(12) United States Patent
Karp et al.

(10) Patent No.: US 7,772,271 B2
(45) Date of Patent: *Aug. 10, 2010

(54) METHODS FOR TREATING HEPATITIS C

(75) Inventors: Gary Mitchell Karp, Princeton Junction, NJ (US); Peter Seongwoo Hwang, Edison, NJ (US); James J. Takasugi, Lawrenceville, NJ (US); Hongyu Ren, Dayton, NJ (US); Richard Gerald Wilde, Somerville, NJ (US); Anthony Turpoff, Edison, NJ (US); Alexander Arefolov, Newton, MA (US); Guangming Chen, Bridgewater, NJ (US); Jeffrey Allen Campbell, Bethlehem, PA (US); Chunshi Li, East Brunswick, NJ (US); Steven Paget, Hillsborough, NJ (US); Nanjing Zhang, Princeton, NJ (US); Xiaoyan Zhang, Belle Mead, NJ (US); Jin Zhu, Raritan, NJ (US)

(73) Assignee: PTC Therapeutics, Inc., South Plainfield, NJ (US)

( * ) Notice: Subject to any disclaimer, the term of this patent is extended or adjusted under 35 U.S.C. 154(b) by 327 days.

This patent is subject to a terminal disclaimer.

(21) Appl. No.: 11/653,448

(22) Filed: Jan. 16, 2007

(65) Prior Publication Data
US 2007/0299068 A1 Dec. 27, 2007

Related U.S. Application Data

(63) Continuation-in-part of application No. 11/331,180, filed on Jan. 13, 2006, which is a continuation-in-part of application No. 11/180,961, filed on Jul. 14, 2005.

(60) Provisional application No. 60/587,487, filed on Jul. 14, 2004, provisional application No. 60/634,979, filed on Dec. 13, 2004, provisional application No. 60/645,586, filed on Jan. 24, 2005, provisional application No. 60/665,349, filed on Mar. 28, 2005, provisional application No. 60/675,440, filed on Apr. 28, 2005, provisional application No. 60/758,527, filed on Jan. 13, 2006, provisional application No. 60/921,482, filed on Jan. 13, 2007.

(51) Int. Cl.
C07D 209/10 (2006.01)
A61K 31/404 (2006.01)
(52) U.S. Cl. .................................. 514/415; 548/491
(58) Field of Classification Search .................. 548/491; 514/415
See application file for complete search history.

(56) References Cited

U.S. PATENT DOCUMENTS

| 4,788,206 A | 11/1988 | Guthrie et al. |
|---|---|---|
| 4,874,756 A | 10/1989 | Mertens et al. |
| 5,072,003 A | 12/1991 | Behnred et al. |
| 5,190,942 A | 3/1993 | Poss |
| 5,215,980 A | 6/1993 | Jones |
| 5,217,996 A | 6/1993 | Ksander |
| 5,354,759 A | 10/1994 | Oku et al. |
| 5,369,120 A | 11/1994 | Woodruff |
| 5,413,999 A | 5/1995 | Vacca et al. |
| 5,474,994 A | 12/1995 | Leonardi et al. |
| 5,527,819 A | 6/1996 | Williams et al. |
| 5,559,127 A | 9/1996 | Hartman et al. |
| 5,605,896 A | 2/1997 | Leonardi et al. |
| 5,633,388 A | 5/1997 | Diana et al. |
| 5,639,906 A | 6/1997 | London et al. |
| 5,681,954 A | 10/1997 | Yamamoto et al. |
| 5,693,643 A | 12/1997 | Gilbert et al. |
| 5,714,496 A | 2/1998 | Brown et al. |
| 5,880,137 A | 3/1999 | Miller et al. |
| 5,922,898 A | 7/1999 | Miller et al. |
| 5,958,086 A | 9/1999 | Adam et al. |
| 5,977,090 A | 11/1999 | Slusher et al. |
| 5,985,910 A | 11/1999 | Miller et al. |
| 6,030,785 A | 2/2000 | Katze et al. |
| 6,057,093 A | 5/2000 | Han et al. |
| 6,124,311 A | 9/2000 | Chandrasekhar et al. |
| 6,132,966 A | 10/2000 | Draper |
| 6,194,599 B1 | 2/2001 | Miller et al. |
| 6,221,902 B1 | 4/2001 | Malamas et al. |
| 6,326,392 B1 | 12/2001 | Gast et al. |
| 6,335,445 B1 | 1/2002 | Chabrier de Lassauniere et al. |
| 6,358,992 B1 | 3/2002 | Pamukeu et al. |
| 6,376,529 B1 | 4/2002 | Tang et al. |
| 6,380,166 B1 | 4/2002 | Miller et al. |

(Continued)

FOREIGN PATENT DOCUMENTS

| CA | 2099060 | 12/1993 |
|---|---|---|
| CN | 1333206 A | 1/2002 |
| DE | 25 26 317 A1 | 1/1976 |
| DE | 29 09 779 | 9/1980 |
| DE | 258014 | 6/1988 |

(Continued)

OTHER PUBLICATIONS

Cecil Textbook of Medicine (20th Edition, vol. 2, 1996, pp. 1739-1747).*

Ahlquist et al., "Host Factors in Positive-Strand RNA Virus Genome Replication", *Journal of Virology*, 77(15):8181-8186 (2003).

Ali et al., "Human La Antigen is Required for the Hepatitis C Virus Internal Ribosome Entry Site-mediated Translation", *J Biol Chem*, 275(36):27531-27540 (2000).

(Continued)

*Primary Examiner*—Kahsay T Habte
(74) *Attorney, Agent, or Firm*—Hoffmann & Baron, LLP

(57) ABSTRACT

The present invention provides compounds, pharmaceutical compositions, and methods of using such compounds or compositions for treating infection by a virus, or for affecting viral IRES activity.

7 Claims, No Drawings

U.S. PATENT DOCUMENTS

| | | |
|---|---|---|
| 6,384,022 B1 | 5/2002 | Jackson et al. |
| 6,555,555 B1 | 4/2003 | Konishi et al. |
| 6,589,570 B1 | 7/2003 | Thyagarajan |
| 6,589,954 B1 | 7/2003 | Mavunkel et al. |
| 6,685,931 B1 | 2/2004 | Grint et al. |
| 6,690,975 B2 | 2/2004 | Yamamoto et al. |
| 6,974,870 B2 | 12/2005 | Cywin et al. |
| 2002/0055651 A1 | 5/2002 | Moran et al. |
| 2002/0091116 A1 | 7/2002 | Zhu et al. |
| 2002/0099054 A1 | 7/2002 | Connor et al. |
| 2002/0099080 A1 | 7/2002 | Gagliardi et al. |
| 2002/0103210 A1 | 8/2002 | Furuya et al. |
| 2002/0143022 A1 | 10/2002 | Pamukeu et al. |
| 2002/0169101 A1 | 11/2002 | Gonzalez et al. |
| 2002/0169107 A1 | 11/2002 | Rajagopalan et al. |
| 2003/0004119 A1 | 1/2003 | Ganguly et al. |
| 2003/0050320 A1 | 3/2003 | Hashimoto et al. |
| 2003/0078420 A1 | 4/2003 | Chabrier de Lassauniere et al. |
| 2003/0096825 A1 | 5/2003 | Wang et al. |
| 2003/0176433 A1 | 9/2003 | Beaulieu et al. |
| 2003/0176697 A1 | 9/2003 | Overman et al. |
| 2003/0199689 A1 | 10/2003 | Nazare et al. |
| 2003/0220377 A1 | 11/2003 | Chesworth |
| 2003/0232866 A1 | 12/2003 | Watterson et al. |
| 2003/0236391 A1 | 12/2003 | Klunk et al. |
| 2004/0044059 A1 | 3/2004 | Pinney et al. |
| 2004/0059131 A1 | 3/2004 | Dell et al. |
| 2004/0067996 A1 | 4/2004 | Sheppeck |
| 2004/0180945 A1 | 9/2004 | Artico et al. |
| 2004/0186125 A1 | 9/2004 | Poupart et al. |
| 2005/0026969 A1 | 2/2005 | Cheng et al. |
| 2005/0075242 A1 | 4/2005 | Holtcamp et al. |
| 2005/0075384 A1 | 4/2005 | Sheppeck et al. |
| 2005/0085529 A1 | 4/2005 | Brown et al. |
| 2005/0113283 A1 | 5/2005 | Solow-Cordero et al. |
| 2005/0119318 A1 | 6/2005 | Hudyma et al. |
| 2005/0123560 A1 | 6/2005 | Sinnott |
| 2005/0227291 A1 | 10/2005 | Kinsella |

FOREIGN PATENT DOCUMENTS

| | | |
|---|---|---|
| DE | 258015 | 6/1988 |
| DE | 258016 | 6/1988 |
| DE | 37 06 427 A1 | 9/1988 |
| DE | 41 39 851 A1 | 6/1992 |
| DE | 41 29 603 A1 | 3/1993 |
| DE | 44 37 262 A1 | 4/1995 |
| DE | 44 37 265 A1 | 4/1995 |
| DE | 196 48 793 A1 | 5/1998 |
| DE | 198 38 705 A1 | 3/2000 |
| DE | 199 46 289 A1 | 3/2001 |
| EP | 0 196 096 A2 | 10/1986 |
| EP | 0 290 153 A1 | 11/1988 |
| EP | 0 318 902 A2 | 6/1989 |
| EP | 0 387 201 A1 | 9/1990 |
| EP | 0 406 734 A2 | 1/1991 |
| EP | 0 414 386 A1 | 2/1991 |
| EP | 0 425 434 A2 | 5/1991 |
| EP | 0 427 225 A1 | 5/1991 |
| EP | 0 430 186 A1 | 6/1991 |
| EP | 0 436 199 A1 | 7/1991 |
| EP | 0 471 372 A1 | 2/1992 |
| EP | 0 480 204 A1 | 4/1992 |
| EP | 0 488 532 | 6/1992 |
| EP | 0 497 659 | 8/1992 |
| EP | 0 527 458 A1 | 2/1993 |
| EP | 0 527 704 A2 | 2/1993 |
| EP | 0 528 762 A1 | 2/1993 |
| EP | 0 530 149 | 3/1993 |
| EP | 0 548 798 A1 | 6/1993 |
| EP | 0 553 682 A1 | 8/1993 |
| EP | 0 556 949 | 8/1993 |
| EP | 0 558 245 A1 | 9/1993 |
| EP | 0 502 424 B1 | 1/1994 |
| EP | 0 586 331 A2 | 3/1994 |
| EP | 0 617 968 A1 | 10/1994 |
| EP | 0 622 356 A1 | 11/1994 |
| EP | 0 624 584 A1 | 11/1994 |
| EP | 0 628 559 | 12/1994 |
| EP | 0 630 895 A1 | 12/1994 |
| EP | 0 639 573 | 2/1995 |
| EP | 0 657 508 A1 | 6/1995 |
| EP | 0 697 172 | 2/1996 |
| EP | 0 708 091 | 4/1996 |
| EP | 0 714 955 A1 | 6/1996 |
| EP | 0 716 855 A2 | 6/1996 |
| EP | 0 719 837 A2 | 7/1996 |
| EP | 0 802 183 | 10/1997 |
| EP | 0 802 184 | 10/1997 |
| EP | 0 826 743 A2 | 3/1998 |
| EP | 1 118 323 | 7/2001 |
| EP | 1 120 114 | 8/2001 |
| EP | 1 125 582 | 8/2001 |
| EP | 1 149 579 | 10/2001 |
| EP | 1 177 787 | 2/2002 |
| EP | 1 192 945 | 4/2002 |
| EP | 1 199 069 | 4/2002 |
| EP | 1 226 823 | 7/2002 |
| EP | 1 314 733 A1 | 5/2003 |
| EP | 1 457 485 A1 | 9/2004 |
| EP | 1 532 980 | 5/2005 |
| EP | 1 574 502 A1 | 9/2005 |
| FR | 2 854 159 | 10/2004 |
| FR | 2 865 208 | 7/2005 |
| GB | 2 282 808 A | 4/1995 |
| GB | 2 292 149 A | 2/1996 |
| JP | 57-085055 A2 | 5/1982 |
| JP | 01273040 | 10/1989 |
| JP | 3-32801 | 2/1991 |
| JP | 3-43744 | 2/1991 |
| JP | 4-319959 | 11/1992 |
| JP | 5-58997 | 3/1993 |
| JP | 5-339565 | 12/1993 |
| JP | 06-236010 | 8/1994 |
| JP | 6-306077 | 11/1994 |
| JP | 8-157461 | 6/1996 |
| JP | 8-244353 | 9/1996 |
| JP | 9-20083 | 1/1997 |
| JP | 9-169729 | 6/1997 |
| JP | 9-258399 | 10/1997 |
| JP | 10-45512 | 2/1998 |
| JP | 11-302177 | 11/1999 |
| JP | 2000-63354 | 2/2000 |
| JP | 2001-55332 | 2/2001 |
| JP | 2001-64166 | 3/2001 |
| JP | 2001-64205 | 3/2001 |
| JP | 2001-151751 | 6/2001 |
| JP | 2001-206845 | 7/2001 |
| JP | 2001-242165 | 9/2001 |
| JP | 3246259 | 11/2001 |
| JP | 2002-3368 | 1/2002 |
| JP | 2002 105081 | 4/2002 |
| JP | 2003-300875 | 10/2003 |
| JP | 2004-61583 | 2/2004 |
| JP | 2004-327313 | 11/2004 |
| JP | 2005-2346 | 1/2005 |
| JP | 2005-82701 | 3/2005 |
| JP | 2005-194198 | 7/2005 |
| JP | 2005-225872 | 8/2005 |
| KR | 93-12108 | 12/1993 |
| WO | WO 92/15579 | 9/1992 |
| WO | 93/14758 | 8/1993 |
| WO | WO 93/18030 | 9/1993 |
| WO | WO 93/18765 | 9/1993 |

| | | | | | | |
|---|---|---|---|---|---|---|
| WO | WO 93/18766 | 9/1993 | | WO | WO 02/00651 A2 | 1/2002 |
| WO | WO 93/19067 | 9/1993 | | WO | WO 02/03975 | 1/2002 |
| WO | WO 94/04153 | 3/1994 | | WO | WO 02/03976 | 1/2002 |
| WO | WO 94/04535 | 3/1994 | | WO | WO 02/03977 | 1/2002 |
| WO | WO 94/08583 | 4/1994 | | WO | WO 02/03986 | 1/2002 |
| WO | WO 94/08962 | 4/1994 | | WO | WO 02/03987 | 1/2002 |
| WO | WO 94/11378 | 5/1994 | | WO | WO 02/03988 | 1/2002 |
| WO | WO 94/14435 | 7/1994 | | WO | WO 02/03989 | 1/2002 |
| WO | WO 94/14438 | 7/1994 | | WO | WO 02/03990 | 1/2002 |
| WO | WO 94/14763 | 7/1994 | | WO | WO 02/03991 | 1/2002 |
| WO | WO 94/14771 | 7/1994 | | WO | WO 02/03992 | 1/2002 |
| WO | WO 94/26746 | 11/1994 | | WO | WO 02/04418 | 1/2002 |
| WO | WO 95/02583 | 1/1995 | | WO | WO 02/06226 A1 | 1/2002 |
| WO | WO 95/07910 | 3/1995 | | WO | WO 02/13802 | 2/2002 |
| WO | WO 95/14003 | 5/1995 | | WO | WO 02/16333 A2 | 2/2002 |
| WO | WO 95/32710 | 12/1995 | | WO | WO 02/16353 | 2/2002 |
| WO | WO 95/33720 | 12/1995 | | WO | WO 02/26696 A1 | 4/2002 |
| WO | WO 96/10012 | 4/1996 | | WO | WO 02/26703 A1 | 4/2002 |
| WO | WO 96/16054 | 5/1996 | | WO | WO 02/30358 | 4/2002 |
| WO | WO 96/26207 | 8/1996 | | WO | WO 02/30879 A2 | 4/2002 |
| WO | WO 96/32379 | 10/1996 | | WO | WO 02/36203 A2 | 5/2002 |
| WO | WO 96/40650 | 12/1996 | | WO | WO 02/36562 | 5/2002 |
| WO | WO 96/41800 | 12/1996 | | WO | WO 02/36580 A2 | 5/2002 |
| WO | WO 97/14419 | 4/1997 | | WO | WO 02/42292 | 5/2002 |
| WO | WO 97/45410 | 4/1997 | | WO | WO 02/48099 A1 | 6/2002 |
| WO | WO 98/13044 | 4/1998 | | WO | WO 02/051805 A1 | 7/2002 |
| WO | WO 98/22457 | 5/1998 | | WO | WO 02/053534 A1 | 7/2002 |
| WO | WO 98/25883 | 6/1998 | | WO | WO 02/055496 A1 | 7/2002 |
| WO | WO 98/48797 | 11/1998 | | WO | WO 02/059088 | 8/2002 |
| WO | WO 99/06836 | 2/1999 | | WO | WO 02/059120 | 8/2002 |
| WO | WO 99/11634 | 3/1999 | | WO | WO 02/060374 A2 | 8/2002 |
| WO | WO 99/13714 | 3/1999 | | WO | WO 02/060447 A1 | 8/2002 |
| WO | WO 99/18096 | 4/1999 | | WO | WO 02/066477 A2 | 8/2002 |
| WO | WO 99/23072 | 5/1999 | | WO | WO 02/070462 A1 | 9/2002 |
| WO | WO 99/24027 | 5/1999 | | WO | WO 02/070469 A2 | 9/2002 |
| WO | WO 99/26946 | 6/1999 | | WO | WO 02/070510 A2 | 9/2002 |
| WO | WO 99/33849 | 7/1999 | | WO | WO 02/072549 | 9/2002 |
| WO | WO 99/43651 | 9/1999 | | WO | WO 02/074742 | 9/2002 |
| WO | WO 99/50237 | 10/1999 | | WO | WO 02/076926 | 10/2002 |
| WO | WO 99/58520 | 11/1999 | | WO | WO 02/083134 A1 | 10/2002 |
| WO | WO 99/59581 | 11/1999 | | WO | WO 02/053545 A1 | 11/2002 |
| WO | WO 99/59969 | 11/1999 | | WO | WO 02/089811 | 11/2002 |
| WO | WO 99/61426 | 12/1999 | | WO | WO 02/096426 A1 | 12/2002 |
| WO | WO 99/64035 | 12/1999 | | WO | WO 02/098424 | 12/2002 |
| WO | WO 99/64415 | 12/1999 | | WO | WO 03/000254 A1 | 1/2003 |
| WO | WO 00/15645 | 3/2000 | | WO | WO 03/000690 A1 | 1/2003 |
| WO | WO 00/28991 | 5/2000 | | WO | WO 03/004458 A1 | 1/2003 |
| WO | WO 00/29384 | 5/2000 | | WO | WO 03/005025 A1 | 1/2003 |
| WO | WO 00/35886 | 6/2000 | | WO | WO 03/006447 A2 | 1/2003 |
| WO | WO 00/43393 | 7/2000 | | WO | WO 03/010140 | 2/2003 |
| WO | WO 00/61586 | 10/2000 | | WO | WO 03/010141 | 2/2003 |
| WO | WO 00/73269 A2 | 12/2000 | | WO | WO 03/022214 A2 | 3/2003 |
| WO | WO 01/19798 A2 | 3/2001 | | WO | WO 03/010140 A2 | 6/2003 |
| WO | WO 01/19839 | 3/2001 | | WO | WO 03/048101 A1 | 6/2003 |
| WO | WO 01/21589 A2 | 3/2001 | | WO | WO 03/053359 A2 | 7/2003 |
| WO | WO 01/21609 | 3/2001 | | WO | WO 03/053368 A2 | 7/2003 |
| WO | WO 01/23353 | 4/2001 | | WO | WO 03/053938 A1 | 7/2003 |
| WO | WO 01/23390 A2 | 4/2001 | | WO | WO 03/053941 A2 | 7/2003 |
| WO | WO 01/44182 | 6/2001 | | WO | WO 03/055447 A2 | 7/2003 |
| WO | WO 01/47883 A1 | 7/2001 | | WO | WO 03/059269 A2 | 7/2003 |
| WO | WO 01/55111 A1 | 8/2001 | | WO | WO 03/062392 A2 | 7/2003 |
| WO | WO 01/55136 | 8/2001 | | WO | WO 03/064539 A1 | 8/2003 |
| WO | WO 01/55137 | 8/2001 | | WO | WO 03/066629 A2 | 8/2003 |
| WO | WO 01/55138 | 8/2001 | | WO | WO 03/074047 | 9/2003 |
| WO | WO 01/55139 | 8/2001 | | WO | WO 03/082265 | 10/2003 |
| WO | WO 01/55144 | 8/2001 | | WO | WO 03/087092 | 10/2003 |
| WO | WO 01/58859 A1 | 8/2001 | | WO | WO 03/091211 | 11/2003 |
| WO | WO 01/64678 A2 | 9/2001 | | WO | WO 03/097036 A1 | 11/2003 |
| WO | WO 01/68585 A1 | 9/2001 | | WO | 2005/058315 | 12/2003 |
| WO | WO 01/74773 A2 | 10/2001 | | WO | WO 03/099276 A1 | 12/2003 |
| WO | WO 01/83451 A1 | 11/2001 | | WO | WO 2004/003103 A1 | 1/2004 |
| WO | WO 01/85687 A1 | 11/2001 | | WO | WO 2004/012736 A1 | 2/2004 |
| WO | WO 01/90105 | 11/2001 | | WO | WO 2004/013135 | 2/2004 |

| | | |
|---|---|---|
| WO | WO 2004/014912 | 2/2004 |
| WO | WO 2004/022057 A1 | 3/2004 |
| WO | WO 2004/024060 A2 | 3/2004 |
| WO | WO 2004/024655 A2 | 3/2004 |
| WO | WO 2004/024896 A2 | 3/2004 |
| WO | WO 2004/030630 | 4/2004 |
| WO | WO 2004/035047 A1 | 4/2004 |
| WO | WO 2004/035522 A1 | 4/2004 |
| WO | WO 2004/035525 A1 | 4/2004 |
| WO | WO 2004/035571 | 4/2004 |
| WO | WO 2004/035571 A1 | 4/2004 |
| WO | WO 2004/037788 | 5/2004 |
| WO | WO 2004/037791 A1 | 5/2004 |
| WO | WO 2004/041256 | 5/2004 |
| WO | WO 2004/041781 A1 | 5/2004 |
| WO | WO 2004/050035 A2 | 6/2004 |
| WO | WO 2004/064759 | 8/2004 |
| WO | WO 2004/064925 | 8/2004 |
| WO | WO 2004/065367 | 8/2004 |
| WO | WO 2004/065367 A1 | 8/2004 |
| WO | WO 2004/074447 | 9/2004 |
| WO | WO 2004/082638 | 9/2004 |
| WO | WO 2004/083195 A1 | 9/2004 |
| WO | WO 2004/087714 A1 | 10/2004 |
| WO | WO 2004/093871 | 11/2004 |
| WO | WO 2004/093912 A1 | 11/2004 |
| WO | WO 2004/094409 | 11/2004 |
| WO | WO 2004/096210 | 11/2004 |
| WO | WO 2004/099168 A2 | 11/2004 |
| WO | WO 2004/099170 A2 | 11/2004 |
| WO | WO 2004/099171 A2 | 11/2004 |
| WO | WO 2004/099192 A2 | 11/2004 |
| WO | WO 2004/099239 A1 | 11/2004 |
| WO | WO 2004/111056 A2 | 12/2004 |
| WO | WO 2005/003086 A2 | 1/2005 |
| WO | WO 2005/003131 A1 | 1/2005 |
| WO | WO 2005/009389 | 2/2005 |
| WO | WO 2005/013950 A2 | 2/2005 |
| WO | WO 2005/013976 | 2/2005 |
| WO | WO 2005/013977 | 2/2005 |
| WO | WO 2005/014000 | 2/2005 |
| WO | WO 2005/014045 | 2/2005 |
| WO | WO 2005/014543 A1 | 2/2005 |
| WO | WO 2005/016862 A1 | 2/2005 |
| WO | WO 2005/018531 | 3/2005 |
| WO | WO 2005/020899 | 3/2005 |
| WO | WO 2005/020921 A1 | 3/2005 |
| WO | WO 2005/021505 | 3/2005 |
| WO | WO 2005/028502 | 3/2005 |
| WO | WO 2005/034941 | 4/2005 |
| WO | WO 2005/034941 A1 | 4/2005 |
| WO | WO 2005/034943 | 4/2005 |
| WO | WO 2005/039489 A2 | 5/2005 |
| WO | WO 2005/042018 | 5/2005 |
| WO | WO 2005/055940 A2 | 6/2005 |
| WO | WO 2005/061519 A1 | 7/2005 |
| WO | WO 2005/062676 A1 | 7/2005 |
| WO | WO 2005/066180 A1 | 7/2005 |
| WO | WO 2005/072132 A2 | 8/2005 |
| WO | WO 2005/076861 A2 | 8/2005 |
| WO | WO 2005/077122 A2 | 8/2005 |
| WO | WO 2005/077969 | 8/2005 |
| WO | WO 2005/080335 | 9/2005 |
| WO | WO 2005/080388 A1 | 9/2005 |
| WO | WO 2005/082895 A1 | 9/2005 |
| WO | WO 2005/082905 A1 | 9/2005 |
| WO | WO 2005/086754 A2 | 9/2005 |
| WO | WO 2005/090282 | 9/2005 |
| WO | WO 2005/092855 | 10/2005 |
| WO | WO 2005/107747 | 11/2005 |
| WO | WO 2005/112519 | 11/2005 |
| WO | WO 2005/113529 | 12/2005 |
| WO | 2006/019831 | 2/2006 |
| WO | WO 2006/019831 A1 | 2/2006 |
| WO | WO 2006/024699 | 3/2006 |
| WO | WO 2006/041874 | 4/2006 |
| WO | WO 2006/049013 | 5/2006 |
| WO | WO 2006/050236 | 5/2006 |
| WO | WO 2006/057354 | 6/2006 |
| WO | WO 2006/083458 | 8/2006 |

OTHER PUBLICATIONS

Ali et al., "Interaction of Polypyrimidine Tract-Binding Protein with the 5' Noncoding Region of the Hepatitis C Virus RNA Genome and its Functional Requirement in Internal Initiation of Translation", *J Virol*, 69(10):6367-6375 (1995).

Ali et al., "The La Antigen Binds 5' Noncoding Region of the Hepatitis C Virus RNA in the Context of the Initiator AUG Codon and Stimulates Internal Ribosome Entry Site-Mediated Translation", *Proc Natl Acad Sci USA*, 94:2249-2254 (1997).

Almerico et al., "Glycosidopyrroles Part 3. Effect of the Benzocondesnation on Acyclic Derivatives: 1-(2-hydroxyethoxy) Methylindoles as Potential Antiviral Agents", *Il Farmaco*, 53:409-414 (1998).

Almerico et al., "Glycosidopyrroles. part 4. 1-β-D-ribofuranosyl-pyrroles and Indoles as Potential Antiviral agents", *ARKIVOC*, 1(4):486-496 (2000).

Anwar et al., "Demonstration of Functional Requirement of Polypyrimidine Tract-binding Protein by SELEX RNA during Hepatitis C Virus Internal Ribosome Entry Site-mediated Translation Initiation", *J Biol Chem*, 275(44):34231-34235 (2000).

Attaby et al., "Synthesis and Antimicrobial Evaluation of Several New Pyridine, Thienopyridine and Pyridothienopyrazole Derivatives", *Phosphorus, Sulfur and Silicon*, 149:49-64 (1999).

Beales et al., "The Internal Ribosome Entry Site (IRES) of Hepatitis C Virus Visualized by Electron Microscopy", *RNA*, 7:661-670 (2001).

Belsham et al., "A Region of the 5' Noncoding Region of Foot-and-Mouth Disease Virus RNA Directs Efficient Internal Initiation of Protein Synthesis within Cells: Involvement with the Role of L Protease in Translational Control", *J Virol*, 64(11):5389-5395 (1990).

Belsham et al., "Translation Initiation on Picornavirus RNA", p. 869-900, Cold Spring Harbor Laboratory Press, New York (2000).

Blight et al., "Efficient Initiation of HCV RNA Replication in Cell Culture", *Science*, 290:1972-1974 (2000).

Blight et al., "Highly Permissive Cell Lines for Subgenomic and Genomic Hepatitis C Virus RNA Replication", *J Virol*, 76(24):13001-13014 (2002).

Boni et al., "Hepatitis C Virus Core Protein Acts as a *trans*-Modulating Factor on Internal Translation Initiation of the Viral RNA", *J Biol Chem*, 280(18):17737-17748 (2005).

Borovjagin et al., "Pyrimidine Tract Binding Protein Strongly Stimulates in vitro Encephalomyocarditis Virus RNA Translation at the Level of the Preinitiation Complex Formation" *FEBS Lett*, 351:291-302 (1994).

Brown et al., "Secondary Structure of the 5' Nontranslated Regions of Hepatitis C Virus and Pestivirus Genomic RNAs", *Nucleic Acids Res*, 20(19):5041-5045 (1992).

Buck et al., "The Human Immunodeficiency Virus Type 1 *gag* Gene Encodes an Internal Ribosome Entry Site", *J Virol*, 75(1):181-191 (2001).

Bukh et al. "Sequence Analysis of the 5' Noncoding Region of Hepatitis C Virus", *Proc Natl Acad Sci USA*, 89:4942-4946 (1992).

Bukh et al., "Sequence Analysis of the Core Gene of 14 Hepatitis C Virus Genotypes", *Proc Natl Acad Sci USA*, 91:8239-8243 (1994).

Buratti et al., "Functional Analysis of the Interaction Between HCV 5'UTR and Putative Subunits of Eukaryotic Translation Initiation Factor eIF3", *Nucleic Acids Res*, 26(13):3179-3187 (1998).

Cacchi et al., "2-Aryl and 2-Heteroaryl Indoles from 1-Alkynes and o-Iodotrifluoroacetanilide through a Domino Copper-Catalyzed Coupling-Cyclization Process", *Organic Letters*, 5(21):3843-3846 (2003).

Carson et al., "The Synthesis and Properties of 2-p-Dimthylaminophenyl-1,3,3-trimethyl-3H-indolium Salts", *Journal of the Chemical Society*, 5819-5825 (1965).

Chappell et al., "A Mutation in the c-*myc*-IRES Leads to Enhanced Internal Ribosome Entry in Multiple Myeloma: A Novel Mechanism of Oncogene De-Regulation", *Oncogene*, 19:4437-4440 (2000).
Chung et al., "Hepatitis C Virus Replication is Directly Inhibited by IFN-α in a Full-Length Binary Expression System", *Proc Natl Acad Sci USA*, 98(17):9847-9852 (2001).
Chikvaidze et al., "Synthesis and Antimicrobial Activity of New Derivatives of 2-Phenylindone", *Pharmaceutical Chemistry Journal*, 28(10):751-755 (1994).
Coldwell et al., "Initiation of Apaf-1 Translation by Internal Ribosome Entry", *Oncogene*, 19:899-905 (2000).
Créancier et al., "Fibroblast Growth Factor 2 Internal Ribosome Entry Site (IRES) Activity Ex Vivo and in Transgenic Mice Reveals a Stringent Tissue-specific Regulation", *J Cell Biol*, 150(1):275-281 (2000).
Danilova et al., "Synthesis and Transformations of Aminoethyl Derivatives of Cyclic β-Diketones", *Zhurnal Obshchei Khimii*, 1(9):1708-9 (1965).
Das et al., "Inhibition of Internal Entry Site (IRES)-Mediated Translation by a Small Yeast RNA: a Novel Strategy to Block Hepatitis C Virus Protein Synthesis" *Front Biosci*, (3)d1241-1252 (1998).
Dever, "Gene-Specific Regulation by General Translation Factors", *Cell*, 108:545-556 (2002).
Dhar et al., "3-Cyanoindole-Based Inhibitors of Inosine Monophosphate Dehydrogenase: Synthesis and Initial Structure-Activity Relationships", *Bioorganic & Medicinal Chemistry Letters*, 13:3557-3560 (2003).
Dumas et al., "A Promoter Activity is Present in the DNA Sequence Corresponding to the Hepatitis C Virus 5' UTR", *Nucleic Acids Res*, 31(4):1275-1281 (2003).
Font et al., "indoles and Pyridazino[4,5-*b*]indoles as Nonnucleoside Analog Inhibitors of HIV-1 Reverse Transcriptase", *Eur J Med Chem*, 30:963-971 (1995).
Fukushi et al., "Complete 5' Noncoding Region is Necessary for the Efficient Internal Initiation of Hepatitis C Virus RNA", *Biochem Biophys. Res Commun.*, 199(2):425-432 (1994).
Fukushi et al., "The Sequence Element of the Internal Ribosome Entry Site and a 25-Kilodalton Cellular Protein Contribute to Efficient Internal Initiation of Translation of Hepatitis C Virus RNA", *J Virol*, 71(2):1662-1666 (1997).
Fukushi et al., "Specific Interaction of a 25-Kilodalton Cellular Protein, a 40S Ribosomal Subunit Protein, with the Internal Ribosome Entry Site of Hepatitis C Virus Genome", *Virus Genes*, 19(2):153-161 (1999).
Fukushi et al., "Ribosomal Protein S5 Interacts with the Internal Ribosomal Entry Site of Hepatitis C Virus", *J Biol Chem*, 276(24):20824-20826 (2001).
Funkhouser et al., "Hepatitis A Virus Translation is Rate-Limiting for Virus Replication in MRC-5 Cells", *Virology*, 254:268-278 (1999).
Germain Sanit-Ruf et al., "Analogues Méso-Hétérocycliques du dihydro-9,10 anthracéne. XII—Sur quelques Indoes Dérivés de la Dibenzo-p-Dioxine", *Notes*, 1069-1071 (1975).
Glass et al., "Identification of the Hepatitis A Virus Internal Ribosome Entry Site: In vivo and in vitro Analysis of Bicistronic RNAs Containing the HAV 5' Noncoding Region", *Virology*, 193:842-852 (1993).
Gordon et al., "A Phase II, 12-Week Study of ISIS 14803, an Antisense Inhibitor of HCV for the Treatment of Chronic Hepatitis C" AASLD Abst., 795, *Hepatology*, 36:362A (2002).
Gosert et al., "Transient Expression of Cellular Polypyrimidine-Tract Binding Protein Stimulates Cap-Independent Translation Directed by Both Picornaviral and Flaviviral Internal Ribosome Entry Sites In Vivo", *Mol Cell Biol*, 20(5):1583-1595 (2000).
Gray et al., "Control of Translation Initiation in Animals", *Annu Rev Cell Dev Biol*, 14:399-458 (1998).
Griffith et al., "An Unusual Internal Ribosome Entry Site in the Herpes Simplex Virus Thymidine Kinase Gene", *Proc Natl Acad Sci USA*, 102(27):9667-72 (2005).
Guo et al., "Effect of Alpha Interferon on the Hepatitis C Virus Replicon", *J Virol*, 75(18):8516-8523 (2001).
Hahm et al., "Heterogeneous Nuclear Ribonucleoprotein L Interacts with the 3' Border of the Internal Ribosomal Entry Site of Hepatitis C Virus", *J Virol*, 72(11):8782-8788 (1998).

Haller et al., "Attenuation Stem-Loop Lesions in the 5' Noncoding Region of Poliovirus RNA: Neuronal Cell-Specific Translation Defects", *J Virol*, 70(3):1467-1474 (1996).
He et al., "The Regulation of Hepatitis C Virus (HCV) Internal Ribosome-Entry Site-Mediated Translation by HCV Replicons and Nonstructural Proteins", *J Gen Virol*, 84:535-543 (2003).
Hellen et al., "Translation of Hepatitis C Virus RNA", *J Viral Hepat*, 6:79-87 (1999).
Hellen et al., "A Cytoplasmic 57-kDa Protein that is Required for Translation of Picornavirus RNA by Internal Ribosomal Entry is Identical to the Nuclear Pyrimidine Tract-Binding Protein", *Proc Natl Acad Sci USA*, 90:7642-7646 (1993).
Hendrix et al., "Direct Observation of Aminoglycoside-RNA Interactions by Surface Plasmon Resonance" *Journal of the American Chemical Society*, 119(16):3641-8 (1997).
Holcik et al., "Functional Characterization of the X-Linked Inhibitor of Apoptosis (XIAP) Internal Ribosome Entry Site Element: Role of La Autoantigen in XIAP Translation", *Mol Cell Biol*, 20(13):4648-4657 (2000).
Holcik et al., "A new Internal-Ribosome-Entry-Site Motif Potentiates XIAP-Mediated Cytoprotection", *Nat Cell Biol*, 1:190-192 (1999).
Honda et al., "A Phylogenetically Conserved Stem-Loop Structure at the 5' Border of the Internal Ribosome Entry Site of Hepatitis C Virus is Required for Cap-Independent Viral Translation", *J Virol*, 73(2):1165-1174 (1999).
Honda et al., "Stability of a Stem-Loop Involving the Initiator AUG Controls the Efficiency of Internal Initiation of Translation on Hepatitis C Virus RNA", *RNA*, 2:955-968 (1996).
Honda et al., "Structural Requirements for Initiation of Translation by Internal Ribosome Entry within Genome-Length Hepatitis C Virus RNA", *Virology*, 222:31-42 (1996).
Honda et al., "Natural Variation in Translational Activities of the 5' Nontranslated RNAs of Hepatitis C Virus Genotypes 1a and 1b: Evidence for a Long- Range RNA-RNA Interaction Outside of the Internal Ribosomal Entry Site", *J Virol*, 73(6):4941-4951 (1999).
Huez et al., "New Vascular Endothelial Growth Factor Isoform Generated by Internal Ribosome Entry Site-Driven CUG Translation Initiation", *Mol Endocrinol.*, 15(12):2197-2210 (2001).
Huez et al., "Two Independent Internal Ribosome Entry Sites Are Involved in Translation Initiation of Vascular Endothelial Growth Factor mRNA", *Mol Cell Biol*, 18(11):6178-6190 (1998).
Ikeda et al., "Selectable Subgenomic and Genome-Length Dicistronic RNAs Derived from an Infectious Molecular Clone of the HCV-N Strain of Hepatitis C Virus Replicate Efficiently in Cultured Huh7 Cells" *J Virol*, 76(6):2997-3006 (2002).
International Search Report for International Application No. PCT/US2005/024881, mailed Feb. 3, 2006.
Irvine et al., "MDCK (Madin-Darby Canine Kidney) Cells: A Tool for Membrane Permeability Screening", *J Pharm Sci*, 88(1):28-33 (1999).
Isoyama et al., "Lower Concentration of La Protein Required for Internal Ribosome Entry on Hepatitis C Virus RNA than on Poliovirus RNA", *J Gen Virol*, 80( 9):2319-2327 (1999).
Ito et al., "An Internal Polypyrimidine-Tract-Binding Protein-Binding Site in the Hepatitis C Virus RNA Attenuates Translation, Which is Relieved by the 3'-Untranslated Sequence", *Virology* 254:288-296 (1999).
Jang et al., "A Segment of the 5' Nontranslated Region of Encephalomyocarditis Virus RNA Directs Internal Entry of Ribosomes during In Vitro Translation", *J Virol*, 62(8):2636-2643 (1988).
Jubin et al., "Hepatitis C Virus Internal Ribosome Entry Site (IRES) Stem Loop IIId Contains a Phylogenetically Conserved GGG Triplet Essential for Translation and IRES Folding", *J Virol*, 74(22):10430-10437 (2000).
Kalliampakou et al., "Mutational Analysis of the Apical Region of Domain II of the HCV IRES", *FEBS Lett*, 511:79-84 (2002).
Kaminski et al., "Direct Evidence that Polypyrimidine Tract Binding Protein (PTB) is Essential for Internal Initiation of Translation of Encephalomyocarditis Virus RNA", *RNA*, 1:924-938 (1995).

Kamoshita et al., "Genetic Analysis of Internal Ribosomal Entry Site on Hepatitis C Virus RNA: Implication for Involvement of the Highly Ordered Structure and Cell Type-Specific Transacting Factors", *Virology*, 233:9-18 (1997).

Kato et al., "Hepatitis C Virus NS4A and NS4B Proteins Suppress Translation in Vivo", *J Med Virol*, 66:187-199 (2002).

Kieft et al., "The Hepatitis C Virus Internal Ribosome Entry Site Adopts an Ion-dependent Tertiary Fold", *J Mol Biol*, 292:513-529 (1999).

Kieft et al., "Mechanism of Ribosome Recruitment by Hepatitis C IRES RNA", *RNA*, 7:194-206 (2001).

Klinck et al., "A Potential RNA Drug Target in the Hepatitis C Virus Internal Ribosomal Entry Site", *RNA*, 6:1423-1431 (2000).

Kolupaeva et al., "An Enzymatic Footprinting Analysis of the Interaction of 40S Ribosomal Subunits with the Internal Ribosomal Entry Site of Hepatitis C Virus", *J Virol*, 74(14):6242-6250 (2000).

Kolupaeva et al., "Structural Analysis of the Interaction of the Pyrimidine Tract-Binding Protein with the Internal Ribosomal Entry Site of Encephalomyocarditis Virus and Foot-and-Mouth Disease Virus RNAs", *RNA*, 2:1199-1212 (1996).

Kolupaeva et al., "Translation Eukaryotic Initiation Factor 4G Recognizes a Specific Structural Element within the Internal Ribosome Entry Site of Encephalomyocarditis Virus RNA", *J Biol Chem*, 273(29):18599-18604 (1998).

Kozak, "Initiation of Translation in Prokaryotes and Eukaryotes", *Gene*, 234:187-208 (1999).

Krüger et al., "Involvement of Proteasome α-Subunit PSMA7 in Hepatitis C Virus Internal Ribosome Entry Site-Mediated Translation", *Mol Cell Biol*, 21(24): 8357-8364 (2001).

La Monica et al., "Differences in Replication of Attenuated and Neurovirulent Polioviruses in Human Neuroblastoma Cell Line SH-SY5Y", *J Virol*, 63(5):2357-2360 (1989).

Le et al., "Unusual Folding Regions and Ribosome Landing Pad within Hepatitis C Virus and Pestivirus RNAs", *Gene*, 154:137-143 (1995).

Lerat et al., "Cell Type-Specific Enhancement of Hepatitis C Virus Internal Ribosome Entry Site-Directed Translation due to 5' Nontranslated Region Substitutions Selected during Passage of Virus in Lymphoblastoid Cells", *J Virol*, 74(15):7024-7031 (2000).

Li et al., "A Heterocyclic Inhibitor of the Rev-RRE Complex Binds to RRE as a Dimer", Biochemistry, 40:1150-1158 (2001).

Li et al., "Amino Acids 1-20 of the Hepatitis C Virus (HCV) Core Protein Specifically Inhibit HCV IRES-Dependent Translation in HepG2 Cells, and Inhibit Both HCV IRES- and Cap-Dependent Translation in HuH7 and CV-1 Cells", *J Gen Virol*, 84:815-825 (2003).

Lipinski, "Drug-Like Properties and the Causes of Poor Solubility and Poor Permeability", *J Pharm Tox Meth*, 44:235-249 (2000).

Llinàs-Brunet, "NS3 Serine Protease Inhibitors as Potential Antiviral Agents for the Treatment of Hepatitis C Virus Infections", The 3rd Internatl Antiviral & Vaccine Discovery & Development Summit, Princeton, NJ (Mar. 13-14, 2002).

Lohmann et al., "Mutations in Hepatitis C Virus RNAs Conferring Cell Culture Adaptation", *J Virol*, 75(3):1437-1449 (2001).

Lohmann et al., "Replication of Subgenomic Hepatitis C Virus RNAs in a Hepatoma Cell Line", *Science*, 285:110-113 (1999).

Lopez et al., "IRES Interaction with Translation Initiation Factors: Functional Characterization of Novel RNA Contacts with eIF3, eIF4B, and eIF4GII", *RNA*, 7:1213-1226 (2001).

Lopez et al., "Interaction of the eIF4G Initiation Factor with the Aphthovirus IRES is Essential for Internal Translation Initiation In Vivo", *RNA*, 6:1380-1392 (2000).

Lu et al., "Poliovirus Chimeras Replicating Under the Translational Control of Genetic Elements of Hepatitis C Virus Reveal Unusual Properties of the Internal Ribosomal Entry Site of Hepatitis C Virus", *Proc Natl Acad Sci USA*, 93:1412-1417 (1996).

Lukavsky et al., "Structures of Two RNA Domains Essential for Hepatitis C Virus Internal Ribosome Entry Site Function", *Nat Struct Bio*, 7(12):1105-1110 (2000).

Lyons et al., "Hepatitis C Virus Internal Ribosome Entry Site RNA Contains a Tertiary Structural Element in a Functional Domain of Stem-Loop II", *Nucleic Acids Res*, 29(12):2535-2541 (2001).

Lukavsky et al., "Structure of HCV IRES Domain II Determined by NMR", *Nat Struct Biol*, 10(12):1033-1038 (2003).

Macejak et al., "Inhibition of Hepatitis C Virus (HCV)-RNA-Dependent Translation and Replication of a Chimeric HCV Poliovirus Using Synthetic Stabilized Ribozymes", *Hepatology*, 31:769-76 (2000).

Macejak et al., "Enhanced Antiviral Effect in Cell Culture of Type 1 Interferon and Ribozymes Targeting HCV RNA", *J Viral Hepatitis*, 8:400-405 (2001).

Macejak et al., "Internal Initiation of Translation Mediated by the 5' Leader of a Cellular mRNA", *Nature*, 353:90-94 (1991).

Major et al., "Hepatitis C Viruses.", p. 1127-1161. In D. Knipe and P. Howley (eds.), Fields Virology, vol. 1, 4th Ed. Lippincott Williams and Wilkins, Philadelphia, PA (2001).

Manns et al., "Peginterferon alfa-2b Plus Ribavirin Compared with Interferon Alfa-2b Plus Ribavirin for Initial Treatment of Chronic Hepatitis C: A Randomised Trial", *The Lancet*, 358:958-965 (2001).

Martinez-Saks et al., "Functional Interactions in Internal Translation Initiation Directed by Viral and Cellular IRES Elements", *J Gen Virol*, 82:973-984 (2001).

Mazur et al., "A Thermodynamic and Structural Analysis of DNA Minor-groove Complex Formation", *J Mol Biol*, 300:321-337 (2000).

McHutchison et al., "Combination Therapy With Interferon Plus Ribavirin for the Initial Treatment of Chronic Hepatitis C", *Semin Liver Dis*, 19 Suppl 1:57-65 (1999).

McHutchison et al., "Hepatic HCV RNA Before and After Treatment With Interferon Alone or Combined With Ribavirin", *Hepatology*, 35(3):688-693 (2002).

Meerovitch et al., "A Cellular Protein that Binds to the 5'-Noncoding Region of Poliovirus RNA: Implications for Internal Translation Initiation", *Genes Dev*, 3:1026-1034 (1989).

Meerovitch et al., "La Autoantigen Enhances and Corrects Aberrant Translation of Poliovirus RNA in Reticulocyte Lysate", *J Virol*, 67(7): 3798-3807 (1993).

Mercer et al., "Hepatitis C Virus Replication in Mice with Chimeric Human Livers", *Nature Medicine*, 7(8):927-933 (2001).

Michel et al., "Eukaryotic Initiation Factor 4G-Poly(A) Binding Protein Interaction Is Required for Poly(A) Tail-Mediated Stimulation of Picornavirus Internal Ribosome Entry Segment-Driven Translation but Not for X-Mediated Stimulation of Hepatitis C Virus Translation", *Mol Cell Biol*, 21(13): 4097-4109 (2001).

Mitchell et al., "Protein Factor Requirements of the Apaf-1 Internal Ribosome Entry Segment: Roles of Polypyrimidine Tract Binding Protein and Upstream of N-ras", *Mol Cell Biol*, 21(10):3364-3374 (2001).

Moriguchi, et al., "Simple Method of Calculating Octanol/Water Partition Coefficient", *Chem Pharm Bull*, 40(1):127-130 (1992).

Nanbru et al., "Alternative Translation of the Proto-oncogene c-*myc* by an Internal Ribosome Entry Site", *J Biol Chem*, 272(51):32061-32066 (1997).

Niepmann et al., "Functional Involvement of Polypyrimidine Tract-Binding Protein in Translation Initiation Complexes with the Internal Ribosome Entry Site of Foot-and-Mouth Disease Virus", *J Virol*, 71(11):8330-8339 (1997).

Odreman-Macchioli et al., "Mutational Analysis of the Different Bulge Regions of Hepatitis C Virus Domain II and Their Influence on Internal Ribosome Entry Site Translational Ability", *J Biol Chem*, 276(45):41648-41655 (2001).

Odreman-Macchioli et al., "Influence of Correct Secondary and Tertiary RNA Folding on the Binding of Cellular Factors to the HCV IRES", *Nucleic Acids Res*, 28(4):875-885 (2000).

Ohlmann et al., "An Internal Ribosome Entry Segment Promotes Translation of the Simian Immunodeficiency Virus Genomic RNA", *J Biol Chem*, 275(16):11899-11906 (2000).

Otto et al., "The Pathway of HCV IRES-Mediated Translation Initiation", *Cell*, 119:369-380 (2004).

Pain, "Initiation of Protein Synthesis in Eukaryotic Cells", *Eur J Biochem*, 236:747-771 (1996).

Patent Abstracts of Japan of JP 01273040 a published Oct. 31, 1989.
Patent Abstracts of Japan of JP 06236010 a published Aug. 23, 1994.
Patent Abstracts of Japan of JP 09169729 a published Jun. 30, 1997.

Pelletier et al., "Internal Initiation of Translation of Eukaryotic mRNA Directed by a Sequence Derived from Poliovirus RNA", *Nature*, 334:320-325 (1988).

Pelletier et al., "Internal Binding of Eucaryotic Ribosomes on Poliovirus RNA: Translation in HeLa Cell Extracts", *J Virol*, 63(1):441-444 (1989).

Perola et al., "Successful Virtual Screening of a Chemical Database for Farnesyltransferase Inhibitor Leads", *J. Med. Chem.*, 43:401-408 (2000).

Pestova et al., "Eukaryotic Ribosomes Require Initiation Factors 1 and 1A to Locate Initiation Codons", *Nature* 394:854-859 (1998).

Pestova et al., "A Prokaryotic-Like Mode of Cytoplasmic Eukaryotic Ribosome Binding to the Initiation Codon During Internal Translation Initiation of Hepatitis C and Classical Swine Fever Virus RNAs", *Genes Dev*, 12: 67-83 (1998).

Pestova et al., "Functional Dissection of Eukaryotic Initiation Factor 4F: the 4A Subunit and the Central Domain of the 4G Subunit Are Sufficient to Mediate Internal Entry of 43S Preinitiation Complexes", *Mol Cell Biol*, 16(12):6870-6878 (1996).

Peytou et al., "Synthesis and Antiviral Activity of Ethidium-Arginine Conjugates Directed Against the TAR RNA of HIV-1", *J Med Chem*, 42(20):4042-53 (1999).

Pietschmann et al., "Persistent and Transient Replication of Full-Length Hepatitis C Virus Genomes in Cell Culture", *J Virol*, 76(8):4008-4021 (2002).

Pietschmann et al., "Characterization of Cell Lines Carrying Self-Replicating Hepatitis C Virus RNAs", *J Virol*, 75(3):1252-1264 (2001).

Poole et al., "Pestivirus Translation Initiation Occurs by Internal Ribosome Entry", *Virology*, 206:750-754 (1995).

Pringle, "Virus Taxonomy—1999. The Universal System of Virus Taxonomy, Updated to Include the New Proposals Ratified by the International Committee on Taxonomy of Viruses During 1998", *Arch Virol*, 144/2:421-429 (1999).

Psaridi et al., "Mutational Analysis of a Conserved Tetraloop in the 5' Untranslated Region of Hepatitis C Virus Identifies a Novel RNA Element Essential for the Internal Ribosome Entry Site Function", *FEBS Lett*, 453:49-53 (1999).

Reynolds et al., "Internal Initiation of Translation of Hepatitis C Virus RNA: The Ribosome Entry Site is at the Authentic Initiation Codon", *RNA*, 2:867-878 (1996).

Reynolds et al., "Unique Features of Internal Initiation of Hepatitis C Virus RNA Translation", *EMBO J*, 14(23):6010-6020 (1995).

Rijnbrand et al., "Almost the Entire 5' Non-Translated Region of Hepatitis C Virus is Required for Cap-Independent Translation", *FEBS Lett*, 365:115-119 (1995).

Rijnbrand et al., "Internal Ribosome Entry Site-Mediated Translation in Hepatitis C Virus Replication", *Curr Top Microbiol Immunol*, 242:85-116 (2000).

Rijnbrand et al., "The Influence of Downstream Protein-Coding Sequence on Internal Ribosome Entry on Hepatitis C Virus and Other Flavivirus RNAs", *RNA*, 7:585-597 (2001).

Rijnbrand et al., "The Influence of AUG Codons in the Hepatitis C Virus 5' Nontranslated Region on Translation and Mapping of the Translation Initiation Window", *Virology*, 226:47-56 (1996).

Sachs et al., "Starting at the Beginning, Middle, and End: Translation Initiation in Eukaryotes", *Cell*, 89:831-838 (1997).

Saito et al., "Hepatitis C Virus Infection is Associated with the Development of Hepatocellular Carcinoma", *Proc Natl Acad Sci USA*, 87:6547-6549 (1990).

Schultz et al., "Mutations within the 5' Nontranslated RNA of Cell Culture-Adapted Hepatitis A Virus Which Enhance Cap-Independent Translation in Cultured African Green Monkey Kidney Cells", *J Virol*, 70(2):1041-1049 (1996).

Shimazaki et al., "Inhibition of Internal Ribosomal Entry Site-Directed Translation of HCV by Recombinant IFN-α Correlates With a Reduced La Protein", *Hepatology*, 35(1):199-208 (2002).

Simmonds, "Variability of Hepatitis C Virus", *Hepatology*, 21(2):570-583 (1995).

Sinha Roy et al., "Direct Interaction of a Vancomycin Derivative with Bacterial Enzymes Involved in Cell Wall Biosynthesis", *Chem Biol*, 8:1095-1106 (2001).

Sizova et al., "Specific Interaction of Eukaryotic Translation Initiation Factor 3 with the 5' Nontranslated Regions of Hepatitis C Virus and Classical Swine Fever Virus RNAs", *J Virol*, 72(6):4775-4782 (1998).

Smith, "Design of Drugs Through a Consideration of Drug Metabolism and Pharmacokinetics", *Eur J Drug Metab Pharm*, 3:193-199 (1994).

Smith et al., "Variation of the Hepatitis C Virus 5' Non-Coding Region: Implications for Secondary Structure, Virus Detection and Typing", *J Gen Virol*, 76(7):1749-1761 (1995).

Sonenberg et al., "Translational Control of Gene Expression", Cold Spring Harbor. Cold Spring Harbor Laboratory Press, New York (2000).

Spahn et al., "Hepatitis C Virus IRES RNA-Induced Changes in the Conformation of the 40s Ribosomal Subunit", *Science*, 291:1959-1962 (2001).

Spatzenegger et al., "Clinical Importance of Hepatic Cytochrome P450 in Drug Metabolism", *Drug Metab Rev* 27(3):397-417 (1995).

Subkhankulova et al., "Internal Ribosome Entry Segment-Mediated Initiation of c-Myc Protein Synthesis Following Genotoxic Stress", *Biochem J*, 359:183-192 (2001).

Tang et al., "Alterations to Both the Primary and Predicted Secondary Structure of Stem-Loop IIIc of the Hepatitis C Virus 1b 5' Untranslated Region (5'UTR) Lead to Mutants Severely Defective in Translation Which Cannot Be Complemented in *trans* by the Wild-Type 5'UTR Sequence", *J Virol*, 73(3):2359-2364 (1999).

Terent'ev et al., "Synthesis of Derivatives of 5-Methoxyinodle", *Doklady Akademii Nauk SSSR*, 114:560-563 (1957).

Thiel et al., "Internal Ribosome Entry in the Coding Region of Murine Hepatitis Virus mRNA 5", *J Gen Virol.*, 75(11):3041-3046 (1994).

Tsukiyama-Kohara et al., "Internal Ribosome Entry Site within Hepatitis C Virus RNA", *J Virol*, 66(3):1476-1483 (1992).

Vagner et al., "Alternative Translation of Human Fibroblast Growth Factor 2 mRNA Occurs by Internal Entry of Ribosomes", *Mol Cell Biol*, 15(1):35-44 (1995).

Varaklioti et al., "Mutational Analysis of Two Unstructured Domains of the 5' Untranslated Region of HCV RNA", *Biochem Biophys. Res Commun.*, 253:678-685 (1998).

Wang et al., "An RNA Pseudoknot is an Essential Structural Element of the Internal Ribosome Entry Site Located Within the Hepatitis C Virus 5' Noncoding Region", *RNA*, 1:526-537 (1995).

Wang et al., "Translation of Human Hepatitis C Virus RNA in Cultured Cells is Mediated by an Internal Ribosome-Binding Mechanism", *J Virol*, 67(6):3338-3344 (1993).

Wang et al., "A Conserved Helical Element is Essential for Internal Initiation of Translation of Hepatitis C Virus RNA", *J Virol*, 68(11):7301-7307 (1994).

Wang et al., "Screening poly(dA/dT) cDNAs for Gene Identification", *PNAS USA*, 97(8):4162-7 (2000).

Wang et al., "Core Protein-Coding Sequence, but Not Core Protein, Modulates the Efficiency of Cap-Independent Translation Directed by the Internal Ribosome Entry Site of Hepatitis C Virus", *J Virol*, 74(23):11347-11358 (2000).

Wang et al., "Alpha Interferon Induces Distinct Translational Control Programs to Suppress Hepatitis C Virus RNA Replication", *Journal of Virology*, 77(7):3898-3912 (2003).

Wimmer et al., "Genetics of Poliovirus", *Annu Rev Genet*, 27:353-436 (1993).

Wong et al., "Cost-Effectiveness of 24 or 48 Weeks of Interferon α-2b Alone or With Ribavirin as Initial Treatment of Chronic Hepatitis C", *Am J Gastroenterol*, 95(6):1524-1530 (2000).

Zhao et al., "Genetic Analysis of a Poliovirus/Hepatitis C Virus Chimera: New Structure for Domain II of the Internal Ribosomal Entry Site of Hepatitis C Virus", *J Virol*, 75(8):3719-3730 (2001).

Zhao et al., "Poliovirus/Hepatitis C Virus (Internal Ribosomal Entry Site-Core) Chimeric Viruses: Improved Growth Properties through Modification of a Proteolytic Cleavage Site and Requirement for Core RNA Sequences but Not for Core-Related Polypeptides", *J Virol*, 73(2):1546-1554 (1999).

Al-Omran, STN Accession No. 2000:825367 Document No. 134:131488; Abstract of the Journal of Heterocyclic Chemistry, 37(5):1219-1223 (2000).

Boehm et al., STN Accession No. 1993:756686 Document No. 118:233974; Abstract of Pharmazie, 47(12):897-901 (1992).

Dyachenko et al., STN Accession No. 1996:756686 Document No. 126:74777; Abstract of Khimiya Geterotsiklicheskikh Soedinenii, 9:1232-1234 (1996).

Elgemeie et al., STN Accession No. 1994:54466 Document No. 120:54466; Abstract of Journal of Chemical Research, Synopses, 7:256-257 (1993).

Frolova et al., STN Accession No. 1996:396582 Document No. 125:167833; Abstract of Izvestiya Akademii Nauk, Seriya Khimicheskaya, 4:938-942 (1996).

Frolova et al., STN Accession No. 1997:73192 Document No. 126:131360; Abstract of Izvestiya Akademii Nauk, Seriya Khimicheskaya, 11:2719-2721 (1996).

International Search Report in PCT/US2007/000996 mailed Sep. 19, 2007.

Leistner et al., STN Accession No. 1992:235578 Document No. 116:235578; Abstract of Pharmazie, 47(1):11-14 (1992).

Paronikyan et al., STN Accession No. 01998:173599 Document No. 128:243969, Abstract of Khimiko-Farmatsevticheskii Zhurnal, 31(10):34-36 (1997).

Partial International Search Report in PCT/US2007/000996 mailed Jul. 16, 2007.

Patent Abstracts of Japan of Pubklication No. 08183260 Published Jul. 16, 1996.

Quintela et al., STN Accession No. 1999:643470 Document No. 132:22945; Abstract of Journal of Medicinal Chemistry, 42(22):4720-4724 (1999).

Sharanin et al., STN Accession No. 1985:113330 Document No. 102:113330, Abstract of Zhurnal Organicheskoi Khimii, 20(9):2002-2011 (1984).

Vieweg et al., STN Accession No. 1993:449330, Document No. 119:49330, Abstract of Pharmazie, 48(1):26-30 (1993).

\* cited by examiner

METHODS FOR TREATING HEPATITIS C

CROSS REFERENCE TO RELATED APPLICATIONS

This application claims the benefit of priority under 35 U.S.C. 119(e) of U.S. Provisional Application No. 60/758,527, filed Jan. 13, 2006 and U.S. Provisional application Ser. No. 60/921,482, filed Jan. 13, 2007 (converted on May 4, 2007 from U.S. application Ser. No. 11/653,436); and is a continuation-in-part of U.S. application Ser. No. 11/331,180, filed Jan. 13, 2006, which is a continuation-in-part of U.S. application Ser. No. 11/180,961, filed Jul. 14, 2005 (having corresponding International Application No. PCT/US2005/024881, filed Jul. 14, 2005) which claims the benefit of each of U.S. Provisional Application No. 60/587,487, filed Jul. 14, 2004, U.S. Provisional Application No. 60/634,979, filed Dec. 13, 2004, U.S. Provisional Application No. 60/645,586, filed Jan. 24, 2005, U.S. Provisional Application No. 60/665,349, filed Mar. 28, 2005, and U.S. Provisional Application No. 60/675,440, filed Apr. 28, 2005; the entire contents of which applications are incorporated herein by reference.

GOVERNMENT SUPPORT

The present invention was made with U.S. Government support under DHHS Grant No. 5R44AI054029-03. The U.S. Government has certain rights in the invention.

FIELD OF THE INVENTION

The present invention provides compounds, pharmaceutical compositions, and methods of using such compounds or compositions for treating infection by a virus, or for affecting viral IRES activity.

BACKGROUND OF THE INVENTION

An estimated 170 million people worldwide are reported to be infected with hepatitis C virus (HCV), the causative agent of hepatitis C. Seventy to eighty percent of HCV infections lead to chronic liver infection, which in turn may result in severe liver disease, including liver fibrosis, cirrhosis, and hepatocellular carcinoma (115).

HCV constitutes the *Hepacivirus* genus of the family Flaviviridae (106), and contains a positive-stranded 9.6 kb RNA genome. The features of the HCV genome include a 5'-untranslated region (UTR) that encodes an internal ribosome entry site (IRES) that directs the translation of a single long open reading frame (ORF) encoding a polyprotein of 3,010 amino acids. The HCV ORF is followed by a 3'-UTR of variable length, depending on the HCV variant, that encodes the sequences required for the initiation of antigenomic strand synthesis (79).

The HCV IRES and 3'-UTR both encode regions of RNA structures that are required for genome translation and replication. The HCV polyprotein is posttranslationally processed into at least 10 mature viral proteins, including the structural proteins core (putative nucleocapsid), E1 and E2 and the nonstructural (NS) proteins NS2 to NS5B.

Three distinct elements have been shown to be involved in HCV IRES-mediated translation: (1) integrity of the global structure of HCV IRES, (2) the 3'-terminal region of the HCV genome; and (3) trans-acting cellular factors that interact with the HCV IRES element and assist in translation initiation (35).

The initiation of protein synthesis in eukaryotic cells predominantly follows the 5' cap-dependent, first AUG rule (61). However, an increasing number of viral (6, 12, 28, 31a, 50, 95, 97, 98, 105, 128) and cellular mRNAs (18, 39, 45, 78, 91, 130) have been shown to use an IRES element to direct translation initiation. In 1992, an IRES element was reported in the 5' UTR of the HCV RNA genome (129), indicating that synthesis of the viral protein is initiated in a cap-independent fashion.

A bicistronic expression system can be used to define and evaluate the function of IRES elements. This test system harbors two different reporter genes in which the 5'-proximal reporter gene is expressed by a cap dependent translation mechanism while the second reporter is expressed only if an upstream sequence inserted in the intergenic space contains an IRES sequence element. Using this system, a putative IRES in the HCV 5' UTR was unambiguously demonstrated to function as an IRES involved in translational control of viral proteins (133). In vitro translation, RNA transfection, and mutagenesis studies provided further evidence that the HCV 5' UTR contains an IRES element (23, 41, 42, 108, 129, 132, 133, 134). Both in vitro and cell-based studies demonstrated that the HCV IRES guides cellular translation initiation factors to an internal site of the viral RNA (56, 58, 120), thus functionally demonstrating the HCV IRES activity. Taken together, these results demonstrate that the HCV 5'-UTR contains an IRES element that plays an active and crucial role in the mechanism of internal initiation for HCV protein translation.

The IRES is one of the most conserved regions of the HCV genome, reflecting its essential nature for viral replication and protein synthesis (13, 118, 122). Although both 5' and 3' sequences of the IRES appear to play a role in the control of initiation of translation (42, 109, 110, 113, 136), the minimal sequence requirement for HCV IRES function has been mapped to a region between nucleotides 44-354 (40).

Biochemical probing and computer modeling indicate that the HCV IRES and its 5' sequence is folded into a distinct structure that consists of four major domains and a pseudoknot (11, 42, 122). Domain I contains a small stem-loop structure that does not appear to be a functional part of the IRES element while domains II, III, and IV contain the HCV IRES activity (43, 111). The relationships between secondary and tertiary structures of the HCV IRES and their function have recently been established (5, 55, 56, 99, 124). Both domains II and III consist of multiple stems, loops, and bulges and are important for IRES activity (23, 40, 51, 52, 54, 56, 64, 74, 75, 93, 107, 108, 110, 124, 127, 131, 139, 141, 142). Domain II can induce conformational changes on the ribosome that have been implicated in the decoding process (124). Domain III has the highest degree of structural conservation among the different HCV strains. It comprises the core of the flavivirus IRES and has 6 subdomains (40). Various studies have shown that subdomain IIId forms complex secondary/tertiary structures and is critical for initiation activity (55, 56, 57, 124, 129). Domain IV has one stem-loop that spans the initiation codon and is specific for the HCV IRES (41, 122), but the precise role of domain IV in IRES activity remains controversial (41, 112).

The role of the HCV IRES is to position the translational machinery near an internal initiator codon in the viral mRNA. The translation initiation mechanism of the HCV and other viral IRES differs significantly from that of 5'-cap-dependent translation initiation (7, 21, 31, 35, 61, 71, 72, 81, 88, 96, 114, 123). Most cellular capped mRNAs utilize a number of initiation factors (eIFs) that are required for the translation initiation process. The initial steps of the process require proteins that interact with the 5' cap structure and recruit the 40S ribosomal subunit to the cap-proximal region of mRNA. This complex then scans 3' of the cap, until reaching an AUG codon at which translation will initiate (21, 114). However, in the case of HCV, the IRES functionally replaces the 5' cap structure, allowing the 40S ribosomal subunit and eIF3 to bind directly to the RNA. Subdomain IIId of the HCV IRES harbors the binding site for the 40S ribosomal subunit and the only initiation factors required for translation initiation are eIF2, eIF3, and eIF4E (15, 58, 94, 100, 120, 124).

The polypyrimidine track-binding protein (PTB) and La autoantigen are noncanonical translation initiation factors that bind to and enhance HCV IRES activity (1, 2, 3, 4, 5, 30, 48, 49, 53). PTB, a 57-kDa protein involved in RNA splicing, is also necessary for efficient IRES-mediated translation initiation of picornavirus mRNA, and some cellular mRNAs (10, 11, 36, 53, 59, 89, 92). The La autoantigen, a 52 kDa double-stranded RNA unwinding protein, also increases the activity of poliovirus and cellular IRES (38, 85, 86). Other cellular factors involved in HCV IRES-mediated translation initiation include proteasome α-subunit PSMA7 (62), ribosomal protein S5 (26), ribosomal protein S9 (24, 25, 100), and hnRNPL (33). However, the role of these RNA-binding proteins in HCV IRES-mediated initiation of translation is unclear. Recently, it was reported that the activity of interferon (IFN) α against HCV replication might target HCV IRES-mediated translation initiation by causing a reduction of La protein levels (117) Some HCV proteins, such as NS5A, core and NS4A/4B, also reported to be involved in the HCV IRES function (143-146). Thus, an inhibitor that blocks interaction between the IRES and the noncanonical factors might efficiently inhibit HCV replication and lack cytotoxicity.

Currently, only IFN α and the nucleoside analogue ribavirin, in combination, are marketed for the treatment of HCV infection. However, these two agents are immunomodulators and have limited efficacy, relatively high toxicity, and high cost (80, 83, 84, 138). Although the treatment outcome is variable among the six major HCV genotypes, only about one-half of all treated patients respond to therapy, suggesting that the virus encodes protein products that may directly or indirectly attenuate the antiviral action of IFN. IFNs are naturally produced in response to virus infection, and cellular exposure to IFN leads to the induced expression of a variety of IFN-stimulated genes (ISGs), many of which have an antiviral function. ISG action can limit virus replication at multiple points within the replicative cycle.

There remains a need for a more effective means of treating patients afflicted with HCV. Specifically, a need exists for novel antiviral drugs that have no cross-resistance with existing treatment modalities, and which demonstrate synergy with other anti-HCV agents.

All documents referred to herein are incorporated by reference into the present application as though fully set forth herein.

SUMMARY OF THE INVENTION

The present invention provides compounds, pharmaceutical compositions, and methods of using such compounds or compositions for treating infection by a virus, or for affecting viral IRES activity.

DETAILED DESCRIPTION OF THE INVENTION

A. Compounds of the Invention

In another embodiment, the present invention includes a compound of Formula (I)

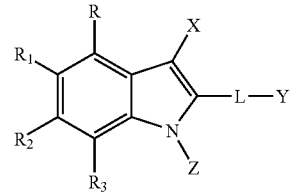

(I)

wherein:

X is:

hydrogen;

a cyano group;

a nitro group;

a formyl group;

a —COOH group;

a $COR_x$ group, wherein $R_x$ is a $C_1$ to $C_6$ alkyl;

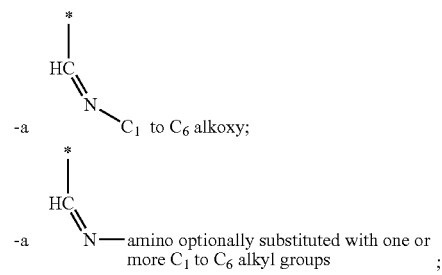

a halo;

an alkyl optionally substituted with one or more halo;

an alkyne optionally substituted with a $C_1$ to $C_6$ alkyl optionally substituted with one or more independently selected halo or cyano groups;

an oxime;

—$SO_2R_x$;

—$SO_2NH_2$;

—$SO_2NH(R_x)$;

—$SO_2N(R_x)_2$;

an amino optionally substituted with one or more $C_1$ to $C_6$ alkyl groups or $C_1$ to $C_6$ alkylcarbonyl groups;

an amide group optionally substituted with one or more independently selected $C_1$ to $C_6$ alkyl group;

a 5 or 6 membered heterocycle;

a 5 or 6 membered heteroaryl optionally substituted with one or more $C_1$ to $C_6$ alkyl groups optionally substituted with one or more halos;

a $C_6$ to $C_8$ aryl group optionally substituted with one or more of the following:

—$C_1$ to $C_6$ alkyl optionally substituted with one or more halos, halo, or cyano;

Y is:

a hydrogen;

a haloalkyl;

a halo;

a benzofuran;

a benzothiophene;

a dibenzofuran;
a dibenzothiophene;
a benzothiazole optionally substituted with an amino group optionally substituted with one or more $C_1$ to $C_6$ alkyls;
a naphthalene;
an indole, optionally substituted on the nitrogen with a $C_1$ to $C_6$ alkyl or an —$SO_2R_x$ group;

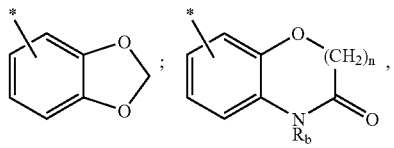

where $R_b$ is a hydrogen or a $C_1$ to $C_6$ alkyl, and n is 0 or 1;

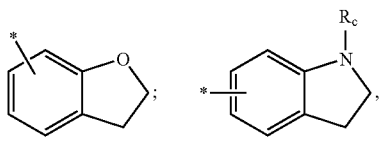

where $R_c$ is a hydrogen, a —$CONHR_x$, where $R_x$ is a $C_1$ to $C_6$ alkyl, or an —$SO_2R_x$, where $R_x$ is a $C_1$ to $C_6$ alkyl; or

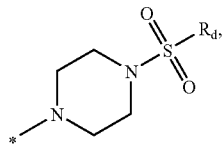

where $R_d$ is a $C_1$ to $C_6$ alkyl or a $C_6$ to $C_8$ aryl;
a —$NHCOR_e$ group, where $R_e$ is:
 a $C_1$ to $C_6$ alkyl;
 a $C_6$ to $C_8$ aryl optionally substituted with:
  a $C_1$ to $C_6$ alkyl,
  an alkoxy,
  a cyano group,
  a nitro group, or
  a halo;
a —$NHCOOR_x$ group, where $R_x$ is a $C_1$ to $C_6$ alkyl;
a —$NR_gR_h$ group, where $R_g$ is a $C_1$ to $C_6$ alkyl or a hydrogen and $R_h$ is a hydrogen, $C_1$ to $C_6$ alkyl, or $C_6$ to $C_8$ aryl, the $C_1$ to $C_6$ alkyl or $C_6$ to $C_8$ aryl optionally substituted with an alkoxy;
a $C_1$ to $C_6$ alkyl;
a 5 or 6 membered heteroaryl, optionally substituted with one or more of the following:
 a $C_1$ to $C_6$ alkyl, optionally substituted with one or more halos or a $C_6$ to $C_8$ aryl,
 a $C_6$ to $C_8$ aryl, optionally substituted with —$COOR_x$, where $R_x$ is a $C_1$ to $C_6$ alkyl,
 an amino group, or
 a substituent from Group A;
a 5 or 6 membered heterocycle optionally substituted with:
 a —$COOR_x$ group, where $R_x$ is as defined above, or
 a —$NHCOOR_x$ group, where $R_x$ is as defined above;
a $C_6$ to $C_8$ aryl, optionally substituted with one or more of the following:
 an alkoxy, optionally substituted with:
  an alkoxy,
  hydroxy,
  one or more halos,
  a 5 or 6 membered heterocycle, optionally substituted with:
   a $C_1$ to $C_6$ alkyl, or
   a hydroxy,
  a $C_6$ to $C_8$ aryl, optionally substituted with one or more substituents independently selected from Group A,
  a a 5 or 6 membered heteroaryl optionally substituted with one or more substituents independently selected from Group A,
  an amino optionally substituted with one or more $C_1$ to $C_6$ alkyls,
  a —$NR_iSO_2R_x$ group, where $R_x$ is a $C_1$ to $C_6$ alkyl and $R_i$ is:
   a hydrogen,
   a $C_1$ to $C_6$ alkyl,
   a —$COR_x$ group, where $R_x$ is as defined above,
   a haloalkyl, or
   a haloalkoxy,
  a —$NR_jCOR_k$ group, where $R_k$ is:
   a $C_1$ to $C_6$ alkyl,
   a hydrogen, or
   an amino optionally substituted with one or more $C_1$ to $C_6$ alkyls,
  and $R_j$ is:
   a hydrogen,
   a $C_1$ to $C_6$ alkyl,
   a —$COR_x$ group, where $R_x$ is a $C_1$ to $C_6$ alkyl,
   a haloalkyl, or
   a haloalkoxy,
  a —N=$N^+$=$N^-$ group, or
  a —$COR_1$, where $R_1$ is a 5 or 6 membered heterocycle optionally substituted with a hydroxy,
 an amino,
 a $C_1$ to $C_6$ alkyl group, optionally substituted with:
  a —$NHSO_2R_x$ group, where $R_x$ is as defined above, or
  a —$NR_xSO_2R_x$ group, where $R_x$ is as defined above,
 a haloalkoxy,
 a halo,
 a hydroxy,
 —$OC(O)NHR_x$,
 —$OC(O)N(R_x)_2$,
 —$OC(O)NH(OR_x)$,
 —$OC(O)NR_x(OR_x)$,
 —$OC(O)R_{ab}$, wherein $R_{ab}$ is a 5 or 6 membered heterocycle group,
 a —$COOR_x$ group, where $R_x$ is a $C_1$ to $C_6$ alkyl,
 a —$COR_m$ group, where $R_m$ is:
  an amino optionally substituted with one or more $C_1$ to $C_6$ alkyls, where the $C_1$ to $C_6$ alkyls are optionally substituted with:
   a hydroxy
   a 5 or 6 membered heterocycle,
   an amino optionally substituted with one or more $C_1$ to $C_6$ alkyls,
   an alkoxy,
  a 3 to 7 membered heterocycle, optionally substituted with a $C_1$ to $C_6$ alkyl, optionally substituted with a dialkyl-amino,
  a —$NHR_n$ group, where $R_n$ is:
   a —$CH_2CONH_2$, or
   a $C_6$ to $C_8$ aryl optionally substituted with:
    an alkyl,
    one or more halos, a nitro group, or
one or more alkoxys,
a —$NR_oCOR_p$ group, where $R_p$ is:
  a $C_1$ to $C_6$ alkyl optionally substituted with:
    a halo,
    an alkoxy, or
    a $C_6$ to $C_8$ aryl,
  a 5 or 6 membered heterocycle, optionally substituted with one or more $C_1$ to $C_6$ alkyl or $C_6$ to $C_8$ aryl groups,
  a $C_6$ to $C_8$ aryl, optionally substituted with a halo,
  a 5 or 6 membered heteroaryl optionally substituted with one or more $C_1$ to $C_6$ alkyls,
  a hydrogen,

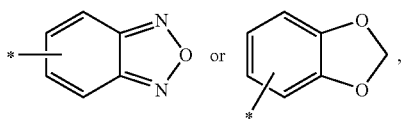

and where $R_o$ is:
  a hydrogen,
  a $C_1$ to $C_6$ alkyl,
  a —$COR_x$ group, where $R_x$ is a $C_1$ to $C_6$ alkyl,
  a haloalkyl, or
  a haloalkoxy,
a —$NR_qCONR_qR_r$ group, where $R_q$ is:
  a hydrogen,
  a $C_1$ to $C_6$ alkyl,
  a haloalkyl,
  a haloalkoxy, or
  a —$COR_x$ group, where $R_x$ is as defined above,
and where $R_r$ is:
  a $C_6$ to $C_8$ aryl optionally substituted with:

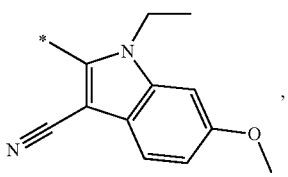

halo,
  a $C_1$ to $C_6$ alkyl optionally and independently substituted with one or more $C_6$ to $C_8$ aryl, halo and/or $C_1$ to $C_6$ alkoxy groups,
  a $C_1$ to $C_6$ alkoxy,
  a $C_1$ to $C_6$ haloalkoxy,
  a —$OR_s$ group, where $R_s$ is a $C_6$ to $C_8$ aryl, or
  a —$COOR_x$ group, where $R_x$ is as defined above,
  a $C_1$ to $C_6$ alkyl optionally substituted with one or more of the following:
    a halo,
    a hydroxyl,
    an alkoxy,
    an alkylene,
    a 5 or 6 membered heterocycle optionally substituted with one or more halo, $C_1$ to $C_6$ alkyl, $C_1$ to $C_6$ haloalkyl, $C_1$ to $C_6$ alkoxy, $C_1$ to $C_6$ haloalkoxy,
    a 5 or 6 membered heteroaryl optionally substituted with one or more halo, $C_1$ to $C_6$ alkyl, $C_1$ to $C_6$ haloalkyl, $C_1$ to $C_6$ alkoxy, $C_1$ to $C_6$ haloalkoxy,
    a $C_6$ to $C_8$ aryl optionally substituted with with one or more halo, $C_1$ to $C_6$ alkyl, $C_1$ to $C_6$ haloalkyl, $C_1$ to $C_6$ alkoxy, $C_1$ to $C_6$ haloalkoxy, or
    a —$COOR_x$ group, where $R_x$ is as defined above,
  a $C_2$ to $C_6$ alkylene group,
  a $C_1$ to $C_6$ alkoxy group,
  a 5 or 6 membered heterocycle group optionally substituted with with one or more halo, $C_1$ to $C_6$ alkyl, $C_1$ to $C_6$ haloalkyl, $C_1$ to $C_6$ alkoxy, $C_1$ to $C_6$ haloalkoxy,
  a —$COOR_x$ group, where $R_x$ is as defined above,
a —$NR_tCOOR_u$ group, where $R_u$ is:
  a $C_1$ to $C_{12}$ alkyl, optionally substituted with one or more groups independently selected from the following:
    a $C_6$ to $C_8$ aryl optionally substituted with one or more halo, $C_1$ to $C_6$ alkyl, $C_1$ to $C_6$ haloalkyl, $C_1$ to $C_6$ alkoxy, $C_1$ to $C_6$ haloalkoxy,
    an alkylene,
    an alkoxy,
    an alkyne,
    an alkoxy group optionally substituted with one or more alkoxy groups,
    an amino optionally substituted with one or more $C_1$ to $C_6$ alkyl,
    halo, or
    a 5 or 6 membered heterocycle,
    a 5 or 6 membered heteroaryl,
  a $C_2$ to $C_6$ alkylene,
  a $C_6$ to $C_8$ aryl, optionally substituted with:
    an alkoxy,
    a halo, or
    a $C_1$ to $C_6$ alkyl, or
  a 5 or 6 membered heterocycle,
and $R_t$ is:
  a hydrogen,
  a $C_1$ to $C_6$ alkyl,
  a —$COR_x$ group, where $R_x$ is as defined above,
  a haloalkyl, or
  a haloalkoxy,
a —$NR_vSO_2R_w$ group, where $R_v$ is:
  a hydrogen,
  a —$COR_x$, where $R_x$ is as defined above, or
  a $C_1$ to $C_6$ alkyl, optionally substituted with:
    a halo,
    a —$COR_x$ group, where $R_x$ is as defined above,
    a —$OCOR_x$ group, where $R_x$ is as defined above,
    a hydroxyl, or
    an alkoxy,
and where $R_w$ is:
  a $C_1$ to $C_6$ alkyl optionally substituted with:
    a halo,
    a haloalkyl,
    a $C_6$ to $C_8$ aryl, or
    a 5 or 6 membered heterocycle,
  a $C_2$ to $C_6$ alkylene,
  an alkyl- or dialkyl-amino optionally substituted with a halo,
  a 5 or 6 membered heterocycle, or
  a 5 or 6 membered heteroaryl optionally substituted with one or more of the following:
    halo,
    a $C_1$ to $C_6$ alkyl,
    —$C_1$ to $C_6$ haloalkyl,
    —$C_1$ to $C_6$ alkoxy,
    —$C_1$ to $C_6$ haloalkoxy,
    a 5 or 6 membered heterocycle, or

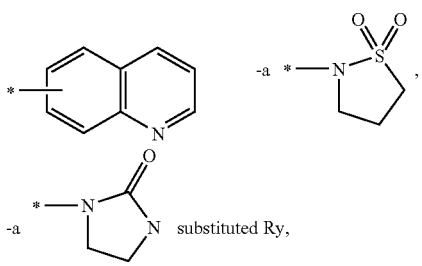

where R$_y$ is a hydrogen, C$_1$ to C$_6$ alkyl optionally substituted with a C$_1$ to C$_6$ alkoxy, C$_1$ to C$_6$ haloalkyl, C$_6$ to C$_8$ aryl, 5 or 6 membered heteroaryl, or 5 or 6 membered heterocycle, where the C$_6$ to C$_8$ aryl, 5 or 6 membered heteroaryl, and 5 or 6 membered heterocycle are each optionally and independently substituted with one or more halo, C$_1$ to C$_6$ alkyl, C$_1$ to C$_6$ alkoxy, C$_1$ to C$_6$ haloalkyl, C$_1$ to C$_6$ haloalkoxy,

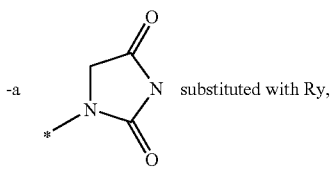

where R$_y$ is as described above,

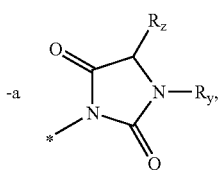

where R$_y$ is as described above and R$_z$ is hydrogen or a C$_1$ to C$_6$ alkyl optionally substituted with a C$_6$ to C$_8$ aryl,

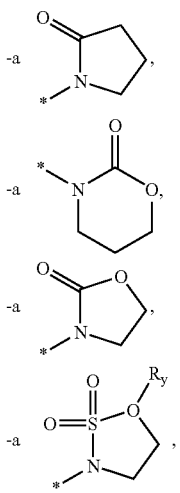

where R$_y$ is as described above, a —SR$_x$ group, where R$_x$ is as defined above,
a —SO$_2$R$_{aa}$ group, where R$_{aa}$ is:
  a C$_1$ to C$_6$ alkyl,
  an amino group,
  an alkyl- or dialkyl-amino group optionally substituted with a hydroxy, a 5 or 6 membered heterocycle, a 5 or 6 membered heteroaryl, or a —COOR$_x$ group, where R$_x$ is as defined above,
  a 5 or 6 membered heteroaryl,
  a 5 or 6 heterocycle optionally substituted with hydroxy, a C$_1$ to C$_6$ alkoxy, or a
a C$_1$ to C$_6$ alkyl, where the alkyl is optionally substituted with one or more hydroxy,
a C$_6$ to C$_8$ aryl, or
a —NHR$_{bb}$ group, where R$_{bb}$ is:

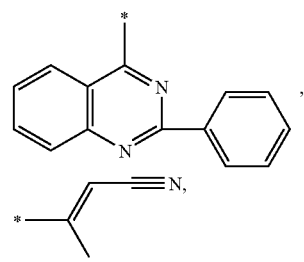

a —C(=S)NH$_2$ group, or
a —PO(OR$_x$)$_2$, where R$_x$ is as defined above;
a —≡—R$_{cc}$ group, where R$_{cc}$ is:
  a naphthalene,
  a 5 or 6 membered heteroaryl,

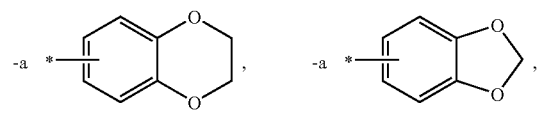

a C$_6$ to C$_8$ aryl, optionally substituted with one or more of the following:
  an alkoxy,
  an hydroxy,
  a halo,
  a C$_1$ to C$_6$ alkyl, optionally substituted with a cyano group,
  an amino optionally substituted with one or more C$_1$ to C$_6$ alkyls,
  a —NHPOR$_x$R$_x$, where R$_x$ is as defined above,
  a —NR$_{ee}$CONR$_{ff}$R$_{ff}$ group, where R$_{ee}$ is a hydrogen or a C$_1$ to C$_6$ alkyl, optionally substituted with a halo, and R$_{ff}$ is:
    a hydrogen,
    a haloalkyl,
    a haloalkoxy,
    a C$_1$ to C$_6$ alkyl, or
    a —COR$_x$, where R$_x$ is as defined above,
  a —NR$_{gg}$COR$_{hh}$ group, where R$_{hh}$ is:
    a hydrogen,
    a C$_1$ to C$_6$ alkyl optionally substituted with:
      an alkoxy,
      a halo, or
      an amino optionally substituted with one or more C$_1$ to C$_6$ alkyls, an amino optionally substituted with one or more C₁ to C₆ alkyls, where the alkyls are optionally substituted with a halo,
a 5 or 6 membered heterocycle,
a 5 or 6 membered heteroaryl,
and R_gg is:
a hydrogen,
a C₁ to C₆ alkyl,
a haloalkyl,
a haloalkoxy, or
a —COR_x group, where R_x is as defined above,
a haloalkyl,
5 or 6 membered heterocycle groups,
an amino optionally substituted with one or more C₁ to C₆ alkyls,
a —NR_{ii}SO₂R_x group, where R_x is as defined above, and R_{ii} is:
a hydrogen,
a C₁ to C₆ alkyl,
a haloalkyl,
a haloalkoxy,
a —COR_x group, where R_x is as defined above;
Z is:
a hydrogen;
a C₁ to C₆ alkyl optionally substituted with:
an alkoxy,
one or more halos,
a 5 or 6 membered heterocycle, or
a C₆ to C₈ aryl;
a 5 or 6 membered heterocycle;
a C₂ to C₆ alkylene;
a C₆ to C₈ aryl optionally substituted with an alkoxy or one or more C₁ to C₆ alkyls;
a —COOR_x group, where R_x is as defined above; or

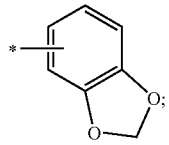

R is a hydrogen, a halo or an alkoxy;
R₁ is:
a hydrogen;
a hydroxy;
a halo;
a haloalkyl;
a nitro group;
a 5 or 6 membered heteroaryl;
a 5 or 6 membered heterocycle;
an alkoxy optionally substituted with:
one or more halos,
a C₆ to C₈ aryl optionally substituted with one or more halo, C₁ to C₆ alkyl, C₁ to C₆ alkoxy, C₁ to C₆ haloalkyl, C₁ to C₆ haloalkoxy, C₁ to C₆ hydroxy, and/or SO₂R_x groups,
a 5 or 6 membered heterocycle optionally substituted with one or more halo, C₁ to C₆ alkyl, C₁ to C₆ alkoxy, C₁ to C₆ haloalkyl, C₁ to C₆ haloalkoxy, C₁ to C₆ hydroxy, and/or SO₂R_x groups,
a 5 or 6 membered heteroaryl optionally substituted with one or more halo, C₁ to C₆ alkyl, C₁ to C₆ alkoxy, C₁ to C₆ haloalkyl, C₁ to C₆ haloalkoxy, C₁ to C₆ hydroxy, and/or SO₂R_x groups,
an amino optionally substituted with a heterocycle;
a C₆ to C₈ aryl optionally substituted with an alkoxy;
a —COR_x group, where R_x is as defined above;
a C₁ to C₆ alkyl optionally substituted with one or more dialkyl-amino, a C₆ to C₈ aryl, a 5 or 6 membered heteroaryl, and/or a 5 or 6 membered heterocycle, where each of the C₆ to C₈ aryl, 5 or 6 membered heteroaryl, and 5 or 6 membered heterocycle is optionally substituted with one or more halo, C₁ to C₆ alkyl, C₁ to C₆ alkoxy, C₁ to C₆ haloalkyl, C₁ to C₆ haloalkoxy, C₁ to C₆ hydroxy, and/or SO₂R_x groups; or
R₁ joins together with R₂ to form:

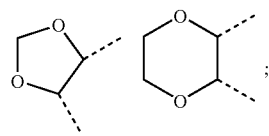

R₂ is:
a nitro group;
a hydrogen;
a halo;
a hydroxy group;
a C₁ to C₆ alkyl group, optionally substituted with one or more of the following:
halos,
5 or 6 membered heterocycle group, optionally substituted with one or more halo, C₁ to C₆ alkyl, C₁ to C₆ alkoxy, C₁ to C₆ haloalkyl, C₁ to C₆ haloalkoxy, C₁ to C₆ hydroxy, and/or SO₂R_x groups,
5 or 6 membered heteroaryl group, is optionally substituted with one or more halo, C₁ to C₆ alkyl, C₁ to C₆ alkoxy, C₁ to C₆ haloalkyl, C₁ to C₆ haloalkoxy, C₁ to C₆ hydroxy, and/or SO₂R_x groups,
—C₆ to C₈ aryl group, is optionally substituted with one or more halo, C₁ to C₆ alkyl, C₁ to C₆ alkoxy, C₁ to C₆ haloalkyl, C₁ to C₆ haloalkoxy, C₁ to C₆ hydroxy, and/or SO₂R_x groups,
amino groups optionally substituted with one or more alkoxy groups or alkyl groups optionally substituted with one or more alkoxy groups,
an amino group optionally substituted with one or more C₁ to C₆ alkyl groups;
an alkoxy group optionally substituted with one or more groups independently selected from the following:
halos,
hydroxy group,
an alkoxy group optionally substituted with an alkoxy group,
an —OCOR_x group, where R_x is as defined above,
an amino group optionally substituted with one or more 5 or 6 membered heterocycle groups or alkyl groups, the alkyl groups optionally and independently substituted with one or more of the following:
a 5 or 6 membered heterocycle, or
an amino optionally substituted with one or more alkyl groups;
a dialkyl-amino optionally substituted with an alkoxy,
a 4 to 7 membered heterocycle group optionally substituted with one or more independently selected hydroxy group or C₁ to C₆ alkyl group, the C₁ to C₆ alkyl group optionally substituted with one or more independently selected C₁ to C₆ alkoxy group,
a 5 or 6 membered heteroaryl group optionally substituted with one or more independently selected halo, C₁ to C₆ alkyl, $C_1$ to $C_6$ alkoxy, $C_1$ to $C_6$ haloalkyl, $C_1$ to $C_6$ haloalkoxy, $C_1$ to $C_6$ hydroxy, and/or $SO_2R_x$ groups, or
a $C_6$ to $C_8$ aryl group optionally substituted with one or more independently selected halo, $C_1$ to $C_6$ alkyl, $C_1$ to $C_6$ alkoxy, $C_1$ to $C_6$ haloalkyl, $C_1$ to $C_6$ haloalkoxy, $C_1$ to $C_6$ hydroxy, and/or $SO_2R_x$ groups;

a —C(O)-5 or 6 membered heterocycle optionally substituted with one or more $C_6$ to $C_8$ aryl groups;

a —COOH group;

a —COOR$_x$ group, where $R_x$ is as defined above;

a haloalkyl;

a —C(O)NH$_2$ optionally substituted with one or more of the following:
  —$C_1$ to $C_6$ alkyl groups optionally substituted with one or more independently selected halo, $C_1$ to $C_6$ alkoxy, $C_1$ to $C_6$ hydroxy, a 5 or 6 membered heterocycle and/or a 5 or 6 membered heteroaryl,
  hydroxy groups, or
  —$C_6$ to $C_8$ aryl groups;

a 5 or 6 membered heterocycle, optionally substituted with one or more of the following:
  —$C_1$ to $C_6$ alkyl,
  —$SO_2R_x$,
  —C(O)—$C_6$ to $C_8$ aryl,
  —C(O)OR$_x$; or
  hydroxy, a 5 or 6 membered heteroaryl optionally substituted with one or more independently selected halo, $C_1$ to $C_6$ alkyl, $C_1$ to $C_6$ alkoxy, $C_1$ to $C_6$ haloalkyl, $C_1$ to $C_6$ haloalkoxy, $C_1$ to $C_6$ hydroxy, and/or $SO_2R_x$ groups;

a —OCOR$_x$ group, where $R_x$ is as defined above;

a —NHCOR$_{jj}$ group, where $R_{jj}$ is:
  an alkyl,
  a $C_6$ to $C_8$ aryl,
  an alkoxy, or
  an amino optionally substituted with one or more $C_1$ to $C_6$ alkyls;

an —OR$_{kk}$ group, where $R_{kk}$ is
  a $C_6$ to $C_8$ aryl optionally substituted with one or more independently selected halo, $C_1$ to $C_6$ alkyl, $C_1$ to $C_6$ alkoxy, $C_1$ to $C_6$ haloalkyl, $C_1$ to $C_6$ haloalkoxy, $C_1$ to $C_6$ hydroxy, and/or $SO_2R_x$ groups,
  a 5 to 6 membered heteroaryl, optionally substituted with a halo, $C_1$ to $C_6$ alkyl, $C_1$ to $C_6$ alkoxy, $C_1$ to $C_6$ haloalkyl, $C_1$ to $C_6$ haloalkoxy, $C_1$ to $C_6$ hydroxy, and/or $SO_2R_x$ groups,
  a 5 to 6 membered heterocycle substituted with a $C_1$ to $C_6$ alkyl, optionally substituted with a $C_6$ to $C_8$ aryl group, or
  an $Si(R_x)_3$;

a —NHSO$_2$R$_x$ group, where $R_x$ is as defined above; or $R_2$ joins together with $R_1$ to form:

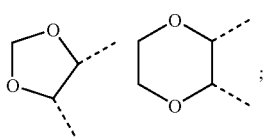

$R_3$ is:
a hydrogen; or
—CH$_2$OCOR$_x$, and $R_x$ is as defined above;

Group A is
a halo,
—$C_1$ to $C_6$ alkyl,
—$C_1$ to $C_6$ alkoxy,
—$C_1$ to $C_6$ haloalkyl,
—$C_1$ to $C_6$ haloalkoxy, a —NR$_o$COR$_p$ group, where $R_p$ is:
  a $C_1$ to $C_6$ alkyl optionally substituted with:
    a halo,
    an alkoxy, or
    a $C_6$ to $C_8$ aryl,
  a 5 or 6 membered heterocycle, optionally substituted with one or more $C_1$ to $C_6$ alkyl or $C_6$ to $C_8$ aryl groups,
  a $C_6$ to $C_8$ aryl, optionally substituted with a halo,
  a 5 or 6 membered heteroaryl optionally substituted with one or more $C_1$ to $C_6$ alkyls,
  a hydrogen,

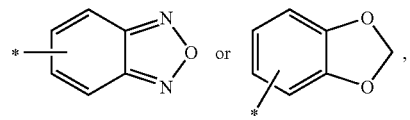

and where $R_o$ is:
  a hydrogen,
  a $C_1$ to $C_6$ alkyl,
  a —COR$_x$ group, where $R_x$ is a $C_1$ to $C_6$ alkyl,
  a haloalkyl, or
  a haloalkoxy, a —NR$_q$CONR$_q$R$_r$ group, where $R_q$ is:
  a hydrogen,
  a $C_1$ to $C_6$ alkyl,
  a haloalkyl,
  a haloalkoxy, or
  a —COR$_x$ group, where $R_x$ is as defined above,
and where $R_r$ is:
  a $C_6$ to $C_8$ aryl optionally substituted with:

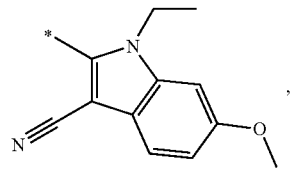

halo,
a $C_1$ to $C_6$ alkyl optionally and independently substituted with one or more $C_6$ to $C_8$ aryl, halo and/or $C_1$ to $C_6$ alkoxy groups,
a $C_1$ to $C_6$ haloalkoxy,
a —OR$_s$ group, where $R_s$ is a $C_6$ to $C_8$ aryl, or
a —COOR$_x$ group, where $R_x$ is as defined above, a $C_1$ to $C_6$ alkyl optionally substituted with one or more of the following:
  a halo,
  a hydroxyl,
  an alkoxy,
  an alkylene,
  a 5 or 6 membered heterocycle optionally substituted with one or more halo, $C_1$ to $C_6$ alkyl, $C_1$ to $C_6$ haloalkyl, $C_1$ to $C_6$ alkoxy, $C_1$ to $C_6$ haloalkoxy,
  a 5 or 6 membered heteroaryl optionally substituted with one or more halo, $C_1$ to $C_6$ alkyl, $C_1$ to $C_6$ haloalkyl, $C_1$ to $C_6$ alkoxy, $C_1$ to $C_6$ haloalkoxy, a C$_6$ to C$_8$ aryl optionally substituted with with one or more halo, C$_1$ to C$_6$ alkyl, C$_1$ to C$_6$ haloalkyl, C$_1$ to C$_6$ alkoxy, C$_1$ to C$_6$ haloalkoxy, or a —COOR$_x$ group, where R$_x$ is as defined above, a C$_2$ to C$_6$ alkylene group, a C$_1$ to C$_6$ alkoxy group, a 5 or 6 membered heterocycle group optionally substituted with with one or more halo, C$_1$ to C$_6$ alkyl, C$_1$ to C$_6$ haloalkyl, C$_1$ to C$_6$ alkoxy, C$_1$ to C$_6$ haloalkoxy, a —COOR$_x$ group, where R$_x$ is as defined above, a —NR$_t$COOR$_u$ group, where R$_u$ is:

a C$_1$ to C$_{12}$ alkyl, optionally substituted with one or more groups independently selected from the following:
  a C$_6$ to C$_8$ aryl optionally substituted with one or more halo, C$_1$ to C$_6$ alkyl, C$_1$ to C$_6$ haloalkyl, C$_1$ to C$_6$ alkoxy, C$_1$ to C$_6$ haloalkoxy,
  an alkylene,
  an alkoxy,
  an alkyne,
  an alkoxy group optionally substituted with one or more alkoxy groups,
  an amino optionally substituted with one or more C$_1$ to C$_6$ alkyl,
  halo, or
  a 5 or 6 membered heterocycle,
  a 5 or 6 membered heteroaryl,
  a C$_2$ to C$_6$ alkylene,
  a C$_6$ to C$_8$ aryl, optionally substituted with:
    an alkoxy,
    a halo, or
    a C$_1$ to C$_6$ alkyl, or
  a 5 or 6 membered heterocycle, and R$_t$ is:
  a hydrogen,
  a C$_1$ to C$_6$ alkyl,
  a —COR$_x$ group, where R$_x$ is as defined above,
  a haloalkyl, or
  a haloalkoxy, a —NR$_v$SO$_2$R$_w$ group, where R$_v$ is:
  a hydrogen,
  a —COR$_x$, where R$_x$ is as defined above, or
  a C$_1$ to C$_6$ alkyl, optionally substituted with:
    a halo,
    a —COR$_x$ group, where R$_x$ is as defined above,
    a —OCOR$_x$ group, where R$_x$ is as defined above,
    a hydroxyl, or
    an alkoxy, and where R$_w$ is:
  a C$_1$ to C$_6$ alkyl optionally substituted with:
    a halo,
    a haloalkyl,
    a C$_6$ to C$_8$ aryl, or
    a 5 or 6 membered heterocycle,
  a C$_2$ to C$_6$ alkylene,
  an alkyl- or dialkyl-amino optionally substituted with a halo,
  a 5 or 6 membered heterocycle, or
  a 5 or 6 membered heteroaryl optionally substituted with one or more of the following:
    halo,
    a C$_1$ to C$_6$ alkyl,
    —C$_1$ to C$_6$ haloalkyl,
    —C$_1$ to C$_6$ alkoxy,
    —C$_1$ to C$_6$ haloalkoxy,
    a 5 or 6 membered heterocycle, or

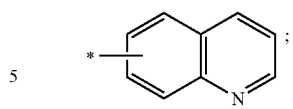

a —SO$_2$R$_{aa}$ group, where R$_{aa}$ is:
  a C$_1$ to C$_6$ alkyl,
  an amino group,
  an alkyl- or dialkyl-amino group optionally substituted with a hydroxy, a 5 or 6 membered heterocycle, a 5 or 6 membered heteroaryl, or a —COOR$_x$ group, where R$_x$ is as defined above,
  a 5 or 6 membered heteroaryl,
  a 5 or 6 heterocycle optionally substituted with hydroxy, a C$_1$ to C$_6$ alkoxy, or a a C$_1$ to C$_6$ alkyl, where the alkyl is optionally substituted with one or more hydroxy, a —NHR$_{bb}$ group, where R$_{bb}$ is:
  a —C(=S)NH$_2$ group, or
  a —PO(OR$_x$)$_2$, where R$_x$ is as defined above;

a —COR$_m$ group, where R$_m$ is:
  an amino optionally substituted with one or more C$_1$ to C$_6$ alkyls, where the C$_1$ to C$_6$ alkyls are optionally substituted with:
    a hydroxy,
    a 5 or 6 membered heterocycle,
    an amino optionally substituted with one or more C$_1$ to C$_6$ alkyls,
    an alkoxy,
  a 3 to 7 membered heterocycle, optionally substituted with a C$_1$ to C$_6$ alkyl, optionally substituted with a dialkyl-amino,
  a —NHR$_n$ group, where R$_n$ is:
    a —CH$_2$CONH$_2$, or
    a C$_6$ to C$_8$ aryl optionally substituted with:
      an alkyl,
      one or more halos,
      a nitro group, or
      one or more alkoxys;

and

L is a direct bond, C$_1$ to C$_{12}$ alkylene, C$_2$ to C$_{12}$ alkenylene or C$_2$ to C$_{12}$ alkynylene, wherein one or more —CH$_2$— group(s) of the alkylene, alkenylene or alkynylene is/are optionally replaced with —O—, —S—, —SO$_2$— and/or —NR$_{mm}$—, and the alkylene, alkenylene or alkynylene is optionally substituted with one or more carbonyl oxygen(s), halos, and/or hydroxy(s), where R$_{mm}$ is hydrogen or C$_1$ to C$_6$ alkyl;

or a pharmaceutical salt thereof.

In a further embodiment, the present invention includes compounds of Formula I, with the proviso that at least one of Y, Z, R$_1$ and R$_2$ is selected from the following:

Y is:

a benzothiazole substituted with an amino group optionally substituted with one or more C$_1$ to C$_6$ alkyls;

an indole substituted on the nitrogen with an —SO$_2$R$_x$ group;

a C$_6$ to C$_8$ aryl substituted with one or more of the following:
  an amino optionally substituted with one or more of the following:
    —SO$_2$R$_x$, or
    —C$_1$ to C$_6$ alkyl substituted with one or more 5 or 6 membered heteroaryl group,
  —OC(O)NHR$_x$,
  —OC(O)N(R$_x$)$_2$,
  —OC(O)NH(OR$_x$), —OC(O)NR(OR$_x$),
—OC(O)N(OR$_x$)$_2$,
—OC(O)R$_{ab}$, wherein R$_{ab}$ is a 5 or 6 membered heterocycle group,
a —NR$_o$COR$_p$ group, where R$_p$ is:
  an amino group optionally substituted with one or more C$_1$ to C$_6$ alkyl groups where the C$_1$ to C$_6$ alkyl groups are optionally and independently substituted with one or more C$_6$ to C$_8$ aryl groups and/or alkoxy groups, or
  a 5 or 6 membered heterocycle, substituted with one or more C$_1$ to C$_6$ alkyl or C$_6$ to C$_8$ aryl groups,
a —NR$_q$CONR$_q$R$_r$ group, where R$_r$ is:
  a C$_1$ to C$_6$ alkyl substituted with one or more of the following:
    a hydroxyl,
    an alkoxy,
    a 5 or 6 membered heterocycle,
    a 5 or 6 membered heteroaryl, or
    a C$_6$ to C$_8$ aryl substituted with a halo,
  a C$_2$ to C$_6$ alkylene group,
  a C$_1$ to C$_6$ alkoxy group, or
  a 5 or 6 membered heterocycle group,
a —NR$_t$COOR$_u$ group, where R$_u$ is:
  a C$_1$ to C$_{12}$ alkyl, substituted with one or more of the following:
    an alkoxy group substituted with one or more alkoxy groups,
    an amino optionally substituted with one or more C$_1$ to C$_6$ alkyl, or
    a 5 or 6 membered heteroaryl,
  a C$_2$ to C$_6$ alkylene, or -a [N-containing heterocycle structure with carbonyl and O], Z is:
a C$_1$ to C$_6$ alkyl substituted with a 5 or 6 membered heterocycle, or
a 5 or 6 membered heterocycle; or
R$_1$ is an alkoxy substituted with an amino, where the amino is optionally substituted with a heterocycle;
R$_2$ is:
a C$_1$ to C$_6$ alkyl group, substituted with one or more of the following:
  5 or 6 membered heterocycle groups, or
  amino groups optionally substituted with one or more alkoxy groups or alkyl groups optionally substituted with one or more alkoxy groups,
an alkoxy group substituted with one or more groups independently selected from the following:
  a hydroxy group,
  an alkoxy group optionally substituted with an alkoxy group,
  an amino group substituted with one or more 5 or 6 membered heterocycle groups or alkyl groups, the alkyl groups optionally and independently substituted with one or more of the following:
    a 5 or 6 membered heterocycle, or
    an amino optionally substituted with one or more alkyl groups;
a 7 membered heterocycle group;
a 5 to 7 membered heterocycle group substituted with one or more independently selected hydroxy groups or substituted with one or more independently selected C$_1$ to C$_6$ alkyl groups substituted with C$_1$ to C$_6$ alkoxy, or
a 5 or 6 membered heteroaryl group substituted with one or more C$_1$ to C$_6$ alkyl groups;
a —C(O)-5 or 6 membered heterocycle optionally substituted with one or more C$_6$ to C$_8$ aryl groups;
a —COOH group;
an amide group substituted with one or more C$_1$ to C$_6$ alkyl groups;
a 5 or 6 membered heterocycle, optionally substituted with one or more of the following:
  —C$_1$ to C$_6$ alkyl,
  —SO$_2$R$_x$,
  —C(O)—C$_6$ to C$_8$ aryl, or
  —C(O)OR$_x$ groups;
an —OR$_{kk}$ group, where R$_{kk}$ is:
  a 5 to 6 membered heterocycle, optionally substituted with a C$_1$ to C$_6$ alkyl, optionally substituted with a C$_6$ to C$_8$ aryl group, or
  an —Si(R$_x$)$_3$;
or a pharmaceutically acceptable salt thereof.

In another embodiment, a compound of Formula I is included, with the proviso that at least one of X, Y, Z, R$_1$, and R$_2$ is selected from the following:
X is:
a —COOH group;

-a [N=CH group]—C$_1$ to C$_6$ alkoxy;

-a [N=CH group]—amino optionally substituted with one or more C$_1$ to C$_6$ alkyl groups ;

a halo;
an alkyl optionally substituted with one or more halo;
an alkyne optionally substituted with a C$_1$ to C$_6$ alkyl optionally substituted with one or more halo or cyano groups;
an oxime;
—SO$_2$R$_x$;
—SO$_2$NH$_2$;
—SO$_2$NH(R$_x$);
—SO$_2$N(R$_x$)$_2$;
an amino optionally substituted with one or more C$_1$ to C$_6$ alkyl groups or C(O)—C$_1$ to C$_6$ alkyl groups;
an amide group optionally substituted with one or more independently selected C$_1$ to C$_6$ alkyl group;
a 5 or 6 membered heterocycle;
a 5 or 6 membered heteroaryl substituted with one or more C$_1$ to C$_6$ alkyl groups substituted with one or more halos; or
a C$_6$ to C$_8$ aryl group substituted with one or more of the following:
  —C$_1$ to C$_6$ alkyl optionally substituted with one or more halos,
  halo, or
  cyano;
Y is:
a benzothiazole substituted with an amino group optionally substituted with one or more C$_1$ to C$_6$ alkyls;
an indole substituted on the nitrogen with an SO$_2$R$_x$ group;
a C$_6$ to C$_8$ aryl substituted with one or more of the following:

an amino optionally substituted with one or more of the following:
—$SO_2R_x$, or
—$C_1$ to $C_6$ alkyl substituted with one or more 5 or 6 membered heteroaryl group,
—$OC(O)NHR_x$,
—$OC(O)N(R_x)_2$,
—$OC(O)NH(OR_x)$,
—$OC(O)NR_x(OR_x)$,
—$OC(O)N(OR_x)_2$,
—$OC(O)R_{ab}$, wherein $R_{ab}$ is a 5 or 6 membered heterocycle group,
a —$NR_oCOR_p$ group, where $R_p$ is:
an amino group optionally substituted with one or more $C_1$ to $C_6$ alkyl groups where the $C_1$ to $C_6$ alkyl groups are optionally and independently substituted with one or more $C_6$ to $C_8$ aryl groups and/or alkoxy groups, or
a 5 or 6 membered heterocycle, substituted with one or more $C_1$ to $C_6$ alkyl or $C_6$ to $C_8$ aryl groups,
a —$NR_qCONR_qR_r$ group, where $R_r$ is:
a $C_1$ to $C_6$ alkyl substituted with one or more of the following:
a hydroxyl,
an alkoxy,
a 5 or 6 membered heterocycle,
a 5 or 6 membered heteroaryl, or
a $C_6$ to $C_8$ aryl substituted with a halo,
a $C_2$ to $C_6$ alkylene group,
a $C_1$ to $C_6$ alkoxy group,
a 5 or 6 membered heterocycle group,
a —$NR_tCOOR_u$ group, where $R_u$ is:
a $C_1$ to $C_{12}$ alkyl, substituted with one or more groups independently selected from the following:
an alkoxy group substituted with one or more alkoxy groups,
an amino optionally substituted with one or more $C_1$ to $C_6$ alkyl, or
a 5 or 6 membered heteroaryl,
a $C_2$ to $C_6$ alkylene, or

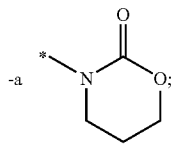

Z is:
a $C_1$ to $C_6$ alkyl substituted with a 5 or 6 membered heterocycle, or
a 5 or 6 membered heterocycle;
$R_1$ is:
a $C_1$ to $C_6$ alkyl substituted with:
an amide optionally substituted with a $C_1$ to $C_6$ alkyl, or
a 5 or 6 membered heteroaryl;
a $C_1$ to $C_6$ alkoxy substituted with:
an amino optionally substituted with a heterocycle,
an amide optionally substituted with a $C_1$ to $C_6$ alkyl,
a 5 or 6 membered heterocycle substituted with a $C_1$ to $C_6$ alkyl, or
a 5 or 6 membered heteroaryl;
an (O)-5 or 6 membered heterocycle;
an (O)-5 or 6 membered heteroaryl;
an —$SO_2R_x$ group optionally substituted with the following:
a 5 or 6 membered heterocycle,
a $C_6$ to $C_8$ aryl,
a 5 or 6 membered heteroaryl; or
alkylthio optionally substituted with the following:
a 5 or 6 membered heterocycle,
a $C_6$ to $C_8$ aryl,
a 5 or 6 membered heteroaryl; or
$R_2$ is:
a $C_1$ to $C_6$ alkyl group, substituted with one or more of the following:
5 or 6 membered heterocycle groups,
5 or 6 membered heteroaryl groups,
—$C_6$ to $C_8$ aryl groups,
an amide optionally substituted with a $C_1$ to $C_6$ alkyl, or
amino groups optionally substituted with one or more heterocycle, alkoxy groups or alkyl groups optionally substituted with one or more alkoxy groups;
an alkylthio group optionally substituted with a 5 or 6 membered heteroaryl group optionally substituted with an alkyl group;
an alkylthio group optionally substituted with a 5 or 6 membered heterocycle group;
an alkylthio group optionally substituted with a $C_6$ to $C_8$ aryl group;
an alkylthio group optionally substituted with a $C_1$ to $C_6$ alkyl group;
an $SO_2R_x$ group optionally substituted with a 5 or 6 membered heteroaryl optionally substituted with one or more $C_1$ to $C_6$ alkyl groups;
an $SO_2R_x$ group optionally substituted with a 5 or 6 membered heterocycle group;
an $SO_2R_x$ group optionally substituted with a $C_6$ to $C_8$ aryl group;
an $SO_2R_x$ group optionally substituted with a $C_1$ to $C_6$ alkyl group;
an $S(O)R_x$ group optionally substituted with a 5 or 6 membered heteroaryl group;
an $S(O)R_x$ group optionally substituted with a 5 or 6 membered heterocycle group;
an $S(O)R_x$ group optionally substituted with a $C_6$ to $C_8$ aryl group;
an $S(O)R_x$ group optionally substituted with a $C_1$ to $C_6$ alkyl group;
an alkoxy group substituted with an alkoxy group,
an amino group substituted with one or more 5 or 6 membered heteroaryl, 5 or 6 membered heterocycle groups or alkyl groups, the alkyl groups optionally and independently substituted with one or more of the following:
a 5 or 6 membered heterocycle, or
an amino optionally substituted with one or more alkyl groups;
an amide optionally substituted with a $C_1$ to $C_6$ alkyl,
—S-5 or 6 membered heterocycle,
—S-5 or 6 membered heteroaryl optionally substituted with a $C_1$ to $C_6$ alkyl,
—S—$C_1$ to $C_6$ alkyl,
—S—$C_6$ to $C_8$ aryl,
sulfinyl-5 or 6 membered heterocycle,
sulfinyl-5 or 6 membered heteroaryl,
sulfinyl-$C_1$ to $C_6$ alkyl,
sulfinyl-$C_6$ to $C_8$ aryl,
sulfonyl-5 or 6 membered heterocycle,
sulfonyl-5 or 6 membered heteroaryl optionally substituted with a $C_1$ to $C_6$ alkyl,
sulfonyl-$C_1$ to $C_6$ alkyl,
sulfonyl-$C_6$ to $C_8$ aryl, a 5 to 7 membered heterocycle group substituted with one or more independently selected hydroxy groups or substituted with one or more independently selected $C_1$ to $C_6$ alkyl groups substituted with $C_1$ to $C_6$ alkoxy, or a 5 or 6 membered heteroaryl group substituted with one or more $C_1$ to $C_6$ alkyl groups a $C_6$ to $C_8$ aryl group;

a —C(O)-5 or 6 membered heterocycle optionally substituted with one or more $C_6$ to $C_8$ aryl groups;

a —C(O)—$C_6$ to $C_8$ aryl;

a —COOH group;

an amide group substituted with one or more $C_1$ to $C_6$ alkyl groups optionally substituted with one or more $C_1$ to $C_6$ alkoxy;

a 5 or 6 membered heterocycle, substituted with one or more of the following:
hydroxy,
—$C_1$ to $C_6$ alkyl,
—$SO_2R_x$ groups,
—C(O)—$C_6$ to $C_8$ aryl, or
—C(O)O$R_x$ groups;

an —O$R_{kk}$ group, where $R_{kk}$ is:
a $C_6$ to $C_8$ aryl,
a 5 to 6 membered heterocycle, optionally substituted with a $C_1$ to $C_6$ alkyl, optionally substituted with a $C_6$ to $C_8$ aryl group, or
an —Si($R_x$)$_3$;

an (O)-5 or 6 membered heterocycle; or an (O)-5 or 6 membered heteroaryl optionally substituted with one or more independently selected $C_1$ to $C_6$ alkyl groups;

or a pharmaceutically acceptable salt thereof.

In another embodiment the present invention includes compounds of Formula I, with the proviso that with the proviso that at least one of Y, Z, and $R_2$ is selected from the following:

Y is:

a benzothiazole substituted with an amino group optionally substituted with one or more $C_1$ to $C_6$ alkyls;

an indole substituted on the nitrogen with an —$SO_2R_x$ group;

a $C_6$ to $C_8$ aryl substituted with one or more of the following:
an amino optionally substituted with one or more of the following:
—$SO_2R_x$, or
—$C_1$ to $C_6$ alkyl substituted with one or more 5 or 6 membered heteroaryl group,
—OC(O)NH$R_x$,
—OC(O)N($R_x$)$_2$,
—OC(O)NH(O$R_x$),
—OC(O)N$R_x$(O$R_x$),
—OC(O)N(O$R_x$)$_2$,
—OC(O)$R_{ab}$, wherein $R_{ab}$ is a 5 or 6 membered heterocycle group,
a —N$R_o$CO$R_p$ group, where $R_p$ is:
an amino group optionally substituted with one or more $C_1$ to $C_6$ alkyl groups where the $C_1$ to $C_6$ alkyl groups are optionally and independently substituted with one or more $C_6$ to $C_8$ aryl groups and/or alkoxy groups,
a 5 or 6 membered heterocycle, substituted with one or more $C_1$ to $C_6$ alkyl or $C_6$ to $C_8$ aryl groups,
a —N$R_q$CON$R_q R_r$ group, where $R_r$ is:
a $C_1$ to $C_6$ alkyl substituted with one or more of the following:
a hydroxyl,
an alkoxy, a 5 or 6 membered heterocycle,
a 5 or 6 membered heteroaryl, or
a $C_6$ to $C_8$ aryl substituted with a halo,
a $C_2$ to $C_6$ alkylene group,
a $C_1$ to $C_6$ alkoxy group,
a 5 or 6 membered heterocycle group,
a —N$R_t$COO$R_u$ group, where $R_u$ is:
a $C_1$ to $C_{12}$ alkyl, substituted with one or more groups independently selected from the following:
an alkoxy group substituted with one or more alkoxy groups,
an amino optionally substituted with one or more $C_1$ to $C_6$ alkyl, or
a 5 or 6 membered heteroaryl,
a $C_2$ to $C_6$ alkylene,

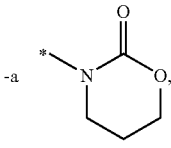

Z is:
a $C_1$ to $C_6$ alkyl substituted with a 5 or 6 membered heterocycle, or
a 5 or 6 membered heterocycle;

$R_2$ is:
a $C_1$ to $C_6$ alkyl group, substituted with one or more of the following:
5 or 6 membered heterocycle groups,
amino groups optionally substituted with one or more alkoxy groups or alkyl groups optionally substituted with one or more alkoxy groups,
an alkoxy group substituted with one or more groups independently selected from the following:
hydroxy group,
an alkoxy group optionally substituted with an alkoxy group,
an amino group substituted with one or more 5 or 6 membered heterocycle groups or alkyl groups, the alkyl groups optionally and independently substituted with one or more of the following:
a 5 or 6 membered heterocycle, or
an amino optionally substituted with one or more alkyl groups;
a 7 membered heterocycle group;
a 5 to 7 membered heterocycle group substituted with one or more independently selected hydroxy groups or substituted with one or more independently selected $C_1$ to $C_6$ alkyl groups substituted with $C_1$ to $C_6$ alkoxy, or
a 5 or 6 membered heteroaryl group substituted with one or more $C_1$ to $C_6$ alkyl groups;

a —C(O)-5 or 6 membered heterocycle optionally substituted with one or more $C_6$ to $C_8$ aryl groups;

a —COOH group;

an amide group substituted with one or more $C_1$ to $C_6$ alkyl groups;

a 5 or 6 membered heterocycle, optionally substituted with one or more of the following:
—$C_1$ to $C_6$ alkyl,
—$SO_2R_x$ group,
—C(O)—$C_6$ to $C_8$ aryl, or
—C(O)O$R_x$ groups;

an —OR$_{kk}$ group, where R$_{kk}$ is:
  a 5 to 6 membered heterocycle, optionally substituted with a C$_1$ to C$_6$ alkyl, optionally substituted with a C$_6$ to C$_8$ aryl group, or
  an —Si(R$_x$)$_3$;
or a pharmaceutically acceptable salt thereof.

As used herein, the term "alkyl" generally refers to saturated hydrocarbyl radicals of straight or branched configuration, including methyl, ethyl, n-propyl, isopropyl, n-butyl, isobutyl, sec-butyl, tert-butyl, n-pentyl, n-hexyl, n-heptyl, octyl, n-octyl, and the like. In some embodiments, alkyl substituents may be C$_1$ to C$_{12}$, or C$_1$ to C$_8$ or C$_1$ to C$_6$ alkyl groups.

As used herein, "alkylene" generally refers to straight, branched or cyclic alkene radicals having one or more carbon-carbon double bonds, such as C$_2$ to C$_6$ alkylene groups including 3-propenyl.

As used herein, "aryl" refers to a carbocyclic aromatic ring structure. Included in the scope of aryl groups are aromatic rings having from five to twenty carbon atoms. Aryl ring structures include compounds having one or more ring structures, such as mono-, bi-, or tricyclic compounds. Examples of aryl groups that include phenyl, tolyl, anthracenyl, fluorenyl, indenyl, azulenyl, phenanthrenyl (i.e., phenanthrene), and napthyl (i.e., napthalene) ring structures. In certain embodiments, the aryl group may be optionally substituted.

As used herein, "heteroaryl" refers to cyclic aromatic ring structures in which one or more atoms in the ring, the heteroatom(s), is an element other than carbon. Heteroatoms are typically O, S or N atoms. Included within the scope of heteroaryl, and independently selectable, are O, N, and S heteroaryl ring structures. The ring structure may include compounds having one or more ring structures, such as mono-, bi-, or tricyclic compounds. In some embodiments, the heteroaryl groups may be selected from heteroaryl groups that contain two or more heteroatoms, three or more heteroatoms, or four or more heteroatoms. Heteroaryl ring structures may be selected from those that contain five or more atoms, six or more atoms, or eight or more atoms. Examples of heteroaryl ring structures include: acridine, benzimidazole, benzoxazole, benzodioxole, benzofuran, 1,3-diazine, 1,2-diazine, 1,2-diazole, 1,4-diazanaphthalene, furan, furazan, imidazole, indole, isoxazole, isoquinoline, isothiazole, oxazole, purine, pyridazine, pyrazole, pyridine, pyrazine, pyrimidine, pyrrole, quinoline, quinoxaline, thiazole, thiophene, 1,3,5-triazine, 1,2,4-triazine, 1,2,3-triazine, tetrazole and quinazoline.

As used herein, "heterocycle" refers to cyclic ring structures in which one or more atoms in the ring, the heteroatom(s), is an element other than carbon. Heteroatoms are typically O, S or N atoms. Included within the scope of heterocycle, and independently selectable, are O, N, and S heterocycle ring structures. The ring structure may include compounds having one or more ring structures, such as mono-, bi-, or tricyclic compounds. Example of heterocyclo groups include morpholinyl, pyrrolidinonyl, pyrrolidinyl, piperidinyl, piperazinyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl or tetrahydrothiopyranyl and the like. In certain embodiments, the heterocycle may optionally be substituted.

As used herein, "alkoxy" generally refers to a group with the structure —O—R, where R is an alkyl group as defined above.

For the purposes of this invention, halo substituents may be independently selected from the halogens such as fluorine, chlorine, bromine, iodine, and astatine. A haloalkyl is an alkyl group, as defined above, substituted with one or more halogens. A haloalkoxy is an alkoxy group, as defined above, substituted with one or more halogens.

For the purposes of this invention, where one or more functionalities encompassing X, Y, Z, R, R$_1$, R$_2$, and R$_3$, are incorporated into a compound of the present invention, each functionality appearing at any location within the disclosed compound may be independently selected, and as appropriate, independently substituted. Further, where a more generic substituent is set forth for any position in the molecules of the present invention, it is understood that the generic substituent may be replaced with more specific substituents, and the resulting molecules are within the scope of the molecules of the present invention.

By "substituted" or "optionally substituted" it is meant that the particular substituent may be substituted with a chemical group known to one of skill in the art to be appropriate for the referred-to substituent, unless a chemical group is specifically mentioned.

In another embodiment, the present invention includes compounds of Formula (I-X)

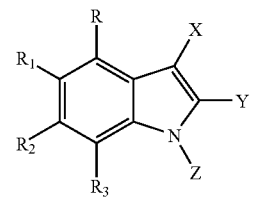

(I-X)

wherein:

X is:

a cyano group;

Y is:

a hydrogen;

a haloalkyl;

a halo;

an amino optionally substituted with one or more C$_1$ to C$_6$ alkyls;

a benzofuran;

a benzothiophene;

a dibenzofuran;

a dibenzothiophene;

a benzothiazole optionally substituted with an amino group optionally substituted with one or more C$_1$ to C$_6$ alkyls;

a naphthalene;

an indole, optionally substituted on the nitrogen with a C$_1$ to C$_6$ alkyl or an —SO$_2$R$_x$ group;

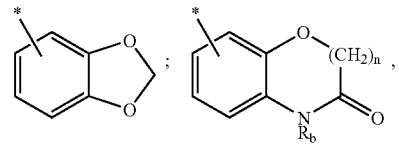

where R$_b$ is a hydrogen or a C$_1$ to C$_6$ alkyl, and n is 0 or 1;

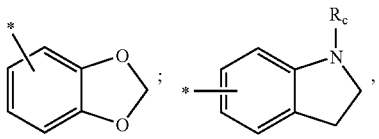

where $R_c$ is a hydrogen, a —CONHR$_x$, where R$_x$ is a C$_1$ to C$_6$ alkyl, or an —SO$_2$R$_x$, where R$_x$ is a C$_1$ to C$_6$ alkyl; or

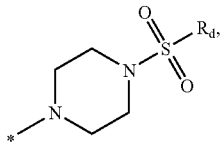

where $R_d$ is a C$_1$ to C$_6$ alkyl or a C$_6$ to C$_8$ aryl;
a —NHCOR$_e$ group, where R$_e$ is:
 a C$_1$ to C$_6$ alkyl;
 a C$_6$ to C$_8$ aryl optionally substituted with:
  a C$_1$ to C$_6$ alkyl,
  an alkoxy,
  a cyano group,
  a nitro group, or
  a halo;
a —NHCOOR$_x$ group, where R$_x$ is a C$_1$ to C$_6$ alkyl;
a —CH$_2$O—R$_f$ group, where R$_f$ is a C$_6$ to C$_8$ aryl;
a —NR$_g$R$_h$ group, where R$_g$ is a C$_1$ to C$_6$ alkyl or a hydrogen and R$_h$ is a C$_6$ to C$_8$ aryl optionally substituted with an alkoxy;
a C$_1$ to C$_6$ alkyl;
a 5 or 6 membered heteroaryl, optionally substituted with:
 a C$_1$ to C$_6$ alkyl, optionally substituted with a C$_6$ to C$_8$ aryl,
 a C$_6$ to C$_8$ aryl, optionally substituted with —COOR$_x$, where R$_x$ is a C$_1$ to C$_6$ alkyl, or
 an amino group;
a 5 or 6 membered heterocycle optionally substituted with:
 a —COOR$_x$ group, where R$_x$ is as defined above, or
 a —NHCOOR$_x$ group, where R$_x$ is as defined above;
a C$_6$ to C$_8$ aryl, optionally substituted with one or more of the following:
 an alkoxy, optionally substituted with:
  an alkoxy,
  a hydroxy,
  one or more halos,
  a 5 or 6 membered heterocycle, optionally substituted with:
   a C$_1$ to C$_6$ alkyl, or
   a hydroxy,
  an amino optionally substituted with one or more C$_1$ to C$_6$ alkyls,
 a —NR$_i$SO$_2$R$_x$ group, where R$_x$ is a C$_1$ to C$_6$ alkyl and R$_i$ is:
  a hydrogen,
  a C$_1$ to C$_6$ alkyl,
  a —COR$_x$ group, where R$_x$ is as defined above,
  a haloalkyl, or
  a haloalkoxy,
 a —NR$_j$COR$_k$ group, where R$_k$ is:
  a C$_1$ to C$_6$ alkyl,
  a hydrogen, or
  an amino optionally substituted with one or more C$_1$ to C$_6$ alkyls,
 and R$_j$ is:
  a hydrogen,
  a C$_1$ to C$_6$ alkyl,
  a —COR$_x$ group, where R$_x$ is a C$_1$ to C$_6$ alkyl,
  a haloalkyl, or
  a haloalkoxy,
 a —N=N$^+$=N$^-$ group, or
 a —COR$_1$, where R$_1$ is a 5 or 6 membered heterocycle optionally substituted with a hydroxy,
an amino optionally substituted with one or more of the following:
 —SO$_2$(R$_x$), or
 —C$_1$ to C$_6$ alkyl, the C$_1$ to C$_6$ alkyl optionally and independently substituted with one or more 5 or 6 membered heteroaryl group,
a nitro group,
a C$_1$ to C$_6$ alkyl group, optionally substituted with:
 a —NHSO$_2$R$_x$ group, where R$_x$ is as defined above, or
 a —NR$_x$SO$_2$R$_x$ group, where R$_x$ is as defined above,
a haloalkoxy,
a halo,
a hydroxy,
—OC(O)NHR$_x$,
—OC(O)N(R$_x$)$_2$,
—OC(O)NH(OR$_x$),
—OC(O)NR$_x$(OR$_x$),
—OC(O)N(OR$_x$)$_2$,
—OC(O)R$_{ab}$, wherein R$_{ab}$ is a 5 or 6 membered heterocycle group,
a —COOR$_x$ group, where R$_x$ is a C$_1$ to C$_6$ alkyl,
a —COR$_m$ group, where R$_m$ is:
 an amino optionally substituted with one or more C$_1$ to C$_6$ alkyls, where the C$_1$ to C$_6$ alkyls are optionally substituted with:
  a hydroxy,
  a 5 or 6 membered heterocycle,
  an amino optionally substituted with one or more C$_1$ to C$_6$ alkyls, or
  an alkoxy,
 a 3 to 7 membered heterocycle, optionally substituted with a C$_1$ to C$_6$ alkyl, optionally substituted with a dialkyl-amino, or
 a —NHR$_n$ group, where R$_n$ is:
  a —CH$_2$CONH$_2$, or
  a C$_6$ to C$_8$ aryl optionally substituted with:
   an alkyl,
   one or more halos,
   a nitro group, or
   one or more alkoxys,
a —NR$_o$COR$_p$ group, where R$_p$ is:
 a C$_1$ to C$_6$ alkyl optionally substituted with:
  a halo,
  an alkoxy, or
  a C$_6$ to C$_8$ aryl,
 an amino group optionally substituted with one or more C$_1$ to C$_6$ alkyl groups where the C$_1$ to C$_6$ alkyl groups are optionally and independently substituted with one or more C$_6$ to C$_8$ aryl groups and/or alkoxy groups,
 a 5 or 6 membered heterocycle, optionally substituted with one or more C$_1$ to C$_6$ alkyl or C$_6$ to C$_8$ aryl groups,
 a C$_6$ to C$_8$ aryl, optionally substituted with a halo,
 a 5 or 6 membered heteroaryl optionally substituted with one or more C$_1$ to C$_6$ alkyls,
 a hydrogen,

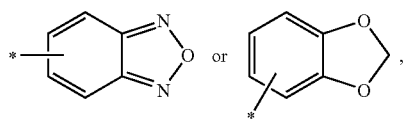

and where $R_o$ is:
  a hydrogen,
  a $C_1$ to $C_6$ alkyl,
  a —$COR_x$ group, where $R_x$ is a $C_1$ to $C_6$ alkyl,
  a haloalkyl, or
  a haloalkoxy,
a —$NR_qCONR_qR_r$ group, where $R_q$ is:
  a hydrogen,
  a $C_1$ to $C_6$ alkyl,
  a haloalkyl,
  a haloalkoxy, or
  a —$COR_x$ group, where $R_x$ is as defined above,
and where $R_r$ is:
  a $C_6$ to $C_8$ aryl optionally substituted with:

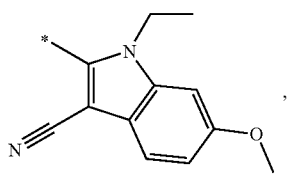

a $C_1$ to $C_6$ alkyl,
  a haloalkyl,
  a —$OR_s$ group, where $R_s$ is a $C_6$ to $C_8$ aryl, or
  a —$COOR_x$ group, where $R_x$ is as defined above,
  a $C_1$ to $C_6$ alkyl optionally substituted with one or more of the following:
    a halo,
    a hydroxyl,
    an alkoxy,
    an alkylene,
    a 5 or 6 membered heterocycle,
    a 5 or 6 membered heteroaryl,
    a $C_6$ to $C_8$ aryl optionally substituted with a halo, or
    a —$COOR_x$ group, where $R_x$ is as defined above,
  a $C_2$ to $C_6$ alkylene group,
  a $C_1$ to $C_6$ alkoxy group,
  a 5 or 6 membered heterocycle group, or
  a —$COOR_x$ group, where $R_x$ is as defined above,
a —$NR_tCOOR_u$ group, where $R_u$ is:
  a $C_1$ to $C_{12}$ alkyl, optionally substituted with one or more groups independently selected from the following:
    a $C_6$ to $C_8$ aryl optionally substituted with halo, $C_1$ to $C_6$ alkyl, or alkoxy,
    an alkylene,
    an alkoxy,
    an alkyne,
    an alkoxy group optionally substituted with one or more alkoxy groups,
    an amino optionally substituted with one or more $C_1$ to $C_6$ alkyl,
    halo,
    a 5 or 6 membered heterocycle, or
    a 5 or 6 membered heteroaryl,
  a $C_2$ to $C_6$ alkylene,
  a $C_6$ to $C_8$ aryl, optionally substituted with:
    an alkoxy,
    a halo, or
    a $C_1$ to $C_6$ alkyl, or
  a 5 or 6 membered heterocycle,
and $R_t$ is:
  a hydrogen,
  a $C_1$ to $C_6$ alkyl,
  a —$COR_x$ group, where $R_x$ is as defined above,
  a haloalkyl, or
  a haloalkoxy,
a —$NR_vSO_2R_w$ group, where $R_v$ is:
  a hydrogen,
  a —$COR_x$, where $R_x$ is as defined above, or
  a $C_1$ to $C_6$ alkyl, optionally substituted with:
    a halo,
    a —$COR_x$ group, where $R_x$ is as defined above,
    a —$OCOR_x$ group, where $R_x$ is as defined above,
    a hydroxyl, or
    an alkoxy,
and where $R_w$ is:
  a $C_1$ to $C_6$ alkyl optionally substituted with:
    a halo,
    a haloalkyl,
    a $C_6$ to $C_8$ aryl, or
    a 5 or 6 membered heterocycle,
  a $C_2$ to $C_6$ alkylene,
  an alkyl- or dialkyl-amino optionally substituted with a halo,
  a 5 or 6 membered heterocycle, or
  a 5 or 6 membered heteroaryl optionally substituted with:
    a $C_1$ to $C_6$ alkyl,
    a 5 or 6 membered heterocycle, or optionally substituted with a $C_1$ to $C_6$ alkyl, where $R_y$ is a $C_1$ to $C_6$ alkyl or hydrogen,

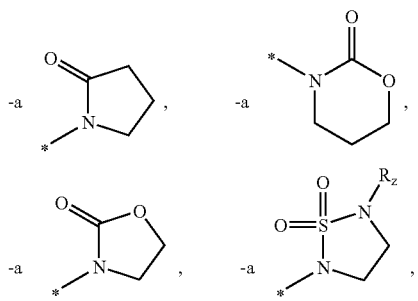

where $R_z$ is hydrogen or a $C_1$ to $C_6$ alkyl, optionally substituted with a $C_6$ to $C_8$ aryl,
a —$SR_x$ group, where $R_x$ is as defined above,
a —$SO_2R_{aa}$ group, where $R_{aa}$ is:
  a $C_1$ to $C_6$ alkyl,
  an amino group,
  an alkyl- or dialkyl-amino group optionally substituted with a hydroxy or a —$COOR_x$ group, where $R_x$ is as defined above, or
  a 5 or 6 membered heteroaryl,
a $C_6$ to $C_8$ aryl, or
a —$NHR_{bb}$ group, where $R_{bb}$ is:
  a —C(=S)NH$_2$ group, or
  a —PO(O$R_x$)$_2$, where $R_x$ is as defined above; or
a ≡$R_{cc}$ group, where $R_{cc}$ is:
  a naphthalene,
  a 5 or 6 membered heteroaryl,

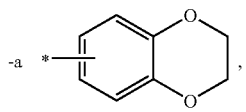

a $C_6$ to $C_8$ aryl, optionally substituted with one or more of the following:
  an alkoxy,
  a hydroxy,
  a halo,
  a $C_1$ to $C_6$ alkyl, optionally substituted with a cyano group,
  an amino optionally substituted with one or more $C_1$ to $C_6$ alkyls,
  a —NHPO$R_xR_x$, where $R_x$ is as defined above,
  a —$NR_{ee}CONR_{ff}R_{ff}$ group, where $R_{ee}$ is a hydrogen or a $C_1$ to $C_6$ alkyl, optionally substituted with a halo, and $R_{ff}$ is:
    a hydrogen,
    a haloalkyl,
    a haloalkoxy,
    a $C_1$ to $C_6$ alkyl, or
    a —$COR_x$, where $R_x$ is as defined above,
  a —$NR_{gg}COR_{hh}$ group, where $R_{hh}$ is:
    a hydrogen,
    a $C_1$ to $C_6$ alkyl optionally substituted with:
      an alkoxy,
      a halo, or
      an amino optionally substituted with one or more $C_1$ to $C_6$ alkyls,
    an amino optionally substituted with one or more $C_1$ to $C_6$ alkyls, where the alkyls are optionally substituted with a halo,
    a 5 or 6 membered heterocycle, or
    a 5 or 6 membered heteroaryl,
  and $R_{gg}$ is:
    a hydrogen,
    a $C_1$ to $C_6$ alkyl,
    a haloalkyl,
    a haloalkoxy, or
    a —$COR_x$ group, where $R_x$ is as defined above,
  a haloalkyl,
  5 or 6 membered heterocycle groups,
  an amino optionally substituted with one or more $C_1$ to $C_6$ alkyls, or
  a —$NR_{ii}SO_2R_x$ group, where $R_x$ is as defined above, and $R_{ii}$ is:
    a hydrogen,
    a $C_1$ to $C_6$ alkyl,
    a haloalkyl,
    a haloalkoxy, or
    a —$COR_x$ group, where $R_x$ is as defined above;
Z is:
  a hydrogen;
  a $C_1$ to $C_6$ alkyl optionally substituted with:
    an alkoxy,
    one or more halos,
    a 5 or 6 membered heterocycle, or
    a $C_6$ to $C_8$ aryl;
  a 5 or 6 membered heterocycle;
  a $C_2$ to $C_6$ alkylene;
  a $C_6$ to $C_8$ aryl optionally substituted with an alkoxy or one or more $C_1$ to $C_6$ alkyls;
  a —$COOR_x$ group, where $R_x$ is as defined above; or

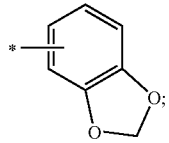

R is a hydrogen, a halo or an alkoxy;
$R_1$ is:
  a hydrogen;
  a hydroxy;
  a halo;
  a haloalkyl;
  a nitro group;
  a 5 or 6 membered heteroaryl;
  a 5 or 6 membered heterocycle;
  an alkoxy optionally substituted with:
    one or more halos,
    a $C_6$ to $C_8$ aryl,
    a 5 or 6 membered heterocycle, or
    an amino optionally substituted with a heterocycle;
  a $C_6$ to $C_8$ aryl optionally substituted with an alkoxy;
  a —$COR_x$ group, where $R_x$ is as defined above; or
  a $C_1$ to $C_6$ alkyl optionally substituted with a dialkyl-amino or a 5 or 6 membered heterocycle; or $R_1$ joins together with $R_2$ to form:

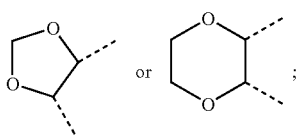

$R_2$ is:
a nitro group;
a hydrogen;
a halo;
a hydroxy group;
a $C_1$ to $C_6$ alkyl group, optionally substituted with one or more of the following:
  halos,
  5 or 6 membered heterocycle groups, or
  amino groups optionally substituted with one or more alkoxy groups or alkyl groups optionally substituted with one or more alkoxy groups,
an amino group;
an alkoxy group optionally substituted with one or more groups independently selected from the following:
  halos,
  a hydroxy group,
  an alkoxy group optionally substituted with an alkoxy group,
  an —$OCOR_x$ group, where $R_x$ is as defined above, or
  an amino group optionally substituted with one or more 5 or 6 membered heterocycle groups or alkyl groups, the alkyl groups optionally and independently substituted with one or more of the following:
    a 5 or 6 membered heterocycle, or
    an amino optionally substituted with one or more alkyl groups;
  a dialkyl-amino optionally substituted with an alkoxy,
  a 5 to 7 membered heterocycle group optionally substituted with one or more independently selected hydroxy group or $C_1$ to $C_6$ alkyl group, the $C_1$ to $C_6$ alkyl group optionally substituted with one or more independently selected $C_1$ to $C_6$ alkoxy group,
  a 5 or 6 membered heteroaryl group optionally substituted with one or more $C_1$ to $C_6$ alkyl groups, or
  a $C_6$ to $C_8$ aryl group;
a —C(O)-5 or 6 membered heterocycle optionally substituted with one or more $C_6$ to $C_8$ aryl groups;
a —COOH group;
a —$COOR_x$ group, where $R_x$ is as defined above;
a haloalkyl;
an amide group optionally substituted with one or more of the following:
  —$C_1$ to $C_6$ alkyl groups,
  hydroxy groups, or
  —$C_6$ to $C_8$ aryl groups;
a 5 or 6 membered heterocycle, optionally substituted with one or more of the following:
  —$C_1$ to $C_6$ alkyl,
  —$SO2R_x$,
  —C(O)—$C_6$ to $C_8$ aryl, or
  —C(O)$OR_x$ groups;
a 5 or 6 membered heteroaryl;
a —$OCOR_x$ group, where $R_x$ is as defined above;

a —$NHCOR_{jj}$ group, where $R_{jj}$ is:
  an alkoxy, or
  an amino optionally substituted with one or more $C_1$ to $C_6$ alkyls;
an —$OR_{kk}$ group, where $R_{kk}$ is:
  a 5 to 6 membered heteroaryl,
  a 5 to 6 membered heterocycle, optionally substituted with a $C_1$ to $C_6$ alkyl, optionally substituted with a $C_6$ to $C_8$ aryl group, or
  an $Si(R_x)_3$; or
a —$NHSO_2R_x$ group, where $R_x$ is as defined above; or
$R_2$ joins together with $R_x$ to form:

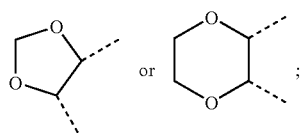

and
$R_3$ is:
a hydrogen; or
—$CH_2OCOR_x$, and $R_x$ is as defined above;
or a pharmaceutically acceptable salt thereof.

In another embodiment, the present invention includes compounds of Formula (I-Xa)

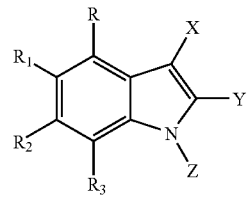

(I-Xa)

wherein
X is:
a cyano group;
Y is:
a hydrogen;
a haloalkyl;
a halo;
an amino optionally substituted with one or more $C_1$ to $C_6$ alkyls;
a benzofuran;
a benzothiophene;
a dibenzofuran;
a dibenzothiophene;
a benzothiazole optionally substituted with an amino group optionally substituted with one or more $C_1$ to $C_6$ alkyls;
a naphthalene;
an indole, optionally substituted on the nitrogen with a $C_1$ to $C_6$ alkyl or an —$SO_2R_x$;

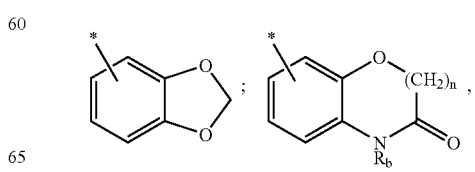

where $R_b$ is a hydrogen or a $C_1$ to $C_6$ alkyl, and n is 0 or 1;

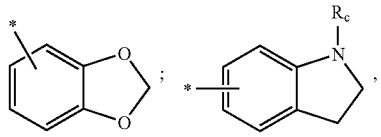

where $R_c$ is a hydrogen, a —CONHR$_x$, where $R_x$ is a $C_1$ to $C_6$ alkyl, or an —SO$_2$R$_x$, where $R_x$ is a $C_1$ to $C_6$ alkyl; or

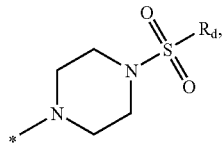

where $R_d$ is a $C_1$ to $C_6$ alkyl or a $C_6$ to $C_8$ aryl;
a —NHCOR$_e$ group, where $R_e$ is:
  a $C_1$ to $C_6$ alkyl;
  a $C_6$ to $C_8$ aryl optionally substituted with:
    a $C_1$ to $C_6$ alkyl,
    an alkoxy,
    a cyano group,
    a nitro group, or
    a halo;
a —NHCOOR$_x$ group, where $R_x$ is a $C_1$ to $C_6$ alkyl;
a —CH$_2$O—R$_f$ group, where $R_f$ is a $C_6$ to $C_8$ aryl;
a —NR$_g$R$_h$ group, where $R_g$ is a $C_1$ to $C_6$ alkyl or a hydrogen and $R_h$ is a $C_6$ to $C_8$ aryl optionally substituted with an alkoxy;
a $C_1$ to $C_6$ alkyl;
a 5 or 6 membered heteroaryl, optionally substituted with:
  a $C_1$ to $C_6$ alkyl, optionally substituted with a $C_6$ to $C_8$ aryl,
  a $C_6$ to $C_8$ aryl, optionally substituted with —COOR$_x$, where $R_x$ is a $C_1$ to $C_6$ alkyl, or
  an amino group;
a 5 or 6 membered heterocycle optionally substituted with:
  a —COOR$_x$ group, where $R_x$ is as defined above, or
  a —NHCOOR$_x$ group, where $R_x$ is as defined above;
a $C_6$ to $C_8$ aryl, optionally substituted with one or more of the following:
  an alkoxy, optionally substituted with:
    an alkoxy,
    a hydroxy,
    one or more halos,
    a 5 or 6 membered heterocycle, optionally substituted with:
      a $C_1$ to $C_6$ alkyl, or
      a hydroxy,
    an amino optionally substituted with one or more $C_1$ to $C_6$ alkyls,
  a —NR$_i$SO$_2$R$_x$ group, where $R_x$ is a $C_1$ to $C_6$ alkyl and $R_i$ is:
    a hydrogen,
    a $C_1$ to $C_6$ alkyl,
    a —COR$_x$ group, where $R_x$ is as defined above,
    a haloalkyl, or
    a haloalkoxy,
  a —NR$_j$COR$_k$ group, where $R_k$ is:
    a $C_1$ to $C_6$ alkyl,
    a hydrogen, or
    an amino optionally substituted with one or more $C_1$ to $C_6$ alkyls,
  and $R_j$ is:
    a hydrogen,
    a $C_1$ to $C_6$ alkyl,
    a —COR$_x$ group, where $R_x$ is a $C_1$ to $C_6$ alkyl,
    a haloalkyl, or
    a haloalkoxy,
    a —N=N$^+$=N$^-$ group, or
    a —COR$_1$, where $R_1$ is a 5 or 6 membered heterocycle optionally substituted with a hydroxy,
  an amino optionally substituted with one or more of the following:
    —SO$_2$(R$_x$), or
    —$C_1$ to $C_6$ alkyl, the $C_1$ to $C_6$ alkyl optionally and independently substituted with one or more 5 or 6 membered heteroaryl group,
  a nitro group,
  a $C_1$ to $C_6$ alkyl group, optionally substituted with:
    a —NHSO$_2$R$_x$ group, where $R_x$ is as defined above, or
    —NR$_x$SO$_2$R$_x$ group, where $R_x$ is as defined above,
  a haloalkoxy,
  a halo,
  a hydroxy,
  —OC(O)NHR$_x$,
  —OC(O)N(R$_x$)$_2$,
  —OC(O)NH(OR$_x$),
  —OC(O)NR$_x$(OR$_x$),
  —OC(O)N(OR$_x$)$_2$,
  —OC(O)R$_{ab}$, wherein $R_{ab}$ is a 5 or 6 membered heterocycle group,
  a —COOR$_x$ group, where $R_x$ is a $C_1$ to $C_6$ alkyl,
  a —COR$_m$ group, where $R_m$ is:
    an amino optionally substituted with one or more $C_1$ to $C_6$ alkyls, where the $C_1$ to $C_6$ alkyls are optionally substituted with:
      a hydroxy
      a 5 or 6 membered heterocycle,
      an amino optionally substituted with one or more $C_1$ to $C_6$ alkyls, or
      an alkoxy,
    a 3 to 7 membered heterocycle, optionally substituted with a $C_1$ to $C_6$ alkyl, optionally substituted with a dialkyl-amino,
  a —NHR$_n$ group, where $R_n$ is:
    a —CH$_2$CONH$_2$, or
    a $C_6$ to $C_8$ aryl optionally substituted with:
      an alkyl,
      one or more halos,
      a nitro group, or
      one or more alkoxys,
  a —NR$_o$COR$_p$ group, where $R_p$ is:
    a $C_1$ to $C_6$ alkyl optionally substituted with:
      a halo,
      an alkoxy, or
      a $C_6$ to $C_8$ aryl,
    an amino group optionally substituted with one or more $C_1$ to $C_6$ alkyl groups where the $C_1$ to $C_6$ alkyl groups are optionally and independently substituted with one or more $C_6$ to $C_8$ aryl groups and/or alkoxy groups,
    a 5 or 6 membered heterocycle, optionally substituted with one or more $C_1$ to $C_6$ alkyl or $C_6$ to $C_8$ aryl groups,
    a $C_6$ to $C_8$ aryl, optionally substituted with a halo,
    a 5 or 6 membered heteroaryl optionally substituted with one or more $C_1$ to $C_6$ alkyls,
    a hydrogen,

[structures: benzofurazan, benzodioxole]

and where $R_o$ is:
- a hydrogen,
- a $C_1$ to $C_6$ alkyl,
- a —$COR_x$ group, where $R_x$ is a $C_1$ to $C_6$ alkyl,
- a haloalkyl, or
- a haloalkoxy, a —$NR_qCONR_qR_r$ group, where $R_q$ is:
- a hydrogen,
- a $C_1$ to $C_6$ alkyl,
- a haloalkyl,
- a haloalkoxy, or
- a —$COR_x$ group, where $R_x$ is as defined above, and where $R_r$ is:
- a $C_6$ to $C_8$ aryl optionally substituted with:

[structure: indole with CN and OMe substituents]

- a $C_1$ to $C_6$ alkyl,
- a haloalkyl,
- a —$OR_s$ group, where $R_s$ is a $C_6$ to $C_8$ aryl, or
- a —$COOR_x$ group, where $R_x$ is as defined above,
- a $C_1$ to $C_6$ alkyl optionally substituted with one or more of the following:
  - a halo,
  - a hydroxyl,
  - an alkoxy,
  - an alkylene,
  - a 5 or 6 membered heterocycle,
  - a 5 or 6 membered heteroaryl,
  - a $C_6$ to $C_8$ aryl optionally substituted with a halo, or
  - a —$COOR_x$ group, where $R_x$ is as defined above,
- a $C_2$ to $C_6$ alkylene group,
- a $C_1$ to $C_6$ alkoxy group,
- a 5 or 6 membered heterocycle group, or
- a —$COOR_x$ group, where $R_x$ is as defined above, a —$NR_tCOOR_u$ group, where $R_u$ is:
- a $C_1$ to $C_{12}$ alkyl, optionally substituted with one or more of the following:
  - a $C_6$ to $C_8$ aryl optionally substituted with halo, $C_1$ to $C_6$ alkyl, or alkoxy,
  - an alkylene,
  - an alkoxy,
  - an alkyne,
  - an alkoxy group optionally substituted with one or more alkoxy groups,
  - an amino optionally substituted with one or more $C_1$ to $C_6$ alkyl,
  - halo,
  - a 5 or 6 membered heterocycle, or
  - a 5 or 6 membered heteroaryl,
- a $C_2$ to $C_6$ alkylene,
- a $C_6$ to $C_8$ aryl, optionally substituted with:
  - an alkoxy,
  - a halo, or
  - a $C_1$ to $C_6$ alkyl, or
- a 5 or 6 membered heterocycle, and $R_t$ is:
- a hydrogen,
- a $C_1$ to $C_6$ alkyl,
- a —$COR_x$ group, where $R_x$ is as defined above,
- a haloalkyl, or
- a haloalkoxy, a —$NR_vSO_2R_w$ group, where $R_v$ is:
- a hydrogen,
- a —$COR_x$, where $R_x$ is as defined above, or
- a $C_1$ to $C_6$ alkyl, optionally substituted with:
  - a halo,
  - a —$COR_x$ group, where $R_x$ is as defined above,
  - a —$OCOR_x$ group, where $R_x$ is as defined above,
  - a hydroxyl, or
  - an alkoxy, and where $R_w$ is:
- a $C_1$ to $C_6$ alkyl optionally substituted with:
  - a halo,
  - a haloalkyl,
  - a $C_6$ to $C_8$ aryl, or
  - a 5 or 6 membered heterocycle,
- a $C_2$ to $C_6$ alkylene,
- an alkyl- or dialkyl-amino optionally substituted with a halo,
- a 5 or 6 membered heterocycle, or
- a 5 or 6 membered heteroaryl optionally substituted with:
  - a $C_1$ to $C_6$ alkyl,
  - a 5 or 6 membered heterocycle, or

[structures: quinoline, isothiazolidine dioxide, imidazolidinone-NH, imidazolidinedione-NH, hydantoin with $R_y$ groups]

optionally substituted with a $C_1$ to $C_6$ alkyl, where $R_y$ is a $C_1$ to $C_6$ alkyl or hydrogen,

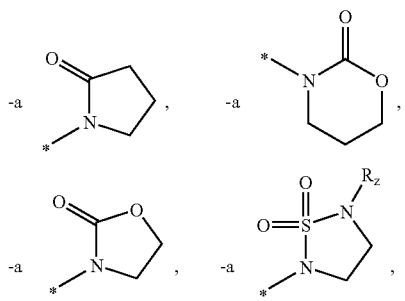

where $R_z$ is hydrogen or a $C_1$ to $C_6$ alkyl, optionally substituted with a $C_6$ to $C_8$ aryl,
  a —$SR_x$ group, where $R_x$ is as defined above,
  an —$SO_2R_{aa}$ group, where $R_{aa}$ is:
    a $C_1$ to $C_6$ alkyl,
    an amino group,
    an alkyl- or dialkyl-amino group optionally substituted with a hydroxy or a —$COOR_x$ group, where $R_x$ is as defined above, or
    a 5 or 6 membered heteroaryl,
  a $C_6$ to $C_8$ aryl, or
  a —$NHR_{bb}$ group, where $R_{bb}$ is:

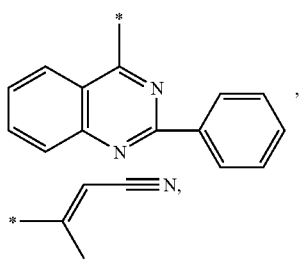

a —$C(=S)NH_2$ group, or
  a —$PO(OR_x)_2$, where $R_x$ is as defined above; or
a ·≡≡—$R_{cc}$ group, where $R_{cc}$ is:
  a naphthalene,
  a 5 or 6 membered heteroaryl,

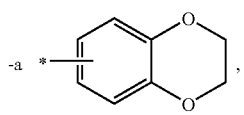

or
  a $C_6$ to $C_8$ aryl, optionally substituted with one or more of the following:
    an alkoxy,
    a hydroxy,
    a halo,
    a $C_1$ to $C_6$ alkyl, optionally substituted with a cyano group,
    an amino optionally substituted with one or more $C_1$ to $C_6$ alkyls,
    a —$NHPOR_xR_x$, where $R_x$ is as defined above,
    a —$NR_{ee}CONR_{ff}R_{ff}$ group, where $R_{ee}$ is a hydrogen or a $C_1$ to $C_6$ alkyl, optionally substituted with a halo, and $R_{ff}$ is:
      a hydrogen,
      a haloalkyl,
      a haloalkoxy,
      a $C_1$ to $C_6$ alkyl, or
      a —$COR_x$, where $R_x$ is as defined above,
    a —$NR_{gg}COR_{hh}$ group, where $R_{hh}$ is:
      a hydrogen,
      a $C_1$ to $C_6$ alkyl optionally substituted with:
        an alkoxy,
        a halo, or
        an amino optionally substituted with one or more $C_1$ to $C_6$ alkyls,
      an amino optionally substituted with one or more $C_1$ to $C_6$ alkyls, where the alkyls are optionally substituted with a halo,
      a 5 or 6 membered heterocycle, or
      a 5 or 6 membered heteroaryl,
    and $R_{gg}$ is:
      a hydrogen,
      a $C_1$ to $C_6$ alkyl,
      a haloalkyl,
      a haloalkoxy, or
      a —$COR_x$ group, where $R_x$ is as defined above,
    a haloalkyl,
    5 or 6 membered heterocycle groups,
    an amino optionally substituted with one or more $C_1$ to $C_6$ alkyls, or
    a —$NR_{ii}SO_2R_x$ group, where $R_x$ is as defined above, and $R_{ii}$ is:
      a hydrogen,
      a $C_1$ to $C_6$ alkyl,
      a haloalkyl,
      a haloalkoxy, or
      a —$COR_x$ group, where $R_x$ is as defined above;
Z is:
  a hydrogen;
  a $C_1$ to $C_6$ alkyl optionally substituted with:
    an alkoxy,
    one or more halos,
    a 5 or 6 membered heterocycle, or
    a $C_6$ to $C_8$ aryl;
  a 5 or 6 membered heterocycle;
  a $C_2$ to $C_6$ alkylene;
  a $C_6$ to $C_8$ aryl optionally substituted with an alkoxy or one or more $C_1$ to $C_6$ alkyls;
  a —$COOR_x$ group, where $R_x$ is as defined above; or

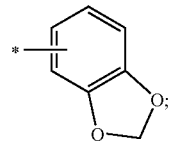

R is a hydrogen, a halo or an alkoxy;
$R_1$ is:
  a hydrogen;
  a hydroxy;
  a halo;
  a haloalkyl;
  a nitro group;
  a 5 or 6 membered heteroaryl;
  a 5 or 6 membered heterocycle;

an alkoxy optionally substituted with:
  one or more halos,
  a $C_6$ to $C_8$ aryl,
  a 5 or 6 membered heterocycle, or
  an amino optionally substituted with a 5 or 6 membered heterocycle;
a $C_6$ to $C_8$ aryl optionally substituted with an alkoxy;
a —$COR_x$ group, where $R_x$ is as defined above; or
a $C_1$ to $C_6$ alkyl optionally substituted with a dialkyl-amino or a 5 or 6 membered heterocycle; or
$R_1$ joins together with $R_2$ to form:

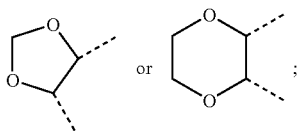

$R_2$ is:
a nitro group;
a hydrogen;
a halo;
a hydroxy group;
a $C_1$ to $C_6$ alkyl group, optionally substituted with one or more of the following:
  halos,
  5 or 6 membered heterocycle groups, or
  amino groups optionally substituted with one or more alkoxy groups or alkyl groups optionally substituted with one or more alkoxy groups,
an amino group;
an alkoxy group optionally substituted with one or more of the following:
  halos,
  a hydroxy group,
  an alkoxy group optionally substituted with an alkoxy group,
  an —$OCOR_x$ group, where $R_x$ is as defined above,
  an amino group optionally substituted with one or more 5 or 6 membered heterocycle groups or alkyl groups, the alkyl groups optionally and independently substituted with one or more of the following:
    a 5 or 6 membered heterocycle, or
    an amino optionally substituted with one or more alkyl groups;
  a dialkyl-amino optionally substituted with an alkoxy,
  a 5 to 7 membered heterocycle group optionally substituted with one or more independently selected hydroxy group or $C_1$ to $C_6$ alkyl group, the $C_1$ to $C_6$ alkyl group optionally substituted with one or more independently selected $C_1$ to $C_6$ alkoxy group,
  a 5 or 6 membered heteroaryl group optionally substituted with one or more $C_1$ to $C_6$ alkyl groups, or
  a $C_6$ to $C_8$ aryl group;
a —C(O)-5 or 6 membered heterocycle optionally substituted with one or more $C_6$ to $C_8$ aryl groups;
a —COOH group;
a —$COOR_x$ group, where $R_x$ is as defined above;
a haloalkyl;
an amide group optionally substituted with one or more of the following:
  —$C_1$ to $C_6$ alkyl groups,
  hydroxy groups, or
  —$C_6$ to $C_8$ aryl groups;
a 5 or 6 membered heterocycle, optionally substituted with one or more of the following:
  —$C_1$ to $C_6$ alkyl,
  —$SO_2R_x$ groups,
  —C(O)—$C_6$ to $C_8$ aryl, or
  —$C(O)OR_x$ groups;
a 5 or 6 membered heteroaryl;
a —$OCOR_x$ group, where $R_x$ is as defined above;
a —$NHCOR_{jj}$ group, where $R_{jj}$ is:
  an alkoxy, or
  an amino optionally substituted with one or more $C_1$ to $C_6$ alkyls;
an —$OR_{kk}$ group, where $R_{kk}$ is:
  a 5 to 6 membered heteroaryl,
  a 5 to 6 membered heterocycle, optionally substituted with a $C_1$ to $C_6$ alkyl, optionally substituted with a $C_6$ to $C_8$ aryl group, or
  an —$Si(R_x)_3$;
a —$NHSO_2R_x$ group, where $R_x$ is as defined above; or
$R_2$ joins together with $R_1$ to form:

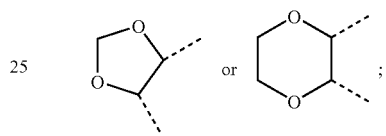

$R_3$ is:
a hydrogen; or
—$CH_2OCOR_x$, and $R_x$ is as defined above;
with the proviso that at least one of Y, Z, $R_1$ and $R_2$ is selected from the following:
Y is:
a benzothiazole substituted with an amino group optionally substituted with one or more $C_1$ to $C_6$ alkyls;
an indole substituted on the nitrogen with an —$SO_2R_x$ group;
a $C_6$ to $C_8$ aryl substituted with one or more of the following:
  an amino optionally substituted with one or more of the following:
    —$SO_2R_x$, or
    —$C_1$ to $C_6$ alkyl substituted with one or more 5 or 6 membered heteroaryl group,
  —$OC(O)NHR_x$,
  —$OC(O)N(R_x)_2$,
  —$OC(O)NH(OR_x)$,
  —$OC(O)NR_x(OR_x)$,
  —$OC(O)N(OR_x)_2$,
  —$OC(O)R_{ab}$, wherein $R_{ab}$ is a 5 or 6 membered heterocycle group,
  a —$NR_oCOR_p$ group, where $R_p$ is:
    an amino group optionally substituted with one or more $C_1$ to $C_6$ alkyl groups where the $C_1$ to $C_6$ alkyl groups are optionally and independently substituted with one or more $C_6$ to $C_8$ aryl groups and/or alkoxy groups, or
    a 5 or 6 membered heterocycle, substituted with one or more $C_1$ to $C_6$ alkyl or $C_6$ to $C_8$ aryl groups,
  a —$NR_qCONR_qR_r$ group, where $R_r$ is:
    a $C_1$ to $C_6$ alkyl substituted with one or more of the following:
      a hydroxyl,
      an alkoxy,
      a 5 or 6 membered heterocycle,
      a 5 or 6 membered heteroaryl, or
      a $C_6$ to $C_8$ aryl substituted with a halo, a $C_2$ to $C_6$ alkylene group,
a $C_1$ to $C_6$ alkoxy group, or
a 5 or 6 membered heterocycle group,
a —$NR_tCOOR_u$ group, where $R_u$ is:
  a $C_1$ to $C_{12}$ alkyl, substituted with one or more of the following:
    an alkoxy group substituted with one or more alkoxy groups,
    an amino optionally substituted with one or more $C_1$ to $C_6$ alkyl, or
    a 5 or 6 membered heteroaryl,
  a $C_2$ to $C_6$ alkylene, or -a—[structure]

Z is:
a $C_1$ to $C_6$ alkyl substituted with a 5 or 6 membered heterocycle, or
a 5 or 6 membered heterocycle; or
$R_1$ is an alkoxy substituted with an amino, where the amino is optionally substituted with a heterocycle;
$R_2$ is:
a $C_1$ to $C_6$ alkyl group, substituted with one or more of the following:
  5 or 6 membered heterocycle groups, or
  amino groups optionally substituted with one or more alkoxy groups or alkyl groups optionally substituted with one or more alkoxy groups,
an alkoxy group substituted with one or more groups independently selected from the following:
  a hydroxy group,
  an alkoxy group optionally substituted with an alkoxy group,
  an amino group substituted with one or more 5 or 6 membered heterocycle groups or alkyl groups, the alkyl groups optionally and independently substituted with one or more of the following:
    a 5 or 6 membered heterocycle, or
    an amino optionally substituted with one or more alkyl groups;
a 7 membered heterocycle group;
a 5 to 7 membered heterocycle group substituted with one or more independently selected hydroxy groups or substituted with one or more independently selected $C_1$ to $C_6$ alkyl groups substituted with $C_1$ to $C_6$ alkoxy, or
a 5 or 6 membered heteroaryl group substituted with one or more $C_1$ to $C_6$ alkyl groups;
a —C(O)-5 or 6 membered heterocycle optionally substituted with one or more $C_6$ to $C_8$ aryl groups;
a —COOH group;
an amide group substituted with one or more $C_1$ to $C_6$ alkyl groups;
a 5 or 6 membered heterocycle, optionally substituted with one or more of the following:
  —$C_1$ to $C_6$ alkyl,
  —$SO_2R_x$,
  —C(O)—$C_6$ to $C_8$ aryl, or
  —C(O)$OR_x$ groups;
an —$OR_{kk}$ group, where $R_{kk}$ is:
  a 5 to 6 membered heterocycle, optionally substituted with a $C_1$ to $C_6$ alkyl, optionally substituted with a $C_6$ to $C_8$ aryl group, or
  an —$Si(R_x)_3$;
or a pharmaceutically acceptable salt thereof.

In some embodiments, R is selected from the R substituents of compounds 1330-2128 and 2600-3348.

In some embodiments of the invention, compounds are provided wherein R is selected from the following non-limiting substituents:

In other embodiments of the invention, R is hydrogen.

In some embodiments of the invention, $R_1$ is selected from the following non-limiting substituents:

In some embodiments of the invention, $R_2$ is selected from the following non-limiting substituents:

-continued
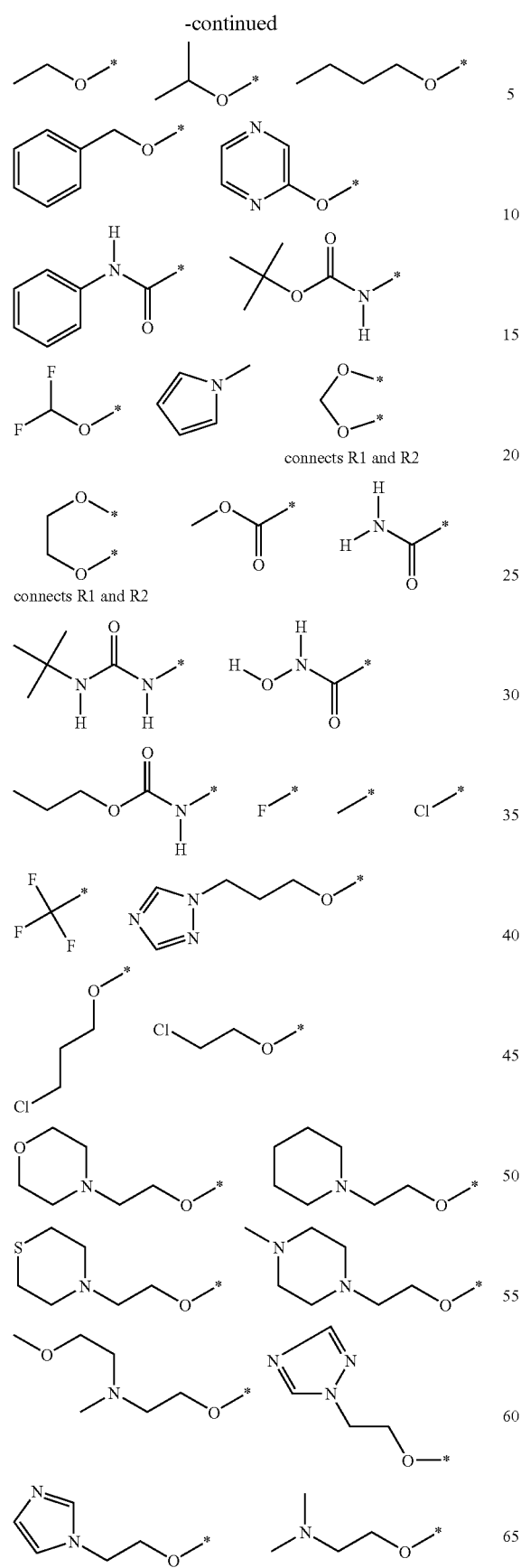
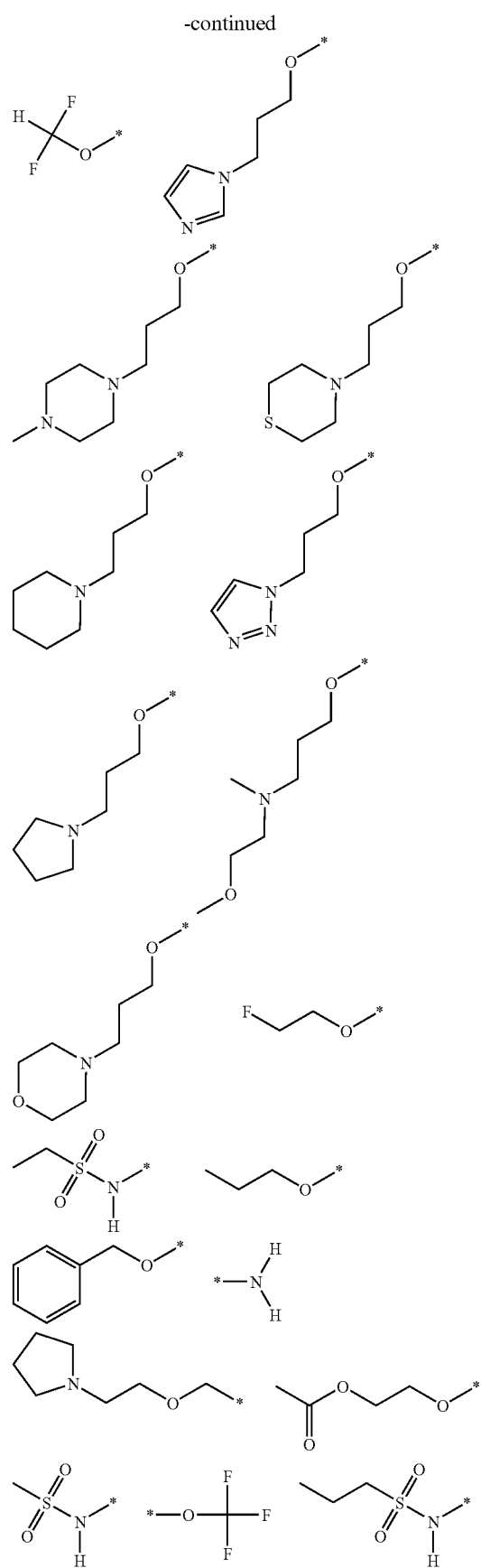

-continued

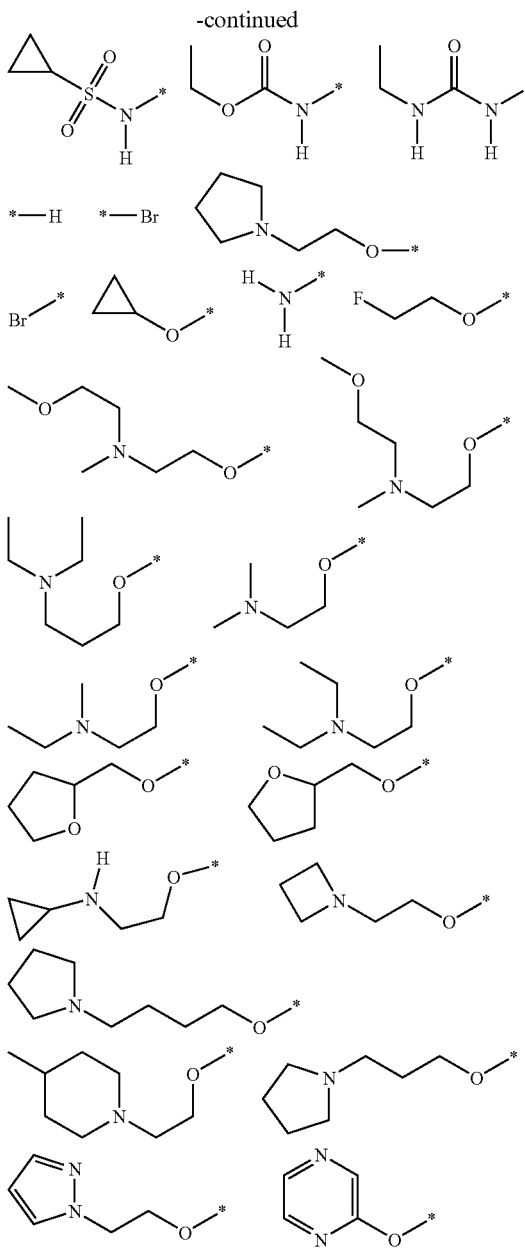

In some embodiments, R₃ is selected from the R₃ substituents of compounds 1330-2128, and 2600-3348.

In some embodiments of the invention, compounds are provided wherein R₃ is selected from the following non-limiting substituents:

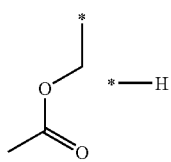

In other embodiments of the invention, compounds are provided wherein R₃ is hydrogen.

In another embodiment, the present invention includes a compound of Formula (I-XI)

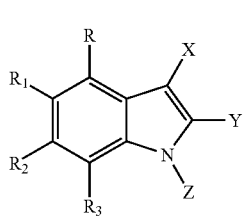

(I-XI)

wherein:
X is:
hydrogen;
a cyano group;
a nitro group;
a formyl group;
a —COOH group;
a CORx group, wherein Rx is a $C_1$ to $C_6$ alkyl;

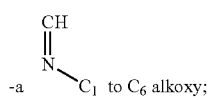

a halo;
an alkyl optionally substituted with one or more halo;
an alkyne optionally substituted with a $C_1$ to $C_6$ alkyl optionally substituted with one or more independently selected halo or cyano groups;
an oxime;
—SO₂Rₓ;
—SO₂NH₂;
—SO₂NH(Rₓ);
—SO₂N(Rₓ)₂;
an amino optionally substituted with one or more $C_1$ to $C_6$ alkyl groups or C(O)—$C_1$ to $C_6$ alkyl groups;
an amide group optionally substituted with one or more independently selected $C_1$ to $C_6$ alkyl group;
a 5 or 6 membered heterocycle;
a 5 or 6 membered heteroaryl optionally substituted with one or more $C_1$ to $C_6$ alkyl groups optionally substituted with one or more halos; or
a $C_6$ to $C_8$ aryl group optionally substituted with one or more of the following:
—$C_1$ to $C_6$ alkyl optionally substituted with one or more halos,
halo, or
cyano;
Y is:
a benzothiazole optionally substituted with an amino group optionally substituted with one or more $C_1$ to $C_6$ alkyls;
an indole, optionally substituted on the nitrogen with an —SO₂Rₓ group; or
a $C_6$ to $C_8$ aryl, optionally substituted with one or more of the following:
halo;
a $C_1$ to $C_6$ alkyl;
an alkoxy, an amino optionally substituted with one or more of the following:
—SO₂Rₓ,
—C₁ to C₆ alkyl, the C₁ to C₆ alkyl optionally and independently substituted with one or more 5 or 6 membered heteroaryl group, or
—PO₂Rₓ,
—OC(O)NHRₓ,
—OC(O)N(Rₓ)₂,
—OC(O)NH(ORₓ),
—OC(O)NRₓ(ORₓ),
—OC(O)N(ORₓ)₂,
—OC(O)Rₐᵦ, wherein Rₐᵦ is a 5 or 6 membered heterocycle group,
a —NR₀COR_p group, where R_p is:
  a C₁ to C₆ alkyl,
  an amino group optionally substituted with one or more C₁ to C₆ alkyl groups where the C₁ to C₆ alkyl groups are optionally and independently substituted with one or more C₆ to C₈ aryl groups and/or alkoxy groups, or
  a 5 or 6 membered heterocycle, optionally substituted with one or more C₁ to C₆ alkyl or C₆ to C₈ aryl groups,
and where R₀ is:
  a hydrogen, or
  a C₁ to C₆ alkyl,
a —NR_qCONR_qR_r group, where R_q is a hydrogen,
and where R_r is:
  a C₁ to C₆ alkyl optionally substituted with one or more of the following:
    halo,
    hydroxyl,
    an alkoxy,
    a 5 or 6 membered heterocycle,
    a 5 or 6 membered heteroaryl, or
    a C₆ to C₈ aryl optionally substituted with a halo,
  a C₂ to C₆ alkylene group optionally substituted with one or more halo,
  a C₁ to C₆ alkoxy group, or
  a 5 or 6 membered heterocycle group,
a —NR_tCOOR_u group, where R_u is:
  a C₁ to C₁₂ alkyl, optionally substituted with one or more groups independently selected from the following:
    a C₆ to C₈ aryl optionally substituted with halo,
    an alkoxy group optionally substituted with one or more alkoxy groups,
    an amino optionally substituted with one or more C₁ to C₆ alkyl,
    halo, or
    a 5 or 6 membered heteroaryl,
  a C₂ to C₆ alkylene, or
  a C₆ to C₈ aryl, optionally substituted with halo,
and R_t is:
  a hydrogen;
a —NHR_bb group, where R_bb is:
  a —C(=S)NH₂ group, or
  a —PO(ORₓ)₂, where Rₓ is as defined above;
a —NR_vSO₂R_w group, where R_v is a hydrogen, and where R_w is a C₁ to C₆ alkyl,

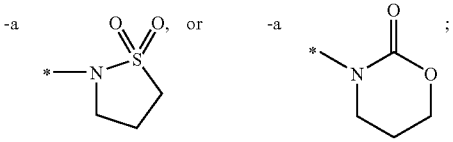

Z is:
  a C₁ to C₆ alkyl optionally substituted with a 5 or 6 membered heterocycle, or
  a 5 or 6 membered heterocycle;
R is a hydrogen;
R₁ is:
  a hydrogen;
  a C₁ to C₆ alkyl optionally substituted with:
    an amino optionally substituted with a heterocycle,
    an amide optionally substituted with a C₁ to C₆ alkyl,
    a 5 or 6 membered heterocycle optionally substituted with a C₁ to C₆ alkyl,
    a 5 or 6 membered heteroaryl, or
    a C₆ to C₈ aryl;
  a C₁ to C₆ alkoxy optionally substituted with:
    an amino optionally substituted with a heterocycle,
    an amide optionally substituted with a C₁ to C₆ alkyl,
    a 5 or 6 membered heterocycle optionally substituted with a C₁ to C₆ alkyl,
    a 5 or 6 membered heteroaryl, or
    a C₆ to C₈ aryl;
  an (O)-5 or 6 membered heterocycle;
  an (O)-5 or 6 membered heteroaryl;
  an —SO₂Rₓ group optionally substituted with the following:
    a 5 or 6 membered heterocycle,
    a C₆ to C₈ aryl,
    a 5 or 6 membered heteroaryl; or
  alkylthio optionally substituted with the following:
    a 5 or 6 membered heterocycle,
    a C₆ to C₈ aryl,
    a 5 or 6 membered heteroaryl;
R₂ is:
  a C₁ to C₆ alkyl group, optionally substituted with one or more of the following:
    5 or 6 membered heterocycle groups,
    5 or 6 membered heteroaryl groups,
    —C₆ to C₈ aryl groups,
    an amide optionally substituted with a C₁ to C₆ alkyl, or
    amino groups optionally substituted with one or more heterocycle, alkoxy groups or alkyl groups optionally substituted with one or more alkoxy groups;
  an alkylthio group optionally substituted with a 5 or 6 membered heteroaryl group optionally substituted with an alkyl group;
  an alkylthio group optionally substituted with a 5 or 6 membered heterocycle group;
  an alkylthio group optionally substituted with a C₆ to C₈ aryl group;
  an alkylthio group optionally substituted with a C₁ to C₆ alkyl group;
  an SO₂Rₓ group optionally substituted with a 5 or 6 membered heteroaryl optionally substituted with one or more C₁ to C₆ alkyl groups;
  an SO₂Rₓ group optionally substituted with a 5 or 6 membered heterocycle group;
  an SO₂Rₓ group optionally substituted with a C₆ to C₈ aryl group;

an SO$_2$R$_x$ group optionally substituted with a C$_1$ to C$_6$ alkyl group;
an S(O)R$_x$ group optionally substituted with a 5 or 6 membered heteroaryl group;
an S(O)R$_x$ group optionally substituted with a 5 or 6 membered heterocycle group;
an S(O)R$_x$ group optionally substituted with a C$_6$ to C$_8$ aryl group;
an S(O)R$_x$ group optionally substituted with a C$_1$ to C$_6$ alkyl group;
an alkoxy group optionally substituted with one or more groups independently selected from the following:
 halo,
 hydroxy group,
 an alkoxy group optionally substituted with an alkoxy group,
 an amino group optionally substituted with one or more 5 or 6 membered heteroaryl groups, 5 or 6 membered heterocycle groups or alkyl groups, the alkyl groups optionally and independently substituted with one or more of the following:
  5 or 6 membered heterocycle, or
  amino optionally substituted with one or more alkyl groups,
 an amide optionally substituted with a C$_1$ to C$_6$ alkyl,
 —S-5 or 6 membered heterocycle,
 —S-5 or 6 membered heteroaryl optionally substituted with a C$_1$ to C$_6$ alkyl,
 —S—C$_1$ to C$_6$ alkyl,
 —S—C$_6$ to C$_8$ aryl,
 sulfinyl-5 or 6 membered heterocycle,
 sulfinyl-5 or 6 membered heteroaryl,
 sulfinyl-C$_1$ to C$_6$ alkyl,
 sulfinyl-C$_6$ to C$_8$ aryl,
 sulfonyl-5 or 6 membered heterocycle,
 sulfonyl-5 or 6 membered heteroaryl optionally substituted with a C$_1$ to C$_6$ alkyl,
 sulfonyl-C$_1$ to C$_6$ alkyl,
 sulfonyl-C$_6$ to C$_8$ aryl,
 a 5 to 7 membered heterocycle group optionally substituted with one or more independently selected hydroxy group or C$_1$ to C$_6$ alkyl group, the C$_1$ to C$_6$ alkyl group optionally substituted with one or more independently selected C$_1$ to C$_6$ alkoxy group,
 a 5 or 6 membered heteroaryl group optionally substituted with one or more C$_1$ to C$_6$ alkyl groups,
 a C$_6$ to C$_8$ aryl group;
a C$_6$ to C$_8$ aryl group;
an (O)-5 or 6 membered heterocycle;
an (O)-5 or 6 membered heteroaryl optionally substituted with one or more independently selected C$_1$ to C$_6$ alkyl groups;
a —C(O)-5 or 6 membered heterocycle optionally substituted with one or more C$_6$ to C$_8$ aryl groups;
a —C(O)-5 or 6 membered heteroaryl;
a —C(O)—C$_6$ to C$_8$ aryl;
a —COOH group;
an amide group optionally substituted with one or more C$_1$ to C$_6$ alkyl groups optionally substituted with one or more C$_1$ to C$_6$ alkoxy;
a 5 or 6 membered heterocycle, optionally substituted with one or more of the following:
 hydroxy,
 —C$_1$ to C$_6$ alkyl,
 —SO$_2$R$_x$,
 —C(O)—C$_6$ to C$_8$ aryl, or
 —C(O)OR$_x$ groups;
an —OR$_{kk}$ group, where R$_{kk}$ is:
 a C$_6$ to C$_8$ aryl,
 a 5 to 6 membered heteroaryl,
 a 5 to 6 membered heterocycle, optionally substituted with a C$_1$ to C$_6$ alkyl, optionally substituted with a C$_6$ to C$_8$ aryl group, or
 an —Si(R$_x$)$_3$; and
R$_3$ is a hydrogen;
or a pharmaceutically acceptable salt thereof.

In a further embodiment of the present invention, compounds of the present invention include compounds of Formula (I-XIa)

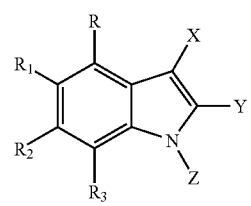

(I-XIa)

wherein:
X is:
hydrogen;
a cyano group;
a nitro group;
a formyl group;
a —COOH group;
a CORE group, wherein R$_x$ is a C$_1$ to C$_6$ alkyl;

$$\text{-a}\overset{\underset{\parallel}{CH}}{A}\diagdown C_1 \text{ to } C_6 \text{ alkoxy;}$$

$$\text{-a}\overset{\underset{\parallel}{CH}}{N}\diagdown \text{amino optionally substituted with one or more } C_1 \text{ to } C_6 \text{ alkyl groups};$$

a halo;
an alkyl optionally substituted with one or more halo;
an alkyne optionally substituted with a C$_1$ to C$_6$ alkyl optionally substituted with one or more halo or cyano groups;
an oxime;
—SO$_2$R$_x$;
—SO$_2$NH$_2$;
—SO$_2$NH(R$_x$);
—SO$_2$N(R$_x$)$_2$;
an amino optionally substituted with one or more C$_1$ to C$_6$ alkyl groups or C(O)—C$_1$ to C$_6$ alkyl groups;
an amide group optionally substituted with one or more independently selected C$_1$ to C$_6$ alkyl group;
a 5 or 6 membered heterocycle;
a 5 or 6 membered heteroaryl optionally substituted with one or more C$_1$ to C$_6$ alkyl groups optionally substituted with one or more halos; or
a C$_6$ to C$_8$ aryl group optionally substituted with one or more of the following:
 —C$_1$ to C$_6$ alkyl optionally substituted with one or more halos,
 halo, or
 cyano;

Y is:
a benzothiazole optionally substituted with an amino group optionally substituted with one or more $C_1$ to $C_6$ alkyls;
an indole, optionally substituted on the nitrogen with a —$SO_2R_x$ group;
a $C_6$ to $C_8$ aryl, optionally substituted with one or more of the following:
halo;
a $C_1$ to $C_6$ alkyl;
an alkoxy,
an amino optionally substituted with one or more
—$SO_2R_x$ groups,
—$C_1$ to $C_6$ alkyl, the $C_1$ to $C_6$ alkyl optionally and independently substituted with one or more 5 or 6 membered heteroaryl group, or
—$PO_2R_x$ groups,
—$OC(O)NHR_x$,
—$OC(O)N(R_x)_2$,
—$OC(O)NH(OR_x)$,
—$OC(O)NR_x(OR_x)$,
—$OC(O)N(OR_x)_2$,
—$OC(O)R_{ab}$, wherein $R_{ab}$ is a 5 or 6 membered heterocycle group,
a —$NR_oCOR_p$ group, where $R_p$ is:
a $C_1$ to $C_6$ alkyl,
an amino group optionally substituted with one or more $C_1$ to $C_6$ alkyl groups where the $C_1$ to $C_6$ alkyl groups are optionally and independently substituted with one or more $C_6$ to $C_8$ aryl groups and/or alkoxy groups,
a 5 or 6 membered heterocycle, optionally substituted with one or more $C_1$ to $C_6$ alkyl or $C_6$ to $C_8$ aryl groups,
and where $R_o$ is:
a hydrogen,
a $C_1$ to $C_6$ alkyl,
a —$NR_qCONR_qR_r$ group, where $R_q$ is a hydrogen, and where $R_r$ is:
a $C_1$ to $C_6$ alkyl optionally substituted with one or more of the following:
halo,
hydroxyl,
an alkoxy,
a 5 or 6 membered heterocycle,
a 5 or 6 membered heteroaryl, or
a $C_6$ to $C_8$ aryl optionally substituted with a halo,
a $C_2$ to $C_6$ alkylene group optionally substituted with one or more halo,
a $C_1$ to $C_6$ alkoxy group, or
a 5 or 6 membered heterocycle group,
a —$NR_tCOOR_u$ group, where $R_u$ is:
a $C_1$ to $C_{12}$ alkyl, optionally substituted with one or more groups independently selected from the following:
a $C_6$ to $C_8$ aryl optionally substituted with halo,
an alkoxy group optionally substituted with one or more alkoxy groups,
an amino optionally substituted with one or more $C_1$ to $C_6$ alkyl,
halo, or
a 5 or 6 membered heteroaryl,
a $C_2$ to $C_6$ alkylene,
a $C_6$ to $C_8$ aryl, optionally substituted with halo,
and $R_t$ is a hydrogen;
a —$NHR_{bb}$ group, where $R_{bb}$ is:
a —$C(=S)NH_2$ group, or
a —$PO(OR_x)_2$, where $R_x$ is as defined above;
a —$NR_vSO_2R_w$ group, where $R_v$ is a hydrogen, and where $R_w$ is a $C_1$ to $C_6$ alkyl,

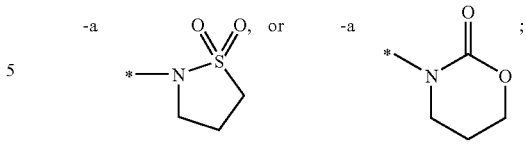

Z is:
a $C_1$ to $C_6$ alkyl optionally substituted with a 5 or 6 membered heterocycle, or
a 5 or 6 membered heterocycle;
R is a hydrogen;
$R_1$ is:
a hydrogen;
a $C_1$ to $C_6$ alkyl optionally substituted with:
an amino optionally substituted with a heterocycle,
an amide optionally substituted with a $C_1$ to $C_6$ alkyl,
a 5 or 6 membered heterocycle optionally substituted with a $C_1$ to $C_6$ alkyl,
a 5 or 6 membered heteroaryl, or
a $C_6$ to $C_8$ aryl;
a $C_1$ to $C_6$ alkoxy optionally substituted with:
an amino optionally substituted with a heterocycle,
an amide optionally substituted with a $C_1$ to $C_6$ alkyl,
a 5 or 6 membered heterocycle optionally substituted with a $C_1$ to $C_6$ alkyl,
a 5 or 6 membered heteroaryl, or
a $C_6$ to $C_8$ aryl;
an (O)-5 or 6 membered heterocycle;
an (O)-5 or 6 membered heteroaryl;
an —$SO_2R_x$ group optionally substituted with the following:
a 5 or 6 membered heterocycle,
a $C_6$ to $C_8$ aryl,
a 5 or 6 membered heteroaryl; or
alkylthio optionally substituted with the following:
a 5 or 6 membered heterocycle,
a $C_6$ to $C_8$ aryl,
a 5 or 6 membered heteroaryl;
$R_2$ is:
a $C_1$ to $C_6$ alkyl group, optionally substituted with one or more of the following:
5 or 6 membered heterocycle groups,
5 or 6 membered heteroaryl groups,
—$C_6$ to $C_8$ aryl groups,
an amide optionally substituted with a $C_1$ to $C_6$ alkyl, or
amino groups optionally substituted with one or more heterocycle, alkoxy groups or alkyl groups optionally substituted with one or more alkoxy groups;
an alkylthio group optionally substituted with a 5 or 6 membered heteroaryl group optionally substituted with an alkyl group;
an alkylthio group optionally substituted with a 5 or 6 membered heterocycle group;
an alkylthio group optionally substituted with a $C_6$ to $C_8$ aryl group;
an alkylthio group optionally substituted with a $C_1$ to $C_6$ alkyl group;
an $SO_2R_x$ group optionally substituted with a 5 or 6 membered heteroaryl optionally substituted with one or more $C_1$ to $C_6$ alkyl groups;
an $SO_2R_x$ group optionally substituted with a 5 or 6 membered heterocycle group;
an $SO_2R_x$ group optionally substituted with a $C_6$ to $C_8$ aryl group;

an SO$_2$R$_x$ group optionally substituted with a C$_1$ to C$_6$ alkyl group;
an S(O)R$_x$ group optionally substituted with a 5 or 6 membered heteroaryl group;
an S(O)R$_x$ group optionally substituted with a 5 or 6 membered heterocycle group;
an S(O)R$_x$ group optionally substituted with a C$_6$ to C$_8$ aryl group;
an S(O)R$_x$ group optionally substituted with a C$_1$ to C$_6$ alkyl group;
an alkoxy group optionally substituted with one or more groups independently selected from the following:
halo,
hydroxy group,
an alkoxy group optionally substituted with an alkoxy group,
an amino group optionally substituted with one or more 5 or 6 membered heteroaryl groups, 5 or 6 membered heterocycle groups or alkyl groups, the alkyl groups optionally and independently substituted with one or more of the following:
a 5 or 6 membered heterocycle, or
an amino optionally substituted with one or more alkyl groups,
an amide optionally substituted with a C$_1$ to C$_6$ alkyl,
—S-5 or 6 membered heterocycle,
—S-5 or 6 membered heteroaryl optionally substituted with a C$_1$ to C$_6$ alkyl,
—S—C$_1$ to C$_6$ alkyl,
—S—C$_6$ to C$_8$ aryl,
sulfinyl-5 or 6 membered heterocycle,
sulfinyl-5 or 6 membered heteroaryl,
sulfinyl-C$_1$ to C$_6$ alkyl,
sulfinyl-C$_6$ to C$_8$ aryl,
sulfonyl-5 or 6 membered heterocycle,
sulfonyl-5 or 6 membered heteroaryl optionally substituted with a C$_1$ to C$_6$ alkyl,
sulfonyl-C$_1$ to C$_6$ alkyl,
sulfonyl-C$_6$ to C$_8$ aryl,
a 5 to 7 membered heterocycle group optionally substituted with one or more independently selected hydroxy group or C$_1$ to C$_6$ alkyl group, the C$_1$ to C$_6$ alkyl group optionally substituted with one or more independently selected C$_1$ to C$_6$ alkoxy group,
a 5 or 6 membered heteroaryl group optionally substituted with one or more C$_1$ to C$_6$ alkyl groups,
a C$_6$ to C$_8$ aryl group;
a C$_6$ to C$_8$ aryl group;
an (O)-5 or 6 membered heterocycle;
an (O)-5 or 6 membered heteroaryl optionally substituted with one or more independently selected C$_1$ to C$_6$ alkyl groups;
a —C(O)-5 or 6 membered heterocycle optionally substituted with one or more C$_6$ to C$_8$ aryl groups;
a —C(O)-5 or 6 membered heteroaryl;
a —C(O)—C$_6$ to C$_8$ aryl;
a —COOH group;
an amide group optionally substituted with one or more of the following:
—C$_1$ to C$_6$ alkyl groups optionally substituted with one or more C$_1$ to C$_6$ alkoxy,
a 5 or 6 membered heterocycle, optionally substituted with one or more of the following:
hydroxy,
—C$_1$ to C$_6$ alkyl,
—SO$_2$R$_x$,
—C(O)—C$_6$ to C$_8$ aryl, or
—C(O)OR$_x$ groups;
an —OR$_{kk}$ group, where R$_{kk}$ is:
a C$_6$ to C$_8$ aryl,
a 5 to 6 membered heteroaryl,
a 5 to 6 membered heterocycle, optionally substituted with a C$_1$ to C$_6$ alkyl, optionally substituted with a C$_6$ to C$_8$ aryl group, or
an —Si(R$_x$)$_3$; and
R$_3$ is a hydrogen;
with the proviso that at least one of X, Y, Z, R$_1$, and R$_2$ is selected from the following:
X is:
a —COOH group;

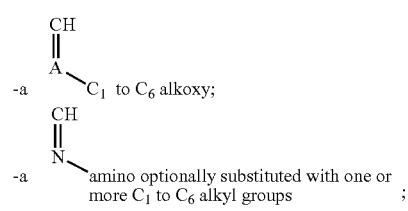

a halo;
an alkyl optionally substituted with one or more halo;
an alkyne optionally substituted with a C$_1$ to C$_6$ alkyl optionally substituted with one or more halo or cyano groups;
an oxime;
—SO$_2$R$_x$;
—SO$_2$NH$_2$;
—SO$_2$NH(R$_x$);
—SO$_2$N(R$_x$)$_2$;
an amino optionally substituted with one or more C$_1$ to C$_6$ alkyl groups or C(O)—C$_1$ to C$_6$ alkyl groups;
an amide group optionally substituted with one or more independently selected C$_1$ to C$_6$ alkyl group;
a 5 or 6 membered heterocycle;
a 5 or 6 membered heteroaryl substituted with one or more C$_1$ to C$_6$ alkyl groups substituted with one or more halos; or
a C$_6$ to C$_8$ aryl group substituted with one or more of the following:
—C$_1$ to C$_6$ alkyl optionally substituted with one or more halos,
halo, or
cyano;
Y is:
a benzothiazole substituted with an amino group optionally substituted with one or more C$_1$ to C$_6$ alkyls;
an indole substituted on the nitrogen with an SO$_2$R$_x$ group;
a C$_6$ to C$_8$ aryl substituted with one or more of the following:
an amino optionally substituted with one or more of the following:
—SO$_2$R$_x$, or
—C$_1$ to C$_6$ alkyl substituted with one or more 5 or 6 membered heteroaryl group,
—OC(O)NHR$_x$,
—OC(O)N(R$_x$)$_2$,
—OC(O)NH(OR$_x$),
—OC(O)NR$_x$(OR$_x$),
—OC(O)N(OR$_x$)$_2$,
—OC(O)R$_{ab}$, wherein R$_{ab}$ is a 5 or 6 membered heterocycle group,
a —NR$_o$COR$_p$ group, where R$_p$ is:
an amino group optionally substituted with one or more C$_1$ to C$_6$ alkyl groups where the C$_1$ to C$_6$ alkyl groups are optionally and independently substituted with one or more C$_6$ to C$_8$ aryl groups and/or alkoxy groups, or
a 5 or 6 membered heterocycle, substituted with one or more C$_1$ to C$_6$ alkyl or C$_6$ to C$_8$ aryl groups,
a —NR$_q$CONR$_q$R$_r$ group, where R$_r$ is:
  a C$_1$ to C$_6$ alkyl substituted with one or more of the following:
    a hydroxyl,
    an alkoxy,
    a 5 or 6 membered heterocycle,
    a 5 or 6 membered heteroaryl, or
    a C$_6$ to C$_8$ aryl substituted with a halo,
  a C$_2$ to C$_6$ alkylene group,
  a C$_1$ to C$_6$ alkoxy group,
  a 5 or 6 membered heterocycle group,
a —NR$_t$COOR$_u$ group, where R$_u$ is:
  a C$_1$ to C$_{12}$ alkyl, substituted with one or more groups independently selected from the following:
    an alkoxy group substituted with one or more alkoxy groups,
    an amino optionally substituted with one or more C$_1$ to C$_6$ alkyl, or
    a 5 or 6 membered heteroaryl,
  a C$_2$ to C$_6$ alkylene, or

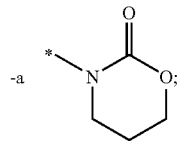

Z is:
a C$_1$ to C$_6$ alkyl substituted with a 5 or 6 membered heterocycle, or
a 5 or 6 membered heterocycle;
R$_1$ is:
a C$_1$ to C$_6$ alkyl substituted with:
  an amide optionally substituted with a C$_1$ to C$_6$ alkyl, or
  a 5 or 6 membered heteroaryl;
a C$_1$ to C$_6$ alkoxy substituted with:
  an amino optionally substituted with a heterocycle,
  an amide optionally substituted with a C$_1$ to C$_6$ alkyl,
  a 5 or 6 membered heterocycle substituted with a C$_1$ to C$_6$ alkyl, or
  a 5 or 6 membered heteroaryl;
an (O)-5 or 6 membered heterocycle;
an (O)-5 or 6 membered heteroaryl;
an —SO$_2$R$_x$ group optionally substituted with the following:
  a 5 or 6 membered heterocycle,
  a C$_6$ to C$_8$ aryl,
  a 5 or 6 membered heteroaryl; or
alkylthio optionally substituted with the following:
  a 5 or 6 membered heterocycle,
  a C$_6$ to C$_8$ aryl,
  a 5 or 6 membered heteroaryl; or
R$_2$ is:
a C$_1$ to C$_6$ alkyl group, substituted with one or more of the following:
  5 or 6 membered heterocycle groups,
  5 or 6 membered heteroaryl groups,
  —C$_6$ to C$_8$ aryl groups,
  an amide optionally substituted with a C$_1$ to C$_6$ alkyl, or
  amino groups optionally substituted with one or more heterocycle, alkoxy groups or alkyl groups optionally substituted with one or more alkoxy groups;
an alkylthio group optionally substituted with a 5 or 6 membered heteroaryl group optionally substituted with an alkyl group;
an alkylthio group optionally substituted with a 5 or 6 membered heterocycle group;
an alkylthio group optionally substituted with a C$_6$ to C$_8$ aryl group;
an alkylthio group optionally substituted with a C$_1$ to C$_6$ alkyl group;
an SO$_2$R$_x$ group optionally substituted with a 5 or 6 membered heteroaryl optionally substituted with one or more C$_1$ to C$_6$ alkyl groups;
an SO$_2$R$_x$ group optionally substituted with a 5 or 6 membered heterocycle group;
an SO$_2$R$_x$ group optionally substituted with a C$_6$ to C$_8$ aryl group;
an SO$_2$R$_x$ group optionally substituted with a C$_1$ to C$_6$ alkyl group;
an S(O)R$_x$ group optionally substituted with a 5 or 6 membered heteroaryl group;
an S(O)R$_x$ group optionally substituted with a 5 or 6 membered heterocycle group;
an S(O)R$_x$ group optionally substituted with a C$_6$ to C$_8$ aryl group;
an S(O)R$_x$ group optionally substituted with a C$_1$ to C$_6$ alkyl group;
an alkoxy group substituted with an alkoxy group,
  an amino group substituted with one or more 5 or 6 membered heteroaryl, 5 or 6 membered heterocycle groups or alkyl groups, the alkyl groups optionally and independently substituted with one or more of the following:
    a 5 or 6 membered heterocycle, or
    an amino optionally substituted with one or more alkyl groups;
an amide optionally substituted with a C$_1$ to C$_6$ alkyl,
—S-5 or 6 membered heterocycle,
—S-5 or 6 membered heteroaryl optionally substituted with a C$_1$ to C$_6$ alkyl,
—S—C$_1$ to C$_6$ alkyl,
—S—C$_6$ to C$_8$ aryl,
sulfinyl-5 or 6 membered heterocycle,
sulfinyl-5 or 6 membered heteroaryl,
sulfinyl-C$_1$ to C$_6$ alkyl,
sulfinyl-C$_6$ to C$_8$ aryl,
sulfonyl-5 or 6 membered heterocycle,
sulfonyl-5 or 6 membered heteroaryl optionally substituted with a C$_1$ to C$_6$ alkyl,
sulfonyl-C$_1$ to C$_6$ alkyl,
sulfonyl-C$_6$ to C$_8$ aryl,
a 5 to 7 membered heterocycle group substituted with one or more independently selected hydroxy groups or substituted with one or more independently selected C$_1$ to C$_6$ alkyl groups substituted with C$_1$ to C$_6$ alkoxy, or
a 5 or 6 membered heteroaryl group substituted with one or more C$_1$ to C$_6$ alkyl groups
a C$_6$ to C$_8$ aryl group;
a —C(O)-5 or 6 membered heterocycle optionally substituted with one or more C$_6$ to C$_8$ aryl groups;
a —C(O)—C$_6$ to C$_8$ aryl;
a —COOH group;
an amide group substituted with one or more C$_1$ to C$_6$ alkyl groups optionally substituted with one or more C$_1$ to C$_6$ alkoxy;
a 5 or 6 membered heterocycle, substituted with one or more of the following:

hydroxy,
—$C_1$ to $C_6$ alkyl,
—$SO_2R_x$ groups,
—C(O)—$C_6$ to $C_8$ aryl, or
—C(O)O$R_x$ groups;

an —O$R_{kk}$ group, where $R_{kk}$ is:
  a $C_6$ to $C_8$ aryl,
  a 5 to 6 membered heterocycle, optionally substituted with a $C_1$ to $C_6$ alkyl, optionally substituted with a $C_6$ to $C_8$ aryl group, or
  an —Si($R_x$)$_3$;

an (O)-5 or 6 membered heterocycle; or an (O)-5 or 6 membered heteroaryl optionally substituted with one or more independently selected $C_1$ to $C_6$ alkyl groups;

or a pharmaceutically acceptable salt thereof.

In another embodiment, Formula I-XIb, a compound is provided wherein all substituents except X are as stated for Formula I-XI, and X is an electron withdrawing group. In a further embodiment, Formula I-XIc, a compound is provided wherein all substituents except X are as stated for Formula I-XIa, and X is an electron withdrawing group. As an example, an electron withdrawing group includes any electronegative element, which may be attached to or adjacent to an aromatic ring. By way of non-limiting example, an electron withdrawing group can include a cyano group, an alkynyl group, a nitro group, an oxime, a halo, a halosubstituted alkyl, a carbonyl group, a sulfonyl group, and a heterocycle. In an embodiment of the present invention, X is a cyano group. In another embodiment of Formulas I, I-XI, I-XIa, I-XIb, I-XIc, IIa, IIb, IIc, IId, or IIe, X is a halo. In an embodiment of Formulas I, I-XI, I-XIa, I-XIb, I-XIc, IIa, IIb, IIc, IId, or IIe, X is a fluorine, chlorine, bromine or iodine. In an embodiment of I, I-XI, I-XIa, I-XIb, I-XIc, IIa, IIb, IIc, IId, or IIe, X is a fluorine, bromine or iodine. In an embodiment of Formulas I, I-XI, I-XIa, I-XIb, I-XIc, IIa, IIb, IIc, IId, or IIe, X is a fluorine or chlorine. In an embodiment of Formulas I, I-XI, I-XIa, I-XIb, I-XIc, IIa, IIb, IIc, IId, or IIe, X is a fluorine. In an embodiment of Formulas I, I-XI, I-XIa, I-XIb, I-XIc, IIa, IIb, IIc, IId, or IIe, X is a chlorine. In an embodiment of Formulas I, I-XI, I-XIa, I-XIb, I-XIc, IIa, IIb, IIc, IId, or IIe, X is bromine. In an embodiment of Formulas I, I-XI, I-XIa, I-XIb, I-XIc, IIa, IIb, IIc, IId, or IIe, X is iodine. In a further embodiment of Formulas I, I-XI, I-XIa, I-XIb, I-XIc, IIa, IIb, IIc, IId, or IIe, X is an alkyl substituted with one or more halos. In another embodiment, X is a trifluoromethyl group.

In some embodiments, X is selected from the X substituents of compounds 1330-2128, and 2600-3348.

In an embodiment of Formulas I, I-XI, I-XIa, I-XIb, I-XIc, IIa, IIb, IIc, IId, or IIe, X is selected from the group consisting of:

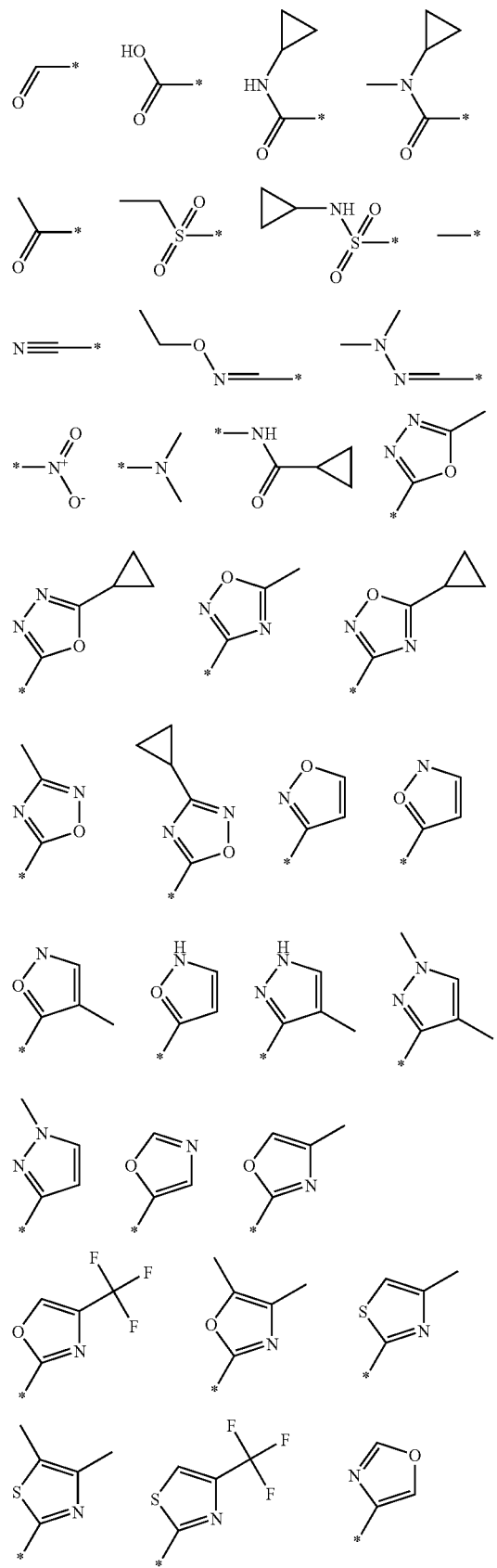

In other non-limiting examples of Formulas I, I-XI, I-XIa, I-XIb, I-XIc, IIa, IIb, IIc, or IIe, X is selected from the group consisting of In some embodiments, $R_1$ is selected from the $R_1$ substituents of compounds 1330-2128, and 2600-3348.

In an embodiment of Formulas I, I-XI, I-XIa, I-XIb, I-XIc, IIa, IIb, IIc, IId, or IIe, $R_1$ is selected from the group consisting of In another embodiment, the present invention includes compounds of Formula (I-XII)

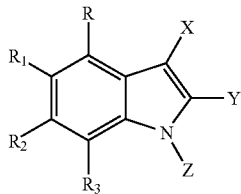

(I-XII)

wherein:
X is:
a cyano group;
Y is:
a benzothiazole optionally substituted with an amino group optionally substituted with one or more $C_1$ to $C_6$ alkyls;
an indole, optionally substituted on the nitrogen with an $SO_2R_x$ group;
a $C_6$ to $C_8$ aryl, optionally substituted with one or more of the following:
an alkoxy,
an amino optionally substituted with one or more of the following:
—$SO_2R_x$ group, or
—$C_1$ to $C_6$ alkyl, the $C_1$ to $C_6$ alkyl optionally and independently substituted with one or more 5 or 6 membered heteroaryl group,
—OC(O)NHR$_x$,
—OC(O)N(R$_x$)$_2$,
—OC(O)NH(OR$_x$),
—OC(O)NR$_x$(OR$_x$),
—OC(O)N(OR$_x$)$_2$,
—OC(O)R$_{ab}$, wherein R$_{ab}$ is a 5 or 6 membered heterocycle group,
a —NR$_o$COR$_p$ group, where R$_p$ is:
a $C_1$ to $C_6$ alkyl,
an amino group optionally substituted with one or more $C_1$ to $C_6$ alkyl groups where the $C_1$ to $C_6$ alkyl groups are optionally and independently substituted with one or more $C_6$ to $C_8$ aryl groups and/or alkoxy groups,
a 5 or 6 membered heterocycle, optionally substituted with one or more $C_1$ to $C_6$ alkyl or $C_6$ to $C_8$ aryl groups,
and where R$_o$ is:
a hydrogen,
a $C_1$ to $C_6$ alkyl,
a —NR$_q$CONR$_q$R$_r$ group, where R$_q$ is a hydrogen, and where R$_r$ is:
a $C_1$ to $C_6$ alkyl optionally substituted with one or more of the following:
a hydroxyl,
an alkoxy,
a 5 or 6 membered heterocycle,
a 5 or 6 membered heteroaryl, or
a $C_6$ to $C_8$ aryl optionally substituted with a halo,
a $C_2$ to $C_6$ alkylene group,
a $C_1$ to $C_6$ alkoxy group,
a 5 or 6 membered heterocycle group,
a —NR$_t$COOR$_u$ group, where R$_u$ is:
a $C_1$ to $C_{12}$ alkyl, optionally substituted with one or more groups independently selected from the following:
a $C_6$ to $C_8$ aryl optionally substituted with halo,
an alkoxy group optionally substituted with one or more alkoxy groups,
an amino optionally substituted with one or more $C_1$ to $C_6$ alkyl,
halo, or
a 5 or 6 membered heteroaryl,
a $C_2$ to $C_6$ alkylene,
a $C_6$ to $C_8$ aryl, optionally substituted with halo,
and R$_t$ is:
a hydrogen;
a —NHR$_{bb}$ group, where R$_{bb}$ is:
a —C(=S)NH$_2$ group, or
a —PO(OR$_x$)$_2$, where R$_x$ is as defined above;
a —NR$_v$SO$_2$R$_w$ group, where R$_v$ is a hydrogen, and where R$_w$ is a $C_1$ to $C_6$ alkyl,

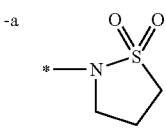 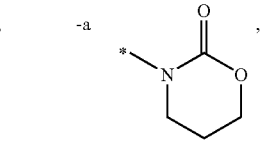

Z is:
a $C_1$ to $C_6$ alkyl optionally substituted with a 5 or 6 membered heterocycle, or
a 5 or 6 membered heterocycle;
R is a hydrogen;
$R_1$ is a hydrogen;
$R_2$ is:
a $C_1$ to $C_6$ alkyl group, optionally substituted with one or more of the following:
5 or 6 membered heterocycle groups,
amino groups optionally substituted with one or more alkoxy groups or alkyl groups optionally substituted with one or more alkoxy groups,
an alkoxy group optionally substituted with one or more groups independently selected from the following:
halo,
hydroxy group,
an alkoxy group optionally substituted with an alkoxy group,
an amino group optionally substituted with one or more 5 or 6 membered heterocycle groups or alkyl groups, the alkyl groups optionally and independently substituted with one or more of the following:
a 5 or 6 membered heterocycle, or
an amino optionally substituted with one or more alkyl groups;
a 5 to 7 membered heterocycle group optionally substituted with one or more independently selected hydroxy group or $C_1$ to $C_6$ alkyl group, the $C_1$ to $C_6$ alkyl group optionally substituted with one or more independently selected $C_1$ to $C_6$ alkoxy group,
a 5 or 6 membered heteroaryl group optionally substituted with one or more $C_1$ to $C_6$ alkyl groups,
a —C(O)-5 or 6 membered heterocycle optionally substituted with one or more $C_6$ to $C_8$ aryl groups;
a —COOH group;
an amide group optionally substituted with one or more —$C_1$ to $C_6$ alkyl groups;
a 5 or 6 membered heterocycle, optionally substituted with one or more of the following:
—$C_1$ to $C_6$ alkyl,
—$SO_2R_x$,
—C(O)—$C_6$ to $C_8$ aryl, or
—C(O)OR$_x$ groups;

an —OR$_{kk}$ group, where R$_{kk}$ is:
a 5 to 6 membered heterocycle, optionally substituted with a C$_1$ to C$_6$ alkyl, optionally substituted with a C$_6$ to C$_8$ aryl group, or
an —Si(Rx)$_3$;
R$_3$ is a hydrogen;
or a pharmaceutically acceptable salt thereof.

In another embodiment, the present invention includes compound of Formula (I-XIIa)

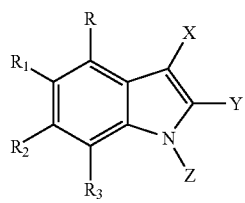

(I-XIIa)

wherein:
X is:
a cyano group;
Y is:
a benzothiazole optionally substituted with an amino group optionally substituted with one or more C$_1$ to C$_6$ alkyls;
an indole, optionally substituted on the nitrogen with an SO$_2$R$_x$ group;
a C$_6$ to C$_8$ aryl, optionally substituted with one or more of the following:
an alkoxy,
an amino optionally substituted with one or more of the following:
—SO$_2$R$_x$, or
—C$_1$ to C$_6$ alkyl, the C$_1$ to C$_6$ alkyl optionally and independently substituted with one or more 5 or 6 membered heteroaryl group,
—OC(O)NHR$_x$,
—OC(O)N(R$_x$)$_2$,
—OC(O)NH(OR$_x$),
—OC(O)NR$_x$(OR$_x$),
—OC(O)N(OR$_x$)$_2$,
—OC(O)R$_{ab}$, wherein R$_{ab}$ is a 5 or 6 membered heterocycle group,
a —NR$_o$COR$_p$ group, where R$_p$ is:
a C$_1$ to C$_6$ alkyl,
an amino group optionally substituted with one or more C$_1$ to C$_6$ alkyl groups where the C$_1$ to C$_6$ alkyl groups are optionally and independently substituted with one or more C$_6$ to C$_8$ aryl groups and/or alkoxy groups,
a 5 or 6 membered heterocycle, optionally substituted with one or more C$_1$ to C$_6$ alkyl or C$_6$ to C$_8$ aryl groups,
and where R$_o$ is:
a hydrogen,
a C$_1$ to C$_6$ alkyl,
a —NR$_q$CONR$_q$R$_r$ group, where R$_q$ is a hydrogen, and where R$_r$ is:
a C$_1$ to C$_6$ alkyl optionally substituted with one or more of the following:
a hydroxyl,
an alkoxy,
a 5 or 6 membered heterocycle,
a 5 or 6 membered heteroaryl, or
a C$_6$ to C$_8$ aryl optionally substituted with a halo, a C$_2$ to C$_6$ alkylene group,
a C$_1$ to C$_6$ alkoxy group,
a 5 or 6 membered heterocycle group,
a —NR$_t$COOR$_u$ group, where R$_u$ is:
a C$_1$ to C$_{12}$ alkyl, optionally substituted with one or more groups independently selected from the following:
a C$_6$ to C$_8$ aryl optionally substituted with halo,
an alkoxy group optionally substituted with one or more alkoxy groups,
an amino optionally substituted with one or more C$_1$ to C$_6$ alkyl,
halo, or
a 5 or 6 membered heteroaryl,
a C$_2$ to C$_6$ alkylene,
a C$_6$ to C$_8$ aryl, optionally substituted with halo,
and R$_t$ is:
a hydrogen;
a —NHR$_{bb}$ group, where R$_{bb}$ is:
a —C(=S)NH$_2$ group, or
a —PO(OR$_x$)$_2$, where R$_x$ is as defined above;
a —NR$_v$SO$_2$R$_w$ group, where R$_v$ is a hydrogen, and where R$_w$ is a C$_1$ to C$_6$ alkyl, -a 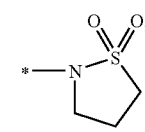 -a 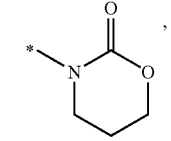

Z is:
a C$_1$ to C$_6$ alkyl optionally substituted with: a 5 or 6 membered heterocycle, or
a 5 or 6 membered heterocycle;
R is a hydrogen;
R$_1$ is a hydrogen;
R$_2$ is:
a C$_1$ to C$_6$ alkyl group, optionally substituted with one or more of the following:
5 or 6 membered heterocycle groups,
amino groups optionally substituted with one or more alkoxy groups or alkyl groups optionally substituted with one or more alkoxy groups,
an alkoxy group optionally substituted with one or more groups independently selected from the following:
halo,
hydroxy group,
an alkoxy group optionally substituted with an alkoxy group,
an amino group optionally substituted with one or more 5 or 6 membered heterocycle groups or alkyl groups, the alkyl groups optionally and independently substituted with one or more of the following:
a 5 or 6 membered heterocycle, or
an amino optionally substituted with one or more alkyl groups;
a 5 to 7 membered heterocycle group optionally substituted with one or more independently selected hydroxy group or C$_1$ to C$_6$ alkyl group, the C$_1$ to C$_6$ alkyl group optionally substituted with one or more independently selected C$_1$ to C$_6$ alkoxy group,
a 5 or 6 membered heteroaryl group optionally substituted with one or more C$_1$ to C$_6$ alkyl groups,
a —C(O)-5 or 6 membered heterocycle optionally substituted with one or more C$_6$ to C$_8$ aryl groups;
a —COOH group;

an amide group optionally substituted with one or more $C_1$ to $C_6$ alkyl groups;
a 5 or 6 membered heterocycle, optionally substituted with one or more of the following:
—$C_1$ to $C_6$ alkyl,
—$SO_2R_x$,
—C(O)—$C_6$ to $C_8$ aryl, or
—$C(O)OR_x$ groups;
an —$OR_{kk}$ group, where $R_{kk}$ is:
a 5 to 6 membered heterocycle, optionally substituted with a $C_1$ to $C_6$ alkyl, optionally substituted with a $C_6$ to $C_8$ aryl group, or
an —$Si(Rx)_3$;
$R_3$ is a hydrogen;
with the proviso that at least one of Y, Z, and $R_2$ is selected from the following:
Y is:
a benzothiazole substituted with an amino group optionally substituted with one or more $C_1$ to $C_6$ alkyls;
an indole substituted on the nitrogen with an —$SO_2R_x$ group;
a $C_6$ to $C_8$ aryl substituted with one or more of the following:
an amino optionally substituted with one or more of the following:
—$SO_2R_x$, or
—$C_1$ to $C_6$ alkyl substituted with one or more 5 or 6 membered heteroaryl group,
—$OC(O)NHR_x$,
—$OC(O)N(R_x)_2$,
—$OC(O)NH(OR_x)$,
—$OC(O)NR_x(OR_x)$,
—$OC(O)N(OR_x)_2$,
—$OC(O)R_{ab}$, wherein $R_{ab}$ is a 5 or 6 membered heterocycle group,
a —$NR_oCOR_p$ group, where $R_p$ is:
an amino group optionally substituted with one or more $C_1$ to $C_6$ alkyl groups where the $C_1$ to $C_6$ alkyl groups are optionally and independently substituted with one or more $C_6$ to $C_8$ aryl groups and/or alkoxy groups,
a 5 or 6 membered heterocycle, substituted with one or more $C_1$ to $C_6$ alkyl or $C_6$ to $C_8$ aryl groups,
a —$NR_qCONR_qR_r$ group, where $R_r$ is:
a $C_1$ to $C_6$ alkyl substituted with one or more of the following:
a hydroxyl,
an alkoxy,
a 5 or 6 membered heterocycle,
a 5 or 6 membered heteroaryl, or
a $C_6$ to $C_8$ aryl substituted with a halo,
a $C_2$ to $C_6$ alkylene group,
a $C_1$ to $C_6$ alkoxy group,
a 5 or 6 membered heterocycle group,
a —$NR_tCOOR_u$ group, where $R_u$ is:
a $C_1$ to $C_{12}$ alkyl, substituted with one or more groups independently selected from the following:
an alkoxy group substituted with one or more alkoxy groups,
an amino optionally substituted with one or more $C_1$ to $C_6$ alkyl, or
a 5 or 6 membered heteroaryl,
a $C_2$ to $C_6$ alkylene,

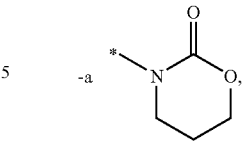

Z is:
a $C_1$ to $C_6$ alkyl substituted with a 5 or 6 membered heterocycle, or
a 5 or 6 membered heterocycle;
$R_2$ is:
a $C_1$ to $C_6$ alkyl group, substituted with one or more of the following:
5 or 6 membered heterocycle groups,
amino groups optionally substituted with one or more alkoxy groups or alkyl groups optionally substituted with one or more alkoxy groups,
an alkoxy group substituted with one or more groups independently selected from the following:
hydroxy group,
an alkoxy group optionally substituted with an alkoxy group,
an amino group substituted with one or more 5 or 6 membered heterocycle groups or alkyl groups, the alkyl groups optionally and independently substituted with one or more of the following:
a 5 or 6 membered heterocycle, or
an amino optionally substituted with one or more alkyl groups;
a 7 membered heterocycle group;
a 5 to 7 membered heterocycle group substituted with one or more independently selected hydroxy groups or substituted with one or more independently selected $C_1$ to $C_6$ alkyl groups substituted with $C_1$ to $C_6$ alkoxy, or
a 5 or 6 membered heteroaryl group substituted with one or more $C_1$ to $C_6$ alkyl groups;
a —C(O)-5 or 6 membered heterocycle optionally substituted with one or more $C_6$ to $C_8$ aryl groups;
a —COOH group;
an amide group substituted with one or more $C_1$ to $C_6$ alkyl groups;
a 5 or 6 membered heterocycle, optionally substituted with one or more of the following:
—$C_1$ to $C_6$ alkyl,
—$SO_2R_x$ group,
—C(O)—$C_6$ to $C_8$ aryl, or
—$C(O)OR_x$ groups;
an —$OR_{kk}$ group, where $R_{kk}$ is:
a 5 to 6 membered heterocycle, optionally substituted with a $C_1$ to $C_6$ alkyl, optionally substituted with a $C_6$ to $C_8$ aryl group, or
an —$Si(R_x)_3$;
or a pharmaceutically acceptable salt thereof.

In another embodiment, the present invention includes compounds of Formulas I, I-X, I-XI, I-XII, I-Xa, I-XIa, I-XIIa, I-XIb, I-XIc, IIa, IIb, IIc, IId, or IIe, wherein Y is a $C_6$ to $C_8$ aryl, optionally substituted with one or more of the following:
a —$NR_qCONR_qR_r$ group, where $R_q$ is a hydrogen, and where $R_r$ is:
a $C_1$ to $C_6$ alkyl optionally substituted with one or more of the following:

a hydroxyl,
an alkoxy,
a 5 or 6 membered heterocycle,
a 5 or 6 membered heteroaryl, or
a $C_6$ to $C_8$ aryl optionally substituted with a halo,
a $C_2$ to $C_6$ alkylene group,
a $C_1$ to $C_6$ alkoxy group,
a 5 or 6 membered heterocycle group,
a —$NR_tCOOR_u$ group, where $R_u$ is:
 a $C_1$ to $C_{12}$ alkyl, optionally substituted with one or more groups independently selected from the following:
  a $C_6$ to $C_8$ aryl optionally substituted with halo,
  an alkoxy group optionally substituted with one or more alkoxy groups,
  an amino optionally substituted with one or more $C_1$ to $C_6$ alkyl,
  halo, or
  a 5 or 6 membered heteroaryl,
 a $C_2$ to $C_6$ alkylene,
 a $C_6$ to $C_8$ aryl, optionally substituted with halo,
 and $R_t$ is:
  a hydrogen;
a —$NHR_{bb}$ group, where $R_{bb}$ is:
 a —C(=S)NH$_2$ group, or
 a —PO(OR$_x$)$_2$, where $R_x$ is as defined above;
or
a —$NR_vSO_2R_w$ group, where $R_v$ is a hydrogen, and where $R_w$ is a $C_1$ to $C_6$ alkyl.

In another embodiment, the present invention includes compounds wherein Y is a $C_6$ to $C_8$ aryl, optionally substituted with:
 a —$NR_qCONR_qR_r$ group, where $R_q$ is a hydrogen,
 and where $R_r$ is:
  a $C_1$ to $C_6$ alkyl optionally substituted with one or more of the following:
   a hydroxyl,
   an alkoxy,
   a 5 or 6 membered heterocycle,
   a 5 or 6 membered heteroaryl, or
   a $C_6$ to $C_8$ aryl optionally substituted with a halo,
  a $C_2$ to $C_6$ alkylene group,
  a $C_1$ to $C_6$ alkoxy group, or
  a 5 or 6 membered heterocycle group.

In a further embodiment, the present invention includes compounds wherein Y is a —$NR_tCOOR_u$ group, where $R_u$ is:
 a $C_1$ to $C_{12}$ alkyl, optionally substituted with one or more groups independently selected from the following:
  a $C_6$ to $C_8$ aryl optionally substituted with halo,
  an alkoxy group optionally substituted with one or more alkoxy groups,
  an amino optionally substituted with one or more $C_1$ to $C_6$ alkyl,
  halo, or
  a 5 or 6 membered heteroaryl,
 a $C_2$ to $C_6$ alkylene,
 a $C_6$ to $C_8$ aryl, optionally substituted with halo,
 and $R_t$ is:
  a hydrogen.

In yet another embodiment, the present invention includes compounds of the following:

1. A compound of formula IIa

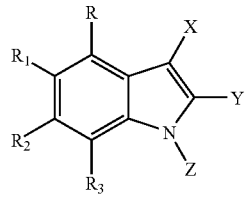

(IIa)

or a pharmaceutically acceptable salt thereof, wherein:
X is:
 cyano;
 nitro;
 formyl;
 —COOH;
 —COR$_x$, wherein $R_x$ is $C_1$ to $C_6$ alkyl;
 —CH=N—($C_1$ to $C_6$ alkoxy);
 —CH=N-(amino optionally substituted with one or more $C_1$ to $C_6$ alkyls);
 halo;
 alkyl optionally substituted with one or more halos;
 alkynyl optionally substituted with $C_1$ to $C_6$ alkyl, which alkyl is optionally substituted with one or more halos and/or cyanos;
 oximyl;
 —SO$_2$R$_x$;
 —SO$_2$NH$_2$;
 —SO$_2$NH(R$_x$);
 —SO$_2$N(R$_x$)$_2$;
 amino optionally substituted with one or more $C_1$ to $C_6$ alkyls and/or —C(O)—$C_1$ to $C_6$ alkyls;
 amido optionally substituted with one or more independently selected $C_1$ to $C_6$ alkyls;
 5 or 6 membered heterocyclo;
 5 or 6 membered heteroaryl optionally substituted with one or more $C_1$ to $C_6$ alkyls, which alkyls are optionally substituted with one or more halos; or
 —$C_6$ to $C_8$ aryl optionally substituted with one or more substituents independently selected from:
  —$C_1$ to $C_6$ alkyl optionally substituted with one or more halos;
  halo; and
  cyano;
Y is:
 benzothiazolyl optionally substituted with amino, which amino is optionally substituted with one or more $C_1$ to $C_6$ alkyls;
 indolyl optionally substituted on the nitrogen with —SO$_2$R$_x$;
 —$C_6$ to $C_8$ aryl optionally substituted with one or more substituents independently selected from:
  halos;
  —$C_1$ to $C_6$ alkyl;
  alkoxy optionally substituted with one or more substituents independently selected from:
   one or more halos; and
   5 or 6 membered heterocyclo;
  hydroxy;
  amino optionally substituted with one or more substituents independently selected from:

—SO$_2$R$_x$;
—C$_1$ to C$_6$ alkyl optionally and independently substituted with one or more 5 or 6 membered heteroaryls; and
—PO$_2$R$_x$;
—OC(O)NHR$_x$;
—OC(O)N(R$_x$)$_2$;
—OC(O)NH(OR$_x$);
—OC(O)NR$_x$(OR$_x$);
—OC(O)N(OR$_x$)$_2$;
—OC(O)R$_{ab}$, wherein R$_{ab}$ is 5 or 6 membered heterocyclo;
—NR$_o$COR$_p$, wherein R$_p$ is:
—C$_1$ to C$_6$ alkyl;
amino optionally substituted with one or more C$_1$ to C$_6$ alkyls, which alkyls are optionally and independently substituted with one or more C$_6$ to C$_8$ aryls and/or alkoxys; or
5 or 6 membered heterocyclo optionally substituted with one or more C$_1$ to C$_6$ alkyls and/or C$_6$ to C$_8$ aryls;
and wherein R$_o$ is:
hydrogen; or
—C$_1$ to C$_6$ alkyl;
—NR$_q$CONR$_q$R$_r$, wherein R$_q$ is hydrogen;
and wherein R$_r$ is:
—C$_1$ to C$_6$ alkyl optionally substituted with one or more substituents independently selected from:
halo;
hydroxy;
alkoxy;
5 or 6 membered heterocyclo;
5 or 6 membered heteroaryl; and
—C$_6$ to C$_8$ aryl optionally substituted with one or more halos;
—C$_2$ to C$_6$ alkenyl optionally substituted with one or more halos;
—C$_1$ to C$_6$ alkoxy; or
5 or 6 membered heterocyclo;
—SO$_2$R$_{aa}$, wherein R$_{aa}$ is:
5 or 6 heterocyclo optionally substituted with hydroxy;
—C$_1$ to C$_6$ alkoxy; or
—C$_1$ to C$_6$ alkyl;
—COR$_m$, wherein R$_m$ is:
amino optionally substituted with one or more C$_1$ to C$_6$ alkyls, wherein the C$_1$ to C$_6$ alkyls are optionally substituted with a 5 or 6 membered heterocyclo; or
3 to 7 membered heterocyclo optionally substituted with C$_1$ to C$_6$ alkyl, which alkyl is optionally substituted with dialkyl-amino;
—NR$_t$COOR$_u$, wherein R$_t$ is hydrogen, and wherein R$_u$ is:
—C$_1$ to C$_{12}$ alkyl optionally substituted with one or more substituents independently selected from:
—C$_6$ to C$_8$ aryl optionally substituted with one or more halos and/or haloalkyls;
alkoxy optionally substituted with one or more alkoxys;
amino optionally substituted with one or more C$_1$ to C$_6$ alkyls;
halo;
5 or 6 membered heteroaryl; and
5 or 6 membered heterocyclo;
—C$_2$ to C$_6$ alkenyl; or
—C$_6$ to C$_8$ aryl optionally substituted with halo;
—NHR$_{bb}$, wherein R$_{bb}$ is:
—C(=S)N—H$_2$; or
—PO(OR$_x$)$_2$;
—NR$_v$SO$_2$R$_w$, wherein R$_v$ is hydrogen, and wherein R$_w$ is:
—C$_1$ to C$_6$ alkyl; or
alkyl- or dialkyl-amino optionally substituted with halo;

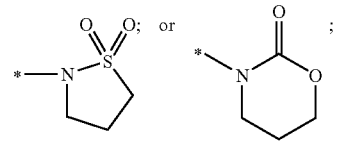

Z is:
—C$_1$ to C$_6$ alkyl optionally substituted with 5 or 6 membered heterocyclo; or
5 or 6 membered heterocyclo;
R is hydrogen;
R$_1$ is:
hydrogen;
5 or 6 membered heterocyclo;
—C$_1$ to C$_6$ alkyl optionally substituted with one or more substituents independently selected from:
amino optionally substituted with heterocyclo;
amido optionally substituted with C$_1$ to C$_6$ alkyl;
5 or 6 membered heterocyclo optionally substituted with C$_1$ to C$_6$ alkyl;
5 or 6 membered heteroaryl; and
—C$_6$ to C$_8$ aryl;
—C$_1$ to C$_6$ alkoxy optionally substituted with one or more substituents independently selected from:
amino optionally substituted with heterocyclo;
amido optionally substituted with C$_1$ to C$_6$ alkyl;
5 or 6 membered heterocyclo optionally substituted with C$_1$ to C$_6$ alkyl;
5 or 6 membered heteroaryl; and
—C$_6$ to C$_8$ aryl;
—(O)-5 or 6 membered heterocyclo;
—(O)-5 or 6 membered heteroaryl;
—SO$_2$R$_x$ optionally substituted with one or more substituents independently selected from:
5 or 6 membered heterocyclo;
—C$_6$ to C$_8$ aryl; and
5 or 6 membered heteroaryl; or
alkylthio optionally substituted with one or more substituents independently selected from:
5 or 6 membered heterocyclo;
—C$_6$ to C$_8$ aryl; and
5 or 6 membered heteroaryl;
R$_2$ is:
—C$_1$ to C$_6$ alkyl optionally substituted with one or more substituents independently selected from:
5 or 6 membered heterocyclo;
5 or 6 membered heteroaryl;
—C$_6$ to C$_8$ aryl;
amido optionally substituted with C$_1$ to C$_6$ alkyl; and
amino optionally substituted with one or more substituents independently selected from heterocyclo, alkoxy and alkyl, which alkyl is optionally substituted with one or more alkoxys;
alkylthio optionally substituted with 5 or 6 membered heteroaryl, which heteroaryl is optionally substituted with alkyl;

alkylthio optionally substituted with 5 or 6 membered heterocyclo;
alkylthio optionally substituted with $C_6$ to $C_8$ aryl;
alkylthio optionally substituted with $C_1$ to $C_6$ alkyl;
—$SO_2R_x$ optionally substituted with 5 or 6 membered heteroaryl, which heteroaryl is optionally substituted with one or more $C_1$ to $C_6$ alkyls;
—$SO_2R_x$ optionally substituted with 5 or 6 membered heterocyclo;
—$SO_2R_x$ optionally substituted with $C_6$ to $C_8$ aryl;
—$SO_2R_x$ optionally substituted with $C_1$ to $C_6$ alkyl;
—$S(O)R_x$ optionally substituted with 5 or 6 membered heteroaryl;
—$S(O)R_x$ optionally substituted with 5 or 6 membered heterocyclo;
—$S(O)R_x$ optionally substituted with $C_6$ to $C_8$ aryl;
—$S(O)R_x$ optionally substituted with $C_1$ to $C_6$ alkyl;
alkoxy optionally substituted with one or more substituents independently selected from:
halo;
hydroxy;
alkoxy optionally substituted with alkoxy;
amino optionally substituted with one or more substituents independently selected from 5 or 6 membered heteroaryl, 5 or 6 membered heterocyclo and alkyl, which alkyl is optionally substituted with one or more substituents independently selected from:
5 or 6 membered heterocyclo; and
amino optionally substituted with one or more alkyls;
amido optionally substituted with $C_1$ to $C_6$ alkyl;
—S-5 or 6 membered heterocyclo;
—S-5 or 6 membered heteroaryl optionally substituted with $C_1$ to $C_6$ alkyl;
—S—$C_1$ to $C_6$ alkyl;
—S—$C_6$ to $C_8$ aryl;
sulfinyl-5 or 6 membered heterocyclo;
sulfinyl-5 or 6 membered heteroaryl;
sulfinyl-$C_1$ to $C_6$ alkyl;
sulfinyl-$C_6$ to $C_8$ aryl;
sulfonyl-5 or 6 membered heterocyclo;
sulfonyl-5 or 6 membered heteroaryl optionally substituted with $C_1$ to $C_6$ alkyl;
sulfonyl-$C_1$ to $C_6$ alkyl;
sulfonyl-$C_6$ to $C_8$ aryl;
5 to 7 membered heterocyclo optionally substituted with one or more substituents independently selected from hydroxy and $C_1$ to $C_6$ alkyl, which alkyl is optionally substituted with one or more $C_1$ to $C_6$ alkoxys;
5 or 6 membered heteroaryl optionally substituted with one or more $C_1$ to $C_6$ alkyls; and
—$C_6$ to $C_8$ aryl;
—$C_6$ to $C_8$ aryl;
—(O)-5 or 6 membered heteroaryl optionally substituted with one or more independently selected $C_1$ to $C_6$ alkyls;
—C(O)-5 or 6 membered heterocyclo optionally substituted with one or more $C_6$ to $C_8$ aryls;
—C(O)—$C_6$ to $C_8$ aryl;
—COOH;
—C(O)$NH_2$ optionally substituted with one or more substituents independently selected from:
—$C_1$ to $C_6$ alkyl optionally substituted with one or more substituents independently selected from halo, $C_1$ to $C_6$ alkoxy, hydroxy, 5 or 6 membered heterocyclo and 5 or 6 membered heteroaryl;
amido optionally substituted with one or more $C_1$ to $C_6$ alkyls, which alkyls are optionally substituted with one or more $C_1$ to $C_6$ alkoxys;
5 or 6 membered heteroaryl optionally substituted with one or more substituents independently selected from:
—$C_1$ to $C_6$ alkyl; and
5 or 6 membered heterocyclo optionally substituted with one or more substituents independently selected from:
hydroxy;
—$C_1$ to $C_6$ alkyl;
—$SO_2R_x$;
—C(O)—$C_6$ to $C_8$ aryl; and
—C(O)$OR_x$; or
—$OR_{kk}$, wherein $R_{kk}$ is:
—$C_6$ to $C_8$ aryl;
5 or 6 membered heterocyclo optionally substituted with $C_1$ to $C_6$ alkyl, which alkyl is optionally substituted with $C_6$ to $C_8$ aryl;
5 or 6 membered heteroaryl optionally substituted with one or more substituents independently selected from halo, $C_1$ to $C_6$ alkyl, $C_1$ to $C_6$ alkoxy, and $C_1$ to $C_6$ haloalkyl;
—$SO_2R_x$; or
—$Si(R_x)_3$; and
$R_3$ is hydrogen;
with the proviso that at least one of X, Y, Z, $R_1$, and $R_2$ is selected from the following:
X is:
—COOH;
—CH=N—($C_1$ to $C_6$ alkoxy);
—CH=N-(amino optionally substituted with one or more $C_1$ to $C_6$ alkyls);
halo;
alkyl optionally substituted with one or more halos;
alkynyl optionally substituted with $C_1$ to $C_6$ alkyl, which alkyl is optionally substituted with one or more halos and/or cyanos;
oximyl;
—$SO_2R_x$;
—$SO_2NH_2$;
—$SO_2NH(R_x)$;
—$SO_2N(R_x)_2$;
amino optionally substituted with one or more $C_1$ to $C_6$ alkyls and/or —C(O)—$C_1$ to $C_6$ alkyls;
amido optionally substituted with one or more independently selected $C_1$ to $C_6$ alkyls;
5 or 6 membered heterocyclo;
5 or 6 membered heteroaryl substituted with one or more $C_1$ to $C_6$ alkyls, which alkyls are substituted with one or more halos; or
—$C_6$ to $C_8$ aryl substituted with one or more substituents independently selected from:
—$C_1$ to $C_6$ alkyl optionally substituted with one or more halos;
halo; and
cyano;
Y is:
benzothiazolyl substituted with amino, which amino is optionally substituted with one or more $C_1$ to $C_6$ alkyls;
indolyl substituted on the nitrogen with $SO_2R_x$; or
—$C_6$ to $C_8$ aryl substituted with one or more substituents independently selected from:
amino optionally substituted with one or more substituents independently selected from:
—$SO_2R_x$, and
—$C_1$ to $C_6$ alkyl substituted with one or more 5 or 6 membered heteroaryls;
—OC(O)$NHR_x$;
—OC(O)$N(R_x)_2$;
—OC(O)NH($OR_x$);

—OC(O)NR$_x$(OR$_x$);
—OC(O)N(OR$_x$)$_2$;
—OC(O)R$_{ab}$, wherein R$_{ab}$ is 5 or 6 membered heterocyclo;
—NR$_o$COR$_p$, wherein R$_p$ is:
  amino optionally substituted with one or more C$_1$ to C$_6$ alkyls, which alkyls are optionally and independently substituted with one or more C$_6$ to C$_8$ aryls and/or alkoxys, or
  5 or 6 membered heterocyclo substituted with one or more C$_1$ to C$_6$ alkyls and/or C$_6$ to C$_8$ aryls,
—NR$_q$CONR$_q$R$_r$, wherein R$_r$ is:
  —C$_1$ to C$_6$ alkyl substituted with one or more substituents independently selected from:
    hydroxy;
    alkoxy;
    5 or 6 membered heterocyclo;
    5 or 6 membered heteroaryl; and
    —C$_6$ to C$_8$ aryl substituted with one or more halos;
  —C$_2$ to C$_6$ alkenyl;
  —C$_1$ to C$_6$ alkoxy; or
  5 or 6 membered heterocyclo;
—NR$_t$COOR$_u$, wherein R$_u$ is:
  —C$_1$ to C$_{12}$ alkyl substituted with one or more substituents independently selected from:
    alkoxy substituted with one or more alkoxys;
    amino optionally substituted with one or more C$_1$ to C$_6$ alkyls; and
    5 or 6 membered heteroaryl; or
  —C$_2$ to C$_6$ alkenyl; and

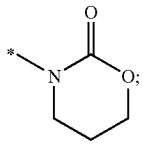

Z is:
  —C$_1$ to C$_6$ alkyl substituted with 5 or 6 membered heterocyclo; or
  5 or 6 membered heterocyclo;
R$_1$ is:
  —C$_1$ to C$_6$ alkyl substituted with:
    amido optionally substituted with C$_1$ to C$_6$ alkyl; and/or
    5 or 6 membered heteroaryl;
  —C$_1$ to C$_6$ alkoxy substituted with:
    amino optionally substituted with heterocyclo;
    amido optionally substituted with C$_1$ to C$_6$ alkyl;
    5 or 6 membered heterocyclo substituted with C$_1$ to C$_6$ alkyl; and/or
    5 or 6 membered heteroaryl;
  —(O)-5 or 6 membered heterocyclo;
  —(O)-5 or 6 membered heteroaryl;
  —SO$_2$R$_x$ optionally substituted with:
    5 or 6 membered heterocyclo;
    —C$_6$ to C$_8$ aryl; and/or
    5 or 6 membered heteroaryl; or
  alkylthio optionally substituted with:
    5 or 6 membered heterocyclo;
    —C$_6$ to C$_8$ aryl; and/or
    5 or 6 membered heteroaryl;
R$_2$ is:
  —C$_1$ to C$_6$ alkyl substituted with one or more substituents independently selected from:
    5 or 6 membered heterocyclo;
    5 or 6 membered heteroaryl;
    —C$_6$ to C$_8$ aryl;
    amido optionally substituted with C$_1$ to C$_6$ alkyl; and
    amino optionally substituted with one or more substituents independently selected from heterocyclo, alkoxy and alkyl, which alkyl is optionally substituted with one or more alkoxys;
  alkylthio optionally substituted with 5 or 6 membered heteroaryl, which heteroaryl is optionally substituted with alkyl;
  alkylthio optionally substituted with 5 or 6 membered heterocyclo;
  alkylthio optionally substituted with C$_6$ to C$_8$ aryl;
  alkylthio optionally substituted with C$_1$ to C$_6$ alkyl;
  —SO$_2$R$_x$ optionally substituted with 5 or 6 membered heteroaryl, which heteroaryl is optionally substituted with one or more C$_1$ to C$_6$ alkyls;
  —SO$_2$R$_x$ optionally substituted with 5 or 6 membered heterocyclo;
  —SO$_2$R$_x$ optionally substituted with C$_6$ to C$_8$ aryl;
  —SO$_2$R$_x$ optionally substituted with C$_1$ to C$_6$ alkyl;
  —S(O)R$_x$ optionally substituted with 5 or 6 membered heteroaryl;
  —S(O)R$_x$ optionally substituted with 5 or 6 membered heterocyclo;
  —S(O)R$_x$ optionally substituted with C$_6$ to C$_8$ aryl;
  —S(O)R$_x$ optionally substituted with C$_1$ to C$_6$ alkyl;
  alkoxy substituted with:
    alkoxy;
    amino substituted with one or more substituents independently selected from 5 or 6 membered heteroaryl, 5 or 6 membered heterocyclo and alkyl, which alkyl is optionally substituted with one or more substituents independently selected from:
      5 or 6 membered heterocyclos; and
      amino optionally substituted with one or more alkyls;
    amido optionally substituted with C$_1$ to C$_6$ alkyl;
  —S-5 or 6 membered heterocyclo;
  —S-5 or 6 membered heteroaryl optionally substituted with C$_1$ to C$_6$ alkyl;
  —S—C$_1$ to C$_6$ alkyl;
  —S—C$_6$ to C$_8$ aryl;
  sulfinyl-5 or 6 membered heterocyclo;
  sulfinyl-5 or 6 membered heteroaryl;
  sulfinyl-C$_1$ to C$_6$ alkyl;
  sulfinyl-C$_6$ to C$_8$ aryl;
  sulfonyl-5 or 6 membered heterocyclo;
  sulfonyl-5 or 6 membered heteroaryl optionally substituted with C$_1$ to C$_6$ alkyl;
  sulfonyl-C$_1$ to C$_6$ alkyl;
  sulfonyl-C$_6$ to C$_8$ aryl;
  5 to 7 membered heterocyclo substituted with one or more substituents independently selected from hydroxy and C$_1$ to C$_6$ alkyl, which alkyl is substituted with one or more C$_1$ to C$_6$ alkoxys;
  5 or 6 membered heteroaryl substituted with one or more C$_1$ to C$_6$ alkyls; or
  —C$_6$ to C$_8$ aryl;
  —C(O)-5 or 6 membered heterocyclo optionally substituted with one or more C$_6$ to C$_8$ aryls;
  —C(O)—C$_6$ to C$_8$ aryl;
  —COOH;
  amido substituted with one or more C$_1$ to C$_6$ alkyls optionally substituted with one or more C$_1$ to C$_6$ alkoxys;
  5 or 6 membered heterocyclo substituted with one or more substituents independently selected from:

hydroxy;
—$C_1$ to $C_6$ alkyl;
—$SO_2R_x$;
—C(O)—$C_6$ to $C_8$ aryl; and
—C(O)$OR_x$;
—$OR_{kk}$, wherein $R_{kk}$ is:
 —$C_6$ to $C_8$ aryl;
 5 or 6 membered heterocyclo optionally substituted with $C_1$ to $C_6$ alkyl and/or $C_6$ to $C_8$ aryl; or
 —Si$(R_x)_3$;
—(O)-5 or 6 membered heterocyclo optionally substituted with one or more independently selected $C_1$ to $C_6$ alkyls; or
—(O)-5 or 6 membered heteroaryl optionally substituted with one or more independently selected $C_1$ to $C_6$ alkyls.

2. The compound of embodiment 1, wherein:
X is:
—COOH;
—CH=N—($C_1$ to $C_6$ alkoxy);
—CH=N-(amino optionally substituted with one or more $C_1$ to $C_6$ alkyls);
halo;
alkyl optionally substituted with one or more halos;
alkynyl optionally substituted with $C_1$ to $C_6$ alkyl, which alkyl is optionally substituted with one or more halos and/or cyanos;
oximyl;
—$SO_2R_x$;
—$SO_2NH_2$;
—$SO_2NH(R_x)$;
—$SO_2N(R_x)_2$;
amino optionally substituted with one or more $C_1$ to $C_6$ alkyls and/or —C(O)—$C_1$ to $C_6$ alkyls;
amido optionally substituted with one or more independently selected $C_1$ to $C_6$ alkyls;
5 or 6 membered heterocyclo;
5 or 6 membered heteroaryl substituted with one or more $C_1$ to $C_6$ alkyls, which alkyls are substituted with one or more halos; or
—$C_6$ to $C_8$ aryl substituted with one or more substituents independently selected from:
 —$C_1$ to $C_6$ alkyl optionally substituted with one or more halos;
 halo; and
 cyano.

3. The compound of embodiment 2, wherein X is cyano, halo, or alkyl substituted with one or more halos.

4. The compound of embodiment 3, wherein X is cyano.

5. The compound of embodiment 3, wherein X is fluoro, bromo, chloro, or iodo.

6. The compound of embodiment 3, wherein X is trifluoromethyl.

7. The compound of embodiment 1, wherein:
Y is $C_6$ to $C_8$ aryl substituted with one or more of the following:
 amino optionally substituted with one or more substituents independently selected from:
  —$SO_2R_x$; and
  —$C_1$ to $C_6$ alkyl substituted with one or more 5 or 6 membered heteroaryls;
 —OC(O)$NHR_x$;
 —OC(O)$N(R_x)_2$;
 —OC(O)NH($OR_x$);
 —OC(O)$NR_x(OR_x)$;
 —OC(O)$N(OR_x)_2$;
 —OC(O)$R_{ab}$, wherein $R_{ab}$ is 5 or 6 membered heterocyclo;
 —$NR_oCOR_p$, wherein $R_p$ is:
  amino optionally substituted with one or more $C_1$ to $C_6$ alkyls, which alkyls are optionally and independently substituted with one or more $C_6$ to $C_8$ aryls and/or alkoxys; or
  5 or 6 membered heterocyclo substituted with one or more $C_1$ to $C_6$ alkyls and/or $C_6$ to $C_8$ aryls;
 —$NR_qCONR_qR_r$, wherein $R_r$ is:
  —$C_1$ to $C_6$ alkyl substituted with one or more substituents independently selected from:
   hydroxy;
   alkoxy;
   5 or 6 membered heterocyclo;
   5 or 6 membered heteroaryl; and
   —$C_6$ to $C_8$ aryl substituted with halo;
  —$C_2$ to $C_6$ alkenyl;
  —$C_1$ to $C_6$ alkoxy; or
  5 or 6 membered heterocyclo;
 —$NR_tCOOR_u$, wherein $R_u$ is:
  —$C_1$ to $C_{12}$ alkyl substituted with one or more substituents independently selected from the following:
   alkoxy substituted with one or more alkoxys;
   amino optionally substituted with one or more $C_1$ to $C_6$ alkyls; and
   5 or 6 membered heteroaryl;
  —$C_2$ to $C_6$ alkenyl, or 8. The compound of embodiment 7, wherein $C_6$ to $C_8$ aryl is phenyl.

9. The compound of embodiment 8, wherein phenyl has at least one substituent at the para position.

10. The compound of embodiment 1, wherein Z is:
—$C_1$ to $C_6$ alkyl substituted with 5 or 6 membered heterocyclo; or
5 or 6 membered heterocyclo.

11. The compound of embodiment 1, wherein Z is $C_1$ to $C_6$ alkyl.

12. The compound of embodiment 11, wherein Z is cyclobutyl, cyclopropyl, cyclopropylmethyl, ethyl or cyclopentyl.

13. The compound of embodiment 1, wherein:
$R_1$ is:
 —$C_1$ to $C_6$ alkyl substituted with:
  amido optionally substituted with $C_1$ to $C_6$ alkyl; and/or
  5 or 6 membered heteroaryl;
 —$C_1$ to $C_6$ alkoxy substituted with:
  amino optionally substituted with heterocyclo;
  amido optionally substituted with $C_1$ to $C_6$ alkyl;
  5 or 6 membered heterocyclo substituted with $C_1$ to $C_6$ alkyl; and/or
  5 or 6 membered heteroaryl;
 —(O)-5 or 6 membered heterocyclo;
 —(O)-5 or 6 membered heteroaryl;
 —$SO_2R_x$ optionally substituted with:
  5 or 6 membered heterocyclo;
  —$C_6$ to $C_8$ aryl; and/or
  5 or 6 membered heteroaryl; or
 alkylthio optionally substituted with:
  5 or 6 membered heterocyclo;
  —$C_6$ to $C_8$ aryl; and/or
  5 or 6 membered heteroaryl.

14. The compound of embodiment 1, wherein:
$R_2$ is:
—$C_1$ to $C_6$ alkyl substituted with one or more substituents independently selected from:
5 or 6 membered heterocyclo;
5 or 6 membered heteroaryl;
—$C_6$ to $C_8$ aryl;
amido optionally substituted with $C_1$ to $C_6$ alkyl; and
amino optionally substituted with one or more substituents independently selected from heterocyclo, alkoxy and alkyl, which alkyl is optionally substituted with one or more alkoxys;
alkylthio optionally substituted with 5 or 6 membered heteroaryl, which heteroaryl is optionally substituted with alkyl;
alkylthio optionally substituted with 5 or 6 membered heterocyclo;
alkylthio optionally substituted with $C_6$ to $C_8$ aryl;
alkylthio optionally substituted with $C_1$ to $C_6$ alkyl;
—$SO_2R_x$ optionally substituted with 5 or 6 membered heteroaryl, which heteroaryl is optionally substituted with one or more $C_1$ to $C_6$ alkyls;
—$SO_2R_x$ optionally substituted with 5 or 6 membered heterocyclo;
—$SO_2R_x$ optionally substituted with $C_6$ to $C_8$ aryl;
—$SO_2R_x$ optionally substituted with $C_1$ to $C_6$ alkyl;
—$S(O)R_x$ optionally substituted with 5 or 6 membered heteroaryl;
—$S(O)R_x$ optionally substituted with 5 or 6 membered heterocyclo;
—$S(O)R_x$ optionally substituted with $C_6$ to $C_8$ aryl;
—$S(O)R_x$ optionally substituted with $C_1$ to $C_6$ alkyl;
alkoxy substituted with:
alkoxy;
amino substituted with one or more substituents independently selected from 5 or 6 membered heteroaryl, 5 or 6 membered heterocyclo and alkyl, which alkyl is optionally substituted with one or more substituents independently selected from:
5 or 6 membered heterocyclos; and
amino optionally substituted with one or more alkyls;
amido optionally substituted with $C_1$ to $C_6$ alkyl;
—S-5 or 6 membered heterocyclo;
—S-5 or 6 membered heteroaryl optionally substituted with $C_1$ to $C_6$ alkyl;
—S—$C_1$ to $C_6$ alkyl;
—S—$C_6$ to $C_8$ aryl;
sulfinyl-5 or 6 membered heterocyclo;
sulfinyl-5 or 6 membered heteroaryl;
sulfinyl-$C_1$ to $C_6$ alkyl;
sulfinyl-$C_6$ to $C_8$ aryl;
sulfonyl-5 or 6 membered heterocyclo;
sulfonyl-5 or 6 membered heteroaryl optionally substituted with $C_1$ to $C_6$ alkyl;
sulfonyl-$C_1$ to $C_6$ alkyl;
sulfonyl-$C_6$ to $C_8$ aryl;
5 to 7 membered heterocyclo substituted with one or more substituents independently selected from hydroxy and $C_1$ to $C_6$ alkyl, which alkyl is substituted with $C_1$ to $C_6$ alkoxy;
5 or 6 membered heteroaryl substituted with one or more $C_1$ to $C_6$ alkyls; or
—$C_6$ to $C_8$ aryl;
—C(O)-5 or 6 membered heterocyclo optionally substituted with one or more $C_6$ to $C_8$ aryls;
—C(O)—$C_6$ to $C_8$ aryl;
—COOH;
amido substituted with one or more $C_1$ to $C_6$ alkyls optionally substituted with one or more $C_1$ to $C_6$ alkoxys;
5 or 6 membered heterocyclo substituted with one or more substituents independently selected from:
hydroxy;
—$C_1$ to $C_6$ alkyl;
—$SO_2R_x$;
—C(O)—$C_6$ to $C_8$ aryl; and
—C(O)$OR_x$;
—$OR_{kk}$, wherein $R_{kk}$ is:
—$C_6$ to $C_8$ aryl;
5 or 6 membered heterocyclo optionally substituted with $C_1$ to $C_6$ alkyl and/or $C_6$ to $C_8$ aryl; or
—$Si(R_x)_3$;
—(O)-5 or 6 membered heterocyclo; or
—(O)-5 or 6 membered heteroaryl optionally substituted with one or more independently selected $C_1$ to $C_6$ alkyls.

15. The compound of embodiment 1, wherein:
X is:
cyano;
halo; or
alkynyl optionally substituted with $C_1$ to $C_6$ alkyl;
Y is:
—$C_6$ to $C_8$ aryl substituted with one or more substituents independently selected from:
halo;
hydroxy;
alkoxy optionally substituted with:
one or more halos; or
5 or 6 membered heterocyclo;
—$C_1$ to $C_6$ alkyl;
amino optionally substituted with one or more substituents independently selected from:
—$SO_2R_x$; and
—$C_1$ to $C_6$ alkyl optionally and independently substituted with one or more 5 or 6 membered heteroaryls;
—OC(O)$NHR_x$;
—$NR_oCOR_p$, wherein $R_p$ is:
—$C_1$ to $C_6$ alkyl; or
amino optionally substituted with one or more $C_1$ to $C_6$ alkyls;
and wherein $R_o$ is hydrogen;
—$NR_qCONR_qR_r$, wherein $R_q$ is hydrogen, and wherein $R_r$ is:
—$C_1$ to $C_6$ alkyl optionally substituted with one or more halos; or
—$C_6$ to $C_8$ aryl optionally substituted with halo;
—$SO_2R_{aa}$, wherein $R_{aa}$ is:
5 or 6 heterocyclo optionally substituted with hydroxy;
—$C_1$ to $C_6$ alkoxy; or
—$C_1$ to $C_6$ alkyl;
—$COR_m$ wherein $R_m$ is:
amino optionally substituted with one or more $C_1$ to $C_6$ alkyls, wherein the $C_1$ to $C_6$ alkyls are optionally substituted with a 5 or 6 membered heterocyclo; or
3 to 7 membered heterocyclo optionally substituted with $C_1$ to $C_6$ alkyl, which alkyl is optionally substituted with dialkyl-amino;
—$NR_tCOOR_u$, wherein $R_t$ is hydrogen, and wherein $R_u$ is:
—$C_1$ to $C_{12}$ alkyl optionally substituted with one or more substituents independently selected from:

—$C_6$ to $C_8$ aryl optionally substituted with one or more halos and/or haloalkyls;
halo; and
5 or 6 membered heteroaryl;
—$C_6$ to $C_8$ aryl optionally substituted with halo; or
5 or 6 membered heterocyclo;
—$NHR_{bb}$, wherein $R_{bb}$ is:
—$C(=S)NH_2$; or
—$PO(OR_x)_2$;
—$NR_vSO_2R_w$, wherein $R_v$ is hydrogen, and wherein $R_w$ is:
—$C_1$ to $C_6$ alkyl; or
alkyl- or dialkyl-amino optionally substituted with halo; or

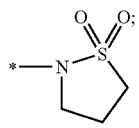

Z is:
—$C_1$ to $C_6$ alkyl; or
5 or 6 membered heterocyclo;
R is hydrogen;
$R_1$ is:
hydrogen;
—$C_1$ to $C_6$ alkoxy substituted with one or more substituents independently selected from:
5 or 6 membered heterocyclo; and
5 or 6 membered heteroaryl;
—(O)-5 or 6 membered heterocyclo;
—(O)-5 or 6 membered heteroaryl; or
5 or 6 membered heterocyclo;
$R_2$ is:
alkoxy substituted with one or more substituents independently selected from:
halo;
hydroxy;
alkoxy optionally substituted with alkoxy;
amino optionally substituted with one or more substituents independently selected from 5 or 6 membered heteroaryl, 5 or 6 membered heterocyclo and alkyl, which alkyl is optionally substituted with one or more substituents independently selected from:
5 or 6 membered heterocyclo; and
amino optionally substituted with one or more alkyl;
amido optionally substituted with $C_1$ to $C_6$ alkyl;
—S-5 or 6 membered heteroaryl optionally substituted with $C_1$ to $C_6$ alkyl;
—S—$C_1$ to $C_6$ alkyl;
sulfinyl-$C_1$ to $C_6$ alkyl;
sulfonyl-$C_1$ to $C_6$ alkyl;
5 to 7 membered heterocyclo optionally substituted with one or more substituents independently selected from hydroxy and $C_1$ to $C_6$ alkyl, which alkyl is optionally substituted with one or more independently selected $C_1$ to $C_6$ alkoxys; and
5 or 6 membered heteroaryl optionally substituted with one or more $C_1$ to $C_6$ alkyls;
—$SO_2R_x$ optionally substituted with $C_1$ to $C_6$ alkyl;
—$S(O)R_x$ optionally substituted with $C_1$ to $C_6$ alkyl;
—(O)-5 or 6 membered heteroaryl optionally substituted with one or more independently selected $C_1$ to $C_6$ alkyls;
—C(O)-5 or 6 membered heterocyclo optionally substituted with one or more $C_6$ to $C_8$ aryls;
—C(O)—$C_6$ to $C_8$ aryl;
—COOH;
—$C(O)NH_2$ optionally substituted with one or more substituents independently selected from:
—$C_1$ to $C_6$ alkyl optionally substituted with one or more substituents independently selected from halo, $C_1$ to $C_6$ alkoxy, hydroxy, 5 or 6 membered heterocyclo and 5 or 6 membered heteroaryl;
5 or 6 membered heteroaryl optionally substituted with one or more substituents independently selected from:
—$C_1$ to $C_6$ alkyl; and;
5 or 6 membered heterocyclo optionally substituted with one or more substituents independently selected from:
one or more halos;
—$C_1$ to $C_6$ alkyl; and
—$SO_2R_x$;
amido optionally substituted with one or more $C_1$ to $C_6$ alkyls, which alkyls are optionally substituted with one or more $C_1$ to $C_6$ alkoxys; or
—$OR_{kk}$, wherein $R_{kk}$ is:
5 or 6 membered heteroaryl optionally substituted with one or more substituents independently selected from halo, $C_1$ to $C_6$ alkyl, $C_1$ to $C_6$ alkoxy, and $C_1$ to $C_6$ haloalkyl; or
5 or 6 membered heterocyclo optionally substituted with $C_1$ to $C_6$ alkyl, which alkyl is optionally substituted with $C_6$ to $C_8$ aryl; and
$R_3$ is hydrogen.

16. The compound of embodiment 15, wherein:
X is:
cyano; or
halo;
Y is:
phenyl substituted with one or more substituents independently selected from:
halo; and
—$NR_tCOOR_u$, wherein $R_t$ is hydrogen, and wherein $R_u$ is:
—$C_1$ to $C_{12}$ alkyl optionally substituted with one or more substituents independently selected from:
—$C_6$ to $C_8$ aryl optionally substituted with one or more halos;
halo; and
5 or 6 membered heteroaryl;
—$C_6$ to $C_8$ aryl optionally substituted with halo; or
5 or 6 membered heterocyclo;
Z is $C_1$ to $C_6$ alkyl;
R is hydrogen;
$R_1$ is hydrogen;
$R_2$ is:
alkoxy substituted with one or more substituents independently selected from:
halo; and
alkoxy optionally substituted with alkoxy;
—(O)-5 or 6 membered heterocyclo;
amido optionally substituted with one or more $C_1$ to $C_6$ alkyls, which alkyls are optionally substituted with one or more $C_1$ to $C_6$ alkoxys;
5 or 6 membered heterocyclo optionally substituted with one or more substituents independently selected from:
one or more halos;
—$C_1$ to $C_6$ alkyl; and
—$SO_2R_x$; and
$R_3$ is hydrogen.

17. The compound of embodiment 15, wherein:
X is cyano;
Y is $C_6$ to $C_8$ aryl substituted with one or more substituents independently selected from $NR_tCOOR_u$, wherein is hydrogen, and wherein $R_u$ is $C_1$ to $C_{12}$ alkyl optionally substituted with one or more $C_6$ to $C_8$ aryls;
Z is 5 or 6 membered heterocyclo;
R is hydrogen;
$R_1$ is hydrogen;
$R_2$ is alkoxy; and
$R_3$ is hydrogen.
18. The compound of embodiment 15, wherein:
X is cyano;
Y is $C_6$ to $C_8$ aryl substituted with one or more substituents independently selected from:
amino optionally substituted with $C_1$ to $C_6$ alkyl;
—$NR_qCONR_qR_r$, wherein $R_q$ is hydrogen, and wherein $R_r$ is $C_1$ to $C_6$ alkyl;
—$COR_m$, wherein $R_m$ is:
amino optionally substituted with one or more $C_1$ to $C_6$ alkyls, wherein the $C_1$ to $C_6$ alkyls are optionally substituted with a 5 or 6 membered heterocyclo; or
3 to 7 membered heterocyclo; and
—$NR_tCOOR_u$, wherein $R_t$ is hydrogen, and wherein $R_u$ is:
—$C_1$ to $C_{12}$ alkyl optionally substituted with one or more substituents independently selected from:
—$C_6$ to $C_8$ aryl optionally substituted with one or more haloalkyls; and
halo; or
5 or 6 membered heterocyclo;
Z is $C_1$ to $C_6$ alkyl;
R is hydrogen;
$R_1$ is hydrogen;
$R_2$ is alkoxy substituted with alkoxy; and
$R_3$ is hydrogen.
19. The compound of embodiment 15, wherein:
X is cyano;
Y is $C_6$ to $C_8$ aryl substituted with one or more substituents independently selected from:
—$NR_tCOOR_u$, wherein $R_t$ is hydrogen, and wherein $R_u$ is $C_1$ to $C_{12}$ alkyl optionally substituted with one or more halos; and
—$NR_vSO_2R_w$, wherein $R_v$ is hydrogen, and wherein $R_w$ is $C_1$ to $C_6$ alkyl;
Z is $C_1$ to $C_6$ alkyl;
R is hydrogen;
$R_1$ is hydrogen;
$R_2$ is amido optionally substituted with one or more $C_1$ to $C_6$ alkyls, which alkyls are substituted with one or more $C_1$ to $C_6$ alkoxys; and
$R_3$ is hydrogen.
20. The compound of embodiment 15, wherein:
X is cyano;
Y is $C_6$ to $C_8$ aryl substituted with one or more substituents independently selected from:
amino optionally substituted with one or more $C_1$ to $C_6$ alkyls;
—$NR_tCOOR_u$, wherein $R_t$ is hydrogen, and wherein $R_u$ is $C_1$ to $C_{12}$ alkyl optionally substituted with one or more halos;
—$NR_vSO_2R_w$, wherein $R_v$ is hydrogen, and wherein $R_w$ is $C_1$ to $C_6$ alkyl; and

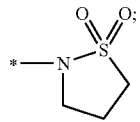

Z is $C_1$ to $C_6$ alkyl;
R is hydrogen;
$R_1$ is hydrogen;
$R_2$ is alkoxy substituted with sulfonyl-$C_1$ to $C_6$ alkyl; and
$R_3$ is hydrogen.
21. The compound of embodiment 15, wherein Y is $C_6$ to $C_8$ aryl substituted with one or more substituents independently selected from $NR_tCOOR_u$, wherein $R_t$ is hydrogen, and wherein $R_u$ is $C_1$ to $C_{12}$ alkyl optionally substituted with one or more halos.
22. The compound of embodiment 15, wherein:
X is cyano;
Y is $C_6$ to $C_8$ aryl substituted with one or more substituents independently selected from:
—$C_1$ to $C_6$ alkyl;
amino optionally substituted with one or more $C_1$ to $C_6$ alkyls;
—$NR_qCONR_qR_r$, wherein $R_q$ is hydrogen, and wherein $R_r$ is $C_1$ to $C_6$ alkyl;
—$NR_tCOOR_u$, wherein $R_t$ is hydrogen, and wherein $R_u$ is $C_1$ to $C_{12}$ alkyl;
—$NR_vSO_2R_w$, wherein $R_t$ is hydrogen and wherein $R_w$ is:
—$C_1$ to $C_6$ alkyl; or
alkyl- or dialkyl-amino;
Z is $C_1$ to $C_6$ alkyl;
R is hydrogen;
$R_1$ is hydrogen;
$R_2$ is $OR_{kk}$, wherein $R_{kk}$ is 5 or 6 membered heteroaryl substituted with one or more substituents independently selected from halo, $C_1$ to $C_6$ alkyl, $C_1$ to $C_6$ alkoxy, and $C_1$ to $C_6$ haloalkyl; and
$R_3$ is hydrogen.
23. The compound of embodiment 22, wherein:
X is cyano;
Y is $C_6$ to $C_8$ aryl substituted with one or more substituents independently selected from:
—$NR_tCOOR_u$, wherein $R_t$ is hydrogen, and wherein $R_u$ is $C_1$ to $C_{12}$ alkyl; and
—$NR_vSO_2R_w$, wherein $R_v$ is hydrogen, and wherein $R_w$ is:
—$C_1$ to $C_6$ alkyl; or
alkyl- or dialkyl-amino;
Z is $C_1$ to $C_6$ alkyl;
R is hydrogen;
$R_1$ is hydrogen;
$R_2$ is $OR_{kk}$, wherein $R_{kk}$ is 5 or 6 membered heteroaryl substituted with one or more substituents independently selected from halo, $C_1$ to $C_6$ alkyl, $C_1$ to $C_6$ alkoxy, and $C_1$ to $C_6$ haloalkyl; and
$R_3$ is hydrogen.
24. The compound of embodiment 22, wherein $R_2$ is $OR_{kk}$, wherein $R_{kk}$ is 5 or 6 membered heteroaryl substituted with one or more $C_1$ to $C_6$ haloalkyls.
25. The compound of embodiment 22, wherein $R_2$ is $OR_{kk}$, wherein $R_{kk}$ is 5 or 6 membered heteroaryl substituted with one or more $C_1$ to $C_6$ alkyls.
26. The compound of embodiment 1, wherein:
X is cyano;
Y is $C_6$ to $C_8$ aryl substituted with one or more substituents independently selected from:

—NR$_t$COOR$_u$, wherein R$_t$ is hydrogen, and wherein R$_u$ is C$_1$ to C$_{12}$ alkyl; and
—NR$_v$SO$_2$R$_w$, wherein R$_v$ is hydrogen, and wherein R$_w$ is C$_1$ to C$_6$ alkyl;
Z is C$_1$ to C$_6$ alkyl;
R is hydrogen;
R$_1$ is hydrogen;
R$_2$ is C(O)-5 or 6 membered heterocyclo; and
R$_3$ is hydrogen.
27. The compound of embodiment 1, wherein:
X is halo;
Y is C$_6$ to C$_8$ aryl substituted with one or more substituents independently selected from:
  amino;
  —NR$_q$CONR$_q$R$_r$, wherein R$_q$ is hydrogen, and wherein R$_r$ is C$_1$ to C$_6$ alkyl; and
  —NR$_t$COOR$_u$, wherein R$_t$ is hydrogen, and wherein R$_u$ is C$_1$ to C$_{12}$ alkyl;
Z is C$_1$ to C$_6$ alkyl;
R is hydrogen;
R$_1$ is hydrogen;
R$_2$ is alkoxy; and
R$_3$ is hydrogen.
28 The compound of embodiment 15 wherein:
X is cyano;
Y is C$_6$ to C$_8$ aryl substituted with one or more substituents independently selected from:
  halo;
  —NR$_q$CONR$_q$R$_r$, wherein R$_q$ is hydrogen, and wherein R$_r$ is C$_1$ to C$_6$ alkyl;
  —NR$_t$COOR$_u$, wherein R$_t$ is hydrogen, and wherein R$_u$ is C$_1$ to C$_{12}$ alkyl optionally substituted with one or more substituents independently selected from:
    —C$_6$ to C$_8$ aryl optionally substituted with one or more halos; and
    halo;
  —NR$_v$SO$_2$R$_w$, wherein R$_v$ is hydrogen, and wherein R$_w$ is:
    —C$_1$ to C$_6$ alkyl; or
    alkyl- or dialkyl-amino optionally substituted with halo; and

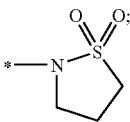

Z is C$_1$ to C$_6$ alkyl;
R is hydrogen;
R$_1$ is hydrogen;
R$_2$ is 5 or 6 membered heterocyclo; and
R$_3$ is hydrogen.
29. The compound of embodiment 28, wherein Y is C$_6$ to C$_8$ aryl substituted with NR$_v$SO$_2$R$_w$, wherein R$_v$ is hydrogen, and wherein R$_w$ is C$_1$ to C$_6$ alkyl.
30. The compound of embodiment 28 wherein Y is C$_6$ to C$_8$ aryl substituted with

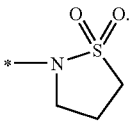

31. The compound of embodiment 15, wherein:
X is cyano;
Y is C$_6$ to C$_8$ aryl substituted with one or more substituents independently selected from:
  halo;
  amino optionally substituted with one or more C$_1$ to C$_6$ alkyls;
  —OC(O)NHR$_x$;
  —NR$_q$CONR$_q$R$_r$, wherein R$_q$ is hydrogen, and wherein R$_r$ is C$_1$ to C$_6$ alkyl;
  —NR$_t$COOR$_u$, wherein R$_t$ is hydrogen, and wherein R$_u$ is C$_1$ to C$_{12}$ alkyl optionally substituted with one or more substituents independently selected from:
    —C$_6$ to C$_8$ aryl optionally substituted with one or more halos and/or haloalkyls; and
    halo;
  —NHR$_{bb}$, wherein R$_{bb}$ is —C(=S)NH$_2$;
  —NR$_v$SO$_2$R$_w$, wherein R$_v$ is hydrogen, and wherein R$_w$ is:
    —C$_1$ to C$_6$ alkyl; or
    alkyl- or dialkyl-amino optionally substituted with halo; and

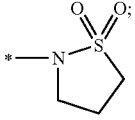

Z is C$_1$ to C$_6$ alkyl;
R is hydrogen;
R$_1$ is hydrogen;
R$_2$ is (O)-5 or 6 membered heterocyclo; and
R$_3$ is hydrogen.
32. The compound of embodiment 31, wherein Y is C$_6$ to C$_8$ aryl substituted with NR$_t$COOR$_u$, wherein R$_t$ is hydrogen, and wherein R$_u$ is C$_1$ to C$_{12}$ alkyl optionally substituted with one or more substituents independently selected from C$_6$ to C$_8$ aryl optionally substituted with one or more halos and/or haloalkyls.
33. The compound of embodiment 15, wherein:
X is cyano;
Y is C$_6$ to C$_8$ aryl substituted with one or more substituents independently selected from NR$_t$COOR$_u$, wherein R$_t$ is hydrogen, and wherein R$_u$ is C$_1$ to C$_{12}$ alkyl substituted with one or more halos;
Z is C$_1$ to C$_6$ alkyl;
R is hydrogen;
R$_1$ is
  hydrogen;
  —(O)-5 or 6 membered heterocyclo; or
  5 or 6 membered heterocyclo;
R$_2$ is:
  alkoxy substituted with one or more substituents independently selected from:
    halo;
    alkoxy;
    sulfonyl-C$_1$ to C$_6$ alkyl;
    5 to 7 membered heterocyclo;
    5 or 6 membered heteroaryl;
  —(O)-5 or 6 membered heterocyclo;
  —(O)-5 or 6 membered heteroaryl;
  5 or 6 membered heteroaryl;
  5 or 6 membered heterocyclo; or
  —OR$_{kk}$, wherein R$_{kk}$ is 5 or 6 membered heteroaryl optionally substituted with one or more C$_1$ to C$_6$ alkoxys; and
R$_3$ is hydrogen.

34. The compound of embodiment 33, wherein $R_1$ is hydrogen, and $R_2$ is alkoxy substituted with one or more halos.

35. The compound of embodiment 33, wherein $R_1$ is hydrogen; and $R_2$ is alkoxy substituted with one or more alkoxys.

36. The compound of embodiment 15, wherein:
X is cyano;
Y is $C_6$ to $C_8$ aryl substituted with one or more substituents independently selected from:
—$NR_qCONR_qR_r$, wherein $R_q$ is hydrogen; and wherein $R_r$ is $C_6$ to $C_8$ aryl substituted with halo; and
—$NR_tCOOR_u$, wherein $R_t$ is hydrogen, and wherein $R_u$ is $C_1$ to $C_{12}$ alkyl substituted with $C_6$ to $C_8$ aryl, which aryl is substituted with one or more halos and/or haloalkyls;
Z is $C_1$ to $C_6$ alkyl;
R is hydrogen;
$R_1$ is hydrogen;
$R_2$ is:
alkoxy substituted with one or more substituents independently selected from:
alkoxy; and
5 or 6 membered heteroaryl;
—(O)-5 or 6 membered heterocyclo; or
—(O)-5 or 6 membered heteroaryl; and
$R_3$ is hydrogen.

37. The compound of embodiment 36, wherein Y is $C_6$ to $C_8$ aryl substituted with $NR_qCONR_qR_r$, wherein $R_q$ is hydrogen, and wherein $R_r$ is $C_6$ to $C_8$ aryl substituted with halo.

38. The compound of embodiment 36, wherein Y is $C_6$ to $C_8$ aryl substituted with one or more substituents independently selected from $NR_tCOOR_u$, wherein $R_t$ is hydrogen, and wherein $R_u$ is $C_1$ to $C_{12}$ alkyl substituted with $C_6$ to $C_8$ aryl, which aryl is substituted with one or more halos and/or haloalkyls.

39. A compound of formula IIb

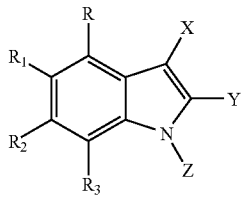

(IIb)

or a pharmaceutically acceptable salt thereof, wherein:
X is cyano;
Y is $C_6$ to $C_8$ aryl substituted with one or more substituents independently selected from:
—$C_1$ to $C_6$ alkyl;
amino substituted with $C_1$ to $C_6$ alkyl
—$NR_tCOOR_u$, wherein $R_t$ is hydrogen, and wherein $R_u$ is $C_1$ to $C_{12}$ alkyl optionally substituted with one or more halos;
—$NR_vSO_2R_w$, wherein $R_v$ is hydrogen, and wherein $R_w$ is $C_1$ to $C_6$ alkyl;
Z is $C_1$ to $C_6$ alkyl;
R is hydrogen;
$R_1$ is hydrogen;
$R_2$ is:
alkoxy substituted with one or more halos;
5 or 6 membered heterocyclo;
5 or 6 membered heteroaryl optionally substituted with one or more substituents independently selected from:
—$C_1$ to $C_6$ alkyl; and
—$NO_2$;
—C(O)-3 to 7 membered heterocyclo or —C(O)-5 membered heterocyclo; and
—$OR_{kk}$, wherein $R_{kk}$ is:
5 or 6 membered heteroaryl optionally substituted with one or more substituents independently selected from cyano, and $C_1$ to $C_6$ alkyl; or
5 or 6 membered heterocyclo optionally substituted with one or more =O; and
$R_3$ is hydrogen.

40. The compound of embodiment 39, wherein:
X is a cyano group;
Y is $C_6$ to $C_8$ aryl substituted with $NR_tCOOR_u$, wherein $R_t$ is hydrogen, and wherein $R_u$ is $C_1$ to $C_{12}$ alkyl substituted with one or more halos;
Z is $C_1$ to $C_6$ alkyl;
R is a hydrogen,
$R_1$ is a hydrogen;
$R_2$ is alkoxy substituted with one or more halos; and
$R_3$ is a hydrogen.

41. The compound of embodiment 40, wherein the $C_6$ to $C_8$ aryl is phenyl.

42. The compound of embodiment 41, wherein the phenyl is substituted at the para position.

43. The compound of embodiment 41, wherein $R_u$ is $C_1$ to $C_{12}$ alkyl substituted with fluoro.

44. The compound of embodiment 39, wherein:
X is cyano;
Y is $C_6$ to $C_8$ aryl substituted with one or more substituents independently selected from:
—$C_1$ to $C_6$ alkyl;
amino substituted with $C_1$ to $C_6$ alkyl; and
—$NR_vSO_2R_w$, wherein $R_v$ is hydrogen, and wherein $R_w$ is $C_1$ to $C_6$ alkyl;
Z is $C_1$ to $C_6$ alkyl;
R is hydrogen;
$R_1$ is hydrogen;
$R_2$ is $OR_{kk}$, wherein $R_{kk}$ is 5 or 6 membered heteroaryl substituted with cyano; and
$R_3$ is hydrogen.

45. The compound of embodiment 44, wherein Y is $C_6$ to $C_8$ aryl para substituted with $NR_vSO_2R_w$, wherein $R_v$ is hydrogen, and wherein $R_w$ is $C_1$ to $C_6$ alkyl.

46. The compound of embodiment 44, wherein Y is $C_6$ to $C_8$ aryl para substituted with $C_1$ to $C_6$ alkyl and $NR_vSO_2R_w$, wherein $R_v$ is hydrogen, and wherein $R_w$ is $C_1$ to $C_6$ alkyl.

47. The compound of embodiment 44, wherein Y is $C_6$ to $C_8$ aryl para substituted with amino substituted with $C_1$ to $C_6$ alkyl.

48. The compound of embodiment 44, wherein $R_2$ is $OR_{kk}$, wherein $R_{kk}$ is 5 or 6 membered heteroaryl substituted with cyano at the ortho position.

49. The compound of embodiment 39, wherein:
X is cyano;
Y is $C_6$ to $C_8$ aryl substituted with one or more substituents independently selected from:
—$NR_tCOOR_u$, wherein $R_t$ is hydrogen, and wherein $R_u$ is $C_1$ to $C_{12}$ alkyl; and
—$NR_vSO_2R_w$, wherein $R_v$ is hydrogen, and wherein $R_w$ is $C_1$ to $C_6$ alkyl;
Z is $C_1$ to $C_6$ alkyl;
R is hydrogen;
$R_1$ is hydrogen;
$R_2$ is $OR_{kk}$, wherein $R_{kk}$ is 5 or 6 membered heteroaryl substituted with $C_1$ to $C_6$ alkyl; and
$R_3$ is hydrogen.

50. The compound of embodiment 49, wherein the $C_6$ to $C_8$ aryl is phenyl.

51. The compound of embodiment 50, wherein Y is phenyl substituted at the para position with $NR_vSO_2R_w$, wherein $R_v$ is hydrogen, and wherein $R_w$ is $C_1$ to $C_6$ alkyl.
52. The compound of embodiment 50, wherein Y is phenyl substituted at the para position with $NR_tCOOR_u$, wherein $R_t$ is hydrogen, and wherein $R_u$ is $C_1$ to $C_{12}$ alkyl.
53. The compound of embodiment 39, wherein:
X is cyano;
Y is $C_6$ to $C_8$ aryl substituted with $NR_tCOOR_u$, wherein $R_t$ is hydrogen, and wherein $R_u$ is $C_1$ to $C_{12}$ alkyl substituted with one or more halos;
Z is $C_1$ to $C_6$ alkyl;
R is hydrogen;
$R_1$ is hydrogen;
$R_2$ is $OR_{kk}$, wherein $R_{kk}$ is 5 or 6 membered heteroaryl; and
$R_3$ is hydrogen.
54. The compound of embodiment 53, wherein the $C_6$ to $C_8$ aryl is phenyl.
55. The compound of embodiment 54, wherein the phenyl is substituted at the para position.
56. The compound of embodiment 55, wherein $R_u$ is $C_1$ to $C_{12}$ alkyl substituted with fluoro.
57. The compound of embodiment 39, wherein:
X is cyano;
Y is $C_6$ to $C_8$ aryl substituted with $NR_tCOOR_u$, wherein $R_t$ is hydrogen, and wherein $R_u$ is $C_1$ to $C_{12}$ alkyl optionally substituted with one or more halos;
Z is $C_1$ to $C_6$ alkyl;
R is hydrogen;
$R_1$ is hydrogen;
$R_2$ is 5 or 6 membered heteroaryl optionally substituted with $C_1$ to $C_6$ alkyl; and
$R_3$ is hydrogen.
58. The compound of embodiment 57, wherein the $C_6$ to $C_8$ aryl is phenyl.
59. The compound of embodiment 58, wherein Y is phenyl substituted at the para position with $NR_tCOOR_u$, wherein $R_t$ is hydrogen, and wherein $R_u$ is $C_1$ to $C_{12}$ alkyl.
60. The compound of embodiment 58, wherein Y is phenyl substituted at the para position with $NR_tCOOR_u$, wherein $R_t$ is hydrogen, and wherein $R_u$ is $C_1$ to $C_{12}$ alkyl substituted with one or more halos.
61. The compound of embodiment 60, wherein $R_u$ is $C_1$ to $C_{12}$ alkyl substituted with fluoro.
62. The compound of embodiment 39, wherein:
X is cyano;
Y is $C_6$ to $C_8$ aryl substituted with $NR_tCOOR_u$, wherein $R_t$ is hydrogen, and wherein $R_u$ is $C_1$ to $C_{12}$ alkyl;
Z is $C_1$ to $C_6$ alkyl;
R is hydrogen;
$R_1$ is hydrogen;
$R_2$ is $OR_{kk}$, wherein $R_{kk}$ is 5 or 6 membered heterocyclo; and
$R_3$ is hydrogen.
63. The compound of embodiment 62, wherein the $C_6$ to $C_8$ aryl is phenyl.
64. The compound of embodiment 63, wherein the phenyl is substituted at the para position.
65. The compound of embodiment 39, wherein:
X is cyano;
Y is $C_6$ to $C_8$ aryl substituted with $NR_tCOOR_u$, wherein $R_t$ is hydrogen, and wherein $R_u$ is $C_1$ to $C_{12}$ alkyl;
Z is $C_1$ to $C_6$ alkyl;
R is hydrogen;
$R_1$ is hydrogen;
$R_2$ is 5 or 6 membered heterocyclo; and
$R_3$ is hydrogen.
66. The compound of embodiment 65, wherein the $C_6$ to $C_8$ aryl is phenyl.
67. The compound of embodiment 66, wherein the phenyl is substituted at the para position.
68. The compound of embodiment 39, wherein:
X is cyano;
Y is $C_6$ to $C_8$ aryl substituted with $NR_tCOOR_u$, wherein $R_t$ is hydrogen, and wherein $R_u$ is $C_1$ to $C_{12}$ alkyl;
Z is $C_1$ to $C_6$ alkyl;
R is hydrogen;
$R_1$ is hydrogen;
$R_2$ is 5 or 6 membered heteroaryl substituted with $NO_2$; and
$R_3$ is hydrogen.
69. The compound of embodiment 68, wherein the $C_6$ to $C_8$ aryl is phenyl.
70. The compound of embodiment 69, wherein the phenyl is substituted at the para position.
71. The compound of embodiment 39, wherein:
X is cyano;
Y is $C_6$ to $C_8$ aryl substituted with $NR_tCOOR_u$, wherein $R_t$ is hydrogen, and wherein $R_u$ is $C_1$ to $C_{12}$ alkyl;
Z is $C_1$ to $C_6$ alkyl;
R is hydrogen;
$R_1$ is hydrogen;
$R_2$ is —C(O)-3 to 7 membered heterocyclo or —C(O)-5 membered heterocyclo; and
$R_3$ is hydrogen.
72. The compound of embodiment 71, wherein the $C_6$ to $C_8$ aryl is phenyl.
73. The compound of embodiment 72, wherein the phenyl is substituted at the para position.
74. The compound of embodiment 39, wherein:
X is cyano;
Y is $C_6$ to $C_8$ aryl substituted with $NR_tCOOR_u$, wherein $R_t$ is hydrogen, and wherein $R_u$ is $C_1$ to $C_{12}$ alkyl;
Z is $C_1$ to $C_6$ alkyl;
R is hydrogen;
$R_1$ is hydrogen;
$R_2$ is $OR_{kk}$, wherein $R_{kk}$ is -5 or 6 membered heterocycle substituted with one or more =O; and
$R_3$ is hydrogen.
75. The compound of embodiment 74, wherein the $C_6$ to $C_8$ aryl is phenyl.
76. The compound of embodiment 75, wherein the phenyl is substituted at the para position.
77. A compound of formula IIc (IIc)

or a pharmaceutically acceptable salt thereof, wherein:
X is cyano;
Y is $C_6$ to $C_8$ aryl substituted with one or more substituents independently selected from:
—$NR_qCONR_qR_r$, wherein $R_q$ is hydrogen, and wherein $R_r$ is $C_1$ to $C_6$ alkyl;
—$NR_tCOOR_u$, wherein $R_t$ is hydrogen, and wherein $R_u$ is $C_1$ to $C_{12}$ alkyl optionally substituted with one or more substituents independently selected from:

—$C_6$ to $C_8$ aryl optionally substituted with one or more halos;
halo; and
5 or 6 membered heteroaryl; and
—$NR_vSO_2R_w$, wherein $R_v$ is hydrogen, and wherein $R_w$ is $C_1$ to $C_6$ alkyl;

Z is:
—$C_1$ to $C_6$ alkyl; or
5 or 6 membered heterocyclo;

R is hydrogen;

$R_1$ is:
—$C_1$ to $C_6$ alkoxy substituted with one or more substituents independently selected from:
5 or 6 membered heterocyclo; and
5 or 6 membered heteroaryl;
—(O)-5 or 6 membered heterocyclo;
—(O)-5 or 6 membered heteroaryl; or
5 or 6 membered heterocyclo;

$R_2$ is hydrogen; and
$R_3$ is hydrogen;
with the proviso that when $R_1$ is $C_1$ to $C_6$ alkoxy substituted with a 5 or 6 membered heterocyclo or when $R_1$ is a 5 or 6 membered heterocyclo, Y is a $C_6$ to $C_8$ aryl substituted with $NR_tCOOR_u$, wherein $R_t$ is hydrogen, and wherein $R_u$ is:
$C_1$ to $C_{12}$ alkyl substituted with one or more halos; or
aryl substituted with one or more halos.

78. The compound of embodiment 77, wherein:
Y is $C_6$ to $C_8$ aryl substituted with $NR_tCOOR_u$, wherein $R_t$ is hydrogen, and wherein $R_u$ is $C_1$ to $C_{12}$ alkyl;
Z is $C_1$ to $C_6$ alkyl; and
$R_1$ is $C_1$ to $C_6$ alkoxy substituted with 5 or 6 membered heteroaryl.

79. The compound of embodiment 77, wherein $R_1$ is $C_1$ to $C_6$ alkoxy substituted with 5 or 6 membered heteroaryl.

80. The compound of embodiment 77, wherein $R_1$ is (O)-5 or 6 membered heterocyclo.

81. The compound of embodiment 77, wherein $R_1$ is (O)-5 or 6 membered heteroaryl.

82. The compound of embodiment 77, wherein Z is cyclobutyl, cyclopropyl, cyclopropylmethyl, or cyclopentyl.

83. A compound of formula IId

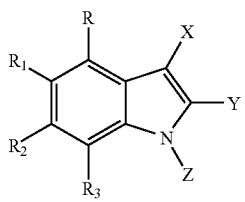

(IId)

or a pharmaceutically acceptable salt thereof, wherein:
X is hydrogen;
Y is $C_6$ to $C_8$ aryl substituted with one or more substituents independently selected from:
—$NR_qCONR_qR_r$, wherein $R_q$ is hydrogen, and wherein $R_r$ is $C_1$ to $C_6$ alkyl; and
—$NR_tCOOR_u$, wherein $R_t$ is hydrogen, and wherein $R_u$ is $C_1$ to $C_{12}$ alkyl optionally substituted with one or more halos;
Z is $C_1$ to $C_6$ alkyl;
R is hydrogen;
$R_1$ is hydrogen;

$R_2$ is $OR_{kk}$, wherein $R_{kk}$ is:
5 or 6 membered heteroaryl;
5 or 6 membered heterocyclo; or
5 or 6 membered heteroaryl optionally substituted with one or more independently selected halos; and
$R_3$ is hydrogen.

84. The compound of embodiment 83, wherein:
X is hydrogen;
Y is $C_6$ to $C_8$ aryl substituted with $NR_tCOOR_u$, wherein $R_t$ is hydrogen, and wherein $R_u$ is $C_1$ to $C_{12}$ alkyl substituted with one or more halos;
Z is $C_1$ to $C_6$ alkyl;
R is hydrogen;
$R_1$ is hydrogen;
$R_2$ is $OR_{kk}$, wherein $R_{kk}$ is 5 or 6 membered heteroaryl; and
$R_3$ is hydrogen.

85. The compound of embodiment 84, wherein the $C_6$ to $C_8$ aryl is phenyl.

86. The compound of embodiment 84, wherein Y is phenyl substituted at the para position with $NR_tCOOR_u$, wherein $R_t$ is hydrogen, and wherein $R_u$ is $C_1$ to $C_{12}$ alkyl substituted with fluoro.

87. The compound of embodiment 84, wherein Z is cyclobutyl, cyclopropyl, cyclopropylmethyl, ethyl or cyclopentyl.

88. The compound of embodiment 83, wherein $R_2$ is (O)-5 or 6 membered heterocyclo.

89. A compound of formula IIe

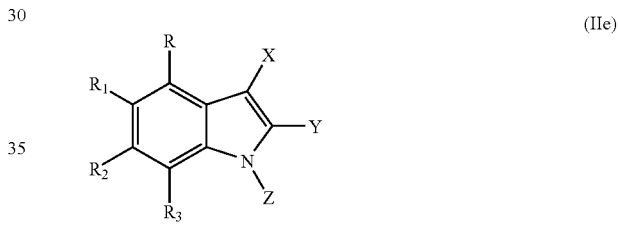

(IIe)

or a pharmaceutically acceptable salt thereof, wherein:
X is:
hydrogen;
cyano;
nitro;
formyl;
—COOH;
—$COR_x$, wherein $R_x$ is $C_1$ to $C_6$ alkyl;
—CH=N—($C_1$ to $C_6$ alkoxy);
—CH=N-(amino optionally substituted with one or more $C_1$ to $C_6$ alkyls);
halo;
alkyl optionally substituted with one or more halos;
alkynyl optionally substituted with $C_1$ to $C_6$ alkyl, which alkyl is optionally substituted with one or more halos and/or cyanos;
oximyl;
—$SO_2R_x$;
—$SO_2NH_2$;
—$SO_2NH(R_x)$;
—$SO_2N(R_x)_2$;
amino optionally substituted with one or more independently selected $C_1$ to $C_6$ alkyls and/or —C(O)—$C_1$ to $C_6$ alkyls;
amido optionally substituted with one or more independently selected $C_1$ to $C_6$ alkyls;
5 or 6 membered heterocyclo;

5 or 6 membered heteroaryl optionally substituted with one or more $C_1$ to $C_6$ alkyls, which alkyls are optionally substituted with one or more halos; or
—$C_6$ to $C_8$ aryl optionally substituted with one or more substituents independently selected from:
—$C_1$ to $C_6$ alkyl optionally substituted with one or more halos;
halo; and
cyano;

Y is:
benzothiazolyl optionally substituted with amino, which amino is optionally substituted with one or more $C_1$ to $C_6$ alkyls;
indolyl optionally substituted on the nitrogen with —$SO_2R_x$;
—$C_6$ to $C_8$ aryl optionally substituted with one or more substituents independently selected from:
halo;
—$C_1$ to $C_6$ alkyl;
alkoxy, optionally substituted with one or more substituents independently selected from:
halo;
5 or 6 membered heterocyclo;
—$C(O)NH_2$ optionally substituted with $C_6$ to $C_8$ alkyl;
—$C(O)NH$—($C_1$ to $C_6$)-alkyl;
hydroxy;
haloalkyl;
cyano;
nitro;
—COOH;
—$N=CHN(R_x)_2$;
amino optionally substituted with one or more substituents independently selected from:
—$SO_2R_x$;
6 to 8 membered aryl optionally substituted with one or more substituents independently selected from alkyl, halo, haloalkyl, cyano, alkoxy, $COR_x$ and haloalkoxy;
5 or 6 membered heteroaryl optionally substituted with one or more substituents independently selected from alkyl, halo, haloalkyl, cyano, alkoxy, haloalkoxy and $C_6$ to $C_8$ aryl optionally substituted with halo;
5 or 6 membered heterocyclo optionally substituted with one or more substituents independently selected from hydroxy, =O, alkyl and haloalkyl;
—$C_1$ to $C_7$ alkyl optionally substituted with one or more substituents independently selected from:
5 or 6 membered heteroaryl optionally substituted with one more substituents independently selected from alkyl, halo, and haloalkyl;
—$C_6$ to $C_8$ aryl optionally substituted with one or more substituents independently selected from alkyl, halo, and haloalkyl;
alkoxy; and
halo; and
—$PO_2R_x$;
—$OC(O)NHR_x$ wherein $R_x$ is optionally substituted with vinyl;
—$OC(O)N(R_u)_2$, wherein $R_u$ is alkyl or $C_6$ to $C_8$ aryl, which alkyl or aryl is optionally substituted with dialkylamino;
—$OC(O)NH(OR_{uu})$, wherein $R_{uu}$ is —$C_6$ to $C_8$ aryl optionally substituted with dialkylamino;
—$OC(O)NR_x(OR_x)$;
—$OC(O)N(OR_x)_2$;
—$OC(O)R_{ab}$, wherein $R_{ab}$ is 5 or 6 membered heterocyclo optionally substituted with heteroaryl, which heteroaryl is optionally substituted with alkyl or haloalkyl;
—$NR_oC(O)R_p$, wherein $R_p$ is:
—$C_1$ to $C_6$ alkyl;
amino optionally substituted with one or more $C_1$ to $C_6$ alkyls, which alkyls are optionally substituted with one or more substituents independently selected from $C_6$ to $C_8$ aryl and alkoxy; or
5 or 6 membered heterocyclo optionally substituted with one or more substituents independently selected from $C_1$ to $C_6$ alkyl and $C_6$ to $C_8$ aryl;
and wherein $R_o$ is:
hydrogen; or
—$C_1$ to $C_6$ alkyl;
—$NR_qCONR_qR_r$, wherein $R_q$ is hydrogen, and wherein $R_r$ is:
—$C_1$ to $C_6$ alkyl optionally substituted with one or more substituents independently selected from:
halo;
hydroxy;
alkoxy;
5 or 6 membered heterocyclo;
5 or 6 membered heteroaryl; and
—$C_6$ to $C_8$ aryl optionally substituted with halo;
—$C_2$ to $C_6$ alkenyl optionally substituted with one or more halos;
—$C_1$ to $C_6$ alkoxy;
5 or 6 membered heterocyclo; or
5 to 6 membered heteroaryl optionally substituted with alkyl;
—$SO_2R_{aa}$, wherein $R_{aa}$ is:
5 or 6 heterocyclo optionally substituted with one or more substituents independently selected from:
hydroxy;
—$C_1$ to $C_6$ alkoxy; and
—$C_1$ to $C_6$ alkyl;
amino optionally substituted with alkyl, which alkyl is optionally substituted with one or more substituents independently selected from:
alkoxy;
hydroxy;
halo;
—$COR_m$, wherein $R_m$ is:
amino optionally substituted with one or more $C_1$ to $C_6$ alkyls, which alkyls are optionally substituted with 5 or 6 membered heterocyclo or $C_6$ to $C_8$ aryl, which heterocyclo or aryl is optionally substituted one or more substituents independently selected from halo and alkoxy;
heterocyclo optionally substituted with hydroxy;
3 to 7 membered heterocyclo optionally substituted with $C_1$ to $C_6$ alkyl, which alkyl is optionally substituted with dialkyl-amino;
—$NR_tCOOR_u$, wherein $R_t$ is hydrogen, and wherein $R_u$ is:
—$C_1$ to $C_{12}$ alkyl optionally substituted with one or more substituents independently selected from:
—$C_6$ to $C_8$ aryl optionally substituted with one or more halos and/or haloalkyls;
alkoxy optionally substituted with one or more alkoxys;
amino optionally substituted with one or more $C_1$ to $C_6$ alkyls;
halo;
—$SO_2R_w$;

—SO$_2$R$_x$;
5 or 6 membered heteroaryl; and
5 or 6 membered heterocyclo;
—C$_2$ to C$_6$ alkenyl;
—C$_6$ to C$_8$ aryl optionally substituted with halo;
4 to 7 membered heterocyclo optionally substituted with one or more substituents independently selected from:
=O;
—SO$_2$R$_w$;
—COR$_p$; and
—(CO)O—(C$_1$ to C$_4$ alkyl)-O—(C$_1$ to C$_4$ alkyl);
—NHR$_{bb}$, wherein R$_{bb}$ is:
—C(=S)NH$_2$;
—C(=S)NHR$_x$;
—C(=S)NR$_x$R$_x$;
—C(=N—CN)NHR$_x$; or
—PO(OR$_x$)$_2$;
—N(CONHR$_w$)$_2$;
—NH(SOR$_w$);
—N(SO$_2$R$_w$)$_2$;
—NR$_v$SO$_2$R$_w$, wherein R$_v$ is hydrogen or alkyl optionally substituted with 4 to 7 membered heterocyclo; and wherein R$_w$ is:
—C$_1$ to C$_6$ alkyl optionally substituted with C$_6$ to C$_8$ aryl, which aryl is optionally substituted with one or more substituents independently selected from haloalkyl, halo, alkoxy, and alkyl;
—C$_6$ to C$_8$ aryl;
—C$_6$ to C$_8$ heteroaryl; or
amino optionally substituted with heterocyclo or alkyl, which heterocyclo or alkyl is optionally substituted with one or more substituents independently selected from halo, C$_1$ to C$_6$ alkoxy, alkoxycarbonyl, (CO)O—(C$_1$ to C$_6$) alkyl), hydroxy, cyano, 5 or 6 membered heterocyclo, and 5 or 6 membered heteroaryl;

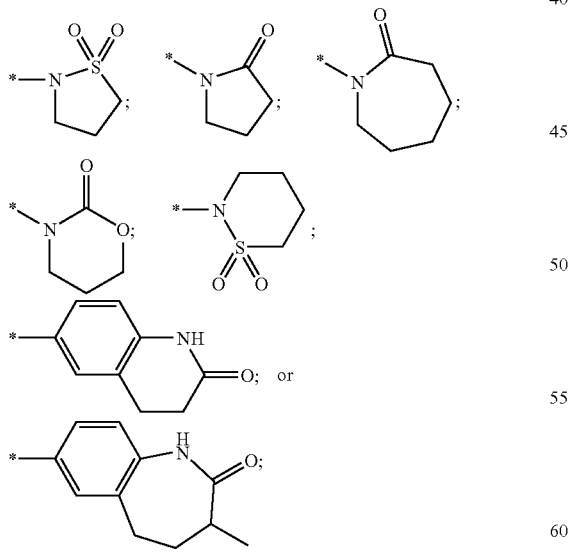

5 to 6 membered heteroaryl optionally substituted with one or more substituents independently selected from:
halo;
—C$_1$ to C$_6$ alkyl;

alkoxy optionally substituted with one or more substituents independently selected from:
halo;
5 or 6 membered heterocyclo; and
—C(O)NH$_2$ optionally substituted with C$_6$ to C$_8$ alkyl;
hydroxy;
haloalkyl;
cyano;
nitro;
—COOH;
amino optionally substituted with one or more substituents independently selected from:
—SO$_2$R$_x$;
6 to 8 membered aryl optionally substituted with one or more substituents independently selected from alkyl, halo, haloalkyl, cyano, alkoxy, COR$_x$ and haloalkoxy;
5 or 6 membered heteroaryl optionally substituted with one or more substituents independently selected from alkyl, halo, haloalkyl, cyano, alkoxy, haloalkoxy and —C$_6$ to C$_8$ aryl optionally substituted with halo;
—C$_5$ to C$_6$ heterocyclo optionally substituted with one or more substituents independently selected from hydroxy, alkyl and haloalkyl; and
—C$_1$ to C$_7$ alkyl optionally substituted with one or more substituents independently selected from:
5 or 6 membered heteroaryl optionally substituted with one or more alkyls, halos, and/or haloalkyls;
—C$_6$ to C$_8$ aryl optionally substituted with one or more substituents independently selected from alkyl, halo and haloalkyl;
alkoxy; and
halo;
—NR$_o$COR$_p$, wherein R$_p$ is:
—C$_1$ to C$_6$ alkyl;
amino optionally substituted with one or more C$_1$ to C$_6$ alkyls, which alkyls are optionally and independently substituted with one or more C$_6$ to C$_8$ aryls and/or alkoxys; or
5 or 6 membered heterocyclo optionally substituted with one or more C$_1$ to C$_6$ alkyls and/or C$_6$ to C$_8$ aryls;
and wherein R$_o$ is:
hydrogen; or
C$_1$ to C$_6$ alkyl;
—NR$_q$CONR$_q$R$_r$, wherein R$_q$ is hydrogen, and wherein R$_r$ is:
—C$_1$ to C$_6$ alkyl optionally substituted with one or more substituents independently selected from:
halo;
hydroxy;
alkoxy;
5 or 6 membered heterocyclo;
5 or 6 membered heteroaryl; and
—C$_6$ to C$_8$ aryl optionally substituted with halo;
—C$_2$ to C$_6$ alkenyl optionally substituted with one or more halos;
—C$_1$ to C$_6$ alkoxy;
5 or 6 membered heterocyclo; or
5 to 6 membered heteroaryl optionally substituted with alkyl;
—NR$_t$COOR$_u$, wherein R$_t$ is hydrogen, and wherein R$_u$ is:

—$C_1$ to $C_{12}$ alkyl optionally substituted with one or more substituents independently selected from:
—$C_6$ to $C_8$ aryl optionally substituted with one or more halos and/or haloalkyls;
alkoxy optionally substituted with one or more alkoxys;
amino optionally substituted with one or more $C_1$ to $C_6$ alkyls;
halo;
—$SO_2R_w$;
—$SO_2R_x$;
5 or 6 membered heteroaryl; and
5 or 6 membered heterocyclo; and
—$NR_vSO_2R_w$, wherein $R_v$ is hydrogen or alkyl optionally substituted with 4 to 7 membered heterocyclo; and wherein $R_w$ is:
—$C_1$ to $C_6$ alkyl optionally substituted with $C_6$ to $C_8$ aryl, which aryl is optionally substituted with one or more substituents independently selected from haloalkyl, halo, alkoxy, and alkyl;
—$C_6$ to $C_8$ aryl;
—$C_6$ to $C_8$ heteroaryl;
amino optionally substituted with heterocyclo or alkyl, which heterocyclo or alkyl is optionally substituted with one or more substituents independently selected from halo, $C_1$ to $C_6$ alkoxy, alkoxycarbonyl, hydroxy, cyano, 5 or 6 membered heterocyclo and 5 or 6 membered heteroaryl;

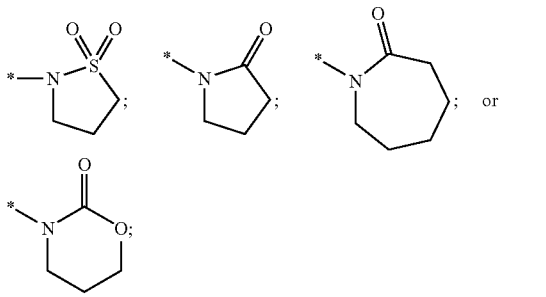

Z is:
—$C_1$ to $C_6$ alkyl optionally substituted with 5 or 6 membered heterocyclo; or
5 or 6 membered heterocyclo;
R is hydrogen;
$R_1$ is:
hydrogen;
a 5 or 6 membered heterocyclo optionally substituted with one or more substituents independently selected from:
hydroxy;
—$C_1$ to $C_6$ alkyl;
—$SO_2R_x$;
—$C(O)$—$C_6$ to $C_8$ aryl;
—$COR_p$; and
—$C(O)OR_x$; or
5 or 6 membered heteroaryl optionally substituted with one or more independently selected from:
—$C_1$ to $C_6$ alkyl optionally substituted with one or more substituents independently selected from halo, $C_1$ to $C_6$ alkoxy, hydroxy, 5 or 6 membered heterocyclo, and 5 or 6 membered heteroaryl;
-alkoxy;
-halo;
-alkylthio;
-haloalkyl;
-cyano;
amino optionally substituted with alkyl, which alkyl is optionally substituted with one or more substituents independently selected from halo, $C_1$ to $C_6$ alkoxy, hydroxy, cyano, 5 or 6 membered heterocyclo, and 5 or 6 membered heteroaryl;
heterocyclo;
nitro;
hydroxy;
—COOH;
—$CO_2R_x$;
$COR_x$;
—$C(O)NH_2$ optionally substituted with one or more $C_1$ to $C_6$ alkyls, which alkyls are optionally substituted with one or more substituents independently selected from halo, $C_1$ to $C_6$ alkoxy, hydroxy, 5 or 6 membered heterocyclo, and 5 or 6 membered heteroaryl;
amido optionally substituted with one or more or more substituents independently selected from halo, $C_1$ to $C_6$ alkoxy, hydroxy, 5 or 6 membered heterocycle, 5 or 6 membered heteroaryl, and $C_1$ to $C_6$ alkyl, which alkyl is optionally substituted with one or more $C_1$ to $C_6$ alkoxys;
—$C_1$ to $C_6$ alkyl optionally substituted with one or more substituents independently selected from:
amino optionally substituted with one or more substituents independently selected from heterocyclo, alkoxy and alkyl, which alkyl is optionally substituted with one or more alkoxys;
amido optionally substituted with $C_1$ to $C_6$ alkyl;
5 or 6 membered heterocyclo optionally substituted with $C_1$ to $C_6$ alkyl;
5 or 6 membered heteroaryl; and
—$C_6$ to $C_8$ aryl;
—$SO_2R_x$;
—$C_2$ to $C_6$ alkenyl optionally substituted with —$SO_2R_x$;
—$C_1$ to $C_6$ alkoxy optionally substituted with one or more substituents independently selected from:
halo;
hydroxy;
cyano;
alkoxy optionally substituted with alkoxy;
amino optionally substituted with one or more independently selected from 5 or 6 membered heteroaryl, 5 or 6 membered heterocyclo and alkyl, which alkyl is optionally substituted with one or more substituents independently selected from:
5 or 6 membered heterocyclo; and
amino optionally substituted with one or more alkyl;
amino optionally substituted with heterocyclo;
amido optionally substituted with $C_1$ to $C_6$ alkyl;
5 to 7 membered heterocyclo optionally substituted with one or more substituents independently selected from hydroxy and $C_1$ to $C_6$ alkyl, which alkyl is optionally substituted with one or more substituents independently selected from:
—$C_1$ to $C_6$ alkoxy; and
—$C_6$ to $C_8$ alryl;
5 or 6 membered heteroaryl optionally substituted with one or more substituents independently selected from:
—$C_1$ to $C_6$ alkyl; and
4 to 7 membered heterocyclo;
alkoxy; and
—$C_6$ to $C_8$ aryl;

—(O)-5 or 6 membered heterocyclo optionally substituted with one or more substituents independently selected from:
hydroxy;
—$C_1$ to $C_6$ alkyl;
—$SO_2R_x$;
—C(O)—$C_6$ to $C_8$ aryl;
—$COR_p$; and
—$C(O)OR_x$; or
—(O)-5 or 6 membered heteroaryl optionally substituted with one or more substituents independently selected from:
—$C_1$ to $C_6$ alkyl optionally substituted with one or more substituents independently selected from halo, $C_1$ to $C_6$ alkoxy, hydroxy, 5 or 6 membered heterocyclo and 5 or 6 membered heteroaryl;
alkoxy;
halo;
alkylthio;
haloalkyl;
cyano;
amino optionally substituted with alkyl, which alkyl is optionally substituted with one or more substituents independently selected from halo, $C_1$ to $C_6$ alkoxy, hydroxy, cyano, 5 or 6 membered heterocyclo and 5 or 6 membered heteroaryl;
heterocyclo;
nitro;
hydroxy;
—COOH;
—$CO_2R_x$;
—$COR_x$;
—$C(O)NH_2$ optionally substituted with one or more substituents independently selected from:
—$C_1$ to $C_6$ alkyl optionally substituted with one or more substituents independently selected from halo, $C_1$ to $C_6$ alkoxy, hydroxy, 5 or 6 membered heterocyclo and 5 or 6 membered heteroaryl; and
amido optionally substituted with one or more or more substituents independently selected from halo, $C_1$ to $C_6$ alkoxy, hydroxy, 5 or 6 membered heterocyclo, 5 or 6 membered heteroaryl, and $C_1$ to $C_6$ alkyl, which alkyl is optionally substituted with one or more $C_1$ to $C_6$ alkoxys;
—$C(O)NH_2$ optionally substituted with one or more $C_1$ to $C_6$ alkyls, which alkyls are optionally substituted with one or more substituents independently selected from halo, $C_1$ to $C_6$ alkoxy, hydroxy, 5 or 6 membered heterocyclo and 5 or 6 membered heteroaryl;
—C(O)-3 to 7 membered heterocyclo optionally substituted with one or more substituents independently selected from:
—$C_6$ to $C_8$ aryl;
5 or 6 membered heteroaryl; and
—$C_1$ to $C_6$ alky further optionally substituted with one or more substituted with hydroxys;
—$SO_2R_x$ optionally substituted with one or more substituents independently selected from:
5 or 6 membered heterocyclo;
—$C_6$ to $C_8$ aryl; and
5 or 6 membered heteroaryl; or
alkylthio optionally substituted with one or more substituents independently selected from:
5 or 6 membered heterocyclo;
—$C_6$ to $C_8$ aryl; and
5 or 6 membered heteroaryl;
—$C_6$ to $C_8$ aryl;
—C(O)-5 or 6 membered heteroaryl;
—C(O)—$C_6$ to $C_8$ aryl;
—COOH; or
—$OR_{kk}$, wherein $R_{kk}$ is:
—$C_6$ to $C_8$ aryl optionally substituted with one or more substituents independently selected from halo, $C_1$ to $C_6$ alkyl, $C_1$ to $C_6$ alkoxy, and $C_1$ to $C_6$ haloalkyl;
$R_2$ is:
—$C_1$ to $C_6$ alkyl optionally substituted with one or more substituents independently selected from:
5 or 6 membered heterocyclo;
5 or 6 membered heteroaryl;
—$C_6$ to $C_8$ aryl;
amido optionally substituted with $C_1$ to $C_6$ alkyl; and
amino optionally substituted with one or more substituents independently selected from heterocyclo, alkoxy and alkyl, which alkyl is optionally substituted with one or more alkoxy; and
—$SO_2R_x$;
—$C_2$ to $C_6$ alkenyl optionally substituted with $SO_2R_x$;
-alkylthio optionally substituted with one or more substituents independently selected from:
5 or 6 membered heteroaryl optionally substituted with alkyl;
5 or 6 membered heterocyclo;
—$C_6$ to $C_8$ aryl; and
—$C_1$ to $C_6$ alkyl;
—$SO_2R_x$ optionally substituted with one or more substituents independently selected from:
5 or 6 membered heteroaryl optionally substituted with one or more $C_1$ to $C_6$ alkyls;
5 or 6 membered heterocyclo;
—$C_6$ to $C_8$ aryl; and
—$C_1$ to $C_6$ alkyl;
—$S(O)R_x$ optionally substituted with one or more substituents independently selected from:
5 or 6 membered heteroaryl;
5 or 6 membered heterocyclo;
—$C_6$ to $C_8$ aryl; and
—$C_1$ to $C_6$ alkyl;
alkoxy optionally substituted with one or more substituents independently selected from:
halo;
hydroxy;
cyano;
alkoxy optionally substituted with alkoxy;
amino optionally substituted with one or more substituents independently selected from —$SO_2$—$C_1$ to $C_4$ alkyl, 5 or 6 membered heteroaryl, 5 or 6 membered heterocyclo and alkyl, which alkyl is optionally substituted with one or more substituents independently selected from:
5 or 6 membered heterocyclo; and
amino optionally substituted with one or more alkyls;
amido optionally substituted with $C_1$ to $C_6$ alkyl;
—S-5 or 6 membered heterocyclo;
—S-5 or 6 membered heteroaryl optionally substituted with $C_1$ to $C_6$ alkyl;
—S—$C_1$ to $C_6$ alkyl optionally substituted with one or more substituents independently selected from:
—$C_6$ to $C_8$ aryl optionally substituted with one or more substituents independently selected from alkyl, haloakyl and halo; and
—$C_5$ to $C_6$ heteroaryl optionally substituted with one or more substituents independently selected from alkyl, haloakyl and halo;

—S—$C_6$ to $C_8$ aryl;
sulfinyl-5 or 6 membered heterocyclo;
sulfinyl-5 or 6 membered heteroaryl;
sulfinyl-$C_1$ to $C_6$ alkyl optionally substituted with one or more substituents independently selected from:
  —$C_6$ to $C_8$ aryl optionally substituted with one or more substituents independently selected from alkyl, haloakyl and halo; and
  —$C_5$ to $C_6$ heteroaryl optionally substituted with one or more substituents independently selected from alkyl, haloakyl and halo;
sulfinyl-$C_6$ to $C_8$ aryl;
sulfonyl-5 or 6 membered heterocyclo;
sulfonyl-5 or 6 membered heteroaryl optionally substituted with $C_1$ to $C_6$ alkyl;
sulfonyl-$C_1$ to $C_6$ alkyl optionally substituted with one or more substituents independently selected from:
  —$C_6$ to $C_8$ aryl optionally substituted with one or more substituents independently selected from alkyl, haloakyl and halo; and
  —$C_5$ to $C_6$ heteroaryl optionally substituted with one or more substituents independently selected from alkyl, haloakyl and halo;
sulfonyl-$C_6$ to $C_8$ aryl;
5 to 7 membered heterocyclo optionally substituted with one or more substituents independently selected from hydroxy, =O, heterocyclo, and $C_1$ to $C_6$ alkyl, which alkyl is optionally substituted with one or more substituents independently selected from:
  —$C_1$ to $C_6$ alkoxy; and
  $C_6$ to $C_8$ aryl;
5 or 6 membered heteroaryl optionally substituted with one or more substituents independently selected from:
  —$C_1$ to $C_6$ alkyl optionally substituted with one or more alkoxys;
  4 to 7 membered heterocyclo; and
  alkoxy; and
  —$C_6$ to $C_8$ aryl;
—$C_6$ to $C_8$ aryl;
—(O)-5 or 6 membered heterocyclo optionally substituted with one or more substituents independently selected from:
  hydroxy;
  =O;
  —$C_1$ to $C_6$ alkyl;
  —$SO_2R_x$;
  —C(O)—$C_6$ to $C_8$ aryl;
  —$COR_p$; and
  —$C(O)OR_x$; or
—(O)-5 or 6 membered heteroaryl optionally substituted with one or more substituents independently selected from:
  —$C_1$ to $C_6$ alkyl optionally substituted with one or more substituents independently selected from halo, $C_1$ to $C_6$ alkoxy, hydroxy, 5 or 6 membered heterocyclo and 5 or 6 membered heteroaryl;
  alkoxy;
  halo;
  alkylthio;
  haloalkyl;
  cyano;
  amino optionally substituted with alkyl, which alkyl is optionally substituted with one or more substituents independently selected from halo, $C_1$ to $C_6$ alkoxy, hydroxy, cyano, 5 or 6 membered heterocyclo and 5 or 6 membered heteroaryl;
  heterocyclo;
  nitro;
  hydroxy;
  —COOH;
  —$CO_2R_x$;
  —$COR_x$;
  —$C(O)NH_2$ optionally substituted with one or more $C_1$ to $C_6$ alkyls, which alkyls are optionally substituted with one or more substituents independently selected from halo, $C_1$ to $C_6$ alkoxy, hydroxy, 5 or 6 membered heterocyclo and 5 or 6 membered heteroaryl;
  amido optionally substituted with one or more substituents independently selected from halo, $C_1$ to $C_6$ alkoxy, hydroxy, 5 or 6 membered heterocyclo, 5 or 6 membered heteroaryl, and $C_1$ to $C_6$ alkyl, which alkyl is optionally substituted with one or more $C_1$ to $C_6$ alkoxys;
—C(O)-3 to 7 membered heterocyclo optionally substituted with one or more substituents independently selected from:
  —$C_6$ to $C_8$ aryl;
  5 or 6 membered heteroaryl; and
  —$C_1$ to $C_6$ alkyl optionally substituted with one or more hydroxys;
—C(O)-5 or 6 membered heteroaryl;
—C(O)—$C_6$ to $C_8$ aryl;
—COOH;
—$C(O)NH_2$ optionally substituted with one or more $C_1$ to $C_6$ alkyls, which alkyls are optionally substituted with one or more substituents independently selected from halo, $C_1$ to $C_6$ alkoxy, hydroxy, 5 or 6 membered heterocyclo and 5 or 6 membered heteroaryl;
amido optionally substituted with one or more $C_1$ to $C_6$ alkyls, which alkyls are optionally substituted with one or more $C_1$ to $C_6$ alkoxys;
amino optionally substituted with one or more substituents independently selected from:
  —$SO_2R_x$;
  6 to 8 membered aryl optionally substituted with one or more substituents independently selected from alkyl, halo, haloalkyl, cyano, alkoxy, $COR_x$ and haloalkoxy;
  5 or 6 membered heteroaryl optionally substituted with one or more substituents independently selected from alkyl, halo, haloalkyl, cyano, alkoxy, haloalkoxy and —$C_6$ to $C_8$ aryl optionally substituted with halo;
  —$C_5$ to $C_6$ heterocyclo optionally substituted with one or more substituents independently selected from hydroxy, alkyl and haloalkyl;
  —$C_1$ to $C_7$ alkyl optionally substituted with one or more substituents independently selected from:
    5 or 6 membered heteroaryl optionally substituted with one or more substituents independently selected from alkyl, halo and haloalkyl;
    —$C_6$ to $C_8$ aryl optionally substituted with one or more substituents independently selected from alkyl, halo and haloalkyl;
    alkoxy; and
    halo;
5 or 6 membered heteroaryl optionally substituted with one or more substituents independently selected from:
  —$C_1$ to $C_6$ alkyl optionally substituted with one or more substituents independently selected from halo, $C_1$ to $C_6$ alkoxy, hydroxy, 5 or 6 membered heterocyclo and 5 or 6 membered heteroaryl;
  alkoxy;
  halo;
  alkylthio;

haloalkyl;
cyano;
amino optionally substituted with one more alkyls, which alkyls are optionally substituted with one or more substituents independently selected from halo, $C_1$ to $C_6$ alkoxy, hydroxy, cyano, 5 or 6 membered heterocyclo and 5 or 6 membered heteroaryl;
heterocyclo;
nitro;
hydroxy;
—COOH;
—$CO_2R_x$;
—$COR_x$;
—$C(O)NH_2$ optionally substituted with one or more $C_1$ to $C_6$ alkyls, which alkyls are optionally substituted with one or more substituents independently selected from halo, $C_1$ to $C_6$ alkoxy, hydroxy, 5 or 6 membered heterocyclo and 5 or 6 membered heteroaryl;
amido optionally substituted with one or more substituents independently selected from halo, $C_1$ to $C_6$ alkoxy, hydroxy, 5 or 6 membered heterocyclo, 5 or 6 membered heteroaryl, and $C_1$ to $C_6$ alkyl, which alkyl is optionally substituted with one or more $C_1$ to $C_6$ alkoxys;
5 or 6 membered heterocyclo optionally substituted with one or more substituents independently selected from:
hydroxy;
═O;
—$C_1$ to $C_6$ alkyl;
—$SO_2R_x$;
—C(O)—$C_6$ to $C_8$ aryl;
—$COR_p$; and
—$C(O)OR_x$;
—$OR_{kk}$, wherein $R_{kk}$ is:
—$C_6$ to $C_8$ aryl optionally substituted with one or more substituents independently selected from halo, $C_1$ to $C_6$ alkyl, $C_1$ to $C_6$ alkoxy, and $C_1$ to $C_6$ haloalkyl;
5 to 6 membered heterocyclo optionally substituted with $C_1$ to $C_6$ alkyl, which alkyl is optionally substituted with $C_6$ to $C_8$ aryl; or
5 to 6 membered heteroaryl optionally substituted with one or more substituents independently selected from halo, $C_1$ to $C_6$ alkyl, $C_1$ to $C_6$ alkoxy, and $C_1$ to $C_6$ haloalkyl;
—$SO_2R_x$; or
—$Si(R_x)_3$;
—$OC(O)NHR_x$ wherein $R_x$ is optionally substituted with —$C_6$ to $C_8$ aryl;
—$OC(O)N(R_x)_2$; or

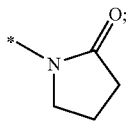

and
$R_3$ is hydrogen; or nitro;
with the proviso that at least one of X, Y, Z, $R_1$, $R_2$ and $R_3$ is selected from the following:
X is:
—CH═N—($C_1$ to $C_6$ alkoxy);
—CH═N-(amino optionally substituted with one or more $C_1$ to $C_6$ alkyls);
halo;
alkyl optionally substituted with one or more halos;
alkynyl optionally substituted with $C_1$ to $C_6$ alkyl, which alkyl is optionally substituted with one or more halos and/or cyanos;
oximyl;
—$SO_2R_x$;
—$SO_2NH_2$;
—$SO_2NH(R_x)$;
—$SO_2N(R_x)_2$;
amino optionally substituted with one or more independently selected $C_1$ to $C_6$ alkyls and/or —C(O)—$C_1$ to $C_6$ alkyls;
amido optionally substituted with one or more independently selected $C_1$ to $C_6$ alkyls;
5 or 6 membered heterocyclo;
5 or 6 membered heteroaryl substituted with one or more $C_1$ to $C_6$ alkyls, which alkyls are optionally substituted with one or more halos; or
—$C_6$ to $C_8$ aryl substituted with one or more substituents independently selected from:
—$C_1$ to $C_6$ alkyl optionally substituted with one or more halos;
halo; and
cyano;
Y is:
benzothiazolyl substituted with amino, which amino is optionally substituted with one or more $C_1$ to $C_6$ alkyls;
indolyl substituted on the nitrogen with —$SO_2R_x$;
—$C_6$ to $C_8$ aryl substituted with one or more substituents independently selected from:
alkoxy substituted with one or more substituents independently selected from:
—$C(O)NH_2$ optionally substituted with $C_6$ to $C_8$ alkyl; and
—C(O)NH—($C_1$ to $C_6$)-alkyl;
haloalkyl;
cyano;
—COOH;
—N═$CHN(R_x)_2$;
amino substituted with one or more substituents independently selected from:
—$SO_2R_x$;
6 to 8 membered aryl optionally substituted with one or more substituents independently selected from alkyl, halo, haloalkyl, cyano, alkoxy, $COR_x$ and haloalkoxy;
5 or 6 membered heteroaryl optionally substituted with one or more substituents independently selected from alkyl, halo, haloalkyl, cyano, alkoxy, haloalkoxy and $C_6$ to $C_8$ aryl optionally substituted with halo;
5 or 6 membered heterocyclo optionally substituted with one or more substituents independently selected from hydroxy, ═O, alkyl and haloalkyl;
—$C_1$ to $C_7$ alkyl substituted with one or more substituents independently selected from:
5 or 6 membered heteroaryl optionally substituted with one more substituents independently selected from alkyl, halo, and haloalkyl;

C$_6$ to C$_8$ aryl optionally substituted with one or more substituents independently selected from alkyl, halo, and haloalkyl;
alkoxy; and
halo; and
—PO$_2$R$_x$;
—OC(O)NHR$_x$ wherein R$_x$ is optionally substituted with vinyl;
—OC(O)N(R$_u$)$_2$, wherein R$_u$ is alkyl or C$_6$ to C$_8$ aryl, which alkyl or aryl is optionally substituted with dialkylamino;
—OC(O)NH(OR$_{uu}$), wherein R$_{uu}$ is —C$_6$ to C$_8$ aryl optionally substituted with dialkylamino;
—OC(O)NR$_x$(OR$_x$);
—OC(O)N(OR$_x$)$_2$;
—OC(O)R$_{ab}$, wherein R$_{ab}$ is 5 or 6 membered heterocyclo optionally substituted with heteroaryl, which heteroaryl is optionally substituted with alkyl or haloalkyl;
—NR$_o$C(O)R$_p$, wherein R$_p$ is:
amino optionally substituted with one or more C$_1$ to C$_6$ alkyls, which alkyls are optionally substituted with one or more substituents independently selected from C$_6$ to C$_8$ aryl and alkoxy; or
5 or 6 membered heterocyclo substituted with one or more substituents independently selected from C$_1$ to C$_6$ alkyl and C$_6$ to C$_8$ aryl;
—NR$_q$CONR$_q$R$_r$, wherein R$_r$ is:
—C$_1$ to C$_6$ alkyl substituted with one or more substituents independently selected from:
hydroxy;
alkoxy;
5 or 6 membered heterocyclo;
5 or 6 membered heteroaryl; and
—C$_6$ to C$_8$ aryl substituted with halo;
—C$_2$ to C$_6$ alkenyl optionally substituted with one or more halos;
—C$_1$ to C$_6$ alkoxy;
5 or 6 membered heterocyclo; or
5 to 6 membered heteroaryl optionally substituted with alkyl;
—SO$_2$R$_{aa}$, wherein R$_{aa}$ is:
5 or 6 heterocyclo optionally substituted with one or more substituents independently selected from:
hydroxy;
—C$_1$ to C$_6$ alkoxy; and
—C$_1$ to C$_6$ alkyl;
amino optionally substituted with alkyl, which alkyl is optionally substituted with one or more substituents independently selected from:
alkoxy;
hydroxy;
halo;
—COR$_m$, wherein R$_m$ is:
amino substituted with one or more C$_1$ to C$_6$ alkyls, which alkyls are substituted with 5 or 6 membered heterocyclo or C$_6$ to C$_8$ aryl, which heterocyclo is substituted with one or more halos and/or alkoxys, and which aryl is optionally substituted with one or more halos and/or alkoxys;
heterocyclo substituted with hydroxy;
—NR$_t$COOR$_u$, wherein R$_u$ is:
—C$_1$ to C$_{12}$ alkyl substituted with one or more substituents independently selected from:
—C$_6$ to C$_8$ aryl substituted with one or more halos and/or haloalkyls;

alkoxy substituted with one or more alkoxys;
amino optionally substituted with one or more C$_1$ to C$_6$ alkyls;
—SO$_2$R$_w$;
—SO$_2$R$_x$; and
5 or 6 membered heteroaryl;
—C$_2$ to C$_6$ alkenyl;
4 to 7 membered heterocyclo substituted with one or more substituents independently selected from:
=O;
—SO$_2$R$_w$;
—COR$_p$; and
—(CO)O—(C$_1$ to C$_4$ alkyl)-O—(C$_1$ to C$_4$ alkyl);
4 or 7 membered heterocyclo optionally substituted with one or more substituents independently selected from:
=O;
—SO$_2$R$_w$;
—COR$_p$; and
—(CO)O—(C$_1$ to C$_4$ alkyl)-O—(C$_1$ to C$_4$ alkyl);
—NHR$_{bb}$, wherein R$_{bb}$ is:
—C(=S)NHR$_x$;
—C(=S)NR$_x$R$_x$; or
—C(=N—CN)NHR$_x$;
—N(CONHR$_w$)$_2$;
—NH(SOR$_w$);
—N(SO$_2$R$_w$)$_2$;
—NR$_v$SO$_2$R$_w$, wherein R$_v$ is alkyl substituted with 4 or 7 membered heterocyclo;
or wherein R$_w$ is:
—C$_1$ to C$_6$ alkyl substituted with C$_6$ to C$_8$ aryl, which aryl is substituted with one or more substituents independently selected from haloalkyl, halo, alkoxy, and alkyl;
amino optionally substituted with heterocyclo or alkyl, which heterocyclo or alkyl is optionally substituted with one or more substituents independently selected from halo, C$_1$ to C$_6$ alkoxy, alkoxycarbonyl, (CO)O—(C$_1$ to C$_6$) alkyl), hydroxy, cyano, 5 or 6 membered heterocyclo, and 5 or 6 membered heteroaryl;

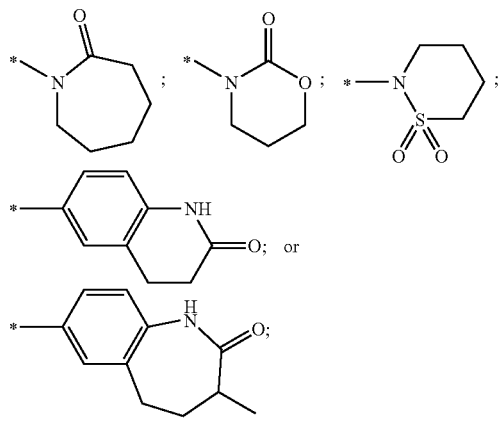

5 to 6 membered heteroaryl optionally substituted with one or more substituents independently selected from:

halo;

$C_1$ to $C_6$ alkyl;

alkoxy optionally substituted with one or more substituents independently selected from:
  halo;
  5 or 6 membered heterocyclo; and
  —C(O)NH$_2$ optionally substituted with $C_6$ to $C_8$ alkyl;

hydroxy;

haloalkyl;

cyano;

nitro;

—COOH;

amino optionally substituted with one or more substituents independently selected from:
  —SO$_2$R$_x$;
  6 to 8 membered aryl optionally substituted with one or more substituents independently selected from alkyl, halo, haloalkyl, cyano, alkoxy, COR$_x$ and haloalkoxy;
  5 or 6 membered heteroaryl optionally substituted with one or more substituents independently selected from alkyl, halo, haloalkyl, cyano, alkoxy, haloalkoxy and —C$_6$ to C$_8$ aryl optionally substituted with halo;
  —C$_5$ to C$_6$ heterocyclo optionally substituted with one or more substituents independently selected from hydroxy, alkyl and haloalkyl; and
  —C$_1$ to C$_7$ alkyl optionally substituted with one or more substituents independently selected from:
    5 or 6 membered heteroaryl optionally substituted with one or more alkyls, halos, and/or haloalkyls;
    —C$_6$ to C$_8$ aryl optionally substituted with one or more substituents independently selected from alkyl, halo and haloalkyl;
    alkoxy; and
    halo;

—NR$_o$COR$_p$, wherein R$_p$ is:
  amino optionally substituted with one or more $C_1$ to $C_6$ alkyls, which alkyls are optionally and independently substituted with one or more $C_6$ to $C_8$ aryls and/or alkoxys; or
  5 or 6 membered heterocyclo optionally substituted with one or more $C_1$ to $C_6$ alkyls and/or $C_6$ to $C_8$ aryls;

—NR$_q$CONR$_q$R$_r$, wherein R$_r$ is:
  —C$_1$ to C$_6$ alkyl substituted with one or more substituents independently selected from:
    hydroxy;
    alkoxy;
    5 or 6 membered heterocyclo;
    5 or 6 membered heteroaryl; and
    —C$_6$ to C$_8$ aryl substituted with halo;
  —C$_2$ to C$_6$ alkenyl optionally substituted with one or more halos;
  —C$_1$ to C$_6$ alkoxy;
  5 or 6 membered heterocyclo; or
  5 to 6 membered heteroaryl optionally substituted with alkyl;

—NR$_t$COOR$_u$, wherein R$_u$ is:
  —C$_1$ to C$_{12}$ alkyl substituted with one or more substituents independently selected from:
    —C$_6$ to C$_8$ aryl substituted with one or more halos and/or haloalkyls;
    alkoxy substituted with one or more alkoxys;
    amino optionally substituted with one or more $C_1$ to $C_6$ alkyls;
    —SO$_2$R$_w$;
    SO$_2$R$_x$; and
    5 or 6 membered heteroaryl;
  —NR$_v$SO$_2$R$_w$, wherein R$_v$ is alkyl substituted with 4 to 7 membered heterocyclo; or wherein R$_w$ is:
    —C$_1$ to C$_6$ alkyl substituted with C$_6$ to C$_8$ aryl, which aryl is substituted with one or more substituents independently selected from haloalkyl, halo, alkoxy, and alkyl;
    —C$_6$ to C$_8$ aryl;
    amino substituted with heterocyclo or alkyl, which heterocyclo is optionally substituted with one or more substituents independently selected from halo, $C_1$ to $C_6$ alkoxy, alkoxycarbonyl, hydroxy, cyano, 5 or 6 membered heterocyclo and 5 or 6 membered heteroaryl, and which alkyl is substituted with one or more substituents independently selected from halo, $C_1$ to $C_6$ alkoxy, alkoxycarbonyl, hydroxy, cyano, 5 or 6 membered heterocyclo and 5 or 6 membered heteroaryl;

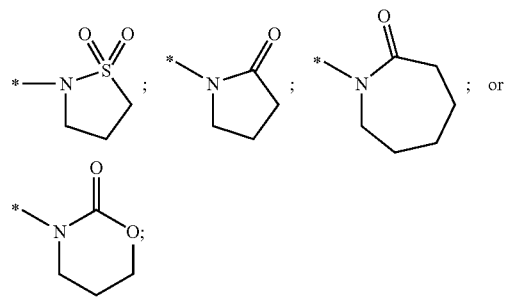

Z is:
  —C$_1$ to C$_6$ alkyl substituted with 5 or 6 membered heterocyclo; or
  5 or 6 membered heterocyclo;

R$_1$ is:
  a 5 or 6 membered heterocyclo substituted with one or more substituents independently selected from:
    hydroxy;
    —C$_1$ to C$_6$ alkyl;
    —SO$_2$R$_x$;
    —C(O)—C$_6$ to C$_8$ aryl;
    —COR$_p$; and
    —C(O)OR$_x$; or
  5 or 6 membered heteroaryl substituted with one or more independently selected from:
    —C$_1$ to C$_6$ alkyl optionally substituted with one or more substituents independently selected from halo, $C_1$ to $C_6$ alkoxy, hydroxy, 5 or 6 membered heterocyclo, and 5 or 6 membered heteroaryl;
    alkoxy;
    halo;
    alkylthio;
    haloalkyl;
    cyano;
    amino optionally substituted with alkyl, which alkyl is optionally substituted with one or more substituents independently selected from halo, $C_1$ to $C_6$ alkoxy, hydroxy, cyano, 5 or 6 membered heterocyclo, and 5 or 6 membered heteroaryl;

heterocyclo;
nitro;
hydroxy;
—COOH;
—CO$_2$R$_x$;
—COR$_x$;
—C(O)NH$_2$ optionally substituted with one or more C$_1$ to C$_6$ alkyls, which alkyls are optionally substituted with one or more substituents independently selected from halo, C$_1$ to C$_6$ alkoxy, hydroxy, 5 or 6 membered heterocyclo, and 5 or 6 membered heteroaryl;
amido optionally substituted with one or more or more substituents independently selected from halo, C$_1$ to C$_6$ alkoxy, hydroxy, 5 or 6 membered heterocyclo, 5 or 6 membered heteroaryl, and C$_1$ to C$_6$ alkyl, which alkyl is optionally substituted with one or more C$_1$ to C$_6$ alkoxys;
—C$_1$ to C$_6$ alkyl substituted with one or more substituents independently selected from:
  amino optionally substituted with one or more substituents independently selected from heterocyclo, alkoxy and alkyl, which alkyl is substituted with one or more alkoxys;
  amido optionally substituted with C$_1$ to C$_6$ alkyl;
  5 or 6 membered heterocyclo substituted with C$_1$ to C$_6$ alkyl;
  5 or 6 membered heteroaryl; and
  —C$_6$ to C$_8$ aryl;
  —SO$_2$R$_x$;
—C$_2$ to C$_6$ alkenyl optionally substituted with —SO$_2$R$_x$;
—C$_1$ to C$_6$ alkoxy substituted with one or more substituents independently selected from:
  hydroxy;
  cyano;
  alkoxy optionally substituted with alkoxy;
  amino optionally substituted with one or more independently selected from 5 or 6 membered heteroaryl, 5 or 6 membered heterocyclo and alkyl, which alkyl is optionally substituted with one or more substituents independently selected from:
    5 or 6 membered heterocyclo; and
    amino optionally substituted with one or more alkyl;
  amino optionally substituted with heterocyclo;
  amido optionally substituted with C$_1$ to C$_6$ alkyl;
  5 to 7 membered heterocyclo substituted with one or more substituents independently selected from hydroxy and C$_1$ to C$_6$ alkyl, which alkyl is optionally substituted with one or more substituents independently selected from:
    —C$_1$ to C$_6$ alkoxy; and
    —C$_6$ to C$_8$ alryl;
  5 or 6 membered heteroaryl optionally substituted with one or more substituents independently selected from:
    —C$_1$ to C$_6$ alkyl; and
    4 to 7 membered heterocyclo; and
  alkoxy;
—(O)-5 or 6 membered heterocyclo optionally substituted with one or more substituents independently selected from:
  hydroxy;
  —C$_1$ to C$_6$ alkyl;
  —SO$_2$R$_x$;
  —C(O)—C$_6$ to C$_8$ aryl;
  —COR$_p$; and
  —C(O)OR$_x$; or
—(O)-5 or 6 membered heteroaryl optionally substituted with one or more substituents independently selected from:
  —C$_1$ to C$_6$ alkyl optionally substituted with one or more substituents independently selected from halo, C$_1$ to C$_6$ alkoxy, hydroxy, 5 or 6 membered heterocyclo and 5 or 6 membered heteroaryl;
alkoxy;
halo;
alkylthio;
haloalkyl;
cyano;
amino optionally substituted with alkyl, which alkyl is optionally substituted with one or more substituents independently selected from halo, C$_1$ to C$_6$ alkoxy, hydroxy, cyano, 5 or 6 membered heterocyclo and 5 or 6 membered heteroaryl;
heterocyclo;
nitro;
hydroxy;
—COOH;
—CO$_2$R$_x$;
—COR$_x$;
—C(O)NH$_2$ optionally substituted with one or more substituents independently selected from:
  —C$_1$ to C$_6$ alkyl optionally substituted with one or more substituents independently selected from halo, C$_1$ to C$_6$ alkoxy, hydroxy, 5 or 6 membered heterocyclo and 5 or 6 membered heteroaryl; and
  amido optionally substituted with one or more or more substituents independently selected from halo, C$_1$ to C$_6$ alkoxy, hydroxy, 5 or 6 membered heterocyclo, 5 or 6 membered heteroaryl, and C$_1$ to C$_6$ alkyl, which alkyl is optionally substituted with one or more C$_1$ to C$_6$ alkoxys;
—C(O)NH$_2$ optionally substituted with one or more C$_1$ to C$_6$ alkyls, which alkyls are optionally substituted with one or more substituents independently selected from halo, C$_1$ to C$_6$ alkoxy, hydroxy, 5 or 6 membered heterocyclo and 5 or 6 membered heteroaryl;
—C(O)-3 to 7 membered heterocyclo optionally substituted with one or more substituents independently selected from:
  —C$_6$ to C$_8$ aryl;
  5 or 6 membered heteroaryl; and
  —C$_1$ to C$_6$ alky further optionally substituted with one or more substituted with hydroxys;
—SO$_2$R$_x$ optionally substituted with one or more substituents independently selected from:
  5 or 6 membered heterocyclo;
  —C$_6$ to C$_8$ aryl; and
  5 or 6 membered heteroaryl; or
alkylthio optionally substituted with one or more substituents independently selected from:
  5 or 6 membered heterocyclo;
  —C$_6$ to C$_8$ aryl; and
  5 or 6 membered heteroaryl;
—C(O)-5 or 6 membered heteroaryl;
—C(O)—C$_6$ to C$_8$ aryl;
—COOH;
—OR$_{kk}$, wherein R$_{kk}$ is:
  —C$_6$ to C$_8$ aryl optionally substituted with one or more substituents independently selected from halo, C$_1$ to C$_6$ alkyl, C$_1$ to C$_6$ alkoxy, and C$_1$ to C$_6$ haloalkyl;
R$_2$ is:
  —C$_1$ to C$_6$ alkyl substituted with one or more substituents independently selected from:

5 or 6 membered heterocyclo;
5 or 6 membered heteroaryl;
—$C_6$ to $C_8$ aryl;
amido optionally substituted with $C_1$ to $C_6$ alkyl; and
amino optionally substituted with one or more substituents independently selected from heterocyclo, alkoxy and alkyl, which alkyl is optionally substituted with one or more alkoxy; and
—$SO_2R_x$;
—$C_2$ to $C_6$ alkenyl optionally substituted with $SO_2R_x$;
alkylthio optionally substituted with one or more substituents independently selected from:
  5 or 6 membered heteroaryl optionally substituted with alkyl;
  5 or 6 membered heterocyclo;
  —$C_6$ to $C_8$ aryl; and
  —$C_1$ to $C_6$ alkyl;
—$SO_2R_x$ optionally substituted with one or more substituents independently selected from:
  5 or 6 membered heteroaryl optionally substituted with one or more $C_1$ to $C_6$ alkyls;
  5 or 6 membered heterocyclo;
  —$C_6$ to $C_8$ aryl; and
  —$C_1$ to $C_6$ alkyl;
—$S(O)R_x$ optionally substituted with one or more substituents independently selected from:
  5 or 6 membered heteroaryl;
  5 or 6 membered heterocyclo;
  —$C_6$ to $C_8$ aryl; and
  —$C_1$ to $C_6$ alkyl;
alkoxy substituted with one or more substituents independently selected from:
  halo;
  hydroxy;
  cyano;
  alkoxy optionally substituted with alkoxy;
  amino substituted with one or more substituents independently selected from —$SO_2$—$C_1$ to $C_4$ alkyl and alkyl, which alkyl is substituted with one or more substituents independently selected from:
    5 or 6 membered heterocyclo; and
    amino optionally substituted with one or more alkyls;
  amido substituted with $C_1$ to $C_6$ alkyl;
—S-5 or 6 membered heterocyclo;
—S-5 or 6 membered heteroaryl optionally substituted with $C_1$ to $C_6$ alkyl;
—S—$C_1$ to $C_6$ alkyl optionally substituted with one or more substituents independently selected from:
  —$C_6$ to $C_8$ aryl optionally substituted with one or more substituents independently selected from alkyl, haloakyl and halo; and
  —$C_5$ to $C_6$ heteroaryl optionally substituted with one or more substituents independently selected from alkyl, haloakyl and halo;
—S—$C_6$ to $C_8$ aryl;
sulfinyl-5 or 6 membered heterocyclo;
sulfinyl-5 or 6 membered heteroaryl;
sulfinyl-$C_1$ to $C_6$ alkyl optionally substituted with one or more substituents independently selected from:
  —$C_6$ to $C_8$ aryl optionally substituted with one or more substituents independently selected from alkyl, haloakyl and halo; and
  —$C_5$ to $C_6$ heteroaryl optionally substituted with one or more substituents independently selected from alkyl, haloakyl and halo;
sulfinyl-$C_6$ to $C_8$ aryl;
sulfonyl-5 or 6 membered heterocyclo;
sulfonyl-5 or 6 membered heteroaryl optionally substituted with $C_1$ to $C_6$ alkyl;
sulfonyl-$C_1$ to $C_6$ alkyl optionally substituted with one or more substituents independently selected from:
  —$C_6$ to $C_8$ aryl optionally substituted with one or more substituents independently selected from alkyl, haloakyl and halo; and
  —$C_5$ to $C_6$ heteroaryl optionally substituted with one or more substituents independently selected from alkyl, haloakyl and halo;
sulfonyl-$C_6$ to $C_8$ aryl;
5 to 7 membered heterocyclo optionally substituted with one or more substituents independently selected from hydroxy, =O, heterocyclo, and $C_1$ to $C_6$ alkyl, which alkyl is optionally substituted with one or more substituents independently selected from:
  —$C_1$ to $C_6$ alkoxy; and
  —$C_6$ to $C_8$ aryl;
5 or 6 membered heteroaryl optionally substituted with one or more substituents independently selected from:
  —$C_1$ to $C_6$ alkyl optionally substituted with one or more alkoxys;
  4 to 7 membered heterocyclo; and
  alkoxy; and
  —$C_6$ to $C_8$ aryl;
—$C_6$ to $C_8$ aryl;
—(O)-5 or 6 membered heterocyclo substituted with one or more substituents independently selected from:
  hydroxy;
  =O;
  —$C_1$ to $C_6$ alkyl;
  —$SO_2R_x$;
  —$C(O)$—$C_6$ to $C_8$ aryl;
  —$COR_p$; and
  —$C(O)OR_x$; or
—(O)-5 or 6 membered heteroaryl substituted with one or more substituents independently selected from:
  —$C_1$ to $C_6$ alkyl optionally substituted with one or more substituents independently selected from halo, $C_1$ to $C_6$ alkoxy, hydroxy, 5 or 6 membered heterocyclo and 5 or 6 membered heteroaryl;
  alkoxy;
  halo;
  alkylthio;
  haloalkyl;
  cyano;
  amino optionally substituted with alkyl, which alkyl is optionally substituted with one or more substituents independently selected from halo, $C_1$ to $C_6$ alkoxy, hydroxy, cyano, 5 or 6 membered heterocyclo and 5 or 6 membered heteroaryl;
  heterocyclo;
  nitro;
  hydroxy;
  —COOH;
  —$CO_2R_x$;
  —$COR_x$;
  —$C(O)NH_2$ optionally substituted with one or more $C_1$ to $C_6$ alkyls, which alkyls are optionally substituted with one or more substituents independently selected from halo, $C_1$ to $C_6$ alkoxy, hydroxy, 5 or 6 membered heterocyclo and 5 or 6 membered heteroaryl;
  amido optionally substituted with one or more substituents independently selected from halo, $C_1$ to $C_6$ alkoxy, hydroxy, 5 or 6 membered heterocyclo, 5 or 6 membered heteroaryl, and $C_1$ to $C_6$ alkyl, which alkyl is optionally substituted with one or more $C_1$ to $C_6$ alkoxys;
—C(O)-3 to 7 membered heterocyclo optionally substituted with one or more substituents independently selected from:
—$C_6$ to $C_8$ aryl;
5 or 6 membered heteroaryl; and
—$C_1$ to $C_6$ alkyl optionally substituted with one or more hydroxys;
—C(O)-5 or 6 membered heteroaryl;
—C(O)—$C_6$ to $C_8$ aryl;
—COOH;
—C(O)$NH_2$ optionally substituted with one or more $C_1$ to $C_6$ alkyls, which alkyls are optionally substituted with one or more substituents independently selected from halo, $C_1$ to $C_6$ alkoxy, hydroxy, 5 or 6 membered heterocyclo and 5 or 6 membered heteroaryl;
amido substituted with one or more $C_1$ to $C_6$ alkyls, which alkyls are optionally substituted with one or more $C_1$ to $C_6$ alkoxys;
amino substituted with one or more substituents independently selected from:
—$SO_2R_x$;
6 to 8 membered aryl optionally substituted with one or more substituents independently selected from alkyl, halo, haloalkyl, cyano, alkoxy, $COR_x$ and haloalkoxy;
5 or 6 membered heteroaryl optionally substituted with one or more substituents independently selected from alkyl, halo, haloalkyl, cyano, alkoxy, haloalkoxy and —$C_6$ to $C_8$ aryl optionally substituted with halo;
—$C_5$ to $C_6$ heterocyclo optionally substituted with one or more substituents independently selected from hydroxy, alkyl and haloalkyl;
—$C_1$ to $C_7$ alkyl optionally substituted with one or more substituents independently selected from:
5 or 6 membered heteroaryl optionally substituted with one or more substituents independently selected from alkyl, halo and haloalkyl;
—$C_6$ to $C_8$ aryl optionally substituted with one or more substituents independently selected from alkyl, halo and haloalkyl;
alkoxy; and
halo;
5 or 6 membered heteroaryl substituted with one or more substituents independently selected from:
—$C_1$ to $C_6$ alkyl optionally substituted with one or more substituents independently selected from halo, $C_1$ to $C_6$ alkoxy, hydroxy, 5 or 6 membered heterocyclo and 5 or 6 membered heteroaryl;
alkoxy;
halo;
alkylthio;
haloalkyl;
cyano;
amino optionally substituted with one more alkyls, which alkyls are optionally substituted with one or more substituents independently selected from halo, $C_1$ to $C_6$ alkoxy, hydroxy, cyano, 5 or 6 membered heterocyclo and 5 or 6 membered heteroaryl;
heterocyclo;
nitro;
hydroxy;
—COOH;
—$CO_2R_x$;
—$COR_x$;
—C(O)$NH_2$ optionally substituted with one or more $C_1$ to $C_6$ alkyls, which alkyls are optionally substituted with one or more substituents independently selected from halo, $C_1$ to $C_6$ alkoxy, hydroxy, 5 or 6 membered heterocyclo and 5 or 6 membered heteroaryl;
amido optionally substituted with one or more substituents independently selected from halo, $C_1$ to $C_6$ alkoxy, hydroxy, 5 or 6 membered heterocyclo, 5 or 6 membered heteroaryl, and $C_1$ to $C_6$ alkyl, which alkyl is optionally substituted with one or more $C_1$ to $C_6$ alkoxys;
5 or 6 membered heterocyclo optionally substituted with one or more substituents independently selected from:
hydroxy;
=O;
—$C_1$ to $C_6$ alkyl;
—$SO_2R_x$;
—C(O)—$C_6$ to $C_8$ aryl;
—$COR_p$; and
—C(O)$OR_x$;
—$OR_{kk}$, wherein $R_{kk}$ is:
—$C_6$ to $C_8$ aryl optionally substituted with one or more substituents independently selected from halo, $C_1$ to $C_6$ alkyl, $C_1$ to $C_6$ alkoxy, and $C_1$ to $C_6$ haloalkyl;
5 to 6 membered heterocyclo optionally substituted with $C_1$ to $C_6$ alkyl, which alkyl is optionally substituted with $C_6$ to $C_8$ aryl; or
5 to 6 membered heteroaryl substituted with one or more substituents independently selected from halo, $C_1$ to $C_6$ alkyl, $C_1$ to $C_6$ alkoxy, and $C_1$ to $C_6$ haloalkyl;
—$SO_2R_x$; or
—Si($R_x$)$_3$;
—OC(O)$NHR_x$ wherein $R_x$ is optionally substituted with —$C_6$ to $C_8$ aryl;
—OC(O)N($R_x$)$_2$; or

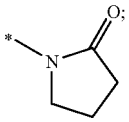

and
$R_3$ is nitro.
90. The compound of embodiment 89, wherein:
X is:
—CH=N—($C_1$ to $C_6$ alkoxy);
—CH=N-(amino optionally substituted with one or more $C_1$ to $C_6$ alkyls);
halo;
alkyl optionally substituted with one or more halos;
alkynyl optionally substituted with $C_1$ to $C_6$ alkyl, which alkyl is optionally substituted with one or more halos and/or cyanos;
oximyl;
—$SO_2R_x$;
—$SO_2NH_2$;
—$SO_2NH(R_x)$;
—$SO_2N(R_x)_2$;
amino optionally substituted with one or more independently selected $C_1$ to $C_6$ alkyls and/or —C(O)—$C_1$ to $C_6$ alkyls;
amido optionally substituted with one or more independently selected $C_1$ to $C_6$ alkyls;
5 or 6 membered heterocyclo;

5 or 6 membered heteroaryl substituted with one or more $C_1$ to $C_6$ alkyls, which alkyls are optionally substituted with one or more halos; or —$C_6$ to $C_8$ aryl substituted with one or more substituents independently selected from:
  —$C_1$ to $C_6$ alkyl optionally substituted with one or more halos;
  halo; and
  cyano.

91. The compound of embodiment 89, wherein:
Y is:
  benzothiazolyl substituted with amino, which amino is optionally substituted with one or more $C_1$ to $C_6$ alkyls;
  indolyl substituted on the nitrogen with —$SO_2R_x$; or
  —$C_6$ to $C_8$ aryl substituted with one or more substituents independently selected from:
    alkoxy substituted with one or more substituents independently selected from:
      —$C(O)NH_2$ optionally substituted with $C_6$ to $C_8$ alkyl; and
      —$C(O)NH$—($C_1$ to $C_6$)-alkyl;
    haloalkyl;
    cyano;
    —COOH;
    —N=$CHN(R_x)_2$;
    amino substituted with one or more substituents independently selected from:
      —$SO_2R_x$;
      6 to 8 membered aryl optionally substituted with one or more substituents independently selected from alkyl, halo, haloalkyl, cyano, alkoxy, $COR_x$ and haloalkoxy;
      5 or 6 membered heteroaryl optionally substituted with one or more substituents independently selected from alkyl, halo, haloalkyl, cyano, alkoxy, haloalkoxy and $C_6$ to $C_8$ aryl optionally substituted with halo;
      5 or 6 membered heterocyclo optionally substituted with one or more substituents independently selected from hydroxy, =O, alkyl and haloalkyl;
      —$C_1$ to $C_7$ alkyl substituted with one or more substituents independently selected from:
        5 or 6 membered heteroaryl optionally substituted with one or more substituents independently selected from alkyl, halo, and haloalkyl;
        —$C_6$ to $C_8$ aryl optionally substituted with one or more substituents independently selected from alkyl, halo, and haloalkyl;
        alkoxy; and
        halo; and
      —$PO_2R_x$;
    —$OC(O)NHR_x$ wherein $R_x$ is optionally substituted with vinyl;
    —$OC(O)N(R_u)_2$, wherein $R_u$ is alkyl or $C_6$ to $C_8$ aryl, which alkyl or aryl is optionally substituted with dialkylamino;
    —$OC(O)NH(OR_{uu})$, wherein $R_{uu}$ is —$C_6$ to $C_8$ aryl optionally substituted with dialkylamino;
    —$OC(O)NR_x(OR_x)$;
    —$OC(O)N(OR_x)_2$;
    —$OC(O)R_{ab}$, wherein $R_{ab}$ is 5 or 6 membered heterocyclo optionally substituted with heteroaryl, which heteroaryl is optionally substituted with alkyl or haloalkyl;
    —$NR_oC(O)R_p$, wherein $R_p$ is:
      amino optionally substituted with one or more $C_1$ to $C_6$ alkyls, which alkyls are optionally substituted with one or more substituents independently selected from $C_6$ to $C_8$ aryl and alkoxy; or
      5 or 6 membered heterocyclo substituted with one or more substituents independently selected from $C_1$ to $C_6$ alkyl and $C_6$ to $C_8$ aryl;
    —$NR_qCONR_qR_r$, wherein $R_r$ is:
      —$C_1$ to $C_6$ alkyl substituted with one or more substituents independently selected from:
        hydroxy;
        alkoxy;
        5 or 6 membered heterocyclo;
        5 or 6 membered heteroaryl; and
        —$C_6$ to $C_8$ aryl substituted with halo;
      —$C_2$ to $C_6$ alkenyl optionally substituted with one or more halos;
      —$C_1$ to $C_6$ alkoxy;
      5 or 6 membered heterocyclo; or
      5 to 6 membered heteroaryl optionally substituted with alkyl;
    —$SO_2R_{aa}$, wherein $R_{aa}$ is:
      5 or 6 heterocyclo optionally substituted with one or more substituents independently selected from:
        hydroxy;
        —$C_1$ to $C_6$ alkoxy; and
        —$C_1$ to $C_6$ alkyl;
      amino optionally substituted with alkyl, which alkyl is optionally substituted with one or more substituents independently selected from:
        alkoxy;
        hydroxy;
        halo;
    —$COR_m$, wherein $R_m$ is:
      amino substituted with one or more $C_1$ to $C_6$ alkyls, which alkyls are substituted with 5 or 6 membered heterocyclo or $C_6$ to $C_8$ aryl, which heterocyclo is substituted with one or more halos and/or alkoxys, and which aryl is optionally substituted with one or more halos and/or alkoxys;
      heterocyclo substituted with hydroxy;
    —$NR_tCOOR_u$, wherein $R_u$ is:
      —$C_1$ to $C_{12}$ alkyl substituted with one or more substituents independently selected from:
        —$C_6$ to $C_8$ aryl substituted with one or more halos and/or haloalkyls;
        alkoxy substituted with one or more alkoxys;
        amino optionally substituted with one or more $C_1$ to $C_6$ alkyls;
        —$SO_2R_w$;
        —$SO_2R_x$; and
        5 or 6 membered heteroaryl;
      —$C_2$ to $C_6$ alkenyl;
      4 to 7 membered heterocyclo substituted with one or more substituents independently selected from:
        =O;
        —$SO_2R_w$;
        —$COR_p$; and
        —(CO)O—($C_1$ to $C_4$ alkyl)-O—($C_1$ to $C_4$ alkyl);
      4 or 7 membered heterocyclo optionally substituted with one or more substituents independently selected from:
        =O;
        —$SO_2R_w$;
        —$COR_p$; and
        —(CO)O—($C_1$ to $C_4$ alkyl)-O—($C_1$ to $C_4$ alkyl);

—NHR$_{bb}$, wherein R$_{bb}$ is:
—C(=S)NHR$_x$;
—C(=S)NR$_x$R$_x$; or
—C(=N—CN)NHR$_x$;
—N(CONHR$_w$)$_2$;
—NH(SOR$_w$);
—N(SO$_2$R$_w$)$_2$;
—NR$_v$SO$_2$R$_w$, wherein R$_v$ is alkyl substituted with 4 or 7 membered heterocyclo;
or wherein R$_w$ is:
—C$_1$ to C$_6$ alkyl substituted with C$_6$ to C$_8$ aryl, which aryl is substituted with one or more substituents independently selected from haloalkyl, halo, alkoxy, and alkyl;
amino optionally substituted with heterocyclo or alkyl, which heterocyclo or alkyl is optionally substituted with one or more substituents independently selected from halo, C$_1$ to C$_6$ alkoxy, alkoxycarbonyl, (CO)O—(C$_1$ to C$_6$) alkyl), hydroxy, cyano, 5 or 6 membered heterocyclo, and 5 or 6 membered heteroaryl;

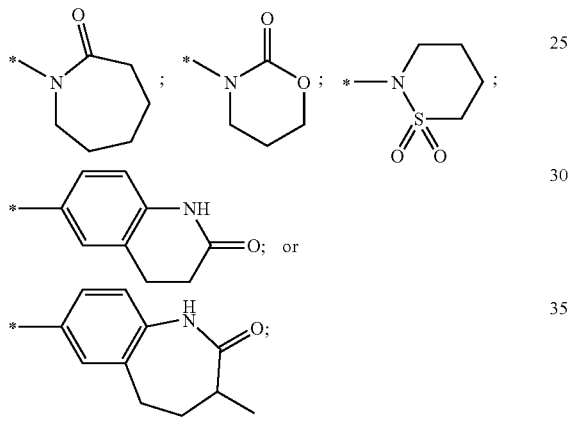

5 to 6 membered heteroaryl optionally substituted with one or more substituents independently selected from:
halo;
—C$_1$ to C$_6$ alkyl;
alkoxy optionally substituted with one or more substituents independently selected from:
halo;
5 or 6 membered heterocyclo; and
—C(O)NH$_2$ optionally substituted with C$_6$ to C$_8$ alkyl;
hydroxy;
haloalkyl;
cyano;
nitro;
—COOH;
amino optionally substituted with one or more substituents independently selected from:
—SO$_2$R$_x$;
6 to 8 membered aryl optionally substituted with one or more substituents independently selected from alkyl, halo, haloalkyl, cyano, alkoxy, COR$_x$ and haloalkoxy;
5 or 6 membered heteroaryl optionally substituted with one or more substituents independently selected from alkyl, halo, haloalkyl, cyano, alkoxy, haloalkoxy and —C$_6$ to C$_8$ aryl optionally substituted with halo;
—C$_5$ to C$_6$ heterocyclo optionally substituted with one or more substituents independently selected from hydroxy, alkyl and haloalkyl; and
—C$_1$ to C$_7$ alkyl optionally substituted with one or more substituents independently selected from:
5 or 6 membered heteroaryl optionally substituted with one or more alkyls, halos, and/or haloalkyls;
—C$_6$ to C$_8$ aryl optionally substituted with one or more substituents independently selected from alkyl, halo and haloalkyl;
alkoxy; and
halo;
—NR$_o$COR$_p$, wherein R$_p$ is:
amino optionally substituted with one or more C$_1$ to C$_6$ alkyls, which alkyls are optionally and independently substituted with one or more C$_6$ to C$_8$ aryls and/or alkoxys; or
5 or 6 membered heterocyclo optionally substituted with one or more C$_1$ to C$_6$ alkyls and/or C$_6$ to C$_8$ aryls;
—NR$_q$CONR$_q$R$_r$, wherein R$_r$ is:
—C$_1$ to C$_6$ alkyl substituted with one or more substituents independently selected from:
hydroxy;
alkoxy;
5 or 6 membered heterocyclo;
5 or 6 membered heteroaryl; and
—C$_6$ to C$_8$ aryl substituted with halo;
—C$_2$ to C$_6$ alkenyl optionally substituted with one or more halos;
—C$_1$ to C$_6$ alkoxy;
5 or 6 membered heterocyclo; or
5 to 6 membered heteroaryl optionally substituted with alkyl;
—NR$_t$COOR$_u$, wherein R$_u$ is:
—C$_1$ to C$_{12}$ alkyl substituted with one or more substituents independently selected from:
—C$_6$ to C$_8$ aryl substituted with one or more halos and/or haloalkyls;
alkoxy substituted with one or more alkoxys;
amino optionally substituted with one or more C$_1$ to C$_6$ alkyls;
—SO$_2$R$_w$;
—SO$_2$R$_x$; and
5 or 6 membered heteroaryl; and
—NR$_v$SO$_2$R$_w$, wherein R$_v$ is alkyl substituted with 4 to 7 membered heterocyclo;
or wherein R$_w$ is:
—C$_1$ to C$_6$ alkyl substituted with C$_6$ to C$_8$ aryl, which aryl is substituted with one or more substituents independently selected from haloalkyl, halo, alkoxy, and alkyl;
—C$_6$ to C$_8$ aryl;
amino substituted with heterocyclo or alkyl, which heterocyclo is optionally substituted with one or more substituents independently selected from halo, C$_1$ to C$_6$ alkoxy, alkoxycarbonyl, hydroxy, cyano, 5 or 6 membered heterocyclo and 5 or 6 membered heteroaryl, and which alkyl is substituted with one or more substituents independently selected from halo, C$_1$ to C$_6$ alkoxy, alkoxycarbonyl, hydroxy, cyano, 5 or 6 membered heterocyclo and 5 or 6 membered heteroaryl;

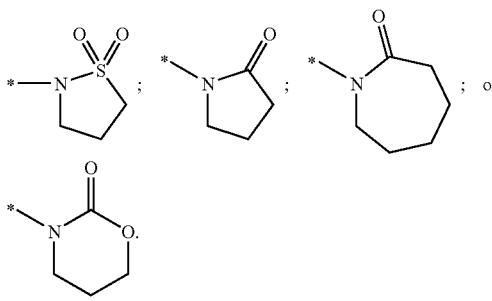

92. The compound of embodiment 89, wherein:
Z is:
- —$C_1$ to $C_6$ alkyl substituted with 5 or 6 membered heterocyclo; or
- 5 or 6 membered heterocyclo.

93. The compound of embodiment 89, wherein:
$R_1$ is:
- a 5 or 6 membered heterocyclo substituted with one or more substituents independently selected from:
  - hydroxy;
  - —$C_1$ to $C_6$ alkyl;
  - —$SO_2R_x$;
  - —C(O)—$C_6$ to $C_8$ aryl;
  - —$COR_p$; and
  - —$C(O)OR_x$; or
- 5 or 6 membered heteroaryl substituted with one or more independently selected from:
  - —$C_1$ to $C_6$ alkyl optionally substituted with one or more substituents independently selected from halo, $C_1$ to $C_6$ alkoxy, hydroxy, 5 or 6 membered heterocyclo, and 5 or 6 membered heteroaryl;
  - alkoxy;
  - halo;
  - alkylthio;
  - haloalkyl;
  - cyano;
  - amino optionally substituted with alkyl, which alkyl is optionally substituted with one or more substituents independently selected from halo, $C_1$ to $C_6$ alkoxy, hydroxy, cyano, 5 or 6 membered heterocyclo, and 5 or 6 membered heteroaryl;
  - heterocyclo;
  - nitro;
  - hydroxy;
  - —COOH;
  - —$CO_2R_x$;
  - —$COR_x$;
  - —$C(O)NH_2$ optionally substituted with one or more $C_1$ to $C_6$ alkyls, which alkyls are optionally substituted with one or more substituents independently selected from halo, $C_1$ to $C_6$ alkoxy, hydroxy, 5 or 6 membered heterocyclo, and 5 or 6 membered heteroaryl;
  - amido optionally substituted with one or more or more substituents independently selected from halo, $C_1$ to $C_6$ alkoxy, hydroxy, 5 or 6 membered heterocyclo, 5 or 6 membered heteroaryl, and $C_1$ to $C_6$ alkyl, which alkyl is optionally substituted with one or more $C_1$ to $C_6$ alkoxys;
  - —$C_1$ to $C_6$ alkyl substituted with one or more substituents independently selected from:
    - amino optionally substituted with one or more substituents independently selected from heterocyclo, alkoxy and alkyl, which alkyl is substituted with one or more alkoxys;
    - amido optionally substituted with $C_1$ to $C_6$ alkyl;
    - 5 or 6 membered heterocyclo substituted with $C_1$ to $C_6$ alkyl;
    - 5 or 6 membered heteroaryl; and
    - —$C_6$ to $C_8$ aryl;
    - —$SO_2R_x$;
  - —$C_2$ to $C_6$ alkenyl optionally substituted with —$SO_2R_x$;
  - —$C_1$ to $C_6$ alkoxy substituted with one or more substituents independently selected from:
    - hydroxy;
    - cyano;
    - alkoxy optionally substituted with alkoxy;
    - amino optionally substituted with one or more independently selected from 5 or 6 membered heteroaryl, 5 or 6 membered heterocyclo and alkyl, which alkyl is optionally substituted with one or more substituents independently selected from:
      - 5 or 6 membered heterocyclo; and
      - amino optionally substituted with one or more alkyl;
    - amino optionally substituted with heterocyclo;
    - amido optionally substituted with $C_1$ to $C_6$ alkyl;
    - 5 to 7 membered heterocyclo substituted with one or more substituents independently selected from hydroxy and $C_1$ to $C_6$ alkyl, which alkyl is optionally substituted with one or more substituents independently selected from:
      - —$C_1$ to $C_6$ alkoxy; and
      - —$C_6$ to $C_8$ alryl;
    - 5 or 6 membered heteroaryl optionally substituted with one or more substituents independently selected from:
      - —$C_1$ to $C_6$ alkyl; and
      - 4 to 7 membered heterocyclo; and
    - alkoxy;
  - —(O)-5 or 6 membered heterocyclo optionally substituted with one or more substituents independently selected from:
    - hydroxy;
    - —$C_1$ to $C_6$ alkyl;
    - —$SO_2R_x$;
    - —C(O)—$C_6$ to $C_8$ aryl;
    - —$COR_p$; and
    - —$C(O)OR_x$; or
  - —(O)-5 or 6 membered heteroaryl optionally substituted with one or more substituents independently selected from:
    - —$C_1$ to $C_6$ alkyl optionally substituted with one or more substituents independently selected from halo, $C_1$ to $C_6$ alkoxy, hydroxy, 5 or 6 membered heterocyclo and 5 or 6 membered heteroaryl;
    - alkoxy;
    - halo;
    - alkylthio;
    - haloalkyl;
    - cyano;
    - amino optionally substituted with alkyl, which alkyl is optionally substituted with one or more substituents independently selected from halo, $C_1$ to $C_6$ alkoxy, hydroxy, cyano, 5 or 6 membered heterocyclo and 5 or 6 membered heteroaryl;
    - heterocyclo;
    - nitro;
    - hydroxy;

—COOH;
—CO$_2$R$_x$;
—COR$_x$;
—C(O)NH$_2$ optionally substituted with one or more substituents independently selected from:
  —C$_1$ to C$_6$ alkyl optionally substituted with one or more substituents independently selected from halo, C$_1$ to C$_6$ alkoxy, hydroxy, 5 or 6 membered heterocyclo and 5 or 6 membered heteroaryl; and
  amido optionally substituted with one or more or more substituents independently selected from halo, C$_1$ to C$_6$ alkoxy, hydroxy, 5 or 6 membered heterocyclo, 5 or 6 membered heteroaryl, and C$_1$ to C$_6$ alkyl, which alkyl is optionally substituted with one or more C$_1$ to C$_6$ alkoxys;
—C(O)NH$_2$ optionally substituted with one or more C$_1$ to C$_6$ alkyls, which alkyls are optionally substituted with one or more substituents independently selected from halo, C$_1$ to C$_6$ alkoxy, hydroxy, 5 or 6 membered heterocyclo and 5 or 6 membered heteroaryl;
—C(O)-3 to 7 membered heterocyclo optionally substituted with one or more substituents independently selected from:
  —C$_6$ to C$_8$ aryl;
  5 or 6 membered heteroaryl; and
  —C$_1$ to C$_6$ alky further optionally substituted with one or more substituted with hydroxys;
—SO$_2$R$_x$ optionally substituted with one or more substituents independently selected from:
  5 or 6 membered heterocyclo;
  —C$_6$ to C$_8$ aryl; and
  5 or 6 membered heteroaryl; or
alkylthio optionally substituted with one or more substituents independently selected from:
  5 or 6 membered heterocyclo;
  —C$_6$ to C$_8$ aryl; and
  5 or 6 membered heteroaryl;
—C(O)-5 or 6 membered heteroaryl;
—C(O)—C$_6$ to C$_8$ aryl;
—COOH; or
—OR$_{kk}$, wherein R$_{kk}$ is:
  —C$_6$ to C$_8$ aryl optionally substituted with one or more substituents independently selected from halo, C$_1$ to C$_6$ alkyl, C$_1$ to C$_6$ alkoxy, and C$_1$ to C$_6$ haloalkyl.

94. The compound of embodiment 89, wherein:
R$_2$ is:
—C$_1$ to C$_6$ alkyl substituted with one or more substituents independently selected from:
  5 or 6 membered heterocyclo;
  5 or 6 membered heteroaryl;
  —C$_6$ to C$_8$ aryl;
  amido optionally substituted with C$_1$ to C$_6$ alkyl; and
  amino optionally substituted with one or more substituents independently selected from heterocyclo, alkoxy and alkyl, which alkyl is optionally substituted with one or more alkoxy; and
  —SO$_2$R$_x$;
—C$_2$ to C$_6$ alkenyl optionally substituted with SO$_2$R$_x$;
alkylthio optionally substituted with one or more substituents independently selected from:
  5 or 6 membered heteroaryl optionally substituted with alkyl;
  5 or 6 membered heterocyclo;
  —C$_6$ to C$_8$ aryl; and
  —C$_1$ to C$_6$ alkyl;
—SO$_2$R$_x$ optionally substituted with one or more substituents independently selected from:
  5 or 6 membered heteroaryl optionally substituted with one or more C$_1$ to C$_6$ alkyls;
  5 or 6 membered heterocyclo;
  —C$_6$ to C$_8$ aryl; and
  —C$_1$ to C$_6$ alkyl;
—S(O)R$_x$ optionally substituted with one or more substituents independently selected from:
  5 or 6 membered heteroaryl;
  5 or 6 membered heterocyclo;
  —C$_6$ to C$_8$ aryl; and
  —C$_1$ to C$_6$ alkyl;
alkoxy substituted with one or more substituents independently selected from:
  halo;
  hydroxy;
  cyano;
  alkoxy optionally substituted with alkoxy;
  amino substituted with one or more substituents independently selected from —SO$_2$—C$_1$ to C$_4$ alkyl and alkyl, which alkyl is substituted with one or more substituents independently selected from:
    5 or 6 membered heterocyclo; and
    amino optionally substituted with one or more alkyls;
  amido substituted with C$_1$ to C$_6$ alkyl;
—S-5 or 6 membered heterocyclo;
—S-5 or 6 membered heteroaryl optionally substituted with C$_1$ to C$_6$ alkyl;
—S—C$_1$ to C$_6$ alkyl optionally substituted with one or more substituents independently selected from:
  —C$_6$ to C$_8$ aryl optionally substituted with one or more substituents independently selected from alkyl, haloakyl and halo; and
  —C$_5$ to C$_6$ heteroaryl optionally substituted with one or more substituents independently selected from alkyl, haloakyl and halo;
—S—C$_6$ to C$_8$ aryl;
sulfinyl-5 or 6 membered heterocyclo;
sulfinyl-5 or 6 membered heteroaryl;
sulfinyl-C$_1$ to C$_6$ alkyl optionally substituted with one or more substituents independently selected from:
  —C$_6$ to C$_8$ aryl optionally substituted with one or more substituents independently selected from alkyl, haloakyl and halo; and
  —C$_5$ to C$_6$ heteroaryl optionally substituted with one or more substituents independently selected from alkyl, haloakyl and halo;
sulfinyl-C$_6$ to C$_8$ aryl;
sulfonyl-5 or 6 membered heterocyclo;
sulfonyl-5 or 6 membered heteroaryl optionally substituted with C$_1$ to C$_6$ alkyl;
sulfonyl-C$_1$ to C$_6$ alkyl optionally substituted with one or more substituents independently selected from:
  —C$_6$ to C$_8$ aryl optionally substituted with one or more substituents independently selected from alkyl, haloakyl and halo; and
  —C$_5$ to C$_6$ heteroaryl optionally substituted with one or more substituents independently selected from alkyl, haloakyl and halo;
sulfonyl-C$_6$ to C$_8$ aryl;
5 to 7 membered heterocyclo optionally substituted with one or more substituents independently selected from hydroxy, =O, heterocyclo, and C$_1$ to C$_6$ alkyl, which alkyl is optionally substituted with one or more substituents independently selected from:
  —C$_1$ to C$_6$ alkoxy; and
  —C$_6$ to C$_8$ aryl;

5 or 6 membered heteroaryl optionally substituted with one or more substituents independently selected from:
- —$C_1$ to $C_6$ alkyl optionally substituted with one or more alkoxys;
- 4 to 7 membered heterocyclo; and
- alkoxy; and —$C_6$ to $C_8$ aryl;

—$C_6$ to $C_8$ aryl;

—(O)-5 or 6 membered heterocyclo substituted with one or more substituents independently selected from:
- hydroxy;
- =O;
- —$C_1$ to $C_6$ alkyl;
- —$SO_2R_x$;
- —C(O)—$C_6$ to $C_8$ aryl;
- —$COR_p$; and
- —$C(O)OR_x$; or —(O)-5 or 6 membered heteroaryl substituted with one or more substituents independently selected from:
- —$C_1$ to $C_6$ alkyl optionally substituted with one or more substituents independently selected from halo, $C_1$ to $C_6$ alkoxy, hydroxy, 5 or 6 membered heterocyclo and 5 or 6 membered heteroaryl;
- alkoxy;
- halo;
- alkylthio;
- haloalkyl;
- cyano;
- amino optionally substituted with alkyl, which alkyl is optionally substituted with one or more substituents independently selected from halo, $C_1$ to $C_6$ alkoxy, hydroxy, cyano, 5 or 6 membered heterocyclo and 5 or 6 membered heteroaryl;
- heterocyclo;
- nitro;
- hydroxy;
- —COOH;
- —$CO_2R_x$;
- —$COR_x$;
- —$C(O)NH_2$ optionally substituted with one or more $C_1$ to $C_6$ alkyls, which alkyls are optionally substituted with one or more substituents independently selected from halo, $C_1$ to $C_6$ alkoxy, hydroxy, 5 or 6 membered heterocyclo and 5 or 6 membered heteroaryl;
- amido optionally substituted with one or more substituents independently selected from halo, $C_1$ to $C_6$ alkoxy, hydroxy, 5 or 6 membered heterocyclo, 5 or 6 membered heteroaryl, and $C_1$ to $C_6$ alkyl, which alkyl is optionally substituted with one or more $C_1$ to $C_6$ alkoxys;

—C(O)-3 to 7 membered heterocyclo optionally substituted with one or more substituents independently selected from:
- —$C_6$ to $C_8$ aryl;
- 5 or 6 membered heteroaryl; and
- —$C_1$ to $C_6$ alkyl optionally substituted with one or more hydroxys;

—C(O)-5 or 6 membered heteroaryl;

C(O)—$C_6$ to $C_8$ aryl;

—COOH;

—$C(O)NH_2$ optionally substituted with one or more $C_1$ to $C_6$ alkyls, which alkyls are optionally substituted with one or more substituents independently selected from halo, $C_1$ to $C_6$ alkoxy, hydroxy, 5 or 6 membered heterocyclo and 5 or 6 membered heteroaryl;

amido substituted with one or more $C_1$ to $C_6$ alkyls, which alkyls are optionally substituted with one or more $C_1$ to $C_6$ alkoxys;

amino substituted with one or more substituents independently selected from:
- —$SO_2R_x$;
- 6 to 8 membered aryl optionally substituted with one or more substituents independently selected from alkyl, halo, haloalkyl, cyano, alkoxy, $COR_x$ and haloalkoxy;
- 5 or 6 membered heteroaryl optionally substituted with one or more substituents independently selected from alkyl, halo, haloalkyl, cyano, alkoxy, haloalkoxy and —$C_6$ to $C_8$ aryl optionally substituted with halo;
- —$C_5$ to $C_6$ heterocyclo optionally substituted with one or more substituents independently selected from hydroxy, alkyl and haloalkyl;
- —$C_1$ to $C_7$ alkyl optionally substituted with one or more substituents independently selected from:
  - 5 or 6 membered heteroaryl optionally substituted with one or more substituents independently selected from alkyl, halo and haloalkyl;
  - —$C_6$ to $C_8$ aryl optionally substituted with one or more substituents independently selected from alkyl, halo and haloalkyl;
  - alkoxy; and
  - halo;

5 or 6 membered heteroaryl substituted with one or more substituents independently selected from:
- —$C_1$ to $C_6$ alkyl optionally substituted with one or more substituents independently selected from halo, $C_1$ to $C_6$ alkoxy, hydroxy, 5 or 6 membered heterocyclo and 5 or 6 membered heteroaryl;
- alkoxy;
- halo;
- alkylthio;
- haloalkyl;
- cyano;
- amino optionally substituted with one more alkyls, which alkyls are optionally substituted with one or more substituents independently selected from halo, $C_1$ to $C_6$ alkoxy, hydroxy, cyano, 5 or 6 membered heterocyclo and 5 or 6 membered heteroaryl;
- heterocyclo;
- nitro;
- hydroxy;
- —COOH;
- —$CO_2R_x$;
- —$COR_x$;
- —$C(O)NH_2$ optionally substituted with one or more $C_1$ to $C_6$ alkyls, which alkyls are optionally substituted with one or more substituents independently selected from halo, $C_1$ to $C_6$ alkoxy, hydroxy, 5 or 6 membered heterocyclo and 5 or 6 membered heteroaryl;
- amido optionally substituted with one or more substituents independently selected from halo, $C_1$ to $C_6$ alkoxy, hydroxy, 5 or 6 membered heterocyclo, 5 or 6 membered heteroaryl, and $C_1$ to $C_6$ alkyl, which alkyd is optionally substituted with one or more $C_1$ to $C_6$ alkoxys;

5 or 6 membered heterocyclo optionally substituted with one or more substituents independently selected from:
- hydroxy;
- =O;
- —$C_1$ to $C_6$ alkyl;
- —$SO_2R_x$;
- —C(O)—$C_6$ to $C_8$ aryl;

—COR$_p$; and
—C(O)OR$_x$;
OR$_{kk}$, wherein R$_{kk}$ is:
- —C$_6$ to C$_8$ aryl optionally substituted with one or more substituents independently selected from halo, C$_1$ to C$_6$ alkyl, C$_1$ to C$_6$ alkoxy, and C$_1$ to C$_6$ haloalkyl;
- 5 to 6 membered heterocyclo optionally substituted with C$_1$ to C$_6$ alkyl, which alkyl is optionally substituted with C$_6$ to C$_8$ aryl; or
- 5 to 6 membered heteroaryl substituted with one or more substituents independently selected from halo, C$_1$ to C$_6$ alkyl, C$_1$ to C$_6$ alkoxy, and C$_1$ to C$_6$ haloalkyl;
- —SO$_2$R$_x$; or
- —Si(R$_x$)$_3$;

—OC(O)NHR$_x$ wherein R$_x$ is optionally substituted with
- —C$_6$ to C$_8$ aryl;

—OC(O)N(R$_x$)$_2$; or

95. The compound of embodiment 89, wherein R$_3$ is nitro.
96. The compound of embodiment 89, wherein:
X is cyano or hydrogen;
Y is:
- —C$_6$ to C$_8$ aryl optionally substituted with one or more substituents independently selected from:
  - halo;
  - —C$_1$ to C$_6$ alkyl;
  - amino optionally substituted with one or more substituents independently selected from:
    - —SO$_2$R$_x$;
    - 5 or 6 membered heteroaryl optionally substituted with one or more alkyl;
    - —C$_1$ to C$_7$ alkyl;
  - —NR$_t$COOR$_u$, wherein R$_t$ is hydrogen, and wherein R$_u$ is C$_1$ to C$_{12}$ alkyl;
  - —NR$_v$SO$_2$R$_w$, wherein R$_v$ is hydrogen, and wherein R$_w$ is C$_1$ to C$_6$ alkyl or amino optionally substituted with alkyl;

Z is C$_1$ to C$_6$ alkyl;
R is hydrogen;
R$_1$ is hydrogen;
R$_2$ is —(O)-5 or 6 membered heteroaryl substituted with cyano; and
R$_3$ is hydrogen.

97. The compound of embodiment 96, wherein the C$_6$ to C$_8$ aryl is phenyl.
98. The compound of embodiment 97, wherein:
X is cyano;
Y is phenyl para substituted with NR$_v$SO$_2$R$_w$, wherein R$_v$ is hydrogen, and wherein R$_w$ is C$_1$ to C$_6$ alkyl; and
R$_2$ is —(O)-5 or 6 membered heteroaryl substituted with cyano at the ortho position.

99. The compound of embodiment 97, wherein:
X is cyano;
Y is phenyl substituted with C$_1$ to C$_6$ alkyl and NR$_v$SO$_2$R$_w$, wherein R$_v$ is hydrogen, and wherein R$_w$ is C$_1$ to C$_6$ alkyl; and
R$_2$ is —(O)-5 or 6 membered heteroaryl substituted with cyano at the ortho position.

100. The compound of embodiment 97, wherein:
X is cyano;
Y is phenyl substituted with halo and NR$_v$SO$_2$R$_w$, wherein R$_v$ is hydrogen, and wherein R$_w$ is C$_1$ to C$_6$ alkyl; and
R$_2$ is —(O)-5 or 6 membered heteroaryl substituted with cyano at the ortho position.

101. The compound of embodiment 97, wherein:
X is hydrogen;
Y is phenyl is para substituted with —NR$_t$COOR$_u$, wherein R$_t$ is hydrogen, and wherein R$_u$ is C$_1$ to C$_{12}$ alkyl;
Z is cyclobutyl, cyclopropyl, cyclopropylmethyl, ethyl or cyclopentyl; and
R$_2$ is —(O)-5 or 6 membered heteroaryl substituted with cyano at the ortho position.

102. The compound of embodiment 89, wherein:
X is cyano;
Y is:
- —C$_6$ to C$_8$ aryl optionally substituted with one or more substituents independently selected from:
  - —NR$_t$COOR$_u$, wherein R$_t$ is hydrogen, and wherein R$_u$ is C$_1$ to C$_{12}$ alkyl optionally substituted with one or more halo; or
  - —NR$_v$SO$_2$R$_w$, wherein R$_v$ is hydrogen, and wherein R$_w$ is C$_1$ to C$_6$ alkyl;

Z is C$_1$ to C$_6$ alkyl;
R is hydrogen;
R$_1$ is hydrogen;
R$_2$ is —(O)-5 or 6 membered heterocyclo substituted with one or more =O; and
R$_3$ is hydrogen.

103. A compound which is selected from the compound range: 1330-2128 and 2600-3348.
104. The compound of embodiment 103 selected from:

2696

2722

125
-continued
2701
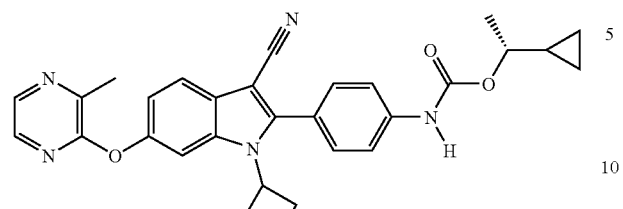
2788
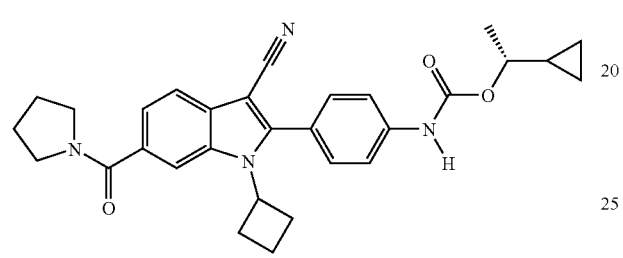
2852
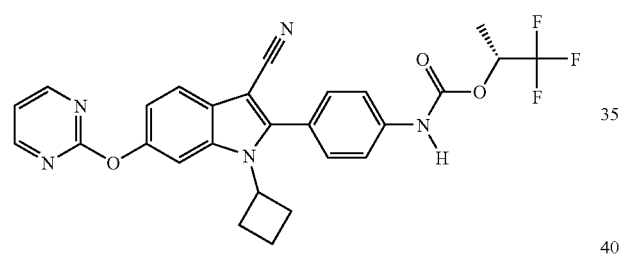
2866
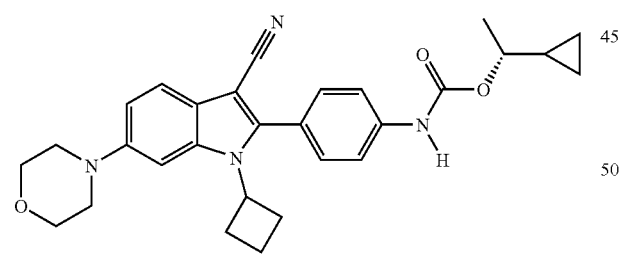
2879

126
-continued
2888
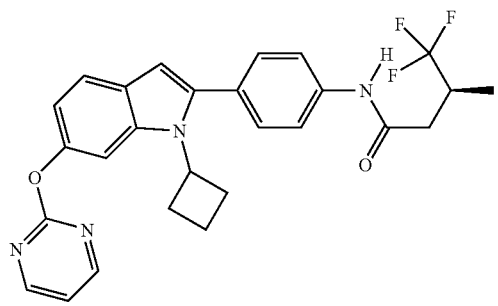
2892
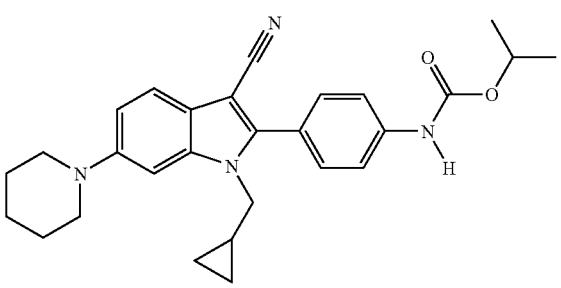
2895
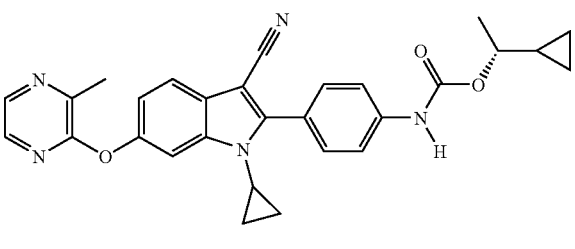
2907
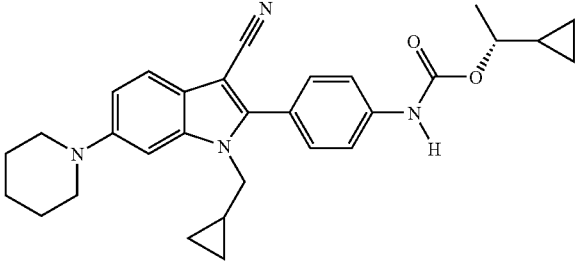
2922
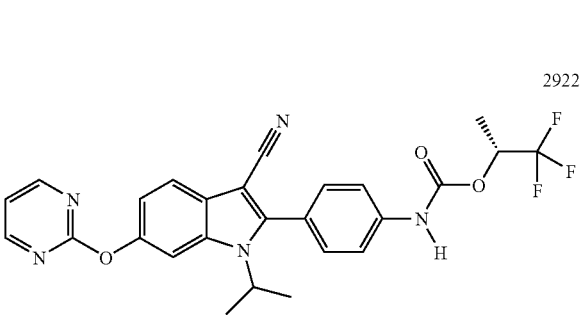

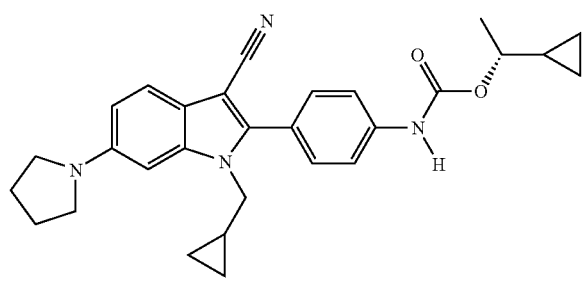
2976

3194

3239
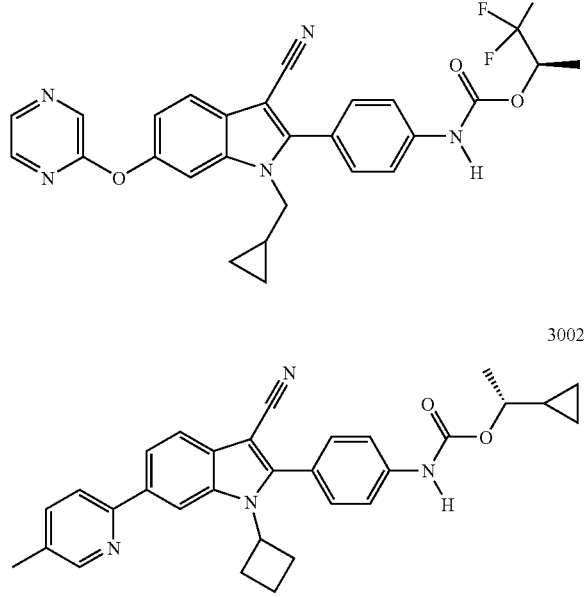
2978
2925
3002
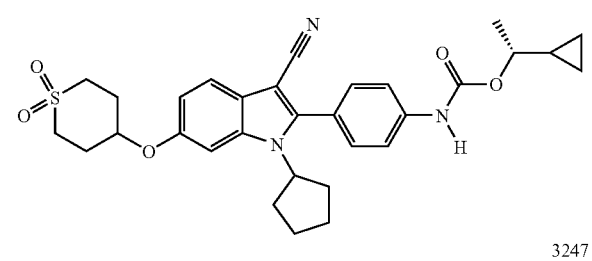
3245
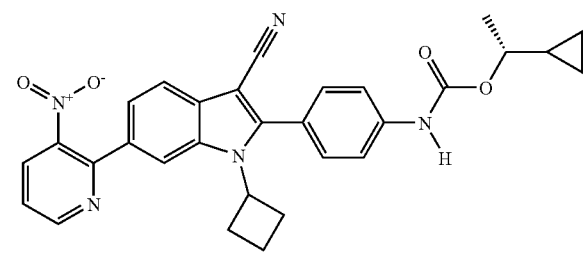
3247
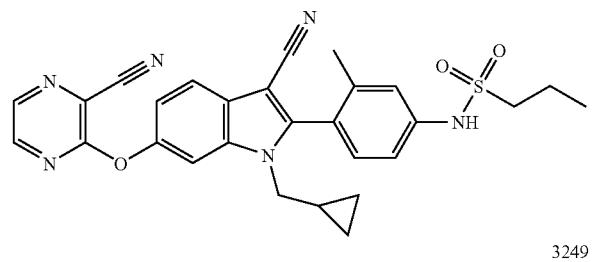
3248
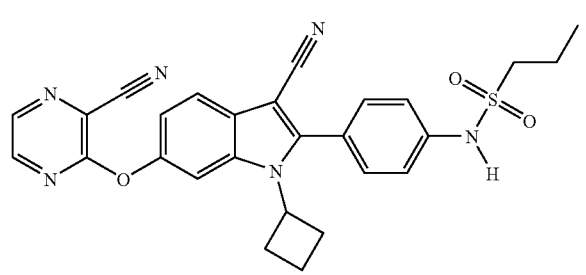
3192
3249

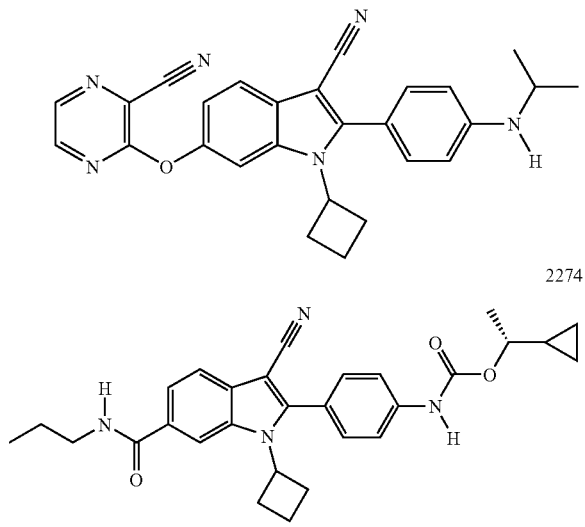

105. A composition comprising the compound of embodiment 1 and one or more pharmaceutically acceptable excipient(s).
106. A composition comprising the compound of embodiment 39 and one or more pharmaceutically acceptable excipient(s).
107. A composition comprising the compound of embodiment 77 and one or more pharmaceutically acceptable excipient(s).
108. A composition comprising the compound of embodiment 83 and one or more pharmaceutically acceptable excipient(s).
109. A composition comprising the compound of embodiment 89 and one or more pharmaceutically acceptable excipient(s).
110. A method for treating Hepatitis C viral infection in a subject in need thereof, comprising administering to the subject an effective amount of one or more compound(s) according to embodiment 1 or a pharmaceutical composition comprising an effective amount of one or more compound(s) according to embodiment 1.
111. A method for treating Hepatitis C viral infection in a subject in need thereof, comprising administering to the subject an effective amount of one or more compound(s) according to embodiment 39 or a pharmaceutical composition comprising an effective amount of one or more compound(s) according to embodiment 39.
112. A method for treating Hepatitis C viral infection in a subject in need thereof, comprising administering to the subject an effective amount of one or more compound(s) according to embodiment 77 or a pharmaceutical composition comprising an effective amount of one or more compound(s) according to embodiment 77.
113. A method for treating Hepatitis C viral infection in a subject in need thereof, comprising administering to the subject an effective amount of one or more compound(s) according to embodiment 83 or a pharmaceutical composition comprising an effective amount of one or more compound(s) according to embodiment 83.
114. A method for treating Hepatitis C viral infection in a subject in need thereof, comprising administering to the subject an effective amount of one or more compound(s) according to embodiment 89 or a pharmaceutical composition comprising an effective amount of one or more compound(s) according to embodiment 89.
115. A method for treating an infection by a virus in a subject in need thereof, wherein the virus comprises an internal ribosome entry site, comprising administering to the subject an effective amount of one or more compound(s) according to embodiment 1 or a pharmaceutical composition comprising an effective amount of one or more compound(s) according to embodiment 1.
116. A method for treating an infection by a virus in a subject in need thereof, wherein the virus comprises an internal ribosome entry site, comprising administering to the subject an effective amount of one or more compound(s) according to embodiment 39 or a pharmaceutical composition comprising an effective amount of one or more compound(s) according to embodiment 39.
117. A method for treating an infection by a virus in a subject in need thereof, wherein the virus comprises an internal ribosome entry site, comprising administering to the subject an effective amount of one or more compound(s) according to embodiment 77 or a pharmaceutical composition comprising an effective amount of one or more compound(s) according to embodiment 77.
118. A method for treating an infection by a virus in a subject in need thereof, wherein the virus comprises an internal ribosome entry site, comprising administering to the subject an effective amount of one or more compound(s) according to embodiment 83 or a pharmaceutical composition comprising an effective amount of one or more compound(s) according to embodiment 83.
119. A method for treating an infection by a virus in a subject in need thereof, wherein the virus comprises an internal ribosome entry site, comprising administering to the subject an effective amount of one or more compound(s) according to embodiment 89 or a pharmaceutical composition comprising an effective amount of one or more compound(s) according to embodiment 89.

In yet another embodiment, the present invention includes compounds of Formulas I, I-X, I-XI, I-XII, I-Xa, I-XIa, I-XIIa, I-XIb, I-XIc, IIa, IIb, IIc, IId, or IIe, wherein Y is a —NR$_t$COOR$_u$ group and R$_u$ is a C$_1$ to C$_6$ alkyl. In an embodiment, compounds are provided wherein Y is a —NR$_t$COOR$_u$ group and R$_u$ is a C$_1$ to C$_6$ alkyl in the para position. In another embodiment, the present invention includes compounds of Formulas I, I-X, I-XI, I-XII, I-Xa, I-XIa, I-XIIa, I-XIb, I-XIc, IIa, IIb, IIc, IId, or IIe, wherein Y is a —NR$_t$COOR$_u$ group and R$_u$ is a branched C$_1$ to C$_6$ alkyl. In an embodiment of Formulas I, I-X, I-XI, I-XII, I-Xa, I-XIa, I-XIIa, I-XIb, I-XIc, IIa, IIb, IIc, IId, or IIe, Y is a —NR$_t$COOR$_u$ group and R$_u$ is a branched C$_1$ to C$_6$ alkyl in the para position. In another embodiment, the present invention includes compounds of Formulas I, I-X, I-XI, I-XII, I-Xa, I-XIa, I-XIIa, I-XIb, I-XIc, IIa, IIb, IIc, IId, or IIe, wherein Y is a —NR$_t$COOR$_u$ group and R$_u$ is an isopropyl. In another embodiment, the present invention includes compounds of I-X, I-XI, I-XII, I-Xa, I-XIa, I-XIIa, I-XIb, I-XIc, IIa, IIb, IIc, IId, or IIe, wherein Y is a —NR$_t$COOR$_u$ group and R$_u$ is a methyl cyclopropyl. In another embodiment, the present invention includes compounds of I-X, I-XI, I-XII, I-Xa, I-XIa, I-XIIa, I-XIb, I-XIc, IIa, IIb, IIc, IId, or IIe, wherein Y is a —NR$_t$COOR$_u$ group and R$_u$ is an ethyl cyclopropyl.

In another embodiment, the present invention includes compounds of I-X, I-XI, I-XII, I-Xa, I-XIa, I-XIIa, I-XIb, I-XIc, IIa, IIb, IIc, IId, or IIe, wherein Y is a —NR$_v$SO$_2$R$_w$ group, R$_v$ is a hydrogen, and where R$_w$ is a C$_1$ to C$_6$ alkyl. In a further embodiment, the present invention includes compounds wherein Y is a —NR$_v$SO$_2$R$_w$ group and R$_w$ is a propyl group.

In an embodiment of the present invention, compounds are provided wherein Y is a C$_6$ to C$_8$ aryl that is substituted. In an embodiment of the present invention, compounds are provided wherein Y is a phenyl that is substituted. In an embodiment of the present invention, compounds are provided wherein Y is a C$_6$ to C$_8$ aryl that has one, two, three, or four substituents. In another embodiment of the compounds of the present invention, Y is a C$_6$ to C$_8$ aryl that has one, two, or three substituents. In another embodiment, Y is a C$_6$ to C$_8$ aryl that has one or two substituents. In a further embodiment, Y is a C$_6$ to C$_8$ aryl that has three substituents. In a further embodiment, Y is a C$_6$ to C$_8$ aryl that has two substituents. In a further embodiment, Y is a C$_6$ to C$_8$ aryl that has one substituent.

In another embodiment of the present invention, compounds are provided wherein Y is a C$_6$ to C$_8$ aryl with at least one substituent in the ortho, meta, or para position. In a further embodiment, Y is a C$_6$ to C$_8$ aryl with at least one substituent in the meta or para position. In yet another embodiment, Y is a C$_6$ to C$_8$ aryl with a substituent in the para position.

In an embodiment of the present invention, compounds are provided wherein Y is a C$_6$ to C$_8$ aryl, optionally substituted with one of the following in the para position:
an alkoxy,
an amino optionally substituted with one or more of the following:
—SO$_2$R$_x$ groups, or
—C$_1$ to C$_6$ alkyl, the C$_1$ to C$_6$ alkyl optionally and independently substituted with one or more 5 or 6 membered heteroaryl group,
—OC(O)NHR$_x$,
—OC(O)N(R$_x$)$_2$,
—OC(O)NH(OR$_x$),
—OC(O)NR$_x$(OR$_x$),
—OC(O)N(OR$_x$)$_2$,
—OC(O)R$_{ab}$, wherein R$_{ab}$ is a 5 or 6 membered heterocycle group,
a —NR$_o$COR$_p$ group, where R$_p$ is:
a C$_1$ to C$_6$ alkyl,
an amino group optionally substituted with one or more C$_1$ to C$_6$ alkyl groups where the C$_1$ to C$_6$ alkyl groups are optionally and independently substituted with one or more C$_6$ to C$_8$ aryl groups and/or alkoxy groups,
a 5 or 6 membered heterocycle, optionally substituted with one or more C$_1$ to C$_6$ alkyl or C$_6$ to C$_8$ aryl groups,
and where R$_o$ is:
a hydrogen,
a C$_1$ to C$_6$ alkyl,
a —NR$_q$CONR$_q$R$_r$ group, where R$_q$ is a hydrogen, and where R$_r$ is:
a C$_1$ to C$_6$ alkyl optionally substituted with one or more of the following:
a hydroxyl,
an alkoxy,
a 5 or 6 membered heterocycle,
a 5 or 6 membered heteroaryl, or
a C$_6$ to C$_8$ aryl optionally substituted with a halo,
a C$_2$ to C$_6$ alkylene group,
a C$_1$ to C$_6$ alkoxy group,
a 5 or 6 membered heterocycle group,
a —NR$_t$COOR$_u$ group, where R$_u$ is:
a C$_1$ to C$_{12}$ alkyl, optionally substituted with one or more groups independently selected from the following:

a C$_6$ to C$_8$ aryl optionally substituted with halo,
an alkoxy group optionally substituted with one or more alkoxy groups,
an amino optionally substituted with one or more C$_1$ to C$_6$ alkyl,
halo, or
a 5 or 6 membered heteroaryl,
a C$_2$ to C$_6$ alkylene,
a C$_6$ to C$_8$ aryl, optionally substituted with halo,
and R$_t$ is:
a hydrogen;
a —NHR$_{bb}$ group, where R$_{bb}$ is:
a —C(=S)NH$_2$ group, or
a —PO(OR$_x$)$_2$, where R$_x$ is as defined above;
a —NR$_v$SO$_2$R$_w$ group, where R$_v$ is a hydrogen, and where R$_w$ is a C$_1$ to C$_6$ alkyl,

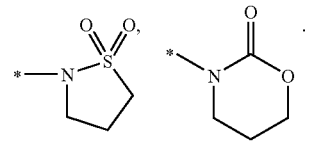

In some embodiments, Y is selected from the Y substituents of compounds 1330-2128, and 2600-3348.

In other embodiments of the present invention, compounds are provided wherein Y is selected from the group consisting of the following substituents:

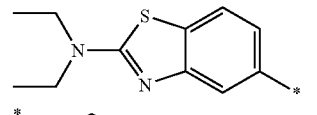

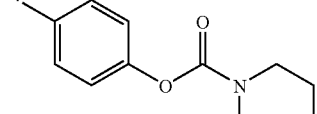

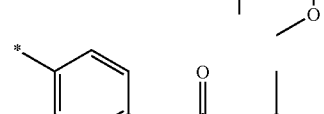

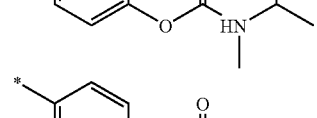

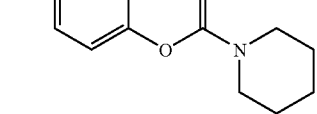

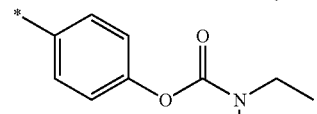

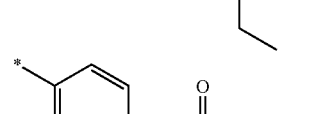

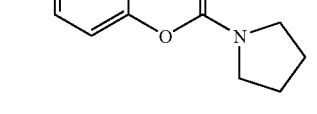

-continued
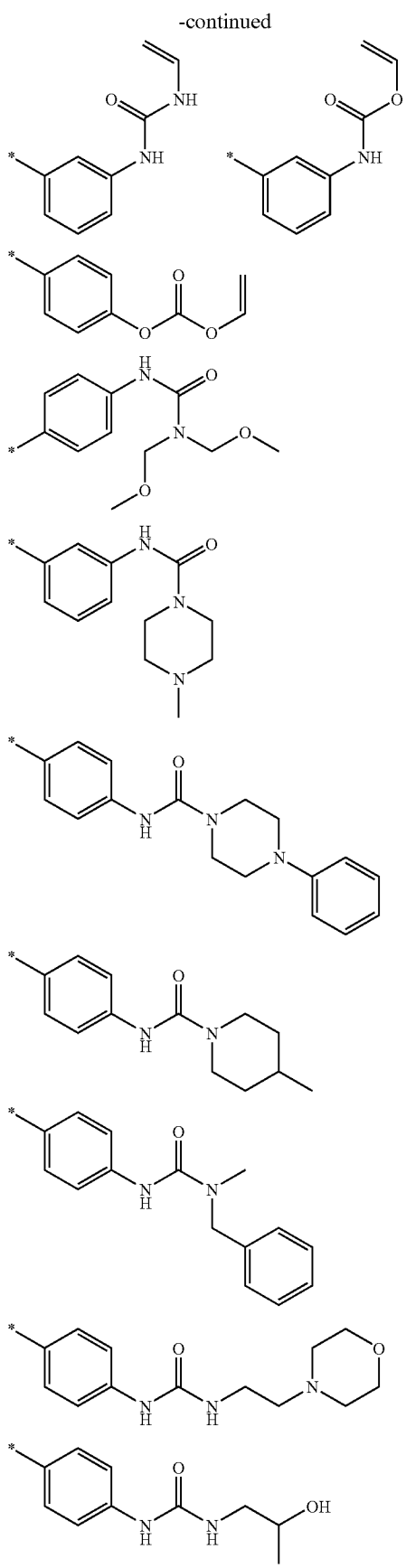
-continued
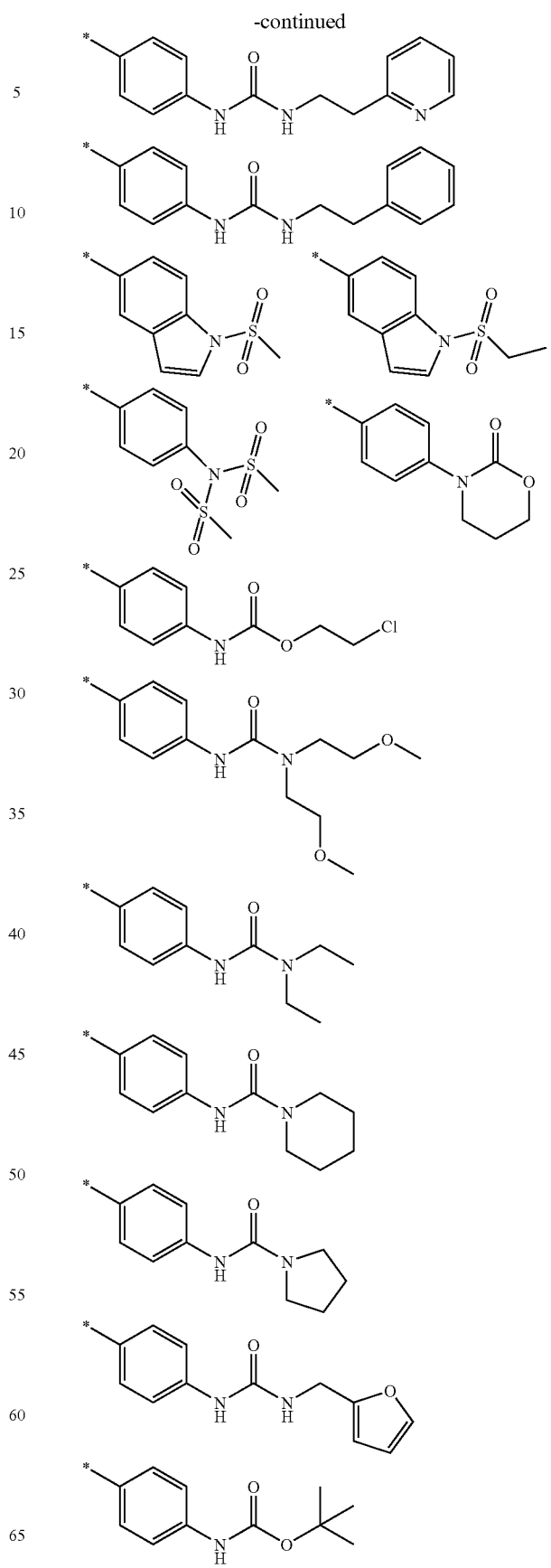

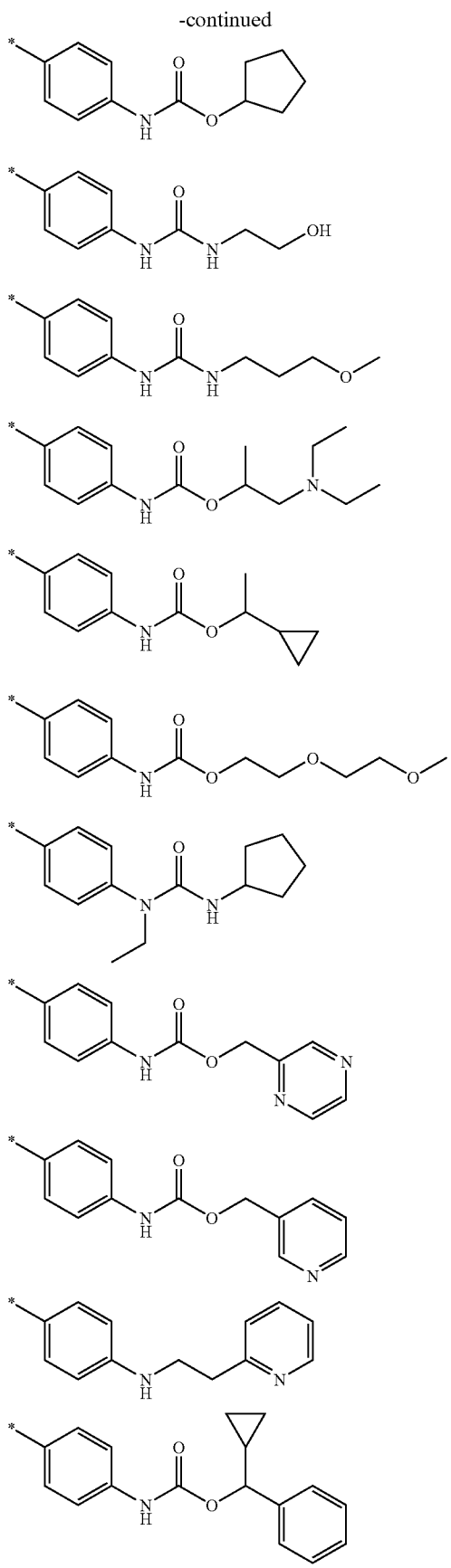
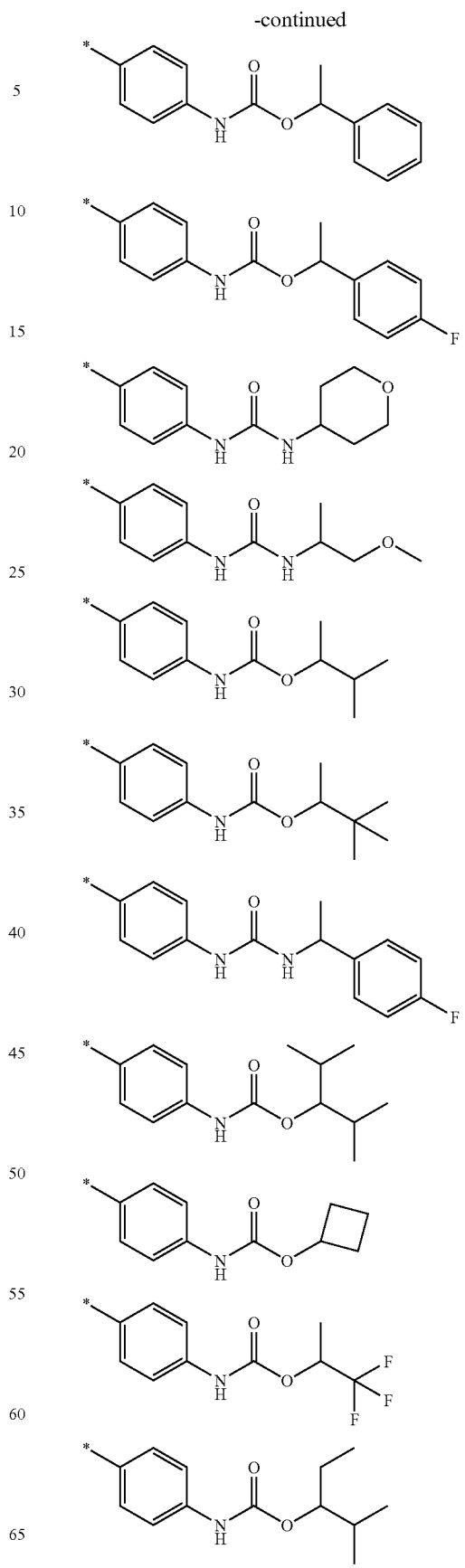

-continued
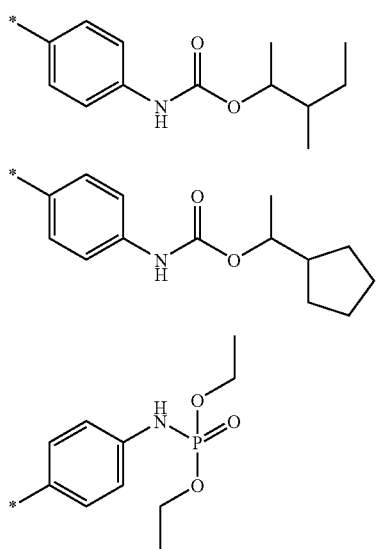
In other non-limiting embodiments of the present invention, compounds are provided wherein Y is selected from the group consisting of
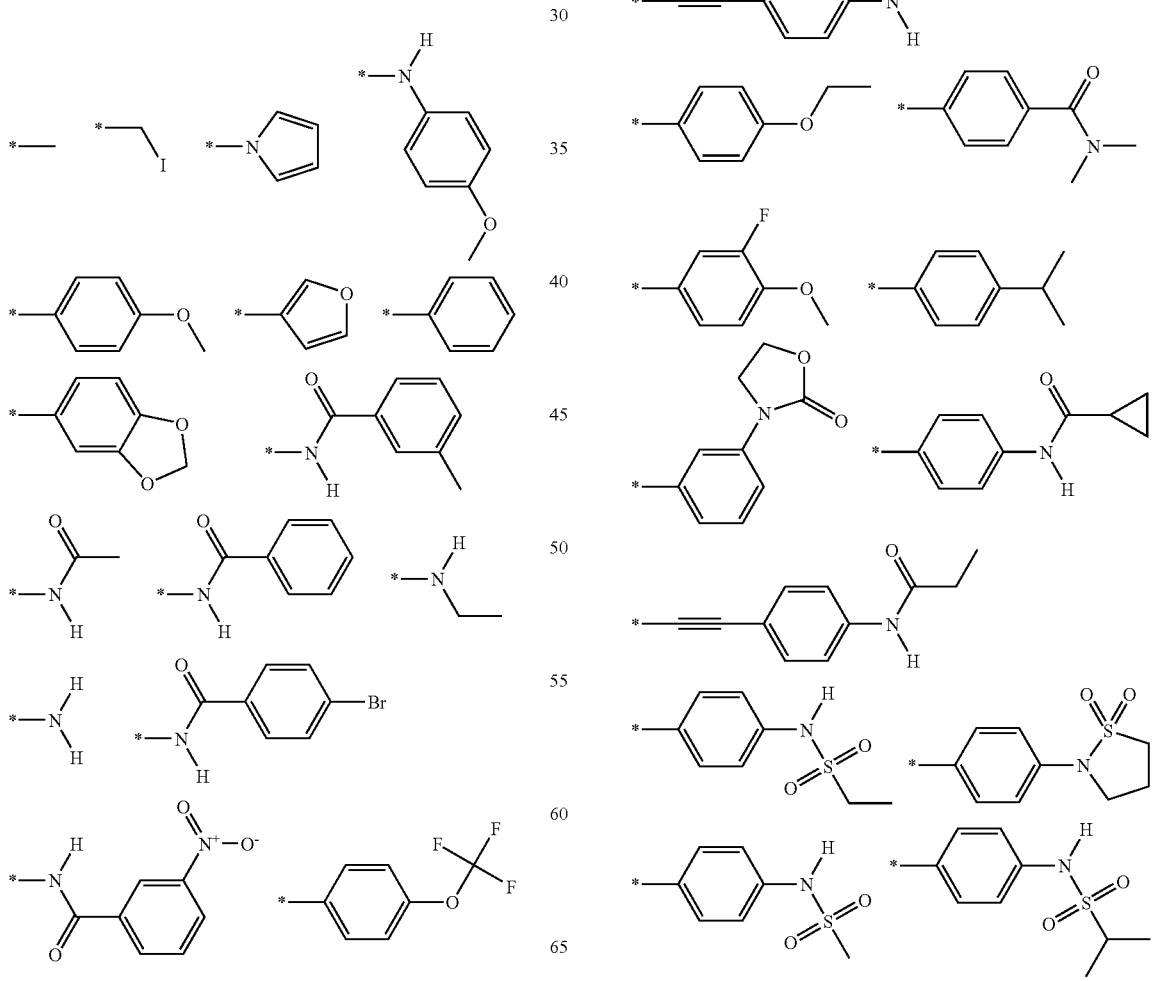

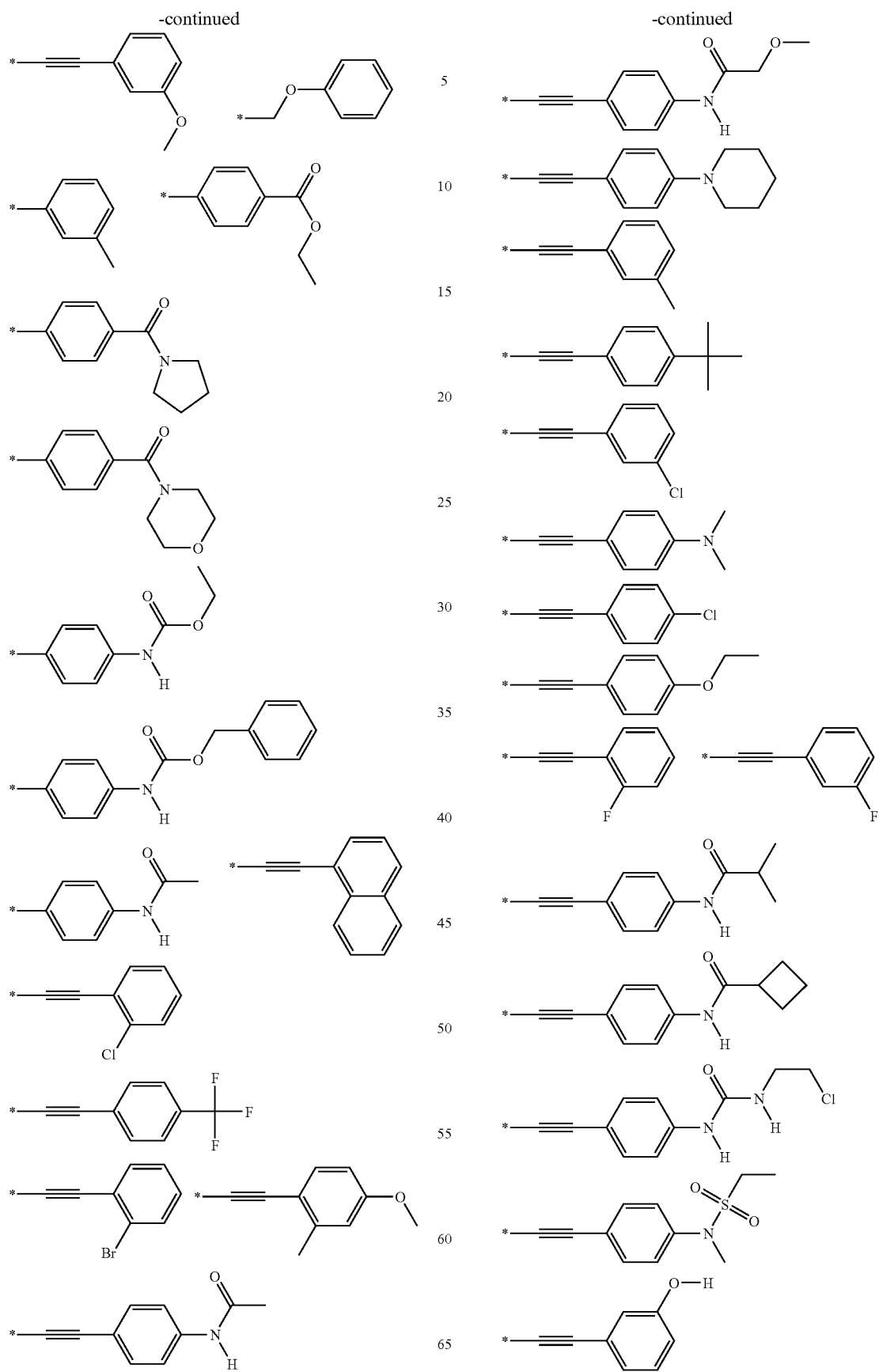

-continued
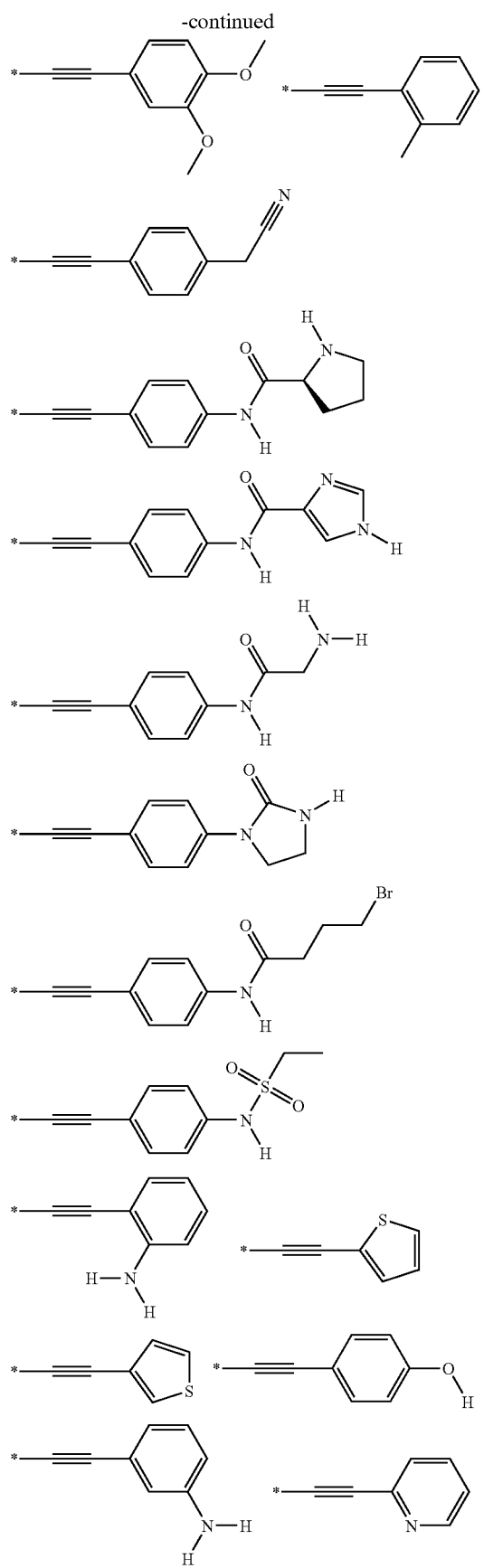
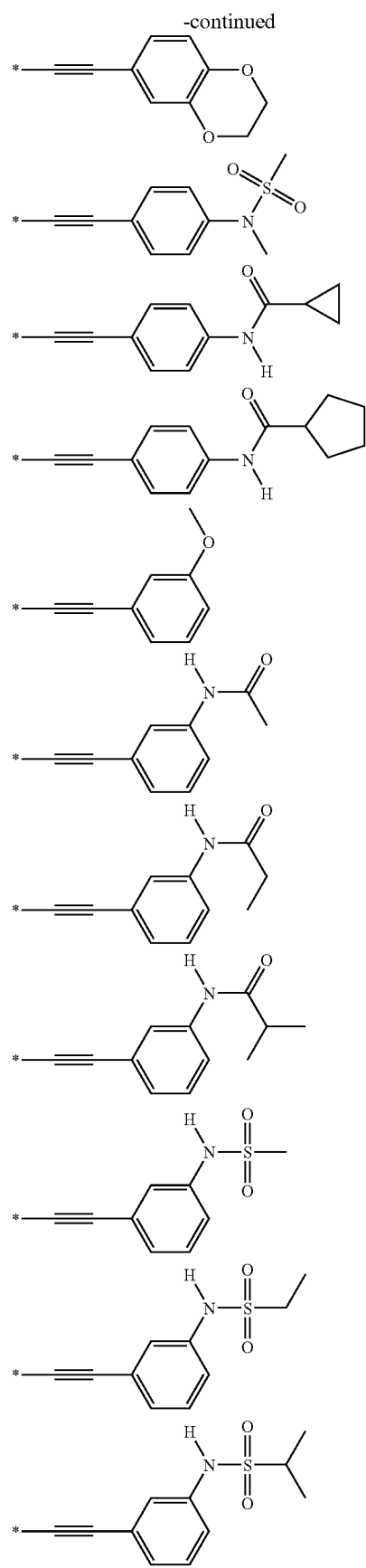

-continued
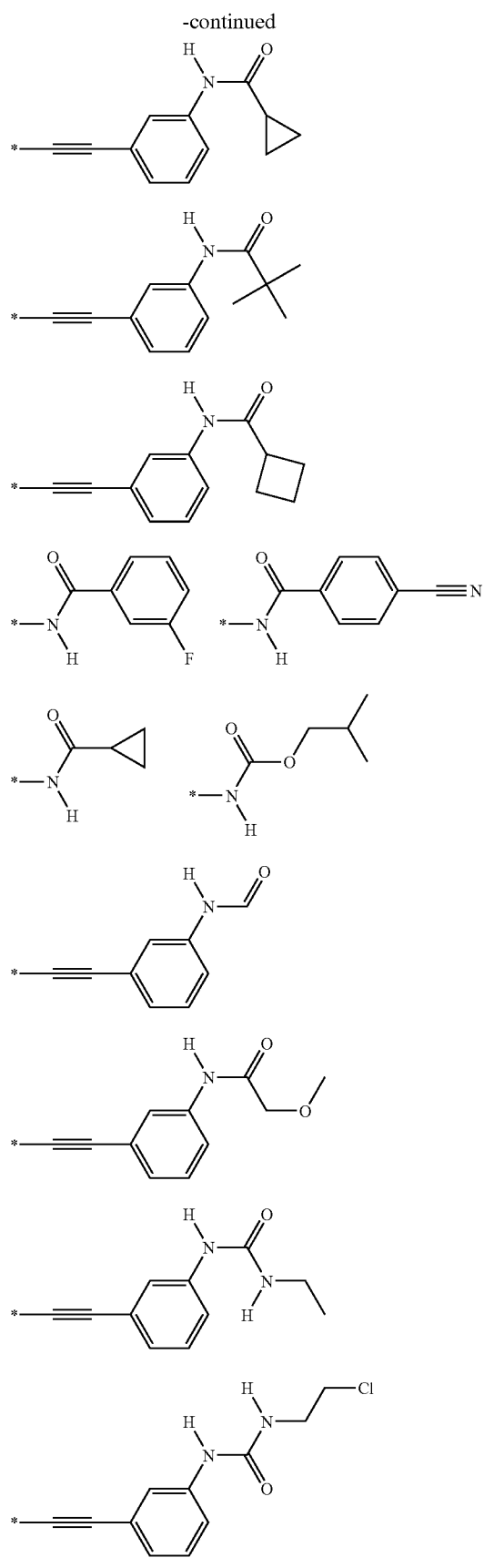
-continued
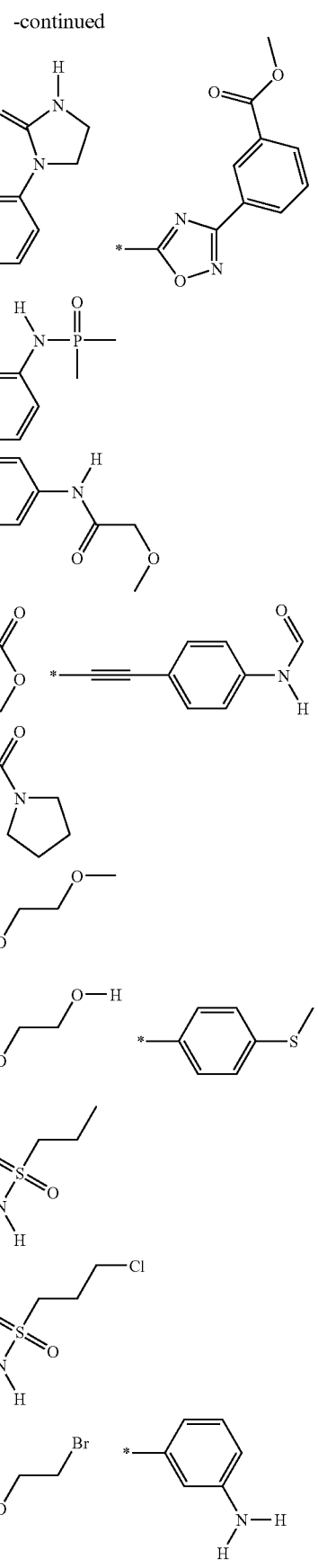

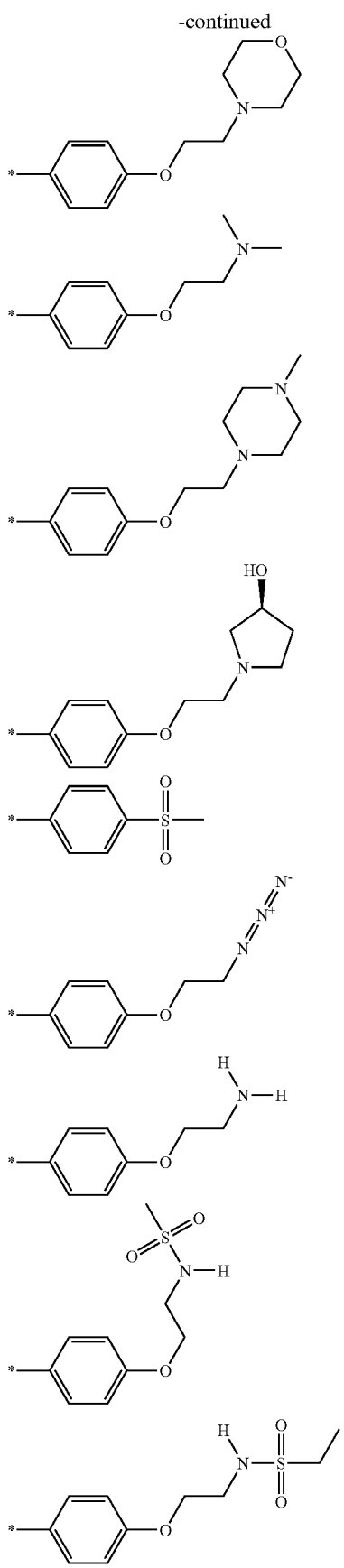
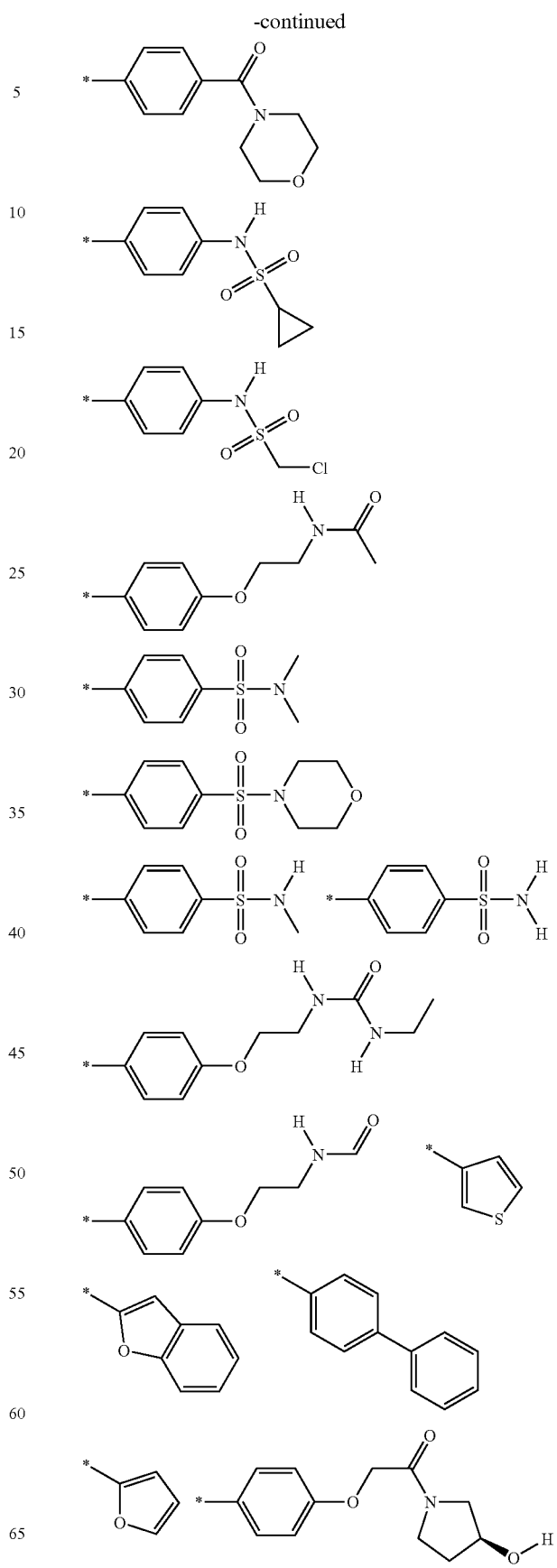

-continued
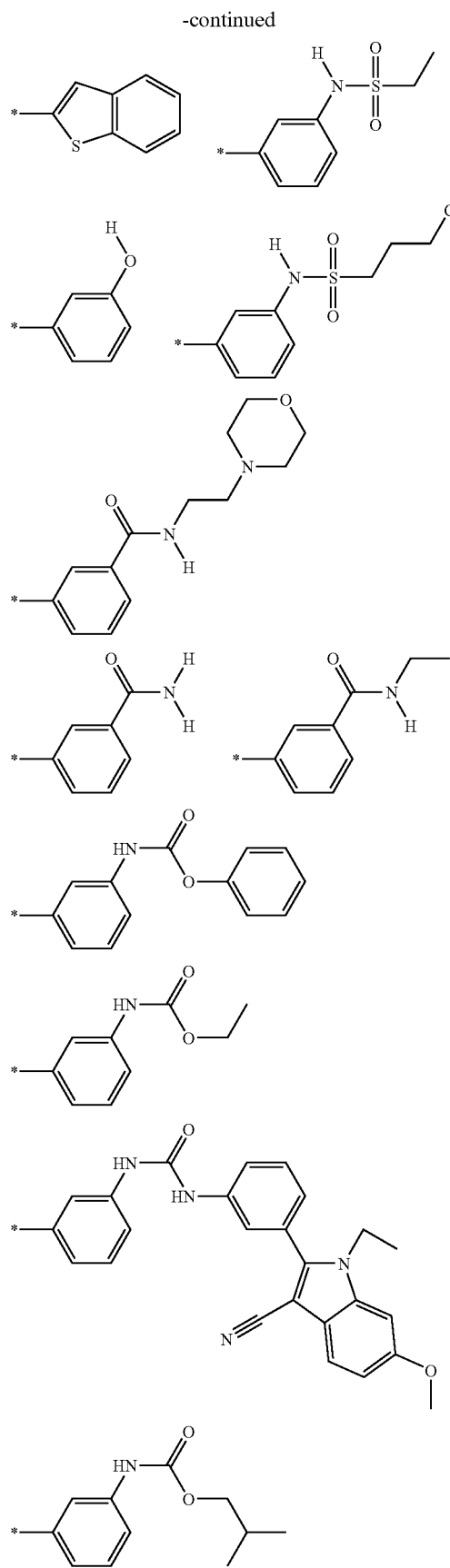
-continued
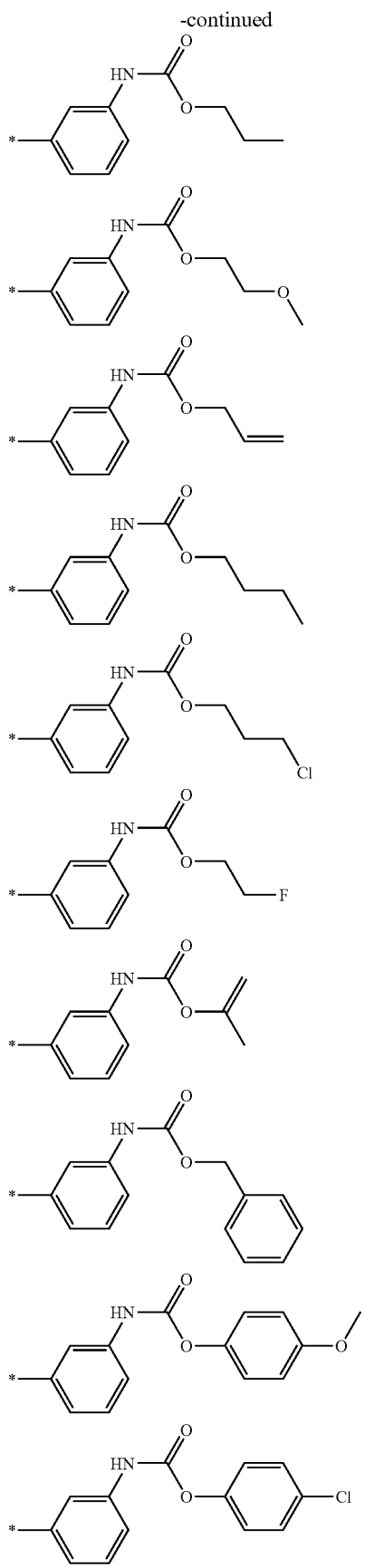

-continued
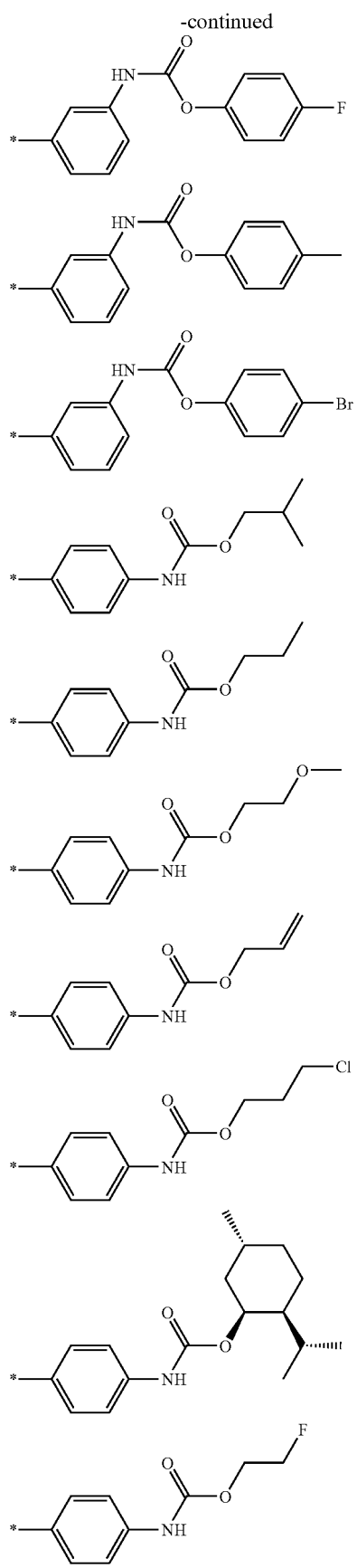
-continued
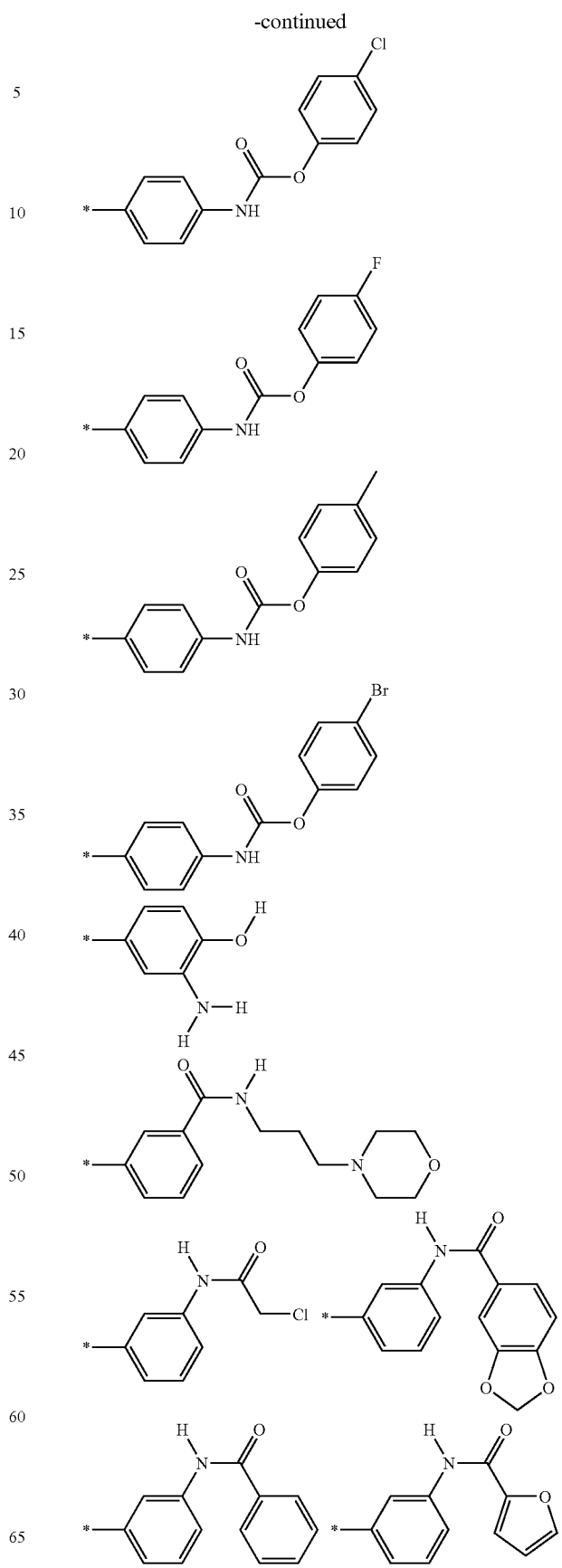

-continued
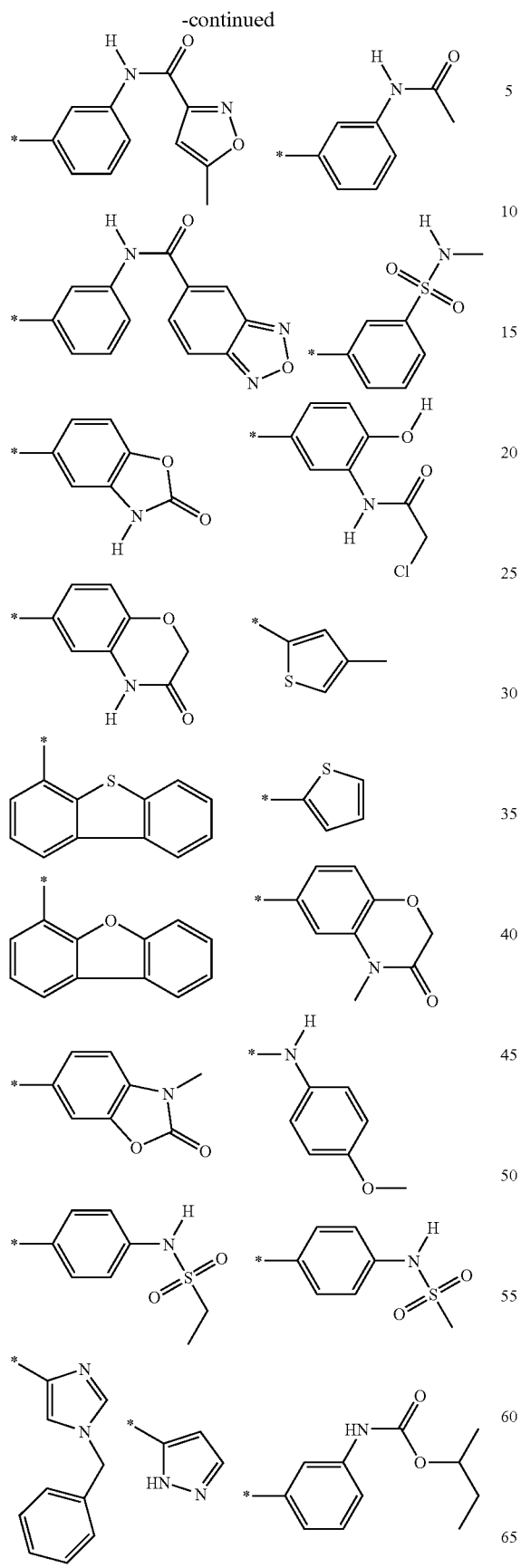
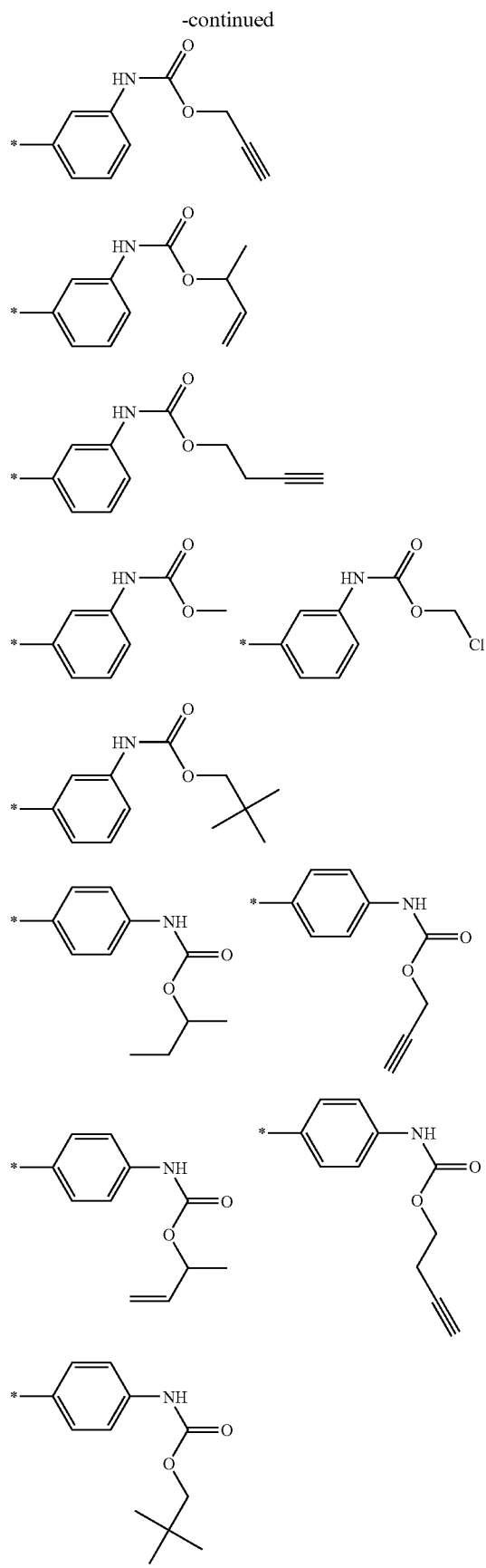

-continued
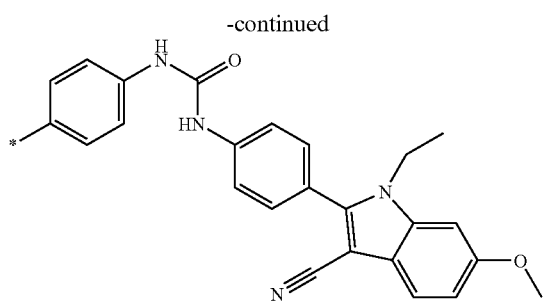
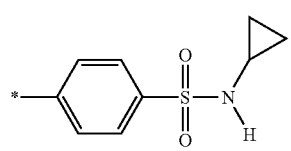
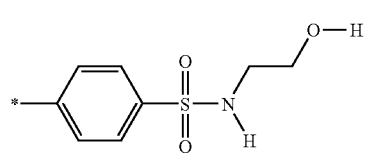
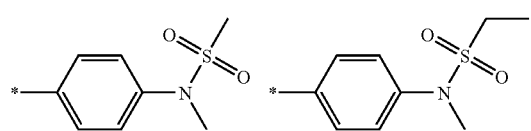
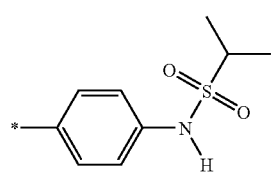
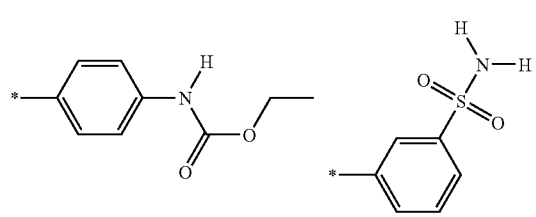
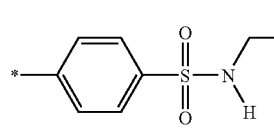
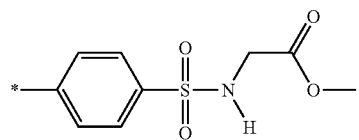
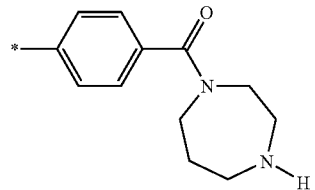
-continued
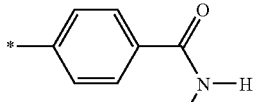
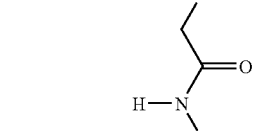

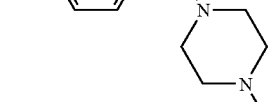 
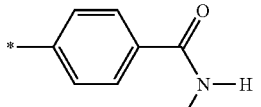 
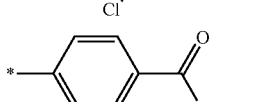 
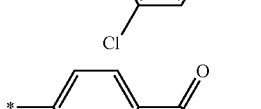 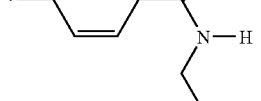
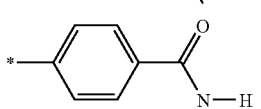 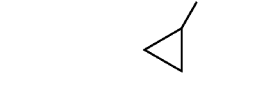
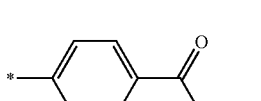 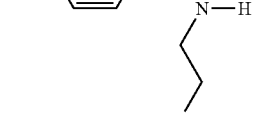
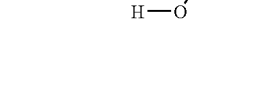

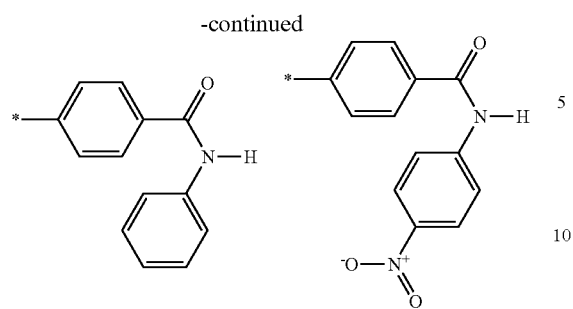
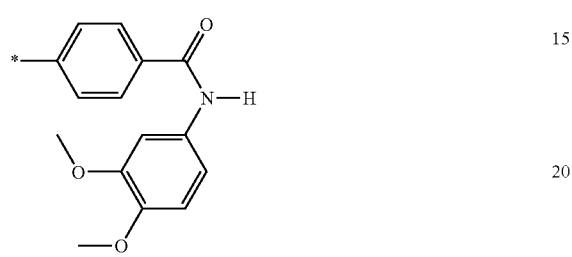
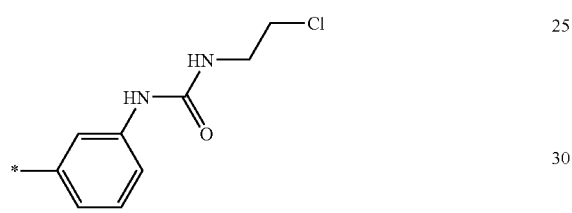

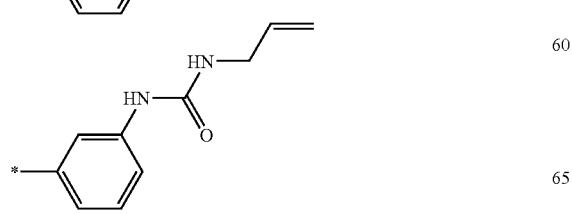
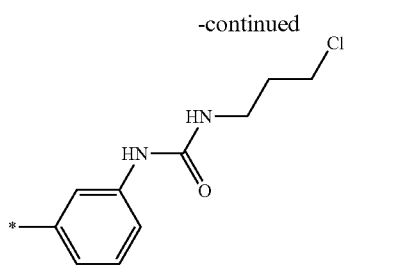
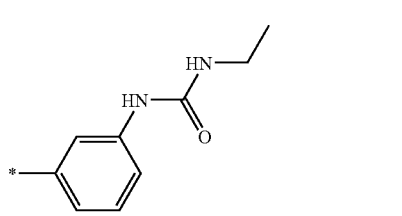
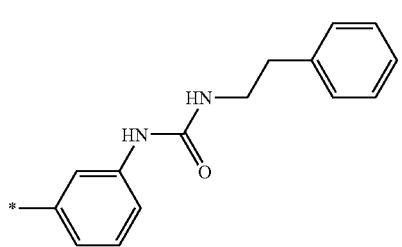

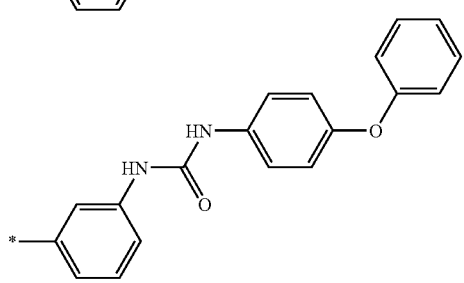

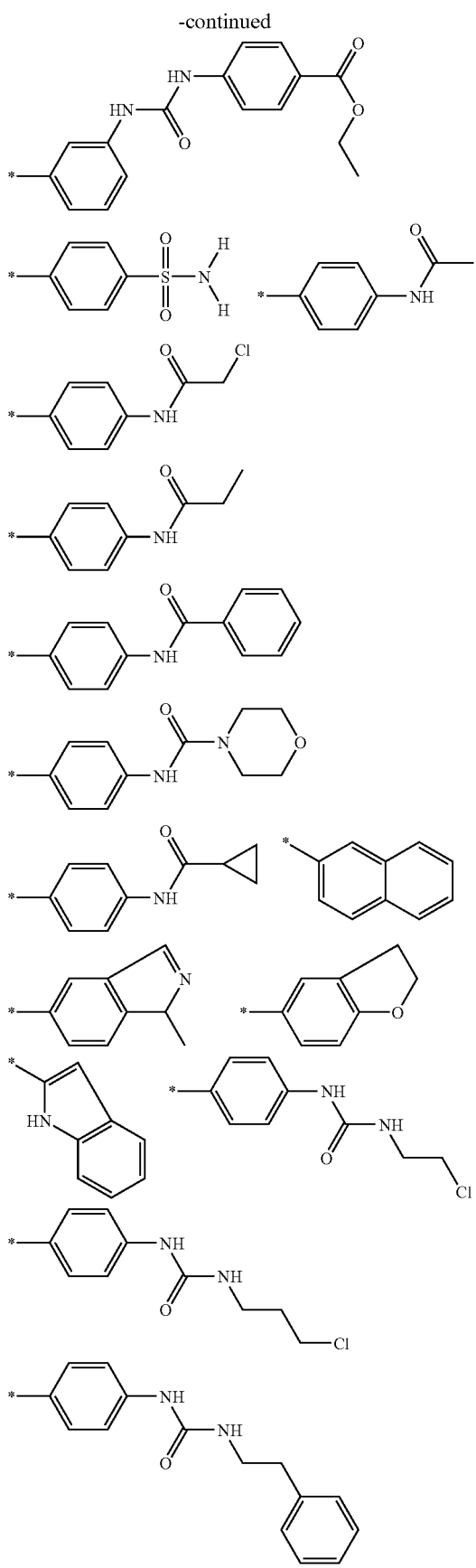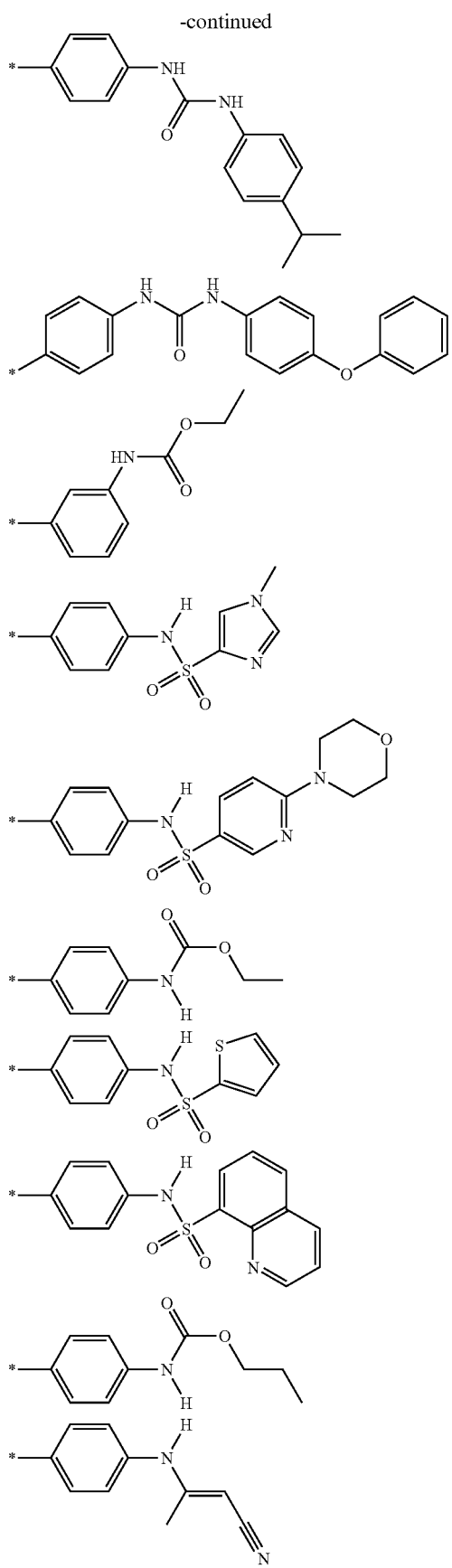

-continued
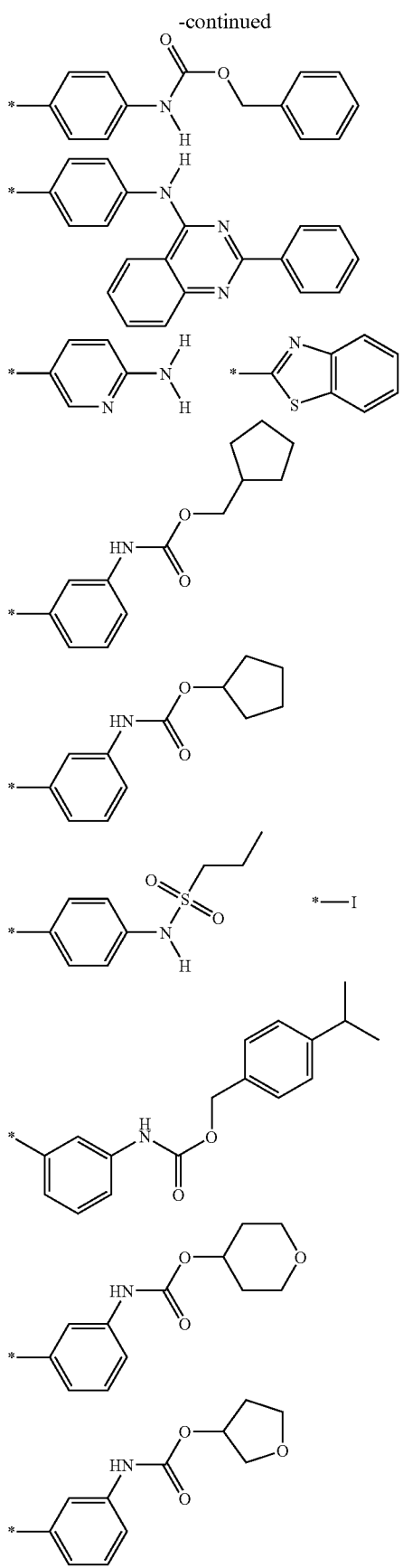
-continued
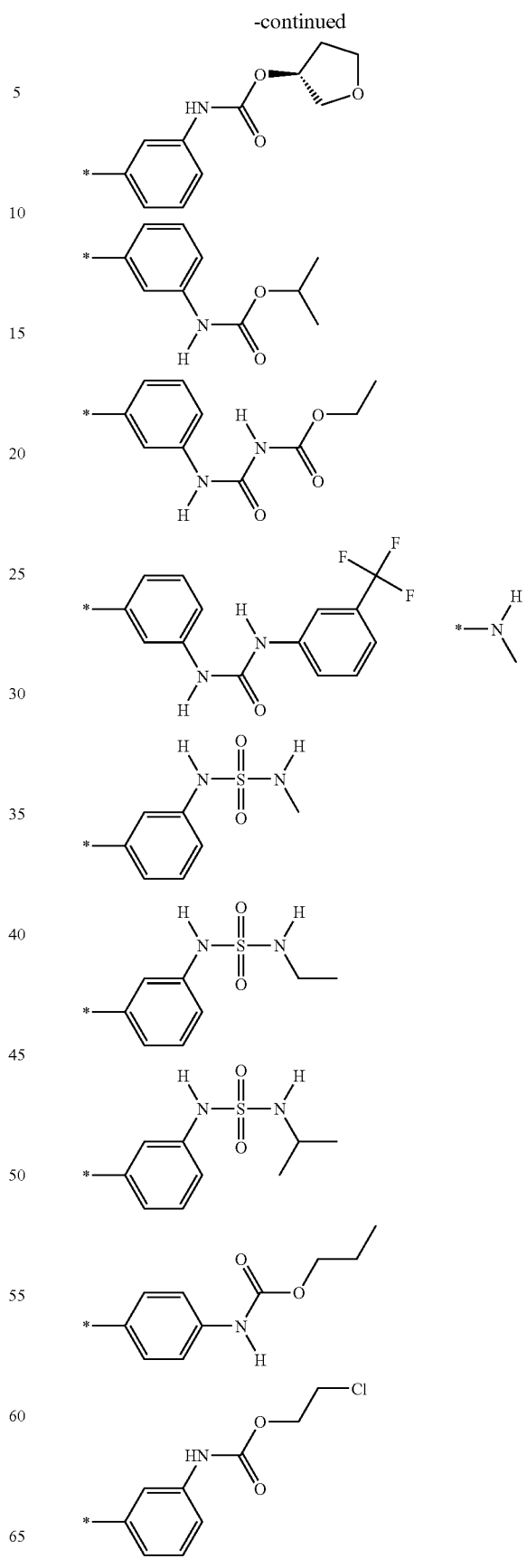

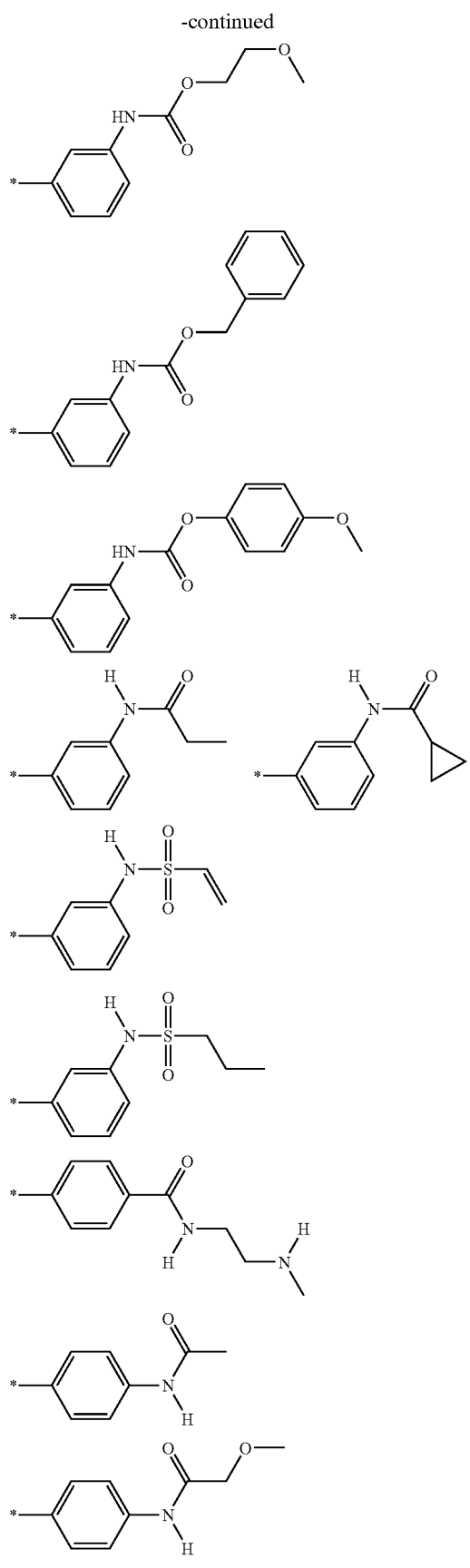

163                                  164
-continued                           -continued
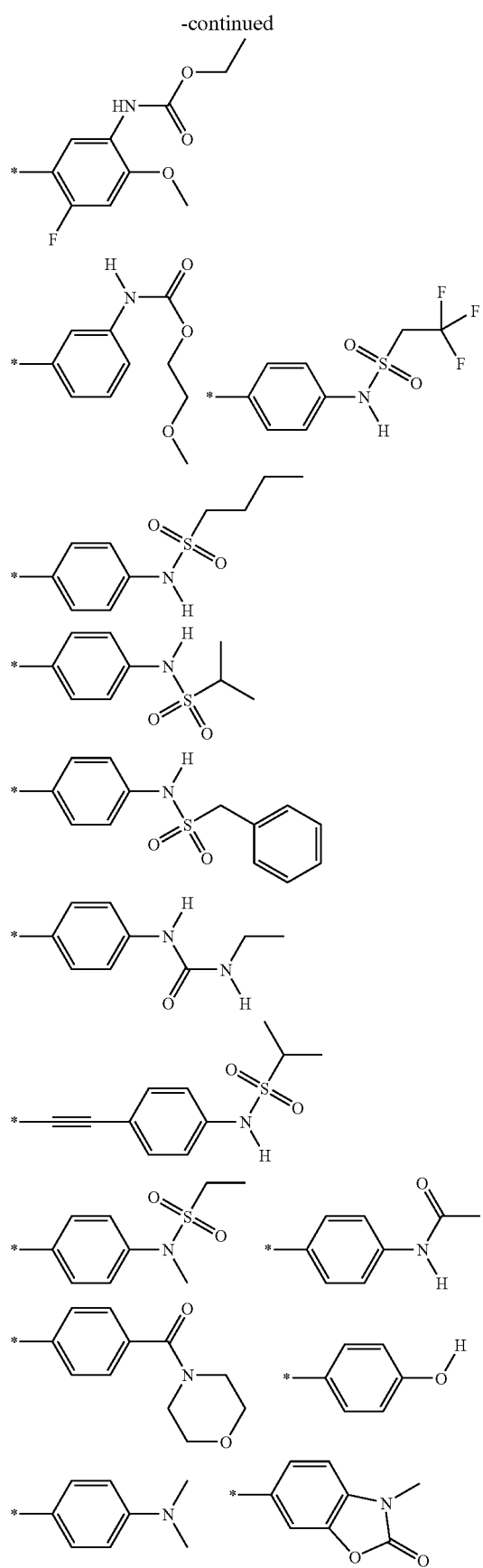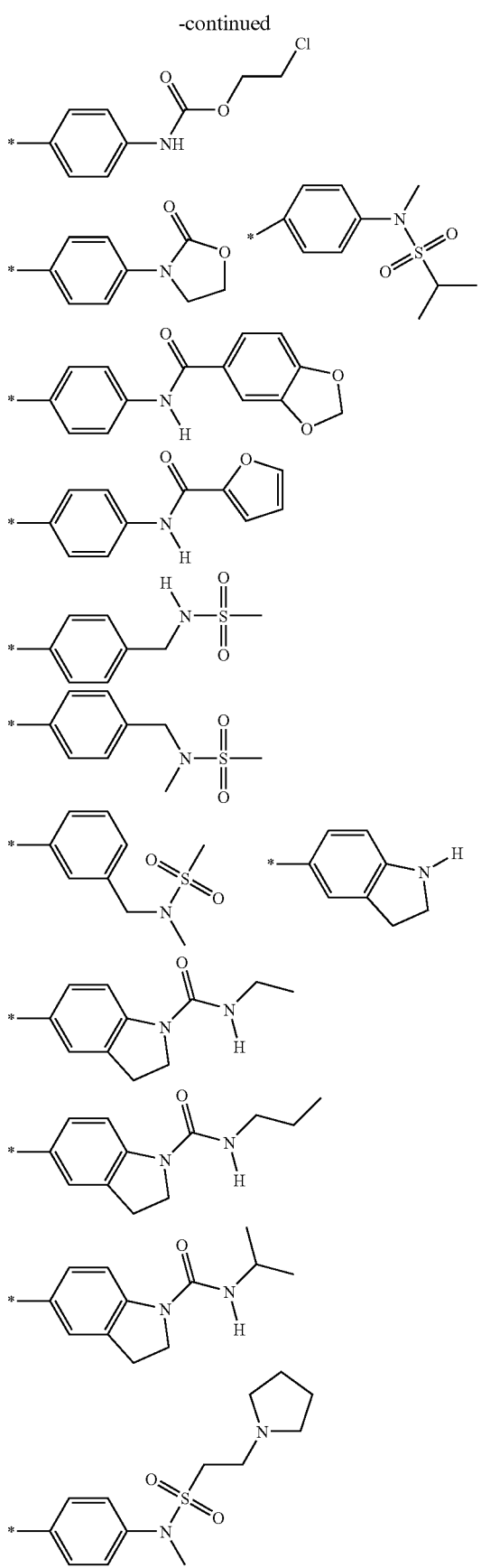

-continued
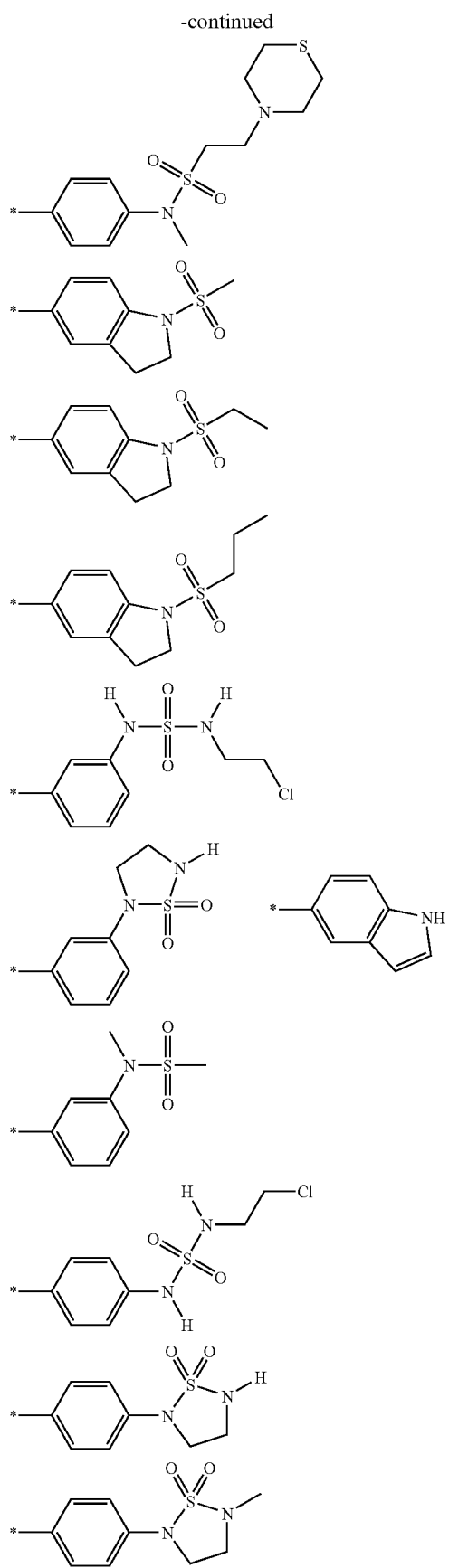
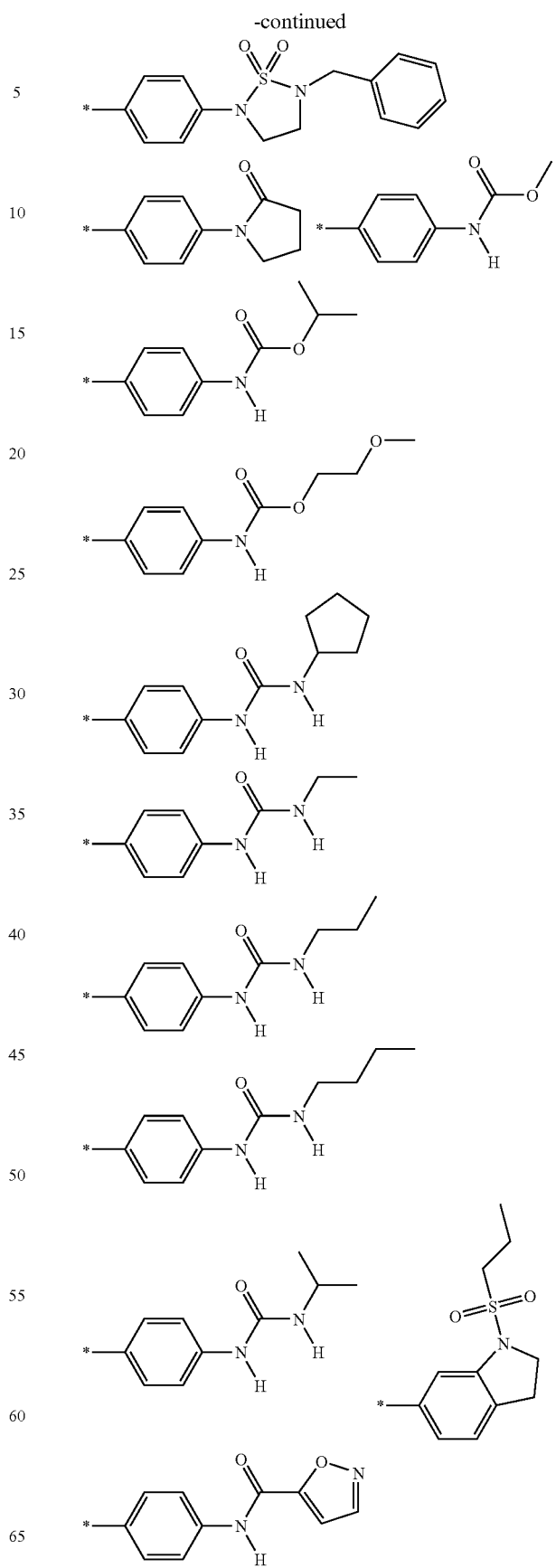

-continued
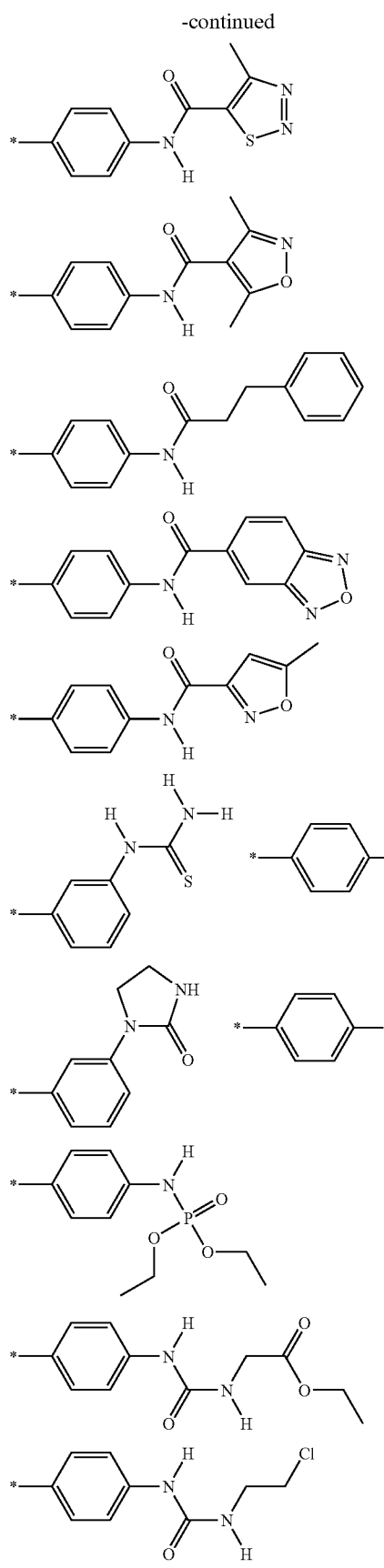
-continued
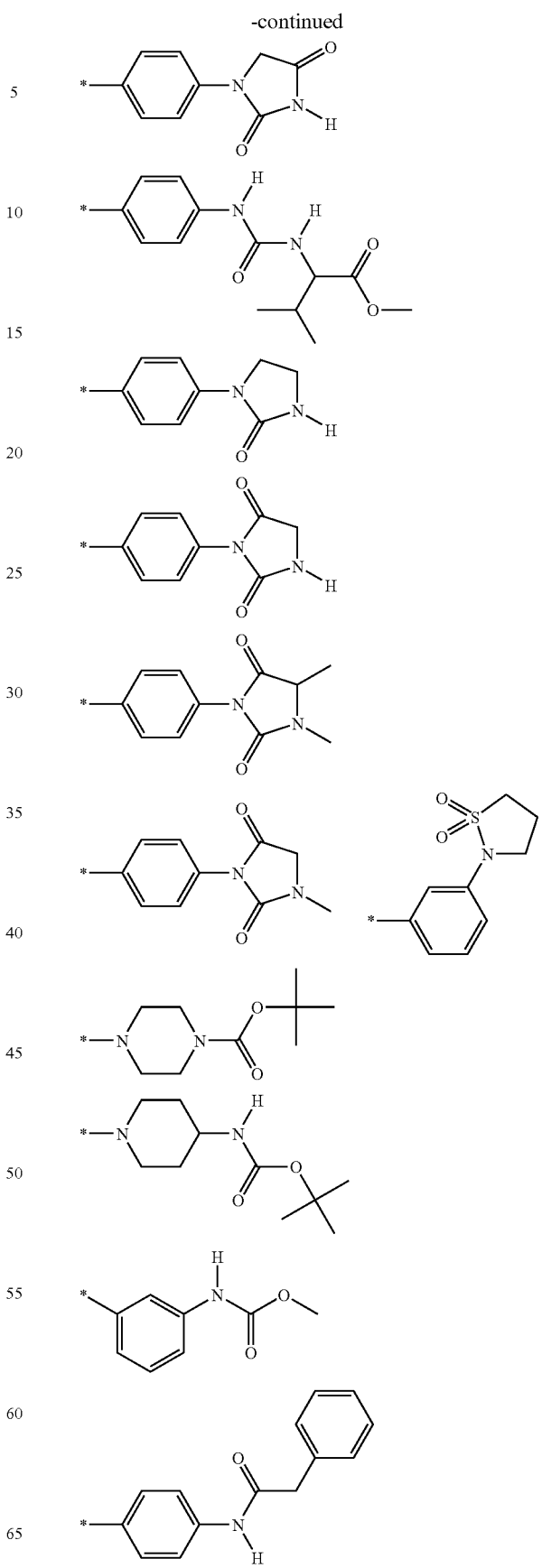

-continued
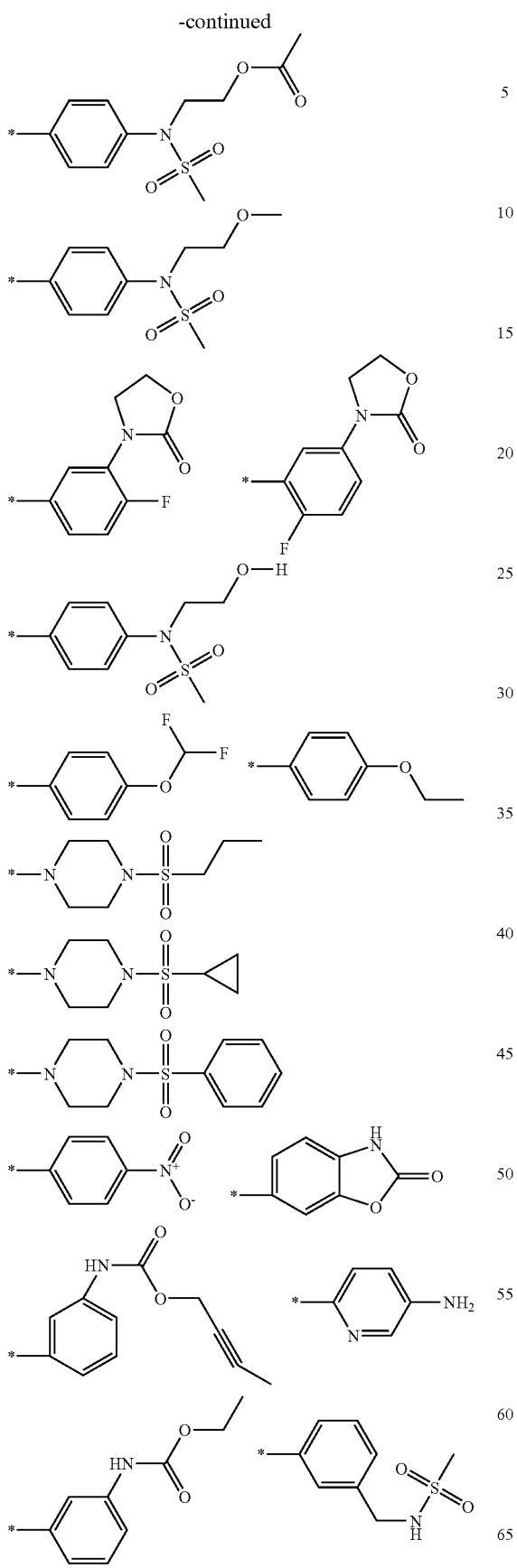
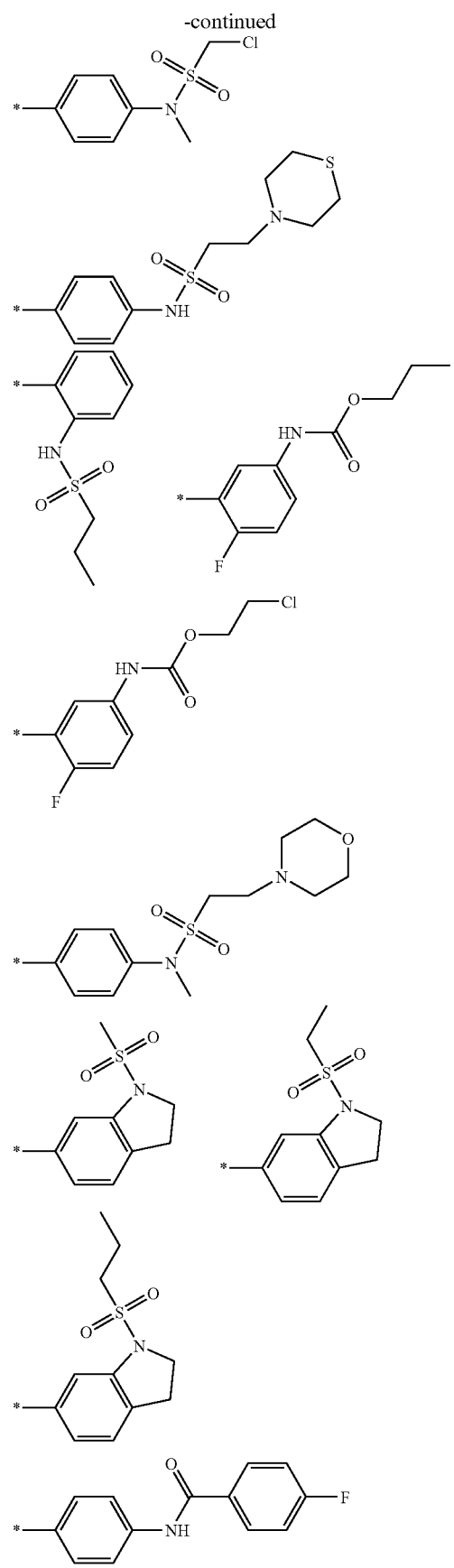

-continued
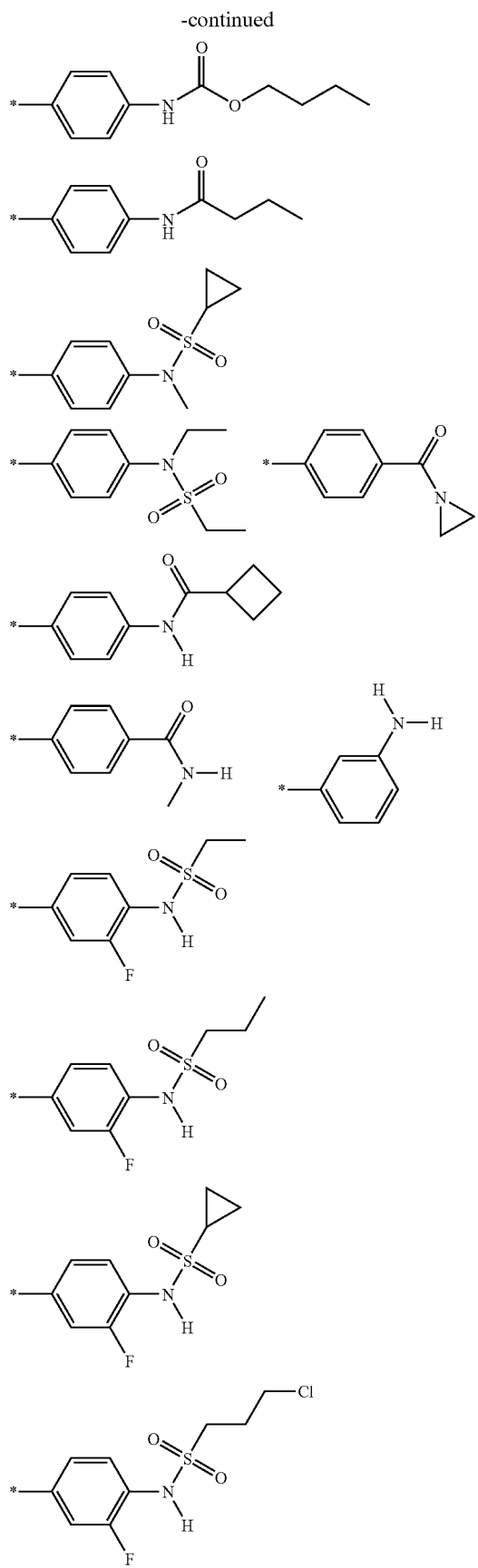
-continued
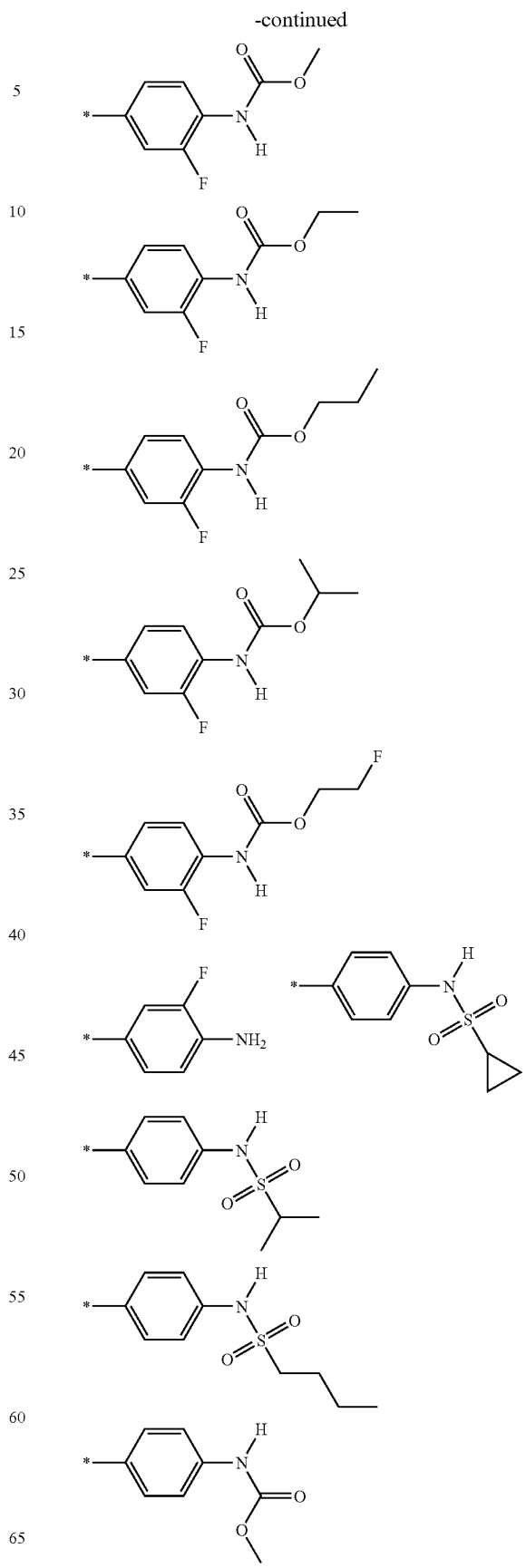

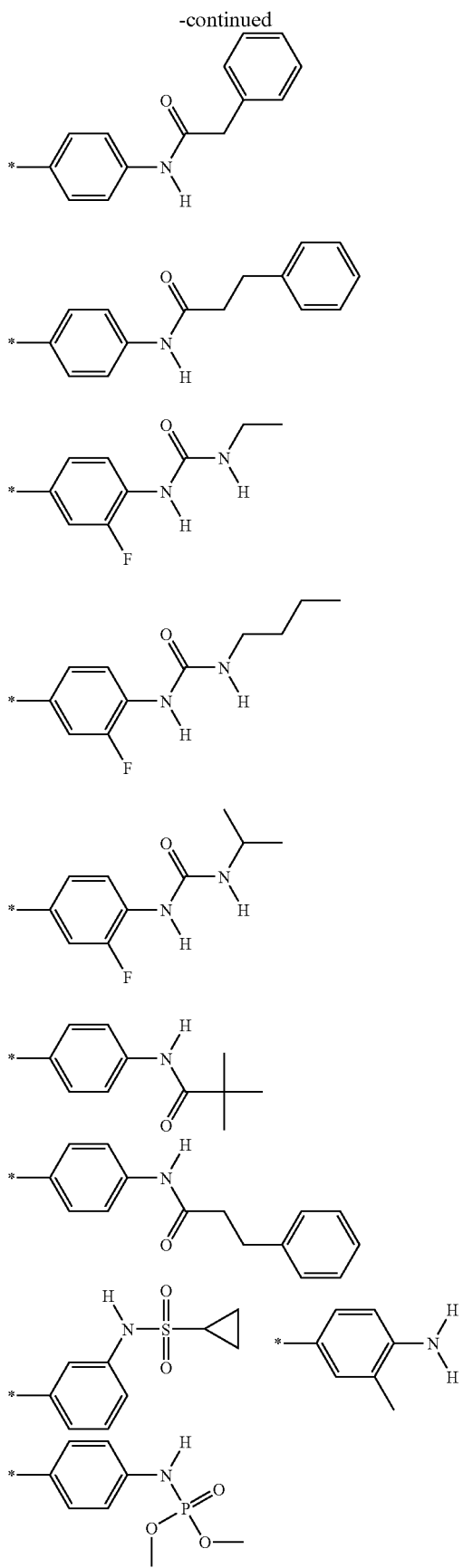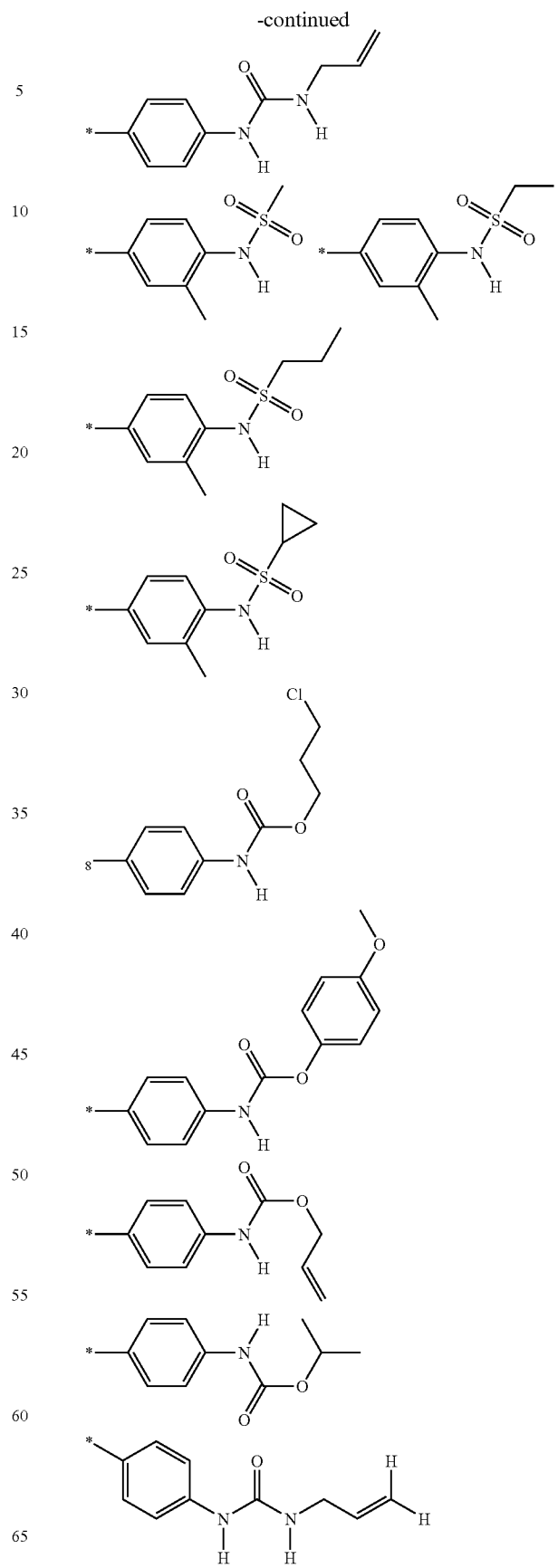

-continued
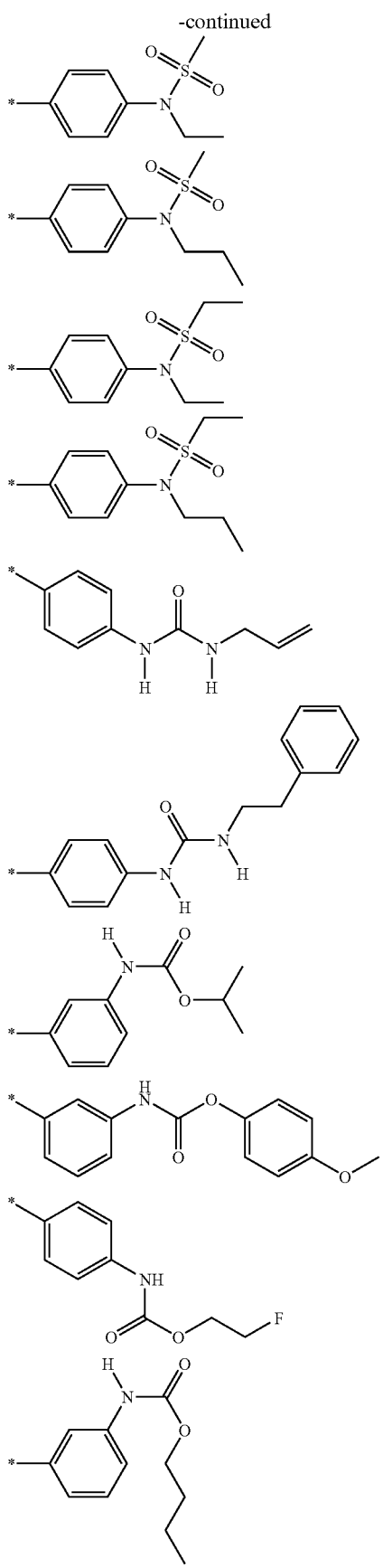
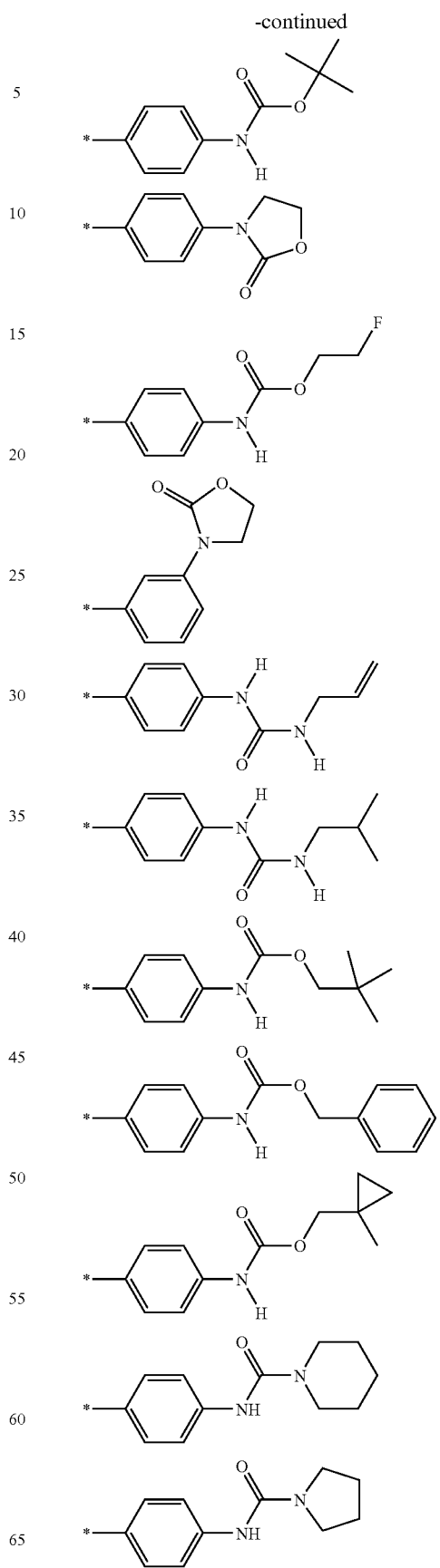

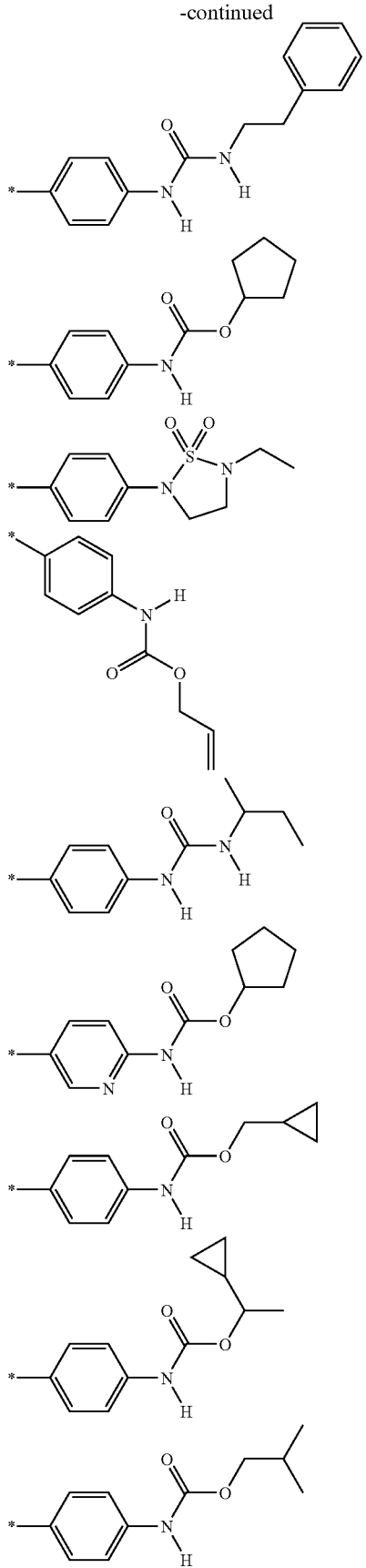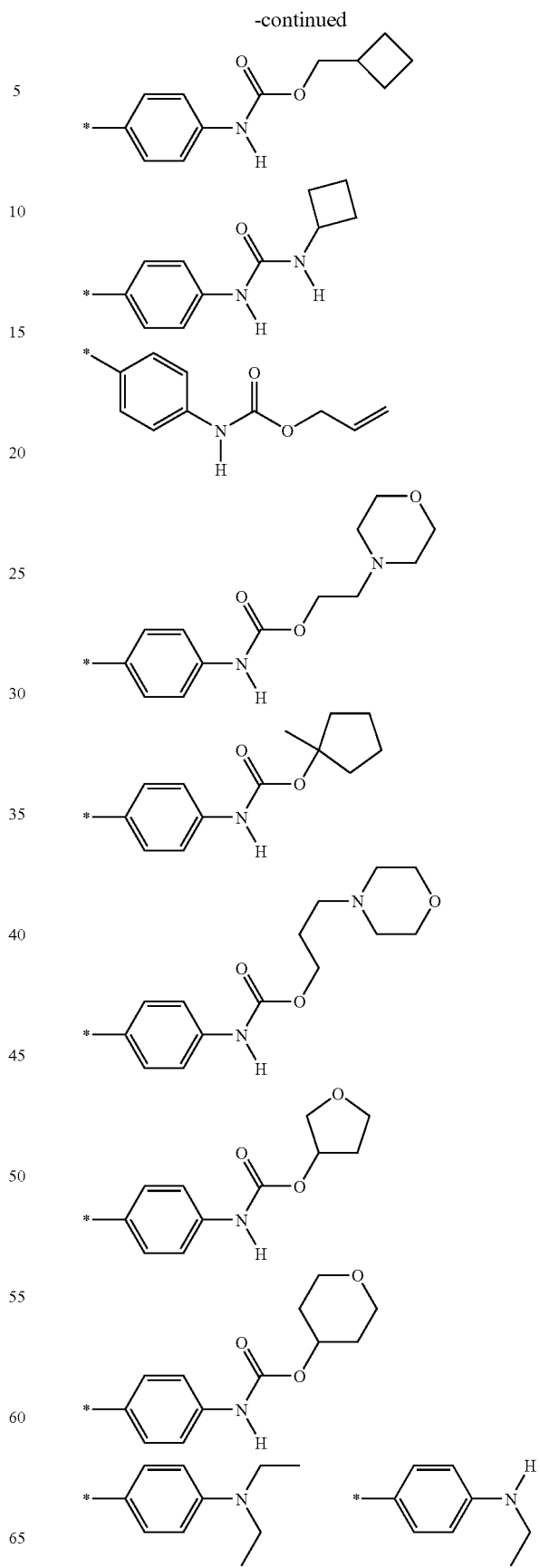

-continued
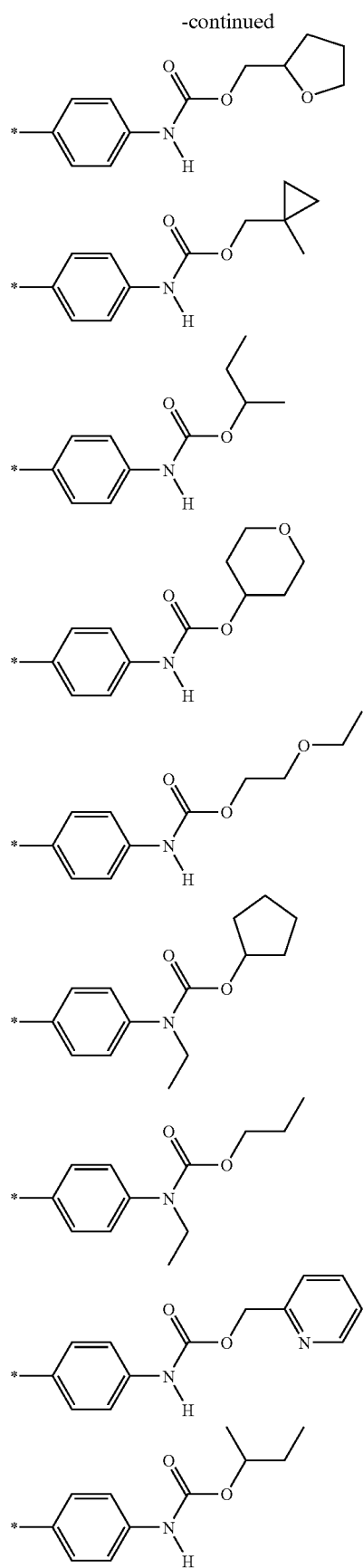
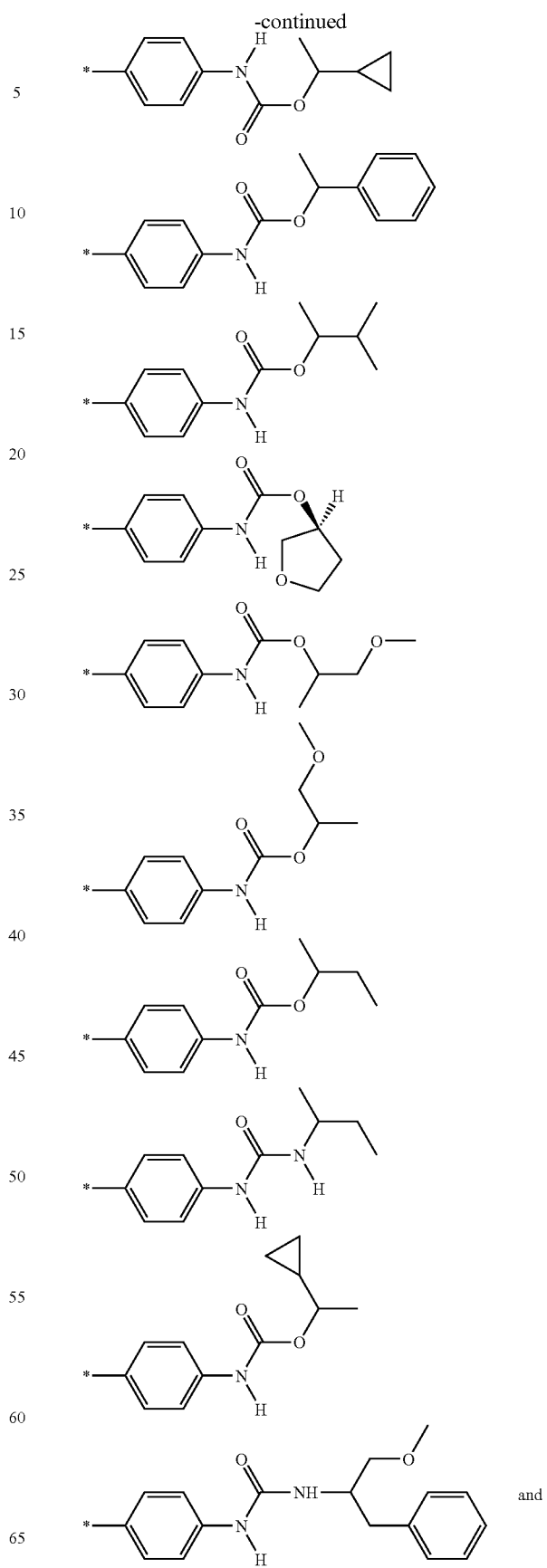
and

-continued

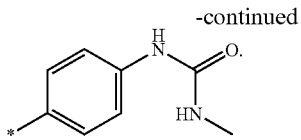

In an embodiment, the present invention includes compounds of Formulas I, I-X, I-XI, I-XII, I-Xa, I-XIa, I-XIIa, I-XIb, I-XIc, IIa, IIb, IIc, IId, or IIe, wherein Z is a 5 or 6 membered heterocycle. In another embodiment of Formulas I, I-X, I-XI, I-XII, I-Xa, I-XIa, I-XIIa, I-XIb, I-XIc, IIa, IIb, IIc, IId, or IIe, Z is a 5 membered heterocycle. In a further embodiment of Formulas I, I-X, I-XI, I-XII, I-Xa, I-XIa, I-XIIa, I-XIb, I-XIc, IIa, IIb, IIc, IId, or IIe, Z is a 6 membered heterocycle. In another embodiment, the present invention includes compounds of Formulas I, I-X, I-XI, I-XII, I-Xa, I-XIa, I-XIIa, I-XIb, I-XIc, IIa, IIb, IIc, IId, or IIe, wherein Z is a $C_1$ to $C_6$ alkyl optionally substituted with a 5 or 6 membered heterocycle. In another embodiment, the present invention includes compounds wherein Z is a $C_1$ to $C_6$ alkyl. In another embodiment, the present invention includes compounds wherein Z is a $C_1$ alkyl. In another embodiment, the present invention includes compounds wherein Z is a $C_2$ alkyl. In another embodiment, the present invention includes compounds wherein Z is a $C_3$ alkyl. In another embodiment, the present invention includes compounds wherein Z is a $C_4$ alkyl. In another embodiment, the present invention includes compounds wherein Z is a $C_5$ alkyl. In another embodiment, the present invention includes compounds wherein Z is a $C_6$ alkyl.

In another embodiment, the present invention includes compounds wherein Z is a straight chain $C_1$ to $C_6$ alkyl. In another embodiment, the present invention includes compounds wherein Z is a cyclic $C_1$ to $C_6$ alkyl. In another embodiment, the present invention includes compounds wherein Z is a $C_1$ to $C_6$ alkyl that is a combination of straight and cyclic. In yet another embodiment, the present invention includes compounds wherein Z is selected from the group consisting of cyclobutyl, cyclopropyl, cyclopropyl methyl, ethyl, cyclopentyl, and isopropyl. In a further embodiment, the present invention includes compounds wherein Z is cyclobutyl, cyclopropyl or ethyl. In a further embodiment, the present invention includes compounds wherein Z is cyclobutyl, cyclopropyl, or cyclopropyl methyl. In an embodiment, the present invention includes compounds wherein Z is cyclobutyl or cyclopropyl. In an embodiment of the present invention, a compound is provided wherein Z is cyclobutyl.

In some embodiments, Z is selected from the Z substituents of compounds 1330-2128, and 2600-3348.

In a non-limiting embodiment of the compounds of the present invention, Z is selected from the group consisting of

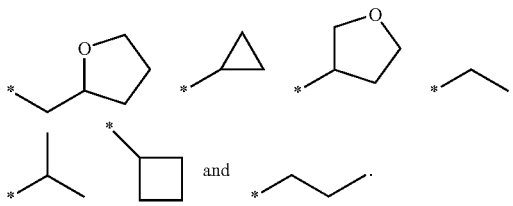

In another non-limiting embodiment of the present invention, compounds are provided wherein Z is selected from the following:

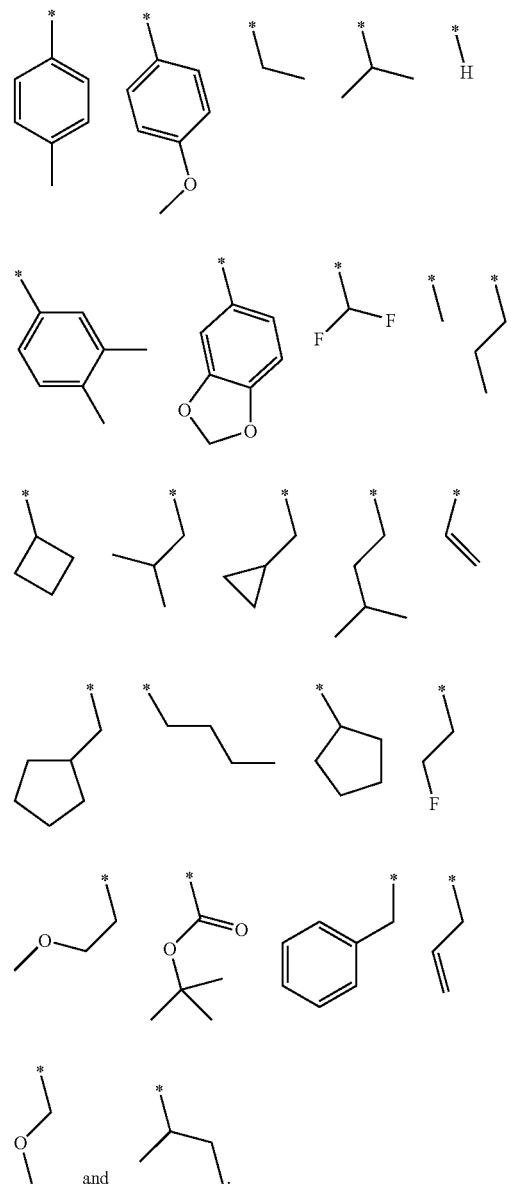

In some embodiments, the Z substituent is a hydrogen. In other embodiments, Z is a $C_1$ to $C_6$ alkyl optionally substituted with a five membered heterocycle. In other embodiments, Z is a $C_1$ to $C_6$ alkyl optionally substituted with a six membered heterocycle. In an embodiment of the present invention, compounds are provided wherein $R_2$ is an alkoxy group. In an embodiment, the present invention provides compounds wherein $R_2$ is a methoxy or an ethoxy group. In an embodiment of the compounds of the present invention, $R_2$ is a methoxy group. In an embodiment of the compounds of the present invention, $R_2$ is an ethoxy group. In an embodiment, the present invention provides compounds wherein $R_2$ is an alkoxy group optionally substituted with one or more groups independently selected from the following:

a 5 to 7 membered heterocycle group optionally substituted with one or more independently selected $C_1$ to $C_6$ alkyl, alkoxy, or hydroxy groups, or a 5 or 6 membered heteroaryl group optionally substituted with one or more $C_1$ to $C_6$ alkyl groups.

In an embodiment, the present invention provides compounds wherein $R_2$ is an alkoxy group substituted with an imidazole, a triazole, a thiazole. In another embodiment, $R_2$ is an alkoxy group substituted with a hydroxy group and an imidazole, a triazole, or a thiazole.

In an embodiment, the present invention provides compounds wherein $R_2$ is an —$OR_{kk}$ group, where $R_{kk}$ is a 5 to 6 membered heterocycle, optionally substituted with a $C_1$ to $C_6$ alkyl, optionally substituted with a $C_6$ to $C_8$ aryl group.

In an embodiment of the present invention, compounds are provided wherein $R_2$ is a $C_1$ to $C_6$ alkyl group, optionally substituted with one or more 5 or 6 membered heterocycle groups. In a further embodiment of the present invention, compounds are provided wherein $R_2$ is a —C(O)-5 or 6 membered heterocycle optionally substituted with one or more $C_6$ to $C_8$ aryl groups.

In some embodiments, $R_2$ is selected from the $R_2$ substituents of compounds 1330-2128, and 2600-3348.

In an embodiment of the present invention, compounds are provided wherein $R_2$ is selected from the group consisting of the following substituents:

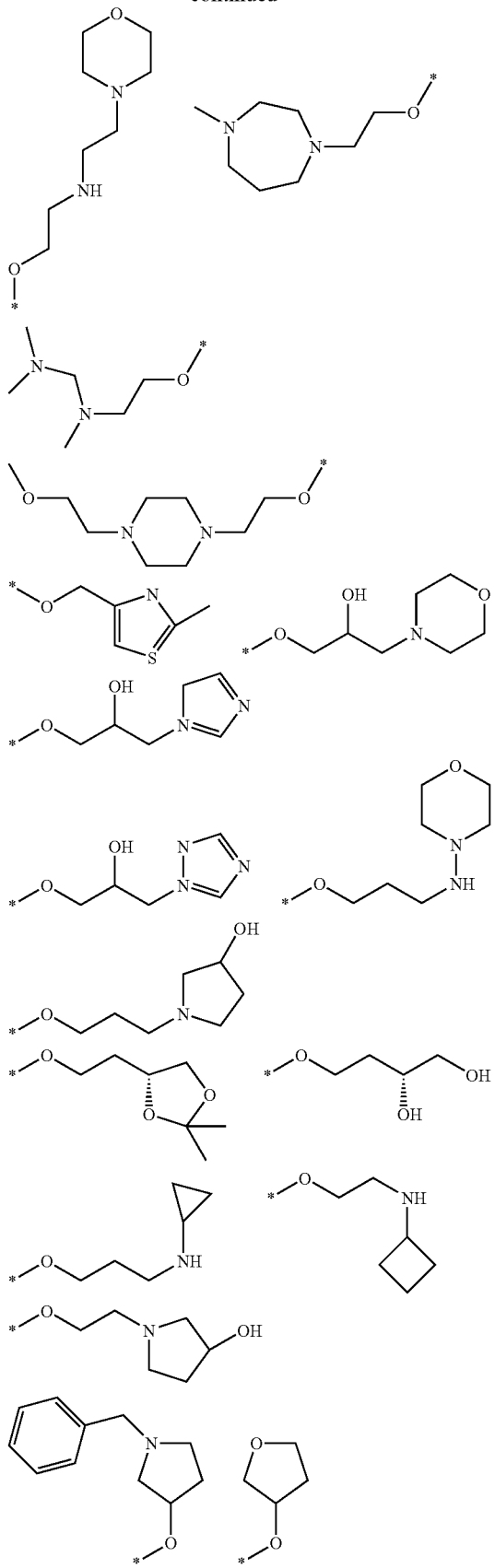

-continued

-continued
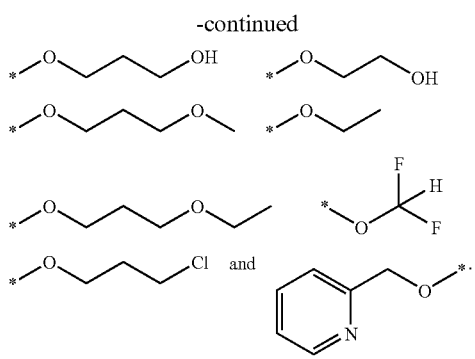
In another embodiment, compounds of the present invention are provided wherein $R_2$ is selected from the group consisting of the following substituents:
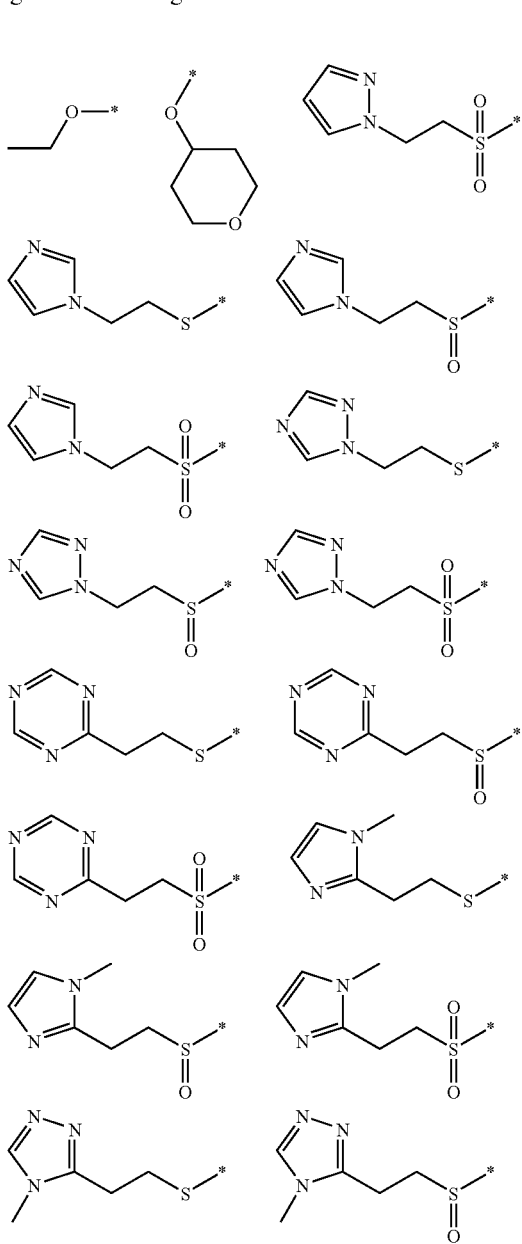
-continued
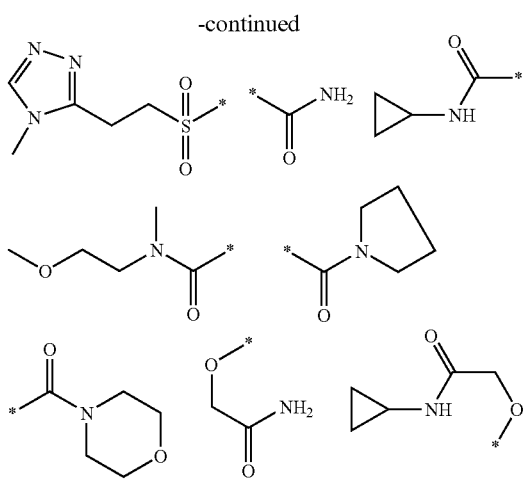
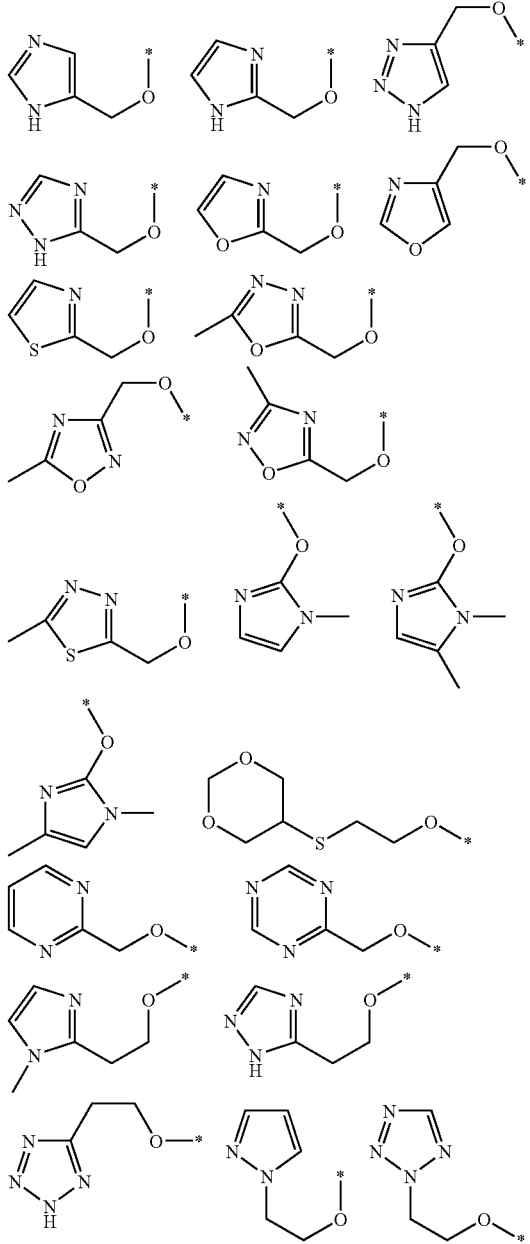

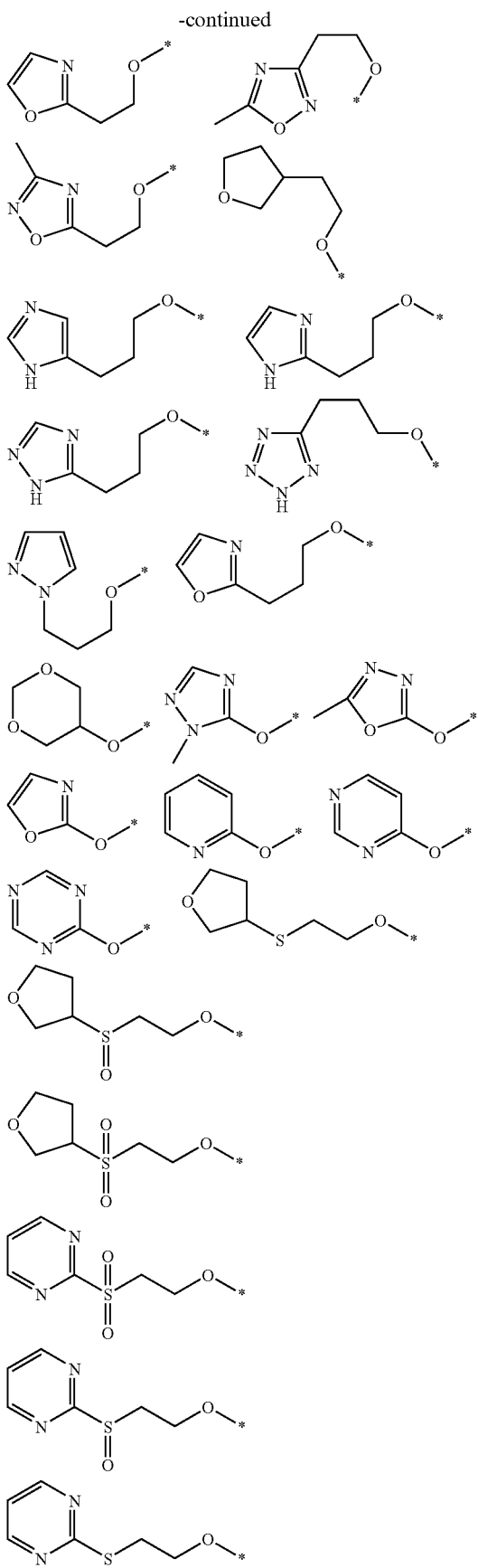
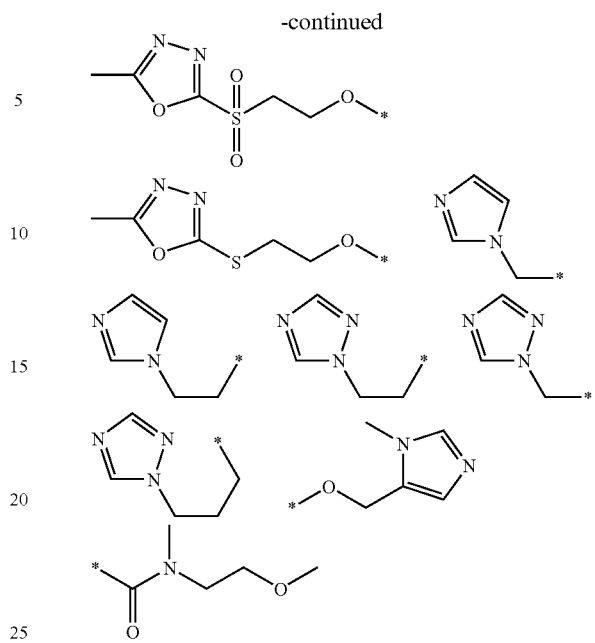

In an embodiment of the present invention, Z is a $C_1$ to $C_6$ alkyl group, Y is a —$NR_tCOOR_u$ group, where $R_u$ is—a $C_1$ to $C_{12}$ alkyl and $R_t$ is—a hydrogen, and $R_2$ is:
an alkoxy group optionally substituted with one or more groups independently selected from the following:
  an amino group optionally substituted with one or more 5 or 6 membered heterocycle groups or alkyl groups, the alkyl groups optionally and independently substituted with one or more 5 or 6 membered heterocycle,
  a 5 to 7 membered heterocycle group optionally substituted with one or more independently selected hydroxy group or $C_1$ to $C_6$ alkyl group, the $C_1$ to $C_6$ alkyl group optionally substituted with one or more independently selected $C_1$ to $C_6$ alkoxy group,
  a 5 or 6 membered heteroaryl group optionally substituted with one or more $C_1$ to $C_6$ alkyl groups,
an —$OR_{kk}$ group, where $R_{kk}$ is a 5 to 6 membered heterocycle, optionally substituted with a $C_1$ to $C_6$ alkyl, optionally substituted with a $C_6$ to $C_8$ aryl group.

In another embodiment of the present invention, Z is a $C_1$ to $C_6$ alkyl group, Y is a —$NR_tCOOR_u$ group, where $R_u$ is—a $C_1$ to $C_{12}$ alkyl and $R_t$ is—a hydrogen, and $R_2$ is:
an alkoxy group optionally substituted with one or more groups independently selected from the following:
  a 5 to 7 membered heterocycle group optionally substituted with one or more independently selected hydroxy group or $C_1$ to $C_6$ alkyl group, the $C_1$ to $C_6$ alkyl group optionally substituted with one or more independently selected $C_1$ to $C_6$ alkoxy group,
  a 5 or 6 membered heteroaryl group optionally substituted with one or more $C_1$ to $C_6$ alkyl groups,
an —$OR_{kk}$ group, where $R_{kk}$ is a 5 to 6 membered heterocycle, optionally substituted with a $C_1$ to $C_6$ alkyl, optionally substituted with a $C_6$ to $C_8$ aryl group.

In another embodiment of the present invention, Z is a $C_1$ to $C_6$ alkyl group, Y is a —$NR_tCOOR_u$ group, where $R_u$ is—a $C_1$ to $C_{12}$ alkyl and $R_t$ is—a hydrogen, and $R_2$ is:
an alkoxy group optionally substituted with one or more groups independently selected from the following:

a 5 to 7 membered heterocycle group optionally substituted with one or more independently selected hydroxy group or $C_1$ to $C_6$ alkyl group, the $C_1$ to $C_6$ alkyl group optionally substituted with one or more independently selected $C_1$ to $C_6$ alkoxy group, a 5 or 6 membered heteroaryl group optionally substituted with one or more $C_1$ to $C_6$ alkyl groups.

In another embodiment of the present invention, Z is a $C_1$ to $C_6$ alkyl group, Y is a —$NR_tCOOR_u$ group, where $R_u$ is —a $C_1$ to $C_{12}$ alkyl and $R_t$ is —a hydrogen, and $R_2$ is:

an alkoxy group optionally substituted with one or more groups independently selected from the following:

a 5 to 7 membered heterocycle group optionally substituted with one or more independently selected hydroxy group or $C_1$ to $C_6$ alkyl group, the $C_1$ to $C_6$ alkyl group optionally substituted with one or more independently selected $C_1$ to $C_6$ alkoxy group.

In another embodiment of the present invention, Z is a $C_1$ to $C_6$ alkyl group, Y is a —$NR_tCOOR_u$ group, where $R_u$ is —a $C_1$ to $C_{12}$ alkyl and $R_t$ is —a hydrogen, and $R_2$ is:

an alkoxy group optionally substituted with one or more groups independently selected from the following:

Exemplary compounds include the following:

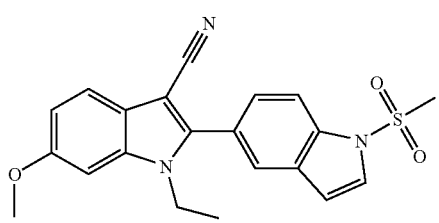

1330

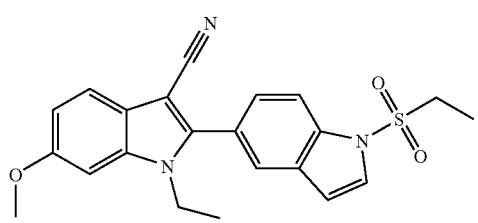

1331

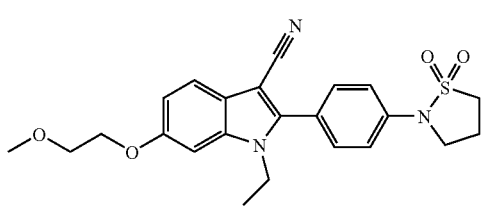

1332

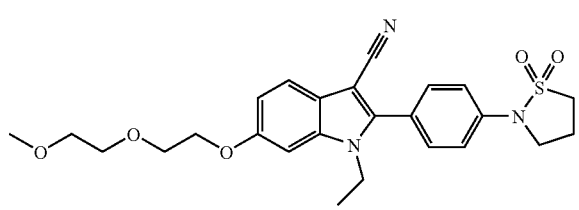

1333

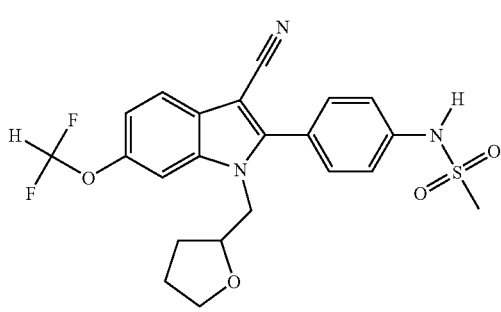

1334

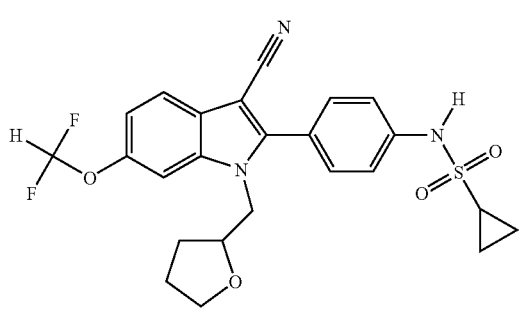

1335

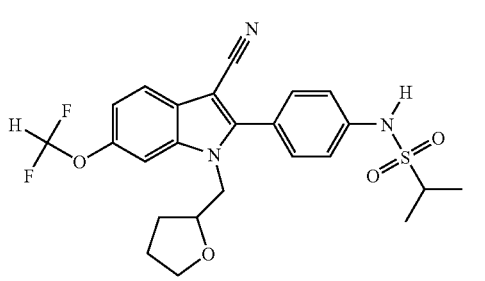

1336

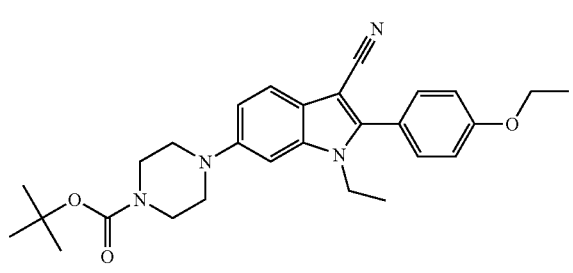

1337

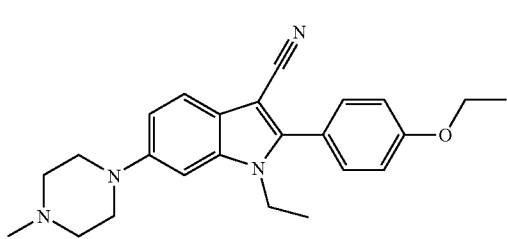

1338

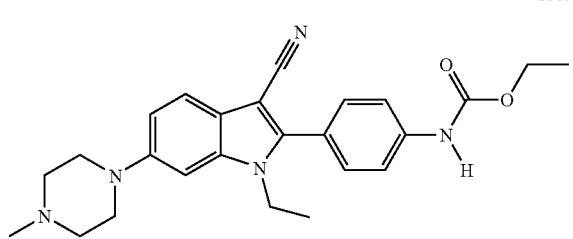

1339

-continued
1340
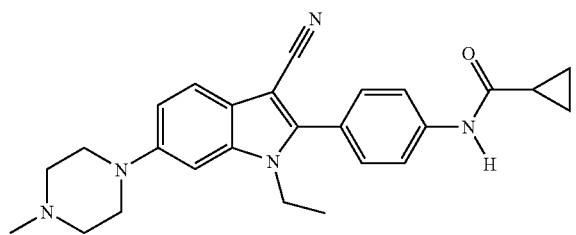
1341
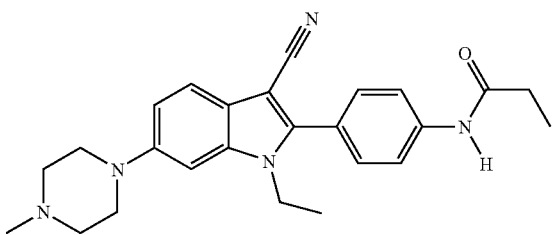
1342
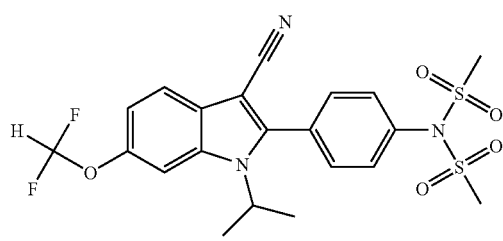
1343
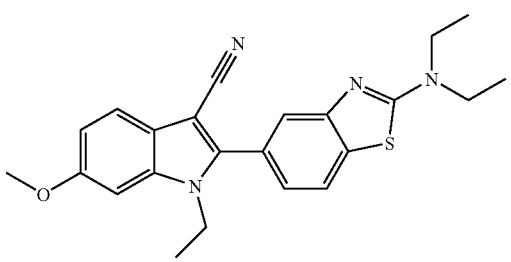
1344
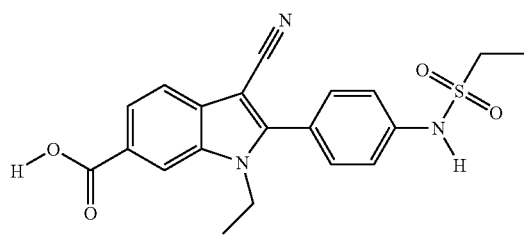
1345
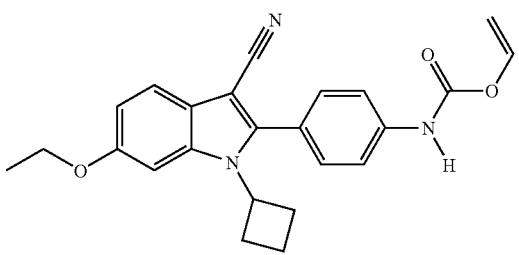
1346
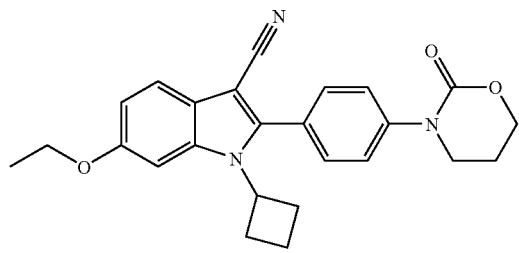
1347
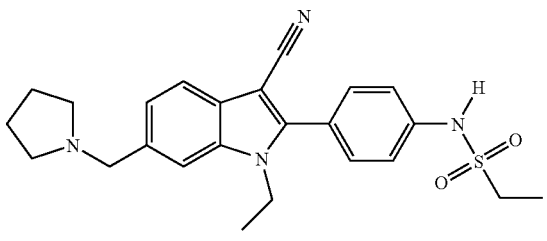
1348
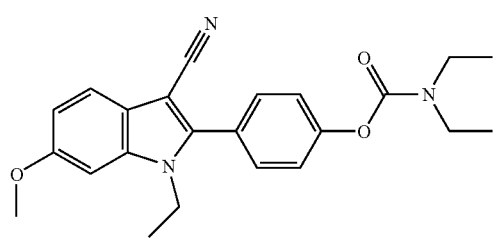
1349
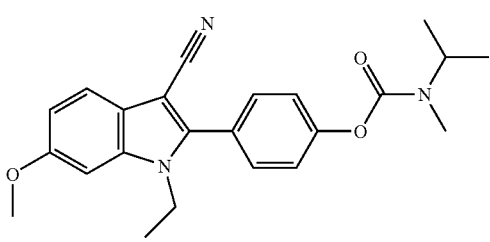
1350
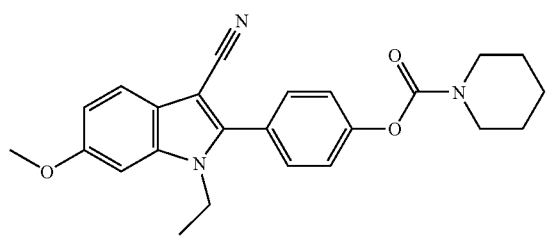
1351
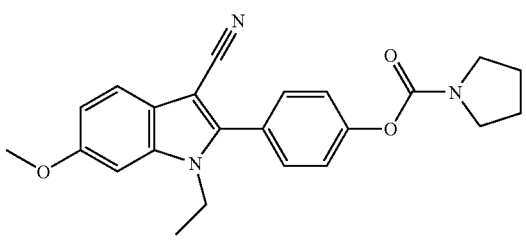

-continued
1352
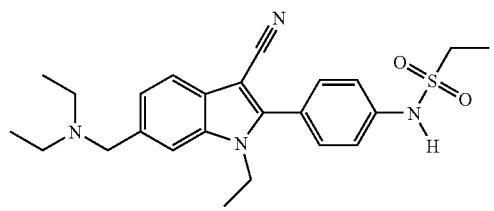
1353
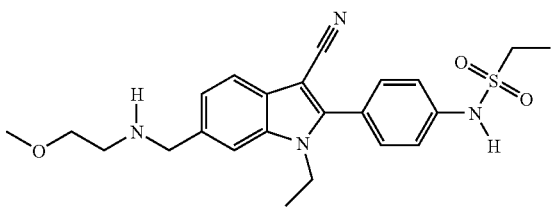
1354
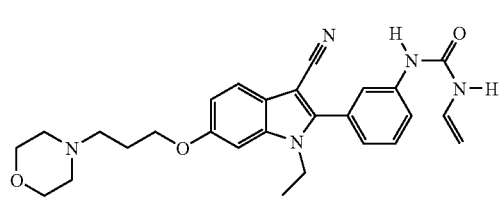
1355
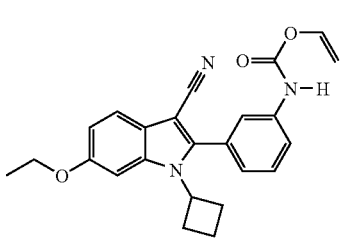
1356
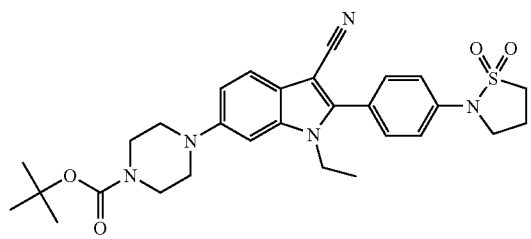
1357
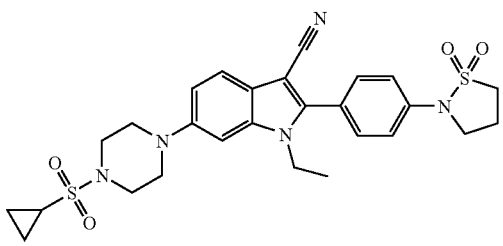
1358
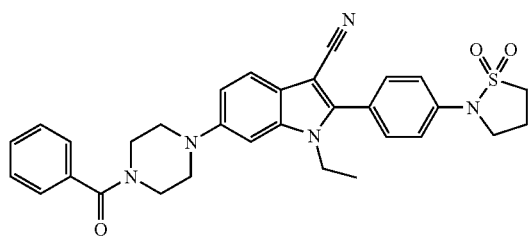
1359
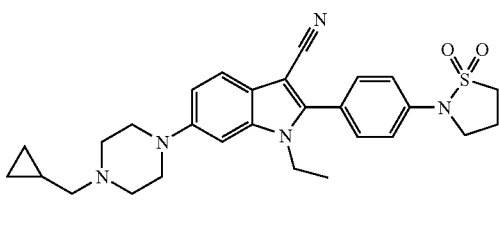
1360
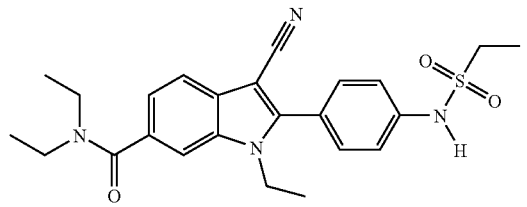
1361
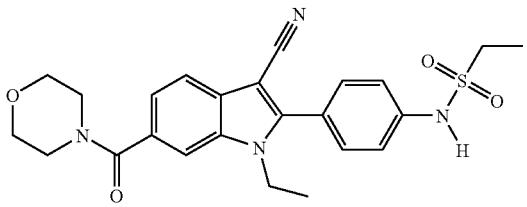
1362
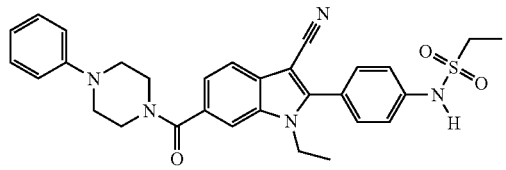
1363
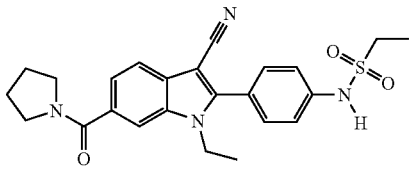
1364
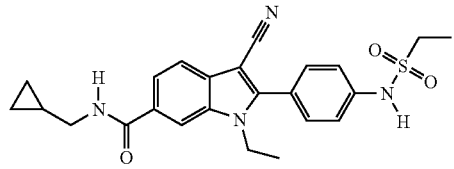
1365
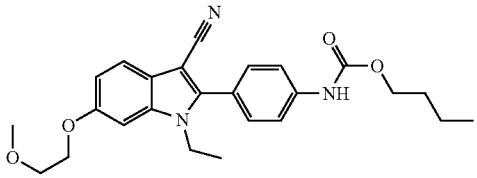

-continued
1366
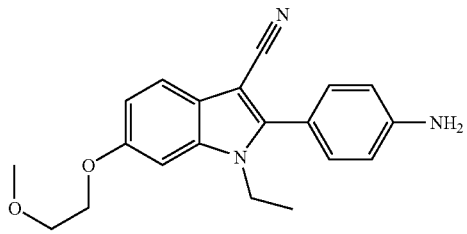
1367
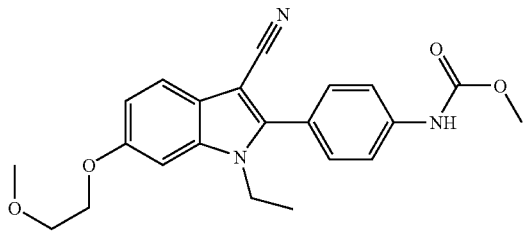
1368
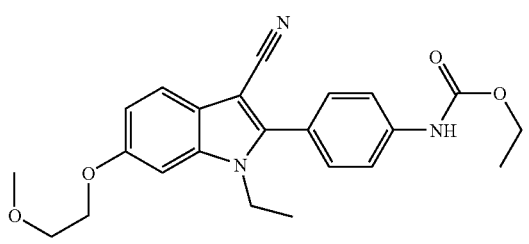
1369
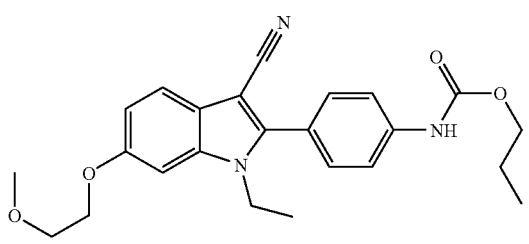
1370
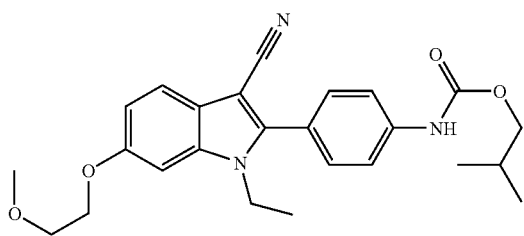
1371
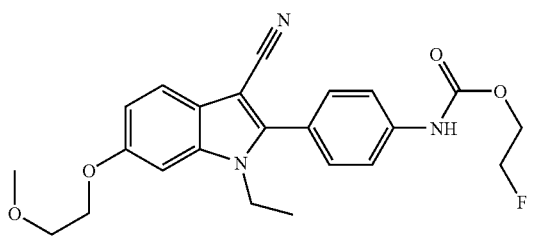
1372
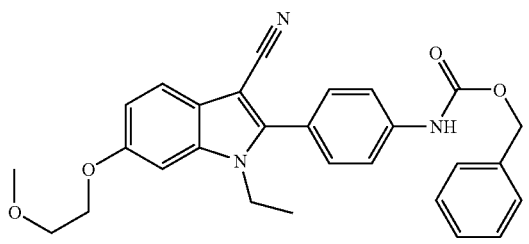
1373
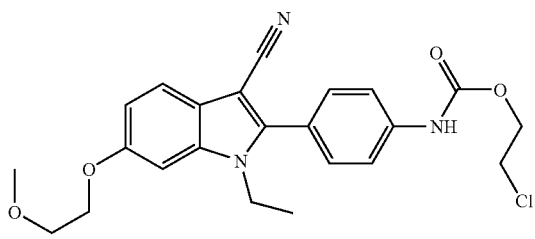
1374
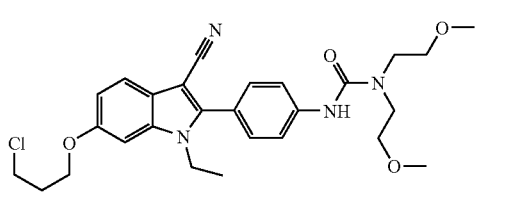
1375
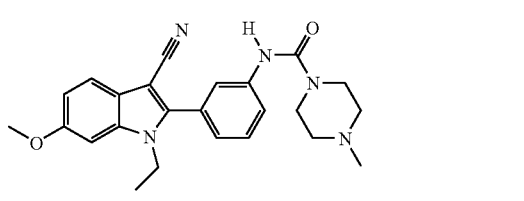
1376
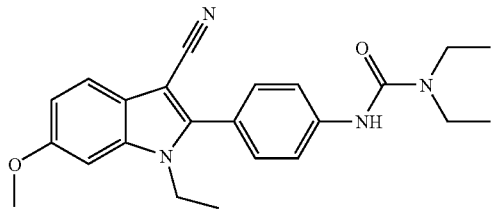
1377
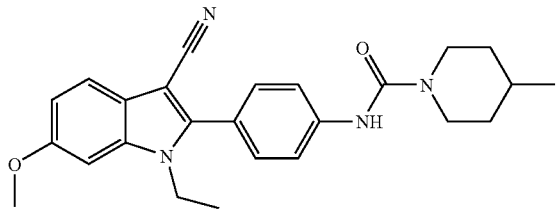

-continued
| 1378 | 1379 |
|---|---|
| 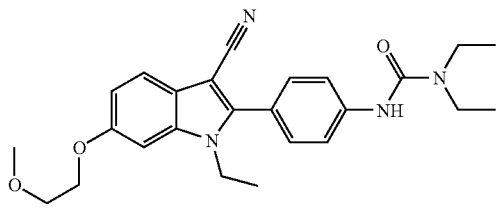 | 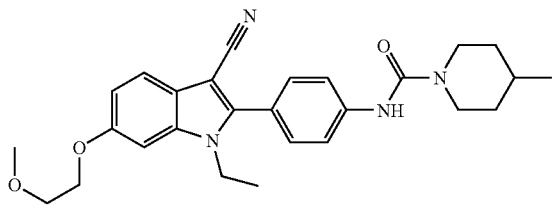 |
| 1380 | 1381 |
| 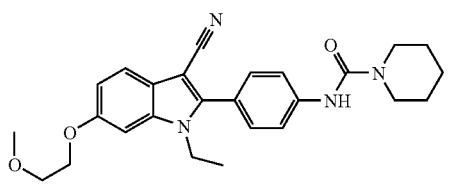 | 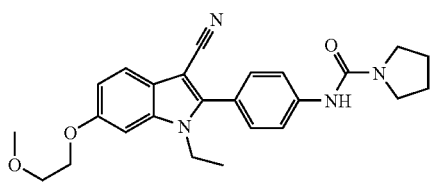 |
| 1382 | 1383 |
| 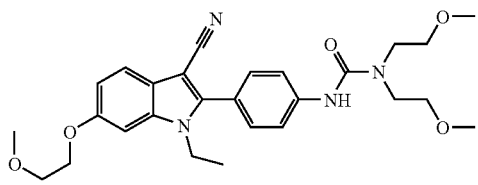 | 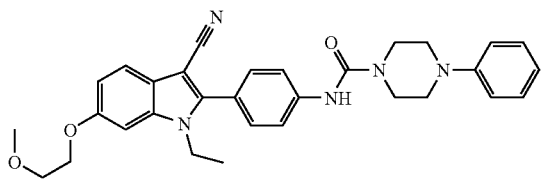 |
| 1384 | 1385 |
| 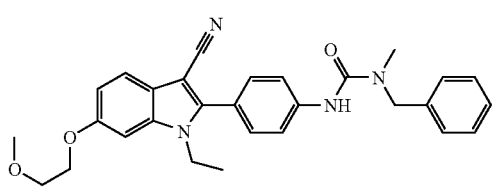 | 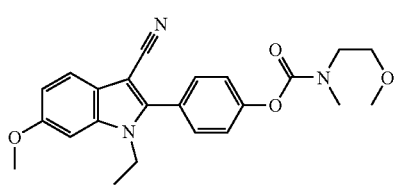 |
| 1386 | 1387 |
| 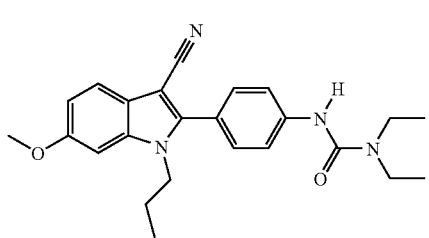 | 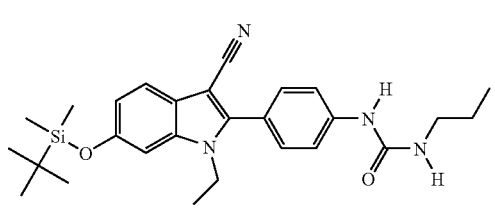 |
| 1388 | 1389 |
| 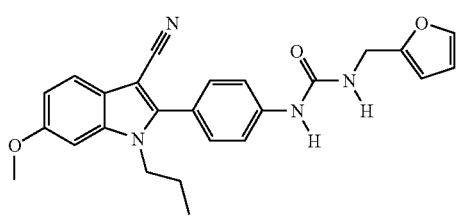 | 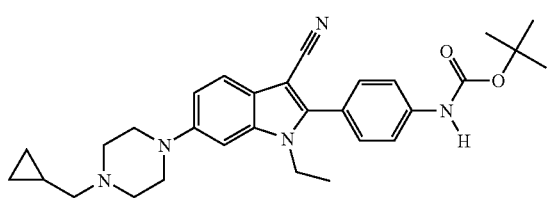 |
| 1390 | 1391 |
| 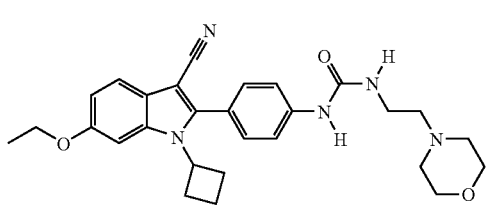 | 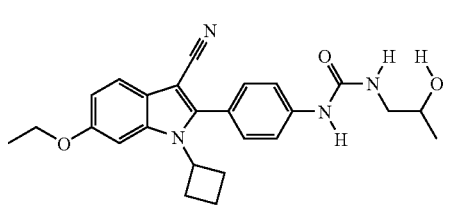 |

-continued
| 1392 | 1393 |
|---|---|
| 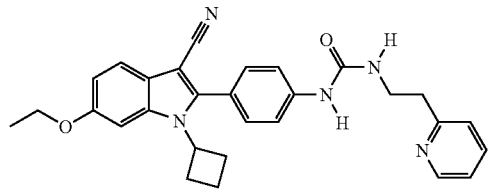 | 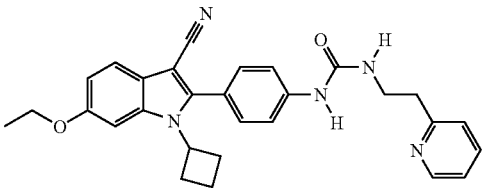 |
| 1394 | 1395 |
| 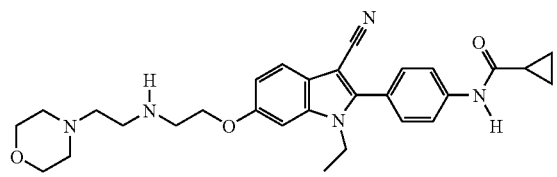 | 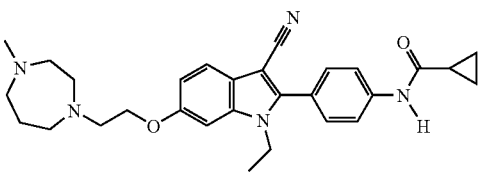 |
| 1396 | 1397 |
|  | |
| 1398 | 1399 |
| | 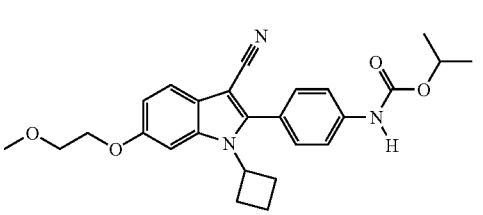 |
| 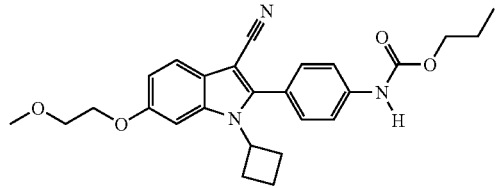 | |
| 1400 | 1401 |
| | 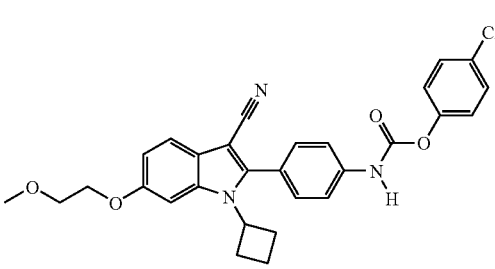 |
| 1402 | 1403 |
| 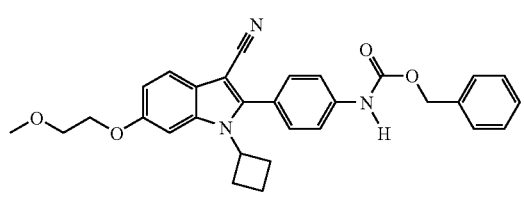 | 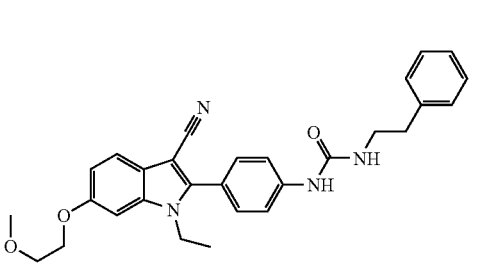 |
| 1404 | 1405 |
| | 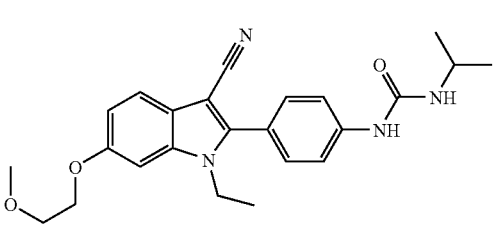 |

-continued
| | |
|---|---|
| 1406 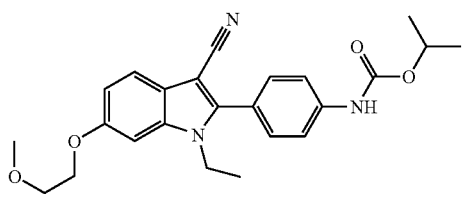 | 1407 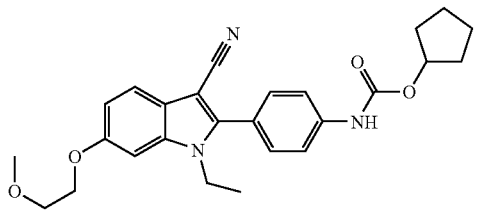 |
| 1408 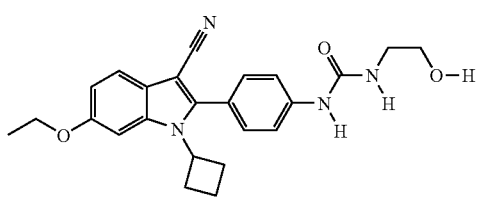 | 1409 |
| 1410 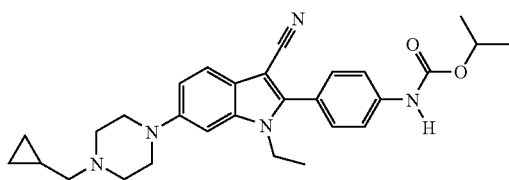 | 1411 |
| 1412 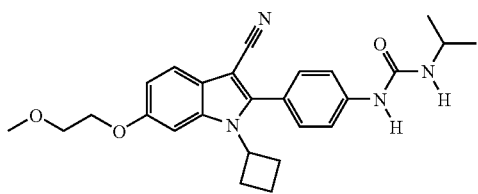 | 1413 |
| 1414 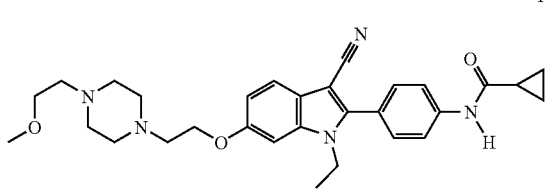 | 1415 |
| 1416 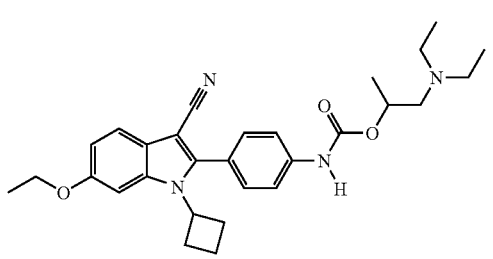 | 1417 |
| 1418 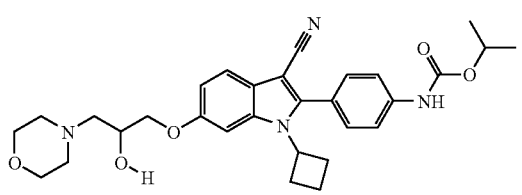 | 1419 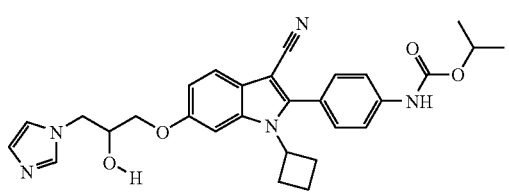 |

-continued
1420
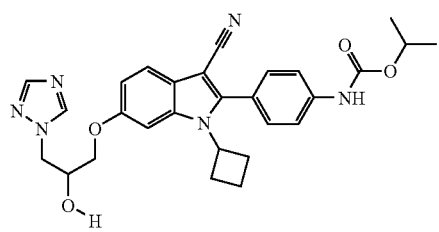
1421
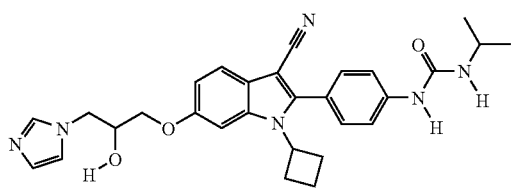
1422
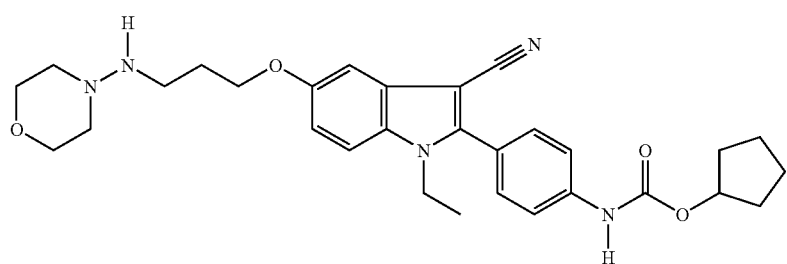
1423
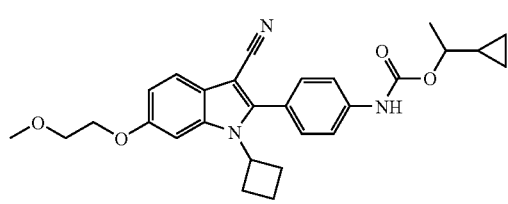
1424
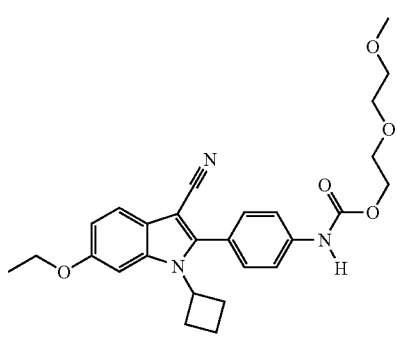
1425
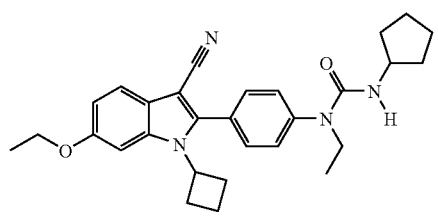
1426
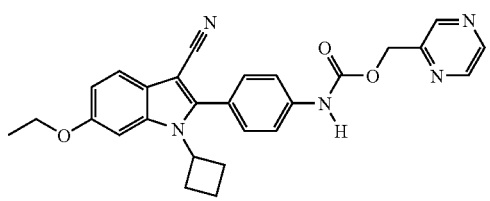
1427
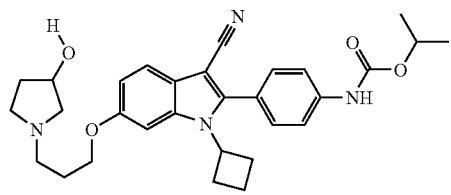
1428
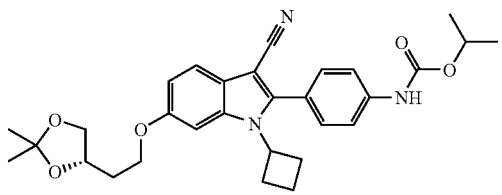
1429
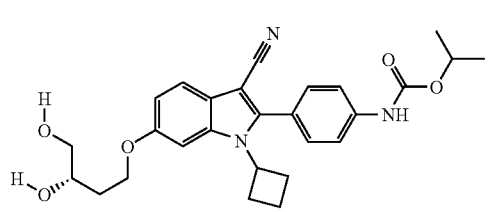
1430
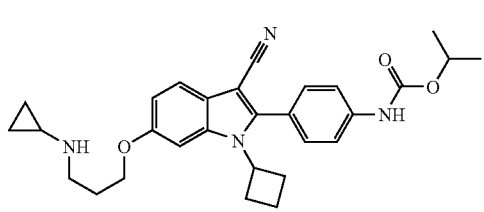

-continued
| 1431 | 1432 |
|---|---|
| 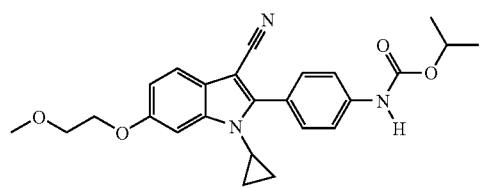 | 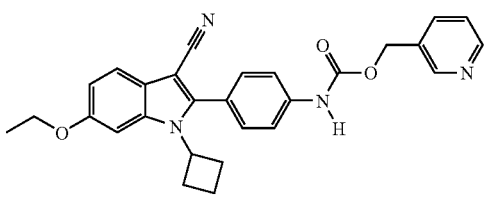 |
| 1433 | 1434 |
| 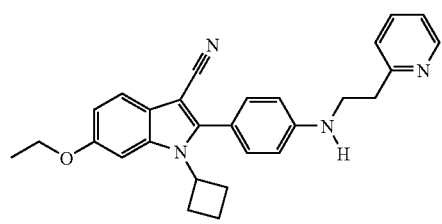 | 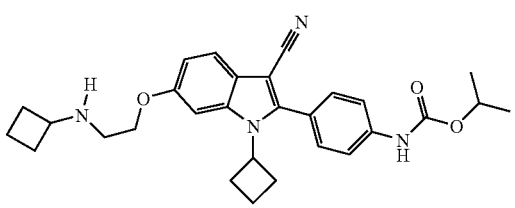 |
| 1435 | 1436 |
| 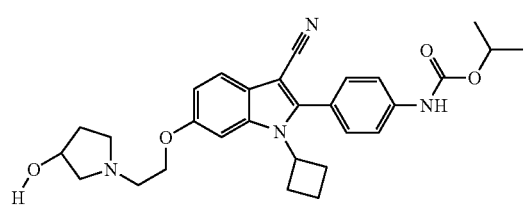 | 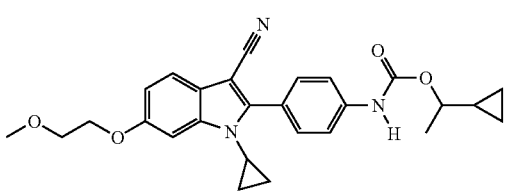 |
| 1437 | 1438 |
| 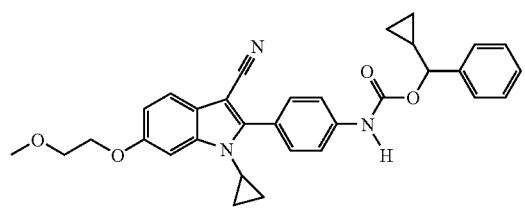 | 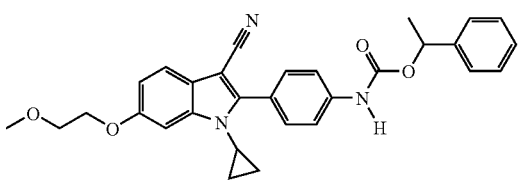 |
1439
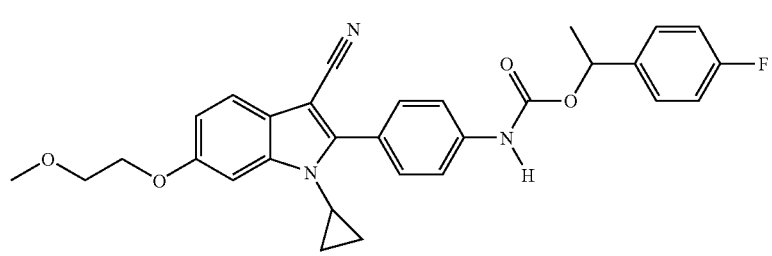
| 1440 | 1441 |
|---|---|
| 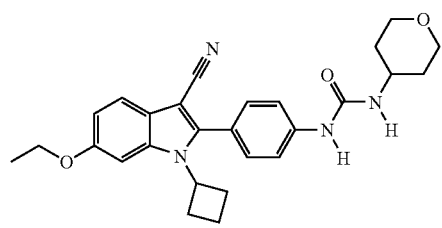 | 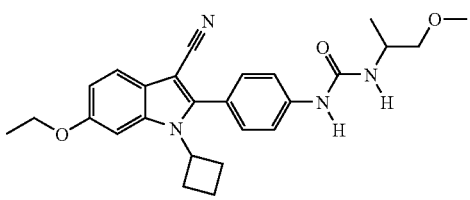 |
| 1442 | 1443 |
| 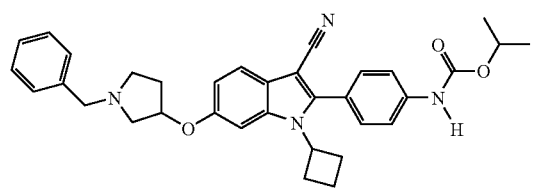 | 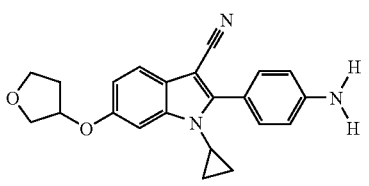 |

-continued
| | |
|---|---|
| 1444 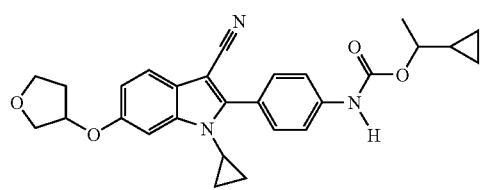 | 1445 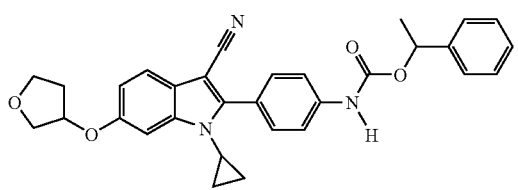 |
| 1446 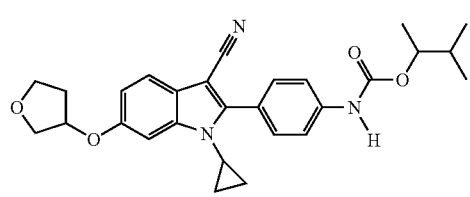 | 1447 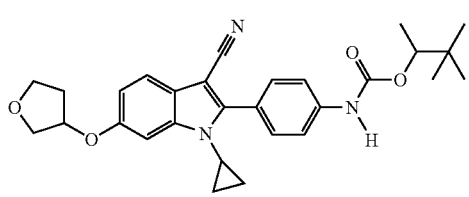 |
| 1448 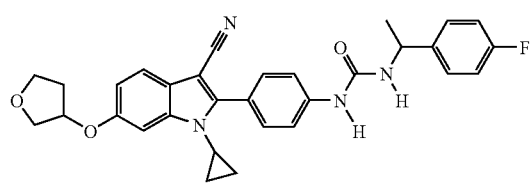 | 1449 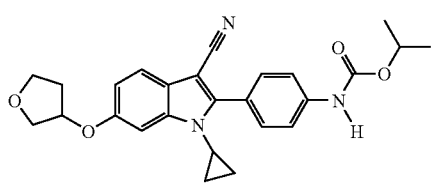 |
| 1450 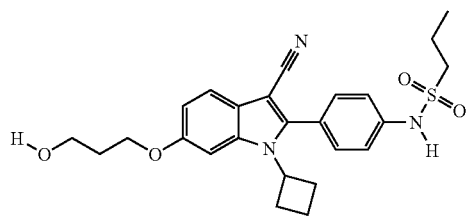 | 1451 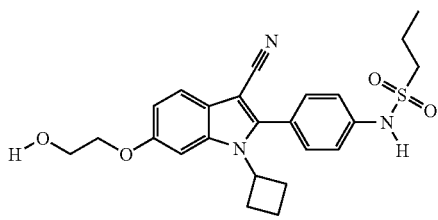 |
| 1452 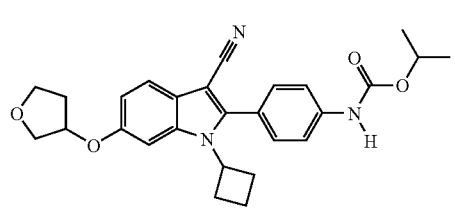 | 1453 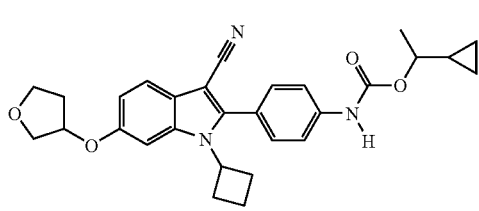 |
| 1454 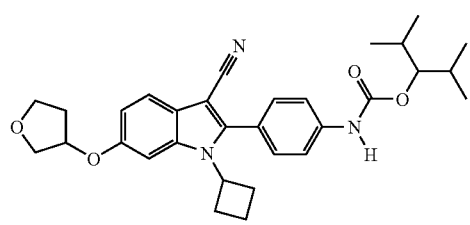 | 1455 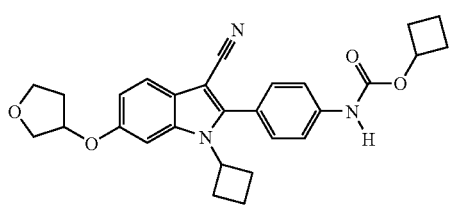 |
| 1456 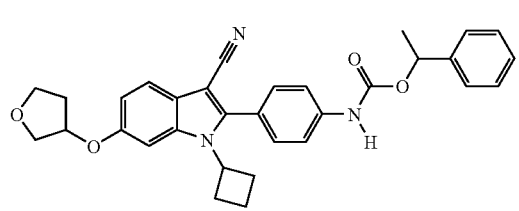 | 1457 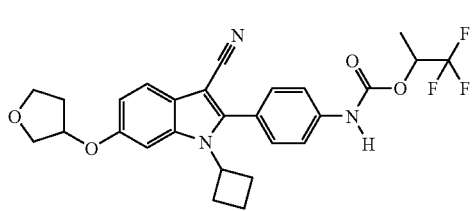 |

-continued
| 1458 | 1459 |
|---|---|
| 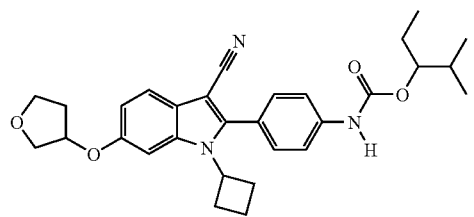 | 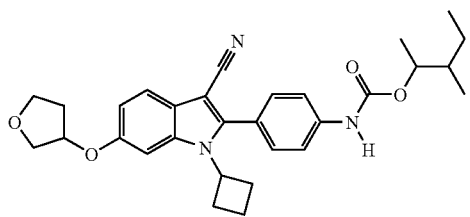 |
| 1460 | 1461 |
| 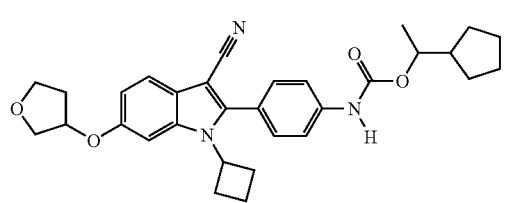 | 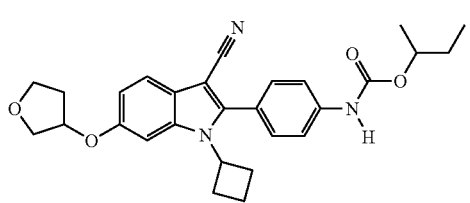 |
| 1462 | 1463 |
| 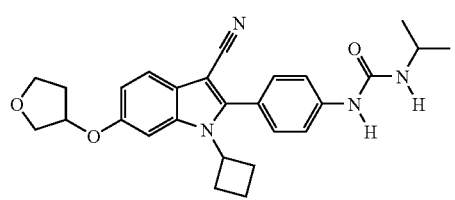 | 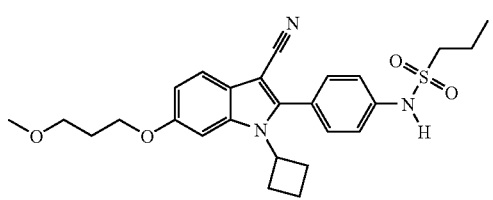 |
| 1464 | 1465 |
| 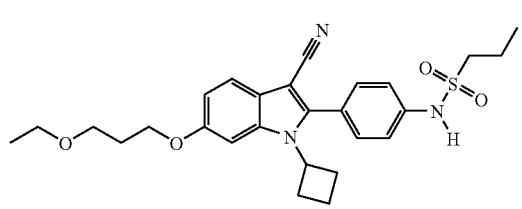 | 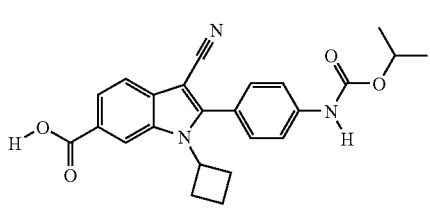 |
| 1466 | 1467 |
| 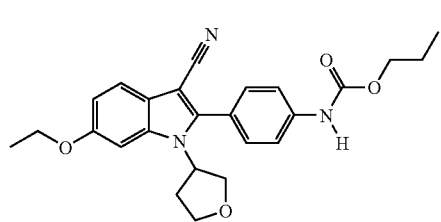 | 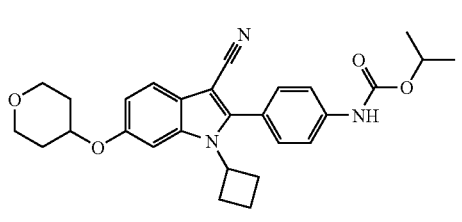 |
| 1468 | 1469 |
| 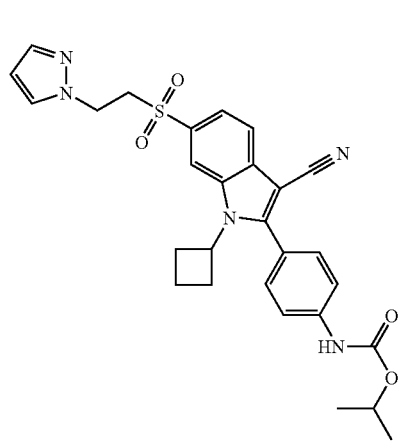 | 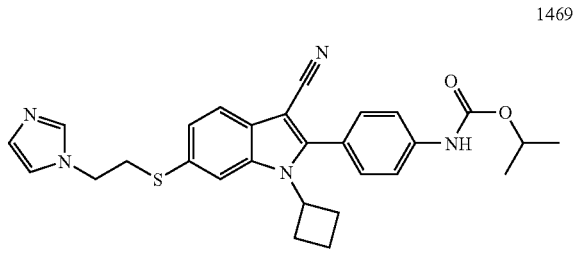 |

-continued
1470
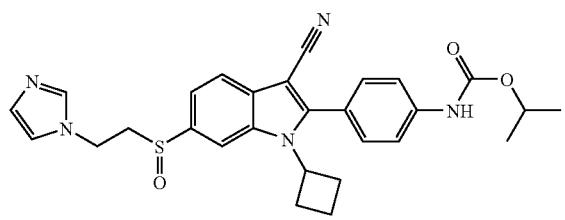
1471
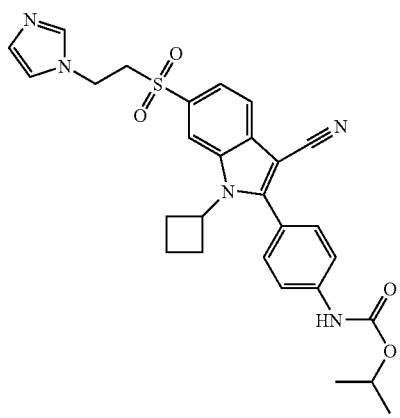
1472
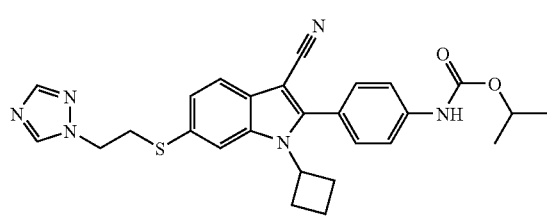
1473
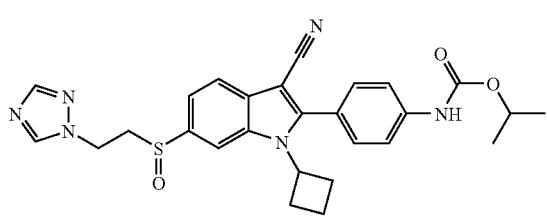
1474
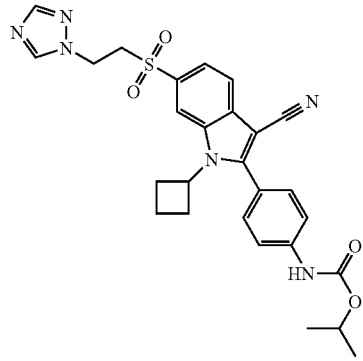
1475
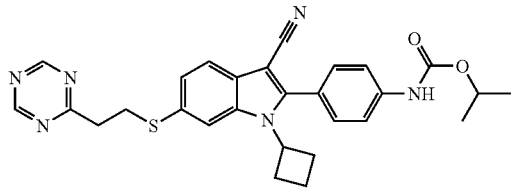
1476
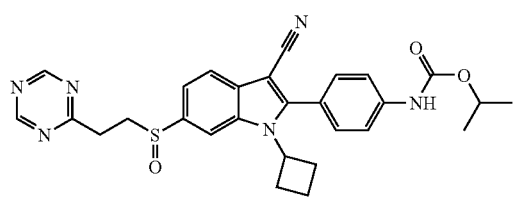
1477
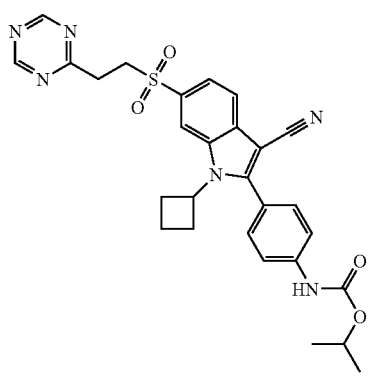
1478
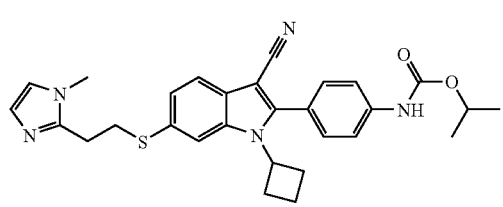
1479
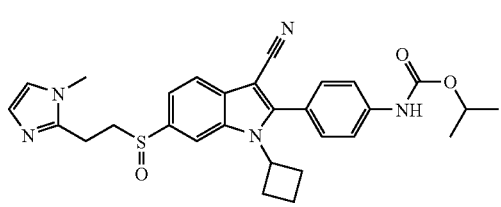

| 213 | 214 |
|---|---|
| | 1480 |
| | 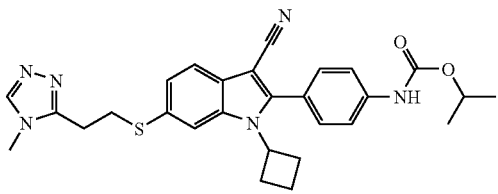 1481 |
| 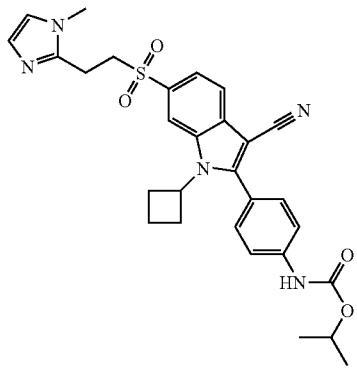 | |
| 1482 | |
| 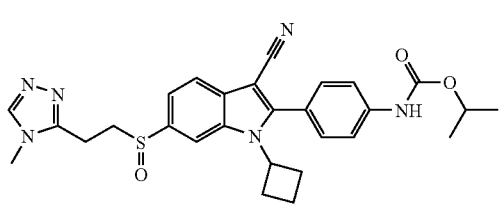 | 1483 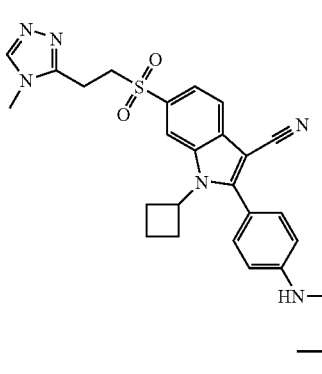 |
| 1485 | 1486 |
| 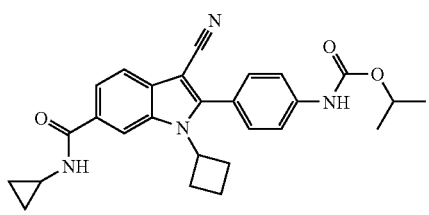 | 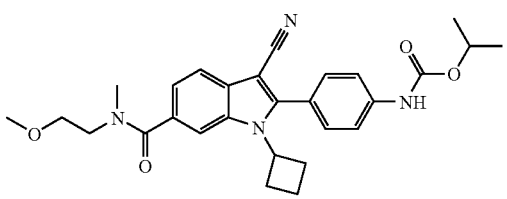 |
| 1487 | 1488 |
| 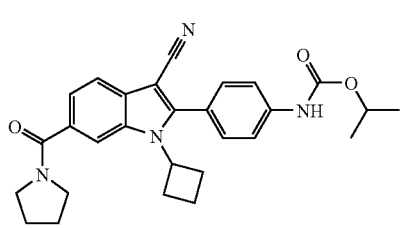 | 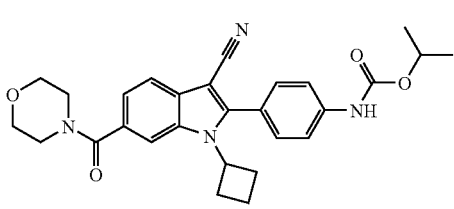 |
| 1489 | 1490 |
| 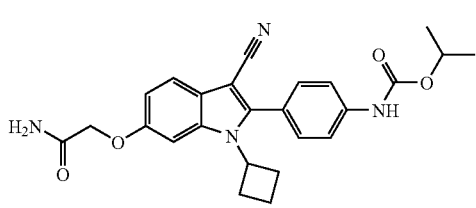 | 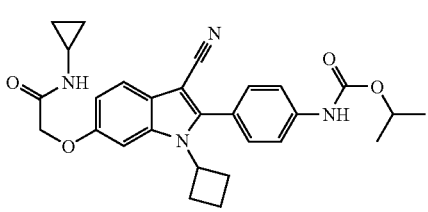 |
| 1498 | 1499 |
| 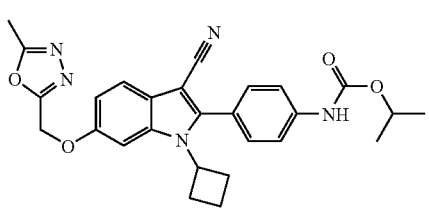 | 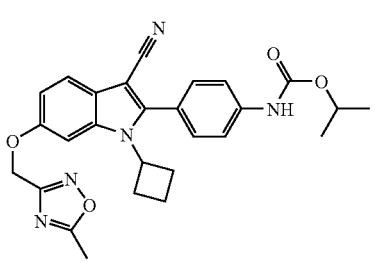 |

-continued
1500
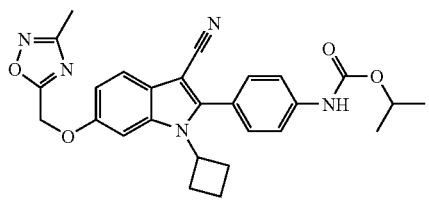
1501
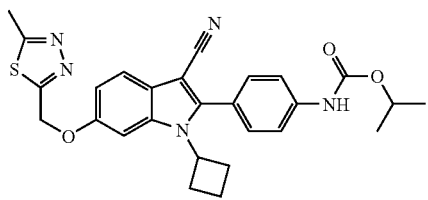
1502
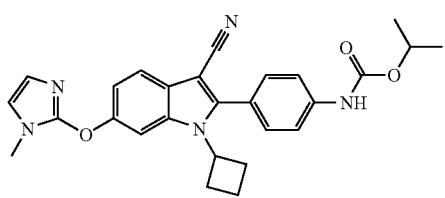
1503
1504
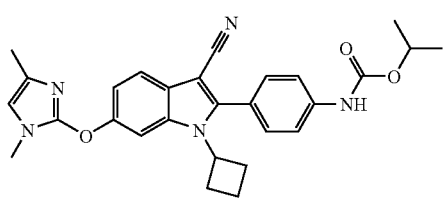
1505
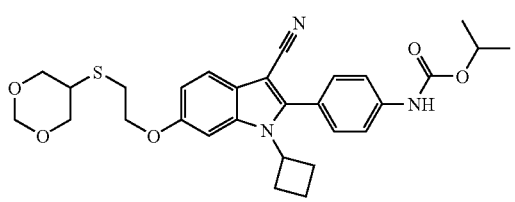
1508
1509
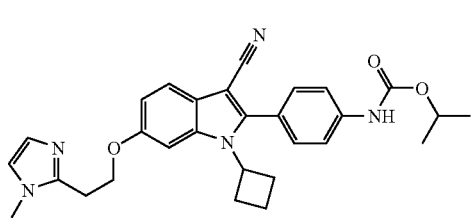
1515
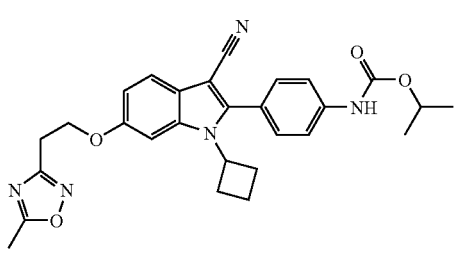
1516
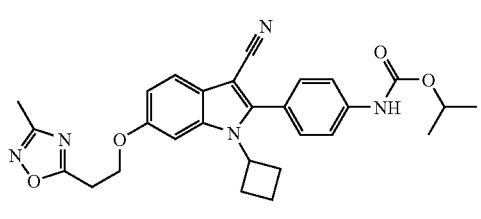
1524
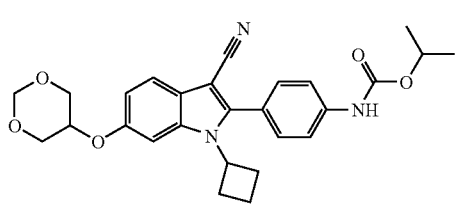
1525
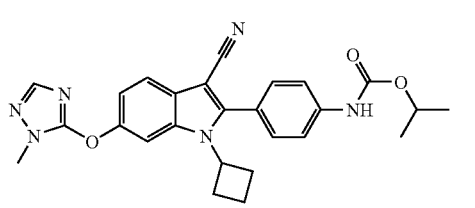
1526
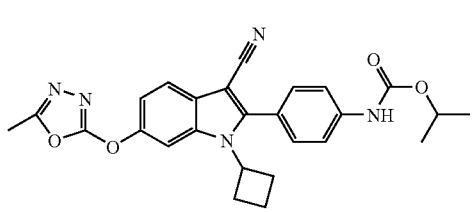
1527
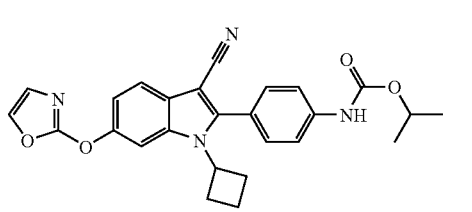

-continued
1528 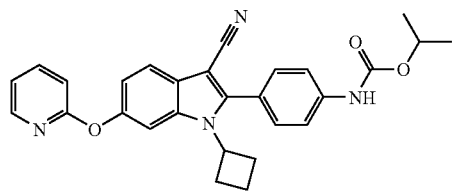
1529 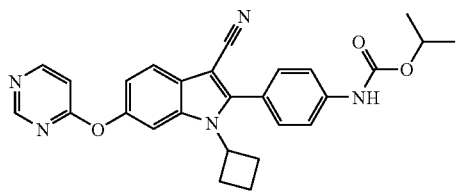
1530 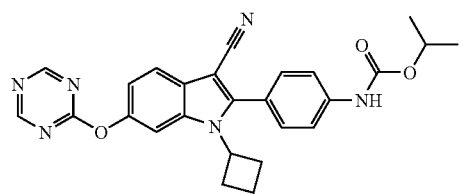
1531 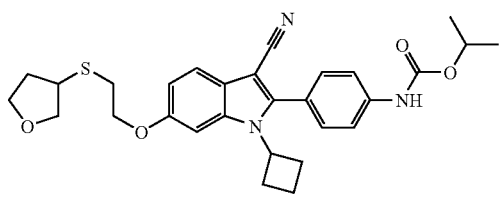
1532 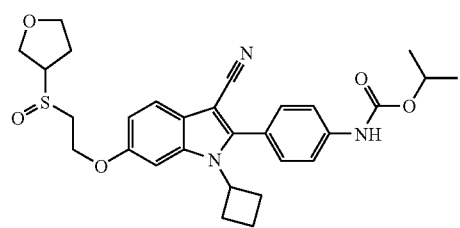
1533 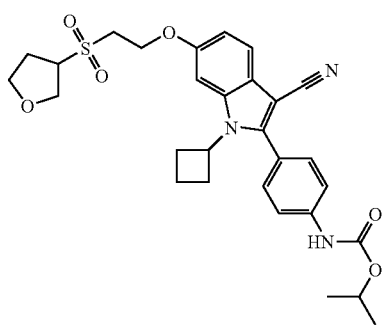
1534 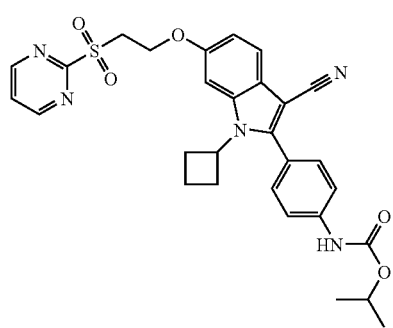
1535 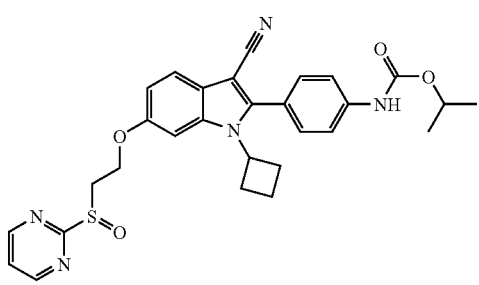
1536 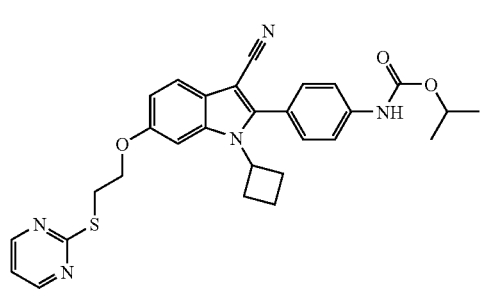
1537 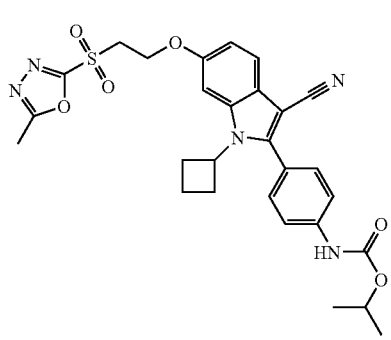

-continued
| | |
|---|---|
| 1538 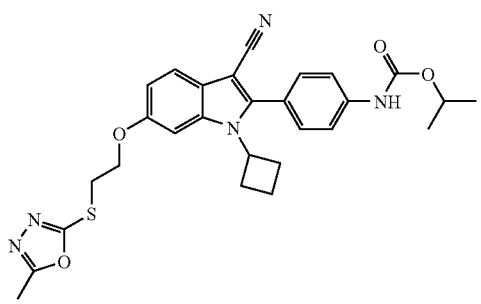 | 1539 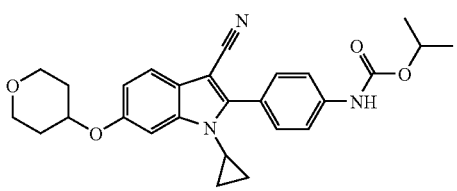 |
| 1543 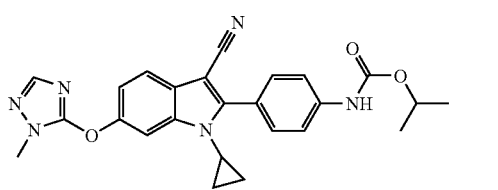 | 1544 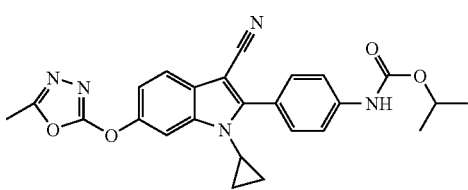 |
| 1545 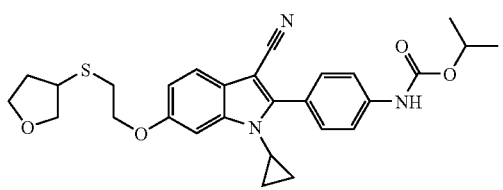 | 1546 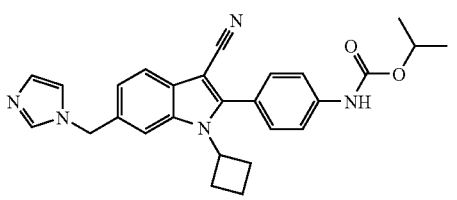 |
| 1547 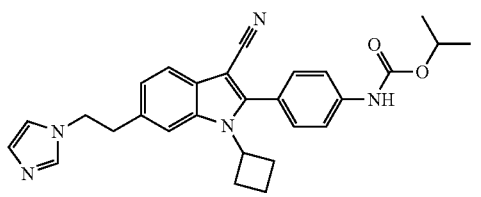 | 1548 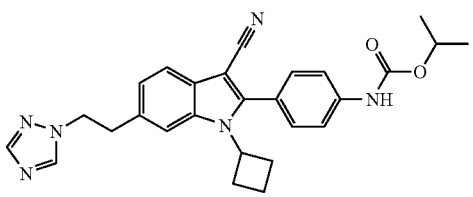 |
| 1549 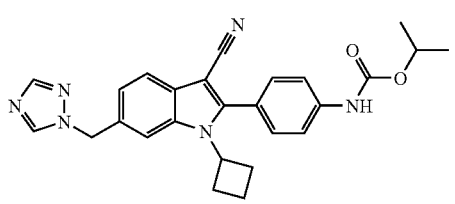 | 1550 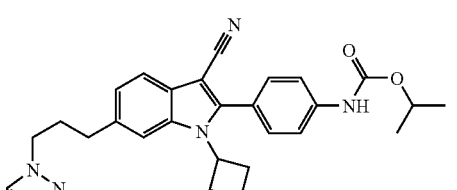 |
| 1551 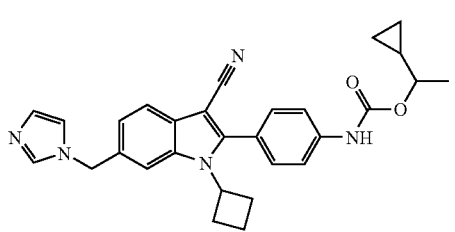 | 1552 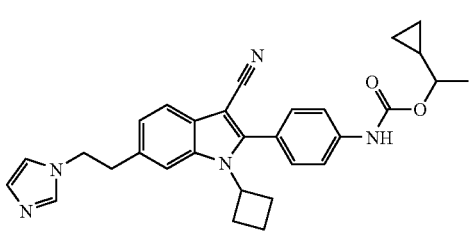 |
| 1553 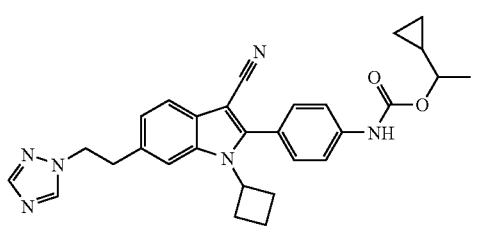 | 1554 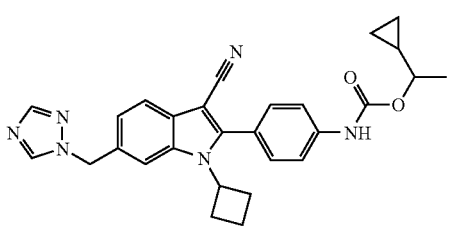 |

-continued
| 1555 | 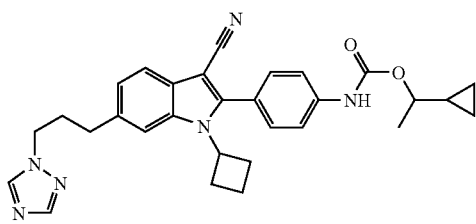 | 1557 | 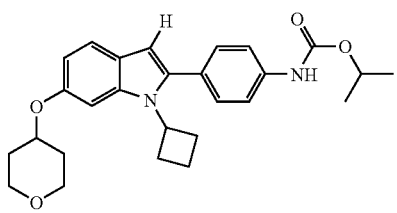 |
| 1558 | 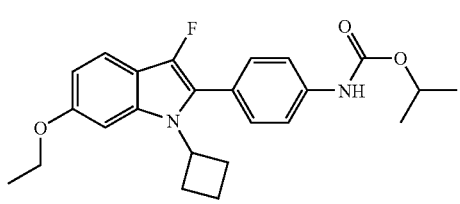 | 1559 | 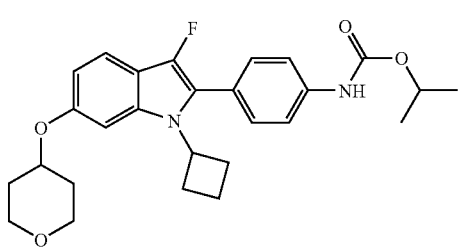 |
| 1560 | 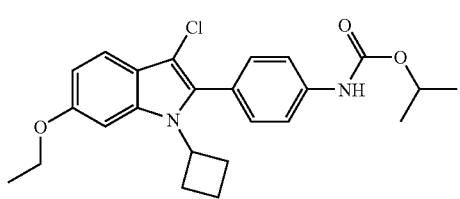 | 1561 | 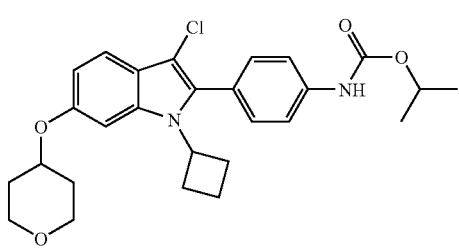 |
| 1562 | 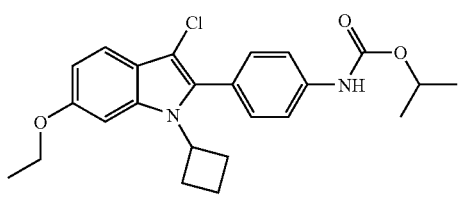 | 1563 | 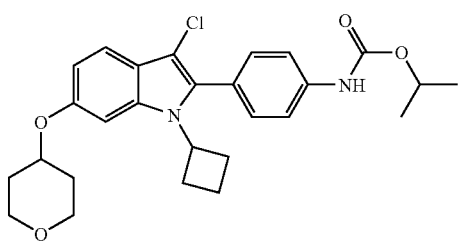 |
| 1564 | 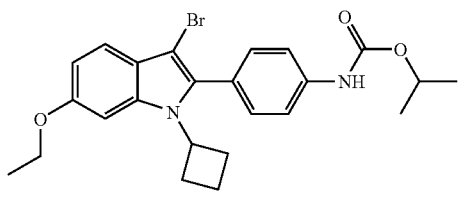 | 1565 | 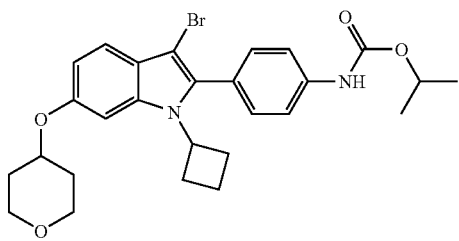 |
| 1566 | 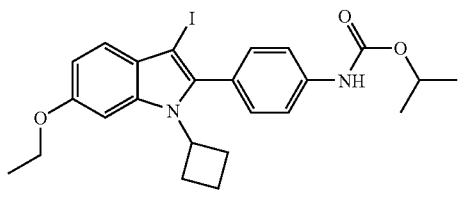 | 1567 | 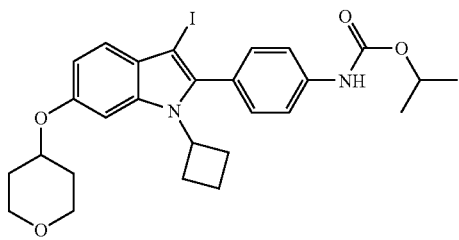 |

-continued
| | |
|---|---|
| 1568 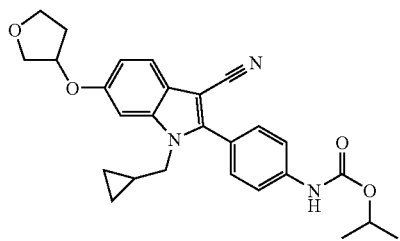 | 1569 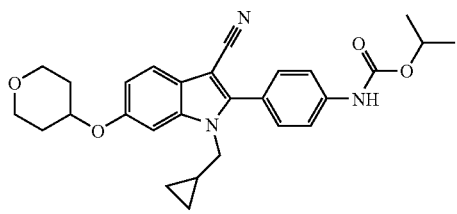 |
| 1570 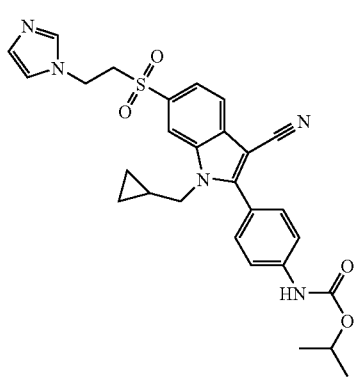 | 1571 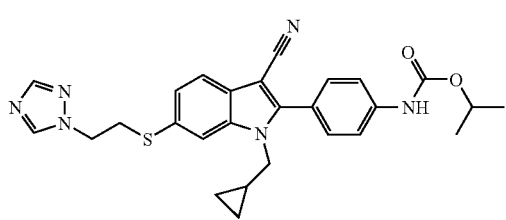 |
| 1572 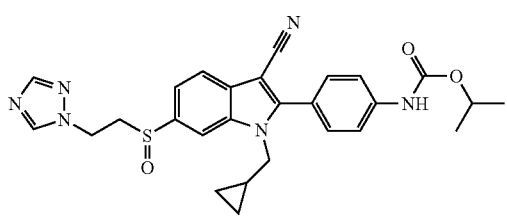 | 1573 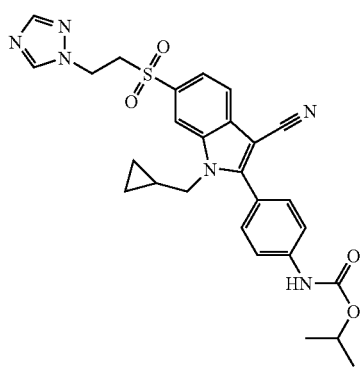 |
| 1575 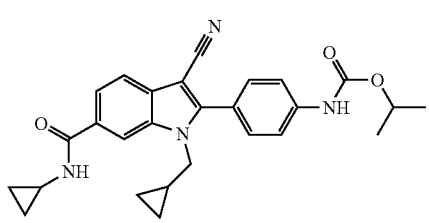 | 1576 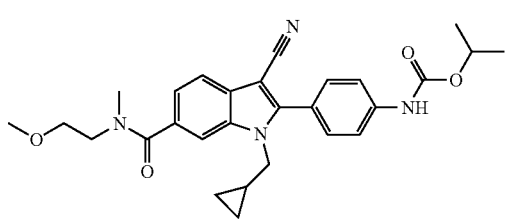 |
| 1577 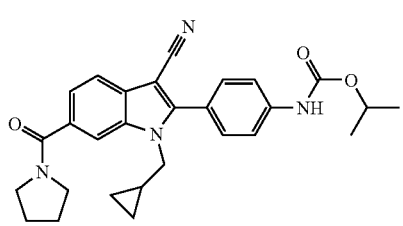 | 1578 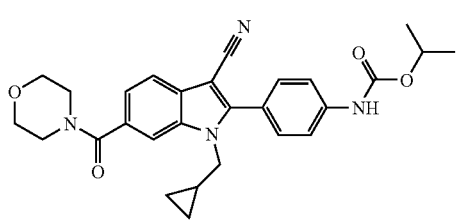 |

-continued
| | |
|---|---|
| 1579 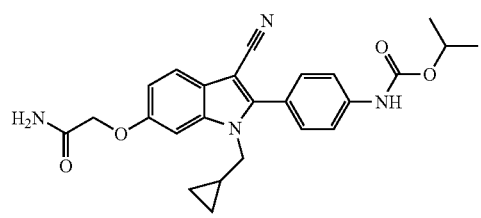 | 1580 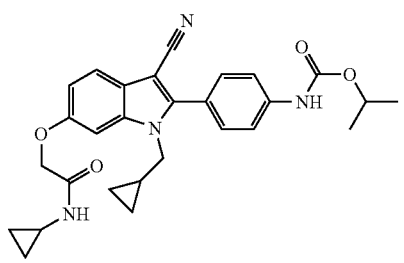 |
| 1585 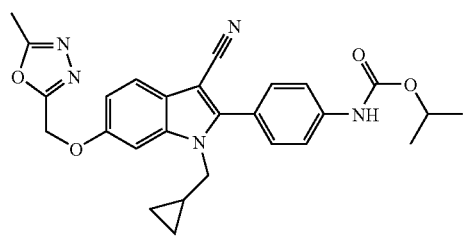 | 1586 |
| 1587 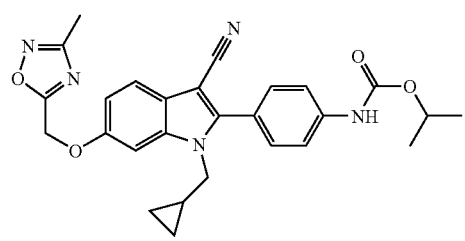 | 1588 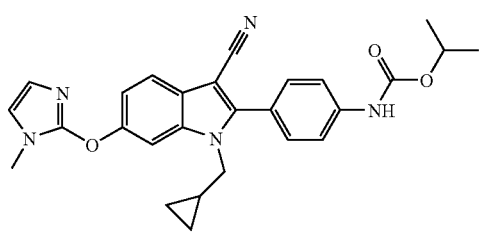 |
| 1589 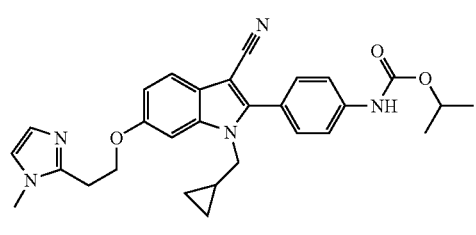 | 1594 |
| 1595 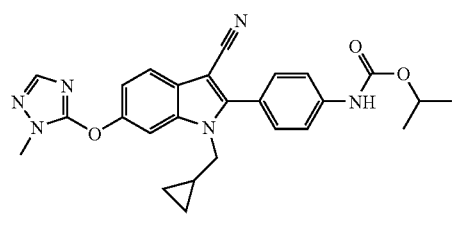 | 1596 |
| 1597 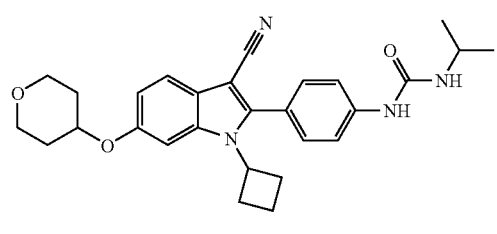 | 1598 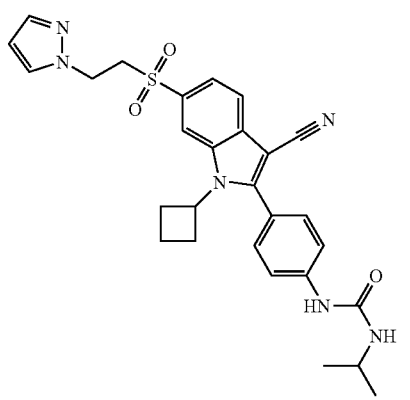 |

227   228
-continued
1599 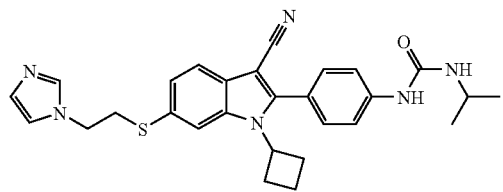   1600 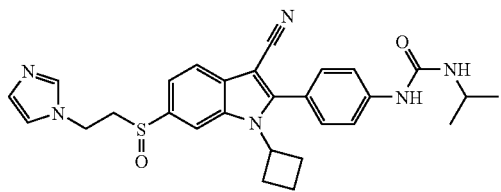
1601 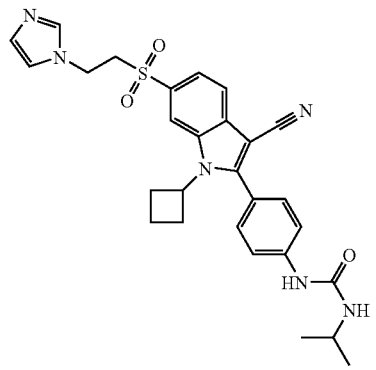   1602 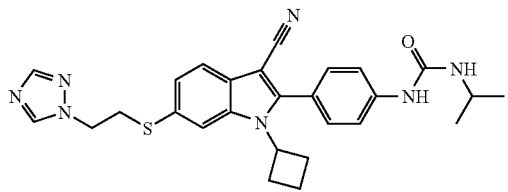
1603 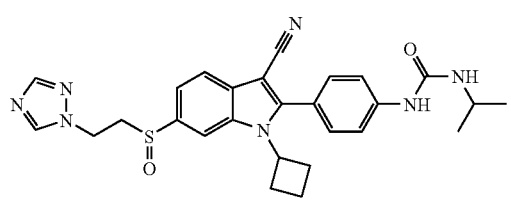   1604 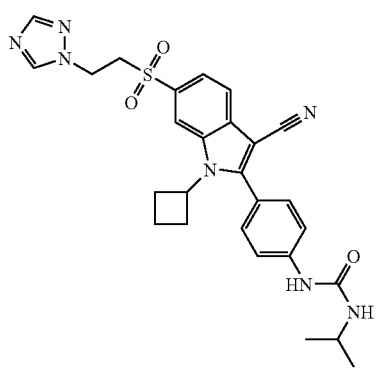
1605 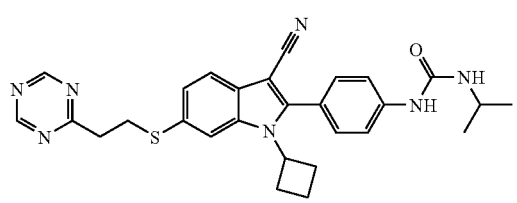   1606 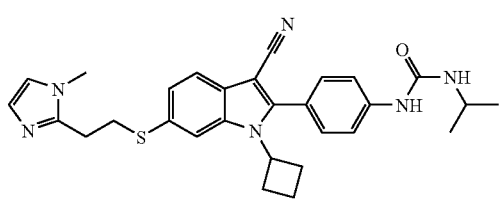
1607 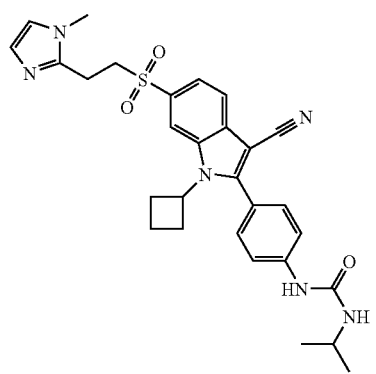   1608 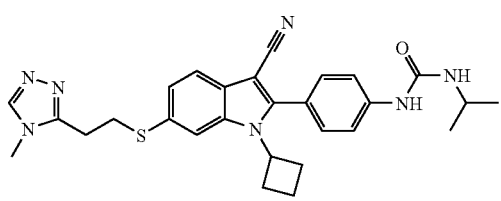

-continued
1609 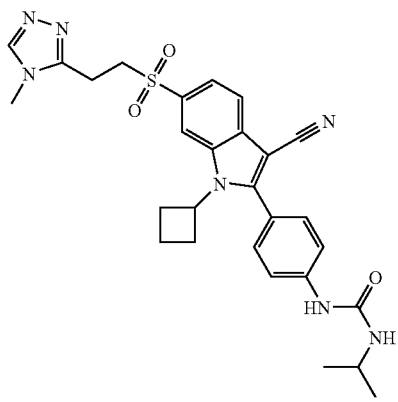
1611 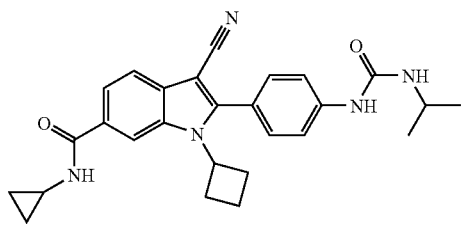
1612 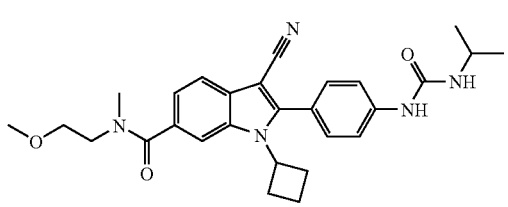
1613 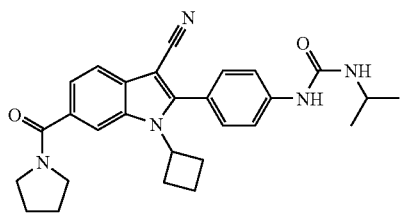
1614 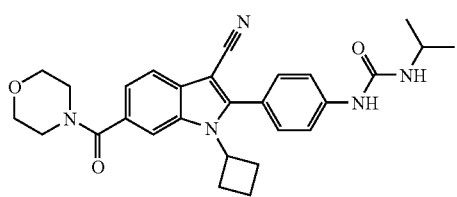
1615 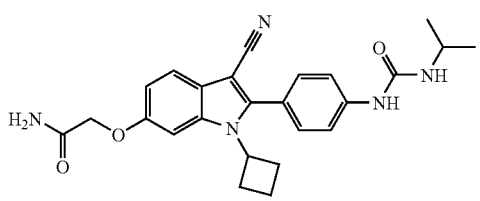
1616 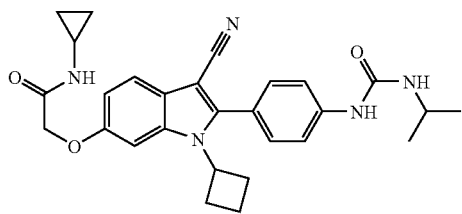
1624 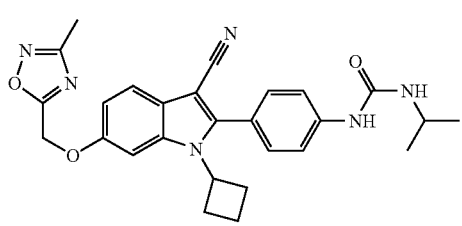
1625 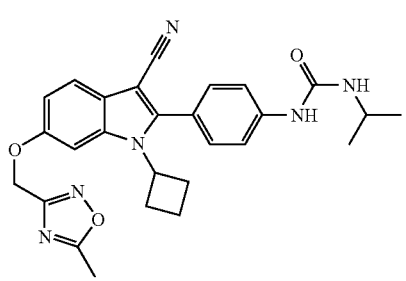
1626 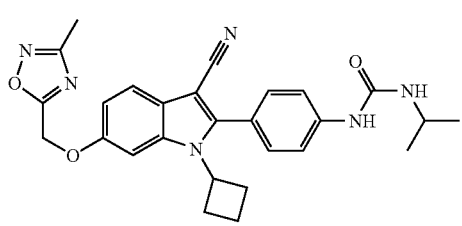
1627 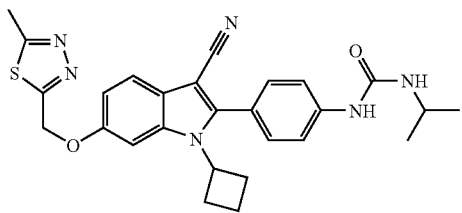
1628 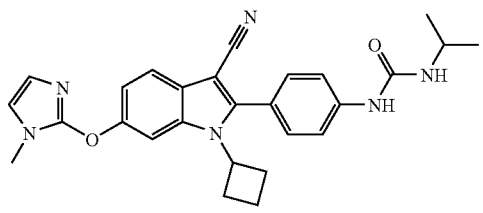

-continued
| | |
|---|---|
| 1629 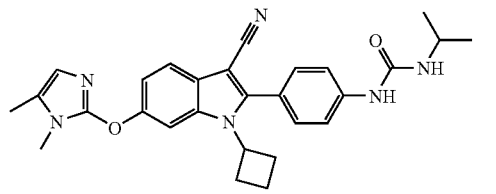 | 1630 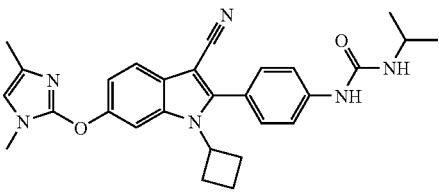 |
| 1631 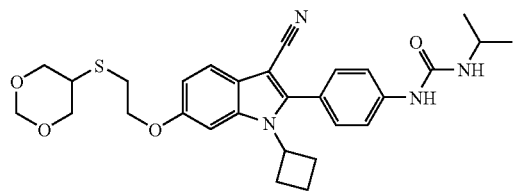 | 1634 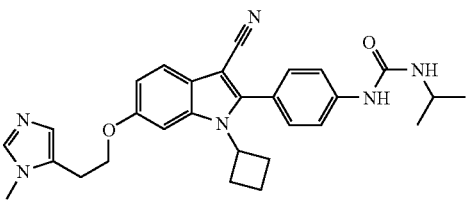 |
| 1635 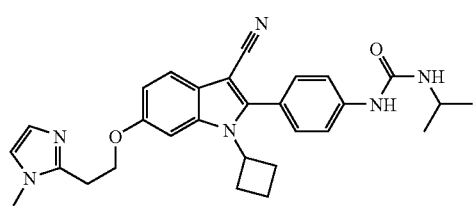 | 1641 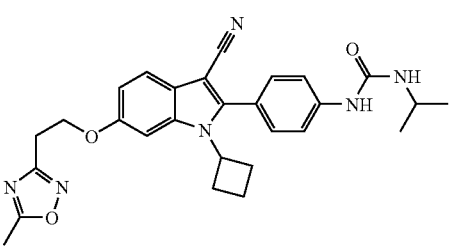 |
| 1642 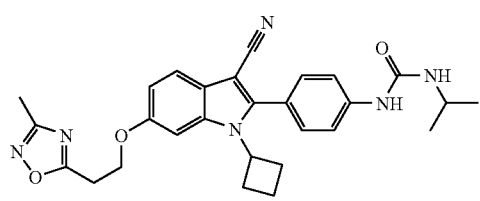 | 1650 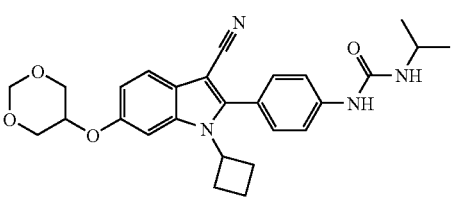 |
| 1651 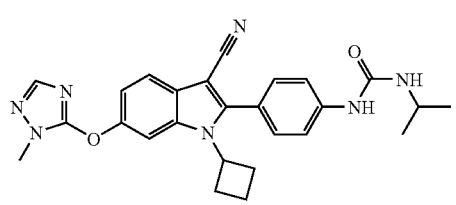 | 1652 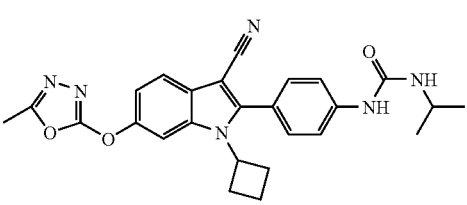 |
| 1653 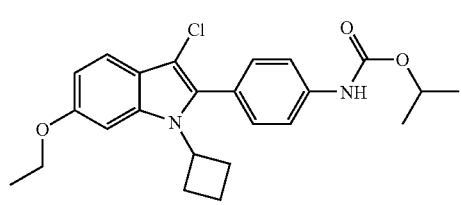 | 1654 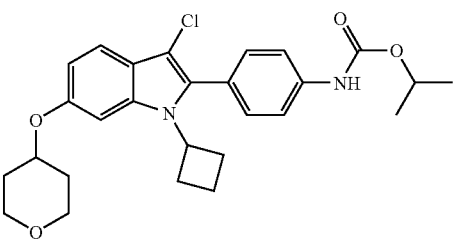 |
| 1655 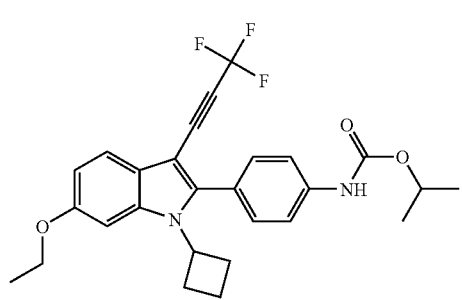 | 1656 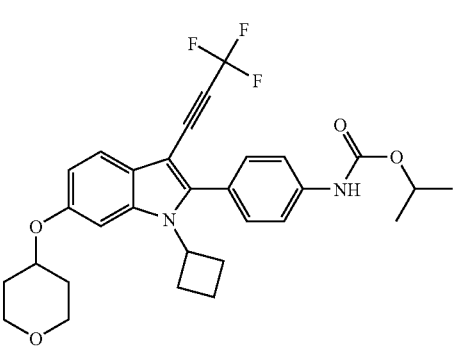 |

-continued
| 1657 | 1658 |
|---|---|
| 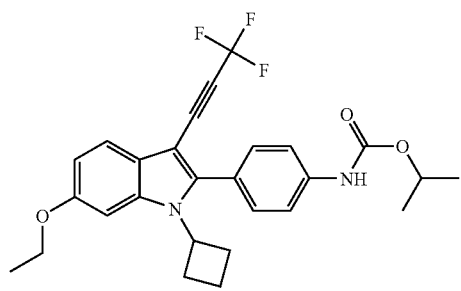 | 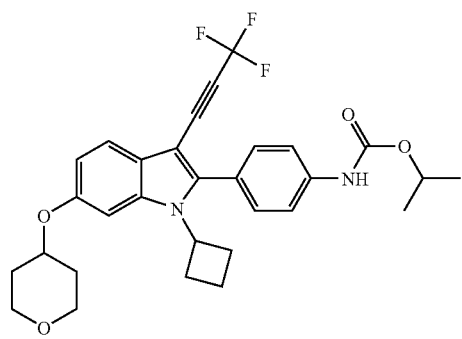 |
| 1659 | 1660 |
| 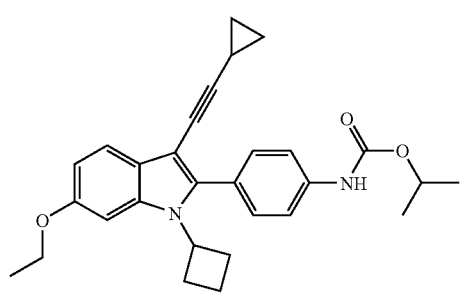 | 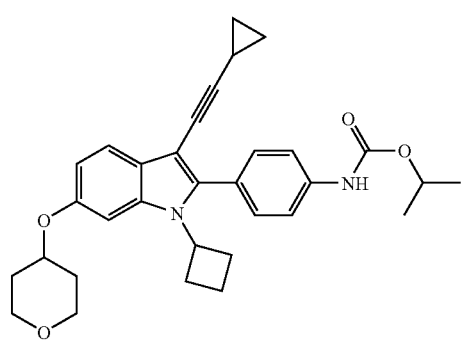 |
| 1661 | 1662 |
| 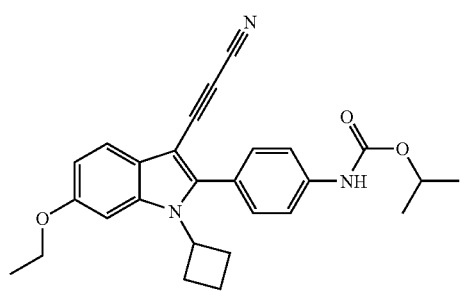 | 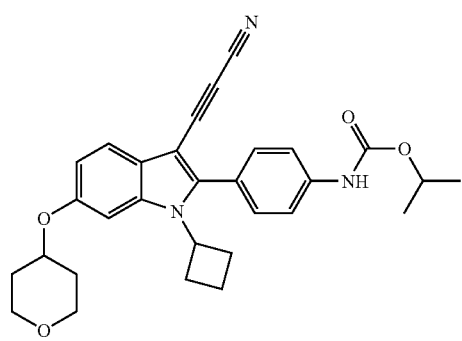 |
| 1663 | 1664 |
| 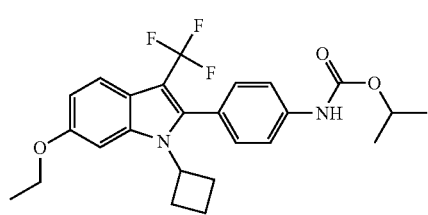 | 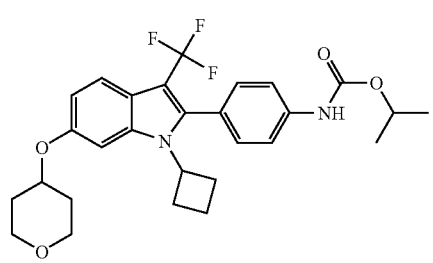 |
| 1665 | 1666 |
| 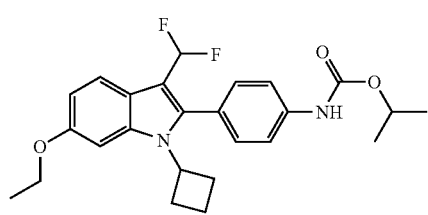 | 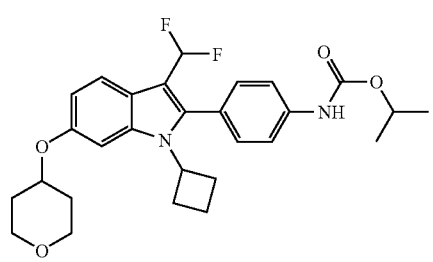 |

235 236
-continued
1668 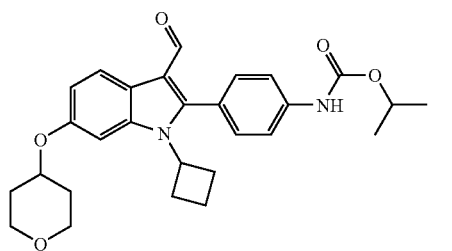 1669 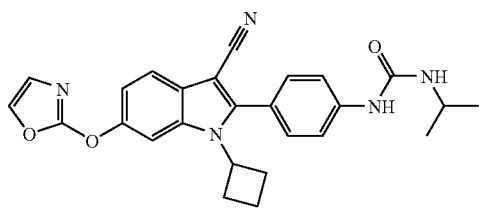
1670 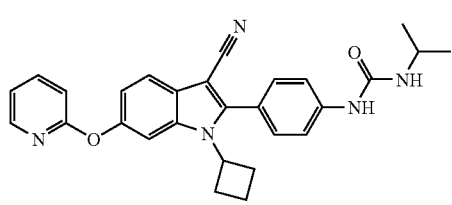 1671
1672 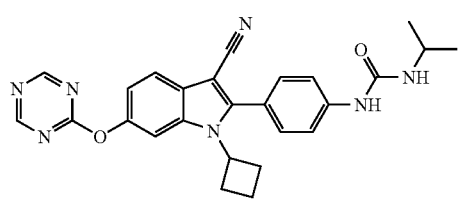 1673
1674 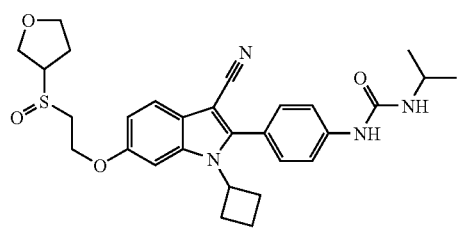 1675
1676 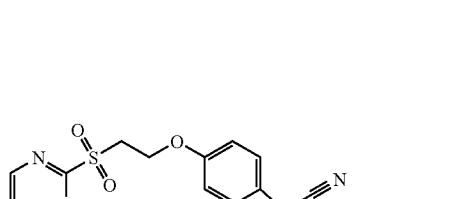 1677
1678 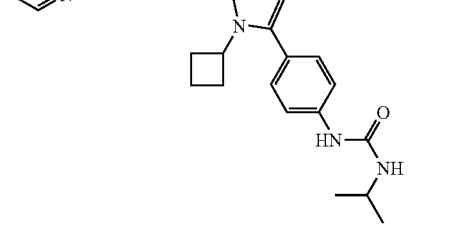 1679 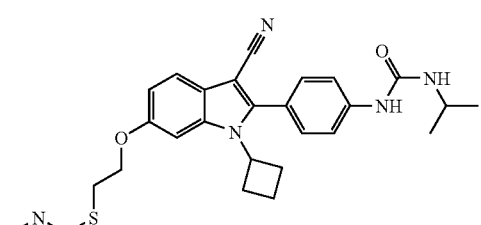

1680 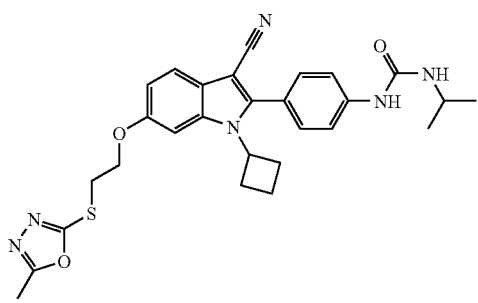
1681 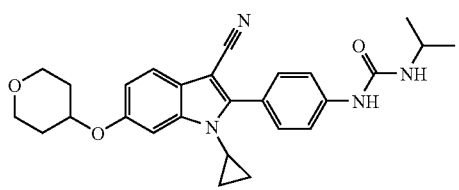
1682 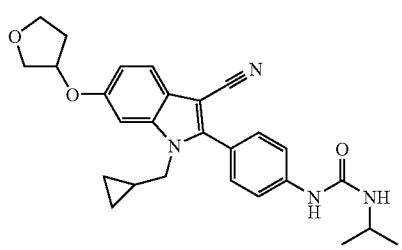
1683 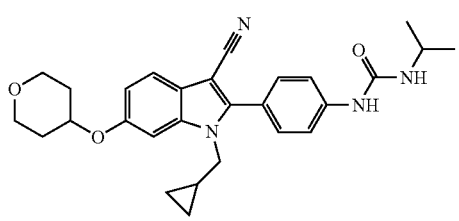
1684 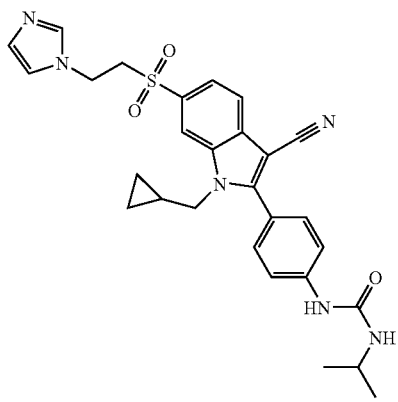
1685 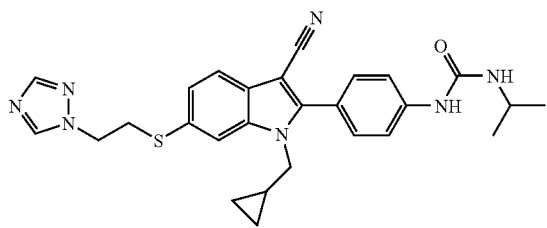
1686 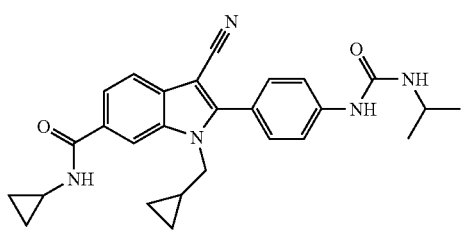
1691 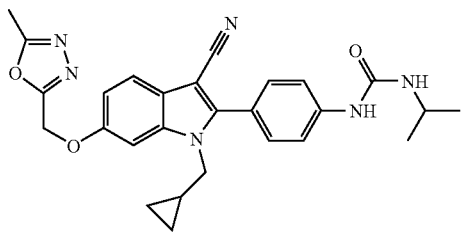
1692 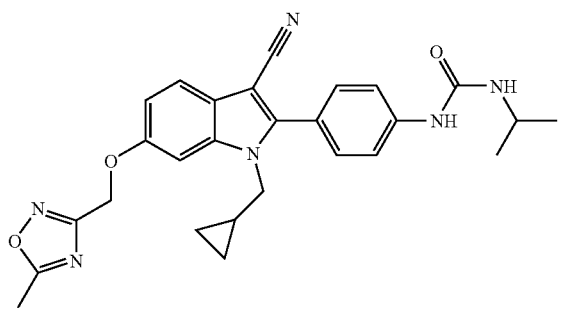
1693 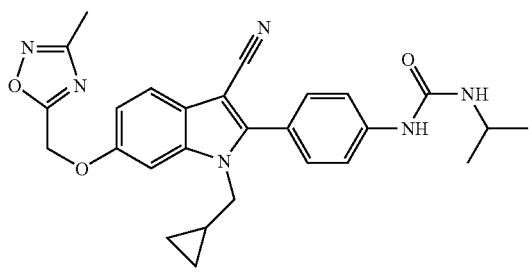

-continued
1694
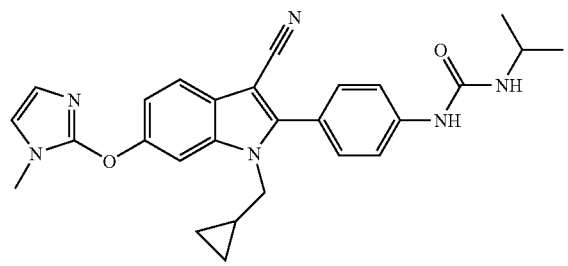
1696
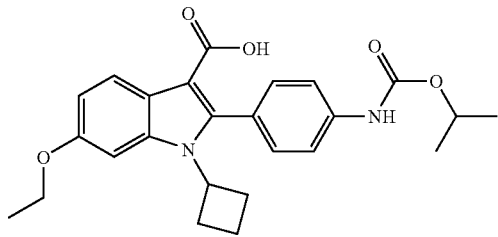
1697
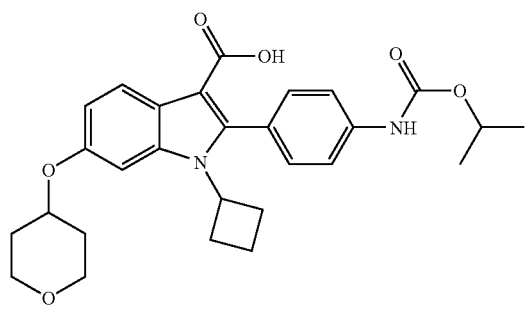
1698
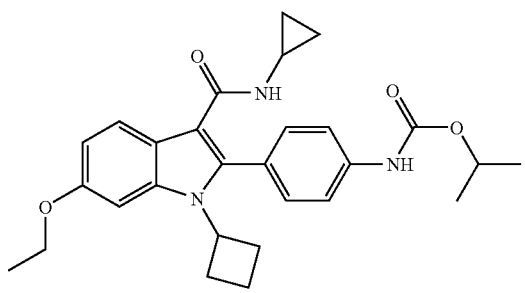
1699
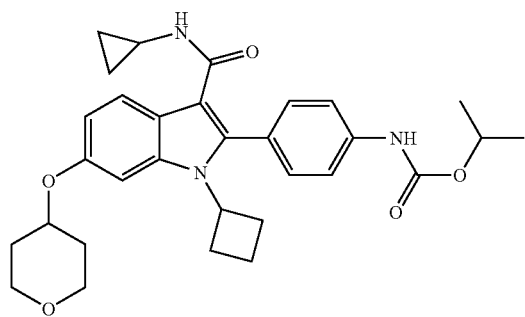
1700
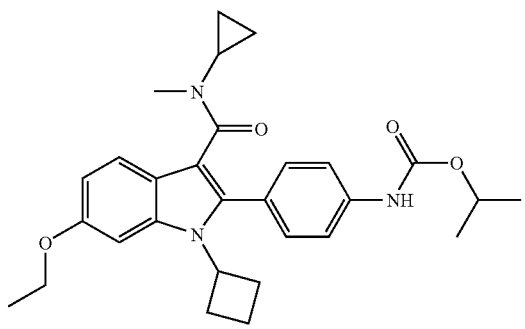
1701
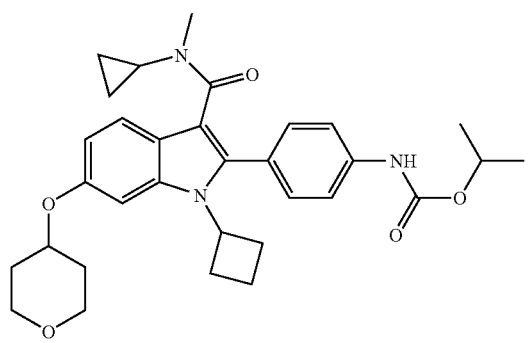
1703
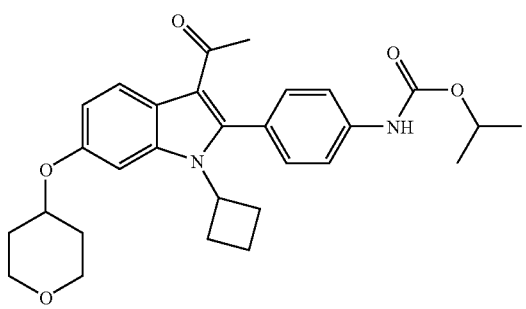

241 242
-continued
| 1704 | 1705 |
|---|---|
| 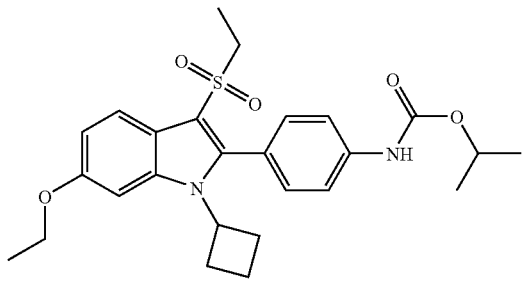 | 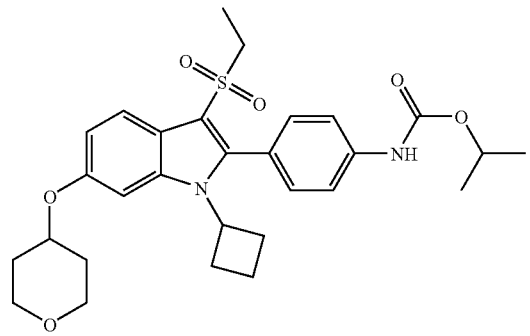 |
| 1706 | 1707 |
| 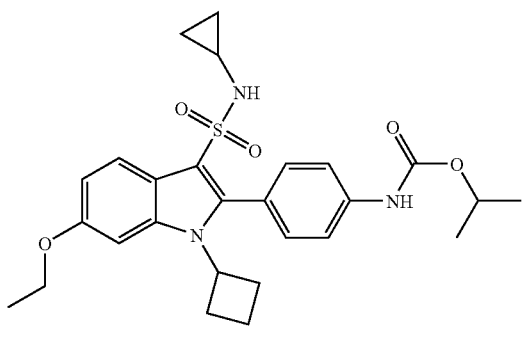 | 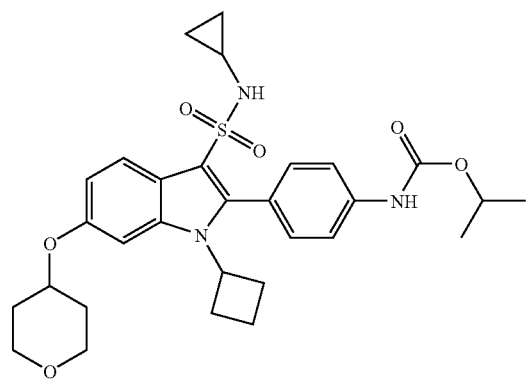 |
| 1708 | 1709 |
| 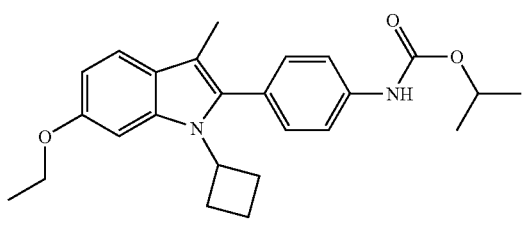 | 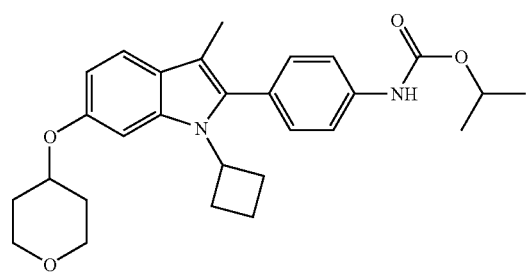 |
| 1710 | 1711 |
| 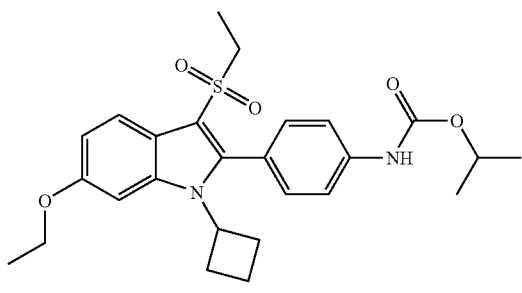 | 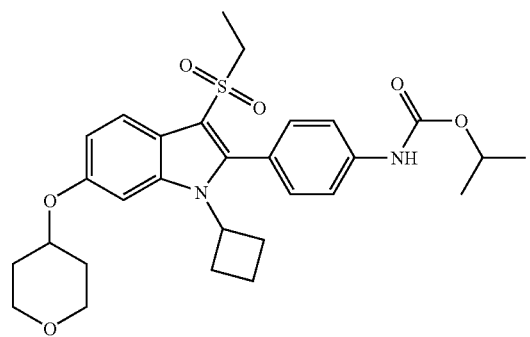 |

-continued
1712
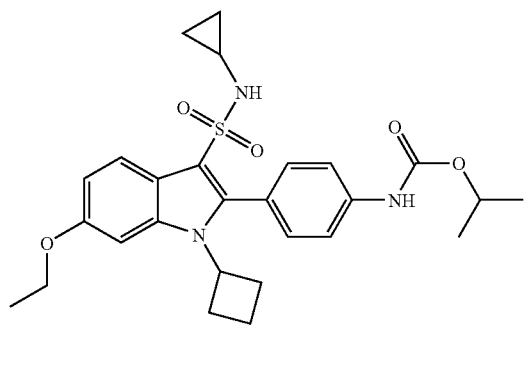
1713
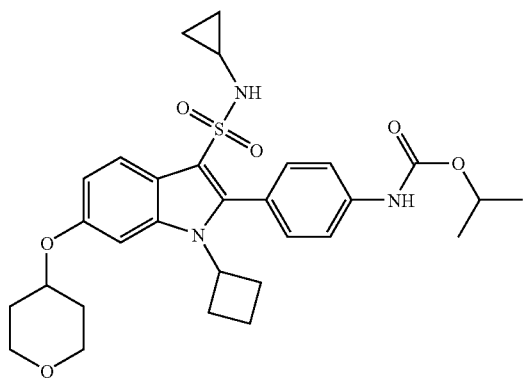
1714
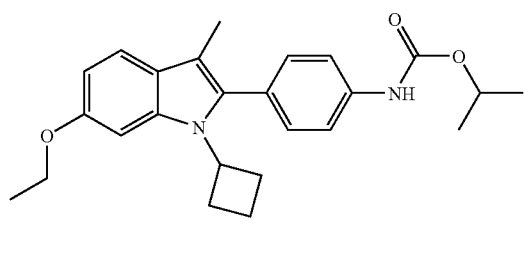
1715
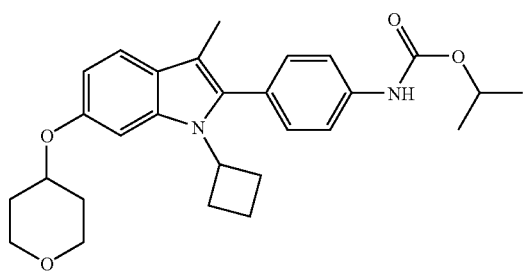
1716
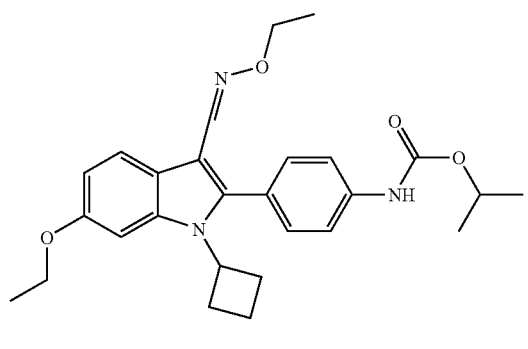
1717
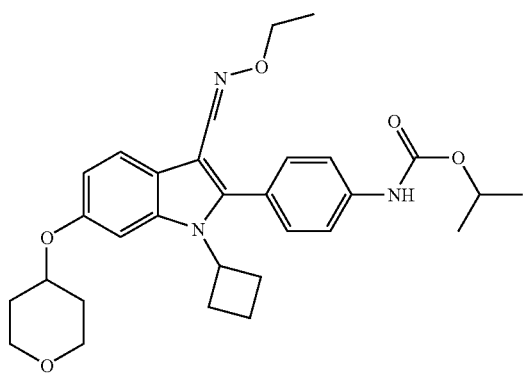
1718
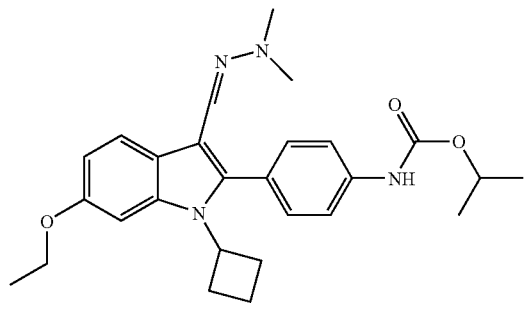
1719
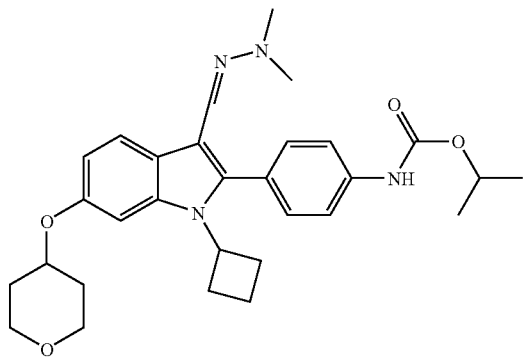

-continued
1721
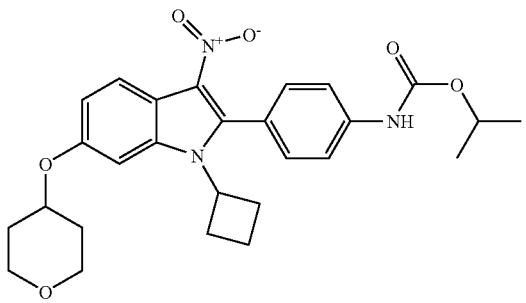
1722
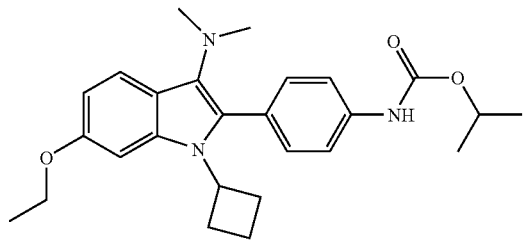
1723
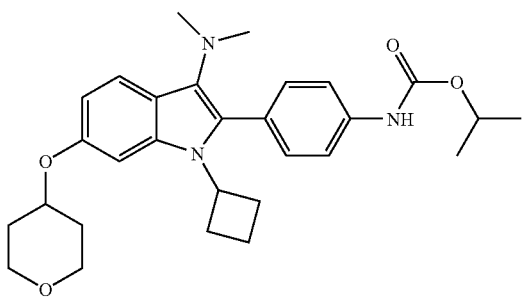
1724
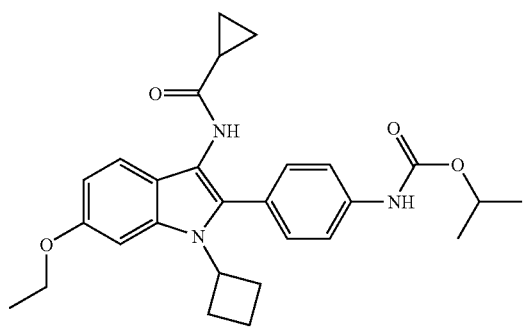
1725
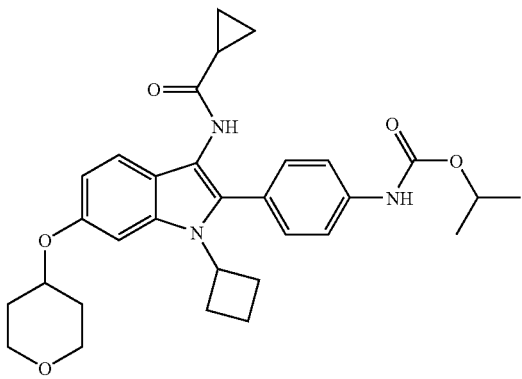
1727
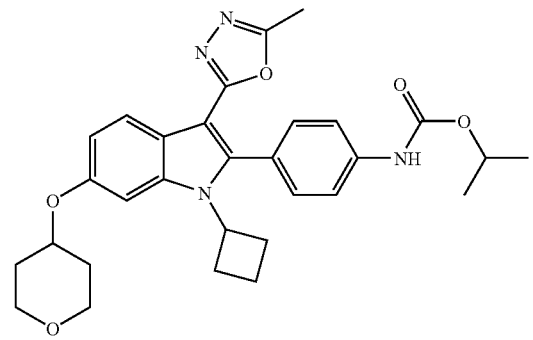
1729
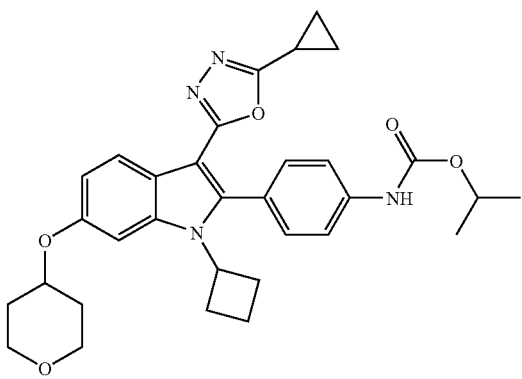
1731
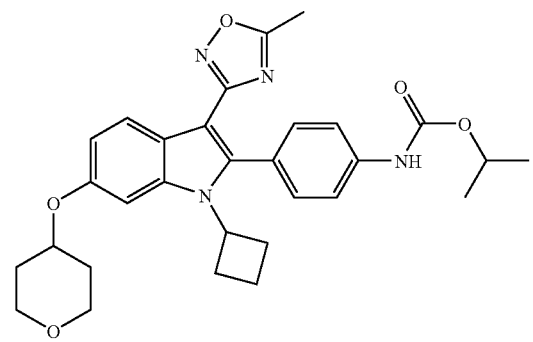

-continued
1733
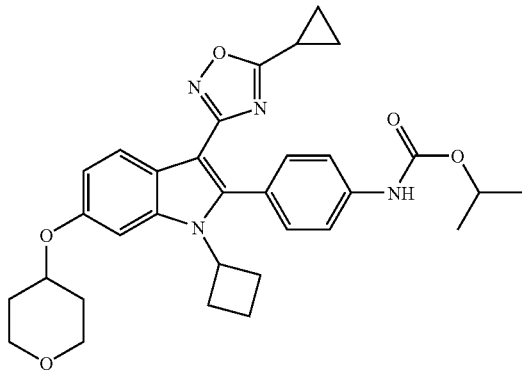
1735
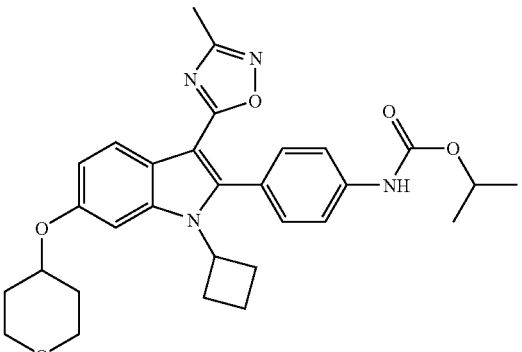
1737
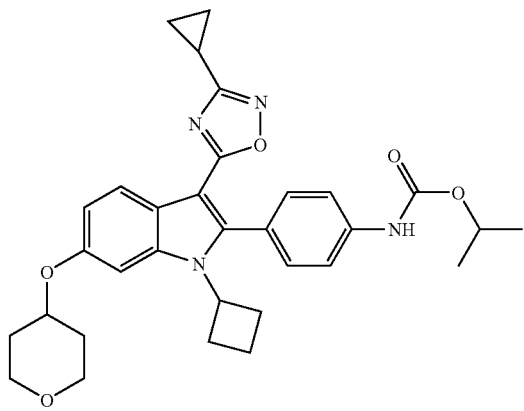
1739
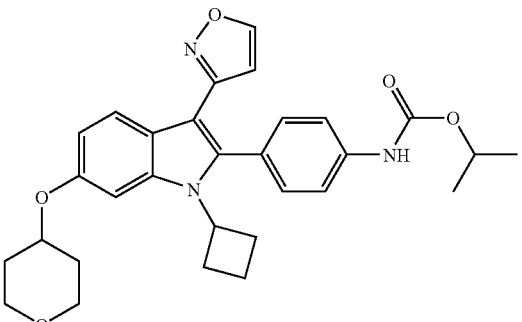
1741
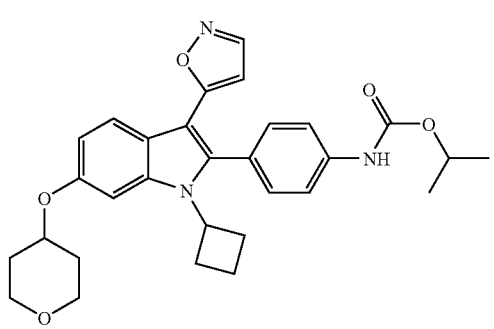
1742
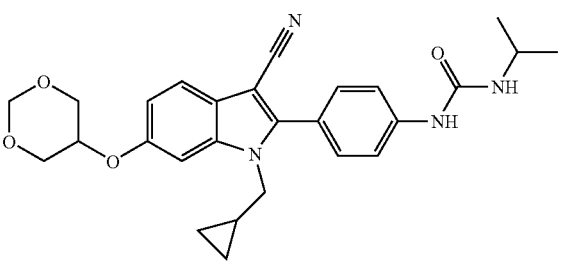
1743
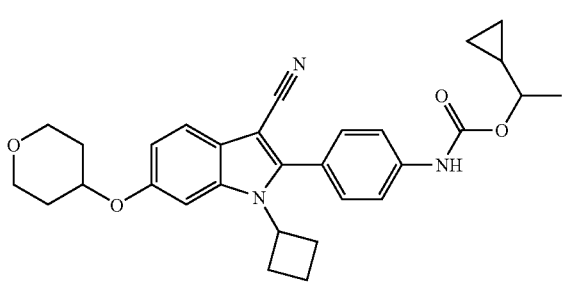
1744
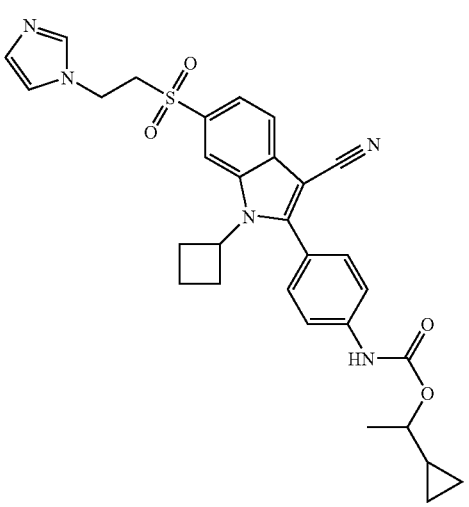

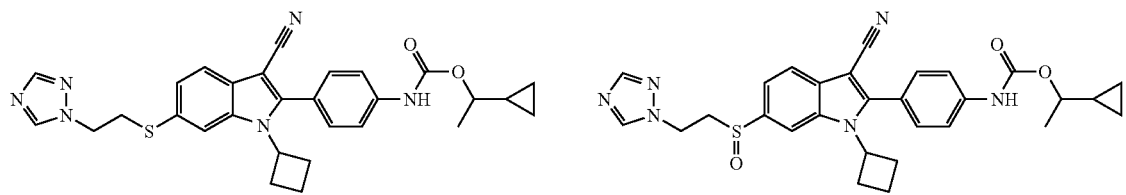
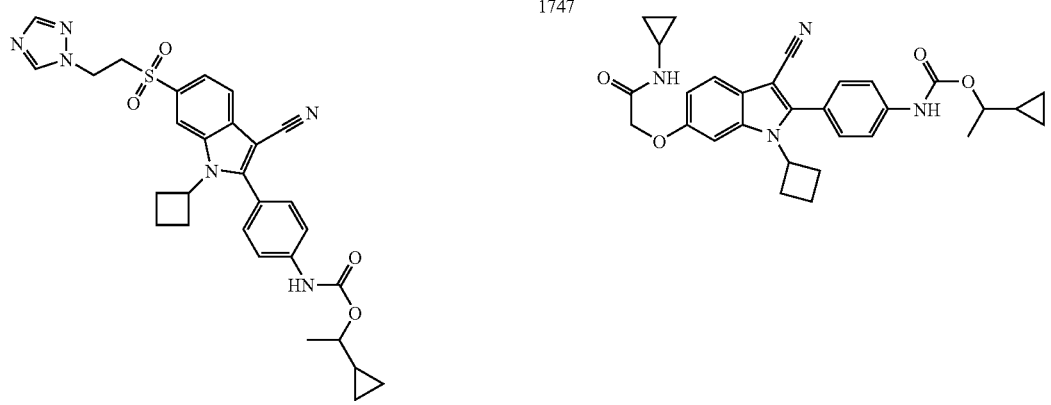
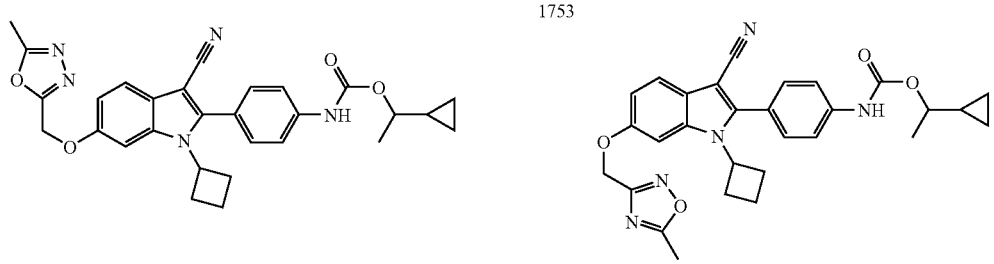
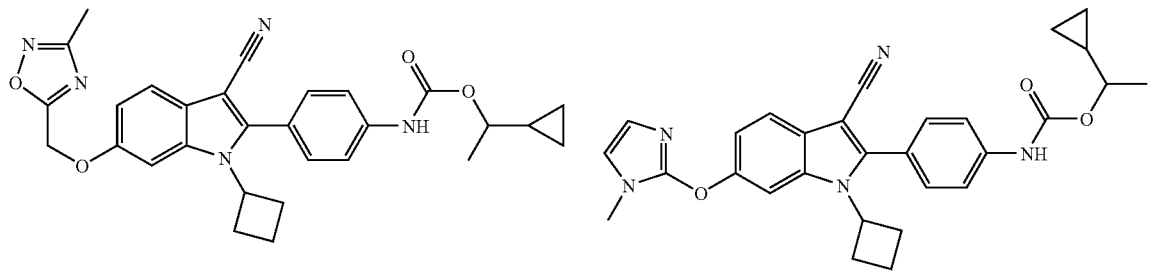
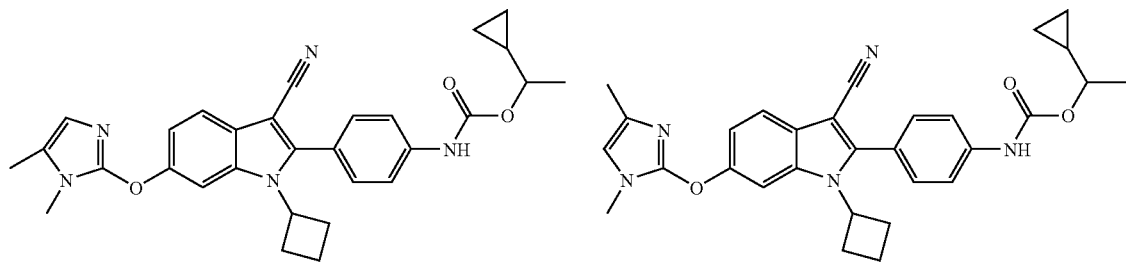

-continued
1760
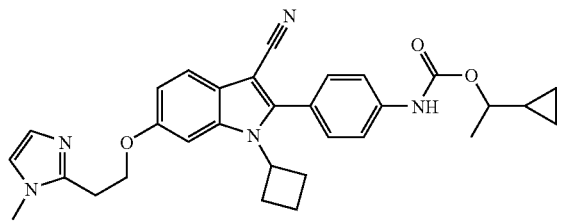
1764
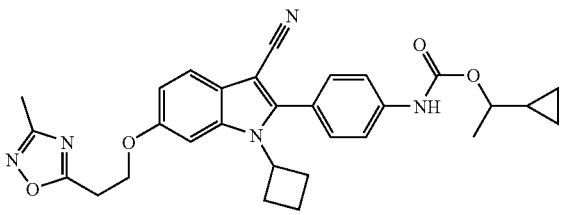
1767
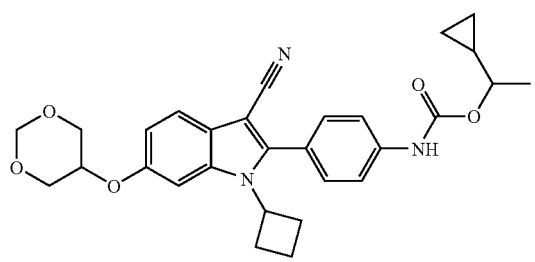
1768
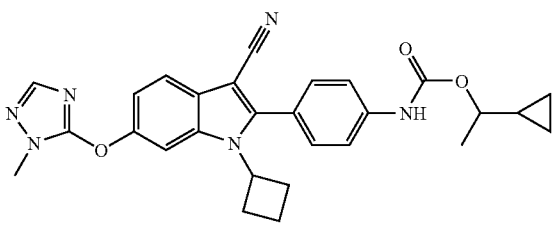
1769
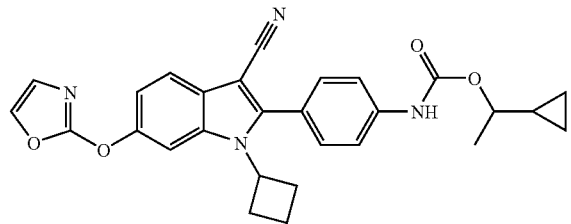
1770
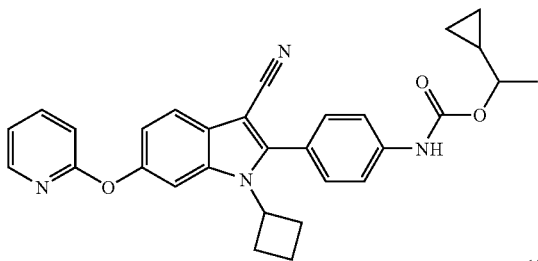
1772
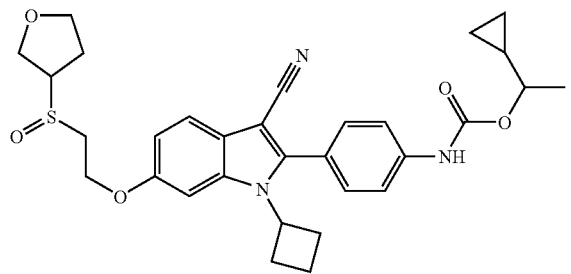
1773
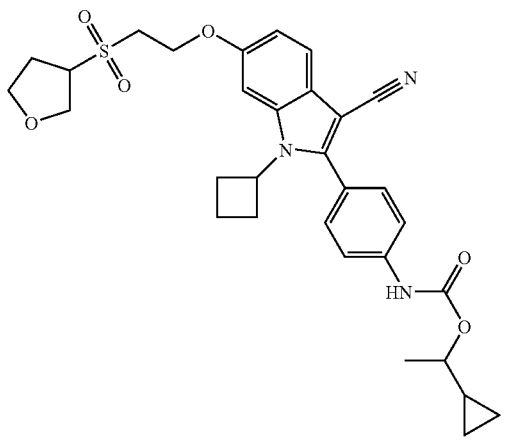
1774
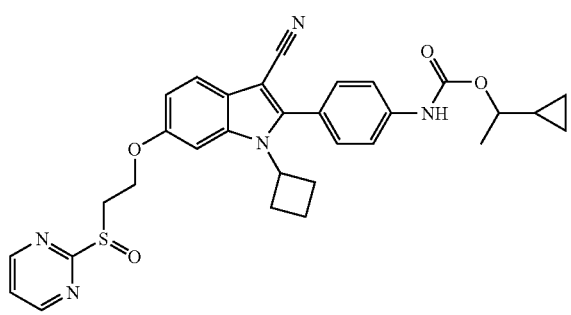
1775
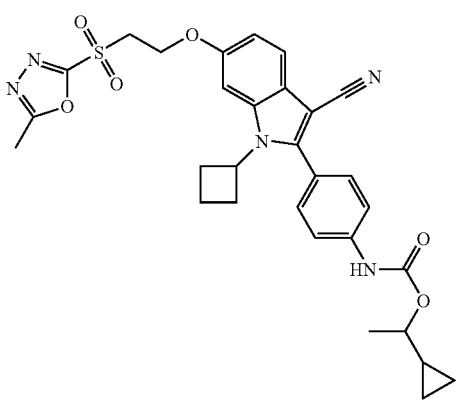

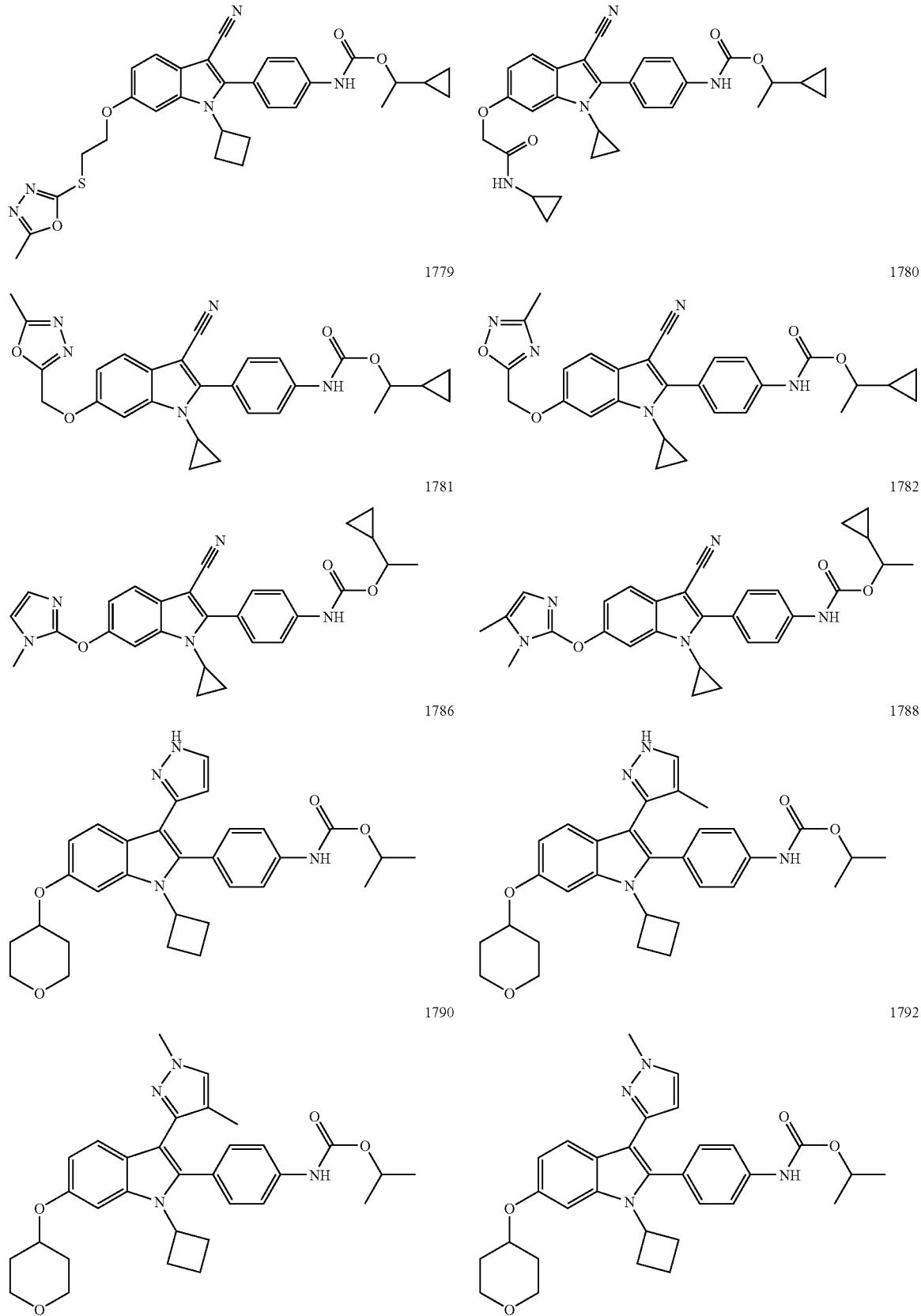

-continued
1794
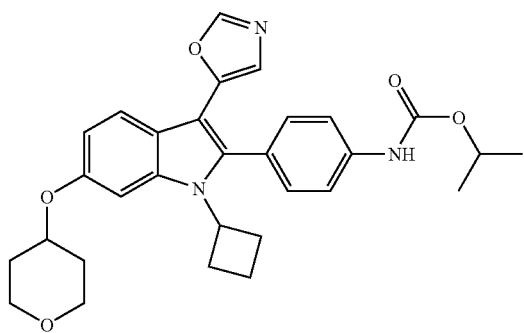
1796
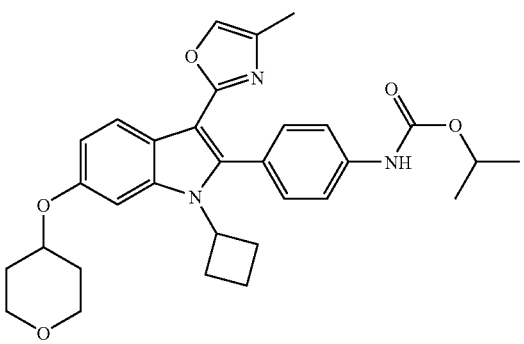
1797
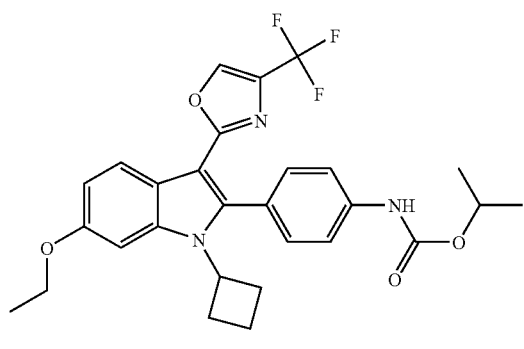
1798
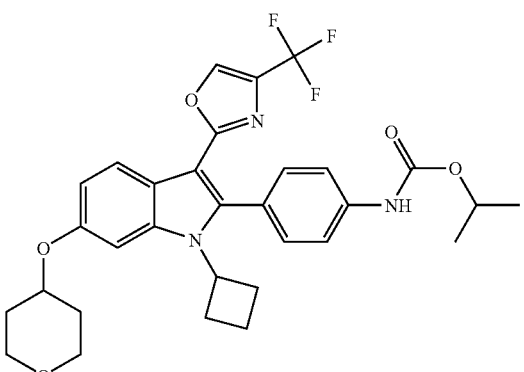
1800
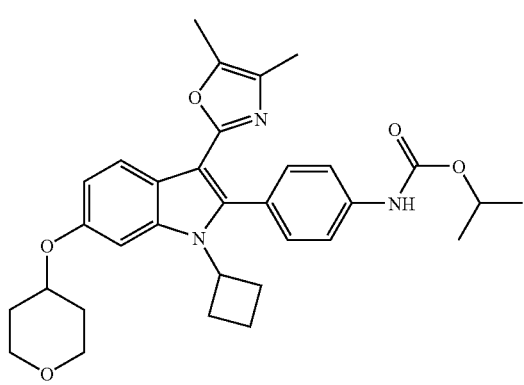
1802
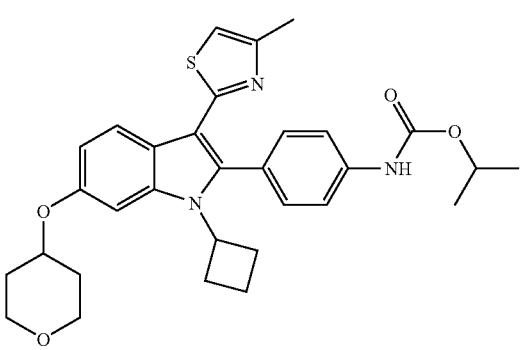
1804
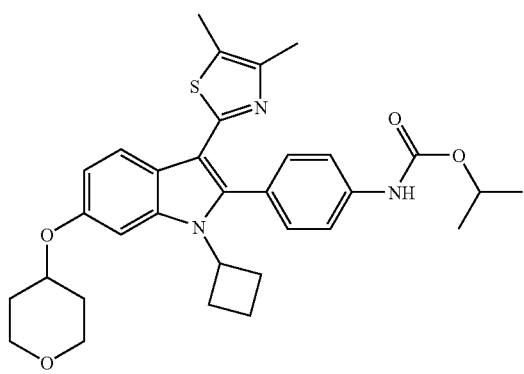
1805
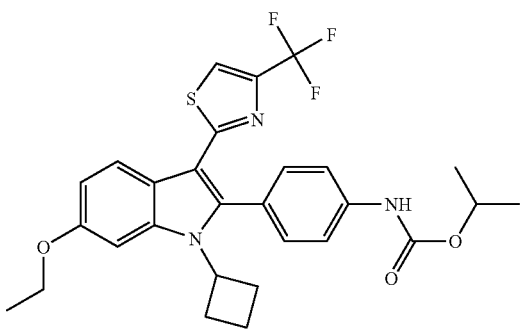

-continued
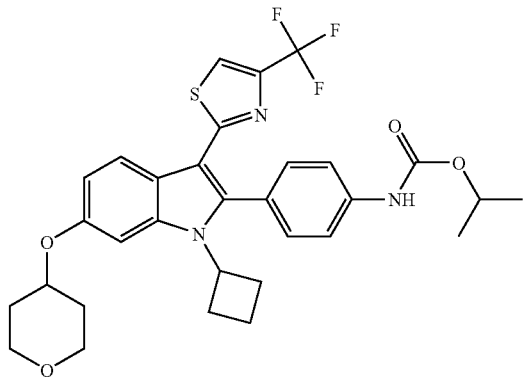
1806
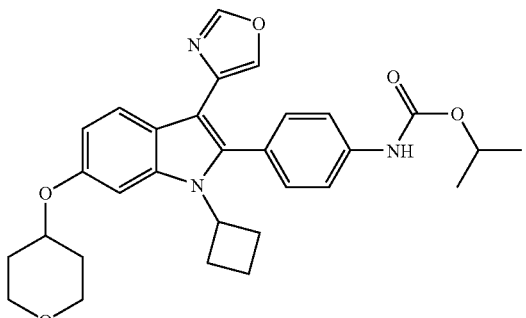
1808
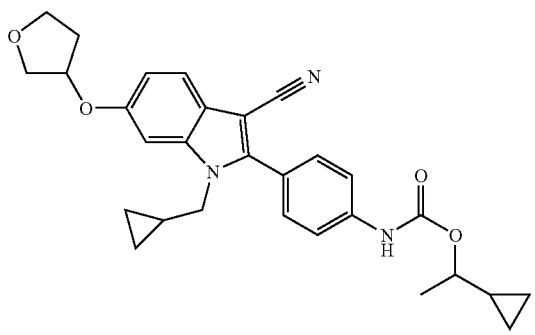
1810
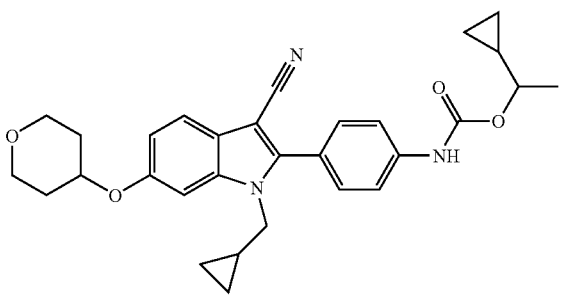
1811
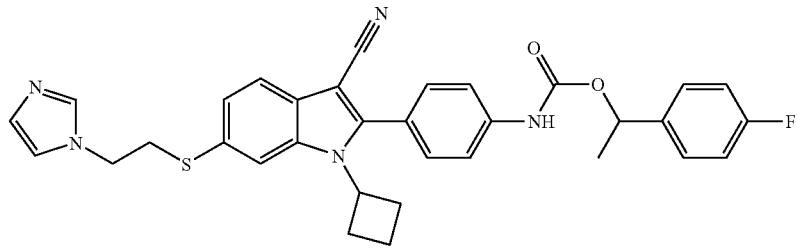
1814
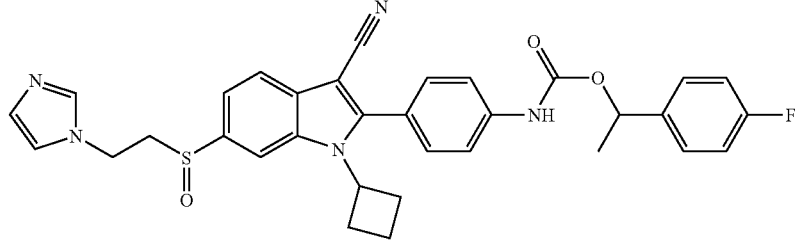
1815
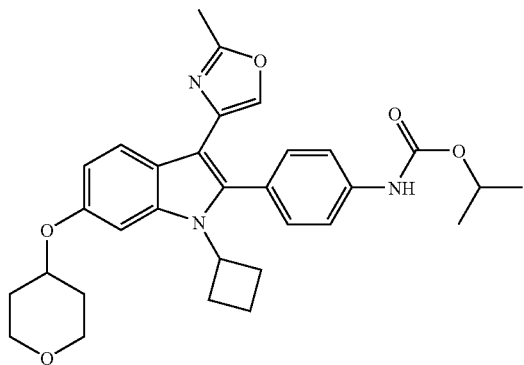
1817
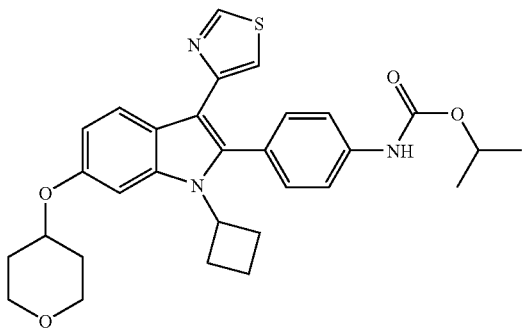
1819

-continued
1821
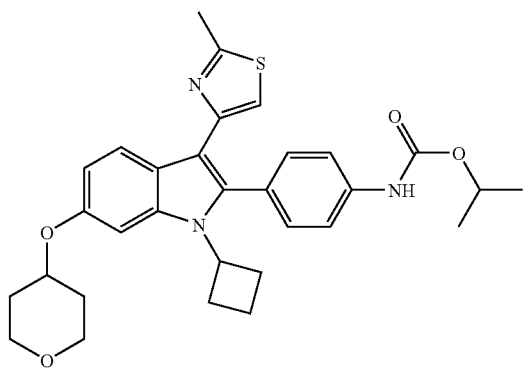
1822
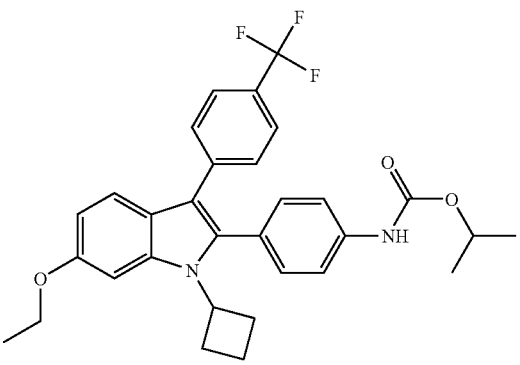
1823
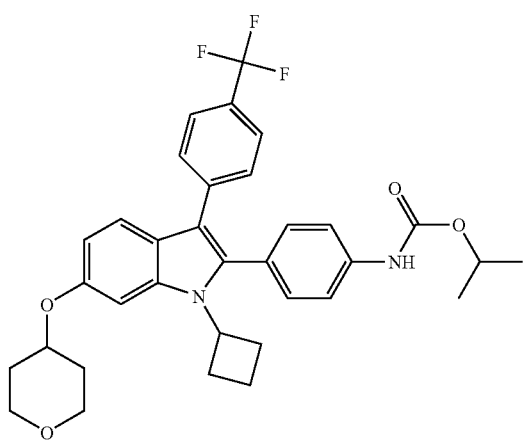
1824
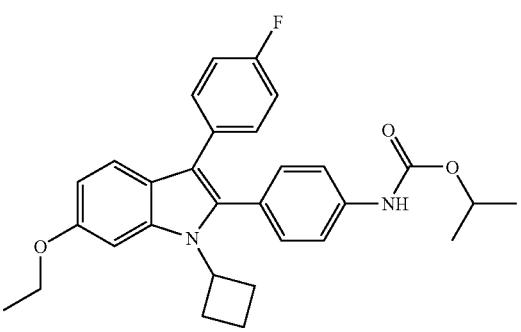
1825
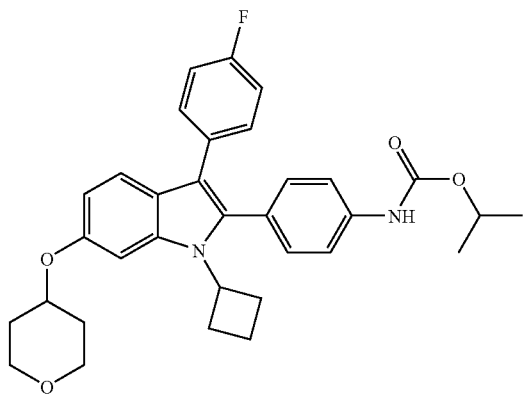
1826
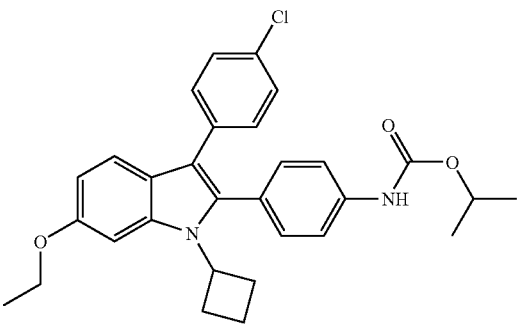
1827
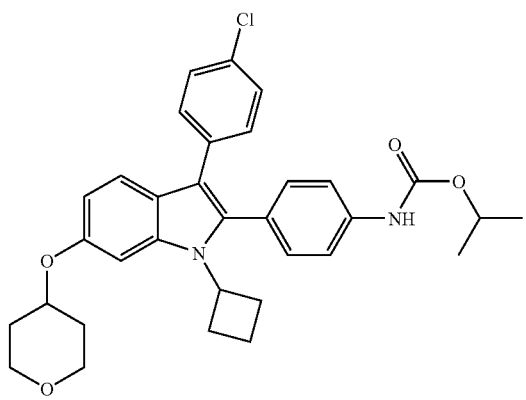
1828
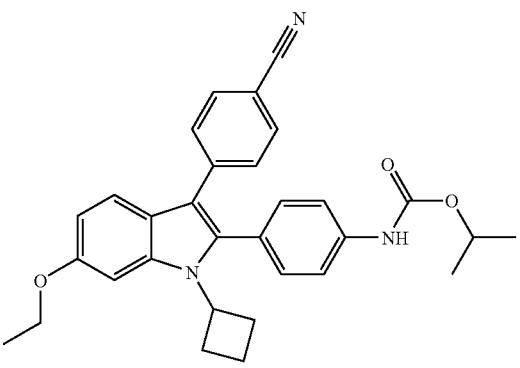

-continued
1829
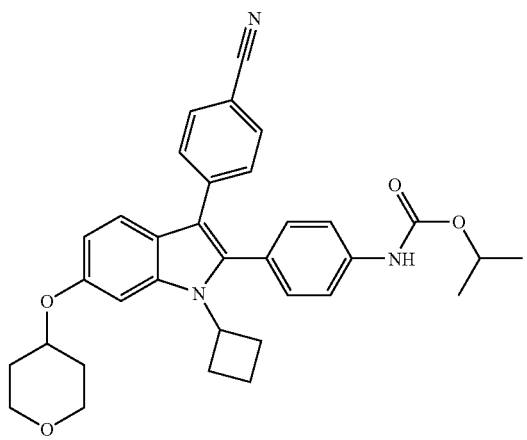
1831
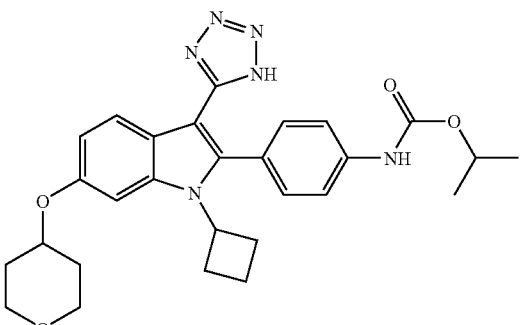
1833
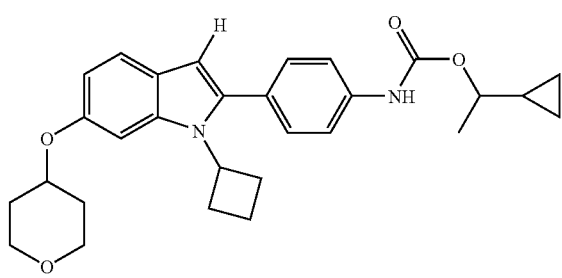
1834
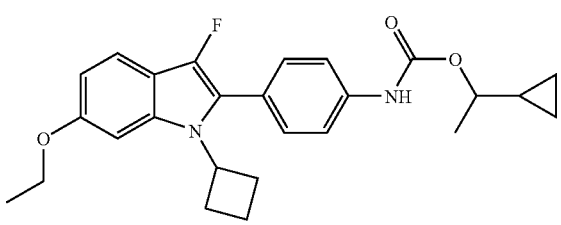
1835
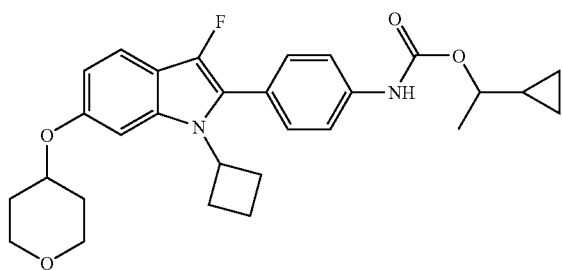
1836
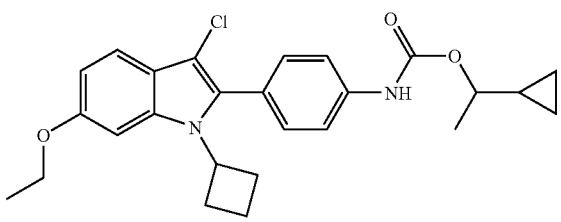
1837
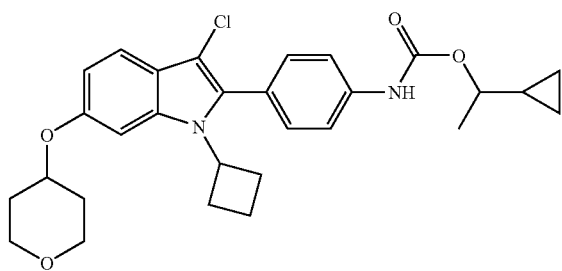
1838
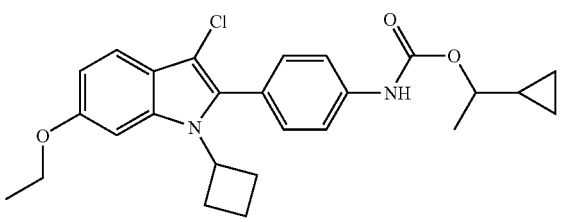
1839
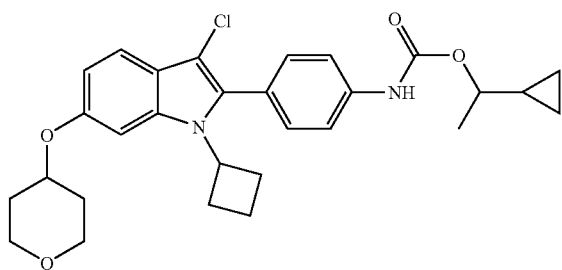
1840
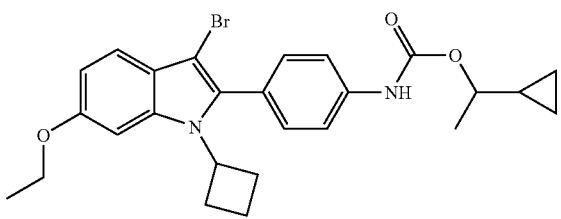

-continued
1841
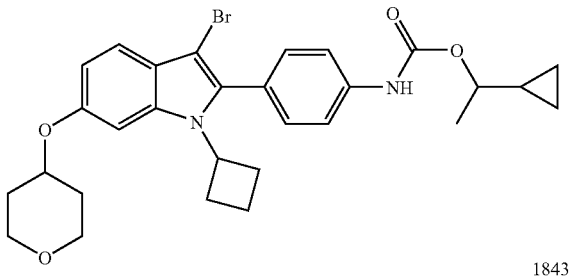
1842
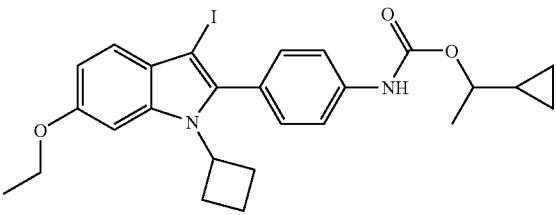
1843
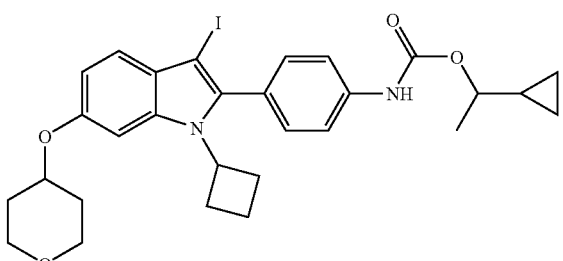
1844
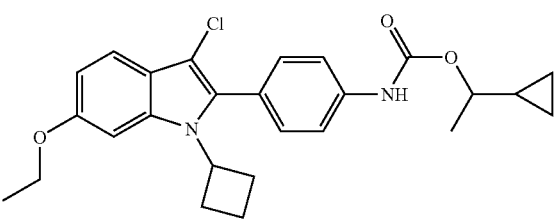
1845
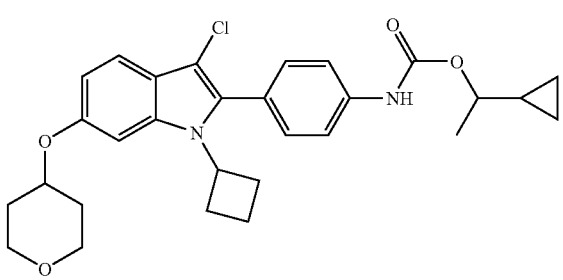
1846
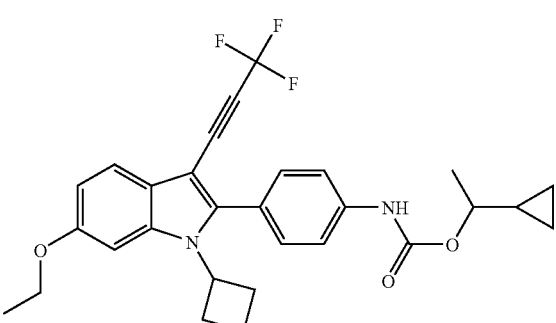
1847
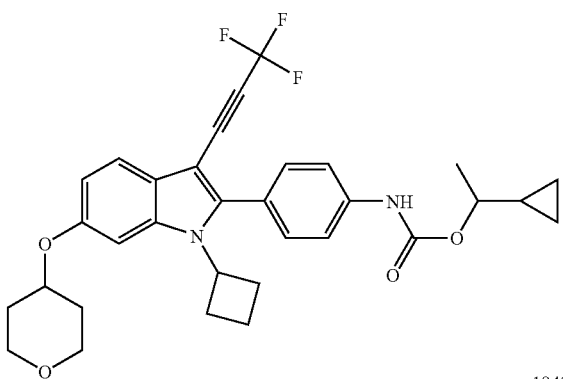
1848
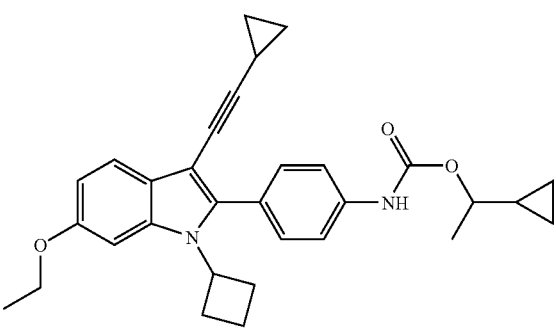
1849
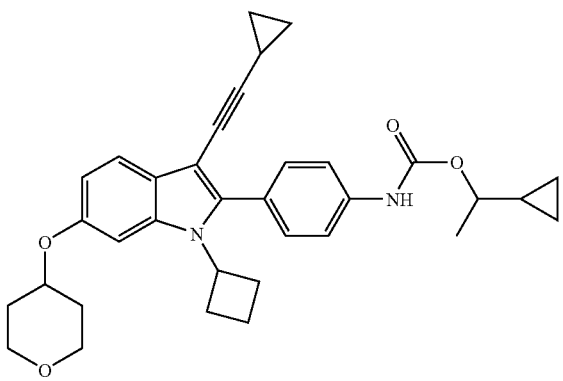
1850
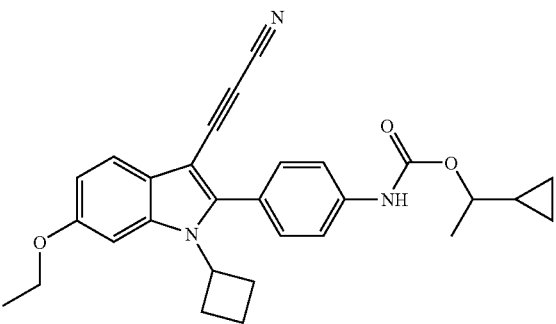

-continued
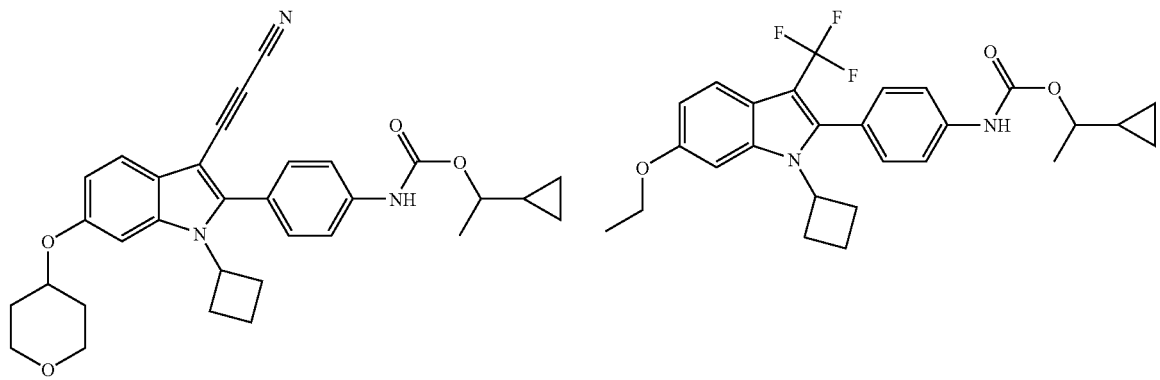
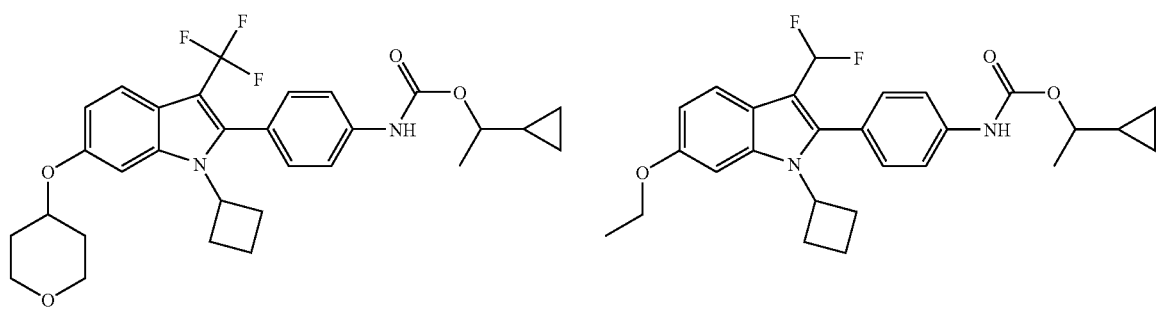
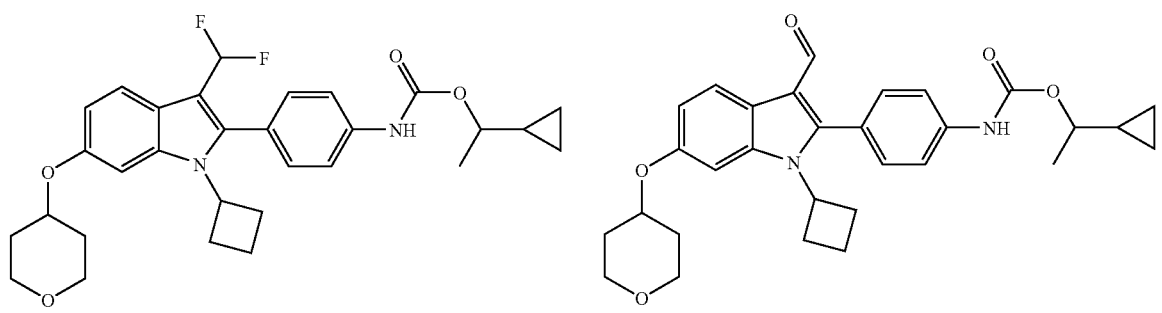
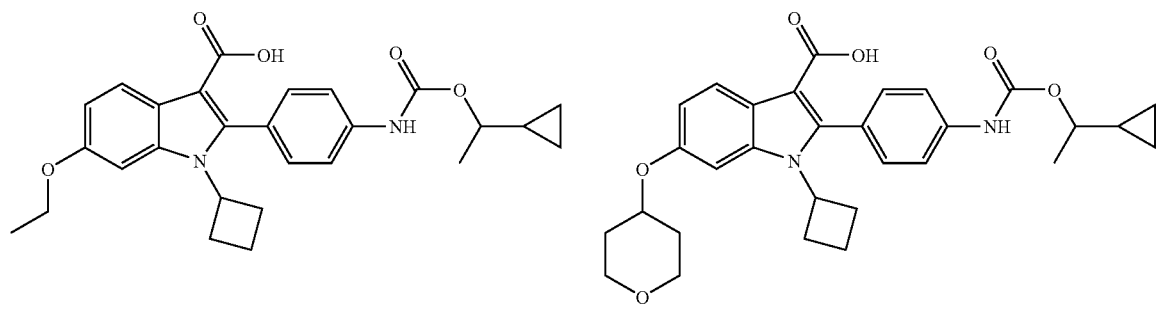

-continued
| 1860 | 1861 |
|---|---|
| 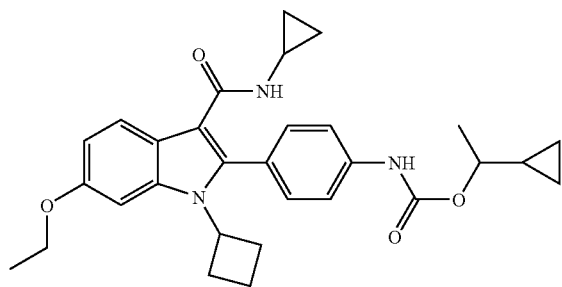 | 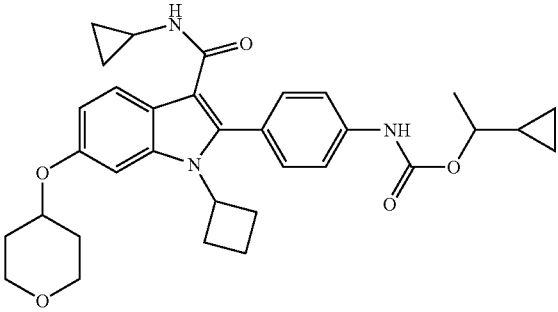 |
| 1863 | 1864 |
| 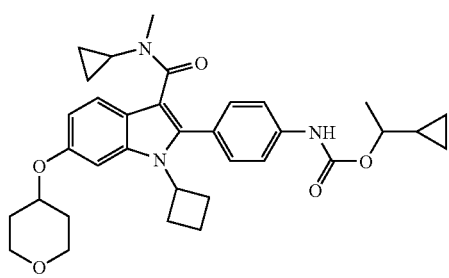 | 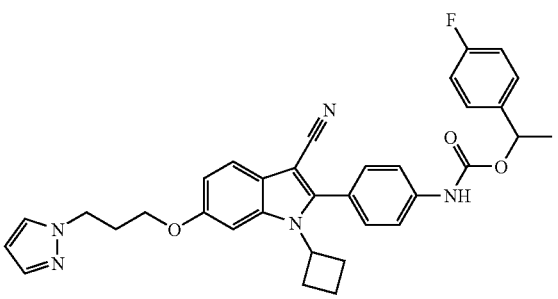 |
| 1865 | 1866 |
| 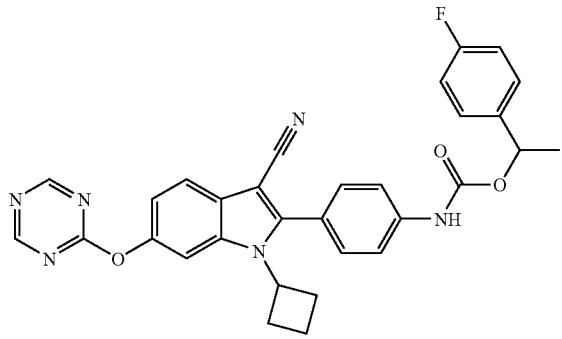 | 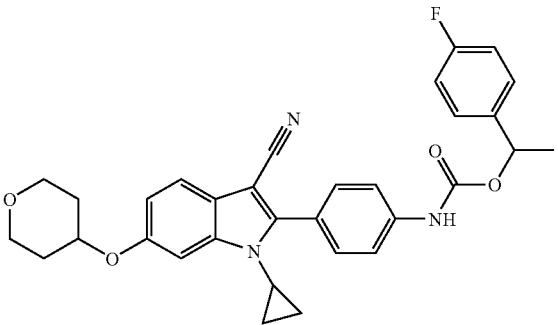 |
| 1867 | 1868 |
| 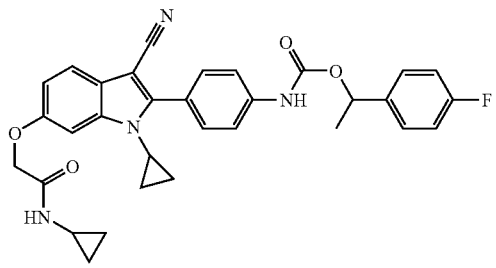 | 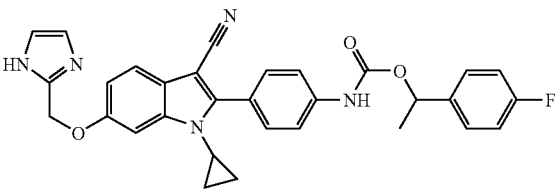 |
| 1869 | 1870 |
| 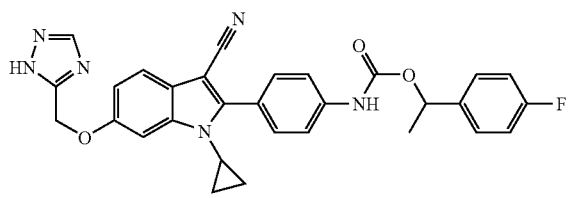 | 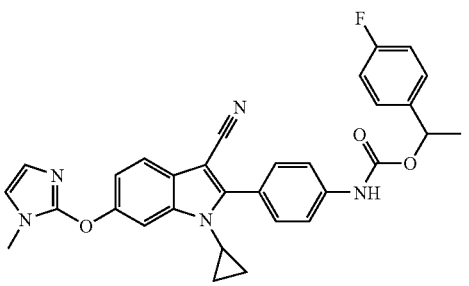 |

-continued
1871
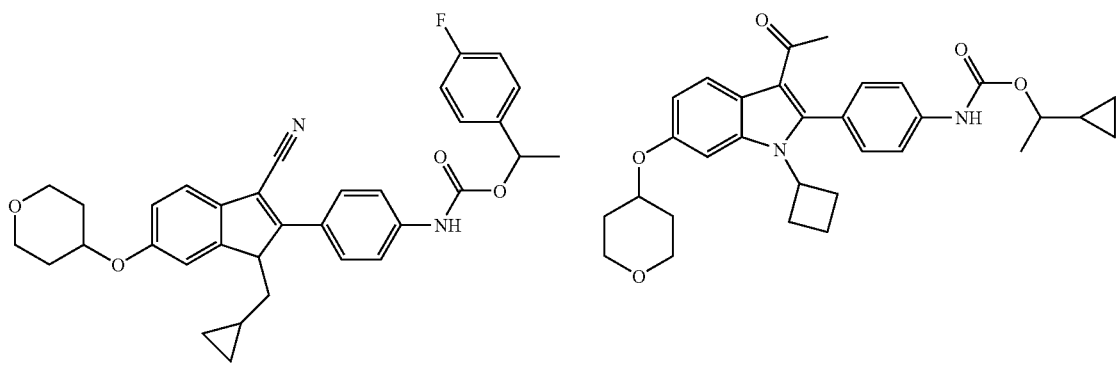
1873
1874
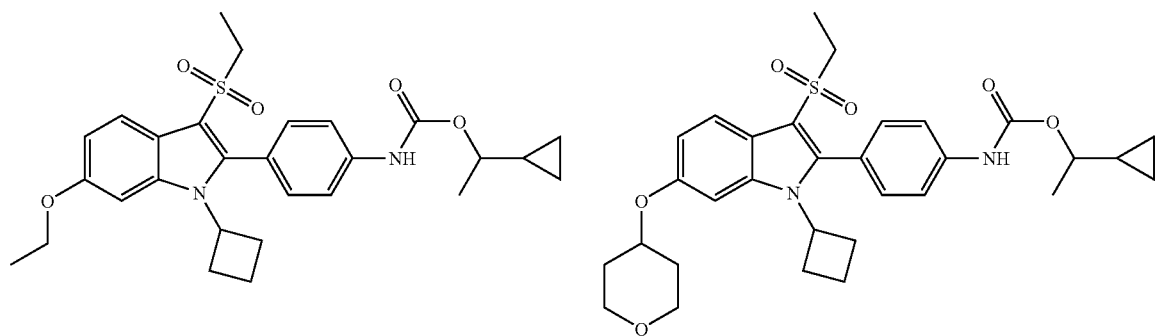
1875
1876
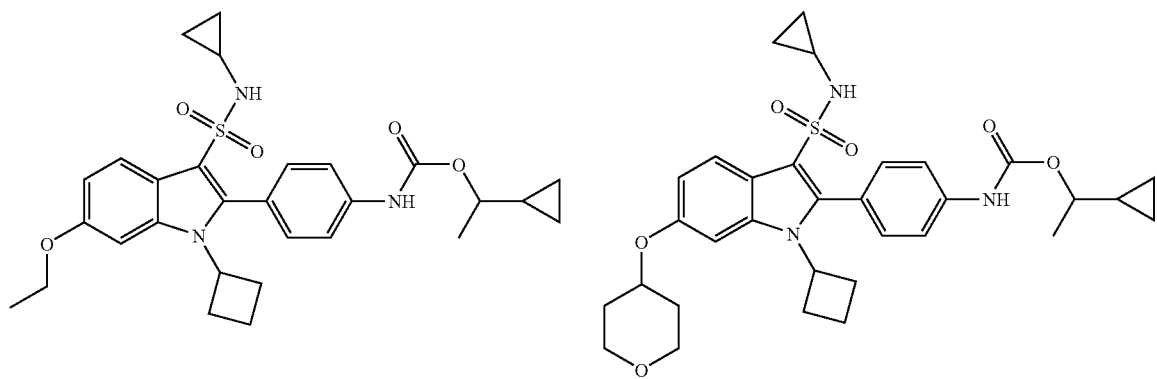
1877
1878
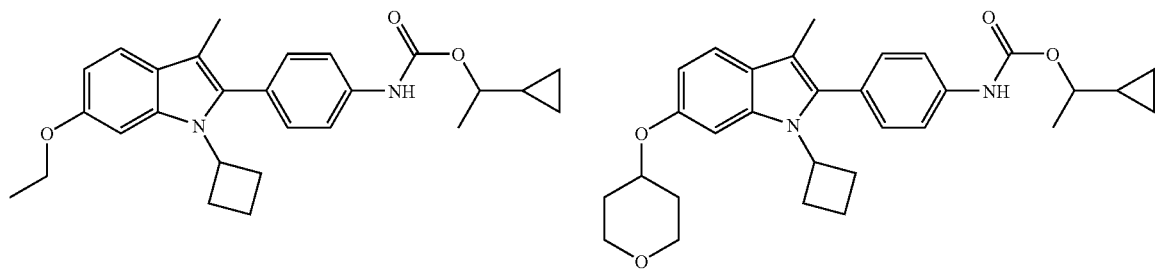
1879

271 272
-continued
1880
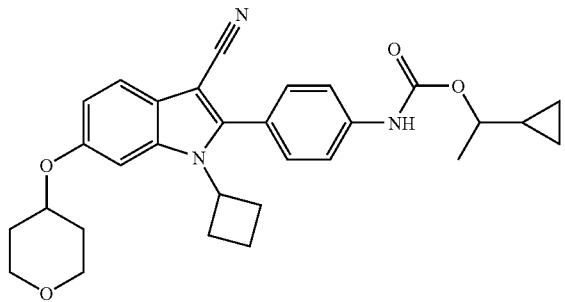
1881
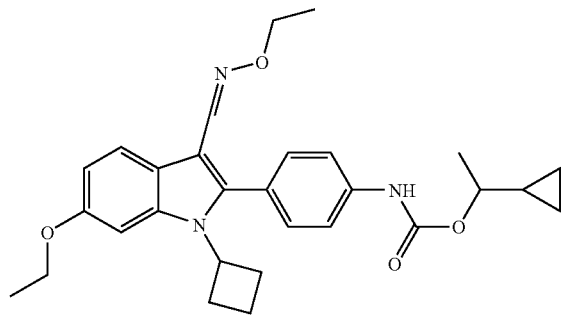
1882
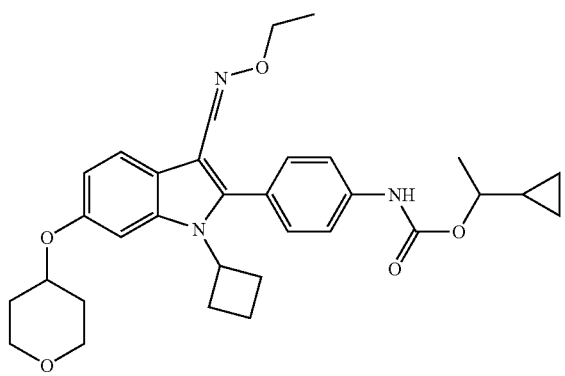
1883
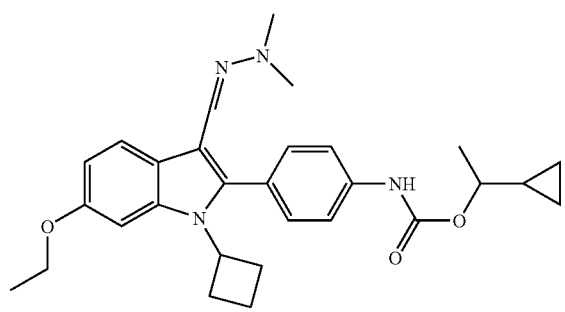
1884
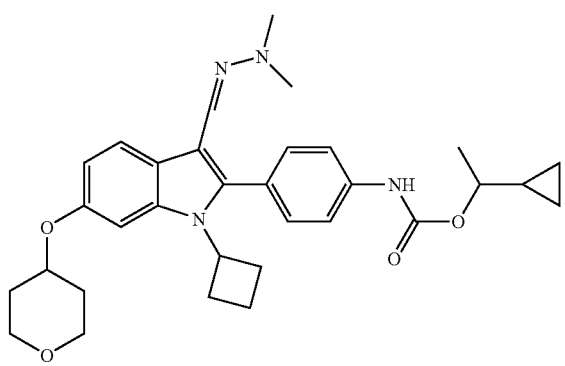
1886
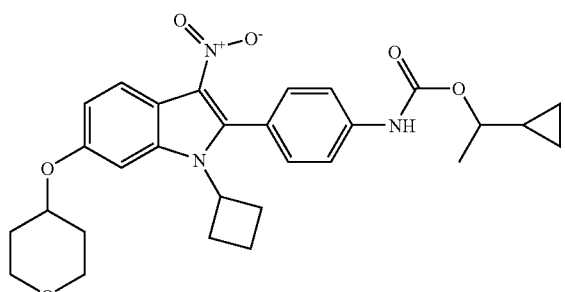
1887
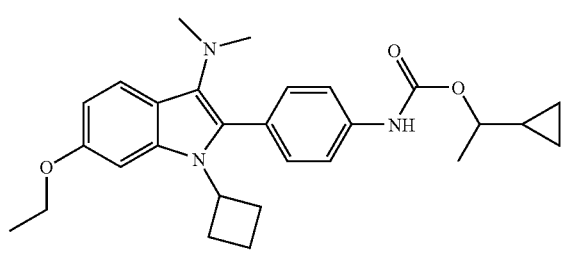
1888
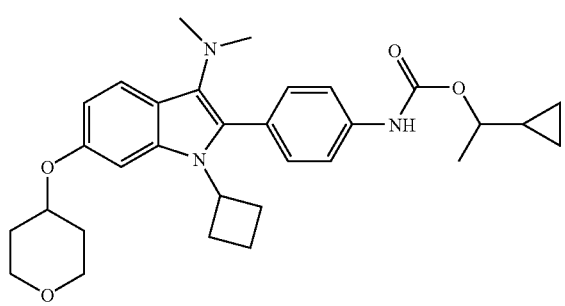

-continued
1889
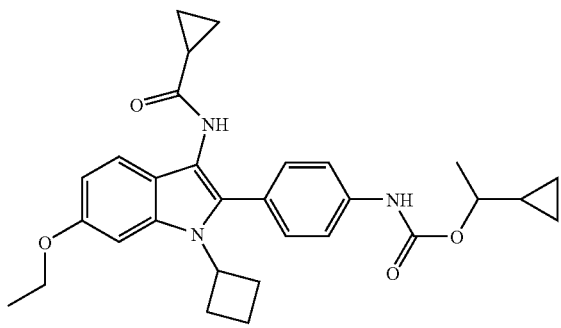
1890
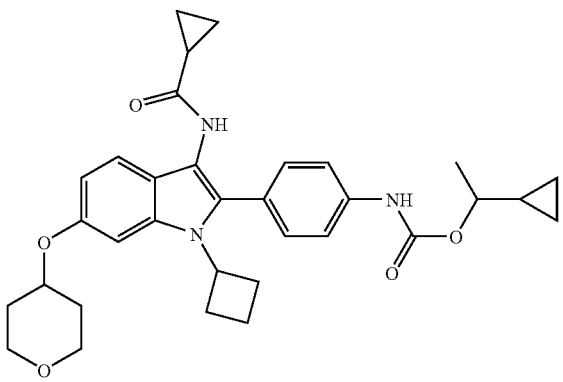
1892
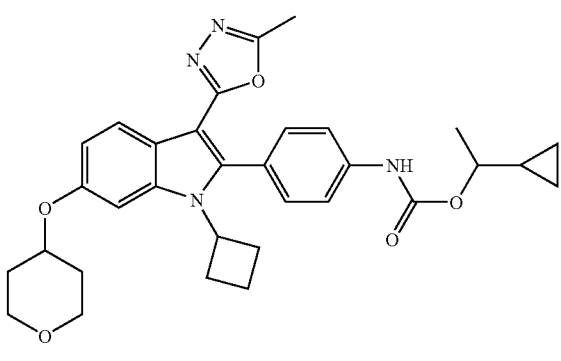
1894
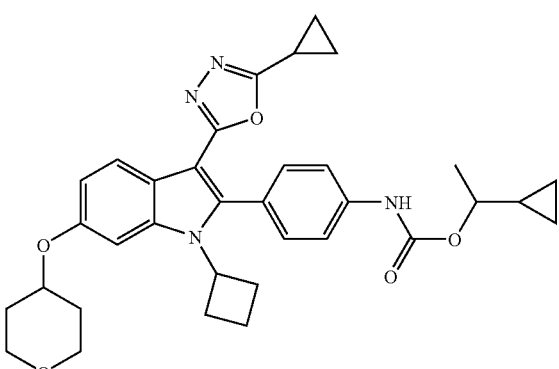
1896
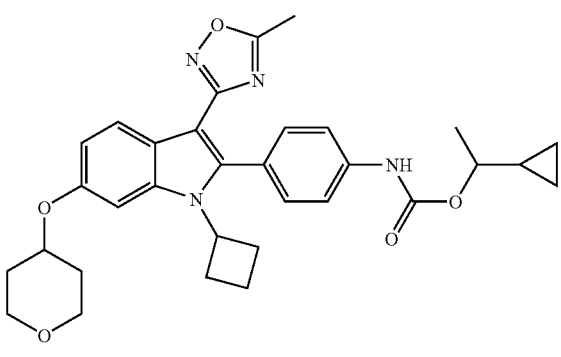
1898
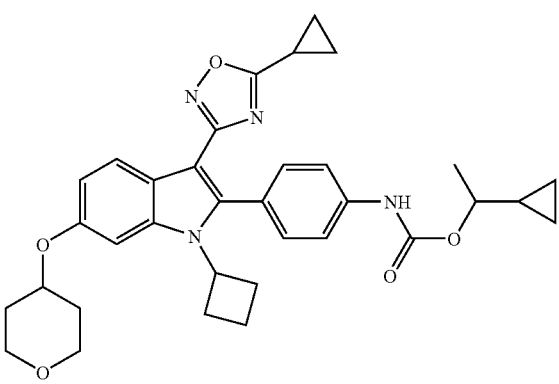
1900
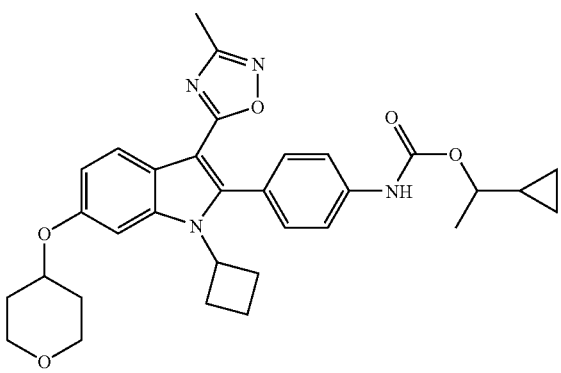
1902
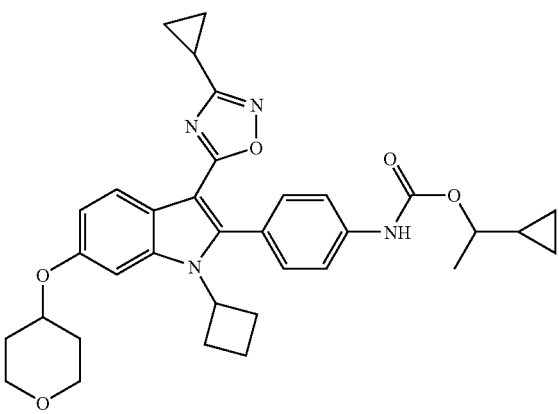

-continued
1904
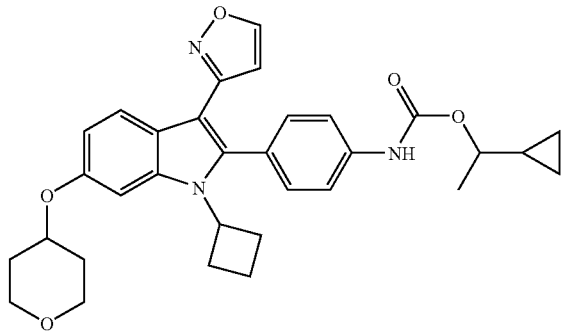
1906
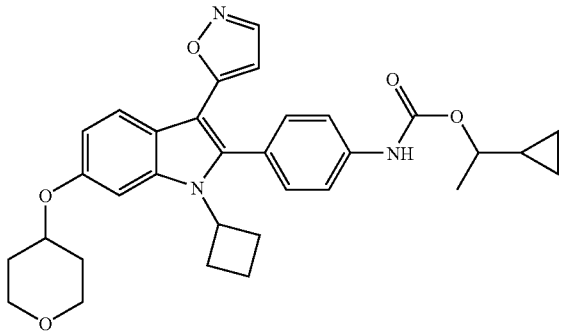
1908
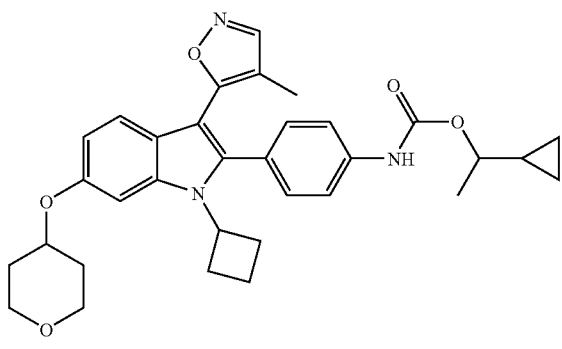
1910
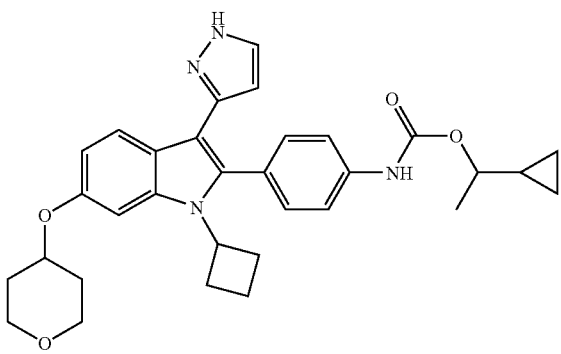
1912
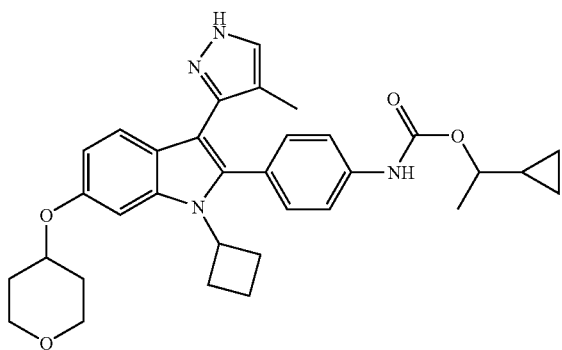
1914
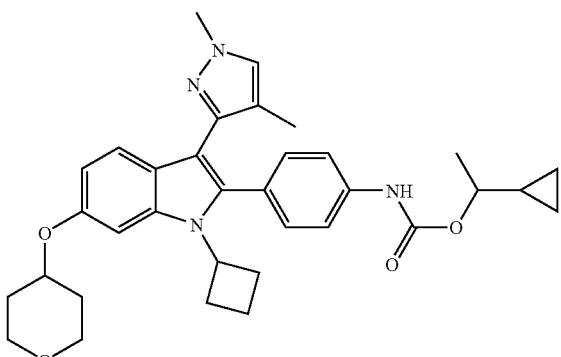
1916
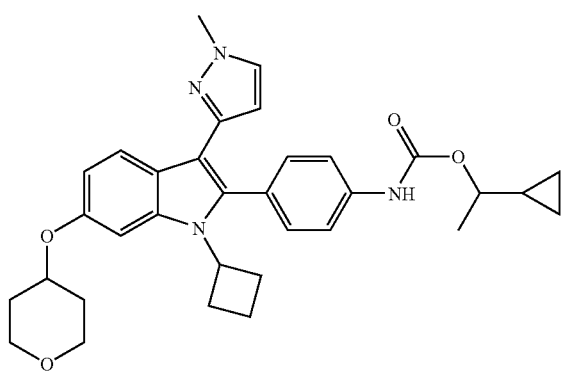
1917
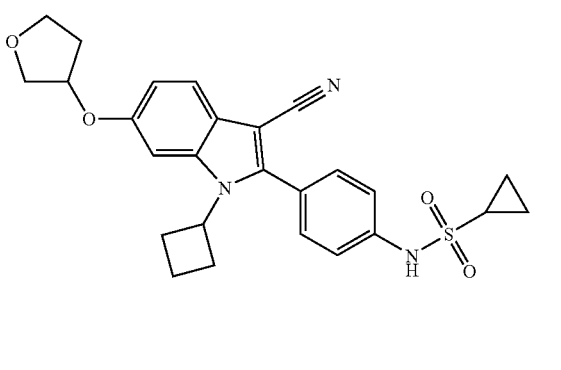

-continued
1918
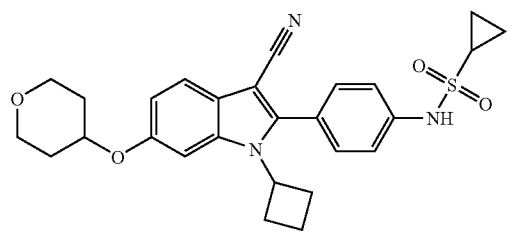
1920
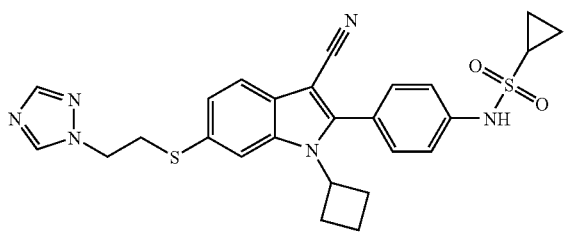
1922
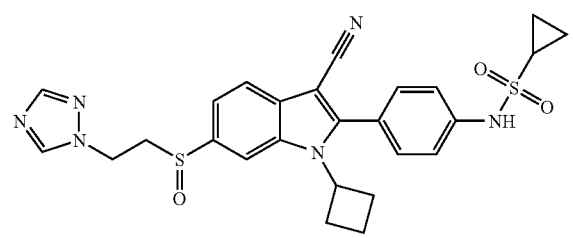
1923
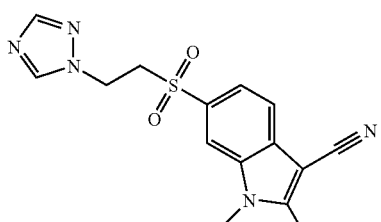
1924
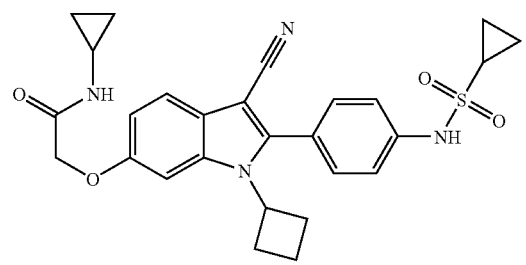
1926
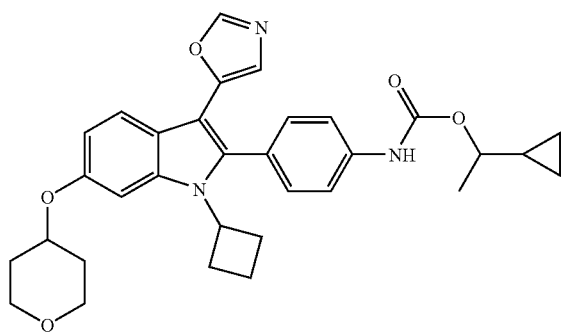
1928
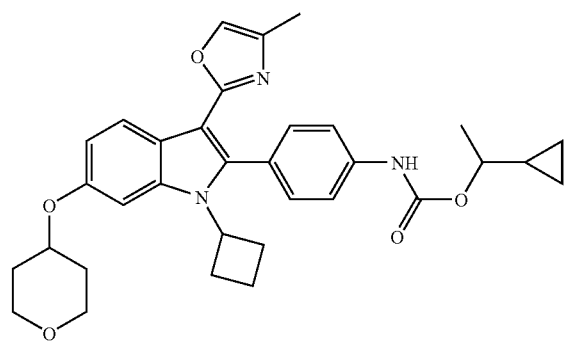
1930
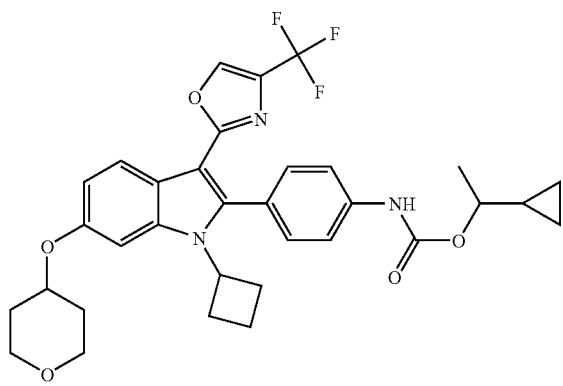

-continued
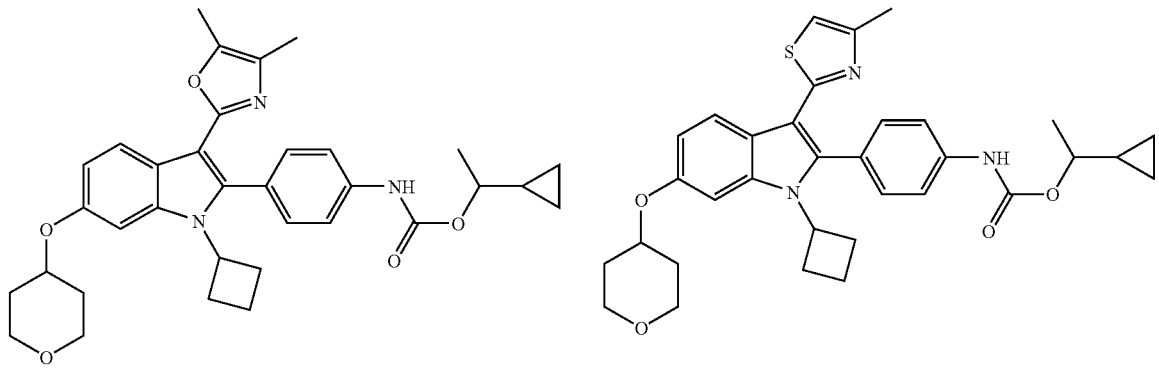
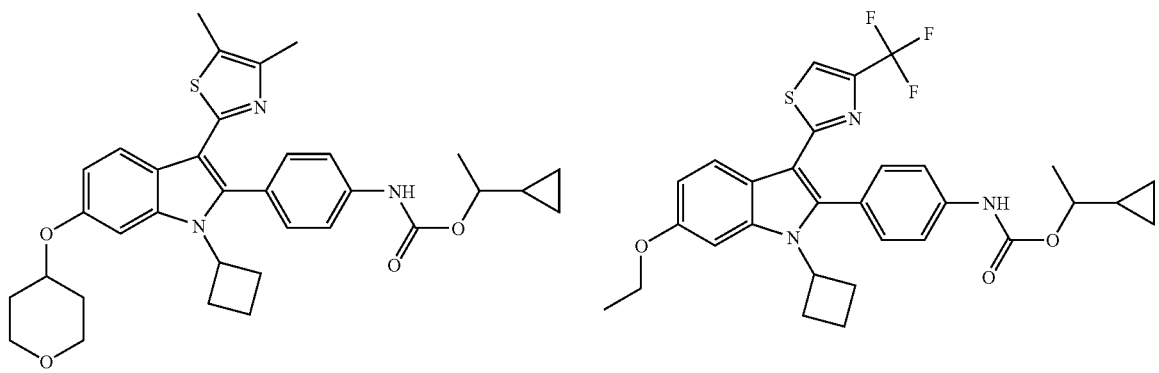
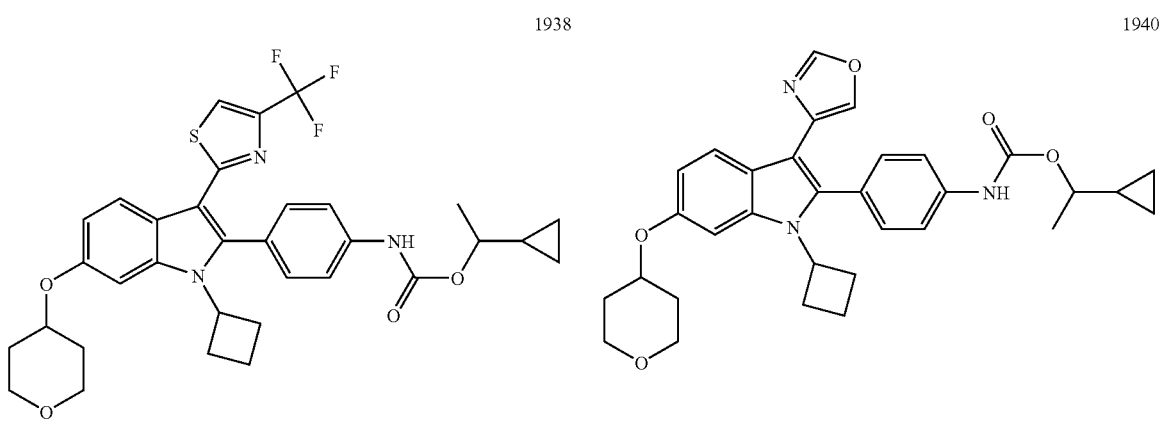
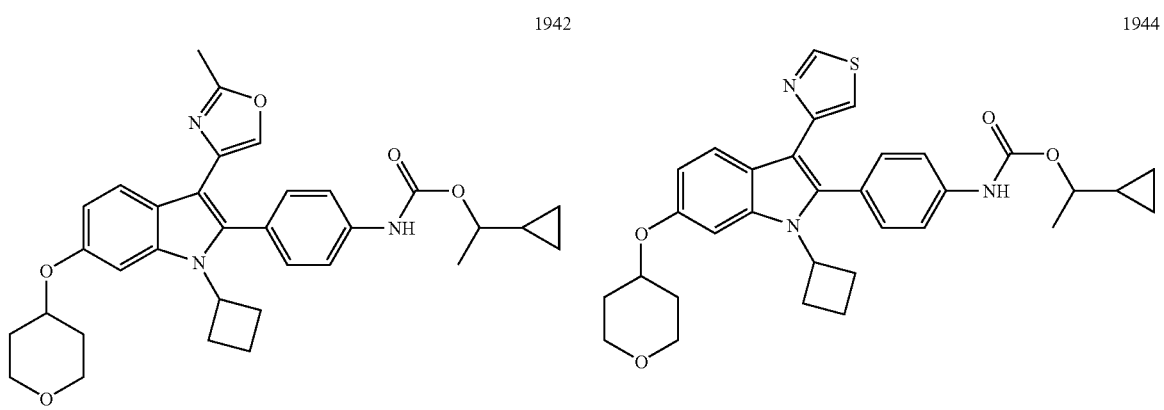

-continued
| 1946 | 1947 |
|---|---|
| 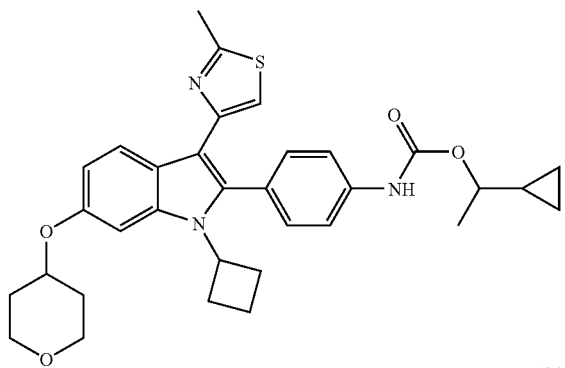 | 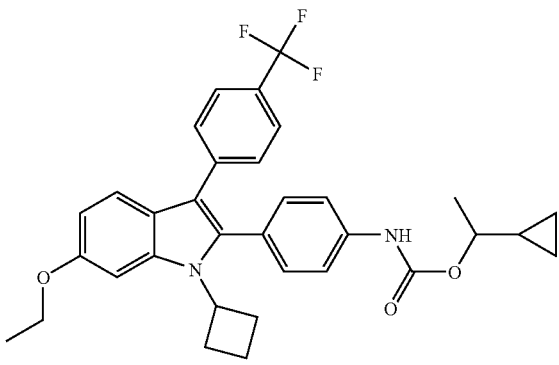 |
| 1948 | 1949 |
|---|---|
| 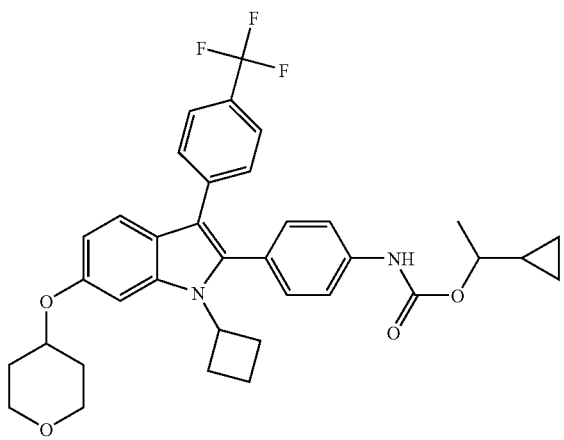 | 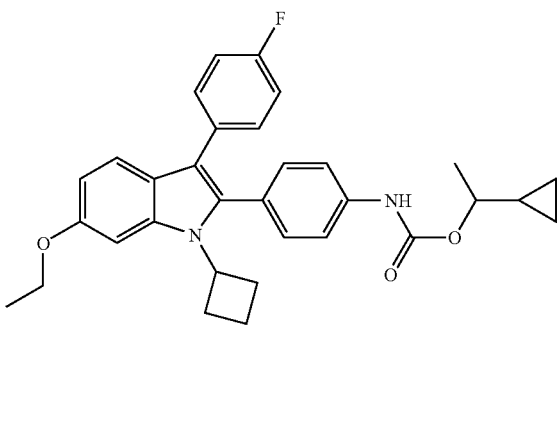 |
| 1950 | 1951 |
|---|---|
| 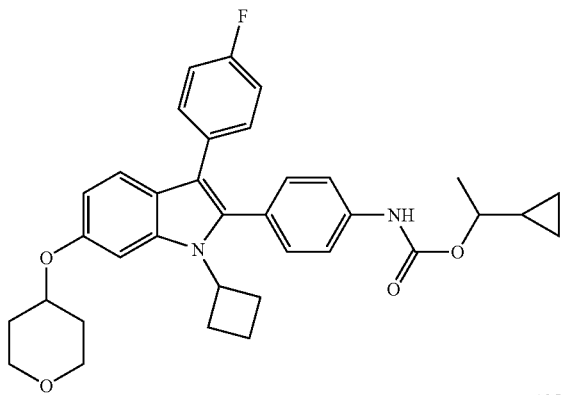 | 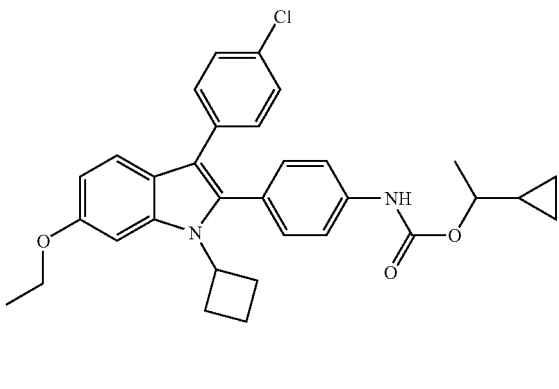 |
| 1952 | 1953 |
|---|---|
| 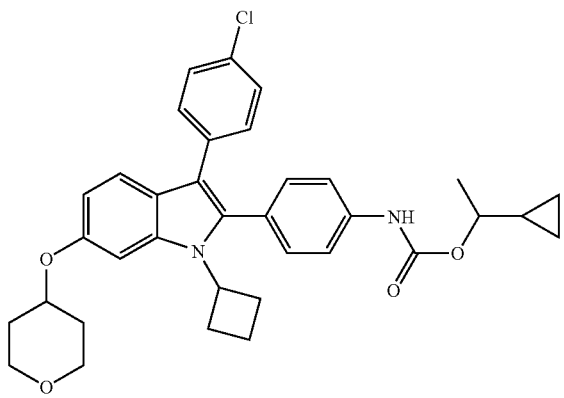 | 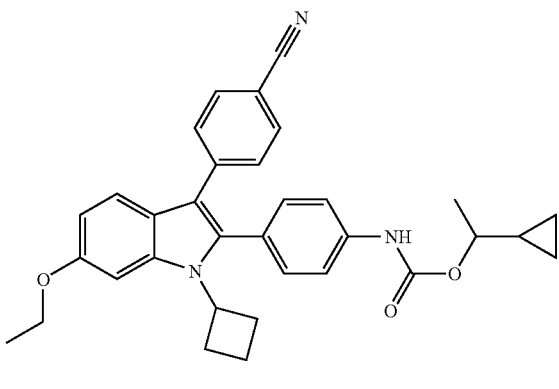 |

-continued
1954
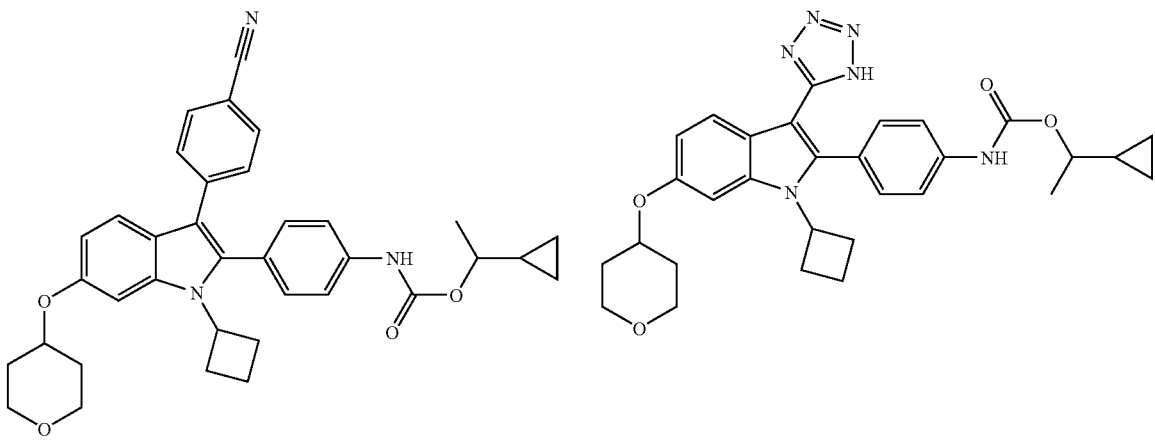
1956
1958
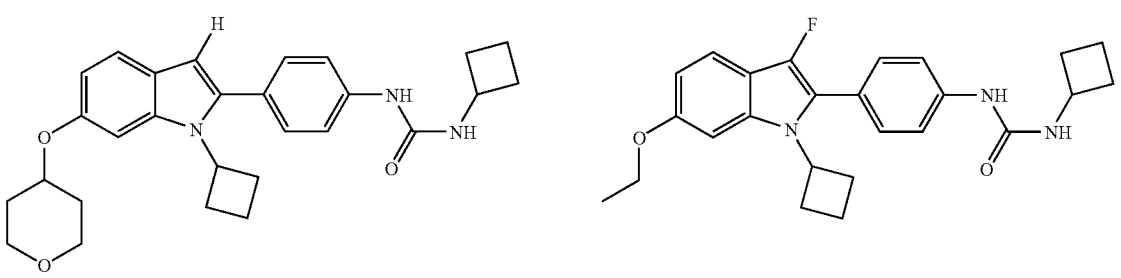
1959
1960
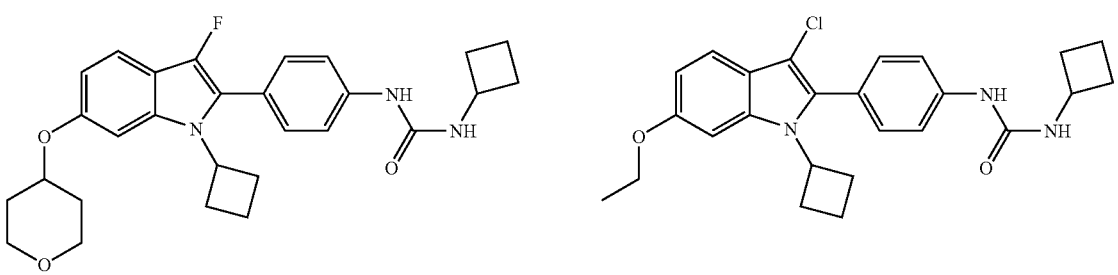
1961
1962
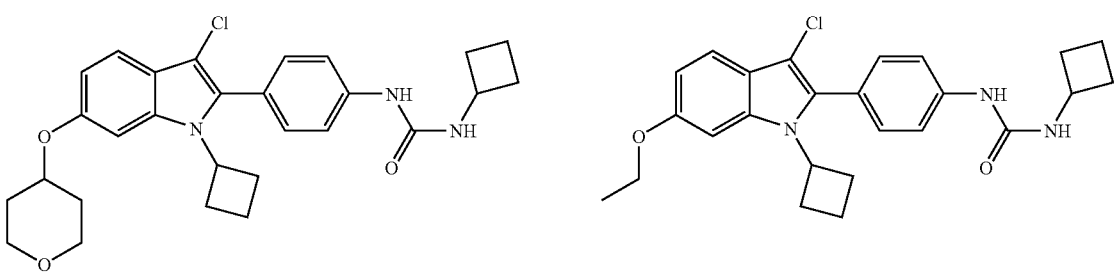
1963
1964
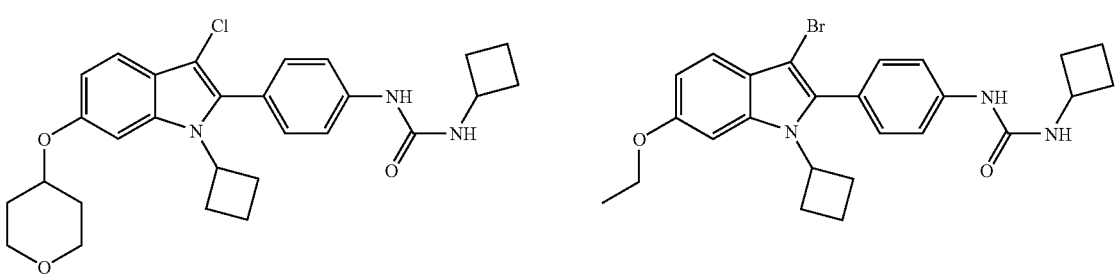
1965

-continued
1966
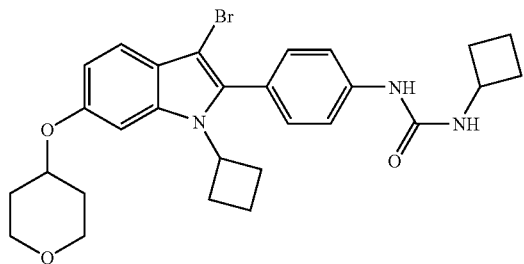
1970
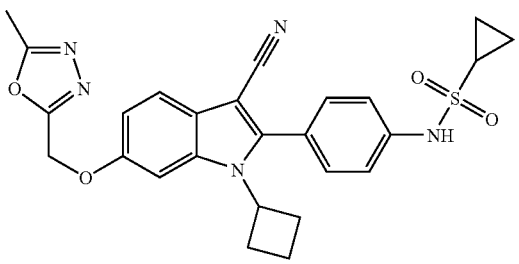
1971
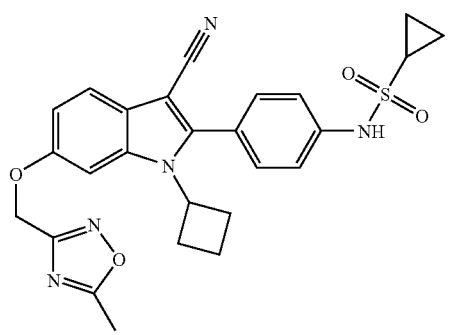
1972
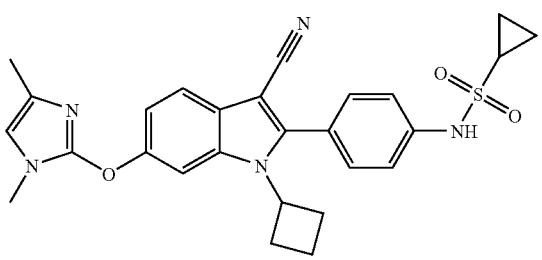
1973
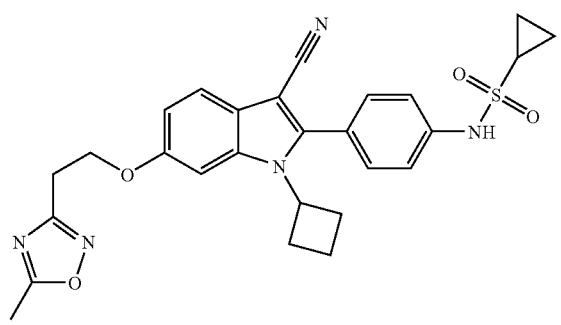
1974
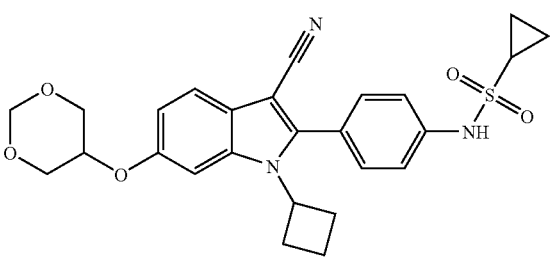
1975
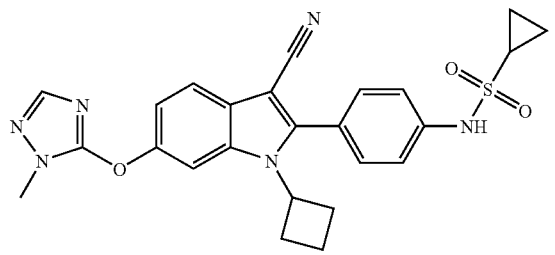
1976
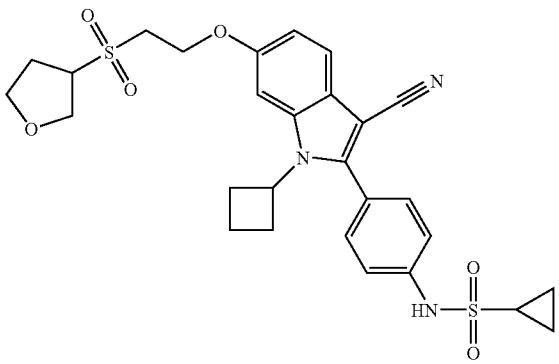
1977
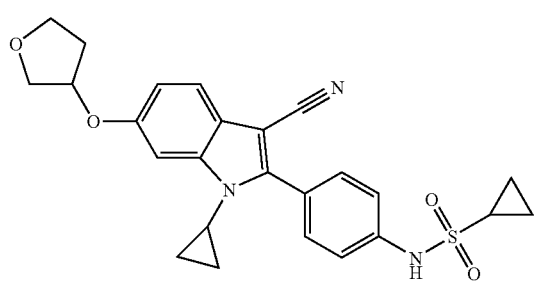
1978
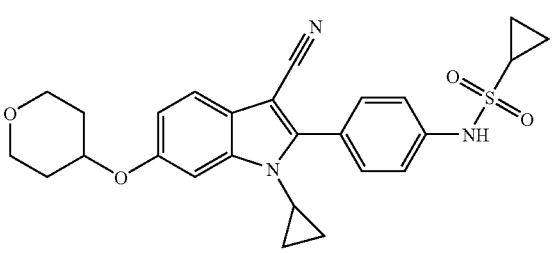

-continued
1979
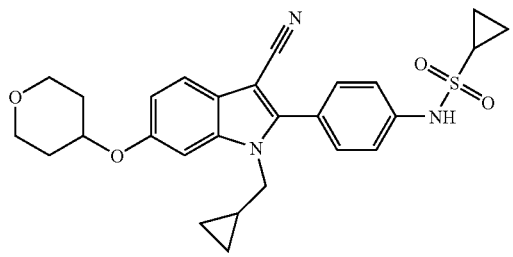
1980
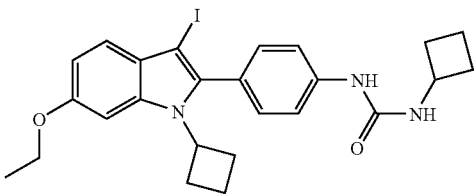
1981
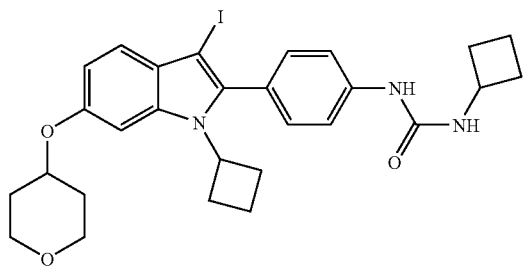
1982
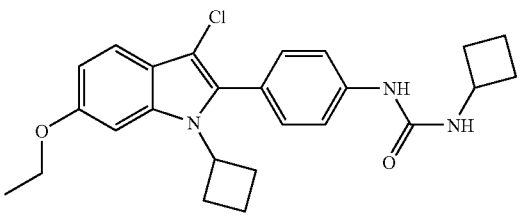
1983
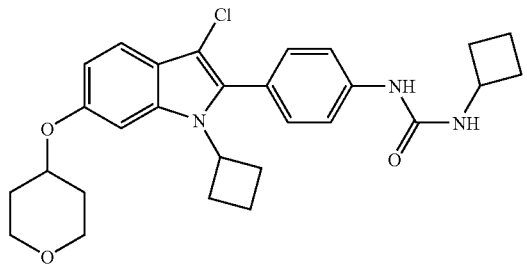
1984
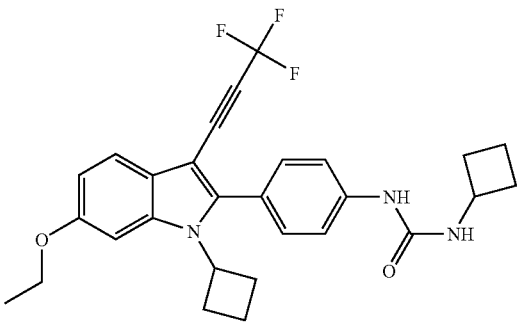
1985
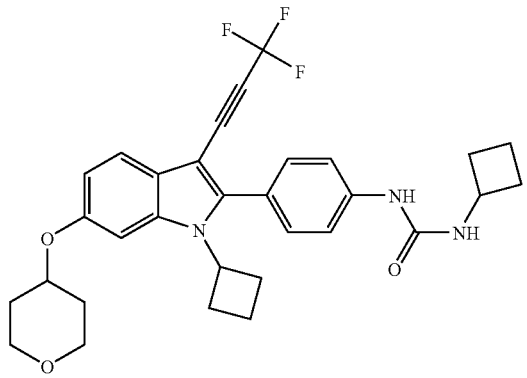
1986
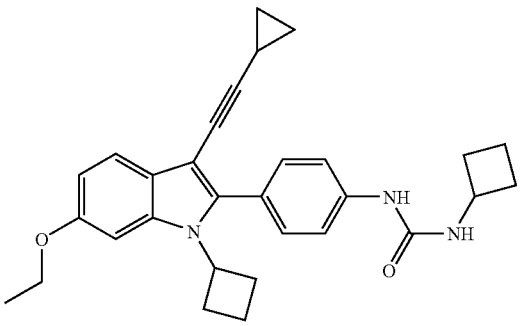
1987
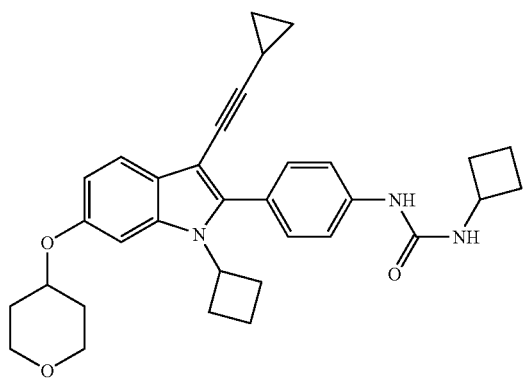
1988
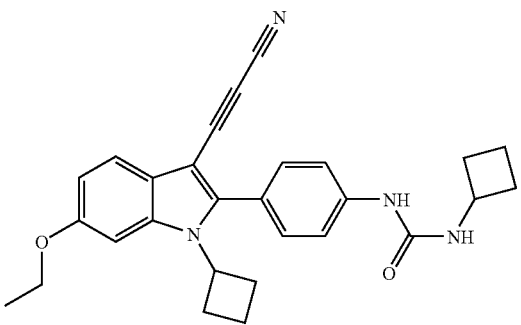

-continued
1989
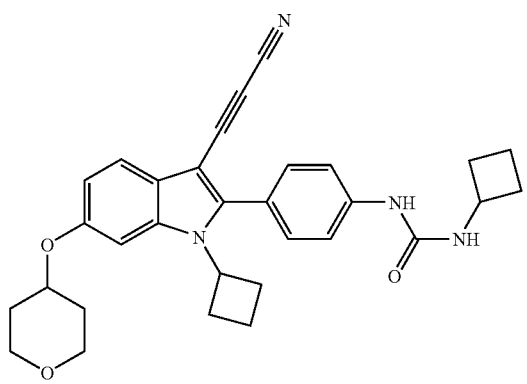
1990
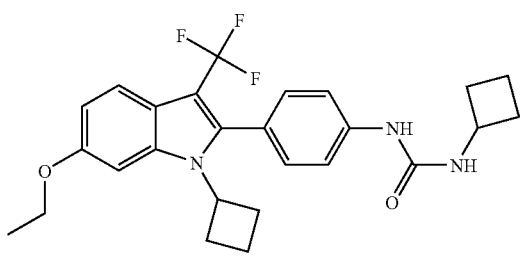
1991
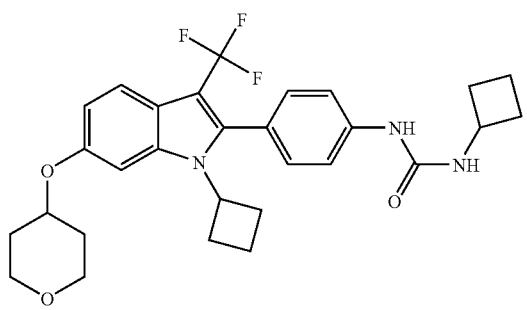
1992
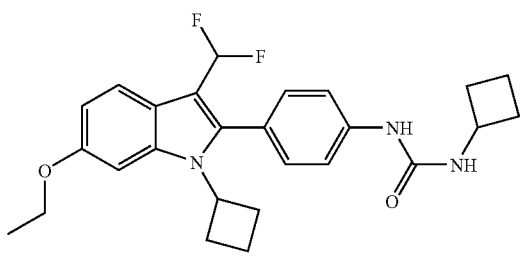
1993
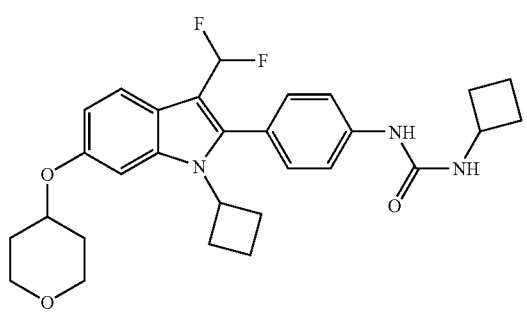
1995
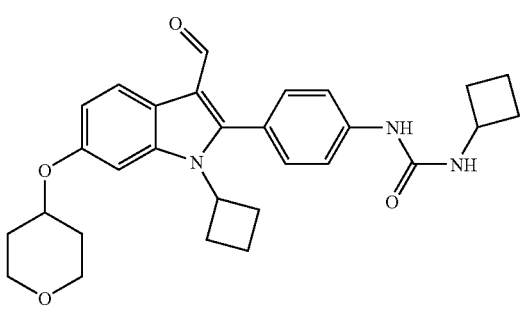
1996
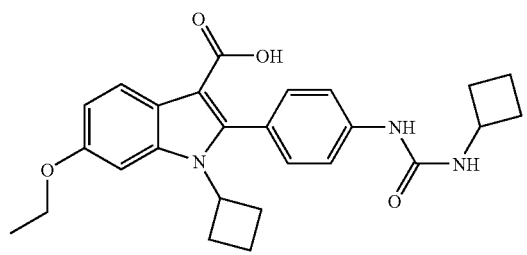
1997
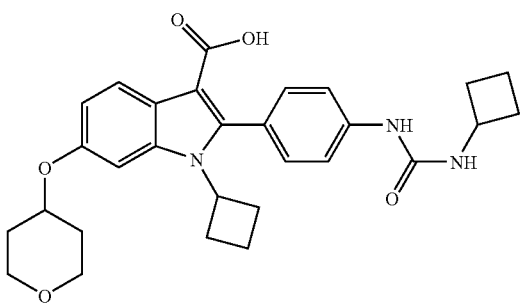

-continued
1998
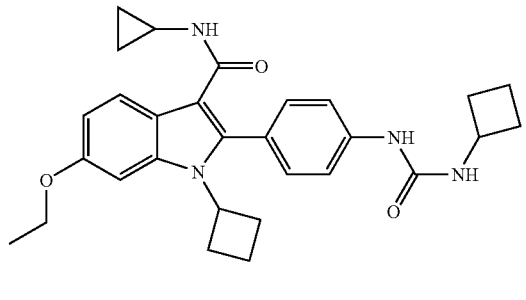
1999
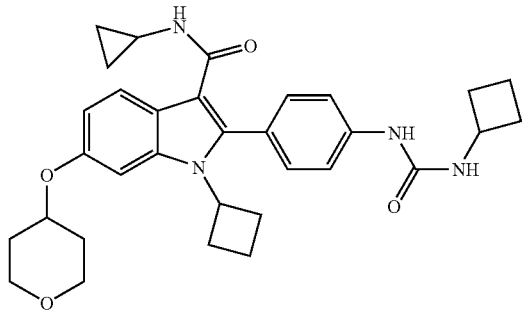
2001
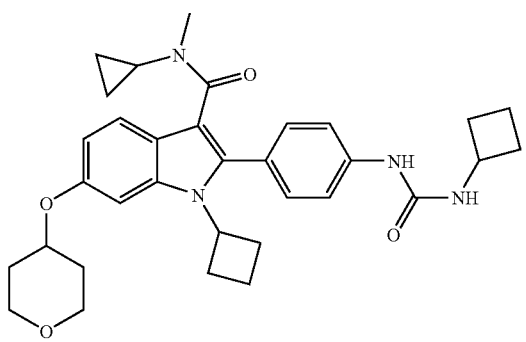
2003
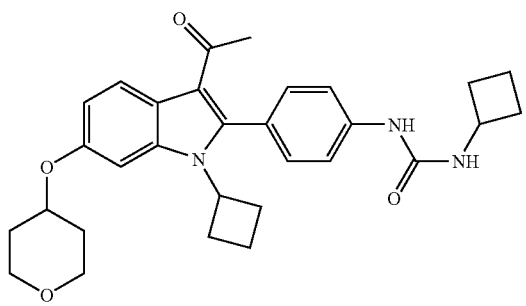
2004
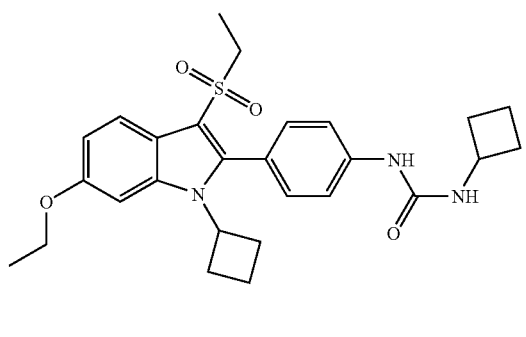
2005
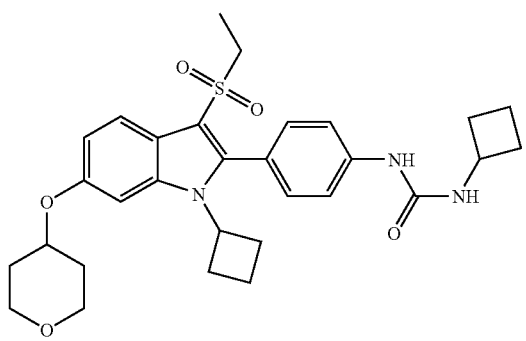
2006
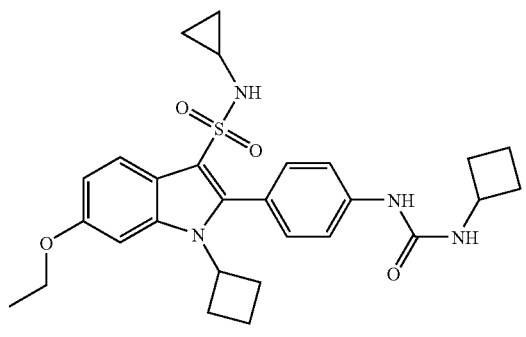
2007
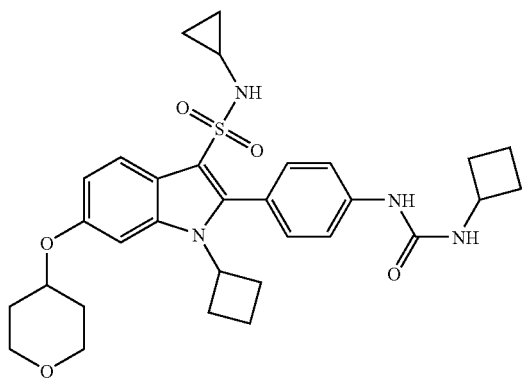

-continued
2008
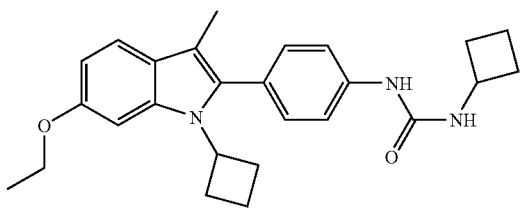
2009
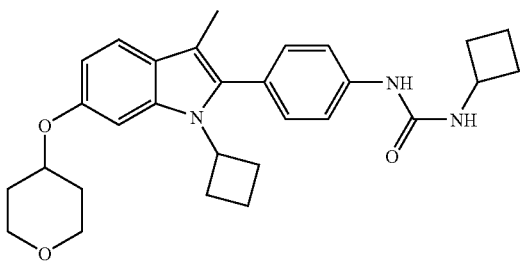
2010
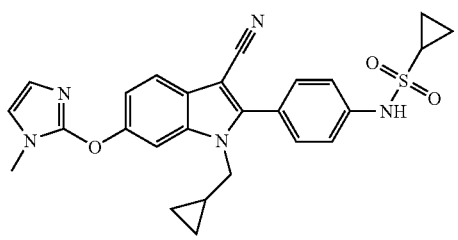
2011
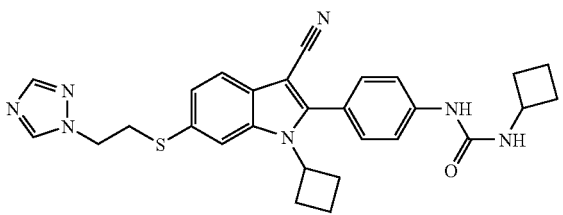
2012
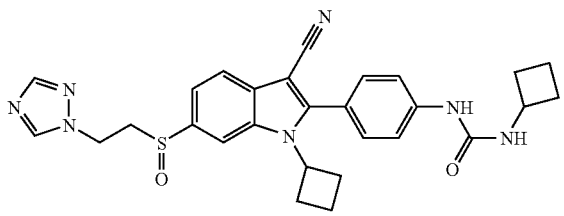
2013
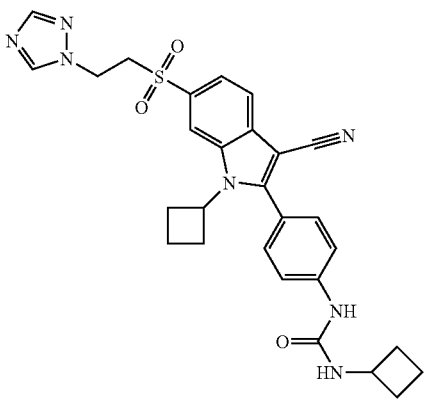
2014
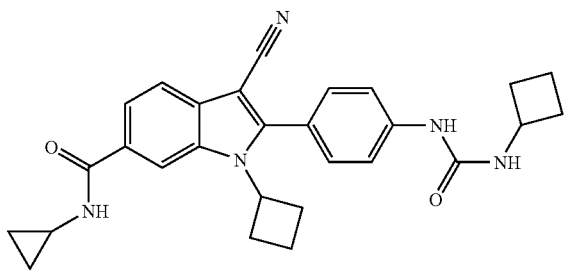
2018
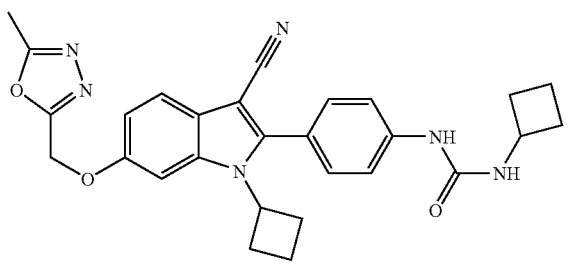
2019
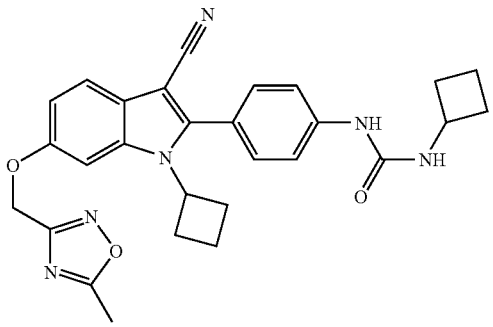
2020
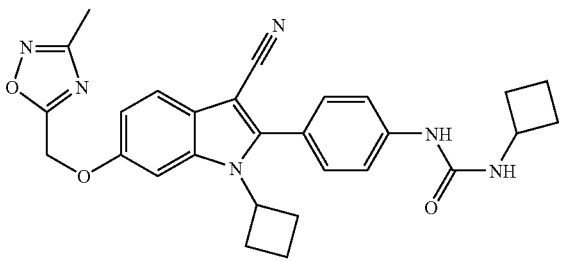

-continued
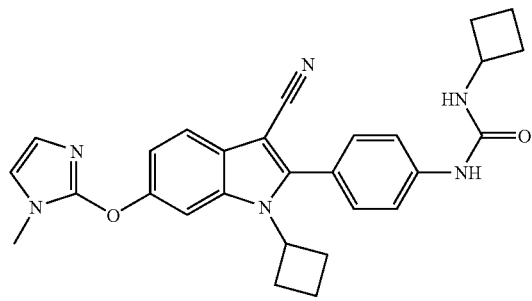
2021
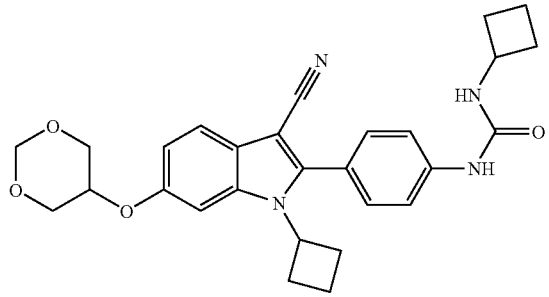
2025
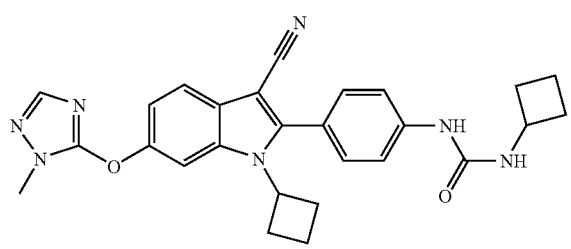
2026
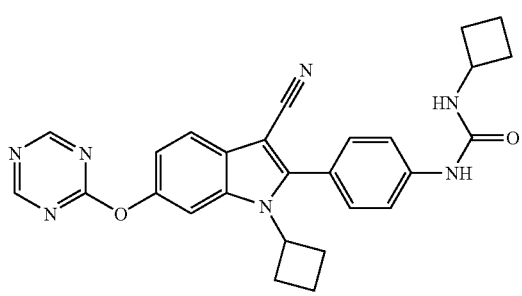
2027
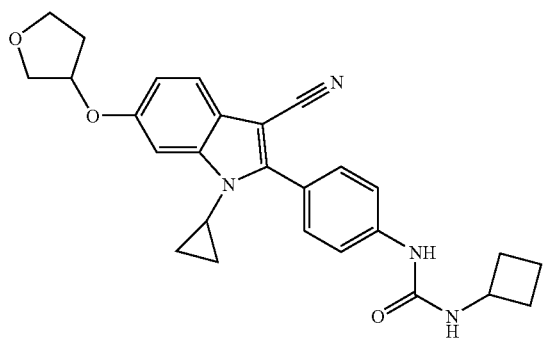
2028
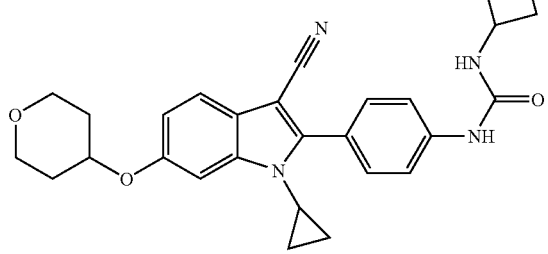
2029
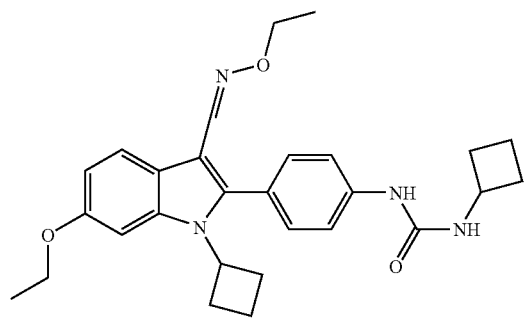
2030
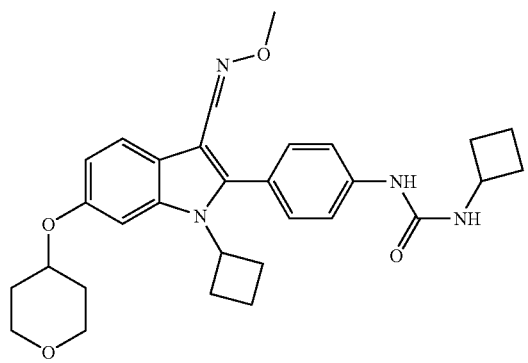
2031

-continued
2032
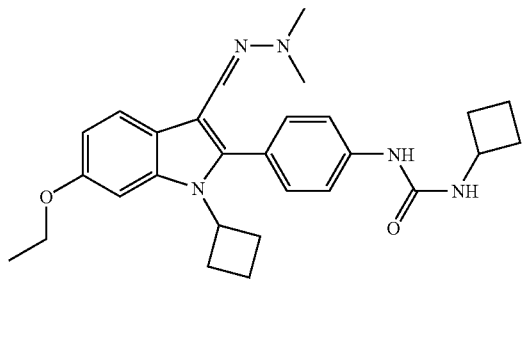
2033
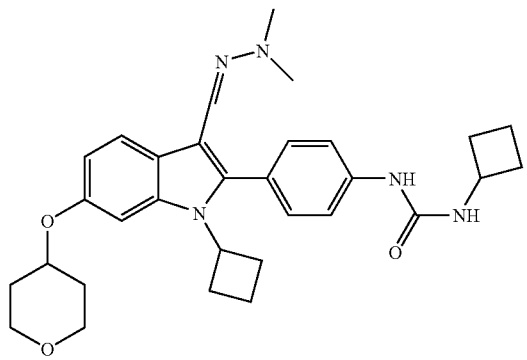
2035
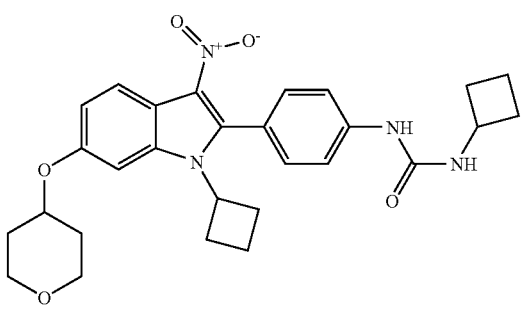
2036
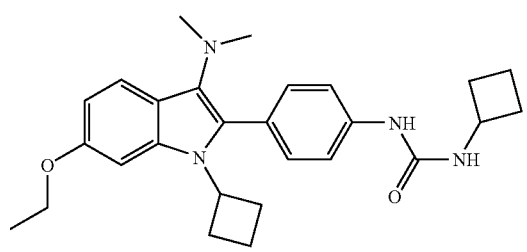
2037
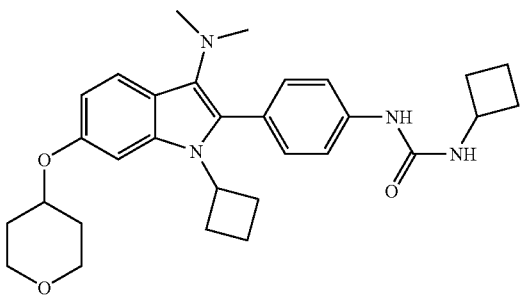
2038
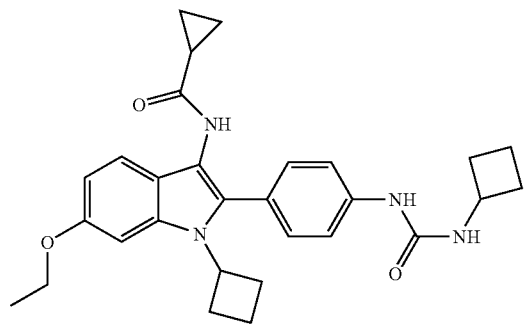
2039
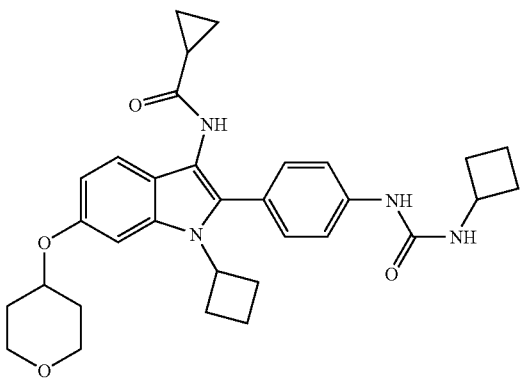
2041
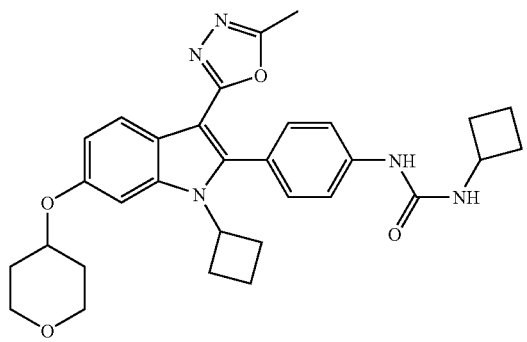

-continued
2043
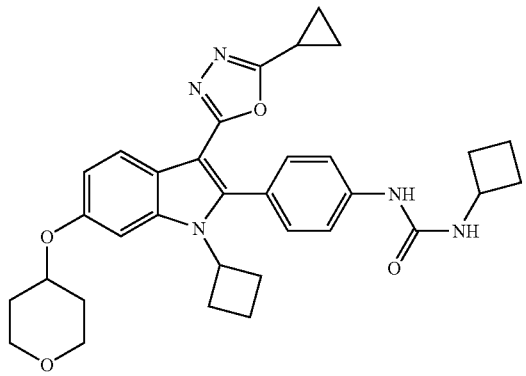
2045
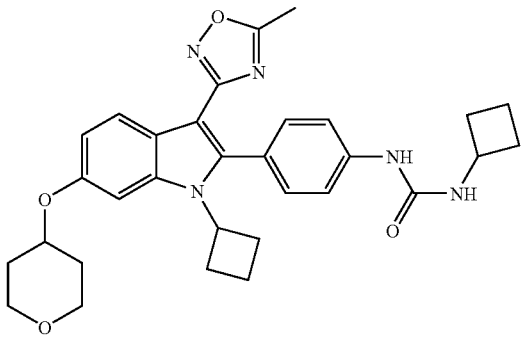
2047
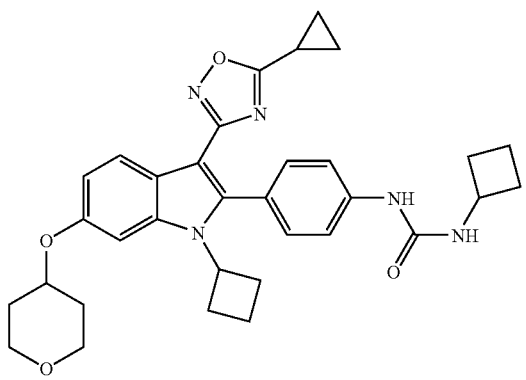
2049
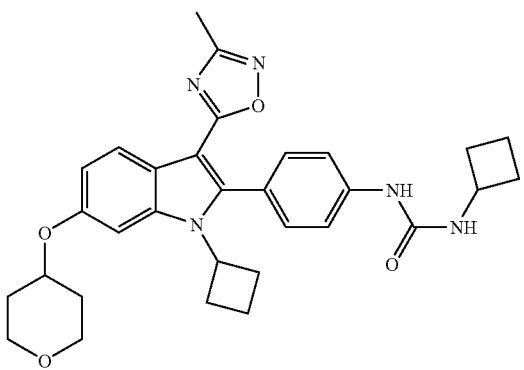
2051
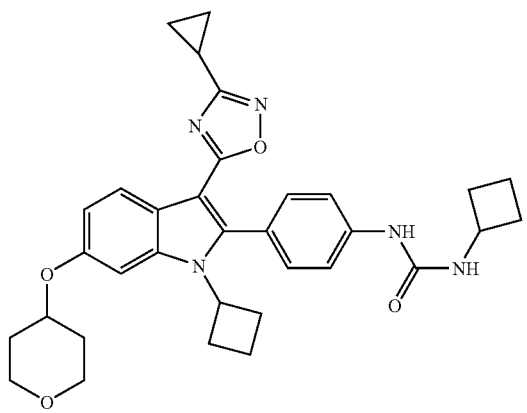
2052
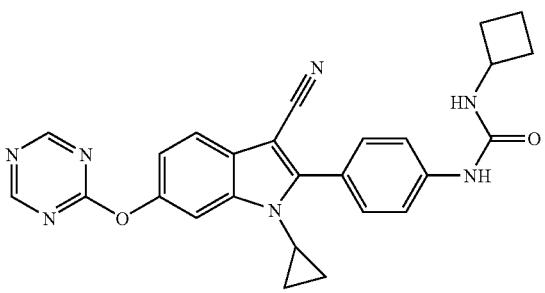
2053
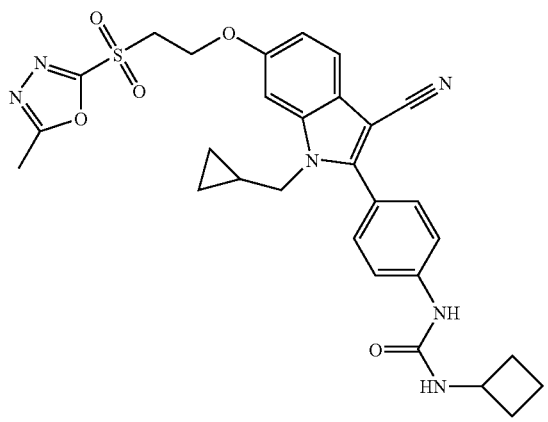
2054
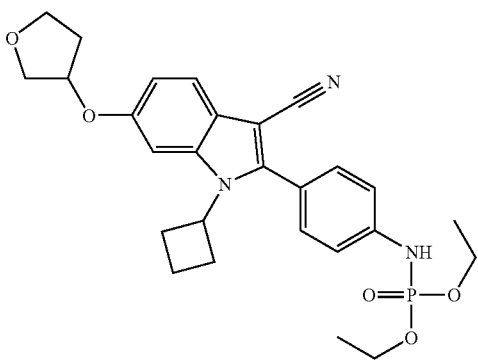

-continued
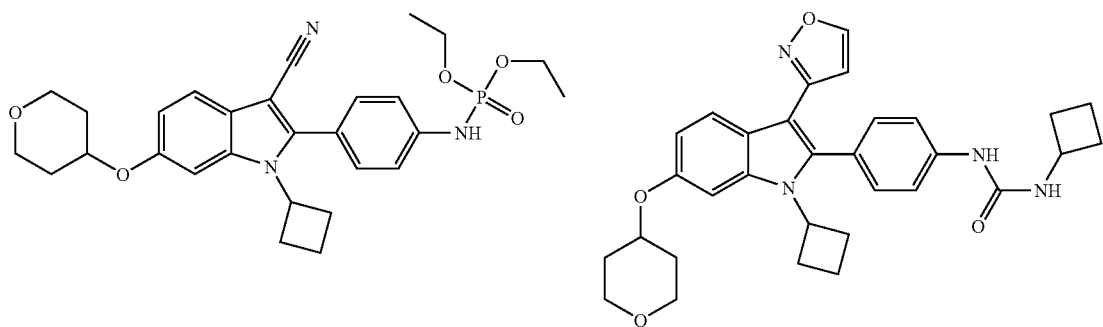
2055 2057
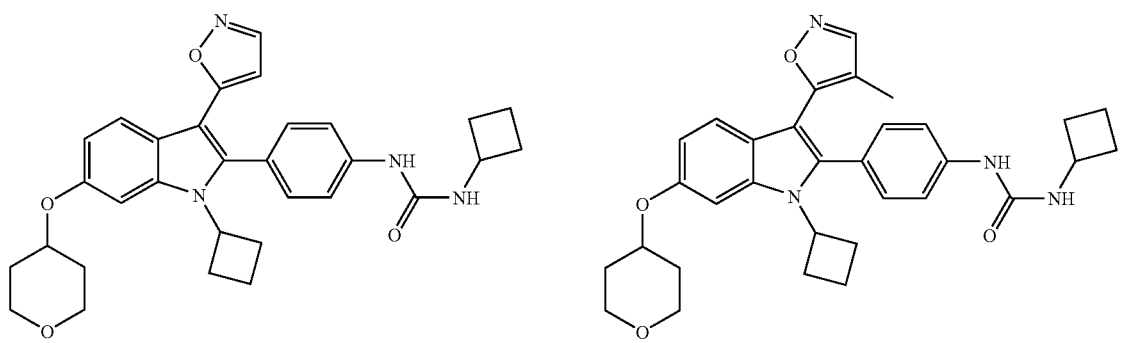
2059 2061
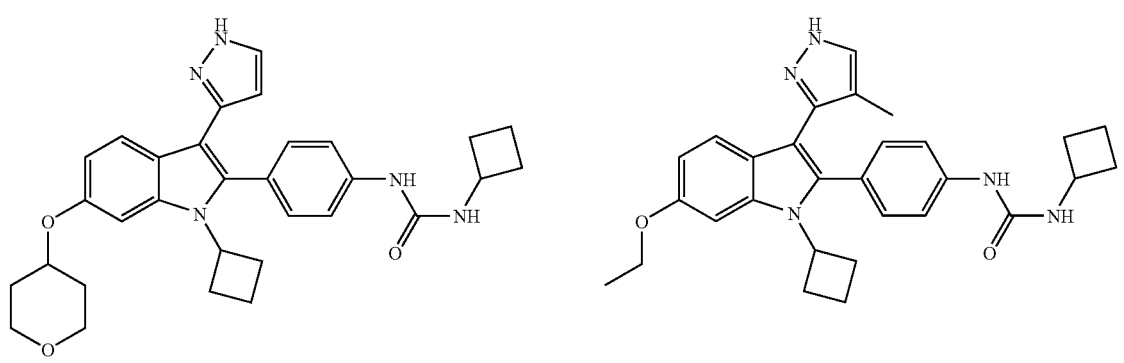
2063 2064
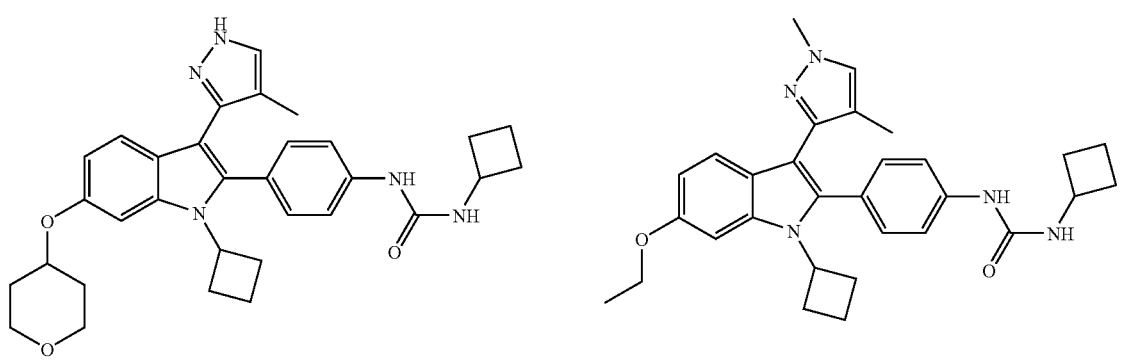
2065 2066

-continued
2067
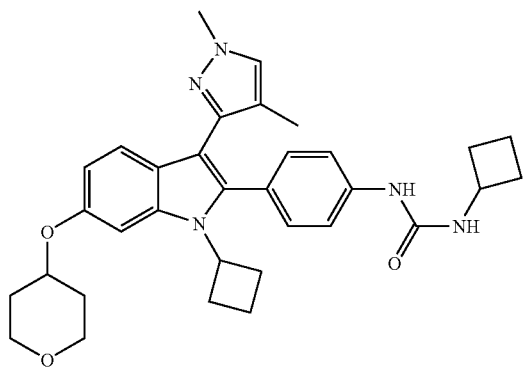
2069
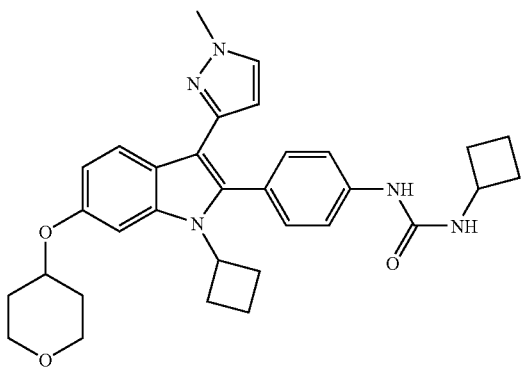
2071
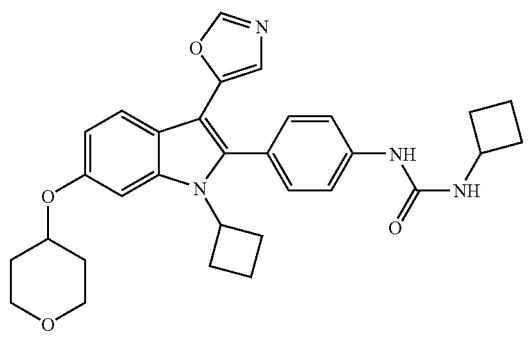
2073
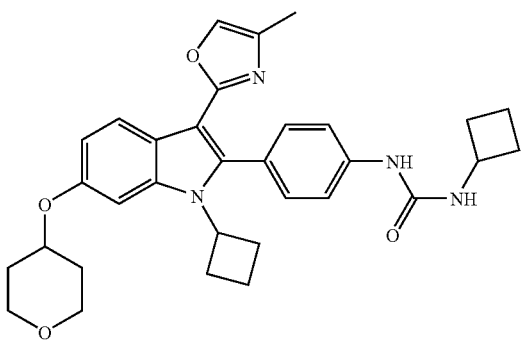
2074
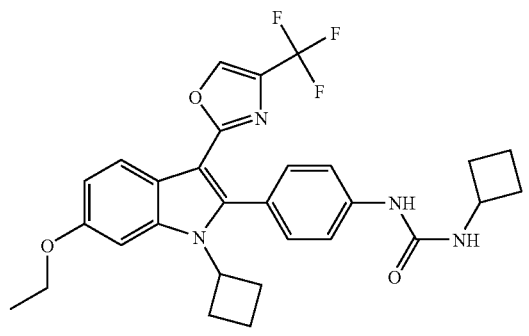
2075
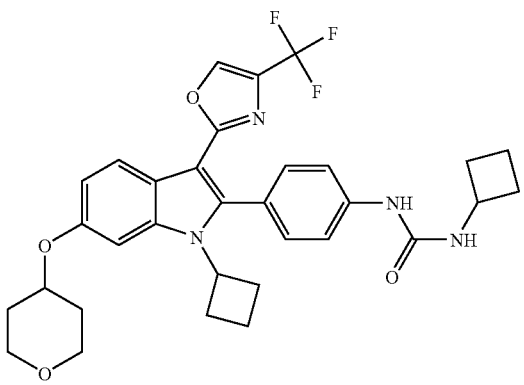
2077
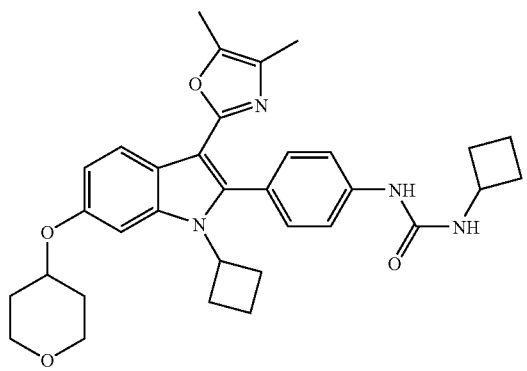
2079
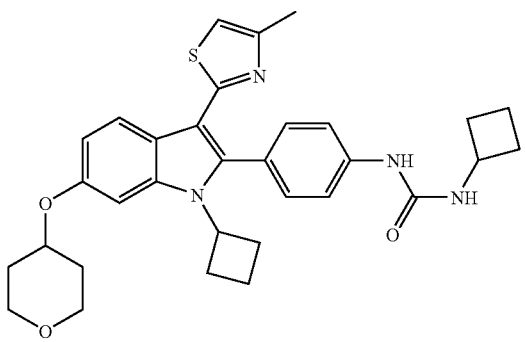

-continued
2081
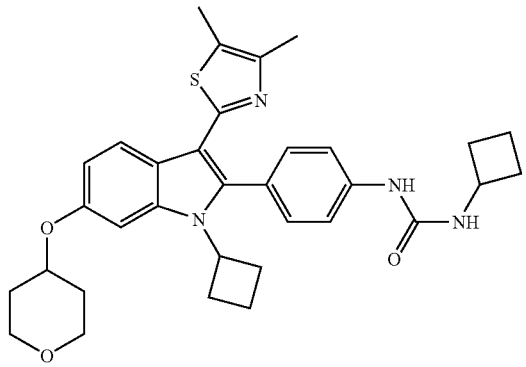
2082
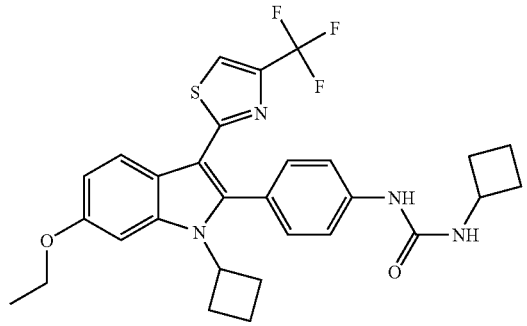
2083
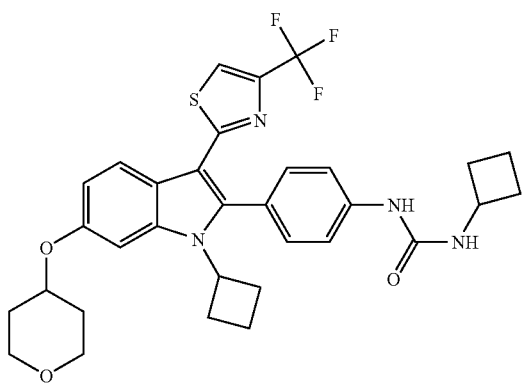
2085
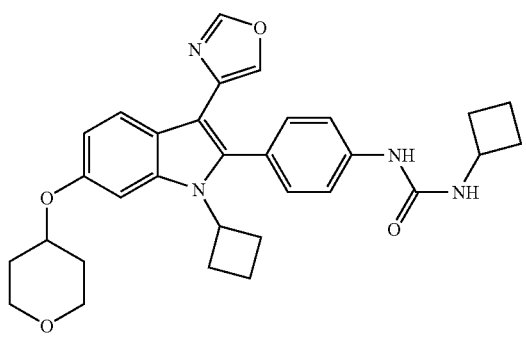
2087
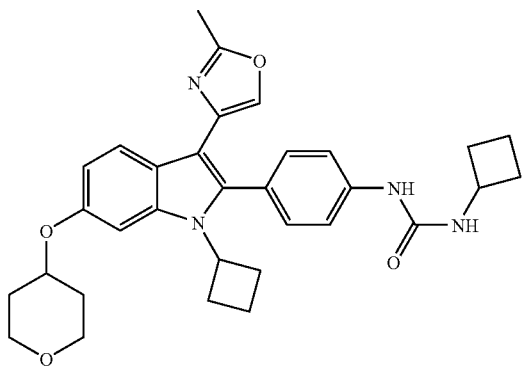
2089
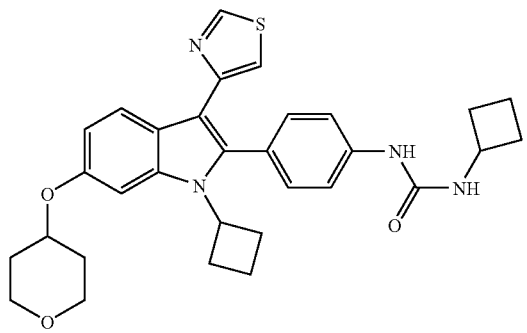
2091
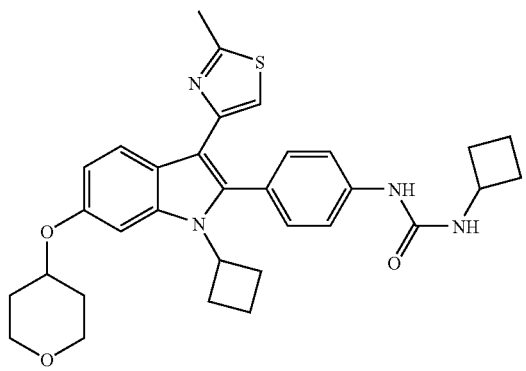
2092
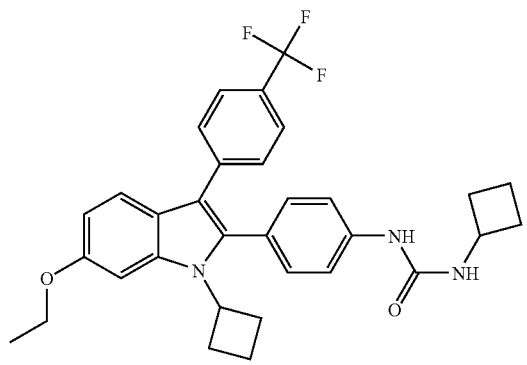

-continued
2093
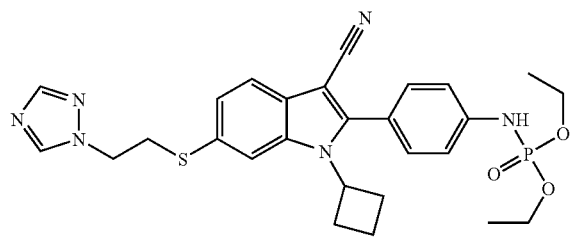
2094
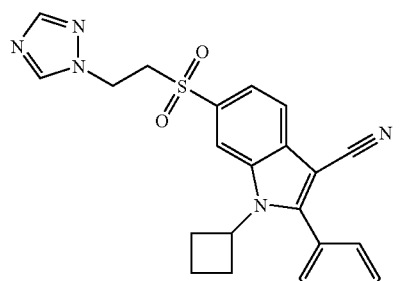
2095
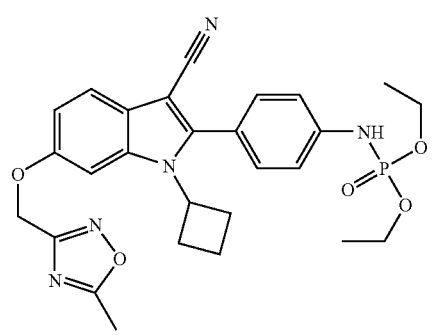
2096
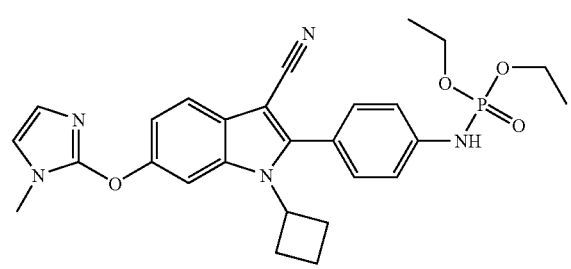
2097
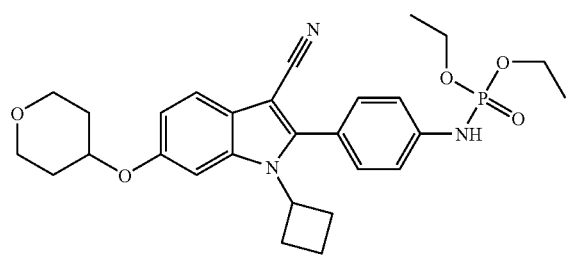
2098
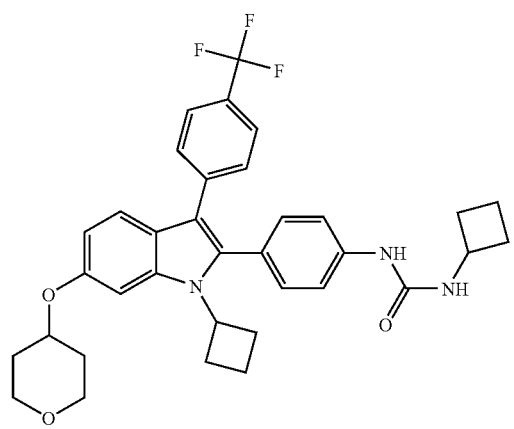
2099
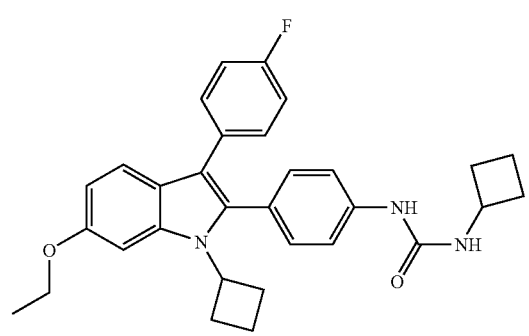
2100
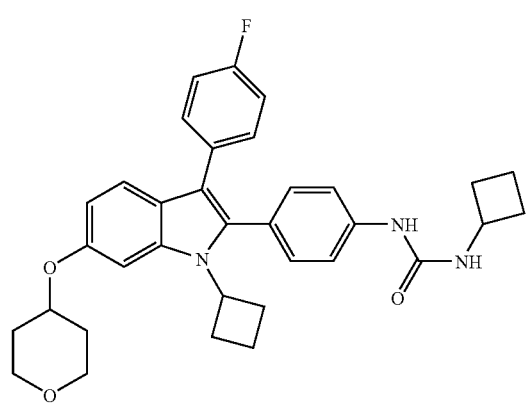

-continued
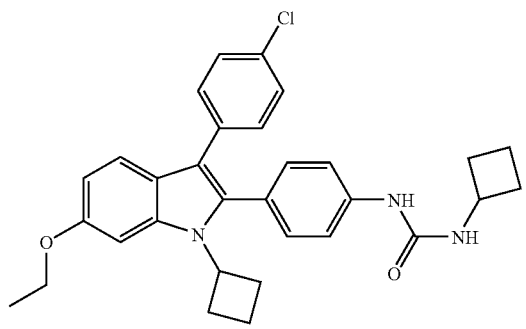
2101
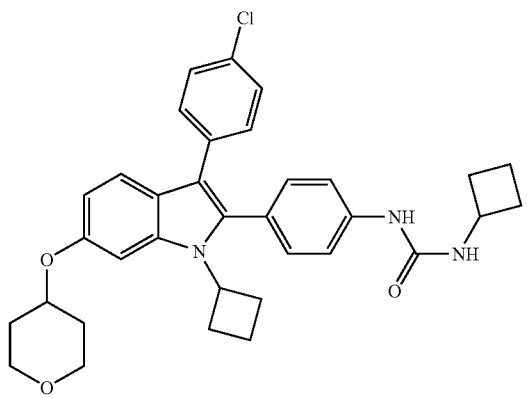
2102
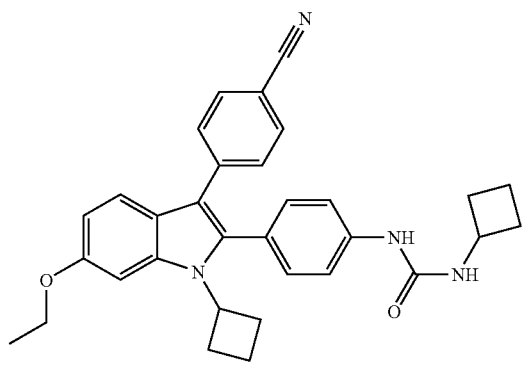
2103
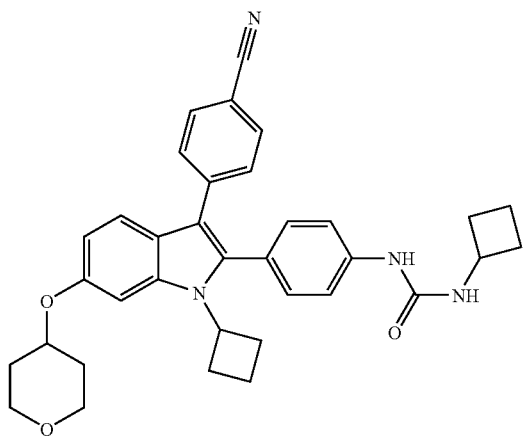
2104
Exemplary compounds include the following:
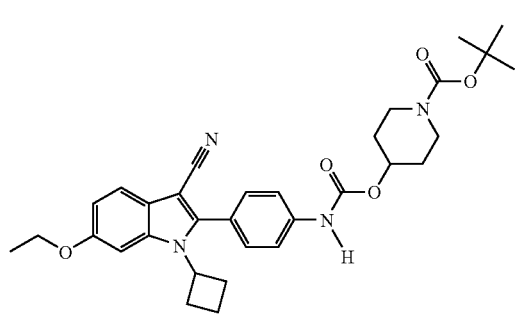
3069
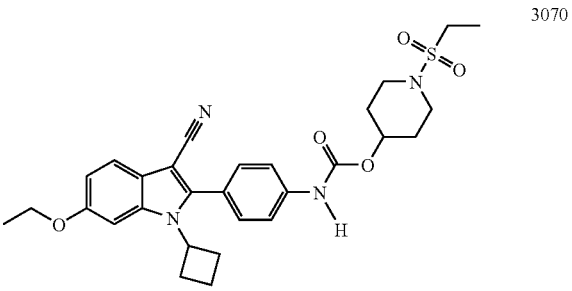
3070
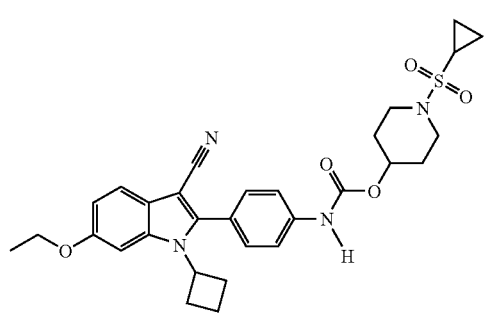
3071
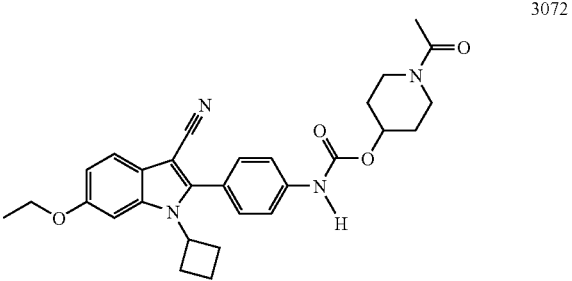
3072

-continued
3073
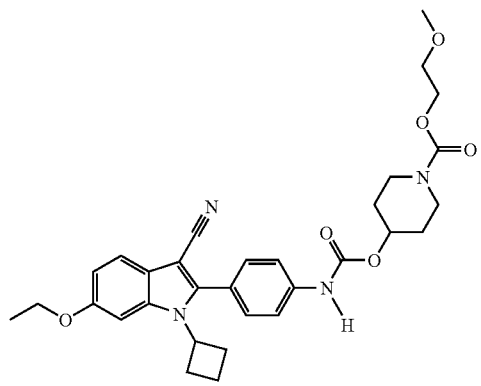
3074
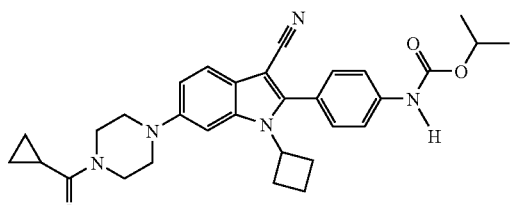
3075
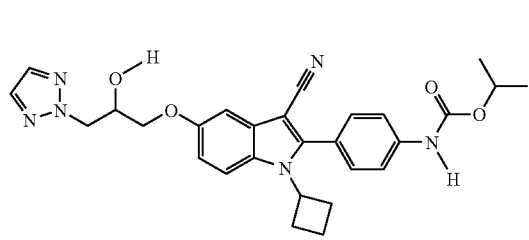
3076
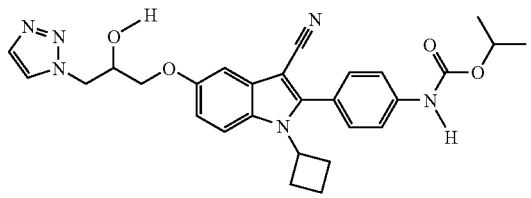
3077
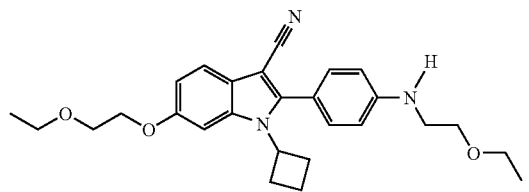
3078
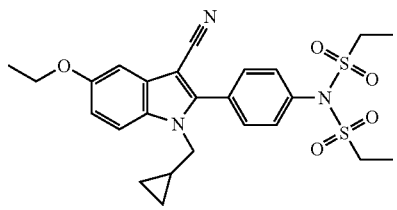
3079
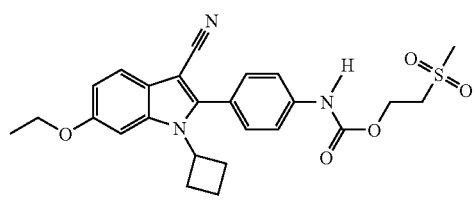
3080
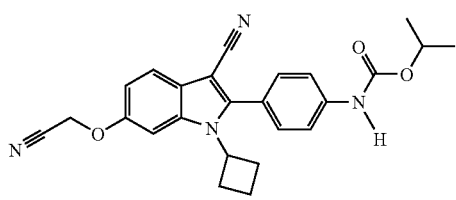
3081
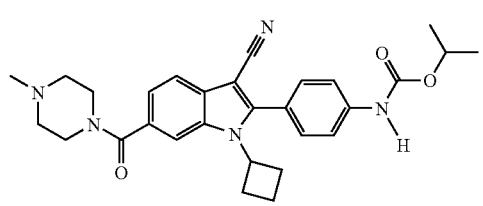
3082
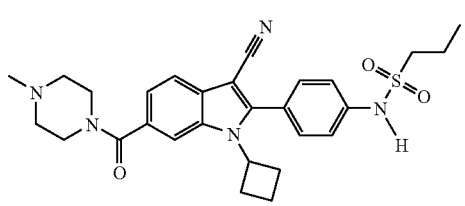
3083
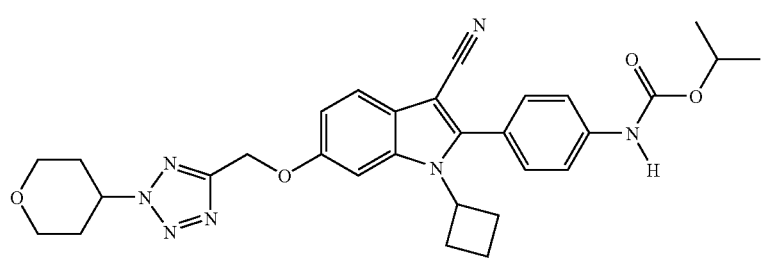

-continued
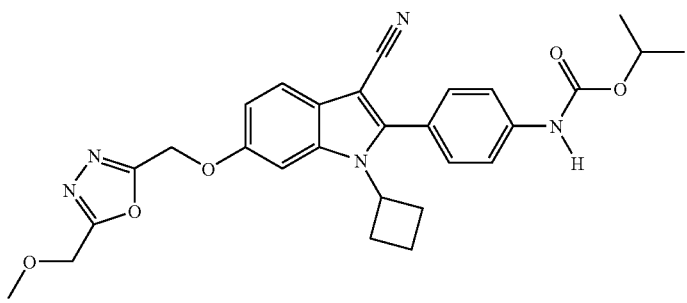
3084
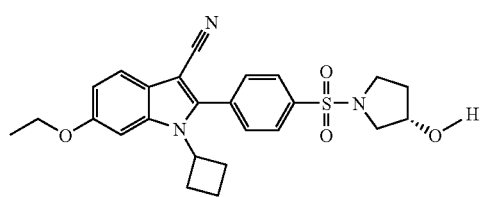
3085
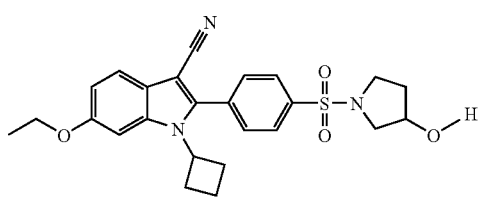
3086
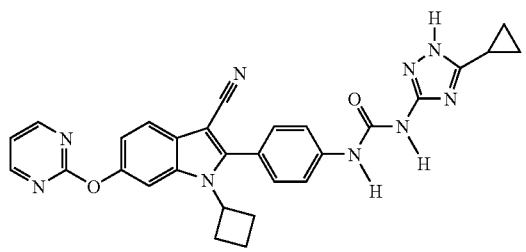
3087
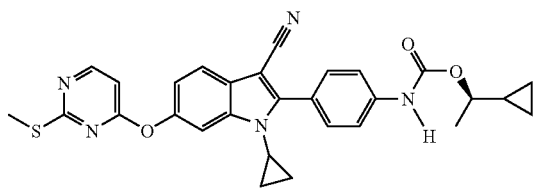
3088
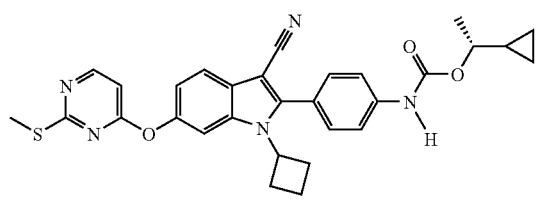
3089
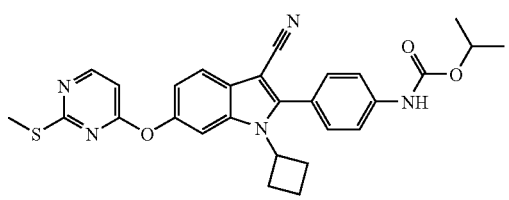
3090
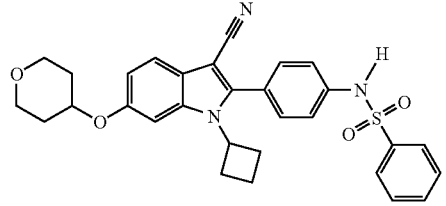
3091
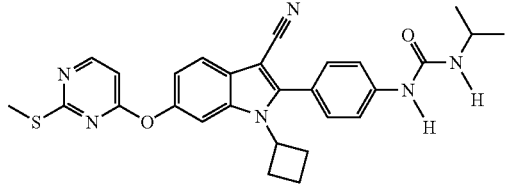
3092
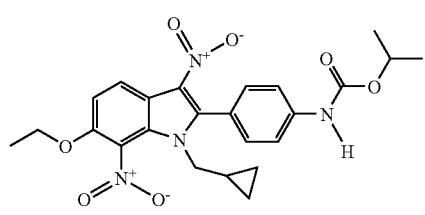
3093
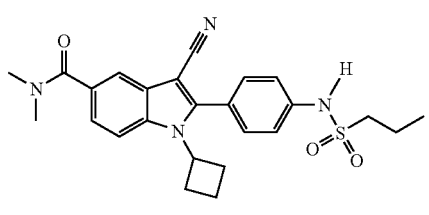
3094
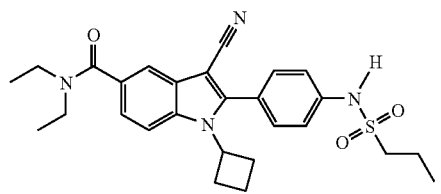
3095
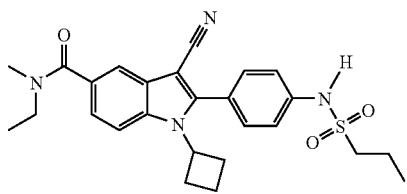
3096

-continued
| | |
|---|---|
| 3097 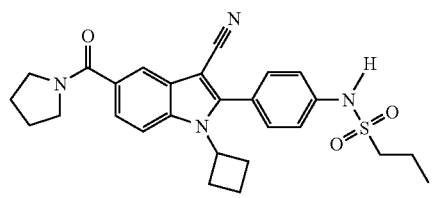 | 3098 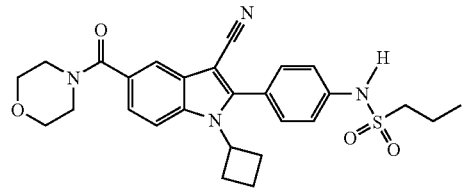 |
| 3099 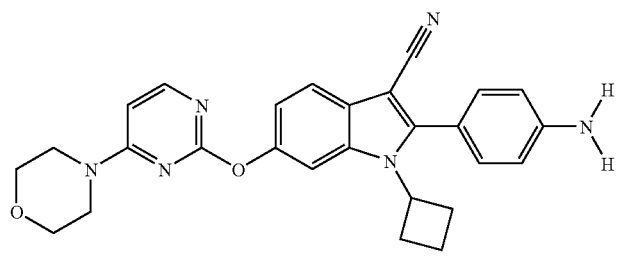 | |
| 3100 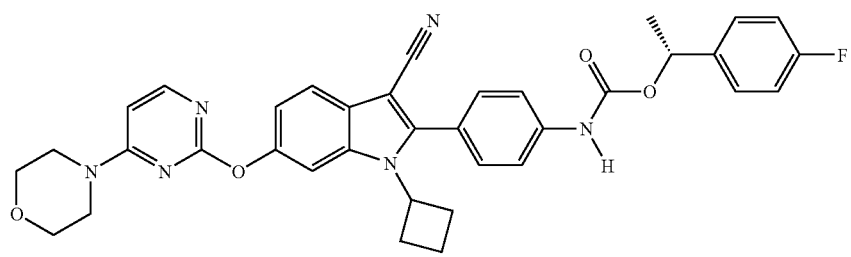 | |
| 3101 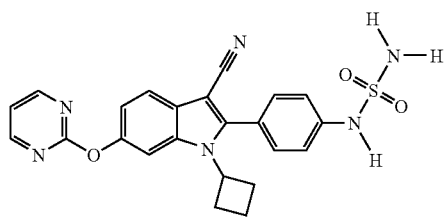 | 3102 |
| 3103 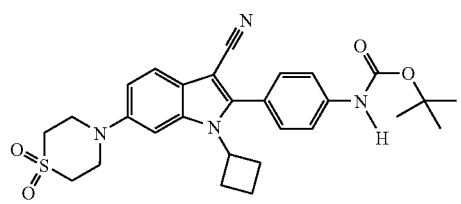 | 3104 |
| 3105 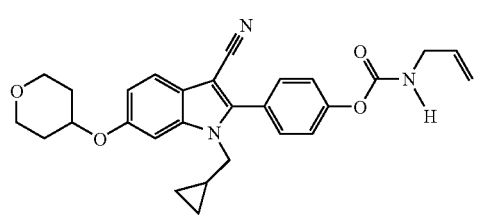 | 3106 |
| 3107 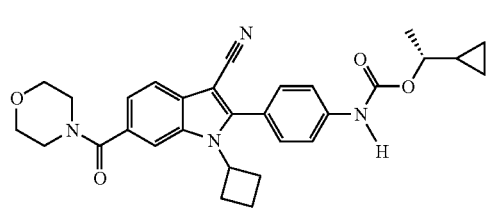 | 3108 |

-continued
3109 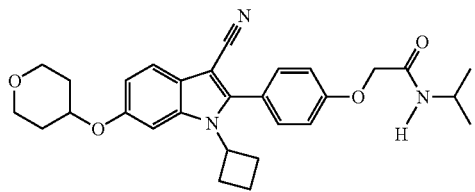
3110 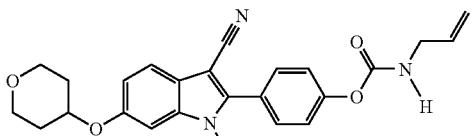
3111 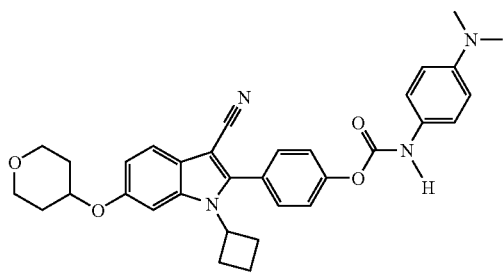
3112 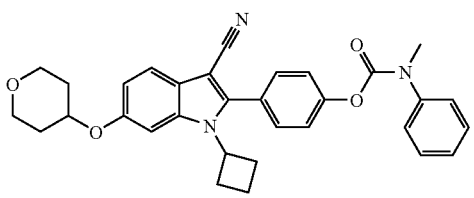
3113 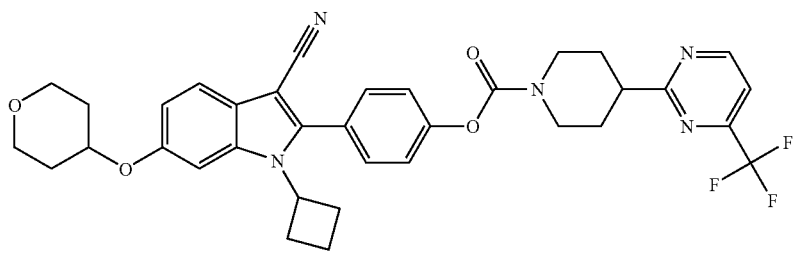
3114 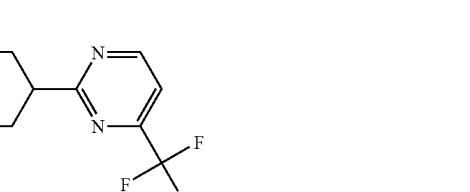
3115 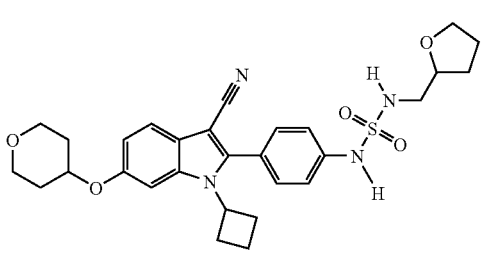
3116 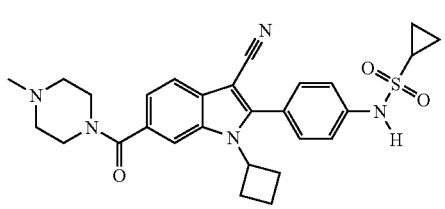
3117 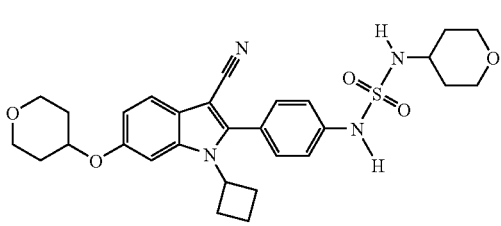
3118 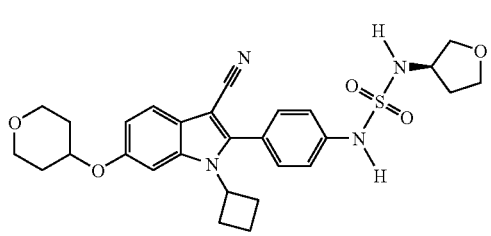
3119 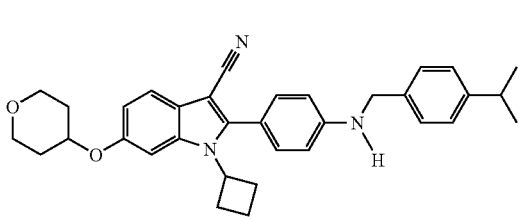
3120 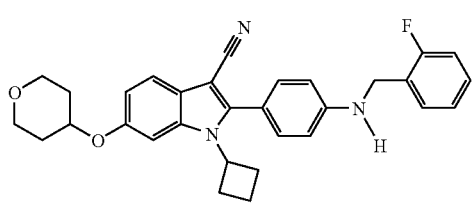
3121 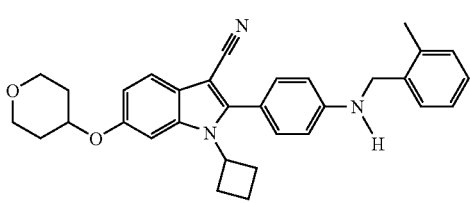

-continued
| 3122 | 3123 |
|---|---|
| 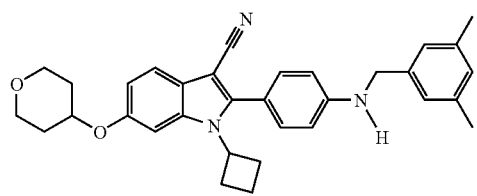 | 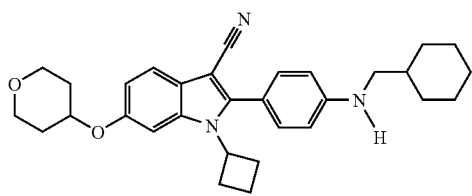 |
| 3124 | 3125 |
| 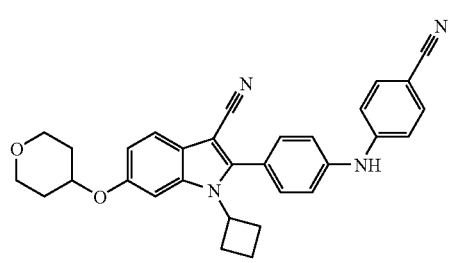 | 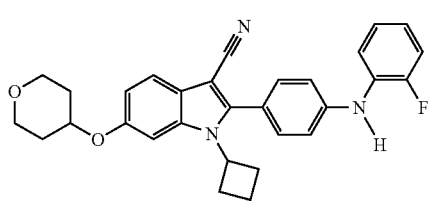 |
| 3126 | 3127 |
| 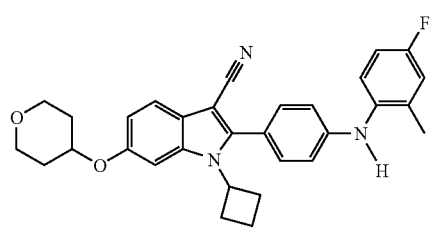 | 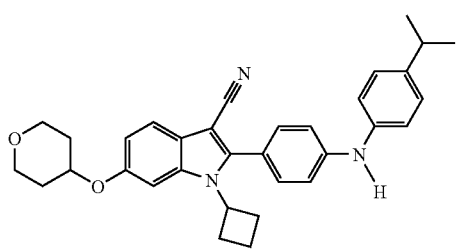 |
| 3128 | 3129 |
| 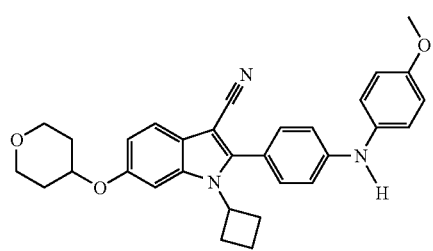 | 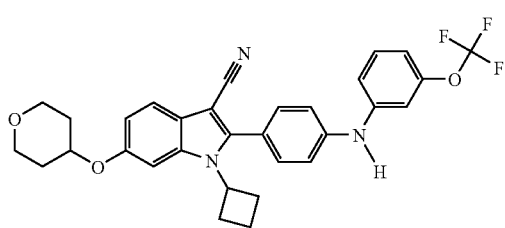 |
| 3130 | 3131 |
| 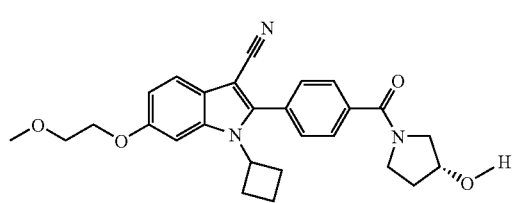 | 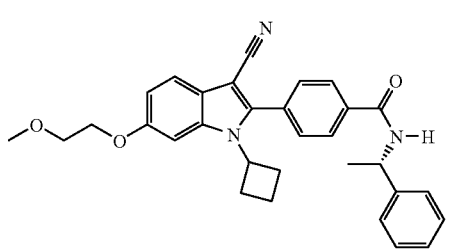 |
| 3132 | 3133 |
| 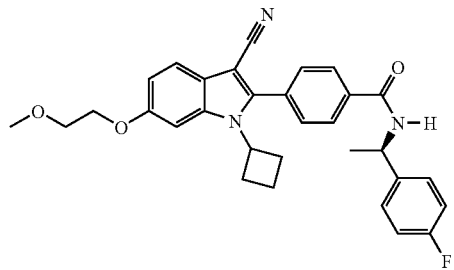 | 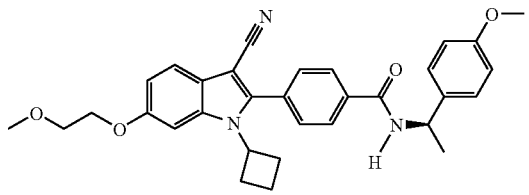 |

-continued
3134 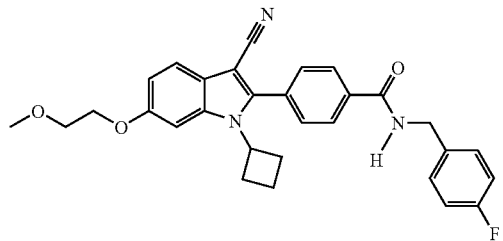 3135 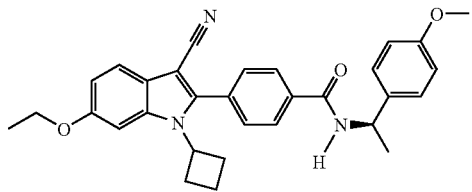
3136 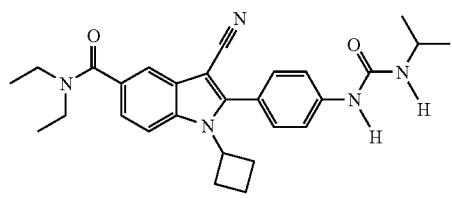 3137 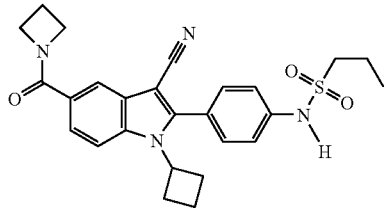
3138 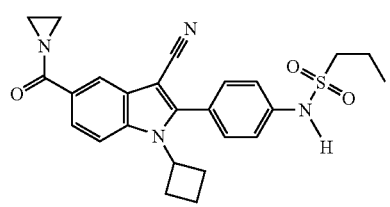 3139 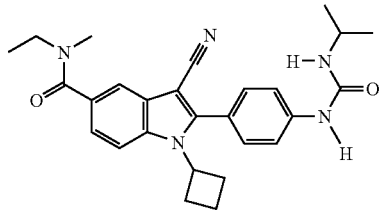
3140 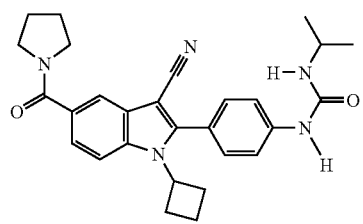 3141 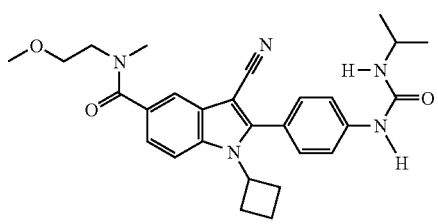
3142 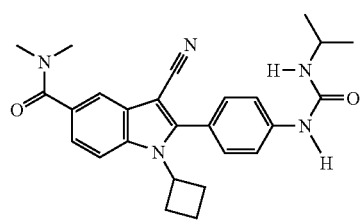 3413 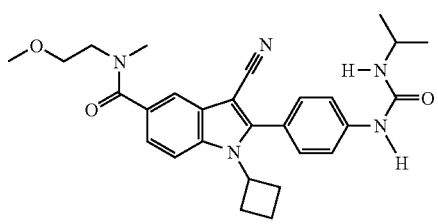
3144 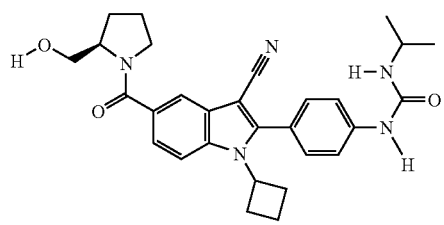 3145 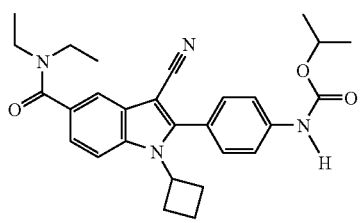
3146 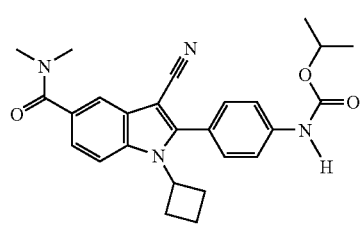 3147 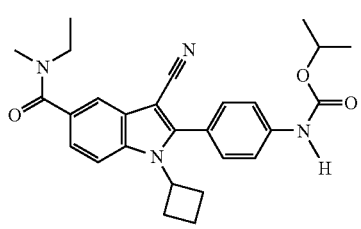

-continued
| | |
|---|---|
| 3148 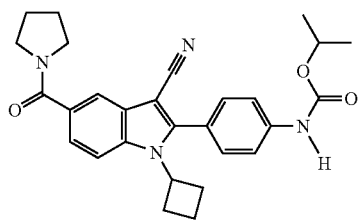 | 3149 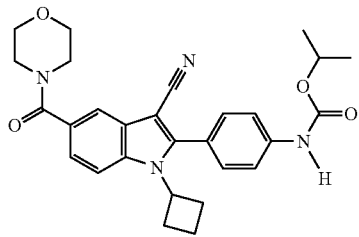 |
| 3150 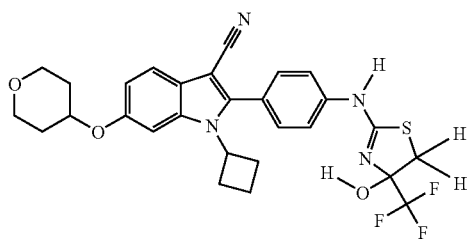 | 3151 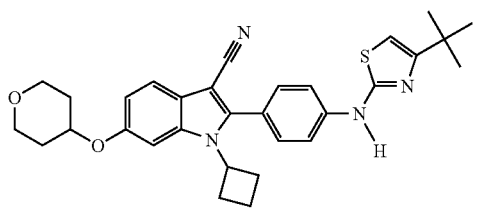 |
| 3152 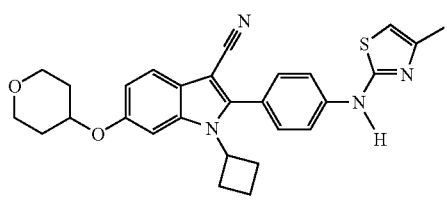 | 3153 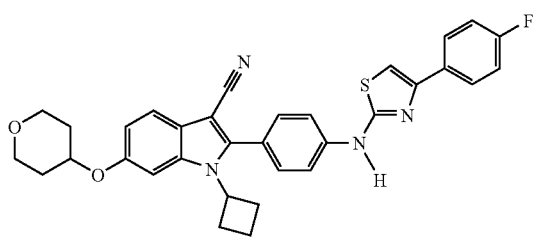 |
| 3154 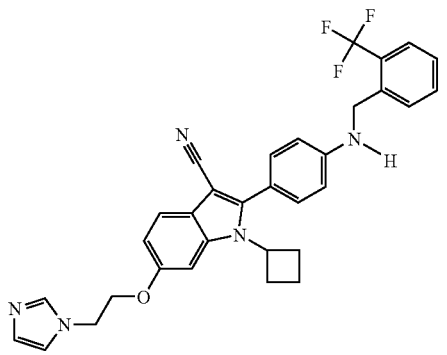 | 3155 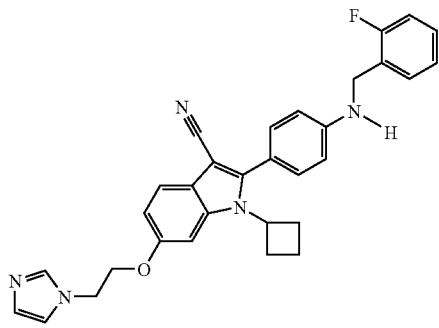 |
| 3156 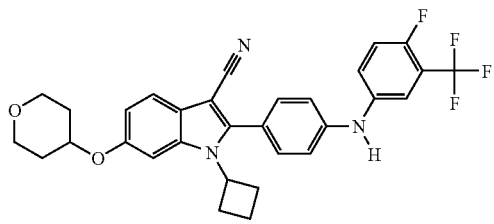 | 3157 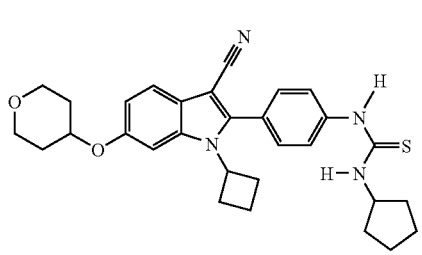 |
| 3158 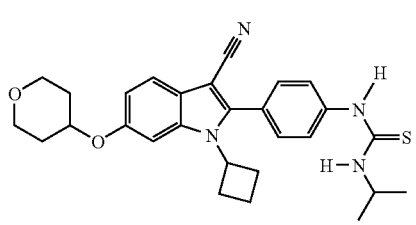 | 3159 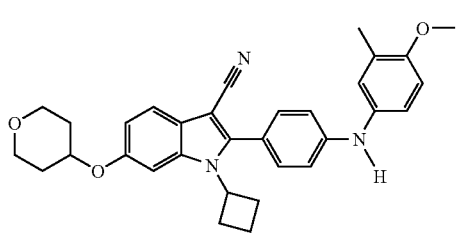 |

-continued
| | |
|---|---|
| 3160 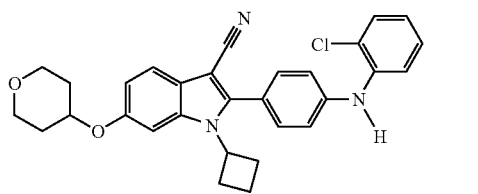 | 3161 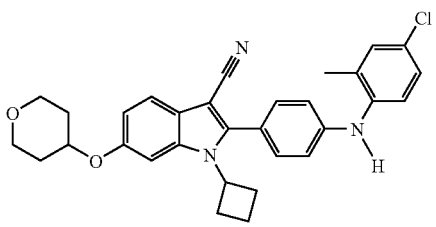 |
| 3162 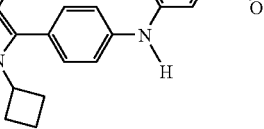 | 3163 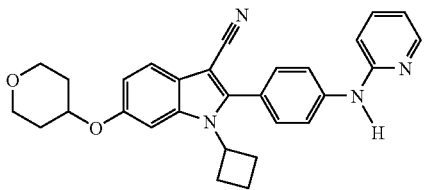 |
| 3164 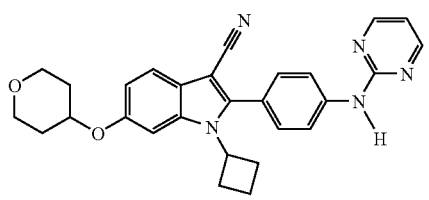 | 3165 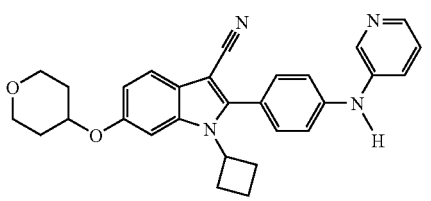 |
| 3166 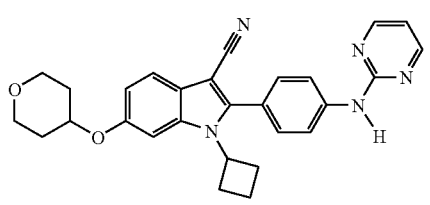 | 3167 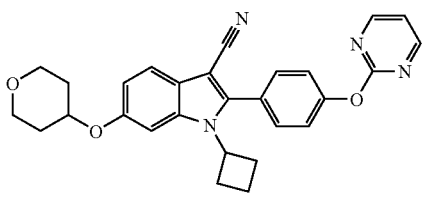 |
| 3168 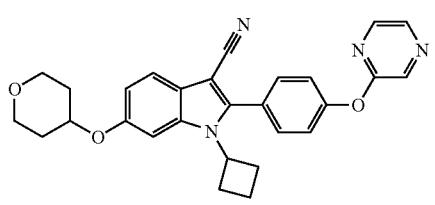 | 3169 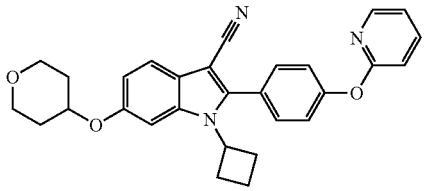 |
| 3170 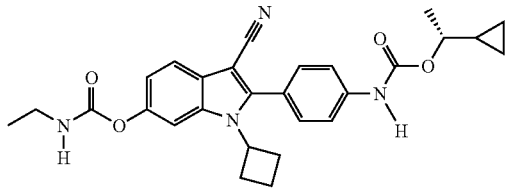 | 3171 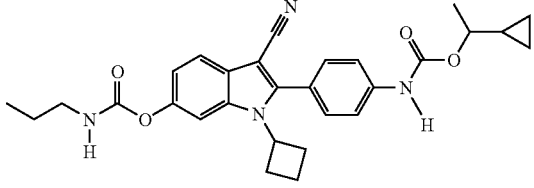 |
| 3172 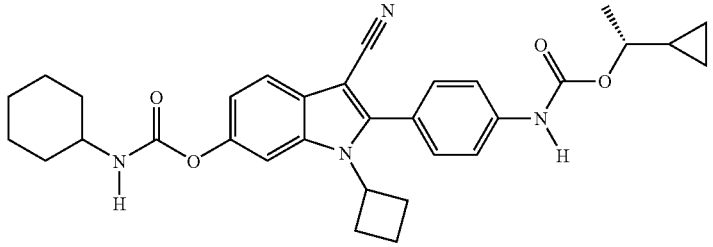 | |

-continued
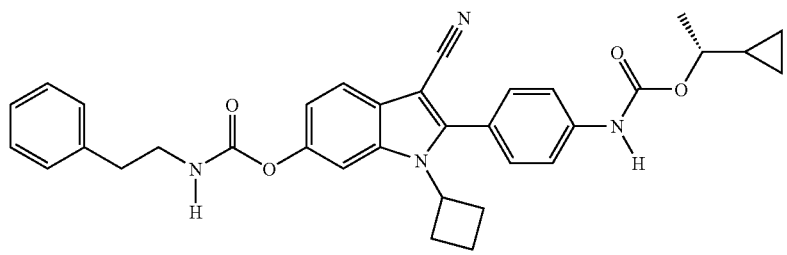
3173
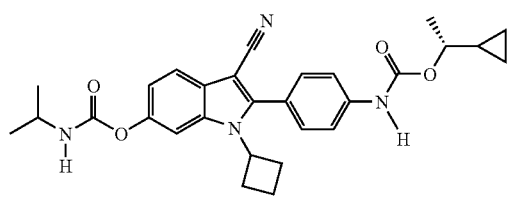
3174
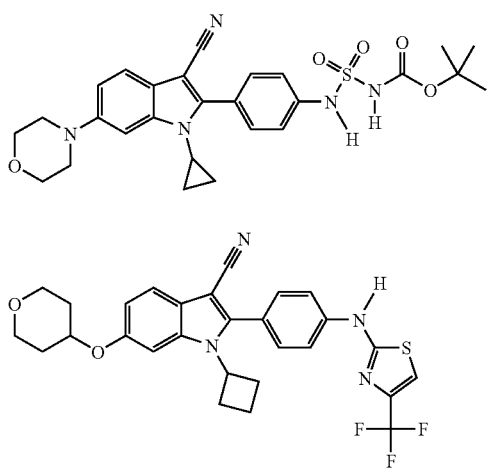
3175
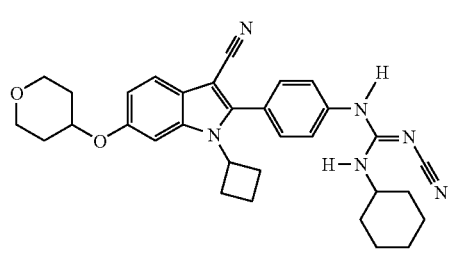
3176
3177
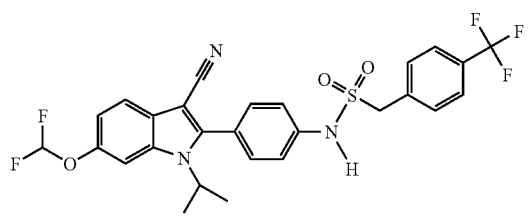
3178
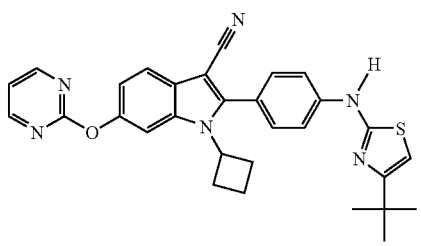
3179
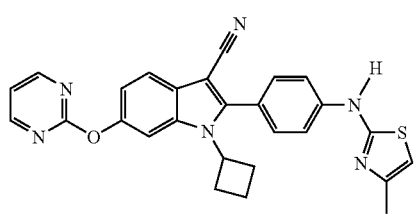
3180
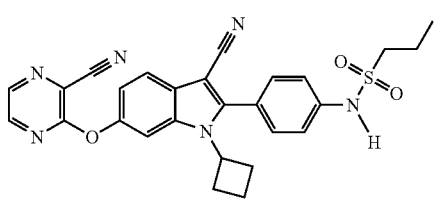
3181
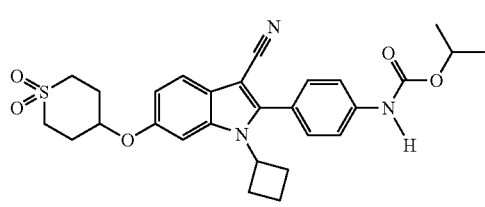
3182
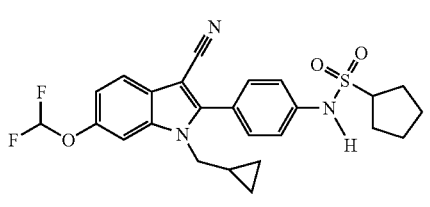
3183
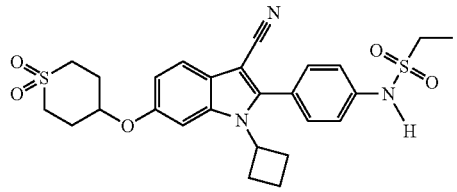
3184
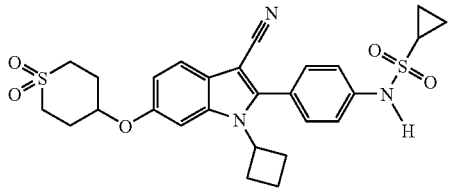
3185

329 330
-continued
| 3186 | 3187 |
|---|---|
| 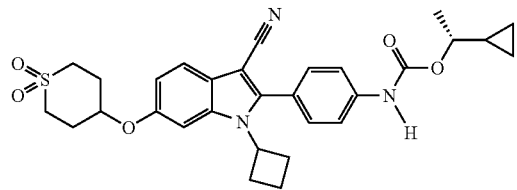 | 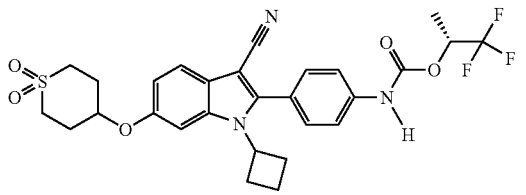 |
| 3188 | 3189 |
| 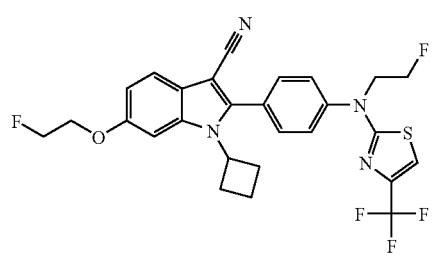 | 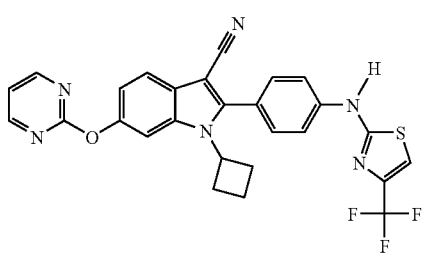 |
| 3190 | 3191 |
| 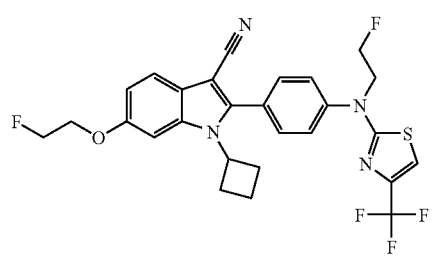 | 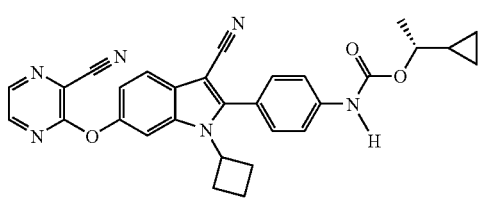 |
| 3192 | 3193 |
| 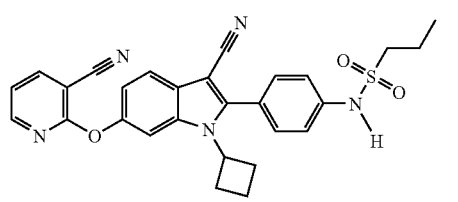 | 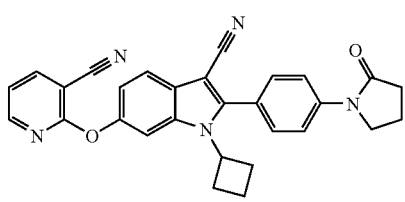 |
| 3194 | 3195 |
| 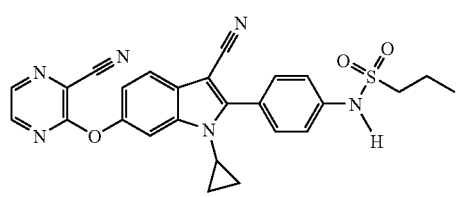 | 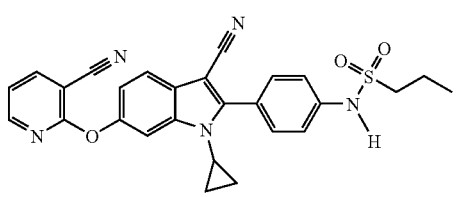 |
| 3196 | 3197 |
| 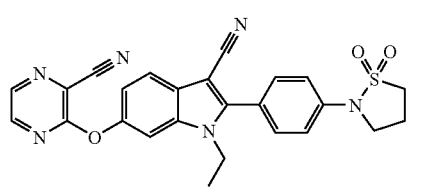 | 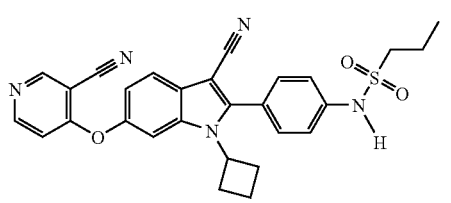 |
| 3198 | 3199 |
| 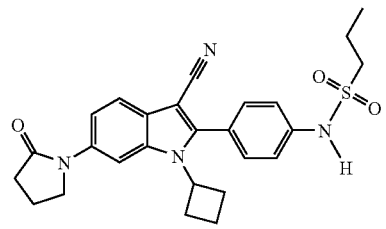 | 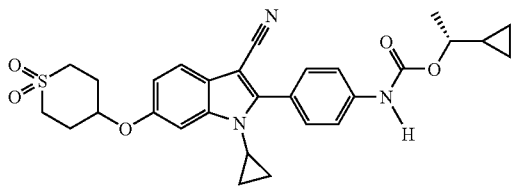 |

-continued
| 3200 | 3201 |
|---|---|
| 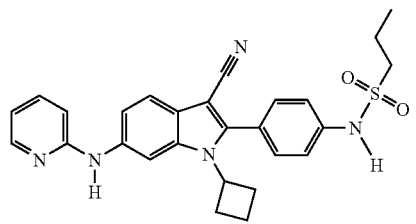 | 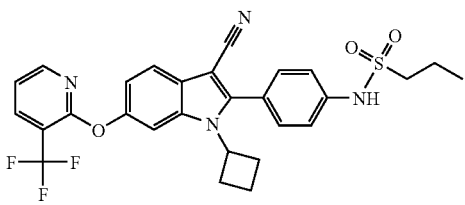 |
| 3202 | 3023 |
|---|---|
| 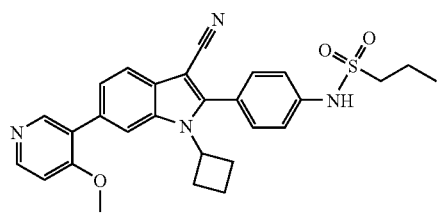 | |
| 3204 | 3205 |
|---|---|
| 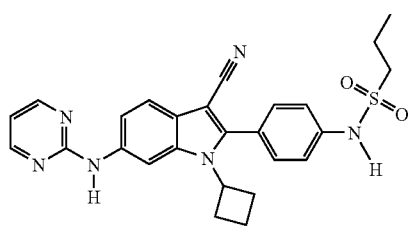 | |
| 3208 | 3209 |
|---|---|
| 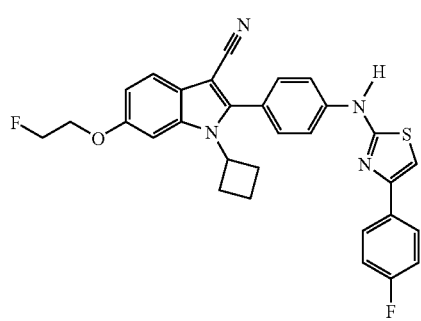 | |
| 3208 | 3209 |
|---|---|
| 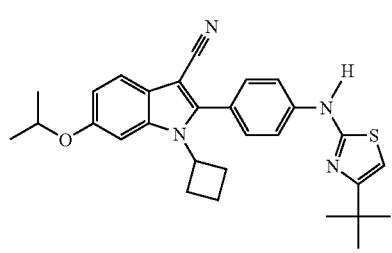 | |
| 3210 | 3211 |
|---|---|
| 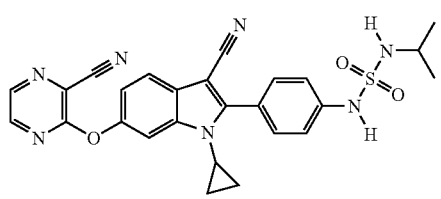 | 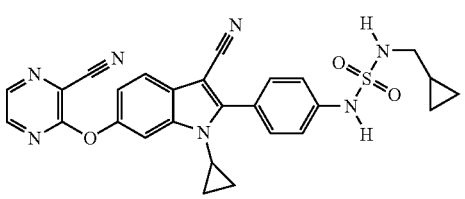 |

-continued
| 3212 | 3213 |
|---|---|
| 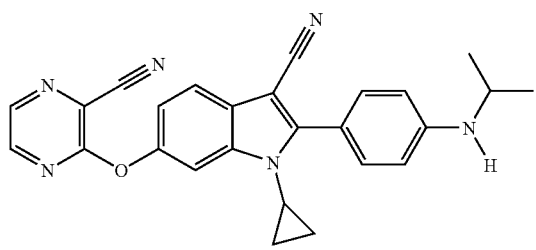 | 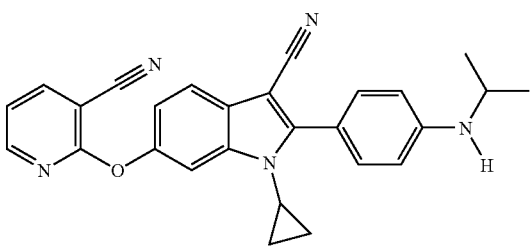 |
| 3214 | 3215 |
| 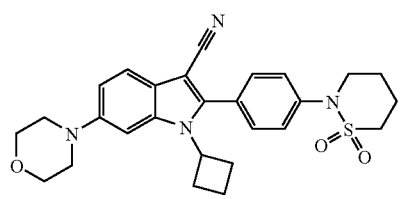 | 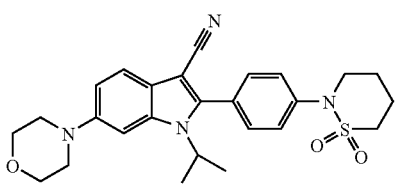 |
| 3216 | 3217 |
| 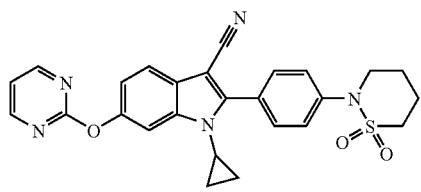 | 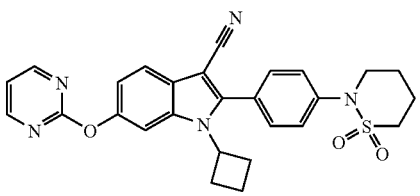 |
| 3218 | 3219 |
| 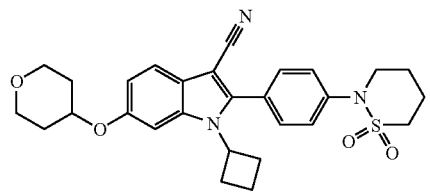 | 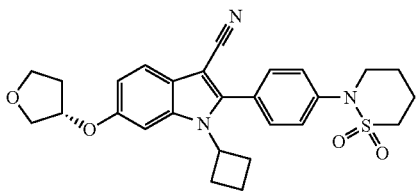 |
| 3220 | 3221 |
| 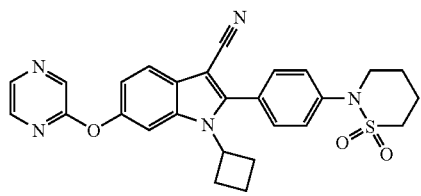 | 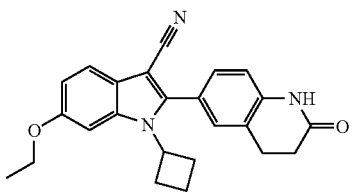 |
| 3222 | 3223 |
| 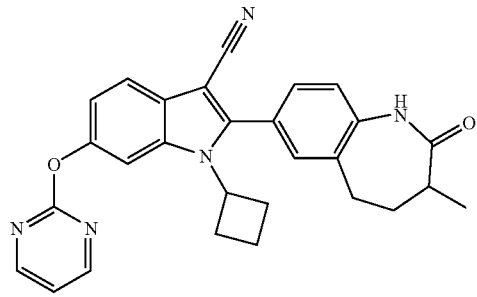 | 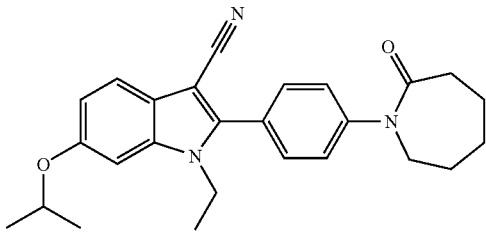 |
| 3224 | 3225 |
| 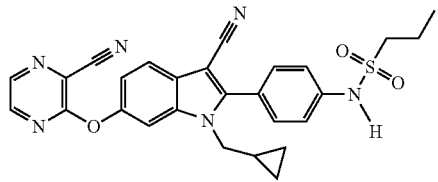 | 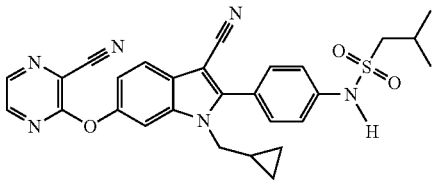 |

-continued
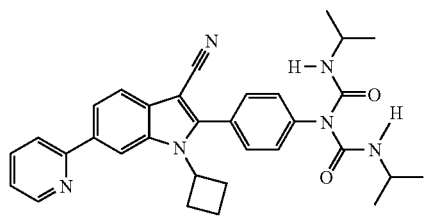
3226
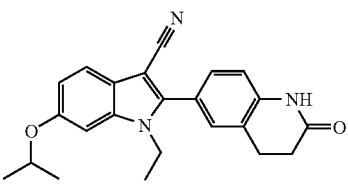
3227
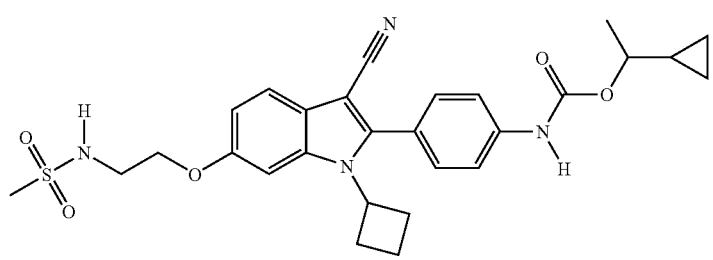
3228
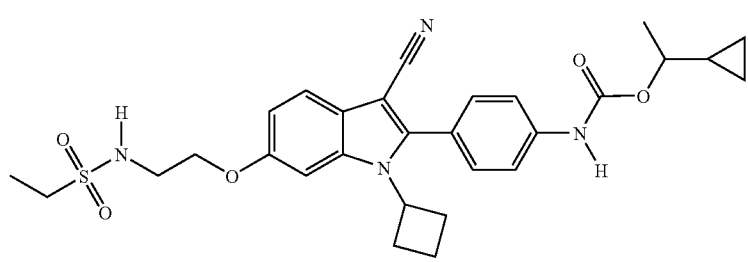
3229
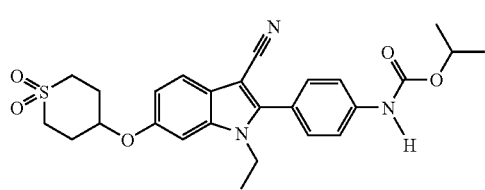
3230
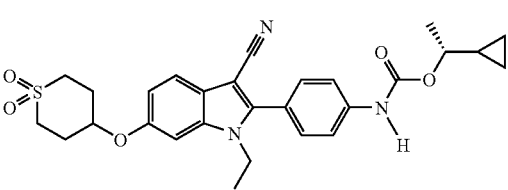
3231
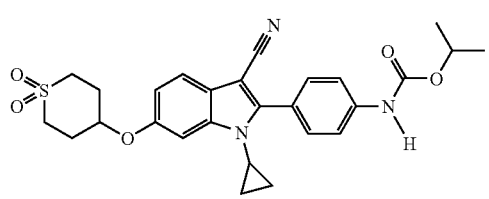
3232
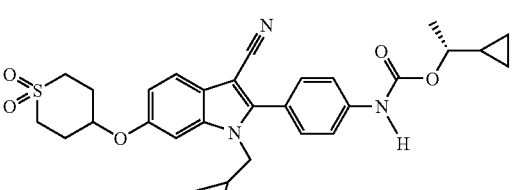
3233
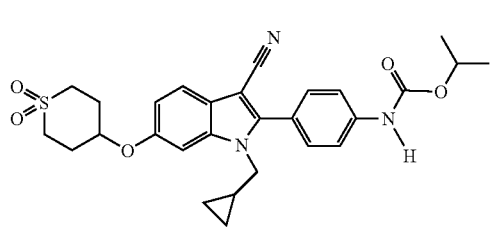
3234
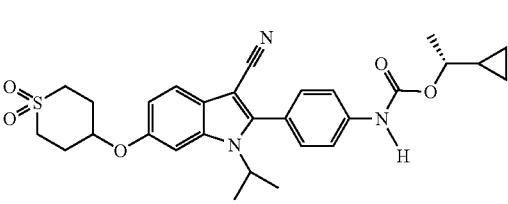
3235
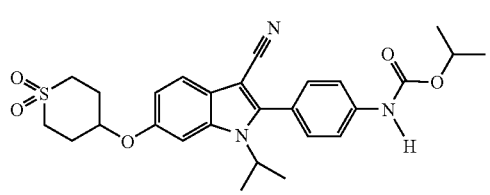
3236
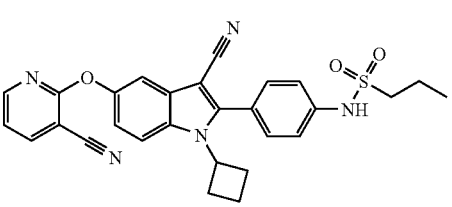
3237

| 337 | 338 |
|---|---|
| 3238 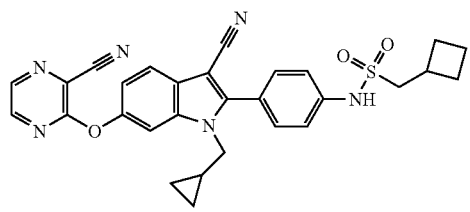 | 3239 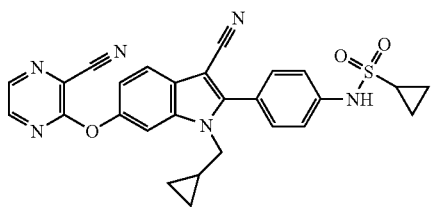 |
| 3240 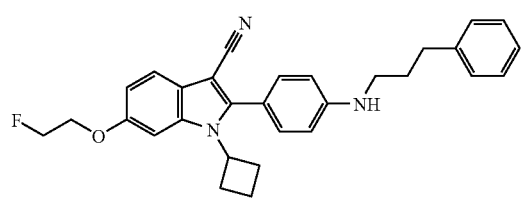 | 3241 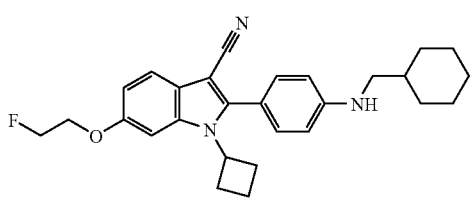 |
| 3242 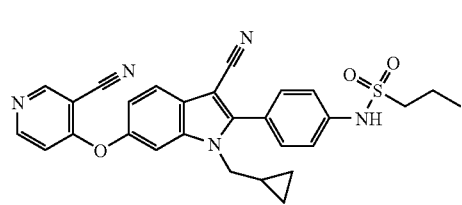 | 3243 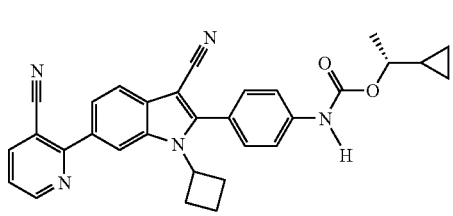 |
| 3244 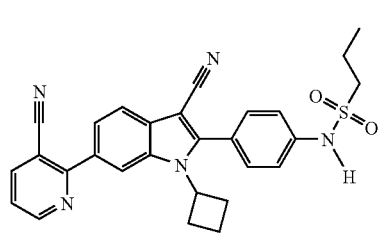 | 3245 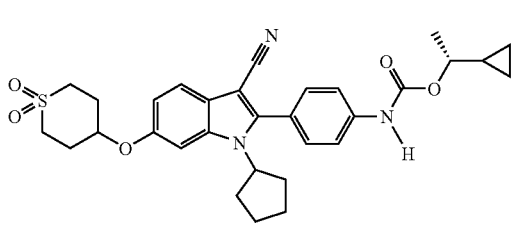 |
| 3246 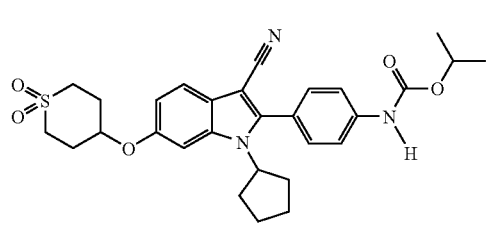 | 3247 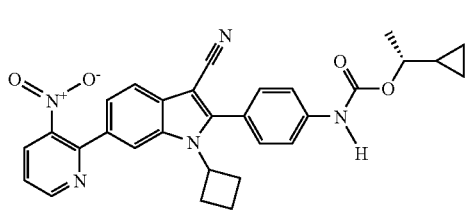 |
| 3248 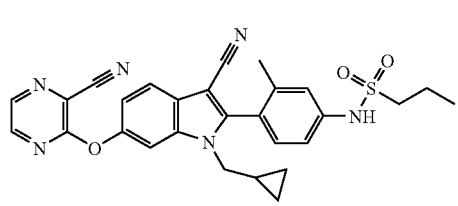 | 3249 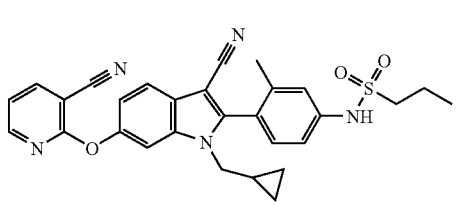 |
| 3250 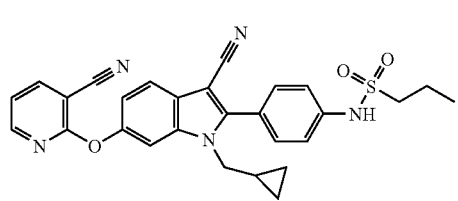 | 3251 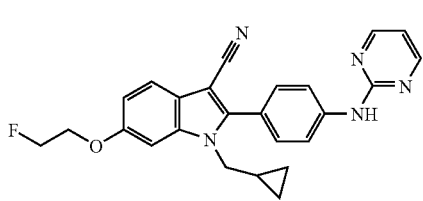 |

-continued
3252 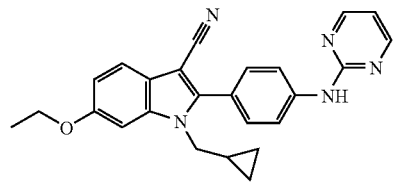 3253 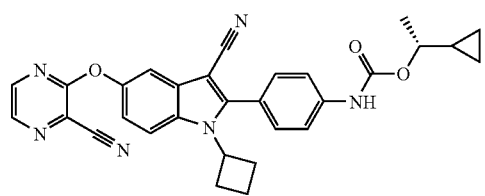
3254 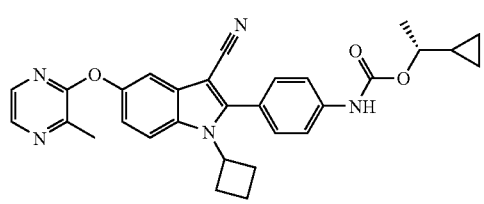 3255 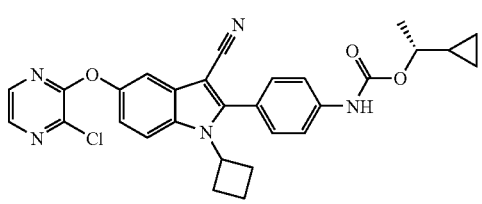
3256 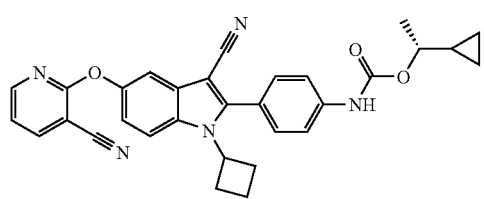 3257 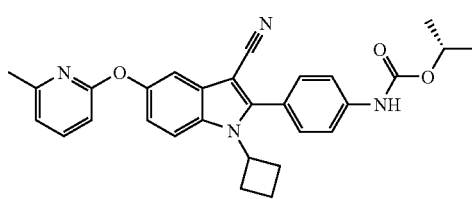
3258 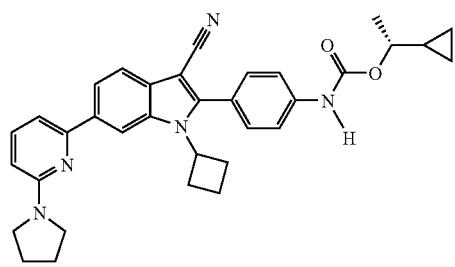 3259 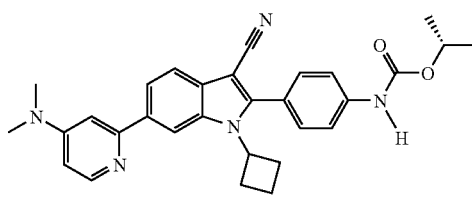
3260 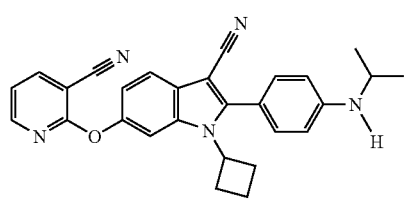 3261 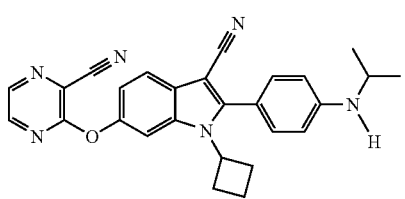
3262 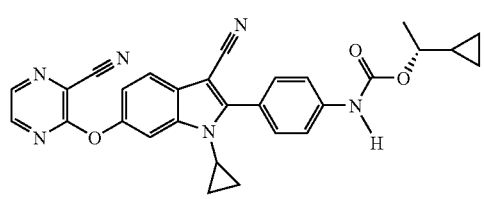 3263 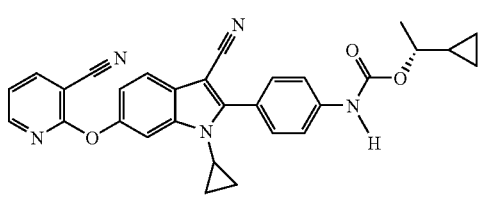
3264 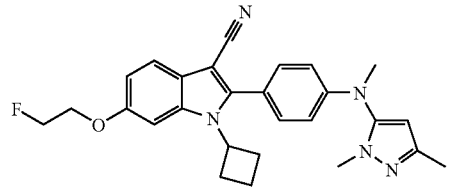 3265 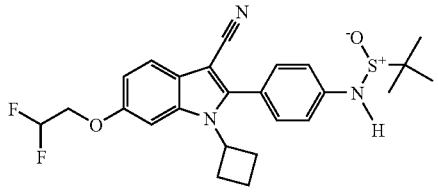

-continued
| 3266 | 3267 |
|---|---|
| 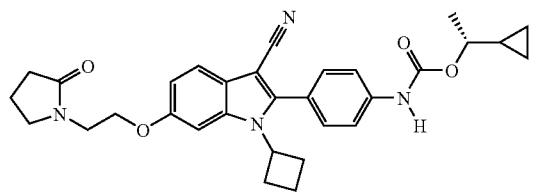 | 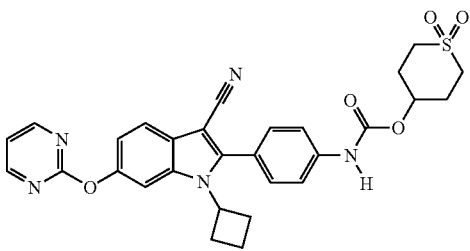 |
| 3268 | 3269 |
| 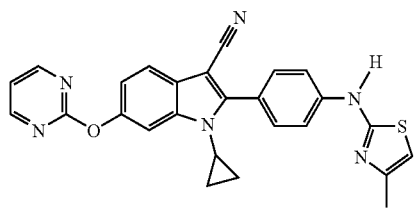 | 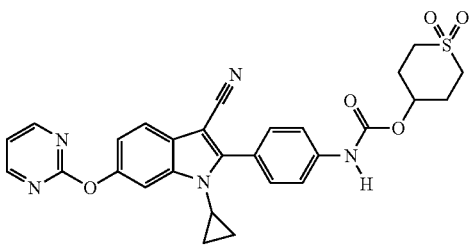 |
| 3270 | 3271 |
| 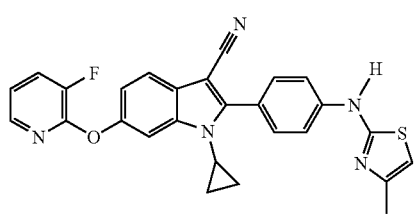 | 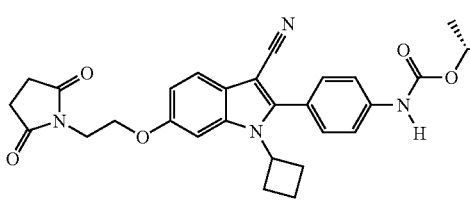 |
| 3272 | 3273 |
| 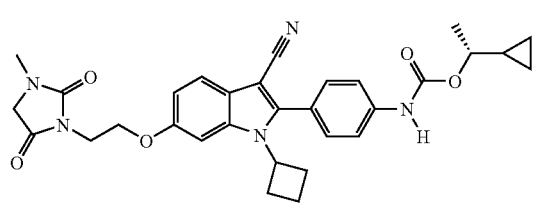 | 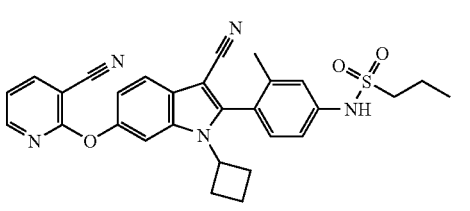 |
| 3274 | 3275 |
| 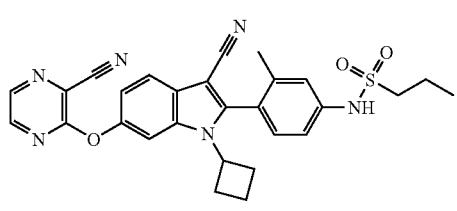 | 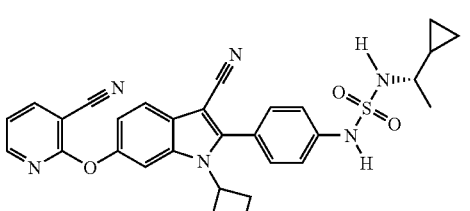 |
| 3276 | 3277 |
| 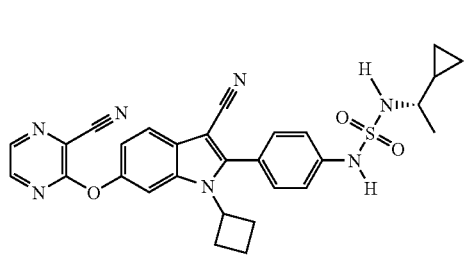 | 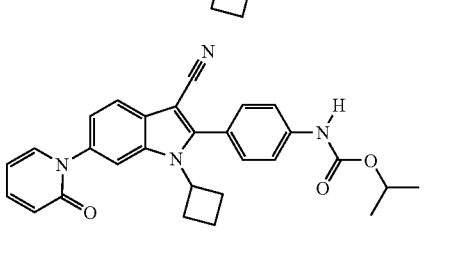 |
| 3278 | 3279 |
| 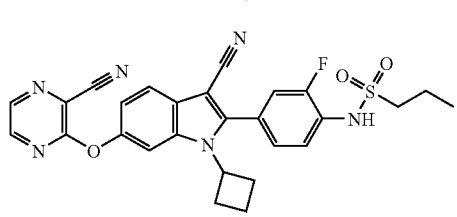 | 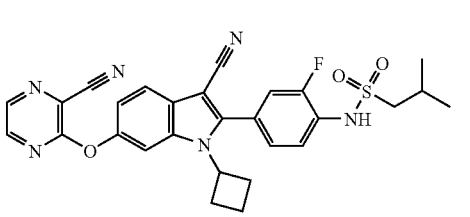 |

-continued
| 3280 | 3281 |
|---|---|
| 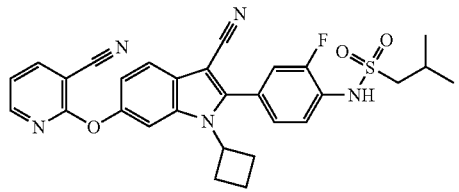 | 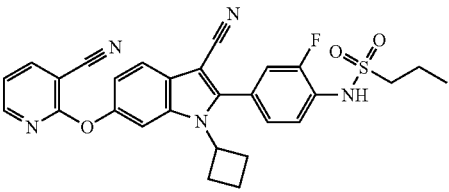 |
| 3282 | 3283 |
| 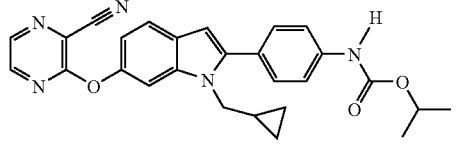 | 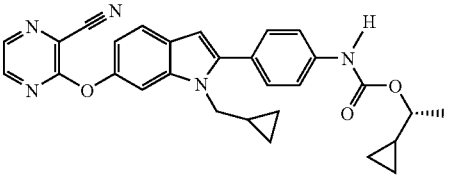 |
| 3284 | 3285 |
| 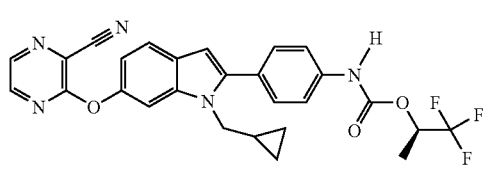 | 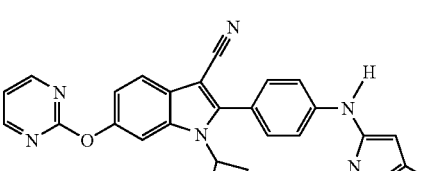 |
| 3286 | 3287 |
| 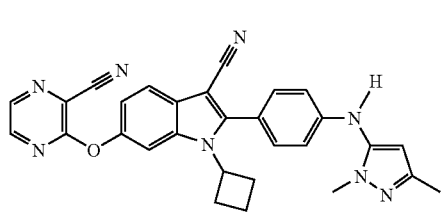 | 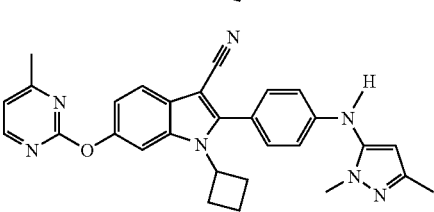 |
| 3288 | 3289 |
| 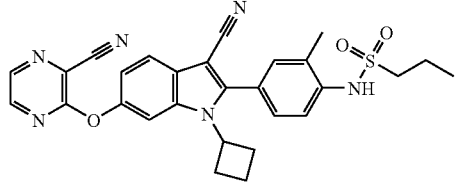 | |
| 3290 | 3291 |
| | 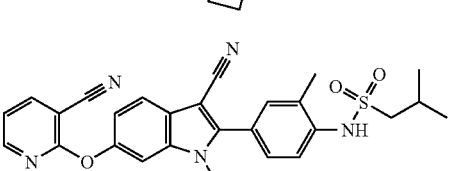 |
| 3292 | 3293 |
| 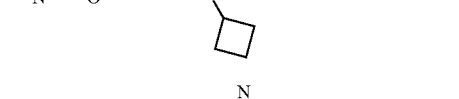 | |
| 3294 | 3295 |
| | 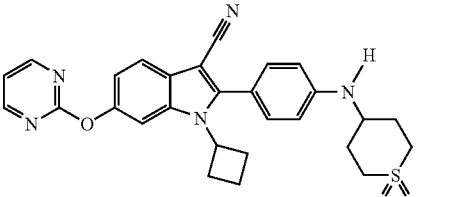 |
| 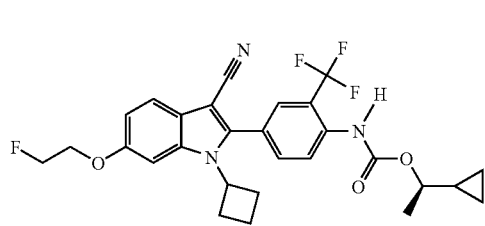 | |

-continued
3296
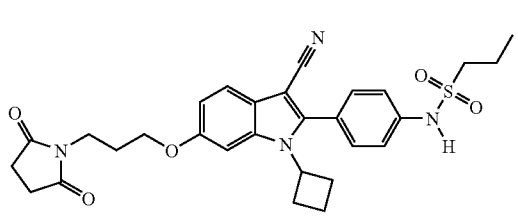
3297
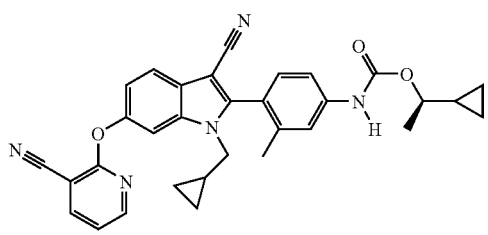
3298
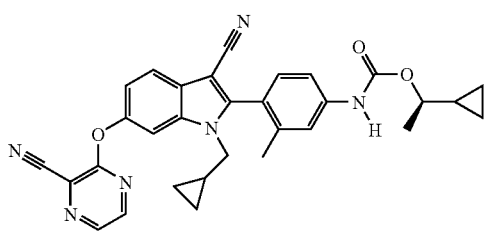
3299
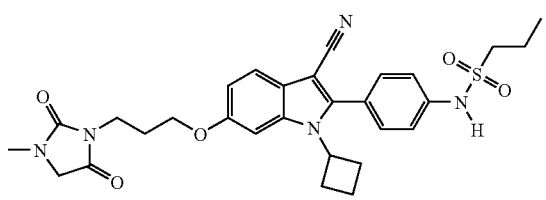
3300
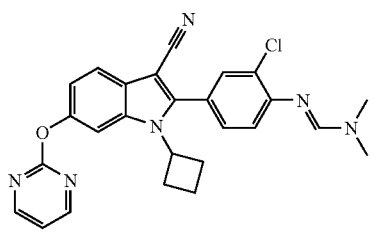
3301
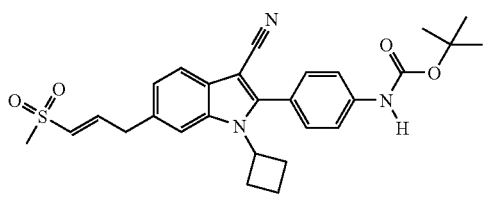
3302
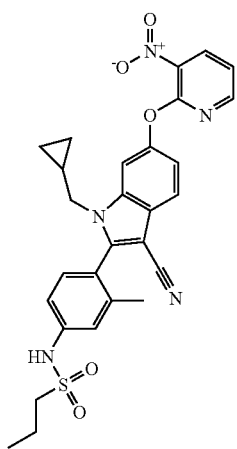
3303
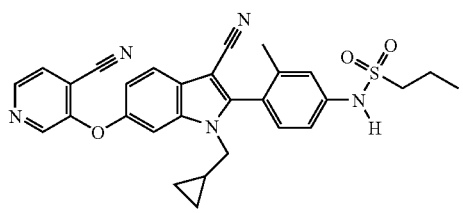
3304
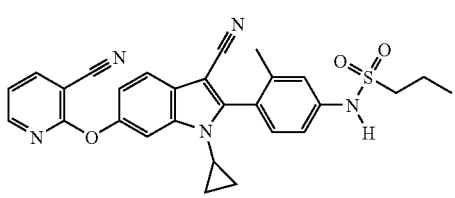
3305
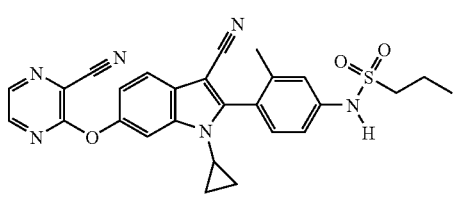
3306
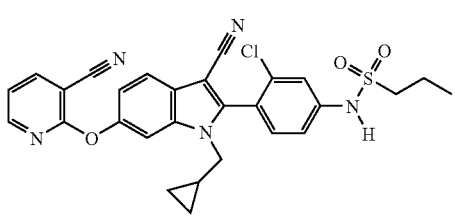
3307
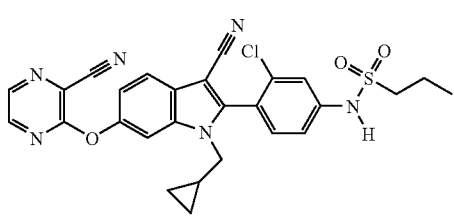

-continued
347
3308
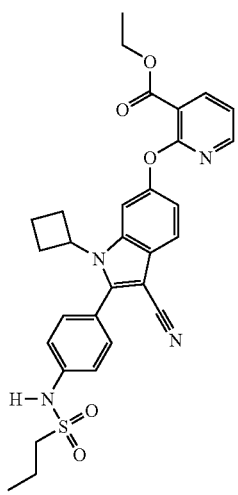
3309
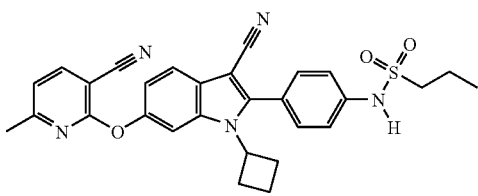
3310
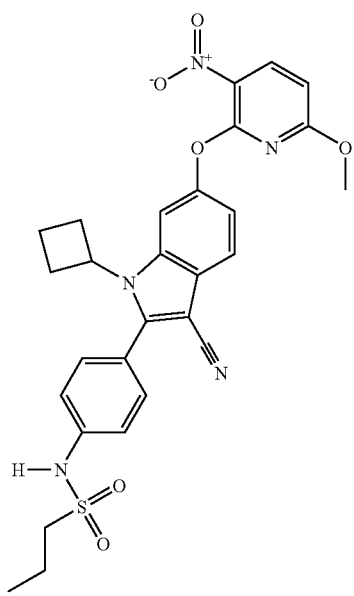
348
3311
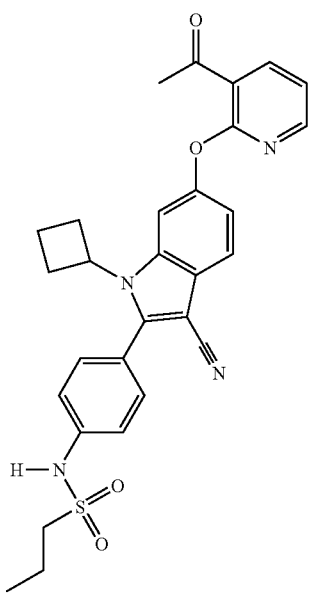
3312
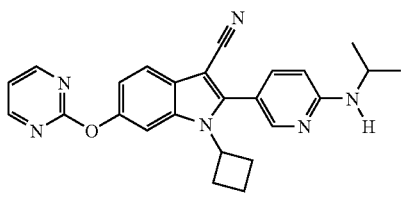
3313
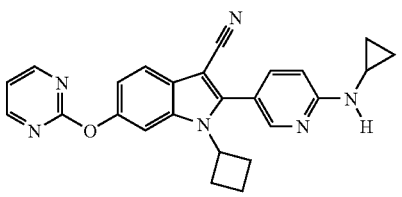
3314
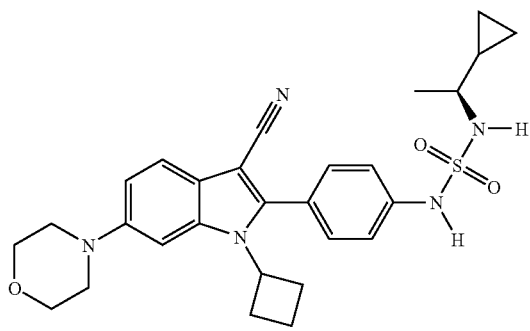
3315
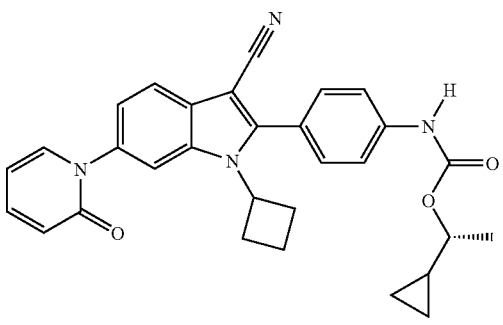

-continued
3316 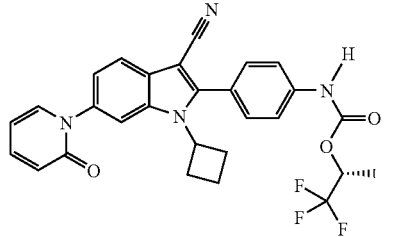 3317 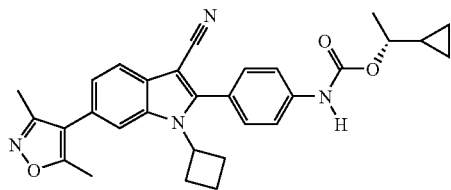
3318 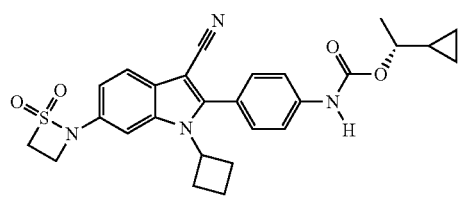 3319 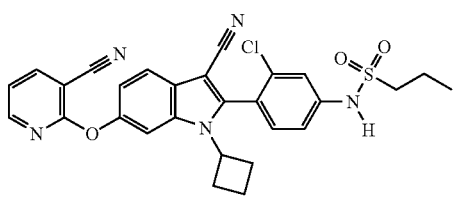
3320 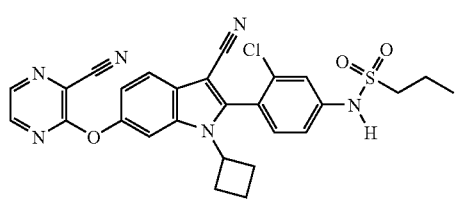 3321 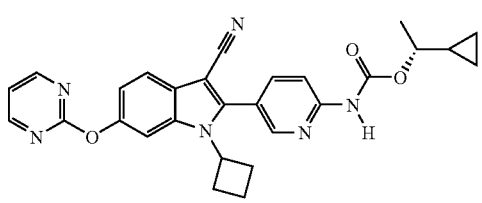
3322 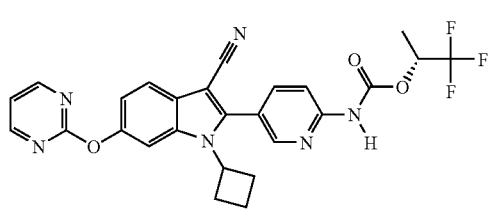 3323 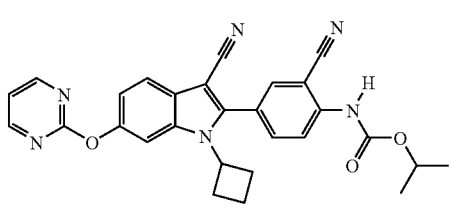
3324 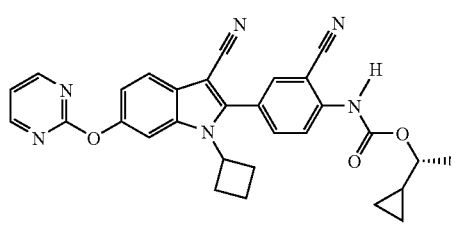 3325 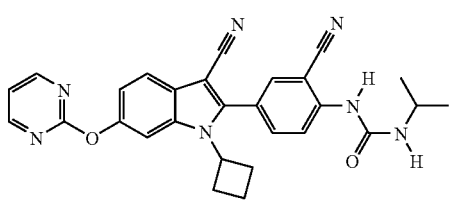
3326 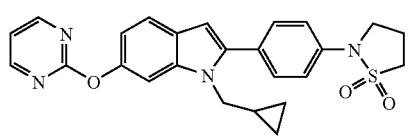 3327 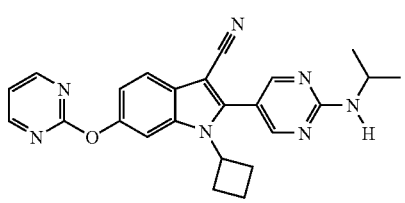
3328 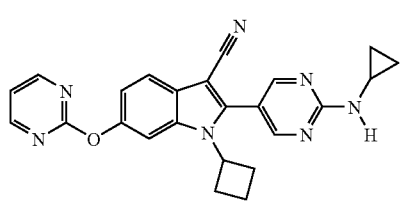 3329 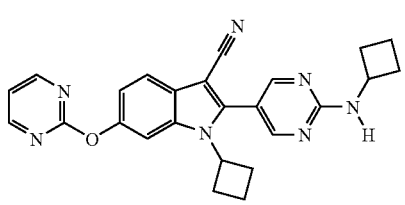

-continued
3330 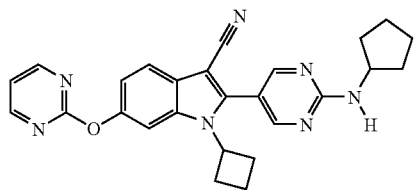
3331 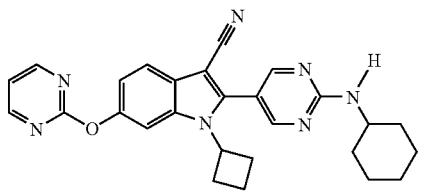
3332 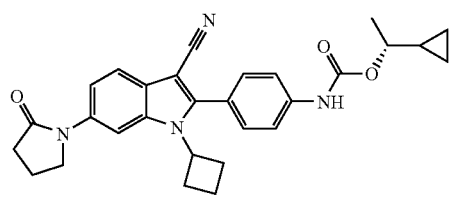
3333 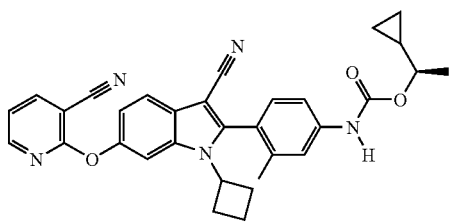
3334 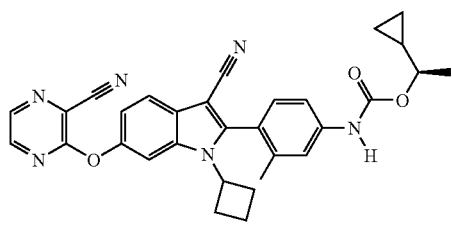
3335 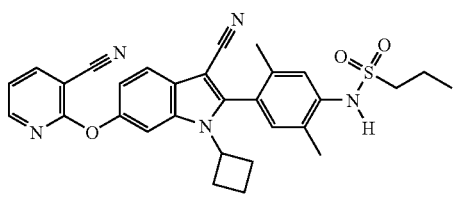
3336 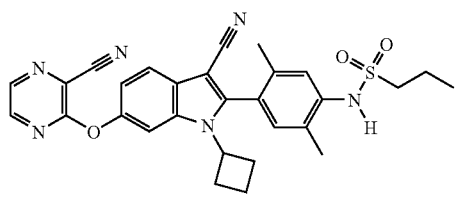
3337 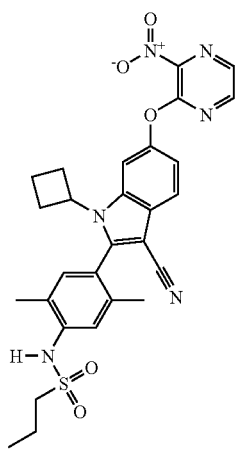
3338 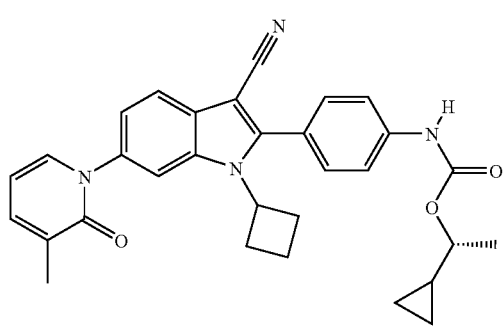
3339 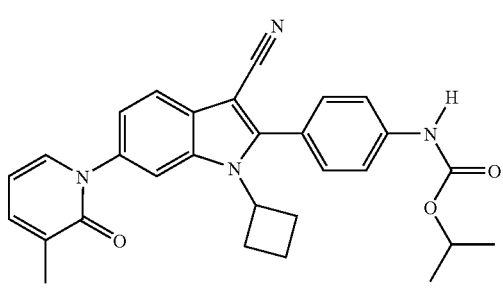

-continued
3340
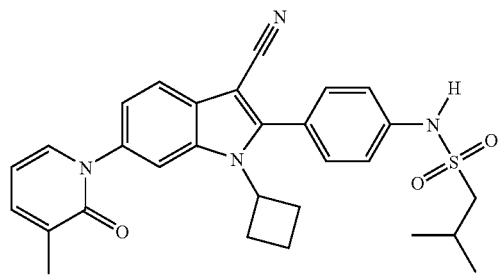
3341
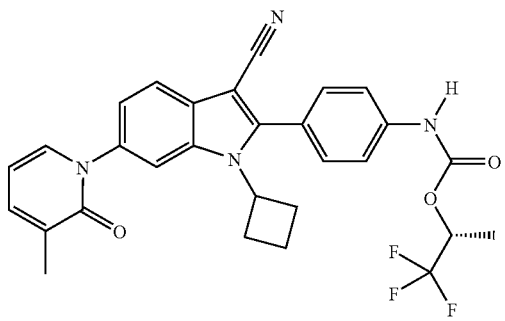
3342
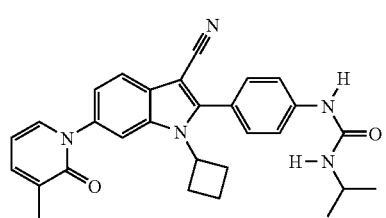
3343
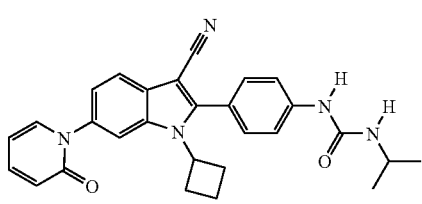
3344
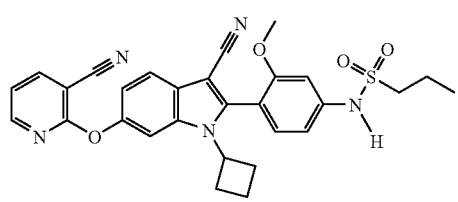
3345
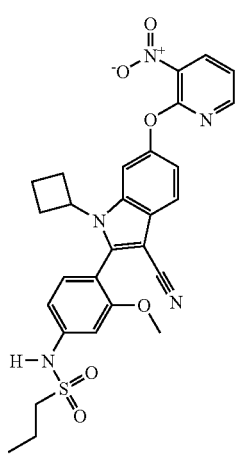
3346
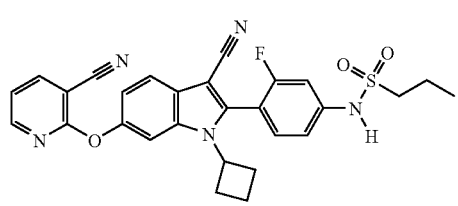
3347
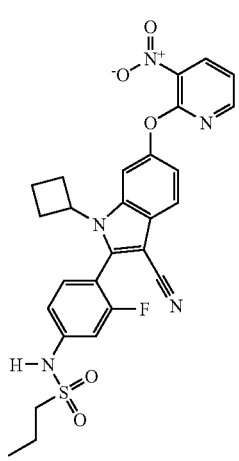
3348
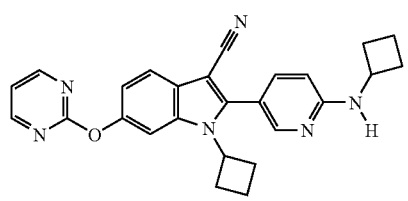
2150
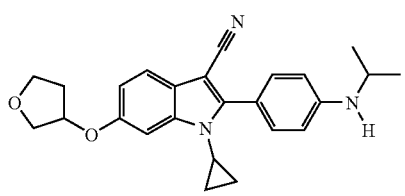

-continued
| | |
|---|---|
| 2186 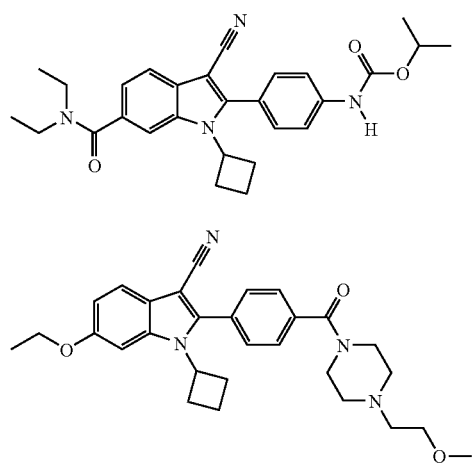 | 2194 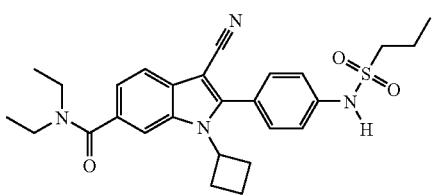 |
| 2249 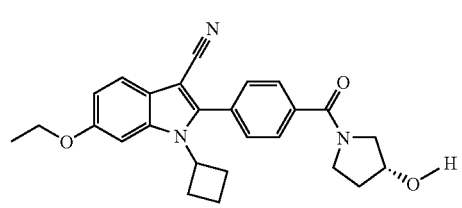 | 2250 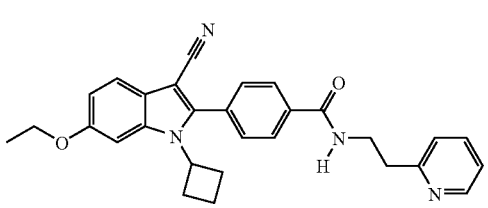 |
| 2251 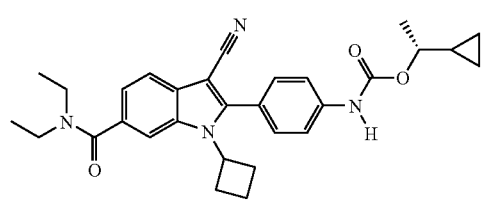 | 2271 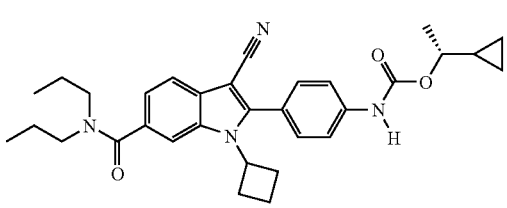 |
| 2272 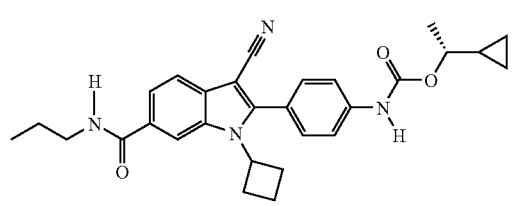 | 2273 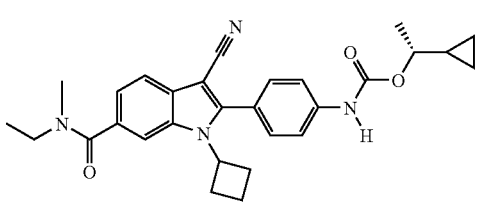 |
| 2274 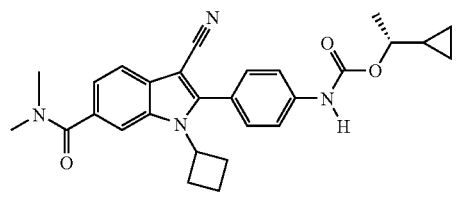 | 2275 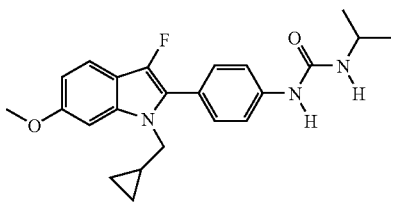 |
| 2276 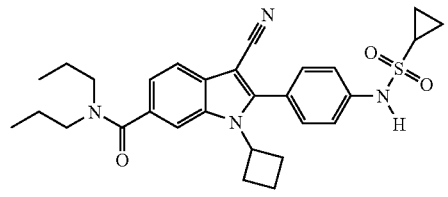 | 2277 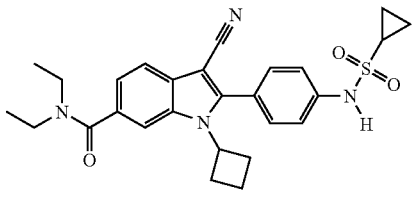 |
| 2293 | 2294 |

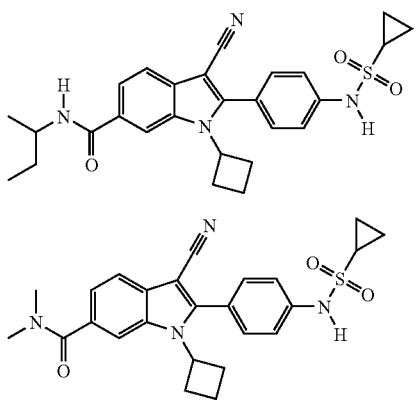
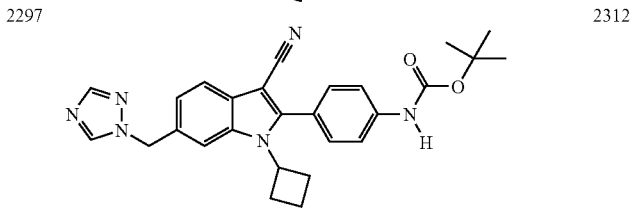

B. Preparation of Compounds of the Invention

Indole compounds of the present invention can be obtained via standard, well-known synthetic methodology. Many of the indole starting materials can be prepared the routes described below or by those skilled in the art.

Compounds of formula I, represented by structure II can be prepared by the methodology depicted in Scheme A below:

An α-nitroketone derivative A2 can be derived from treatment of the anion of nitromethane, obtained from the treatment of nitromethane with a base, such as, e.g., sodium or potassium t-butoxide or sodium hydride, with an activated carboxylic acid derivative, e.g., the acyl imidazolide A1. Reaction of the α-nitroketone A2 with amine derivative A3 can afford the nitro enamine A4 by mixing the components A3 and A4 and heating in a suitable solvent such as an alcohol or an aprotic solvent. Treatment of the nitro enamine A4 with quinone A5 in a polar protic solvent such as acetic acid at or near ambient temperature gives the compound of formula II.

I. Scheme A

Compounds of formula I, represented by structure II can be prepared as shown in Scheme A below:

Treatment of nitromethane with base followed by reaction with an activated carboxylic acid, e.g., an imidazolide, such as compound A1 gives compounds of type A2. Treatment of compounds of type A2 with an amine of structure A3 gives the compound A4. Reaction of compound A4 with quinine in the presence of acid, e.g., acetic acid gives the hydroxyindoles of structure II.

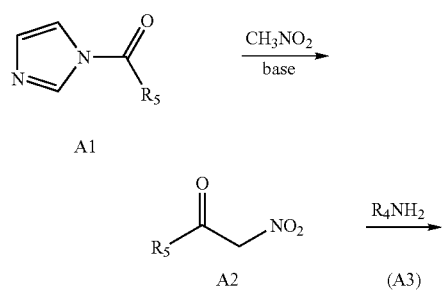

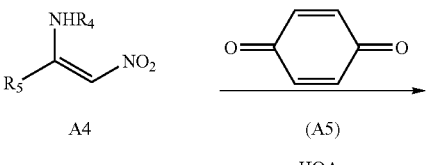

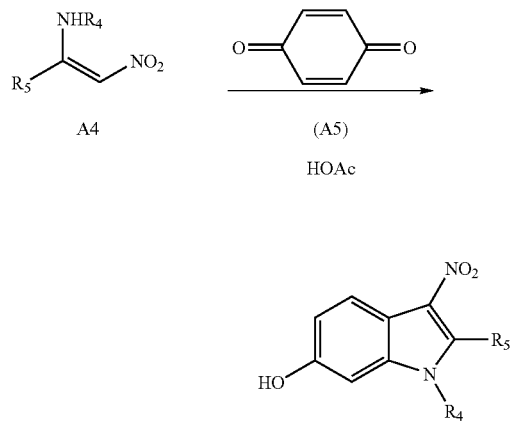

Compounds of formula I, represented by structure III can be prepared as shown in Scheme B below:

Treatment of B1 with a reactive alkyl or aryl group containing a leaving group L in a suitable solvent, with or without heat in the presence of a base, such an inorganic base, e.g., sodium or potassium carbonate or an organic base, e.g., triethylamine, can afford the compound of structure III. Examples of leaving groups include but are not limited to halogens (e.g., chlorine, bromine or iodine) or alkyl or arylsulfonates.

II. Scheme B

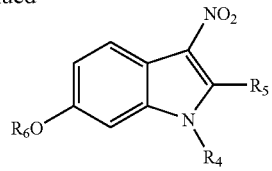

III

Compounds of formula I, represented by structure IV can be prepared as shown in Scheme C below:

Compounds of structure IV can be obtained by nitrating an indole of structure C1, to give the 3-nitroindole C2. The nitration can be carried out by treatment of C1 with a nitrating agent, such as nitric acid or sodium nitrite in a solvent such as acetic acid, acetic anhydride, sulfuric acid or in a mixed solvent system containing an organic solvent such as dichloromethane. The reaction can be carried out a temperature of −30° C. to +50° C. Treatment of C2 with a reactive functional group $R_9$ containing a suitable leaving group L (C3) can give compounds of structure IV. Reactive functional groups can consist of but are not limited to alkyl and aralkyl. L can represent a halide, particularly chloro, bromo or iodo or an alkylsulfonate. The reaction between C2 and C3 can be carried out in a suitable solvent in the presence of an inorganic base such as potassium carbonate or sodium hydride or an organic base such as a trialkylamine. Alternatively, the group $R_9$ can represent an aryl or heteroaryl group and L can represent a halide, particularly chloro, bromo or iodo. The reaction can be carried out in a polar or nonpolar solvent at a temperature from ambient to 200° C. in the presence of a copper catalyst, e.g., CuI, a base such as $Cs_2CO_3$ or $K_3PO_4$, and optionally an amine ligand such as 1,2-bis(methylamino)ethane or 1,2-cyclohexanediamine.

An alternative pathway is to convert C1 into C4 in similar fashion as described above and then carry out the nitration reaction to afford compounds of structure IV.

III. Scheme C

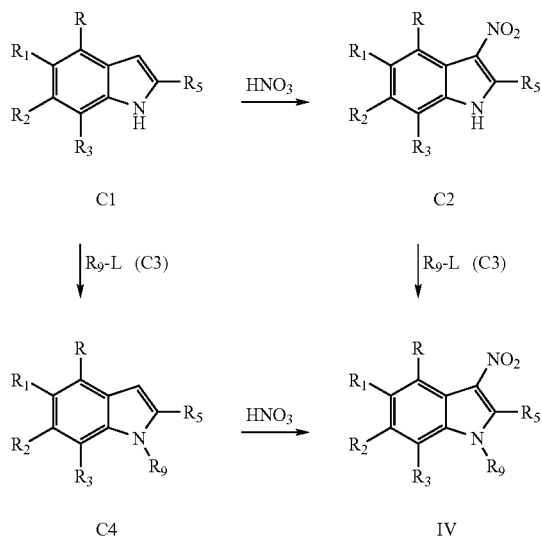

Compounds of formula I, represented by structure V can be prepared as shown in Scheme D.

Treatment of β-ketoesters of structure D1 with amines D2 gives the amino crotonate derivatives D3 by heating in a suitable solvent such as an alcohol or an aprotic solvent. Reaction between D3 and quinone D4 in a polar protic solvent, such as acetic acid gives compounds of structure V.

IV. Scheme D

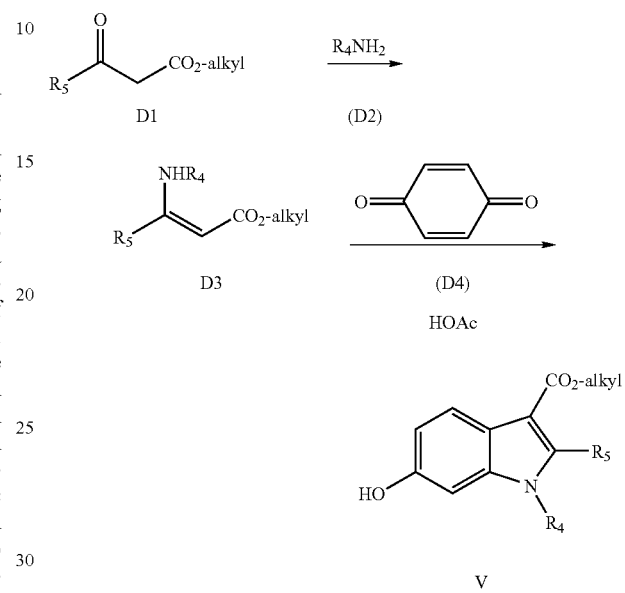

Compounds of the present invention, represented by structure VI compounds can be prepared by the chemistry described in scheme E below.

Indole-3-carboxylic esters E1 can be converted to indole-3-carboxylic acids E2 by treatment of compounds of structure E1 with, for example, either acid or base in aqueous or mixed aqueous-organic solvents at ambient or elevated temperature or by treatment with nucleophilic agents, for example, boron tribromide or trimethylsilyl iodide, in a suitable solvent. Compounds of type E2 can then be activated and treated with amines of type E3 to give compounds E4. Activation of the carboxylic acid can be carried out, for example, by any of the standard methods. For example, the acid E2 can be activated with coupling reagents such as EDCI or DCC with or without HOBt in the presence of the amine E3, or alternatively the acid can be activated as the acid chloride by treatment of the acid with, e.g., thionyl chloride or oxalyl chloride or as the acyl imidazolide, obtained by treatment of the acid with carbonyl diimidazole, followed by treatment of the amine E3. Compounds E4 can be converted to compounds of structure VI by treatment of E4 with a reactive functional group $R_9$ containing a suitable leaving group L (E5) as described previously. Alternatively, compounds of type E1 can be converted to compounds of structure E6 by treatment with E5. Indole-3-carboxylic esters E6 can then be converted to indole-3-carboxylic acids E7 by the methods described above. Conversion of E7 to compounds of structure VI can be carried out by the activation and reaction with an amine E3 as described above.

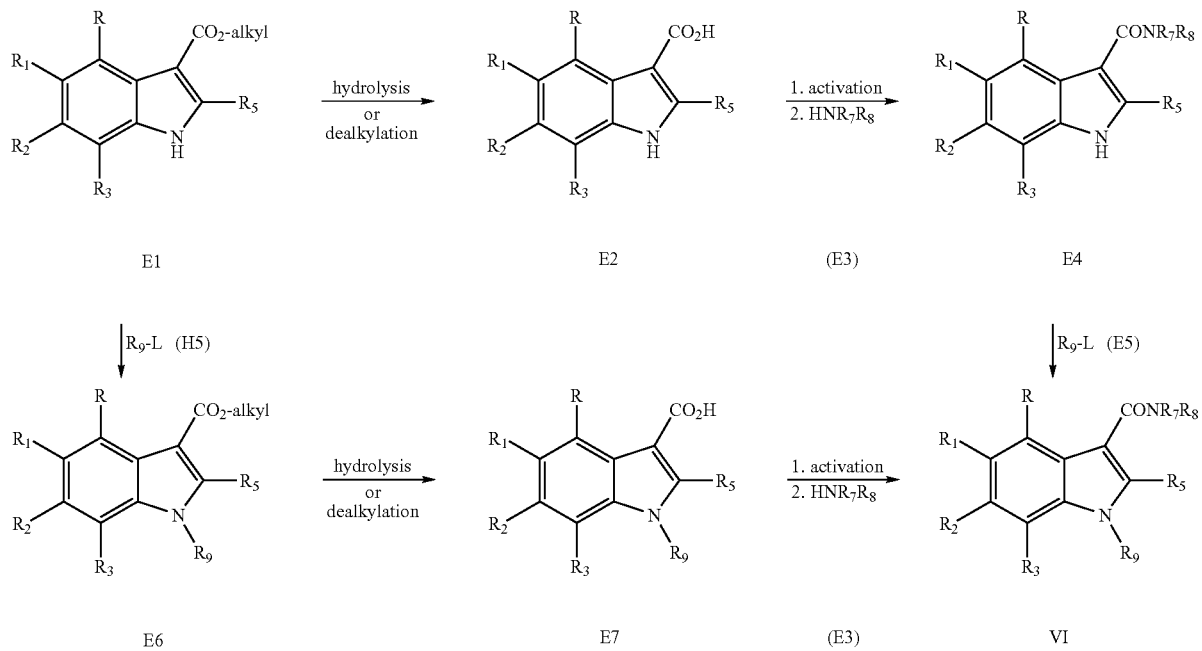

Compounds of the present invention, represented by structure VII compounds can be prepared by the chemistry described in scheme F below.

Indoles F1 can be formylated with reagents such as phosphorous oxychloride in the presence of DMF to give the indole-3-carboxaldehydes F2. Conversion to compounds of structure VII can be accomplished by treatment of F2 with compounds F3 as described previously. Alternatively, compounds of type F1 can first be converted to F4 and then be formylated to compounds of structure VII.

Compounds of formula G, represented by structure VIII can be prepared as shown in Scheme G.

Indole-3-carboxaldehydes of structure G1 can be converted to the indole-3-carboxylic acid derivatives by oxidation with reagents such as potassium permanganate under aqueous conditions.

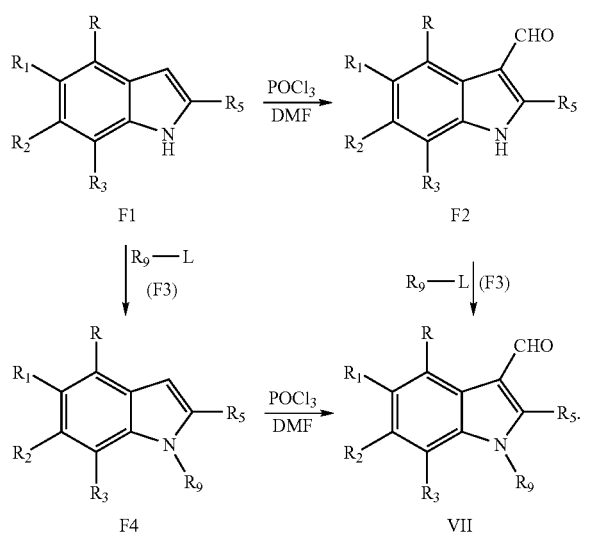

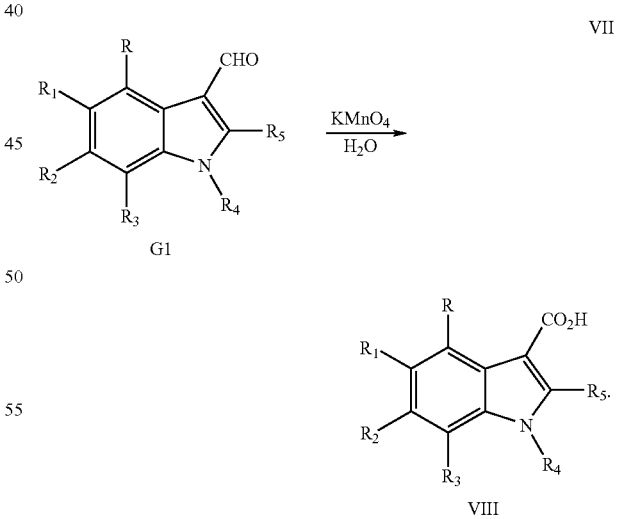

Compounds of formula H, represented by structure IX can be prepared as shown in Scheme H.

Indole-3-carboxaldehydes of structure H1 can be converted to the indole-3-carbonitrile derivatives H2 by a variety of methods. Treatment of H1 with a nitroalkane, e.g., nitropropane, in the presence of an amine source, e.g., ammonium hydrogen phosphate gives the indole-3-carbonitrile H2 derivative. An alternative pathway to compound H2 is via the intermediate H3. Conversion of H1 to the oxime derivative H3 can be followed by dehydration, e.g., treatment of the oxime with acetic anhydride and a base, or reaction of the oxime with thionyl chloride to give H2. The compound H2 can then be reacted with a reactive functional group $R_9$ containing a suitable leaving group L (H4) as described previously to afford compounds of structure IX.

Alternatively, H1 can be reacted with a reactive functional group $R_9$ containing a suitable leaving group L (H4) to give the intermediate H5, which can be reacted with a nitroalkane as above to give the indole-3-carbonitrile IX compound. Compound IX can also be obtained by conversion to the oxime H6 followed by a dehydration reaction as described above.

Compounds of the present invention, represented by structure X can also be prepared as described in scheme I below.

Indoles I1 can be cyanated with an appropriate cyanating agent, e.g., chlorosulfonyl isocyanate (I2) or a dialkyl phosphoryl isocyanate in a suitable solvent or solvent mixture, e.g. DMF, $CH_3CN$ or dioxane, to afford compounds of structure I3. The compound I3 can then be reacted with a reactive functional group $R_9$ containing a suitable leaving group L (I4) as described previously afford the compound X.

Alternatively, compound I1 can be reacted with a reactive functional group $R_9$ containing a suitable leaving group L to give compounds of structure I5 that can then be cyanated as above to give compounds of formula X.

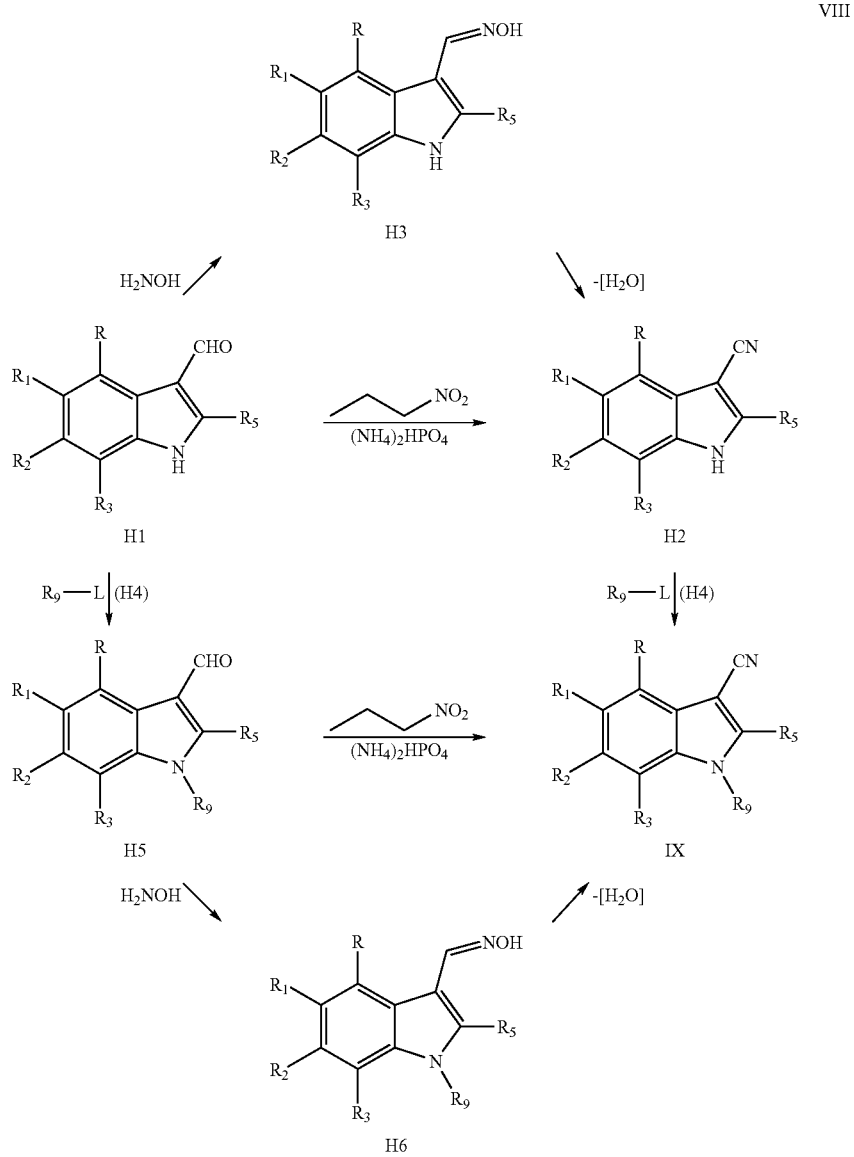

Scheme H

VIII

Scheme I

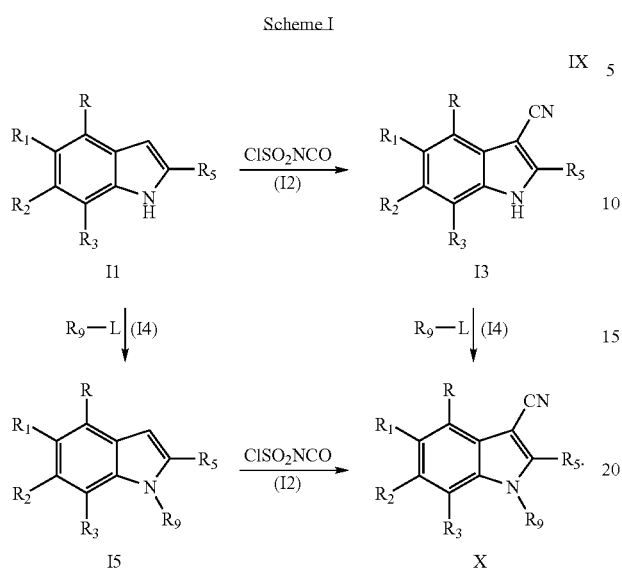

Compounds of formula J, represented by structure XI can be prepared as shown in Scheme J.

Amino crotonates J1 can be reacted with amines J2 to give J3. Reaction of J3 with quinone in the presence of a polar, protic solvent, e.g., acetic acid, gives the compound of structure XI.

Scheme J

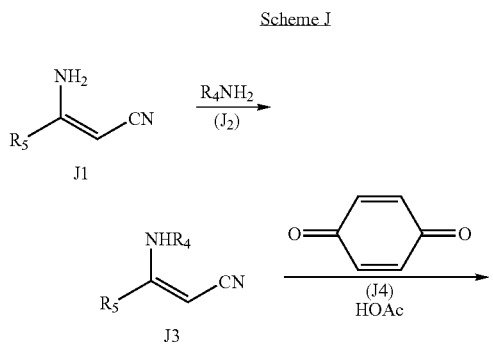

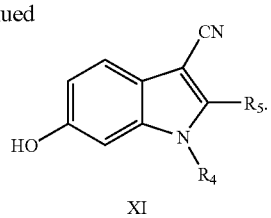

Compounds of the present invention, represented by structure XII and XIII can be prepared as described in scheme K below.

Aldehydes of structure K1 can be reacted with an alkyl azidoacetate K2 by heating the components together in a suitable organic solvent, e.g., a protic or non-protic solvent, in the presence of an organic or inorganic base, to give the α-azidoacrylate K3. Heating K3 in the presence of a suitable non-reactive organic solvent, e.g., toluene or xylenes can give the 2-alkoxycarbonylindoles K4. Reduction of the ester functionality with a suitable reducing reagent, for example, lithium aluminum hydride, in a suitable solvent, e.g., ether or THF can give the intermediate K5. Reaction of K5 with a reactive functional group $R_9$ containing a suitable leaving group L (K6) as described in previously affords the compound K7. Cyanation of K7 with a cyanating agent, e.g., chlorosulfonyl isocyanate as described previously can give compound XII. Alternatively, cyanation of K5 with chlorosulfonyl isocyanate gives K8, which can be reacted with a reactive functional group $R_9$ containing a suitable leaving group L (K6) as described previously, affords, the compound XII.

An alternative use of intermediate K4 is exemplified below. Hydrolysis of the 2-alkoxycarbonyl group of the indole K4 either under acidic or basic conditions followed by decarboxylation can give the intermediate K9. Decarboxylation can be carried out thermally, i.e., heating in an appropriate solvent, e.g., toluene, xylenes, or quinoline. Alternatively, a source of copper can be added, for example, copper bronze, to facilitate decarboxylation. Reaction of K9 with a reactive functional group $R_9$ containing a suitable leaving group L (K6) as described above can afford the compounds K10. Cyanation of K10 with a cyanating agent, e.g., chlorosulfonyl isocyanate as described previously can give compound XIII. Alternatively, cyanation of K9 with chlorosulfonyl isocyanate gives K11, which can be reacted with a reactive functional group $R_9$ containing a suitable leaving group L (K6) as described in previously, affords the compound XIII.

Scheme K

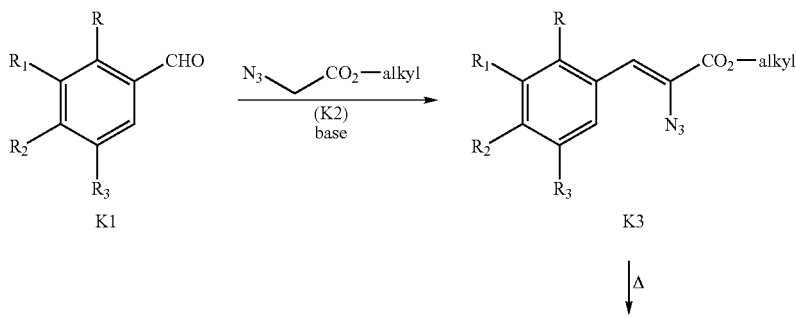

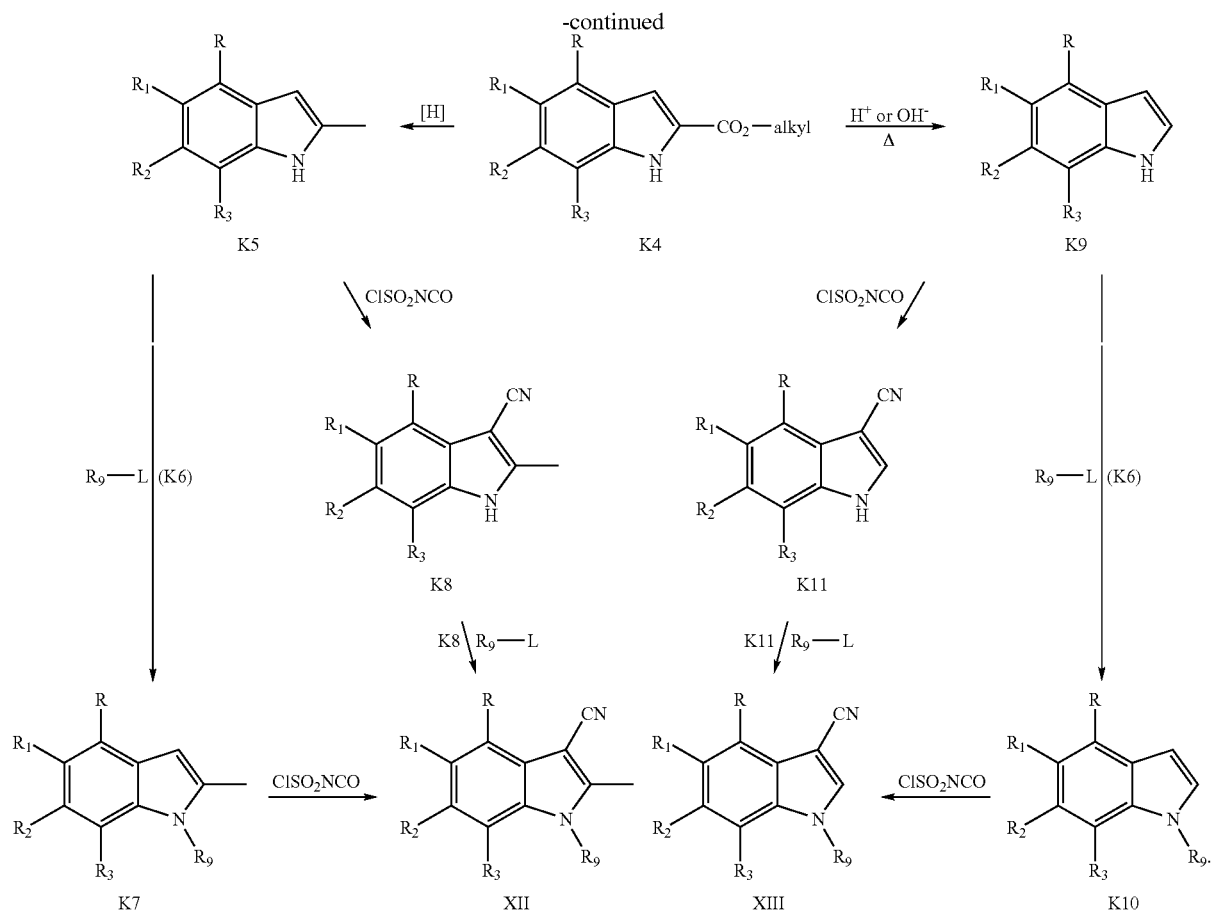

Compounds of formula L, represented by structure XIV can be prepared as shown in Scheme L.

Compounds of formula L1 can be halogenated on the 2-methyl group to give 2-bromomethyl or chloromethyl indoles L2. The halogenation reaction can be conducted with reagents, e.g., N-bromo- or chlorosuccinimide. The reaction can be conducted in a suitable solvent, such as chloroform, carbon tetrachloride, or THF and carried out in a range between ambient temperature and 80° C. Optionally, a radical initiator may be added, e.g., benzoyl peroxide or AIBN. The compound L2 can then be reacted with a nucleophile $R_5$—W (L3) to give compounds of structure XIV. The reaction can be conducted in a suitable solvent, e.g., THF, $CH_2Cl_2$ or DMF, within a temperature range of 0° C. to 120° C. A base, e.g., an inorganic base, such as potassium carbonate or an organic base, such as a trialkylamine can be used to remove the acid formed in the reaction. The group W can refer to an N, O or S atom.

Scheme L

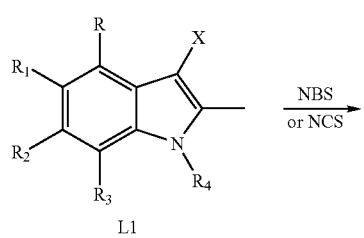

XII

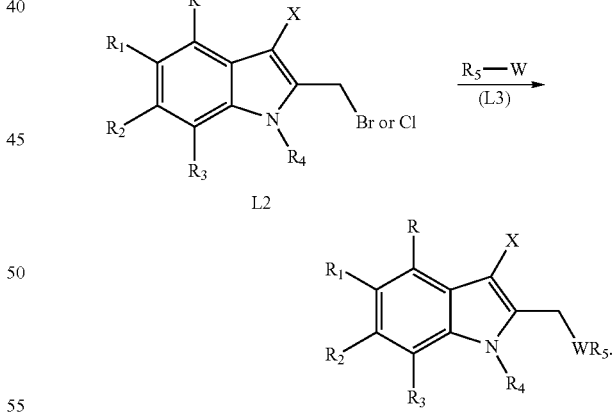

Compounds of the present invention, represented by structure XV can be prepared as described in scheme M below.

Anilines of structure M1 can be diazotized and the resulting diazonium salt can be reduced to give the phenyl hydrazine compound M2. Reaction between the hydrazine M2 and a ketone M3 under acidic conditions can give the indole compound M4. The conditions for the cyclization reaction can be carried out under typical conditions utilized by one skilled in the art, for example, acidic conditions, utilizing acids such as a Bronstead acid, e.g., acetic acid, hydrochloric acid or polyphosphoric acid or a Lewis acid, e.g., zinc chloride. The reaction can be carried out in the presence of a co-solvent, e.g., $CH_2Cl_2$ or THF typically within a temperature range of 0° C. to 120° C. Reaction of M4 with a reactive functional group $R_9$ containing a suitable leaving group L (M5) as described previously, can afford compounds M6. Cyanation of the indole M6 with a cyanating agent such as chlorosulfonyl isocyanate can give the compound of structure XV.

Alternatively, the indoles M4 can be cyanated to give compounds of structure M7. Reaction of M7 with a reactive functional group $R_9$ containing a suitable leaving group L (M5) as described above can give compounds of structure XV.

the nitro group of compounds of type N3 under standard conditions can give the indole compounds of structure N4. The reduction can be carried out via hydrogenation, using a sub-stoichiometric amount of a hydrogenation catalyst, e.g., platinum or palladium, in the presence of a hydrogen source in a protic or aprotic solvent. The reduction can be carried out in a temperature range of ambient to 80° C. Alternatively, the reduction can be carried out via chemical reduction, e.g., in the presence of stoichiometric amounts of Fe or Sn compounds in a suitable solvent at a temperature range of ambient to 100° C. The compound N4 can then be reacted with a reactive functional group $R_9$ containing a suitable leaving group L (N5) as described previously to afford compounds of structure N6. Cyanation of N6 with a cyanating agent such as

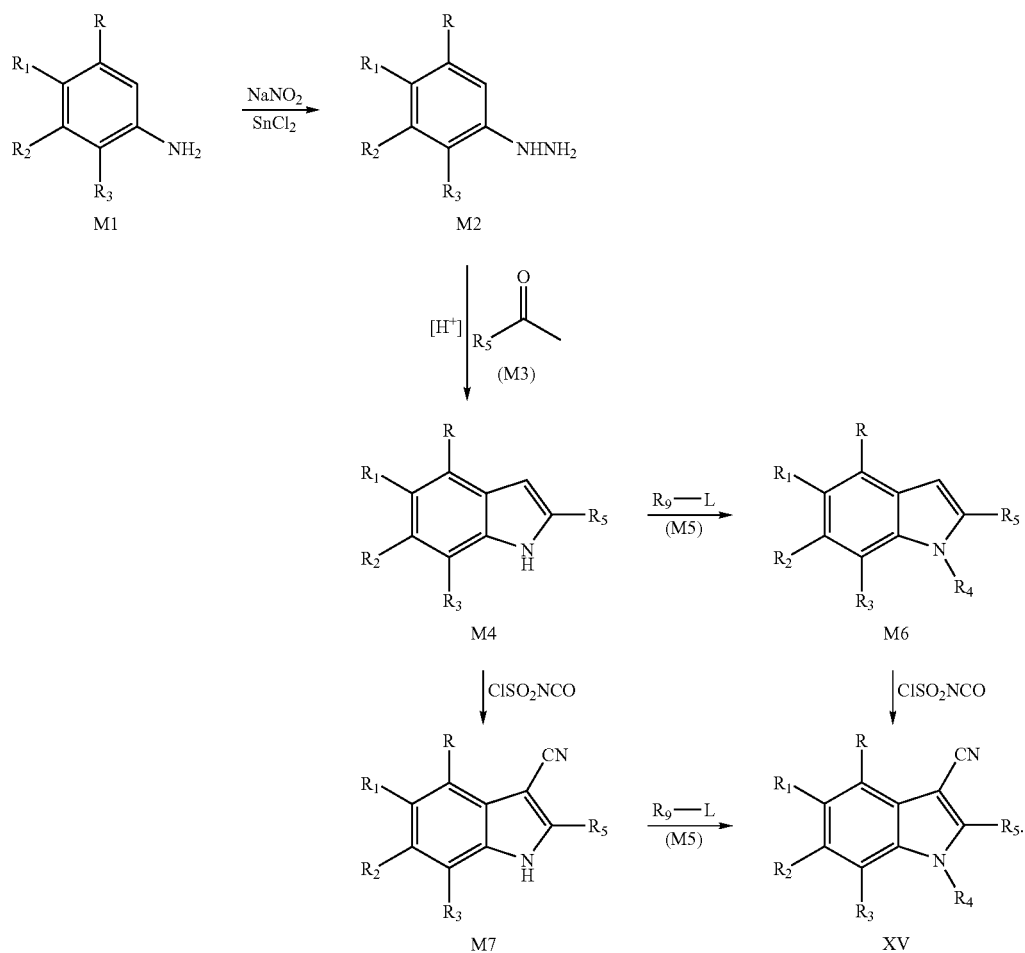

Compounds of formula I, represented by structure XVI can be prepared as shown in Scheme N.

Compounds of formula N1 can be reacted with a dialkylformamide dialkyl acetal, N2, e.g., dimethylformamide dimethyl acetal, optionally in the presence of a suitable solvent, e.g., DMF or dioxane, at a temperature range from ambient to 150° C. to give the compound of structure N3. Reduction of chlorosulfonyl isocyanate in a suitable solvent can give the compounds of structure XVI.

Alternatively, compounds of structure N4 can be cyanated to give compounds of structure N7. Reaction with N7 with a reactive functional group $R_9$ containing a suitable leaving group L (N5) as described above can give compounds of structure XVI.

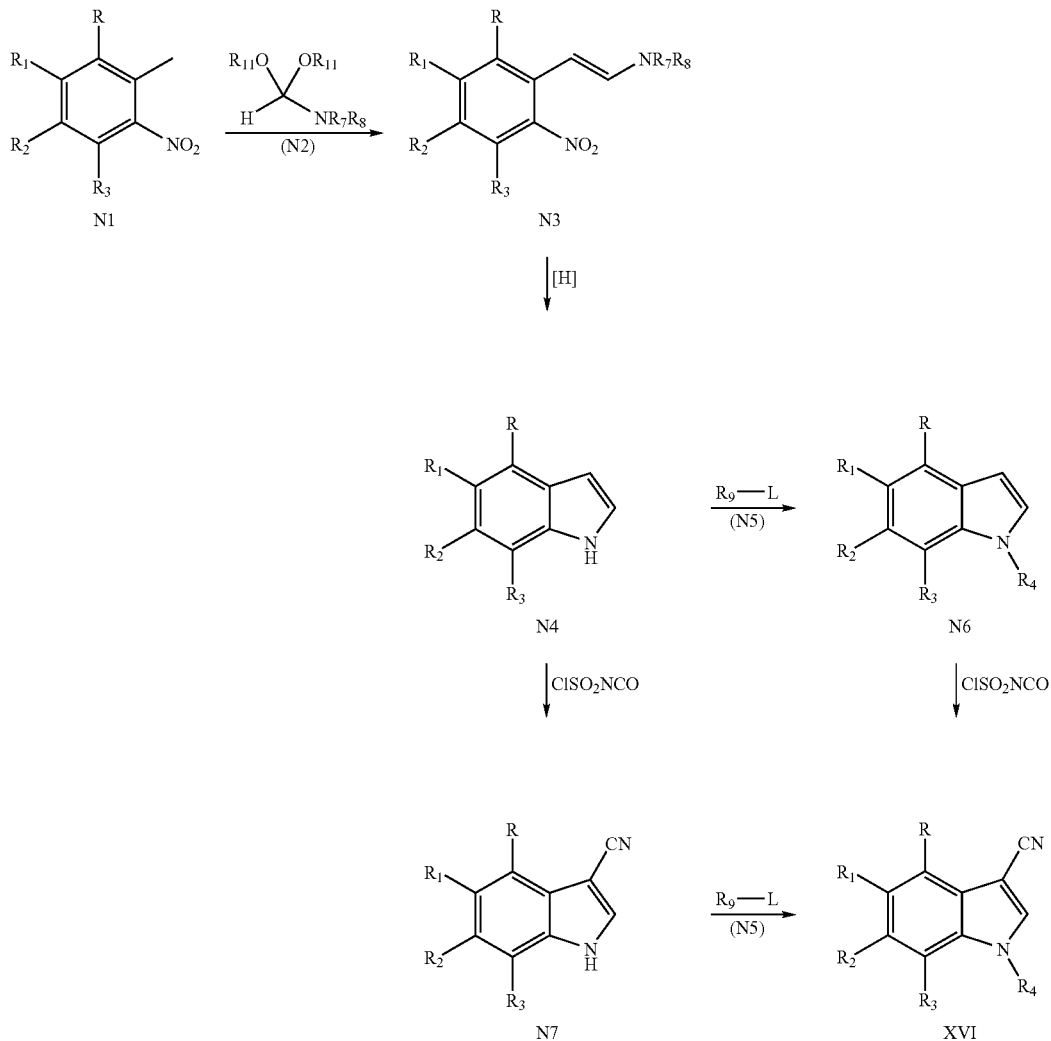

Compounds of formula I, represented by structure XVII can be prepared as shown in Scheme O.

Compounds of structure O1 can be converted to 2-iodo- or bromoindoles O2. Typically, a strong base, such as n-butyllithium or s-butyllithium or lithium diisopropylamide or lithium or potassium hexamethyldisilazide is employed, with formation of the 2-indolyl anion generated in a suitable unreactive solvent, e.g., ether or THF, or solvent mixtures containing them. The reaction is typically carried out in the range of −78° C. to ambient temperature. The 2-indolyl anion can then be quenched with an electrophilic source of halogen, including but not limited to iodine, bromine or N-bromosuccinimide to give compounds of structure O2. Reaction of 2-iodo- or bromoindoles O2 with a boronic acid (commonly referred to as a Suzuki reaction) or trialkyl stannane (commonly referred to as a Stille reaction) can give the compounds of structure XVII. The coupling reactions are carried out by methods known to those skilled in the art and include conducting the reaction in the presence of a catalyst, such as tetrakis(triphenylphosphine)palladium (0), bis(triphenylphosphine)palladium (II) dichloride or palladium acetate with added phosphine ligand. The reactions are carried out in a suitable solvent, e.g., DMF, toluene, dimethoxy ethane or dioxane at a temperature range of ambient to 150° C. For the Suzuki reaction, a base is usually added. The base can be in aqueous solution, e.g., aqueous sodium carbonate or sodium bicarbonate, or the base can be employed under anhydrous conditions, e.g., cesium or potassium fluoride. For the Stille reaction a copper co-catalyst, e.g., copper iodide, can be added.

Alternatively, indoles O1 can be converted to the indole-2-boronic acid or indole-2-trialkylstannane derivatives O3 by reacting the 2-indolyl anion described above with a trialkylborate or chlorotrialkyl stannane derivative, respectively. Compounds of type O3 can be reacted with aryl and heteroaryl bromides and iodides under similar conditions to those described above to form compounds of structure XVII.

Scheme O

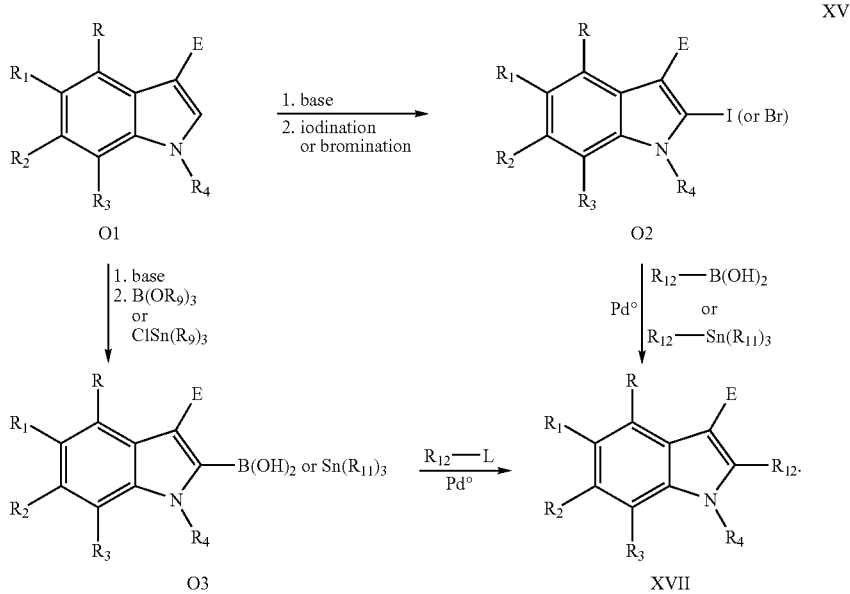

Compounds of formula I, represented by structure XVIII can be prepared as shown in Scheme P.

Compounds of structure P1 can be converted to compounds P3 by treatment of P1 with an aryl or heteroaryl halide (P2) in the presence of organometallic catalysis. Such catalyst combinations can include palladium catalysts, e.g., palladium acetate and a source of copper, e.g., copper iodide. The reaction can be carried out in the presence of a base, e.g., cesium carbonate. The reaction can be carried out within a temperature range of ambient temperature to 150° C.

Scheme P

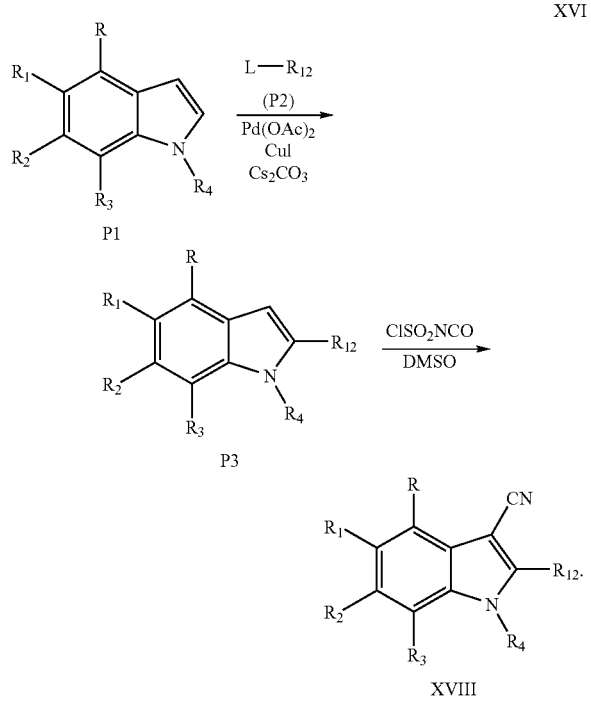

Compounds of the present invention, represented by structure XIX can be prepared as described in scheme Q below.

Compounds of structure XIX can be prepared by protecting an indole compound of structure Q1 as e.g., the N-Boc derivative Q2. Alternatively, other protecting groups that can be utilized but not limited to include, e.g., benzyl, alkyl or aryl sulfonyl, or trialkyl silyl. Treatment of Q2 with a strong base, e.g., lithium diisopropyl amide in an aprotic solvent, e.g., THF followed by quenching with a trialkylborate derivative can give the indolyl-2-boronic acid Q3. Reaction with an aryl or heteroaryl halide Q4 in the presence of palladium catalysis, e.g., tetrakis(triphenylphosphine)palladium (0), bis(triphenylphosphine)palladium (II) dichloride or palladium acetate with added phosphine ligand, can give the compound Q5. Removal of the protecting group can give Q6. Reaction with Q6 with a reactive functional group $R_9$ containing a suitable leaving group L as described above can give compounds of structure Q7. Cyanation of compound Q7 can give the compounds of structure XIX.

Scheme Q

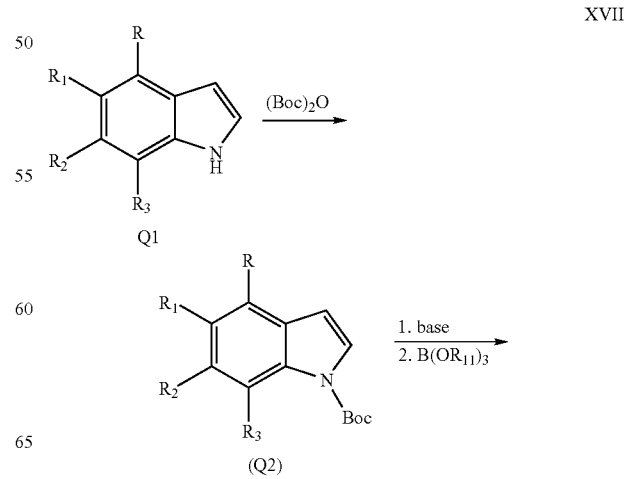

-continued

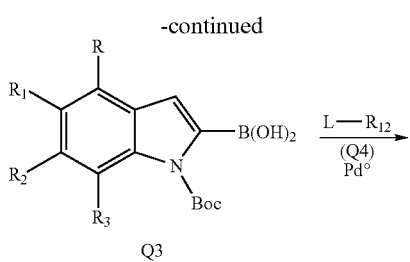
Q3

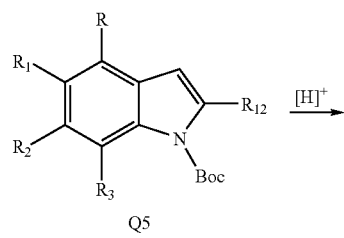
Q5

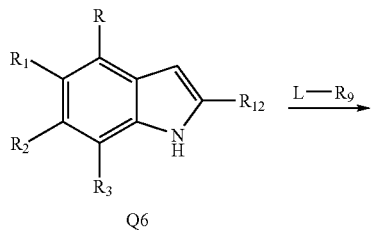
Q6

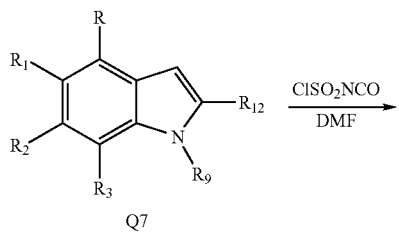
Q7

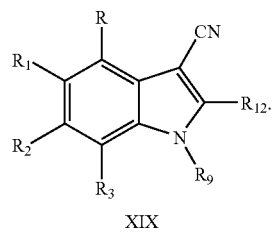
XIX

Compounds of formula I, represented by structure XX can be prepared as shown in Scheme R.

Compounds of structure R1 can be prepared by protecting an indole compound of structure R1 as e.g., the N-Boc derivative R2 as above. Compounds of structure R2 can be converted to 2-iodo- or bromoindoles R3. Typically, a strong base, such as n-butyllithium or s-butyllithium or lithium diisopropylamide or lithium or potassium hexamethyldisilazide is employed, with formation of the 2-indolyl anion generated in a suitable unreactive solvent, e.g., ether or THF, or solvent mixtures containing them. The reaction is typically carried out in the range of –78° C. to ambient temperature. The 2-indolyl anion can then be quenched with an electrophilic source of halogen, including but not limited to iodine, bromine or N-bromosuccinimide to give compounds of structure R3. After removal of the protecting group, compounds of R4 can be reacted with aryl or heteroaryl boronic acids or esters (R5) (commonly referred to as a Suzuki reaction) to give compounds of structure R6. The coupling reactions are carried out by methods known to those skilled in the art and include conducting the reaction in the presence of a catalyst, such as tetrakis(triphenylphosphine)palladium (0), bis(triphenylphosphine)palladium (II) dichloride or palladium acetate with added phosphine ligand. Reaction with R6 with a reactive functional group $R_9$ containing a suitable leaving group L as described above can give compounds of structure XX.

Scheme R

XVIII

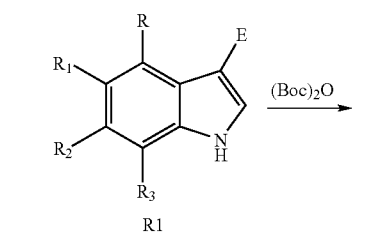
R1

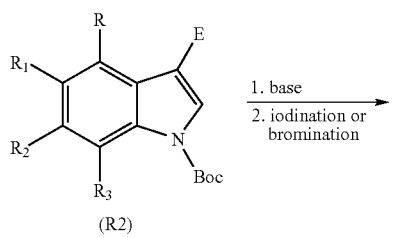
(R2)

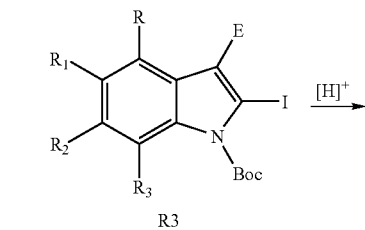
R3

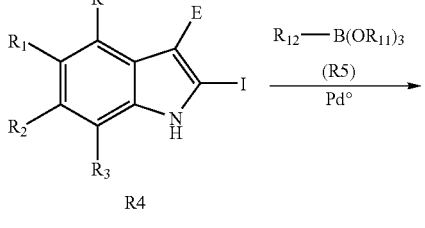
R4

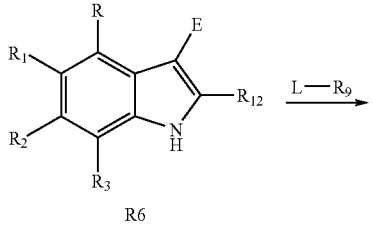
R6

-continued

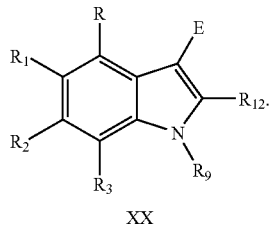

XX

Compounds of the present invention, represented by structure XXI can be prepared as described in scheme S below.

2-iodo- or bromoindoles of structure S1 can be reacted with alkenes in the presence of a palladium catalyst (commonly referred to as the Heck reaction) to give compounds of type XXI. The coupling reactions can be carried out by methods known to those skilled in the art. The choice of catalyst and solvents are similar to those described previously.

Scheme S

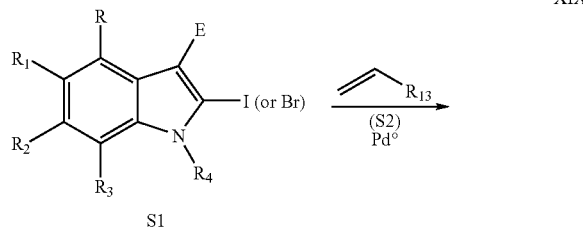

XIX

XXI

Compounds of formula I, represented by structure XXII can be prepared as shown in Scheme T.

2-Iodo- or 2-bromoindoles of structure T1 can be reacted with acetylenes in the presence of a palladium catalyst (commonly referred to as the Sonagashira reaction) to give compounds of type XXII. The coupling reactions can be carried out by methods known to those skilled in the art. A typical set of reaction conditions includes reacting the indoles of structure T1 with an acetylene compound T2 in the presence of a source of palladium, a copper co-catalyst and an amine source. The reaction is carried out in a suitably unreactive solvent and conducted within a temperature range from ambient to 150° C.

Scheme T

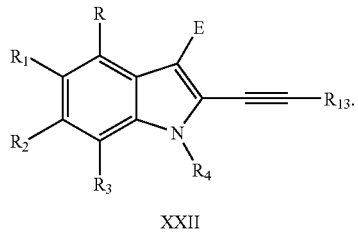

XX

T1

XXII

Compounds of formula I, represented by structure XXIII can be prepared as shown in Scheme U.

Compounds of structure XXIII can be obtained from the reduction of compounds XXI and XXII. Conditions for the reduction can include, but are not limited to catalytic reduction, e.g., hydrogenation over a source of platinum or palladium in a suitable solvent, e.g., $CH_2Cl_2$, ether, THF, methanol or solvent combinations.

Scheme U

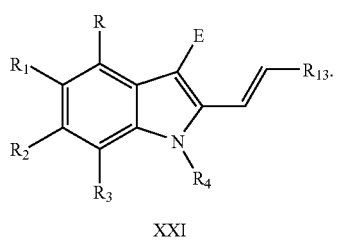

XXI

XXI

XXIII

XXII

Compounds of the present invention, represented by structure XXIV can be prepared as described in scheme V below.

Indoles of structure V1 can be reacted with a suitable base, such as lithium diisopropylamide or potassium hexamethyldisilazide to generate the 2-indolyl anion in a suitable unreactive solvent, e.g., ether or THF, or solvent mixtures containing them. The reaction is typically carried out in the range of −78° C. to ambient temperature. The 2-indolyl anion can then be quenched with a source of zinc halide, e.g., zinc halide metal or solutions containing them to give organozinc compounds of structure V2. Reaction of V2 with an arylhalide (V3) in the presence of a palladium catalyst (commonly referred to as the Negishi reaction) gives compounds of structure XXIV. Alternatively, 2-iodo or bromoindoles of structure V4, prepared from compounds V1 as described previously, can be reacted with organozinc compounds of structure V5 in the presence of a suitable palladium catalyst to give compounds of structure XXIV. The organozinc compound V5 can be derived from, e.g., an alkyl or alkenyl halide after treatment with activated zinc or an aryl or heteroaryl lithium or magnesium compound after treatment with zinc halide. Furthermore, the reactions of V2 or V4 can be carried out in the presence of a palladium source, e.g., as tetrakis(triphenylphosphine)palladium (0) or bis(triphenylphosphine)palladium (II) dichloride in a suitable solvent and at a temperature range from ambient to 150° C.

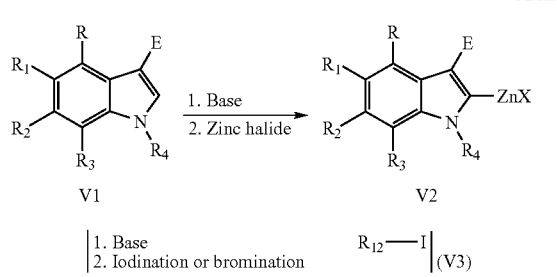

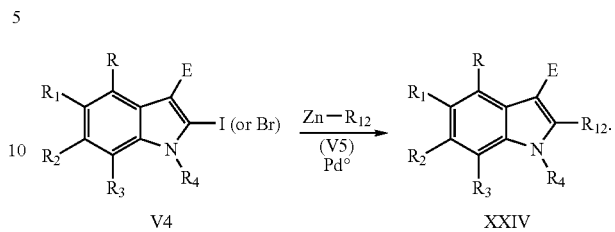

Compounds of formula I, represented by structure XXV-XXVIII can be prepared as shown in Scheme W.

2-Iodo- or bromoindoles of structure W1 can be reacted with acetylenes of structure W2 in the presence of a palladium catalyst (commonly referred to as the Sonagashira reaction) to give compounds of type XXV. The coupling reactions can be carried out by methods known to those skilled in the art. A typical set of reaction conditions includes reacting the indoles of structure W1 with an acetylene compound W2 in the presence of a source of palladium, an optional copper co-catalyst and an amine source. The reaction is carried out in a suitably unreactive solvent and conducted within a temperature range from ambient to 150° C. Reaction with XXV with a reactive functional group $R_9$ containing a suitable leaving group L as described above can give compounds of structure XXVI.

2-iodo- or bromoindoles of structure W1 can also be reacted with alkenes in the presence of a palladium catalyst (commonly referred to as the Heck reaction) to give compounds of type XXVII. The coupling reactions can be carried out by methods known to those skilled in the art. The choice of catalyst and solvents are similar to those described previously. Reaction with XXVII with a reactive functional group $R_9$ containing a suitable leaving group L as described above can give compounds of structure XXVIII.

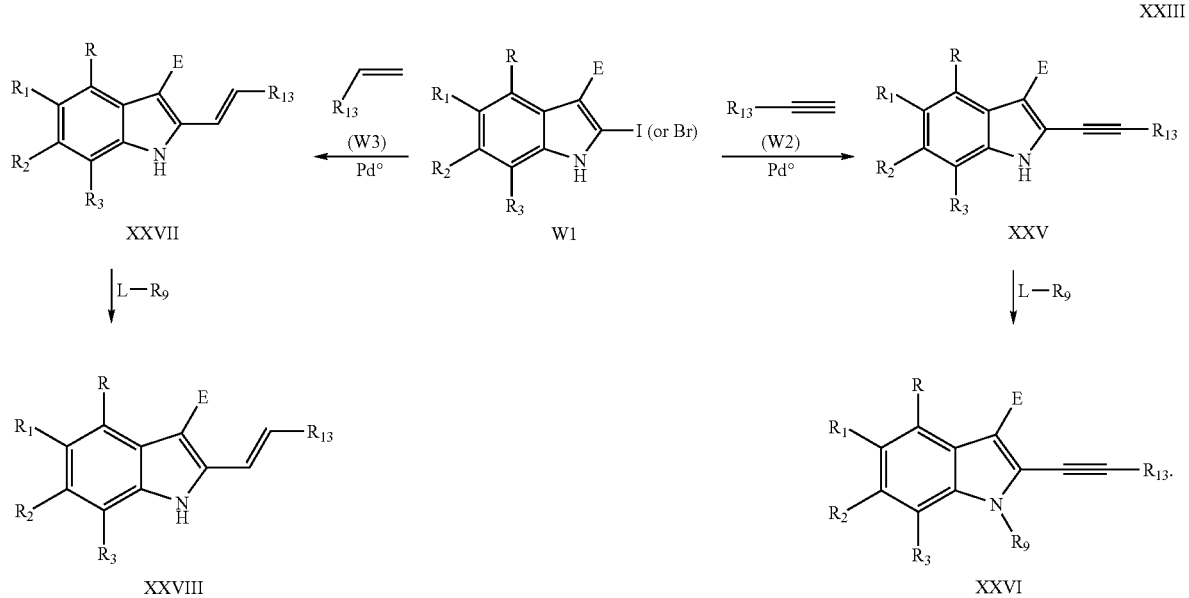

Compounds of formula I, represented by structure XXIX can be prepared as shown in Scheme X.

Indoles of structure X1 and be acylated with acyl halides of structure X2 to give compounds of structure XXIX. The reaction can be promoted with a Lewis acid. The choice of Lewis acid can be chosen from, but is not limited to aluminum chloride, ferric chloride, stannic chloride or diethyl aluminum. The reaction is typically carried out in a suitable non-reactive solvent including $CH_2Cl_2$, carbon disulfide or dichloroethane and is typically conducted within a temperature range of $-20°$ C. to $80°$ C.

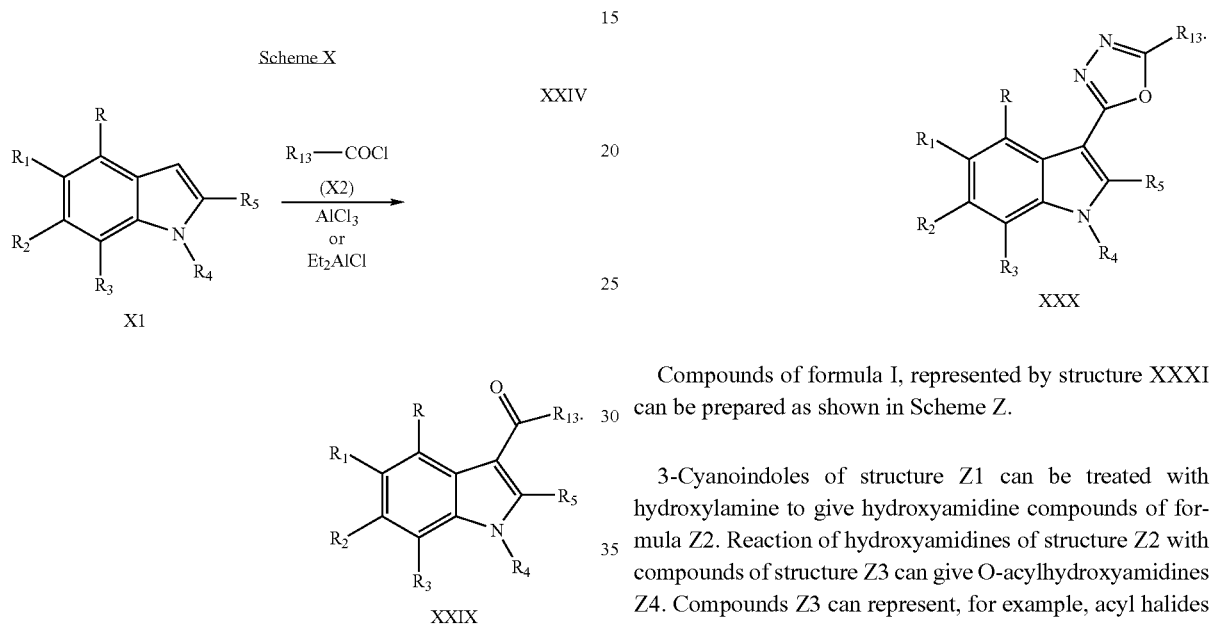

Compounds of formula I, represented by structure XXX can be prepared as shown in Scheme Y.

3-Cyanoindoles of structure Y1 can be converted to tetrazoles of structure Y2 by treatment with, e.g., sodium azide. Heating a mixture of Y2 and the reagent Y3 can give the 3-(1,2,4-oxadiazolyl)indole compound XXX. The reagent Y3 can be, e.g., an acyl halide or an acid derivative activated with a reagent such as dicyclohexyl carbodiimide or diisopropyl carbodiimide. The reaction can be carried out in a variety of solvents, including e.g., toluene, dioxane, pyridine and dichloroethane and can be carried out by heating Y2 and Y3 at a temperature range of $30°$ to $130°$ C.

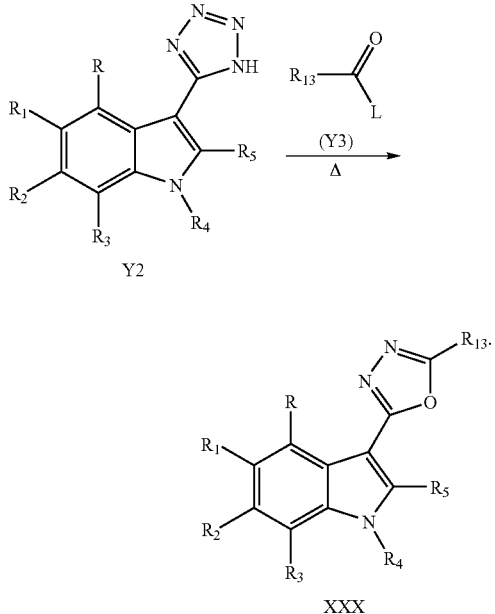

Compounds of formula I, represented by structure XXXI can be prepared as shown in Scheme Z.

3-Cyanoindoles of structure Z1 can be treated with hydroxylamine to give hydroxyamidine compounds of formula Z2. Reaction of hydroxyamidines of structure Z2 with compounds of structure Z3 can give O-acylhydroxyamidines Z4. Compounds Z3 can represent, for example, acyl halides or carboxylic acids activated with a reagent such as dicyclohexyl carbodiimide or diisopropyl carbodiimide. Heating compounds of structure Z4 in a non-reactive organic solvent, e.g., toluene, dichloroethane or dioxane in a temperature range of $30°$ C. to $150°$ C. can give compounds of structure XXXI.

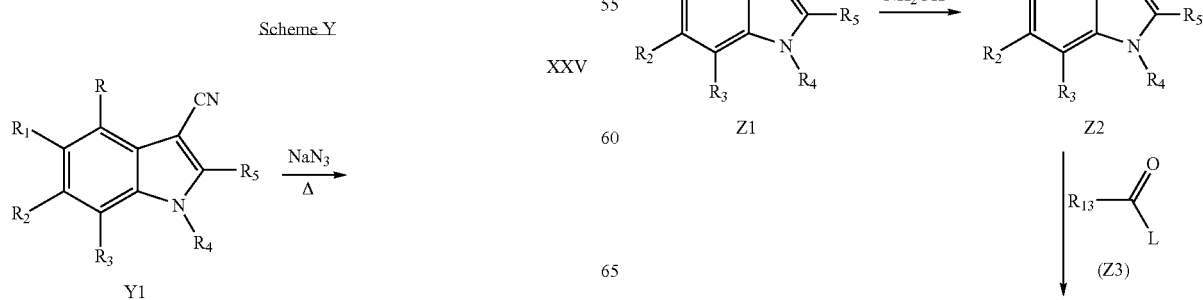

-continued

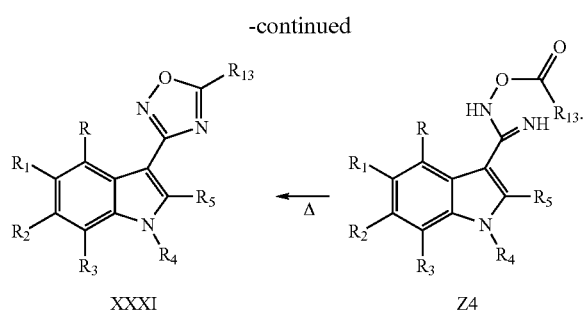

Compounds of the present invention, represented by structure XXXII can be prepared as described in scheme AA below.

Ketoindoles of type AA1 can be converted to oximes of structure AA2 by heating the ketoindoles with hydroxylamine (free base or acid salt) in a suitable solvent. Bis-deprotonation of compounds of type AA2 with a strong organic base (e.g., n-butyllithium or sec-butyllithium or tert-butyllithium) followed by reaction with DMF can give compounds of formula XXXII.

Scheme AA

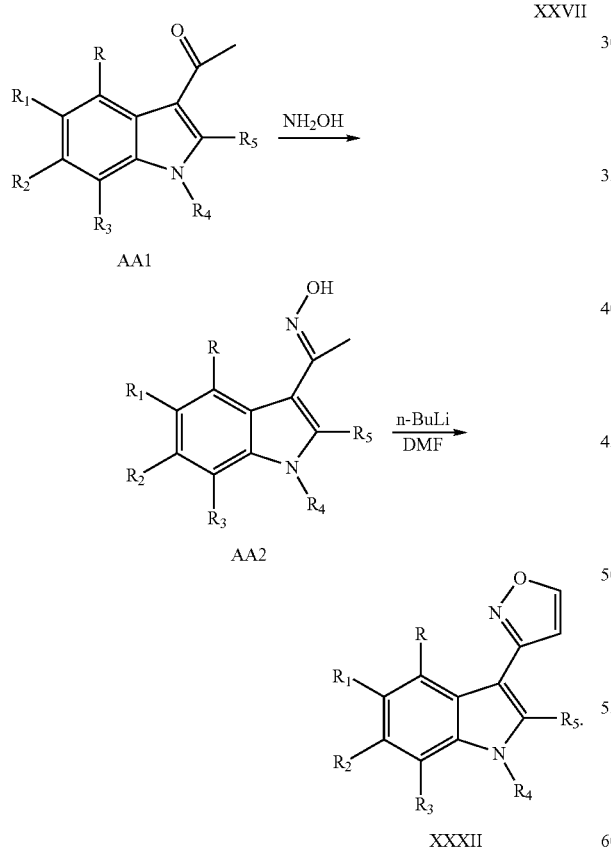

Compounds of formula I, represented by structure XXXIII can be prepared as shown in Scheme AB.

3-Ketoindoles of structure AB1 can be homologated to vinylogous amides of structure AB3 by reaction with dialkyl amide dialkyl acetals AB2. The dialkyl amides can include e.g., lower alkyl amides such as formamide, acetamide and propionamide. Examples would include dimethlformamide dimethyl acetal and dimethyl acetamide dimethyl acetal. The reaction can be conducted by reacting AB1 and AB2 with or without additional solvent at a temperature from ambient to 150° C. Treatment of AB3 with hydroxylamine (free base or acid salt) in a suitable solvent can give compounds of structure XXXIII. The reaction is typically conducted within a temperature range from ambient to 120° C.

Scheme AB

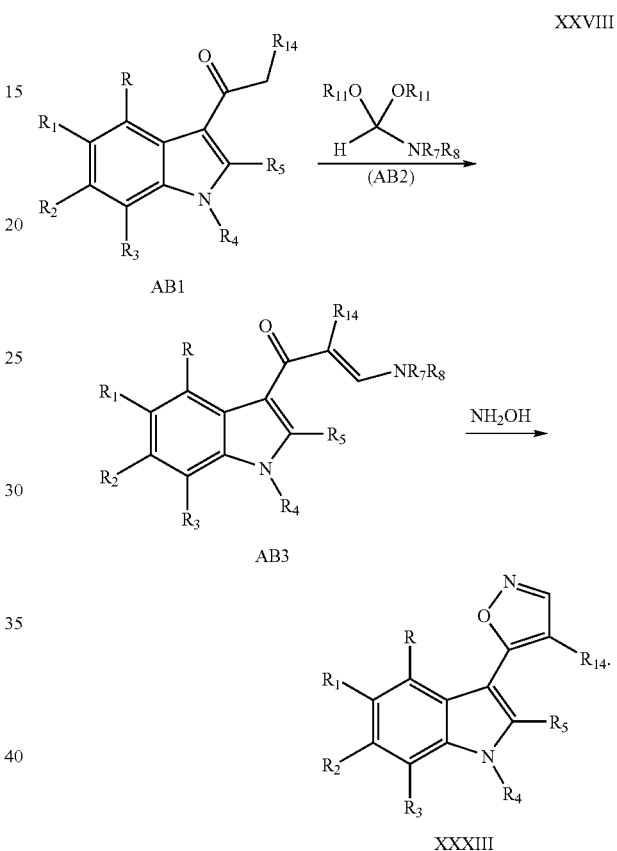

Compounds of formula I, represented by structure XXXIV can be prepared as shown in Scheme AC.

Vinylogous amides of structure AC1 (as prepared above) can be treated with hydrazines AC2 in a suitable organic solvent (DMF, alcohol or acetic acid) at temperatures ranging from ambient temperature to 150° C. to give compounds of structure XXXIV.

Scheme AC

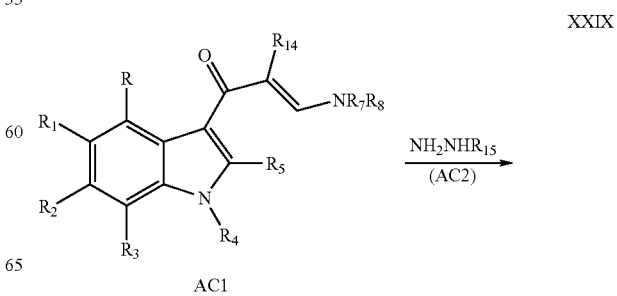

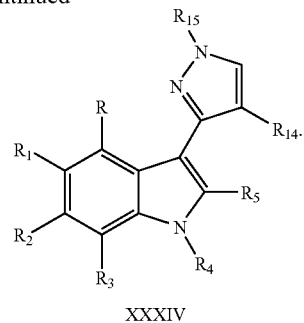

XXXIV

Compounds of the present invention, represented by structure XXXV can be prepared as described in scheme AD below.

Indole-3-carboxaldehydes of structure AD1 (as prepared in Scheme F) can be reacted with p-(toluenesulfonyl)methyl isocyanate (TOSMIC) in the presence of a base to give compounds of structure XXXV. Bases can include potassium carbonate or 1,8-diazabicyclo[5.4.0]undec-7-ene and the reaction can be carried out in a suitable organic solvent from ambient temperature to 150° C.

Scheme AD

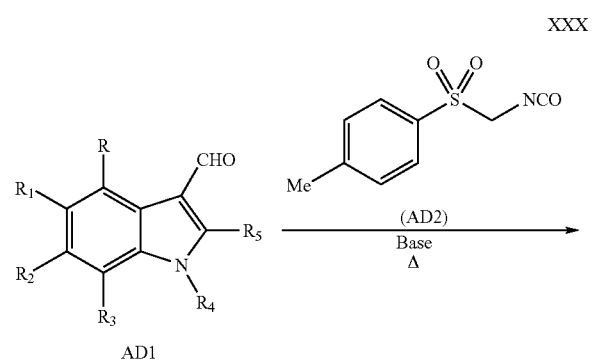

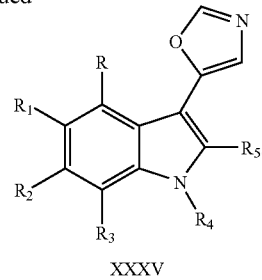

XXXV

Compounds of formula I, represented by structures XXXVI and XXXVII can be prepared as shown in Scheme AE.

3-Indolecarboxylic acids of structure AE1 (from Scheme E) can be converted to amides of structure AE2. Compounds of structure AE2 can be activated by any of the standard methods. For example, the acid AE1 can be activated with coupling reagents such as EDCI or DCC with or without HOBt in the presence of ammonia. Alternatively, the acid can be activated as the acid chloride or as the acyl imidazolide as described previously, followed by treatment of ammonia.

The indole-3-carboxamides of structure AE2 can be reacted with substituted aldehydes or ketones (AE3) containing a suitable leaving group L, in a suitable solvent at temperatures above ambient and up to 200° C. The reaction can be performed with or without added base to afford oxazoles of structure XXXVI.

The indole-3-carboxamides of structure AE2 can also be converted to thioamides of structure AE4 by treating the primary amides with Lawesson's reagent or phosphorous pentasulfide at or above ambient temperature in a suitable organic solvent. The resulting thioamides AE4 can be reacted with substituted aldehydes or ketones containing a suitable leaving group L (AE3), in a suitable solvent at temperatures above ambient and up to 150° C. The reaction can be performed with or without added base to afford thiazoles of structure XXXVII.

Scheme AE

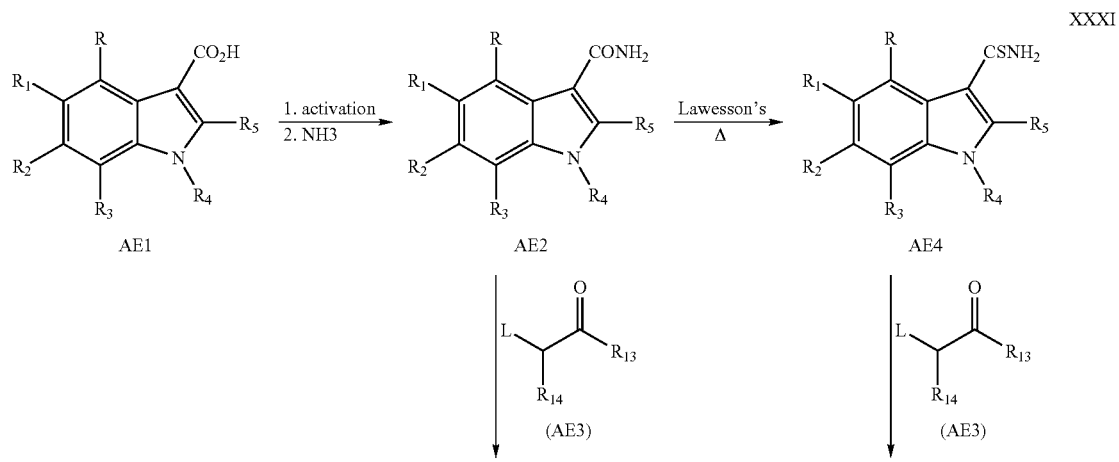

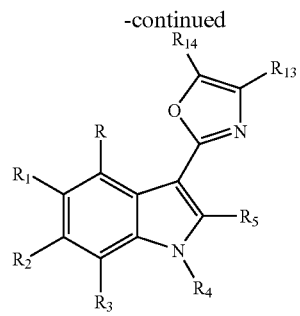

XXXVI

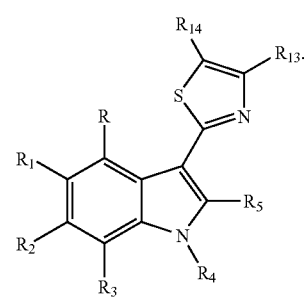

XXXVII

Compounds of the present invention, represented by structure XXXVIII and XXXIX can be prepared as described in scheme AF below.

3-Ketoindoles of structure AF1 can be halogenated (e.g., brominated) to give compounds of structure AF3. Suitable brominating agents can include but are not limited to phenyltrimethylammonium tribromide (AF2), N-bromosuccinimide or bromine and can be carried out in a variety of organic solvents.

Treatment of compounds AF3 with amides of type AF4 in a suitable solvent at temperatures above ambient and up to 200° C. with or without added base can give oxazoles of structure XXXVIII.

Treatment of compounds AF3 with thioamides of type AF5 in a suitable solvent at temperatures above ambient and up to 150° C. with or without added base can give thiazoles of structure XXXIX.

Scheme AF

XXXII

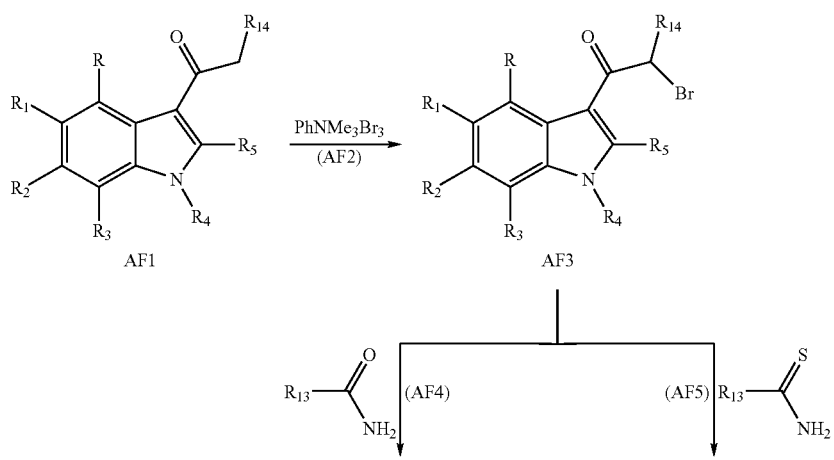

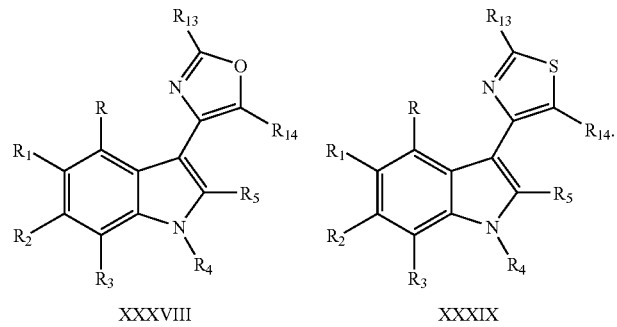

XXXVIII      XXXIX

Compounds of formula I, represented by structure XL can be prepared as shown in Scheme AG.

Indoles of structure AG1 can be brominated or iodinated to give compounds of structure AG2. Brominating agents may include but are not limited to bromine or N-bromosuccinimide and iodinating reagents may include iodine monochloride or bis-trifluoroacetoxy iodobenzene. Reaction of 3-iodo- or bromoindoles AG2 with a boronic acid AG3 (commonly referred to as a Suzuki reaction) can give the compounds of structure XL. The coupling reactions are carried out by methods known to those skilled in the art and include conducting the reaction in the presence of a catalyst, such as tetrakis(triphenylphosphine)palladium (0), bis(triphenylphosphine)palladium (II) dichloride or palladium acetate with added phosphine ligand. The reactions are carried out in a suitable solvent, e.g., DMF, toluene, dimethoxy ethane or dioxane at a temperature range of ambient to 150° C. and typically in the presence of a base e.g., aqueous sodium carbonate or sodium bicarbonate, or the base can be employed under anhydrous conditions, e.g., cesium or potassium fluoride.

Alternatively, indole AG2 can be converted to the indole-3-boronic acid derivative AG5 by reacting the 3-haloindole AG2 with a strong organic base (alkyllithium or Grignard reagent) and reacting the resultant anion with a trialkylborate reagent AG4. Compounds of type AG5 can be reacted with aryl and heteroaryl bromides and iodides under similar conditions to those described above to form compounds of structure XL.

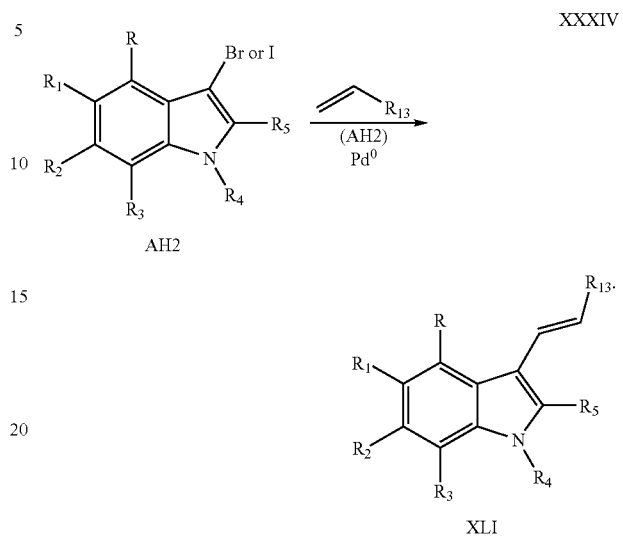

Compounds of formula I, represented by structure XLII can be prepared as shown in Scheme AI.

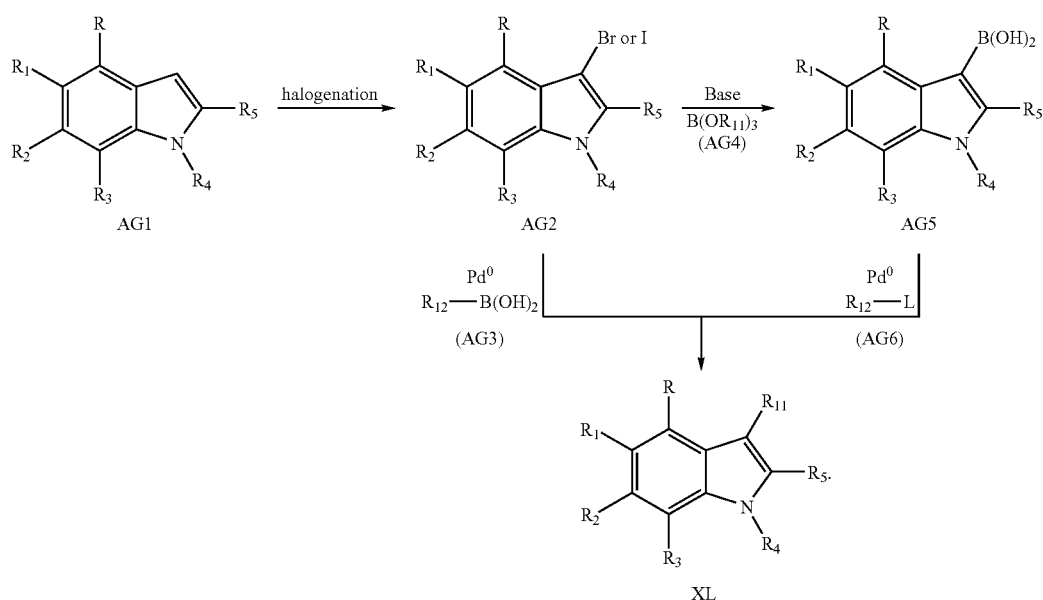

Compounds of the present invention, represented by structure XLI can be prepared as described in scheme AH below.

3-iodo- or bromoindoles of structure AH1 can be reacted with alkenes AH2 in the presence of a palladium catalyst (commonly referred to as the Heck reaction) to give compounds of type XLI. The coupling reactions can be carried out by methods known to those skilled in the art. The choice of catalyst and solvents are similar to those described in Scheme AG.

3-Iodo- or bromoindoles of structure AI1 can be reacted with acetylenes AI2 in the presence of a palladium catalyst (commonly referred to as the Sonagashira reaction) to give compounds of type XLII. The coupling reactions can be carried out by methods known to those skilled in the art. A typical set of reaction conditions includes reacting the indole of structure AI1 with an acetylene compound AI2 in the presence of a source of palladium, a copper co-catalyst and an amine source and carrying out the reaction at a temperature range of ambient to 150° C.

Scheme AI

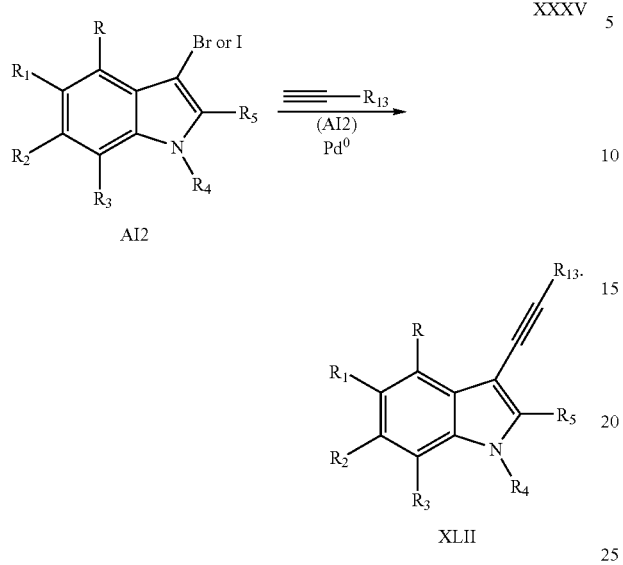

Scheme AJ

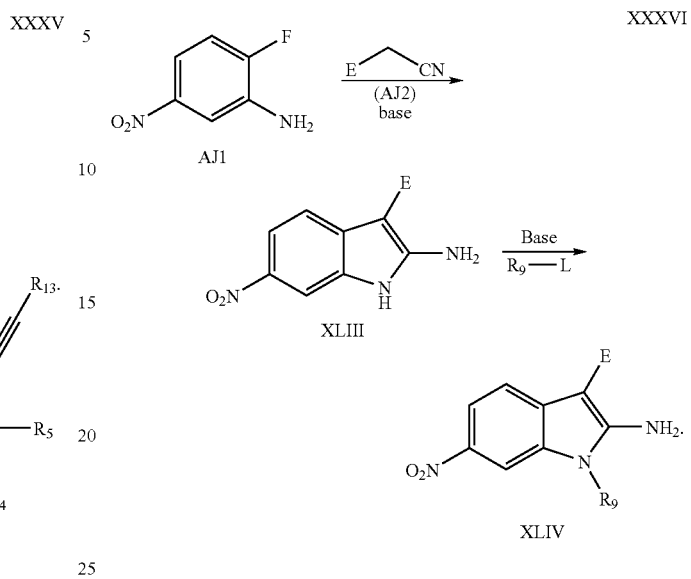

Compounds of the present invention, represented by structure XLIII and XLIV can be prepared as described in scheme AJ below.

Nitroanilines of structure AJ1 can be converted to indoles of structure XLIII by condensation and cyclization with nitriles of structure AJ2. The reaction can be carried out in a suitable organic solvent, e.g., DMF or dioxane. Treatment of compounds of structure XLIII with a base followed by reaction with a reactive functional group $R_9$ containing a suitable leaving group L can give the compounds of formula XLIV.

Compounds of formula I, represented by structure XLV-XLVIII can be prepared as shown in Scheme AK.

2-aminoindoles of structure XLV can be alkylated with a reactive functional group $R_{15}$ containing a suitable leaving group L in the presence of a base, e.g., sodium hydride or potassium carbonate in a suitable organic solvent to give compounds of structure XLVI. A second alkylation utilizing a reactive functional group $R'_{15}$ containing a suitable leaving group L similarly can give compounds of structure XLVII.

Acylation of compounds of structure XLV with acyl chlorides of structure AK1 can give compounds of structure XLVIII. The reaction is typically carried out in the presence of an organic base, e.g., a trialkylamine or an inorganic base, e.g., potassium carbonate in a suitable organic solvent.

Scheme AK

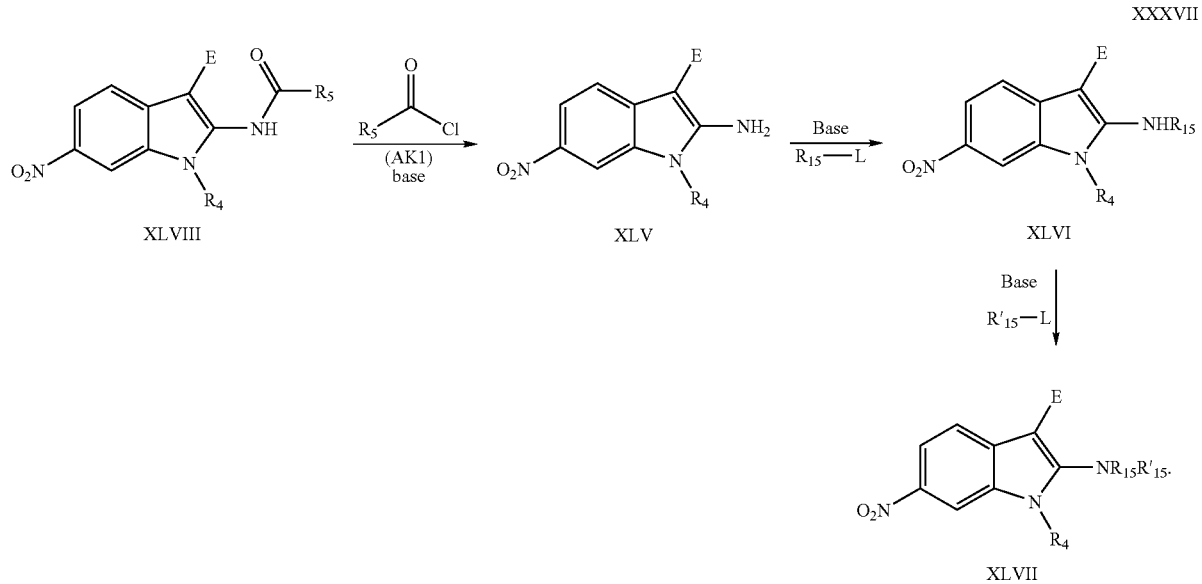

Compounds of the present invention, represented by structure XLIX can be prepared as described in scheme AL below.

Indole-3-carboxylic acids of structure AL1 can be activated to give compounds of structure AL2. Compounds of structure AL2 can represent, for example, acyl halides or carboxylic acids activated with a reagent such as dicyclohexyl carbodiimide or diisopropyl carbodiimide. Reaction of compounds of structure AL2 with hydroxyamidines of structure AL3 can give O-acylhydroxyamidines AL4. Hydroxyamidines may be obtained commercially or by treatment of nitrile compounds with hydroxylamine. Heating compounds of structure AL4 in a non-reactive organic solvent, e.g., toluene, dichloroethane or dioxane in a temperature range of 30° C. to 150° C. can give compounds of structure XLIX.

3-Cyanoindoles of structure AM1 can be converted to tetrazoles of structure AM2 by treatment with, e.g., sodium azide. Heating a mixture of AM2 and the reagent AM3 can give the 3-(1,2,4-oxadiazolyl)indole compound L. The reagent AM3 can be, e.g., an acyl halide or an acid derivative activated with a reagent such as dicyclohexyl carbodiimide or diisopropyl carbodiimide. The reaction can be carried out in a variety of solvents, including e.g., toluene, dioxane, pyridine and dichloroethane and can be carried out by heating AM2 and AM3 at a temperature range of 30° to 130° C.

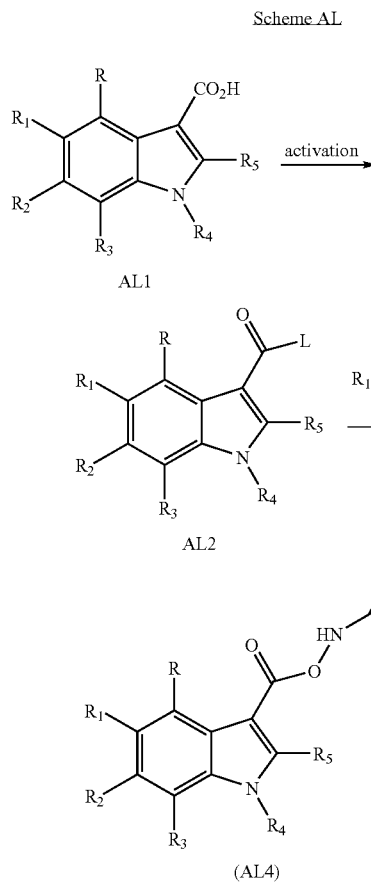

Compounds of formula I, represented by structure L can be prepared as shown in Scheme AM.

Compounds of formula I, represented by structure LI can be prepared as shown in Scheme AN.

3-Cyanoindoles of structure AN1 can be treated with hydroxylamine to give hydroxyamidine compounds of formula AN2. Reaction of hydroxyamidines of structure AN2 with compounds of structure AN3 can give O-acylhydroxyamidines AN4. Compounds AN3 can represent, for example, acyl halides or carboxylic acids activated with a reagent such as dicyclohexyl carbodiimide or diisopropyl carbodiimide. Heating compounds of structure AN4 in a non-reactive organic solvent, e.g., toluene, dichloroethane or dioxane in a temperature range of 30° C. to 150° C. can give compounds of structure LI.

Scheme AN

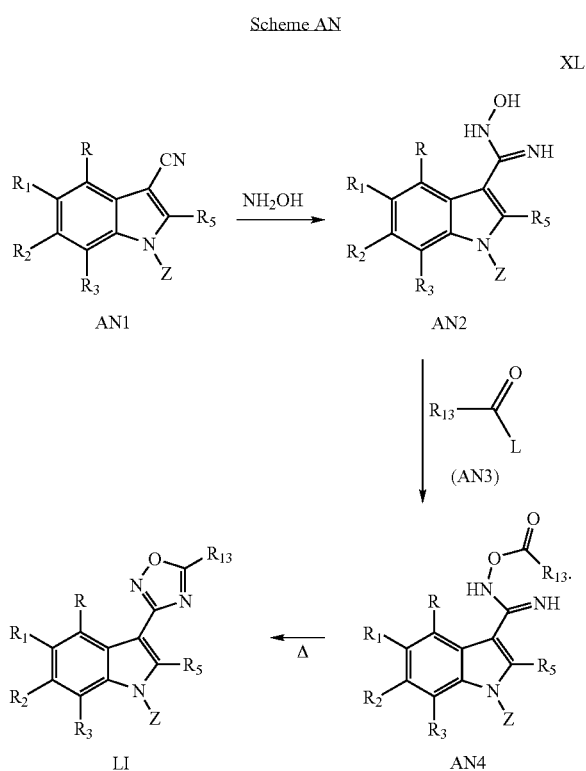

Compounds of the present invention, represented by structure LII can be prepared as described in scheme AO below.

Ketoindoles of type AO1 can be converted to oximes of structure AO2 by heating the ketoindoles with hydroxylamine (free base or acid salt) in a suitable solvent. Bis-deprotonation of compounds of type AO2 with a strong organic base (e.g., n-butyllithium or sec-butyllithium or tert-butyllithium) followed by reaction with DMF can give compounds of formula LII.

Scheme AO

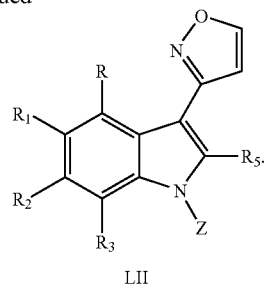

Compounds of formula I, represented by structure LIII can be prepared as shown in Scheme AP.

3-Ketoindoles of structure AP1 can be homologated to vinylogous amides of structure AP3 by reaction with dialkyl amide dialkyl acetals AP2. The dialkyl amides can include e.g., lower alkyl amides such as formamide, acetamide and propionamide. Examples would include dimethlformamide dimethyl acetal and dimethyl acetamide dimethyl acetal. The reaction can be conducted by reacting AP1 and AP2 with or without additional solvent at a temperature from ambient to 150° C. Treatment of AP3 with hydroxylamine (free base or acid salt) in a suitable solvent can give compounds of structure LIII. The reaction is typically conducted within a temperature range from ambient to 120° C.

Scheme AP

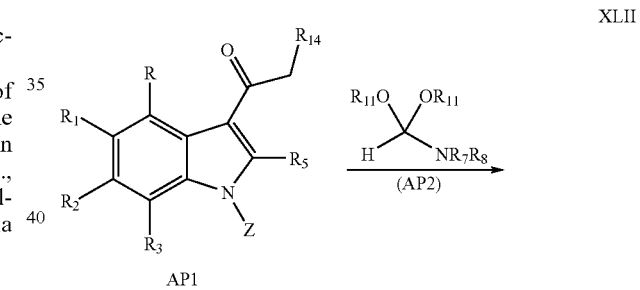

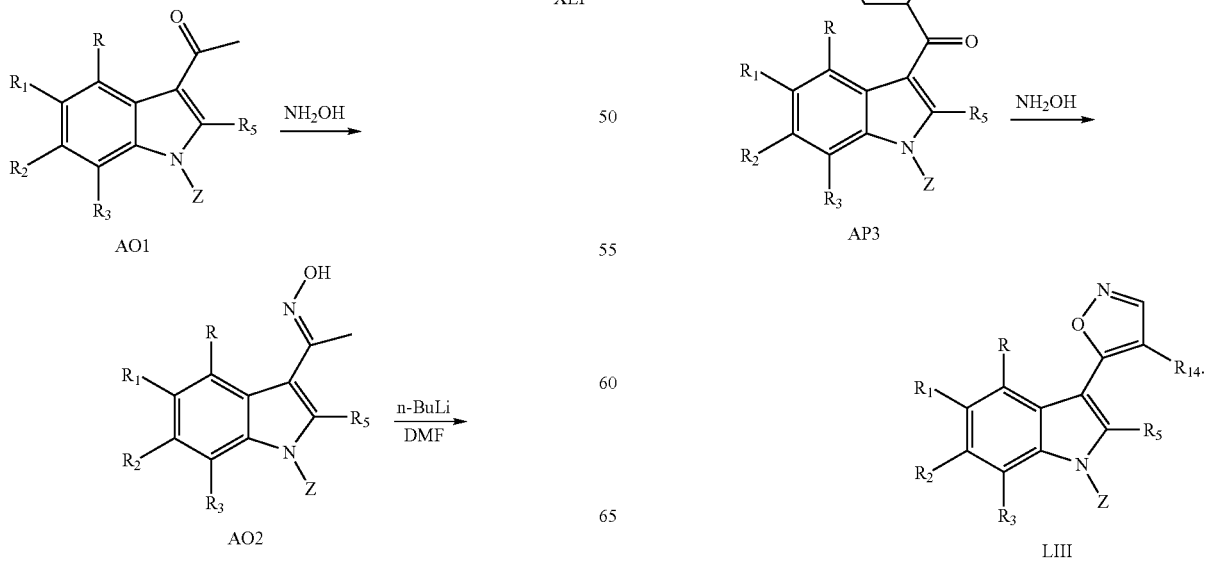

Compounds of formula I, represented by structure LIV can be prepared as shown in Scheme AQ.

Vinylogous amides of structure AQ1 (as prepared above) can be treated with hydrazines AQ2 in a suitable organic solvent (DMF, alcohol or acetic acid) at temperatures ranging from ambient temperature to 150° C. to give compounds of structure LIV.

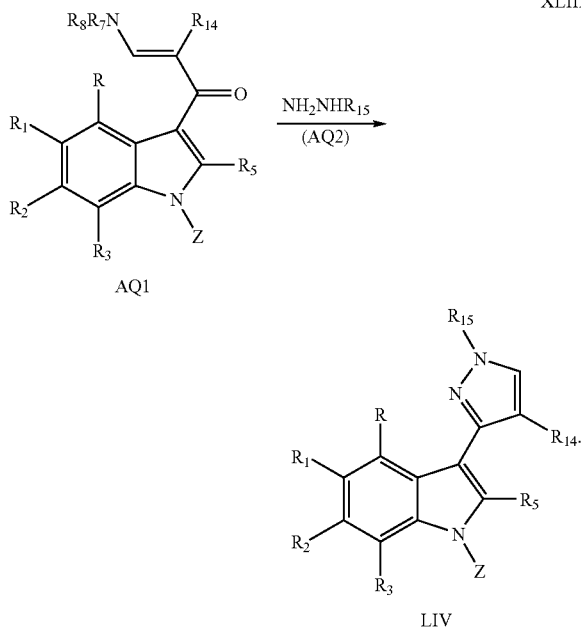

Compounds of the present invention, represented by structure LV can be prepared as described in scheme AR below.

Indole-3-carboxaldehydes of structure AR1 (as prepared in Scheme F) can be reacted with p-(toluenesulfonyl)methyl isocyanate (TOSMIC, AR2) in the presence of a base to give compounds of structure LV. Bases can include potassium carbonate or 1,8-diazabicyclo[5.4.0]undec-7-ene and the reaction can be carried out in a suitable organic solvent from ambient temperature to 150° C.

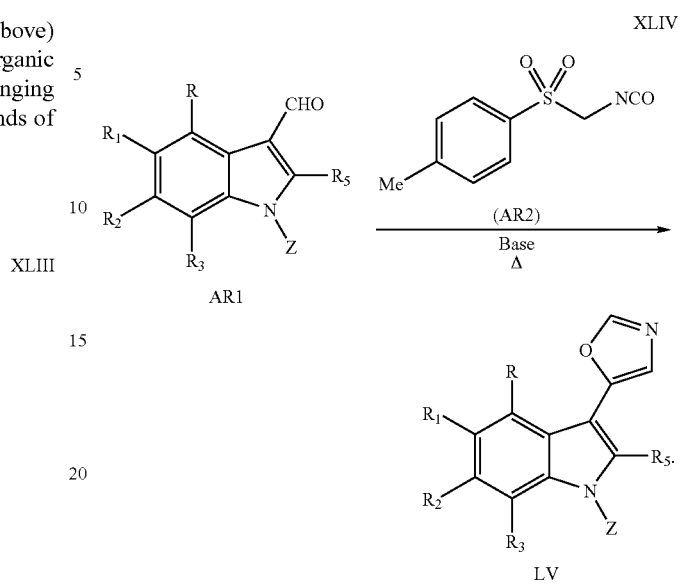

Compounds of formula I, represented by structures LVI and LVII can be prepared as shown in Scheme AS.

3-Indolecarboxylic acids of structure AS1 (from Scheme F) can be converted to amides of structure AS2. Compounds of structure AS1 can be activated by any of the standard methods. For example, the acid AS1 can be activated with coupling reagents such as EDCI or DCC with or without HOBt in the presence of ammonia. Alternatively, the acid can be activated as the acid chloride or as the acyl imidazolide as described previously, followed by treatment of ammonia.

The indole-3-carboxamides of structure AS2 can be reacted with substituted aldehydes or ketones (AS3) containing a suitable leaving group L, in a suitable solvent at temperatures above ambient and up to 200° C. The reaction can be performed with or without added base to afford oxazoles of structure LVI.

The indole-3-carboxamides of structure AS2 can also be converted to thioamides of structure AS4 by treating the primary amides with Lawesson's reagent or phosphorous pentasulfide at or above ambient temperature in a suitable organic solvent. The resulting thioamides AS4 can be reacted with substituted aldehydes or ketones containing a suitable leaving group L (AS3), in a suitable solvent at temperatures above ambient and up to 150° C. The reaction can be performed with or without added base to afford thiazoles of structure LVII.

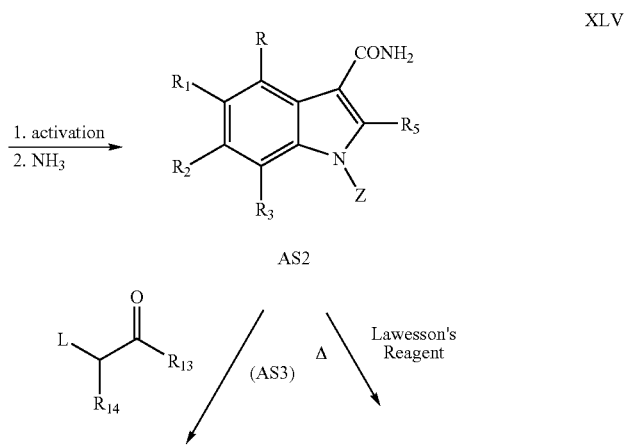

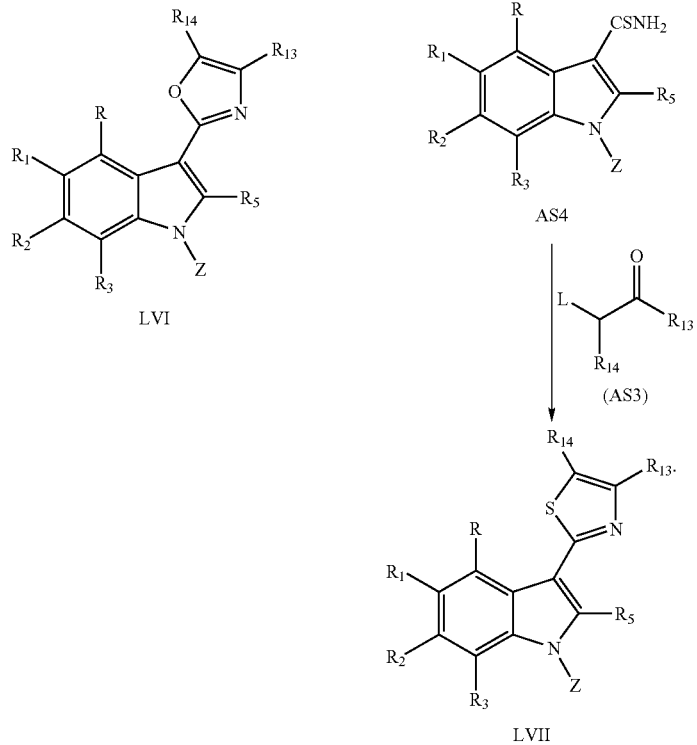

Compounds of the present invention, represented by structure LVIII and LIX can be prepared as described in scheme AT below.

3-Ketoindoles of structure AT1 can be halogenated (e.g., brominated) to give compounds of structure AT3. Suitable brominating agents can include but are not limited to phenyltrimethylammonium tribromide (AT2), N-bromosuccinimide or bromine and can be carried out in a variety of organic solvents.

Treatment of compounds AT3 with amides of type AT4 in a suitable solvent at temperatures above ambient and up to 200° C. with or without added base can give oxazoles of structure LVIII.

Treatment of compounds AT3 with thioamides of type AT5 in a suitable solvent at temperatures above ambient and up to 150° C. with or without added base can give thiazoles of structure LIX.

XLVI. Scheme AT

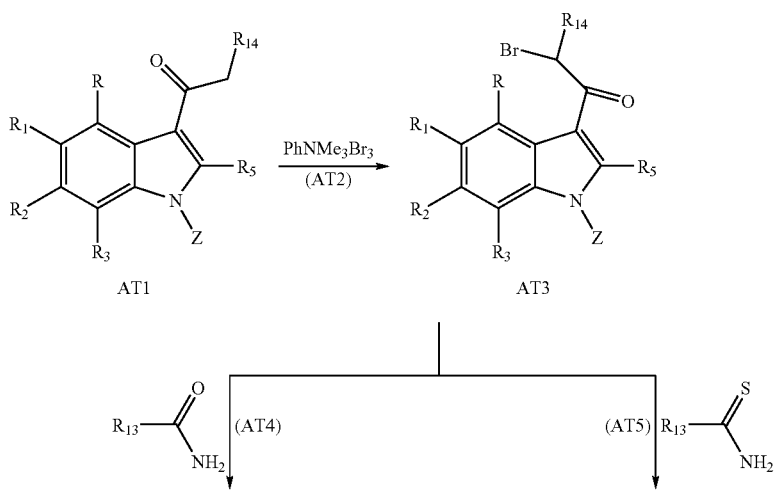

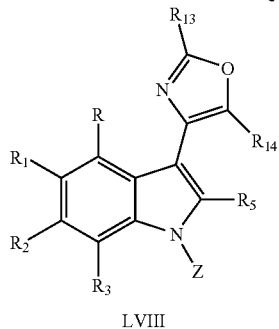

LVIII

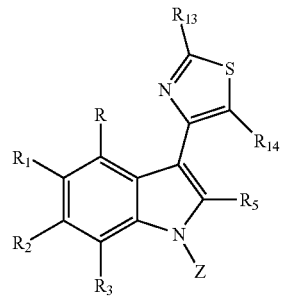

LIX

Compounds of the present invention, represented by structure LX can be prepared as described in scheme AU below.

Indole-3-carboxylic acids of structure AU1 can be activated to give compounds of structure AU2. Compounds of structure AU2 can represent, for example, acyl halides or carboxylic acids activated with a reagent such as dicyclohexyl carbodiimide or diisopropyl carbodiimide. Reaction of compounds of structure AU2 with hydroxyamidines of structure AU3 can give O-acylhydroxyamidines AU4. Hydroxyamidines may be obtained commercially or by treatment of nitrile compounds with hydroxylamine. Heating compounds of structure AU4 in a non-reactive organic solvent, e.g., toluene, dichloroethane or dioxane in a temperature range of 30° C. to 150° C. can give compounds of structure LX.

XLVII. Scheme AU

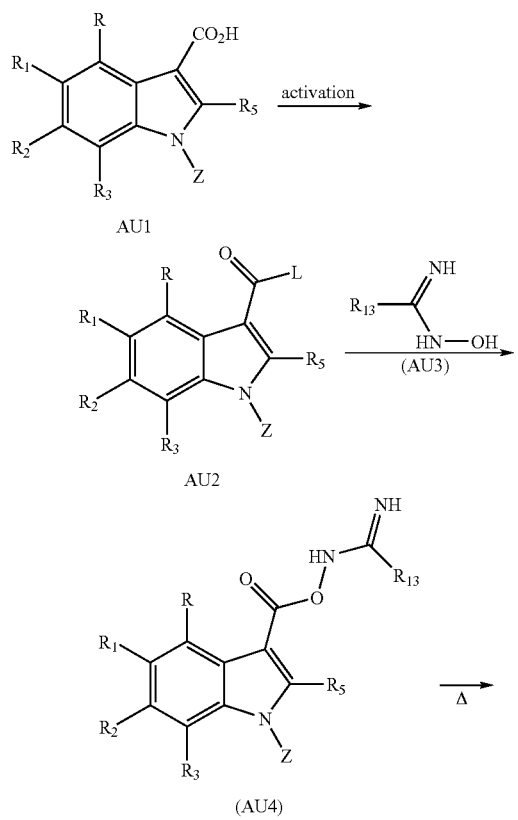

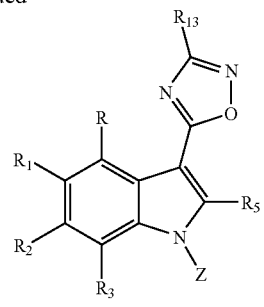

LX

Compounds of formula I, represented by structure LXI can be prepared as shown in Scheme AV.

Reaction of 3-iodo- or bromoindoles AV1 with a boronic acid AV2 (commonly referred to as a Suzuki reaction) can give the compounds of structure LXI. The coupling reactions are carried out by methods known to those skilled in the art and include conducting the reaction in the presence of a catalyst, such as tetrakis(triphenylphosphine)palladium (0), bis(triphenylphosphine)palladium (II) dichloride or palladium acetate with added phosphine ligand. The reactions are carried out in a suitable solvent, e.g., DMF, toluene, dimethoxy ethane or dioxane at a temperature range of ambient to 150° C. and typically in the presence of a base e.g., aqueous sodium carbonate or sodium bicarbonate, or the base can be employed under anhydrous conditions, e.g., cesium or potassium fluoride.

Alternatively, indole AV1 can be converted to the indole-3-boronic acid derivative AV3 by reacting the 3-haloindole AV1 with a strong organic base (alkyllithium or Grignard reagent) and reacting the resultant anion with a trialkylborate reagent AV4. Compounds of type AV3 can be reacted with aryl and heteroaryl bromides and iodides AV6 under similar conditions to those described above to form compounds of structure LXI.

XLVIII. Scheme AV

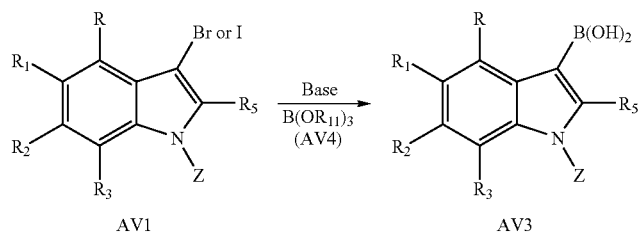

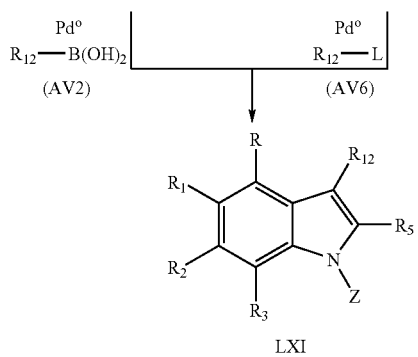

Compounds of formula I, represented by structure LXII, can be prepared as shown in Scheme AW.

Compounds of formula AW1 can be reacted with a protecting group, e.g., di-tert-butyl dicarbonate, to form the boc-protected indole, in the presence of a suitable base and solvent at ambient temperature to give compounds of structure AW2. Treatment of compounds of structure AW2 with base in a polar aprotic solvent at temperatures from −78° C. to ambient temperature, followed by addition of a trialkyl borate would yield compounds of type AW3 upon hydrolytic workup. Reaction of reactive aryl halides or triflates (of the type AW4) with compounds of formula AW3 at or around ambient temperature, in a suitable solvent system containing base and catalytic amounts of palladium catalyst, can give compounds of formula AW5. Removal of the protecting group in compounds of structure AW5, e.g., acid treatment to remove the Boc group would yield compounds of structure AW6. Compounds of type AW6 can be alkylated at the indole nitrogen to give compounds of structure LXII. The alkylation can be carried out in the presence of a suitable alkylating agent and base in a polar solvent at temperatures ranging from ambient temperature to 150° C. to yield compounds of formula LXII.

XLIX. Scheme AW

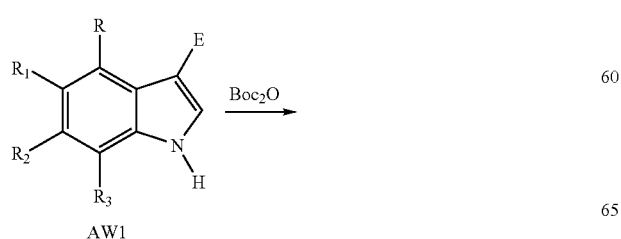

-continued

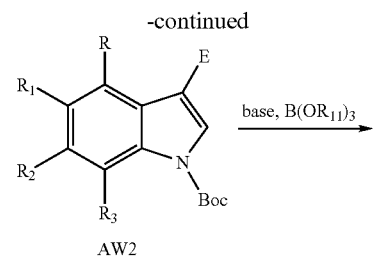

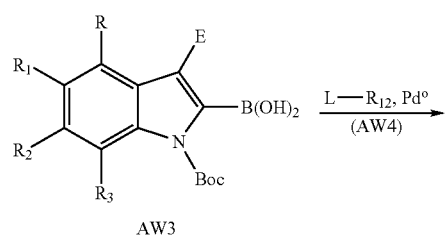

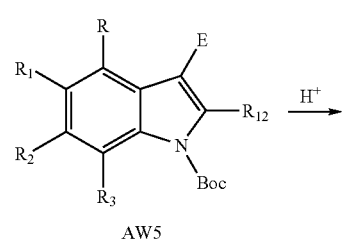

-continued

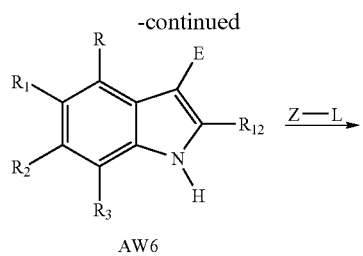

AW6

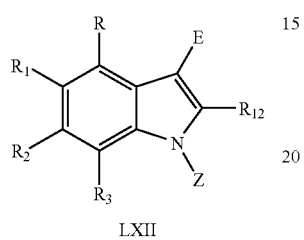

LXII

Compounds of formula I, represented by structure LXIII, can be prepared as shown in Scheme AX.

Compounds of formula AX1 can be fluorinated at the 3-position with an electrophilic fluorinating agent, e.g., N-fluorocollidine tetrafluoroborate, in a suitable non-polar solvent at temperatures ranging from −78° C. to 100° C. to yield compounds of structure LXIII.

L. Scheme AX

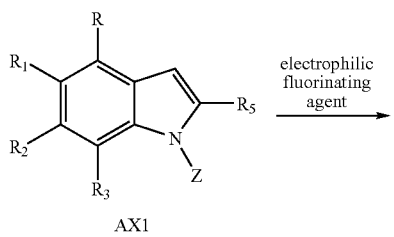

AX1

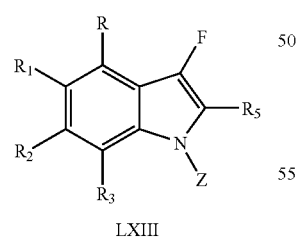

LXIII

Compounds of formula I, represented by structure LIV, can be prepared as shown in Scheme AY.

Compounds of formula AY1 can be chlorinated at the 3-position with an electrophilic chlorinating agent, e.g., N-chlorosuccinimide or chlorine, in a suitable solvent at temperatures ranging from −78° C. to 100° C. to yield products of structure LXIV.

LI. Scheme AY

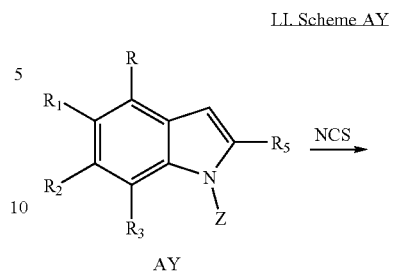

AY

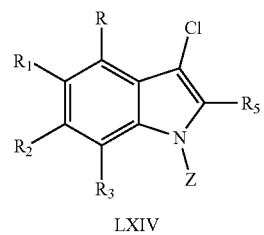

LXIV

Compounds of formula I, represented by structure LXV, can be prepared as shown in scheme AZ.

Compounds of formula AZ1 can be brominated at the 3-position with an electrophilic brominating agent, e.g., N-bromosuccinimide or bromine) in a suitable solvent at temperatures ranging from −78° C. to 100° C. to yield products of structure LXV.

LII. Scheme AZ

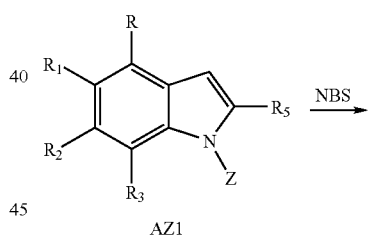

AZ1

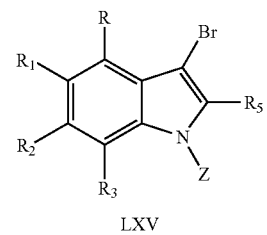

LXV

Compounds of formula I, represented by structure LXVI, can be prepared as shown in Scheme BA.

Compounds of formula BA1 can be iodinated at the 3-position with an electrophilic iodinating agent, e.g., N-iodosuccinimide, (bis-trifluoroacetoxy)iodobenzene, or ICl, in a suitable solvent at temperatures ranging from −78° C. to 100° C. to yield products of structure LXVI.

LIII. Scheme BA

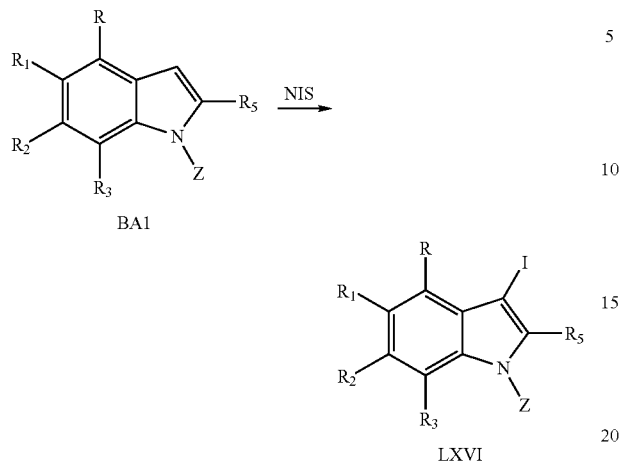

Compounds of formula I, represented by structure LXVII can be prepared as shown in Scheme BB.

3-Iodo- or bromoindoles of structure BB1 can be reacted with acetylenes BB2 in the presence of a palladium catalyst (commonly referred to as the Sonagashira reaction) to give compounds of type LXVII. The coupling reactions can be carried out by methods known to those skilled in the art. A typical set of reaction conditions includes reacting the indole of structure BB1 with an acetylene compound BB2 in the presence of a source of palladium, a copper co-catalyst and an amine and carrying out the reaction at a temperature range of ambient to 150° C.

LIV. Scheme BB

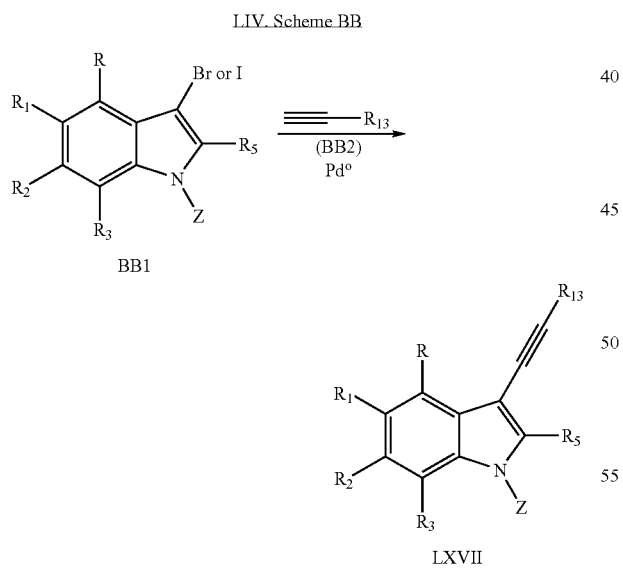

Compounds of formula I, represented by structure LXVIII, can be prepared as shown in Scheme BC.

Compounds of formula BC1 can react with a mixture of POCl$_3$ and DMF at temperatures ranging from ambient to 140° C. to yield 3-carboxaldehydes of structure LXVIII after hydrolysis of the intermediate imminium salt with aqueous NaOH.

LV. Scheme BC

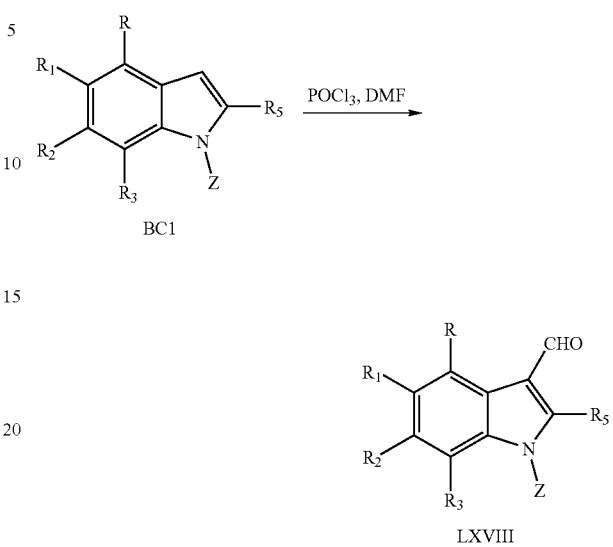

Compounds of formula I, represented by structure LXIX, can be prepared as shown in Scheme BD.

Carboxaldehydes of formula BD1 can be treated with a fluorinating reagent, e.g., (diethylammonium sulfur trifluoride) in a suitable solvent at temperatures ranging from 0° C. to 80° C. to yield compounds of formula LXIX.

Scheme BD

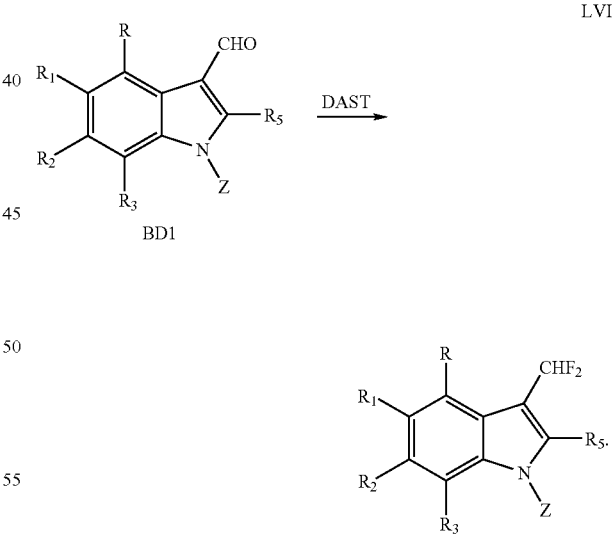

Compounds of formula I, represented by structure LXX, can be prepared as shown in Scheme BE.

Carboxaldehydes of formula BE1 can react with hydroxylamines of structure BE2 in the presence of a suitable polar solvent system and base at temperatures ranging from ambient to 100° C. to yield compounds of formula LXX.

Scheme BE

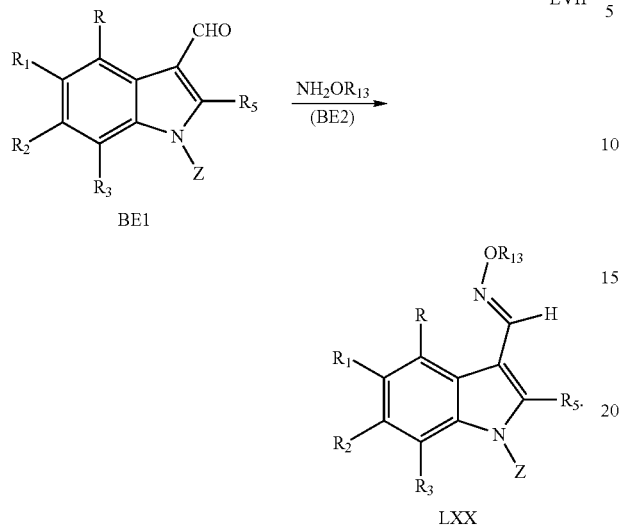

Compounds of formula I, represented by structure LXXI, can be prepared as shown in Scheme BF.

Carboxaldehydes of formula BF1 can react with hydrazines of structure BF2, in the presence of a suitable solvent and base at temperatures ranging from ambient to 100° C. to yield compounds of formula LXXI.

Scheme BF

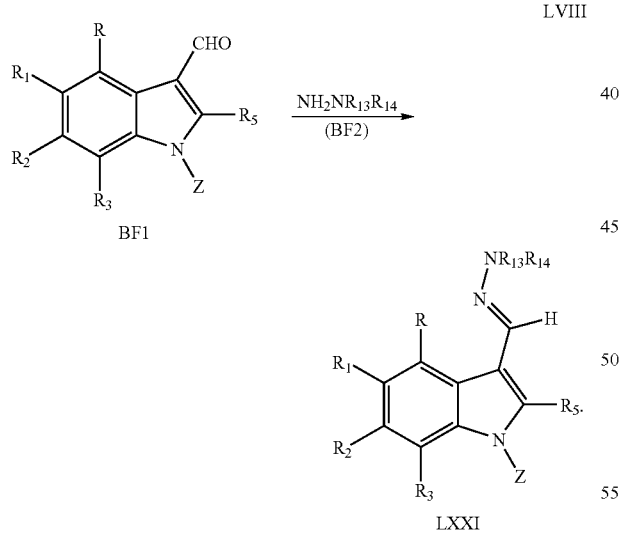

Compounds of formula I, represented by structure LXXII, can be prepared as shown in Scheme BG.

Indolecarboxaldehydes of formula BG1 can be oxidized to carboxylic acids of formula LXXII, using reagents known to those skilled in the art, e.g., KMnO$_4$ or chromic acid. The oxidation can usually be carried out in aqueous or mixed-aqueous/organic solvent systems and carried out at ambient or elevated temperature.

Scheme BG

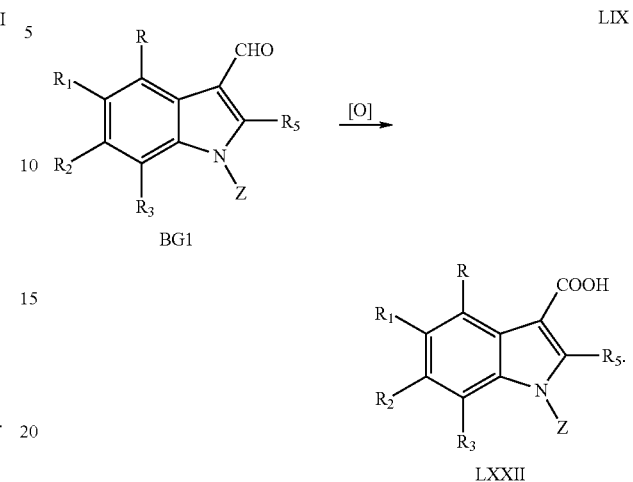

Compounds of formula I, represented by structure LXXIII, can be prepared as shown in Scheme BH.

Carboxylic acids of formula BH1 can be converted to amides by treatment of the carboxylic acid with a suitable activating reagent (thionyl chloride, oxalyl chloride or carbonyldiimidazole) and then treated with amines of formula BH2 to give compounds of formula LXXIII.

Scheme BH

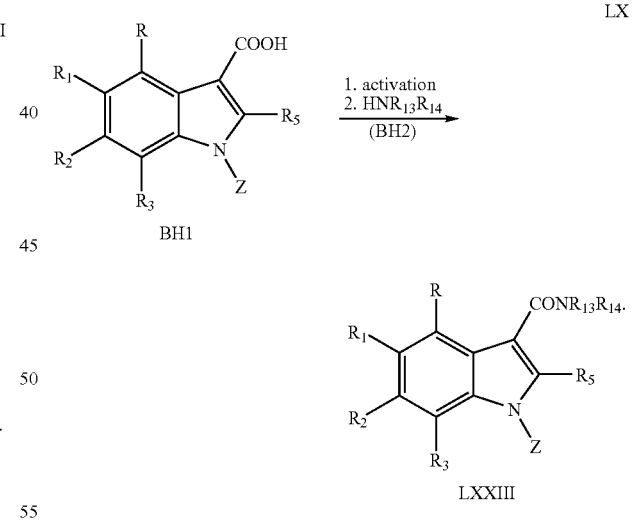

Compounds of formula I, represented by structure LXXIV, can be prepared as shown in Scheme BI.

Carboxylic acids of formula BI1 can be converted to hydrazides and N-alkoxyamides by treatment of the carboxylic acid with a suitable activating reagent (thionyl chloride, oxalyl chloride or carbonyldiimidazole) and then treating the activated carboxylic acids with hydrazines and alkoxylamines of formula BI2 to give compounds of formula LXXIV.

Scheme BI

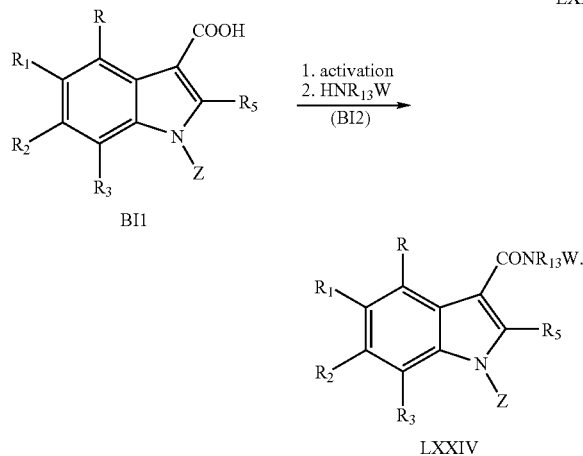

Compounds of formula I, represented by structure LXXV, can be prepared as shown in Scheme BJ.

Carboxaldehydes of formula BJ1 can be treated with the appropriate alkyllithium or Grignard reagent of formula BJ2 at temperatures between −78° C. to ambient temperature in a suitable aprotic solvent to produce secondary alcohols of formula LXXV. An alternative reduction of the carboxaldehydes with an appropriate hydride reducing agent at −78° C. to ambient temperatures can produce primary alcohols of formula LXXV.

Scheme BJ

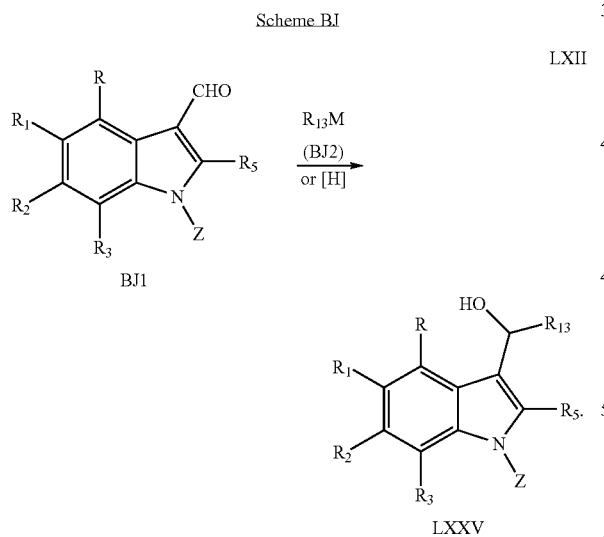

Compounds of formula I, represented by structure LXXVI, can be prepared as shown in Scheme BK.

Compounds of structure BK1 can be sulfonated at the 3-position with sulfur trioxide or some similar sulfuric acid equivalent to produce compounds of formula BK2. Compounds of formula BK2 can be treated with reagents such as, but not limited to, $POCl_3$ at temperatures from 50° C. to 100° C. to convert them into sulfonyl chlorides of formula BK3. Alternatively, treatment of compounds of structure BK1 with reagents such as chlorosulfonic acid can directly afford compounds of structure BK3. Compounds BK3 can react with amines of formula BK4 at ambient temperature in the presence of a suitable base and solvent to produce sulfonamides of formula LXXVI.

Scheme BK

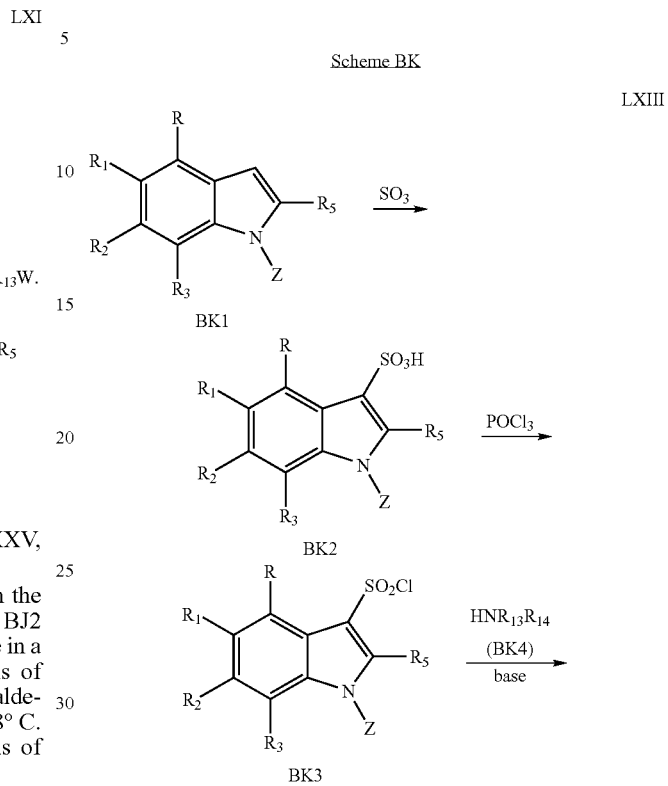

Compounds of formula I, represented by structure LXXVII, can be prepared as shown in Scheme BL.

Iodides or bromides of structure BL1 can be transformed into 3-thioalkyl indoles using an appropriate copper catalyst, e.g., CuI, and a suitable thiol or disulfide. The reaction can generally be carried out at temperatures between ambient and 150° C. to yield compounds of structure BL2. Compounds of structure BL2 can be oxidized to sulfones of formula LXXVII, using oxidizing agents such as, but not limited to, m-CPBA in chloroform at ambient or elevated temperatures.

Scheme BL

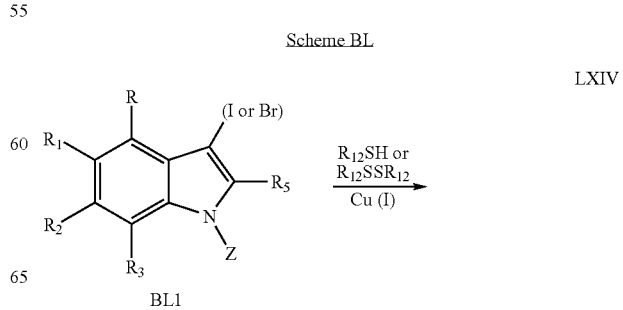

-continued

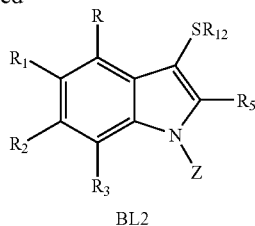
BL2

↓ [O]

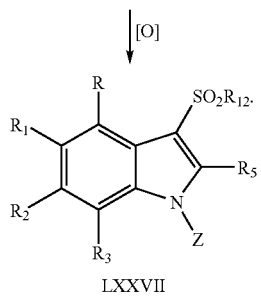
LXXVII

Compounds of formula I, represented by structure LXX-VIII, can be prepared as shown in Scheme BM.

Iodides or bromides of structure BM1 can be transformed into 3-thioalkyl indoles using an appropriate copper catalyst, e.g., CuI, and a suitable thiol or disulfide. The reaction can generally be carried out at temperatures between ambient and 150° C. to yield compounds of structure BM2. Compounds of structure BM2 can be selectively oxidized to sulfoxides of formula LXXVIII, using oxidizing agents such as, but not limited to, sodium periodate in methanol at ambient temperature.

Scheme BM

LXV

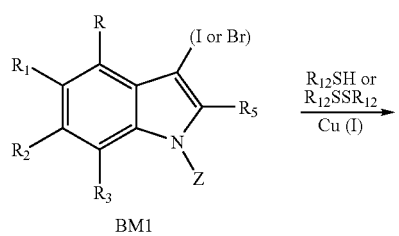
BM1

BM2

↓ [O]

LXXVIII

Compounds of formula I, represented by structure LXXIX, can be prepared as shown in Scheme BN.

Compounds of structure BN1 can be converted to ketones of formula LXXIX via a Friedel-Crafts reaction using an acid chloride of formula BN2. The reaction can typically be carried out in a non-polar solvent such as dichloromethane or $CS_2$ in the presence of a suitable Lewis acid, e.g., $AlCl_3$ or $FeCl_3$ and carried out in a temperature range of 0° C. to 100° C.

Scheme BN

LXVI

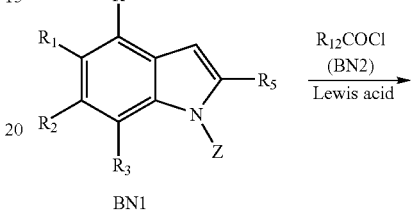
BN1

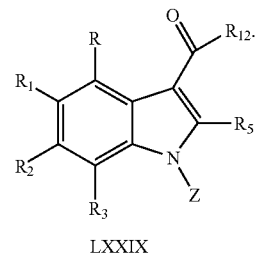
LXXIX

Compounds of formula I, represented by structure LXXX, can be prepared as shown in Scheme BO.

Compounds of structure BO1 can be selectively nitrated at the 3-position using stoichiometric amounts of nitric acid under mild reaction conditions to produce compounds of formula LXXX. These conditions may include, but are not limited to, the use of nitric acid in acetic anhydride at a temperature range of −40° C. to room temperature.

Scheme BO

LXVII

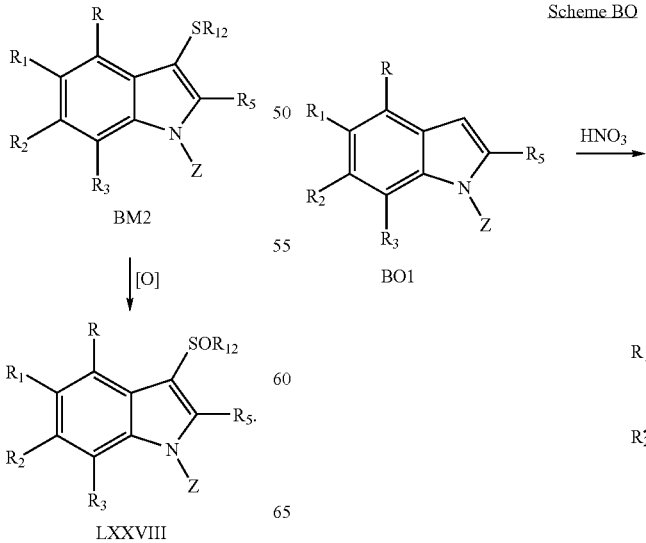
BO1

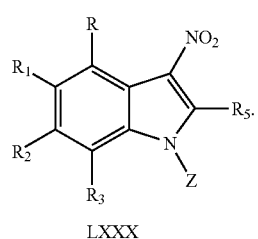
LXXX

Compounds of formula I, represented by structure LXXXI, can be prepared in several ways, as shown in Scheme BP.

3-Nitroindoles of structure BP1 can be reduced to 3-aminoindoles of structure BP2 using any number of standard conditions familiar to chemist skilled in the art, such as hydrogenation or iron reduction. Compounds of formula BP2 can be further elaborated by mono- or di-alkylation of the amino group, using the appropriate alkylating agent, solvent, and base at temperatures ranging from ambient to 150° C. to yield compounds of formula LXXXI.

Alternatively, 3-haloindoles of structure BP3 can undergo Buchwald coupling with mono- or di-alkylamines of formula BP4 in the presence of copper or palladium catalysts, using conditions familiar to chemists skilled in the art, to produce compounds of formula LXXXI.

-continued

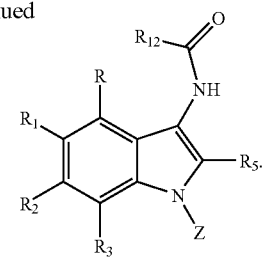

LXXXII

Compounds of formula I, represented by structure LXXXIII, can be prepared as shown in Scheme BR.

3-Aminoindoles of structure BR1 can react with chloroformates or carbonates or dicarbonates of formula BR2 in the presence of a suitable base and solvent at ambient or elevated temperature to yield carbamates of structure LXXXIII. Alternative conditions involve the synthesis of a reactive carbamoyl intermediate of compounds BR1, e.g., by treatment of the amine BR1 with p-nitrophenyl chloroformate or phosgene, followed by reaction of the activated carbamoyl intermediate with alcohols of formula BR3 at temperatures ranging from ambient to 100° C. in a suitable solvent to form carbamates of formula LXXXIII.

Scheme BP

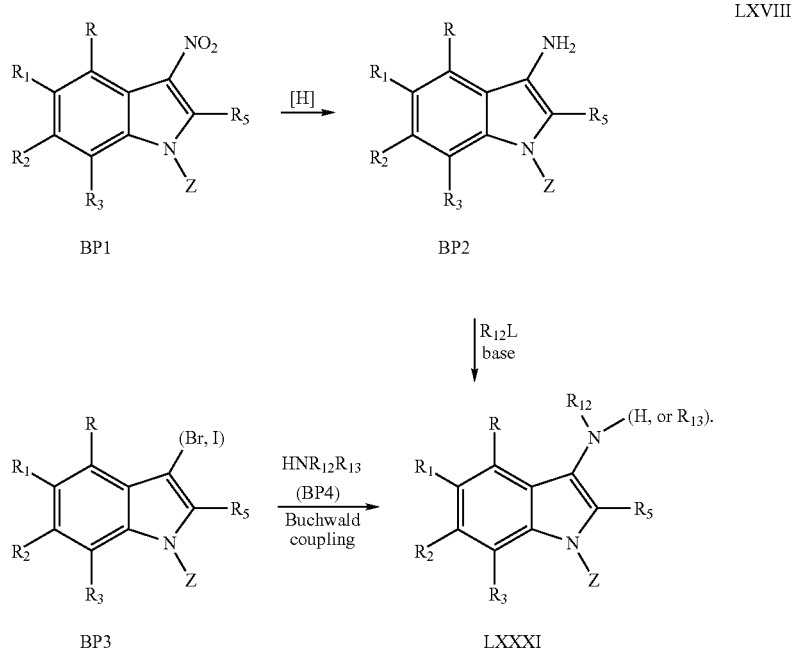

Compounds of formula I, represented by structure LXXXII, can be prepared as shown in BQ.

3-Aminoindoles of structure BQ1 can be reacted with acyl halides or anhydrides of formula BQ2 in the presence of a suitable base and solvent at ambient temperature to yield amides of structure LXXXII.

Scheme BQ

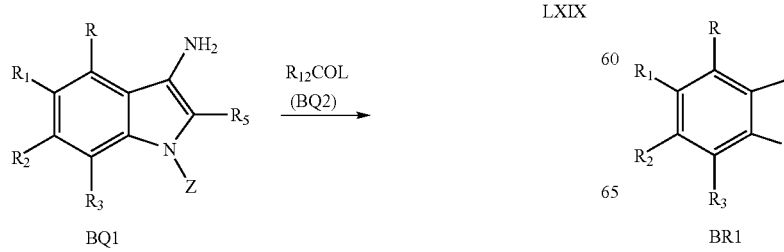

Scheme BR

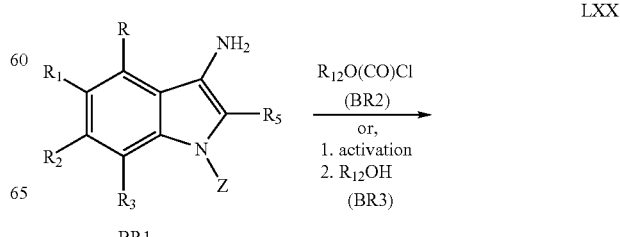

-continued

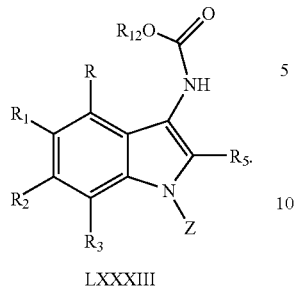

LXXXIII

Compounds of formula I, represented by structure LXXXIV, can be prepared as shown in Scheme BS.

3-Aminoindoles of structure BS1 can react with isocyanates of formula BS2 in the presence of a suitable base and solvent at ambient or elevated temperature to yield ureas of structure LXXXIV. Alternative conditions involve the synthesis of a reactive carbamoyl intermediate of compounds BS1, e.g., by treatment of the amine BS1 with p-nitrophenyl chloroformate or phosgene, followed by reaction of the activated carbamoyl intermediate with amines of formula BS3 at ambient temperature to form ureas of structure LXXXIV.

Scheme BS

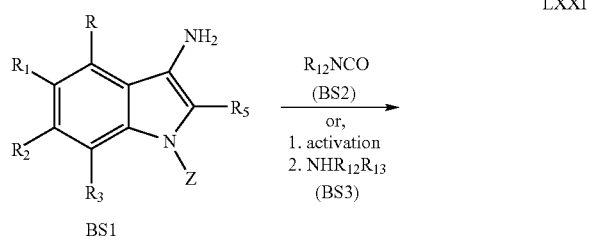

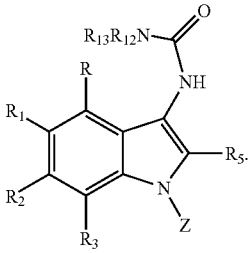

LXXXIV

Compounds of formula I, represented by structure LXXXV, can be prepared as shown in Scheme BT.

3-Aminoindoles of structure BT1 can be reacted with sulfonyl chlorides of formula BT2 in the presence of a suitable base and solvent and reacted at temperatures in the range of −20° C. to 50° C. to yield sulfonamides of structure LXXXV.

Scheme BT

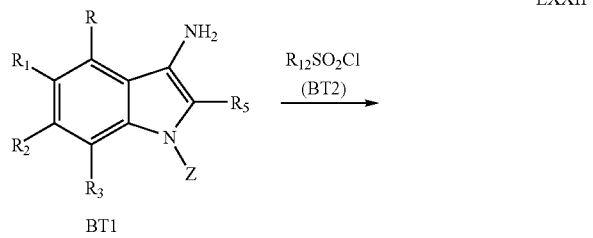

-continued

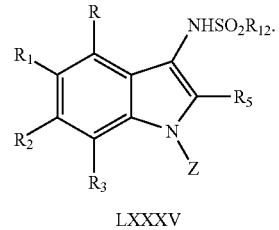

LXXXV

Compounds of formula I, represented by structure LXXXVI can be prepared as shown in Scheme BU.

3-Iodo- or bromoindoles of structure BU1 can be reacted with alkenes BU2 in the presence of a palladium catalyst (commonly referred to as the Heck reaction) to give compounds of structure LXXXVI. The coupling reactions can be carried out by methods known to those skilled in the art. The choice of catalyst and solvents are similar to those described in Scheme AG.

Scheme BU

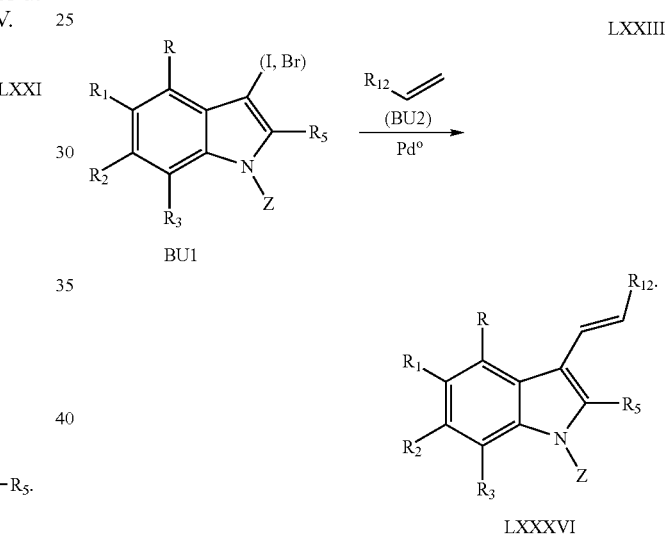

Compounds of formula I, represented by structure LXXXVII can be prepared as shown in Scheme BV.

Hydrazines of structure BV1 can react with 3,3,3-trifluoropropanal to form hydrazone intermediates. Heating the hydrazone intermediates in a suitable solvent and at temperatures from ambient to 150° C. can form indoles of formula BV2. Typically, a Lewis acid catalyst is used, e.g., AlCl$_3$, TiCl$_4$ or ZnCl$_4$. Compounds of formula BV2 can be reacted with a protecting group, e.g., di-tert-butyl dicarbonate, to prepare the Boc derivative BV3. Treatment of compounds of structure BV3 with a strong base, e.g., lithium diisopropyl amide, in an aprotic solvent, e.g., THF or DME at temperatures from −78° C. to ambient temperature, followed by addition of a trialkyl borate can yield compounds BV4 upon hydrolytic workup. Reaction of compounds BV4 with reactive aryl halides or triflates, e.g., BV5 at temperatures in the range of −20° C. to 100° C., in a suitable solvent system containing base and sub-stoichiometric amounts of a palladium catalyst, can give compounds of formula BV6. Proteolytic cleavage of the Boc group of compounds of type BV6 can give compounds of structure BV7. The indole BV7 can be alkylated in the presence of a suitable alkylating agent and base in a suitable solvent at temperatures ranging from 0° C. to 150° C. to yield indoles of formula LXXXVII.

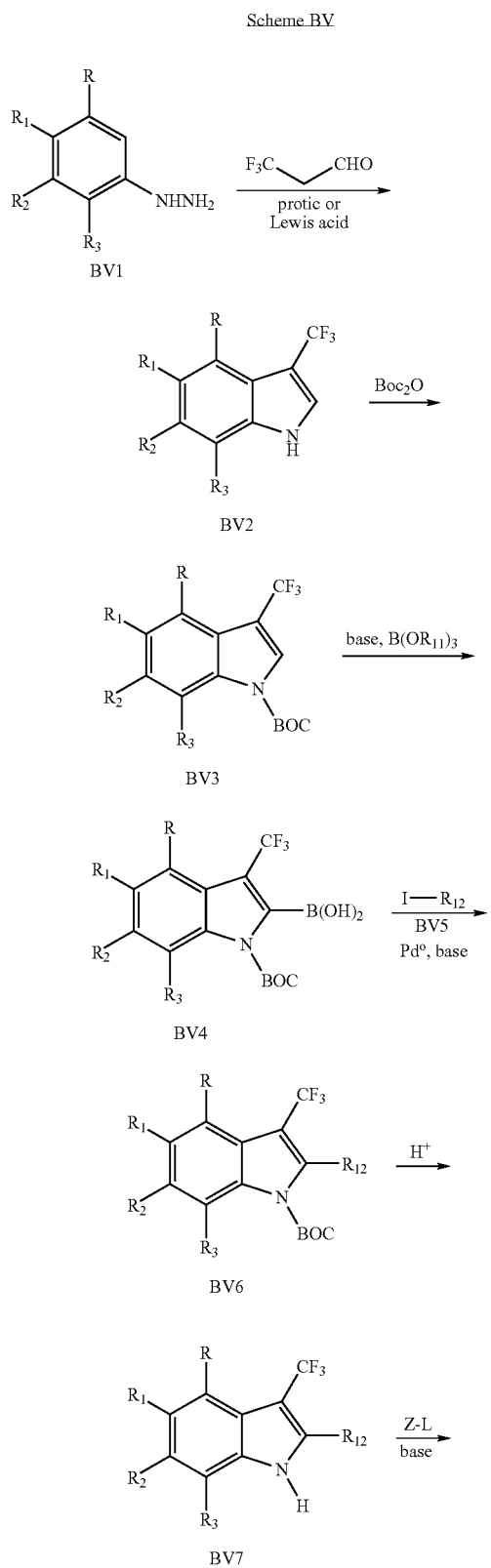

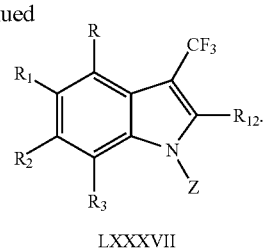

LXXXVII

Compounds of formula I, represented by structure LXXX-VIII can be prepared as shown in Scheme BW.

Compounds of structure BW1 are commercially available, or can be prepared by well-known methodology, e.g., from the hydrolysis of substituted phenylacetonitriles. BW1 can then be activated, e.g., using peptide coupling reagents, or converted to an acid halide, and then reacted with amines (BW2) to provide substituted acetamides BW3. Compounds of type BW3 can undergo cyclization in the presence of a base, such as potassium carbonate or sodium hydride, and a catalyst, such as CuI or CuBr to form compounds of structure BW4. Reduction of compounds BW4 with a reducing agent, such as DIBALH or lithium aluminum hydride can furnish indoles of type BW5. Compounds of type BW5 can then be cyanated with a reagent such as chlorosulfonyl isocyanate (BW6) to afford compounds of type BW7. Treatment of compounds BW7 with a base, e.g., lithium diisopropyl amide in a solvent such as THF or DME and a trialkyl borate can give a 2-indolylboronic acid intermediate. Reaction of the 2-indolylboronic acid intermediate with a group L-$R_{12}$ in the presence of a palladium catalyst can afford compounds of structure LXXXVIII.

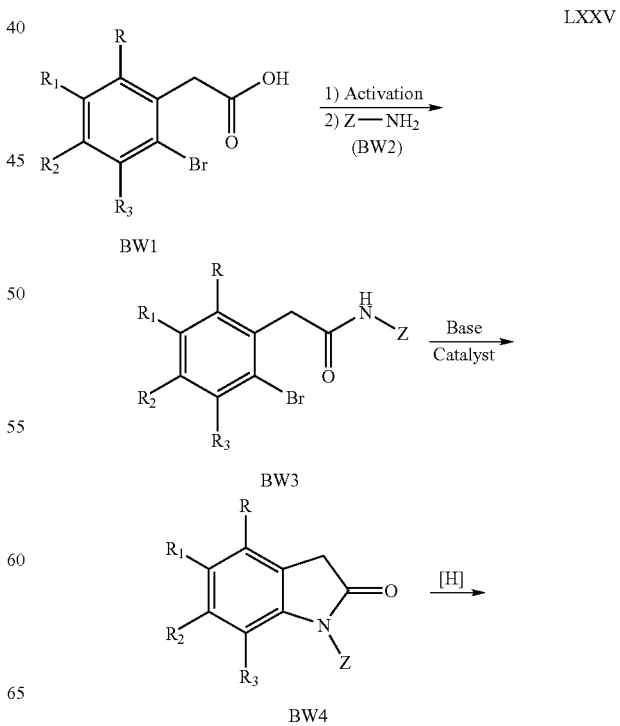

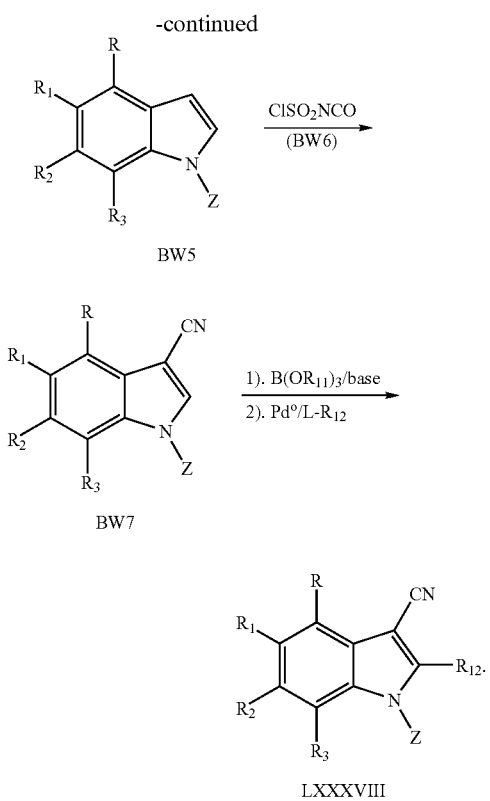

Compounds of formula I, represented by structure LXXXIX can be prepared as shown in Scheme BX.

Indoles BX1 can be cyanated with an appropriate cyanating agent, e.g., chlorosulfonyl isocyanate (BX2) or a dialkyl phosphoryl isocyanate in a suitable solvent or solvent mixture, e.g. DMF, CH$_3$CN or dioxane, and carrying out the reaction at or above ambient temperature to afford compounds of structure BX3. Treatment of BX3 with a reactive functional group Z containing a suitable leaving group L (BX4) can give compounds of structure BX5. L can represent a halide, particularly chloro, bromo or iodo or an alkylsulfonate. The reaction between BX3 and BX4 can be carried out in a suitable solvent in the presence of an inorganic base such as potassium carbonate or sodium hydride or an organic base such as a trialkylamine to afford compounds of formula BX5.

Compounds of structure BX5 can be converted to indolyl-2-boronic acids BX6. Typically, a strong base, such as lithium diisopropylamide or lithium or potassium hexamethyldisilazide is employed in a suitable unreactive solvent, e.g., ether or THF, or solvent mixtures containing them. The reaction is typically carried out in the range of −78° C. to ambient temperature. Quenching with a trialkylborate derivative can give the indolyl-2-boronic acid BX6. Reaction of the indolyl-2-boronic acid BX6 with an aryl or heteroaryl halide BX7 (commonly referred to as a Suzuki reaction) can give the compounds of structure BX8. The coupling reactions are carried out by methods known to those skilled in the art and include conducting the reaction in the presence of a catalyst, such as 1,1'-bis(diphenylphosphino)ferrocene palladium(II) dichloride dichloromethane complex. The reactions are carried out in a suitable solvent, e.g., DMF, toluene, dimethoxyethane or dioxane at a temperature range of ambient to 150° C. in the presence of a base. The base can be in aqueous solution, e.g., aqueous sodium carbonate or sodium bicarbonate, or the base can be employed under anhydrous conditions, e.g., cesium or potassium fluoride.

Compounds BX8 can be de-methylated to give compounds of structure BX9. Suitable de-methylating reagents can include, but are not limited to boron tribromide, boron trichloride or iodotrimethylsilane in a variety of organic solvents, such as methylene chloride. Indoles of structure BX9 can be alkylated with an electrophile, L(CH$_2$)$_n$OP (BX10), to give compounds of structure BX11. L can represent a halide, particularly chloro, bromo or iodo or an alkylsulfonate. N can be equal 2, 3 or 4. P can represent any acid-labile protecting group, such as tert-butyldimethylsilyl, triethylsilyl or tetrahydropyranyl. The reaction can be conducted in a suitable solvent, e.g., THF, CH$_2$Cl$_2$ or DMF, within a temperature range of 20° C. to 100° C. A base, e.g., an inorganic base, such as potassium or cesium carbonate or an organic base, such as a trialkylamine can be used to remove the acid formed in the reaction. Compounds BX11 can be deprotected to give compounds of structure BX12. Suitable deprotecting reagents can include, but are not limited to any mild organic acid, such as para-toluenesulfonic acid or pyridinium para-toluenesulfonate or an inorganic acid, such as acetic or hydrochloric acid in a variety of organic solvents, such as methylene chloride, THF or methanol.

Oxidation of compounds BX12 to carboxylic acids with structure BX13 can be accomplished with various oxidating reagents such as potassium permanganate or pyridinium dichromate. Compounds of type BX13 can then be activated and treated with amines of type BX14 to form compounds of structure LXXXIX. Activation of the carboxylic acid can be carried out by any of the standard methods. For example, the acid BX13 can be activated with coupling reagents such as EDCI or DCC with or without HOBt in the presence of the amine BX14, or alternatively the acid can be activated as the acid chloride by treatment of the acid with, e.g., thionyl chloride or oxalyl chloride or as the acyl imidazolide, obtained by treatment of the acid with carbonyl diimidazole, followed by treatment of the amine BX14.

Scheme BX

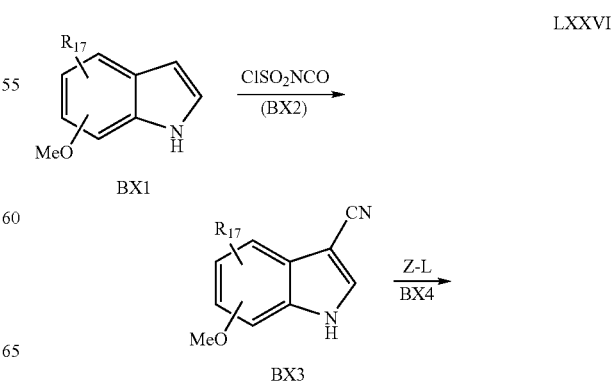

-continued

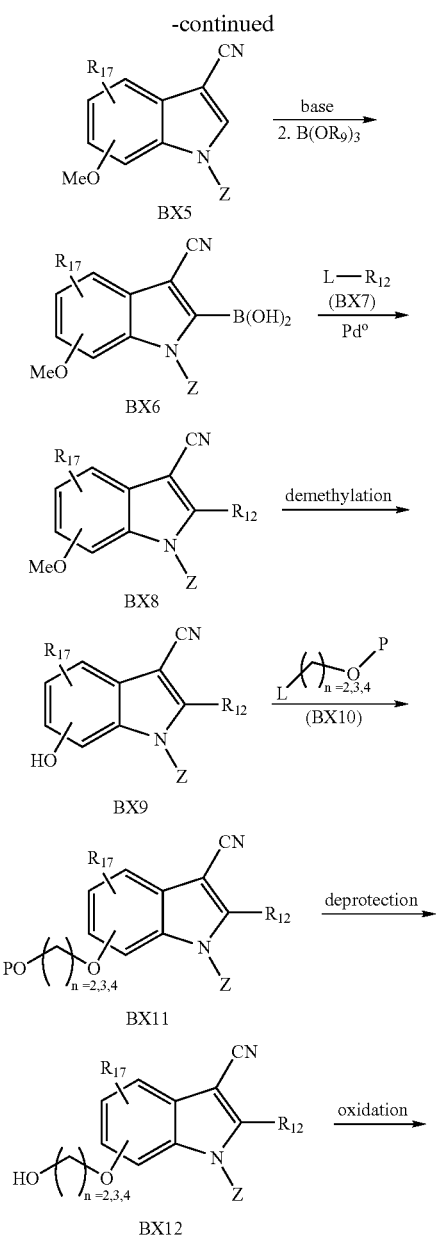

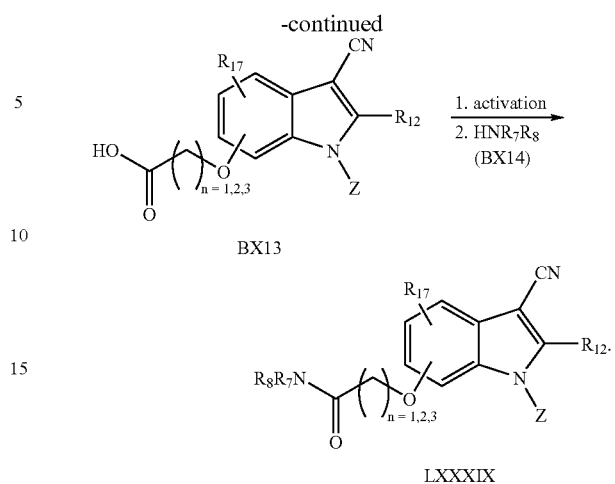

Compounds of the present invention represented by structure XC and XCI can be prepared by the methodology depicted in Scheme BY below, wherein p is an integer between 2 and 6.

A compound of formula BY1 is treated with a reagent of structure BY2, wherein L and L' represent leaving groups (halogen, arylsulfonate, etc.) and can be the same or different. If different, the more reactive of the two will be displaced by the phenol oxygen atom to give compound BY3. Conditions for this reaction include solvents such as, but not limited to, acetonitrile, acetone, 2-butanone or dimethylformamide; bases such as sodium carbonate, potassium carbonate, cesium carbonate, tertiary amine bases or sodium hydride; and reaction temperatures from ambient to the reflux temperature of the chosen solvent. The remaining leaving group in this molecule may be displaced by a reagent of formula $R_{18}SH$ (BY4), wherein $R_{18}$ may be alkyl, aryl or heteroaryl to give compounds of structure XC. The conditions for this reaction may be similar but not necessarily the same as used for the transformation of BY1 to BY3.

Oxides of the resulting sulfide group in compound XC may be prepared, utilizing oxidizing reagents, such as m-chloroperbenzoic acid, potassium permanganate, potassium peroxymonosulfate or dimethyldioxirane, in stoichiometries chosen to optimize the particular oxidation state, using solvents such as dichloromethane, ethanol, methanol or acetone, and at temperatures ranging from −30° C. to 120° C. to afford compounds of structure XCI.

Scheme BY

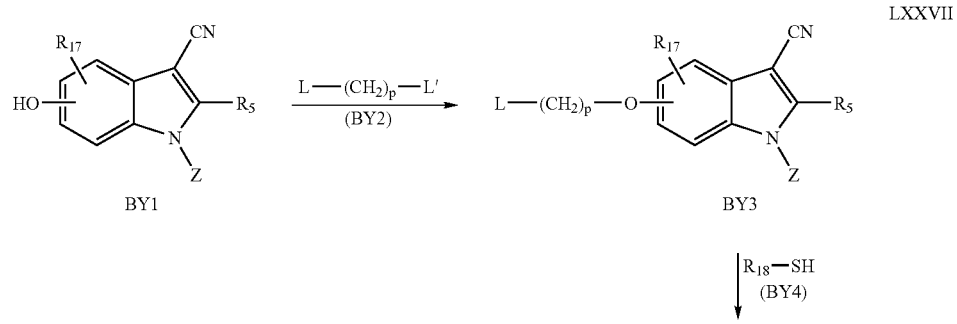

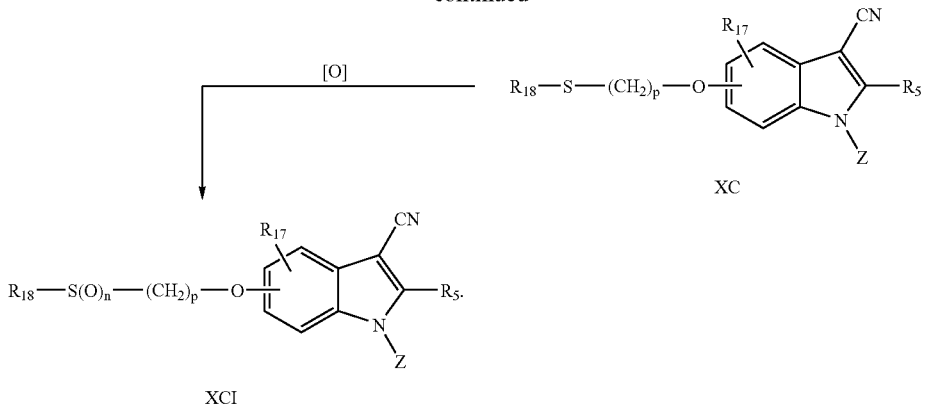

Compounds of this invention represented by structure XCII can be prepared by the methodology depicted in Scheme BZ below, wherein p is 1-6:

A compound of formula BZ1 is treated with a reagent of structure BZ2, wherein L and L' represent leaving groups (halogen, arylsulfonate, etc.) and can be the same or different. The resulting compounds of formula BZ3 may be alkylated by an amine of formula $R_{18}R_{19}NH$ to prepare compounds of formula XCII. Conditions for this alkylation reaction may include solvents such as ethanol, tetrahydrofuran or dimethylformamide. The presence of a basic reagent, such as pyridine, diisopropylethylamine or potassium carbonate, may be utilized.

Scheme BZ

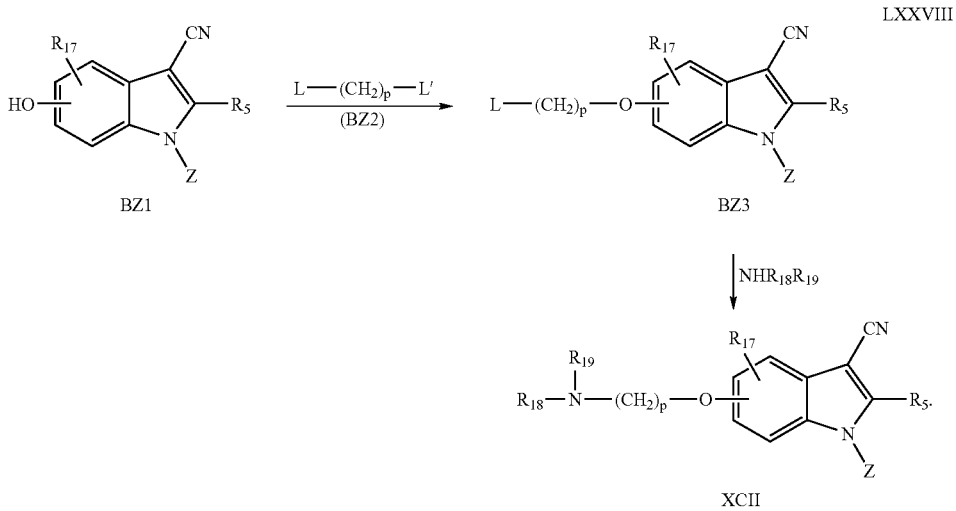

Compounds of this invention represented by structure XCIII can be prepared by the methodology depicted in Scheme CA below.

A phenol compound, CA1, can be reacted with an alkylating agent CA3, which can be derived from a compound of structure CA2. Compounds of structure CA2, wherein Rig taken together with the hydroxyl-bearing carbon atom to which $R_{19}$ is attached, represent a 4-7 membered ring. Such atoms may be all carbon, but may also include up to two heteroatoms, chosen from N, O, S or $SO_2$. A reagent of the formula CA2 may be purchased from commercial sources or be prepared by means familiar to those skilled in the art of organic synthesis and is then converted to compounds of structure CA3, wherein L represents a leaving group. Compound CA3 is then used in an alkylation reaction with the phenol compound CA1, employing the usual alkylation reaction conditions discussed above, to give the compound of formula XCIII.

Scheme CA

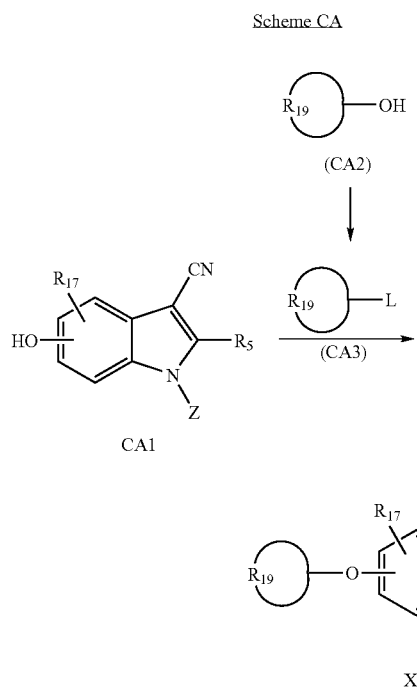

Compounds of this invention represented by structure XCIV and XCV can be prepared by the methodology depicted in Scheme CB below.

Compounds of structure CB1 can be prepared starting from bromo-substituted indoles using the methodology discussed elsewhere in this invention (introduction of the Z group, installation of the cyano group at C-3 of the indole ring, and cross-coupling of the indole with an aryl reagent to give the corresponding 2-aryl group). Alternatively, the bromide may be introduced at a later stage by bromination of the indole ring, employing brominating reagents such as bromine, N-bromosuccinimide or HOBr. The bromide compound can be then subjected to a metal-halogen exchange reaction to generate an organometallic compound CB2, which is not isolated but taken on directly to the next reaction, wherein M is a metal atom such as magnesium or lithium. Organomagnesium reagents may be prepared from aryl bromides by treating with magnesium metal in refluxing ether-like solvents, or treatment with other organomagnesium reagents such as isopropyl magnesium chloride. Organolithium reagents may be prepared from aryl bromides by treating with lithium metal in refluxing solvents, or by treatment with other organolithium reagents such as sec- or tert-butyllithium. The metallated indole may then be treated in situ with a thionating reagent to afford compounds such as XCIV or CB3. If the group $R_{18}$—$(CH_2)_p$— is relatively simple, it may prove convenient to employ a reagent of the structure $R_{18}$—$(CH_2)_p$—S—S—$(CH_2)_p$—$R_{18}$, which will give sulfide compound XCIV directly. Otherwise, it may be more efficient to react compound CB2 with a reagent such as atomic sulfur ($S_8$), which will afford a thiol compound CB3. The thiol group may be alkylated with a reagent of structure CB4, where L represents a suitable leaving group. Typical alkylation conditions known to those skilled in the art can be employed.

Oxides of the resulting sulfide group in compound XCV can be prepared using oxidizing reagents, such as m-chloroperbenzoic acid, potassium permanganate, potassium peroxymonosulfate or dimethyldioxirane in stoichiometries chosen to optimize the particular oxidation state desired, in solvents such as dichloromethane, ethanol, methanol or acetone, and at temperatures ranging from –30° C. to 120° C.

Scheme CB

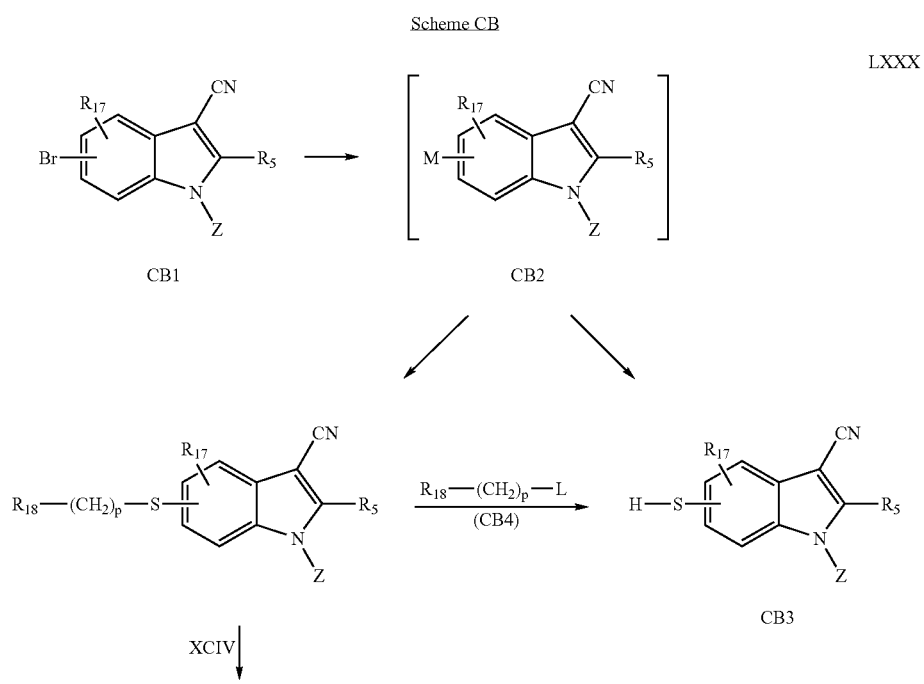

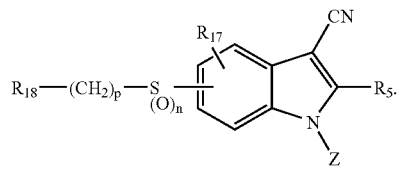

XCV

-continued

Compounds of this invention represented by structures XCVI and XCVII can be prepared by the methodology depicted in Scheme CC below.

A compound of formula CC1 may be nitrated at the indole C-5 position with reagents such as concentrated nitric acid optionally with solvents such as acetic acid or sulfuric acid. The resulting nitro group in compound CC2 may be reduced to the amino compounds of structure CC3 with the use of reducing reagents such as hydrogen (with a catalyst such as palladium on carbon), tin dichloride (in the presence of HCl), sodium thiosulfate (in the presence of ammonia) or iron powder. The amino and hydroxyl groups of compound CC3 may be used to construct a ring; for example, cyclocondensation of CC3 with a reagent CC4, such as phosgene, carbonyldiimidazole or trichloromethyl chloroformate in the presence of a basic reagent to afford compounds of structure CC5. Alternatively, reacting compounds of structure CC3 with compounds of structure CC6 in the presence of a base gives compounds of structure CC7. Compounds CC5 and CC7 can be alkylated with groups of structure L-$R_{21}$ to give compounds XCVI and XCVII.

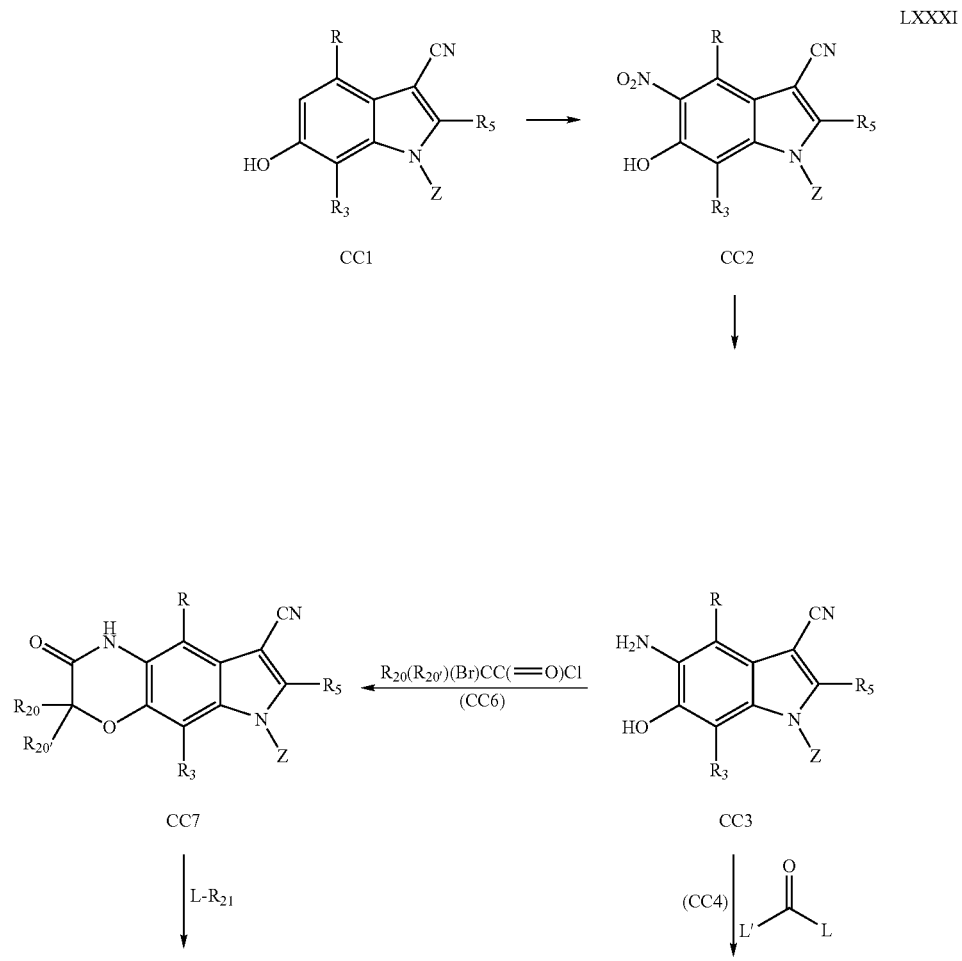

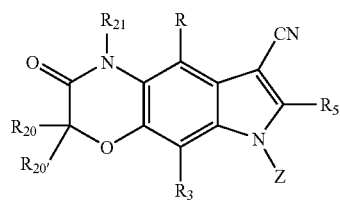

XCVII

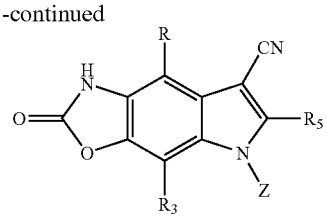

CC5

↓ L-R21

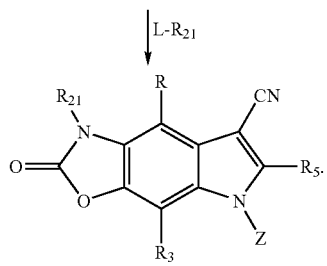

XCVI

Compounds of this invention represented by structures CXVIII, XCIX and C can be prepared by the methodology depicted in Scheme CD, below.

Commercially available 5,6-dihydroxyindole may be protected on the phenol groups with group P to give compound CD1. Suitable protecting groups include e.g., tert-butyldimethylsilyl, benzyl, or tetrahydropyranyl, and their synthesis and subsequent removal are well known to those skilled in the art. Functionalization of the indole nitrogen to give compound CD2, followed by cyanation of CD2 to give CD3, and aryl cross-coupling of CD3 to give CD4 have been discussed elsewhere in this invention. The protecting groups on the phenol oxygen atoms may then be removed, and the oxygens used in various cyclocondensation reactions. For example, reaction with a reagent of structure CD6 in the presence of a suitable base can afford the dioxanyl-fused ring system of compound XCIX. Treatment of CD5 with phosgene or a phosgene equivalent (CD7) can give compounds of structure XCVIII. Condensation of CD5 with ketones of formula CD8 or ketal derivatives of the ketone CD8 can afford the cyclic ketal compounds of structure C.

Scheme CD

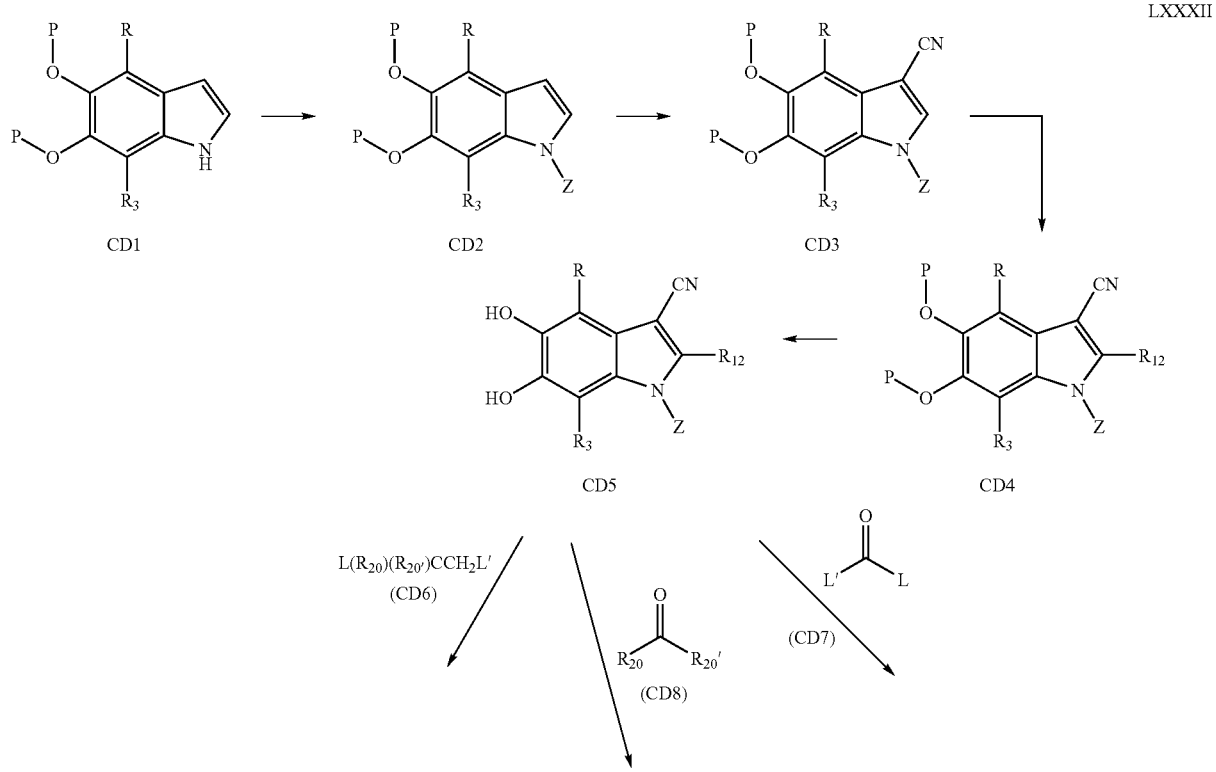

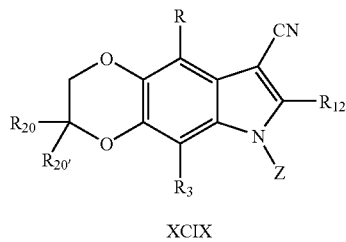

XCIX

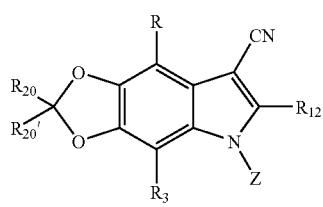

C

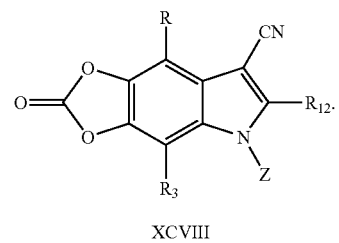

XCVIII

Compounds of formula I, represented by structure CI can be prepared by the methodology depicted in Scheme CE below.

Treatment of CE1 with a reactive heteroaryl group containing a leaving group L in a suitable solvent, with or without heat in the presence of a base, such an inorganic base, e.g., sodium or potassium carbonate or an organic base, e.g., a trialkylamine, can afford the compound of structure CI. The leaving group L can be a halide, particularly choro, bromo or iodo. $R_{18}$ can be an alkyl, aryl or heteroaryl group.

Scheme CE

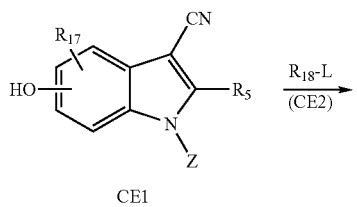

CE1

LXXXIII

CI

Compounds of formula I, represented by structure CII can be prepared by the methodology depicted in Scheme CF below.

Treatment of CF1 with the compound CF2 containing leaving groups L and L' in a suitable solvent, with or without heat in the presence of a base, such an inorganic base, e.g., sodium or potassium carbonate or an organic base, e.g., triethylamine, can afford the compound of structure CF3. L and L' independently represent a leaving group, including but are not limited to halogens (e.g., chlorine, bromine or iodine) or alkyl or arylsulfonates, and p is an integer between 1 and 6. The reactive heterocycle or heteroaryl compound CF4 can be reacted with the compound CF3 in a suitable solvent, with or without heat in the presence of a base, such an inorganic base, e.g., sodium or potassium carbonate or an organic base, e.g., triethylamine, diisopropylamine, to afford the compound of structure CII.

Alternatively, the compound CF1 can be treated with a reactive compound CF5 containing a suitable leaving group L as described above to afford the compound of structure CII.

Scheme CF

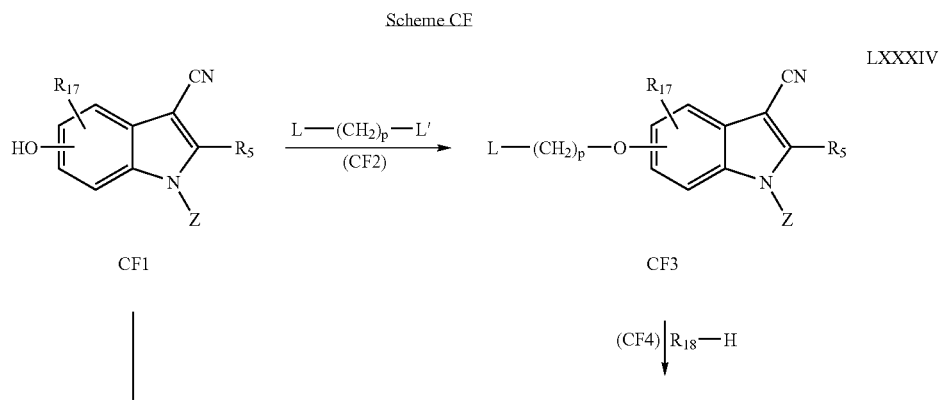

LXXXIV

-continued

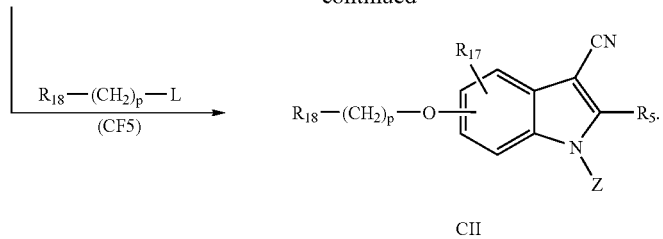

CII

Compounds of formula I, represented by structure CIII can be prepared by the methodology depicted in Scheme CG below:

Indoles CG1 can be cyanated with an appropriate cyanating agent, e.g., chlorosulfonyl isocyanate (CG2) or a dialkyl phosphoryl isocyanate in a suitable solvent or solvent mixture, e.g. DMF, $CH_3CN$ or dioxane, carrying out the reaction at a temperature between $-20°$ C. and $80°$ C. to afford compounds of structure CG3. The compounds CG3 can then be reacted with a reactive functional group Z containing a suitable leaving group L (CG4) as described previously to afford the compound CG6. Alternatively, compound CG1 can be reacted with a reactive functional group Z containing a suitable leaving group L to give compounds of structure CG5, which can then be cyanated as above to give compounds of formula CG6.

Compounds of structure CG6 can be converted to indolyl-2-boronic acid CG7. Typically, a strong base, such as lithium diisopropylamide or lithium or potassium hexamethyldisilazide is employed in a suitable unreactive solvent, e.g., ether or THF, or solvent mixtures containing them. The reaction is typically carried out in the range of $-78°$ C. to ambient temperature. Quenching with a trialkylborate derivative can give the indolyl-2-boronic acid CG7. Reaction of indolyl-2-boronic acid CG7 with aryl or heteroaryl halide CG8 (commonly referred to as a Suzuki reaction) can give the compounds of structure CG9. The coupling reactions are carried out by methods known to those skilled in the art and include conducting the reaction in the presence of a catalyst, such as 1,1'-bis(diphenylphosphino)ferrocene palladium (II) dichloride dichloromethane complex. The reactions are carried out in a suitable solvent, e.g., DMF, toluene, dimethoxy ethane or dioxane at a temperature range of ambient to $150°$ C. in the presence of a base. The base can be in aqueous solution, e.g., aqueous sodium carbonate or sodium bicarbonate, or the base can be employed under anhydrous conditions, e.g., cesium or potassium fluoride.

Indole-carboxylic esters CG9 can be converted to indole-carboxylic acids CG10 by treatment of compounds of structure CG9 with, for example, either acid or base in aqueous or mixed aqueous-organic solvents at ambient or elevated temperature or by treatment with nucleophilic agents, for example, boron tribromide or trimethylsilyl iodide, in a suitable solvent. Compounds of type CG10 can then be activated and treated with amines of type CG11 to form compounds of structure CIII. Activation of the carboxylic acid can be carried out by any of the standard methods. For example, the acid CG10 can be activated with coupling reagents such as EDCI or DCC with or without HOBt in the presence of the amine CG11, or alternatively the acid can be activated as the acid chloride by treatment of the acid with, e.g., thionyl chloride or oxalyl chloride or as the acyl imidazolide, obtained by treatment of the acid with carbonyl diimidazole, followed by treatment with amines CG11.

Scheme CG

LXXXV

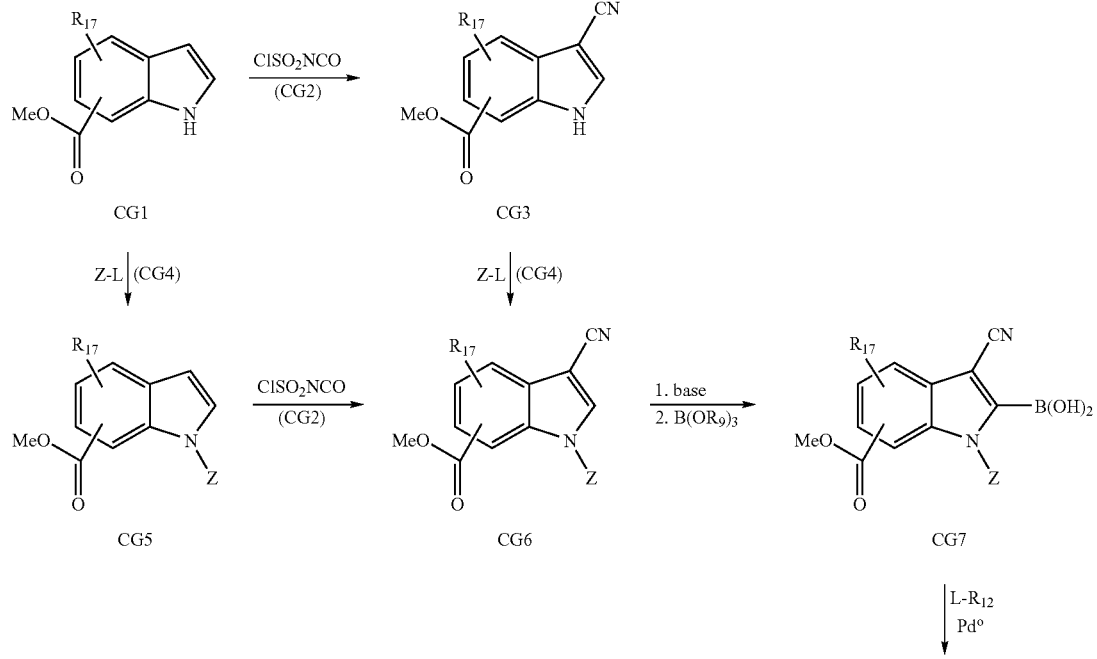

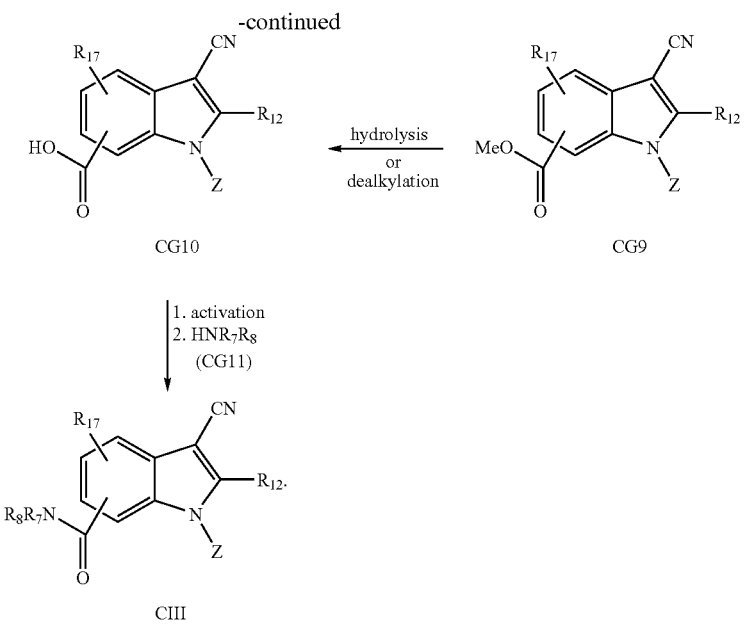

Compounds of formula I, represented by structure CWV can be prepared as shown in Scheme CH.

Compounds of formula CH1 can be reduced at the 6-ester group to give 6-hydroxymethyl indoles CH2. The reduction reaction can be carried out using a hydride regent such as lithium borohydride, in an ethereal solvent such as THF, ethyl ether or DME at temperatures ranging from ambient to reflux to give the alcohol CH2. The benzylic alcohol group in CH2 can be converted to a leaving group L (halogen, aryl sulfonate or alkyl sulfonate) by treatment with reagents such as thionyl chloride, phosphorous trichloride, thionyl bromide, methane sulfonyl chloride or toluenesulfonyl chloride in a solvent such as but not limited to dichloromethane, 1,2-dichloroethane or chloroform. The leaving group L in compounds of formula CH3 can be displaced by a reagent of formula $R_{18}H$ to afford compounds of formula CIV, wherein $R_{18}$ maybe a heterocycle or a heteroaryl compound. Conditions for this reaction include solvents such as but not limited to acetonitrile, tetrahydrofuran, dimethylformamide or dimethyl sulfoxide; bases such as potassium carbonate, cesium carbonate or sodium hydride; and reaction temperatures ranging from ambient to reflux.

Scheme CH
LXXXVI

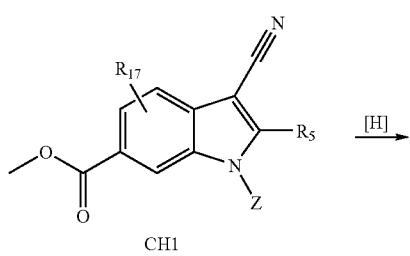

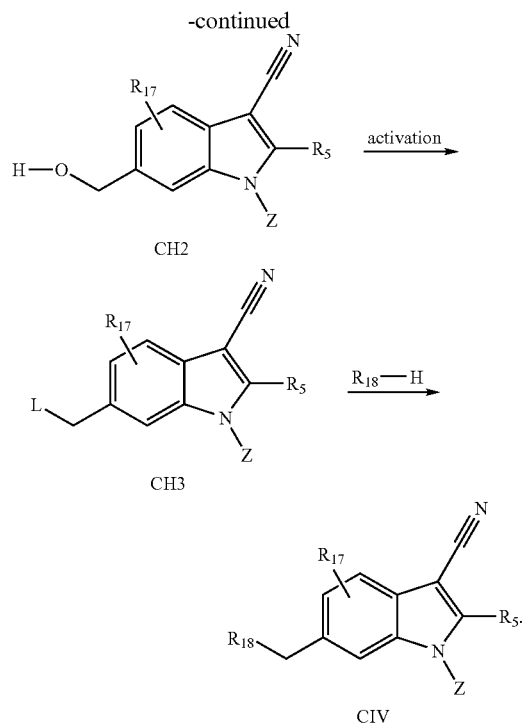

Compounds of formula I, represented by structure CV can be prepared as shown in Scheme CI Compounds of formula CI1 in which V represents bromide or iodide, can undergo reaction with alkyl vinyl ethers such as ethyl vinyl ether in the presence of palladium catalysts such as but not limited to palladium acetate, palladium (tetrakis) triphenylphosphine, in solvents such as but not limited to dimethyl formamide or dimethoxyethane to give the addition products of formula CI2. Vinyl ethers of formula CI2 can be hydrolyzed to aldehydes of formula CI3 using aqueous acids, such as but not limited to, hydrochloric acid, sulfuric acid or acetic acid. Compounds of formula CI3 can be reduced to the alcohol using hydrides such as lithium borohydride or sodium borohydride, in solvents such as methanol or tetrahydrofuran to give primary alcohols CI4.

The alcohol group in CI4 can be converted to a leaving group L (halogen or aryl sulfonate or alkyl sulfonate) by treatment with reagents such as thionyl chloride, phosphorous trichloride, thionyl bromide, methane sulfonyl chloride or toluenesulfonyl chloride in a solvent such as but not limited to dichloromethane, 1,2-dichloroethane or chloroform. The leaving group L in compounds of formula CI5 can be displaced by a reagent of formula $R_{18}H$ to afford compounds of formula CV, wherein $R_{18}$ maybe a heterocycle or a heteroaryl group. Conditions for this reaction include using solvents such as but not limited to acetonitrile, tetrahydrofuran, dimethylformamide or dimethyl sulfoxide; bases such as potassium carbonate, cesium carbonate or sodium hydride; and reaction temperatures ranging from ambient to reflux.

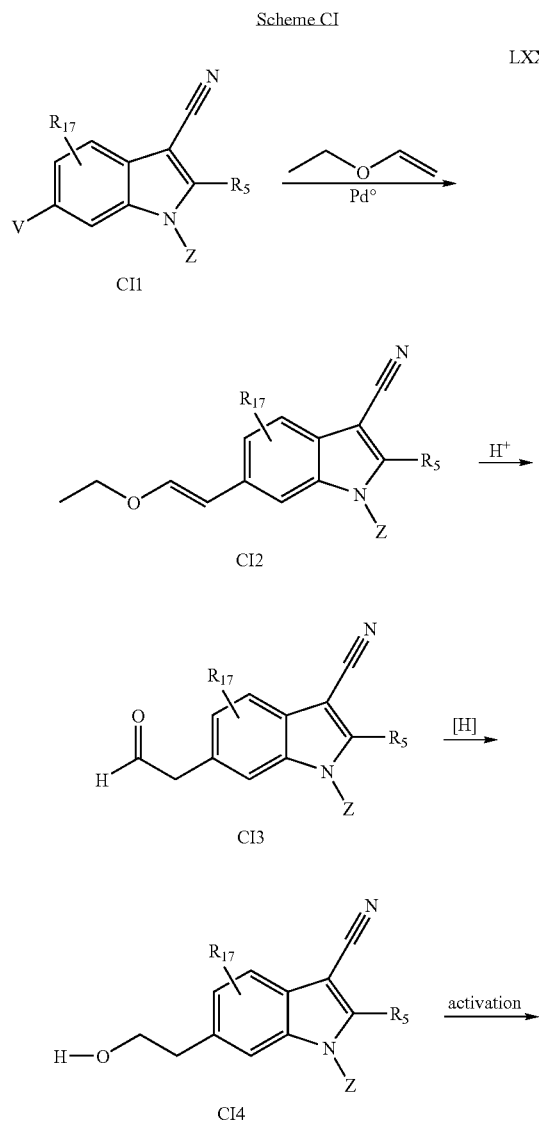

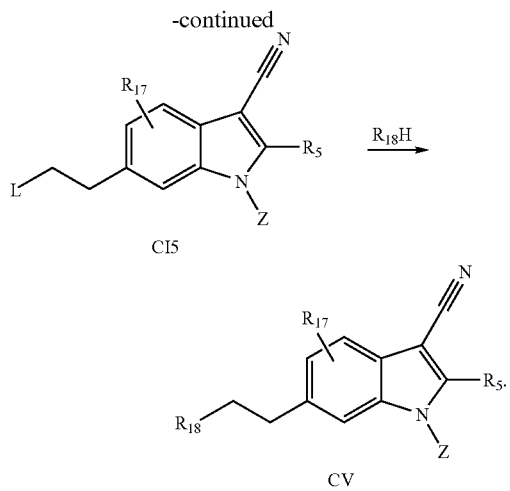

Compounds of formula I, represented by structure CVI can be prepared as shown in Scheme CJ.

Compounds of formula CJ1 in which V represents iodine or bromine, can undergo reaction with acrylic esters in the presence of palladium catalysts such as palladium acetate, palladium (tetrakis)triphenylphosphine or palladium (bis)-triphenylphosphinedichloride, and ligands such as triphenylphosphine or tri-ortho-tolylphosphine, in solvents such as but not limited to, dimethyl formamide, dimethoxyethane or toluene to give compounds of structure CJ2. Hydrogenation of compounds of type CJ2 can give products of type CJ3 by addition of hydrogen in the presence of a catalyst such a palladium or platinum in a solvent such as, but not limited to, methanol, ethanol or acetic acid at pressures ranging from 1-5 atmospheres. Reduction of the ester group in compounds CJ3 can be accomplished using hydride reagents such as lithium borohydride to give the alcohols CJ4. Conversion of the alcohol in CJ4 to a leaving group L (halogen or aryl sulfonate or alkyl sulfonate) can be accomplished by treatment with reagents such as thionyl chloride, phosphorous trichloride, thionyl bromide, methane sulfonyl chloride or toluenesulfonyl chloride in a solvent such as but not limited to dichloromethane, 1,2-dichloroethane or chloroform. The leaving group L in compounds of formula CJ5 can be displaced by a reagent of formula $R_{18}H$ to afford compounds of formula CVI, wherein $R_{18}$ maybe a heterocycle or a heteroaryl group. Conditions for this reaction include solvents such, as but not limited to, acetonitrile, tetrahydrofuran, dimethylformamide or dimethyl sulfoxide; bases such as potassium carbonate, cesium carbonate or sodium hydride; and reaction temperatures ranging from ambient to reflux.

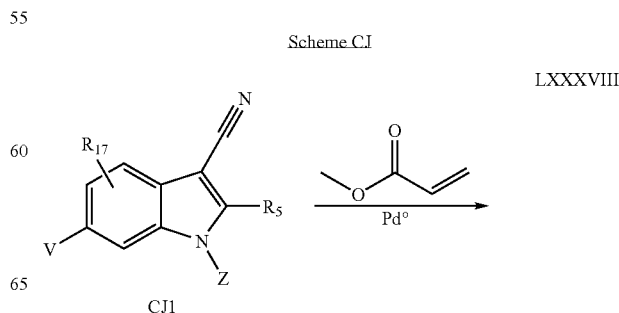

-continued

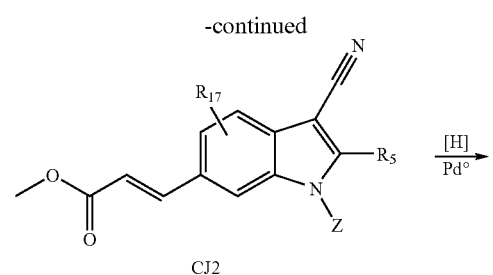
CJ2

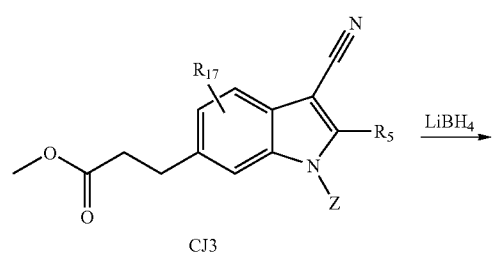
CJ3

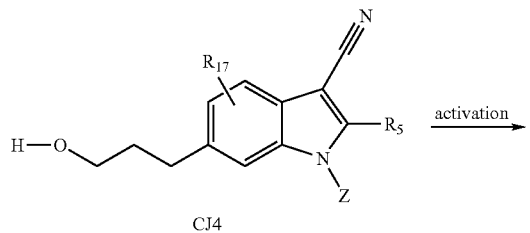
CJ4

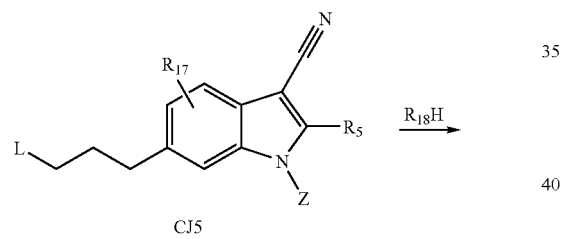
CJ5

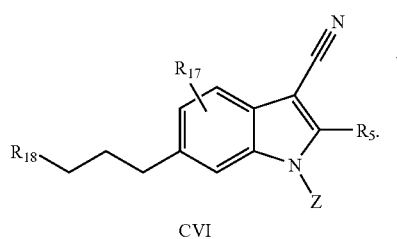
CVI

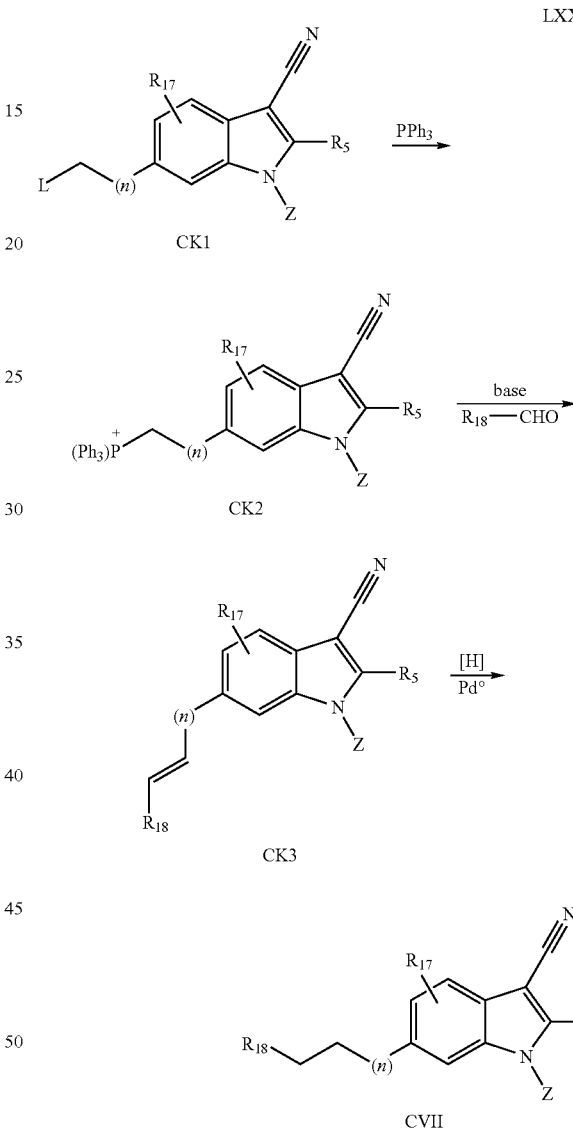

heteroaryl) at temperatures ranging from ambient to reflux. Hydrogenation of compounds of type CK3 can be accomplished in the presence of a catalyst such a palladium or platinum in a solvent such as but not limited to methanol, ethanol or acetic acid at pressures ranging from ambient to 100° C. under a hydrogen atmosphere to give compounds of formula CVII.

Compounds of formula I, represented by structure CVII can be prepared as shown in Scheme CK.

Compounds of formula CK1 (in which L is a leaving group such as chloride, bromide, iodide or sulfonate and n is 0 or 1) can undergo reaction with triphenylphosphine in a solvent such as but not limited to tetrahydrofuran, toluene or dichloromethane; at a temperature ranging from ambient or to reflux to give the phosphonium salt CK2. Phosphonium salt CK2 can be converted to olefin compounds of type CK3 by treatment with a base such as butyllithium, sodium hydride, sodium amide or potassium t-butoxide in a solvent such as tetrahydrofuran, ethyl ether or DME followed by addition of an aldehyde $R_{18}$CHO (in which $R_{18}$ is an aryl, heterocycle or Compounds of formula I, represented by structure CVIII can be prepared as shown in Scheme CL.

Compounds of formula CL1 (in which L represents iodide, bromide or chloride or methanesulfonate) can undergo reaction with boronic acids of structure $R_{18}B(OH)_2$ (in which $R_{18}$ is an aryl or heteroaryl) in the presence of palladium catalysts such as palladium acetate, palladium tetrakis triphenylphosphine or palladium dichloride; and ligands such as triphenylphosphine or tri-ortho-tolylphosphine in solvents such as but not limited to acetone, dimethyl formamide or toluene at temperatures from ambient to reflux to give the addition product CVIII.

Scheme CL

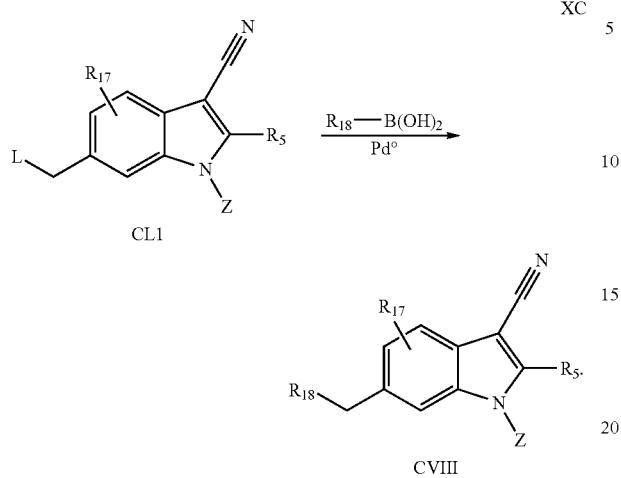

Compounds of formula I, represented by structure CIX can be prepared as shown in Scheme CM.

Compounds of formula CM1 (in which L represents iodide, bromide or chloride or methanesulfonate) can undergo reaction with metal sulfinates (in which $R_{18}$ is an alkyl, aryl or heteroaryl) in solvents such as but not limited to acetone, dimethylformamide or toluene at temperatures from ambient to reflux to give the addition product CIX.

Scheme CM

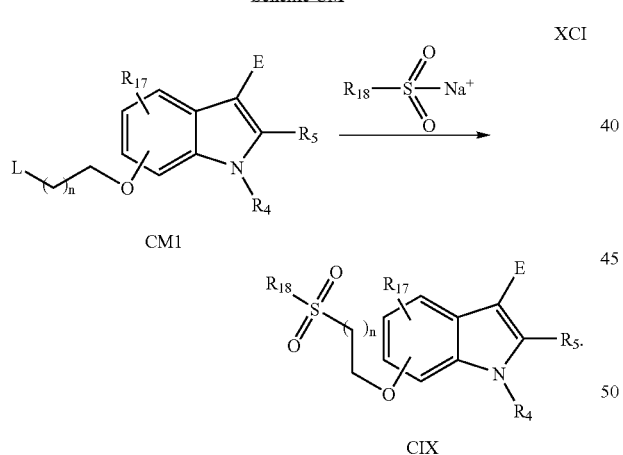

Compounds of formula I, represented by structure CX can be prepared as shown in Scheme CN.

Compounds of formula CL1 (in which $R_{17}$, defined above, is 1-3 substituents placed on the indole ring) when treated with a base such as potassium hydride, sodium hydride or the like, and then an alkyl lithium such as tert-butyl lithium form a carbanion that reacts with disulfide $R_{18}SSR_{18}$ (in which $R_{18}$ is an alkyl, aryl or heteroaryl) in solvents such as but not limited to THF, diethyl ether, or toluene at temperatures from −78° C. to ambient to provide intermediate. Cyanation (CN3), alkylation of the indole nitrogen (CN4) and metal coupling to form product CX are described above.

Scheme CN

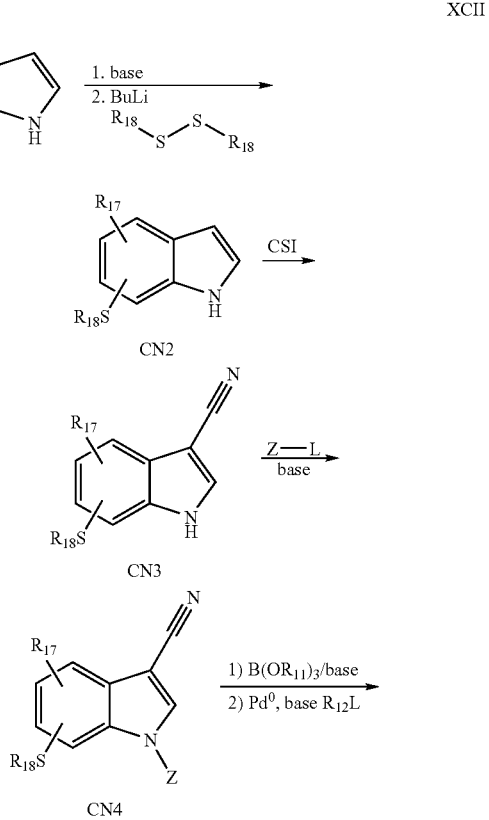

Compounds of formula I, represented by structure CXI, can be prepared as shown in Scheme CO.

Compounds of formula CO1 (in which $R_{17}$, defined above, is 1-3 substituents placed on the indole) when treated with a base, copper (I) iodide and a substituted amine (Z-$NH_2$ where Z is defined above) to provide compounds of formula CO2. Acylation with 2-chloroacetyl chloride and a base such as triethylamine in solvents such as but not limited to dichloromethane, tetrahydrofuran or toluene at temperatures from ambient to reflux provides intermediate CO3 which is subsequently cyclized to form compounds of structure CO4 employing palladium (II) acetate as catalyst, a phosphine ligand and a base such as triethylamine in solvents such as but not limited to tetrahydrofuran, dimethylformamide or toluene at temperatures from ambient to reflux. Reduction and elimination with a hydride source such as DIBAL-H in solvents such as but not limited to dichloromethane, tetrahydrofuran or toluene at temperatures from 0° C. to reflux provides intermediate CO5. The subsequent steps leading to product CXI are described above.

Scheme CO

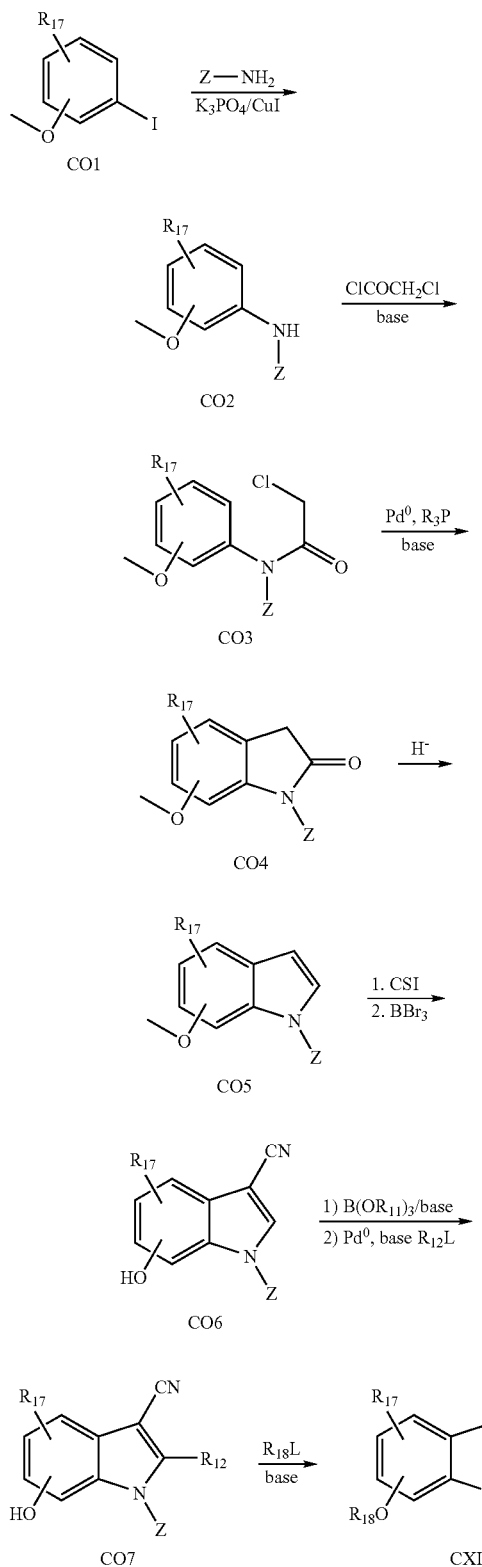

Compounds of formula I, represented by structure CXII can be prepared as shown in Scheme CP.

Compounds of formula CP1 was elaborated using conditions as described above provide CP3 which can be subsequently hydrogenated using a metal such as palladium on carbon and a source of hydrogen such as hydrogen gas or ammonium formate to provide the aniline intermediate CP4. Bis-alkylation using CP5 where X can be $CH_2$, S, SO, $SO_2$, O, C=O, etc. and n=0 to 3, with two leaving groups (L), as described above, and an appropriate base such as triethylamine or potassium hydroxide in solvents such as but not limited to tetrahydrofuran, dimethylformamide or toluene at temperatures from ambient to reflux will provide intermediate CP6. Employing conditions described above then provides product CXII.

Scheme CP

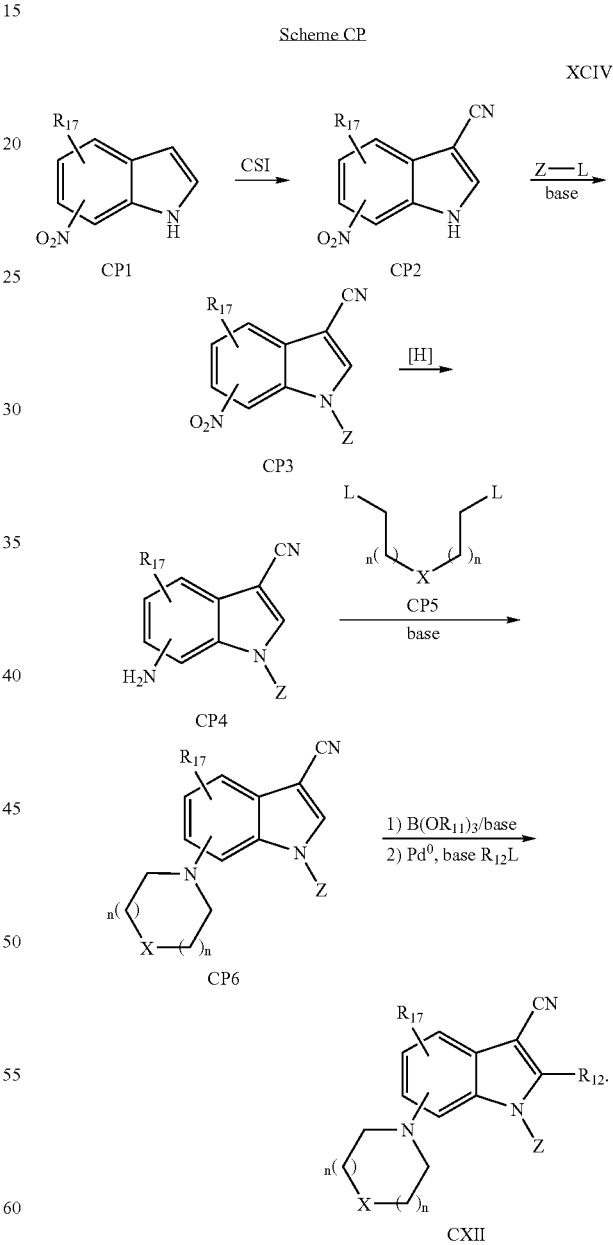

Compounds of formula I, represented by structure CXIII, can be prepared as shown in Scheme CQ.

Compounds of formula CQ1 can be elaborated using conditions described above to provide product CXIII.

Scheme CQ

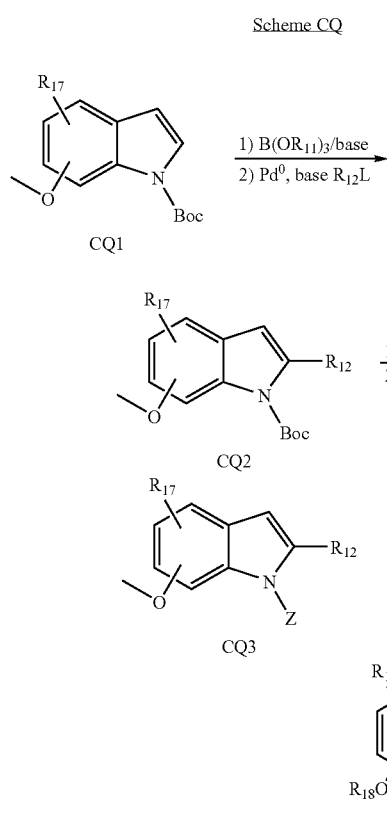

Compounds of formula I, represented by structure CXIV, can be prepared as shown in Scheme CR.

Compounds of formula CR1 can be elaborated using conditions described above to provide intermediate CR4. Treatment of indole CR4 with a halogen source, such as halogen substituted succinimides, in solvents such as but not limited to tetrahydrofuran, dimethylformamide or toluene at temperatures from ambient to reflux provide halogen substituted product CXIV.

Scheme CR

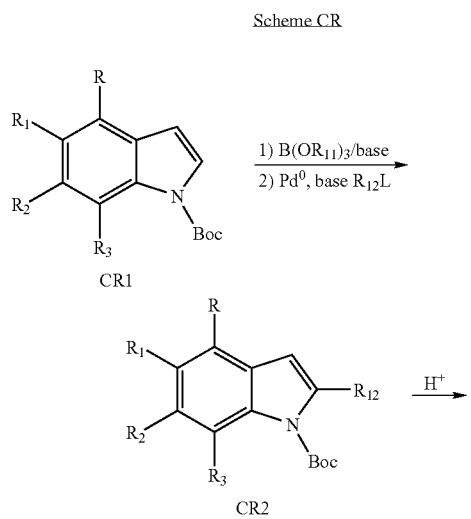

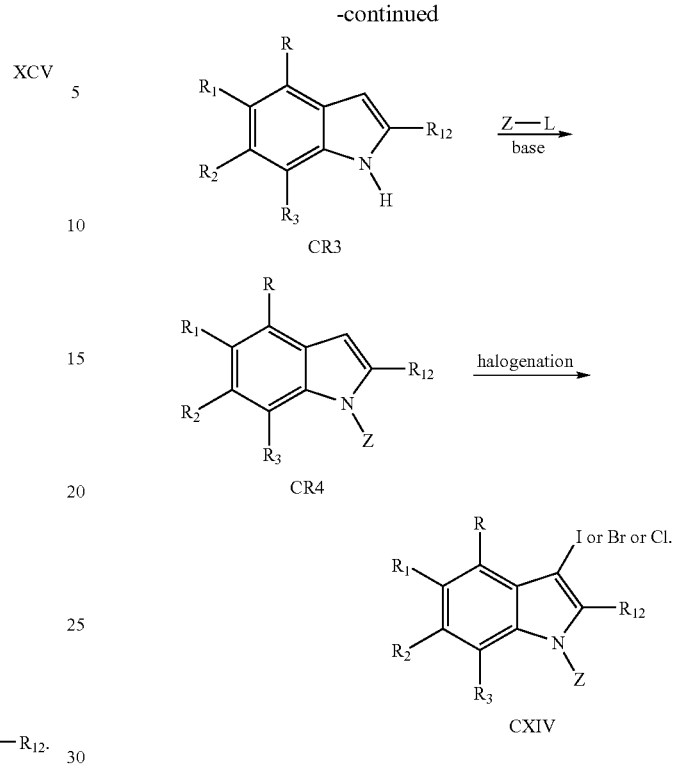

Compounds of formula I, represented by structure CXV, can be prepared as shown in Scheme CS.

Compounds of formula CS1 can be treated with a triflate source, such as triflic anhydride, and a base, such as pyridine, in solvents such as but not limited to tetrahydrofuran, dichloromethane or toluene at temperatures from ambient to reflux to provide intermediate CS2. CS2 can either be directly reacted with palladium (0) and a $R_{12}$ substituted trialkyl tin compound in the presence of cesium fluoride and copper (I) iodide in solvents such as but not limited to tetrahydrofuran, dimethylformamide or toluene at temperatures from ambient to reflux to provide product CXV or reacted in a two step sequence of coupling with a pinacol borane source such as bis-pinacol diborane in the presence of palladium (II) and a base, such as potassium acetate, in solvents such as but not limited to tetrahydrofuran, dioxane or toluene at temperatures from ambient to reflux and then a second palladium coupling with palladium (0), cesium fluoride and an appropriate $R_{12}L$ compound in solvents such as but not limited to tetrahydrofuran, dimethoxy ethane or toluene at temperatures from ambient to reflux to provide CXV.

Scheme CS

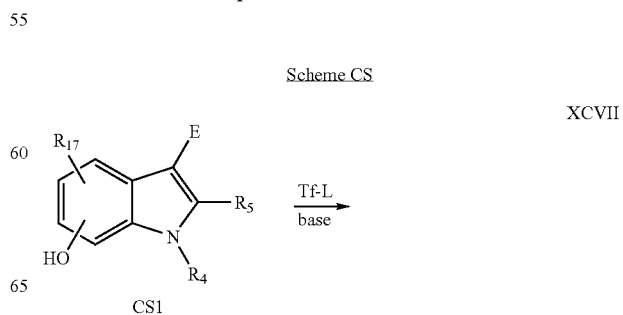

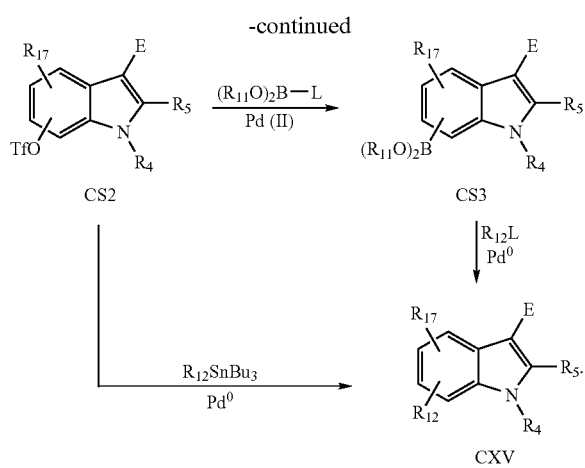

C. Methods of the Invention

Another aspect of the invention relates to a method for treating Hepatitis C viral (HCV) infection in a subject in need thereof, comprising administering to the subject an effective amount of one or more compound(s) of the invention or one or more pharmaceutically acceptable salt(s) thereof, or a pharmaceutical composition comprising an effective amount of one of more compound(s) of the invention or one or more pharmaceutically acceptable salt(s) thereof, as described above.

As used herein, the term "treating" refers to: (i) preventing a disease, disorder or condition from occurring in a subject that may be predisposed to the disease, disorder and/or condition but has not yet been diagnosed as having it; (ii) inhibiting a disease, disorder or condition, i.e., arresting its development; and/or (iii) relieving a disease, disorder or condition, i.e., causing regression of the disease, disorder and/or condition.

As used herein, the term "subject" refers to an animal or any living organism having sensation and the power of voluntary movement, and which requires for its existence oxygen and organic food. Nonlimiting examples include members of the human, equine, porcine, bovine, murine, canine and feline species. In some embodiments, the subject is a mammal or a warm-blooded vertebrate animal. In other embodiments, the subject is a human. As used herein, the term "patient" may be used interchangeably with "human".

Without being limited to any particular theory, it is believed that the compounds of the present invention inhibit IRES-mediated initiation, elongation and termination, i.e., translation by interfering with function of the IRES directly and/or with the interaction of the IRES and a cellular and/or viral factor. Thus, another aspect of the invention relates to a method for treating an infection by a wild type virus or a virus that is resistant to a currently available antiviral agent, in a subject in need thereof, wherein the wild type or resistant virus comprises an internal ribosome entry site (IRES), comprising administering to the subject an effective amount of one or more compound(s) of the invention or one or more pharmaceutically acceptable salt(s) thereof, or a pharmaceutical composition comprising an effective amount of one of more compound(s) of the invention or one or more pharmaceutically acceptable salt(s) thereof, as described above. Nonlimiting examples of such virus include viruses of the picornavirus genus, such as poliovirus, hepatitis A virus, coxsackievirus and rhinovirus; viruses of the coronaviridae genus, such as SARS; viruses of the arbovirus genus; viruses of the flavivirus genus, such as yellow fever, dengue, and West Nile virus; herpesviruses, such as herpes simplex virus and Kaposi's sarcoma-associated herpesvirus, and other viruses with a similar mode of replication; and HIV, human leukemia viruses (HTLV) and other viruses with a similar mode of translation.

Yet another aspect of the invention relates to a method for inhibiting HCV IRES-mediated initiation and/or translation in a subject in need thereof, comprising administering to the subject an effective amount of one or more compound(s) of the invention or one or more pharmaceutically acceptable salt(s) thereof, or a pharmaceutical composition comprising an effective amount of one of more compound(s) of the invention or one or more pharmaceutically acceptable salt(s) thereof, as described above.

As used herein, the term "effective amount" refers to the amount required to produce a desired effect. For example, the effective amount may be the amount required to treat a Hepatitis C viral (HCV) infection, the amount required to treat an infection by a virus which comprises an internal ribosome entry site (IRES), the amount required to inhibit HCV IRES-mediated initiation and/or translation, or the amount required to inhibit viral replication or infectivity, in a subject or, more specifically, in a human. In some instances, the desired effect can be determined by analyzing (1) the presence of HCVRNA; (2) the presence of anti-HCV antibodies; (3) the level of serum alanine amino transferase (ALT) and aspartate aminotransferase (AST) (ALT and AST are elevated in patients chronically infected with HCV); (4) hepatocellular damage resulting from HCV infection, including steatosis, fibrosis and cirrhosis; (5) hepatocellular carcinoma as a result of chronic HCV infection; and (5) extrahepatic sequelae (non-limiting examples include pruritus, encephalopathies, mental disorders such as anxiety or depression) of infection with HCV or other viruses which contain an IRES element. The effective amount for a subject will depend upon various factors, including the subject's body weight, size and health. Effective amounts for a given patient can be determined by routine experimentation that is within the skill and judgment of the clinician.

For any compound, the effective amount can be estimated initially either in cell culture assays or in relevant animal models, such as marmosets and tarmarins. The animal model may also be used to determine the appropriate concentration range and route of administration. Such information can then be used to determine useful doses and routes for administration in humans. Therapeutic efficacy and toxicity may be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between therapeutic and toxic effects is the therapeutic index, and it can be expressed as the ratio, $ED_{50}/LD_{50}$. In some embodiments, the effective amount is such that a large therapeutic index is achieved. In further embodiments, the dosage is within a range of circulating concentrations that include an $ED_{50}$ with little or no toxicity. The dosage may vary within this range depending upon the dosage form employed, sensitivity of the patient, and the route of administration.

More specifically, the concentration-biological effect relationships observed with regard to the compound(s) of the present invention indicate an initial target plasma concentration ranging from approximately 0.1 µg/ml to approximately 100 µg/mL, from approximately 1 µg/mL to approximately 50 µg/mL, from approximately 5 µg/mL to approximately 50

µg/mL, or from approximately 10 µg/mL to approximately 25 µg/mL. To achieve such plasma concentrations, the compounds of the invention may be administered at doses that vary from 0.1 µg to 100,000 mg, depending upon the route of administration. Guidance as to particular dosages and methods of delivery is provided in the literature and is generally available to practitioners in the art. In general, the dose will be in the range of about 1 mg/day to about 10 g/day, or about 0.1 g to about 3 g/day, or about 0.3 g to about 3 g/day, or about 0.5 g to about 2 g/day, in single, divided, or continuous doses for a patient weighing between about 40 to about 100 kg (which dose may be adjusted for patients above or below this weight range, particularly children under 40 kg).

The exact dosage will be determined by the practitioner, in light of factors related to the subject. Dosage and administration may be adjusted to provide sufficient levels of the active agent(s) or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

The compounds and compositions of the present invention may be administered to the subject via any drug delivery route known in the art. Nonlimiting examples include oral, ocular, rectal, buccal, topical, nasal, ophthalmic, subcutaneous, intramuscular, intravenous (bolus and infusion), intracerebral, transdermal, and pulmonary routes of administration.

D. Metabolites of the Compounds of the Invention

Also falling within the scope of the present invention are the in vivo metabolic products of the compounds described herein. Such products may result, for example, from the oxidation, reduction, hydrolysis, amidation, esterification and the like of the administered compound, primarily due to enzymatic processes. Accordingly, the invention includes compounds produced by a process comprising contacting a compound of this invention with a mammalian tissue or a mammal for a period of time sufficient to yield a metabolic product thereof. Such products typically are identified by preparing a radio-labeled (e.g. $C^{14}$ or $H^3$) compound of the invention, administering it in a detectable dose (e.g., greater than about 0.5 mg/kg) to a mammal such as rat, mouse, guinea pig, monkey, or to man, allowing sufficient time for metabolism to occur (typically about 30 seconds to 30 hours), and isolating its conversion products from urine, blood or other biological samples. These products are easily isolated since they are labeled (others are isolated by the use of antibodies capable of binding epitopes surviving in the metabolite). The metabolite structures are determined in conventional fashion, e.g., by MS or NMR analysis. In general, analysis of metabolites may be done in the same way as conventional drug metabolism studies well-known to those skilled in the art. The conversion products, so long as they are not otherwise found in vivo, are useful in diagnostic assays for therapeutic dosing of the compounds of the invention even if they possess no biological activity of their own.

E. Pharmaceutical Compositions of the Invention

Yet another aspect of the invention relates to a pharmaceutical composition comprising: (i) an effective amount of one or more compound(s) of the invention or one or more pharmaceutically acceptable salt(s) thereof, or a pharmaceutical composition comprising an effective amount of one of more compound(s) of the invention or one or more pharmaceutically acceptable salt(s) thereof, as described above.

A pharmaceutical composition of the present invention may be formulated to achieve a physiologically compatible pH, ranging from a pH of about 3 to a pH of about 11. In some embodiments, the pharmaceutical composition is formulated to achieve a pH of about 3 to a pH of about 7. In other embodiments, the pharmaceutical composition is formulated to achieve a pH of about 5 to a pH of about 8.

The pharmaceutical composition may comprise a combination of compounds of the present invention, or may include a second active ingredient useful in the treatment of viral infections, such as anti-viral agents that include, but are not limited to: pegylated interferon, including by way of non-limiting example pegylated α-interferon; un-pegylated interferon, including by way of non-limiting example, un-pegylated α-interferon; ribavirin or prodrugs or derivatives thereof; a glucosidase inhibitor; protease inhibitors; polymerase inhibitors; p7 inhibitors; entry inhibitors, including fusion inhibitors such as Fuzeon™ (Trimeris); helicase inhibitors; a Toll-like receptor agonist, a caspase inhibitor, anti-fibrotics; drugs that target IMPDH (inosine monophosphate dehydrogenase inhibitors), such as Merimepadib™ (Vertex Pharmaceuticals Inc.); synthetic thymosin alpha 1 (ZADAXIN™, SciClone Pharmaceuticals Inc.); a glycosidase inhibitor; therapeutic viral vaccines, such as those produced by Chiron and Immunogenics; and immunomodulators, such as histamine.

The term "pharmaceutically acceptable excipient" refers to an excipient for administration of a pharmaceutical agent, such as the compounds of the present invention. The term refers to any pharmaceutical excipient that may be administered without undue toxicity. Pharmaceutically acceptable excipients may be determined in part by the particular composition being administered, as well as by the particular mode of administration and/or dosage form. Nonlimiting examples of pharmaceutically acceptable excipients include carriers, solvents, stabilizers, adjuvants, diluents, etc. Accordingly, there exist a wide variety of suitable formulations of pharmaceutical compositions of the present invention (see, e.g., Remington's Pharmaceutical Sciences).

Suitable excipients may be carrier molecules that include large, slowly metabolized macromolecules such as proteins, polysaccharides, polylactic acids, polyglycolic acids, polymeric amino acids, amino acid copolymers, and inactive virus particles. Other exemplary excipients include antioxidants such as ascorbic acid; chelating agents such as EDTA; carbohydrates such as dextrin, hydroxyalkylcellulose, hydroxyalkylmethylcellulose, stearic acid; liquids such as oils, water, saline, glycerol and ethanol; wetting or emulsifying agents; pH buffering substances; and the like. Liposomes are also included within the definition of pharmaceutically acceptable excipients.

The pharmaceutical compositions of the invention may be formulated in any form suitable for the intended method of administration. Suitable formulations for oral administration include solids, liquid solutions, emulsions and suspensions, while suitable inhaleable formulations for pulmonary administration include liquids and powders. Alternative formulations include syrups, creams, ointments, tablets, and lyophilized solids which can be reconstituted with a physiologically compatible solvent prior to administration.

When intended for oral use for example, tablets, troches, lozenges, aqueous or oil suspensions, non-aqueous solutions, dispersible powders or granules (including micronized particles or nanoparticles), emulsions, hard or soft capsules, syrups or elixirs may be prepared. Compositions intended for oral use may be prepared according to any method known to the art for the manufacture of pharmaceutical compositions, and such compositions may contain one or more agents including sweetening agents, flavoring agents, coloring agents and preserving agents, in order to provide a palatable preparation.

Pharmaceutically acceptable excipients suitable for use in conjunction with tablets include, for example, inert diluents, such as celluloses, calcium or sodium carbonate, lactose, calcium or sodium phosphate; disintegrating agents, such as croscarmellose sodium, cross-linked povidone, maize starch, or alginic acid; binding agents, such as povidone, starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may be also presented as hard gelatin capsules where the active ingredient is mixed with an inert solid diluent, for example celluloses, lactose, calcium phosphate or kaolin, or as soft gelatin capsules wherein the active ingredient is mixed with non-aqueous or oil medium, such as glycerin, propylene glycol, polyethylene glycol, peanut oil, liquid paraffin or olive oil.

In other embodiments, pharmaceutical compositions of the invention may be formulated as suspensions comprising one or more compound(s) of the present invention in admixture with at least one pharmaceutically acceptable excipient suitable for the manufacture of a suspension. In yet other embodiments, pharmaceutical compositions of the invention may be formulated as dispersible powders and granules suitable for preparation of a suspension by the addition of one or more excipient(s).

Excipients suitable for use in connection with suspensions include suspending agents, such as sodium carboxymethylcellulose, methylcellulose, hydroxypropyl methylcelluose, sodium alginate, polyvinylpyrrolidone, gum tragacanth, gum acacia, dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycethanol), a condensation product of ethylene oxide with a partial ester derived from a fatty acid and a hexitol anhydride (e.g., polyoxyethylene sorbitan monooleate); and thickening agents, such as carbomer, beeswax, hard paraffin or cetyl alcohol. The suspensions may also contain one or more preservatives such as acetic acid, methyl and/or n-propyl p-hydroxy-benzoate; one or more coloring agents; one or more flavoring agents; and one or more sweetening agents such as sucrose or saccharin.

The pharmaceutical compositions of the invention may also be in the form of oil-in-water emulsions. The oily phase may be a vegetable oil, such as olive oil or arachis oil, a mineral oil, such as liquid paraffin, or a mixture of these. Suitable emulsifying agents include naturally-occurring gums, such as gum acacia and gum tragacanth; naturally occurring phosphatides, such as soybean lecithin, esters or partial esters derived from fatty acids; hexitol anhydrides, such as sorbitan monooleate; and condensation products of these partial esters with ethylene oxide, such as polyoxyethylene sorbitan monooleate. The emulsion may also contain sweetening and flavoring agents. Syrups and elixirs may be formulated with sweetening agents, such as glycerol, sorbitol or sucrose. Such formulations may also contain a demulcent, a preservative, a flavoring or a coloring agent.

Additionally, the pharmaceutical compositions of the invention may be in the form of a sterile injectable preparation, such as a sterile injectable aqueous emulsion or oleaginous suspension. Such emulsion or suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,2-propane-diol. The sterile injectable preparation may also be prepared as a lyophilized powder. Among the acceptable vehicles and solvents that may be employed are water, Ringer's solution, and isotonic sodium chloride solution. In addition, sterile fixed oils may be employed as a solvent or suspending medium. For this purpose any bland fixed oil may be employed including synthetic mono- or di-glycerides. In addition, fatty acids such as oleic acid may likewise be used in the preparation of injectables.

The compounds of the invention may be substantially insoluble in water and sparingly soluble in most pharmaceutically acceptable protic solvents and vegetable oils, but generally soluble in medium-chain fatty acids (e.g., caprylic and capric acids) or triglycerides and in propylene glycol esters of medium-chain fatty acids. Thus, contemplated in the invention are compounds which have been modified by substitutions or additions of chemical or biochemical moieties which make them more suitable for delivery (e.g., increase solubility, bioactivity, palatability, decrease adverse reactions, etc.), for example by esterification, glycosylation, PEGylation, etc.

In some embodiments, the compound of the invention is formulated for oral administration in a lipid-based composition suitable for low solubility compounds. Lipid-based formulations can generally enhance the oral bioavailability of such compounds. As such, pharmaceutical compositions of the invention may comprise a effective amount of one or more compound(s) of the invention, together with at least one pharmaceutically acceptable excipient selected from medium chain fatty acids or propylene glycol esters thereof (e.g., propylene glycol esters of edible fatty acids such as caprylic and capric fatty acids) and pharmaceutically acceptable surfactants, such as polyoxyl 40 hydrogenated castor oil.

In alternative embodiments, the pharmaceutical composition may further comprise one or more aqueous solubility enhancer(s), such as a cyclodextrin. Nonlimiting examples of cyclodextrin include hydroxypropyl, hydroxyethyl, glucosyl, maltosyl and maltotriosyl derivatives of $\alpha$-, $\beta$-, and $\gamma$-cyclodextrin, and hydroxypropyl-$\beta$-cyclodextrin (HPBC). In some embodiments, the pharmaceutical composition further comprises about 0.1% to about 20% hydroxypropyl-$\beta$-cyclodextrin, about 1% to about 15% hydroxypropyl-$\beta$-cyclodextrin, or about 2.5% to about 10% hydroxypropyl-$\beta$-cyclodextrin. The amount of solubility enhancer employed may depend on the amount of the compound of the present invention in the composition.

F. Combination Therapy

It is also possible to combine any compound of the present invention with one or more other active ingredients useful in the treatment of HCV infection, including compounds, in a unitary dosage form, or in separate dosage forms intended for simultaneous or sequential administration to a patient in need of treatment. When administered sequentially, the combination may be administered in two or more administrations. In an alternative embodiment, it is possible to administer one or more compounds of the present invention and one or more additional active ingredients by different routes.

The skilled artisan will recognize that a variety of active ingredients may be administered in combination with the compounds of the present invention that may act to augment or synergistically enhance the viral inhibiting activity of the compounds of the invention. Such active ingredients include anti-HCV agents. Anti-HCV agents include agents that target the virus as well as agents that have an immunomodulatory effect. For example, anti-HCV agents include, but are not limited to, interferon, including, for example without limitation, IFN-α, ribavirin or prodrugs or derivatives thereof; a glucosidase inhibitor, protease inhibitors, polymerase inhibitors, helicase inhibitors, a Toll-like receptor agonist, a caspase inhibitor and a glycosidase inhibitor. Furthermore, the compounds of the invention may also be administered in combination with other compounds that affect IRES activity.

According to the methods of the invention, the combination of active ingredients may be: (1) co-formulated and administered or delivered simultaneously in a combined formulation; (2) delivered by alternation or in parallel as separate formulations; or (3) by any other combination therapy regimen known in the art. When delivered in alternation therapy, the methods of the invention may comprise administering or delivering the active ingredients sequentially, e.g., in separate solution, emulsion, suspension, tablets, pills or capsules, or by different injections in separate syringes. In general, during alternation therapy, an effective dosage of each active ingredient is administered sequentially, i.e., serially, whereas in simultaneous therapy, effective dosages of two or more active ingredients are administered together. Various sequences of intermittent combination therapy may also be used.

To assist in understanding the present invention, the following Examples are included. The experiments relating to this invention should not, of course, be construed as specifically limiting the invention and such variations of the invention, now known or later developed, which would be within the purview of one skilled in the art are considered to fall within the scope of the invention as described herein and hereinafter claimed.

It will be apparent to those skilled in the art that specific embodiments of the present invention may be directed to one, some or all of the above-indicated aspects as well as other aspects, and may encompass one, some or all of the above- and below-indicated embodiments, as well as other embodiments.

Other than in the working examples, or where otherwise indicated, all numbers expressing quantities of ingredients, reaction conditions, and so forth used in the specification and claims are to be understood as being modified by the term "about". Accordingly, unless indicated to the contrary, such numbers are approximations that may vary depending upon the-desired properties sought to be obtained by the present invention. At the very least, and not as an attempt to limit the application of the doctrine of equivalents to the scope of the claims, each numerical parameter should be construed in light of the number of significant digits and ordinary rounding techniques.

While the numerical ranges and parameters setting forth the broad scope of the invention are approximations, the numerical values set forth in the working examples are reported as precisely as possible. Any numerical value, however, inherently contains certain errors necessarily resulting from the standard deviation found in their respective testing measurements.

EXAMPLES

The present invention is described in more detail with reference to the following non-limiting examples, which are offered to more fully illustrate the invention, but are not to be construed as limiting the scope thereof. The examples illustrate the preparation of certain compounds of the invention, and the testing of these compounds in vitro or in vivo or both in vitro and in vivo. Those of skill in the art will understand that the techniques described in these examples represent techniques described by the inventors to function well in the practice of the invention, and as such constitute preferred modes for the practice thereof. However, it should be appreciated that those of skill in the art should in light of the present disclosure, appreciate that many changes can be made in the specific methods that are disclosed and still obtain a like or similar result without departing from the spirit and scope of the invention.

Example 1

Preparation of Compounds of the Invention

Example 1A

Preparation of 1-ethyl-6-methoxy-1H-indole-3-carbonitrile (compound 5)

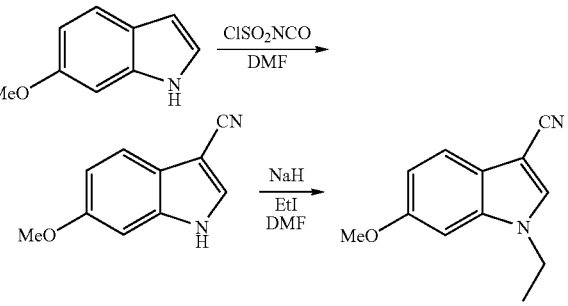

Step A: A solution of 6-methoxyindole (10.0 g, 68.0 mmol) in DMF (120 mL) is cooled to 0° C. and treated with chlorosulfonyl isocyanate (7.72 mL, 88.4 mmol). After the addition, the reaction mixture is stirred at this temperature for I h. The dark solution is poured into ice water (600 mL) and the light brown solid is collected by filtration, washed with additional $H_2O$ and dried to afford 9.9 g (85%) of 6-methoxy-1H-indole-3-carbonitrile as a light brown solid.

Step B: To a solution of 6-methoxy-1H-indole-3-carbonitrile (9.9 g, 57.6 mmol) in DMF (150 mL) is added NaH (60% dispersion in mineral oil, 3.45 g, 86.3 mmol). The reaction mixture is stirred for 15 min and then ethyl iodide (5.53 mL, 69.1 mmol) is added and the mixture is stirred at room temperature overnight. The reaction mixture is then diluted with $H_2O$ and extracted with EtOAc (2×). The organic phases are washed with $H_2O$ (3×) and saturated NaCl and then dried and concentrated to a semi-solid. The crude product is purified via column chromatography on silica gel (200 g) using $CH_2Cl_2$/hexanes (50-100%) as eluent to yield 6-methoxy-1-ethyl-1H-indole-3-carbonitrile as a tan solid.

Utilizing steps A and B above and substituting different indoles and alkyl halides gives the following compounds: Compounds 43, 45, 51, 52, 108, 109, 115, 118, 120, 123, 126, 179 and 714.

Example 1B

Preparation of 6-ethoxy-1-ethyl-1H-indole-3-carbonitrile (compound 9)

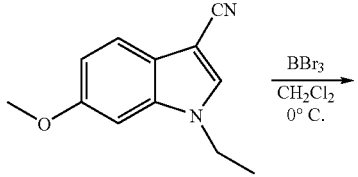

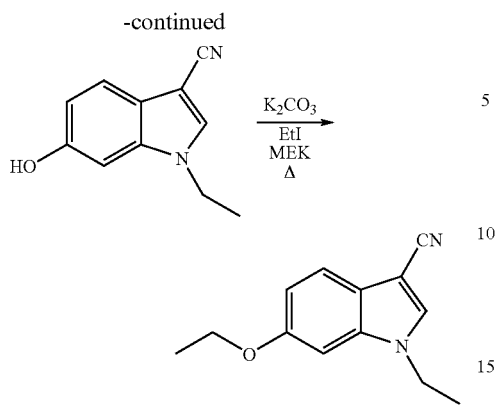

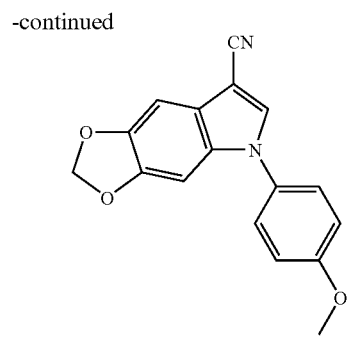

Step A: To a solution of 1-ethyl-6-methoxy-1H-indole-3-carbonitrile (2.85 g, 14.2 mmol), prepared by example 1A, step B, in CH$_2$Cl$_2$ (40 mL) is added a 1M solution of BBr$_3$ in CH$_2$Cl$_2$ (28.5 mL, 28.5 mmol) at 0° C. The mixture is allowed to warm to room temperature and kept for 2.5 h. The dark reaction mixture is then poured onto ice and sufficient 1M NaOH is added until the pH is 8-9. The product is extracted with CH$_2$Cl$_2$ (3×) and the combined organic phases are washed with saturated NaHCO$_3$, H$_2$O and saturated NaCl. After drying over MgSO$_4$, the solution is concentrated and the product is purified by chromatography (EtOAc/CH$_2$Cl$_2$, 0-10%) to afford 2.15 g (82%) of 6-hydroxy-1-ethyl-1H-indole-3-carbonitrile as a yellow solid.

Step B: To a solution 6-hydroxy-1-ethyl-1H-indole-3-carbonitrile (80 mg, 0.43 mmol) in 5 mL of methyl ethyl ketone is added anhydrous K$_2$CO$_3$ (71 mg, 0.52 mmol) and iodomethane (0.05 mL, 0.60 mmol). After stirring overnight at reflux, the reaction mixture is cooled, diluted with H$_2$O and extracted with EtOAc (3×). The combined organic phases are dried and concentrated. Flash chromatography (CH$_2$Cl$_2$) gives 94 mg (100% S) of 6-ethoxy-1-ethyl-1H-indole-3-carbonitrile as a white wax.

In similar fashion, following steps A and B, above, the following compounds are also prepared: Compounds 6, 10, 11, 12 and 24.

Example 1C

Preparation of 5-(4-methoxyphenyl)-5H-[1,3]dioxolo[4,5-f]indole-7-carbonitrile (compound 44)

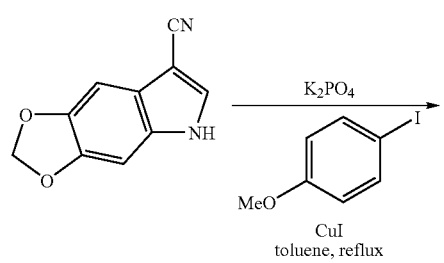

A mixture of p-iodoanisole (85 mg, 0.36 mmol), anhydrous K$_3$PO$_4$ (102 mg, 0.48 mmol), CuI (4.6 mg, 0.024 mmol) and N,N'-Dimethyl cyclohexane-1,2-diamine (14 mg, 0.096 mmol) is added to 5H-[1,3]dioxolo[4,5-f]indole-7-carbonitrile (45 mg, 0.24 mmol), prepared as described by the method of example 1A, step A, in anhydrous toluene (0.4 mL). After heating at reflux for 24 h, the solvent is evaporated under vacuum. The residue is dissolved with CH$_2$Cl$_2$ (5 mL) and the mixture is filtered. The filtrate is concentrated to afford crude product, which is purified by silica gel chromatography using EtOAc/petroleum ether (1:4) as eluent to yield 5-(4-methoxyphenyl)-5H-[1,3]dioxolo[4,5-f]indole-7-carbonitrile.

Utilizing the procedure above and substituting different aryl iodides gives the following compounds: Compounds 4, 8, 102, 103, 111, 112, 117, 119, 124, 125, 127, 154.

Example 1D

Preparation of 1-ethyl-6-(pyrazin-2-yloxy)-1H-indole-3-carbonitrile (compound 13)

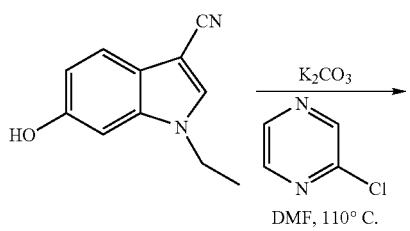

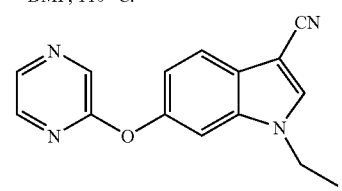

To a solution of 1-ethyl-6-hydroxy-1H-indole-3-carbonitrile (60 mg, 0.32 mmol) prepared as described in example 1A, step A, in DMF (5 mL) is added K$_2$CO$_3$ (55 mg, 0.40 mmol) and 2-chloropyridazine (45 mg, 0.40 mmol). The mixture is heated at 110° C. for 18 h. After cooling to room temperature, the reaction mixture is diluted with H$_2$O and extracted with EtOAc (3×). The combined organic phases are washed with H$_2$O and saturated NaCl, dried and concentrated. The product is isolated by chromatography (EtOAc/CH$_2$Cl$_2$, 1-3%) over silica gel to afford 76 mg (96%) of the title compound, 1-ethyl-6-(pyrazin-2-yloxy)-1H-indole-3-carbonitrile, as an off-white solid.

Example 1E

Preparation of 3-cyano-1-ethyl-1H-indole-6-carboxylic acid phenylamide (compound 15)

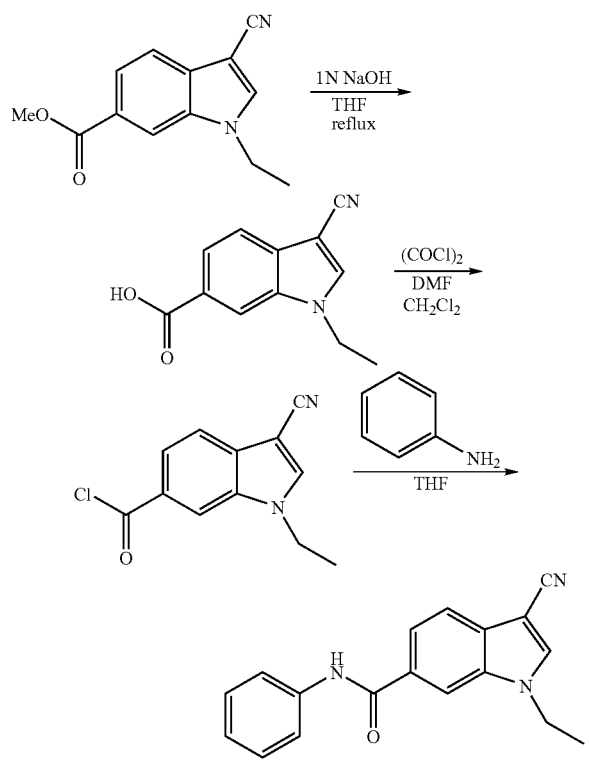

Step A: A solution of methyl 3-cyano-1-ethyl-1H-indole-6-carboxylate (1.60 g, 7.02 mmol), prepared by the method described in example 1A from methyl 1H-indole-6-carboxylate, in THF (35 mL) is treated with 1N NaOH (7.7 mL, 7.7 mmol) and heated at reflux for 2.5 h. After cooling to room temperature, most of the THF is removed and the solution is diluted with $H_2O$ and extracted with ether (2x). The ether extracts are discarded. The aqueous phase is then acidified with 6N HCl to pH 2 and then extracted with EtOAc (3x). The EtOAc layers are combined, washed with saturated NaCl and then dried and concentrated to afford 1.43 g (95%) of 3-cyano-1-ethyl-1H-indole-6-carboxylic acid as a white solid.

Step B: A suspension of 3-cyano-1-ethyl-1H-indole-6-carboxylic acid (0.42 g, 1.96 mmol) in $CH_2Cl_2$ (15 mL) is cooled to 0° C. The suspension is treated with DMF (2 drops) and then oxalyl chloride (0.34 mL, 3.92 mmol) is added via syringe during 2 minutes after which the ice bath is removed and the reaction mixture is allowed to warm to ambient temperature during 1.5 h during which time the reaction became a yellow solution. The solution is then concentrated in vacuo to afford 0.46 g (quantitative yield) of 3-cyano-1-ethyl-1H-indole-6-carbonyl chloride as a yellow solid.

Step C: A suspension of 3-cyano-1-ethyl-1H-indole-6-carbonyl chloride (70 mg, 0.30 mmol) in THF (5 mL) is cooled to 0° C. and treated with aniline (0.08 mL, 0.90 mmol). After the addition the reaction is warmed to ambient temperature and after stirring for an additional 16 hours, the reaction mixture is diluted with $H_2O$ and extracted with EtOAc (2x). The combined organic phases are washed with saturated NaCl and then dried and concentrated to afford the product. Chromatography (EtOAc/$CH_2Cl_2$, 2/98) over silica gel gives 44 mg (51%) of 3-cyano-1-ethyl-1H-indole-6-carboxylic acid phenylamide.

Utilizing essentially the procedure above gives the following compound: Compound 89.

Example 1F

Preparation of t-butyl (3-cyano-1-ethyl-1H-indol-6-yl)-carbamate (compound 16)

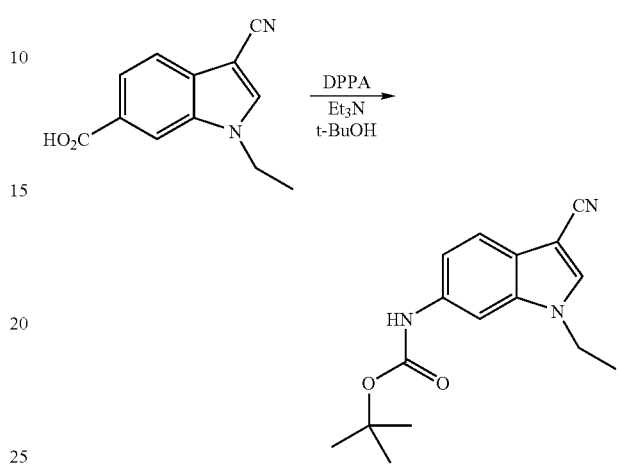

A solution of 3-cyano-1-ethyl-1H-indole-6-carboxylic acid (0.60 g, 2.80 mmol) from Example 1E, step A, in t-butanol (20 mL) is treated with $Et_3N$ (0.46 mL, 3.36 mmol) and diphenylphosphoryl azide (0.73 mL, 3.36 mmol) and then heated at reflux for 4 h. After cooling to room temperature, most of the t-butanol is removed in vacuo to give an oil, which is then dissolved in EtOAc. After washing with $H_2O$, the organic phase is back-extracted with EtOAc and the organic layers are combined and washed sequentially with additional $H_2O$, saturated $NaHCO_3$ and saturated NaCl. The organic phase is dried, concentrated and the resulting crude product is purified by chromatography over silica gel using EtOAc/$CH_2Cl_2$ (0-1%) to afford 0.52 g (65%) of t-butyl (3-cyano-1-ethyl-1H-indol-6-yl)-carbamate as a white solid.

The following compound is made in similar fashion: Compound 90.

Example 1Ga

Preparation of 2-(4-aminophenyl)-1-ethyl-6-methoxy-1H-indole-3-carbonitrile via Suzuki route (compound 55)

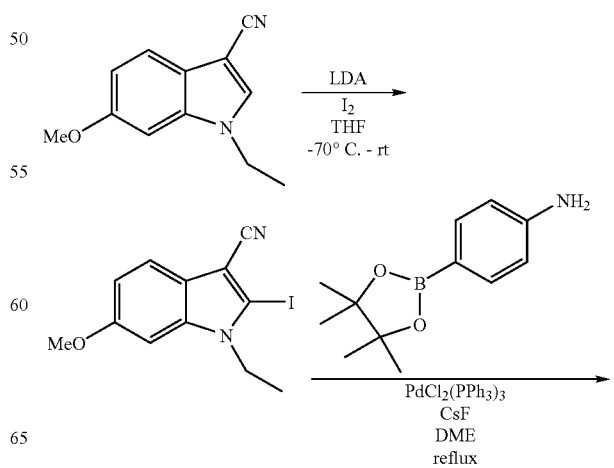

-continued

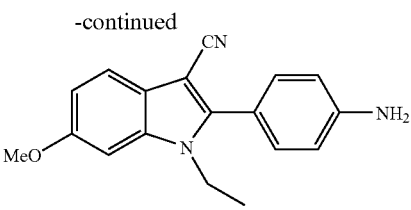

Step A: A 2M solution of lithium diisopropyl amide in THF/hexanes (Acros) (3.9 mL, 7.8 mmol) is diluted with THF (5 mL) in a flame-dried flask. After cooling the reaction to −30° C., a solution of 1-ethyl-6-methoxy-1H-indole-3-carbonitrile (1.30 g, 6.5 mmol) in THF (10 mL) is added dropwise during 10 min, maintaining the temperature at −30° C. After stirring for an additional 30 min at this temperature, a solution of iodine (2.31 g, 9.1 mmol) in THF (5 mL) is added during 10 min. After the addition, the reaction is warmed to ambient temperature during 1 h. The reaction is then diluted with ice-$H_2O$ and extracted with EtOAc (2×). The combined organic phases are washed with 1M sodium thiosulfate and saturated NaCl and then concentrated to a brown solid. Chromatography ($CH_2Cl_2$/hexanes, 1/1) over silica gel gives 1.31 g (62%) of 1-ethyl-2-iodo-6-methoxy-1H-indole-3-carbonitrile as an off-white solid.

Step B: A mixture of 1-ethyl-2-iodo-6-methoxy-1H-indole-3-carbonitrile (1.25 g, 3.83 mmol), 4-(4,4,5,5-tetramethyl)-1,3-2-dioxaboralanyl-2-yl-aniline (0.96 g, 4.90 mmol), CsF (1.46 g, 9.58 mmol) and $Pd(PPh_3)_2Cl_2$ (110 mg, 0.15 mmol) in DME (20 mL) is added to a flask and alternatively evacuated and flushed with $N_2$. The reaction is then heated at reflux for 24 h and then cooled to room temperature. The reaction mixture is diluted with $H_2O$ and extracted with EtOAc (2×). The combined organic phases are washed with $H_2O$ and saturated NaCl and then dried over $MgSO_4$ and concentrated. The crude reaction mix is purified by flash chromatography on silica gel using EtOAc/$CH_2Cl_2$ (5/95) as eluent to afford 765 mg (69%) of 2-(4-aminophenyl)-1-ethyl-6-methoxy-1H-indole-3-carbonitrile as a yellow solid.

Utilizing essentially the same procedure described above and substituting different boronic acids gives the following compounds: Compounds 19, 20, 21, 22, 53, 63, 70, 71, 74, 76, 77, 79, 80, 100, 110, 229, 239, 240, 247, 250, 254, 255, 256, 257, 258, 259, 260, 281, 282, 283, 284, 286, 335, 336, 337, 338, 339, 347, 348, 426, 427, 428, 429, 476, 543, 578, 758.

Example 1Gb

Preparation of 2-(4-aminophenyl)-1-butyl-6-methoxy-1H-indole-3-carbonitrile via alternative Suzuki route

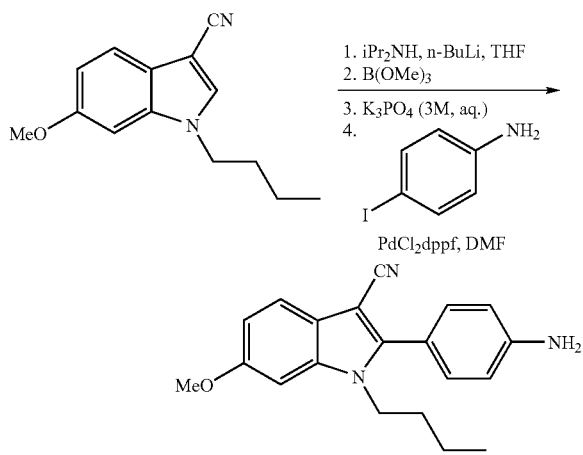

To a solution of (i-$Pr)_2NH$ (1.35 mL, 9.65 mmol) in THF (30 mL) cooled to −78° C. is added n-BuLi (3.7 mL, 2.5M in hexanes, 9.21 mmol) in one portion. The acetone/dry ice bath is exchanged for ice/water bath and the solution is stirred further for 40 min. The solution is cooled to −78° C. and solution of 1-butyl-6-methoxy-1H-indole-3-carbonitrile, prepared as in example 1A (2.0 g, 8.77 mmol) in THF (10 mL) is added dropwise. This solution is stirred for 15 min at −78° C., following by 20 min at −20° C. Trimethyl borate (1.0 mL, 8.77 mmol) is added, the reaction mixture is stirred for 15 min at −20° C. after which the cooling bath is removed and this solution is stirred further at room temperature for 1 h. A solution of $K_3PO_4$ is added (11.7 mL, 3M aqueous solution, 35.1 mmol) followed by a solution of 4-iodoaniline (2.5 g, 11.40 mmol) and $PdCl_2$dppf catalyst (640 mg, 0.88 mmol) in DMF (40 mL, plus a 5 mL rinse). The reaction mixture is stirred overnight (ca. 18 h) and then water (80 mL) is added and the product is extracted with EtOAc (3×50 mL). The combined organic fractions are dried over $MgSO_4$, filtered and concentrated under reduced pressure. The crude product is purified via flush chromatography on silica gel (5→60% EtOAc/Hexanes as eluant) to afford the desired 2-(4-aminophenyl)-1-butyl-6-methoxy-1H-indole-3-carbonitrile as a tan solid (2.4 g, 86% yield).

The following compounds are prepared in similar fashion utilizing other indole and aryl and heteroaryl bromides and iodides: Compounds 656, 659, 660, 661, 682, 683, 712, 731, 732, 733, 806, 807, 808, 809, 810, 811, 812, 813, 814, 827.

Example 1Gc

Preparation of 2-(4-aminophenyl)-6-methoxy-1-propyl-1H-indole-3-carbonitrile via Negishi route

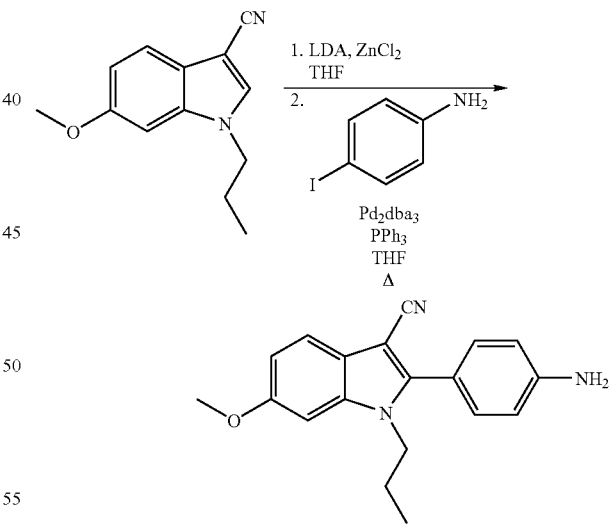

A nitrogen-purged flask fitted with a septum and a nitrogen needle is charged with dry THF (all additions performed by syringe) (20 mL). Diisopropylamine (Aldrich Sure-Seal, 2.00 mL, 14.3 mmol) is added, and the solution is cooled to 0° C. n-Butyllithium (8.50 mL of 1.6 M solution in hexane, 13.6 mmol) is added slowly. The flask is allowed to warm to room temperature briefly, and then is cooled to −78° C. A concentrated THF solution of 6-methoxy-1-propyl-1H-indole-3-carbonitrile (2.77 g, 12.9 mmol; prepared analogously to compound 5 of Example 1A) is added slowly, and the resulting solution is maintained at −78° C. for 30 min. The flask is then transferred to a water-ice bath and allowed to come to 0° C. for about 15 minutes. The solution is once again cooled to −78° C., and ZnCl$_2$ (0.5 M solution in THF, 27.0 mL, 13.5 mmol) is slowly added. A precipitate is observed at this point, which may be the bis(indole)zinc compound, but the solution becomes homogeneous when the entire volume of zinc chloride solution is added. After about 10 minutes, the solution is allowed to come to room temperature, and a THF solution (5 mL) of 4-iodoaniline (3.47 g, 15.8 mmol) and triphenylphosphine (338 mg, 1.29 mmol) is added. The septum is removed, and solid Pd$_2$(dba)$_3$ (295 mg, 0.322 mmol) is added. A reflux condenser is fitted to the flask, and the solution is degassed by three successive cycles of vacuum pumping/N$_2$ purging. The solution is then heated to reflux overnight. After cooling to room temperature, the solution is poured into 4 volumes of water, and 4 volumes of ethyl acetate are added. The resulting mixture is vigorously stirred for 30 minutes, then filtered through celite (with ethyl acetate washing) to remove solid Zn- and Pd-containing material. The phases are separated, and the aqueous phase is extracted with more ethyl acetate. The organic phases are washed in sequence with saturated brine, combined, dried over anhydrous sodium sulfate, filtered and evaporated. A solid precipitate forms at this point, which is sufficiently pure product and is collected by trituration with ether and filtration. The remaining material is purified by column chromatography (eluting 1:2 ethyl acetate-hexane on silica gel 60). Total yield of the product, 2-(4-amino-phenyl)-6-methoxy-1-propyl-1H-indole-3-carbonitrile, is 2.75 g (8.99 mmol, 70%).

The following compounds are made using essentially the same procedure and substituting other aryl or heteroaryl iodides or bromides: Compounds 393, 408, 430, 431, 436, 437, 438, 459, 460, 461, 462, 483, 484, 632, 633, 634, 635, 636, 650, 651.

Example 1Gd

Preparation of 1-ethyl-2-(3-hydroxyphenyl)-6-methoxy-1H-indole-3-carbonitrile (Compound 288)

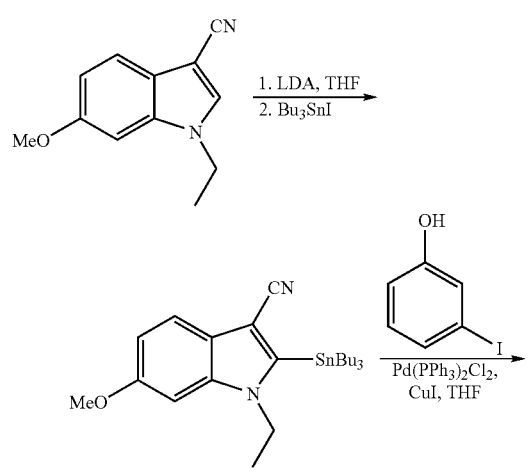

-continued

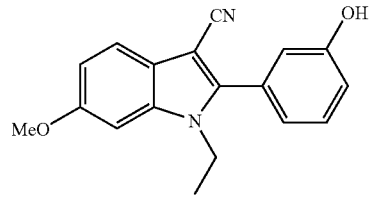

Step A: A solution of THF (60 mL) and diisopropylamine (5.5 mL, 39 mmol) is cooled to −78° C. n-Butyllithium (14.5 mL, 2.5M in hexanes, 36.2 mmol) is added dropwise over 5 minutes. The LDA mixture is stirred at −78° C. for 10 minutes, and then at 0° C. for 20 minutes. The solution is re-cooled to −78° C. 1-ethyl-6-methoxy-1H-indole-3-carbonitrile (5.0 g, 25 mmol), prepared as in example 1A, is taken up in THF (30 mL) and added dropwise to the LDA mixture over 15 minutes. The reaction is stirred at −78° C. for 10 minutes, and at 0° C. for 30 minutes. Once again, the reaction mixture is cooled to −78° C. Tributyltin iodide (10 mL, 35 mmol) is added dropwise. This is stirred at −78° C. for 15 minutes, and then at 0° C. for 30 minutes. The reaction mixture is absorbed onto silica gel and concentrated. Purification by chromatography (CH$_2$Cl$_2$) yields 1-ethyl-6-methoxy-2-tributylstannanyl-1H-indole-3-carbonitrile (12.05 g, 98%).

Step B: 1-Ethyl-6-methoxy-2-tributylstannanyl-1H-indole-3-carbonitrile (1.0 g, 2.05 mmol), prepared in step A, is combined with 3-iodophenol (474 mg, 2.15 mmol), Pd(PPh$_3$)$_2$Cl$_2$ (67 mg, 0.102 mmol), CuI (75 mg, 0.39 mmol) and THF (4.0 mL). This mixture is heated at 65° C. overnight. The reaction mixture is diluted in EtOAc, and is filtered through celite. The filtrate is concentrated and the residue is purified by silica gel chromatography (4:1, CH$_2$Cl$_2$/EtOAc) to yield crude product. Ether trituration yields 1-ethyl-2-(3-hydroxy-phenyl)-6-methoxy-1H-indole-3-carbonitrile (430 mg, 72%) as a yellow-white solid.

The following compounds are prepared similarly as above, using other commercially available iodides and bromides, or using iodides derived from a one step amidation of p-iodophenylsulfonyl chloride: Compounds 275, 276, 277, 278, 331, 363, 364, 373, 374, 375, 474, 475, 678.

Example 1Ge

Preparation of ethanesulfonic acid [4-(3-cyano-6-difluoromethoxy-1-ethyl-1H-indol-2-yl)-phenyl]-amide via Heck route (compound 519)

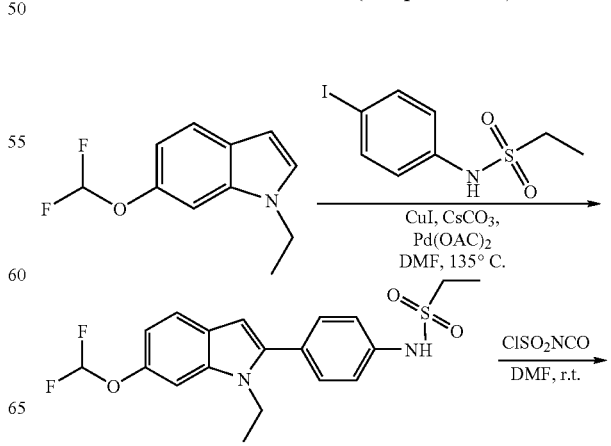

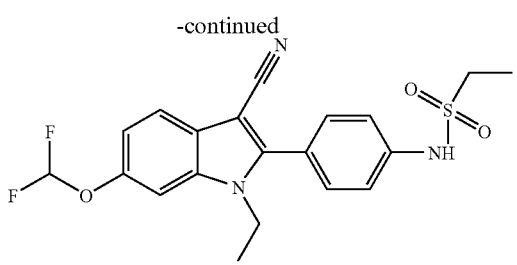

Step A: A solution of 6-difluoromethoxy-1-ethyl-1H-indole (402.8 mg, 2.04 mmol), ethanesulfonic acid (4-iodophenyl)-amide (712.1 mg, 2.29 mmol), cesium carbonate (733.2 mg, 3.82 mmol), triphenylphosphine (33.1 mg, 0.13 mmol) and palladium acetate (5.7 mg, 0.025 mmol) in DMA (5 ml) is heated to 135° C. for 48 h. The reaction mixture is diluted with water and extracted with EtOAc (2×10 mL). The combined organic phases are washed with brine, dried over MgSO$_4$, and then concentrated. The residue is purified via column chromatography on silica gel (25 g) using EtOAc/Hexanes (10-20%) as eluent to afford 298.2 mg (37.1% yield) of ethanesulfonic acid [4-(6-difluoromethoxy-1-ethyl-1H-iodo-2-yl)-phenyl]-amide, compound 516, as a light brown solid.

Step B: Following the procedure 1A, step A, ethanesulfonic acid [4-(6-difluoromethoxy-1-ethyl-1H-iodo-2-yl)-phenyl]-amide is converted to ethanesulfonic acid [4-(3-cyano-6-difluoromethoxy-1-ethyl-1H-indol-2-yl)-phenyl]-amide, compound 519.

Following steps A and B above, the following compounds are prepared in similar fashion: Compounds 343, 344, 345, 346, 409, 410, 411, 412, 413, 414, 415, 416, 417, 418, 419, 463, 464, 465, 466, 467, 468, 469, 470, 471, 472, 473, 515, 517, 518, 520, 521, 522, 523, 524, 575, 577, 579, 580, 611, 612, 613, 614.

Example 1H

Preparation of 1-ethyl-2-(4-fluorophenylethynyl)-6-methoxy-1H-indole-3-carbonitrile (compound 67)

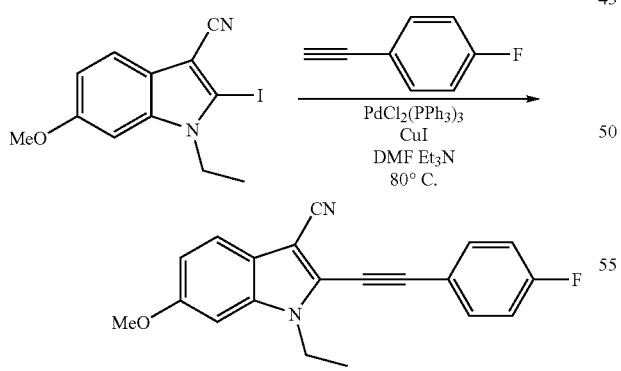

A mixture of 1-ethyl-2-iodo-6-methoxy-1H-indole-3-carbonitrile (150 mg, 0.46 mmol), prepared as described in example 1Ga, step A, 4-fluorophenylacetylene (80 mg, 0.0.69 mmol), bis(triphenylphosphine)palladium (II) dichloride (6 mg, 0.009 mmol) and CuI (4 mg, 0.018 mmol) is added to a sealable tube and alternatively evacuated and flushed with N$_2$. To the tube is then added DMF (4 mL) and Et$_3$N (0.25 mL, 1.84 mmol) and the reaction is heated at 80° C. for 20 h and then cooled to room temperature. The reaction mixture is diluted with H$_2$O and extracted with EtOAc (2×). The combined organic phases are washed with H$_2$O (3×) and saturated NaCl and then dried over MgSO4 and concentrated. The crude reaction mix is absorbed on silica gel (0.6 g) and chromatographed over silica gel using EtOAc/hexanes (10-20%) as eluent to afford 120 mg (82%) of 1-ethyl-2-(4-fluorophenylethynyl)-6-methoxy-1H-indole-3-carbonitrile as a yellow solid.

Utilizing essentially the same procedure described above and substituting different acetylene derivatives gives the following compounds: Compounds 64, 65, 66, 68, 69, 91, 92, 93, 94, 95, 96, 133, 134, 135, 136, 137, 143, 144, 145, 146, 147, 148, 149, 150, 151, 158, 159, 160, 161, 169, 170, 171, 172, 173, 174, 175, 176, 177, 178, 184, 185, 186, 187, 188, 196, 197, 198, 199, 200, 201, 202, 223, 230, 231, 232, 233, 234, 235, 236, 237, 238.

Example 1I

Preparation of 1-ethyl-3-(5-ethyl-[1,2,4]oxadiazol-3-yl)-6-methoxy-1H-indole (compound 28)

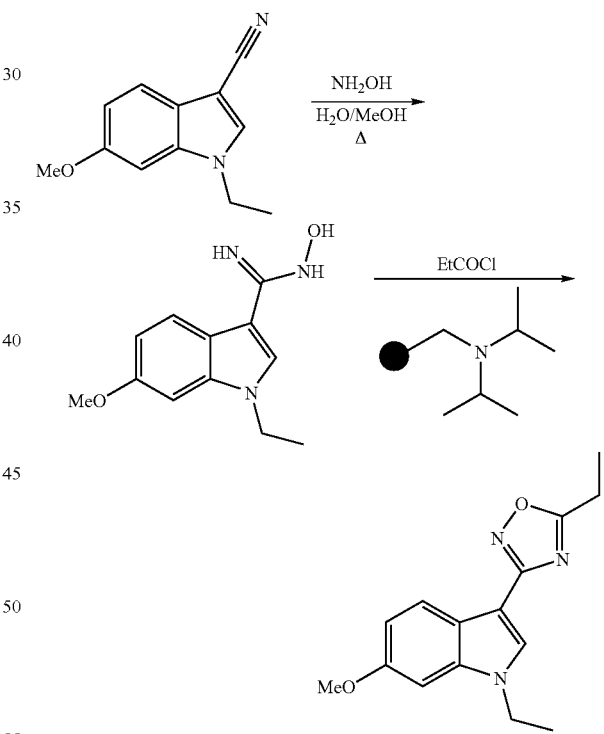

Step A: A solution of 1-ethyl-6-methoxy-1H-indole-3-carbonitrile (1.00 g, 5.00 mmol) in MeOH (10 mL) is treated with a 50% aqueous solution of hydroxylamine (0.38 mL, 6.25 mmol) and heated at reflux for 18 h. After cooling to room temperature, the heterogeneous mixture is filtered to afford 525 mg of desired product as a tan solid. The filtrate is concentrated to an oil, which is then dissolved in CH$_2$Cl$_2$ and chromatographed over silica gel using EtOAc/CH$_2$Cl$_2$ (15-50%) to afford an additional 295 mg of product as a tan solid. Total yield of 1-ethyl-N-hydroxy-6-methoxy-1H-indole-3-carboxamidine is 820 mg (70%).

Step B: The N-hydroxycarboxamidine above (50 mg, 0.21 mmol), polystyrene-diisopropylethylamine 165 mg, 3.90 mmol/g loading) and propionyl chloride (0.03 mL, 0.32 mmol) in CH$_2$Cl$_2$ (10 mL) are placed in a tube and rotated for 22 h at room temperature. After this time, trisamine resin (77 mg, 2.71 mmol/g loading) is then added and the tube rotated for an additional 30 min at room temperature. Solids are filtered and then the filtrate is concentrated and diluted with toluene (5 mL) and heated at 110° C. overnight. The crude reaction mixture is concentrated and purified by chromatography (EtOAc/CH$_2$Cl$_2$, 2/98) to afford 27 mg (46%) of 1-ethyl-3-(5-ethyl-[1,2,4]oxadiazol-3-yl)-6-methoxy-1H-indole as a white solid.

The following compound is prepared utilizing the above procedure with substitution of the appropriate acyl halide: Compound 29.

Example 1J

Preparation of 1-ethyl-6-methoxy-3-(5-ethyl-[1,3,4]oxadiazol-2-yl)-1H-indole (compound 54)

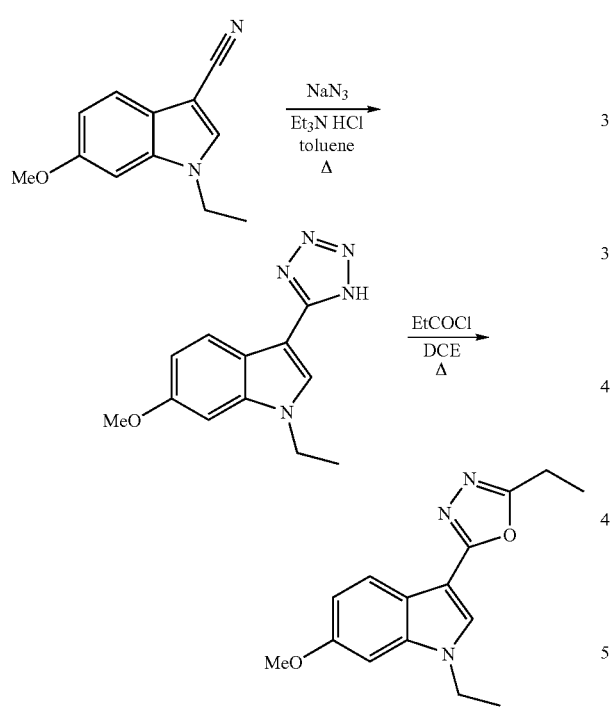

Step A: A mixture of 1-ethyl-6-methoxy-1H-indole-3-carbonitrile (1.00 g, 5.00 mmol) in toluene (30 mL) is treated with triethylamine hydrochloride (1.03 g, 7.50 mmol) and sodium azide (0.49 g, 7.50 mmol) and is heated at reflux for 16 h. After cooling to room temperature, the reaction mixture is diluted with saturated NaHCO$_3$ and extracted with EtOAc. The organic layer is then washed with additional NaHCO$_3$ (2×). The combined aqueous phases are acidified to pH 2 with 6N HCl. The resultant thick precipitate is extracted with hot EtOAc (3×) and the combined organic phases are washed with saturated NaCl and dried and concentrated to give 0.55 g (45%) of 1-ethyl-6-methoxy-3-(1H-tetrazol-5-yl)-1H-indole as a yellow solid.

Step B: A suspension of the tetrazole above (50 mg, 0.21 mmol) and propionyl chloride (0.03 mL, 0.31 mmol) in dichloroethane (5 mL) is heated at reflux for 21 h. After cooling the reaction mixture to room temperature, polystyrene trisamine resin (70 mg, 3.4 meq/g) is added and the reaction is rotated for 4 h at room temperature. After filtering off the resin, and removal of the solvent, the crude product is absorbed on silica gel and the product is isolated by silica gel chromatography (EtOAc/CH$_2$Cl$_2$, 5-10%) to afford 30 mg (53Y %) of 1-ethyl-6-methoxy-3-(5-ethyl-[1,3,4]oxadiazol-2-yl)-1H-indole as a tan solid.

Example 1K

Preparation of ethyl 5-difluoromethoxy-1-(4-methoxyphenyl)-2-methyl-1H-indole-3-carboxylate (compound 49)

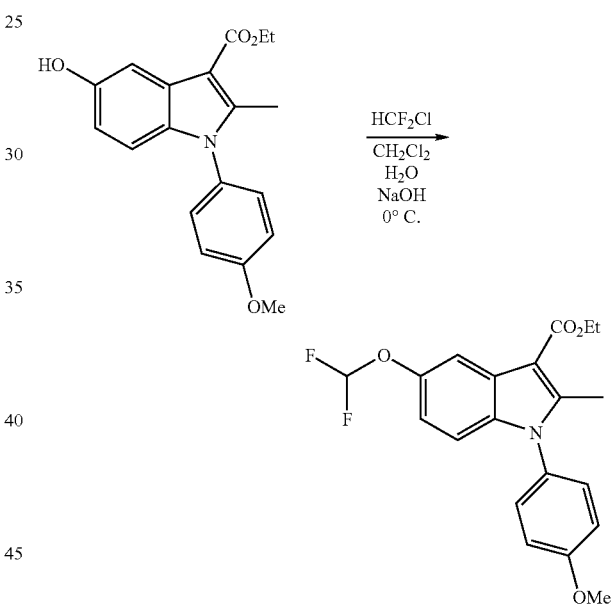

Freon-22 (HCF$_2$Cl) gas is bubbled into a solution of ethyl 5-hydroxy-1-(4-methoxyphenyl)-2-methyl-1H-indole-3-carboxylate (250 mg, 0.77 mmol) in CH$_2$Cl$_2$ (5 mL) at 0° C. containing a small amount of tetrabutylammonium bromide as a phase transfer catalyst. A 50% solution of NaOH is added dropwise at 0° C. After the addition, the mixture is stirred at 0° C. for 2 h. After the addition of H$_2$O, the organic phase is separated and washed with brine and dried over Na$_2$SO$_4$. The solvent is then concentrated and the residue is purified by column chromatography over silica gel using EtOAc/petroleum ether (1/2) as eluent to yield the desired product in 40% yield.

The following compounds are prepared utilizing the above procedure with substitution of the appropriate hydroxyindole: Compounds 18, 46, and 50.

Example 1L

Preparation of 1-[5-methoxy-1-(4-methoxyphenyl)-1-H-indol-3-yl]-ethanone (compound 42)

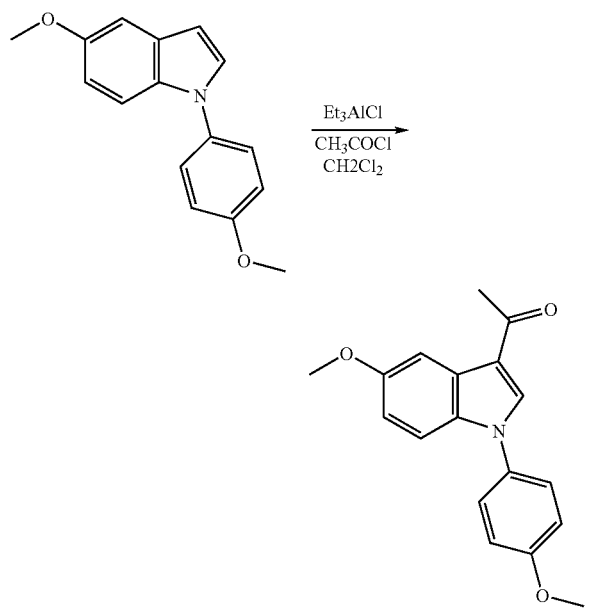

5-Methoxy-1-(4-methoxyphenyl)-1-H-indole (50 mg, 0.2 mmol), prepared by the method of example 1C, is dissolved in 1 mL of CH$_2$Cl$_2$ at 0° C. Et$_2$AlCl (300 μL, 1 M in hexanes, 0.3 mmol) is then added. After stirring at 0° C. for 30 min, a solution of acetyl chloride (22 μL, 0.3 mmol) in 1 mL of CH$_2$Cl$_2$ is added dropwise. This is stirred at 0° C. for a further 90 min. The reaction mixture is quenched with H$_2$O and is extracted with CH$_2$Cl$_2$ and concentrated in vacuo. Purification by column chromatography on silica gel EtOAc/CH$_2$Cl$_2$ (5/95) yields the title compound as a white solid (42 mg, 71%).

Utilizing essentially the same procedure described above and substituting different acyl chlorides, the following compounds are prepared: Compounds 32, 33, 34, 37, 38, 39, 47, 48.

Example 1M

Preparation of 1-ethyl-3-isoxazol-3-yl-6-methoxy-1-H-indole (compound 57)

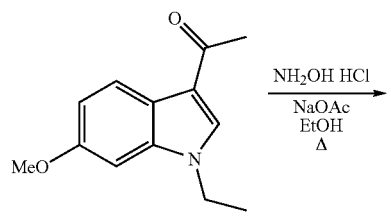

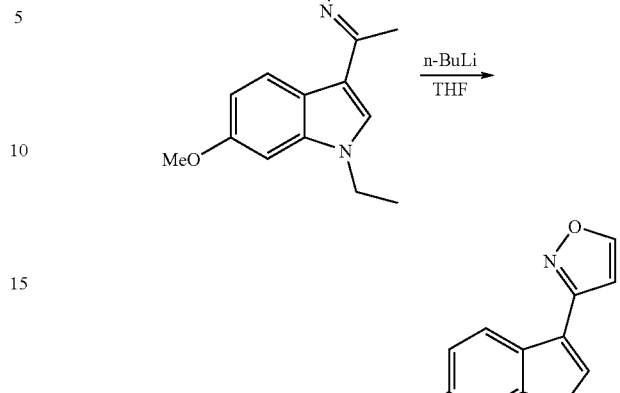

Step A: A mixture of 1-(1-ethyl-6-methoxy-1-H-indole-3-yl)ethanone (200 mg, 0.92 mmol), prepared from 1-ethyl-6-methoxy-1H-indole by the procedure described in example 1L, hydroxylamine hydrochloride (128 mg, 1.84 mmol), NaOAc (151 mg, 1.84 mmol) and EtOH (7 mL) is heated at 85° C. for 4 h. The reaction mixture is then partitioned between H$_2$O and EtOAc. The organic phase is dried and concentrated in vacuo. Purification by column chromatography using EtOAc/CH$_2$Cl$_2$ (1/9) yields 1-(1-ethyl-6-methoxy-1-H-indole-3-yl)ethanone oxime as a white solid (189 mg, 92%).

Step B: 1-(1-Ethyl-6-methoxy-1-H-indole-3-yl)ethanone oxime (100 mg, 0.43 mmol) is dissolved in THF (900 μL) at 0° C. n-BuLi (450 μL, 2.5 M in hexanes, 1.12 mol) is added dropwise, resulting in instant precipitation of solids. DMF (70 μL, 0.9 mol) in 260 μL of is then added dropwise. This is stirred at 0° C. for 1 h, then at room temperature for 1 h. The reaction mixture is pipetted into a mixture containing 1 mL of H$_2$O, 1 mL of THF, and 100 μL of concentrated H$_2$SO$_4$. This mixture is heated at 75° C. for 1 h and then is partitioned between H$_2$O and EtOAc. The organic phase is dried and concentrated. Purification by column chromatography (CH$_2$Cl$_2$) yields 1-ethyl-3-isoxazol-3-yl-6-methoxy-1-H-indole product as a white solid (13 mg, 12%).

Example 1N

Preparation of 1-ethyl-3-isoxazol-5-yl-6-methoxy-1H-indole (compound 58)

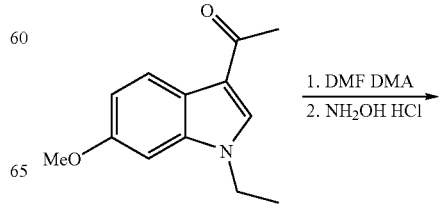

-continued

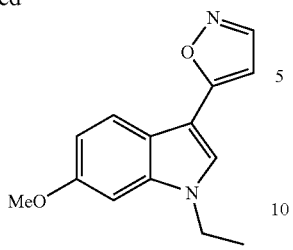

1-(1-Ethyl-6-methoxy-1H-indol-3-yl)ethanone (100 mg, 0.46 mmol), prepared from 1-ethyl-6-methoxy-1H-indole by the procedure described in example 1L, is heated with 1.5 mL of dimethylformamide dimethylacetal and 100 µL of pyrrolidine at 110° C. overnight. The dimethylformamide dimethylacetal is then concentrated in vacuo. The residue is redissolved in 1.25 mL of EtOH and 250 µL of $H_2O$, and is treated with hydroxylamine hydrochloride (66 mg, 0.95 mmol) and heated at 80° C. for 2 h. Partitioning between $H_2O$ and EtOAc and drying and concentration of the organic phase followed by purification by silica gel chromatography (EtOAc/$CH_2Cl_2$, 5/95) gives 1-ethyl-3-isoxazol-5-yl-6-methoxy-1H-indole as a white solid (72 mg, 66%).

Utilizing essentially the same procedure described above, the following compound is prepared: Compound 60.

Example 1O

Preparation of 1-ethyl-6-methoxy-3-(2H-pyrazol-3-yl)-1H-indole (compound 59)

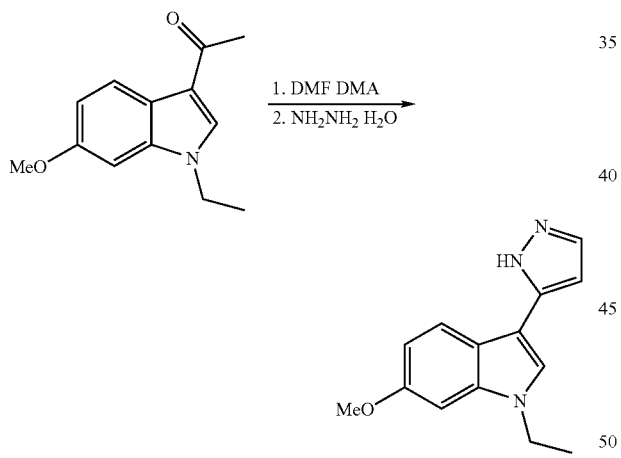

1-(1-Ethyl-6-methoxy-1H-indol-3-yl)-ethanone (100 mg, 0.46 mmol), prepared from 1-ethyl-6-methoxy-1H-indole by the procedure described in example 1L, is heated with 1.5 mL of dimethylformamide dimethyl acetal and 100 µL pyrrolidine at 110° C. overnight. The DMF dimethyl acetal is removed in vacuo. The residue is redissolved in 3 mL of acetic acid, hydrazine hydrate (70 µL, 1.38 mmol) is added, and the mixture is heated to 100° C. for 2 h. The acetic acid is removed in vacuo, and the residue is partitioned between EtOAc and saturated $NaHCO_3$. The organic phase is dried and concentrated and the product purified by silica gel chromatography (EtOAc/Hex, 1/1) to give 59 mg of 1-ethyl-6-methoxy-3-(2H-pyrazol-3-yl)-1H-indole (54%) as a colorless semisolid. Trituration in $Et_2O$ gives a white crystalline powder.

The following compound is prepared utilizing the above procedure: Compound 61.

Example 1P

Preparation of methyl 1-ethyl-3-oxazol-5-yl-1H-indole-6-carboxylate (compound 72)

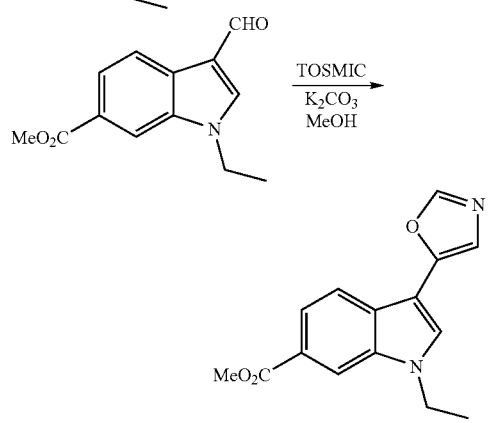

Step A: 1-Ethyl-1H-indole-6-carboxylic acid methyl ester (900 mg, 4.45 mmol) is dissolved in DMF (3.3 mL). This is added dropwise to an ice-cold solution of $POCl_3$ (430 µL, 4.5 mmol) in DMF (1.5 mL). The reaction mixture is stirred at room temperature for 90 minutes. The reaction mixture is then treated with 6N NaOH (3.5 ml). The mixture is then partitioned between $H_2O$ and ethyl acetate. Purification by silica gel chromatography (5-10% EtOAc/$CH_2Cl_2$) yields 1-ethyl-3-formyl-1H-indole-6-carboxylic acid methyl ester (985 mg, 96%) as a white solid.

Step B: 1-Ethyl-3-formyl-1H-indole-6-carboxylic acid methyl ester (100 mg, 0.42 mmol), TOSMIC (100 mg, 0.52 mmol), $K_2CO_3$ (178 mg, 1.29 mmol), and MeOH (800 µL) are heated at 80° C. overnight. The reaction mixture is then partitioned between $H_2O$ and ether. After drying and concentrating the organic phase, the product is purified by silica gel chromatography (EtOAc/$CH_2Cl_2$, 10/90) to give methyl 1-ethyl-3-oxazol-5-yl-1H-indole-6-carboxylate (26 mg, 23%) as an off-white solid.

Example 1Q

Preparation of methyl 1-ethyl-3-oxazol-2-yl-1H-indole-6-carboxylate (compound 75)

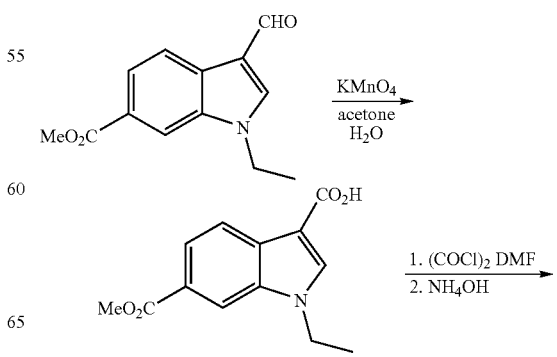

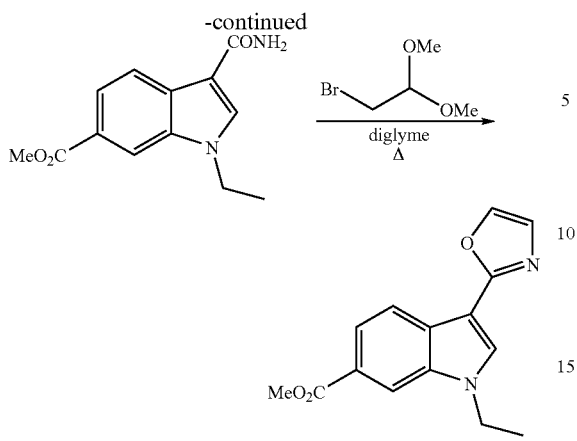

Step A: 1-Ethyl-3-formyl-1H-indole-6-carboxylic acid methyl ester (800 mg, 3.5 mmol), prepared as shown in example 1P, step A, is dissolved in acetone (98 mL). A solution of $KMnO_4$ (655 mg, 4.15 mmol) in $H_2O$ (31 mL) is added. The reaction mixture is stirred at room temperature for 90 minutes. Another addition of $KMnO_4$ (108 mg) in $H_2O$ (6 mL), followed by stirring for another 45 minutes is required to drive the reaction to completion. The reaction mixture is then quenched with 10% $H_2O_2$ (1.5 mL). The mixture is filtered through celite. The filtrate is stripped down under vacuum to roughly ⅓ of the volume. The residue is acidified with 6N HCl, and is extracted into ethyl acetate. The solids isolated from the ethyl acetate layer are triturated with acetone to yield 1-ethyl-1H-indole-3,6-dicarboxylic acid 6-methyl ester (696 mg, 79%) as a light orange solid.

Step B: 1-Ethyl-1H-indole-3,6-dicarboxylic acid 6-methyl ester (600 mg, 2.43 mmol) is suspended in a solution of $CH_2Cl_2$ (27 ml) and DMF (20 µL). Oxalyl chloride (470 µL, 5.38 mmol) is added, and the reaction mixture is stirred for 1 hour at room temperature. This mixture is then slowly poured into a rapidly stirring solution of concentrated $NH_4OH$ (10 mL). This is then partitioned in $H_2O$ and EtOAc. The residue from the ethyl acetate layer is triturated with acetone to yield 6-methoxycarbonyl-1-ethyl-1H-indole-3-carboxamide (511 mg, 85%) as a white solid.

Step C: A mixture of 150 mg (0.61 mmol) of 6-methoxycarbonyl-1-ethyl-1H-indole-3-carboxamide in diglyme (3.6 mL), and bromoacetaldehyde dimethyl acetal (430 µL, 3.7 mmol) is heated at 125° C. for 2 h. The reaction mixture is cooled and partitioned in $H_2O$ and EtOAc. The organic phase is dried and concentrated and the product is purified by silica gel chromatography (EtOAc/$CH_2Cl_2$ 5-10%). The product containing fractions are combined and concentrated and the solid is triturated with hexanes to yield methyl 1-ethyl-3-oxazol-2-yl-1H-indole-6-carboxylate (75 mg, 46%) as a yellow solid.

Example 1R

Preparation of 1-ethyl-6-methoxy-3-thiazol-2-yl-1H-indole (compound 73)

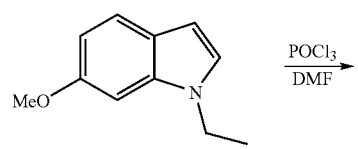

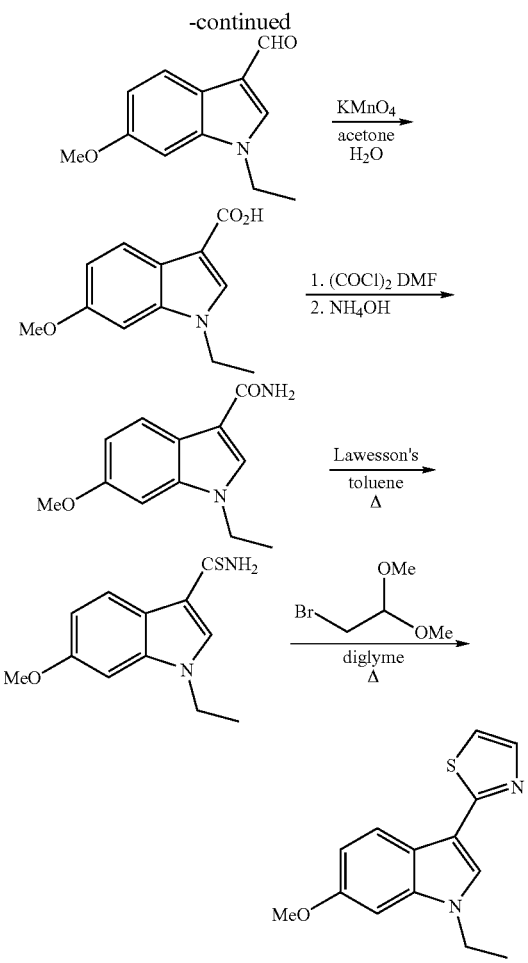

Step A: 1-Ethyl-6-methoxy-1H-indole (900 mg, 5.14 mmol) is dissolved in DMF (1.5 mL). This is added dropwise to an ice-cold solution of $POCl_3$ (500 µL, 5.2 mmol) in DMF (1.75 ml). After stirring at room temperature for 90 minutes, the reaction mixture is re-cooled in an ice bath and is slowly quenched with 6N NaOH (4 mL). The reaction mixture is partitioned between EtOAc and $H_2O$. Purification by silica gel chromatography (EtOAc/$CH_2Cl_2$, 5/95) yields 1-ethyl-6-methoxy-1H-indole-3-carbaldehyde (849 mg, 81%) as a yellow solid.

Step B: 1-Ethyl-6-methoxy-1H-indole-3-carbaldehyde (600 mg, 2.95 mmol) is dissolved in acetone (85 mL). A solution of $KMnO_4$ (450 mg, 2.85 mmol) in $H_2O$ (28 mL) is added. This is stirred at room temperature for 5 hours. Another solution of $KMnO_4$ (450 mg, 2.85 mmol) in $H_2O$ (25 mL) is then added. After stirring for another hour at room temperature, the reaction is complete. The reaction mixture is quenched with 10% $H_2O_2$ (1.5 mL), and is then filtered through celite. The filtrate is stripped down under vacuum to roughly ⅓ of the volume. The residue is acidified with 6N HCl, and is extracted into ethyl acetate. Purification by silica gel column (hexanes/acetone/acetic acid, 70/30/1) yields crude product. Trituration with ether yields pure 1-ethyl-6-methoxy-1H-indole-3-carboxylic acid (365 mg, 56%) as a yellow solid.

Step C: 1-Ethyl-6-methoxy-1H-indole-3-carboxylic acid (250 mg, 1.14 mmol) is suspended in a solution of $CH_2Cl_2$ (12.5 mL) and DMF (10 µL). Oxalyl chloride (230 µL, 2.64 mmol) is added, and the reaction mixture is stirred for 1 hour at room temperature. This mixture is then slowly poured into a rapidly stirring solution of concentrated NH$_4$OH (5 mL). This is then partitioned in H$_2$O and EtOAc. The residue from the ethyl acetate layer is triturated with acetone to yield 1-ethyl-6-methoxy-1H-indole-3-carboxamide (134 mg, 54%) as a white solid.

Step D: 1-Ethyl-6-methoxy-1H-indole-3-carboxamide (120 mg, 0.55 mmol), Lawesson's reagent (240 mg, 0.6 mmol), and toluene (2 mL) are heated at 90° C. for 90 min. The reaction mixture is concentrated and purified by silica gel chromatography (EtOAc/CH$_2$Cl$_2$, 1/9) to yield 1-ethyl-6-methoxy-1H-indole-3-thiocarboxamide as a yellow solid (92 mg, 71%).

Step E: 1-Ethyl-6-methoxy-1H-indole-3-thiocarboxamide (83 mg, 0.36 mmol), glyme (3.6 mL) and bromoacetaldehyde dimethyl acetal (220 μL, 1.86 mmol) are heated at 80° C. for 16 h. More bromoacetaldehyde dimethyl acetal (250 μL is added. This is heated at 80° C. for 2 h. Addition of 250 μL more bromoacetaldehyde dimethyl acetal is followed by heating for another 2 hours. The reaction mixture is cooled to room temperature, absorbed onto silica and purified by silica gel chromatography (hexanes/EtOAc, 7/3) to afford 1-ethyl-6-methoxy-3-thiazol-2-yl-1H-indole as a brown oil (44 mg, 47%).

The following compounds are prepared following the procedure described above: Compounds 78, 101, 104, 105 and 106.

Example 1S

Preparation of 1-ethyl-6-methoxy-2-phenoxymethyl-1H-indole-3-carbonitrile (compound 99)

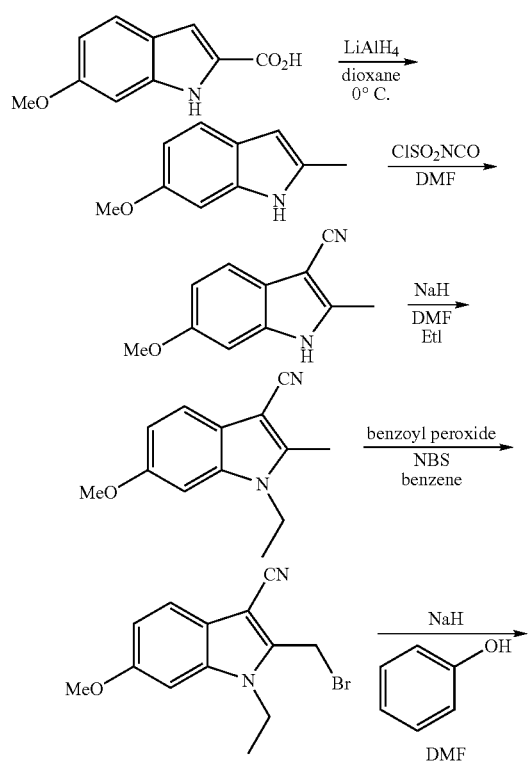

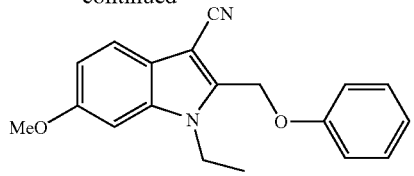

Step A: To a suspension of LiAlH$_4$ (7.6 g, 0.2 mol) in dioxane (100 mL) is added dropwise a solution of methyl 6-methoxy-1H-indole-2-carboxylate (8.2 g, 0.04 mol) in dioxane (50 mL) at 0° C. After the addition, the mixture is stirred at room temperature for 1 h and then heated at reflux for 5 h. After cooling to 0° C., the reaction is quenched by water (dropwise) and then 15% aqueous NaOH. After stirring at room temperature for 1 h, the mixture is filtered through Celite. The solid is washed with a large amount of EtOAc. The solvent is washed with brine, dried over Na$_2$SO$_4$ and evaporated under vacuum. The residue is purified by flash column chromatography on silica gel using EtOAc/petroleum ether (1/5) as eluent to yield 61% of 6-methoxy-2-methyl-1H-indole.

Step B: To a solution of 6-methoxy-2-methyl-1H-indole (3.9 g, 24 mmol) in acetonitrile (200 mL) and DMF (20 mL) is added dropwise a solution of ClSO$_2$NCO (4 mL, 1.3 eq.) in acetonitrile (31 mL) at 0° C. After the addition, the mixture is stirred at room temperature for 3 h. Then it is poured into ice water and saturated NaHCO$_3$ is added to it until it becomes basic. The aqueous phase is extracted with CH$_2$Cl$_2$ and then evaporated. The residue is purified with flash column chromatography on silica gel using EtOAc/petroleum ether (1/5) as eluent to yield 81% of 6-methoxy-2-methyl-1H-indole-3-carbonitrile.

Step C: To a suspension of NaH (0.6 g, 2 eq.) in DMF (7 mL) is added a solution of 6-methoxy-2-methyl-1H-indole-3-carbonitrile (1.3 g, 7.0 mmol) in DMF (8 mL) followed by ethyl iodide (1.2 mL, 2 eq.) at 0° C. After stirring for 1 h, the mixture is poured into ice water and the mixture is extracted with CH$_2$Cl$_2$. The organic layer is washed with brine and dried with Na$_2$SO$_4$. The solvent is evaporated under vacuum and purified with flash column chromatography on silica gel using EtOAc/petroleum ether (1/5) as eluent to yield 92% of 1-ethyl-6-methoxy-2-methyl-1H-indole-3-carbonitrile.

Step D: To a solution of 1-ethyl-6-methoxy-2-methyl-1H-indole-3-carbonitrile (1.38 g, 6.45 mmol) in benzene (130 mL) is added benzoyl peroxide (226 mg) and NBS (1.21 g, 1.05 eq.). Then the mixture is heated to reflux for 3 h. After cooling and filtering, the filtrate is concentrated under vacuum. The crude 2-bromomethyl-1-ethyl-6-methoxy-1H-indole-3-carbonitrile (1.6 g, 86%) is used without further purification.

Step E: To a solution of NaH (44 mg, 4 eq.) in DMF (0.5 mL) is added 2-bromomethyl-1-ethyl-6-methoxy-1H-indole-3-carbonitrile (80 mg, 0.274 mmol) and phenol (2 eq.). After stirring for 20 h, the mixture is poured into ice water and extracted with CH$_2$Cl$_2$. The organic layer is washed with brine and dried with Na$_2$SO$_4$. The solvent is evaporated under vacuum and purified with flash column chromatography on silica gel using EtOAc/petroleum ether (1/5) as eluent to yield 1-ethyl-6-methoxy-2-phenoxymethyl-1H-indole-3-carbonitrile, compound 99.

Example 1T

Preparation of 6-nitro-2-pyrrol-1-yl-1H-indole-3-carbonitrile (compound 7)

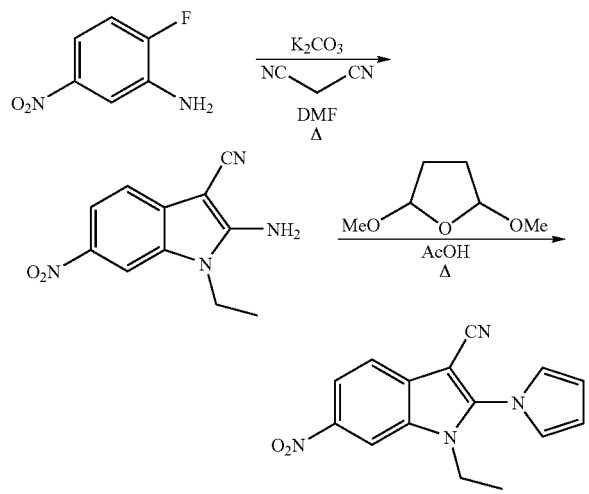

Step A: A solution of 2-fluoro-5-nitroaniline (11.7 g, 74.9 mmol) in dimethylformamide (120 mL) is treated with malononitrile (5.28 g, 80.0 mmol) and potassium carbonate (11.05 g, 80.0 mmol) (Modification of *Chem. Heterocyclic Cpd.* (*Engl. Trans.*, 9, 37 (2001). The resulting heterogeneous mixture is heated to gentle reflux for 3 h, then cooled and poured into water (500 mL). The resulting precipitate is collected by filtration and taken up into ethyl acetate (300 mL). This solution is dried over $Na_2SO_4$, filtered and partially evaporated to give a precipitate, which is collected by filtration. Further evaporation and filtration gives a second crop. The two crops are combined and dried under vacuum to give 2-amino-1-ethyl-6-nitro-1H-indole-3-carbonitrile (7.90 g, 52%) as an orange powder.

Step B: A solution of 2-amino-6-nitro-1H-indole-3-carbonitrile (362 mg, 1.79 mmol) in acetic acid (5 mL) is treated with 2,5-dimethoxytetrahydrofuran (0.30 mL, 2.27 mmol), and the solution is heated to reflux for 14 h. After cooling to ambient temperature, the solution is poured into water (100 mL), and solid sodium bicarbonate is added until $CO_2$ evolution ceased. The mixture is extracted with EtOAc (2×100 mL), and the extracts are washed with saturated brine, combined, dried over $MgSO_4$, filtered and concentrated. The residual material is separated by silica gel chromatography (EtOAc/hexanes, 1/4) to afford 6-nitro-2-pyrrol-1-yl-1H-indole-3-carbonitrile, compound 5, as a yellow solid (232 mg, 51%).

Example 1U

Preparation of N-(3-cyano-1-ethyl-6-nitro-1H-indol-2-yl)acetamide (compound 25)

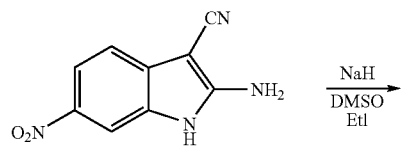

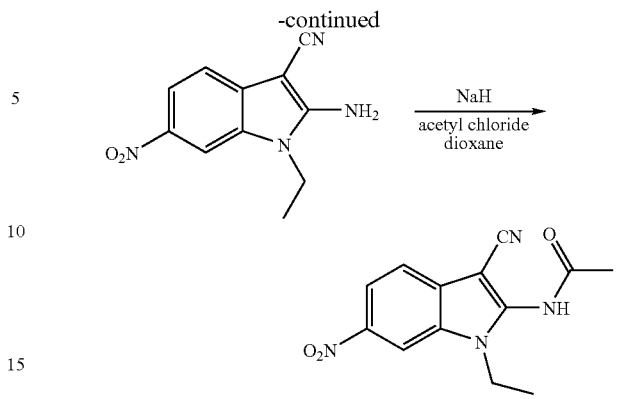

Step A: Sodium hydride (42 mg, 1.05 mmol, 60% w/w suspension in mineral oil) is washed with hexane and taken up in dimethylsulfoxide (1 mL). A solution of 2-amino-6-nitro-1H-indole-3-carbonitrile, prepared in procedure 1T) in dimethylsulfoxide (1 mL) is added by syringe, and the resulting mixture is stirred for 20 min. Then, iodoethane (77 µL, 0.96 mmol) is added by syringe, and the mixture is stirred for 14 h. The reaction is then poured into EtOAc (50 mL), and this solution is washed with water (3×50 mL) and saturated brine (40 mL). The aqueous phases are back-extracted with EtOAc, and the organic extracts are combined, dried over $Na_2SO_4$, filtered and evaporated. The residual material is separated by column chromatography over silica gel (EtOAc/hexanes, 1/1) to afford first a small amount of a dialkylated analog, then the desired compound, 2-amino-1-ethyl-6-nitro-1H-indole-3-carbonitrile (114 mg, 52%), and finally unreacted starting material. The desired product is isolated as an orange powder.

Step B: Sodium hydride (44 mg, 1.10 mmol, 60% w/w in mineral oil) is washed with hexanes and suspended in 1,4-dioxane (3 mL). A solution of 2-amino-1-ethyl-6-nitro-1H-indole-3-carbonitrile (120 mg, 0.521 mmol), prepared in step B, above, in dioxane (2 mL) is added, and the resulting mixture is allowed to stir for 30 min. Then, acetyl chloride (45 µL, 0.63 mmol) is added by syringe, and the solution is stirred for an additional 12 h. The reaction is partitioned between water and EtOAc (20 mL each), and the organic phase is washed with brine. The aqueous phases are back-extracted in sequence with ethyl acetate, and the organic extracts are combined, dried over $MgSO_4$, filtered and evaporated. The resulting solid is triturated with $Et_2O$, collected by filtration and dried under vacuum to afford N-(3-cyano-1-ethyl-6-nitro-1H-indol-2-yl)-acetamide (100 mg, 71%), compound 25, as an off-white powder.

Using this procedure and substituting the appropriate acid chlorides or chloroformates gives the following compounds: Compounds 23, 26, 35, 36, 203, 204, 214, 215, 216.

Example 1V

Preparation of N-ethyl-3-phenyl-5-nitroindole (compound 41)

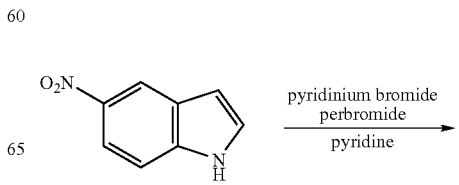

479
-continued

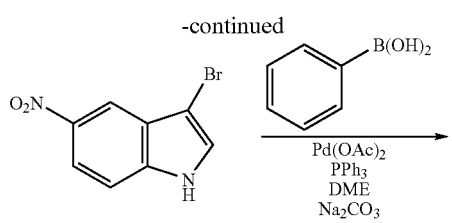

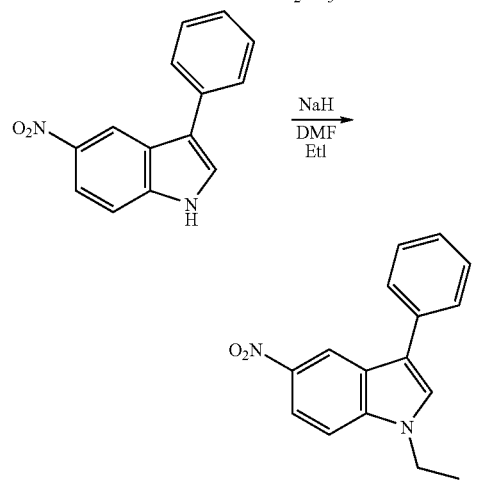

Step A: To a solution of 5-nitroindole (5.00 g, 30.8 mmol) in pyridine (200 mL) at −4° C. is added a solution of pyridinium bromide perbromide (10.99 g, 34.3 mmol) in pyridine (200 mL) dropwise under nitrogen with stirring. After complete addition, the reaction mixture is stirred for 5 min at 0° C. The reaction mixture is diluted in 0° C. water (200 mL) and extracted with 200 mL of Et$_2$O. The organic layer is washed with 6 M HCl (300 mL), 5% NaHCO$_3$ (300 mL), and brine (300 mL). The organic phase is dried over MgSO$_4$ and solvent is removed to give 3-bromo-5-nitroindole as a yellow powder, 80% pure with 20% 5-nitroindole (6.80 g, 74% yield).

Step B: A solution of 3-bromo-5-nitroindole from above (625 mg, 2.1 mmol), phenylboronic acid (381 mg, 3.13 mmol), triphenylphosphine (109.3 mg, 0.417 mmol) in dimethoxyethane (4.16 mL) is degassed. To this mixture 2N sodium carbonate (6.25 mL) is added, and reaction mixture is degassed again. To the reaction is added palladium (II) acetate (23.4 mg, 0.104 mmol), and the reaction is refluxed under dry nitrogen with stirring for 8 hours. The reaction mixture is then diluted with 1 M HCl (100 mL), and extracted with ethyl acetate (100 mL). The organic phase is washed with water (100 mL), and brine (100 mL). The organic phase is dried over MgSO$_4$ and concentrated in vacuo. The crude product is purified by chromatography over silica gel (EtOAc/hexanes, 10/90) to afford 3-phenyl-5-nitroindole as an orange powder (45 mg, 9% yield).

Step C: To a mixture of 60% NaH in mineral oil (8.7 mg, 0.630 mmol) and DMF (1.0 mL) is added dropwise a solution of 3-phenyl-5-nitroindole (40.0 mg, 2.1 mmol) in DMF (0.75 mL). The reaction mixture is stirred for 20 min at 0° C. under N$_2$. Ethyl iodide (14.8 μL, 0.185 mmol) is added dropwise and the reaction mixture is stirred for an additional 3 hours. The reaction mixture is diluted with water (250 mL), and extracted with EtOAc (30 mL). The organic phase is washed with water (250 mL) and is then dried over MgSO$_4$ and the solvent is removed in vacuo. The desired N-ethyl-3-phenyl-5-nitroindole is obtained as a yellow powder (40.0 mg, 89.5% yield).

480

In similar fashion the following compound is prepared: Compound 40.

Example 1W

Preparation of [3-Cyano-1-(4-methoxyphenyl)-1H-indol-6-yl]-carbamic acid propyl ester (compound 97)

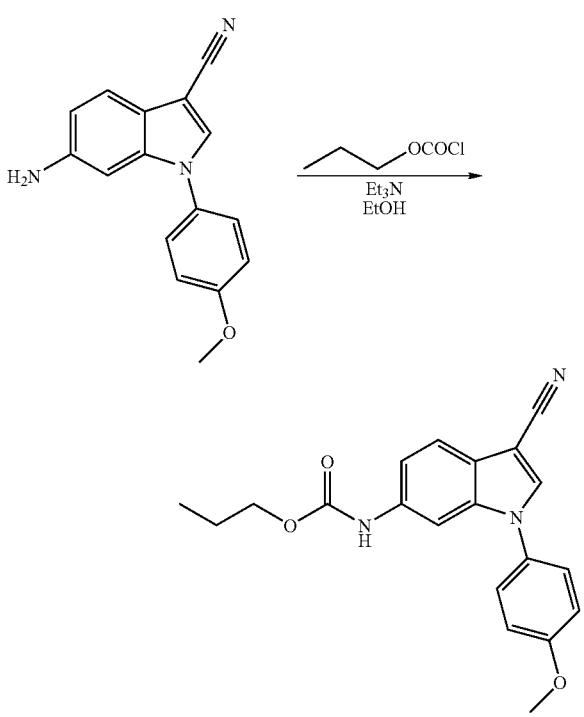

6-Amino-1-(4-methoxyphenyl)-1H-indole-3-carbonitrile (30 mg, 0.12 mmol), is suspended in EtOH (300 μL). Propyl chloroformate (168 μL, 1.5 mmol) is added, and this mixture is stirred at room temperature overnight. The addition of triethylamine (300 μL), followed by another hour of stirring at room temperature, completes the reaction. This reaction mixture is loaded directly onto a silica column, and is eluted with CH$_2$Cl$_2$. Another silica column (3/2, ether/hexanes) is needed to fully purify the product, [3-cyano-1-(4-methoxyphenyl)-1H-indol-6-yl]-carbamic acid propyl ester (19 mg, 45%), as a white solid.

Example 1X

Preparation of N-[4-(3-cyano-1-ethyl-6-methoxy-1H-indol-2-ylethynyl)-phenyl]-methanesulfonamide (compound 130)

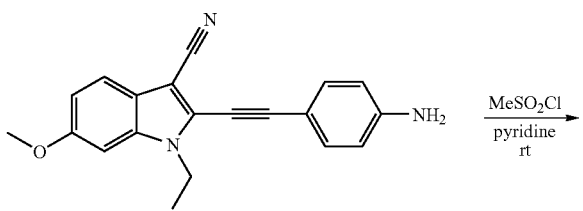

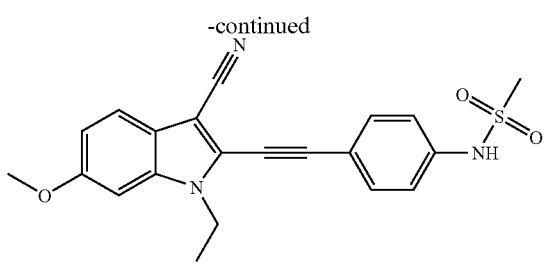

2-(4-Aminophenylethynyl)-1-ethyl-6-methoxy-1H-indole-3-carbonitrile (50 mg, 0.16 mmol), prepared as described by the method of Example 1H, is dissolved in pyridine (550 µL) at room temperature. Methanesulfonyl chloride (17 µL, 0.21 mmol) is added dropwise. This is stirred overnight at room temperature. The reaction mixture is then diluted in ethyl acetate and is washed with aqueous HCl, followed by brine. The organic layer is dried and concentrated. Purification by silica gel chromatography (9/1, $CH_2Cl_2$/EtOAc) yields N-[4-(3-cyano-1-ethyl-6-methoxy-1H-indol-2-ylethynyl)-phenyl]-methanesulfonamide (58 mg, 92%) as an off-white solid.

The following compounds are made using the procedure shown above, by substituting the appropriate aminophenylethynyl indoles and sulfonyl chlorides: Compounds 131, 132, 208, 209, and 210.

Example 1Y

Preparation of N-[4-(3-Cyano-1-ethyl-6-methoxy-1H-indol-2-yl)-phenyl]-methanesulfonamide (compound 129)

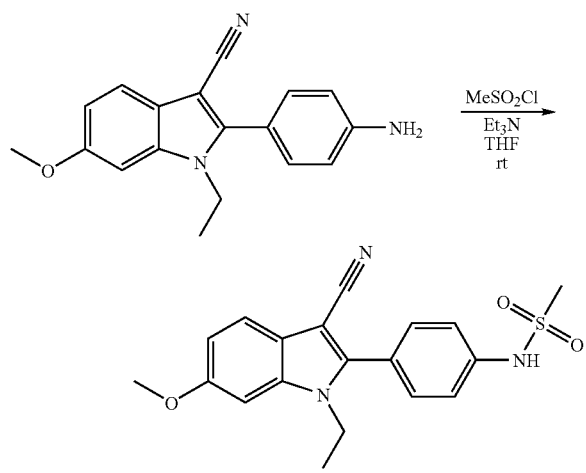

A solution of 2-(4-aminophenyl)-1-ethyl-6-methoxy-1H-indole-3-carbonitrile (70 mg, 0.24 mmol), prepared as described in Example 1Ga, step B in THF (3 mL) is cooled to 0° C. and treated with triethylamine (0.04 mL, 0.31 mmol) and methanesulfonylchloride (0.02 mL, 0.29 mmol) and stirred, warming to room temperature overnight. The reaction mixture is then diluted with $H_2O$ and extracted with ethyl acetate (3×). The organic phase is washed with $H_2O$ and saturated NaCl, dried and concentrated and purified by flash chromatography using EtOAc/hexanes (30-50%) to afford 60 mg (68%) of N-[4-(3-Cyano-1-ethyl-6-methoxy-1H-indol-2-yl)-phenyl]-methanesulfonamide as a tan solid.

Using essentially the same procedure as above and substituting the appropriate aminophenylindole and sulfonyl chloride or carrying out the reaction in pyridine as both base and solvent gives the following compounds: Compounds 83, 85, 86, 87, 88, 243, 251, 252, 272, 273, 287, 289, 365, 366, 367, 368, 369, 370, 371, 394, 439, 440, 448, 449, 451, 452, 477, 487, 488, 495, 505, 510, 548, 549, 550, 551, 552, 562, 563, 598, 599, 601, 602, 608, 609, 610, 615, 616, 617, 621, 622, 623, 629, 630, 631, 639, 655, 657, 658, 662, 669, 670, 671, 674, 675, 701, 702, 703, 706, 707, 708, 709, 710, 711, 713, 715, 720, 789, 790, 791, 850, 851, 867, 868, 890, 891, 912, 919, 920, 921, 922, 923, 924, 932, 933, 934, 935, 941, 953, 968, 982, 988, 990, 995, 996, 997, 998, 1035, 1038, 1041, 1103, 1105, 1115, 1116, 1117, 1123, 1140, 1141, 1155, 1160, 1161, 1170, 1175, 1181, 1182, 1188, 1189, 1228, 1229, 1230, 1231, 1280.

Example 1Za

Preparation of N-[4-(3-cyano-1-ethyl-6-methoxy-1H-indol-2-ylethynyl)-phenyl]-acetamide (compound 138)

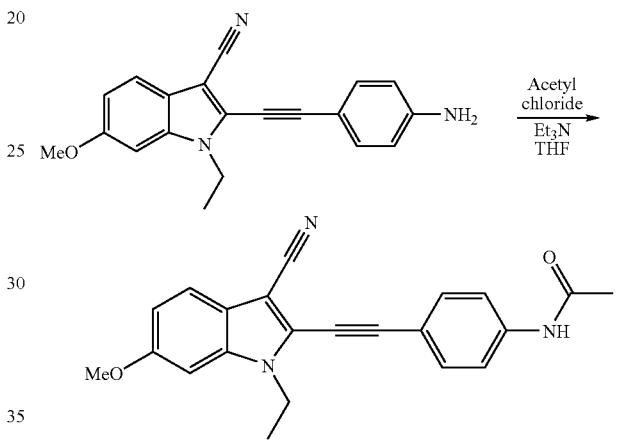

2-(4-Aminophenylethynyl)-1-ethyl-6-methoxy-1H-indole-3-carbonitrile (95 mg, 0.29 mmol), prepared as described in Example 1H, is dissolved in THF (1.4 mL). Triethylamine (84 µL, 0.6 mmol) is added, followed by dropwise addition of acetyl chloride (44 µL, 0.5 mmol). This is stirred at room temperature for 1 h. The reaction mixture is partitioned between $H_2O$ and EtOAc. The organic layer is dried and concentrated. Purification by silica chromatography (9/1, $CH_2Cl_2$/EtOAc) yields N-[4-(3-cyano-1-ethyl-6-methoxy-1H-indol-2-ylethynyl)-phenyl]-acetamide (103 mg, 96%) as a yellow solid.

The following compounds are prepared by the procedure shown above, substituting the appropriate aminophenylethynyl indoles and acid chlorides: Compounds 82, 139, 152, 153, 162, 163, 165, 167, 205, 206, 207, 211, 212, 213, 219, 224, 225, 228.

Example 1Zb

Preparation of N-[4-(3-cyano-1-ethyl-6-methoxy-1H-indol-2-ylethynyl)-phenyl]-formamide (compound 241)

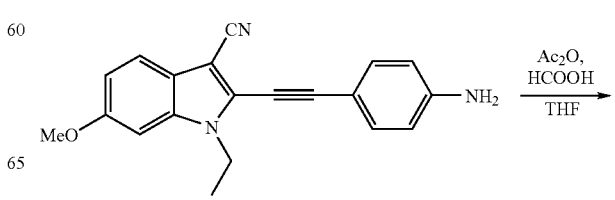

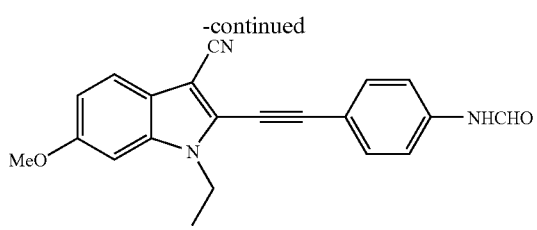

Acetic anhydride (2.5 mL) and 98% formic acid (1.0 mL) are heated at 65° C. for 1 hour. This is cooled to 0° C. 2-(4-Aminophenylethynyl)-1-ethyl-6-methoxy-1H-indole-3-carbonitrile (100 mg, 0.32 mmol), prepared as in example 1H, is taken up in THF (1.2 mL) and added to the formic acetic anhydride mixture. This is stirred at 0° C. for 30 minutes. The reaction mixture is then partitioned between H₂O and EtOAc. The EtOAc layer is washed with saturated NaHCO₃, followed by saturated brine. The organic layer is dried and concentrated. Purification by silica gel chromatography (4/1, CH₂Cl₂/EtOAc) yields N-[4-(3-cyano-1-ethyl-6-methoxy-1H-indol-2-ylethynyl)-phenyl]-formamide (105 mg, 96%) as a yellow solid.

The following compound is prepared similarly as described above: Compound 218.

Example 1AA

Preparation of N-[4-(3-Cyano-1-ethyl-6-methoxy-1H-indol-2-yl)-phenyl]-acetamide (compound 128)

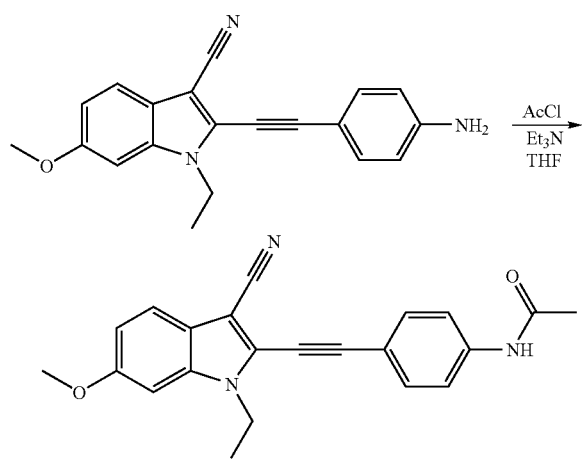

A solution of 2-(4-aminophenyl)-1-ethyl-6-methoxy-1H-indole-3-carbonitrile (70 mg, 0.24 mmol), prepared as described in Example 1Ga, step B in THF (3 mL) is cooled to 0° C. and treated with triethylamine (0.04 mL, 0.31 mmol) and acetyl chloride (0.02 mL, 0.29 mmol) and stirred, warming to room temperature overnight. The reaction mixture is then diluted with H₂O and extracted with ethyl acetate (3×). The organic phase is washed with H₂O and saturated NaCl, dried and concentrated and purified by flash chromatography using EtOAc/hexanes (30-50%) to afford 57 mg (71%) of N-[4-(3-cyano-1-ethyl-6-methoxy-1H-indol-2-yl)-phenyl] acetamide as a tan solid.

Using essentially the same procedure as above and substituting appropriate aminophenyl indoles and the acid chlorides, the following compounds are prepared: Compounds 81, 242, 244, 324, 325, 326, 327, 328, 329, 330, 383, 420, 421, 422, 423, 424, 425, 544, 558, 559, 560, 561, 565, 566, 567, 644, 645, 646, 755, 756, 757, 759, 760, 761, 762, 763, 764, 765, 766, 798, 799, 801, 802, 803, 804, 854, 855, 856, 857, 858, 859, 895, 896, 897, 898, 899, 900, 901, 913, 914, 915, 916, 983.

Example 1AB

Preparation of 1-[3-(3-cyano-1-ethyl-6-methoxy-1H-indol-2-ylethynyl)phenyl]-3-ethyl urea (compound 220)

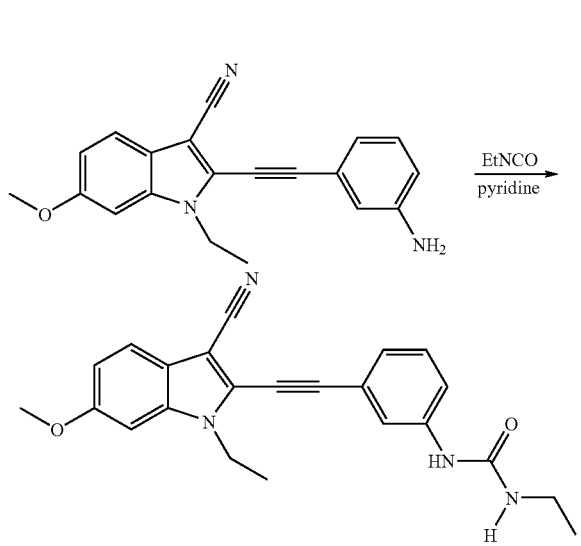

2-(3-Aminophenylethynyl)-1-ethyl-6-methoxy-1H-indole-3-carbonitrile (100 mg, 0.32 mmol), prepared as described in Example 1H, is dissolved in pyridine (670 µL). Ethyl isocyanate (62 µL, 0.75 mmol) is added. The reaction mixture is then heated at 100° C. for 2 h. The mixture is then diluted in EtOAc, and is washed with aqueous HCl, followed by brine. The organic layer is dried and concentrated. Purification by silica chromatography (4/1, CH₂Cl₂/EtOAc), followed by trituration with hexanes/acetone (1/1), yields 1-[3-(3-cyano-1-ethyl-6-methoxy-1H-indol-2-ylethynyl)-phenyl]-3-ethyl urea (44 mg, 36%) as a white solid.

Example 1AC

Preparation of 1-(2-chloroethyl)-3-[4-(3-cyano-1-ethyl-6-methoxy-1H-indol-2-ylethynyl)-phenyl]urea (compound 156)

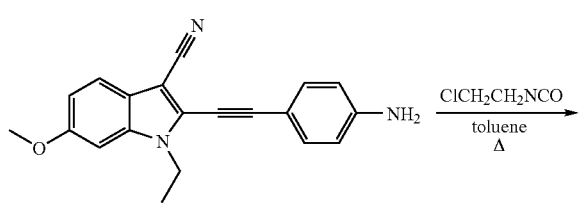

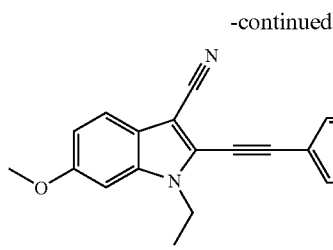

2-(4-Aminophenylethynyl)-1-ethyl-6-methoxy-1H-indole-3-carbonitrile (100 mg, 0.32 mmol), prepared as described in Example 1H, is suspended in toluene (600 μL). 2-Chloroethyl isocyanate (32 μL, 0.37 mmol) is added, and the mixture is heated at 100° C. for 5 h. The reaction mixture is then cooled, diluted in acetone, and absorbed onto silica. Purification by column chromatography (5-10% EtOAc in $CH_2Cl_2$) yields 1-(2-chloro-ethyl)-3-[4-(3-cyano-1-ethyl-6-methoxy-1H-indol-2-ylethynyl)-phenyl]urea (73 mg, 54%) as a yellow solid.

The following compound is prepared using the procedure above: Compound 221.

Example 1AD

Preparation of Ethanesulfonic acid [4-(3-cyano-1-ethyl-6-methoxy-1H-indol-2-ylethynyl)-phenyl]methyl amide (compound 157)

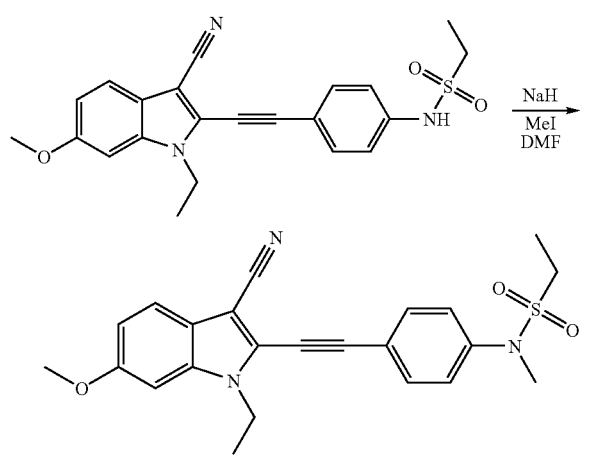

N-[4-(3-cyano-1-ethyl-6-methoxy-1H-indol-2-ylethynyl)phenyl]ethanesulfonamide (70 mg, 0.17 mmol), prepared as in Example 1X, is combined with $K_2CO_3$ (49 mg, 0.35 mmol), and DMF (1.0 mL). Iodomethane (16 μL, 0.26 mmol) is added, and the mixture is stirred at room temperature for 1 hour. The reaction mixture is then diluted in EtOAc, and is washed with $H_2O$ and then brine. The organic layer is dried and concentrated. Purification by silica chromatography (95/5, $CH_2Cl_2$/EtOAc) yields a light tan solid. Trituration gives ethanesulfonic acid [4-(3-cyano-1-ethyl-6-methoxy-1H-indol-2-ylethynyl)-phenyl]methyl amide (61 mg, 85%) as an orange-white solid.

The following compounds are prepared using the procedure above, substituting the appropriate sulfonamide: Compound 182, 652, 840.

Example 1AE

Preparation of 1-ethyl-5-methoxy-2-[4-(morpholine-4-carbonyl)-phenyl]-1H-indole-3-carbonitrile (compound 245)

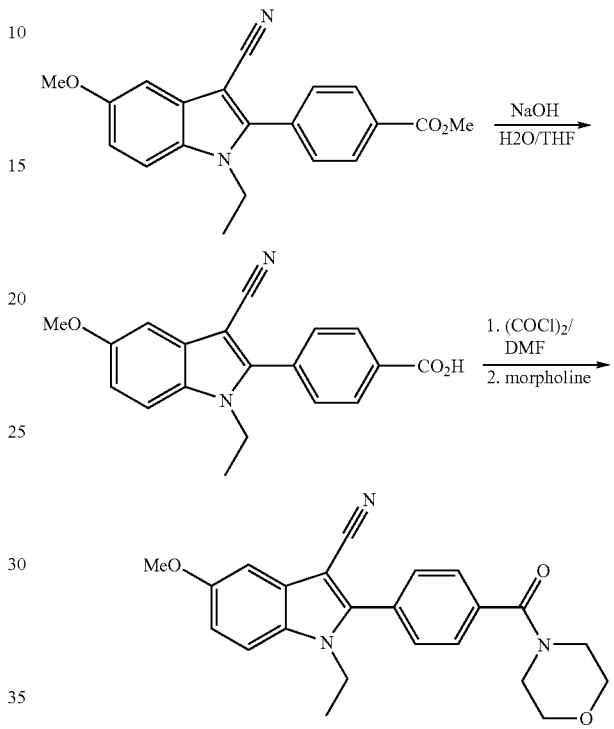

Step A: Methyl 4-(3-cyano-1-ethyl-5-methoxy-1H-indol-2-yl)-benzoate (350 mg, 1.05 mmol), prepared as described in Example 1Ga step B, is combined with NaOH (40 mg, 1 mmol), $H_2O$ (0.8 mL), and THF (3.4 mL) and is heated at 80° C. for 1 hour. The reaction mixture is diluted in $H_2O$ and is then ether-washed. The aqueous layer is acidified with aqueous HCl, and is extracted into EtOAc. The organic layer is dried and concentrated to yield 4-(3-cyano-1-ethyl-6-methoxy-1H-indol-2-yl)-benzoic acid (311 mg, 92%) as a pure white solid.

Step B: 4-(3-cyano-1-ethyl-6-methoxy-1H-indol-2-yl)-benzoic acid (50 mg, 0.16 mmol) is suspended in $CH_2Cl_2$ (2.2 mL) and catalytic DMF (2 μL). Oxalyl chloride (22 μL, 0.25 mmol) is added. The reaction mixture is stirred at room temperature for 1 hour, at which time full dissolution occurs. This reaction mixture is pipetted dropwise into a vigorously stirring solution of morpholine (1.0 mL) in $CH_2Cl_2$ (5 ml). After addition is complete, the reaction mixture is washed with aqueous HCl solution. The organic layer is dried and concentrated. Purification by silica column (1:1 $CH_2Cl_2$/EtOAc) yields 1-ethyl-6-methoxy-2-[4-(morpholine-4-carbonyl)-phenyl]-1H-indole-3-carbonitrile (56 mg, 90%) as a white solid.

The following compounds are prepared similarly as described above: Compounds 113, 114, 246, 270, 271 290, 291, 292, 323, 377, 378, 379, 380, 381, 382, 384, 385, 386, 387, 388, 389, 390, 391, 392, 432, 433, 564, 568, 569, 570, 571, 572, 573, 647, 648, 853, 860, 861, 862.

Example 1AF

Preparation of cyclopropanecarboxylic acid [4-(3-cyano-1-ethyl-6-hydroxy-1H-indol-2-ylethynyl)-phenyl]amide (compound 194)

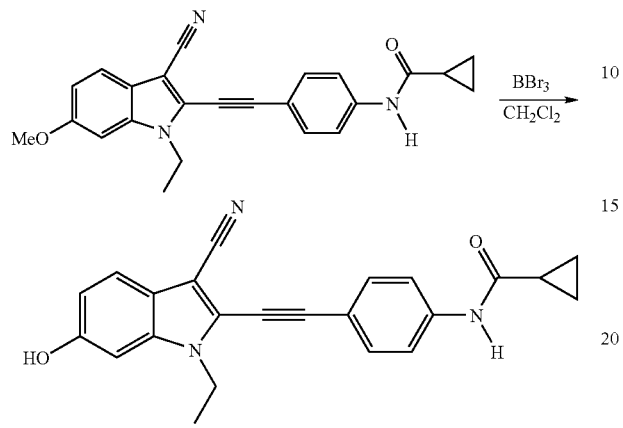

Cyclopropanecarboxylic acid [4-(3-cyano-1-ethyl-6-methoxy-1H-indol-2-ylethynyl)-phenyl]-amide (60 mg, 0.16 mmol), prepared as described in Example 1Za, is stirred in BBr₃ (800 μL, 1M in CH₂Cl₂, 0.8 mmol) at room temperature for 1 hour. The reaction mixture is quenched with H₂O, and is extracted with CH₂Cl₂. The organic layer is dried and concentrated. Purification by silica chromatography (EtOAC) gives impure product. This crude product is triturated with 1/1 hexanes/acetone to yield cyclopropanecarboxylic acid [4-(3-cyano-1-ethyl-6-hydroxy-1H-indol-2-ylethynyl)-phenyl]-amide (32 mg, 54%) as an off-white solid.

The following compounds are prepared using the procedure above, substituting the appropriate sulfonamides (from Example 1X) or amides (from Example 1Z): Compounds 164, 168, 183, 193, 195.

Example 1AG

Preparation of 1-ethyl-6-methoxy-2-[4-(2-oxo-imidazolidin-1-yl)-phenylethynyl]-1H-indole-3-carbonitrile (compound 166)

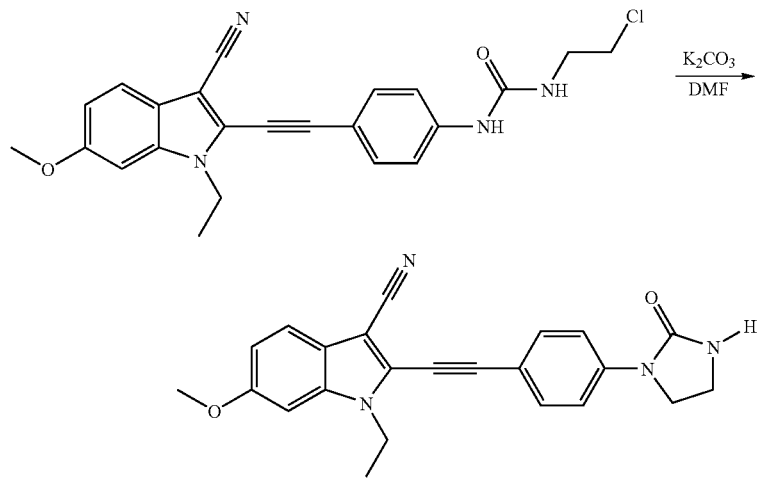

1-(2-Chloroethyl)-3-[4-(3-cyano-1-ethyl-6-methoxy-1H-indol-2-ylethynyl)-phenyl]urea (55 mg, 0.13 mmol), prepared as in Example 1AC, is combined with K₂CO₃ (50 mg, 0.36 mmol) and DMF (550 μL). This mixture is stirred at room temperature for 3 hours. The reaction mixture is diluted in EtOAc, and is washed with H₂O, and then with brine. The organic layer is dried and concentrated. Purification by silica chromatography (10-50%, EtOAc/CH₂Cl₂) yields 1-ethyl-6-methoxy-2-[4-(2-oxo-imidazolidin-1-yl)-phenylethynyl]-1H-indole-3-carbonitrile (47 mg, 94%) as a white solid.

The following compound is prepared using the above procedure, substituting the appropriate urea: Compound 222.

Example 1AH

Preparation of N-[4-(3-cyano-1-ethyl-6-methoxy-1H-indol-2-ylethynyl)-phenyl]-dimethylphosphinic amide (compound 227)

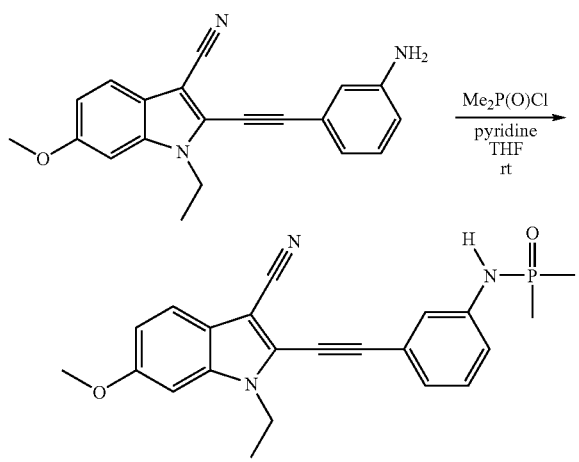

2-(3-Aminophenylethynyl)-1-ethyl-6-methoxy-1H-indole-3-carbonitrile (100 mg, 0.32 mmol), prepared as described in Example 1H, is dissolved in pyridine (300 μL) at 0° C. Dimethylphosphinic chloride (60 mg, 0.53 mmol) in THF (300 μL) is added. The reaction is stirred at room temperature for 2 hours. The reaction mixture is diluted in EtOAc, and is washed with aqueous HCl followed by brine. The organic layer is dried and concentrated. Purification by silica chromatography (acetone) yields N-[4-(3-cyano-1-ethyl-6-methoxy-1H-indol-2-ylethynyl)-phenyl]-dimethylphosphinic amide (65 mg, 52%), compound 227, as a pure white solid. The silica column is then flushed with 9/1 CH$_2$Cl$_2$/MeOH to yield 9 mg of N-[4-(3-cyano-1-ethyl-6-methoxy-1H-indol-2-ylethynyl)-phenyl]-bis-(dimethylphosphinic) amide as a by-product.

Example 1AI

Preparation of 1-ethyl-6-methoxy-3-[5-(4-methoxyphenyl)-isoxazol-3-yl]-1H-indole (compound 116)

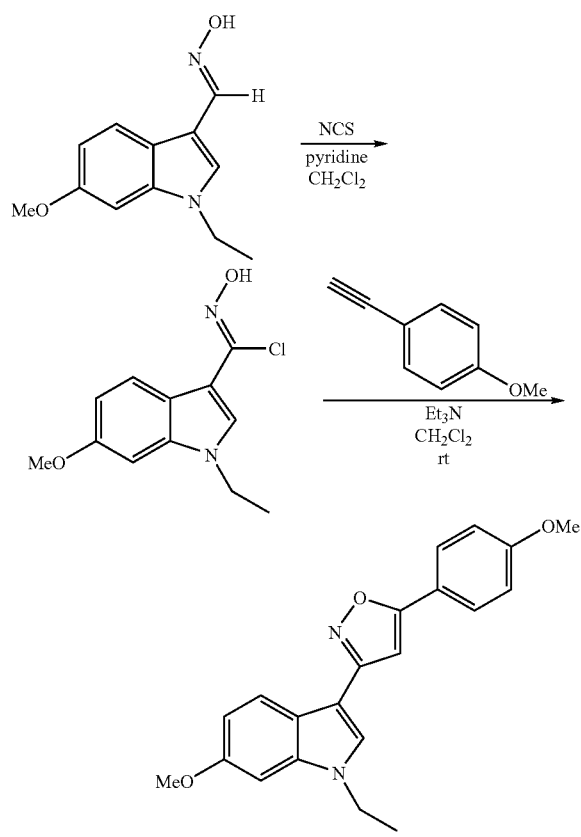

Step A: A mixture of 1-ethyl-6-methoxy-1H-indole-3-carbaldehyde oxime (0.20 g, 0.92 mmol), prepared from the aldehyde precursor in example 1R, in dichloroethane (3 mL) is treated with N-chlorosuccinimide (0.12 g, 0.92 mmol) and pyridine (0.04 mL, 0.46 mmol) and stirred at room temperature for 1 h. The reaction mixture is then poured into H$_2$O and acidified with 1N HCl until the pH is 2. The mixture is extracted with EtOAc and the organic phases are washed with H$_2$O and saturated NaCl and dried and concentrated to a mixture of chlorooximes, which are used in the next step without further purification.

Step B: The mixture of chlorooximes prepared above is dissolved in CH$_2$Cl$_2$ (5 mL) and to this is added 4-methoxyphenylacetylene (0.24 g, 1.84 mmol) and triethylamine (0.25 mL, 1.84 mmol) at 0° C. and the reaction is then stirred overnight warming to room temperature. The reaction is then diluted with H$_2$O and extracted with EtOAc (3×). The organic phases are washed with H$_2$O and saturated NaCl and dried and concentrated. Chromatography over silica gel (EtOAc/hexanes, 10-20%) gives 76 mg (24%) of 1-ethyl-6-methoxy-3-[5-(4-methoxy-phenyl)-isoxazol-3-yl]-1H-indole as a tan solid.

Example 1AJ

Preparation of [4-(3-cyano-1-ethyl-6-methoxy-1H-indol-2-yl)-phenyl]-carbamic acid ethyl ester (compound 121)

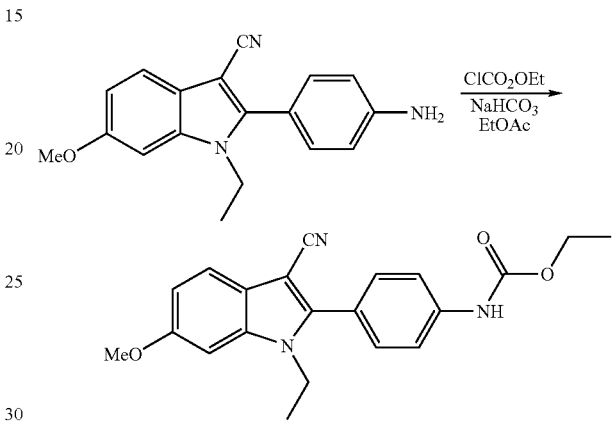

A biphasic mixture of 2-(4-amino-phenyl)-1-ethyl-6-methoxy-1H-indole-3-carbonitrile (70 mg, 0.24 mmol), prepared as described in example 1Ga step B, and ethyl chloroformate (0.03 mL, 0.29 mmol) in EtOAc (3 mL) and saturated NaHCO$_3$ (3 mL) is prepared at 0° C. and then allowed to warm to room temperature and stirred for 24 h. The reaction is then diluted with H$_2$O and extracted with EtOAc (2×). The organic phases are washed with H$_2$O and saturated NaCl and then dried and concentrated. Flash chromatography (EtOAc/hexanes 20-40%) gives 48 mg (55%) of [4-(3-cyano-1-ethyl-6-methoxy-1H-indol-2-yl)-phenyl]-carbamic acid ethyl ester as an off-white solid.

The following compounds are prepared in similar fashion: Compound 122, 293, 294, 296, 297, 298, 299, 300, 301, 302, 303, 304, 305, 306, 307, 308, 309, 310, 311, 312, 313, 314, 315, 316, 317, 318, 319, 320, 321, 349, 350, 351, 352, 353, 354, 355, 356, 357, 358, 359, 360, 361, 372, 434, 435, 450, 453, 454, 455, 457, 485, 486, 489, 490, 500, 501, 502, 503, 506, 507, 508, 509, 545, 546, 547, 553, 554, 555, 556, 557, 581, 582, 583, 584, 585, 585, 586, 587, 588, 589, 590, 591, 592, 593, 594, 595, 596, 597, 603, 604, 605, 606, 607, 618, 619, 624, 625, 637, 640, 641, 664, 665, 676, 677, 721, 722, 723, 734, 735, 736, 737, 738, 739, 744, 745, 746, 747, 787, 788, 792, 793, 794, 795, 796, 797, 819, 822, 823, 824, 825, 826, 849, 925, 926, 945, 946, 947, 948, 949, 950, 951, 970, 971, 972, 973, 974, 975, 976, 977, 978, 979, 981, 984, 985, 986, 991, 992, 993, 1015, 1020, 1021, 1022, 1029, 1030, 1031, 1032, 1033, 1034, 1037, 1040, 1042, 1044, 1055, 1056, 1057, 1058, 1059, 1062, 1063, 1064, 1065, 1071, 1073, 1074, 1075, 1077, 1078, 10791107, 1109, 1111, 1112, 1113, 1114, 1122, 1127, 1128, 1129, 1145, 1148, 1149, 1150, 1151, 1152, 1153, 1154, 1169, 1174, 1176, 1177, 1178, 117911801186, 1193, 1194, 1195, 1196, 1197, 1198, 1199, 1200, 1201, 1202, 1203, 1204, 1205, 1206, 1207, 1211, 1222, 1232, 1233, 1300, 1302.

Example 1AK

Preparation of 1-ethyl-5-thiophen-3-yl-1H-indole-3-carbonitrile (compound 141)

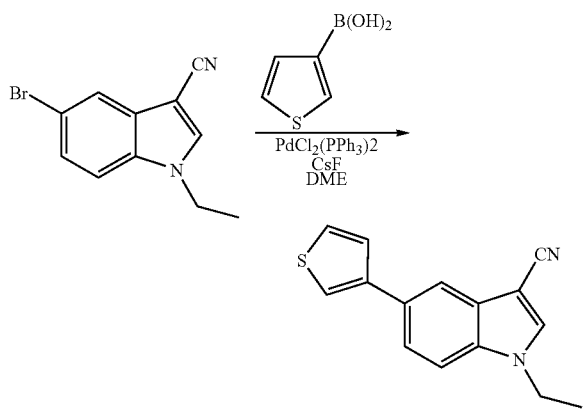

A tube is charged with a mixture of 5-bromo-1-ethyl-1H-indole-3-carbonitrile (100 mg, 0.40 mmol), thiophene-3-boronic acid (72 mg, 0.56 mmol), PdCl$_2$(PPh$_3$)$_2$ (11 mg, 0.016 mmol) and CsF (152 mg, 1 mmol) and then alternately evacuated and filled with nitrogen (3×) and diluted with dimethoxyethane (3 mL) and then heated to 90° C. for 19 h. After cooling, the crude reaction mixture is diluted with saturated NaHCO$_3$ and extracted with EtOAc (2×). The combined organic phases are washed with saturated NaCl and dried and concentrated. Flash chromatography over silica gel (CH$_2$Cl$_2$/hexanes, 40/60) gives 25 mg (25%) of 1-ethyl-5-thiophen-3-yl-1H-indole-3-carbonitrile as a white solid.

The following compounds are prepared in similar fashion: Compounds 140 and 142.

Example 1AL

Preparation of N-[4-(3-cyano-1-ethyl-6-methoxy-1H-indol-2-yl)-phenyl]-N-methyl methanesulfonamide (compound 180)

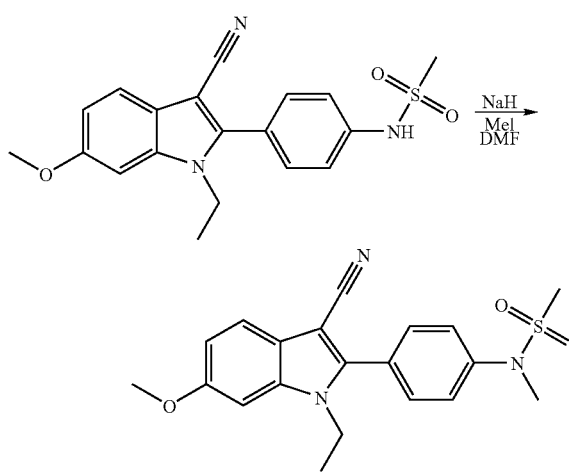

A solution of N-[4-(3-cyano-1-ethyl-6-methoxy-1H-indol-2-yl)-phenyl]methanesulfonamide (130 mg, 0.35 mmol), prepared as in Example 1Y, in DMF (10 mL) is treated with NaH (21 mg, 0.53 mmol), and stirred at room temperature for 10 min. Iodomethane (0.03 mL, 0.53 mmol) is added, and the mixture is stirred at room temperature for 18 h. The reaction mixture is then diluted with H$_2$O, and extracted with EtOAc (2×). The organic phases are washed with H$_2$O and saturated NaCl and then dried and concentrated. Purification by flash chromatography over silica gel (EtOAc/CH$_2$Cl$_2$, 0-1%) gives 60 mg (45%) of N-[4-(3-cyano-1-ethyl-6-methoxy-1H-indol-2-yl)-phenyl]-N-methyl methanesulfonamide as a white solid.

In similar fashion the following compounds are prepared: Compounds 181, 642, 643, 672, 673, 816, 852, 1002, 1003, 1004, 1005, 1006, 1007.

Example 1AM

Preparation of N-[4-(3-cyano-1-ethyl-6-hydroxy-1H-indol-2-yl)-phenyl]-methanesulfonamide (compound 189)

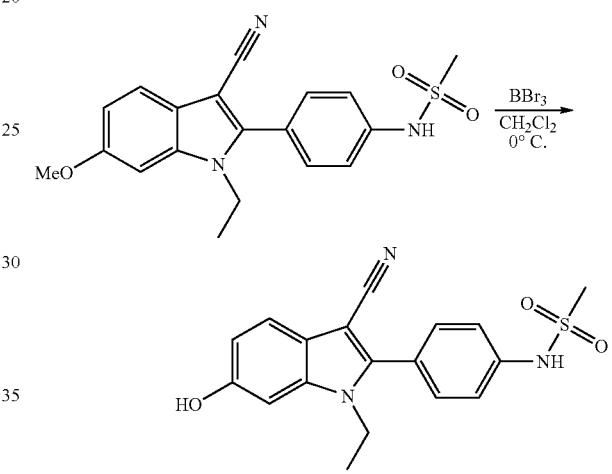

A solution of N-[4-(3-cyano-1-ethyl-6-methoxy-1H-indol-2-yl)-phenyl]methanesulfonamide (85 mg, 0.23 mmol) in CH$_2$Cl$_2$ (2 mL) is cooled to −5° C. A solution of boron tribromide (1.15 mL, 1.15 mmol, 1M solution in CH$_2$Cl$_2$) is added and the reaction mixture is allowed to warm to 10° C. over 4 h. The reaction mixture is poured into H$_2$O and extracted with EtOAc (3×). The combined organic phases are washed with H$_2$O and saturated NaCl and dried and concentrated. Chromatography over silica gel (EtOAc/CH$_2$Cl$_2$, 5-10%) gives 18 mg (22%) of N-[4-(3-cyano-1-ethyl-6-hydroxy-1H-indol-2-yl)-phenyl]methanesulfonamide as a tan solid.

The following compounds are made similarly: Compounds 190, 191, 192.

Example 1AN

Preparation of methyl 3-[5-(3-cyano-6-methoxy-1H-indol-2-yl)-[1,2,4]oxadiazol-3-yl]benzoate (compound 226)

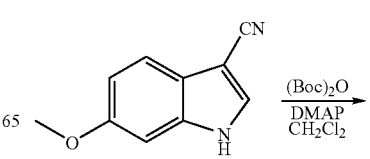

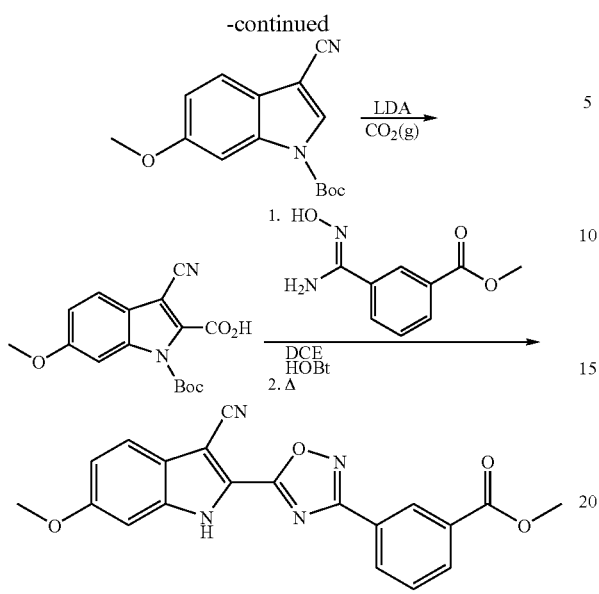

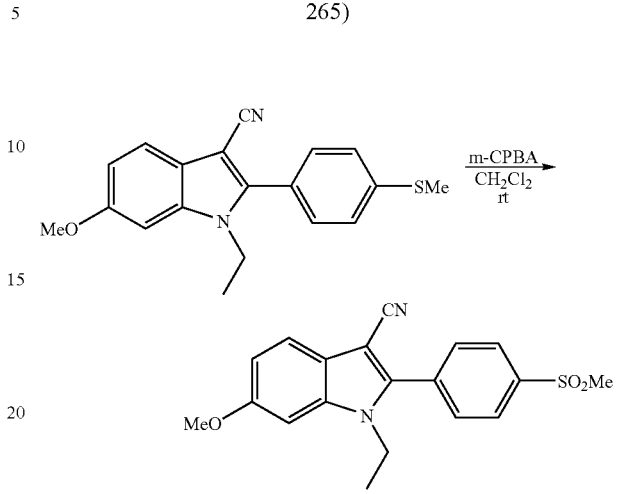

Example 1AO

Preparation of 1-ethyl-2-(4-methanesulfonylphenyl)-6-methoxy-1H-indole-3-carbonitrile (compound 265)

Step A: To a mixture of 6-methoxy-1H-indole-3-carbonitrile (5.88 g, 40 mmol), prepared as described in the previous examples, and (Boc)₂O (9.59 g, 44.0 mmol) in DCM (50 mL) is added DMAP (0.10 g, 0.8 mmol). The mixture is stirred at room temperature for 48 h, then treated with water (30 mL) and dried over anhydrous Na₂SO₄. The crude product is chromatographed over silica gel (hexanes/EtOAc, 7/1) to furnish the desired intermediate, 3-cyano-6-methoxyindole-1-carboxylic acid tert-butyl ester (8.48 g, 86%).

Step B: The above intermediate (2.72 g, 10.0 mmol) is dissolved in anhydrous THF (20 mL), and cooled at –78° C., followed by the addition of LDA (1.5 M mono THF in cyclohexane, 10.0 mL, 15 mmol). After stirring for 45 min, CO₂ gas is introduced for 2 h. The mixture is then brought to room temperature and the solvent is removed in vacuo, and the residue is treated with water and acidified to pH=2 with 6 N HCl. The precipitate is collected and washed with water and dried to provide the acid intermediate, 3-cyano-6-methoxy-indole-1,2-dicarboxylic acid 1-tert-butyl ester (2.40 g, 73%).

Step C: To a solution of 3-cyano-6-methoxyindole-1,2-dicarboxylic acid 1-tert-butyl ester (474 mg, 1.5 mmol) prepared above, and HOBt (200 mg, 1.5 mmol) in DCE/DMF (10 mL/1 mL), is added DCC (310 mg, 1.5 mmol), followed by 3-(N-hydroxycarbamimidoyl)benzoic acid methyl ester (291 mg, 1.5 mmol). The mixture is stirred at room temperature for 2 h and filtered. The filtrate is collected and the solvent is replaced with chlorobenzene, followed by the heating at 150° C. for 48 h. After cooling to room temperature, the solvent is removed in vacuo and the residue is chromatographed (silica gel, CH₂Cl₂/EtOAc, 8/2) to furnish the intermediate, 3-cyano-6-methoxy-2-[3-(3-methoxycarbonylphenyl)-[1,2,4]oxadiazol-5-yl]-indole-1-carboxylic acid tert-butyl ester, which is treated with 50% TFA in DCM (10.0 mL) at room temperature for 1 h. After removal of the volatiles in vacuo, the residue is suspended in water and neutralized with K₂CO₃ to provide the desired product, methyl 3-[5-(3-cyano-6-methoxy-1H-indol-2-yl-)[1,2,4]oxadiazol-3-yl]benzoate, compound 226 (350 mg, 62%).

A solution of 1-ethyl-6-methoxy-2-(4-methylsulfanylphenyl)-1H-indole-3-carbonitrile (0.12 g, 0.37 mmol) in CH₂Cl₂ (5 mL) is treated with m-chloroperbenzoic acid (Aldrich, <77%, 0.26 g) in one portion and the reaction is stirred for 10 h at room temperature. The reaction is then diluted with H₂O and saturated NaHCO₃ and extracted twice with EtOAc. The organic phases are washed with NaHCO₃ (2×) and saturated NaCl and dried and concentrated to a dark semi-solid. The crude product is purified by flash chromatography (EtOAc/CH2C12, 0-3%) through a 5 gram silica cartridge topped with 1 gram of basic alumina to give 72 mg (55%) of 1-ethyl-6-methoxy-2-(4-methylsulfanylphenyl)-1H-indole-3-carbonitrile as an off-white solid.

Example 1AP

Preparation of N-{4-[3-cyano-1-ethyl-6-(2-morpholin-4-yl-ethoxy)-1H-indol-2-yl]-phenyl}methanesulfonamide (compound 478)

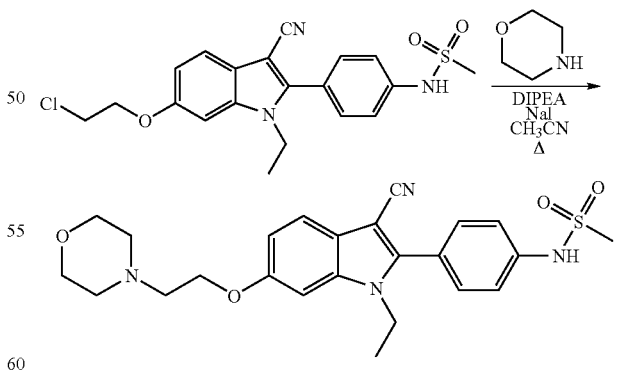

A solution of N-{4-[6-(2-chloroethoxy)-3-cyano-1-ethyl-1H-indol-2-yl]-phenyl}methanesulfonamide (90 mg, 0.21 mmol), morpholine (0.06 mL, 0.65 mmol), NaI (32 mg, 0.21 mmol) and diisopropyl ethylamine (0.06 mL, 0.32 mmol) in CH₃CN (2 mL) is heated in a sealed tube at 100° C. for 25 h. The reaction mixture is cooled to room temperature, diluted

Example 1AQ

Preparation of 2-morpholin-4-yl-ethanesulfonic acid [4-(3-cyano-1-ethyl-6-methoxy-1H-indol-2-yl)-phenyl]amide (compound 653)

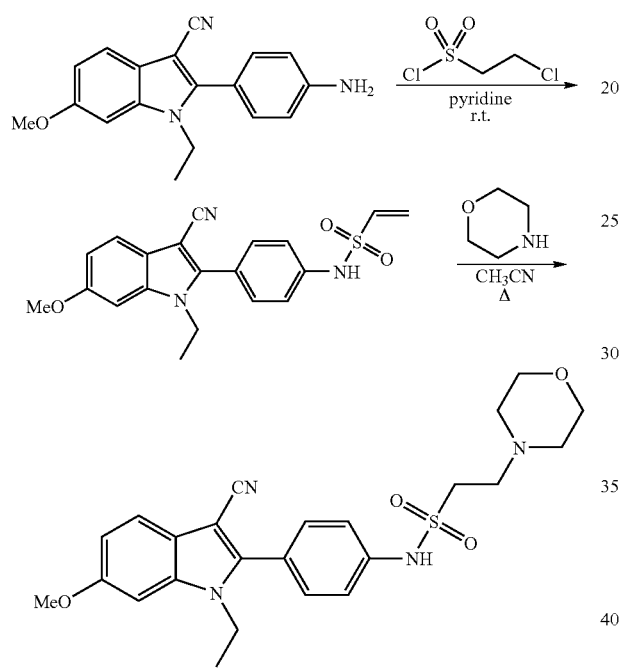

Step A: A solution of 2-(4-aminophenyl)-1-ethyl-6-methoxy-1H-indole-3-carbonitrile, prepared by example 1Ga step B, (0.82 mg, 2.82 mmol), in pyridine (10 mL) is treated dropwise with chloroethyl sulfonylchloride (0.38 mL, 3.66 mmol) at room temperature. After stirring for 4 h, the reaction mixture is quenched with ice-water and enough 6N HCl is added until the pH is lowered to 2. The suspension is extracted with hot EtOAc (3×). The organic phases are then washed sequentially with 1N HCl, $H_2O$ and saturated NaCl and dried and concentrated to give ethenesulfonic acid [4-(3-cyano-1-ethyl-6-methoxy-1H-indol-2-yl)-phenyl]amide as a pale orange solid which is used directly in the next step without further purification.

Step B: A suspension of ethenesulfonic acid [4-(3-cyano-1-ethyl-6-methoxy-1H-indol-2-yl)-phenyl]amide, prepared above, (70 mg, 0.18 mmol), morpholine (0.05 mL, 0.55 mmol) in $CH_3CN$ (1.5 mL) is heated at reflux for 1.5 h. After cooling to room temperature, the reaction is concentrated and the residue is purified by flash chromatography (acetone/EtOAc, 2/98) over silica gel to afford 89 mg (100%) of 2-morpholin-4-yl-ethanesulfonic acid [4-(3-cyano-1-ethyl-6-methoxy-1H-indol-2-yl)-phenyl]amide as a tan foam.

The following compound is made similarly: Compound 654.

Example 1AR

Preparation of 2-morpholin-4-yl-ethanesulfonic acid [4-(3-cyano-1-ethyl-6-methoxy-1H-indol-2-yl)-phenyl]methyl amide (compound 668)

A solution of 2-morpholin-4-yl-ethanesulfonic acid [4-(3-cyano-1-ethyl-6-methoxy-1H-indol-2-yl)-phenyl]amide, prepared in example 1AQ (60 mg, 0.13 mmol) in DMF (3 mL) is treated with $K_2CO_3$ (35 mg, 0.26 mmol) and methyl iodide (0.02 mL, 0.26 mmol). After stirring at room temperature for 1.5 h, the reaction mixture is diluted with $H_2O$ and extracted with EtOAc (2×). The organic phases are then washed with $H_2O$ (3×) and saturated NaCl, and then dried and concentrated to afford a residue. Flash chromatography over silica gel (acetone/EtOAc, 0-2%) gives 31 mg (50%) of 2-morpholin-4-yl-ethanesulfonic acid [4-(3-cyano-1-ethyl-6-methoxy-1H-indol-2-yl)-phenyl]methyl amide as an off white solid.

The following compounds are made similarly: Compounds 684, 685, 686, 687, 688, 689, 690, 691, 692, 693, 694, 695, 696, 697, 698.

Example 1AS

Preparation of 2-[4-(1,1-dioxo-1λ⁶-isothiazolidin-2-yl)phenyl]-1-ethyl-6-methoxy-1H-indole-3-carbonitrile (compound 84)

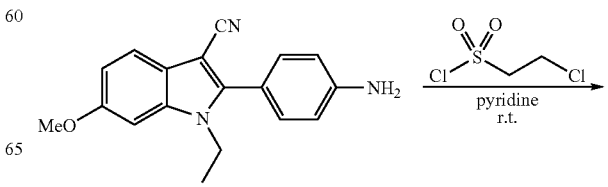

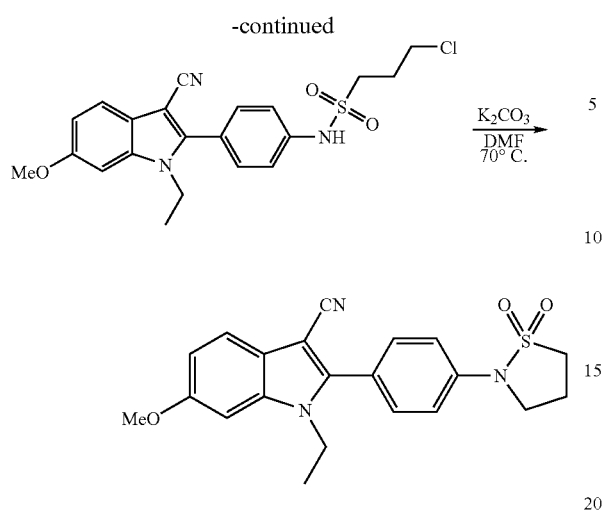

Step A: A solution of 2-(4-aminophenyl)-1-ethyl-6-methoxy-1H-indole-3-carbonitrile, prepared by example 1Ga step B, (2.78 g, 9.55 mmol) in pyridine (40 mL) is treated dropwise with 3-chloropropanesulfonyl chloride (1.45 mL, 11.9 mmol) and the reaction is stirred for 4 h at room temperature. The reaction is diluted with water and enough 6N HCl to lower the pH to 2. The reaction mixture is extracted with EtOAc (3×) and the combined organic layers are washed sequentially with 1N HCl, water and saturated NaCl and then dried and concentrated to give 3.9 g (95%), of 3-chloropropane-1-sulfonic acid [4-(3-cyano-1-ethyl-6-methoxy-1H-indol-2-yl)-phenyl]amide as a brown foam which is used directly in the next step.

Step B: A solution of 3-chloropropane-1-sulfonic acid [4-(3-cyano-1-ethyl-6-methoxy-1H-indol-2-yl)-phenyl]amide, prepared above (3.65 g, 2.33 mmol) in DMF (100 mL) is treated with $K_2CO_3$ and heated at 70° C. for 2 h. After cooling to room temperature, the reaction mixture is diluted with $H_2O$ and extracted 3× with hot EtOAc. The hot organic layers are washed with warm $H_2O$ (3×) and saturated NaCl and dried and concentrated to a solid. Trituration ($CH_2Cl_2$/hexanes) gives 2.27 g (68%) of 2-[4-(1,1-dioxo-1$\lambda^6$-isothiazolidin-2-yl)phenyl]-1-ethyl-6-methoxy-1H-indole-3-carbonitrile as a light brown solid.

The following compounds are made in similar fashion: Compound 649, 775, 809, 969, 980.

Example 1AT

Preparation of 2-[4-(1,1-dioxo-1$\lambda^6$-isothiazolidin-2-yl)phenyl]-1-ethyl-6-methoxy-1H-indole-3-carbonitrile (compound 666)

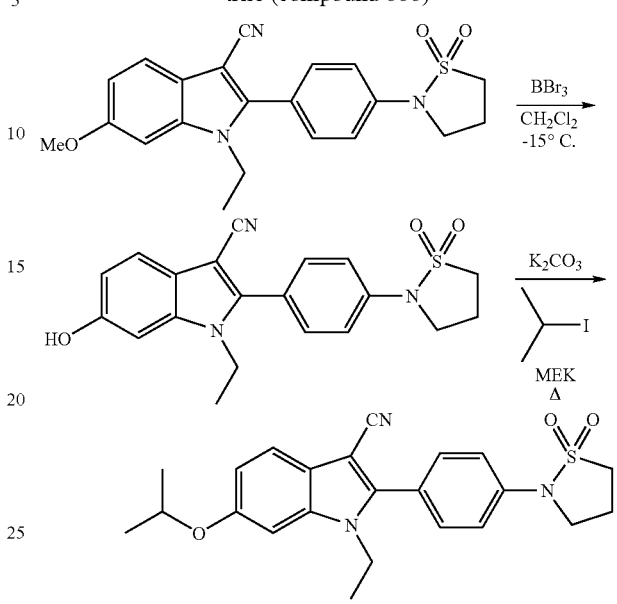

Step A: Following the procedure in example 1B step A, 2-[4-(1,1-dioxo-1$\lambda^6$-isothiazolidin-2-yl)phenyl]-1-ethyl-6-methoxy-1H-indole-3-carbonitrile is treated with 1M $BBr_3$ solution in $CH_2Cl_2$ at −15° C. for 1.5 h and then poured into ice-water and filtered and dried to afford 2-[4-(1,1-dioxo-1$\lambda^6$-isothiazolidin-2-yl)phenyl]-1-ethyl-6-hydroxy-1H-indole carbonitrile in nearly quantitative yield.

Step B: Following the procedure in example 1B step B, 2-[4-(1,1-dioxo-1$\lambda^6$-isothiazolidin-2-yl)phenyl]-1-ethyl-6-hydroxy-1H-indole-3-carbonitrile, $K_2CO_3$, 2-iodopropane and methyl ethyl ketone are heated at reflux to give, after flash chromatography (EtOAc/$CH_2Cl_2$, 0-2%), 61% of 2-[4-(1,1-dioxo-1$\lambda^6$-isothiazolidin-2-yl)phenyl]-1-ethyl-6-isopropoxy-1H-indole-3-carbonitrile as an off-white solid.

The following compounds are made similarly: Compounds 667, 699.

Example 1AU

Preparation of 2-[4-(1,1-dioxo-1$\lambda^6$-isothiazolidin-2-yl)-phenyl]-1-ethyl-6-(2-morpholin-4-yl-ethoxy)-1H-indole-3-carbonitrile (compound 729)

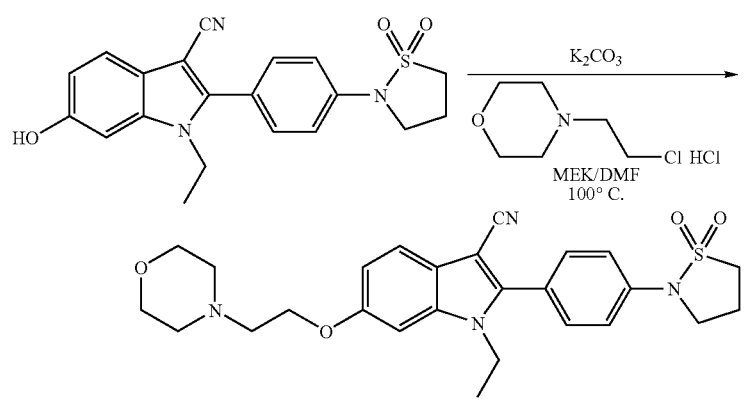

A mixture of 2-[4-(1,1-dioxo-1λ⁶-isothiazolidin-2-yl)phenyl]-1-ethyl-6-hydroxy-1H-indole-3-carbonitrile, prepared in example 1AT above (70 mg, 0.25 mmol), K₂CO₃ (75 mg, 0.51 mmol), sodium iodide (27 mg, 0.18 mmol), 4-(2-chloroethyl)morpholine hydrochloride (42 mg, 0.25 mmol) in methyl ethyl ketone (3 mL) is heated in a sealed tube at 100° C. After 13 hours, DMF (3 mL) is added and the reaction is heated for an additional 6 h. After this time, an additional 42 mg of 4-(2-chloroethyl)morpholine hydrochloride and 135 mg of K₂CO₃ is added and the reaction is heated for an additional 6 h to complete the reaction. The reaction mixture is cooled to room temperature, diluted with water, and extracted with EtOAc (3×). The combined organic phases are washed with water (2×) and saturated NaCl and dried and concentrated. Pure 2-[4-(1,1-dioxo-1λ⁶-isothiazolidin-2-yl)-phenyl]-1-ethyl-6-(2-morpholin-4-yl-ethoxy)-1H-indole-3-carbonitrile is obtained by flash chromatography (MeOH/CH₂Cl₂, 0-6%) to give 29 mg (34%) of a tan solid.

The following compounds are made similarly: Compounds 728 and 730.

Example 1AV

Preparation of 2-[4-(2,5-dioxo-imidazolidin-1-yl)-phenyl]-6-ethoxy-1-ethyl-1H-indole-3-carbonitrile (compound 779)

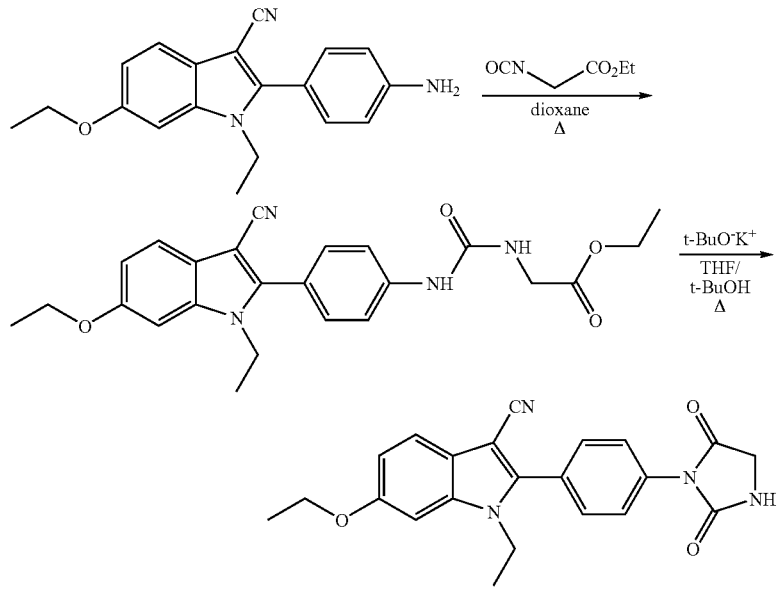

Step A: A solution of 2-(4-aminophenyl)-6-ethoxy-1-ethyl-1H-indole-3-carbonitrile (585 mg, 1.92 mmol) in 10 mL of 1,4-dioxane is treated with ethyl isocyanatoacetate (0.25 mL, 2.12 mmol), and the resulting solution is heated to reflux overnight. The solution is allowed to cool, and the solvent is removed by rotary evaporation. The residual material is triturated with ether, and the resulting precipitate is collected by filtration and dried under vacuum to afford compound 773 (587 mg, 1.35 mmol, 70%).

A similar procedure is used to prepare methyl 2-{3-[4-(3-cyano-6-ethoxy-1-ethyl-1H-indol-2-yl)-phenyl]-ureido}-3-phenyl-propionate (compound 777).

Step B: A solution of ethyl {3-[4-(3-cyano-6-ethoxy-1-ethyl-1H-indol-2-yl)-phenyl]-ureido}-acetate (compound 773, 101 mg, 0.232 mmol) in THF (10 mL) is treated with a solution of potassium tert-butoxide in tert-butanol (0.30 mL, 1.0 M, 0.30 mmol), and the resulting mixture is allowed to stir overnight. The reaction mixture is partitioned between water and ethyl acetate (50 mL each), and the organic phase is washed with saturated brine. The aqueous phases are extracted with more ethyl acetate, and the extracts are combined, dried over anhydrous magnesium sulfate, filtered and evaporated. The residual material is separated by column chromatography (eluting 2/1 ethyl acetate/hexane on silica gel 60) to afford 2-[4-(2,5-dioxo-imidazolidin-1-yl)-phenyl]-6-ethoxy-1-ethyl-1H-indole-3-carbonitrile, compound 779, which is purified farther by trituration with ether, collection by filtration and drying under high vacuum (76 mg, 0.196 mmol, 84%).

Example 1AW

Preparation of 2-[4-(2,4-dioxo-imidazolidin-1-yl) phenyl]-6-ethoxy-1-ethyl-1H-indole-3-carbonitrile (compound 776)

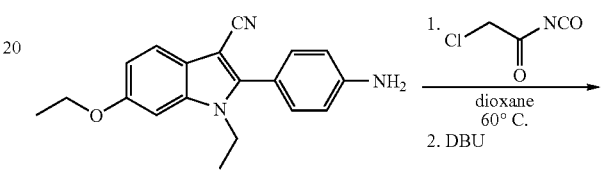

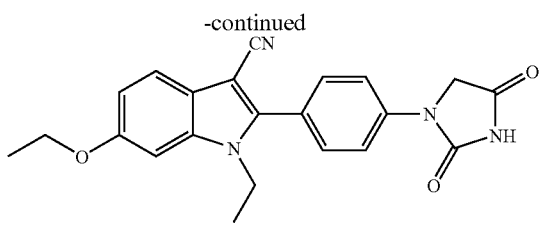

A solution of 2-(4-aminophenyl)-6-ethoxy-1-ethyl-1H-indole-3-carbonitrile (319 mg, 1.04 mmol) in 1,4-dioxane (3 mL) is treated with chloroacetyl isocyanate (0.10 mL, 1.17 mmol), and the resulting solution is warmed to 60° C. overnight. The solution is cooled, and DBU (0.20 mL, 1.31 mmol) is added. This mixture is stirred at ambient temperature overnight, and then is partitioned between water and ethyl acetate (50 mL each). The organic layer is washed with saturated brine, and then dried over anhydrous magnesium sulfate, filtered and evaporated. The residual material is triturated with ether, and the resulting solid is collected by filtration and dried under high vacuum to afford the title product (319 mg, 0.821 mmol, 79%).

Example 1AX

Preparation of N,N-Dimethyl-2-[4-(3,4-dimethyl-2,5-dioxo-imidazolidin-1-yl)-phenyl]-6-ethoxy-1-ethyl-1H-indole-3-carboxamide (compound 780) and N,N-Dimethyl-6-ethoxy-1-ethyl-2-[4-(3-methyl-2,5-dioxo-imidazolidin-1-yl)-phenyl]-1H-indole-3-carboxamide (compound 781)

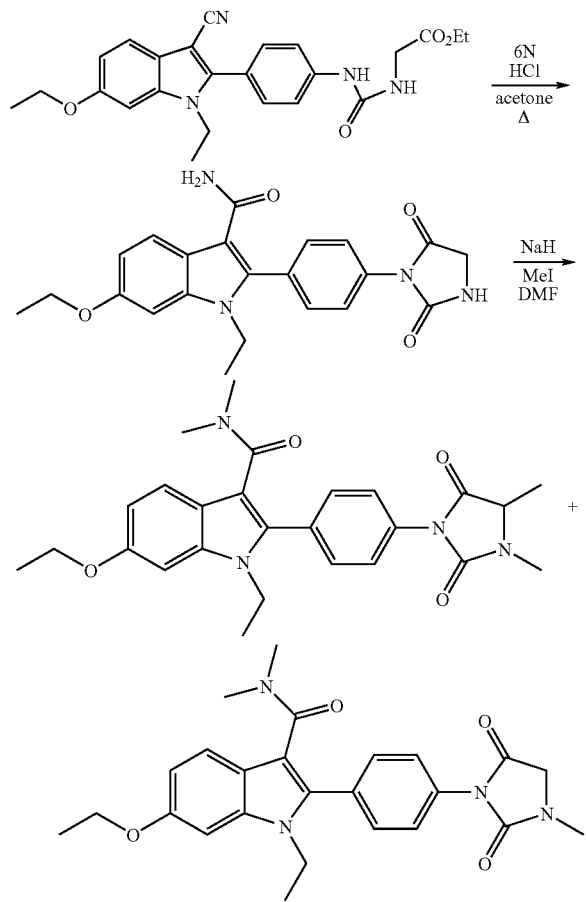

Step A. A solution of ethyl {3-[4-(3-cyano-6-ethoxy-1-ethyl-1H-indol-2-yl)-phenyl]-ureido}acetate (compound 773, 325 mg, 0.748 mmol), prepared in procedure 1AV, step A, in acetone (5 mL) is treated with HCl (3 mL, 6 N), and the resulting solution is heated to reflux overnight. The reaction mixture is cooled, and the resulting precipitate is collected by filtration, washed with ether and dried under high vacuum to afford the product, 6-ethoxy-1-ethyl-2-[4-(2,5-dioxo-imidazolidin-1-yl)-phenyl]-1H-indole-3-carboxamide (264 mg, 0.650 mmol, 87%).

Step B. Sodium hydride dispersion in mineral oil (75 mg) is washed with a small portion of hexane, and the hexane layer is decanted off. A solution of 6-ethoxy-1-ethyl-2-[4-(2,5-dioxo-imidazolidin-1-yl)-phenyl]-1H-indole-3-carboxamide (190 mg, 0.468 mmol) in dimethylformamide (2 mL) is added, and the mixture is stirred for 1 hour. Then, methyl iodide (0.10 mL, 1.61 mmol) is added by syringe. The resulting mixture is allowed to stir at ambient temperature overnight and then is poured into 50 mL of ethyl acetate. The organic phase is washed with water (3×50 mL) and saturated brine (20 mL), then dried over anhydrous magnesium sulfate, filtered and evaporated. The residual material is separated by column chromatography (1/1 ethyl acetate/hexane, eluting on silica gel 60) to afford the title products, compounds 780 and 781.

Example 1AY

Preparation of N-[4-(3-cyano-1-ethyl-6-methoxy-1H-indol-2-yl)-phenyl]-N-(2-hydroxyethyl)-methanesulfonamide (compound 828)

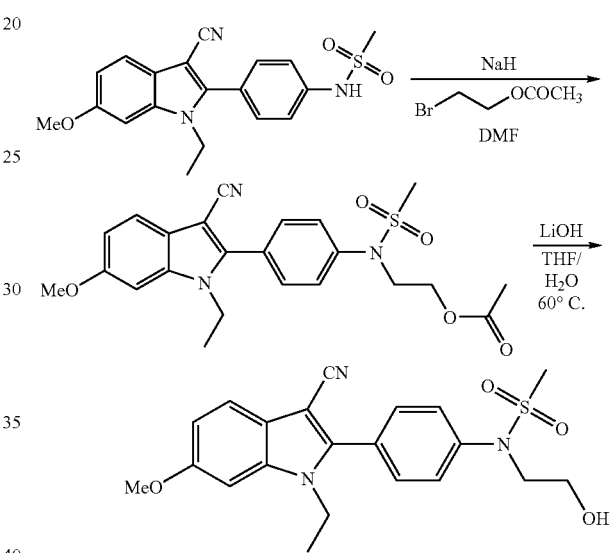

Step A: Sodium hydride dispersion in mineral oil (108 mg) is washed with a small portion of hexane, and the hexane layer is decanted off. A solution of N-[4-(3-cyano-1-ethyl-6-methoxy-1H-indol-2-yl)-phenyl]methanesulfonamide (compound 129, 500 mg, 1.35 mmol) in DMF (5 mL) is slowly added. After gas evolution is complete, 2-bromoethyl acetate (0.30 mL, 2.64 mmol) and sodium iodide (20 mg) are added. The mixture is stirred at ambient temperature overnight, and then is poured into 50 mL of ethyl acetate. This is washed with water (3×50 mL) and saturated brine (20 mL), then dried over anhydrous magnesium sulfate, filtered and evaporated. The residual material is separated by column chromatography (1/1 ethyl acetate/hexane, eluting on silica gel 60) to afford compound 815 (364 mg, 0.799 mmol, 59%).

Step B: A mixture of N-(2-acetoxyethyl)-N-[4-(3-cyano-1-ethyl-6-methoxy-1H-indol-2-yl)-phenyl]methanesulfonamide (compound 815, 164 mg, 0.360 mmol) and lithium hydroxide hydrate (45 mg, 1.07 mmol) in 5 mL THF/1 mL water is warmed to 60° C. overnight. The mixture is cooled and poured into ethyl acetate (50 mL). This is washed with water (50 mL) and brine (20 mL), dried over anhydrous magnesium sulfate, filtered and evaporated to afford a solid. The solid is triturated with ether, collected by filtration and dried under high vacuum to afford N-[4-(3-cyano-1-ethyl-6-methoxy-1H-indol-2-yl)-phenyl]-N-(2-hydroxyethyl)methanesulfonamide, compound 828 (137 mg, 0.331 mmol, 92%).

Example 1AZ

Preparation of 1-ethyl-6-methoxy-2-[4-(2-methoxyethoxy)-phenyl]-1H-indole-3-carbonitrile (compound 248)

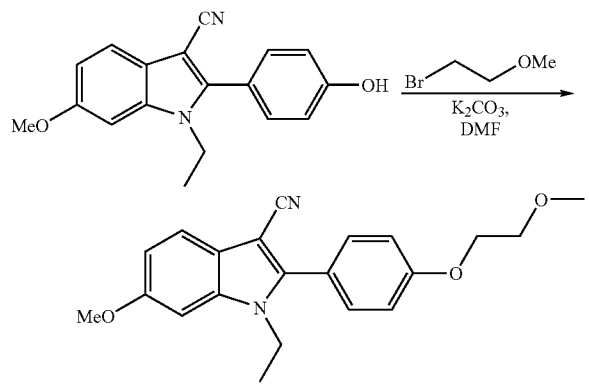

1-Ethyl-2-(4-hydroxy-phenyl)-6-methoxy-1H-indole-3-carbonitrile (40 mg, 0.14 mmol), prepared as in example 1Ga step B, is combined with $K_2CO_3$ (77 mg, 0.56 mmol), bromoethyl methyl ether (26 μL, 0.28 mmol), and DMF (450 μL). This is stirred at room temperature for 1 hour, and then at 75° C. for 3 hours. The reaction mixture is then partitioned between $H_2O$ and EtOAc. The organic layer is dried and concentrated. Purification by silica gel chromatography ($CH_2Cl_2$, 0-5% EtOAc) yields 1-ethyl-6-methoxy-2-[4-(2-methoxyethoxy)-phenyl]-1H-indole-3-carbonitrile (44 mg, 90%) as a white solid.

The following compound is prepared similarly as above: Compound 249.

Example 1BA

Preparation of 1-ethyl-6-methoxy-2-[4-(2-morpholin-4-yl-ethoxy)-phenyl]-1H-indole-3-carbonitrile (compound 261)

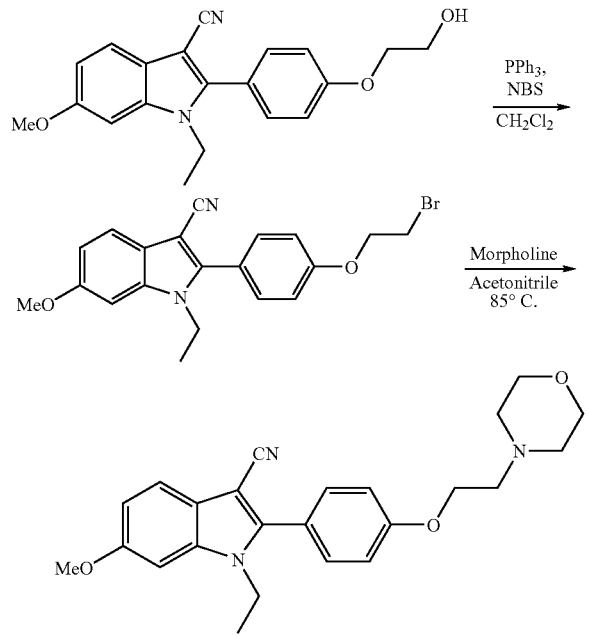

Step A: 1-Ethyl-6-methoxy-2-[4-(2-hydroxyethoxy)-phenyl]-1H-indole-3-carbonitrile (450 mg, 1.34 mmol), prepared as in example 1AZ, is combined with $PPh_3$ (878 mg, 3.35 mmol) in $CH_2Cl_2$ (32 mL) at 0° C. N-bromosuccinimide (600 mg, 3.37 mmol) is added in one portion. The reaction mixture is stirred at room temperature for 30 minutes. The reaction mixture is washed with aqueous $NaHCO_3$. The organic layer is dried and concentrated, and purified by silica gel chromatography ($CH_2Cl_2$) to yield 2-[4-(2-bromoethoxy)-phenyl]-1-ethyl-6-methoxy-1H-indole-3-carbonitrile (506 mg, 95%), compound 253 as a white solid.

Step B: 2-[4-(2-bromoethoxy)-phenyl]-1-ethyl-6-methoxy-1H-indole-3-carbonitrile (40 mg, 0.1 mmol), prepared as in step A above, is combined with morpholine (50 μL, 0.58 mmol) and acetonitrile (1.0 mL). This is heated at 85° C. for 2 h. The reaction mixture is then partitioned between $CH_2Cl_2$ and $H_2O$. The organic layer is dried and concentrated. Purification by silica gel chromatography (6/4, acetone/hexanes) yields 1-ethyl-6-methoxy-2-[4-(2-morpholin-4-yl-ethoxy)-phenyl]-1H-indole-3-carbonitrile (39 mg, 96%) as a white solid.

The following compounds are prepared similarly as above, using different amines: Compounds 262, 263, 264.

Example 1BB

Preparation of N-{2-[4-(3-cyano-1-ethyl-6-methoxy-1H-indol-2-yl)-phenoxy]-ethyl}methanesulfonamide (compound 268)

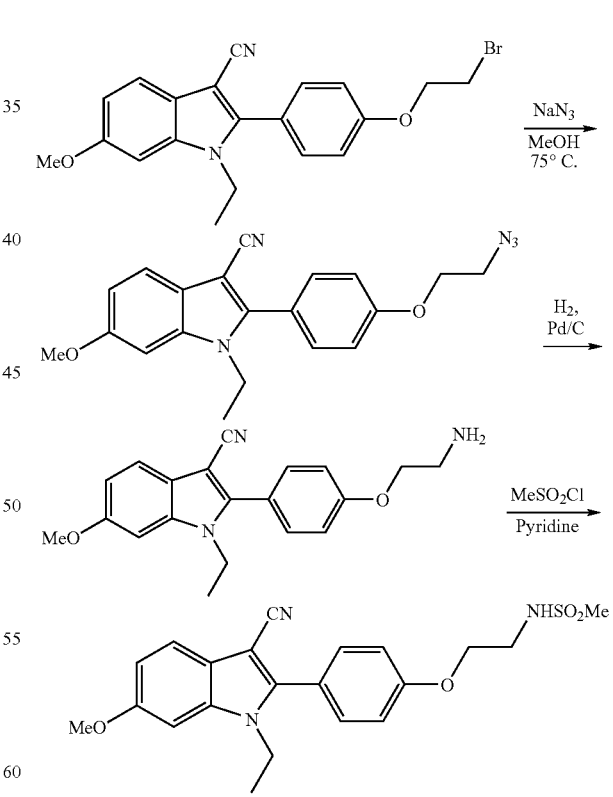

Step A: 2-[4-(2-Bromoethoxy)phenyl]-1-ethyl-6-methoxy-1H-indole-3-carbonitrile (258 mg, 0.65 mmol), prepared in example 1BA, step A, is combined with $NaN_3$ (144 mg, 2.2 mmol), and MeOH (3.2 mL). This is heated overnight at 75° C. The reaction mixture is then partitioned between $CH_2Cl_2$ and H₂O. The organic layer is dried and concentrated. Purification by silica gel chromatography (CH₂Cl₂) yields 2-[4-(2-azidoethoxy)phenyl]-1-ethyl-6-methoxy-1H-indole-3-carbonitrile (187 mg, 80%), compound 266 as a white solid.

Step B: 2-[4-(2-Azidoethoxy)phenyl]-1-ethyl-6-methoxy-1H-indole-3-carbonitrile (410 mg, 1.14 mmol), prepared as in step A, above, is suspended in a solution of MeOH (20 mL) and concentrated HCl (500 EL). Pd/C (150 mg, 10%) is added, and this mixture is hydrogenated at 30 p.s.i. for 1 h. This is filtered and the filtrate is concentrated. The filtrate residue is partitioned between EtOAc and 0.5N NaOH. The organic layer is dried and concentrated. Purification by silica gel chromatography (10-30%, MeOH/CH₂Cl₂) yields 2-[4-(2-aminoethoxy)phenyl]-1-ethyl-6-methoxy-1H-indole-3-carbonitrile (298 mg, 78%), compound 267, as a white solid.

Step C: 2-[4-(2-Aminoethoxy)phenyl]-1-ethyl-6-methoxy-1H-indole-3-carbonitrile (30 mg, 0.09 mmol), prepared in step B, above, is dissolved in pyridine (300 µL). Methanesulfonyl chloride (8 µL, 0.1 mmol) is added. This is stirred at room temperature for 45 minutes. More methanesulfonyl chloride (4 µL, 0.05 mmol) is added. Stirring continues for another hour. The reaction mixture is partitioned between EtOAc and aqueous HCl. The organic layer is dried and concentrated. Purification by silica gel chromatography (1/1 CH₂Cl₂/EtOAc) yields N-{2-[4-(3-cyano-1-ethyl-6-methoxy-1H-indol-2-yl)phenoxy]ethyl}methanesulfonamide, compound 268 (32 mg, 86%) as a white solid.

The following compound is prepared similarly as above: Compound 269.

Example 1BC

Preparation of N-{2-[4-(3-cyano-1-ethyl-6-methoxy-1H-indol-2-yl)-phenoxy]-ethyl}acetamide (compound 274)

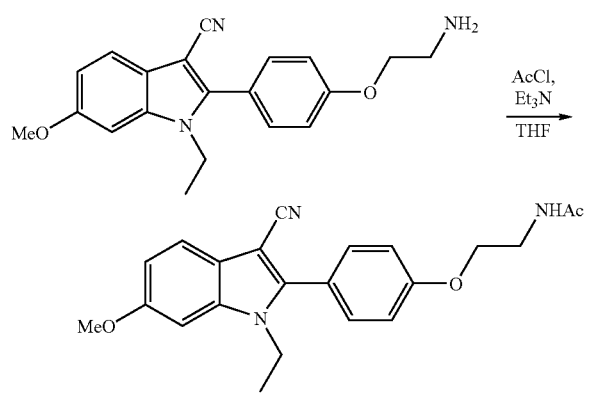

2-[4-(2-Aminoethoxy)phenyl]-1-ethyl-6-methoxy-1H-indole-3-carbonitrile (30 mg, 0.09 mmol), prepared as in example 1BB, step B, is dissolved in THF (400 µL), and Et₃N (24 µL, 0.17 mmol). Acetyl chloride (10 µL, 0.14 mmol) is added, and the reaction mixture is stirred at room temperature for 2 h. The reaction mixture is partitioned between EtOAc and H₂O. The organic layer is dried and concentrated. Purification by silica gel chromatography (EtOAc) yields N-{2-[4-(3-cyano-1-ethyl-6-methoxy-1H-indol-2-yl)phenoxy]ethyl}acetamide (33 mg, 97%) as a white solid.

Example 1BD

Preparation of 1-{2-[4-(3-cyano-1-ethyl-6-methoxy-1H-indol-2-yl)-phenoxy]ethyl}-3-ethyl-urea (Compound 279)

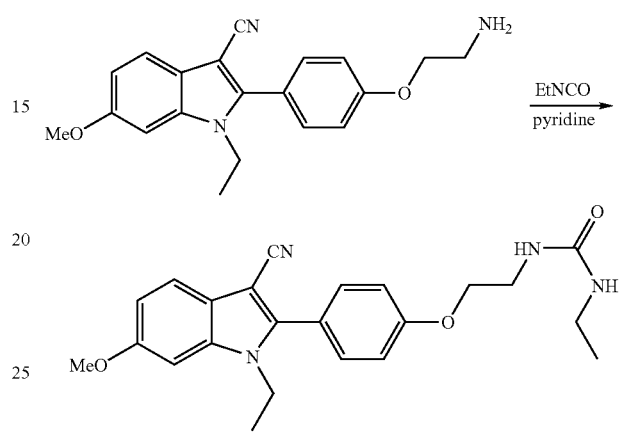

2-[4-(2-Aminoethoxy)phenyl]-1-ethyl-6-methoxy-1H-indole-3-carbonitrile (30 mg, 0.09 mmol), prepared as in example 1BB, is combined with ethyl isocyanate (18 µL, 0.21 mmol) and pyridine (300 µL). This mixture is stirred at room temperature for 90 minutes, and is then partitioned between EtOAc and aqueous HCl. The organic layer is dried and concentrated. Purification by silica gel chromatography (EtOAc) yields 1-{2-[4-(3-cyano-1-ethyl-6-methoxy-1H-indol-2-yl)-phenoxy]-ethyl}-3-ethyl-urea (34 mg, 93%) as a white solid.

Example 1BE

Preparation of N-{2-[4-(3-cyano-1-ethyl-6-methoxy-1H-indol-2-yl)-phenoxy]ethyl}formamide (compound 280)

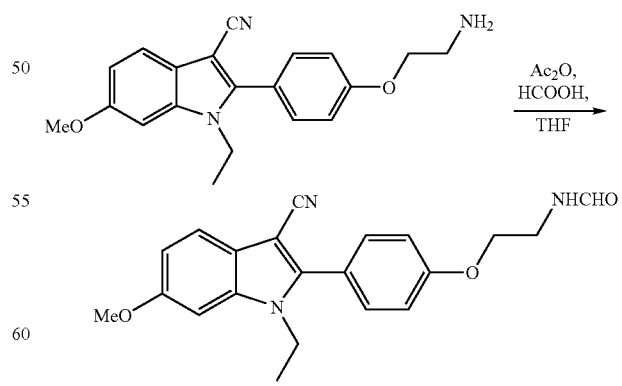

Acetic anhydride (700 µL) and 98% formic acid (280 µL) are heated at 65° C. for 1 h. This is cooled to 0° C. 2-[4-(2-Aminoethoxy)phenyl]-1-ethyl-6-methoxy-1H-indole-3-carbonitrile (30 mg, 0.09 mmol), prepared as in example 1BB, is taken up in THF (400 µL), and added to the mixed anhydride. This is stirred at 0° C. for 45 minutes. The mixture is then portioned between EtOAc and aqueous NaHCO₃. The organic layer is dried and concentrated. Purification by silica gel chromatography (4/1, CH₂Cl₂/acetone) yields N-{2-[4-(3-cyano-1-ethyl-6-methoxy-1H-indol-2-yl)phenoxy]-ethyl}formamide (28 mg, 86%) as a white solid.

Example 1BF

Preparation of 1-ethyl-2-{4-[2-(3-hydroxypyrrolidin-1-yl)-2-oxo-ethoxy]phenyl}-6-methoxy-1H-indole-3-carbonitrile (compound 285)

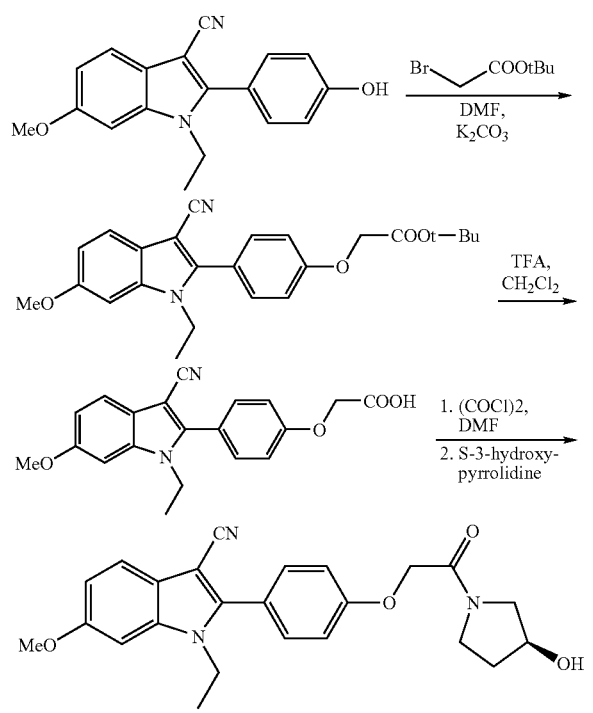

Step A: 1-Ethyl-2-(4-hydroxyphenyl)-6-methoxy-1H-indole-3-carbonitrile (559 mg, 1.91 mmol), is used to prepare [4-(3-cyano-1-ethyl-6-methoxy-1H-indol-2-yl)-phenoxy]-acetic acid tert-butyl ester (780 mg, 100%) utilizing essentially the same procedure as example 1AZ.

Step B: [4-(3-Cyano-1-ethyl-6-methoxy-1H-indol-2-yl)-phenoxy]-acetic acid tert-butyl ester (745 mg, 1.83 mmol) is stirred in 20% TFA in CH₂Cl₂ at room temperature for 3 hours. This is concentrated and the residue is partitioned between H₂O and EtOAc. The organic layer is dried and concentrated. The residue is triturated with CH₂Cl₂ to yield [4-(3-cyano-1-ethyl-6-methoxy-1H-indol-2-yl)-phenoxy]-acetic acid (634 mg, 99%) as a white solid.

Step C: [4-(3-Cyano-1-ethyl-6-methoxy-1H-indol-2-yl)-phenoxy]-acetic acid (40 mg, 0.12 mmol) is suspended in CH₂Cl₂ (1.65 mmol) and DMF (2 µL). Oxalyl chloride (17 µL, 0.19 mmol) is added. This is stirred at room temperature for 30 minutes. The resulting solution is then pipetted into a stirring solution of S-3-hydroxypyrrolidine (150 µL) and CH₂Cl₂ (3.0 mL). The mixture is washed with aqueous HCl. The organic layer is dried and concentrated. Purification by silica gel chromatography (3/2 CH₂Cl₂/acetone) yields 1-ethyl-2-{4-[2-(3-hydroxy-pyrrolidin-1-yl)-2-oxo-ethoxy]-phenyl}-6-methoxy-1H-indole-3-carbonitrile (40 mg, 79%), compound 285 as a white solid.

Example 1BG

Preparation of 1-ethyl-6-methoxy-2-(2-oxo-2,3-dihydro-benzooxazol-5-yl)-1H-indole-3-carbonitrile (Compound 332)

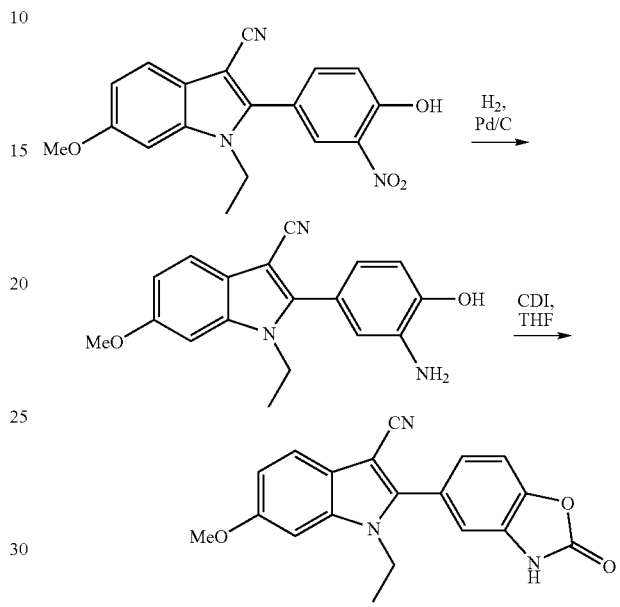

Step A: 1-Ethyl-2-(4-hydroxy-3-nitrophenyl)-6-methoxy-1H-indole-3-carbonitrile (369 mg, 1.1 mmol), prepared as in example 1Gd, is combined with EtOAc (20 mL) and Pd/C (150 mg, 10%). This mixture is hydrogenated at 30 p.s.i. for 1 h. This is filtered through celite. The filtrate is concentrated and triturated with ether to yield 2-(3-amino-4-hydroxyphenyl)-1-ethyl-6-methoxy-1H-indole-3-carbonitrile (307 mg, 91%), compound 322, as a white solid.

Step B: 2-(3-Amino-4-hydroxyphenyl)-1-ethyl-6-methoxy-1H-indole-3-carbonitrile (100 mg, 0.33 mmol), prepared as in step A, is combined with CDI (83 mg, 0.51 mmol), and THF (1.1 mL). This is heated at 65° C. for 1 hour. The reaction mixture is partitioned between EtOAc and aqueous HCl. The organic layer is dried and concentrated. Purification by silica gel chromatography (9/1, CH₂Cl₂/EtOAc) yields 1-ethyl-6-methoxy-2-(2-oxo-2,3-dihydro-benzooxazol-5-yl)-1H-indole-3-carbonitrile (89 mg, 81%) as a white solid.

Example 1BH

Preparation of 1-ethyl-6-methoxy-2-(3-oxo-3,4-dihydro-2H-benzo[1,4]oxazin-6-yl)-1H-indole-3-carbonitrile (compound 334)

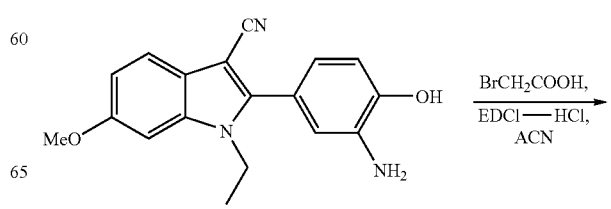

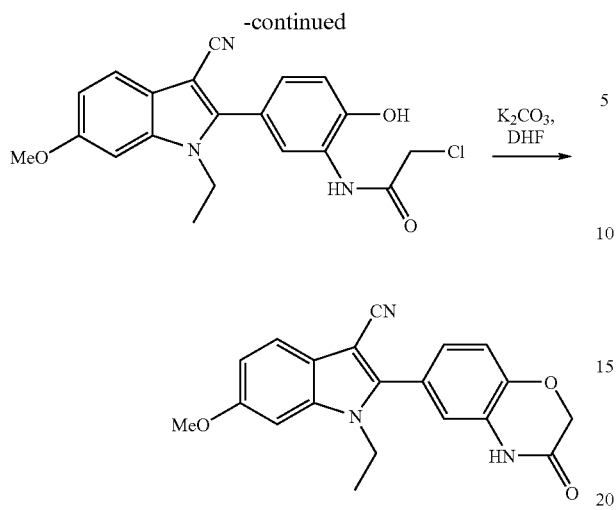

Step A: Bromoacetic acid (52 mg, 0.37 mmol) is combined with EDCI hydrochloride (62 mg, 0.4 mmol) and acetonitrile (900 μL) to form a homogeneous solution. 2-(3-Amino-4-hydroxyphenyl)-1-ethyl-6-methoxy-1H-indole-3-carbonitrile (100 mg, 0.33 mmol), prepared as in example 1BG, step B, is added to the solution. A thick paste soon forms. Another 1.1 mL of acetonitrile is added and the mixture is then stirred at room temperature for 2 hours. The reaction mixture is then partitioned between $H_2O$ and EtOAc. The organic layer is dried and concentrated. Purification by silica gel chromatography (4/1, $CH_2Cl_2$/EtOAc) yields 2-chloro-N-[5-(3-cyano-1-ethyl-6-methoxy-1H-indol-2-yl)-2-hydroxyphenyl]acetamide (82 mg, 60%), compound 333, as a white solid.

Step B: 2-Chloro-N-[5-(3-cyano-1-ethyl-6-methoxy-1H-indol-2-yl)-2-hydroxy-phenyl]acetamide (57 mg, 0.13 mmol), prepared in step A, is combined with $K_2CO_3$ (55 mg, 0.4 mmol), and DMF (400 μL). This is heated at 80° C. for 1 hour. The reaction mixture is then partitioned between $H_2O$ and EtOAc. The organic layer is dried and concentrated. Purification by silica gel chromatography (9/1, $CH_2Cl_2$/EtOAc) yields 1-ethyl-6-methoxy-2-(3-oxo-3,4-dihydro-2H-benzo[1,4]oxazin-6-yl)-1H-indole-3-carbonitrile (45 mg, 90%) as a white solid.

Step A: 4-Aminosalicylic acid (4.0 g, 26 mmol) is suspended in $H_2SO_4$ (26 mL, 2.7M) at −5° C. Sodium nitrite (1.8 g, 26.1 mmol) in $H_2O$ (6.5 mL) is cooled to ice bath temperature and is added dropwise to the aminosalicylic acid mixture over 5 minutes. The resulting suspension is stirred at −5° C. for 15 minutes. A solution of KI (6.8 g, 41 mmol) in $H_2SO_4$ (13 mL, 1M) is added dropwise to the diazonium salt, with considerable evolution of $N_2$. The reaction mixture is heated at 70° C. for 20 minutes. The reaction mixture is then partitioned between $H_2O$ and EtOAc. The organic layer is dried and concentrated. Purification by silica gel chromatography (7/3, hexanes/acetone, 1% acetic acid) yields 4-iodosalicylic acid (5.33 g, 85-90% pure).

Step B: Crude 4-Iodosalicylic acid (1.0 g, 3.8 mmol) is dissolved in THF (28 mL) and $Et_3N$ (1.15 mL, 8.2 mmol). DPPA (1.7 mL, 7.8 mmol) is added. This is heated at 70° C. overnight. The reaction mixture is then partitioned between $H_2O$ and EtOAc. The organic layer is dried and concentrated. Purification by silica gel chromatography (9/1, $CH_2Cl_2$/EtOAc) yields 472 mg crude intermediate. Trituration with ether yields 6-iodo-3H-benzooxazol-2-one (369 mg, 37%) as a white solid.

Step C: 6-Iodo-3H-benzooxazol-2-one (118 mg, 0.45 mmol) is used to prepare 1-ethyl-6-methoxy-2-(2-oxo-2,3-dihydro-benzooxazol-6-yl)-1H-indole-3-carbonitrile, compound 340 (75 mg, 55%), utilizing essentially the same procedure as in example 1Gd.

Example 1BI

Preparation of 1-ethyl-6-methoxy-2-(2-oxo-2,3-dihydro-benzooxazol-6-yl)-1H-indole-3-carbonitrile (Compound 340)

Example 1BJ

Preparation of 1-ethyl-6-methoxy-2-(4-methyl-3-oxo-3,4,-dihydro-2H-benzo[1,4]oxazin-6-yl)-1H-indole-3-carbonitrile (compound 339)

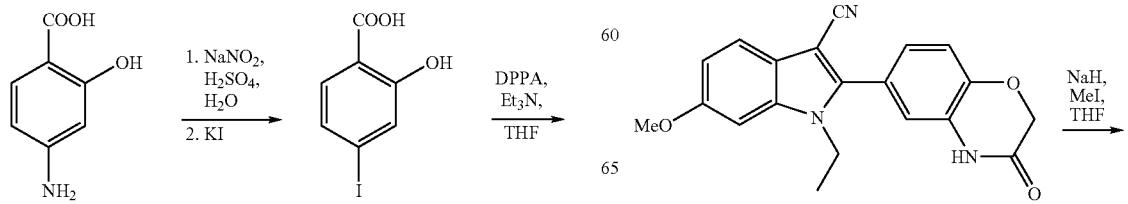

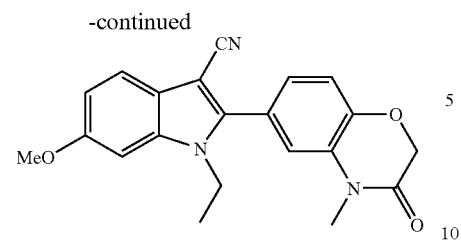

1-Ethyl-6-methoxy-2-(3-oxo-3,4-dihydro-2H-benzo[1,4]oxazin-6-yl)-1H-indole-3-carbonitrile (20 mg, 0.058 mmol), prepared as in example 1BH, is combined with NaH (14 mg, 60% suspension in oil, 0.35 mmol). THF (300 μL) is added. This is stirred at room temperature for 5 minutes. A solution of methyl iodide (4.4 μL) in THF (100 μL) is added. This is stirred at room temperature for 1 hour. The reaction mixture is partitioned between EtOAc and aqueous HCl. The organic layer is dried and concentrated. Purification by silica gel chromatography (9/1, CH$_2$Cl$_2$/EtOAc) yields 1-ethyl-6-methoxy-2-(4-methyl-3-oxo-3,4,-dihydro-2H-benzo[1,4]oxazin-6-yl)-1H-indole-3-carbonitrile (16 mg, 76%) as a white solid.

The following compound is prepared similarly: Compound 341.

Example 1BK

Preparation of 1-ethyl-2-iodo-6-methoxy-5-nitro-1H-indole-3-carbonitrile (compound 499)

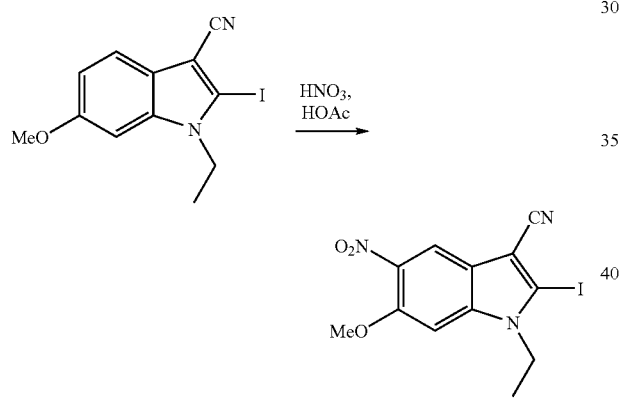

1-Ethyl-2-iodo-6-methoxy-1H-indole-3-carbonitrile (50 mg, 0.15 mmol), prepared as in example 1Ga, Step A, is suspended in acetic acid (620 μL) at 0° C. Nitric acid (4.25M in AcOH) is added. This is stirred at room temperature for 2 hours. The reaction mixture is then partitioned between CH$_2$Cl$_2$ and H$_2$O. The organic layer is washed with aqueous NaHCO$_3$, and then is dried and concentrated. Purification by silica gel chromatography (6/4, CH$_2$Cl$_2$/hexanes), followed by ether trituration, yields 1-ethyl-2-iodo-6-methoxy-5-nitro-1H-indole-3-carbonitrile (16 mg, 29%) as a yellow solid.

Example 1BL

Preparation of 1'-ethanesulfonyl-1-ethyl-6-methoxy-2',3'-dihydro-1H,1H'-[2,6']biindolyl-3-carbonitrile (compound 753)

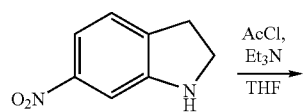

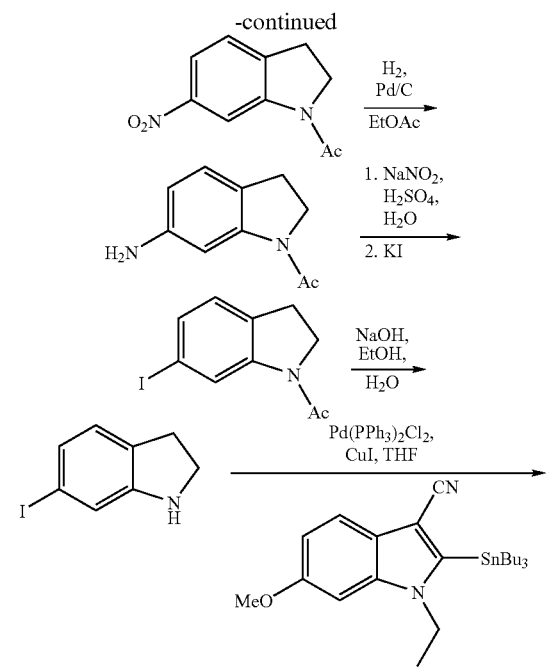

Step A: 6-Nitroindoline (3.0 g, 18.3 mmol) is dissolved in THF (45 mL) and Et$_3$N (3.4 mL, 24.4 mmol) at 0° C. Acetyl chloride (1.5 mL, 21 mmol) is added dropwise. The mixture is stirred at room temperature for 30 minutes. The mixture is partitioned between EtOAc and aqueous HCl. The organic layer is dried and concentrated to yield 1-acetyl-6-nitroindoline (3.8 g, 100%) as a yellow solid.

Step B: 1-Acetyl-6-nitroindoline (3.8 g, 18.3 mmol) is suspended in EtOAc (200 mL). Pd/C (650 mg, 10%) is added, and the mixture is hydrogenated at 40-55 p.s.i. for 2 hours. The mixture is then filtered through celite. The filtrate is concentrated, and the residue is triturated with ether to yield 1-acetyl-6-aminoindoline (3.18 g, 99%) as an orange solid.

Step C: 1-Acetyl-6-aminoindoline (1.5 g, 8.5 mmol) is used to prepare 1-acetyl-6-iodoindoline (1.06 g, 43%), utilizing essentially the same procedure in example 1BI, Step A.

Step D: 1-Acetyl-6-iodoindoline (1.06 g, 3.7 mmol), NaOH (1.16 g, 29 mmol), EtOH (8 mL), and H$_2$O (6 mL) are heated at 90° C. overnight. The reaction mixture is then partitioned between H$_2$O and EtOAc. The organic layer is extracted into aqueous HCl. The aqueous layer is in turn basified with NaOH, and is extracted with EtOAc. The organic layer is dried and concentrated. Hexane trituration yields 6-iodoindoline (577 mg, 64%) as a brown solid.

Step E: 1-Iodoindoline (600 mg, 2.45 mmol) is used to prepare 1-ethyl-6-methoxy-2',3'-dihydro-1H,1H'-[2,6']biindolyl-3-carbonitrile (535 mg, 67%), utilizing essentially the same procedure as in example 1Gd, Step B.

Step F: 1-Ethyl-6-methoxy-2',3'-dihydro-1H,1H'-[2,6']biindolyl-3-carbonitrile (30 mg, 0.095 mmol) is used to prepare 1'-Ethanesulfonyl-1-Ethyl-6-methoxy-2',3'-dihydro-1H,1H'-[2,6']biindolyl-3-carbonitrile (24 mg, 62%), utilizing the procedure in example 1Y.

The following compounds are prepared similarly as above: Compounds 752 and 754.

Example 1BM

Preparation of 5-acetyl-1-ethyl-6-methoxy-2-(4-nitro-phenyl)-1H-indole-3-carbonitrile (compound 844)

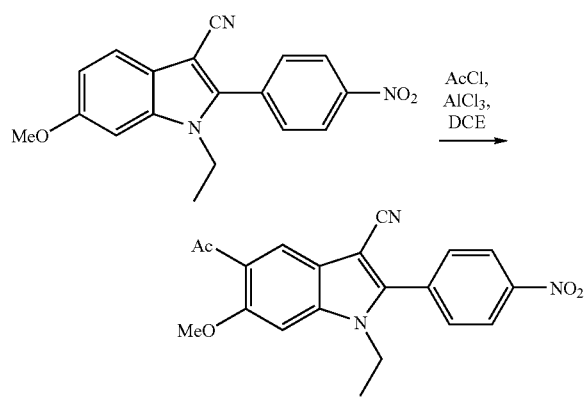

1-Ethyl-6-methoxy-2-(4-nitrophenyl)-1H-indole-3-carbonitrile (100 mg, 0.3 mmol), prepared by the method of example 1Gc, is suspended in 1,2-dichloroethane (500 μL) at 0° C. Acetyl chloride (50 μL, 0.69 mmol) is added, followed by AlCl₃ (55 mg, 0.4 mmol) in one portion. This is stirred at 0° C. for 1 hour, at room temperature for 4 hours, and at 45° C. overnight. The reaction mixture is then partitioned between CH₂Cl₂ and H₂O. The organic layer is dried and concentrated. Purification by silica gel chromatography (195:5 CH₂Cl₂/EtOAc) yields 5-acetyl-1-ethyl-6-methoxy-2-(4-nitro-phenyl)-1H-indole-3-carbonitrile (33 mg, 29%) as an orange solid.

Example 1BN

Preparation of 1-ethyl-6-methoxy-5-morpholin-4-ylmethyl-2-(4-nitro-phenyl)-1H-indole-3-carbonitrile (compound 845)

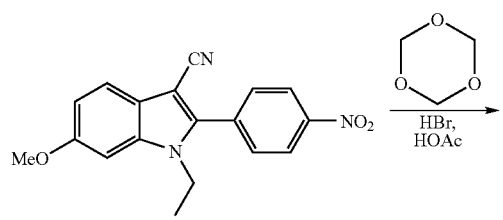

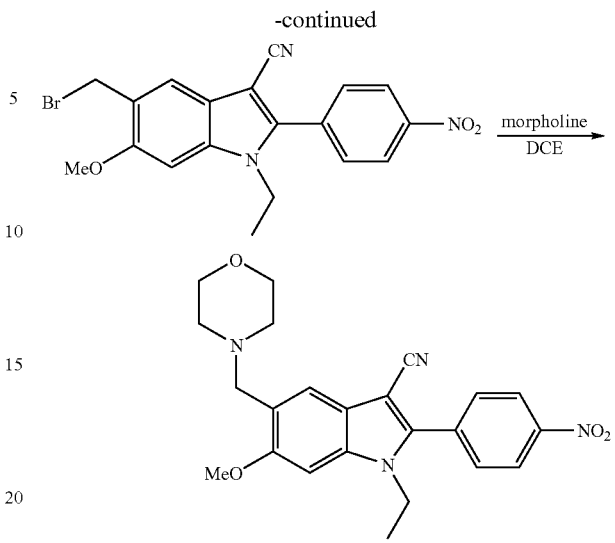

Step A: 1-Ethyl-6-methoxy-2-(4-nitrophenyl)-1H-indole-3-carbonitrile (100 mg, 0.3 mmol), prepared by the method of example 1Gc, is combined with 1,3,5-trioxane (64 mg, 0.71 mmol) and acetic acid (2.0 mL). 33% HBr in acetic acid (2.0 mL) is added. This is stirred at room temperature for 4 hours. The reaction mixture is then partitioned between CH₂Cl₂ and H₂O. The organic layer is washed with aqueous NaHCO₃, and is subsequently dried and concentrated. The crude material is carried through to the next step.

Step B: Crude 6-bromomethyl-1-ethyl-6-methoxy-2-(4-nitro-phenyl)-1H-indole-3-carbonitrile (0.3 mmol) is heated with morpholine (150 μL, 1.75 mmol) and DCE (1.0 mL) at 90° C. overnight. The reaction mixture is then partitioned between H₂O and EtOAc. The organic layer is dried and concentrated. Purification by silica gel chromatography (50-100%, EtOAc/CH₂Cl₂), followed by trituration with 1/1 hexane/acetone yields 1-ethyl-6-methoxy-5-morpholin-4-ylmethyl-2-(4-nitrophenyl)-1H-indole-3-carbonitrile (57 mg, 44% overall yield) as a yellow solid.

Example 1BO

2-[4-(1,1-dioxidoisothiazolidin-2-yl)phenyl]-1-cyclopropylmethyl-6-methoxy-1H-indole-3-carbonitrile (compound 716)

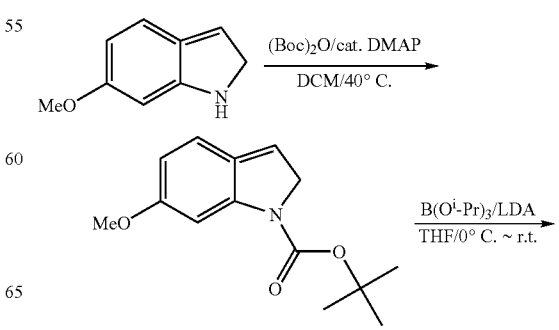

515

-continued

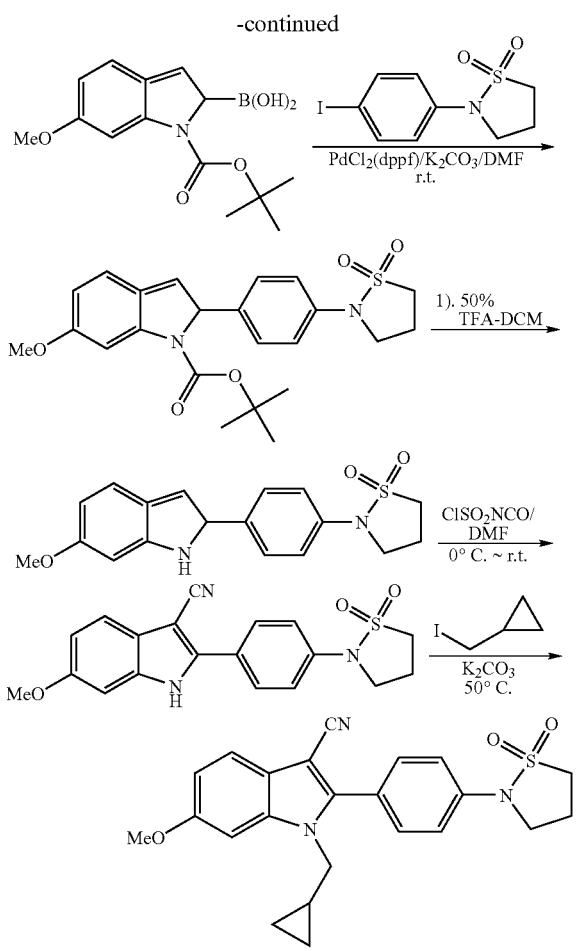

Step A: To a solution of 6-methoxyindole (5.88 g, 40.0 mmol) and di-tert-butyl dicarbonate (9.59 g, 44.0 mmol) in DCM (50 mL) is added, at 40° C. while stirring, DMAP (0.10 g). After stirring overnight, the mixture is washed sequentially with 0.1 N HCl, water and brine and dried over anhydrous Na₂SO₄. The solvent is evaporated and the residue is chromatographed (silica gel, EtOAc/hexanes, 1/7) to provide tert-butyl 6-methoxy-1H-indole-1-carboxylate (8.48 g, 86%).

Step B: The above Boc-indole (3.08 g, 12.5 mmol) and isopropylborate (4.83 mL, 21.9 mmol) are dissolved in anhydrous THF (20 mL) and the solution is cooled at 0° C. While stirring, LDA (12.5 mL, 1.5 M mono-THF complex in cyclohexane, 18.7 mmol) is added dropwise. The mixture is stirred at 0° C. for 15 min and then room temperature for 0.5 h, followed by the addition of HCl (6 N, 3.0 mL, 18 mmol) in an ice-water bath. The organic solvent is removed in vacuo and the residue is suspended in H₂O (100 mL) and acidified with HCl (6 N) to pH 4~5. The precipitate is collected via filtration and washed with water and hexanes and dried in air to provide 1-Boc-6-methoxyindole-2-boronic acid (3.38 g, 93%).

Step C: To a solution of 4-iodoanilline (3.18 g, 14.5 mmol) in pyridine (15 mL) at 0° C., is added 3-chloropropanesulfonyl chloride (2.3 mL, 18.9 mmol). After the addition, the mixture is stirred for 2 hr at room temperature, and poured into ice-water (200 mL). The organic is separated and the aqueous layer is extracted with DCM (2×50 mL). The combined organics are washed with HCl (2 N, 2×15 mL), water (2×50 mL) and brine (20 mL) consecutively and dried over anhydrous Na₂SO₄. The solvent is then evaporated and the residue is chromatographed to furnish 3-chloro-N-(4-iodophenyl)propane-1-sulfonamide (4.68 g, 90%). The chlorosulfonamide obtained (3.47 g, 9.6 mmol) is then treated with K₂CO₃ (3.33 g, 24.1 mmol) in DMF (50 mL) at 50° C. for 2 h. The mixture is poured into ice-water (300 mL) and the precipitate is collected and dried in air to provide essentially pure 2-(4-iodophenyl)isothiazolidine-1,1-dioxide (3.11 g, 100%).

Step D: To a mixture of 1-Boc-6-methoxyindole-2-boronic acid prepared in step B above (0.36 g, 1.25 mmol), 2-(4-iodophenyl)isothiazolidine-1,1-dioxide (0.32 g, 1.0 mmol) and PdCl₂(dppf) (0.037 g, 0.05 mmol) in DMF (4.0 mL), is added aqueous K₂CO₃ solution (1.5 mL, 2.0 M, 3.0 mmol). The mixture is stirred at room temperature overnight and then poured into ice-water (100 mL). The precipitate is collected and washed with water and purified by flash column chromatography (silica gel, DCM/EtOAc, 9/1) to furnish 1-Boc-2-[4-(1,1-dioxidoisothiazolidin-2-yl)phenyl]-6-methoxy-1H-indole (0.43 g, 98%).

The following compound is made similarly: Compound 768.

Step E: 1-Boc-2-[4-(1,1-dioxidoisothiazolidin-2-yl)phenyl]-6-methoxy-1H-indole (1.63 g, 3.7 mmol) is treated with TFA (25 mL) in DCM (25 mL) at room temperature for 4 h. After the removal of the volatiles, the residue is carefully stirred with saturated NaHCO₃ for 0.5 h. The precipitate is collected via filtration and washed with water thoroughly and dried to provide essentially pure 1-H-2-[4-(1,1-dioxidoisothiazolidin-2-yl)phenyl]-6-methoxyindole (1.17 g, 92%).

At 0° C., 1-H-2-[4-(1,1-dioxidoisothiazolidin-2-yl)phenyl]-6-methoxyindole (0.95 g, 2.8 mmol) is dissolved in DMF (10 mL) and treated with chlorosulfonyl isocyanate (0.36 mL, 4.2 mmol). The mixture is then stirred at room temperature overnight and poured into ice-water (150 mL) then stirred for 0.5 h. The precipitate is collected via filtration and washed thoroughly with water and dried in air to furnish 1-H-2-[4-(1,1-dioxidoisothiazolidin-2-yl)phenyl]-6-methoxyindole-3-carbonitrile (0.89 g, 87%).

The following compound is prepared in the same fashion as described above: Compound 829.

Step F: To a solution of 1-H-2-[4-(1,1-dioxidoisothiazolidin-2-yl)phenyl]-6-methoxyindole-3-carbonitrile (73 mg, 0.2 mmol) and K₂CO₃ (69 mg, 0.5 mmol) in DMF (3.0 mL) is added cyclopropylmethyl iodide (0.029 mL, 0.3 mmol). The mixture is stirred at 50° C. overnight and poured into ice-water (10 mL). The precipitate is collected via filtration, washed with water and purified by column chromatography to provide 2-[4-(1,1-dioxidoisothiazolidin-2-yl)phenyl]-6-methoxy-1-cyclopropylmethylindole-3-carbonitrile, compound 716 (73 mg, 87%).

The following compounds are prepared in the same fashion as described above: Compounds 717, 718, 719, 782, 783, 784.

Example 1BP

Preparation of 2-[4-(1,1'-dioxo-1λ⁶-isothiazolidin-2-yl)-6-methoxy-3-oxazol-5-yl-1-propyl-1H-indole (compound 805)

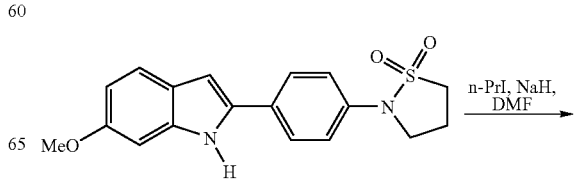

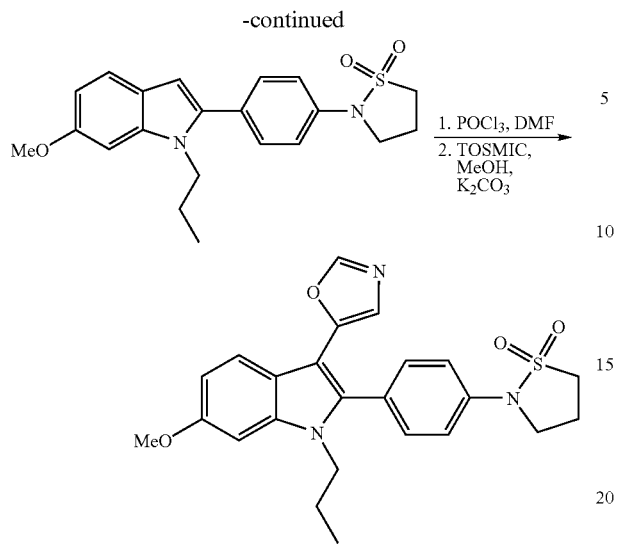

Step A: 2-[4-(1,1'-Dioxo-1λ⁶-isothiazolidin-2-yl)-6-methoxy-indole (900 mg, 2.62 mmol), prepared in example 1BO, step D is used to prepare 2-[4-(1,1'-dioxo-1λ⁶-isothiazolidin-2-yl)-6-methoxy-1-propyl-1H-indole (608 mg, 60%), utilizing essentially the same procedure as example 1A, Step B.

Step B: 2-[4-(1,1'-Dioxo-1λ⁶-isothiazolidin-2-yl)-6-methoxy-1-propyl-1H-indole (50 mg, 0.13 mmol) is used to prepare 2-[4-(1,1'-dioxo-1λ⁶-isothiazolidin-2-yl)-6-methoxy-3-oxazol-5-yl-1-propyl-1H-indole (9 mg, 15% overall yield) according to the protocol in example 1P.

Example 1BQ

Preparation of 2-[4-(cyclopropylsulfonyl)piperazin-1-yl]-1-ethyl-6-(trifluoromethyl)-1H-indole-3-carbonitrile (compound 842)

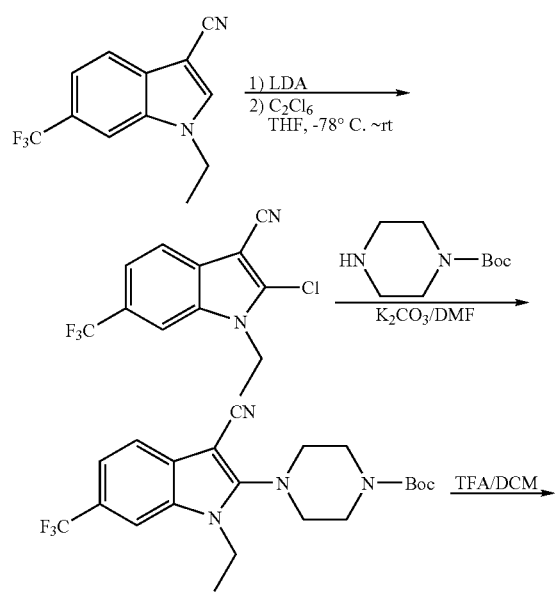

Step A: To a solution of 1-ethyl-6-trifluoromethylindole-3-carbonitrile (2.54 g, 10.0 mmol), prepared by the method of procedure 1A, in anhydrous THF (20.0 mL), at −78° C. is added LDA (8.3 mL, 1.5 M mono-THF in cyclohexane, 12.5 mmol) dropwise. The mixture is continued for 0.5 hr after the addition, followed by the addition of hexachloroethane and the mixture is then brought to room temperature slowly and stirred for 0.5 hr. The solvent is then evaporated and the residue is treated with water. The organics are extracted with dichloromethane, washed with water and brine and dried over anhydrous Na₂SO₄. The crude product obtained after the removal of the solvent is chromatographed (silica gel, dichloromethane/hexanes, 3/2) to provide 2-chloro-1-ethyl-6-(trifluoromethyl)-1H-indole-3-carbonitrile (1.75 g, 64%).

Step B: The chloroindole obtained above (0.27 g, 1.0 mmol), K₂CO₃ (0.35 g, 2.5 mmol) and N-Boc-piperazine (0.28 g, 1.5 mmol) are stirred at 70° C. in DMF (5.0 mL) for 3 days and then poured into water (50 mL). The precipitate is collected via filtration and washed with water. Chromatography of this crude product (silica gel, dichloromethane/ethyl acetate, 9/1) provides 4-(3-cyano-1-ethyl-6-trifluoromethyl-1H-indol-2-yl)-piperazine-1-carboxylic acid tert-butyl ester, compound 785 (0.30 g, 71%).

The following compounds are prepared in the same fashion as described above, by using other amines: Compounds 514, 785, 786.

Step C: 4-(3-cyano-1-ethyl-6-trifluoromethyl-1H-indol-2-yl)-piperazine-1-carboxylic acid tert-butyl ester (0.26 g, 6.1 mmol) is treated with TFA (5 mL) in dichloromethane (5 mL) for 1 hr at room temperature. After the removal of the volatiles, the residue is treated with saturated NaHCO₃ and the precipitate is collected via filtration, washed with water thoroughly and dried in air to furnish essentially pure 1-ethyl-2-piperazin-1-yl-6-(trifluoromethyl)-1H-indole-3-carbonitrile (0.20 g, 100%).

Step D: To a solution of 1-ethyl-2-piperazin-1-yl-6-(trifluoromethyl)-1H-indole-3-carbonitrile (32 mg, 0.1 mmol), pyridine (0.1 mL) in dichloromethane (1.0 mL) is added cyclopropanesulfonyl chloride (28 mg, 0.2 mmol) and the mixture is stirred at room temperature overnight. This is then diluted with dichloromethane (5 mL), washed with HCl (2 N, 2×2 mL), water (2×5 mL) and brine (5 mL) and chromatographed over silica gel (dichloromethane/ethyl acetate, 9/1) to provide 2-[4-(cyclopropylsulfonyl)piperazin-1-yl]-1-ethyl-6-(trifluoromethyl)-1H-indole-3-carbonitrile, compound 842 (30 mg, 70%).

519

The following compounds are prepared in the same fashion as described above, using corresponding sulfonyl chlorides: Compounds 841, 843.

Example 1BR

Ethanesulfonic acid [3-cyano-2-(4-ethoxyphenyl)-1-ethyl-1H-indol-6-yl]-amide (compound 835)

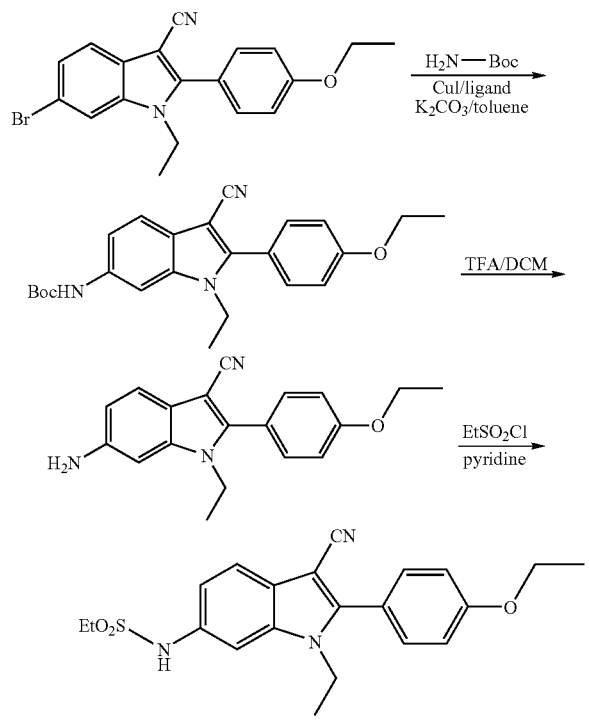

Step A: 6-Bromo-2-(4-ethoxyphenyl)-1-ethyl-1H-indole-3-carbonitrile (0.74 g, 2.0 mmol), compound 831, prepared from 6-bromoindole as described in example 1Gb, is mixed with K₂CO₃ (0.55 g, 4.0 mmol), CuI (0.02 g, 0.1 mmol), tert-butyl carbamate (0.35 g, 3.0 mmol), N,N'-dimethylcyclohexane-1,2-diamine ligand (0.028 g, 0.2 mmol) and anhydrous toluene (5.0 mL) in a sealed tube. The reaction system is flushed with nitrogen and then stirred at 110° C. overnight. After cooling, the solvent is replaced with dichloromethane and chromatographed (silica gel, dichloromethane) to provide [3-cyano-2-(4-ethoxy-phenyl)-1-ethyl-1H-indol-6-yl]-carbamic acid tert-butyl ester (0.68 g, 84%), compound 832.

Step B: Compound 832 prepared in step A above (0.63 g, 1.56 mmol) is treated with TFA/DCM (7.5 mL/7.5 mL) at room temperature for 2 h, and the volatiles are removed in vacuum. The residue is treated with saturated NaHCO₃ and the precipitate is collected via filtration and washed thoroughly with water, dried in air to provide 6-amino-2-(4-ethoxyphenyl)-1-ethyl-1H-indole-3-carbonitrile (0.45 g, 96%), compound 833.

Step C: The above amine (31 mg, 0.1 mmol) is treated with ethanesulfonyl chloride (19 mg, 0.15 mmol) in pyridine (1.0 mL) at room temperature overnight to provide, after purification using column chromatography, ethanesulfonic acid [3-cyano-2-(4-ethoxy-phenyl)-1-ethyl-1H-indol-6-yl]-amide (83%), compound 835.

520

The following compounds are prepared in the same fashion as described above: Compounds 830, 834, 836 and 837.

Example 1BS

Preparation of [3-cyano-2-(4-ethoxyphenyl)-1-ethyl-1H-indol-6-yl]-carbamic acid ethyl ester (compound 838)

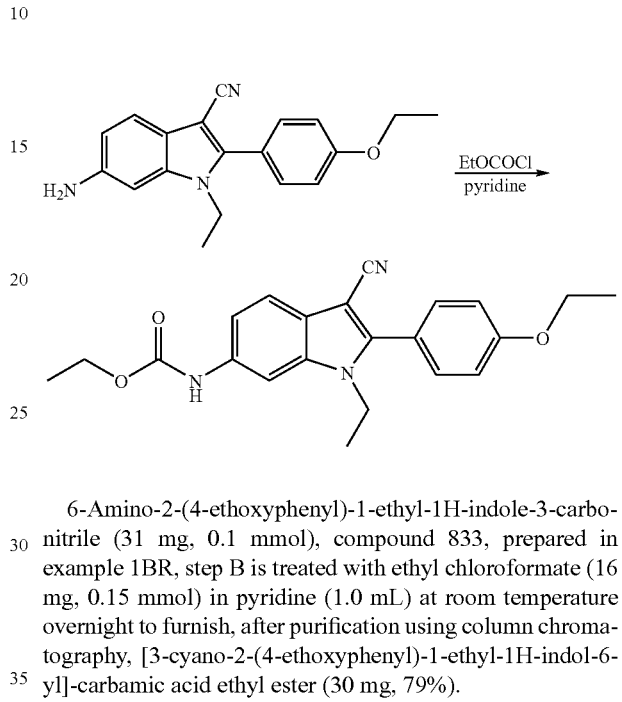

6-Amino-2-(4-ethoxyphenyl)-1-ethyl-1H-indole-3-carbonitrile (31 mg, 0.1 mmol), compound 833, prepared in example 1BR, step B is treated with ethyl chloroformate (16 mg, 0.15 mmol) in pyridine (1.0 mL) at room temperature overnight to furnish, after purification using column chromatography, [3-cyano-2-(4-ethoxyphenyl)-1-ethyl-1H-indol-6-yl]-carbamic acid ethyl ester (30 mg, 79%).

Example 1BT

Preparation of 1-[3-cyano-2-(4-ethoxyphenyl)-1-ethyl-1H-indol-6-yl]-3-ethyl-urea (compound 839)

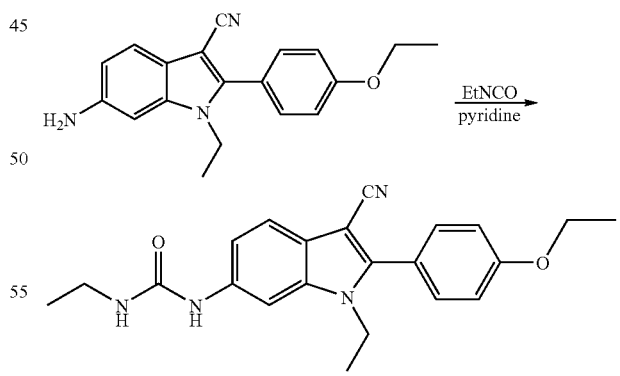

6-Amino-2-(4-ethoxyphenyl)-1-ethyl-1H-indole-3-carbonitrile (31 mg, 0.1 mmol) is treated with ethyl isocyanate (14 mg, 0.2 mmol) in dichloromethane (1.0 mL) at 40° C. overnight. The precipitate is collected via filtration, washed with dichloromethane and dried in air to furnish 1-[3-cyano-2-(4-ethoxy-phenyl)-1-ethyl-1H-indol-6-yl]-3-ethyl-urea (36 mg, 95%).

Example 1BU

Preparation of 1-(2-chloroethyl)-3-[4-(3-cyano-1-ethyl-6-methoxy-1H-indol-2-yl)-phenyl]-urea (compound 442)

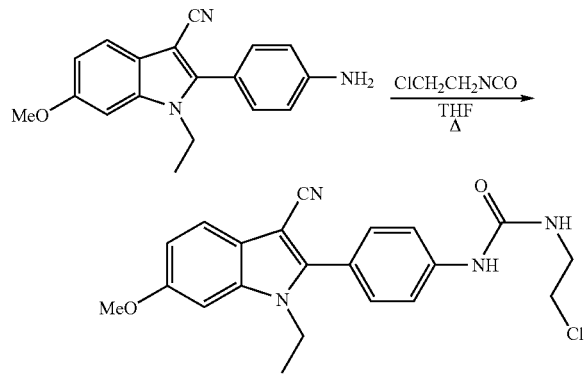

To a solution of 2-(4-aminophenyl)-1-ethyl-6-methoxy-1H-indole-3-carbonitrile (50 mg, 0.172 mmol) in THF (2 mL) is added 2-chloroethyl isocyanate (22 uL, 0.258 mmol) at room temperature. After stirring overnight at reflux, the reaction mixture is concentrated in vacuo and the residue is diluted with ethyl acetate. The resulting semi-solid is triturated with hexane and the precipitate collected is collected by filtration and washed well with 50% ethyl acetate in hexane and dried in vacuo to afford (62 mg, 91%) of 1-(2-chloroethyl)-3-[4-(3-cyano-1-ethyl-6-methoxy-1H-indol-2-yl)-phenyl]-urea.

Utilizing essentially the same procedure, the following compounds are prepared: Compounds 295, 362, 395, 396, 397, 398, 399, 400, 401, 402, 403, 404, 405, 406, 407, 443, 444, 445, 446, 511, 512, 513, 600, 620, 626, 627, 628, 679, 680, 681, 740, 741, 742, 743, 748, 749, 750, 751, 774, 817, 818, 846, 847, 848, 954, 955, 956, 957, 958, 987, 999, 1000, 1001, 1008, 1009, 1010, 1011, 1012, 1013, 1014, 1016, 1017, 1018, 1019, 1023, 1024, 1027, 1036, 1039, 1043, 1045, 1060, 1061, 1066, 1067, 1070, 1080, 1092, 1094, 1095, 1096, 1097, 1098, 1099, 1100, 1101, 1102, 1106, 1108, 1118, 1120, 1124, 1125, 1126, 1136, 1137, 1138, 1139, 1143, 1144, 1156, 1157, 1162, 1163, 1164, 1165, 1171, 1172, 11731197, 1190, 1214, 1221, 1223, 1224, 1225, 1225, 1227, 1256, 1279, 1301, 1303, 1304, 1305.

Example 1BV

Preparation of 1-ethyl-6-methoxy-2-[4-(2-oxo-imidazolidin-1-yl)-phenyl]-1H-indole-3-carbonitrile (compound 771)

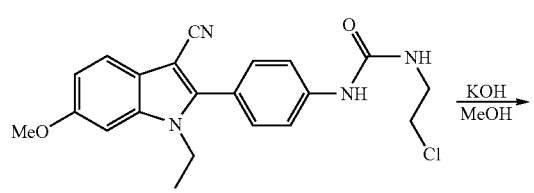

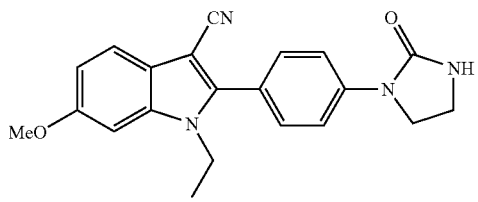

To a solution of 1-(2-chloroethyl)-3-[4-(3-cyano-1-ethyl-6-methoxy-1H-indol-2-yl)-phenyl]-urea (100 mg, 0.252 mmol) in MeOH (10 mL) is added aqueous 1M KOH (504 uL) and then stirred at 49° C. for 24 h. The solvents are removed under reduced pressure. The residue is diluted with ethyl acetate and then washed with water. The organic layer is dried over anhydrous MgSO₄, filtered and concentrated under reduced pressure. The residue is diluted with ethyl acetate and then triturated with hexane and the precipitate collected by filtration and washed well with 50% ethyl acetate in hexane and dried in vacuo to afford 1-ethyl-6-methoxy-2-[4-(2-oxo-imidazolidin-1-yl)-phenyl]-1H-indole-3-carbonitrile (56 mg, 62%).

Using essentially the same procedure, the following compounds are prepared: Compounds 770, 778.

Example 1BW

Preparation of 1-ethyl-6-isopropoxy-2-[4-(2-oxo-oxazolidin-3-yl)-phenyl]-1H-indole-3-carbonitrile (compound 638)

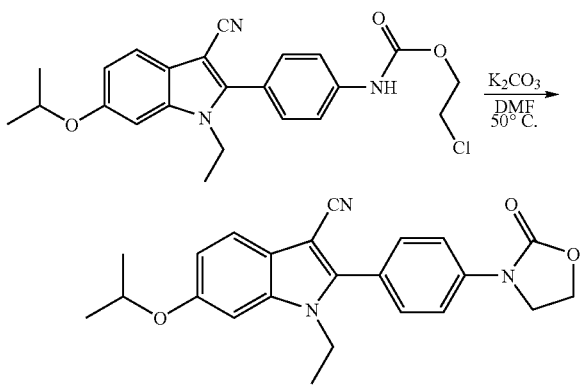

To a solution of [4-(3-cyano-1-ethyl-6-isopropoxy-1H-indol-2-yl)-phenyl]-carbamic acid 2-chloro-ethyl ester (30 mg, 0.07 mmol) in DMF (1 mL) is added aqueous K₂CO₃ (10 mg) and then stirred at 50° C. for 18 h. The reaction mixture is poured into cold water and the precipitate collected by filtration and washed with hexane and dried in vacuo to afford the title compound (21 mg, 81%).

The following compounds are made in similar fashion: Compounds 820, 821, 863, 864.

Example 1BX

Preparation of {3-[3-cyano-1-ethyl-6-(3-pyrrolidin-1-yl-propoxy)-1H-indol-2-yl]-phenyl}-carbamic acid ethyl ester (compound 530)

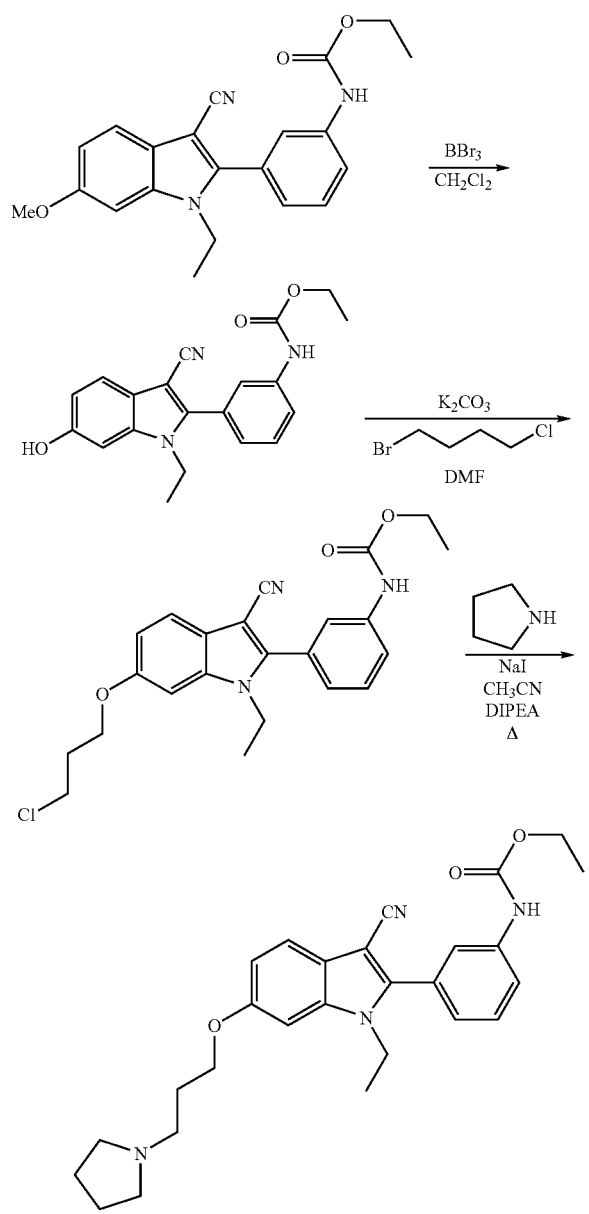

Step A: To a solution of [3-(3-cyano-1-ethyl-6-methoxy-1H-indol-2-yl)-phenyl]-carbamic acid ethyl ester (1.65 g, 4.37 mmol) in DCM (20 mL) is added 1M $BBr_3$ in DCM (13.12 mL) over a period of 20 min. The reaction mixture is stirred further 1 h at room temperature and then the solvents are removed under reduced pressure. The residue is dissolved in MeOH and then poured into cold water. The precipitate is collected by filtration and washed with hexane and dried in vacuo to afford [3-(3-cyano-1-ethyl-6-hydroxy-1H-indol-2-yl)-phenyl]-carbamic acid ethyl ester (1.5 g, 98%).

Step B: To a solution of [3-(3-cyano-1-ethyl-6-hydroxy-1H-indol-2-yl)-phenyl]-carbamic acid ethyl ester (1.2 g, 2.91 mmol) in DMF (10 mL) is added $K_2CO_3$ (538 mg, 3.9 mmol) and 3-bromo-1-chloroproane (383 uL, 3.9 mmol) and the reaction is stirred for overnight at 50° C. The reaction mixture is then poured into cold water and the precipitate is collected by filtration and washed with hexane and dried in vacuo to afford 1.1 g, 89% of the desired product.

Step C: To a solution of {3-[3-cyano-1-ethyl-6-(3-pyrrolidin-1-yl-propoxy)-1H-indol-2-yl]-phenyl}-carbamic acid ethyl ester (50 mg, 0.12 mmol) in $CH_3CN$ (2 mL) is added DIEA (31 uL, 0.18 mmol), sodium iodide (20 mg, 0.132 mmol) and pyrrolidine (30 uL, 0.36 mmol). The resulting mixture is stirred at reflux temperature for overnight. The solvent is evaporated and the residue is diluted with ethyl acetate and then triturated with hexane and the precipitate collected by filtration and washed well with 50% ethyl acetate in hexane and dried in vacuo to afford 1-ethyl-6-isopropoxy-2-[4-(2-oxo-oxazolidin-3-yl)-phenyl]-1H-indole-3-carbonitrile, compound 638 (46 mg, 85%).

The following compounds are made in similar fashion following steps A-C, above: Compounds 441, 447, 491, 492, 493, 504, 525, 526, 527, 528, 529, 531, 532, 533, 534, 535, 536, 537, 538, 539.

Example 1BY

Preparation of [3-(3-cyano-1-ethyl-6-methoxy-1H-indol-2-yl)-phenyl]-thiourea (Compound 767)

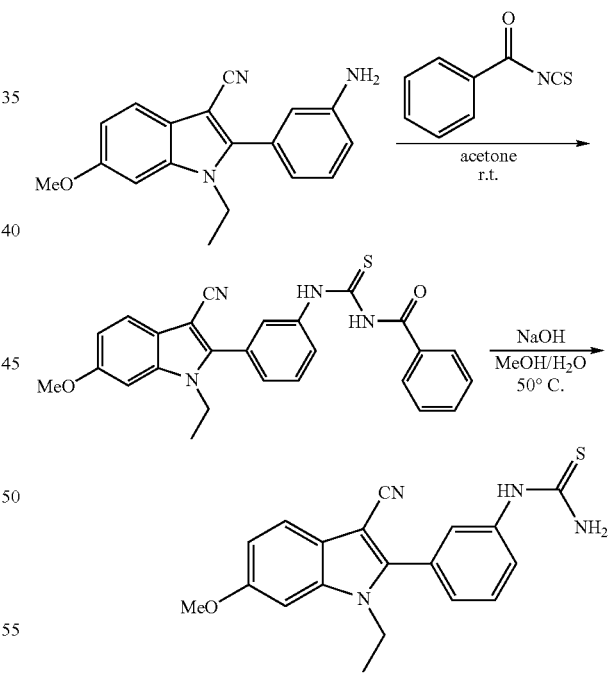

Step A: The starting material 2-(3-amino-phenyl)-1-ethyl-6-methoxy-1H-indole-3-carbonitrile (187 mg, 0.642 mmol) is dissolved in anhydrous acetone (3.0 mL). Benzoyl isothiocyanate (107 mg, 0.656 mmol) is added to the solution at room temperature and the mixture is stirred for 17 h during which time a precipitate forms. The precipitate is filtered, washed with acetone and dried to give 264 mg of 1-benzoyl-3-[3-(3-cyano-1-ethyl-6-methoxy-1H-indol-2-yl)-phenyl]-thiourea (90% yield) as a light yellow solid.

Step B: A suspension of 1-benzoyl-3-[3-(3-cyano-1-ethyl-6-methoxy-1H-indol-2-yl)-phenyl]-thiourea (241 mg, 0.530 mmol) in methyl alcohol (2.0 ml) and water (0.5 mL) is stirred at room temperature as sodium hydroxide (31 mg, 0.78 mmol) is added. The reaction mixture is heated to 50° C. for 17 h. The reaction mixture is concentrated to remove methyl alcohol. Water is added to the mixture and the solid is filtered, washed with water and dried to give 179 mg of [3-(3-cyano-1-ethyl-6-methoxy-1H-indol-2-yl)-phenyl]-thiourea, compound 767 (96% yield) as a white solid.

Example 1BZ

Preparation of 1-ethyl-6-methoxy-2-[4-(2-phenylquinazolin-4-ylamino)-phenyl]-1H-indole-3-carbonitrile (Compound 458)

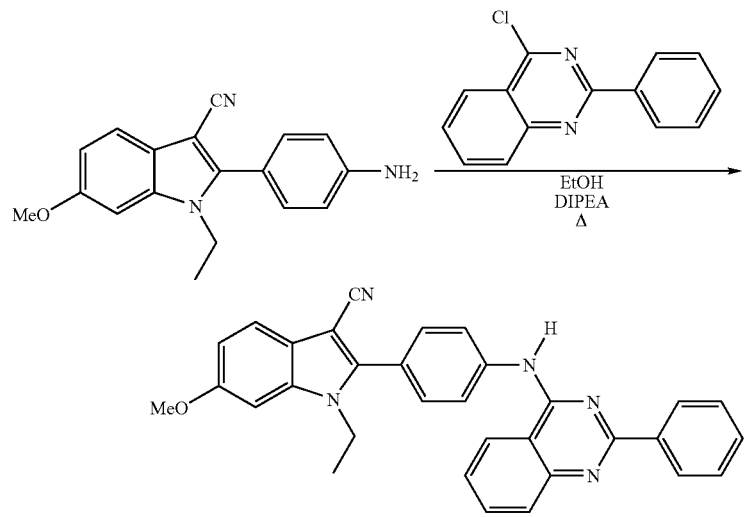

A solution of 2-(4-aminophenyl)-1-ethyl-6-methoxy-1H-indole-3-carbonitrile (100 mg, 0.343 mmol), 4-chloro-2-phenyl-quinazoline (83 mg, 0.34 mmol) and diisopropylethylamine (0.10 mL, 0.57 mmol) in absolute ethanol (3 mL) is heated to reflux overnight. The solution is cooled and evaporated, and the residue taken up in ethyl acetate (50 mL). This is washed with water and saturated brine (50 mL each), then dried over anhydrous sodium sulfate, filtered and evaporated. The resulting solid is triturated with ether, collected by filtration and dried under vacuum to afford 1-ethyl-6-methoxy-2-[4-(2-phenylquinazolin-4-ylamino)-phenyl]-1H-indole-3-carbonitrile (139 mg, 0.280 mmol, 82%).

Example 1CA

Preparation of diethyl [4-(3-cyano-6-ethoxy-1-ethyl-1H-indol-2-yl)-phenyl]-phosphoramidate (compound 772)

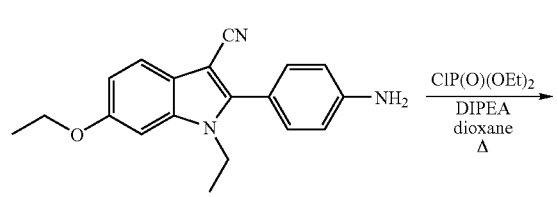

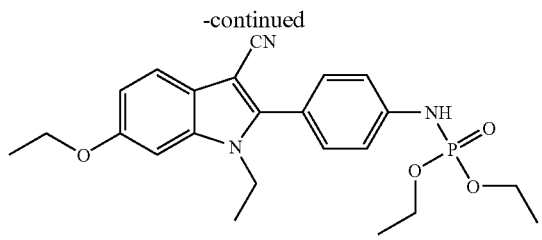

A solution of 2-(4-aminophenyl)-6-ethoxy-1-ethyl-1H-indole-3-carbonitrile (148 mg, 0.484 mmol), diethyl chlorophosphate (0.086 mL, 0.58 mmol) and diisopropylethylamine (0.10 mL, 0.57 mmol) in 1,4-dioxane (5 mL) is stirred at ambient temperature for 12 hours, then heated to 80° C. for an additional 24 hours. The solution is cooled and poured into 50 mL of ethyl acetate. This is washed with water and saturated brine (50 mL each), then dried over anhydrous magnesium sulfate, filtered and evaporated. The residual material is separated by flash chromatography (eluting 2/1 ethyl acetate/hexane on silica gel 60) to afford diethyl [4-(3-cyano-6-ethoxy-1-ethyl-1H-indol-2-yl)-phenyl]-phosphoramidate (108 mg, 0.245 mmol, 51%) as a white powder after evaporation.

The following examples are made in similar fashion: Compounds 936, 937, 942, 943, 944, 1081.

Example 1CB

Preparation of 1-ethyl-6-methoxy-2-[4-(5-methyl-1,1-dioxo-1λ⁶-[1,2,5]thiadiazolidin-2-yl)-phenyl]-1H-indole-3-carbonitrile (compound 726)

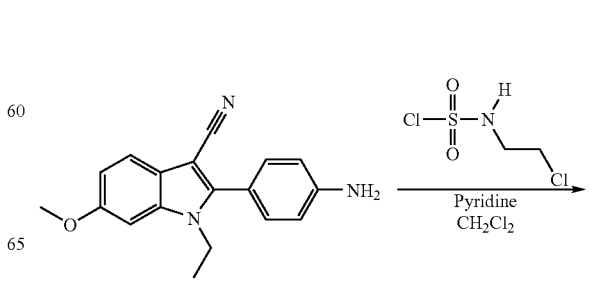

-continued

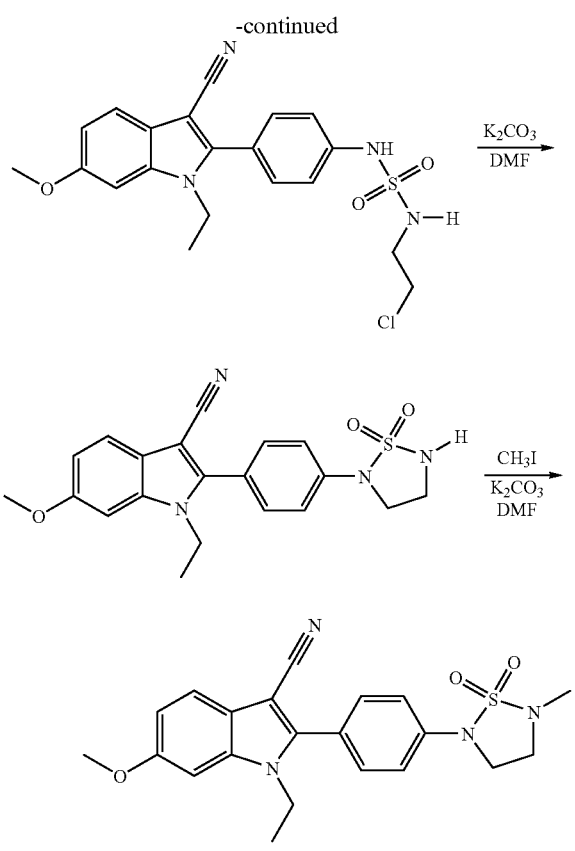

Step A: To a solution of 2-(4-aminophenyl)-1-ethyl-6-methoxy-1H-indole-3-carbonitrile (202 mg, 0.693 mmol) in pyridine (2.0 mL) is added the N-β-(chloroethylamino)sulfonyl chloride (222 mg, 1.39 mmol). The mixture is stirred at room temperature for 17 h then water (12.0 mL) is added and the mixture is extracted with ethyl acetate (3×2 mL). The extract is washed with 10% aqueous HCl (2×2 mL), water (2×2 mL), dried over MgSO$_4$, filtered and concentrated on a rotary evaporator. The crude product is purified by flash chromatography (0-5%, ethyl acetate/methylene chloride) to give 217 mg of N-(2-chloro-ethyl)-N'-[4-(3-cyano-1-ethyl-6-methoxy-1H-indol-2-yl)phenyl]sulfamide, compound 724, as a tan solid (75% yield).

In similar fashion the following compounds are prepared: Compounds 540, 541, 542, 574, 576, 704.

Step B: To a solution of N-(2-chloro-ethyl)-N'-[4-(3-cyano-1-ethyl-6-methoxy-1H-indol-2-yl)phenyl]sulfamide (100 mg, 0.241 mmol) in anhydrous DMF (1.25 mL), is added potassium carbonate (71.0 mg, 0.514 mmol). The mixture is stirred at room temperature for 17 h, then diluted with water (7.5 mL). The reaction mixture is extracted with ethyl acetate (3×2 mL) and the extract is washed with water (2×2 mL), dried over MgSO$_4$ and concentrated to give 2-[4-(1,1-dioxo-1λ$^6$-[1,2,5]thiadiazolidin-2-yl)phenyl]-1-ethyl-6-methoxy-1H-indole-3-carbonitrile, compound 725, as a white solid (84 mg, 88% yield).

In similar fashion the following compound is prepared: Compound: 705.

Step C: To a solution of 2-[4-(1,1-dioxo-1λ$^6$-[1,2,5]thiadiazolidin-2-yl)phenyl]-1-ethyl-6-methoxy-1H-indole-3-carbonitrile (34 mg, 0.086 mmol) in anhydrous DMF (1.0 mL) is added potassium carbonate (25 mg, 0.18 mmol) and iodomethane (20.4 mg, 0.144 mmol). The mixture is stirred at room temperature for 2 h and then diluted with water (6.0 mL) to give a precipitate. The precipitate is filtered, washed with water and dried to give 1-ethyl-6-methoxy-2-[4-(5-methyl-1,1-dioxo-1λ$^6$-[1,2,5]thiadiazolidin-2-yl)-phenyl]-1H-indole-3-carbonitrile, compound 726, as a white solid (35 mg, 98% yield).

In similar fashion the following compounds are prepared: Compound 727, 1110.

Example 1CC

Preparation of [4-(3-cyano-1-ethyl-6-methoxy-1H-indol-2-yl)-2-fluorophenyl]-carbamic acid propyl ester (compound 877)

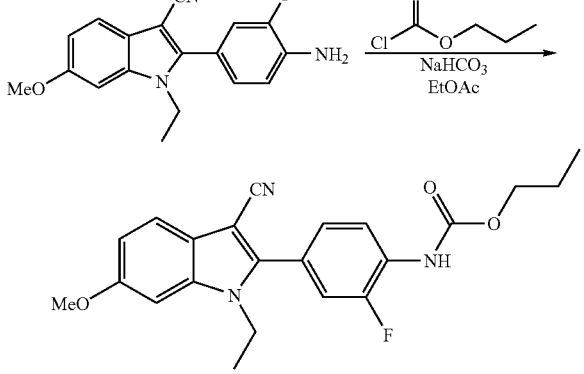

A biphasic mixture of 2-(4-amino-3-fluorophenyl)-1-ethyl-6-methoxy-1H-indole-3-carbonitrile (74 mg, 0.24 mmol), prepared as described in example 1Gb, and propyl chloroformate (0.033 mL, 0.29 mmol) in EtOAc (3 mL) and saturated NaHCO$_3$ (3 mL) is prepared at 0° C. and then allowed to warm to room temperature and stirred for 24 h. The reaction is then diluted with H$_2$O and extracted with EtOAc (2×). The organic phases are washed with H$_2$O and saturated NaCl and then dried and concentrated. Flash chromatography (EtOAc/hexanes 10-40%) gives 60 mg (63%) of [4-(3-cyano-1-ethyl-6-methoxy-1H-indol-2-yl)-2-fluorophenyl]-carbamic acid propyl ester as an off-white solid.

The following compounds are prepared in a similar fashion: Compounds 875, 876, 878, 879. By utilizing 2-(4-amino-3-methylphenyl)-1-ethyl-6-methoxy-1H-indole-3-carbonitrile, the following compounds are prepared: Compounds: 963, 964, 965.

Utilizing the same starting material and procedures described in examples 1Y, the following compounds are prepared: Compounds 871, 872, 873, 874. In similar fashion, utilizing 2-(4-amino-3-methylphenyl)-1-ethyl-6-methoxy-1H-indole-3-carbonitrile, the following compounds are prepared: Compounds 959, 960, 961, 962.

Utilizing the same starting material and procedures described in examples 1BU, the following compounds are prepared: 909, 910, 911. In a similar fashion, utilizing 2-(4-amino-3-methylphenyl)-1-ethyl-6-methoxy-1H-indole-3-carbonitrile, the following compounds are prepared: Compound: 966, 967.

Example CD

Preparation of cyclopropanecarboxylic acid {4-[3-cyano-1-ethyl-6-(2-imidazol-1-yl-ethoxy)-1H-indol-2-yl]-phenyl}-amide (compound 1183)

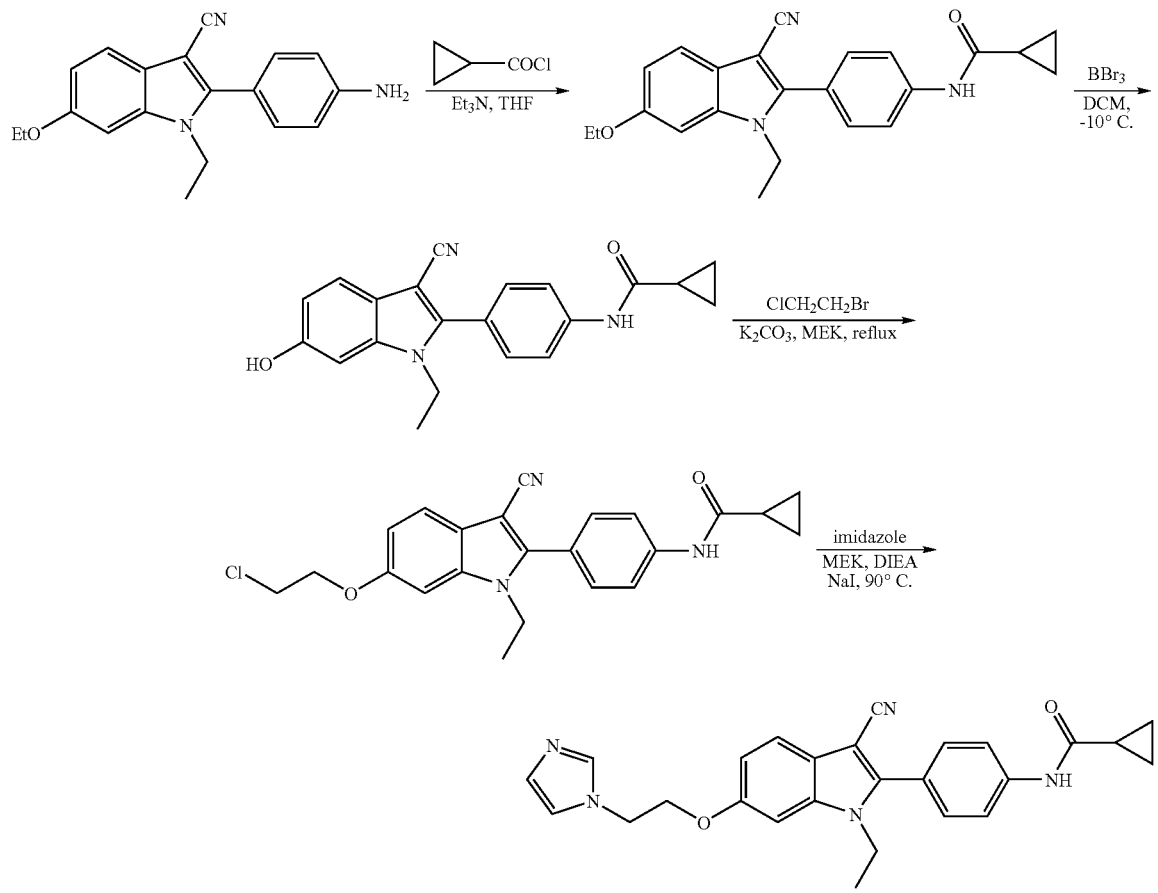

Step A: To a solution of compound 2-(4-aminophenyl)-6-ethoxy-1-ethyl-1H-indole-3-carbonitrile (3.66 g, 12 mmol), prepared as described in example 1Gb, in 20 mL of THF is added Et$_3$N (3.37 ml) and cyclopropanecarbonyl chloride (1.6 mL, 18 mmol). The mixture is stirred for 3 h at room temperature. Then water and ethyl acetate are added to the reaction mixture. The organic layer is separated, washed with brine (2×), dried over anhydrous Na$_2$SO$_4$, filtered and concentrated. The residue is recrystallized with ethyl acetate and hexane to yield 99% of cyclopropanecarboxylic acid [4-(3-cyano-6-ethoxy-1-ethyl-1H-indol-2-yl)-phenyl]-amide.

Step B: To a solution of cyclopropanecarboxylic acid [4-(3-cyano-6-ethoxy-1-ethyl-1H-indol-2-yl)-phenyl]-amide (4.4 g, 11.8 mmol) in 60 mL of DCM is added BBr$_3$ (6.65 mL, 70 mmol) at −10° C. After the addition, the mixture is stirred for 3 h at 0° C. Then aqueous NaHCO$_3$ is added to the mixture carefully until it becomes basic. The crude solid is collected by filtration to give 91% of cyclopropanecarboxylic acid [4-(3-cyano-1-ethyl-6-hydroxy-1H-indol-2-yl)-phenyl]-amide and is used for the next step without further purification.

Step C: To a solution of cyclopropanecarboxylic acid [4-(3-cyano-1-ethyl-6-hydroxy-1H-indol-2-yl)-phenyl]-amide (4 g, 11.6 mmol) in 15 mL of MEK is added K$_2$CO$_3$ (8 g, 58 mmol) and 1-bromo-2-chloro-ethane (6.7 mL, 70 mmol). Then the mixture is heated at reflux overnight. After it is cooled to room temperature, water and ethyl acetate are added. The organic layer is separated, washed with brine (2×), dried over anhydrous Na$_2$SO$_4$, filtered and concentrated to yield 81% of the crude cyclopropanecarboxylic acid {4-[6-(2-chloroethoxy)-3-cyano-1-ethyl-1H-indol-2-yl]-phenyl}-amide.

Step D: To a solution of cyclopropanecarboxylic acid {4-[6-(2-chloroethoxy)-3-cyano-1-ethyl-1H-indol-2-yl]-phenyl}-amide (102 mg, 0.25 mmol) in 1.5 mL of acetonitrile are added NaI (46 mg, 0.275 mmol), K$_2$CO$_3$ (138 mg, 1 mmol) and imidazole (51 mg, 0.75 mmol) in a sealed tube. Then the mixture is heated to 90° C. and stirred overnight. After it is cooled to room temperature, water and ethyl acetate are added. The organic layer is separated, washed with brine (2×), dried over anhydrous Na$_2$SO$_4$, filtered and concentrated. The crude compound is purified by preparative HPLC to give 71% of cyclopropanecarboxylic acid {4-[3-cyano-1-ethyl-6-(2-imidazol-1-yl-ethoxy)-1H-indol-2-yl]-phenyl}-amide.

Using the same procedure and substituting the appropriate nucleophilic reagents gives the following compounds: Compounds 952, 1025, 1054, 1090, 1091, 1092, 1093, 1184, 1394, 1395, 1413, 1414.

Example CE

Preparation of ethanesulfonic acid [4-(3-cyano-1-ethyl-6-trifluoromethoxyindol-2-yl)phenyl]amide (compound 881)

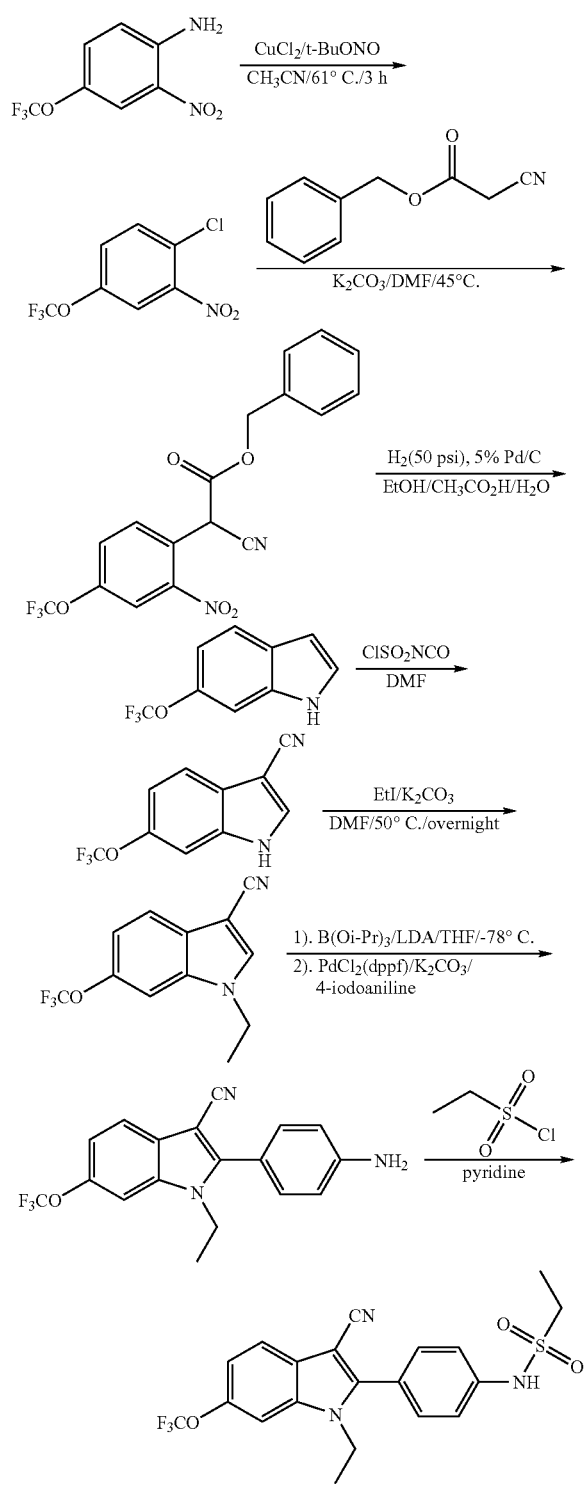

Step A: To a suspension of t-BuONO (8.01 mL, 67.5 mmol) and CuCl$_2$ (7.26 g, 54 mmol) in acetonitrile (50 mL), at 61° C. with gentle stirring, is added 2-nitro-4-trifluoromethoxyaniline (10.0 g, 45.0 mmol) portionwise. The mixture is stirred at this temperature for 2 h after the addition. The solvent is removed on a rotovap and the residue is treated with HCl (6 N, 200 mL), and extracted with dichloromethane (3×100 mL). The extracts are combined, dried over anhydrous Na$_2$SO$_4$, and passed through a short silica gel pad. The solvent is removed and the residue is added to a suspension of benzyl cyanoacetate (7.88 g, 45 mmol) and K$_2$CO$_3$ (12.42 g, 90 mmol) in DMF (100 mL). This mixture is then stirred at 45° C. overnight and poured into ice-water (700 mL), and extracted with dichloromethane (3×100 mL). The organics are dried over anhydrous Na$_2$SO$_4$ and again passed through a short silica gel pad, eluting with ethyl acetate. The solvent is then replaced with EtOH (160 mL), acetic acid (16 mL) and water (16 mL), and the reaction mixture is hydrogenated over 5% Pd/C (2.80 g) at 50 psi overnight. The mixture is filtered over Celite and the volatiles are removed in vacuo. The residue is dissolved in dichloromethane (200 mL), washed with Na$_2$CO$_3$ (2 M, 2×50 mL), water (2×50 mL), brine (50 mL) and dried over anhydrous Na$_2$SO$_4$. The crude product, obtained after the removal of the solvent, is chromatographed (silica gel, DCM/Hexanes, 1/1) to provide 6-trifluoromethoxyindole (5.70 g, 63% based on 2-nitro-4-trifluoromethoxyaniline).

Step B: To a solution of 6-trifluoromethoxyindole (2.68 g, 13.3 mmol) in dry DMF (10 mL) at 0° C., is added chlorosulfonylisocyanate (2.35 g, 1.44 mL, 16.6 mmol). The mixture is then brought to room temperature slowly and stirred for 1 h. The mixture is poured into ice (100 mL) and stirred for 1 h. The precipitate is collected by filtration and washed thoroughly with water and dried in vacuo, which is then dissolved in DMF (15 mL). To the solution is added K$_2$CO$_3$ and EtI (2.59 g, 1.34 mL, 16.6 mmol), and the mixture is stirred at 50° C. overnight. It is then poured into ice-water (200 mL). The precipitate is collected by filtration and washed with water, dried in air and purified by chromatography (silica gel, DCM) to furnish 1-ethyl-6-trifluoromethoxyindole-3-carbonitrile (2.90 g, 86%).

Step C: To a solution of the intermediate (2.03 g, 8.0 mmol) obtained above, triisopropylborate (2.16 g, 2.65 mL, 12.0 mmol) in dry THF (15 mL) at −78° C. is added LDA (6.7 mL, 1.5 M, 10.0 mmol). The mixture is stirred at −78° C. for 15 min after the addition, then slowly brought to room temperature and stirred for 30 min. It is then cooled at −78° C. and followed by the addition of 4-iodoaniline (2.10 g, 9.6 mmol), PdCl$_2$(dppf) (0.29 g, 0.4 mmol), DMF (30 mL) and K$_2$CO$_3$ (12.0 mL, 2.0 M, 24.0 mmol). The mixture is brought to room temperature slowly and stirred overnight and poured into ice-water (400 mL). The precipitate is collected and washed with water, chromatographed (silica gel, EtOAc/DCM, 0.5/9.5) to furnish 2-(4-aminophenyl)-1-ethyl-6-trifluoromethoxyindole-3-carbonitrile (1.99 g, 72%).

Step D: To a solution of the compound obtained in step C (31 mg, 0.1 mmol) in dry pyridine (1.0 mL) is added ethanesulfonyl chloride (14 μL, 0.15 mmol). The mixture is stirred at room temperature overnight and diluted with water (5 mL). The organic is extracted with DCM (5 mL) and washed with HCl (2N, 2×3 mL), water (2×4 mL) and brine (3 mL) and chromatographed (silica gel, EtOAc/DCM, 0.5/9.5) to provide the product, ethanesulfonic acid [4-(3-cyano-1-ethyl-6-trifluoromethoxyindol-2-yl)phenyl]amide (33 mg, 83%).

Compounds 882, 883, 884, 885, 886, 887, 888, 889 are prepared utilizing the above route using either the appropriate alkylsulfonyl chlorides (procedure 1Y) or chloroformates (procedure 1AJ).

Example 1CF

Preparation of 2-[4-(1,1-dioxidoisothiazolidin-2-yl)phenyl]-1-ethyl-6-(trifluoromethoxy)indole-3-carbonitrile (compound 903)

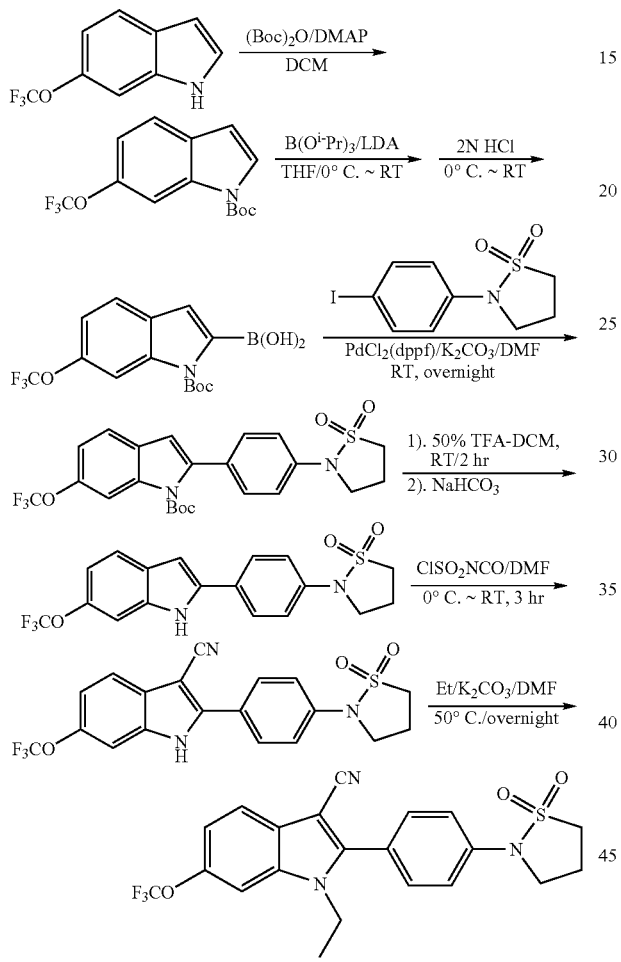

Step A: To a solution of 6-trifluoromethoxyindole (3.01 g, 15.0 mmol) and di-tert-butyl dicarbonate (3.59 g, 16.5 mmol) in DCM (30 mL) at 40° C. is added DMAP (0.04 g) while stirring. After stirring overnight, the mixture is washed sequentially with 0.1 N HCl, water and brine and dried over anhydrous $Na_2SO_4$. The solvent is evaporated and the residue is chromatographed (silica gel, EtOAc/Hexanes, 1/9) to provide tert-butyl 6-trifluoromethoxy-1H-indole-1-carboxylate.

Step B: The above Boc-indole and triisopropylborate (4.73 g, 5.8 mL, 26.3 mmol) are dissolved in anhydrous THF (20 mL) and the solution is cooled to 0° C. While stirring, LDA (15.0 mL, 1.5 M mono-THF complex in cyclohexane, 22.5 mmol) is added dropwise. The mixture is stirred at 0° C. for 15 min and then room temperature for 0.5 h, followed by the addition of HCl (6 N, 3.75 mL, 22.5 mmol) in an ice-water bath. The organic solvent is removed in vacuo and the residue is suspended in $H_2O$ (100 mL) and acidified with HCl (6 N) to pH 4~5. The precipitate is collected via filtration and washed with water and hexanes and dried in air to provide 1-Boc-6-trifluoromehoxyindole-2-boronic acid (2.56 g, 49%).

Step C: To a mixture of 1-Boc-6-trifluoromehoxyindole-2-boronic acid prepared above (0.74 g, 2.1 mmol), 2-(4-iodophenyl)isothiazolidine-1,1-dioxide (0.76 g, 2.4 mmol), and $PdCl_2(dppf)$ (0.08 g, 0.1 mmol) in DMF (6.0 mL), is added $K_2CO_3$ solution (3.2 mL, 2.0 M, 6.4 mmol). The mixture is stirred at room temperature overnight and then poured into ice-water (100 mL). The precipitate is collected and washed with water and purified by flash column chromatography (silica gel, DCM/EtOAc, 9/1) to furnish 1-Boc-2-[4-(1,1-dioxidoisothiazolidin-2-yl)phenyl]-6-methoxyindole, which is treated with 50% TFA in DCM (15 mL) at room temperature for 1 h. After the removal of the volatiles, the residue is carefully stirred with saturated $NaHCO_3$ for 0.5 h. The precipitate is collected via filtration and washed thoroughly with water and dried to provide essentially pure 1-H-2-[4-(1,1-dioxidoisothiazolidin-2-yl)phenyl]-6-trifluoromethoxyindole.

Step D: At 0° C., a solution of the intermediate obtained above in dry DMF (10 mL) is treated with chlorosulfonyl isocyanate (0.38 g, 0.23 mL, 2.68 mmol). The mixture is then stirred at room temperature overnight and poured into ice-water (150 mL) then stirred for 0.5 h. The precipitate is collected via filtration and washed thoroughly with water and dried in air to furnish 1-H-2-[4-(1,1-dioxidoisothiazolidin-2-yl)phenyl]-6-trifluoromethoxyindole-3-carbonitrile (0.81 g, 90%).

Step E: To a solution of 1-H-2-[4-(1,1-dioxidoisothiazolidin-2-yl)phenyl]-6-trifluoromethoxyindole-3-carbonitrile (63 mg, 0.15 mmol) and $K_2CO_3$ (62 mg, 0.45 mmol) in DMF (2.0 mL) is added ethyl iodide (36 µL, 0.45 mmol). The mixture is stirred at 50° C. overnight and poured into ice-water (10 mL). The precipitate is collected via filtration, washed with water and purified by column chromatography to provide 2-[4-(1,1-dioxidoisothiazolidin-2-yl)phenyl]-6-trifluoromethoxy-1-ethylindole-3-carbonitrile (59 mg, 88%).

The following compounds are prepared in the same fashion as described above: Compounds 902, 904, 905, 906.

Example 1CG

Preparation of [4-(3-cyano-1-cyclopropyl-6-methoxyindol-2-yl)phenyl]carbamic acid isopropyl ester (compound 1234)

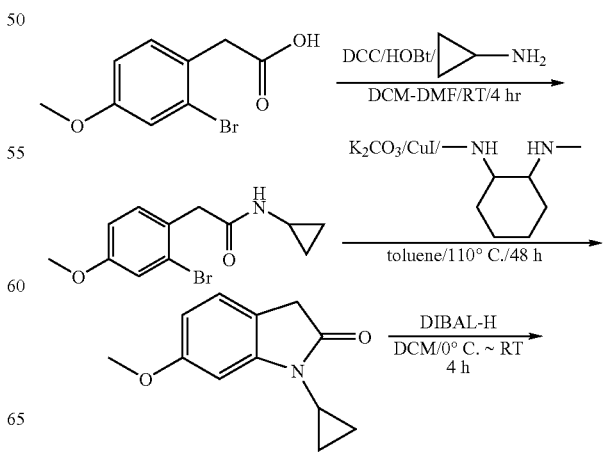

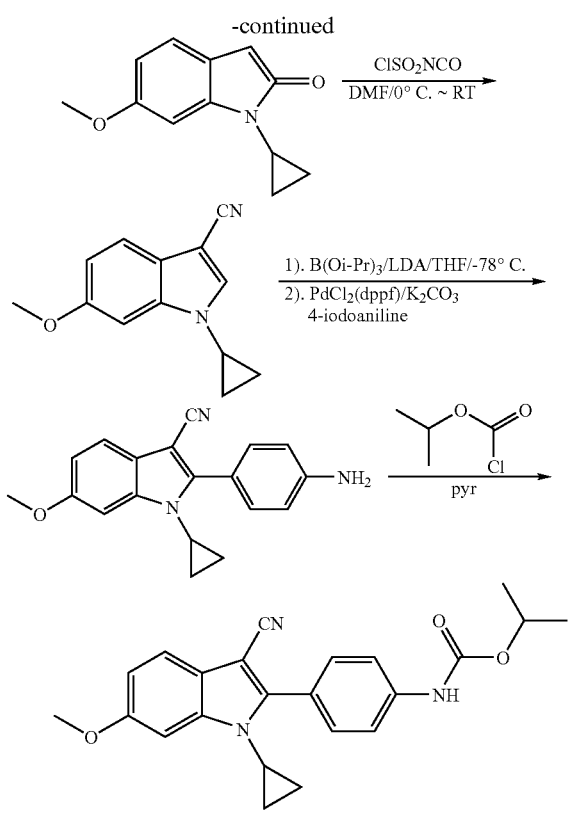

Step A: To a suspension of 2-bromo-4-methoxyphenylacetic acid (24.5 g, 100 mmol) in DCM (100 mL), while stirring, is added DMF (~10 mL) until all the solid disappeared, which is followed by the addition of DCC (22.66 g, 110 mmol) and HOBt (14.85 g, 110 mmol). After stirring at RT for 10 min, cyclopropylamine (8.55 g, 10.4 mL, 150 mmol) is added to the mixture, and the resulting mixture is stirred at room temperature for 4 h. The solid is filtered and washed thoroughly with DCM (300 mL). The filtrate is cooled to −10° C. and gently stirred for 1 h and filtered again to remove additional urea by-product. The filtrate is passed through a silica gel pad and eluted with DCM/EtOAc, 8/2). After the removal of the solvent, the cyclopropyl amide intermediate is obtained as white solid (28.34 g, 100%).

Step B: A mixture of above amide (14.2 g, 50.0 mmol), $K_2CO_3$ (13.8 g, 100 mmol), CuI (0.74 g, 5.0 mmol) and N,N'-dimethylcyclohexanediamine (1.42 g, 1.57 mL, 10.0 mmol) in toluene (150 mL) is stirred at 110° C. under $N_2$ atmosphere for 48 h. After cooling to room temperature, the mixture is filtered over Celite and washed thoroughly with DCM. The filtrate is evaporated under reduced pressure to dryness and the residue is chromatographed (DCM/EtOAc, 9.5/0.5) to provide the product, 1-cyclopropyl-6-methoxyoxindole as pale yellow solid (4.30 g, 42%).

Step C: To a solution of the oxindole obtained above (5.0 g, 24.6 mmol) in dry DCM (25 mL), at 0° C., is added DIBAL-H (1.0 M in DCM, 35.0 mL, 35.0 mmol). After the addition, the mixture is stirred at room temperature for 4 h and re-cooled to 0° C., followed by the addition of HCl (2 N) dropwise. The DCM layer is washed with HCl (2 N, 10 mL) water and brine and dried over anhydrous $Na_2SO_4$. The crude product obtained after the removal of the solvent is chromatographed (hexanes/EtOAc, 9.5/0.5) to provide the 1-cyclopropyl-6-methoxyindole as a colorless oil (4.52 g, 98%).

Step D: To a solution of 1-cyclopropyl-6-methoxyindole (3.29 g, 17.6 mmol) in dry DMF (30 mL), at 0° C., is added chlorosulfonyl isocyanate (3.11 g, 1.91 mL, 22.0 mmol). After the addition, the mixture is stirred at room temperature for 2 h, followed by aqueous work-up. Chromatography (silica gel, hexanes/EtOAc, 9/1) furnishes 3-cyano-1-cyclopropyl-6-methoxyindole (3.05 g, 82%).

Step E: To a solution of the intermediate (2.65 g, 12.5 mmol) obtained above and triisopropyl borate (3.38 g, 4.14 mL, 18.8 mmol) in dry THF (18 mL) at −78° C. is added LDA (10 mL, 1.5 M, 15.0 mmol). The mixture is stirred at −78° C. for 15 min after the addition, then slowly brought to room temperature and stirred for 30 min. It is then cooled at −78° C. and followed by the addition of 4-iodoaniline (3.29 g, 15.0 mmol), $PdCl_2(dppf)$ (0.46 g, 0.6 mmol), DMF (40 mL) and $K_2CO_3$ (18.8 mL, 2.0 M, 37.6 mmol). The mixture is brought to room temperature slowly and stirred overnight and then poured into ice-water (400 mL). The precipitate is collected and washed with water, and after drying, is chromatographed (silica gel, EtOAc/DCM, 0.5/9.5) to furnish 2-(4-aminophenyl)-1-cyclopropyl-6-methoxyindole-3-carbonitrile (2.84 g, 75%).

Step F: To a solution of the compound obtained in step E (61 mg, 0.2 mmol) in dry pyridine (2.0 mL) is added isopropylchloroformate (0.3 mL, 1.0 M, 0.3 mmol) in toluene. The mixture is stirred at room temperature overnight and diluted with water (10 mL). The organic layer is extracted with DCM (10 mL) and washed with HCl (2N, 2×3 mL), water (2×4 mL) and brine (3 mL) and chromatographed (silica gel, EtOAc/DCM, 0.5/9.5) to provide the product, [4-(3-cyano-1-cyclopropyl-6-methoxyindol-2-yl)phenyl]carbamic acid isopropyl ester (66 mg, 85%).

Compounds 1235 and 1236 are prepared by utilizing the above chemistry.

Example 1CH

Preparation of 1-allyl-6-methoxy-2-[4-(2-oxopyrrolidin-1-yl)-phenyl]-1H-indole-3-carbonitrile (compound 938)

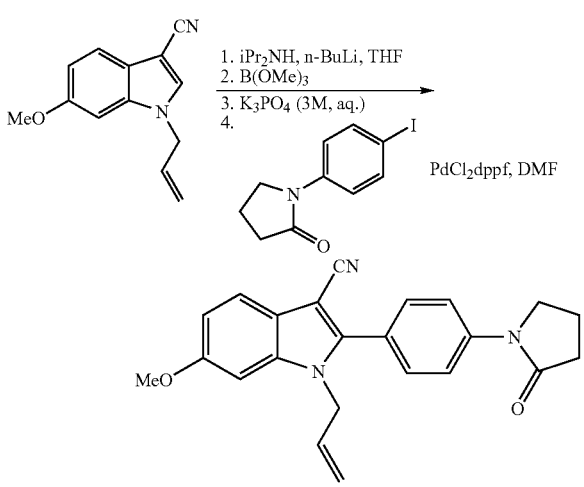

Utilizing the procedure described in Example 1Gb, substituting 1-allyl-6-methoxy-1H-indole-3-carbonitrile (92.3 mg, 0.43 mmol) and 1-(4-iodophenyl)-pyrrolidin-2-one gives 99.0 mg (61.3% yield) of compounds 938.

Example 1CI

Preparation of 6-cyclopropoxy-2-[4-(1,1-dioxo-1λ$^6$-isothiazolidin-2-yl)-phenyl]-1-ethyl-1H-indole-3-carbonitrile (compound 1046)

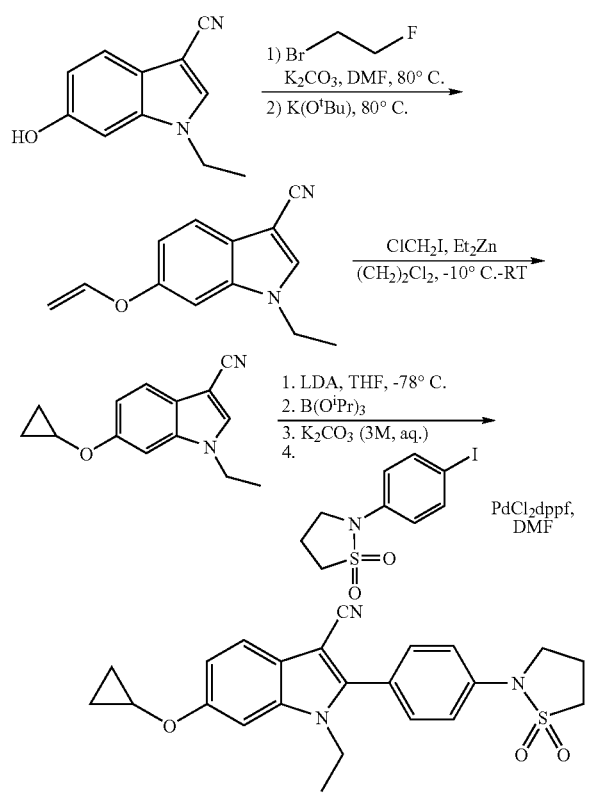

Step A: To a solution of 6-hydroxy-1-ethyl-1H-indole-3-carbonitrile (503.9 mg, 2.70 mmol) in 5 mL of DMF is added anhydrous K$_2$CO$_3$ (1.12 g, 8.12 mmol) and 1-bromo 2-fluoroethane (413.7 mg, 3.29 mmol). The resulting mixture is stirred at 80° C. until complete consumption of the starting material as determined by TLC. The reaction mixture is cooled, potassium tert-butoxide (1M solution in THF, 5.5 ml, 5.43 mmol) is added, and stirring is continued at 80° C. overnight. The mixture is partitioned between EtOAc (30 mL) and 1N HCl (20 mL). The organic phase is washed with saturated NaHCO$_3$, saturated NaCl and dried and concentrated. The product is isolated by chromatography (EtOAc/hexanes, 10-25%) over silica gel to afford 430.2 mg (74.9%) 1-ethyl-6-vinyloxy-1H-indole-3-carbonitrile as a white solid.

Step B: Via a syringe, diethyl zinc is added to a mixture of 1-ethyl-6-vinyloxy-1H-indole-3-carbonitrile (288.1 mg, 1.36 mmol), chloroiodomethane (268.9 mg, 1.53 mmol) and 5 ml of 1,2-dichloroethane over a period of 10 min, maintaining the temperature at −10° C. The mixture is warmed to 20-25° C. for 20 min, and then cooled back to 0° C. Saturated NH$_4$Cl (15 mL), concentrated ammonium hydroxide (15 mL), and ethyl acetate (15 mL) are added in sequence at this temperature, and stirred for 10 min. After the phases are separated, the aqueous phase is back-extracted with ethyl acetate (10 mL). The combined organic phases are washed with saturated NH$_4$Cl (10 mL), dried over MgSO$_4$ and then the solution is concentrated and the product is purified by chromatography, eluting with 15-30% ethyl acetate/hexanes to afford 140.5 mg (45.7% yield) of 6-cyclopropoxy-1-ethyl-1H-indole-3-carbonitrile as a yellow solid.

Step C: Utilizing the same procedure described in Example 1Gb substituting 4-iodoaniline with 2-(4-iodo-phenyl)-isothiazolidine 1,1-dioxide gives the title compound.

In similar fashion, following steps A to C, above, compound 1047 is also prepared.

Example CJ

Propane-1-sulfonic acid [4-(3-cyano-6-difluoromethoxy-1-ethyl-1H-indole-2-yl)-phenyl]-amide (compound 928)

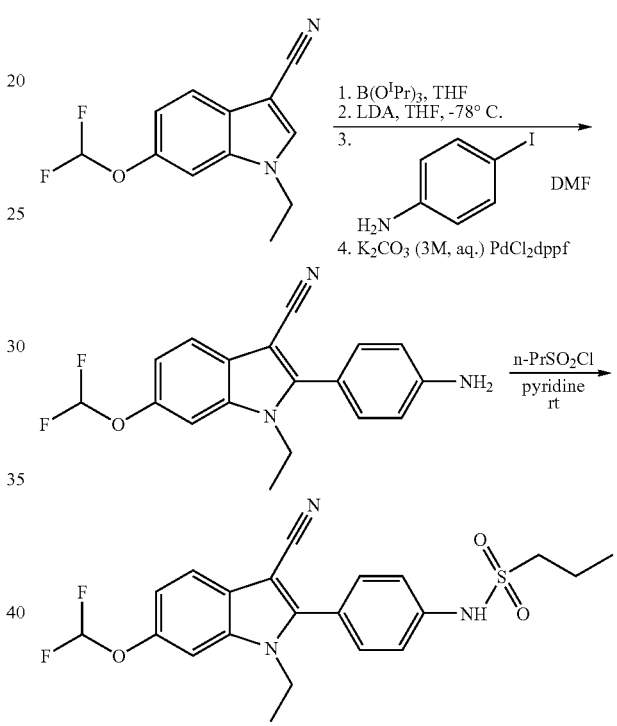

Step A: A solution of 6-difluoromethoxy-1-ethyl-1H-indole-3-carbonitrile (316.3 mg, 1.34 mmol) and triisopropyl borate (402.9 mg, 2.14 mmol) in THF (15 mL) is cooled to −78° C. and treated with LDA (1.5 M mono-THF in cyclohexane, 1.07 mL, 1.61 mmol). After the addition, the acetone/dry ice bath is exchanged for an ice water bath and the solution is stirred further for 30 min. The solution is cooled to −78° C. and a solution of 4-iodoaniline (299.5 mg, 1.37 mmol) in DMF (8 mL), K$_2$CO$_3$ (2M, 2.01 mL, 6.02 mmol) and PdCl$_2$dppf (51.3 mg, 0.07 mmol) are added in sequence. The mixture is degassed by three successive cycles of vacuum pumping/N$_2$ purging and is stirred overnight (ca. 16 h). The reaction mixture is poured into 4 volumes of water, and 4 volumes of ethyl acetate are added. The phases are separated, and the aqueous phase is extracted with more ethyl acetate. The organic phases are washed by water, saturated NaCl and then dried over anhydrous MgSO$_4$, filtered and evaporated. The remaining material is purified by column chromatography, eluting with 5-15% ethyl acetate/hexanes on silica gel to yield 304.5 mg (70%) of the aniline intermediate as a white solid.

Step B: Utilizing the same procedure described in Example 1Y and substituting n-propylsulfonyl chloride gives the title compound.

The following compounds are made using essentially the same procedure and substituting other sulfonyl chlorides: Compounds 929, 930, 931.

Example 1CK

[4-(3-cyano-6-difluoromethoxy-1-ethyl-1H-indol-2-yl)-phenyl]-carbamic acid methyl ester (compound 1130)

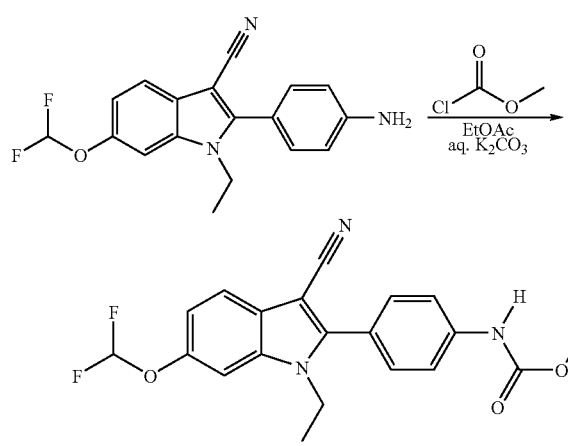

A solution of 2-(4-aminophenyl)-6-difluoromethoxy-1-ethyl-1H-indole-3-carbonitrile (200 mg, 0.611 mmol) and methyl chloroformate (95 µL, 1.23 mmol) in ethyl acetate (2 mL) is treated with 2 M aqueous potassium carbonate solution (0.370 mL, 0.74 mmol), and the resulting mixture is stirred vigorously overnight. Saturated brine solution (1 mL) is added, and the mixture is stirred for 10 minutes. The organic layer is removed, dried over anhydrous magnesium sulfate, filtered and evaporated. The resulting solid is triturated with 1/1 ether-hexane, collected by filtration and dried under vacuum to afford the title product as a white solid.

Similarly prepared from appropriate reagents are: Compounds 1131, 1132, 1133, 1134, 1135.

Example 1CL

1-[4-(3-cyano-6-difluoromethoxy-1-ethyl-1H-indol-2-yl)-phenyl]-3-propyl-urea (Compound 893)

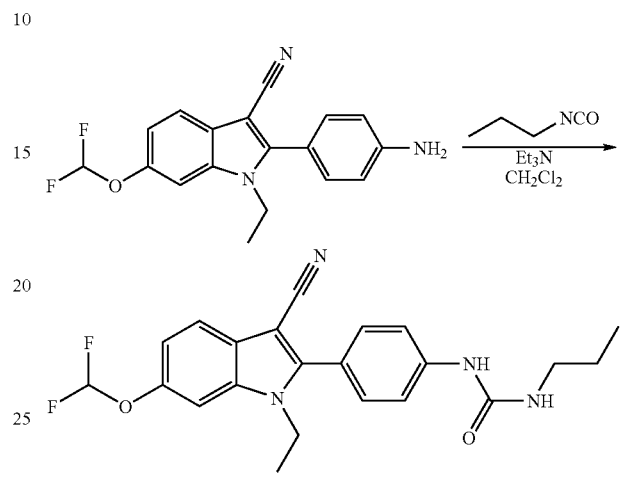

A solution of 2-(4-aminophenyl)-6-difluoromethoxy-1-ethyl-1H-indole-3-carbonitrile (200 mg, 0.611 mmol) in 1,2-dichloroethane (2 mL) is treated with n-propylisocyanate (115 mL, 1.23 mmol) and triethylamine (170 mL, 1.22 mmol). The resulting solution is stirred at ambient temperature for 12 hours, and then concentrated. The residual material is separated by silica gel chromatography (1/2 ethyl acetate-hexane) to afford the title product as a solid.

Similarly prepared from appropriate reagents are: Compounds 892, 894.

Example 1CM

Preparation of morpholine-4-carboxylic acid [4-(3-cyano-1-cyclobutyl-6-ethoxy-1H-indol-2-yl)-phenyl]-amide (compound 1166)

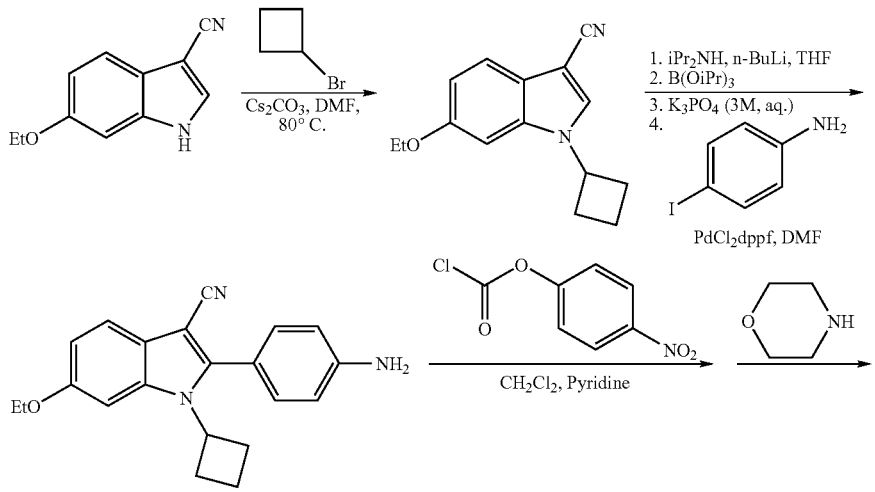

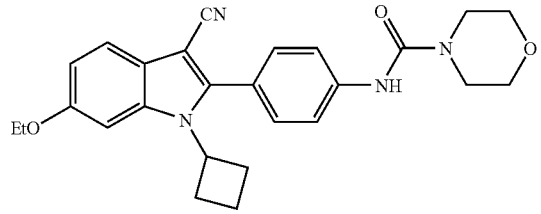

Step A: 6-Ethoxy-1H-indole-3-carbonitrile (2.8 g, 15 mmol), prepared as shown in example 1A, step A, is combined with Cs$_2$CO$_3$ (11.6 g, 35.6 mmol), DMF (21 mL), and cyclobutyl bromide (1.73 mL, 17.9 mmol) in a capped tube. The reaction mixture is heated at 80° C. for 8 h. This is then quenched with H$_2$O (200 mL) and is extracted with EtOAc. The EtOAc layer is backwashed with H$_2$O, and then with brine. The organic phase is dried and concentrated. Purification by silica gel chromatography (hexanes/CH$_2$Cl$_2$, 50-100%) yields 1-cyclobutyl-6-ethoxy-1H-indole-3-carbonitrile (3.00 g, 83%) as a white solid.

Step B: Following essentially the procedure in example 1Gb, 1-cyclobutyl-6-ethoxy-1H-indole-3-carbonitrile (3.0 g, 12.4 mmol) is converted via Suzuki coupling to yield 2-(4-aminophenyl)-1-cyclobutyl-6-ethoxy-1H-indole-3-carbonitrile (2.60 g, 68%) as an off-white solid.

Step C: 2-(4-aminophenyl)-1-cyclobutyl-6-ethoxy-1H-indole-3-carbonitrile (40 mg, 0.12 mmol), 4-nitrophenyl chloroformate (60 mg, 0.30 mmol), CH$_2$Cl$_2$ (400 μL), and pyridine (25 μL, 0.31 mmol) are stirred at room temperature for 1 hour. Morpholine (60 μL, 0.70 mmol) is added. After stirring at room temperature for an additional 30 minutes, the reaction mixture is diluted in CH$_2$Cl$_2$ and is washed with dilute aqueous NaOH to remove the yellow nitrophenol byproduct. The organic layer is dried and concentrated. Purification by silica gel chromatography (CH$_2$Cl$_2$/EtOAc, 7/3) yields morpholine-4-carboxylic acid [4-(3-cyano-1-cyclobutyl-6-ethoxy-1H-indol-2-yl)-phenyl]-amide (53 mg, 100%) as a white solid.

The following compounds are prepared in a similar fashion, using the appropriate amine in the final step: Compounds 1087, 1088, 1089, 1119, 1159, 1168, 1191, 1266, 1288, 1324, 1325, 1326.

Example 1CN

Preparation of rac-[4-(3-cyano-1-cyclobutyl-6-ethoxy-1H-indol-2-yl)-phenyl]-carbamic acid 1-cyclopropyl-ethyl ester (compound 1147)

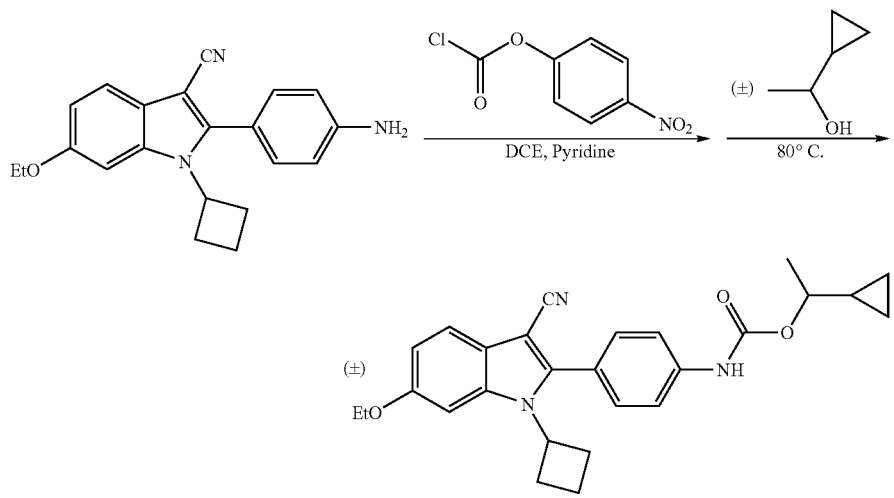

2-(4-Aminophenyl)-1-cyclobutyl-6-ethoxy-1H-indole-3-carbonitrile (50 mg, 0.15 mmol), prepared as in example 1CM, step B, is combined with 4-nitrophenyl chloroformate (76 mg, 0.38 mmol), DCE (0.5 mL), and pyridine (30 μL, 0.37 mmol). This suspension is stirred at room temperature for 1 h. Rac-cyclopropyl methyl carbinol (100 μL, 0.98 mmol) is added. This mixture is heated at 75° C. overnight. The reaction mixture is then diluted in CH$_2$Cl$_2$ and is washed with dilute aqueous NaOH to remove the yellow nitrophenol byproduct. The organic layer is dried and concentrated. Purification by silica gel chromatography (CH$_2$Cl$_2$) yields rac-[4-(3-cyano-1-cyclobutyl-6-ethoxy-1H-indol-2-yl)-phenyl]-carbamic acid 1-cyclopropyl-ethyl ester (40 mg, 60%) as a white solid.

The following compounds are prepared in a similar fashion, using the appropriate alcohols: Compounds 1146, 1158, 1167, 1192, 1208, 1209, 1210, 1215, 1216, 1240, 1241, 1242, 1243, 1244, 1246, 1247, 1248, 1249, 1250, 1264, 1265, 1267, 1268, 1281, 1282, 1283, 1286, 1287, 1289, 1290, 1291, 1292, 1294, 1295, 1296, 1297, 1298, 1299, 1312, 1313.

Example 1CO

Preparation of 1-cyclobutyl-6-ethoxy-2-(4-ethylaminophenyl)-1H-indole-3-carbonitrile (compound 1239)

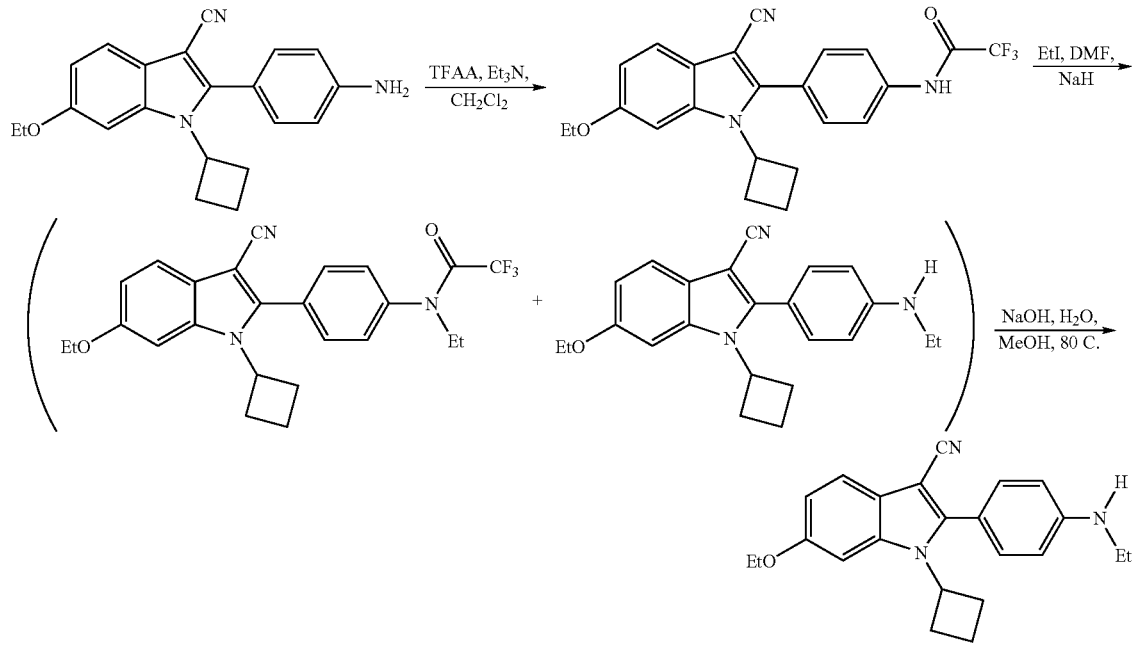

Step A: 2-(4-Aminophenyl)-1-cyclobutyl-6-ethoxy-1H-indole-3-carbonitrile (600 mg, 1.81 mmol), prepared as in example 1CM, step B, is suspended in $CH_2Cl_2$ (18 mL), and $Et_3N$ (390 μL, 2.7 mmol). Trifluoroacetic anhydride (310 μL, 2.2 mmol) is added dropwise. The reaction mixture is stirred at room temperature for 30 minutes, after which time dissolution is complete. The reaction mixture is then washed with saturated $NaHCO_3$ solution. The organic layer is dried and concentrated to yield N-[4-(3-cyano-1-cyclobutyl-6-ethoxy-1H-indol-2-yl)-phenyl]-2,2,2-trifluoro-acetamide (802 mg, 100%) as a yellow solid.

Step B: N-[4-(3-Cyano-1-cyclobutyl-6-ethoxy-1H-indol-2-yl)-phenyl]-2,2,2-trifluoro-acetamide (800 mg, 1.8 mmol) is dissolved in DMF (10 mL). NaH (140 mg, 60% oil suspension, 3.5 mmol) is added. This is stirred at room temperature for a few minutes, after which ethyl iodide (176 μL, 2.2 mmol) is added. This is stirred at room temperature overnight, and then at 75° C. for 6 h. Additional portions of NaH (200 mg, 5.0 mmol) and iodoethane (200 μL, 2.5 mmol) are necessary to push the reaction further. This is heated overnight at 75° C. Additional ethyl iodide (200 μL, 2.5 mmol) is added. This is heated for another 2 h. The reaction mixture is then diluted in $H_2O$ and is extracted into EtOAc. The EtOAc layer is dried and concentrated. Silica gel chromatography ($CH_2Cl_2$) yields 384 mg of an inseparable mixture of expected N-[4-(3-cyano-1-cyclobutyl-6-ethoxy-1H-indol-2-yl)-phenyl]-N-ethyl-2,2,2-trifluoro-acetamide and hydrolyzed 1-cyclobutyl-6-ethoxy-2-(4-ethylamino-phenyl)-1H-indole-3-carbonitrile.

Step C: The crude mixture from the previous step is dissolved in methanol (5 mL). 6N NaOH (1.0 mL, 6 mmol) is added, and the mixture is heated at 80° C. for 1 h. The reaction mixture is then diluted in $H_2O$ and is extracted into $CH_2Cl_2$. The organic layer is dried and concentrated. Purification by silica gel chromatography ($CH_2Cl_2$) yields pure 1-cyclobutyl-6-ethoxy-2-(4-ethylaminophenyl)-1H-indole-3-carbonitrile (343 mg, 53% over two steps) as a white solid.

1-Cyclobutyl-2-(4-diethylamino-phenyl)-6-ethoxy-1H-indole-3-carbonitrile (compound 1217, 77 mg, 11%) is isolated as a byproduct of the reaction described in example 1CO, step B.

Example 1CP

Preparation of [4-(3-cyano-1-cyclobutyl-6-ethoxy-1H-indol-2-yl)-phenyl]-ethyl-carbamic acid cyclopentyl ester (compound 1251)

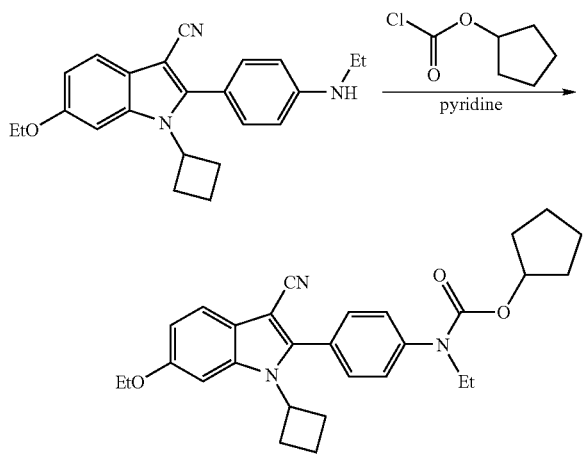

1-Cyclobutyl-6-ethoxy-2-(4-ethylaminophenyl)-1H-indole-3-carbonitrile (35 mg, 0.10 mmol), prepared as in example 1CO, step C, is dissolved in pyridine (300 μL). Cyclopentyl chloroformate (25 μL, 0.17 mmol) is added. The reaction mixture is stirred at room temperature for 2.5 h. More chloroformate (10 μL, 0.07 mmol) is added to drive the reaction to completion. After an additional 90 min of stirring, the reaction mixture is partitioned between aqueous HCl and EtOAc. The organic layer is dried and concentrated. Purification by silica gel chromatography yields [4-(3-cyano-1-cyclobutyl-6-ethoxy-1H-indol-2-yl)-phenyl]-ethyl-carbamic acid cyclopentyl ester (41 mg, 87%) as a white solid.

Compound 1252 is prepared similarly using the appropriate chloroformate.

Example 1CQ

Preparation of {4-[3-cyano-1-cyclobutyl-6-(3-[1,2,4]triazol-1-yl-propoxy)-1H-indol-2-yl]-phenyl}-carbamic acid isopropyl ester (compound 1255)

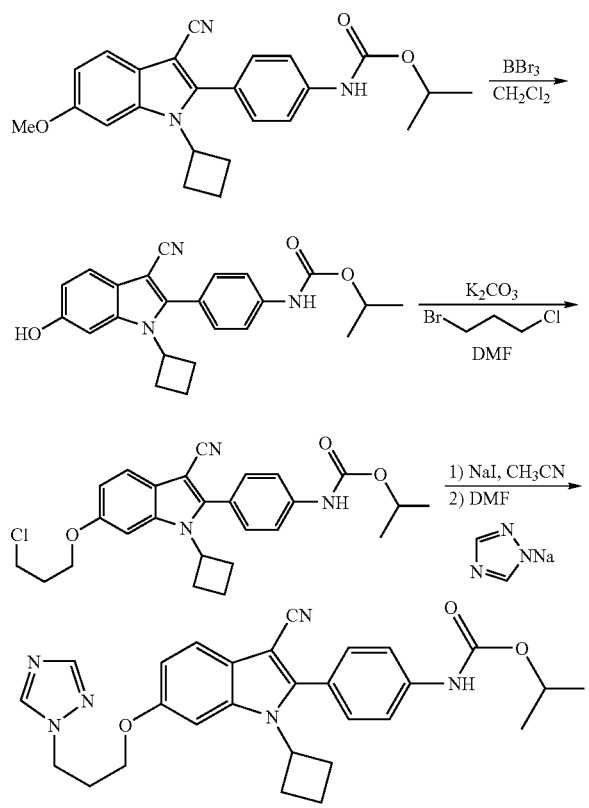

Step A: To a solution [4-(3-cyano-1-cyclobutyl-6-methoxy-1H-indol-2-yl)-phenyl]-carbamic acid isopropyl ester (950 mg, 2.35 mmol) in DCM (10 mL) is added BBr$_3$ (556 uL, 5.9 mmol) over a period of 20 min. The reaction mixture is stirred further for 1 h at room temperature and then water (1 mL) is added. The solvents are removed under reduced pressure. The residue is dissolved in MeOH and then poured into cold water. The precipitate is collected by filtration and washed with hexane and dried in vacuo to afford [4-(3-cyano-1-cyclobutyl-6-hydroxy-1H-indol-2-yl)-phenyl]-carbamic acid isopropyl ester (650 mg, 71%).

Step B: To a solution of [4-(3-cyano-1-cyclobutyl-6-hydroxy-1H-indol-2-yl)-phenyl]-carbamic acid isopropyl ester (340 mg, 0.87 mmol) in DMF (2 mL) is added K$_2$CO$_3$ (132 mg, 0.96 mmol) and 3-bromo-1-chloroproane (172 uL, 1.75 mmol) and the reaction is stirred for 5 h at 60° C. The reaction mixture is then poured into cold water and the precipitate is collected by filtration and washed with hexane and dried in vacuo to afford 370 mg (92%) of the desired product.

Step C: To a solution of {4-[6-(3-chloro-propoxy)-3-cyano-1-cyclobutyl-1H-indol-2-yl]-phenyl}-carbamic acid isopropyl ester (37 mg, 0.08 mmol) in CH$_3$CN (1 mL) is added sodium iodide (71 mg, 0.48 mmol). The resulting mixture is stirred at reflux temperature overnight. The solvent is then evaporated and the residue is diluted with anhydrous DMF (1 mL) and then treated with the sodium salt of 1,2,4-triazole (0.16 mmol) at room temperature overnight. The solvent is removed under reduced pressure and the residue is diluted with ethyl acetate and then washed with water. The organic layer is concentrated and triturated with hexane and the precipitate is collected by filtration and washed well with 50% ethyl acetate in hexane and dried in vacuo to afford {4-[3-cyano-1-cyclobutyl-6-(3-[1,2,4]triazol-1-yl-propoxy)-1H-indol-2-yl]-phenyl}-carbamic acid isopropyl ester, compound 1255 (31 mg, 78%).

The following compounds are made in similar fashion following steps A-C, above: Compounds 1253, 1254, 1260, 1261, 1262, 1427, 1430.

Example 1CR

Preparation of {4-[3-cyano-1-cyclobutyl-6-(2-[1,2,4]triazol-1-yl-ethoxy)-1H-indol-2-yl]-phenyl}-carbamic acid isopropyl ester (compound 1276)

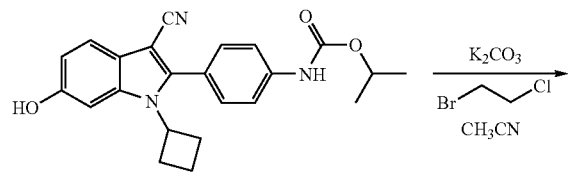

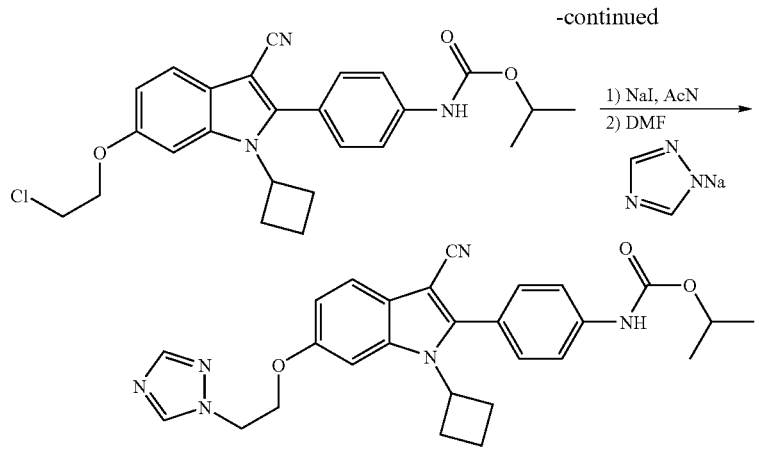

Step A: To a solution of [4-(3-cyano-1-cyclobutyl-6-hydroxy-1H-indol-2-yl)-phenyl]-carbamic acid isopropyl ester (390 mg, 1.0 mmol) in $CH_3CN$ (5 mL) is added $K_2CO_3$ (414 mg, 3.0 mmol) and 3-bromo-1-chloroethane (250 uL, 3.0 mmol) and the reaction is stirred for 18 h at 80° C. The reaction mixture is then poured into cold water and the precipitate is collected by filtration and washed with hexane and dried in vacuo to afford 420 mg, 93% of the desired product.

Step B: To a solution of {4-[6-(3-chloroethoxy)-3-cyano-1-cyclobutyl-1H-indol-2-yl]-phenyl}-carbamic acid isopropyl ester (42 mg, 0.09 mmol) in $CH_3CN$ (1 mL) is added sodium iodide (56 mg, 0.37 mmol). The resulting mixture is stirred at reflux temperature overnight. The solvent is evaporated and the residue is diluted with anhydrous DMF (1 mL) and then treated with the sodium salt of 1,2,4-triazole (0.18 mmol) at room temperature for overnight. The solvent is removed under reduced pressure and the residue is diluted with ethyl acetate and then washed with water. The organic layer is concentrated and triturated with hexane. The precipitate is collected by filtration and washed well with 50% ethyl acetate in hexane and dried in vacuo to afford {4-[3-cyano-1-cyclobutyl-6-(3-[1,2,4]triazol-1-yl-ethoxy)-1H-indol-2-yl]-phenyl}-carbamic acid isopropyl ester, compound 1276 (28 mg, 64%).

The following compounds are made in similar fashion following steps A and B, above: Compounds 1269, 1270, 1271, 1272, 1273, 1274, 1275, 1276, 1277, 1278, 1434, 1435.

Example 1CS

Preparation of {4-[3-cyano-1-cyclobutyl-6-(2-[1,2,4]triazol-1-yl-ethoxy)-1H-indol-2-yl]-phenyl}-carbamic acid 1-cyclopropyl-ethyl ester (compound 1329)

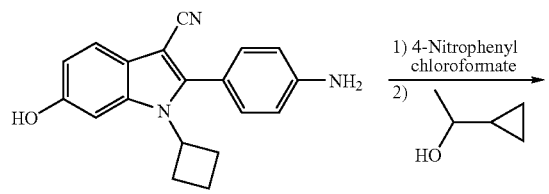

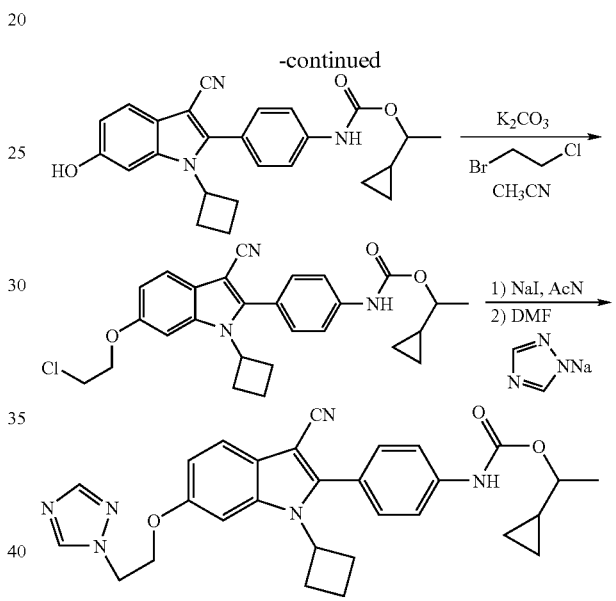

Step A: To a solution 2-(4-aminophenyl)-1-cyclobutyl-6-hydroxy-1H-indole-3-carbonitrile (909 mg, 3 mmol) in pyridine (5 mL) is added 4-nitrophenyl chloroformate (6 mmol) at room temperature and then stirred for 2 h at room temperature. To the reaction is added cyclopropyl methyl carbinol and then stirred for 8 h at 80° C. The reaction mixture is diluted with 1N HCl and then extracted with ethyl acetate. The organic layer is concentrated and the residue is dissolved in EtOAc and triturated with hexane. The precipitate is collected by filtration and washed with hexane and dried in vacuo to afford [4-(3-cyano-1-cyclobutyl-6-hydroxy-1H-indol-2-yl)-phenyl]-carbamic acid 1-cyclopropyl-ethyl ester (996 mg, 80%).

Step B: To a solution of [4-(3-cyano-1-cyclobutyl-6-hydroxy-1H-indol-2-yl)-phenyl]-carbamic acid 1-cyclopropyl-ethyl ester (1.5 g, 3.61 mmol) in $CH_3CN$ (8 mL) is added $K_2CO_3$ (1.5 g, 10.8 mmol) and 2-bromo-1-chloroethane (895 uL, 10.8 mmol) and the reaction is stirred for 18 h at 80° C. The reaction mixture is then poured into cold water and the precipitate is collected by filtration and washed with hexane and dried in vacuo to afford 1.46 g, 84% of the desired product.

Step C: To a solution of {4-[6-(2-chloroethoxy)-3-cyano-1-cyclobutyl-1H-indol-2-yl]-phenyl}-carbamic acid 1-cyclopropyl-ethyl ester (1.46 g, 3.05 mmol) in $CH_3CN$ (10 mL) is added sodium iodide (1.84 g, 12.22 mmol). The resulting mixture is stirred at reflux temperature overnight. The solvent is evaporated and the residue is diluted with anhydrous DMF (20 mL) and then used without further purification. To 1 mL of the DMF solution containing the iodoethyl intermediate (0.153 mmol) is added the sodium salt of 1,2,4-triazole (0.31 mmol) and the reaction is stirred at room temperature overnight. The reaction mixture is diluted with 0.5 mL DMF and the desired product is purified by preparative LC to give {4-[3-cyano-1-cyclobutyl-6-(2-[1,2,4]triazol-1-yl-ethoxy)-1H-indol-2-yl]-phenyl}-carbamic acid 1-cyclopropyl-ethyl ester, compound 1329 (23 mg, 29%).

The following compounds are made in similar fashion following steps A-C, above: Compounds 1327, 1328.

Example 1CT

Preparation of 1-{4-[3-cyano-1-cyclobutyl-6-(3-[1,2,4]triazol-1-yl-propoxy)-1H-indol-2-yl]-phenyl}-3-isopropyl-urea (compound 1314)

Step A: To a solution of 1-[4-(3-cyano-1-cyclobutyl-6-methoxy-1H-indol-2-yl)-phenyl]-3-isopropyl-urea (2.21 g, 5.49 mmol in $CH_2Cl_2$ (30 mL) is added a 1M solution of $BBr_3$ in $CH_2Cl_2$ (16.5 mL, 16.5 mmol) at 0° C. The mixture is allowed to warm to room temperature and kept for 1 h. The reaction mixture is then poured on to ice and aqueous 1M $NaHCO_3$ is added until the pH is 7-8. The product is extracted with 100 mL of ethyl acetate (3×) and the organic phases are washed with 100 mL of saturated NaCl. The organic phases are combined and dried over $MgSO_4$. Solvent is removed to recover 1.95 g (92-) of 1-[4-(3-cyano-1-cyclobutyl-6-hydroxy-1H-indol-2-yl)-phenyl]-3-isopropyl-urea, as a tan solid.

Step B: To a solution of 1-[4-(3-cyano-1-cyclobutyl-6-hydroxy-1H-indol-2-yl)-phenyl]-3-isopropyl-urea (750 mg, 1.93 mmol) in 10 mL of acetonitrile is added anhydrous $K_2CO_3$ (800 mg, 5.79 mmol) and 1-bromo-3-chloropropane (382 μL, 3.86 mmol). After stirring overnight at 80° C., the

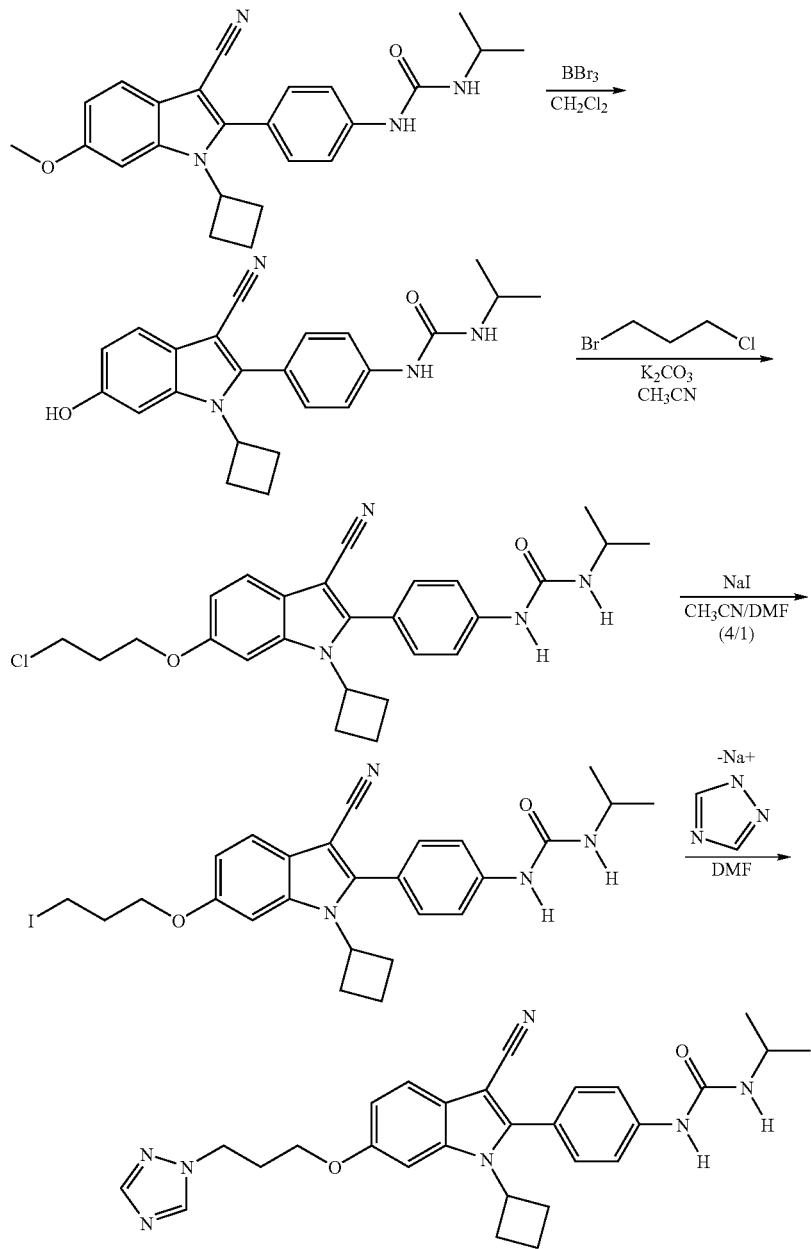

reaction mixture is cooled and solvent is removed. The reaction is re-suspended in 100 mL of ethyl acetate. The organic phase is washed with 200 mL of H₂O, and the aqueous phase is re-extracted 2× with 100 mL of ethyl acetate. The organic phases are combined, dried over MgSO₄ and the solvent is removed to afford 769 mg (86%) of 1-{4-[6-(3-chloropropoxy)-3-cyano-1-cyclobutyl-1H-indol-2-yl]-phenyl}-3-isopropyl-urea as a tan powder.

Step C: To a solution of 1-{4-[6-(3-chloropropoxy)-3-cyano-1-cyclobutyl-1H-indol-2-yl]-phenyl}-3-isopropyl-urea (400 mg, 0.860 mmol) in 8 mL of acetonitrile/DMF, (4/1) is added anhydrous NaI (258 mg, 1.72 mmol). After stirring overnight at 60° C., the reaction shows conversion to product by LCMS-UV. The reaction mixture is cooled, the solvent is removed and redissolved in DMF to 14.0 mL total volume.

Step D: To 1 mL of the DMF solution above, 1-{4-[3-cyano-1-cyclobutyl-6-(3-iodopropoxy)-1H-indol-2-yl]-phenyl}-3-isopropyl-urea (34 mg, 0.062 mmol) is added anhydrous 1,2,4-triazole, sodium salt (10.0 mg, 0.110 mmol). After stirring overnight at rt, the reaction mixture is filtered and purified by preparatory LC/UV purification. The solvent is removed to obtain 12.3 mg (40%) of 1-{4-[3-cyano-1-cyclobutyl-6-(3-[1,2,4]triazol-1-yl-propoxy)-1H-indol-2-yl]-phenyl}-3-isopropyl-urea (compound 1314), as a white powder.

The following compounds are prepared following the above procedure: Compounds 1306, 1307, 1308, 1309, 1315, 1316, 1317, 1318, 1319, 1320, 1321, 1323 and 1324.

Example 1CU

Preparation of 1-ethyl-1'-methanesulfonyl-6-methoxy-1H,1'H-[2,5']biindolyl-3-carbonitrile (compound 1330)

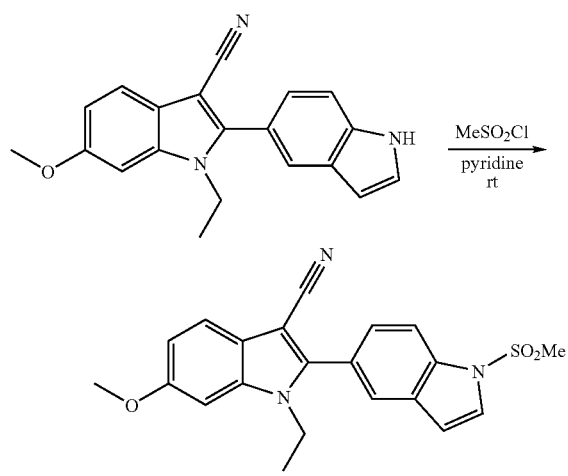

A solution of 1-ethyl-6-methoxy-1H,1'H-[2,5']biindolyl-3-carbonitrile (70 mg, 0.22 mmol), prepared as described in Example 1Gb, in pyridine (2 mL) is treated with methanesulfonyl chloride (0.034 mL, 0.44 mmol) and stirred overnight. The reaction mixture is then diluted with H₂O and extracted with ethyl acetate (3×). The organic phase is washed with H₂O and saturated NaCl, dried and concentrated and purified by flash chromatography using EtOAc/hexanes (30-80%) to afford 70 mg (81%) of 1-ethyl-1'-methanesulfonyl-6-methoxy-1H,1'H-[2,5']biindolyl-3-carbonitrile as a tan solid.

Using the same procedure as above and substituting the appropriate ethanesulfonyl chloride gives the following compound: Compound 1331.

Example 1CV

Preparation of 3-cyano-1-ethyl-2-[4-(propane-1-sulfonylamino)-phenyl]-1H-indole-6-carboxylic acid diethylamide (compound 1360)

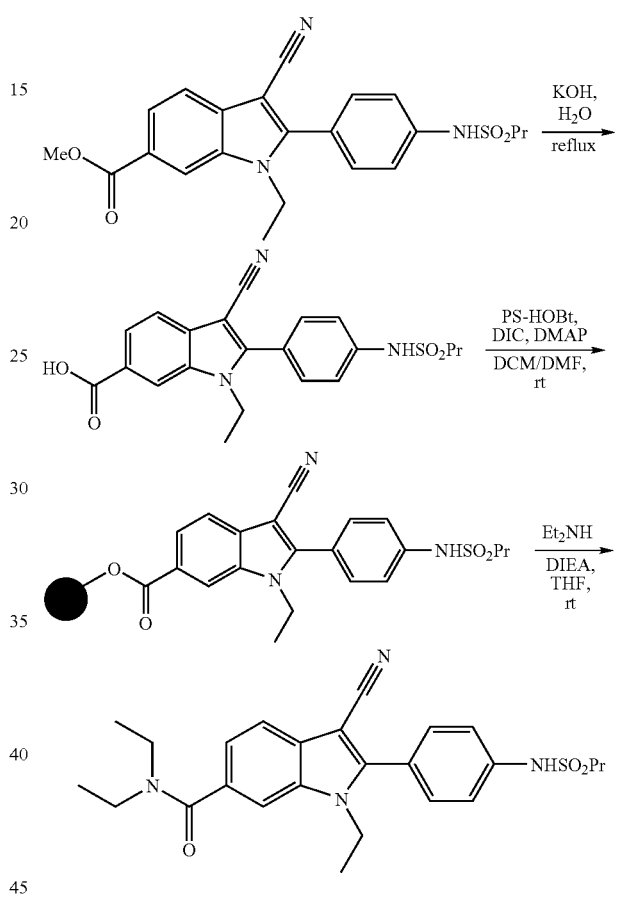

Step A: 3-Cyano-1-ethyl-2-[4-(propane-1-sulfonylamino)-phenyl]-1H-indole-6-carboxylic acid methyl ester (1.25 g, 3.04 mmol), prepared by the method described in example 1Y from methyl 2-(4-aminophenyl)-3-cyano-1-ethyl-1H-indole-6-carboxylate, is treated with 0.5N KOH (30 mL, 15.2 mmol) and heated at reflux for 2.5 h. After cooling to room temperature, the aqueous phase is acidified with 3N HCl to pH 2 and the resultant precipitate is filtered, washed with water (2×) and dried until constant weight to afford 1.15 g (96%) of 3-cyano-1-ethyl-2-[4-(propane-1-sulfonylamino)-phenyl]-1H-indole-6-carboxylic acid as a white solid.

Step B: To a sample of PS-HOBt resin (2.84 g, 1.02 mmol/g loading) is added a solution of DMAP in DCM (0.045M, 39 mL) followed by a solution of 3-cyano-1-ethyl-2-[4-(propane-1-sulfonylamino)-phenyl]-1H-indole-6-carboxylic acid in DMF (0.38M, 7.5 mL). This mixture is stirred for 15 min., then a solution of diisopropylcarbodiimide in DCM (1.65M, 7.9 mL) is added and the reaction mixture is stirred for 18 h at room temperature. The resin is filtered and washed with DMF (3×50 mL), DCM (3×50 mL) and THF (3×50 mL) and then dried under vacuum for 4 h to afford 4.1 g of active ester resin. The loading of this resin is determined by combining a small aliquot of the active ester resin with benzyl amine in $CDCl_3$ directly in NMR tube, shaking the resultant mixture at room temperature overnight, and then comparing the integration of protons of unreacted benzyl amine with the protons of resultant amide.

Step C: The above active ester resin (400 mg, 0.551 mmol/g loading), DIEA (0.036 mL, 0.22 mmol) and THF (3 mL) are combined and diethylamine (0.03 mL, 0.15 mmol) is added to the mixture. The tube is sealed and the reaction mixture is shaken overnight. The resin is filtered, washed with THF (2×5 mL), DCM (2×5 mL) and the combined organic fractions are concentrated. The crude product is purified by preparative HPLC to afford 50 mg (71% yield) of 3-cyano-1-ethyl-2-[4-(propane-1-sulfonylamino)-phenyl]-1H-indole-6-carboxylic acid diethylamide.

The following compounds are prepared utilizing the above procedure with substitution of the appropriate amine: Compounds 1361, 1362, 1363, 1364.

Example 1CW

Preparation of isopropyl-methyl-carbamic acid 4-(3-cyano-1-ethyl-6-methoxy-1H-indol-2-yl)-phenyl ester (compound 1349)

umn chromatography on silica gel using EtOAc/petroleum ether (1/5 to 2/1) as eluant to yield 73% of 1-ethyl-2-(4-hydroxyphenyl)-6-methoxy-1H-indole-3-carbonitrile.

Step B: To a solution of 1-ethyl-2-(4-hydroxyphenyl)-6-methoxy-1H-indole-3-carbonitrile (58 mg, 0.2 mmol) in 4 mL of $Et_3N$ and $CH_2Cl_2$ (1/1) is added p-nitrophenyl chloroformate (100 mg, 0.5 mmol) at room temperature. After the mixture is stirred for about 1 h, N-isopropylmethylamine (0.062 mL, 0.6 mmol) is added. The mixture is stirred for 3 h and then water and ethyl acetate are added to the reaction mixture. The organic layer is separated, washed with aqueous HCl (1N) and brine, dried over anhydrous $Na_2SO_4$, and filtered and concentrated. The crude solid is purified by preparative HPLC to afford 70% of isopropyl-methyl-carbamic acid 4-(3-cyano-1-ethyl-6-methoxy-1H-indol-2-yl)-phenyl ester.

The following compounds are prepared utilizing the above procedure with substitution of the appropriate amines: Compounds 1348, 1350, 1351, 1385.

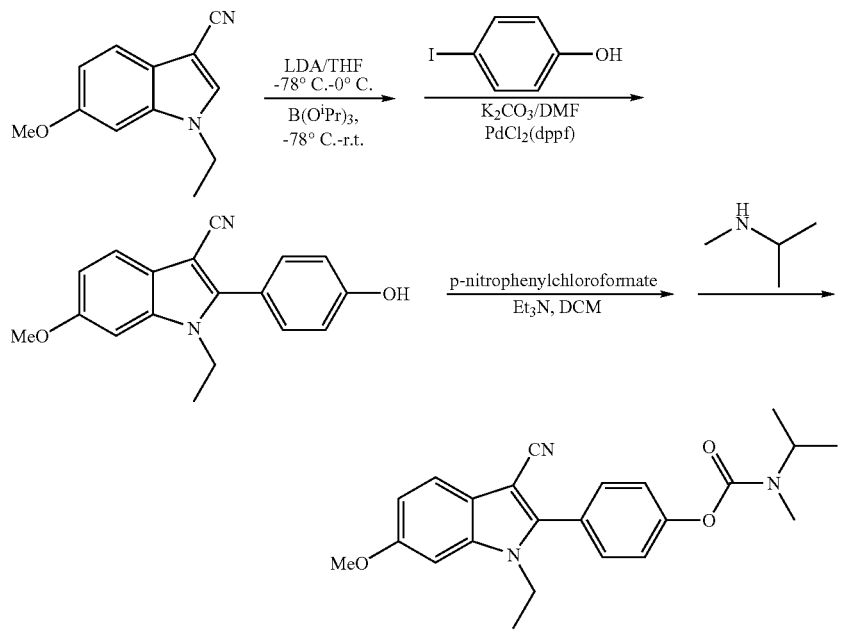

Step A: To a solution of 1-ethyl-6-methoxy-1H-indole-3-carbonitrile (2.5 g, 12.5 mmol) in 21 mL of THF is added LDA (23 mL, 22.5 mmol) at −78° C. After warming to 0° C. and stirring for 10 min, the mixture is re-cooled to −78° C. and $B(O-^iPr)_3$ (4.35 mL, 18.8 mmol) is added. After the addition, the reaction is allowed to warm to room temperature and stirred for about 1 h. 4-iodophenol (2.89 g, 13.1 mmol), $PdCl_2(dppf)$ (510 mg, 0.625 mmol), aqueous $K_2CO_3$ (25 mL, 50 mmol) and DMF (42 mL) is added and the reaction mixture is stirred at room temperature overnight. The organic solvent is evaporated under reduced pressure. The residue is washed with water and the mixture is filtered. The filtrate is concentrated to afford crude solid which is purified via col- Example 1CX Preparation of N-{4-[3-cyano-6-difluoromethoxy-1-(tetrahydro-furan-2-ylmethyl)-1H-indole-2-yl]-phenyl}-methanesulfonamide (compound 1334)

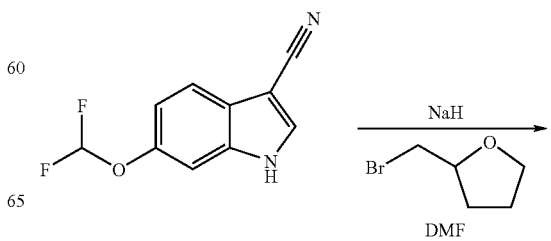

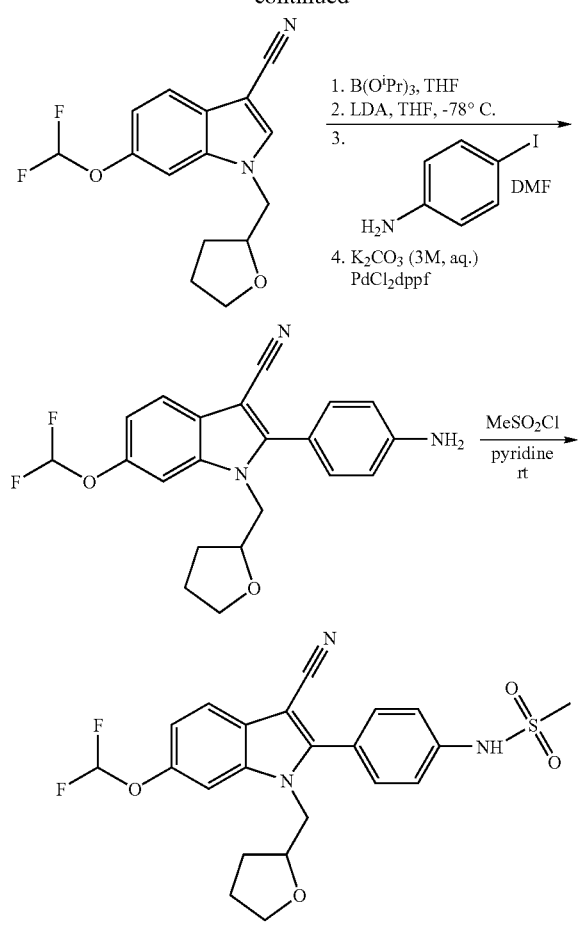

Step A: Utilizing the procedure described in Example 1A (Step B) substituting iodo ethane with 2-bromomethyl tetrahydrofuran affords 6-difluoromethoxy-1-(tetrahydrofuran-2-ylmethyl)-1H-indole-3-carbonitrile.

Step B: A solution of 6-difluoromethoxy-1-ethyl-1H-indole-3-carbonitrile (516.2 mg, 1.77 mmol) and tri-isopropyl borate (532.7 mg, 2.83 mmol) in THF (15 mL) is cooled to −78° C. and treated with LDA (1.5 M mono-THF in cyclohexane, 1.43 ml, 2.04 mmol). After the addition, the acetone/dry ice bath is exchanged for ice/water bath and the solution is stirred further for 30 min. The solution is cooled to −78° C. and a solution of 4-iodoaniline (390.2 mg, 1.78 mmol) in DMF (8 mL), $K_2CO_3$ (2M, 2.7 ml, 5.31 mmol) and $PdCl_2dppf$ (67.4 mg, 0.09 mmol) are added in sequence. The mixture is degassed by three successive cycles of vacuum pumping/$N_2$ purging and is stirred overnight (ca. 16 h), after which it is poured into 4 volumes of water, and 4 volumes of ethyl acetate are added. The phases are separated, and the aqueous phase is extracted with more ethyl acetate. The organic phases are washed by water, saturated NaCl, dried over anhydrous $MgSO_4$, filtered and evaporated. The remaining material is purified by column chromatography, eluting with 5-15% ethyl acetate/hexanes on silica gel to yield 367.5 mg (55.0% yield) of 2-(4-aminophenyl)-6-difluoromethoxy-1-(tetrahydrofuran-2-ylmethyl)-1H-indole-3-carbonitrile as a white solid.

Step C: Utilizing the same procedure described in Example 1Y gives the title compound, N-{4-[3-cyano-6-difluoromethoxy-1-(tetrahydro-furan-2-ylmethyl)-1H-indole-2-yl]-phenyl}-methanesulfonamide (compound 1334).

The following compounds are made using essentially the same procedure and substituting other sulfonyl chlorides: Compounds 1335, 1336.

Example 1CY

Preparation of 1-cyclobutyl-6-ethoxy-2-[4-(2-oxo-[1,3]oxazinan-3-yl)-phenyl]-1H-indole-3-carbonitrile (compound 1346)

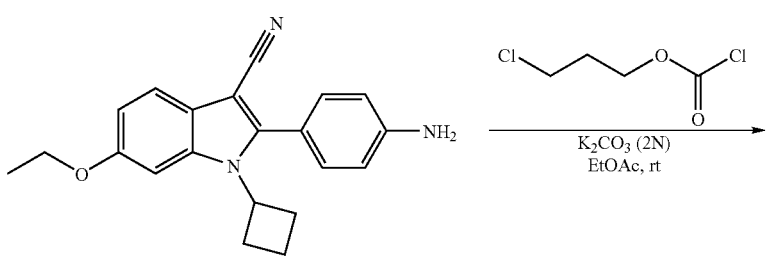

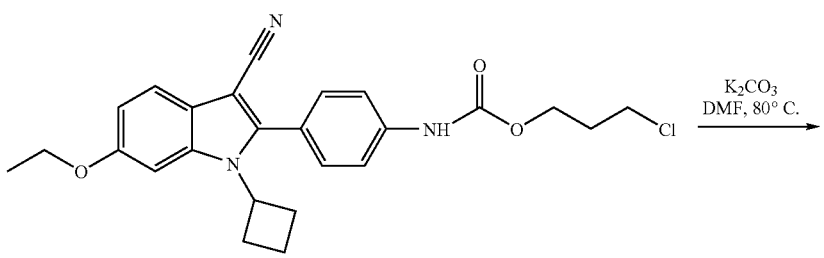

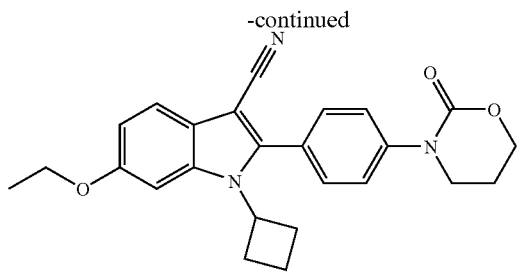

Step A: To a suspension of 2-(4-aminophenyl)-1-cyclobutyl-6-ethoxy-1H-indole-3-carbonitrile (50.0 mg, 0.15 mmol), K$_2$CO$_3$ (2N, 0.45 mL, 0.45 mmol) and 5 mL of ethyl acetate is added 3-chloropropylchlorofromate (35.6 mg, 0.23 mmol). The resulting mixture is stirred at room temperature until complete consumption of the starting material as determined by TLC. The phases are separated and the organic phase is washed by saturated NaCl, dried over MgSO$_4$ and concentrated. The residual oil is crystallized from diethyl ether/hexanes to afford [4-(3-cyano-1-cyclobutyl-6-ethoxy-1H-indole-2-yl)-phenyl]-carbamic acid 3-chloro-propyl ester as a white solid.

Step B: To a solution of [4-(3-cyano-1-cyclobutyl-6-ethoxy-1H-indole-2-yl)-phenyl]-carbamic acid 3-chloro-propyl ester in 5 mL of DMF is added anhydrous K$_2$CO$_3$. The resulting mixture is stirred at 80° C. until complete consumption of the starting material is determined by TLC. After cooling, 10 mL of water is added to the reaction mixture to afford a solid precipitation which is collected by filtration, followed by washing with ether. The desired 1-cyclobutyl-6-ethoxy-2-[4-(2-oxo-[1,3]oxazinan-3-yl)-phenyl]-1H-indole-3-carbonitrile is obtained as a white powder (76.2 mg, 91.8% yield).

Example 1CZ

Preparation of {4-[3-cyano-1-cyclobutyl-6-(2-methoxy-ethoxy)-1H-indole-2-yl]-phenyl}-carbamic acid ethyl ester (compound 1397)

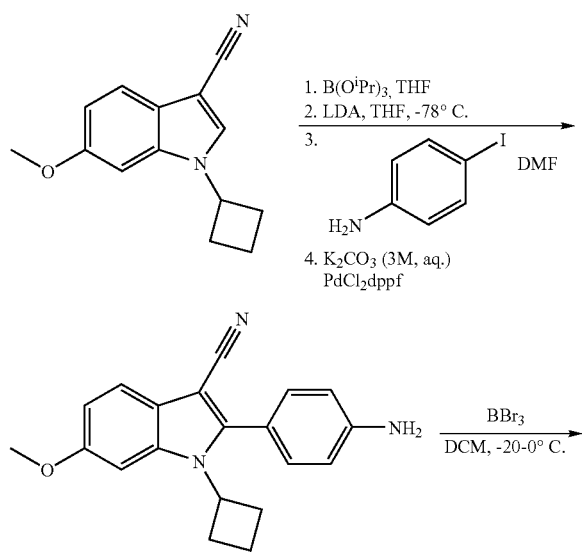

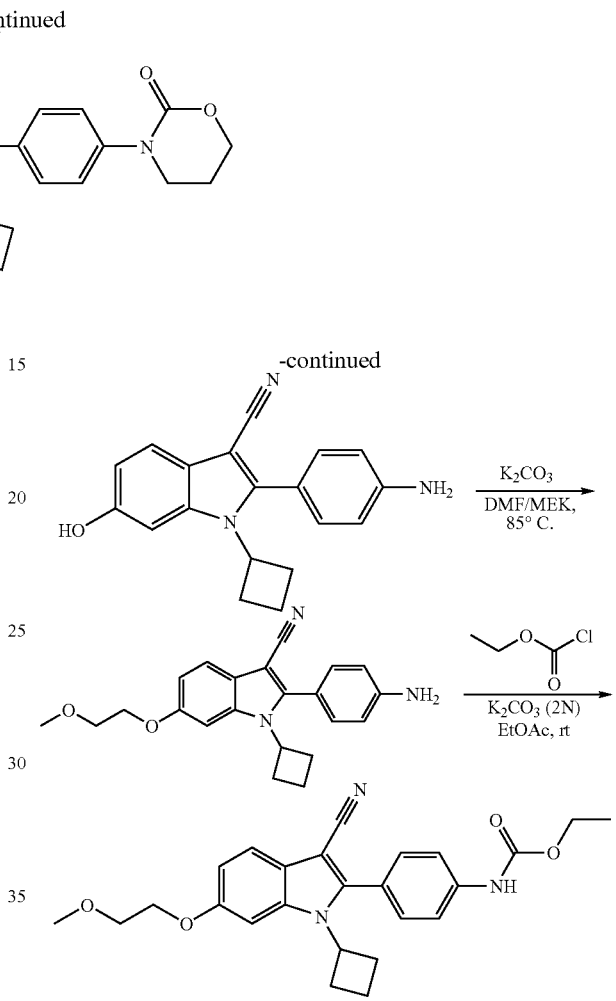

Step A: Utilizing the same procedure described in Example 1CW (Step B) gives 2-(4-aminophenyl)-1-cyclobutyl-6-methoxy-1H-indole-3-carbonitrile.

Step B: Utilizing the procedure described in Example 1B (Step A) gives 2-(4-aminophenyl)-1-cyclobutyl-6-hydroxy-1H-indole-3-carbonitrile.

Step C: To a suspension of 2-(4-aminophenyl)-1-cyclobutyl-6-hydroxy-1H-indole-3-carbonitrile (519.2 mg, 1.71 mmol), K$_2$CO$_3$, 10 mL of methyl ethyl ketone, and 2 mL of DMF is added 2-bromoethyl methyl ether. The resulting mixture is stirred at 85° C. for 8 h. The mixture is concentrated and the residue is partitioned between ethyl acetate (20 mL) and water (20 mL). The aqueous phase is extracted with additional ethyl acetate (20 mL). The combined organic phases are washed with saturated NaCl, dried over MgSO$_4$, and then the solution is concentrated and the product is washed with diethyl ether to afford 505.0 mg (81.7% yield) of 2-(4-aminophenyl)-1-cyclobutyl-6-(2-methoxy-ethoxy)-1H-indole-3-carbonitrile as a yellow solid.

Step D: Utilizing the same procedure described in Example 1AJ gives the desired title compound, {4-[3-cyano-1-cyclobutyl-6-(2-methoxy-ethoxy)-1H-indole-2-yl]-phenyl}-carbamic acid ethyl ester (compound 1397) as a white solid.

In similar fashion, following steps A to D above, the following compounds are prepared: Compounds 1365, 1366, 1367, 1368, 1369, 1370, 1371, 1372, 1373, 1398, 1399, 1400, 1401, 1402, 1407, 1431.

In similar fashion, substituting the procedure described in example 1BU for step D above, gives the following urea derivatives: Compounds 1403, 1404, 1405, 1406, 1412.

Example 1DA

Preparation of [4-(3-cyano-1-cyclobutyl-6-(2-methoxyethoxy)-1H-indol-2-yl)-phenyl]-carbamic acid 1-cyclopropyl-ethyl ester (compound 1423)

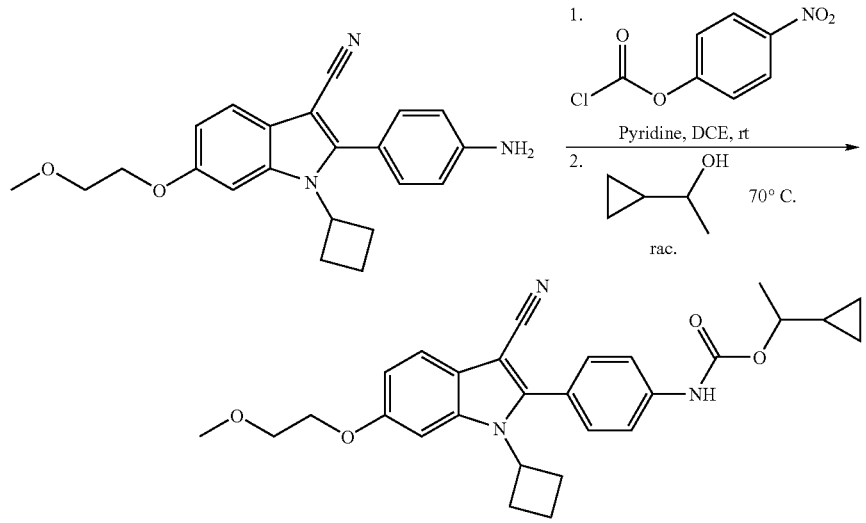

To a solution of 2-(4-aminophenyl)-1-cyclobutyl-6-(2-methoxy-ethoxy)-1H-indol-3-carbonitrile (76.0 mg, 0.21 mmol), pyridine (36.5 mg, 0.46 mmol) in 10 mL of 1,1 dichloroethane is added 4-nitrophenyl chloroformate (93.2 mg, 0.46 mmol). The resulting mixture is stirred at room temperature for 2 h. Then α-methylcyclopropane methanol (54.3 mg, 0.63 mmol) is added. The reaction mixture is heated to 70° C. for 5 h. After cooling, the reaction is partitioned between ethyl acetate (10 mL) and saturated $K_2CO_3$ (10 mL). The organic phase is washed with additional saturated $K_2CO_3$ (2×10 mL), water, and saturated NaCl. The colorless solution is dried over $MgSO_4$, filtered and evaporated. The remaining solid is washed with diethyl ether to yield the title compound, of [4-(3-cyano-1-cyclobutyl-6-(2-methoxyethoxy)-1H-indol-2-yl)-phenyl]-carbamic acid 1-cyclopropyl-ethyl ester (compound 1423) as a white solid.

Example 1DB

Preparation of 4-[3-cyano-2-(4-ethoxyphenyl)-1-ethylindol-6-yl]piperazine-1-carboxylic acid tert-butyl ester (compound 1337)

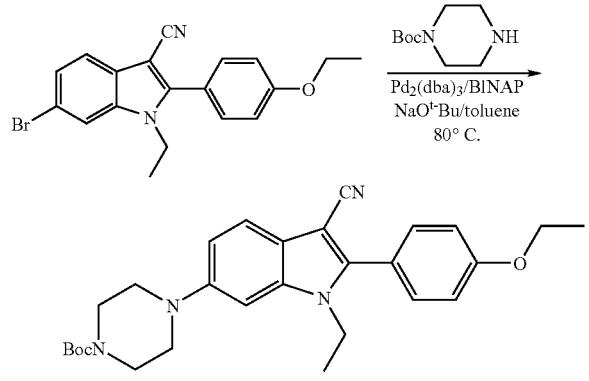

Step A: 6-Bromo-2-(4-ethoxyphenyl)-1-ethyl-indole-3-carbonitrile (0.37 g, 1.0 mmol), prepared from 6-bromoindole using the procedure described in example 1Gb, is mixed with NaO$^t$Bu (0.13 g, 1.4 mmol), $Pd_2(dba)_3$ (0.009 g, 0.01 mmol), BINAP (0.019 g, 0.03 mmol), 1-Boc-piperazine (0.22 g, 1.2 mmol) and dry toluene (3.0 mL). The mixture is stirred at 80° C. for 6 h. After cooling, the solvent is replaced with dichloromethane and chromatographed (silica gel, DCM/EtOAc, 9.5/0.5) to provide 4-[3-cyano-2-(4-ethoxyphenyl)-1-ethylindol-6-yl]piperazine-1-carboxylic acid tert-butyl ester (0.41 g, 86%).

Compound 1338 is prepared in the same fashion as described above.

Example 1DC

Preparation of {N-{4-[3-cyano-1-ethyl-6-(4-methylpiperazin-1-yl)-indol-2-yl]phenyl}propionamide (compound 1341)

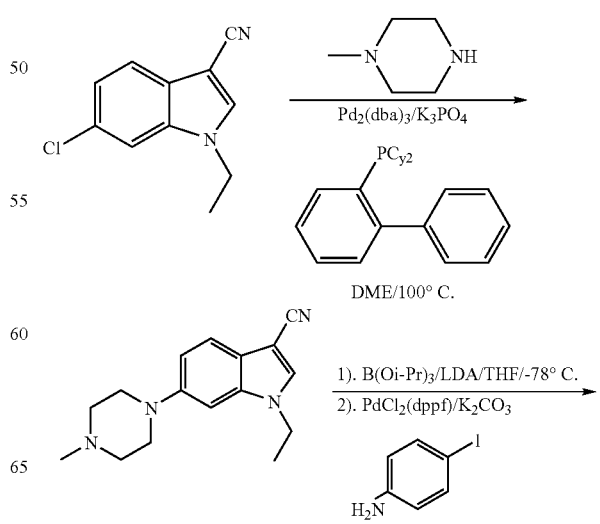

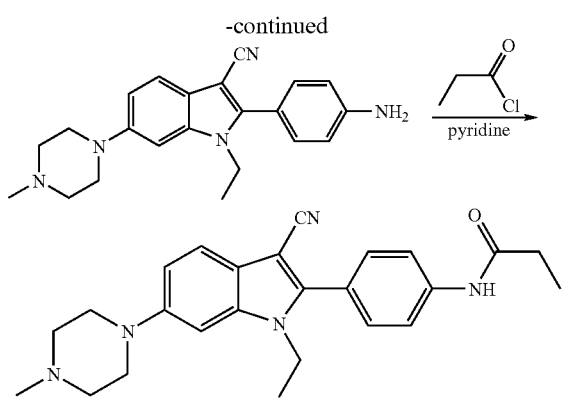

Step A: 6-chloro-1-ethylindole-3-carbonitrile (1.02 g, 5.0 mmol), prepared from 6-chloroindole using the procedures described in example 1A, is mixed with K₃PO₄ (1.48 g, 7.0 mmol), Pd₂(dba)₃ (0.11 g, 0.12 mmol), biphenyl-2-yldicyclohexylphosphane (0.17 g, 0.48 mmol), 1-methylpiperazine (0.60 g, 0.67 mL 6.0 mmol) and dry DME (10.0 mL). The mixture is stirred at 100° C. overnight. After cooling, the solvent is replaced with dichloromethane and chromatographed (silica gel, DCM, then EtOAc, finally DCM/MeOH, 9/1) to provide 1-ethyl-6-(4-methylpiperazin-1-yl)indole-3-carbonitrile (0.96 g, 72%).

Step B: To a solution of 1-ethyl-6-(4-methylpiperazin-1-yl) indole-3-carbonitrile (0.81 g, 3.0 mmol) obtained above and triisopropylborate (0.81 g, 0.99 mL, 4.50 mmol) in dry THF (5 mL) at −78° C. is added LDA (2.5 mL, 1.5 M, 3.75 mmol). The mixture is stirred at −78° C. for 15 min after the addition, then slowly brought to room temperature and stirred for an additional 30 min. The reaction is then cooled to −78° C. followed by the addition of 4-iodoaniline (0.78 g, 3.6 mmol), PdCl₂(dppf) (0.11 g, 0.15 mmol), DMF (10 mL) and K₂CO₃ (4.5 mL, 2.0 M, 9.0 mmol). The mixture is brought to room temperature slowly and stirred overnight and then poured into ice-water (200 mL). The precipitate is collected and washed with water, chromatographed (silica gel, EtOAc/DCM/Et₃N, 6/4/0.02) to furnish 2-(4-aminophenyl)-1-ethyl-6-(4-methylpiperazin-1-yl)indole-3-carbonitrile (0.90 g, 83%).

Step C: To a solution of the compound obtained in step B (54 mg, 0.15 mmol) in dry pyridine (1.5 mL) is added propionyl chloride (26 μL, 0.30 mmol). The mixture is stirred at room temperature overnight and the solvent is removed in vacuo. The residue is dissolved with DCM (5 mL) and washed with water (2×4 mL) and chromatographed (silica gel, MeOH/DCM, 0.5/9.5) to provide product, {N-{4-[3-cyano-1-ethyl-6-(4-methylpiperazin-1-yl)indol-2-yl] phenyl}propionamide (45 mg, 73%).

Compounds 1339 and 1340 are prepared by utilizing the above procedure using ethyl chloroformate and cyclopropane carbonylchloride.

Example 1DD

Preparation of {4-[3-cyano-1-cyclopropyl-6-(2-methoxyethoxy)indol-2-yl]phenyl}carbamic acid 1-cyclopropylethyl ester (compound 1436)

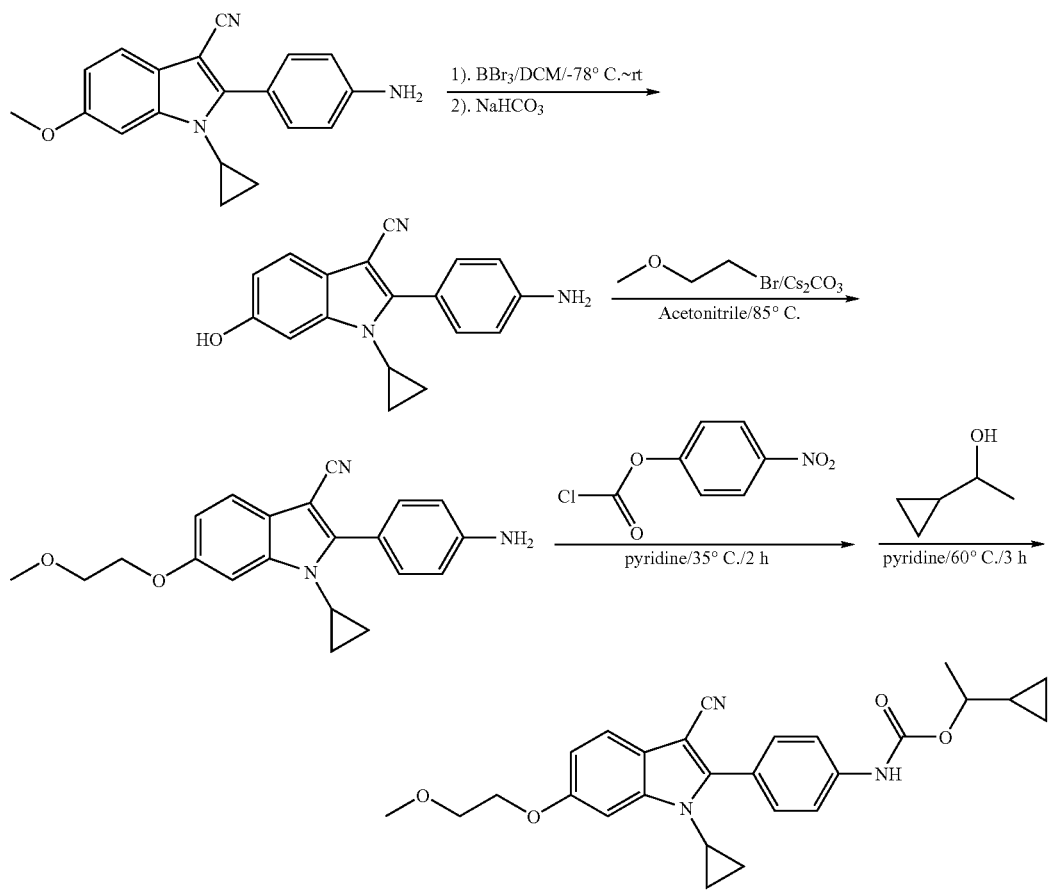

Step A: To a solution of 2-(4-aminophenyl)-1-cyclopropyl-6-methoxyindole-3-carbonitrile (2.02 g, 6.7 mmol), prepared in example 1CG, step E, in dry DCM (30 mL), at −30° C., is added boron tribromide (8.35 g, 3.15 mL, 33.3 mmol). The mixture is stirred at −30° C. ~−15° C. for 1.5 h and then brought to ambient temperature and stirred for 15 min. The mixture is poured into saturated NaHCO₃ and ice and stirred for 1 h. The volatiles are removed on a rotovap and the precipitate is collected via filtration and washed with water and then dried under a stream of N₂ to provide 2-(4-aminophenyl)-1-cyclopropyl-6-hydroxyindole-3-carbonitrile in quantitative yield.

Step B: The intermediate obtained above (0.29 g, 1.0 mmol) is mixed with Cs₂CO₃ (0.98 g, 3.0 mmol), 2-methoxyethyl bromide (0.21 g, 0.14 mL, 1.5 mmol) and acetonitrile (5 mL) and the mixture is stirred at 85° C. overnight. The solvent is removed in vacuum and the residue is treated with DCM and chromatographed (silica gel, DCM/EtOAc, 9/1) to provide 2-(4-aminophenyl)-1-cyclopropyl-6-(2-methoxyethoxy)indole-3-carbonitrile (0.16 g, 46%).

Step C: A mixture of 2-(4-aminophenyl)-1-cyclopropyl-6-(2-methoxyethoxy)indole-3-carbonitrile (35 mg, 0.1 mmol), 4-nitrophenylchloroformate (50 mg, 0.25 mmol) in pyridine (2.0 mL) is stirred at 35° C. for 2 h, followed by the addition of 1-cyclopropylethanol (98 µL, 1.0 mmol). The mixture is then stirred at 60° C. overnight and diluted with water (10 mL) and DCM (5 mL). The organic is washed with water (3×5 mL), HCl (2N, 3×5 mL), saturated NaHCO₃ (3×5 mL) and chromatographed (silica gel, EtOAc/DCM, 0.5/9.5) to provide the title compound, {4-[3-cyano-1-cyclopropyl-6-(2-methoxyethoxy)indol-2-yl]phenyl}carbamic acid 1-cyclopropylethyl ester (22 mg, 48%).

Compounds 1437, 1438 and 1439 are prepared by utilizing the above chemistry.

Example 1DE

Preparation of {4-[3-cyano-1-cyclopropyl-6-(tetrahydrofuran-2-yloxy)-2-yl]-phenyl}carbamic acid 1-cyclopropylethyl ester (compound 1444)

Step A: 2-(4-aminophenyl)-1-cyclopropyl-6-hydroxyindole-3-carbonitrile (0.29 g, 1.0 mmol), prepared in example 1DD, step A, is mixed with K₂CO₃ (0.35 g, 2.5 mmol), toluene-4-sulfonic acid tetrahydrofuran-2-yl ester (0.36 g, 1.5 mmol) and acetonitrile (5 mL) and the mixture is stirred at 80° C. overnight. The solvent is removed in vacuum and the residue is treated with DCM and chromatographed (silica gel, DCM/EtOAc, 9/1) to provide 2-(4-aminophenyl)-1-cyclopropyl-6-(tetrahydrofuran-2-yloxy)indole-3-carbonitrile (0.27 g, 75%).

Step B: A mixture of 2-(4-aminophenyl)-1-cyclopropyl-6-(tetrahydrofuran-2-yloxy)indole-3-carbonitrile (36 mg, 0.1 mmol), 4-nitrophenylchloroformate (50 mg, 0.25 mmol) in pyridine (2.0 mL) is stirred at 35° C. for 2 h, followed by the addition of 1-cyclopropylethanol (98 µL, 1.0 mmol). The mixture is then stirred at 60° C. overnight and diluted with water (10 mL) and DCM (5 mL). The organic is washed with water (3×5 mL), HCl (2N, 3×5 mL), saturated NaHCO₃ (3×5 mL) and chromatographed (silica gel, EtOAc/DCM, 0.5/9.5) to provide the title compound, {4-[3-cyano-1-cyclopropyl-6-(tetrahydrofuran-2-yloxy)indol-2-yl]phenyl}carbamic acid 1-cyclopropylethyl ester (32 mg, 68%).

In similar fashion, the following compounds are prepared following the procedure described above: Compounds 1445, 1446, 1447, 1448, 1449, 1453, 1454, 1455, 1456, 1457, 1458, 1459, 1460, 1461.

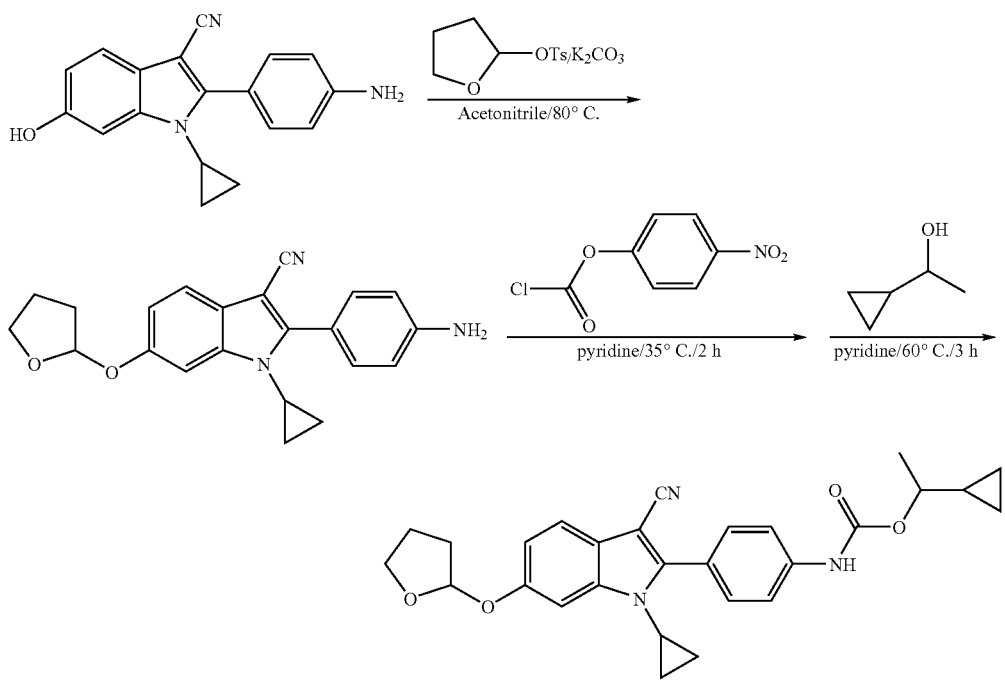

Example 1DF

Preparation of 4-Methyl-piperidine-1-carboxylic acid {4-[3-cyano-1-cyclobutyl-6-(2-methoxy-ethoxy)-1H-indol-2-yl]-phenyl}-amide (compound 1377)

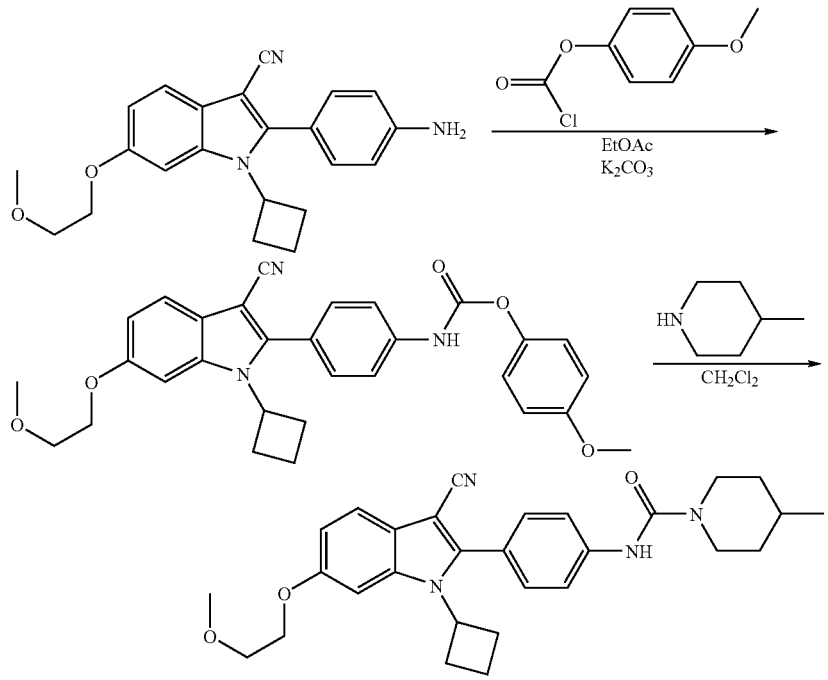

Step A: To a solution 2-(4-aminophenyl)-1-cyclobutyl-6-(2-methoxyethoxy)-1H-indole-3-carbonitrile (530 mg, 1.58 mmol) in EtOAc (10 mL) is added 2M aqueous $K_2CO_3$ (556 uL, 5.9 mmol) and 4-methoxyphenyl chloroformate over a period of 5 min. The reaction mixture is stirred further for 3 h at room temperature. The reaction mixture is diluted with EtOAc (20 mL) and then washed with water (5 mL). The solvents are removed under reduced pressure and the residue is dissolved in EtOAc and then triturated with hexane. The precipitate is collected by filtration and washed with 50% EtOAc/hexane and dried in vacuo to afford {4-[3-cyano-1-cyclobutyl-6-(2-methoxy-ethoxy)-1H-indol-2-yl]-phenyl}-carbamic acid 4-methoxy-phenyl ester (761 mg, 98%).

Step B: To a solution of {4-[3-cyano-1-cyclobutyl-6-(2-methoxy-ethoxy)-1H-indol-2-yl]-phenyl}-carbamic acid 4-methoxy-phenyl ester (40 mg, 0.082 mmol) in DCM (4 mL) is added 4-methylpiperidine (0.16 mmole) and the reaction is stirred for 18 h at reflux temperature. The solvent is removed under reduced pressure. The residue is dissolved in EtOAc and then triturated with hexane. The precipitate is collected by filtration and washed with 50% EtOAc/hexane and dried in vacuo to afford 4-methyl-piperidine-1-carboxylic acid {4-[3-cyano-1-cyclobutyl-6-(2-methoxyethoxy)-1H-indol-2-yl]-phenyl}-amide, compound 1377, (26 mg, 68%).

The following compounds are made in similar fashion following steps A and B, above: Compounds 1378, 1379, 1380, 1381, 1382, 1383, 1384.

Example 1DG

Preparation of {4-[3-Cyano-1-cyclobutyl-6-(2-hydroxy-3-[1,2,4]triazol-1-yl-propoxy)-1H-indol-2-yl]-phenyl}-carbamic acid isopropyl ester (compound 1420)

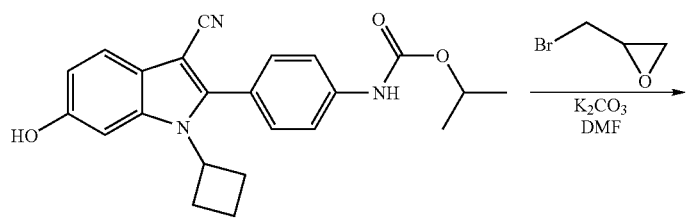

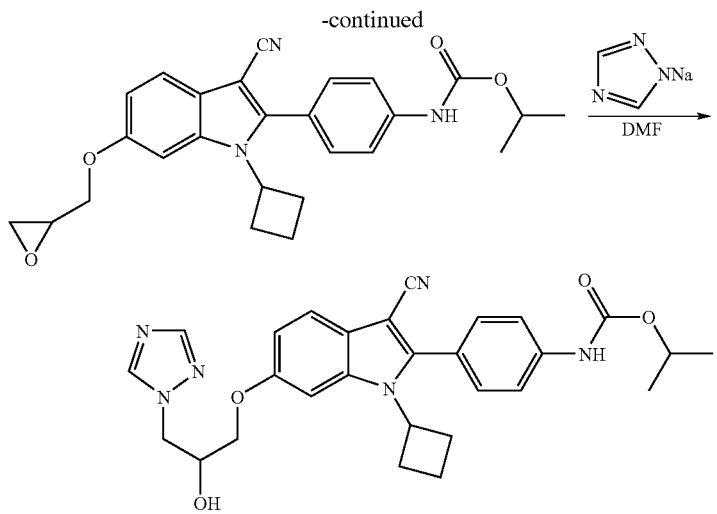

Step A: To a solution of [4-(3-cyano-1-cyclobutyl-6-hydroxy-1H-indol-2-yl)-phenyl]-carbamic acid isopropyl ester (1.0 g, 2.57 mmol) in DMF (10 mL) is added K₂CO₃ (710 mg, 5.13 mmole) and epibromohydrin (436 uL, 5.13 mmole) and the reaction is stirred for 42 h at ambient temperature. The reaction mixture is then poured into cold water and the precipitate is collected by filtration and washed with hexane and dried in vacuo to afford 960 mg, 84% of the desired product.

Step B: To a solution of [4-(3-cyano-1-cyclobutyl-6-oxiranylmethoxy-1H-indol-2-yl)-phenyl]-carbamic acid isopropyl ester (40 mg, 0.09 mmole) in DMF (1 mL) is added the sodium salt of 1,2,4-triazole (30 mg). The resulting mixture is stirred at 60° C. overnight. The solvent is removed under reduced pressure and the residue is diluted with ethyl acetate and then washed with water. The organic layer is concentrated and triturated with hexane. The precipitate is collected by filtration and washed well with 1/1 ethyl acetate/hexane and dried in vacuo to afford {4-[3-cyano-1-cyclobutyl-6-(2-hydroxy-3-[1,2,4]triazol-1-yl-propoxy)-1H-indol-2-yl]-phenyl}-carbamic acid isopropyl ester, compound 1420, (29 mg, 63%).

The following compounds are made in similar fashion following steps A and B, above: Compounds 1418, 1419.

Following the chemistry described above the urea derivative, compound 1421 is prepared similarly.

Example 1DH

Preparation of {4-[3-cyano-1-cyclobutyl-6-(3,4-dihydroxy-butoxy)-1H-indol-2-yl]-phenyl}-carbamic acid isopropyl ester (compound 1429)

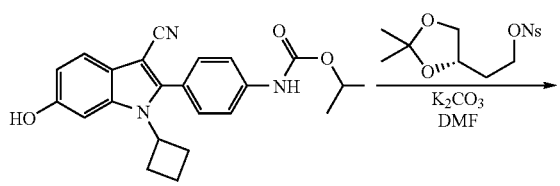

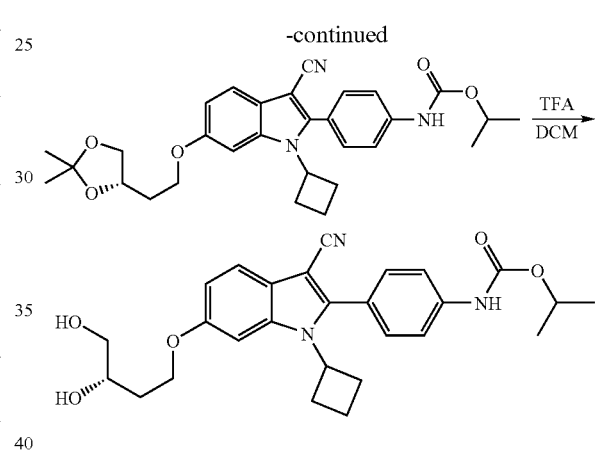

Step A: To a solution of [4-(3-cyano-1-cyclobutyl-6-hydroxy-1H-indol-2-yl)-phenyl]-carbamic acid isopropyl ester (100 mg, 0.26 mmol) in DMF (3 mL) is added K₂CO₃ (43.2 mg, 0.312 mmole) and 4-nitrobenzenesulfonic acid 2-(2,2-dimethyl-[1,3]dioxolan-4-yl)-ethyl ester (129 mg, 0.39 mmole) and the reaction is stirred for 18 h at ambient temperature. The reaction mixture is then poured into cold water and the precipitate is collected by filtration and washed with EtOAc/hexane and dried in vacuo to afford 96 mg, 84% of the desired product, (4-{3-cyano-1-cyclobutyl-6-[2-(2,2-dimethyl-[1,3]dioxolan-4-yl)-ethoxy]-1H-indol-2-yl}carbamic acid isopropyl ester, compound 1428.

Step B: To a solution of (4-{3-cyano-1-cyclobutyl-6-[2-(2,2-dimethyl-[1,3]dioxolan-4-yl)-ethoxy]-1H-indol-2-yl}-phenyl)-carbamic acid isopropyl ester (70 mg, 0.135 mmole) in DCM (2 mL) is added TFA (10 uL). The resulting mixture is stirred at ambient temperature for 2 h. The solvent is removed under reduced pressure and the residue is diluted with ethyl acetate and triturated with hexane and the precipitate collected by filtration and washed well with 50% ethyl acetate in hexane and dried in vacuo to afford {4-[3-cyano-1-cyclobutyl-6-(3,4-dihydroxy-butoxy)-1H-indol-2-yl]-phenyl}-carbamic acid isopropyl ester, compound 1429, 45 mg, (70%).

Example 1DI

Preparation of 1-[4-(3-cyano-1-cyclobutyl-6-ethoxy-1H-indol-2-yl)-phenyl]-3-(2-hydroxy-ethyl)-urea (compound 1408)

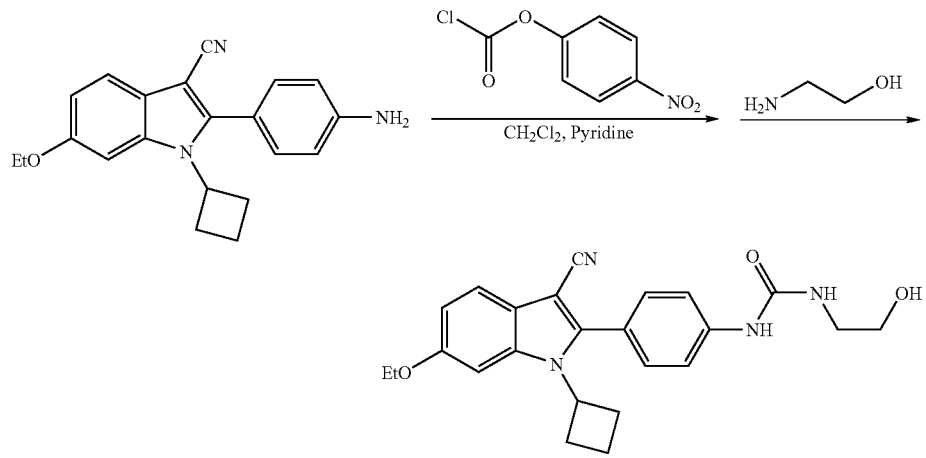

2-(4-Aminophenyl)-1-cyclobutyl-6-ethoxy-1H-indole-3-carbonitrile (40 mg, 0.12 mmol), prepared as in example 1CM, step B, is combined with 4-nitrophenyl chloroformate (60 mg, 0.30 mmol), CH$_2$Cl$_2$ (400 µL), and pyridine (25 µL, 0.31 mmol). This suspension is stirred at room temperature for 1 hour. Ethanolamine (42 µL, 0.70 mmol) is added. After stirring at room temperature for an additional 30 min, the reaction mixture is diluted in CH$_2$Cl$_2$ and is washed with dilute aqueous NaOH to remove the yellow nitrophenol by-product. The organic layer is dried and concentrated. Purification by silica gel chromatography (CH$_2$Cl$_2$/Acetone, 7/3) yields 1-[4-(3-cyano-1-cyclobutyl-6-ethoxy-1H-indol-2-yl)-phenyl]-3-(2-hydroxy-ethyl)-urea (40 mg, 80%) as a white solid.

The following compounds are prepared in a similar fashion, using the appropriate amine and aniline coupling partner: Compounds 1375, 1390, 1391, 1392, 1396, 1409, 1440, and 1441.

Example 1DJ

Preparation of [4-(3-cyano-1-cyclobutyl-6-ethoxy-1H-indol-2-yl)-phenyl]-carbamic acid 2-(2-methoxy-ethoxy)-ethyl ester (compound 1424)

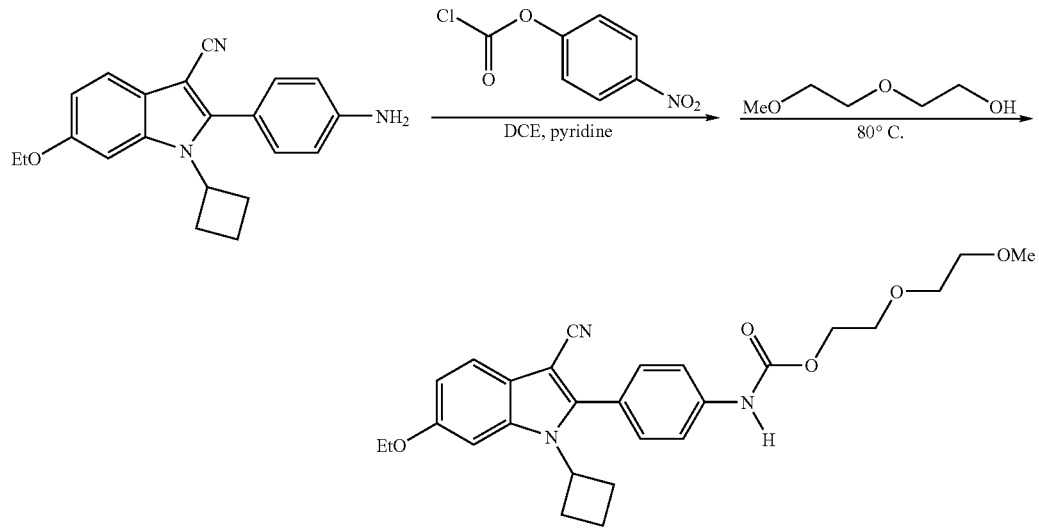

2-(4-Aminophenyl)-1-cyclobutyl-6-ethoxy-1H-indole-3-carbonitrile (40 mg, 0.12 mmol), prepared as in example 1CM, step B, is combined with 4-nitrophenyl chloroformate (60 mg, 0.30 mmol), DCE (0.4 mL), and pyridine (25 μL, 0.31 mmol). This suspension is stirred at room temperature for 1 h. 2-(2-methoxyethoxy)ethanol (150 μL, 1.25 mmol) is added. This mixture is heated at 80° C. overnight. The reaction mixture is then diluted in CH$_2$Cl$_2$ and is washed with dilute aqueous NaOH to remove the yellow nitrophenol by-product. The organic layer is dried and concentrated. Purification by silica gel chromatography (CH$_2$Cl$_2$) yields [4-(3-cyano-1-cyclobutyl-6-ethoxy-1H-indol-2-yl)-phenyl]-carbamic acid 2-(2-methoxy-ethoxy)-ethyl ester (51 mg, 89%) as a white solid.

The following compounds are prepared in a similar fashion, using the appropriate alcohol: Compounds 1416, 1426, 1432.

Example 1DK

Preparation of 1-[4-(3-cyano-1-cyclobutyl-6-ethoxy-1H-indol-2-yl)-phenyl]-3-cyclopenyl-1-ethyl-urea (compound 1425)

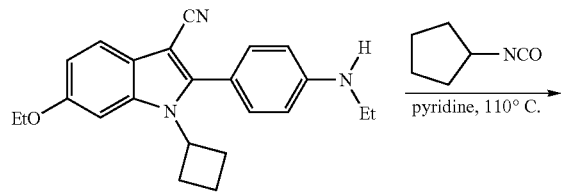

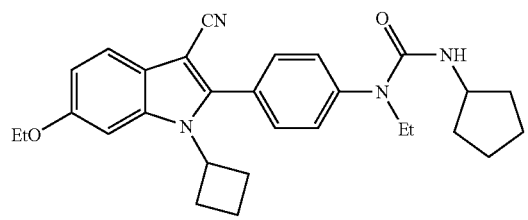

1-Cyclobutyl-6-ethoxy-2-(4-ethylaminophenyl)-1H-indole-3-carbonitrile, prepared in example 1CO, step C, (35 mg, 0.10 mmol) is dissolved in pyridine (300 μL). Cyclopentyl isocyanate (130 μL, 1.08 mmol) is added. The reaction mixture is heated at 110° C. for 2 h. The reaction mixture is then partitioned between aqueous HCl and EtOAc. The organic layer is dried and concentrated. Purification by silica gel chromatography using hexanes/EtOAc (6/4) followed by a second chromatography using CH$_2$Cl$_2$/EtOAc (95/5) is required to remove the dicyclopentyl urea impurity, affording pure 1-[4-(3-cyano-1-cyclobutyl-6-ethoxy-1H-indol-2-yl)-phenyl]-3-cyclopenyl-1-ethyl-urea (39 mg, 82%) as an off-white solid.

Example 1DL

Preparation of 1-cyclobutyl-6-ethoxy-2-[4-(2-pyridin-2-yl-ethylamino)-phenyl]-1H-indole-3-carbonitrile (compound 1433)

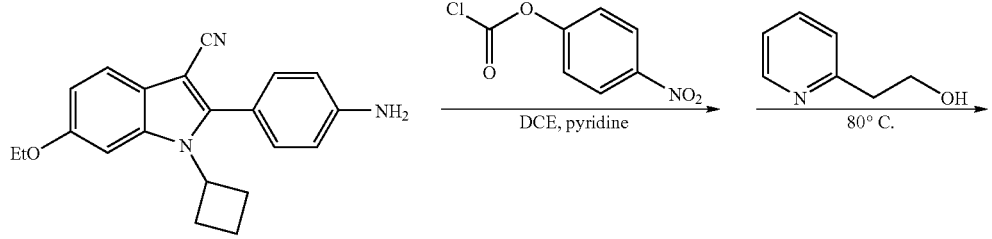

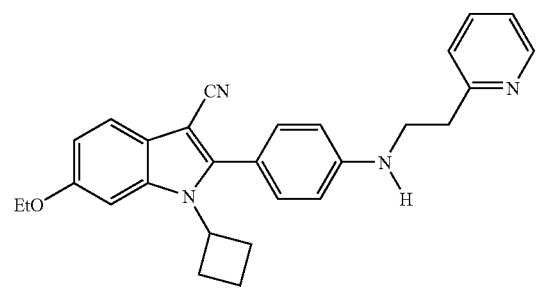

2-(4-Aminophenyl)-1-cyclobutyl-6-ethoxy-1H-indole-3-carbonitrile (40 mg, 0.12 mmol), prepared as in example 1CM, step B, is combined with 4-nitrophenyl chloroformate (60 mg, 0.30 mmol), DCE (0.4 mL), and pyridine (25 μL, 0.31 mmol). This suspension is stirred at room temperature for 1 h. 2-(2-methoxyethoxy)ethanol (150 μL, 1.25 mmol) is added. This mixture is heated at 75° C. overnight. The reaction mixture is then diluted in CH$_2$Cl$_2$ and is washed with dilute aqueous NaOH to remove the yellow nitrophenol by-product. The organic layer is dried and concentrated. Purification by silica gel chromatography (CH$_2$Cl$_2$/EtOAc, 4/1), followed by trituration with hexanes/acetone (2/1) yields 1-cyclobutyl-6-ethoxy-2-[4-(2-pyridin-2-yl-ethylamino)-phenyl]-1H-indole-3-carbonitrile (23 mg, 42%) as a white solid.

Example 1DM

Preparation of 2-(2-Diethylaminobenzothiazol-6-yl)-1-ethyl-6-methoxy-1H-indole-3-carbonitrile (compound 1343)

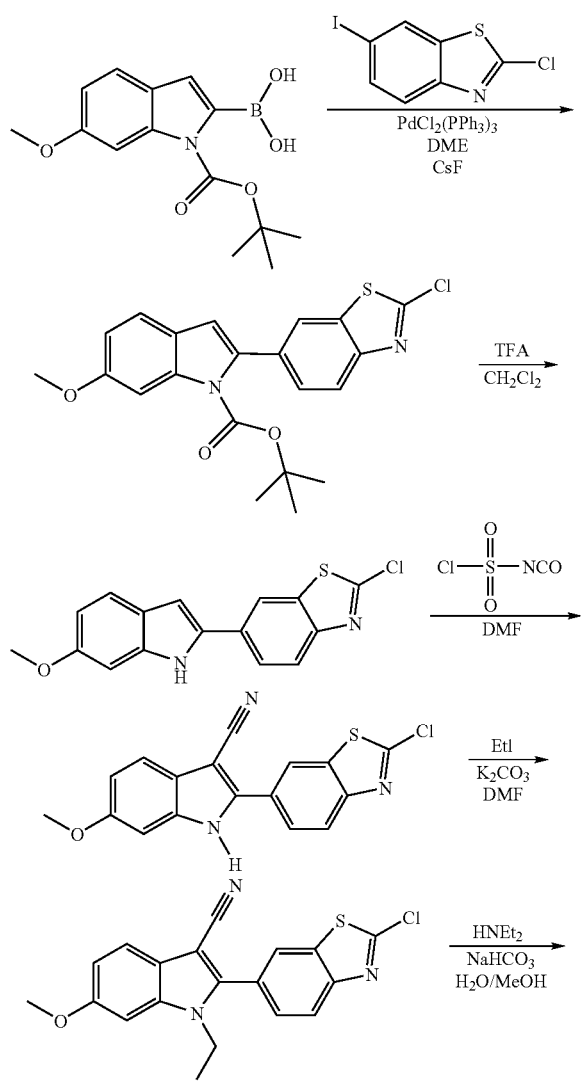

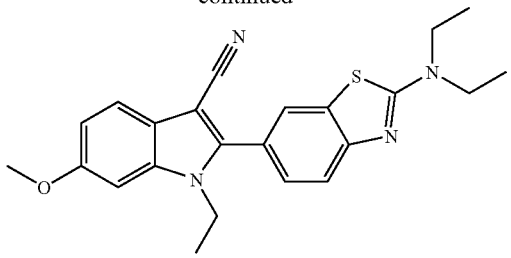

Step A: tert-butyl 6-methoxy-1H-indole-1-carboxylate, from example 1BO, (2.50 g, 8.6 mmol) is dissolved in anhydrous dimethoxyethane (21.5 mL). To the solution is added 2-chloro-6-iodobenzothiazole (2.42 g, 8.2 mmol), cesium fluoride (2.53 g, 16.7 mmol) and PdCl$_2$(PPh$_3$)$_2$ (0.23 g, 0.33 mmol). The reaction mixture is heated at reflux. After 17 h the reaction mixture is cooled to room temperature, diluted with water (100 mL) and extracted with ethyl acetate (4×20 mL). The extract is washed with saturated aqueous NaHCO$_3$ (20 mL), dried over MgSO$_4$ and concentrated under vacuum to give tert-butyl 2-(2-chlorobenzothiazol-6-yl)-6-methoxy-indole-1-carboxylate (2.95 g, 83%) as a hard foam.

Step B: The above Boc indole (2.87 g, 6.9 mmol) is dissolved in anhydrous CH$_2$Cl$_2$ (13 mL). To the solution is added trifluoroacetic acid (3.0 mL, 38.9 mmol) at room temperature. The reaction mixture is stirred at room temperature for 17 h. Water (20 mL) is added and the mixture is extracted with CH$_2$Cl$_2$ (3×10 mL). The extract is washed with water (1×15 mL), saturated aqueous NaHCO$_3$ (20 mL), dried over MgSO$_4$ and concentrated using a rotary evaporator to give the crude product. The product is purified by silica gel chromatography (1-50% ethyl acetate/hexane) to give 2-chloro-6-(-methoxy-1H-indol-2-yl)-benzothiazole (0.40 g, 18%).

Step C: The above indole is dissolved in anhydrous DMF (3.0 mL) and cooled in an ice bath. Chlorosulfonyl isocyanate (0.12 mL, 1.4 mol) is added and the mixture stirred for 2 h in an ice bath. Water (15 mL) is added and the mixture stirred at room temperature for 30 minutes. The precipitate is filtered, washed with water and dried to give 2-(2-chlorobenzothiazol-6-yl)-6-methoxy-1H-indole-3-carbonitrile (0.39 g, 95%).

Step D: The above indole (373 mg, 1.1 mmol) is dissolved in anhydrous DMF (2.2 mL) and stirred at room temperature as iodoethane (0.20 g, 1.3 mmol) and potassium carbonate (0.31 g, 2.2 mmol) are added. The mixture is stirred at 50° C. for 22 h. The mixture is diluted with water (15 mL) and stirred at room temperature for 15 minutes. The solid is filtered, washed with water and dried to give 2-(2-chlorobenzothiazol-6-yl)-1-ethyl-6-methoxy-1H-indole-3-carbonitrile (0.39 g, 96%).

Step E: The above indole (46 mg, 0.13 mmol) is dissolved in 15% water/isopropyl alcohol (1.5 mL). Diethyl amine (25 mg, 0.34 mmol) is added followed by sodium bicarbonate (43 mg, 0.51 mmol). The reaction mixture is heated at reflux for 21 hours. The reaction mixture is cooled to room temperature, and diluted with water (5 mL). The precipitate is filtered, washed with water and dried to give 2-(2-diethylaminobenzothiazol-6-yl)-1-ethyl-6-methoxy-1H-indole-3-carbonitrile (40 mg, 79%).

Example 1DN

Preparation of Ethanesulfonic acid [4-(3-cyano-6-diethylaminomethyl-1-ethyl-1H-indol-2-yl)-phenyl]-amide (compound 1352)

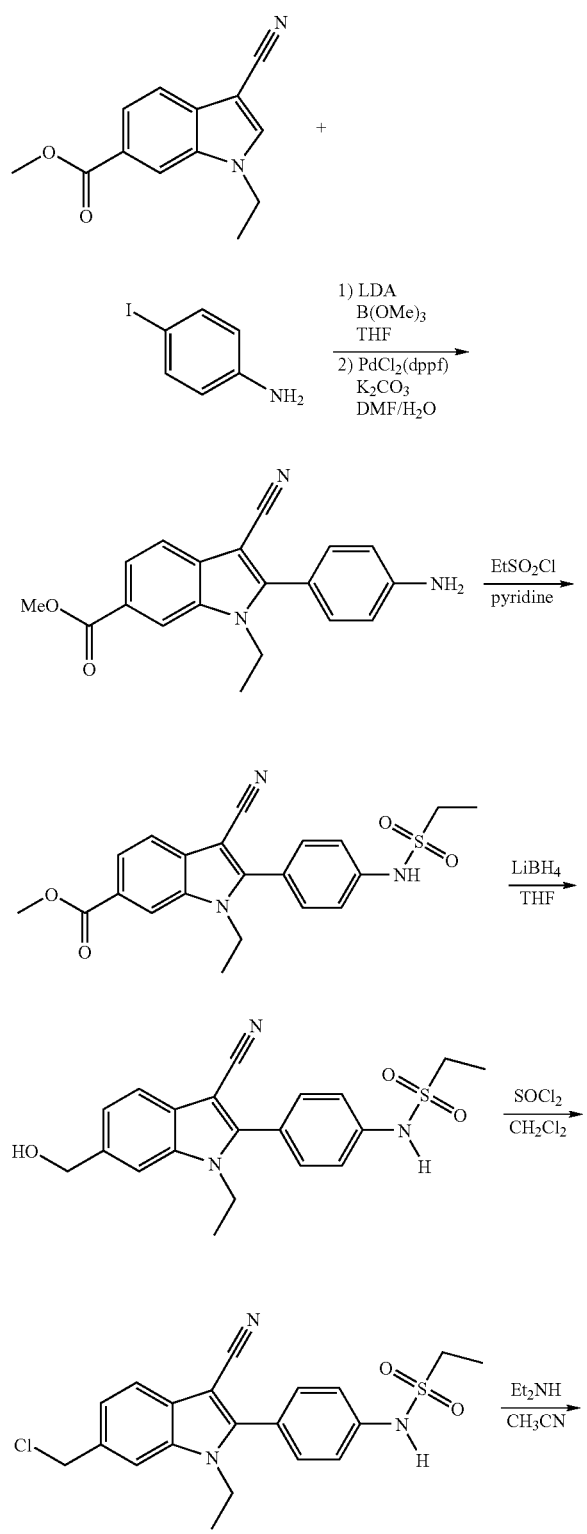

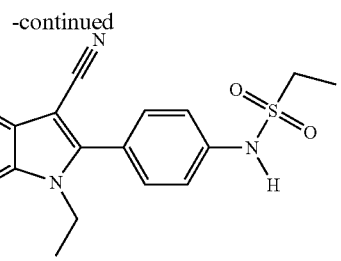

Step A: A solution of methyl 3-cyano-1-ethyl-1H-indole-6-carboxylate (4.11 g, 18.0 mmol), prepared by the method described in example 1A from methyl 1H-indole-6-carboxylate, in anhydrous THF (36 mL) is cooled in a dry ice/ether bath. Lithium diisopropylamide (1.5 M solution in cyclohexane, 14.4 mL, 21.6 mmol) is added at a rate to keep the reaction temperature below −60° C. After the addition, the reaction mixture is stirred at −60° C. for 30 minutes. Trimethylborate (3.1 mL, 27.8 mmol) is added to the reaction and the mixture is stirred at −60° C. for 30 minutes. The reaction mixture is allowed to warm to room temperature and DMF (60 mL), 4-iodoaniline (4.00 g, 18.3 mmol), PdCl$_2$(dppf) (735 mg, 0.90 mmol) and aqueous K$_2$CO$_3$ (2M, 36 mL) are added. The mixture is stirred at 40° C. for 17 h. The mixture is cooled to room temperature and concentrated to remove THF. Water is added to a volume of 500 mL and the mixture is extracted with ethyl acetate (3×50 mL). The extract is washed with water (3×50 mL), dried over MgSO$_4$ and concentrated to give the product as a semi-solid. The product is crystallized from ethyl acetate to give methyl 2-(4-aminophenyl)-3-cyano-1-ethyl-1H-indole-6-carboxylate (2.53 g, 44%) as a tan solid.

Step B: The indole product from above (1.26 g, 3.95 mmol) is dissolved in anhydrous pyridine (6 mL). To the solution is added ethanesulfonyl chloride (0.63 g, 4.90 mmol). The mixture is heated to 50° C. for 17 hours. The reaction mixture is cooled to room temperature and water (30 mL) is added. The mixture is extracted with ethyl acetate (3×5 mL). The extract is washed with 10% aqueous hydrochloric acid (5 mL), water (2×10 mL), dried over MgSO$_4$ and concentrated using a rotary evaporator to give 3-cyano-2-(4-ethanesulfonylaminophenyl)-1-ethyl-1H-indole-6-carboxylic acid methyl ester (1.47 g, 90%).

Step C: The indole product from above (0.72 g, 1.76 mmol) is suspended in anhydrous THF (3.3 mL). A solution of lithium borohydride (2.6 mL, 5.2 mmol, 2M in THF) is added at room temperature. The mixture is heated at reflux for 20 h. The mixture is cooled to room temperature and water (4 mL) is added. The pH is adjusted to 4 by addition of 10% aqueous hydrochloric acid. The mixture is extracted with methylene chloride (4×2 mL). The extract is washed with water (2.2 mL), dried over MgSO$_4$ and concentrated to give ethanesulfonic acid[4-(3-cyano-1-ethyl-6-hydroxymethyl-1H-indol-2-yl)-phenyl]-amide (595 mg, 88%) as a tan solid.

Step D: The indole product from above (471 mg, 1.23 mmol) is suspended in anhydrous methylene chloride (6 mL). Thionyl chloride (0.135 mL, 1.85 mmol) is added and the mixture stirred at room temperature for 2 h. The mixture is concentrated on a rotary evaporator to give ethanesulfonic acid [4-(6-chloromethyl-3-cyano-1-ethyl-1H-indol-2-yl)-phenyl]-amide (493 mg, 99%).

Step E: The indole product from above (50 mg, 0.124 mmol) is dissolved in anhydrous acetonitrile (1.0 mL). Diethylamine (28.1 mg, 0.38 mmol) is added and the mixture is heated at 80° C. for 17 hours. The mixture is cooled to room temperature, concentrated on a rotary evaporator and purified by silica gel chromatography (0-10% MeOH/CH$_2$Cl$_2$) to give ethanesulfonic acid [4-(3-cyano-6-diethylaminomethyl-1-ethyl-1H-indol-2-yl)-phenyl]-amide (33.6 mg, 62%).

Example 1DO

{4-[3-Cyano-1-cyclobutyl-6-(2-methanesulfonyl-ethoxy)-1H-indol-2-yl]-phenyl}-carbamic acid 1-cyclopropyl-ethyl ester (compound 2695)

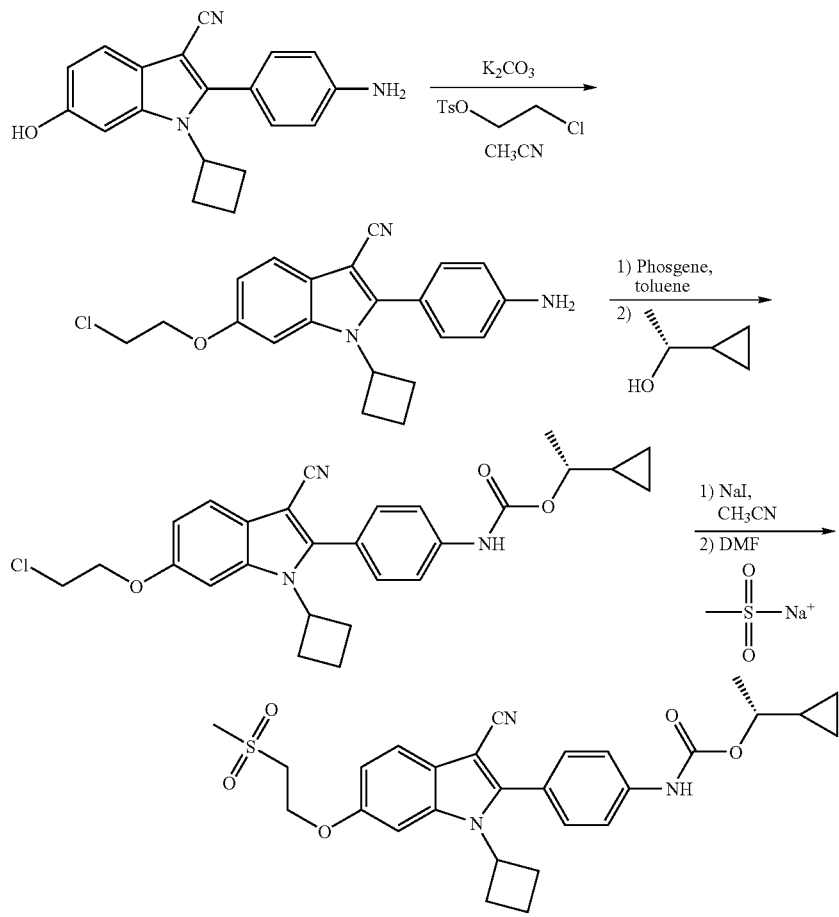

Step A: To a solution of 2-(4-aminophenyl)-1-cyclobutyl-6-hydroxy-1H-indole-3-carbonitrile (3.43 g, 11.3 mmol) in CH$_3$CN (8 mL) was added Cs$_2$CO$_3$ (4.30 g, 73.2 mmol) and 2-chloroethyl-p-tosylate (2.39 mL, 13.2 mmol) and the reaction mixture was stirred for 18 h at 40° C. in a sealed tube. An aqueous workup was performed in 0.5M HCl (500 mL) and the mixture extracted with EtOAc (2×500 mL). Organic layers were combined, dried over MgSO$_4$ and concentrated. The crude product was purified over silica gel column in 10% EtOAc/CH$_2$Cl$_2$. Solvent was removed to provide 4.06 g (98% yield) of 2-(4-Amino-phenyl)-6-(2-chloro-ethoxy)-1-cyclobutyl-1H-indole-3-carbonitrile, as a white solid.

Step B: 2-(4-Amino-phenyl)-6-(2-chloro-ethoxy)-1-cyclobutyl-1H-indole-3-carbonitrile (800 mg, 2.19 mmol) was dissolved in phosgene in toluene (2M, 10 mL, 5.00 mmol) and stirred for 2 h at 80° C. in a sealed tube. Solvent was removed and the white solid obtained was suspended in 1 ml of DCE. To this solution was added (R)-1-cyclopropylethanol (400 uL, 5.28 mmol) and DMAP (268 mg, 2.19 mmol). Solution was stirred in a sealed tube for 16 h at room temperature. An aqueous workup was performed in 0.5M HCl (200 mL) and extracted with EtOAc (2×100 mL). The organic layers were combined, dried over MgSO$_4$ and concentrated. Solid product was triturated with ether to generate 800 mg (77% yield) of {4-[6-(2-Chloro-ethoxy)-3-cyano-1-cyclobutyl-1H-indol-2-yl]-phenyl}-carbamic acid 1-cyclopropyl-ethyl ester, as a white solid.

Step C: To a solution of {4-[6-(2-Chloro-ethoxy)-3-cyano-1-cyclobutyl-1H-indol-2-yl]-phenyl}-carbamic acid 1-cyclopropyl-ethyl ester (800 mg, 1.67 mmol) in 1:4 DMF/CH$_3$CN (8 mL) is added sodium iodide (2.50 g, 16.7 mmol). The resulting mixture was refluxed overnight. An aqueous workup was performed in 0.5M HCl (200 mL) and extracted with EtOAc (2×100 mL). Organic layers were combined, dried over MgSO$_4$ and concentrated. Solid product was triturated with ether and used without further purification. To 4 mL of a DMF solution containing the iodoethyl intermediate (0.56 mmol) was added the sodium methane sulfinate (113 mg, 1.11 mmol), and the reaction was stirred at room temperature overnight. An aqueous workup was performed in 0.5M HCl (200 mL) and extracted with EtOAc (2×100 mL). The organic layers were combined, dried over MgSO$_4$ and concentrated. The mixture was purified over silica gel column (CH$_2$Cl$_2$) to provide 100 mg (35% yield) of {4-[3-Cyano-1-cyclobutyl-6-(2-methanesulfonyl-ethoxy)-1H-indol-2-yl]-phenyl}-carbamic acid 1-cyclopropylethyl ester, as an off-white powder.

Example 1DP

Preparation of [4-(1-cyclopropylmethyl-6-ethoxy-3-iodo-1H-indol-2-yl)-phenyl]-carbamic acid isopropyl ester (compound 2634)

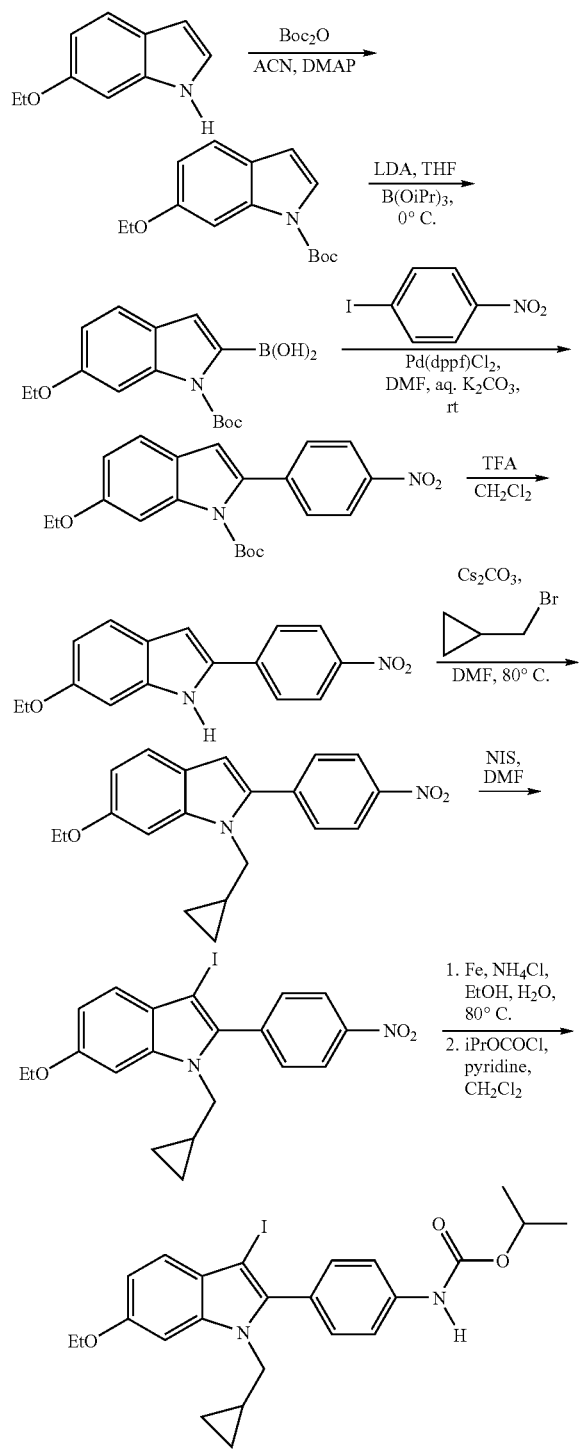

Step A: To a solution 6-Ethoxy-1-H-indole (5.0 g, 31 mmol) in CH$_3$CN (31 mL) was added di-tert-butyldicarbonate (7.2 g, 33 mmol) and DMAP (480 mg, 3.9 mmol). The mixture was stirred overnight at room temperature, concentrated and the residue purified by silica gel chromatography (1:1 CH$_2$Cl$_2$/hexane) provided 6-ethoxy-indole-1-carboxylic acid tert-butyl ester (7.67 g, 95%) as a tan oil.

Step B: A solution of 6-ethoxy-indole-1-carboxylic acid tert-butyl ester (8 g, 30 mmol) and B(OiPr)$_3$ (12 mL, 52 mmol) in THF (48 mL) was cooled to 0° C. and LDA (1.5 M in THF-cyclohexane, 30 mL, 45 mmol) was added dropwise. The reaction mixture was stirred at 0° C. for 20 minutes, and then at room temperature for 30 minutes. HCl (7.5 mL, 6 M) was added and the mixture concentrated to roughly 30 mL of solution. This concentrate was acidified with aqueous HCl to pH 1-2. The solids were filtered, washed with H$_2$O, and dried at 50° C. at reduced pressure for 30 minutes. The product, 2-(6-ethoxy-indole-1-tert-butoxy-carbonyl-indole)-boronic acid trihydrate (10.32 g, 96%) was isolated as a white solid.

Step C: To a mixture of 2-(6-ethoxy-indole-1-tert-butoxy-carbonyl-indole)-boronic acid trihydrate (5.1 g, 14.2 mmol), 1-iodo-4-nitrobenzene (3.6 g, 14.4 mmol), Pd(dppf)Cl$_2$—CH$_2$ (205 mg, 0.25 mmol) and DMF (45 mL) was added aq. K$_2$CO$_3$ (2M, 20 mL, 40 mmol) and the mixture was stirred at room temperature for 1 h. The reaction mixture was diluted with H$_2$O and was extracted with EtOAc. The EtOAc layer was washed with H$_2$O, and then with brine. The organic layer was dried, concentrated and purified by silica gel chromatography (1:1 CH$_2$Cl$_2$/hexane), followed by trituration with 1:1 hexane/ether to provide 6-ethoxy-2-(4-nitro-phenyl)-indole-1-carboxylic acid tert-butyl ester (3.63 g, 67%) as a yellow solid.

Step D: To a solution of 6-ethoxy-2-(4-nitro-phenyl)-indole-1-carboxylic acid tert-butyl ester (8.1 g, 21.2 mmol) in CH$_2$Cl$_2$ (8 mL) was added TFA (8 mL). This mixture was stirred at room temperature for 2 h and concentrated. The residue was diluted in EtOAc and washed with sat.aq. NaHCO$_3$. The organic layer was concentrated and purified by silica gel chromatography (7:3 CH$_2$Cl$_2$/hexane, followed by 100% CH$_2$Cl$_2$) to provide 6-ethoxy-2-(4-nitro-phenyl)-1H-indole (4.5 g, 68%) as an orange-red solid.

Step E: 6-Ethoxy-2-(4-nitro-phenyl)-1H-indole (4.5 g, 16 mmol), Cs$_2$CO$_3$ (7.8 g, 24 mmol), DMF (23 mL), and bromomethylcyclopropane (1.8 mL, 18 mmol) were stirred at 80° C. in a sealed tube for 16 hours. The reaction mixture was diluted with H$_2$O and extracted with EtOAc. The organic layer was washed with H$_2$O and brine and then dried and concentrated. Purification by silica gel chromatography (1:1 CH$_2$Cl$_2$/hexane) provided 1-cyclopropylmethyl-6-ethoxy-2-(4-nitro-phenyl)-1H-indole (4.73 g, 88%) as an orange solid.

Step F: To 1-cyclopropylmethyl-6-ethoxy-2-(4-nitro-phenyl)-1H-indole (800 mg, 2.38 mmol) in DMF (8.6 mL) at room temperature was added a solution of N-iodosuccinimide (585 mg, 2.6 mmol) in DMF (5.6 mL) dropwise. The reaction mixture was stirred at room temperature for 2 h, diluted with H$_2$O and extracted with EtOAc. The organic layer was washed with H$_2$O, and then with sat. aq. NaHCO$_3$ and then dried and concentrated. The residue was triturated with hexane to provide 1-cyclopropylmethyl-6-ethoxy-3-iodo-2-(4-nitro-phenyl)-1H-indole (1.061 g, 96%) as an orange solid.

Step G: A mixture of 1-Cyclopropylmethyl-6-ethoxy-3-iodo-2-(4-nitro-phenyl)-1H-indole (990 mg, 2.14 mmol), iron powder (690 mg, 11.8 mmol), NH$_4$Cl (690 mg, 12.9 mmol), ethanol (22 mL), and H$_2$O (8 mL) were heated at 80° C. for 90 minutes. The reaction mixture was diluted with H$_2$O and extracted with CH$_2$Cl$_2$. The organic layer was dried, concentrated and purified by silica gel chromatography (CH$_2$Cl$_2$). Product containing fractions were used immediately in the next reaction. The compound in CH$_2$Cl$_2$ (80 mL)

was treated with pyridine (15 mL) and isopropylchloroformate (1M in toluene, 2.5 mL, 2.5 mmol) and stirred at room temperature for 15 minutes. The reaction mixture was concentrated and extracted with a mixture of EtOAc and aq. HCl. The organic layer was washed with H₂O and brine and then dried, concentrated and purified by silica gel chromatography (CH₂Cl₂/hexane, 1:1 to 3:1) to provide [4-(1-cyclopropylmethyl-6-ethoxy-3-iodo-1H-indol-2-yl)-phenyl]-carbamic acid isopropyl ester (644 mg, 58%) as a white solid.

Example 1DQ

Preparation of [4-(1-Cyclopropylmethyl-6-ethoxy-3-fluoro-1H-indol-2-yl)-phenyl]-carbamic acid isopropyl ester (compound 2640)

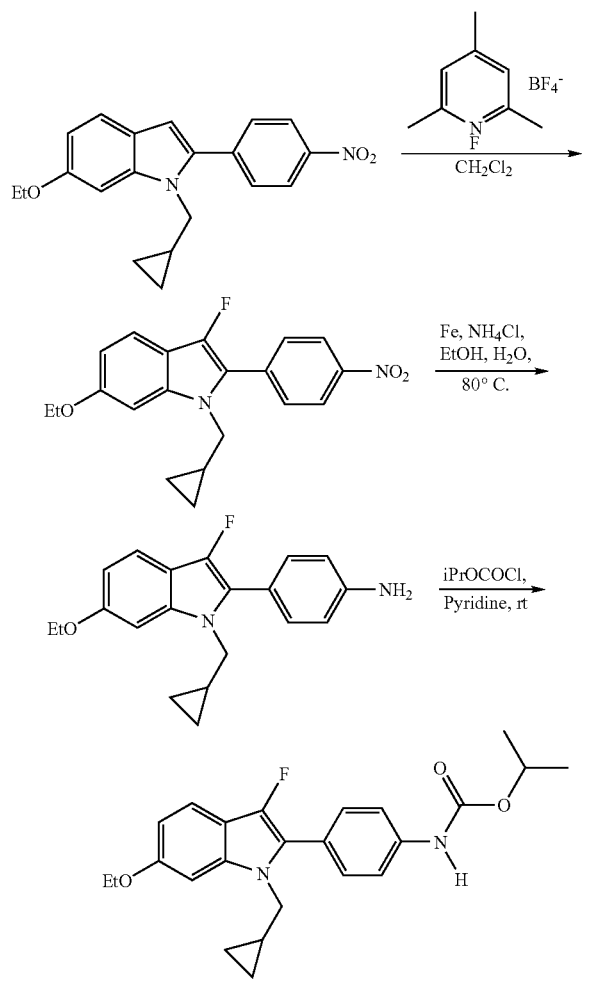

Step A: To 1-cyclopropylmethyl-6-ethoxy-2-(4-nitro-phenyl)-1H-indole (600 mg, 1.79 mmol) in CH₂Cl₂ (4 mL) was added 1-fluoro-2,4,6-trimethyl pyridinium tetrafluoroborate (418 mg, 1.85 mmol). The reaction mixture was stirred at room temperature for 3 days and then diluted in CH₂Cl₂ and washed with aq. NaHCO₃. The organic layer was dried, concentrated and purified by silica gel chromatography (1:1 CH₂Cl₂/hexane) to provide 1-cyclopropylmethyl-6-ethoxy-3-fluoro-2-(4-nitro-phenyl)-1H-indole (161 mg, 25%) as a yellow solid.

Step B: A mixture of 1-cyclopropylmethyl-6-ethoxy-3-fluoro-2-(4-nitro-phenyl)-1H-indole (161 mg, 0.45 mmol), iron powder (170 mg), NH₄Cl (170 mg, 3.2 mmol), ethanol (4 mL) and H₂O (1.5 mL) were heated at 80° C. for 90 minutes. The reaction mixture was diluted with H₂O and was extracted with CH₂Cl₂. The organic layer was dried and concentrated to provide 4-(1-cyclopropylmethyl-6-ethoxy-3-fluoro-1H-indol-2-yl)-phenylamine (122 mg, 83%) as a white solid.

Step C: A mixture of 4-(1-cyclopropylmethyl-6-ethoxy-3-fluoro-1H-indol-2-yl)-phenyl amine (30 mg, 0.093 mmol), pyridine (300 µL), and isopropylchloroformate (1 M in toluene, 110 µL, 0.11 mmol) was stirred at room temperature for 90 minutes. The residue was extracted with a mixture of EtOAc and aqueous HCl. The organic layer was washed with H₂O and brine and then dried, concentrated and purified by silica gel chromatography (CH₂Cl₂/Hex, 1:1) to provide [4-(1-cyclopropylmethyl-6-ethoxy-3-fluoro-1H-indol-2-yl)-phenyl]-carbamic acid isopropyl ester (35 mg, 92%) as a white solid.

Example 1DR

Preparation of [4-(3-cyclopropylethynyl-1-cyclopropylmethyl-6-ethoxy-1H-indol-2-yl)-phenyl]-carbamic acid isopropyl ester (compound 2635)

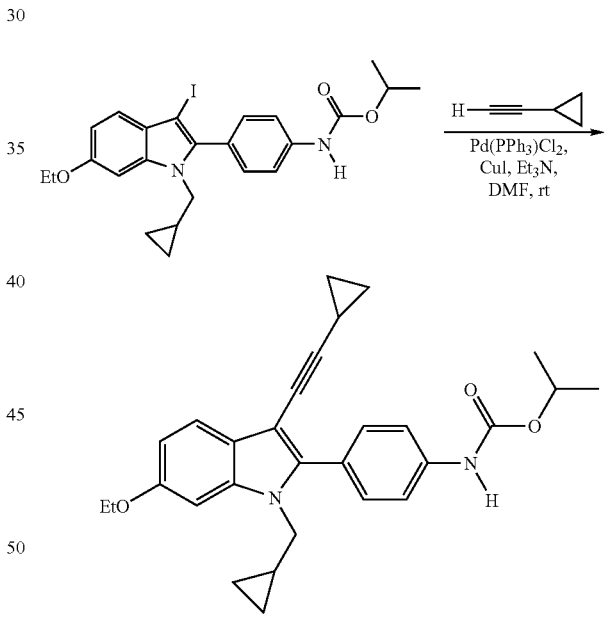

[4-(1-Cyclopropylmethyl-6-ethoxy-3-iodo-1H-indol-2-yl)-phenyl]-carbamic acid isopropyl ester (100 mg, 0.19 mmol), cyclopropylacetylene (50 µL, 70% in toluene, 0.4 mmol), Pd(PPh₃)₂Cl₂ (6.7 mg, 0.0096 mmol), CuI (5 mg, 0.026 mmol), triethylamine (600 µL), and DMF (600 µL) was stirred at room temperature for 5 h. Additional Pd(PPh₃)₂Cl₂ (5 mg), and cyclopropylacetylene (30 µL) was then added and the reaction mixture was stirred overnight. The reaction mixture was diluted with EtOAc and washed with H₂O and aq. HCl. The organic layer was dried, concentrated and purified by silica gel chromatography (3:1 CH₂Cl₂/hexane), followed by a second chromatography (7:3 hexane/ether) to provide

[4-(3-cyclopropylethynyl-1-cyclopropylmethyl-6-ethoxy-1H-indol-2-yl)-phenyl]-carbamic acid isopropyl ester (21 mg, 24%) as a white solid.

Example 1DS

Preparation of [4-(3-bromo-1-cyclopropylmethyl-6-ethoxy-1H-indol-2-yl)-phenyl]-carbamic acid isopropyl ester (compound 2691)

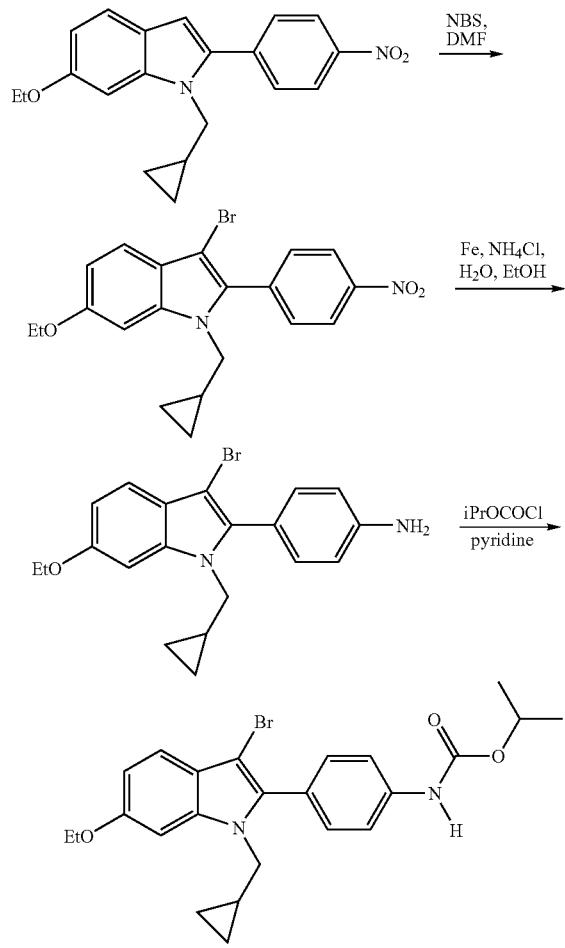

bromo-1-cyclopropylmethyl-6-ethoxy-1H-indol-2-yl)-phenyl]-carbamic acid isopropyl ester (25 mg, 68%) as a white solid.

Example 1DT

Preparation of [4-(3-chloro-1-cyclopropylmethyl-6-methoxy-1H-indol-2-yl)-phenyl]-carbamic acid isopropyl ester (compound 2804)

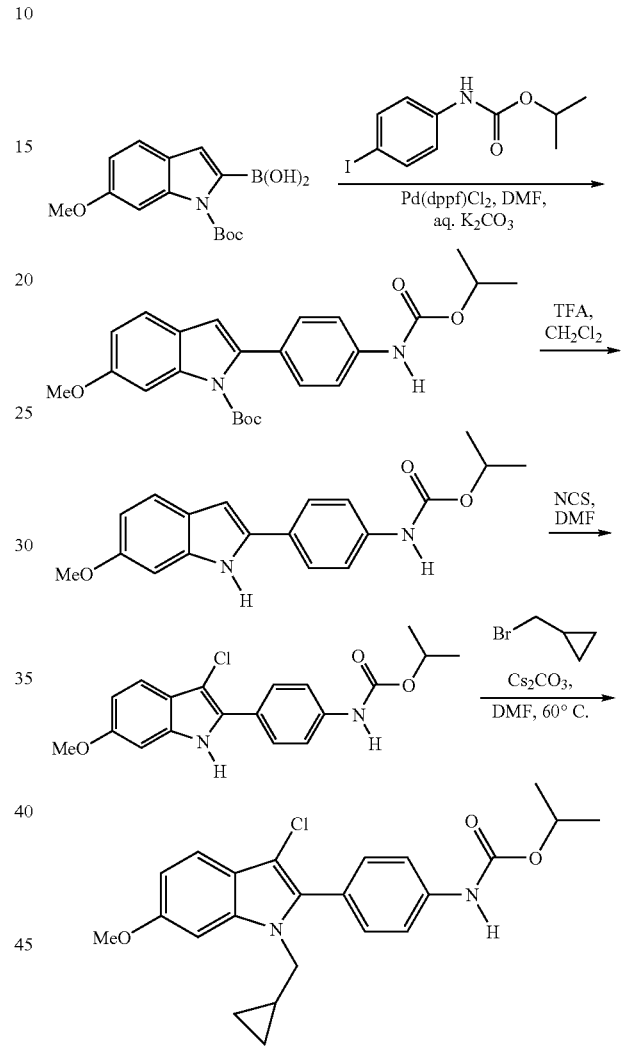

Step A: To 1-cyclopropylmethyl-6-ethoxy-2-(4-nitro-phenyl)-1H-indole (200 mg, 0.6 mmol) in DMF (2.5 mL) was added a solution of N-bromosuccinimide (107 mg, 0.6 mmol) in DMF (1.5 mL) dropwise. The reaction mixture was stirred at room temperature for 90 minutes. The reaction mixture was diluted in H$_2$O and extracted with EtOAc. The organic layer was washed with H$_2$O and brine and then dried, concentrated and purified by silica gel chromatography (1:1 CH$_2$Cl$_2$/hexane) to provide 3-bromo-1-cyclopropylmethyl-6-ethoxy-2-(4-nitro-phenyl)-1H-indole (219 mg, 88%) as a yellow solid.

Step B: Following Example 1DP step B, 3-bromo-1-cyclopropylmethyl-6-ethoxy-2-(4-nitro-phenyl)-1H-indole (205 mg, 0.5 mmol) was reduced to provide 4-(3-bromo-1-cyclopropylmethyl-6-ethoxy-1H-indol-2-yl)-phenylamine (164 mg, 85%) as yellowish solid.

Step C: Following Example 1DP step C, 4-(3-bromo-1-cyclopropylmethyl-6-ethoxy-1H-indol-2-yl)-phenylamine (30 mg, 0.078 mmol) was carbamoylated to provide [4-(3-

Step A: 2-(6-Methoxy-indole-1-tert-butoxy-carbonyl-indole)-boronic acid (14 g, 48 mmol) was combined with N-(4-iodophenyl)-isopropylcarbamate (15.25 g, 50 mmol), Pd(dppf)Cl$_2$ (678 mg, 0.92 mmol), aq. K$_2$CO$_3$ (2M, 66 mL, 132 mmol), and DMF (150 mL). The reaction mixture was stirred overnight at room temperature then diluted with H$_2$O and extracted with EtOAc. The organic layer was washed with H$_2$O and brine and then dried, concentrated and purified by silica gel chromatography (CH$_2$Cl$_2$), followed by trituration with 2:1 hexane/ether to provide 2-(4-isopropoxycarbonylamino-phenyl)-6-methoxy-indole-1-carboxylic acid tert-butyl ester (15.6 g, 76%) as a gray solid.

Step B: A mixture of 2-(4-Isopropoxycarbonylamino-phenyl)-6-methoxy-indole-1-carboxylic acid tert-butyl ester (17.4 g, 41 mmol), CH$_2$Cl$_2$ (50 mL), and TFA (50 mL) was stirred at room temperature for 1 h. The reaction mixture was concentrated, diluted in CH$_2$Cl$_2$, and washed with sat. aq.

NaHCO₃. The organic layer was dried, concentrated, and triturated with ether to provide [4-(6-methoxy-1H-indol-2-yl)-phenyl]-carbamic acid isopropyl ester (11.4 g, 86%) as a grayish solid.

Step C: To [4-(6-Methoxy-1H-indol-2-yl)-phenyl]-carbamic acid isopropyl ester (11.3 g, 34.9 mmol) in DMF (50 mL) was added a solution of N-chlorosuccinimide (5 g, 37.4 mmol) dropwise over 20 minutes and the mixture stirred at room temperature for 1 h. The reaction mixture was diluted with H₂O and extracted with EtOAc. The organic layer was washed with H₂O and brine and then dried, concentrated and triturated with ether to provide [4-(3-chloro-6-Methoxy-1H-indol-2-yl)-phenyl]-carbamic acid isopropyl ester (10.65 g, 85%) as a tan solid.

60° C. for 4 h. The reaction mixture was then stirred at room temperature for 1 h, diluted with H₂O and extracted with EtOAc. The organic layer was washed with H₂O and brine and then dried, concentrated and purified by silica gel chromatography (7:3 CH₂Cl₂/hexane) to provide [4-(3-chloro-1-cyclopropylmethyl-6-methoxy-1H-indol-2-yl)-phenyl]-carbamic acid isopropyl ester (19 mg, 33%) as a white solid.

Example 1DU

Preparation of (R)-[4-(3-cyano-1-cyclobutyl-6-methanesulfonylmethoxy-1H-indol-2-yl)-phenyl]-carbamic acid 1-cyclopropyl-ethyl ester (compound 2988)

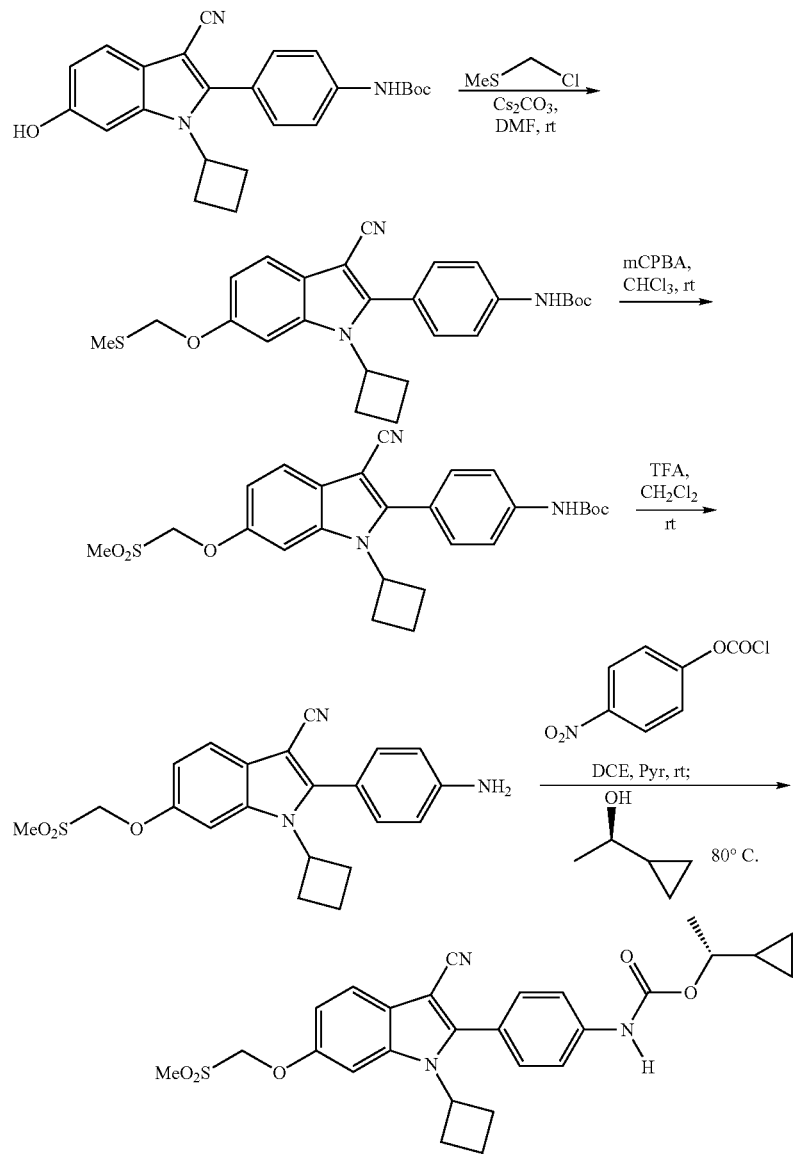

Step D: A mixture of [4-(3-Chloro-6-Methoxy-1H-indol-2-yl)-phenyl]-carbamic acid isopropyl ester (50 mg, 0.14 mmol), Cs₂CO₃ (95 mg, 0.29 mmol), bromomethylcyclopropane (18 μL, 0.18 mmol), and DMF (200 μL) was stirred at Step A: [4-(3-Cyano-1-cyclobutyl-6-hydroxy-1H-indol-2-yl)-phenyl]-carbamic acid tert-butyl ester (1.6 g, 4 mmol) was combined with Cs₂CO₃ (2.6 g, 8 mmol), methyl chloromethyl sulfide (410 μL, 5 mmol), and DMF (16 mL). The reaction mixture was stirred overnight at room temperature, diluted with H₂O and extracted with EtOAc. The organic layer was washed with H₂O and brine and then dried, concentrated and purified by silica gel chromatography (CH₂Cl₂) to provide [4-(3-cyano-1-cyclobutyl-6-methanesulfanylmethoxy-1H-indol-2-yl)-phenyl]-carbamic acid tert-butyl ester (1.72 g, 93%) as an off-white solid.

Step B: To [4-(3-Cyano-1-cyclobutyl-6-methanesulfanyl-methoxy-1H-indol-2-yl)-phenyl]-carbamic acid tert-butyl ester (1.35 g, 2.9 mmol) in CHCl₃ (20 mL) was added 3-Chloroperoxybenzoic acid (1.5 g, 8.7 mmol) in one portion. After 10 minutes the reaction mixture was washed with dilute NaHCO₃ solution, dried, concentrated and purified by silica gel chromatography (95:5 CH₂Cl₂/EtOAc) to yield [4-(3-cyano-1-cyclobutyl-6-methanesulfonylmethoxy-1H-indol-2-yl)-phenyl]-carbamic acid tert-butyl ester (1.11 g, 77%) as an off-white solid.

Step C: To [4-(3-Cyano-1-cyclobutyl-6-methanesulfonylmethoxy-1H-indol-2-yl)-phenyl]-carbamic acid tert-butyl ester (1.21 g, 2.47 mmol) in CH₂Cl₂ (6 mL) was added TFA (2 mL) and stirred at room temperature for 1 h. The reaction mixture was diluted in CH₂Cl₂, washed with aq. NaHCO₃, dried and concentrated. Trituration with acetone (5 mL) provided 2-(4-amino-phenyl)-1-cyclobutyl-6-methanesulfonylmethoxy-1H-indole-3-carbonitrile (891 mg, 91%) as a light pink solid.

Step D: 2-(4-Amino-phenyl)-1-cyclobutyl-6-methanesulfonylmethoxy-1H-indole-3-carbonitrile (100 mg, 0.25 mmol) was combined with p-nitrophenyl chloroformate (120 mg, 0.6 mmol), DCE (1 mL), and pyridine (60 μL, 0.75 mmol) and stirred at room temperature for 1 h. To this mixture was added (R)-1-Cyclopropylethanol (90 μL, 0.92 mmol) and then heated at 80° C. for 2 h. The reaction mixture was diluted with CH₂Cl₂ and washed with dilute aqueous NaOH solution. The organic layer was dried, concentrated and purified by silica gel chromatography (95:5 CH₂Cl₂/EtOAc) to provide (R)-[4-(3-cyano-1-cyclobutyl-6-methanesulfonylmethoxy-1H-indol-2-yl)-phenyl]-carbamic acid 1-cyclopropyl-ethyl ester (105 mg, 83%) as a white solid.

Example 1DV

Preparation of [4-(3-cyano-1-cyclobutyl-6-morpholin-4-yl-1H-indol-2-yl)-phenyl]-carbamic acid isopropyl ester (compound 2800)

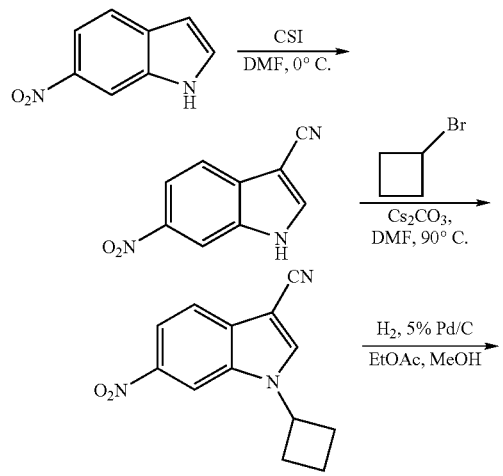

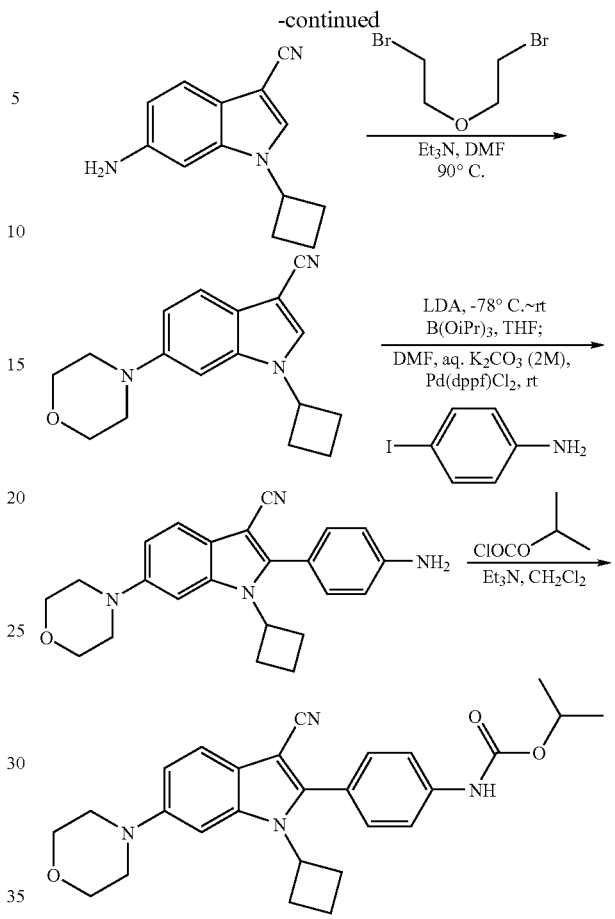

Step A: To a solution of 6-nitroindole (16.2 g, 100 mmol) in DMF (60 mL) at 0° C. was added chlorosulfonylisocyanate (10.9 mL, 125.0 mmol). The mixture was then stirred at room temperature overnight, poured into ice-water (1.0 L) and stirred for 3 h. The precipitate was filtered, washed with water and dried in air to provide 3-cyano-6-nitroindole (17.63 g, 94%).

Step B: A mixture of 3-cyano-6-nitroindole (3.74 g, 20.0 mmol), cyclobutylbromide (2.27 mL, 24.0 mmol), Cs₂CO₃ (13.04 g, 40.0 mmol) in DMF (20 mL) was stirred at 90° C. in a sealed tube for 3 days. After cooling, the mixture was poured into ice-water (200 mL) and the precipitate was filtered, washed with water and transferred to a Paar hydrogenator. The hydrogenation was carried out with 5% Pd/C (1.0 g), in MeOH (50 mL) and EtOAc (50 mL) at 60 psi of H₂ for 24 h. The mixture was filtered through Celite, washed with MeOH and concentrated to dryness to provide 6-amino-1-cyclobutyl-3-cyanoindole (3.13 g, 74%).

Step C: A mixture of 6-amino-1-cyclobutyl-3-cyanoindole (4.60 g, 21.8 mmol), bromoethylether (6.07 g, 26.16 mmol), DIEA (10.79 mL, 65.4 mmol) in DMF (100 mL) was stirred at 90° C. overnight and then poured into ice-water (1.0 L). The precipitate was filtered, washed with water, and purified on silica gel (CH₂Cl₂/EtOAc, 9:1) to provide 1-cyclobutyl-6-morpholin-4-yl-1H-indole-3-carbonitrile (5.24 g, 85%).

Step D: To a solution of 1-cyclobutyl-6-morpholin-4-yl-1H-indole-3-carbonitrile (1.20 g, 4.27 mmol), triisopropylborate (1.28 mL, 5.55 mmol) in THF (15 mL) at −78° C. was added LDA (1.5M mono THF in cyclohexane, 3.27 mL, 4.91 mmol) with stirring. The mixture was stirred at −78° C. for 10 minutes and at room temperature for 30 min followed by the addition of 4-iodoaniline (1.03 g, 4.70 mmol) and PdCl₂ (dppf) (0.16 g, 0.2 mmol). The reaction system was cooled to −78° C., flushed with nitrogen followed by the addition of DMF (30 mL) and aq. K₂CO₃ (2.0M, 6.4 mL, 12.8 mmol). The cooling bath was removed and the mixture was stirred overnight and poured into ice water (500 mL). The precipitate was filtered, washed with water, dried in air and purified on silica gel (CH₂Cl₂/EtOAc, 9:1) to give 2-(4-amino-phenyl)-1-cyclobutyl-6-morpholin-4-yl-1H-indole-3-carbonitrile (1.49 g, 94%).

Step E: A solution of 2-(4-amino-phenyl)-1-cyclobutyl-6-morpholin-4-yl-1H-indole-3-carbonitrile (0.112 g, 0.3 mmol), pyridine (1.0 mL) in CH₂Cl₂ (2.0 mL) was treated with isopropylchloroformate (1.0 M in toluene, 0.6 mL, 0.6 mmol). The mixture was stirred at room temperature for 5 h and diluted with CH₂Cl₂ (5 mL). The organic layer was separated, washed with HCl (1.0 N, 3×2 mL), water (5 mL×2) and brine (5 mL), and purified on silica gel (CH₂Cl₂/EtOAc, 9:1) to provide [4-(3-cyano-1-cyclobutyl-6-morpholin-4-yl-1H-indol-2-yl)-phenyl]-carbamic acid isopropyl ester (0.12 g, 87%).

Example 1DW

Preparation of {4-[3-cyano-1-cyclobutyl-6-(tetrahydro-pyran-4-yloxy)-1H-indole-2-yl]-phenyl}-carbamic acid isopropyl ester (compound 2616)

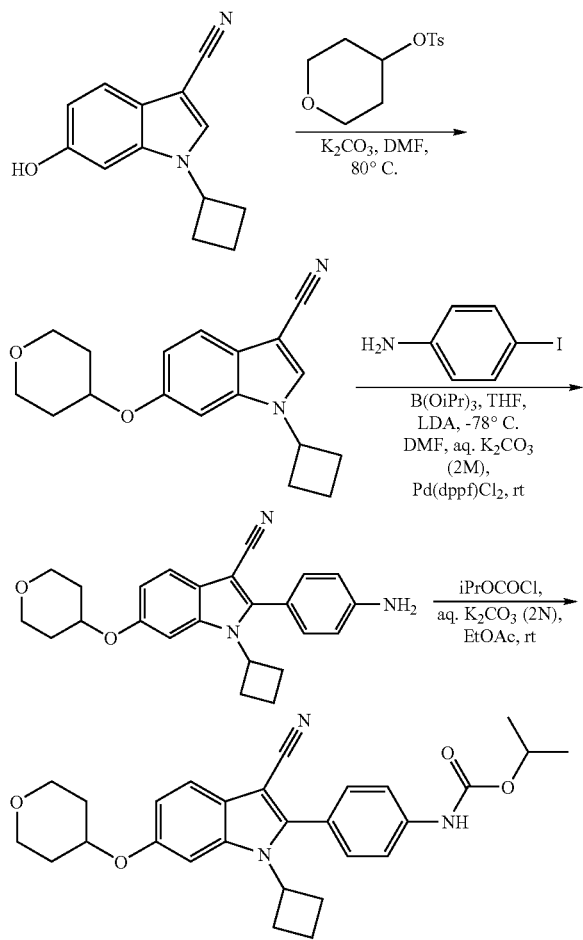

Step A: A mixture of 6-hydroxyindole (1.47 g, 6.93 mmol), toluene-4-sulfonic acid tetrahydro-pyran-4-yl ester (2.65 g, 10.42 mmol), K₂CO₃ (2.87 g, 20.77 mmol) and DMF (15 ml) was stirred at 80° C. overnight. After cooling, the reaction mixture was poured into ice-water (60 ml) to afford precipitate, which was collected by filtration, washed with water and ether/hexanes (1:1). The solid was dried under vacuum to obtain the product (1.76 g, 86%) as a brown solid.

Step B: A solution of 1-cyclobutyl-6-(tetrahydro-pyran-4-yloxy)-1H-indole-3-carbonitrile (1.68 g, 5.68 mmol) and tri-isopropyl borate (1.39 g, 7.38 mmol) in THF (15 mL) was cooled to −78° C. whereupon LDA (1.5 M in THF-cyclohexane, 4.73 mL, 7.10 mmol) was added dropwise. The reaction mixture was allowed to warm up to room temperature and continued stirring for 30 minutes. The reaction mixture was cooled to −78° C. 4-iodoaniline (1.31 g, 5.96 mmol) in DMF (10 mL), K₂CO₃ (2 M, 8.5 mL, 17.0 mmol), and PdCl₂dppf (208 mg, 0.29 mmol) were added to it in sequence. The mixture was de-gassed, back-filled with N₂ and then stirred at room temperature for 3 h. The reaction mixture was partitioned between EtOAc (50 mL) and water (50 mL). The aqueous phase was washed with more EtOAc (40 mL). The combined organic phase was washed with water (2×30 mL), brine and dried over Mg₂SO₄, concentrated and purified on silica gel (EtOAc/hexanes, 10% to 50%) to afford the product (1.81 g, 83%) as a brown solid.

Step C: To a mixture of 2-(4-amino-phenyl)-1-cyclobutyl-6-(tetrahydro-pyran-4-yloxy)-1H-indole-3-carbonitrile (897.8 mg, 2.32 mmol), K₂CO₃ (7 mL), and ethyl acetate (7 mL) was added iPrOCOCl (6.9 mL, 1 M in toluene, 6.96 mmol). The resulting mixture was stirred at room temperature overnight. The organic layer was washed with brine, dried over Mg₂SO₄, concentrated and purified on silica gel (EtOAc/hexanes, 10% to 30%) to provide the product (1.01 g, 92%) as white solid.

Example 1DX

Preparation of [4-(3-cyano-1-cyclobutyl-6-ethylsulfanyl-1H-indole-2-yl)-phenyl}-carbamic acid 1-cyclopropyl-ethyl ester (compound 2720)

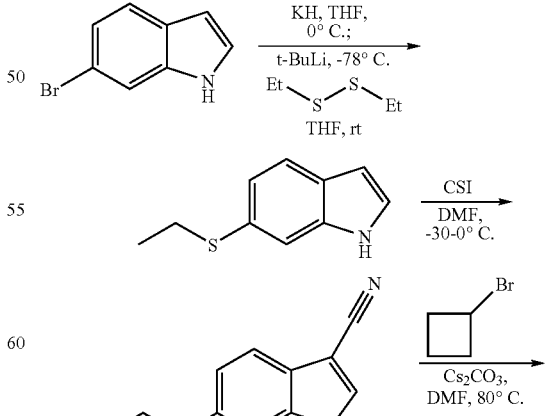

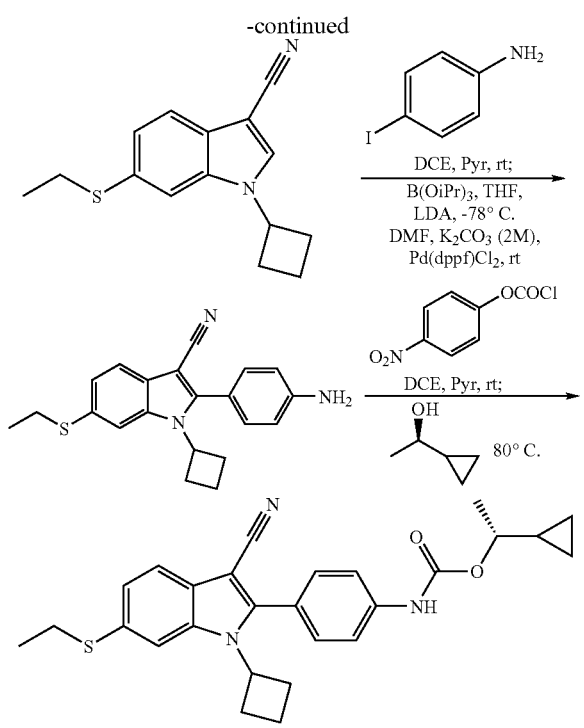

Step A: To a mixture of potassium hydride (30% wt. in mineral oil, 2.71 g, 20.2 mmol) and THF (30 mL) was added a solution of 6-bromoindole (3.98 g, 20.3 mmol) in THF (10 mL) at 0° C. After 15 minutes the solution was cooled to −78° C., and tert-butyllithium (1.5 M in pentane, 27.07 mL, 40.60 mmol) was added via syringe. The mixture was stirred at −78° C. for 10 min then ethyl disulfide (4.97 g, 40.6 mmol) in THF (10 mL) was added. The reaction mixture was allowed to warm to room temperature, poured into ice-sat.aq. NH$_4$Cl (150 mL), and then extracted with EtOAc (150 mL). The organic phase was washed with water (150 mL), brine (150 mL), dried over Mg$_2$SO$_4$, concentrated, and purified on silica gel (EtOAc/hexane 5% to 15%), to provide 6-ethylsulfanyl-1H-indole (2.75 g, 77%) as a clear liquid.

Step B: To a mixture of 6-ethylsulfanyl-1H-indole (2.75 g, 15.54 mmol) in DMF (20 mL) was added chlorosulfonyl isocyante dropwise at −30° C. The temperature was raised to 0° C. after addition and stirred for 30 minutes. The mixture was partitioned between EtOAc and water. The organic layer was washed with water, brine, dried over Mg$_2$SO$_4$, concentrated and purified on silica gel (CH$_2$Cl$_2$) to provide 6-ethylsulfanyl-1H-indole-3-carbonitrile (3.25 g, 84%) as a white solid.

Step C: A mixture of 6-ethylsulfanyl-1H-indole-3-carbonitrile (2.13 g, 10.5 mmol) Cs$_2$CO$_3$ (6.9 g, 21 mmol), cyclobutyl bromide (1.78 g, 13.2 mmol) and DMF (20 mL) was heated to 85° C. overnight and, after cooling, partitioned between ethyl acetate and water. The organic layer was washed with water, brine, dried over Mg$_2$SO$_4$, concentrated and purified on silica gel (EtOAc/hexane 5% to 30%) to provide 1-cyclobutyl-6-ethylsulfanyl-1H-indole-3-carbonitrile (2.58 g, 96%) as a light-yellow oil.

Step D: To a solution of 1-cyclobutyl-6-ethylsulfanyl-1H-indole-3-carbonitrile (2.58 g, 10.08 mmol), triisopropyl borate (2.47 g, 13.13 mmol) in THF (25 mL) was slowly added LDA (1.5 M in THF-cyclohexane, 9.41 mL, 14.1 mmol). The reaction mixture was allowed to warm to room temperature and continued stirring for 30 minutes. The reaction mixture was then cooled to −78° C. and 4-iodoaniline (2.42 g, 11.09 mmol) in DMF (10 mL), K$_2$CO$_3$ (15.5 mL, 31.00 mmol), and PdCl$_2$dppf (368.0 mg, 0.50 mmol) were added. The mixture was degassed, back-filled with N$_2$, stirred at room temperature for 3 h and then partitioned between EtOAc (40 mL) and water (40 mL). The aqueous phase was washed with more ethyl acetate (30 mL) and the combined organics were washed with water (2×40 mL), brine, dried over Mg$_2$SO$_4$, and then concentrated. A precipitate was collected by filtration, washed with water and ether afford 1.45 g of product. The filtrate was condensed and purified on silica gel (EtOAc/hexane 5% to 40) to afford a further 1.65 g of 2-(4-amino-phenyl)-1-cyclobutyl-6-ethylsulfanyl-1H-indole-3-carbonitrile (3.10 g, 89%) as a solid.

Step E: To 2-(4-amino-phenyl)-1-cyclobutyl-6-ethylsulfanyl-1H-indole-3-carbonitrile (230.0 mg, 0.66 mmol) was combined with p-nitrophenyl chloroformate (266 mg, 1.32 mmol), DCE (3.0 mL), and pyridine (104.7 mg, 1.32 mmol) and stirred at room temperature for 2 h. (R)-1-Cyclopropylethanol (115.0, 1.34 mmol) was added and mixture was heated at 80° C. for 2 h. The reaction mixture was diluted with EtOAc and washed with sat. aq. K$_2$CO$_3$ (2×15 mL), water, and brine. The organic layer was dried, concentrated and purified on silica gel (EtOAc/hexane 10%)) to provide (R)-[4-(3-cyano-1-cyclobutyl-6-ethylsulfanyl-1H-indol-2-yl)-phenyl]-carbamic acid 1-cyclopropyl-ethyl ester (209 mg, 69%) as a white solid.

Example 1DY

Preparation of {4-[1-cyclobutyl-6-(pyrimidin-2-yloxy)-1H-indole-2-yl]-phenyl}-carbamic acid 2,2,2-trifluoro-1-methyl-ethyl ester (compound 2888)

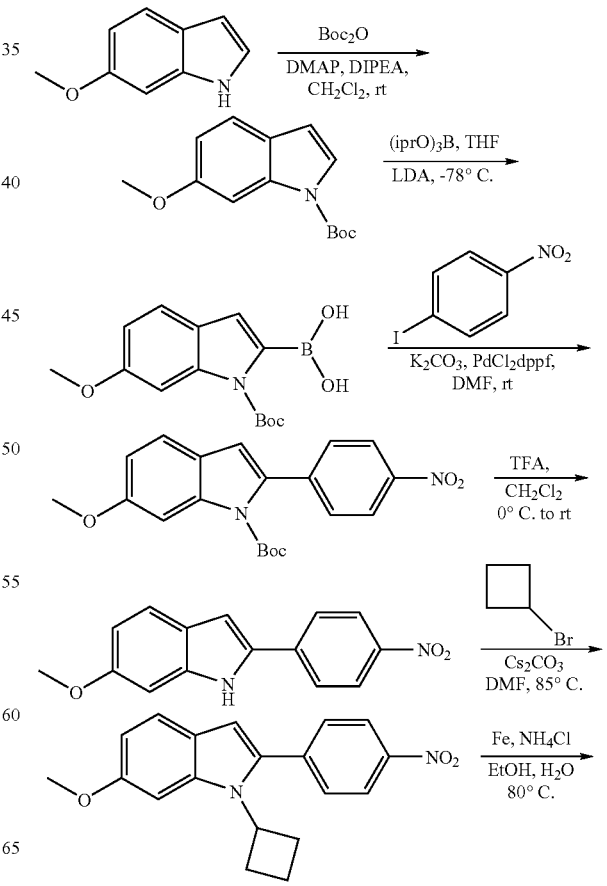

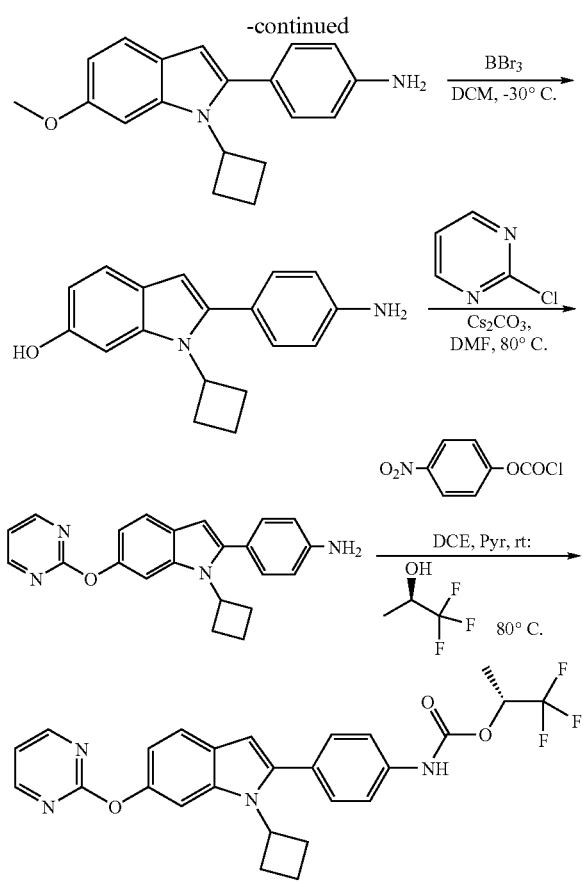

Step A: To a solution of 6-methoxyindole (18.32 g, 124.0 mmol), di-(tert-butyl)dicarbonate (35.3 g, 162.2 mmol) in $CH_2Cl_2$ (120 mL) was added DMAP (200 mg, 1.64 mmol) at 0° C. The resulting mixture was stirred at room temperature for 16 h, concentrated and partitioned between EtOAc and water. The organic layer was washed with water, brine, dried, concentrated and purified on silica gel (EtOAc/hexane 5%) to provide 6-methoxy-indole-1-carboxylic acid t-butyl ester (30.4 g, 99%) as a solid.

Step B: To a solution of 6-methoxy-indole-1-carboxylic acid tert-butyl ester (14.33 g, 57.90 mmol) triisopropyl borate (15.25 g, 81.06 mmol) in THF (80 mL) at −78° C. was added LDA slowly. The resulting mixture was stirred at room temperature for 1 h, concentrated to half of its original volume, poured into ice-water (100 mL) and acidified with 1N HCl. A precipitate was collected by filtration, washed with water and hexanes to provide 2-Boronic acid 6-methoxy-indole-1-carboxylic acid t-butyl ester (14.2 g, 85% yield) as a brown solid.

Step C: To a solution of indole 2-boronic acid from Step B (5.98 g, 20.5 mmol) and 1-iodo-4-nitrobenzene (5.37 g, 21.6 mmol) in DMF (60 mL) was added aq. $K_2CO_3$ (2M, 30.8 mL, 61.6 mmol) dropwise at 0° C. and then $PdCl_2dppf$ (375.4 mg, 0.51 mmol). The mixture was degassed by three successive cycles of vacuum pumping/$N_2$ backfilling, then stirred at room temperature for 5 h and partitioned between EtOAc and water. The organic layer was washed with water, brine, dried and concentrated. The residue was suspended in hexanes and a precipitate collected by filtration and washed with hexanes to afford the product (7.20 g, 95%) as a red solid.

Step D: To a solution of 6-methoxy-2-(4-nitro-phenyl)-indole-1-carboxylic acid tert-butyl ester (7.20 g, 19.55 mmol) in $CH_2Cl_2$ (50 mL) was added TFA (22 mL) dropwise at 0° C. The resulting mixture was stirred at room temperature for 3 h, concentrated and suspended in ether to afford a solid, which was collected by filtration, washed with ether to provide 2.43 g of a red solid as the first crop product. The filtrate was condensed, and the residue was purified on silica gel (EtOAc/hexane 5% to 20%), to provide 1.55 g of a second crop of 6-methoxy-2-(4-nitro-phenyl)-1H-indole (combined: 3.98 g, 76% yield) as a red solid.

Step E: A mixture of 6-methoxy-2-(4-nitro-phenyl)-1H-indole (2.12 g, 7.90 mmol), $Cs_2CO_3$ (5.15 g, 15.80 mmol), cyclobutyl bromide (1.28 g, 9.48 mmol) and DMF (20 mL) was heated at 85° C. for 2 days. After cooling, the reaction mixture was partitioned between EtOAc and water. The organic phase was washed with water, brine, dried, concentrated and purified on silica gel (EtOAc/hexane 5% to 20 to provide the product (0.96 g, 37%) as a yellow solid.

Step F: A mixture of 1-cyclobutyl-6-methoxy-2-(4-nitro-phenyl)-1H-indole (0.83 g, 2.60 mmol), iron powder (0.84 mg, 15.0 mmol), ammonium chloride (0.96 g, 18.0 mmol), and EtOH/water (25 mL/8 mL) was stirred at 80° C. for 1 h and concentrated. The residue was suspended in DMF (20 mL) and MeOH/$CH_2Cl_2$ (1:1, 20 mL). The mixture was passed through a Celite pad, washed with MeOH/$CH_2Cl_2$ (1:1), concentrated and water was added to afford a precipitate which was collected by filtration and washed with water. The solid was dissolved in $CH_2Cl_2$, dried over $MgSO_4$, concentrated and purified on silica gel (EtOAc/hexane 20%) to provide 4-(1-cyclobutyl-6-methoxy-1H-indole-2-yl)-phenylamine (0.57 mg, 75%) as a white solid.

Step G: To a solution of 4-(1-cyclobutyl-6-methoxy-1H-indole-2-yl)-phenylamine (518.5 mg, 1.77 mmol) in $CH_2Cl_2$ (15 mL) was added borontribromide (1.33 g, 5.31 mmol) at 30° C. The resulting mixture was stirred at 0° C. for 2 h, poured into ice-water, neutralized with aq $KHCO_3$ and then extracted with EtOAc. The aqueous phase was washed with more EtOAc and the combined organics were washed with water, brine, dried, concentrated and purified on silica gel (EtOAc/hexane 20%) to afford the product (480 mg, 98%) as a white solid.

Step H: A mixture of 2-(4-amino-phenyl)-1-cyclobutyl-1H-indole-6-ol (480 mg, 1.72 mmol), $Cs_2CO_3$ (1.12 g, 3.45 mmol), 2-chloropyridine (296 mg, 2.60 mmol) and DMF (3 mL) was stirred at 50° C. overnight. After cooling, the mixture was partitioned between EtOAc and water. The aqueous phase was washed with more ethyl acetate and the combined organics were washed with water, brine, dried, concentrated and purified on silica gel (EtOAc/hexane 25%) to afford the product the product (567 mg, 92% yield) as a white sold.

Step I: Prepared as in Example 1DX, step E.

Example 1DZ

Preparation of {4-[3-cyano-1-cyclobutyl-6-(1,1-dioxo-hexahydro-1$\lambda^6$-thiopyran-4-yloxy)-1H-indol-2-yl]-phenyl}-carbamic acid isopropyl ester (compound 3182)

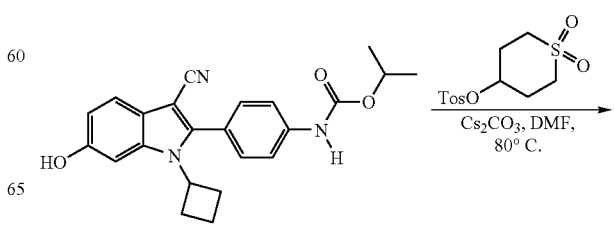

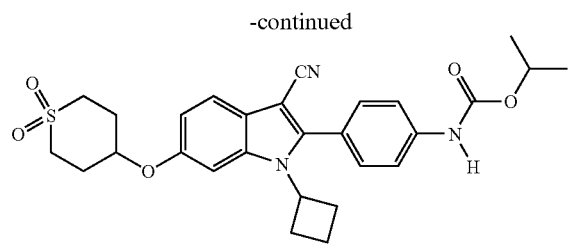

Step A: To tetrahydrothiopyran-4-one in CH₃CN (50 mL) and H₂O (35 mL) at 0° C. was added in portions over 1 hour a mixture of oxone (70.5 g, 115 mmol) and NaHCO₃ (29.9 g, 356 mmol). The reaction mixture was then stirred at room temperature for 1 h, diluted in CH₃CN (250 mL) and filtered. The filtrate was concentrated, suspended in acetone and filtered. 1,1-Dioxo-tetrahydrothiopyran-4-one (6.3 g, quantitative yield) was obtained as a white solid.

Step B: To 1,1-dioxo-tetrahydrothiopyran-4-one (6.3 g, 36 mmol) in H₂O (55 mL) was added, in portions, sodium borohydride (720 mg, 18.9 mmol). The reaction mixture was stirred at room temperature for 30 minutes and then the pH was adjusted to 4 with aq. HCl. The reaction mixture was concentrated and suspended in acetone and filtered. The filtrate was concentrated and triturated with ether/hexane to provide 1,1-dioxo-tetrahydrothiopyran-4-ol (5.63 g, 90%) as a white solid.

Step C: 1,1-Dioxo-tetrahydrothiopyran-4-ol (1.0 g, 6.6 mmol), pyridine (10 mL), and tosyl chloride (1.6 g, 8.4 mmol) were combined and stirred at room temperature overnight. The reaction mixture was concentrated, diluted in EtOAc and washed with aqueous HCl and brine. The organic layer was dried, concentrated and triturated with hexane to yield O-tosyl-1,1-dioxo-tetrahydrothiopyran-4-ol (1.073 g, 53%) as a white solid.

Step D: [4-(3-Cyano-1-cyclobutyl-6-hydroxy-1H-indol-2-yl)-phenyl]-carbamic acid isopropyl ester (90 mg, 0.23 mmol) was combined with Cs₂CO₃ (156 mg, 0.48 mmol), DMF (0.9 mL), and O-tosyl-1,1-dioxo-tetrahydrothiopyran-4-ol (96 mg, 0.32 mmol). The reaction mixture was heated overnight at 80° C., diluted with H₂O and extracted with EtOAc. The organic layer was washed with H₂O and brine and then dried, concentrated and purified by silica gel chromatography (95:5 CH₂Cl₂/EtOAc) to provide 4-[3-cyano-1-cyclobutyl-6-(1,1-dioxo-hexahydro-1λ⁶-thiopyran-4-yloxy)-1H-indol-2-yl]-phenyl}-carbamic acid isopropyl ester (66 mg, 56%) as a white solid.

Example 1EA

Preparation of 1-cyclobutyl-2-[4-(4-methyl-thiazol-2-ylamino)-phenyl]-6-(pyrimidin-2-yloxy)-1H-indole-3-carbonitrile (compound 3180)

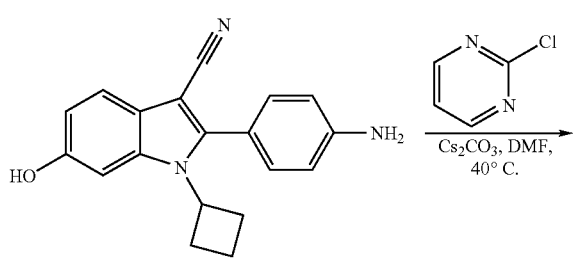

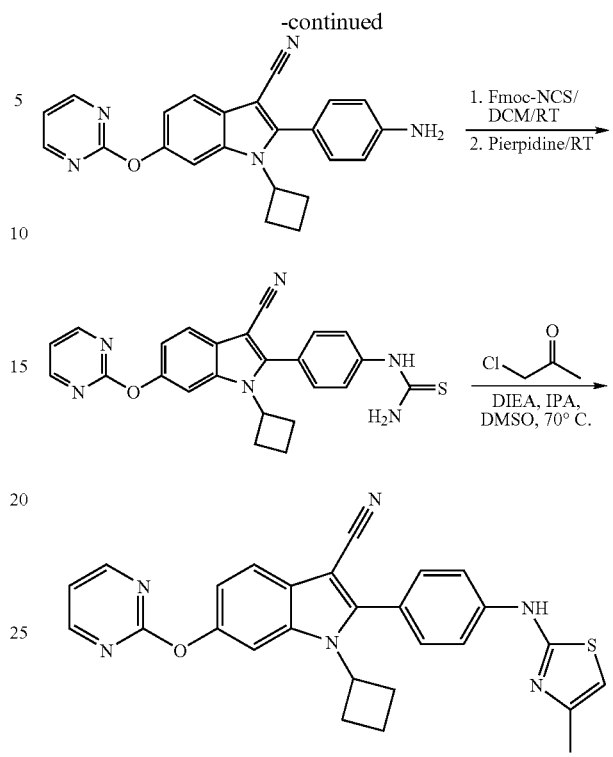

Step A: Prepared as in Example 1EA, step H.

Step B: 1. A solution of 6-pyrimidin-indole aniline (2.25 g, 5.90 mmol) prepared in Step A, Fmoc-NCS (1.74 g, 6.19 mmol) and CH₂Cl₂ (15 mL) was stirred at room temperature for 2 h, concentrated and washed with ethyl ether to afford Fmoc-indole-urea used without further purification. To the above solid was added CH₂Cl₂ (30 mL) and piperidine (5 mL). The resulting mixture was stirred at room temperature for 14 h, concentrated, washed with ether, dried and concentrated to afford the product (2.5 g, 96%) as a light-brown solid.

Step D: To a mixture of indole thiourea obtained in step C (150 mg, 0.34 mmol), DIPEA (88 mg, 0.68 mmol), isopropanol (3.5 mL) and DMSO (2.0 mL) was added 1-chloro-propan-2-one (92.5 mg, 47.6 mmol). The resulting mixture was stirred at 70° C. for 2 days. After cooling, the reaction mixture was partitioned between EtOAc and water and the organic layer was washed with water, brine, dried over MgSO₄, and purified on silica gel (EtOAc/hexane 25%) the product (102 mg, 63% yield) as a brown solid.

Example 1EB

Preparation of 1-cyclobutyl-2-[4-(2,5-dimethyl-2H-pyrazol-3-ylamino)-phenyl]-6-(pyrimidin-2-yloxy)-1H-indole-3-carbonitrile (compound 3285)

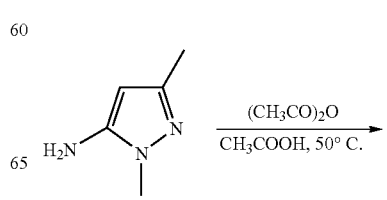

-continued

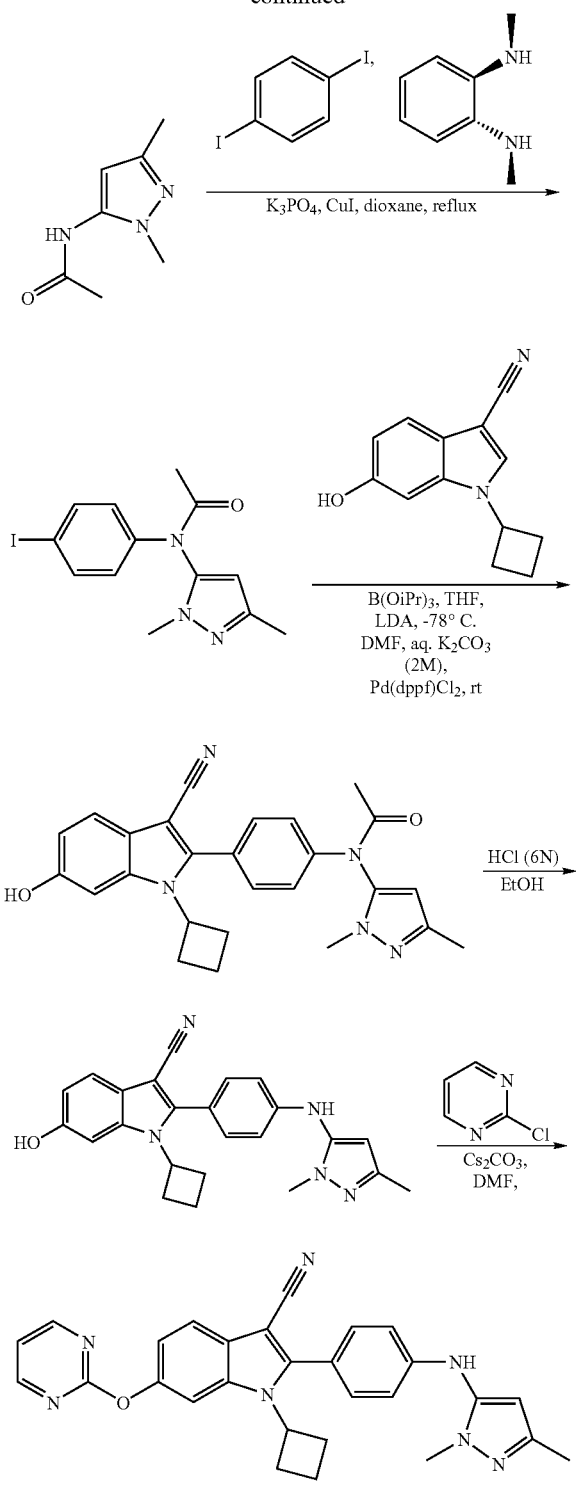

Step A: A mixture of 2,5-dimethyl-2H-pyrazol-3-ylamine (2.53 g, 22.8 mmol), acetic anhydride (2.67 g, 26.2 mmol) and acetic acid (10 mL) was stirred at 50° C. for 3 h. After cooling, the mixture was treated with sat. aq. NaHCO₃ to afford a precipitate, which was collected by filtration, washed with water and hexanes, and dried to provide the product (3.43 g, quant.) as a white solid.

Step B: To N-(2,5-dimethyl-2H-pyrazol-3-yl)-acetamide (2.01 g, 13.1 mmol), 1,4-diiodobenzene (5.20 g, 15.8 mmol), K₃PO₄ (5.57 g, 26.2 mmol), CuI (125 mg, 0.66 mmol), and dioxane (50 mL), was added N,N-dimethyl-cyclohexane-1, 2-diamine. The mixture was degassed by three successive cycles of vacuum pumping/N₂ backfilling, then stirred at reflux for 14 h. After cooling, the mixture was partitioned between EtOAc and water and the organic layer was washed with water, brine, dried over Mg₂SO₄, concentrated and purified on silica gel (EtOAc/CH₂Cl₂ 20%) to afford the product (4.91 g, 69%) as a white solid.

Step C. Prepared N-[4-cyano-1-cyclobutyl-6-hydroxy-1H-indole-yl)-phenyl]-N-(2,5-dimethyl-2H-pyrazol-3-yl)-acetamide (2.12 g, 86% yield) as in Example 1EI, Step D.

Step D. A mixture of N-[4-cyano-1-cyclobutyl-6-hydroxy-1H-indole-yl)-phenyl]-N-(2,5-dimethyl-2H-pyrazol-3-yl)-acetamide (1.54 g, 3.50 mmol) and HCl (6N, 6 mL) was stirred at 80° C. for 15 h. After cooling, the reaction mixture was partitioned between EtOAc and water and organic layer was washed with sat. aq. NaHCO₃, water, brine, dried over MgSO₄, and concentrated. The residual solid was washed with ether to afford the product (1.27 g, 92% yield) as a brown solid.

Step E: 1-cyclobutyl-2-[4-(2,5-dimethyl-2H-pyrazol-3-ylamino)-phenyl]-6-(pyrimidin-2-yloxy)-1H-indole-3-carbonitrile (PS102656) was prepared as in Example 3, step H.

Example 1EC

{4-[3-Cyano-1-cyclobutyl-6-(2-methanesulfonyl-vinyloxy)-1H-indol-2-yl]-phenyl}-carbamic acid tert-butyl ester (compound 3301)

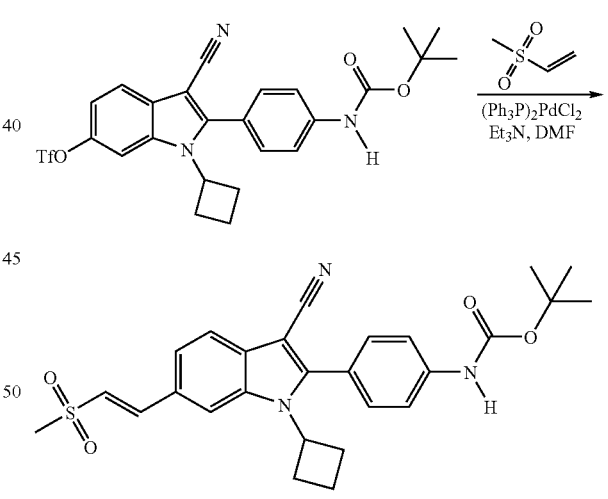

To a solution of the indole triflate (1.07 g, 2.00 mmol) in DMF (2 mL) was added methyl vinyl sulfone (432 mg, 3.99 mmol), bis(triphenylphosphine)palladium(II)chloride (72 mg, 0.103 mmol) and Et₃N (0.84 mL, 6.03 mmol). The mixture was purged with nitrogen and heated at 90° C. for 20 h then additional methyl vinyl sulfone (106 mg, 1 mmol) and bis(triphenylphosphine)palladium (72 mg, 0.10 mmol) were added. The mixture was heated for 20 h at 90° C. then cooled to room temperature. Water (14 mL) was added and the solid was filtered, washed with water, dried and purified on silica gel (EtOAc/1:1 CH₂Cl₂-hexanes 0-10%) to give the product (250 mg, 26%) as a tan solid.

Example 1ED

Preparation of (R)-{4-[3-cyano-1-cyclopropyl-6-(pyrimidin-2-yloxy)-1H-indol-2-yl]-phenyl}-carbamic acid 1-cyclopropylethyl ester (compound 3321)

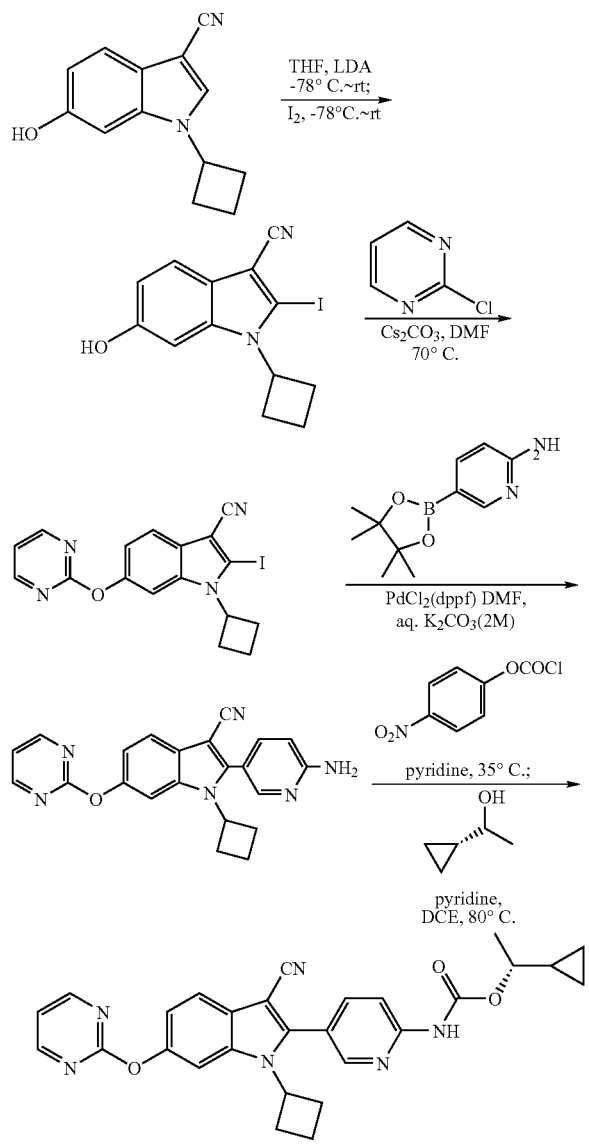

Step A: T6 a solution of 1-cyclobutyl-6-hydroxy-1H-indole-3-carbonitrile (4.24 g, 20 mmol) in THF (60.0 mL) at −78° C. was added LDA (30.7 mL, 46.0 mmol) and iodine (7.62 g, 30.0 mmol). The mixture was stirred at −78° C. for 10 min, warmed to room temperature and stirred for 3 h. The reaction mixture was poured into ice-water (500 mL) and the precipitate was filtered and washed with water and $CH_2Cl_2$. After drying in air the crude iodide obtained (3.99 g) was taken up in DMF (25 mL) and $Cs_2CO_3$ (9.78 g, 30.0 mmol) and 2-chloropyrimidine (2.18 g, 19.0 mmol) were added to this solution. The mixture was stirred at 70° C. for 30 min, poured into ice water (200 mL) and the precipitate was collected on a filter, washed with water and purified on silica gel ($CH_2Cl_2$/EtOAc, 9.75:0.25) to provide 1-cyclobutyl-2-iodo-6-(pyrimidin-2-yloxy)-1H-indole-3-carbonitrile (1.52 g, 47%).

Step B: The iodide obtained in Step A (0.83 g, 2.0 mmol), 5-(4,4,5,5-eetramethyl-[1,3,2]dioxaborolan-2-yl)-pyridin-2-ylamine (0.48 g, 2.2 mmol), $PdCl_2(dppf)$ (0.07 g, 01 mmol) were mixed with DMF (10.0 mL), followed by the addition of aq. $K_2CO_3$ (2.0 M, 3.0 mL, 6.0 mmol). The mixture was stirred at 80° C. overnight and poured into ice-water (100 mL). The precipitate was filtered, washed with water and purified on silica gel ($CH_2Cl_2$/EtOAc/MeOH, 5:5:0.2) to furnish 2-(6-amino-pyridin-3-yl)-1-cyclobutyl-6-(pyrimidin-2-yloxy)-1H-indole-3-carbonitrile (0.61 g, 80%).

Step C: A mixture of 2-(6-amino-pyridin-3-yl)-1-cyclobutyl-6-(pyrimidin-2-yloxy)-1H-indole-3-carbonitrile (115 mg, 0.3 mmol), 4-nitrophenylchloroformate (91 mg, 0.45 mmol) in pyridine (1.0 mL) was stirred at 30° C. for 2 h, followed by the addition of (R)-1-cyclopropylethanol (150 µL, 1.5 mmol). The mixture was stirred at 80° C. overnight and diluted with water (10 mL) and $CH_2Cl_2$ (5 mL). The organic layer was washed with water (3×5 mL), HCl (2N, 3×5 mL), sat. aq. $NaHCO_3$ (3×5 mL) and and purified on silica gel ($CH_2Cl_2$/EtOAc, 1:9) to provide (R)-{4-[3-cyano-1-cyclopropyl-6-(pyrimidin-2-yloxy)-1H-indol-2-yl]-phenyl}-carbamic acid 1-cyclopropylethyl ester (25 mg, 17%).

Example 2

Screening of Low Molecular Weight Compounds Using a Cell-Based HCV IRES Monocistronic Translation Assay Chemical libraries are screened using a cell-based monocistronic HCV IRES-regulated translation assay designed to closely mimic natural HCV mRNA translation and then compound analogs are made based on hits in the chemical libraries and screened as well. A DNA construct is prepared, termed pHCVIRESmono, in which HCV IRES sequences (HCV 2b, nucleotides 18-347) are inserted between a promoter and the firefly luciferase (Fluc) reporter gene. A stably transfected HepG 2 (hepatoblastoma) cell line (termed HepGmono-4) or a Huh7 cell line (termed Huhmono 7), or a Hela-cell line (termed Helamono), are established by transfection with the pHCVIRESmono DNA by selecting for resistance to hygromycin.

Example 3

Determination of Selectivity for HCV IRES-Regulated Translation Using the Cell-Based Cap-Dependent Translation Assays Since translation assays are used to screen HCV IRES inhibitors, the selected hits may specifically act on HCV IRES-driven translation or may modulate general protein synthesis in mammalian cells. The compounds that act on general translation will most likely have significant toxicity. To address this possibility, various cell-based cap-dependent translation assays are established for the further evaluation of all selected compounds. Plasmid DNAs containing 130 nucleotides of vector sequence 5' to Fluc are constructed. This construct is referred to herein as pLuc. A stable cell line is established in cap-dependent translation assays using 293T cells (a human embryonic kidney cell line). HepGmono-4 and pLuc are treated with compound for 20 hours and activity is determined by quantifying the Fluc signal. A five-fold selectivity between the HCV IRES and cap-dependent translation is considered to be desirable. Using these cell-based cap-dependent translation assays, compounds are identified that show $IC_{50}$ values that are at least 5-fold greater in the cap-dependent translation assays than in the HCV IRES translation assay.

Western blotting assays are used to further demonstrate that compounds selectively inhibit HCV IRES-driven translation. Both HepGmono-4 and pLuc cells are treated with the compounds as described above, following treatment with the test compounds for 20 hours, cells are collected and lysed in Laminin buffer containing 0.5% SDS. Proteins are separated on a 10% SDS-PAGE, then transferred onto a nitrocellulose membrane, and blotted using antibodies against Fluc (RDI) and β-actin (Oncogene). For example, some compounds of the present invention are tested in this manner.

Testing conditions for these cell lines are optimized and the effects of mRNA level on activity of the compounds are controlled by quantitating Fluc mRNA levels by RT real-time PCR. For example, some of the compounds of the present invention are tested in this manner.

Example 4

Evaluation of the Selectivity for HCV IRES-Driven Translation Using Cellular IRES-Mediated Translation Assays A number of human mRNAs have been shown to harbor IRES elements (18, 19, 39, 44, 45, 91, 126, 130). Although the primary sequences and secondary structures of the HCV IRES are different from those of cellular IRESs, an important test for selectivity is to determine whether the selected compounds are active against cellular IRESs. The VEGF IRES has poor initiation activity in in vitro assays, but demonstrates substantial activity in cell-based translation assays (18, 45). For example, some of the compounds of the present invention are tested Example 5

Evaluation of Cytotoxicity

Effects on cell proliferation are a critical issue for any drug discovery effort. Therefore, a cell proliferation/cytotoxicity assay is used to eliminate any compounds that affect mammalian cell growth. The effects of the selected hits on cell proliferation are tested in human cell lines 293 T and Huh7 (a human hepatoblastoma cell line). Cells are grown in Dulbecco's modified Eagle's medium supplemented with 10% fetal bovine serum, L-glutamine, penicillin, and streptomycin. Cells in log phase are treated with test compounds for three days, with 250 µM being the highest concentration of test compound used. The effect of the compounds on cell proliferation is assessed by using the CellTiter 96 AQueous One Solution Cell Proliferation Assay (Promega, Madison, Wis.). Compounds that have at least 5-fold higher $CC_{50}$ values relative to $IC_{50}$ values in HepGmono-4 are considered to have a sufficient window between activity and cytotoxicity and are selected for further evaluation.

Example 6

Evaluation of the Efficacy of the Compounds in the HCV Replicon System

The lack of reliable and readily accessible cell-culture and small animal models permissive for HCV replication has limited the development of new anti-HCV agents. Self-replicating subgenomic HCV systems, termed HCV replicons, have recently been described and have been widely used to assess the efficacy of anti-HCV inhibitors (8, 70, 104). Interferon (IFN) α and inhibitors of the HCV protease and polymerase have been reported to be active in the HCV replicon system (8, 17, 32, 68, 69, 117).

HCV replicons that include bicistronic and monocistronic systems are identified and assays for testing the HCV IRES inhibitors are established. In the bicistronic replicons, the HCV IRES directs the expression of the selective marker (Neo and/or a Fluc reporter), and the EMCV IRES mediates the expression of viral non-structural proteins. In the monocistronic replicon, the HCV IRES directly mediates viral protein synthesis. The HCV IRES inhibitors are analyzed in the bicistronic replicon by quantitating the Fluc reporter signal. Replicon-containing cells are cultured with the compounds of the invention for 2 days or for 3 days. Interferon (IFN) α is used as a positive control. For example, some compounds of the present invention are tested in this manner.

TABLE 1A

| Compound | Melting Point (° C.) | Mass Spec [M + H] | Replicon $IC_{50}$ µM 2-day | Replicon $IC_{50}$ µM 3-day | $^1$H NMR Data |
|---|---|---|---|---|---|
| 1330 | 148-151 | 394.18 | ** | | |
| 1331 | 157-160 | 408.20 | ** | | |
| 1332 | 213-215 | 440.2 | ** | | |
| 1333 | 160-164 | 482.2 | ** | | |
| 1334 | 87-88 | 460.25 (M − H+) | ** | *** | |
| 1335 | 179-180 | 488.31 | ** | | |
| 1336 | 173-176 | 488.31 (M − H+) | ** | | |
| 1337 | 183-184 | | ** | | |
| 1338 | 186-187 | 389.4 | ** | | |
| 1339 | 177-178 | 432.3 | ** | | |
| 1340 | 249-250 | 428.3 | *** | | |
| 1341 | 170-171 | 416.3 | ** | | |
| 1342 | 232-234 | 498.17 | *** | *** | |
| 1343 | 155-158 | 405.24 | ** | | |
| 1344 | 294-296 | 398.15 | * | | |
| 1345 | 201-203 | 401.21 (M − H+) | *** | *** | |
| 1346 | 226-228 | 416.29 | * | | |
| 1347 | Foam | 437.10 | ** | | |

TABLE 1A-continued

| Compound | Melting Point (° C.) | Mass Spec [M + H] | Replicon IC$_{50}$ µM 2-day | Replicon IC$_{50}$ µM 3-day | $^1$H NMR Data |
|---|---|---|---|---|---|
| 1348 | 134.2-139.5 | 392.1 | ** | | (CDCl3, 300 MHz), δ 7.63 (d, J = 8.7 Hz, 1H), 7.53 (d, J = 8.7 Hz, 2H), 7.32 (d, J = 8.7 Hz, 2H), 6.96 (dd, J = 2.1 Hz and 8.7 Hz, 1H), 6.87 (d, J = 1.8 Hz, 1H), 4.14 (q, J = 6.9 Hz, 2H), 3.90 (s, 3H), 3.49-3.40 (m, 4H), 1.36-1.21 (m, 9H). |
| 1349 | 111.3-116.5 | 423.4 | ** | | (CDCl3, 300 MHz), δ 7.63 (d, J = 8.7 Hz, 1H), 7.52 (d, J = 8.4 Hz, 2H), 7.31 (d, J = 7.8 Hz, 2H), 6.96 (dd, J = 2.1 Hz and 8.7 Hz, 1H), 6.87 (d, J = 1.8 Hz, 1H), 4.61-4.43 (m, 1H), 4.14 (q, J = 7.5 Hz, 2H), 3.90 (s, 3H), 2.97-2.90 (m, 3H), 1.34 (t, J = 7.2 Hz, 3H), 1.30-1.16 (m, 6H). |
| 1350 | 173.6-182.1 | 435.5 | ** | | (CDCl3, 300 MHz), δ 7.63 (d, J = 8.1 Hz, 1H), 7.52 (d, J = 8.4 Hz, 2H), 7.30 (d, J = 8.4 Hz, 2H), 6.97 (d, J = 7.5 Hz, 1H), 6.87 (s, 1H), 4.14 (q, J = 6.6 Hz, 2H), 3.90 (s, 3H), 3.64-3.48 (m, 4H), 1.72-1.62 (m, 6H), 1.34 (t, J = 6.3 Hz, 3H). |
| 1351 | 197.1-205.3 | 421.5 | ** | | (CDCl3, 300 MHz), δ 7.63 (d, J = 8.7 Hz, 1H), 7.52 (d, J = 8.7 Hz, 2H), 7.33 (d, J = 8.4 Hz, 2H), 6.96 (dd, J = 1.8 Hz and 8.4 Hz, 1H), 6.88 (s, 1H), 4.14 (q, J = 7.2 Hz, 2H), 3.90 (s, 3H), 3.60 (t, J = 6.6 Hz, 2H), 3.51 (t, J = 6.6 Hz, 2H), 2.04-1.91 (m, 4H), 1.34 (t, J = 6.9 Hz, 3H). |
| 1352 | Foam | 439.25 | ** | | |
| 1353 | Foam | 441.24 | ** | | |
| 1354 | 110-115 | 488.3 | ** | | |
| 1355 | 163-164 | 400.26 (M − H+) | ** | | |
| 1356 | 251-252 | 550.4 | ** | *** | |
| 1357 | 278-280 | 554.3 | ** | ** | |
| 1358 | 260-261 | 554.3 | *** | | |
| 1359 | 254-256 | 504.3 | ** | | |
| 1360 | 163-165 | 453.22 | *** | ** | |
| 1361 | 238-241 | 467.22 | ** | | |
| 1362 | 236-238 | 542.27 | ** | | |
| 1363 | 168-171 | 451.21 | ** | ** | |
| 1364 | 128-131 | 451.21 | ** | | |
| 1365 | 112-114 | 436.3 | *** | ** | |
| 1366 | 168-169 | 336.3 | ** | | |
| 1367 | 191-194 | 394.2 | *** | ** | |
| 1368 | 175-177 | 408.2 | *** | *** | |
| 1369 | 154-156 | 422.2 | *** | *** | |
| 1370 | 145-148 | 436.2 | *** | *** | |
| 1371 | 166-168 | 426.2 | *** | *** | |
| 1372 | 107-109 | 470.2 | *** | *** | |
| 1373 | 148-151 | 442.1 | ** | | |
| 1374 | 158-161 | 514.3 | ** | | |
| 1375 | 108-120 | 418.2 | ** | | |
| 1376 | 165-167 | 391.2 | ** | | |
| 1377 | 161-163 | 417.2 | ** | | |
| 1378 | 147-150 | 435.3 | ** | | |
| 1379 | 152-155 | 461.4 | ** | | |
| 1380 | 216-218 | 447.3 | ** | | |
| 1381 | 151-154 | 433.3 | ** | | |
| 1382 | 110-114 | 495.4 | ** | | |
| 1383 | 196-198 | 524.4 | ** | | |
| 1384 | 175-176 | 483.3 | ** | | |
| 1385 | 122-127 | 408.0 | ** | | (CDCl3, 300 MHz), δ 7.63 (d, J = 8.7 Hz, 1H), 7.54-7.51 (m, 2H), 7.34-7.29 (m, 2H), 6.96 (dd, J = 2.4 Hz and 8.7 Hz, 1H), 6.87 (d, J = 2.1 Hz, 1H), 4.13 (q, J = 7.2 Hz, 2H), 3.90 (s, 3H), 3.64-3.56 (m, 4H), 3.40 (d, J = 1.8 Hz, 3H), 3.14 (d, J = 29.7 Hz, 3H), 1.34 (t, J = 7.2 Hz, 3H). |
| 1386 | 213-214 | 405.34 | ** | | $^1$H NMR (300 MHz, DMSO-d$_6$): δ 8.44 (1H, s), 7.72 (2H, d, J = 8.8 Hz), 7.50 (1H, d, J = 8.8 Hz), 7.44 (2H, d, J = 8.8 Hz,), 7.24 (1H, d, J = 2.0 Hz), 6.91 (1H, dd, J = 8.8, 2.0 Hz), 4.15 (2H, t, J = 7.2 Hz), 3.84 (3H, s), 3.36 (4H, q, J = 7.0 Hz), 1.56 (2H, hx, J = 7.0 Hz), 1.10 (6H, t, J = 7.0 Hz), 0.64 (3H, t, J = 7.2 Hz). |

TABLE 1A-continued

| Compound | Melting Point (° C.) | Mass Spec [M + H] | Replicon IC$_{50}$ µM 2-day | Replicon IC$_{50}$ µM 3-day | $^1$H NMR Data |
|---|---|---|---|---|---|
| 1387 | 65-70 | 477.38 | * | | $^1$H NMR (300 MHz, DMSO-d$_6$): δ 8.54 (1H, s), 7.40 (2H, d, J = 8.8 Hz), 7.28 (1H, d, J = 8.5 Hz), 7.24 (2H, d, J = 8.8 Hz), 6.89 (1H, d, J = 2.0 Hz), 6.62 (1H, dd, J = 8.5, 2.0 Hz), 6.06 (1H, t, J = 5.7 Hz), 3.98-3.91 (2H, m), 2.85 (2H, q, J = 6.1 Hz), 1.30-1.20 (2H, m), 0.76 (9H, s), 0.67 (3H, t, J = 7.3 Hz), 0.00 (6H, s). |
| 1388 | 161-164 | 429.25 | ** | | |
| 1389 | 171-173 | 500.2 | *** | | |
| 1390 | 217-223 | No ionization | ** | | |
| 1391 | 195-200 | 433.25 | ** | | |
| 1392 | 193-197 | 478.39 (ES−) | *** | | |
| 1393 | 193-197 | 478.39 (ES−) | *** | | |
| 1394 | 96.5-100.6 | 502.2 | *** | | (MeOD, 300 MHz), δ 7.78 (d, J = 8.4 Hz, 2H), 7.52-7.45 (m, 3H), 7.17 (s, 1H), 7.02 (dd, J = 1.8 Hz and 8.4 Hz, 1H), 4.40 (t, J = 4.2 Hz, 2H), 4.19 (q, J = 6.9 Hz, 2H), 3.89 (t, J = 4.2 Hz, 4H), 3.63-3.59 (m, 4H), 3.45 (t, J = 6.3 Hz, 2H), 3.29-3.23 (m, 4H), 1.85-1.77 (m, 1H), 1.25 (t, J = 7.2 Hz, 3H), 0.98-0.86 (m, 4H). |
| 1395 | 95.9-99 | 486.3 | ** | *** | (MeOD, 300 MHz), δ 7.79 (d, J = 8.4 Hz, 2H), 7.54-7.48 (m, 3H), 7.19 (s, 1H), 7.02 (d, J = 7.8 Hz, 1H), 4.46-4.41 (m, 2H), 4.21 (q, J = 6.9 Hz, 2H), 3.84-3.79 (m, 4H), 3.66-3.61 (m, 4H), 3.51 (br, 2H), 2.96 (s, 3H), 2.32 (br, 2H), 1.81-1.79 (m, 1H), 1.26 (t, J = 7.2 Hz, 3H), 0.97-0.87 (m, 4H). |
| 1396 | 192-198 | 455.30 | *** | *** | |
| 1397 | 170-171 | 434.27 | *** | *** | |
| 1398 | 166-167 | 448.27 | *** | *** | |
| 1399 | 125-126 | 448.27 | *** | *** | |
| 1400 | 168-169 | 474.26 | ** | | |
| 1401 | 182-183 | 516.25 | *** | *** | |
| 1402 | 144-145 | 494.20 (M − H+) | *** | *** | |
| 1403 | 168-171 | 483.1 | *** | | |
| 1404 | 174-176 | 407.2 | *** | | |
| 1405 | 182-185 | 421.3 | *** | *** | |
| 1406 | 141-144 | 422.3 | *** | *** | |
| 1407 | 137-140 | 448.3 | ** | | |
| 1408 | 199-203 | 419.41 | *** | | |
| 1409 | 152-155 | 447.26 | *** | | |
| 1410 | 153-155 | 486.7 | *** | | |
| 1411 | 173-174 | 506.3 | *** | *** | |
| 1412 | 198-200 | 446.00 (M − H+) | ** | | $^1$H NMR (300 MHz, CDCl$_3$): δ 7.61 (1H, d, J = 8.8 Hz), 7.50 (2H, d, J = 8.6 Hz), 7.36 (2H, d, J = 8.6 Hz), 7.29 (1H, d, J = 1.9 Hz), 7.03 (1H, s), 6.99 (1H, dd, J = 8.0, J = 2.2 Hz), 4.95 (2H, m), 4.23 (2H, t, J = 4.7 Hz), 4.00 (1H, m), 2.81 (2H, t, J = 4.7 Hz), 3.49 (3H, s), 2.82 (2H, m), 2.35 (2H, m), 1.80 (2H, m), 1.20 (6H, d, J = 6.3 Hz). |
| 1413 | 90.2-95.4 | 474.1 | ** | | (CD3CN, 300 MHz), δ 9.04 (s, 1H), 7.80 (d, J = 8.7 Hz, 2H), 7.57 (d, J = 8.4 Hz, 1H), 7.50 (d, J = 8.4 Hz, 2H), 7.15 (d, J = 1.5 Hz, 1H), 6.99 (dd, J = 1.5 Hz and 8.7 Hz, 1H), 4.44 (t, J = 4.2 Hz, 2H), 4.15 (q, J = 7.2 Hz, 2H), 3.59-3.51 (m, 6H), 2.90 (s, 3H), 2.84 (s, 6H), 1.78-1.72 (m, 1H), 1.25 (t, J = 7.2 Hz, 3H), 0.93-0.82 (m, 4H). |
| 1414 | 163.9-168.8 | 516.5 | ** | | (CD3CN, 300 MHz), δ 8.90 (s, 1H), 7.79 (d, J = 8.7 Hz, 2H), 7.56 (d, J = 8.7 Hz, 1H), 7.50 (d, J = 8.7 Hz, 2H), 7.11 (d, J = 1.5 Hz, 1H), 6.96 (dd, J = 1.8 Hz and 8.7 Hz, 1H), 4.43 (t, J = 4.2 Hz, 2H), 4.15 (q, J = 7.2 Hz, 2H), 3.71-3.68 (m, 8H), 3.70-3.67 (m, 2H), 3.54 (br, 2H), 3.32-3.29 (m, 5H), 1.95-1.92 (m, 1H), 1.24 (t, J = 7.2 Hz, 3H), 0.90-0.82 (m, 4H). |

TABLE 1A-continued

| Compound | Melting Point (° C.) | Mass Spec [M + H] | Replicon IC$_{50}$ μM 2-day | Replicon IC$_{50}$ μM 3-day | $^1$H NMR Data |
|---|---|---|---|---|---|
| 1415 | 220-222 | 474.22 | *** | | $^1$H NMR (300 MHz, DMSO-d$_6$): δ 8.75 (1H, s), 7.62-7.39 (7H, m), 6.98 (1H, d, J = 8.8 Hz), 6.27 (1H, t, J = 5.4 Hz), 5.19 (2H, s), 4.18 (2H, q, J = 7.3 Hz), 3.05 (2H, q, J = 6.4 Hz), 2.65 (3H, s), 1.44 (2H, hx, J = 7.3 Hz), 1.18 (3H, t, J = 7.0 Hz), 0.87 (3H, t, J = 7.5 Hz). |
| 1416 | 115-121 | 489.35 | ** | | |
| 1417 | 192-193 | 466.28 | *** | | |
| 1418 | 183-185 | 533.4 | *** | *** | |
| 1419 | 121-123 | 514.5 | *** | *** | |
| 1420 | 209-215 | 515.6 | *** | *** | |
| 1421 | 138-140 | 513.3 | ** | | |
| 1422 | 201-203 | 516.6 | *** | *** | |
| 1423 | 192-193 | 474.36 | *** | ** | |
| 1424 | 65-72 | 476.33 (ES−) | ** | | |
| 1425 | 153-160 | 471.48 | *** | *** | |
| 1426 | 159-164 | 468.37 | *** | *** | |
| 1427 | 211-213 | 517.3 | *** | ** | |
| 1428 | 141-145 | 518.4 | *** | | |
| 1429 | 132-134 | 478.4 | | *** | |
| 1430 | 122-125 | 487.3 | | *** | |
| 1431 | 136-138 | 432.3 (ES−) | | *** | |
| 1432 | 187-194 | 467.47 | | *** | |
| 1433 | 153-156 | 437.50 | | *** | |
| 1434 | 221-223 | 487.6 | | *** | |
| 1435 | 161-165 | 503.5 | | *** | |
| 1436 | 76-79 | 463.4 | | *** | |
| 1437 | 74-76 | 522.4 | | *** | |
| 1438 | 76-79 | 496.4 | | *** | |
| 1439 | 74-76 | 514.4 | | ** | |
| 1440 | 232-236 | 459.43 | | *** | |
| 1441 | 192-196 | 447.40 | | ** | |
| 1442 | 144-145 | 549.2 | | ** | |
| 1443 | 199-201 | 360.1 | | *** | |
| 1444 | 189-191 | 472.4 | | *** | |
| 1445 | 112-115 | 508.4 | | *** | |
| 1446 | 207-208 | 474.4 | | *** | |
| 1447 | 220-222 | 488.4 | | *** | |
| 1448 | 182-184 | 525.4 | | *** | |
| 1449 | 180-181 | 446.3 | | *** | |
| 1450 | 162-163 | 468.41 | | ** | |
| 1451 | 163-164 | 453.41 | | *** | |
| 1452 | 183-184 | 460.44 | | *** | |
| 1453 | 183-184 | 486.49 | | *** | |
| 1454 | 183-184 | 514.53 (M − H+) | | *** | |
| 1455 | 183-184 | 472.45 | | *** | |
| 1456 | 183-184 | 520.43 (M − H+) | | *** | |
| 1457 | 183-184 | 514.43 | | *** | |
| 1458 | 183-184 | 500.49 (M − H+) | | *** | |
| 1459 | 183-184 | 500.43 (M − H+) | | *** | |
| 1460 | 183-184 | 512.34 (M − H+) | | *** | |
| 1461 | 183-184 | 472.31 (M − H+) | | ** | |
| 1462 | 183-184 | 459.43 | | ** | |
| 1463 | | 482.35 | | ** | |
| 1464 | | 496.41 | | *** | |
| 1465 | | 418.31 | | *** | |
| 1466 | 223-224 | 434.3 | | *** | |
| 2600 | 200-202 | 446.3 | | *** | |
| 2601 | 191-193 | 432.3 | | *** | |
| 2602 | 202-204 | 458.3 | | *** | |
| 2603 | 167-169 | 480.3 | | *** | |
| 2604 | 256 (decomp.) | 562.5 | | ** | |
| 2605 | 204-205 | 497.4 | | *** | |
| 2606 | 148-150 | 496.4 | | *** | |
| 2607 | 209-211 | 496.4 | | *** | |
| 2608 | 153-155 | 436.4 | | *** | |
| 2609 | 165-166 | 448.4 | | *** | |
| 2610 | 181-183 | 464.4 | | *** | |

TABLE 1A-continued

| Compound | Melting Point (° C.) | Mass Spec [M + H] | Replicon IC$_{50}$ μM 2-day | Replicon IC$_{50}$ μM 3-day | $^1$H NMR Data |
|---|---|---|---|---|---|
| 2611 | 115-116 | 462 | | *** | $^1$H NMR (300 MHz, CDCl$_3$): δ 7.62 (1H, d, J = 8.8 Hz), 7.55 (2H, d, J = 8.8 Hz), 7.42 (2H, d, J = 8.8 Hz), 7.27 (1H, d, J = 2.0 Hz), 6.98 (1H, dd, J = 8.8, 2.0 Hz), 6.73 (1H, s), 5.05 (1H, hp, J = 6.4 Hz), 4.93 (1H, p, J = 8.8 Hz), 4.25-4.21 (2H, m), 3.87-3.83 (2H, m), 3.64 (2H, q, J = 7.0 Hz), 2.91-2.78 (2H, m), 2.40-2.28 (2H, m), 2.00-1.89 (1H, m), 1.88-1.77 (1H, m), 1.32 (6H, d, J = 6.4 Hz), 1.28 (3H, t, J = 7.0 Hz). |
| 2612 | 148-150 | 461 | | *** | $^1$H NMR (300 MHz, CDCl$_3$): δ 7.62 (1H, d, J = 8.8 Hz), 7.49 (2H, d, J = 8.8 Hz), 7.38 (2H, d, J = 8.8 Hz), 7.29 (1H, d, J = 2.3 Hz), 6.99 (1H, dd, J = 8.8, 2.3 Hz), 6.75 (1H, s), 4.96 (1H, p, J = 8.9 Hz), 4.75 (1H, d, J = 7.9 Hz), 4.25-4.21 (2H, m), 4.02 (1H, m, J = 7.3 Hz), 3.90-3.86 (2H, m), 3.64 (2H, q, J = 7.0 Hz), 2.90-2.78 (2H, m), 2.40-2.28 (2H, m), 1.98-1.88 (1H, m), 1.87-1.77 (1H, m), 1.28 (3H, t, J = 7.0 Hz), 1.21 (6H, d, J = 6.6 Hz). |
| 2613 | 141-142 | 488 | | *** | $^1$H NMR (300 MHz, CDCl$_3$): δ 7.62 (1H, d, J = 8.8 Hz), 7.55 (2H, d, J = 8.8 Hz), 7.42 (2H, d, J = 8.8 Hz), 7.27 (1H, d, J = 2.0 Hz), 6.97 (1H, dd, J = 8.8, 2.0 Hz), 6.75 (1H, s), 4.93 (1H, p, J = 8.7 Hz), 4.34 (1H, dq, J = 8.4, 6.4 Hz), 4.27-4.23 (2H, m), 3.88-3.84 (2H, m), 3.64 (2H, q, J = 7.0 Hz), 2.88-2.76 (2H, m), 2.39-2.27 (2H, m), 2.01-1.91 (1H, m), 1.90-1.80 (1H, m), 1.38 (3H, d, J = 6.4 Hz), 1.27 (3H, t, J = 7.0 Hz), 1.08-0.98 (1H, m), 0.62-0.42 (3H, m), 0.37-0.27 (1H, m). |
| 2614 | 181-182 | 464.4 | | ** | |
| 2615 | 118-120 | 500.4 | | *** | |
| 2616 | 197-199 | 474.4 | | *** | |
| 2617 | 127-129 | 502.4 | | *** | |
| 2618 | 96-98 | 534.3 (M − 1) | | *** | |
| 2619 | 102-103 | 534.3 (M − 1) | | *** | |
| 2620 | 146-147 | 488.4 | | *** | |
| 2621 | 145-146 | 486.4 (M − 1) | | *** | |
| 2622 | 198-200 | 527.8 (M − 1) | | *** | |
| 2623 | 190-192 | 486.4 | | *** | |
| 2624 | 160-161 | 514.4 (M − 1) | | *** | |
| 2625 | 187-189 | 473.4 | | *** | |
| 2626 | 130-132 | 485.4 | | *** | |
| 2627 | | 523.1 | | ** | |
| 2628 | | 575.2 | | * | |
| 2629 | 194-195 | 483.4 | | *** | |
| 2630 | 182-184 | 390.2 | | *** | |
| 2631 | 185-188 | 482.4 | | *** | |
| 2632 | 155-161 | 427.1 | | *** | |
| 2633 | 170-175 | 426.3 | | *** | |
| 2634 | 135-140 | 519.2 | | *** | |
| 2635 | 175-180 | 457.3 | | *** | |
| 2636 | 122-124 | 516 | | *** | $^1$H NMR (300 MHz, CDCl$_3$): δ 7.63 (1H, d, J = 8.8 Hz), 7.57 (2H, d, J = 8.8 Hz), 7.45 (2H, d, J = 8.8 Hz), 7.27 (1H, dd, J = 8.8, 2.3 Hz), 6.98 (1H, d, J = 2.3 Hz), 6.93 (1H, br s), 5.35 (1H, hp, J = 6.6 Hz), 4.92 (1H, p, J = 8.9 Hz), 4.23 (2H, m), 3.86 (2H, m), 3.64 (2H, q, J = 7.0 Hz), 2.89-2.72 (2H, m), 2.40-2.29 (2H, m), 2.00-1.78 (2H, m), 1.49 (3H, d, J = 6.7 Hz), 1.28 (3H, t, J = 7.0 Hz). $^{19}$F NMR (282 MHz, CDCl$_3$): δ −79.17 (3F, d, J = 7.9 Hz). |
| 2637 | | 485.4 | | *** | |
| 2638 | 196-197 | 458.3 (M − 1) | | *** | |
| 2639 | 101-109 | 325.4 | | ** | |
| 2640 | 178-184 | 411.3 | | *** | |
| 2641 | 191-197 | 410.3 | | *** | |
| 2642 | 93-95 | 592.5 | | *** | |
| 2643 | 168-169 | 567.3 | | *** | |
| 2644 | 108-110 | 593.5 | | *** | |
| 2645 | 118-120 | 629.2 | | *** | |

TABLE 1A-continued

| Compound | Melting Point (° C.) | Mass Spec [M + H] | Replicon IC$_{50}$ μM 2-day | Replicon IC$_{50}$ μM 3-day | $^1$H NMR Data |
|---|---|---|---|---|---|
| 2646 | 187-189 | 530.3 | | *** | |
| 2647 | 130-133 | 486.4 | | *** | |
| 2648 | 203-205 | 502.3 | | *** | |
| 2649 | 207-209 | 514.4 | | *** | |
| 2650 | | 540.4 | | *** | |
| 2651 | | 590.4 | | *** | |
| 2652 | | 576.4 | | *** | |
| 2653 | 189-192 | 539.4 | | *** | |
| 2654 | 100-104 | 453.3 | | *** | |
| 2655 | 121-122 | 554.3 (M − 1) | | *** | |
| 2656 | 270-272 | 592.4 | | *** | |
| 2657 | 202-205 | 584.3 | | ** | |
| 2658 | | 471.4 | | *** | |
| 2659 | 102-105 | 489.4 | | *** | |
| 2660 | | 487.4 | | *** | |
| 2661 | 195-202 | 464.3 | | * | (CDCl$_3$, 400 MHz), δ 7.91 (d, J = 8.4 Hz, 2H), 7.68-7.64 (m, 3H), 7.18 (d, J = 2.0 Hz, 1H), 7.00 (dd, J = 8.8 Hz and 1.6 Hz, 1H), 4.91-4.87 (m, 1H), 4.14 (q, J = 7.2 Hz, 2H), 3.09 (t, J = 4.8 Hz, 4H), 2.78-2.70 (m, 2H), 2.38-2.31 (m, 2H), 1.96-1.80 (m, 2H), 1.69-1.65 (m, 4H), 1.51-1.48 (m, 5H). |
| 2662 | | 505.4 | | *** | |
| 2663 | | 491.3 | | *** | |
| 2664 | | 509.4 | | *** | |
| 2665 | | 507.3 | | *** | |
| 2666 | 186-191 | 498.4 (M − 1) | | *** | |
| 2667 | 184-190 | 517.4 (M + NH$_4$) | | *** | |
| 2668 | 195-197 | 528.3 | | *** | |
| 2669 | 128-131 | 464.4 | | *** | |
| 2670 | 204-205 | 478.4 | | *** | |
| 2671 | 148-150 | 444.3 | | *** | |
| 2672 | | 510.4 | | *** | |
| 2673 | | 509.4 | | *** | |
| 2674 | | 510.5 | | *** | |
| 2675 | | 511.3 | | *** | |
| 2676 | | 494.3 | | *** | |
| 2677 | 190-192 | 495.4 | | *** | |
| 2678 | | 530.3 | | *** | |
| 2679 | | 531.4 | | *** | |
| 2680 | | 531.4 | | *** | |
| 2681 | | 545.4 | | *** | |
| 2682 | | 544.3 | | *** | |
| 2683 | | 545.4 | | *** | |
| 2684 | 221-223 | 481.3 | | *** | |
| 2685 | 205-206 | 482.4 | | *** | |
| 2686 | 162-165 | 490.2 | | *** | |
| 2687 | 89-112 | 516.3 | | *** | |
| 2688 | 150-155 | 552.4 | | *** | |
| 2689 | 180-183 | 480.0 | | * | (CDCl$_3$, 300 MHz), δ 8.01 (d, J = 8.4 Hz, 2H), 7.69-7.65 (m, 3H), 7.17 (d, J = 2.1 Hz, 1H), 6.99 (dd, J = 8.7 Hz and 1.8 Hz, 1H), 4.92-4.83 (m, 1H), 4.14 (q, J = 7.2 Hz, 2H), 3.77-3.71 (m, 3H), 3.77-3.69 (m, 1H), 3.58-3.51 (m, 1H), 2.80-2.67 (m, 2H), 2.37-2.34 (m, 2H), 2.00-1.79 (m, 5H), 1.70-1.61 (m, 1H), 1.57 (t, J = 7.2 Hz, 3H). |
| 2690 | 170-172 | 480.0 | | *** | (CDCl$_3$, 400 MHz), δ 8.01 (d, J = 8.4 Hz, 2H), 7.68-7.65 (m, 3H), 7.18 (d, J = 2.0 Hz, 1H), 6.99 (d, J = 8.8 Hz and 2.0 Hz, 1H), 4.91-4.87 (m, 1H), 4.14 (q, J = 7.2 Hz, 2H), 3.77-3.70 (m, 3H), 3.58-3.52 (m, 1H), 3.37-3.31 (m, 1H), 2.76-2.71 (m, 2H), 2.36-2.34 (m, 2H), 2.08-1.76 (m, 5H), 1.62-1.56 (m, 1H), 1.47 (t, J = 7.2 Hz, 3H). |
| 2691 | 128-132 | 473.1 | | *** | |
| 2692 | 176-183 | 472.2 | | *** | |
| 2693 | 78-110 | 499.2 | | *** | |
| 2694 | 155-160 | 536.4 | | *** | $^1$H-NMR (CDCl$_3$) δ 7.63 (d, 1H), 7.55 (m, 2H), 7.43 (d, 2H), 7.18 (d, 1H), 6.91 (dd, 1H), 6.78 (s, 1H), 4.94 (q, 1H), 4.34 (m, 1H), 4.21 (t, 2H), 3.32 (t, 2H), 2.93 (s, 3H), 2.81 (m, 2H), 2.41 (m, 4H), 1.93-1.40 (m, 4H), 1.40 (t, 3H), 1.03 (m, 1H), 0.59-0.48 (m, 3H), 0.32 (m, 1H). |

TABLE 1A-continued

| Compound | Melting Point (° C.) | Mass Spec [M + H] | Replicon IC$_{50}$ µM 2-day | Replicon IC$_{50}$ µM 3-day | $^1$H NMR Data |
|---|---|---|---|---|---|
| 2695 | 135-140 | 522.32 | | *** | |
| 2696 | 126-128 | 500.4 | | *** | |
| 2697 | 145-146 | 527.4 | | ** | $^1$H NMR (300 MHz, CDCl$_3$): δ 8.45 (1H, ddd, J = 5.0, 1.9, 1.0 Hz), 7.63 (1H, d, J = 8.8 Hz), 7.55 (2H, d, J = 8.5 Hz), 7.54-7.45 (1H, m), 7.42 (2H, d, J = 8.5 Hz), 7.25-7.21 (2H, m), 7.05-7.00 (2H, m), 6.70 (1H, s), 5.05 (1H, hp, J = 6.3 Hz), 4.93 (1H, p, J = 8.9 Hz), 4.35 (2H, t, J = 6.7 Hz), 3.64 (2H, t, J = 6.7 Hz), 2.85-2.70 (2H, m), 2.37-2.27 (2H, m), 1.97-1.86 (1H, m), 1.83-1.73 (1H, m), 1.32 (6H, d, J = 6.3 Hz). |
| 2698 | 69-72 | 528.4 | | *** | $^1$H NMR (300 MHz, CDCl$_3$): δ 8.54 (2H, d, J = 4.7 Hz), 7.63 (1H, d, J = 8.8 Hz), 7.55 (2H, d, J = 8.8 Hz), 7.42 (2H, d, J = 8.8 Hz), 7.24 (1H, d, J = 2.0 Hz), 7.03 (1H, dd, J = 8.8, 2.0 Hz), 7.01 (1H, t, J = 4.7 Hz), 6.71 (1H, s), 5.05 (1H, hp, J = 6.3 Hz), 4.93 (1H, p, J = 8.7 Hz), 4.37 (1H, t, J = 6.8 Hz), 3.60 (1H, t, J = 6.8 Hz), 2.89-2.70 (2H, m), 2.40-2.29 (2H, m), 2.00-1.89 (1H, m), 1.88-1.77 (1H, m), 1.32 (6H, d, J = 6.3 Hz). |
| 2699 | 150-151 | 549.6 | | *** | $^1$H NMR (300 MHz, CDCl$_3$): δ 7.63 (1H, d, J = 8.8 Hz), 7.55 (2H, d, J = 8.8 Hz), 7.42 (2H, d, J = 8.8 Hz), 7.23 (1H, d, J = 2.0 Hz), 6.96 (1H, dd, J = 8.8, 2.0 Hz), 6.71 (1H, s), 5.05 (1H, hp, J = 6.3 Hz), 4.94 (1H, p, J = 8.6 Hz), 4.46 (2H, t, J = 6.2 Hz), 3.76 (2H, t, J = 6.2 Hz), 2.80-2.68 (2H, m), 2.74 (3H, s), 2.40-2.29 (2H, m), 2.00-1.90 (1H, m), 1.89-1.73 (1H, m), 1.32 (6H, d, J = 6.3 Hz). |
| 2700 | 132-133 | 464.3 | | *** | $^1$H NMR (300 MHz, CDCl$_3$): δ 7.63 (1H, d, J = 8.8 Hz), 7.55 (2H, d, J = 8.5 Hz), 7.42 (2H, d, J = 8.5 Hz), 7.22 (1H, d, J = 2.0 Hz), 6.96 (1H, dd, J = 8.8, 2.0 Hz), 6.71 (1H, s), 5.05 (1H, hp, J = 6.3 Hz), 4.94 (1H, p, J = 8.7 Hz), 4.26 (2H, t, J = 6.8 Hz), 2.95 (2H, t, J = 6.8 Hz), 2.89-2.73 (2H, m), 2.40-2.30 (2H, m), 2.25 (3H, s), 2.00-1.90 (1H, m), 1.88-1.78 (1H, m), 1.33 (6H, d, J = 6.3 Hz). |
| 2701 | foam | 496.1 | | *** | |
| 2702 | 116-117 | 474.4 | | *** | |
| 2703 | 166-168 | 486.4 | | *** | |
| 2704 | 133-140 | 444.0 | | *** | |
| 2705 | 180-183 | 479.1 (M − 1) | | *** | |
| 2706 | 180-183 | 481.2 | | *** | |
| 2707 | 211-213 | 522.3 | | *** | |
| 2708 | 200-202 | 548.4 | | *** | |
| 2709 | 246-248 | 584.4 | | *** | |
| 2710 | 240-242 | 547.4 | | *** | |
| 2711 | 157-159 | 459.4 | | *** | |
| 2712 | 149-151 | 486.4 | | *** | |
| 2713 | 150-152 | 432.4 (M − 1) | | *** | |
| 2714 | 165-168 | 450.1 | | *** | |
| 2715 | 123-125 | 494.1 | | *** | |
| 2716 | 173-175 | 548.1 | | *** | |
| 2717 | foam | 566.3 | | *** | |
| 2718 | 188-191 | 504.2 | | *** | |
| 2719 | 88-100 | 462.3 | | *** | |
| 2720 | 120-122 | 458.1 (M − 1) | | *** | |
| 2721 | 126-128 | 476.2 | | *** | |
| 2722 | 179-181 | 522.3 | | *** | |
| 2723 | 182-184 | 524.3 | | *** | |
| 2724 | 178-180 | 536.3 | | *** | |
| 2725 | 188-190 | 538.3 | | *** | |
| 2726 | 229-231 | 544.3 | | *** | |
| 2727 | 232-234 | 495.3 | | *** | |
| 2728 | 137-138 | 523.3 | | *** | |
| 2729 | 172-173 | 525.3 | | *** | |
| 2730 | 149-150 | 537.3 | | *** | |
| 2731 | 171-172 | 539.4 | | *** | |

TABLE 1A-continued

| Compound | Melting Point (° C.) | Mass Spec [M + H] | Replicon IC$_{50}$ μM 2-day | Replicon IC$_{50}$ μM 3-day | $^1$H NMR Data |
|---|---|---|---|---|---|
| 2732 | 215-217 | 545.4 | | *** | |
| 2733 | 206-208 | 561.4 | | *** | |
| 2734 | 206-208 | 561.3 | | *** | |
| 2735 | 173-174 | 496.3 | | *** | |
| 2736 | 161-164 | 524.5 | | *** | |
| 2737 | glass | 530.2 | | *** | |
| 2738 | glass | 516.7 (M − 1) | | *** | |
| 2739 | 179-183 | 498.5 | | *** | |
| 2740 | glass | 500.6 (M − 1) | | *** | |
| 2741 | 208-210 | 488.3 | | *** | |
| 2742 | 189-192 | 474.3 | | *** | |
| 2743 | 151-153 | 474.3 | | *** | |
| 2744 | 195-197 | 524.3 | | *** | |
| 2745 | 207-209 | 480.6 | | *** | |
| 2746 | 185-187 | 494.2 | | *** | |
| 2747 | 202-204 | 492.5 | | *** | |
| 2748 | 211-213 | 494.5 | | *** | |
| 2749 | 224-226 | 492.5 | | *** | |
| 2750 | 221-225 | 497.5 | | *** | |
| 2751 | glass | 604.4 (M − 1) | | *** | |
| 2752 | 136-138 | 446.3 | | ** | (CDCl3, 300 MHz), δ 7.66 (d, J = 8.7 Hz, 1H), 7.56-7.49 (m, 4H), 7.32 (d, J = 2.1 Hz, 1H), 7.01 (dd, J = 8.7 Hz and 2.4 Hz, 1H), 4.94-4.88 (m., 1H), 4.25-4.22 (m, 2H), 3.84-3.81 (m, 2H), 3.58-3.55 (m, 2H), 3.50 (s, 3H), 3.43-3.35 (m, 2H), 2.89-2.82 (m, 2H), 2.31 (q, J = 8.4 Hz, 2H), 1.97-1.79 (m, 2H), 1.28-1.14 (m, 6H). |
| 2753 | 202-204 | 432.2 | | ** | (MeOD, 300 MHz), δ 7.98 (d, J = 8.4 Hz, 2H), 7.64 (d, J = 8.1 Hz, 2H), 7.56 (d, J = 8.7 Hz, 1H), 7.31 (d, J = 2.1 Hz, 1H), 7.01 (dd, J = 8.7 Hz and 2.1 Hz, 1H), 5.07-4.98 (m, 1H), 4.29-4.20 (m, 2H), 3.82-3.79 (m, 2H), 3.37 (s, 3H), 2.68-2.58 (m, 2H), 2.42-2.34 (m, 2H), 1.92-1.81 (m, 2H), 1.28 (d, J = 6.6 Hz, 6H). |
| 2754 | 148-150 | 460.2 | | ** | (CDCl3, 400 MHz), δ 7.66 (d, J = 8.8 Hz, 1H), 7.59-7.53 (m, 4H), 7.31 (s, 1H), 7.01 (dd, J = 8.4 Hz and 2.0 Hz, 1H), 4.92-4.88 (m, 1H), 4.24 (t, J = 4.4 Hz, 2H), 3.84-3.49 (m, 13H), 2.87-2.82 (m, 2H), 2.36-2.31 (m, 2H), 1.97-1.80 (m, 2H). |
| 2755 | 166-168 | 430.2 | | ** | (CDCl3, 400 Hz) δ 7.78 (d, J = 8.0 Hz, 2H), 7.65 (d, 8.8 Hz, 2H), 7.53 (d, J = 8.0 Hz, 2H), 7.29 (d, J = 2.0 Hz, 1H), 7.01 (d, J = 8.4 Hz, 1H), 4.92-4.88 (m, 1H), 4.37-4.33 (m, 4H), 4.24 (t, J = 4.4 Hz, 2H), 3.82 (t, J = 4.8 Hz, 2H), 3.50 (s, 3H), 2.83-2.77 (m, 2H), 2.44-2.29 (m, 4H), 1.95-1.82 (m, 2H). |
| 2756 | 162-164 | 444.2 | | ** | (CDCl3, 400 MHz), δ 7.13-7.09 (m, 3H), 6.97 (d, J = 8.0 Hz, 2H), 6.76 (s, 1H), 6.46 (d, J = 8.8 Hz, 1H), 4.38-4.34 (m, 1H), 3.71-3.68 (m, 2H), 3.27 (t, J = 4.4 Hz, 2H), 3.14-3.11 (m, 2H), 2.98-2.95 (m, 5H), 2.31-2.26 (m, 2H), 1.78-1.76 (m, 2H), 1.44-1.25 (m, 6H). |
| 2757 | 155-158 | 458.3 | | *** | (CDCl3, 400 MHz), δ 7.66 (d, J = 8.4 Hz, 1H), 7.59-7.50 (m, 4H), 7.32 (s, 1H), 7.01 (d, J = 8.8 Hz, 1H), 4.93-4.86 (m, 1H), 4.25 (t, J = 4.0 Hz, 2H), 3.83 (t, J = 4.4 Hz, 2H), 3.76 (b, 2H), .3.50 (s, 3H), 3.43 (b, 2H), 2.91-2.81 (m, 2H), 2.32 (q, J = 8.8 Hz, 2H), 2.00-1.72 (m, 8H). |
| 2758 | 194-196 | 456.2 | | ** | (CDCl3, 300 MHz), δ 7.97 (dd, J = 6.9 Hz and 2.1 Hz, 2H), 7.63 (dd, J = 6.9 Hz and 2.1 Hz, 2H), 7.55 (d, J = 8.7 Hz, 1H), 7.31 (d, J = 1.8 Hz, 1H), 7.02 (dd, J = 9.0 Hz and 2.4 Hz, 1H), 5.07-5.01 (m, 1H), 4.38-4.33 (m, 1H), 4.24-4.21 (m, 2H), 3.82-3.79 (m, 2H), 3.52 (s, 3H), 2.68-2.58 (m, 2H), 2.43-2.33 (m, 2H), 2.07-2.01 (m, 2H), 1.92-1.76 (m, 8H). |

TABLE 1A-continued

| Compound | Melting Point (° C.) | Mass Spec [M + H] | Replicon IC$_{50}$ μM 2-day | Replicon IC$_{50}$ μM 3-day | $^1$H NMR Data |
|---|---|---|---|---|---|
| 2759 | 199-200 | 444.1 | | ** | (MeOH, 300 MHz), δ 7.99 (dd, J = 6.9 Hz and 1.8 Hz, 2H), 7.64 (dd, J = 6.6 Hz and 2.1 Hz, 2H), 7.56 (d, J = 8.7 Hz, 1H), 7.31 (d, J = 2.1 Hz, 1H), 7.02 (dd, J = 8.7 Hz and 2.1 Hz, 1H), 5.07-5.01 (m, 1H), 4.57-4.51 (m, 1H), 4.25-4.21 (m, 2H), 3.82-3.79 (m, 2H), 3.46 (s, 3H), 2.68-2.61 (m, 2H), 2.43-2.35 (m, 4H), 2.18-2.11 (m, 2H), 1.91-1.80 (m, 4H). |
| 2760 | 228-230 | 430.0 | | ** | (CDCl3, 400 MHz) δ 7.88 (dd, J = 8.0 Hz, 2H), 7.64 (dd, J = 9.2 Hz, 1H), 7.55 (dd, J = 7.6 Hz, 2H), 7.01 (dd, J = 8.8 Hz, 1H), 6.31 (s, 1H), 4.94-4.88 (m, 1H), 4.23 (t, J = 4.4 Hz, 2H), 3.82 (t, J = 4.4 Hz, 2H), 3.50 (s, 3H), 2.95 (b, 1H), 2.82-2.72 (m, 2H), 2.32 (q, J = 8.8 Hz, 2H), 1.97-1.76 (m, 2H), 0.92 (q, J = 6.0 Hz, 2H), 0.66 (q, J = 6.0 Hz, 2H). |
| 2761 | 240-245 | 481.5 | | ** | |
| 2762 | 264-269 | 501.9 | | ** | |
| 2763 | 225-231 | 519.2 | | *** | |
| 2764 | 218-220 | 472.9 | | *** | |
| 2765 | glass | 504.4 | | *** | |
| 2766 | 195-196 | 449.4 | | *** | |
| 2767 | glass | 538.4 | | *** | |
| 2768 | 99-102 | 492.3 | | *** | |
| 2769 | glass | 606.5 | | *** | |
| 2770 | glass | 554.3 (M − 1) | | *** | |
| 2771 | glass | 530.3 | | *** | |
| 2772 | glass | 488.3 | | *** | |
| 2773 | glass | 488.3 | | *** | |
| 2774 | glass | 518.3 | | ** | |
| 2775 | 199-203 | 494.3 | | ** | |
| 2776 | 183-184 | 494.4 (M − 1) | | *** | |
| 2777 | 191 (decomp.) | 488.8 | | *** | |
| 2778 | 222-225 | 444.4 | | *** | |
| 2779 | 146-150 | 518.5 (M − 1) | | ** | |
| 2780 | 155-156 | 477.4 (M + NH$_4$) | | *** | |
| 2781 | 147-148 | 491.4 (M + NH$_4$) | | *** | |
| 2782 | 161-163 | 474.4 | | *** | |
| 2783 | 146-147 | 505.5 (M + NH$_4$) | | *** | |
| 2784 | 169-171 | 500.4 | | *** | |
| 2785 | 158-160 | 514.4 | | *** | |
| 2786 | 183-185 | 509.4 | | *** | |
| 2787 | 148-150 | 511.4 | | *** | |
| 2788 | 124-127 | 497.4 | | *** | |
| 2789 | 133-134 | 473.4 | | ** | |
| 2790 | 188-189 | 519.4 (M + NH$_4$) | | * | |
| 2791 | 96-98 | 515.4 | | *** | |
| 2792 | 90-94 | 515.4 | | *** | |
| 2793 | 148-151 | 529.4 | | *** | |
| 2794 | 75-77 | 559.4 | | *** | |
| 2795 | | 548.4 | | *** | |
| 2796 | 217-221 | 396.4 | | *** | |
| 2797 | glass | 496.3 | | *** | |
| 2798 | glass | 554.3 (M − 1) | | *** | |
| 2799 | 162-169 | 530.2 | | *** | |
| 2800 | 206-208 | 458.8 | | *** | $^1$H NMR (300 MHz, CDCl$_3$): δ 1.33 (d, 6H), 1.73-1.99 (m, 2H), 2.27-2.46 (m, 2H), 2.68-2.88 (m, 2H), 3.16-3.29 (4H), 3.88-4.00 (4H), 4.89-5.13 (m, 2H), 6.69 (s, br, 1H), 7.01-7.04 (dd, 1H), 7.15 (d, 1H), 7.39-7.46 (m, 2H), 7.51-7.59 (m, 2H), 7.64 (d, 1H) |
| 2801 | 220-220 | 479.3 | | *** | |
| 2802 | 222-224 | 476.8 | | *** | |
| 2803 | 203-204 | 479.4 | | *** | |
| 2804 | 171-177 | 413.9 | | *** | |
| 2805 | 174-175 | 591.8 | | *** | |
| 2806 | 175-176 | 589.9 (M − 1) | | *** | |
| 2807 | 205-207 | 477.4 (M + NH$_4$) | | *** | |
| 2808 | 153-154 | 491.4 (M + NH$_4$) | | *** | |
| 2809 | 185-186 | 491.4 (M + NH$_4$) | | *** | |
| 2810 | 137-138 | 505.4 (M + NH$_4$) | | *** | |

TABLE 1A-continued

| Compound | Melting Point (° C.) | Mass Spec [M + H] | Replicon IC$_{50}$ μM 2-day | Replicon IC$_{50}$ μM 3-day | $^1$H NMR Data |
|---|---|---|---|---|---|
| 2811 | 168-169 | 517.4 (M + NH$_4$) | | *** | |
| 2812 | 187-188 | 514.4 | | *** | |
| 2813 | 174-175 | 488.4 | | *** | |
| 2814 | 178-179 | 519.4 (M + NH$_4$) | | *** | |
| 2815 | 179-181 | 503.4 (M + NH$_4$) | | *** | |
| 2816 | 137-138 | 488.4 | | *** | |
| 2817 | 179-181 | 475.4 | | *** | |
| 2818 | 185-187 | 402.5 | | *** | |
| 2819 | 150 (decomp.) | 547.3 | | *** | |
| 2820 | 152 (decomp.) | 547.3 | | *** | |
| 2821 | | 509.2 | | *** | |
| 2822 | 247-249 | 503.3 | | ** | |
| 2823 | 209-211 | 489.3 | | *** | |
| 2824 | 201-203 | 507.3 | | *** | |
| 2825 | 125-128 | 505.3 | | ** | |
| 2826 | 205-207 | 521.3 | | *** | |
| 2827 | 115-120 | 437.4 | | *** | |
| 2828 | 225-230 | 550 | | *** | |
| 2829 | 163-168 | 539.6 | | *** | |
| 2830 | 161-162 | 567.4 | | *** | |
| 2831 | 103-104 | 567.4 | | *** | |
| 2832 | 197-202 | 512.5 | | *** | |
| 2833 | 218-220 | 481.2 | | *** | |
| 2834 | 199-201 | 495.3 | | *** | |
| 2835 | 196-198 | 523.5 | | *** | |
| 2836 | 193-195 | 537.5 | | *** | |
| 2837 | 210-212 | 521.4 | | *** | |
| 2838 | 179-181 | 535.4 | | *** | |
| 2839 | glass | 505.3 (ES−) | | *** | |
| 2840 | | 508.4 | | *** | |
| 2841 | | 508.4 | | *** | |
| 2842 | 203-212 | 512.5 | | *** | |
| 2843 | 203-205 | 479.6 | | *** | |
| 2844 | 169-170 | 503.2 | | ** | (CDCl3, 8.8 MHz) δ 8.00 (b, 1H), 7.65 (d, J = 8.8 Hz, 1H), 7.58 (d, J = 8.0 Hz, 2H), 7.29 (s, 1H), 7.01 (s, 1H), 4.94-4.90 (m, 1H), 4.24 (t, J = 4.4 Hz, 2H) 3.86-3.82 (m, 4H), 3.70-3.68 (m, 2H), 3.50 (s, 3H), 2.84-2.69 (m, 6H), 2.33 (q, J = 8.0 Hz, 2H), 1.98-1.77 (m, 2H), 1.68-1.48 (m, 4H). |
| 2845 | glass | 536.4 (M − 1) | | *** | |
| 2846 | 202-204 | 447.3 | | *** | |
| 2847 | 217-218 | 484.3 | | * | |
| 2848 | 206-207 | 486.3 | | ** | |
| 2849 | 225-227 | 486.3 | | ** | |
| 2850 | 161-163 | 498.3 | | ** | |
| 2851 | 140-145 | 465.4 | | *** | |
| 2852 | 205-207 | 522.3 | | *** | |
| 2853 | 189-190 | 514.3 | | *** | |
| 2854 | 113-116 | 516.3 | | *** | |
| 2855 | 264 | 444.4 | | ** | |
| 2856 | 220-227 | 445.4 | | *** | |
| 2857 | 176-179 | 471.5 | | *** | |
| 2858 | 230-232 | 456.4 | | *** | |
| 2859 | 200-201 | 502.2 (M − 1) | | *** | |
| 2860 | 197-198 | 488.4 | | *** | |
| 2861 | 221-232 decomposed | 516.2 (M − 1) | | *** | |
| 2862 | 234-235 | 458.3 | | *** | |
| 2863 | 172 (decomp.) | 470.4 | | *** | |
| 2864 | 220-222 | 513.3 | | *** | |
| 2865 | 163-165 | 539.3 | | *** | |
| 2866 | 194-195 | 485.3 | | *** | |
| 2867 | 198-200 | 494.3 | | *** | |
| 2868 | 100-104 | 506.4 (M − 1) | | *** | |
| 2869 | 108-111 | 538.4 (M − 1) | | *** | |
| 2870 | glass | 554.2 (M − 1) | | *** | |
| 2871 | 198-199 | 514.2 (M − 1) | | *** | |
| 2872 | 215-216 | 488.4 | | *** | |
| 2873 | 170-180 | 495.4 | | *** | |
| 2874 | glass | 502.3 | | *** | |
| 2875 | 151-153 | 495.6 | | *** | |

TABLE 1A-continued

| Compound | Melting Point (° C.) | Mass Spec [M + H] | Replicon IC$_{50}$ μM 2-day | Replicon IC$_{50}$ μM 3-day | $^1$H NMR Data |
|---|---|---|---|---|---|
| 2876 | 170-230 | 470.4 | | *** | |
| 2877 | 241-243 | 463.6 | | *** | |
| 2878 | 196-199 | 472.4 | | *** | |
| 2879 | 198-200 | 490.3 | | *** | |
| 2880 | 161-162 | 492.1 (M − 1) | | ** | |
| 2881 | 197-203 | 498.4 | | *** | |
| 2882 | 210-212 | 475.4 | | *** | |
| 2883 | glass | 554.5 (M − 1) | | *** | |
| 2884 | glass | 530.4 | | *** | |
| 2885 | 189-190 | 530.4 | | *** | |
| 2886 | 179-780 | 492.6 | | *** | |
| 2887 | 165-166 | 580.7 | | *** | |
| 2888 | 99-101 | 497.5 | | *** | |
| 2889 | 129-130 | 488.6 | | *** | |
| 2890 | 186-189 | 479.6 | | *** | |
| 2891 | 170-180 | 459.6 | | *** | |
| 2892 | 145-148 | 457.5 | | *** | |
| 2893 | glass | 474.6 (M − 1) | | *** | |
| 2894 | 208-210 | 476.6 | | *** | |
| 2895 | 185-187 | 494.7 | | *** | |
| 2896 | 217-219 | 508.7 | | *** | |
| 2897 | 247-249 | | | ** | |
| 2898 | 220-222 | | | *** | |
| 2899 | 169-171 | 506 | | *** | |
| 2900 | 198-200 | | | *** | |
| 2901 | 210-212 | 520 | | *** | |
| 2902 | 223-227 | 502.6 | | *** | |
| 2903 | 172-174 | 500.5 | | *** | |
| 2904 | 182-186 | 532.6 | | *** | |
| 2905 | 248-250 | 477.6 | | *** | |
| 2906 | 208-213 | 479.7 | | *** | |
| 2907 | 127-132 | 483.7 | | *** | |
| 2908 | 191-194 | 475.5 | | *** | |
| 2909 | 201-202 | 508.7 | | *** | |
| 2910 | 162-164 | 515.1 | | *** | |
| 2911 | 205-207 | 452.8 | | *** | |
| 2912 | 212-214 | 466.9 | | *** | |
| 2913 | 172-174 | 508.9 | | *** | |
| 2914 | 290-292 | 477.7 | | ** | |
| 2915 | 269-271 | 451.7 | | ** | |
| 2916 | 235-236 | 465.7 | | *** | |
| 2917 | 175-177 | 510.6 | | *** | |
| 2918 | 195-196 | 520.2 (M − 1) | | *** | |
| 2919 | 200-204 | 508.5 | | *** | |
| 2920 | 196-198 | 496.4 | | *** | |
| 2921 | 241-245 | 477.5 | | ** | |
| 2922 | 108-118 | 510.4 | | *** | |
| 2923 | 158-160 | 522.8 | | *** | |
| 2924 | 119-121 | 562.9 | | *** | |
| 2925 | 231-233 | 522.9 | | *** | |
| 2926 | 247-248 | 451.8 | | ** | |
| 2927 | 260-265 | 463.6 | | ** | |
| 2928 | 216-217 | 494.9 | | ** | |
| 2929 | 221-223 | 496.6 | | *** | |
| 2930 | 227-229 | 522.8 | | *** | |
| 2931 | 227-230 | 502.9 | | *** | |
| 2932 | 224-225 | 489.7 | | ** | |
| 2933 | 167-173 | 485.7 | | *** | |
| 2934 | 192-195 | 447.7 | | *** | |
| 2935 | 216-217 | 541.8 | | ** | |
| 2936 | 209-210 | 507.6 | | *** | |
| 2937 | 183-184 | 508.6 | | *** | |
| 2938 | 191-193 | 488.8 | | *** | |
| 2939 | 239-241 | 488.7 | | *** | |
| 2940 | 222-227 | 466.8 | | ** | |
| 2941 | 219-224 | 478.6 | | ** | |
| 2942 | 191-193 | 473.7 | | *** | |
| 2943 | 215-217 | 508.0 | | *** | |
| 2944 | 234-239 | 488.8 | | * | |
| 2945 | 173-175 | 521.6 | | *** | |
| 2946 | 144-146 | 537.0 | | *** | |
| 2947 | 130 (decomp.) | 523.0 | | *** | |
| 2948 | 206-208 | 549.0 | | *** | |
| 2949 | 181-183 | 534.9 | | ** | |

TABLE 1A-continued

| Compound | Melting Point (° C.) | Mass Spec [M + H] | Replicon IC$_{50}$ μM 2-day | Replicon IC$_{50}$ μM 3-day | $^1$H NMR Data |
|---|---|---|---|---|---|
| 2950 | 224-226 | 435.1 | | *** | |
| 2951 | 196-197 | 443.1 | | *** | |
| 2952 | 148-150 | 501.1 | | *** | |
| 2953 | 231-234 | 527.3 | | *** | |
| 2954 | 241-244 | 443.2 | | *** | |
| 2955 | 229-234 | 463.6 | | *** | |
| 2956 | 198-200 | 490.8 | | *** | |
| 2957 | 203-204 | 528.0 | | * | |
| 2958 | 206-208 | 564.5 | | *** | |
| 2959 | 220-222 | 505.0 | | *** | |
| 2960 | 258-260 | 461.1 | | ** | |
| 2961 | 246-249 | 497.3 | | *** | |
| 2962 | 244-250 | 449.4 | | ** | |
| 2963 | 189-194 | 477.1 | | *** | |
| 2964 | 248-250 | 519.2 | | *** | |
| 2965 | 212-214 | 533.3 | | *** | |
| 2966 | glass | 487.0 | | ** | |
| 2967 | 208-213 | 456 | | *** | |
| 2968 | 233-235 | 477.3 | | *** | |
| 2969 | 181-183 | 502.1 | | ** | |
| 2970 | 183-185 | 508.4 | | *** | |
| 2971 | 208-210 | 511.4 | | *** | |
| 2972 | 235-237 | 504.9 | | *** | |
| 2973 | 220-229 | 493.9 (M − 1) | | *** | |
| 2974 | 203-205 | 463.6 | | *** | |
| 2975 | 256-261 | 463.6 | | *** | |
| 2976 | 168-173 | 443.5 | | *** | |
| 2977 | 112-117 | 490.9 | | *** | |
| 2978 | 210-212 | 484.9 | | *** | |
| 2979 | glass | 569.3 | | *** | |
| 2980 | 167-170 | 515.9 | | ** | |
| 2981 | 174-177 | 570.2 | | * | |
| 2982 | 198-202 | 491 | | *** | |
| 2983 | 232-238 | 475.6 | | *** | |
| 2984 | 229-233 | 449.5 | | ** | |
| 2985 | 205-210 | 469 | | *** | |
| 2986 | 197-202 | 455.5 | | *** | |
| 2987 | 266-273 | 501.8 | | ** | |
| 2988 | 218-223 | 508.0 | | *** | |
| 2989 | 234-238 | 500.0 | | ** | |
| 2990 | 114-143 | 536.3 | | *** | |
| 2991 | 221-225 | 516.0 | | *** | |
| 2992 | 211-213 | 481.9 | | *** | |
| 2993 | 231-237 | 514.0 | | ** | |
| 2994 | 84-94 | 539.1 | | *** | |
| 2995 | 206-208 | 493.8 | | *** | |
| 2996 | 200-202 | 493.9 | | *** | |
| 2997 | 90-98 | 544.7 | | *** | |
| 2998 | | 490.9 | | *** | |
| 2999 | 226-228 | 491.0 | | *** | |
| 3000 | 208-210 | 511.0 | | *** | |
| 3001 | 111-122 | 511.0 | | *** | |
| 3002 | 88-102 | 491.0 | | *** | |
| 3003 | 223-225 | 552.7 | | *** | |
| 3004 | 188-190 | 440.8 | | ** | |
| 3005 | 171-173 | 490.9 | | *** | |
| 3006 | 173-175 | 437.6 | | *** | |
| 3007 | 154-156 | 497.0 | | *** | |
| 3008 | 197-200 | 546.7 | | *** | |
| 3009 | 173-175 | 546.8 | | *** | |
| 3010 | 172-174 | 518.9 | | *** | |
| 3011 | 196-199 | 492.8 | | *** | |
| 3012 | 181-184 | 483.6 | | *** | |
| 3013 | 176-179 | 477.6 | | *** | |
| 3014 | 90-91 | 497.3 | | *** | |
| 3015 | 270 (decomp.) | 501.0 | | ** | |
| 3016 | | 499.6 | | *** | |
| 3017 | 120-125 | 561.8 | | *** | |
| 3018 | 155-157 | 545.9 | | *** | |
| 3019 | 227-229 | 542.8 | | *** | |
| 3020 | 118-124 | 607.7 | | *** | |
| 3021 | 195-196 | 535.7 | | *** | |
| 3022 | 165-168 | 524.8 | | *** | |
| 3023 | 158-160 | 515.9 | | ** | |

TABLE 1A-continued

| Compound | Melting Point (° C.) | Mass Spec [M + H] | Replicon IC$_{50}$ μM 2-day | Replicon IC$_{50}$ μM 3-day | $^1$H NMR Data |
|---|---|---|---|---|---|
| 3024 | 171-174 | 569.8 | | ** | |
| 3025 | 214-220 | 493.7 (M − 1) | | *** | |
| 3026 | 187-190 | 481.9 | | *** | |
| 3027 | 186-189 | 507.9 | | *** | |
| 3028 | | 536.0 | | *** | |
| 3029 | 110-113 | 580.4 | | *** | |
| 3030 | 128-131 | 518.6 | | *** | |
| 3031 | 82-88 | 468.8 | | *** | |
| 3032 | | 452.1 | | *** | |
| 3033 | | 466.1 | | *** | |
| 3034 | 80-81 | 578.0 | | *** | |
| 3035 | 94-96 | 552.0 | | ** | |
| 3036 | 144-154 | 503.8 | | *** | |
| 3037 | | 529.9 | | *** | |
| 3038 | 236-243 | 502.9 | | *** | |
| 3039 | 150-155 | 469.8 (M − 1) | | *** | |
| 3040 | 176-180 | 498.0 | | *** | |
| 3041 | 224-229 | 471.1 | | *** | |
| 3042 | | 555.4 | | ** | |
| 3043 | | 505.6 (M − 1) | | *** | |
| 3044 | | 490.0 | | *** | |
| 3045 | | 484.0 | | *** | |
| 3046 | 195-197 | 480.1 | | *** | |
| 3047 | 225 (decomp.) | 495.1 | | *** | |
| 3048 | 120 (decomp.) | 480.1 | | *** | |
| 3049 | 154-155 | 521.8 | | *** | |
| 3050 | 141-142 | 525.8 | | *** | |
| 3051 | 184-185 | 539.7 (M − 1) | | *** | |
| 3052 | 166-187 | 467.8 | | *** | |
| 3053 | 203-208 | 493.8 | | *** | |
| 3054 | 190-196 | 521.9 | | *** | |
| 3055 | 72-73 | 496.8 | | *** | |
| 3056 | 85-94 | 533.5 | | *** | |
| 3057 | 95-112 | 521.8 | | *** | |
| 3058 | 181-185 | 535.8 | | *** | |
| 3059 | 97-109 | 542.1 | | *** | |
| 3060 | 205-212 | 553.8 | | *** | |
| 3061 | 77-78 | 510.9 | | *** | |
| 3062 | 75-76 | 564.2 | | *** | |
| 3063 | 74-75 | 536.2 | | *** | |
| 3064 | 192-193 | 509.9 | | *** | |
| 3065 | 218-220 | 521.3 | | *** | |
| 3066 | 237-241 | 507.7 (M − 1) | | *** | |
| 3067 | 265-271 | 496.0 | | *** | |
| 3068 | 218-224 | 521.9 | | *** | |
| 3069 | 207-211 | 559.5 | | *** | |
| 3070 | 237-242 | 551.5 | | *** | |
| 3071 | 236-241 | 563.5 | | *** | |
| 3072 | 211-215 | 501.5 | | ** | |
| 3073 | 185-190 | 561.5 | | *** | |
| 3074 | 274 (decomp.) | 526.5 | | ** | |
| 3075 | | 513.4 | | * | |
| 3076 | | 513.4 | | * | |
| 3077 | 109-110 | 448 | | *** | $^1$H NMR (300 MHz, CDCl$_3$): δ 7.60 (1H, d, J = 8.8 Hz), 7.29 (2H, d, J = 8.8 Hz), 7.27 1H (d, J = 2.2 Hz), 6.96 (1H, dd, J = 8.8, 2.2 Hz), 6.73 (2H, d, J = 8.8 Hz), 4.97 (1H, p, J = 8.9 Hz), 4.36 (1H, br), 4.24-4.21 (2H, m), 3.87-3.84 (2H, m), 3.70-3.53 (6H, m), 3.37-3.34 (2H, m), 2.92-2.81 (2H, m), 2.37-2.28 (2H, m), 1.99-1.89 (1H, m), 1.88-1.77 (1H, m), 1.28 (3H, t, J = 7.0 Hz), 1.25 (3H, t, J = 7.0 Hz). |
| 3078 | 180-182 | 516.2 | | * | (CDCl$_3$, 400 MHz), δ 7.64 (d, J = 8.4 Hz, 2H), 7.56 (d, J = 8.4 Hz, 2H), 7.40 (d, J = 8.8 Hz, 1H), 7.19 (d, J = 2.0 Hz, 1H), 7.01 (dd, J = 9.2 Hz and 2.4 Hz, 1H), 4.12 (q, J = 6.8 Hz, 2H), 4.04 (d, J = 6.4 Hz, 2H), 3.65 (q, J = 7.2 Hz, 4H), 1.68-1.46 (m, 9H), 1.07-0.98 (m, 1H), 0.48 (q, J = 9.6 Hz, 2H), 0.11-0.05 (m, 2H). |

TABLE 1A-continued

| Compound | Melting Point (° C.) | Mass Spec [M + H] | Replicon IC$_{50}$ μM 2-day | Replicon IC$_{50}$ μM 3-day | $^1$H NMR Data |
|---|---|---|---|---|---|
| 3079 | 194-195 | 482 | | * | $^1$H NMR (300 MHz, DMSO-d$_6$): δ 10.09 (1H, s), 7.66 (2H, d, J = 8.8 Hz), 7.51 (1H, d, J = 8.8 Hz), 7.48 (2H, d, J = 8.8 Hz), 7.20 (1H, d, J = 2.1 Hz), 6.93 (1H, dd, J = 8.8, 2.1 Hz), 4.97 (1H, p, J = 8.7 Hz), 4.47 (2H, t, J = 5.7 Hz), 4.11 (2H, q, J = 7.0 Hz), 3.55 (2H, t, J = 5.7 Hz), 3.08 (3H, s), 2.59-2.41 (2H, m), 2.37-2.26 (2H, m), 1.83-1.65 (2H, m), 1.36 (3H, t, J = 7.0 Hz). |
| 3080 | 187-192 | 427.1 (M − 1) | | *** | |
| 3081 | | 500.4 | | *** | |
| 3082 | | 520.4 | | ** | |
| 3083 | 192-205 | 556.4 | | ** | |
| 3084 | 156-162 | 516.1 | | ** | |
| 3085 | 195-196 | 466.3 | | ** | (CDCl$_3$, 400 MHz), δ 7.99 (d, J = 8.0 Hz, 2H), 7.65-7.63 (m, 3H), 7.18 (s, 1H), 6.99 (d, J = 8.8 Hz and 1.6 Hz, 1H), 4.94-4.85 (m, 1H), 4.44 (s, 1H), 4.13 (q, J = 6.8 Hz, 2H), 3.50-3.46 (m, 3H), 3.36 (d, J = 11.2 Hz, 1H), 2.79-2.71 (m, 2H), 2.41-2.30 (m, 2H), 2.05-1.83 (m, 4H), 1.49 (t, J = 6.8 Hz, 3H). |
| 3086 | 194-196 | 466.0 | | ** | (CDCl$_3$, 400 MHz), δ 7.99 (d, J = 8.4 Hz, 2H), 7.66-7.64 (m, 3H), 7.18 (d, J = 2.0 Hz, 1H), 6.99 (d, J = 8.8 Hz and 1.6 Hz, 1H), 4.92-4.87 (m, 1H), 4.44-4.43 (m, 1H), 4.13 (q, J = 6.8 Hz, 2H), 3.50-3.46 (m, 3H), 3.36 (d, J = 11.2 Hz, 1H), 2.77-2.72 (m, 2H), 2.41-2.30 (m, 2H), 2.05-1.83 (m, 4H), 1.49 (t, J = 6.8 Hz, 3H). |
| 3087 | 275 (decomp.) | 532.4 | | *** | |
| 3088 | 140 (decomp.) | 526.1 | | ** | |
| 3089 | 172-177 | 540.6 | | *** | |
| 3090 | 196-201 | 514 | | ** | |
| 3091 | 231-233 | 528.7 | | *** | |
| 3092 | 238-243 | 513.2 | | ** | |
| 3093 | 112-119 | 481.0 (M − 1) | | ** | |
| 3094 | 236-237 | 465.2 | | ** | (CDCl$_3$, 400 MHz), δ 7.81-7.77 (m, 2H), 7.48-7.46 (m, 3H), 7.34 (d, J = 8.4 Hz, 2H), 6.76 (s, 1H), 5.00-4.96 (m, 1H), 3.23-3.13 (m, 8H), 2.83-2.76 (m, 2H), 2.37 (q, J = 8.0 Hz, 2H), 2.00-1.82 (m, 4H), 1.09 (t, J = 7.6 Hz, 3H). |
| 3095 | 133-134 | 493.2 | | ** | (CDCl$_3$, 400 MHz), δ 7.78-7.76 (m, 2H), 7.46 (d, J = 8.4 Hz, 2H), 7.39 (d, J = 9.2 Hz, 1H), 7.33 (d, J = 8.4 Hz, 2H), 6.80 (s, 1H), 4.99-4.95 (m, 1H), 3.61 (b, 2H), 3.36 (b, 2H), 3.20 (t, J = 8.0 Hz, 2H), 2.84-2.78 (m, 2H), 2.38 (q, J = 9.6 Hz, 2H), 2.00-1.87 (m, 4H), 1.27-1.18 (m, 6H), 1.09 (t, J = 7.2 Hz, 3H). |
| 3096 | 138-139 | 479.2 | | ** | (CDCl$_3$, 400 MHz), δ 7.80-7.77 (m, 2H), 7.48-7.42 (m, 3H), 7.34 (d, J = 8.4 Hz, 2H), 6.66 (s, 1H), 4.99-4.95 (m, 1H), 3.62-3.32 (m, 2H), 3.23-3.19 (m, 2H), 3.08-3.07 (m, 3H), 2.84-2.79 (m, 2H), 2.42-2.35 (m, 2H), 2.00-1.85 (m, 4H), 1.25-1.22 (m, 3H), 1.10 (t, J = 7.6 Hz, 3H). |
| 3097 | 200-202 | 491.2 | | *** | (CDCl$_3$, 400 MHz), δ 7.93 (s, 1H), 7.78-7.76 (m, 1H), 7.58-7.56 (m, 1H), 7.51 (s, 1H), 7.45-7.43 (m, 2H), 7.38-7.36 (m, 2H), 4.99-4.95 (m, 1H), 3.71 (s, 2H), 3.55 (s, 2H), 3.21-3.17 (m, 2H), 2.82-2.77 (m, 2H), 2.39-2.37 (m, 2H), 1.99-1.84 (m, 7H), 1.07 (t, J = 8.4 Hz, 3H). |
| 3098 | 128-129 | 507.2 | | ** | (CDCl$_3$, 400 MHz), δ 7.81-7.78 (m, 2H), 7.48-7.43 (m, 3H), 7.35 (d, J = 8.4 Hz, 2H), 6.75 (s, 1H), 5.00-4.96 (m, 1H), 4.85-3.62 (m, 8H), 4.29 (s, 2H), 3.23-3.19 (m, 2H), 2.83-2.75 (m, 2H), 2.41-2.36 (m, 2H), 2.01-1.83 (m, 4H), 1.10 (t, J = 7.2 Hz, 3H). |

TABLE 1A-continued

| Compound | Melting Point (° C.) | Mass Spec [M + H] | Replicon IC$_{50}$ μM 2-day | Replicon IC$_{50}$ μM 3-day | $^1$H NMR Data |
|---|---|---|---|---|---|
| 3099 | 149-152 | 467.5 | | ** | |
| 3100 | 201-203 | 633.9 | | * | |
| 3101 | | 461.7 | | *** | |
| 3102 | 244 (decomp.) | 505.4 | | ** | |
| 3103 | 187 (decomp.) | 531.6 | | * | |
| 3104 | 166-168 | 491.4 (M − C$_5$H$_8$O) | | *** | |
| 3105 | 187-189 | 489.4 (M + NH$_4$) | | *** | |
| 3106 | 104-106 | 526.4 | | *** | |
| 3107 | 156-158 | 513.4 | | *** | |
| 3108 | 150-153 | 525.4 | | *** | |
| 3109 | 152-153 | 488.5 | | * | |
| 3110 | 167-168 | 472.3 | | *** | |
| 3111 | 165-166 | 551.5 | | *** | |
| 3112 | 167-169 | 539.4 (M + NH$_4$) | | *** | |
| 3113 | 179-180 | 646.5 | | *** | |
| 3114 | 124-127 | 518.3 | | ** | |
| 3115 | 175-178 | 551.5 | | *** | |
| 3116 | 214-217 | 537.3 | | *** | |
| 3117 | 208-210 | 551.6 | | *** | |
| 3118 | 105-108 | 506.3 | | *** | |
| 3119 | 157-159 | 520.3 | | ** | |
| 3120 | 180-181 | 496.4 | | *** | |
| 3121 | 168-172 | 492.5 | | *** | |
| 3122 | 104-107 | 506.5 | | *** | |
| 3123 | 175-177 | 484.2 | | *** | |
| 3124 | 238-241 | 489.1 | | *** | |
| 3125 | 171-175 | 482.4 | | *** | |
| 3126 | 182-185 | 496.4 | | *** | |
| 3127 | 185-188 | 506.5 | | *** | |
| 3128 | 207-210 | 494.4 | | *** | |
| 3129 | 108-110 | 548.4 | | *** | |
| 3130 | | 460.2 | | *** | (CDCl$_3$, 400 MHz), δ 7.72-7.64 (m, 3H), 7.53 (d, J = 7.6 Hz, 2H), 7.31 (s, 1H), 7.01 (d, J = 9.2 Hz, 1H), 4.93-4.88 (m, 1H), 4.64-4.51 (m, 1H), 4.24 (t, J = 4.0 Hz, 2H), 3.89-3.79 (m, 4H), 3.73-3.60 (m, 2H), 3.50 (s, 3H), 2.88-2.78 (m, 2H), 2.34-2.32 (m, 2H), 2.17-1.91 (m, 3H), 1.85-1.74 (m, 2H). |
| 3131 | 149-152 | 494.0 | | ** | (CDCl$_3$, 400 MHz), δ 7.91 (d, J = 8.4 Hz, 2H), 7.64 (d, J = 9.2 Hz, 1H), 7.56 (d, J = 8.0 Hz, 2H), 7.43-7.39 (m, 4H), 7.32 (d, J = 2.0 Hz, 1H), 7.00 (d, J = 6.8 Hz, 1H), 5.40-5.34 (m, 1H), 4.95-4.88 (m, 1H), 4.23 (t, J = 4.4 Hz, 2H), 3.82 (t, J = 4.4 Hz, 2H), 3.49 (s, 3H), 2.80-2.72 (m, 2H), 2.33 (q, J = 8.8 Hz, 2H), 1.97-1.76 (m, 2H), 1.65 (d, J = 6.8 Hz, 3H). |
| 3132 | 169-170 | 512.0 | | *** | (CDCl$_3$, 400 MHz), δ 7.91 (d, J = 8.0 Hz, 2H), 7.64 (d, J = 8.8 Hz, 1H), 7.56 (dd, J = 8.4 Hz, 2H), 7.41-7.37 (m, 2H), 7.09-7.04 (m, 2H), 7.01 (dd, J = 8.8 Hz and 1.2 Hz, 1H), 6.35 (d, J = 8.4 Hz, 1H), 5.38-5.31 (m, 1H), 4.93-4.88 (m, 1H), 4.23 (t, J = 4.4 Hz, 2H), 3.82 (t, J = 4.4 Hz, 2H), 3.50 (s, 3H), 2.82-2.72 (m, 2H), 2.33 (q, J = 8.4 Hz, 2H), 1.94-1.76 (m, 2H), 1.62 (d, J = 6.8 Hz, 3H). |
| 3133 | 156-157 | 524.8 | | *** | (CDCl$_3$, 400 MHz), δ 7.91 (d, J = 8.0 Hz, 2H), 7.64 (d, J = 8.8 Hz, 1H), 7.55 (d, J = 8.0 Hz, 2H), 7.35 (d, J = 8.8 Hz, 2H), 7.00 (d, J = 7.2 Hz, 1H), 6.91 (d, J = 8.8 Hz, 2H), 6.32 (d, J = 7.6 Hz, 1H), 5.36-5.29 (m, 1H), 4.92-4.86 (m, 1H), 4.23 (t, J = 4.4 Hz, 2H), 3.83-3.82 (m, 5H), 3.50 (s, 3H), 2.82-2.75 (m, 2H), 2.33 (q, J = 8.8 Hz, 2H), 1.96-1.76 (m, 2H), 1.63 (d, J = 6.8 Hz, 3H). |

TABLE 1A-continued

| Compound | Melting Point (° C.) | Mass Spec [M + H] | Replicon IC$_{50}$ μM 2-day | Replicon IC$_{50}$ μM 3-day | $^1$H NMR Data |
|---|---|---|---|---|---|
| 3134 | 154-160 | 498.1 | | *** | (CDCl$_3$, 400 MHz), δ 7.94 (d, J = 8.0 Hz, 2H), 7.65 (d, J = 8.8 Hz, 1H), 7.57 (d, J = 8.4 Hz, 2H), 7.38-7.33 (m, 2H), 7.09-7.04 (m, 2H), 7.03 (d, J = 8.8 Hz, 1H), 7.46 (t, J = 6.8 Hz, 1H), 4.95-4.86 (m, 1H), 4.66 (d, J = 6.0 Hz, 2H), 4.23 (t, J = 4.4 Hz, 2H), 3.82 (t, J = 4.4 Hz, 2H), 3.50 (s, 3H), 2.83-2.72 (m, 2H), 2.32 (q, J = 8.8 Hz, 2H), 1.97-1.79 (m, 2H). |
| 3135 | 216-218 | 493.9 | | * | (CDCl$_3$, 400 MHz), δ 7.90 (d, J = 8.0 Hz, 2H), 7.64 (d, J = 8.8 Hz, 1H), 7.55 (d, J = 8.4 Hz, 2H), 7.35 (d, J = 8.8 Hz, 2H), 7.18 (d, J = 1.6 Hz, 1H), 6.91 ((d, J = 8.4 Hz, 1H), 6.44 (d, J = 7.6 Hz, 1H), 5.34-5.30 (m, 1H), 4.93-4.88 (m, 1H), 4.12 (q, J = 2.8 Hz, 2H), 3.81 (s, 3H), 2.81-2.71 (m, 2H), 2.35-2.30 (m, 2H), 1.94-1.76 (m, 2H), 1.63 (d, J = 6.8 Hz, 3H), 1.49 (t, J = 6.8 Hz, 3H). |
| 3136 | 250 (decomp.) | 472.3 | | ** | (CDCl$_3$, 400 MHz), δ 7.76-7.72 (m, 3H), 7.34 (d, J = 8.0 Hz, 1H), 6.77-6.73 (m, 4H), 4.84-4.80 (m, 1H), 4.00 (t, J = 6.8 Hz, 1H), 3.65 (b, 2H), 3.46 (b, 2H), 2.63-2.58 (m, 2H), 2.32-2.28 (m, 2H), 1.90-1.75 (m, 2H), 1.36-1.23 (m, 12H) |
| 3137 | | 477.2 | | ** | (CDCl$_3$, 400 MHz), δ 7.99 (s, 1H), 7.79-7.77 (m, 1H), 7.73-7.71 (m, 1H), 7.48 (d, J = 8.0 Hz, 2H), 7.36 (d, J = 8.4 Hz, 2H), 6.71 (s, 1H), 4.96 (m, 1H), 4.41 (s, 2H), 4.29 (s, 2H), 3.23-3.19 (m, 2H), 2.84-2.76 (m, 2H), 2.40-2.37 (m, 4H), 2.01-1.83 (m, 4H), 1.10 (t, J = 7.2 Hz, 3H). |
| 3138 | | 463.2 | | ** | (CDCl$_3$, 400 MHz), δ 8.37 (s, 1H), 8.15-8.13 (m, 1H), 7.80 (d, J = 4.4 Hz, 1H), 7.48 (d, J = 8.4 Hz, 2H), 7.38 (d, J = 8.4 Hz, 2H), 7.00 (s, 1H), 5.02-4.93 (m, 1H), 4.63-4.59 (m, 2H), 4.20-4.16 (m, 2H), 4.23-4.19 (m, 2H), 2.85-2.75 (m, 2H), 2.40-2.36 (m, 2H), 2.18-1.84 (m, 4H), 1.09 (t, J = 6.8 Hz, 3H). |
| 3139 | | 458.2 | | *** | (CDCl$_3$, 400 MHz), δ 7.76-7.73 (m, 2H), 7.39-7.32 (m, 2H), 6.88-6.86 (m, 4H), 4.91-4.82 (m, 1H), 4.05-3.97 (m, 1H), 3.75-3.59 (m, 2H), 3.15 (s, 3H), 2.66-2.56 (m, 2H), 2.35-2.29 (m, 2H), 1.95-1.82 (m, 2H), 1.32-1.22 (m, 9H). |
| 3140 | | 470.2 | | *** | (CDCl$_3$, 400 MHz), δ 7.87 (s, 1H), 7.76-7.73 (m, 1H), 7.51-7.46 (m, 1H), 7.34-7.32 (m, 1H), 7.00 (s, 4H), 4.91-4.85 (m, 1H), 4.03-3.99 (m, 1H), 3.80-3.72 (m, 2H), 3.62-3.59 (m, 2H), 2.74-2.61 (m, 2H), 2.33-2.30 (m, 2H), 2.10-1.94 (m, 6H), 1.24 (d, J = 8.4 Hz, 6H). |
| 3141 | | 496.1 | | ** | (CDCl$_3$, 400 MHz), δ 7.78-7.75 (m, 2H), 7.42-7.38 (m, 1H), 7.10 (s, 4H), 5.24 (s, 1H), 4.94-4.88 (m, 1H), 4.03-3.77 (m, 9H), 2.72-2.61 (m, 2H), 2.35-2.29 (m, 2H), 1.94-1.81 (m, 2H), 1.22 (d, J = 7.6 Hz, 6H). |
| 3142 | | 444.2 | | ** | (CDCl$_3$, 400 MHz), δ 7.78-7.75 (m, 2H), 7.42-7.39 (m, 2H), 6.93-6.86 (m, 4H), 5.62 (s, 1H), 4.88-4.82 (m, 1H), 4.02-3.98 (m, 1H), 3.20-3.16 (m, 6H), 2.67-2.60 (m, 2H), 2.35-2.26 (m, 2H), 1.92-1.81 (m, 2H), 1.23 (d, J = 8.8 Hz, 6H). |
| 3143 | | 488.1 | | ** | (CDCl$_3$, 400 MHz), δ 7.83-7.71 (m, 2H), 7.48 (s, 1H), 7.41-7.38 (m, 1H), 6.87 (s, 4H), 5.65 (s, 1H), 4.87-4.81 (m, 1H), 3.80-3.74 (m, 2H), 3.64-3.55 (m, 2H), 3.44-3.36 (m, 3H), 3.20 (s, 3H), 2.66-2.59 (m, 2H), 2.34-2.25 (m, 2H), 1.91-1.81 (m, 2H), 1.22 (d, J = 8.8 Hz, 6H). |

TABLE 1A-continued

| Compound | Melting Point (° C.) | Mass Spec [M + H] | Replicon IC$_{50}$ µM 2-day | Replicon IC$_{50}$ µM 3-day | $^1$H NMR Data |
|---|---|---|---|---|---|
| 3144 | | 500.1 | | ** | (DMSO, 400 MHz), δ 8.65 (s, 1H), 7.88 (d, J = 7.6 Hz, 1H), 7.76 (s, 1H), 7.59-7.57 (m, 2H), 7.44-7.42 (m, 2H), 6.14 (d, J = 8.0 Hz, 1H), 5.04-4.99 (m, 1H), 4.18-4.16 (m, 1H), 3.78-3.74 (m, 1H), 3.57-3.46 (m, 3H), 3.04-3.01 (m, 1H), 2.60-2.55 (m, 2H), 2.32-2.30 (m, 1H), 1.91-1.65 (m, 6H), 1.09 (d, J = 6.8 Hz, 6H). |
| 3145 | 225-226 | 473.3 | | *** | (CDCl$_3$, 400 MHz), δ 7.76 (dd, J = 7.6 Hz and 1.6 Hz, 2H), 7.58 (d, J = 8.4 Hz, 2H), 7.45 (d, J = 8.4 Hz, 2H), 7.37 (d, J = 8.8 Hz, 1H), 6.76 (s, 1H), 5.09-4.97 (m, 2H), 3.60-3.36 (m, 6H), 2.87-2.76 (m, 2H), 2.38 (q, J = 8.8 Hz, 2H), 1.34-1.21 (m, 12H). |
| 3146 | 136-138 | 445.2 | | ** | (CDCl$_3$, 400 MHz), δ 7.81 (d, J = 1.2 Hz, 1H), 7.77 (d, J = 8.8 Hz, 1H), 7.58 (d, J = 8.4 Hz, 2H), 7.46-7.43 (m, 3H), 6.74 (s, 1H), 5.09-4.98 (m, 2H), 3.14-3.09 (m, 6H), 2.87-2.79 (m, 2H), 2.38 (q, J = 8.8 Hz, 2H), 2.01-1.82 (m, 2H), 1.34 (d, J = 6.4 Hz, 6H). |
| 3147 | | 459.2 | | *** | (CDCl$_3$, 400 MHz), δ 7.79-7.75 (m, 2H), 7.58 (d, J = 8.4 Hz, 2H), 7.46-7.40 (m, 3H), 6.76 (s, 1H), 5.09-4.98 (m, 2H), 3.63-3.37 (m, 2H), 3.09 (b, 3H), 2.86-2.76 (m, 2H), 2.38 (q, J = 8.4 Hz, 2H), 3.01-1.80 (m, 2H), 1.34-1.18 (m, 9H). |
| 3148 | 204-205 | 471.3 | | ** | (CDCl$_3$, 400 MHz), δ 7.92 (s, 1H), 7.76 (d, J = 8.4 Hz, 1H), 7.59-7.55 (m, 3H), 7.45 (d, J = 8.8 Hz, 2H), 6.73 (s, 1H), 5.07-5.00 (m, 2H), 3.70 (t, J = 6.4 Hz, 2H), 3.54 (t, J = 5.6 Hz, 2H), 2.84-2.78 (m, 2H), 2.38 (q, J = 10 Hz, 2H), 2.01-1.89 (m, 6H), 1.33 (d, J = 6.0 Hz, 6H). |
| 3149 | | 487.2 | | *** | (CDCl$_3$, 400 MHz), δ 7.80-7.77 (m, 2H), 7.59 (d, J = 8.8 Hz, 2H), 7.46-7.41 (m, 3H), 6.74 (s, 1H), 5.09-4.98 (m, 2H), 3.73 (b, 8H), 2.85-2.77 (m, 2H), 2.38 (q, J = 8.8 Hz, 2H), 2.01-1.80 (m, 2H), 1.34 (d, J = 6.4 Hz, 6H). |
| 3150 | 136-138 | 557.4 | | *** | |
| 3151 | 246-248 | 527.5 | | ** | |
| 3152 | 215-217 | 485.5 | | *** | |
| 3153 | 269-271 | 565.5 | | *** | |
| 3154 | 182-185 | 556.5 | | *** | |
| 3155 | 164-166 | 506.2 | | *** | |
| 3156 | 168-169 | 550.4 | | *** | |
| 3157 | 137-138 | 515.4 | | *** | |
| 3158 | 129-130 | 489.3 | | *** | |
| 3159 | 195-201 | 508.4 | | *** | |
| 3160 | 125-128 | 498.3 | | *** | |
| 3161 | 174-179 | 512.4 | | *** | |
| 3162 | 148-152 | 506.4 | | *** | |
| 3163 | 211-212 | 465.3 | | *** | |
| 3164 | 225-227 | 466.4 | | *** | |
| 3165 | 210-212 | 463.4 (M − 1) | | *** | |
| 3166 | 209-213 | 466.5 | | *** | |
| 3167 | 168-169 | 467.4 | | *** | |
| 3168 | 167-170 | 467.4 | | ** | |
| 3169 | 147-149 | 466.4 | | ** | |
| 3170 | 192-194 | 487.3 | | *** | |
| 3171 | 174-177 | 501.3 | | *** | |
| 3172 | 213-216 | 541.5 | | *** | |
| 3173 | 203-206 | 563.5 | | *** | |
| 3174 | 202-205 | 501.4 | | *** | |
| 3175 | 171-175 | 538.6 | | *** | |
| 3176 | 209-211 | 537.5 | | *** | |
| 3177 | 250-252 | 539.4 | | *** | |
| 3178 | 224-225 | 562.6 | | *** | |
| 3179 | 240-241 | 521.7 | | *** | |
| 3180 | 223-225 | 479.7 | | *** | |
| 3181 | 218-220 | 513.6 | | *** | |
| 3182 | 245-249 | 522.6 | | *** | |
| 3183 | 222-224 | 484.4 | | ** | |

TABLE 1A-continued

| Compound | Melting Point (° C.) | Mass Spec [M + H] | Replicon IC$_{50}$ μM 2-day | Replicon IC$_{50}$ μM 3-day | $^1$H NMR Data |
|---|---|---|---|---|---|
| 3184 | 259-264 | 528.5 | | ** | |
| 3185 | 279-285 | 538.8 (M − 1) | | *** | |
| 3186 | 226-231 | 548.7 | | *** | |
| 3187 | 243-249 | 577.1 | | *** | |
| 3188 | 137-138 | 547.6 | | * | |
| 3189 | 241-245 | 533.5 | | *** | |
| 3190 | 192-193 | 533.6 | | * | |
| 3191 | 227-229 | 519.7 | | *** | |
| 3192 | 201-203 | 512.6 | | *** | $^1$H NMR (300 MHz) δ, 8.32 (dd, 1H, J = 1.8, 4.8 Hz), 8.05 (dd, 1H, J = 1.8, 7.8 Hz), 7.80 (d, 1H, J = 8.7 Hz), 7.58 (d, 1H, J = 1.8 Hz), 7.10-7.49 (m, 6H), 6.73 (s, 1H), 4.95 (m, 1H), 3.21 (t, 2H, J = 7.8 Hz), 2.74-2.82 (m, 2H), 2.33-2.37 (m, 2H), 1.83-1.97 (m, 4H), 1.10 (t, 3H, 7.5 Hz). |
| 3193 | 189-191 | 475.7 | | ** | |
| 3194 | 210-212 | 499.7 | | *** | |
| 3195 | 193-194 | 498.8 | | *** | |
| 3196 | 232-236 | 485.6 | | ** | |
| 3197 | 215-217 | 512.6 | | *** | |
| 3198 | 279-282 | 477.8 | | *** | |
| 3199 | 205-210 | 535.1 | | *** | |
| 3200 | 208-212 | 487.0 | | *** | |
| 3201 | 181-184 | 555.7 | | *** | |
| 3202 | 240-242 | 501.3 | | *** | |
| 3203 | 241-242 | 474.3 | | ** | |
| 3204 | 174-177 | 488.0 | | *** | |
| 3205 | 199-201 | 447.9 | | ** | |
| 3206 | 234-236 | 527.1 | | *** | |
| 3207 | 116-118 | 501.1 | | *** | |
| 3208 | 243-245 | 485.9 | | *** | |
| 3209 | 219-221 | 528.2 | | *** | $^1$H NMR (300 MHz, CDCl$_3$): δ 1.21 (d, 6H), 1.73-2.00 (m, 2H), 2.27-2.44 (m, 2H), 2.66-2.86 (m, 2H), 3.57-3.75 (m, 1H), 3.39 (d, 1H), 4.85-5.06 (m, 1H), 6.62 (d, br, 1H), 7.12-7.15 (m, 1H), 7.27-7.34 (m, 2H), 7.43-7.50 (m, 2H), 7.58 (d, 1H), 7.82 (d, 1H), 8.30 (d, 1H), 8.43 (d, 1H) |
| 3210 | 269-271 | 511.8 | | *** | $^1$H NMR (300 MHz, CDCl$_3$): δ 1.21 (d, 6H), 1.73-2.00 (m, 2H), 2.27-2.44 (m, 2H), 2.66-2.86 (m, 2H), 3.57-3.75 (m, 1H), 3.39 (d, 1H), 4.85-5.06 (m, 1H), 6.62 (d, br, 1H), 7.12-7.15 (m, 1H), 7.27-7.34 (m, 2H), 7.43-7.50 (m, 2H), 7.58 (d, 1H), 7.82 (d, 1H), 8.30 (d, 1H), 8.43 (d, 1H) |
| 3211 | 189-191 | 525.9 | | *** | |
| 3212 | 224-226 | 435.1 | | *** | |
| 3213 | 195-197 | 434.1 | | *** | |
| 3214 | 262-268 | 491.3 | | ** | |
| 3215 | 260-271 | 479.1 | | * | |
| 3216 | 251-256 | 486.2 | | ** | |
| 3217 | 212-223 | 500.2 | | * | |
| 3218 | 180-187 | 506.4 | | ** | |
| 3219 | 203-212 | 492.2 | | ** | |
| 3220 | 187-196 | 500.3 | | * | |
| 3221 | 249-250 | 386.2 | | ** | |
| 3222 | 233-235 | 464.0 | | ** | |
| 3223 | 250-251 | 416.2 | | ** | |
| 3224 | 178-180 | 513.3 | | *** | |
| 3225 | 194-197 | 527.3 | | *** | |
| 3226 | 193-194 | 535.4 | | *** | |
| 3227 | 148-150 | 373.5 | | ** | |
| 3228 | 92-95 | 537.8 | | *** | |
| 3229 | 88-91 | 551.8 | | *** | |
| 3230 | 253-257 | 496.1 | | ** | |
| 3231 | 189-196 | 522.2 | | ** | |
| 3232 | 278-282 | 508.1 | | ** | |
| 3233 | 193-198 | 548.5 | | *** | |
| 3234 | 243-247 | 522.1 | | ** | |
| 3235 | 249-256 | 536.2 | | ** | |
| 3236 | 173-190 | 510.1 | | * | |
| 3237 | | 512.4 | | * | |
| 3238 | 205-208 | 539.2 | | *** | |

TABLE 1A-continued

| Compound | Melting Point (° C.) | Mass Spec [M + H] | Replicon IC$_{50}$ μM 2-day | Replicon IC$_{50}$ μM 3-day | $^1$H NMR Data |
|---|---|---|---|---|---|
| 3239 | 193-196 | 511.1 | | *** | |
| 3240 | 121-124 | 468.4 | | *** | |
| 3241 | 169-173 | 446.0 | | *** | |
| 3242 | 242-245 | 512.2 | | *** | |
| 3243 | 183-185 | 502.3 | | *** | |
| 3244 | 223-225 | 495.9 | | ** | |
| 3245 | 243-250 | 562.3 | | *** | |
| 3246 | 223-227 | 536.2 | | *** | |
| 3247 | 199-201 | 522.0 | | *** | |
| 3248 | 238-241 | 527.0 | | *** | |
| 3249 | 235-239 | 526.0 | | *** | |
| 3250 | 232-235 | 511.8 | | *** | |
| 3251 | 212-213 | 427.6 | | ** | |
| 3252 | 223-224 | 409.5 | | * | |
| 3253 | glass | 516.8 (M − 1) | | *** | |
| 3254 | 214-215 | 508.0 | | *** | |
| 3255 | 209-211 | 527.9 | | ** | |
| 3256 | 217-218 | 517.9 | | ** | |
| 3257 | 205-208 | 507.9 | | *** | |
| 3258 | 250-252 | 546.3 | | *** | |
| 3259 | 203-208 | 520.2 | | *** | |
| 3260 | 202-204 | 447.8 | | *** | |
| 3261 | 207-209 | 448.6 | | *** | |
| 3262 | 223 (decomp.) | 504.9 | | *** | |
| 3263 | 183-185 | 503.9 | | *** | |
| 3264 | 245-247 | 443.9 | | ** | |
| 3265 | 172-174 | 469.8 | | ** | |
| 3266 | 159-162 | 527.1 | | *** | |
| 3267 | 181-212 | 558.5 | | *** | |
| 3268 | 223-225 | 465.0 | | *** | |
| 3269 | 240-246 | 543.9 | | ** | |
| 3270 | 193-195 | 481.9 | | *** | |
| 3271 | 80-83 | 541.1 | | *** | |
| 3272 | 79-81 | 556.1 | | * | |
| 3273 | 227-230 | 526.1 | | *** | |
| 3274 | 222-225 | 527.0 | | *** | |
| 3275 | 130 (decomp.) | 552.8 | | *** | |
| 3276 | 209-212 | 553.9 | | *** | |
| 3277 | 267-268.5 | 467.0 | | *** | |
| 3278 | 165-169 | 529.8 | | *** | |
| 3279 | | 542.5 (M − 1) | | *** | |
| 3280 | | 543.9 | | *** | |
| 3281 | 211-213 | 529.7 | | *** | |
| 3282 | 181-182 | 468.8 | | *** | |
| 3283 | 145-147 | 494.9 | | *** | |
| 3284 | 99-101 | 522.9 | | *** | |
| 3285 | 236-238 | 476.9 | | *** | |
| 3286 | 233-235 | 501.9 | | ** | |
| 3287 | 166-168 | 490.9 | | ** | |
| 3288 | 215-217 | 526.7 | | *** | |
| 3289 | 177-178 | 540.6 | | *** | |
| 3290 | 176-180 | 527.7 | | *** | |
| 3291 | 168-172 | 537.3 (M − 1) | | *** | |
| 3292 | 159-161 | 432.0 | | *** | |
| 3293 | 232-250 | 513.6 | | *** | |
| 3294 | 187-192 | 527.3 (M − 1) | | * | |
| 3295 | 236-238 | 524.8 | | *** | |
| 3296 | 215-216 | 548.8 | | * | |
| 3297 | 112-119 | 442.1 | | *** | |
| 3298 | 126-139 | 496.8 | | *** | |
| 3299 | 178-179 | 563.9 | | ** | |
| 3300 | 215-216 | 470.8 | | ** | |
| 3301 | 253 (decomp.) | 489.8 (M − 1) | | *** | |
| 3302 | 175-179 | 545.8 | | *** | |
| 3303 | 138-142 | 525.8 | | *** | |
| 3304 | 222-226 | 512.4 | | *** | |
| 3305 | 225-228 | 513.4 | | *** | |
| 3306 | 218-220 | 546.0 | | *** | |
| 3307 | 243-246 | 547.0 | | *** | |
| 3308 | 138-142 | 559.1 | | ** | |
| 3309 | 219-221 | 526.0 | | * | |
| 3310 | 272-274 | 561.9 | | ** | |

TABLE 1A-continued

| Compound | Melting Point (° C.) | Mass Spec [M + H] | Replicon IC$_{50}$ μM 2-day | Replicon IC$_{50}$ μM 3-day | $^1$H NMR Data |
|---|---|---|---|---|---|
| 3311 | 191-194 | 529.1 | | *** | |
| 3312 | 206-208 | 425.1 | | *** | |
| 3313 | 244-246 | 423.0 | | *** | |
| 3314 | 198-199 | 519.9 | | *** | |
| 3315 | 237-238 | 493.0 | | *** | |
| 3316 | 244-245 | 520.9 | | *** | |
| 3317 | 225 (decomp.) | 495.1 | | *** | |
| 3318 | 235 (decomp.) | 505.1 | | *** | |
| 3319 | | 545.9 | | *** | |
| 3320 | | 546.9 | | *** | |
| 3321 | 233 (decomp.) | 494.9 | | *** | |
| 3322 | 227-229 | 522.8 | | *** | |
| 3323 | 114-300 | 492.7 | | ** | |
| 3324 | 117-300 | 518.8 | | *** | |
| 3325 | 173-181 | 491.8 | | *** | |
| 3326 | 98-99 | 460.9 | | *** | |
| 3327 | 213-215 | 426.0 | | *** | |
| 3328 | 227-229 | 424.0 | | *** | |
| 3329 | 237-238 | 438.0 | | *** | |
| 3330 | 230-231 | 452.0 | | *** | |
| 3331 | 217-218 | 466.0 | | *** | |
| 3332 | 140 (decomp.) | 483.2 | | *** | |
| 3333 | 108-115 | | | *** | |
| 3334 | 108-116 | 531.6 | | *** | |
| 3335 | 227-230 | 540.0 | | *** | |
| 3336 | 257-259 | 541.0 | | *** | |
| 3338 | 280-281 | 507.0 | | *** | |
| 3337 | 227-230 | 560.0 | | *** | |
| 3339 | 284-285 | 481.0 | | *** | |
| 3340 | 290-291 | 515.4 | | *** | |
| 3341 | 265-266 | 535.0 | | *** | |
| 3342 | 266-267.5 | 480.0 | | *** | |
| 3343 | 109-110 | 466.0 | | *** | |
| 3344 | 227-230 | 541.9 | | *** | |
| 3345 | 167-169 | 561.8 | | *** | |
| 3346 | 113-116 | 529.9 | | *** | |
| 3347 | 160-162 | 549.9 | | *** | |
| 3348 | 229-231 | 436.9 | | *** | |
| 2150 | 170-172 | 402.4 | | *** | |
| 2186 | 189-191 | 473.4 | | *** | |
| 2194 | | 493.4 | | *** | |
| 2249 | 155-156 | 487.3 | | ** | $^1$H NMR (CDCl$_3$, 400 MHz), δ 7.65 (d, J = 8.8 Hz, 1H), 7.58-7.52 (m, 4H), 7.23 (s, 1H), 6.98 (dd, J = 8.8 Hz and 2.4 Hz, 1H), 4.93-4.88 (m, 1H), 4.14 (q, J = 7.2 Hz, 2H), 3.87 (b, 2H), 3.55 (b, 4H), 3.37 (s, 3H), 2.87-2.82 (m, 2H), 2.70-2.44 (m, 6H), 2.34-2.32 (m, 2H) 2.01-2.80 (m, 2H), 1.49 (t, J = 6.8 Hz, 3H). |
| 2250 | 194-195 | 465.2 | | ** | $^1$H NMR (CDCl$_3$, 400 MHz), δ 8.61 (d, J = 5.2 Hz, 1H), 7.96 (d, J = 8.4 Hz, 2H), 7.85 (b, 1H), 7.78-7.74 (m, 1H), 7.64 (d, J = 8.8 Hz, 1H), 7.55 (d, J = 8.4 Hz, 2H), 7.33-7.29 (m, 2H), 7.20 (s, 1H), 6.97 (d, J = 6.8 Hz, 1H), 4.94-4.90 (m, 1H), 4.14 (q, J = 7.2 Hz, 2H), 3.94 (q, J = 5.4 Hz, 2H), 3.22 (t, J = 6.0 Hz, 2H), 2.83-2.72 (m, 2H), 2.37-2.31 (m, 2H), 1.96-1.77 (m, 2H), 1.49 (t, J = 6.8 Hz, 3H). |
| 2251 | 172-173 | 430.2 | | ** | $^1$H NMR (CDCl$_3$, 400 MHz), δ 7.69-7.64 (m, 3H), 7.53 (d, J = 8.0 Hz, 2H), 7.22 (s, 1H), 6.98 (dd, J = 8.8 Hz and 1.2 Hz, 1H), 4.93-4.89 (m, 1H), 4.63-4.52 (m, 1H), 4.14 (q, J = 6.8 Hz, 2H), 3.83-3.49 (m, 4H), 2.85-2.80 (m, 2H), 2.35-2.31 (m, 2H), 2.04-1.78 (m, 5H), 1.49 (t, J = 7.2 Hz, 3H). |
| 2271 | 160-163 | 527.4 | | *** | |
| 2272 | 166-168 | 499.4 | | *** | |
| 2273 | 118-121 | 499.4 | | *** | |
| 2274 | 201-203 | 585.4 | | *** | |
| 2275 | 114-117 | 485.4 | | *** | |

TABLE 1A-continued

| Compound | Melting Point (° C.) | Mass Spec [M + H] | Replicon IC$_{50}$ μM 2-day | Replicon IC$_{50}$ μM 3-day | $^1$H NMR Data |
|---|---|---|---|---|---|
| 2276 | 118-120 | 471.4 | *** | | |
| 2277 | 217-221 | 396.4 | *** | | |
| 2293 | 199-201 | 519.4 | *** | | |
| 2294 | 205-207 | 491.4 | *** | | |
| 2295 | 105-107 | 491.4 | *** | | |
| 2296 | 202-205 | 477.3 | *** | | |
| 2297 | 235-237 | 463.3 | *** | | |
| 2312 | 203-204 | 467.4 | ** | | |

Example 7

Evaluation of the Activity of Compounds Using an HCV-Poliovirus Chimera

In an HCV-poliovirus (HCV-PV) chimera, the PV 5' UTR is replaced by the HCV 5' UTR and partial (the first 123 amino acids) core coding sequences (nucleotides 18 to 710 of HCV 1b) (140). As a consequence, the expression of poliovirus proteins is under regulation of the HCV IRES. Poliovirus is a picornavirus in which protein translation initiation is mediated by an IRES element located in the 5' UTR. At the 5' end of the HCV-PV chimeric genome, there is the cloverleaf-like RNA structure of PV, an essential cis-acting replication signal ending with the genome-linked protein VPg. Replication kinetics of the HCV-PV chimera matches that of the parental poliovirus (Mahoney) and can result in cytopathic effects (CPE) in cell culture. Heptazyme, a ribozyme that targets the HCV IRES, was shown to be active against the chimeric virus in cell culture (76, 77).

To evaluate compounds for activity against the chimeric virus, HeLa cells are seeded and incubated at 37° C. under 5% $CO_2$ for 24 hours. The cells are then infected with HCV-PV at a multiplicity of infection (MOI) at 0.1 for 30 min and then treated with compound for 1 day (treatment time will be optimized). The activity of compounds is determined by a change in cytopathic effect, plaque assay, and/or viral RNA production (see e.g., Tables 1A and 1B).

Example 8

Evaluation of the Activity of Compounds Against a Wild-Type Poliovirus (WT-PV) and the Poliovirus IRES Translation Assay (WT-PV Mono luc)

A DNA construct is prepared, termed pPVIRESmono, in which PV IRES sequences are inserted (nucleotide number 1-742) between a promoter and the firefly luciferase (Fluc) reporter gene. A stably transfected 293 T cell line, is established by transfection with the pPVIRESmono DNA by selecting for resistance to hygromycin. As previously described, cells are treated with compounds for 20 hours, and activity is determined by quantifying the Fluc signal. Additionally, to evaluate compounds activity against wild-type poliovirus, Hela cells are seeded and incubated at 37° C. under 5% $CO_2$ for 24 hours. Cells are then infected with wild-type poliovirus at a MOI at 0.1 for 30 minutes, and then treated with compound for one day. The activity of compounds is determined by changes in cytopathic effect, plaque assay, and RT-PCR using poliovirus IRES primers and probes (see e.g., Table 2).

Furthermore, if compounds are active against the poliovirus and other virus IRESs, then the compounds are useful for treating viral infection by any virus containing an IRES.

TABLE 2

| Compound No. | WT-PV CPE (100 μM)* | WT-PV CPE (10 μM)* | WT-PV CPE (1 μM)* | WTPV mono luc IC$_{50}$ (μM) |
|---|---|---|---|---|
| 4 | 3 | 2 | 1 | 0.8 |
| 5 | 3 | 2 | 1 | 9 |
| 9 | 3 | 2 | 2 | >100 |
| 10 | 3 | 2 | 2 | >100 |
| 19 | 3 | 2 | 1 | 15 |
| 24 | 3 | 2 | 2 | 1.5 |

Example 9

In Vitro Translation Assay

In vitro translation assays can be used to distinguish between the compounds that act on HCV IRES RNA or cellular translation factors. In exemplary assays, the mRNA that will direct translation is a transcribed runoff product from the T7 RNA polymerase promoter of the pHCVIRESmono plasmid DNA generated with Ambion RNA MegaTranscript kit (Ambion, Inc., Austin, Tex.). In vitro translation is performed using HeLa cell lysates using methods known to one of skill in the art. Preliminary results indicate that one or more of the compounds of the present invention has significantly higher activity against HCV IRES regulated translation after preincubating the compound with the HCV IRES RNA transcripts than after preincubating with HeLa cell lysate for 30 min at 37° C. or without preincubation (data not shown). This suggests that this compound may interact with the HCV IRES RNA in the in vitro translation assay. To demonstrate whether the compounds selectively act on the HCV IRES, pLuc is used together with cellular IRES mRNA transcripts as controls for in vitro translation.

All publications and patent applications cited herein are incorporated by reference to the same extent as if each individual publication or patent application was specifically and individually indicated to be incorporated by reference.

Although certain embodiments have been described in detail above, those having ordinary skill in the art will clearly understand that many modifications are possible in the embodiments without departing from the teachings thereof.

All such modifications are intended to be encompassed within the claims of the invention.

REFERENCES

1. Ali, N., G. J. Pruijn, D. J. Kenan, J. D. Keene, and A. Siddiqui. 2000. Human La antigen is required for the hepatitis C virus internal ribosome entry site-mediated translation. J Biol Chem 275:27531-27540.
2. Ali, N. and A. Siddiqui. 1995. Interaction of polypyrimidine tract-binding protein with the 5' noncoding region of the hepatitis C virus RNA genome and its functional requirement in internal initiation of translation. J Virol 69:6367-6375.
3. Ali, N. and A. Siddiqui. 1997. The La antigen binds 5' noncoding region of the hepatitis C virus RNA in the context of the initiator AUG codon and stimulates internal ribosome entry site-mediated translation. Proc Natl Acad Sci USA 94:2249-2254.
4. Anwar, A. N. Ali, R. Tanveer, and A. Siddiqui. 2000. Demonstration of functional requirement of polypyrimidine tract-binding protein by SELEX RNA during hepatitis C virus internal ribosome entry site-mediated translation initiation. J Biol Chem 275:34231-34235.
5. Beales, L. P., D. J. Rowlands, and A. Holzenburg. 2001. The internal ribosome entry site (IRES) of hepatitis C virus visualized by electron microscopy. RNA 7:661-670.
6. Belsham, G. J. and J. K. Brangwyn. 1990. A region of the 5' noncoding region of foot-and-mouth disease virus RNA directs efficient internal initiation of protein synthesis within cells: involvement with the role of L protease in translational control. J Virol 64:5389-5395.
7. Belsham, G. J. and R. J. Jackson. 2000. Translation initiation on picornavirus RNA., p. 869-900. Cold Spring Harbor Laboratory Press, New York.
8. Blight, K J., A. A. Kolykhalov, and C. M. Rice. 2000. Efficient initiation of HCV RNA replication in cell culture. Science 290:1972-1974.
9. Blight, K. J., J. A. McKeating, and C. M. Rice. 2002. Highly permissive cell lines for subgenomic and genomic hepatitis C virus RNA replication. J Virol 76:13001-13014.
10. Borvjagin, G., T. Pestova, and I. Shatsky. 1994. Pyrimidine tract binding protein strongly stimulates in vitro encephalomyocarditis virus RNA translation at the level of the preinitiation complex formation. FEBS Lett 351:291-302.
11. Brown, E. A., H. Zhang, L. H. Ping, and S. M. Lemon. 1992. Secondary structure of the 5' nontranslated regions of hepatitis C virus and pestivirus genomic RNAs. Nucleic Acids Res 20:5041-5045.
12. Buck C B, Shen X, Egan M A, Pierson T C, Walker C M, and Siliciano R F. 2001. The human immunodeficiency virus type 1 gag gene encodes an internal ribosome entry site. J Virol 75:181-191.
13. Bukh, J., R. H. Purcell, and R. H. Miller. 1992. Sequence analysis of the 5' noncoding region of hepatitis C virus. Proc Natl Acad Sci USA 89:4942-4946.
14. Bukh, J., R. H. Purcell, and R. H. Miller. 1994. Sequence analysis of the core gene of 14 hepatitis C virus genotypes. Proc Natl Acad Sci USA 91:8239-8243.
15. Buratti, E., S. Tisminetzky, M. Zotti, and F. E. Baralle. 1998. Functional analysis of the interaction between HCV 5'UTR and putative subunits of eukaryotic translation initiation factor eIF3. Nucleic Acids Res 26:3179-3187.
16. Chappell, S. A., J. P. LeQuesne, F. E. Paulin, M. L. deSchoolmeester, M. Stoneley, R. L. Soutar, S. H. Ralston, M. H. Helfrich, and A. E. Willis. 2000. A mutation in the c-myc-IRES leads to enhanced internal ribosome entry in multiple myeloma: a novel mechanism of oncogene deregulation. Oncogene 19:4437-4440.
17. Chung, R. T., W. He, A. Saquib, A. M. Contreras, R. J. Xavier, A. Chawla, T. C. Wang, and E. V. Schmidt. Hepatitis C virus replication is directly inhibited by IFN-alpha in a full-length binary expression system. 2001. Proc Natl Acad Sci USA 98:9847-9852.
18. Coldwell, M. J., S. A. Mitchell, M. Stoneley, M. MacFarlane, and A. E. Willis. 2000. Initiation of Apaf-1 translation by internal ribosome entry. Oncogene 19:899-905.
19. Creancier, L., D. Morello, P. Mercier, and A. C. Prats. 2000. Fibroblast growth factor 2 internal ribosome entry site (IRES) activity ex vivo and in transgenic mice reveals a stringent tissue-specific regulation. J Cell Biol 150:275-281.
20. Das, S., M. Ott, A. Yamane, A. Venkatesan, S. Gupta, and A. Dasgupta. 1998. Inhibition of internal entry site (IRES)-mediated translation by a small yeast RNA: a novel strategy to block hepatitis C virus protein synthesis. Front Biosci 3:D1241-D1252.
21. Dever, T. E. 2002. Gene-specific regulation by general translation factors. Cell 108:545-556.
22. Dumas, E., C. Staedel, M. Colombat, S. Reigadas, S. Chabas, T. Astier-Gin, A. Cahour, S. Litvak, and M. Ventura. 2003. A promoter activity is present in the DNA sequence corresponding to the hepatitis C virus 5' UTR. Nucleic Acids Res 31:1275-1281.
23. Fukushi, S., K. Katayama, C. Kurihara, N. Ishiyama, F. B. Hoshino, T. Ando, and A. Oya. 1994. Complete 5' noncoding region is necessary for the efficient internal initiation of hepatitis C virus RNA. Biochem Biophys. Res Commun. 199:425-432.
24. Fukushi, S., C. Kurihara, N. Ishiyama, F. B. Hoshino, A. Oya, and K Katayama. 1997. The sequence element of the internal ribosome entry site and a 25-kilodalton cellular protein contribute to efficient internal initiation of translation of hepatitis C virus RNA. J Virol 71:1662-1666.
25. Fukushi, S., M. Okada, T. Kageyama, F. B. Hoshino, and K. Katayama. 1999. Specific interaction of a 25-kilodalton cellular protein, a 40S ribosomal subunit protein, with the internal ribosome entry site of hepatitis C virus genome. Virus Genes 19:153-161.
26. Fukushi, S., M. Okada, J. Stahl, T. Kageyama, F. B. Hoshino, and K. Katayama. 2001. Ribosomal protein S5 interacts with the internal ribosomal entry site of hepatitis C virus. J Biol Chem 276:20824-20826.
27. Funkhouser, A. W., D. E. Schultz, S. M. Lemon, R. H. Purcell, and S. U. Emerson. 1999. Hepatitis A virus translation is rate-limiting for virus replication in MRC-5 cells. Virology 254:268-278.
28. Glass, M. J., X. Y. Jia, and D. F. Summers. 1993 Identification of the hepatitis A virus internal ribosome entry site: in vivo and in vitro analysis of bicistronic RNAs containing the HAV 5' noncoding region. Virology. 193:842-852.
29. Gordon S. C., B. R. Bacon, I. M. Jacobson, M. I. Shiffman, N. H. Afdhal, J. G. McHutchison, T. J. Kwoh, and F. A. Dorr. 2002. A Phase II, 12-week study of ISIS 14803, an antisense inhibitor of HCV for the treatment of chronic hepatitis C. AASLD Abst. 795. Hepatology 36:362A.
30. Gosert, R., K. H. Chang, R. Rijnbrand, M. Yi, D. V. Sangar, and S. M. Lemon. 2000. Transient expression of cellular polypyrimidine-tract binding protein stimulates cap-independent translation directed by both picornaviral and flaviviral internal ribosome entry sites In vivo. Mol Cell Biol 20:1583-1595.

31. Gray, N, and M. Wickens. 1998. Control of translation initiation in animals. Annu Rev Cell Dev Biol 14:399-458.

31a. Griffith, A., and D. M. Coen. 2005. An unusual internal ribosome entry site in the herpes simplex virus thymidine kinase gene. Proc Natl Acad Sci U S A. 102:9667-72.

32. Guo, J. T., V. V. Bichko, and C. Seeger. 2001. Effect of alpha interferon on the hepatitis C virus replicon. J Virol 75:8516-8523.

33. Hahm, B., Y. K. Kim, J. H. Kim, T. Y. Kim, and S. K. Jang. 1998. Heterogeneous nuclear ribonucleoprotein L interacts with the 3' border of the internal ribosomal entry site of hepatitis C virus. J Virol 72:8782-8788.

34. Haller, A. A., S. R. Stewart, and B. L. Semler. 1996. Attenuation stem-loop lesions in the 5' noncoding region of poliovirus RNA: neuronal cell-specific translation defects. J Virol 70:1467-1474.

35. Hellen, C. U. and T. V. Pestova. 1999. Translation of hepatitis C virus RNA. J Viral Hepat 6:79-87.

36. Hellen, C. U., G. W. Witherell, M. Schmid, S. H. Shin, T. V. Pestova, A. Gil, and E. Wimmer. 1993. A cytoplasmic 57-kDa protein that is required for translation of picornavirus RNA by internal ribosomal entry is identical to the nuclear pyrimidine tract-binding protein. Proc Natl Acad Sci USA 90:4672-7646

37. Hendrix, M., E. S. Priestley, G. F. Joyce, and C. H. Wong. 1997. Direct observation of aminoglycoside-RNA interactions by surface plasmon resonance. Journal of the American Chemical Society 119:3641-8.

38. Holcik, M. and R. G. Korneluk. 2000. Functional characterization of the X-linked inhibitor of apoptosis (XIAP) internal ribosome entry site element: role of La autoantigen in XIAP translation. Mol Cell Biol 20:4648-4657.

39. Holcik, M., C. Lefebvre, C. Yeh, T. Chow, and R. G. Korneluk. 1999. A new internal-ribosome-entry-site motif potentiates XIAP-mediated cytoprotection. Nat Cell Biol 1:190-192.

40. Honda, M., M. R. Beard, L. H. Ping, and S. M. Lemon. 1999. A phylogenetically conserved stem-loop structure at the 5' border of the internal ribosome entry site of hepatitis C virus is required for cap-independent viral translation. J Virol 1165-1174.

41. Honda, M., E. A. Brown, and S. M. Lemon. 1996. Stability of a stem-loop involving the initiator AUG controls the efficiency of internal initiation of translation on hepatitis C virus RNA. RNA 2:955-968.

42. Honda, M., L. H. Ping, R. C. Rijnbrand, E. Amphlett, B. Clarke, D. Rowlands, and S. M. Lemon. 1996. Structural requirements for initiation of translation by internal ribosome entry within genome-length hepatitis C virus RNA. Virology 222:31-42.

43. Honda, M., R. Rijnbrand, G. Abell, D. Kim, and S. M. Lemon. 1999. Natural variation in translational activities of the 5' nontranslated RNAs of hepatitis C virus genotypes 1a and 1b: evidence for a long-range RNA-RNA interaction outside of the internal ribosomal entry site. J Virol 73:4941-4951.

44. Huez, I., S. Bornes, D. Bresson, L. Creancier, and H. Prats. 2001. New vascular endothelial growth factor isoform generated by internal ribosome entry site-driven CUG translation initiation. Mol Endocrinol. 15:2197-2210.

45. Huez, I., L. Creancier, S. Audigier, M. C. Gensac, A. C. Prats, and H. Prats. 1998. Two independent internal ribosome entry sites are involved in translation initiation of vascular endothelial growth factor mRNA. Mol Cell Biol 18:6178-6190

46. Ikeda, M., M. Yi, K. Li, and S. M. Lemon. 2002. Selectable subgenomic and genome-length dicistronic RNAs derived from an infectious molecular clone of the HCV-N strain of hepatitis C virus replicate efficiently in cultured Huh7 cells. J Virol 76:2997-3006.

47. Irvine, J. D., L. Takahashi, K. Lockhart, J. Cheong, J. W. Tolan, H. E. Selick, and J. R. Grove. 1999. MDCK (Madin-Darby canine kidney) cells: A tool for membrane permeability screening. J Pharm Sci 88:28-33.

48. Isoyama, T., N. Kamoshita, K. Yasui, A. Iwai, K. Shiroki, H. Toyoda, A. Yamada, Y. Takasaki, and A. Nomoto. 1999. Lower concentration of La protein required for internal ribosome entry on hepatitis C virus RNA than on poliovirus RNA. J Gen Virol 80 (Pt 9):2319-2327.

49. Ito, T. and M. M. Lai. 1999. An internal polypyrimidine-tract-binding protein-binding site in the hepatitis C virus RNA attenuates translation, which is relieved by the 3'-untranslated sequence. Virology 254:288-296.

50. Jang, S. K., H. G. Krausslich, M. J. Nicklin, G. M. Duke, A. C. Palmenberg, and E. Wimmer. 1988. A segment of the 5' nontranslated region of encephalomyocarditis virus RNA directs internal entry of ribosomes during in vitro translation. J Virol 62:2636-2643.

51. Jubin, R., N. E. Vantuno, J. S. Kieft, M. G. Murray, J. A. Doudna, J. Y. Lau, and B. M. Baroudy. 2000. Hepatitis C virus internal ribosome entry site (IRES) stem loop IIId contains a phylogenetically conserved GGG triplet essential for translation and IRES folding. J Virol 74:10430-10437.

52. Kalliampakou, K. I., L. Psaridi-Linardaki, and P. Mavromara. 2002. Mutational analysis of the apical region of domain II of the HCV IRES. FEBS Lett 511:79-84.

53. Kaminski, A., S. L. Hunt, J. G. Patton, and R. J. Jackson. 1995. Direct evidence that polypyrimidine tract binding protein (PTB) is essential for internal initiation of translation of encephalomyocarditis virus RNA. RNA 1:924-938

54. Kamoshita, N., K. Tsukiyama-Kohara, M. Kohara, and A. Nomoto. 1997. Genetic analysis of internal ribosomal entry site on hepatitis C virus RNA: implication for involvement of the highly ordered structure and cell type-specific transacting factors. Virology 233:9-18.

55. Kieft, J. S., K. Zhou, R. Jubin, M. G. Murray, J. Y. Lau, and J. A. Doudna. 1999. The hepatitis C virus internal ribosome entry site adopts an ion-dependent tertiary fold. J Mol Biol 292:513-529.

56. Kieft, J. S., K. Zhou, R. Jubin, M. G. Murray, J. Y. Lau, and J. A. Doudna. 2001. Mechanism of ribosome recruitment by hepatitis C IRES RNA. RNA 7:194-206.

57. Klinck, R., E. Westhof, S. Walker, M. Afshar, A. Collier, and F. Aboul-Ela. 2000. A potential RNA drug target in the hepatitis C virus internal ribosomal entry site. RNA 6:1423-1431.

58. Kolupaeva V G, Pestova T V, and Hellen C U T. 2000. An enzymatic foot-printing analysis of the interaction of 40S ribosomal subunits with the internal ribosomal entry site of hepatitis C virus. J Virol 74:6242-6250.

59. Kolupaeva, V. G., C. U. Hellen, and I. N. Shatsky. 1996. Structural analysis of the interaction of the pyrimidine tract-binding protein with the internal ribosomal entry site of encephalomyocarditis virus and foot-and-mouth disease virus RNAs. RNA 2:1199-1212.

60. Kolupaeva, V. G., T. V. Pestova, C. U. Hellen, and I. N. Shatsky. 1998. Translation eukaryotic initiation factor 4G recognizes a specific structural element within the internal ribosome entry site of encephalomyocarditis virus RNA. J Biol Chem 273:18599-18604.

61. Kozak, M. 1999. Initiation of translation in prokaryotes and eukaryotes. Gene 234:187-208.
62. Kruger, M., C. Beger, P. J. Welch, J. R. Barber, M. P. Manns, and F. Wong-Staal. 2001. Involvement of proteasome alpha-subunit PSMA7 in hepatitis C virus internal ribosome entry site-mediated translation. Mol Cell Biol 21: 8357-8364
63. La Monica, N. and V. R. Racaniello. 1989. Differences in replication of attenuated and neurovirulent polioviruses in human neuroblastoma cell line SH-SY5Y. J Virol 63:2357-2360.
64. Le, S. Y., N. Sonenberg, and J. V. Maizel, Jr. 1995. Unusual folding regions and ribosome landing pad within hepatitis C virus and pestivirus RNAs. Gene 154:137-143.
65. Lerat, H., Y. K. Shimizu, and S. M. Lemon. 2000. Cell type-specific enhancement of hepatitis C virus internal ribosome entry site-directed translation due to 5' nontranslated region substitutions selected during passage of virus in lymphoblastoid cells. J Virol 74:7024-7031.
66. Li, K., T. M. Davis, C. Bailly, A. Kumar, D. W. Boykin, and W. D. Wilson. 2001. A heterocyclic inhibitor of the REV-RRE complex binds to RRE as a dimer. Biochemistry 40:1150-8.
67. Lipinski, J. 2000. J. Pharm. Tox. Meth. 44:235-249.
68. Llinàs-Brunet M. 2002. NS3 serine protease inhibitors as potential antiviral agents for the treatment of hepatitis C virus infections. The 3rd internatl antiviral & vaccine discovery and development summit. March 13-14. Princeton, N. J.
69. Lohmann, V., F. Korner, A. Dobierzewska, and R. Bartenschlager. 2001. Mutations in hepatitis C virus RNAs conferring cell culture adaptation. J Virol 75:1437-1449.
70. Lohmann, V., F. Korner, J. Koch, U. Herian, L. Theilmann, and R. Bartenschlager. 1999. Replication of subgenomic hepatitis C virus RNAs in a hepatoma cell line. Science 285:110-113.
71. Lopez, d. Q., E. Lafuente, and E. Martinez-Salas. 2001. IRES interaction with translation initiation factors: functional characterization of novel RNA contacts with eIF3, eIF4B, and eIF4GII. RNA 7:1213-1226.
72. Lopez, d. Q. and E. Martinez-Salas. 2000. Interaction of the eIF4G initiation factor with the aphthovirus IRES is essential for internal translation initiation in vivo. RNA 6:1380-1392.
73. Lu, H. H. and E. Wimmer. 1996. Poliovirus chimeras replicating under the translational control of genetic elements of hepatitis C virus reveal unusual properties of the internal ribosomal entry site of hepatitis C virus. Proc Natl Acad Sci USA 93:1412-7.
74. Lukavsky, P. J., G. A. Otto, A. M. Lancaster, P. Sarnow, and J. D. Puglisi. 2000. Structures of two RNA domains essential for hepatitis C virus internal ribosome entry site function. Nat Struct Bio 7:1105-1110.
75. Lyons, A. J., J. R. Lytle, J. Gomez, and H. D. Robertson. Hepatitis C virus internal ribosome entry site RNA contains a tertiary structural element in a functional domain of stem-loop II. Nucleic Acids Res 29:2535-2546.
76. Macejak, D. G., K. L. Jensen, S. F. Jamison, K. Domenico, E. C. Roberts, N. Chaudhary, I. von_Carlowitz, L. Bellon, M. J. Tong, A. Conrad, P. A. Pavco, and L. M. Blatt. 2000. Inhibition of hepatitis C virus (HCV)-RNA-dependent translation and replication of a chimeric HCV poliovirus using synthetic stabilized ribozymes. Hepatology (Baltimore, Md.) 31:769-76.
77. Macejak, D. G., K. L. Jensen, P. A. Pavco, K. M. Phipps, B. A. Heinz, J. M. Colacino, and L. M. Blatt. 2001. Enhanced antiviral effect in cell culture of type 1 interferon and ribozymes targeting HCV RNA. J Viral Hepatitis 8:400-405.
78. Macejak, D. G. and P. Sarnow. 1991. Internal initiation of translation mediated by the 5' leader of a cellular mRNA. Nature 353:90-94.
79. Major M E, Rehermann B, and Feinstone. 2001. Hepatitis C viruses., p. 2535-2541. In D. Knipe and P. Howley (eds.), Fields Virology. Lippincott Williams and Wilkins, Philadelphia, Pa.
80. Manns M P, McHutchison J G, Gordon S C, Rustgi V K, Shiffman M, Reindollar R, Goodman Z D, Koury K, Ling M, and Albrecht J K. 2003. Peginterferon alfa-2b plus ribavirin compared with interferon alfa-2b plus ribavirin for initial treatment of chronic hepatitis C: a randomised trial. Lancet 358:958-965.
81. Martinez-Salas, E., R. Ramos, E. Lafuente, and d. Q. Lopez. 2001. Functional interactions in internal translation initiation directed by viral and cellular IRES elements. J Gen Virol 82:973-984.
82. Mazur, S., F. A. Tanious, D. Ding, A. Kumar, D. W. Boykin, I. J. Simpson, S. Neidle, and W. D. Wilson. 2000. A thermodynamic and structural analysis of DNA minor-groove complex formation. Journal of Molecular Biology 300:321-37.
83. McHutchison J G and Poynard T. 1999. Combination therapy with interferon plus ribavirin for the initial treatment of chronic hepatitis C. Semin. Liver Dis. 19 Suppl 1:57-65.
84. McHutchison, J. G., T. Poynard, R. Esteban-Mur, G. L. Davis, Z. D. Goodman, J. Harvey, M. H. Ling, J. J. Garaud, J. K. Albrecht, K. Patel, J. L. Dienstag, and T. Morgan. 2002. Hepatic HCV RNA before and after treatment with interferon alone or combined with ribavirin. Hepatology 35:688-693.
85. Meerovitch, K., J. Pelletier, and N. Sonenberg. 1989. A cellular protein that binds to the 5'-noncoding region of poliovirus RNA: implications for internal translation initiation. Genes Dev 3:1026-1034.
86. Meerovitch, K., Y. V. Svitkin, H. S. Lee, F. Lejbkowicz, D. J. Kenan, E. K. Chan, V. I. Agol, J. D. Keene, and N. Sonenberg. 1993. La autoantigen enhances and corrects aberrant translation of poliovirus RNA in reticulocyte lysate. J Virol 67: 3798-3807.
87. Mercer, D. F., D. E. Schiller, J. F. Elliott, D. N. Douglas, C. Hao, A. Rinfret, W. R. Addison, K P. Fischer, T. A. Churchill, J. R. Lakey, D. L. Tyrrell, and N. M. Kneteman. 2001. Hepatitis C virus replication in mice with chimeric human livers. Nature Medicine 7:927-33.
88. Michel, Y. M., A. M. Borman, S. Paulous, and K. M. Kean. 2001. Eukaryotic initiation factor 4G-poly(A) binding protein interaction is required for poly(A) tail-mediated stimulation of picornavirus internal ribosome entry segment-driven translation but not for X-mediated stimulation of hepatitis C virus translation. Mol Cell Biol 21: 4097-4109.
89. Mitchell, S. A., E. C. Brown, M. J. Coldwell, R. J. Jackson, and A. E. Willis. 2001. Protein factor requirements of the Apaf-1 internal ribosome entry segment: roles of polypyrimidine tract binding protein and upstream of N-ras. Mol Cell Biol 21:3364-3374.
90. Moriguchi, e. al. 1992. Chem Pharm Bull 40:127-130.
91. Nanbru, C., I. Lafon, S. Audigier, M. C. Gensac, S. Vagner, G. Huez, and A. C. Prats. 2003. Alternative translation of the proto-oncogene c-myc by an internal ribosome entry site. J Biol Chem 272:32061-32066.
92. Niepmann, M., A. Petersen, K. Meyer, and E. Beck. 1997. Functional involvement of polypyrimidine tract-binding 93. Odreman-Macchioli, F., F. E. Baralle, and E. Buratti. 2001. Mutational analysis of the different bulge regions of hepatitis C virus domain II and their influence on internal ribosome entry site translational ability. J Biol Chem 276: 41648-41655.
94. Odreman-Macchioli, F. E., S. G. Tisminetzky, M. Zotti, F. E. Baralle, and E. Buratti. 2000. Influence of correct secondary and tertiary RNA folding on the binding of cellular factors to the HCV IRES. Nucleic Acids Res 28:875-885.
95. Ohlmann, T., M. Lopez-Lastra, and J. L. Darlix. 2000. An internal ribosome entry segment promotes translation of the simian immunodeficiency virus genomic RNA. J Biol Chem 275:11899-11906.
96. Pain V M. 1996. Initiation of protein synthesis in eukaryotic cells. Eur J Biochem 236:747-771.
97. Pelletier, J. and N. Sonenberg. 1988. Internal initiation of translation of eukaryotic mRNA directed by a sequence derived from poliovirus RNA. Nature 334:320-325.
98. Pelletier, J. and N. Sonenberg. 1989. Internal binding of eucaryotic ribosomes on poliovirus RNA: translation in HeLa cell extracts. J Virol 63:441-444.
99. Pestova, T. V., S. I. Borukhov, and C. U. Hellen. 1998. Eukaryotic ribosomes require initiation factors 1 and 1A to locate initiation codons. Nature 394:854-859.
100. Pestova, T. V., I. N. Shatsky, S. P. Fletcher, R. J. Jackson, and C. U. Hellen. 1998. A prokaryotic-like mode of cytoplasmic eukaryotic ribosome binding to the initiation codon during internal translation initiation of hepatitis C and classical swine fever virus RNAs. Genes Dev 12: 67-83.
101. Pestova, T. V., I. N. Shatsky, and C. U. Hellen. 1996. Functional dissection of eukaryotic initiation factor 4F: the 4A subunit and the central domain of the 4G subunit are sufficient to mediate internal entry of 43S preinitiation complexes. Mol Cell Biol 16:6870-6878.
102. Peytou, V., R. Condom, N. Patino, R. Guedj, A. M. Aubertin, N. Gelus, C. Bailly, R. Terreux, and D. Cabrol_Bass. 1999. Synthesis and antiviral activity of ethidium-arginine conjugates directed against the TAR RNA of HIV-1. Journal of Medicinal Chemistry 42:4042-53.
103. Pietschmann, T., V. Lohmann, A. Kaul, N. Krieger, G. Rinck, G. Rutter, D. Strand, and R. Bartenschlager. 2002. Persistent and transient replication of full-length hepatitis C virus genomes in cell culture. J Virol 76:4008-4021.
104. Pietschmann, T., V. Lohmann, G. Rutter, K Kurpanek, and R. Bartenschlager. 2001. Characterization of cell lines carrying self-replicating hepatitis C virus RNAs. J Virol 75:1252-1264.
105. Poole, T. L., C. Wang, R. A. Popp, L. N. Potgieter, A. Siddiqui, and M. S. Collett. 1995. Pestivirus translation initiation occurs by internal ribosome entry. Virology 206: 750-754.
106. Pringle, C. 1999. Virus taxonomy—1999. The universal system of virus taxonomy, updated to include the new proposals ratified by the International Committee on Taxonomy of Viruses during 1998. Arch Virol 144:421-429.
107. Psaridi, L., U. Georgopoulou, A. Varaklioti, and P. Mavromara. 1999. Mutational analysis of a conserved tetraloop in the 5' untranslated region of hepatitis C virus identifies a novel RNA element essential for the internal ribosome entry site function. FEBS Lett 453:49-53.
108. Reynolds, J. E., A. Kaminski, A. R. Carroll, B. E. Clarke, D. J. Rowlands, and R. J. Jackson. 1996. Internal initiation of translation of hepatitis C virus RNA: the ribosome entry site is at the authentic initiation codon. RNA 2:867-878.
109. Reynolds, J. E., A. Kaminski, H. J. Kettinen, K. Grace, B. E. Clarke, A. R. Carroll, D. J. Rowlands, and R. J. Jackson. 1995. Unique features of internal initiation of hepatitis C virus RNA translation. EMBO J 14: 6010-6020.
110. Rijnbrand R, Bredenbeek P, van der Straaten T, Whetter L, Inchauspe G, Lemon S, and Spaan W. 1995. Almost the entire 5' non-translated region of hepatitis C virus is required for cap-independent translation. FEBS Lett 365: 115-119.
111. Rijnbrand R C and Lemon S M. 2000. Internal ribosome entry site-mediated translation in hepatitis C virus replication. Curr Top. Microbiol Inmunol. 242:85-116.
112. Rijnbrand, R., P. J. Bredenbeek, P. C. Haasnoot, J. S. Kieft, W. J. Spaan, and S. M. Lemon. 2001. The influence of downstream protein-coding sequence on internal ribosome entry on hepatitis C virus and other flavivirus RNAs. RNA 7:585-597.
113. Rijnbrand, R. C., T. E. Abbink, P. C. Haasnoot, W. J. Spaan, and P. J. Bredenbeek. 1996. The influence of AUG codons in the hepatitis C virus 5' nontranslated region on translation and mapping of the translation initiation window. Virology 226:47-56.
114. Sachs, A. B., P. Sarnow, and M. W. Hentze. 1997. Starting at the beginning, middle, and end: translation initiation in eukaryotes. Cell 89:831-838.
115. Saito I, Miyamura T, Ohbayashi A, Harada H, Katayama T, Kikuchi S, Watanabe Y, Koi S, Onji M, Ohta Y, Choo Q, Houghton M, and Kuo G. 2003. Hepatitis C virus infection is associated with the development of hepatocellular carcinoma. Proc Natl Acad Sci U. S. A 87:6547-6549.
116. Schultz, D. E., M. Honda, L. E. Whetter, K. L. McKnight, and S. M. Lemon. 1996. Mutations within the 5' nontranslated RNA of cell culture-adapted hepatitis A virus which enhance cap-independent translation in cultured African green monkey kidney cells. J Virol 70:1041-1049.
117. Shimazaki, T., M. Honda, S. Kaneko, and K. Kobayashi. 2002. Inhibition of internal ribosomal entry site-directed translation of HCV by recombinant IFN-alpha correlates with a reduced La protein. Hepatology 35:199-208.
118. Simmonds, P. 2003. Variability of hepatitis C virus. Hepatology 21:570-583.
119. Sinha, R., P. Yang, S. Kodali, Y. Xiong, R. M. Kim, P. R. Griffin, H. R. Onishi, J. Kohler, L. L. Silver, and K. Chapman. 2001. Direct interaction of a vancomycin derivative with bacterial enzymes involved in cell wall biosynthesis. Chem Biol 8:1095-1106.
120. Sizova, D. V., V. G. Kolupaeva, T. V. Pestova, I. N. Shatsky, and C. U. Hellen. 1998. Specific interaction of eukaryotic translation initiation factor 3 with the 5' non-translated regions of hepatitis C virus and classical swine fever virus RNAs. J Virol 72:4775-4782.
121. Smith. 1994. Eur J Drug Metab Pharm 3:193-199.
122. Smith, D. B., J. Mellor, L. M. Jarvis, F. Davidson, J. Kolberg, M. Urdea, P. L. Yap, and P. Simmonds. 1995. Variation of the hepatitis C virus 5' non-coding region: implications for secondary structure, virus detection and typing. The International HCV Collaborative Study Group. J Gen Virol 76 (Pt 7): 1749-1761.
123. Sonenberg N, Mathews M B, and Hershey J W B. 2000. Translational control of gene expression. Cold Spring Harbor. Cold Spring Harbor Laboratory Press, New York.
124. Spahn, C. M., J. S. Kieft, R. A. Grassucci, P. A. Penczek, K Zhou, J. A. Doudna, and J. Frank. 2001. Hepatitis C virus IRES RNA-induced changes in the conformation of the 40s ribosomal subunit. Science 291:1959-1962.
125. Spatzenegger, M. and W. Jaeger. 1995. Clinical importance of hepatic cytochrome P450 in drug metabolism. Drug Metab Rev 27:397-417.
126. Subkhankulova, T., S. A. Mitchell, and A. E. Willis. 2001. Internal ribosome entry segment-mediated initiation of c-Myc protein synthesis following genotoxic stress. Biochem J 359:183-192.
127. Tang, S., A. J. Collier, and R. M. Elliott. 1999. Alterations to both the primary and predicted secondary structure of stem-loop IIIc of the hepatitis C virus 1b 5' untranslated region (5'UTR) lead to mutants severely defective in translation which cannot be complemented in trans by the wild-type 5'UTR sequence. J Virol 73:2359-2364.
128. Thiel, V. and S. G. Siddell. 1994. Internal ribosome entry in the coding region of murine hepatitis virus mRNA 5. J Gen Virol. 75 (Pt 11):3041-3046.
129. Tsukiyama-Kohara, K., N. Iizuka, M. Kohara, and A. Nomoto. 1992. Internal ribosome entry site within hepatitis C virus RNA. J Virol 66:1476-1483.
130. Vagner, S., M. C. Gensac, A. Maret, F. Bayard, F. Amalric, H. Prats, and A. C. Prats. 1995. Alternative translation of human fibroblast growth factor 2 mRNA occurs by internal entry of ribosomes. Mol Cell Biol 15:35-44.
131. Varaklioti A, Georgopoulou U, Kakkanas A, Psaridi L, Serwe M, Caselmann W H, and Mavromara P. 1998. Mutational analysis of two unstructured domains of the 5, untranslated region of HCV RNA. Biochem Biophys. Res Commun. 253:678-685.
132. Wang, C., S. Y. Le, N. Ali, and A. Siddiqui. 1995. An RNA pseudoknot is an essential structural element of the internal ribosome entry site located within the hepatitis C virus 5' noncoding region. RNA 1:526-537.
133. Wang, C., P. Sarnow, and A. Siddiqui. 1993. Translation of human hepatitis C virus RNA in cultured cells is mediated by an internal ribosome-binding mechanism. J Virol 67:3338-3344.
134. Wang, C., P. Sarnow, and A. Siddiqui. 1994. A conserved helical element is essential for internal initiation of translation of hepatitis C virus RNA. J Virol 68:7301-7307.
135. Wang, S. M., S. C. Fears, L. Zhang, J. J. Chen, and J. D. Rowley. 2000. Screening poly(dA/dT)-cDNAs for gene identification. Proceedings of the National Academy of Sciences of the United States of America 97:4162-7.
136. Wang, T. H., R. C. Rijnbrand, and S. M. Lemon. 2000. Core protein-coding sequence, but not core protein, modulates the efficiency of cap-independent translation directed by the internal ribosome entry site of hepatitis C virus. J Virol 74:11347-11358.
137. Wimmer, E., C. U. Hellen, and X. Cao. 1993. Genetics of poliovirus. Annu Rev Genet 27:353-436.
138. Wong, J. B., T. Poynard, M. H. Ling, J. K. Albrecht, and S. G. Pauker. 2000. Cost-effectiveness of 24 or 48 weeks of interferon alpha-2b alone or with ribavirin as initial treatment of chronic hepatitis C. International Hepatitis Interventional Therapy Group. Am. J Gastroenterol. 95:1524-1530.
139. Zhao, W. D. and E. Wimmer. 2001. Genetic analysis of a poliovirus/hepatitis C virus chimera: new structure for domain II of the internal ribosomal entry site of hepatitis C virus. J Virol 75:3719-3730.
140. Zhao, W. D., E. Wimmer, and F. C. Lahser. 1999. Poliovirus/Hepatitis C virus (internal ribosomal entry site-core) chimeric viruses: improved growth properties through modification of a proteolytic cleavage site and requirement for core RNA sequences but not for core-related polypeptides. Journal of Virology 73:1546-54.

We claim:
1. A compound of formula IIa

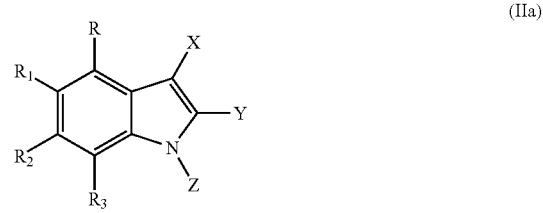

(IIa)

or a pharmaceutically acceptable salt thereof, wherein:
X is -cyano;
Y is -aryl substituted with one or more substituents independently selected from:
(1) -halos;
(2) —$C_1$ to $C_6$ alkyl; haloalkyl; cyclopropyl; cyclobutyl; cyclopentyl; cyclohexyl; or cyclopropylmethyl;
(3) -alkoxy optionally substituted with one or more substituents independently selected from:
  (i) -one or more halos;
  (ii) -5 or 6 membered heterocyclo;
  (iii) —$SO_2$-alkyl; or (iv) —C(O)NH-alkyl;
(4) -hydroxy;
(5) -amino
  (a) optionally substituted with one or more substituents independently selected from:
    (i) —$SO_2R_x$, wherein $R_x$ is —$C_1$ to $C_6$ alkyl, cyclopropyl, cyclobutyl, cyclopentyl or cyclohexyl,
    (ii) —$C_1$ to $C_6$ alkyl optionally and independently substituted with one or more alkoxy, halo, cyclopropyl, cyclobutyl, cyclopentyl, cyclohexyl, aryl, or 5 or 6 membered heteroaryls, wherein aryl is optionally substituted with one or more $C_1$ to $C_6$ alkyls, alkoxy, halos, haloalkyls or haloalkoxys;
    (iii) -5 or 6 membered heteroaryl optionally substituted with one or more substituents independently selected from aryl, $C_1$ to $C_6$ alkyls, hydroxyls, halos or haloalkyls, wherein aryl is optionally substituted with one or more $C_1$ to $C_6$ alkyls, halos, or haloalkyls; (iv) -aryl optionally substituted with one or more substituents independently selected from cyano, $C_1$ to $C_6$ alkyls, alkoxys, —C(O)-alkyl, halos, haloalkyls or haloalkoxys; (v) —C(O)-amino-$(R_x)_2$, wherein $R_x$ is hydrogen or $C_1$ to $C_6$ alkyl;
(6) —OC(O)NH$R_x$, wherein $R_x$, is $C_1$ to $C_6$ alkyl; $C_2$ to $C_6$ alkenyl; -aryl optionally substituted with one or more—mono- or dialkyl-amino; cyclopropyl; cyclobutyl; cyclopentyl or cyclohexyl;
(7) —OC(O)N$(R_x)_2$; wherein $R_x$ is independently selected from $C_1$ to $C_6$ alkyl optionally and independently substituted with alkoxy or aryl
(8) —OC(O)NH(O$R_x$), wherein $R_x$ is —$C_1$ to $C_6$ alkyl;
(9) —OC(O)N$R_x$(O$R_x$), wherein $R_x$ is independently selected from —$C_1$ to $C_6$ alkyl;
(10) —OC(O)N(O$R_x$)$_2$, wherein $R_x$ is independently selected from —$C_1$ to $C_6$ alkyl;
(11) —OC(O)$R_{ab}$, wherein $R_{ab}$ is a 5 or 6 membered heterocyclo optionally substituted with a 5 or 6 membered heteroaryl, wherein heteroaryl is optionally substituted with one or more haloalkyls;

(12) —NR$_p$COR$_p$, wherein R$_p$ is:
(i) —C$_1$ to C$_6$ alkyl;
(ii) -amino optionally substituted with cyclopropyl; cyclobutyl; cyclopentyl; cyclohexyl; or one or more C$_1$ to C$_6$ alkyls, which C$_1$ to C$_6$ alkyls are optionally and independently substituted with one or more aryls or alkoxys;

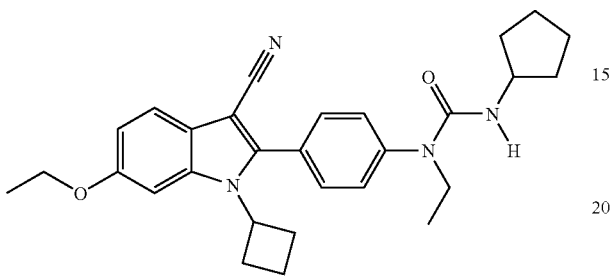

(iii) -5 or 6 membered heterocyclo optionally substituted with one or more C$_1$ to C$_6$ alkyls or aryls;
(iv) -cyclopropyl;
(v) -cyclobutyl;
(vi) -cyclopentyl;
(vii) -cyclohexyl; or
(viii) -cyclopropylmethyl;
and wherein R$_o$ is: -hydrogen; or —C$_1$ to C$_6$ alkyl;

(13) —NR$_q$CONR$_q$R$_r$, wherein R$_q$ is hydrogen;
and wherein R$_r$ is:
(i) —C$_1$ to C$_6$ alkyl optionally substituted with one or more substituents independently selected from: -halo; -hydroxy; -alkoxy; -5 or 6 membered heterocyclo; -5 or 6 membered heteroaryl; and -aryl optionally substituted with one or more halos;
(ii) —C$_2$ to C$_6$ alkenyl optionally substituted with one or more halos;
(iii) —C$_1$ to C$_6$ alkoxy;
(iv) -5 or 6 membered heterocyclo;
(v) -5 or 6 membered heteroaryl optionally substituted with cyclopropyl; cyclobutyl; cyclopentyl; cyclohexyl;
(vi) -cyclobutyl;
(vii) -cyclopentyl;
(viii) -cyclopropyl;
(ix) -cyclohexyl; or
(x) -cyclopropylmethyl;

(14) —SO$_2$R$_{aa}$, wherein R$_{aa}$ is:
(i) -5 or 6 membered heterocyclo optionally substituted with hydroxyl or one or more C$_1$ to C$_6$ alkyls, wherein C$_1$ to C$_6$ alkyl is optionally substituted with hydroxyl;
(ii) —C$_1$ to C$_6$ alkoxy; or
(iii) —C$_1$ to C$_6$ alkyl;

(15) —COR$_m$, wherein R$_m$ is:
(i) -amino optionally substituted with cyclopropyl, cyclobutyl, cyclopentyl or cyclohexyl or one or more C$_1$ to C$_6$ alkyls, wherein the C$_1$ to C$_6$ alkyls are optionally substituted with an aryl, 5 or 6 membered heteroaryl or a 5 or 6 membered heterocyclo, wherein aryl is optionally substituted with one or more alkoxy, halos or haloalkyls; or (ii) -3 to 7 membered heterocyclo optionally substituted with hydroxyl or C$_1$ to C$_6$ alkyl, which alkyl is optionally substituted with -alkoxy or dialkylamino;

(16) —NR$_t$COOR$_u$, wherein R$_t$ is hydrogen,
and wherein R$_u$ is:
(i) —C$_1$ to C$_{12}$ alkyl optionally substituted with one or more substituents independently selected from: cyclopropyl; cyclobutyl; cyclopentyl; cyclohexyl; -aryl optionally substituted with one or more halos or haloalkyls; -alkoxy optionally substituted with one or more alkoxys; -amino optionally substituted with one or more C$_1$ to C$_6$ alkyls; -halo; —SO$_2$-alkyl, -5 or 6 membered heteroaryl; and -5 or 6 membered heterocyclo;
(ii) —C$_2$ to C$_6$ alkenyl;
(iii) -aryl optionally substituted with halo;
(iv) -5 or 6 membered heterocyclo optionally substituted with —C(O)-alkyl; —C(O)-alkoxy wherein alkoxy is optionally substituted with one or more alkoxys; —SO$_2$-alkyl; —SO$_2$-cyclopropyl; —SO$_2$-cyclobutyl; —SO$_2$-cyclopentyl or —SO$_2$-cyclohexyl; (v) -dioxo-tetrahydro-thiopyran;
(vi) -cyclobutyl;
(vii) -cyclopentyl;
(viii) -cyclopropyl; or
(ix) -cyclohexyl;

(17) —NHR$_{bb}$, wherein R$_{bb}$ is: —C(=S)NH$_2$; —C(=S)NH-alkyl; —C(=S)NH-cyclopropyl; —C(=S)NH-cyclobutyl; —C(=S)NH-cyclopentyl; —C(=S)NH-cyclohexyl; —C(=N—CN)—NH-cyclopropyl; —C(=N—CN)—NH-cyclobutyl; —C(=N—CN)—NH-cyclopentyl; —C(=N—CN)—NH-cyclohexyl; —S(=O)-alkyl; —S$^+$(O$^-$)-alkyl; PO(OR$_x$)$_2$, wherein R$_x$ is independently selected from —C$_1$ to C$_6$ alkyl or -dioxo-tetrahydro-thiopyran;

(18) —N[=CH-amino-(R$_x$)$_2$], wherein R$_x$ is independently selected from hydrogen or C$_1$ to C$_6$ alkyl;

(19) -5 or 6 membered heteroaryloxy;

(20) —NR$_v$SO$_2$R$_w$, wherein R$_v$ is hydrogen
and wherein R$_w$ is:
(i) —C$_1$ to C$_6$ alkyl optionally substituted with cyclopropyl, cyclobutyl, cyclopentyl, cyclohexyl or aryl, wherein aryl is optionally substituted with one or more halos or haloalkyls;
(ii) -amino optionally substituted with —C(O)O-alkyl or a -5 or 6 membered heterocyclo;
(iii) mono- or -dialkyl-amino optionally substituted on alkyl with halo, cyclopropyl, cyclobutyl, cyclopentyl, cyclohexyl or -5 or 6 membered heterocyclo;
(iv) -aryl;
(v) -cyclopropyl;
(vi) -cyclobutyl;
(vii) -cyclopentyl;

(viii) -1-methylcyclopropyl; or
(ix) -1-ethylcyclopropyl;

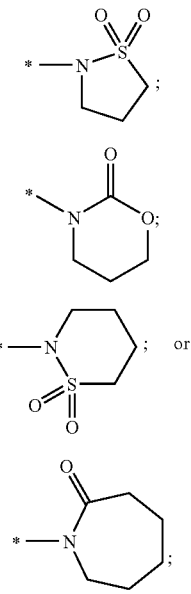

(21)

(22)

(23)

(24)

Z is:
(a) —C₁ to C₆ alkyl,
(b) -cyclopropyl,
(c) -cyclobutyl,
(d) -cyclopentyl,
(e) -cyclopropylmethyl; or
(f) -cyclohexyl;
R is hydrogen;
R₁ is (a) -hydrogen;
(b) -5 or 6 membered heterocyclo;
(c) —C₁ to C₆ alkyl optionally substituted with one or more substituents independently selected from:
(1) -amino optionally substituted with heterocyclo;
(2) -amido optionally substituted with C₁ to C₆ alkyl;
(3) -5 or 6 membered heterocyclo optionally substituted with C₁ to C₆ alkyl;
(4) -5 or 6 membered heteroaryl; and
(5) -aryl;
(d) —C₁ to C₆ alkoxy optionally substituted with one or more substituents independently selected from:
(1) -amino optionally substituted with heterocyclo;
(2) -amido optionally substituted with C₁ to C₆ alkyl, cyclopropyl, cyclobutyl, cyclopentyl or cyclohexyl;
(3) -5 or 6 membered heterocyclo optionally substituted with C₁ to C₆ alkyl;
(4) -5 or 6 membered heteroaryl optionally substituted with C₁ to C₆ alkyl; and
(5) -aryl; or
(6) hydroxyl;
(e) —(O)-5 or 6 membered heterocyclo;
(f) —(O)-5 or 6 membered heteroaryl optionally substituted with one or more substituents independently selected from: cyano, halo, nitro, —C₁ to C₆ alkyl, C₁ to C₆ alkoxy, C₁ to C₆ haloalkyl, amino optionally mono or disubstituted with —C₁ to C₆ alkyl, or 5 or 6 membered heterocyclo;
(g) —C(O)-3,4,5 or 6 membered heterocyclo optionally substituted with one or more C₁ to C₆ alkyls, wherein C₁ to C₆ alkyl is optionally substituted with hydroxy;
(h) —CONH₂ optionally substituted with one or more C₁ to C₆ alkyls, wherein C₁ to C₆ alkyl is optionally substituted with alkoxy;
(h) —SO₂R$_x$, wherein R$_x$ is C₁ to C₆ alkyl optionally substituted with one or more substituents independently selected from:
(1) -5 or 6 membered heterocyclo;
(2) -aryl; and
(3) -5 or 6 membered heteroaryl; or
(i) -alkylthio optionally substituted with one or more substituents independently selected from:
(1) -5 or 6 membered heterocyclo;
(2) -aryl; and
(3) -5 or 6 membered heteroaryl;
R₂ is (a) —C₁ to C₆ alkyl optionally substituted with one or more substituents independently selected from:
(1)-5 or 6 membered heterocyclo;
(2)-5 or 6 membered heteroaryl;
(3)-aryl;
(4)-amido optionally substituted with C₁ to C₆ alkyl; and
(5) -amino optionally substituted with one or more substituents independently selected from (i) heterocyclo, (ii) alkoxy and (iii) alkyl, which alkyl is optionally substituted with one or more alkoxys;
(b)-alkylthio optionally substituted with 5 or 6 membered heteroaryl, which heteroaryl is optionally substituted with alkyl;
(c)-alkylthio optionally substituted with 5 or 6 membered heterocyclo;
(d)-alkylthio optionally substituted with aryl;
(e)-alkylthio optionally substituted with C₁ to C₆ alkyl;
(f) —SO₂R$_x$, wherein R₁ to C₆ alkyl optionally substituted with 5 or 6 membered heteroaryl, which heteroaryl is optionally substituted with one or more C₁ to C₆ alkyls;
(g) —SO₂R$_x$, wherein R$_x$ is C₁ to C₆ alkyl optionally substituted with 5 or 6 membered heterocyclo;
(h) —SO₂R$_x$, wherein R$_x$ is C₁ to C₆ alkyl optionally substituted with aryl;
(i) —SO₂R$_x$, wherein R$_x$ is C₁ to C₆ alkyl;
(j) —S(O)R$_x$, wherein R$_x$ is C₁ to C₆ alkyl optionally substituted with 5 or 6 membered heteroaryl, which heteroaryl is optionally substituted with one or more C₁ to C₆ alkyls;
(k) —S(O)R$_x$, wherein R$_x$ is C₁ to C₆ alkyl optionally substituted with 5 or 6 membered heterocyclo;
(l) —S(O)R$_x$, where R$_x$ is C₁ to C₆ alkyl optionally substituted with aryl;
(m) (i) —S(O)R$_x$, wherein R$_x$ is C₁ to C₆ alkyl;
(ii) —SR$_x$, wherein R$_x$ is C₁ to C₆ alkyl;
(iii) —C₂ to C₆ alkenyl-SO₂—R$_x$, wherein R$_x$ is C₁ to C₆ alkyl;
(n)-alkoxy optionally substituted with one or more substituents independently selected from:
(1) -halo;
(2) -hydroxy;
(3) -alkoxy optionally substituted with alkoxy;
(4) -amino optionally substituted with one or more substituents independently selected from cyclopropyl, cyclobutyl, cyclopentyl, cyclohexyl, 5 or 6 membered heteroaryl, 5 or 6 membered heterocyclo, —SO₂-alkyl and alkyl, which alkyl is optionally substituted with one or more substituents independently selected from: cyclopropyl, cyclobutyl, cyclopentyl, cyclohexyl, -5 or 6 membered heterocyclo, -5 or 6 membered heteroaryl; and -amino optionally substituted with one or more alkyls;
(5) -amido optionally substituted with $C_1$ to $C_6$ alkyl, cyclopropyl, cyclobutyl, cyclopentyl or cyclohexyl;
(6) —S-5 or 6 membered heterocyclo;
(7) —S-5 or 6 membered heteroaryl optionally substituted with $C_1$ to $C_6$ alkyl;
(8) —S—$C_1$ to $C_6$ alkyl;
(9) —S-aryl;
(10) -sulfinyl-5 or 6 membered heterocyclo;
(11) -sulfinyl-5 or 6 membered heteroaryl;
(12) -sulfinyl-$C_1$ to $C_6$ alkyl;
(13) -sulfinyl-aryl;
(14) -sulfonyl-5 or 6 membered heterocyclo;
(15) -sulfonyl-5 or 6 membered heteroaryl optionally substituted with $C_1$ to $C_6$ alkyl;
(16) -sulfonyl-$C_1$ to $C_6$ alkyl;
(17) -sulfonyl-aryl;
(18) -5 to 7 membered heterocyclo optionally substituted with one or more substituents independently selected from oxo, hydroxy and $C_1$ to $C_6$ alkyl, which alkyl is optionally substituted with one or more $C_1$ to $C_6$ alkoxys;
(19) -5 or 6 membered heteroaryl optionally substituted with one or more $C_1$ to $C_6$ alkyls or 5 or 6 membered heterocyclo, which alkyl is optionally substituted with one or more $C_1$ to $C_6$ alkoxys;
(20) -aryl; or
(21) -cyano;
(o) -aryl;
(p) —NH-5 or 6 membered heteroaryl optionally substituted with one or more independently selected $C_1$ to $C_6$ alkyls;
(q) —C(O)-5 or 6 membered heterocyclo optionally substituted with one or more $C_1$ to $C_6$ alkyls or aryls;
(r) —C(O)-aryl;
(s) —$CONH_2$ optionally substituted with one or more of the following:
(1) $C_1$ to $C_6$ alkyl, wherein $C_1$ to $C_6$ alkyl is optionally substituted with alkoxy, cyclopropyl, cyclobutyl, cyclopentyl, cyclohexyl, 5 or 6 membered heterocyclo or 5 or 6 membered heteroaryl;
(2) alkoxy,
(3) cyclopropyl,
(4) cyclobutyl,
(5) cyclopentyl or
(6) cyclohexyl;
(t) -5 or 6 membered heteroaryl optionally substituted with one or more substituents independently selected from: cyano, halo, nitro, —$C_1$ to $C_6$ alkyl $C_1$ to $C_6$ alkoxy, $C_1$ to $C_6$ haloalkyl, amino optionally mono or disubstituted with —$C_1$ to $C_6$ alkyl, or 5 or 6 membered heterocyclo;
(u) -4, 5 or 6 membered heterocyclo optionally having a hetero atom ring member selected from sulfinyl or sulfonyl, wherein heterocyclo is optionally substituted with one or more substituents independently selected from:
(1) -hydroxy;
(2) —$C_1$ to $C_6$ alkyl optionally substituted with cyclopropyl, cyclobutyl, cyclopentyl or cyclohexyl;
(3) —$SO_2R_x$, wherein $R_x$ is $C_1$ to $C_6$ alkyl optionally substituted with cyclopropyl, cyclobutyl, cyclopentyl or cyclohexyl;
(4) —C(O)-aryl;
(5) —$C(O)OR_x$, wherein $R_x$ is $C_1$ to $C_6$ alkyl, cyclopropyl, cyclobutyl, cyclopentyl or cyclohexyl;
(6) —$C(O)R_x$, wherein $R_x$ is $C_1$ to $C_6$ alkyl, cyclopropyl, cyclobutyl, cyclopentyl or cyclohexyl;
(7) oxo;
(8) aryl;
(9) cyclopropyl;
(10) cyclobutyl;
(11) cyclopentyl; and
(12) cyclohexyl; or
(v) —$OR_{kk}$, wherein $R_{kk}$ is:
(1) -aryl;
(2) -5 or 6 membered heterocyclo optionally having a hetero atom ring member selected from sulfinyl or sulfonyl, wherein heterocyclo is optionally substituted with $C_1$ to $C_6$ alkyl, which alkyl is optionally substituted with aryl;
(3) -5 or 6 membered heteroaryl optionally substituted with one or more substituents independently selected from cyano, halo, nitro, $C_1$ to $C_6$ alkyl, $C_1$ to $C_6$ alkoxy, —C(O)—$C_1$ to $C_6$ alkyl, —S—$C_1$ to $C_6$ alkyl, —C(O)O—$C_1$ to $C_6$ alkyl, $C_1$ to $C_6$ haloalkyl or 5 or 6 membered heterocyclo;
(4) —$SO_2R_x$, wherein $R_x$ is —$C_1$ to $C_6$ alkyl;
(5) —$Si(R_x)_3$ wherein $R_x$ is independently selected from —$C_1$ to $C_6$ alkyl;
(6) —$CONH_2$ optionally substituted with one or more $C_1$ to $C_6$ alkyl, cyclopropyl, cyclobutyl, cyclopentyl or cyclohexyl, wherein $C_1$ to $C_6$ alkyl is optionally substituted with alkoxy, cyclopropyl, cyclobutyl, cyclopentyl, cyclohexyl, aryl, 5 or 6 membered heterocyclo or 5 or 6 membered heteroaryl;
(w) —C(O)OH;
and
$R_3$ is hydrogen;
with the proviso that at least one of Y, $R_1$, and $R_2$ is selected from the following:
Y is -aryl substituted with one or more substituents independently selected from:
(1) -amino optionally substituted with one or more substituents independently selected from: (i) —$SO_2R_x$, wherein $R_x$ is —$C_1$ to $C_6$ alkyl, cyclopropyl, cyclobutyl, cyclopentyl or cyclohexyl, substituted with one or more 5 or 6 membered heteroaryls; (ii) —$C_1$ to $C_6$ alkyl optionally and independently substituted with one or more alkoxy, halo, cyclopropyl, cyclobutyl, cyclopentyl, cyclohexyl, aryl, or (iii) 5 or 6 membered heteroaryls, wherein aryl is optionally substituted with one or more $C_1$ to $C_6$ alkyls, alkoxy, halos, haloalkyls or haloalkoxys;
(2) —$OC(O)NHR_x$, wherein $R_x$ is $C_1$ to $C_6$ alkyl; $C_1$ to $C_6$ alkenyl; -aryl optionally substituted with one or more mono- or dialkyl-amino; cyclopropyl; cyclobutyl; cyclopentyl or cyclohexyl;
(3) —$OC(O)N(R_x)_2$; wherein $R_x$ is independently selected from $C_1$ to $C_6$ alkyl optionally and independently substituted with alkoxy or aryl;
(4) —$OC(O)NH(OR_x)$, wherein $R_x$ is —$C_1$ to $C_6$ alkyl;
(5) —$OC(O)NR_x(OR_x)$, wherein $R_x$ is independently selected from —$C_1$ to $C_6$ alkyl;
(6) —$OC(O)N(OR_x)_2$, wherein $R_x$ is independently selected from —$C_1$ to $C_6$ alkyl;
(7) —$OC(O)R_{ab}$, wherein $R_{ab}$ is a 5 or 6 membered heterocyclo optionally substituted with a 5 or 6 membered heteroaryl, wherein heteroaryl is optionally substituted with one or more haloalkyls;

(8) —NR$_o$COR$_p$, wherein R$_p$ is:
  (i) -amino optionally substituted with cyclopropyl; cyclobutyl; cyclopentyl; cyclohexyl; or one or more C$_1$ to C$_6$ alkyls, which C$_1$ to C$_6$ alkyls are optionally and independently substituted with one or more aryls or alkoxys, or
  (ii) -5 or 6 membered heterocyclo substituted with one or more C$_1$ to C$_6$ alkyls or aryls;
  (iii) -cyclopropyl;
  (iv) -cyclobutyl;
  (v) -cyclopentyl;
  (vi) -cyclohexyl; or
  (vii) -cyclopropylmethyl;
(9) —NR$_q$CONR$_q$R$_r$, wherein R$_r$ is:
  (i) —C$_1$ to C$_6$ alkyl substituted with one or more substituents independently selected from: hydroxy; -alkoxy; -5 or 6 membered heterocyclo; -5 or 6 membered heteroaryl; and -aryl substituted with one or more halos;
  (ii) —C$_2$ to C$_6$ alkenyl;
  (iii) —C$_1$ to C$_6$ alkoxy; or
  (iv) -5 or 6 membered heterocyclo;
  (v) -5 or 6 membered heteroaryl optionally substituted with cyclopropyl; cyclobutyl; cyclopentyl; cyclohexyl;
  (vi) -cyclobutyl;
  (vii) -cyclopentyl;
  (viii) -cyclopropyl;
  (ix) -cyclohexyl; or
  (x) -cyclopropylmethyl;
(10) —NR$_t$COOR$_u$, wherein R$_u$ is:
  (i) —C$_1$ to C$_{12}$ alkyl substituted with one or more substituents independently selected from: cyclopropyl; cyclobutyl; cyclopentyl; cyclohexyl; -alkoxy substituted with one or more alkoxys; -amino optionally substituted with one or more C$_1$ to C$_6$ alkyls; —SO$_2$-alkyl and -5 or 6 membered heteroaryl;
  (ii) —C$_2$ to C$_6$ alkenyl;
  (iii) -5 or 6 membered heterocyclo optionally substituted with —C(O)-alkyl; —C(O)-alkoxy wherein alkoxy is optionally substituted with one or more alkoxys; —SO$_2$-alkyl; —SO$_2$-cyclopropyl; —SO$_2$-cyclobutyl; —SO$_2$-cyclopentyl or —SO$_2$-cyclohexyl;
  (iv) -dioxo-tetrahydro-thiopyran;
  (v) -cyclobutyl;
  (vi) cyclopentyl;
  (vii) -cyclopropyl; or
  (viii) -cyclohexyl; and

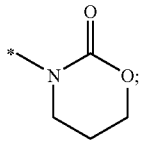

R$_1$ is (a) —C$_1$ to C$_6$ alkyl substituted with:
  (1) -amido optionally substituted with C$_1$ to C$_6$ alkyl; or
  (2) -5 or 6 membered heteroaryl;
  (b) —C$_1$ to C$_6$ alkoxy substituted with:
    (1) -amino optionally substituted with heterocyclo;
    (2) -amido optionally substituted with C$_1$ to C$_6$ alkyl, cyclopropyl, cyclobutyl, cyclopentyl or cyclohexyl;
    (3) -5 or 6 membered heterocyclo substituted with C$_1$ to C$_6$ alkyl;
    (4) -5 or 6 membered heteroaryl optionally substituted with C$_1$ to C$_6$ alkyl; or
    (5) hydroxyl
  (c) —(O)-5 or 6 membered heterocyclo;
  (d) —(O)-5 or 6 membered heteroaryl optionally substituted with one or more substituents independently selected from: cyano, halo, nitro, —C$_1$ to C$_6$ alkyl, C$_1$ to C$_6$ alkoxy, C$_1$ to C$_6$ haloalkyl, amino optionally mono or disubstituted with —C$_1$ to C$_6$ alkyl, or 5 or 6 membered heterocyclo;
  (e) —SO$_2$R$_x$, wherein R$_x$ is C$_1$ to C$_6$ alkyl optionally substituted with:
    (1) -5 or 6 membered heterocyclo;
    (2) -aryl; or
    (3) -5 or 6 membered heteroaryl; or
  (f)-alkylthio optionally substituted with:
    (1)-5 or 6 membered heterocyclo;
    (2) -aryl; or
    (3) -5 or 6 membered heteroaryl;
  (g) —C(O)-3,4,5 or 6 membered heterocyclo optionally substituted with one or more C$_1$ to C$_6$ alkyls, wherein C$_1$ to C$_6$ alkyl is optionally substituted with hydroxy;
  (h) —CONH$_2$ optionally substituted with one or more C$_1$ to C$_6$ alkyls, wherein C$_1$ to C$_6$ alkyl is optionally substituted with alkoxy;
and
R$_2$ is
  (a) —C$_1$ to C$_6$ alkyl substituted with one or more substituents independently selected from:
    (1) -5 or 6 membered heterocyclo;
    (2) -5 or 6 membered heteroaryl;
    (3) -aryl;
    (4) -amido optionally substituted with C$_1$ to C$_6$ alkyl; and
    (5) -amino optionally substituted with one or more substituents independently selected from heterocyclo, alkoxy and alkyl, which alkyl is optionally substituted with one or more alkoxys;
  (b)-alkylthio optionally substituted with 5 or 6 membered heteroaryl, which heteroaryl is optionally substituted with alkyl;
  (c)-alkylthio optionally substituted with 5 or 6 membered heterocyclo;
  (d)-alkylthio optionally substituted with aryl;
  (e)-alkylthio optionally substituted with C$_1$ to C$_6$ alkyl;
  (f) —SO$_2$R$_x$, wherein R$_x$ is C$_1$ to C$_6$ alkyl optionally substituted with 5 or 6 membered heteroaryl, which heteroaryl is optionally substituted with one or more C$_1$ to C$_6$ alkyls;
  (g) —SO$_2$R$_x$, wherein R$_x$ is C$_1$ to C$_6$ alkyl optionally substituted with 5 or 6 membered heterocyclo;
  (h) —SO$_2$R$_x$, wherein R$_x$ is C$_1$ to C$_6$ alkyl optionally substituted with aryl;
  (i) —SO$_2$R$_x$, wherein R$_x$ is C$_1$ to C$_6$ alkyl;
  (j) —S(O)R$_x$, wherein R$_x$ is C$_1$ to C$_6$ alkyl optionally substituted with 5 or 6 membered heteroaryl, which heteroaryl is optionally substituted with one or more C$_1$ to C$_6$ alkyls;
  (k) —S(O)R$_x$, wherein R$_x$ is C$_1$ to C$_6$ alkyl optionally substituted with 5 or 6 membered heterocyclo;
  (l) —S(O)R$_x$, wherein R$_x$ is C$_1$ to C$_6$ alkyl optionally substituted with aryl;

(m) (i) —S(O)R$_x$, wherein R$_x$ is C$_1$ to C$_6$ alkyl;
  (ii) —SR$_x$, wherein R$_x$ is C$_1$ to C$_6$ alkyl;
  (iii) —C$_2$ to C$_6$ alkenyl-SO$_2$—R$_x$, wherein R$_x$ is C$_1$ to C$_6$ alkyl;
(n) -alkoxy substituted with:
  (1) -alkoxy;
  (2) -amino substituted with one or more substituents independently selected from cyclopropyl, cyclobutyl, cyclopentyl, cyclohexyl, 5 or 6 membered heteroaryl, 5 or 6 membered heterocyclo, —SO$_2$-alkyl and alkyl, which alkyl is optionally substituted with one or more substituents independently selected from: cyclopropyl, cyclobutyl, cyclopentyl, cyclohexyl, -5 or 6 membered heterocyclos; -5 or 6 membered heteroaryl and -amino optionally substituted with one or more alkyls;
  (3) -amido optionally substituted with C$_1$ to C$_6$ alkyl; -5 or 6 membered heteroaryl
  (4) —S-5 or 6 membered heterocyclo;
  (5) —S-5 or 6 membered heteroaryl optionally substituted with C$_1$ to C$_6$ alkyl;
  (6) —S—C$_1$ to C$_6$ alkyl;
  (7) —S-aryl;
  (8) -sulfinyl-5 or 6 membered heterocyclo;
  (9) -sulfinyl-5 or 6 membered heteroaryl;
  (10) -sulfinyl-C$_1$ to C$_6$ alkyl;
  (11) -sulfinyl-aryl;
  (12) -sulfonyl-5 or 6 membered deterocyclo;
  (13) -sulfonyl-5 or 6 membered heteroaryl optionally substituted with C$_1$ to C$_6$ alkyl;
  (14) -sulfonyl-C$_1$ to C$_6$ alkyl;
  (15) -sulfonyl-aryl;
  (16) -5 to 7 membered heterocyclo substituted with one or more substituents independently selected from oxo, hydroxy and C$_1$ to C$_6$ alkyl, which alkyl is substituted with one or more C$_1$ to C$_6$ alkoxys;
  (17) -5 or 6 membered heteroaryl substituted with one or more C$_1$ to C$_6$ alkyls or 5 or 6 membered heterocyclo, which alkyl is optionally substituted with one or more C$_1$ to C$_6$ alkoxys;
  (18) -aryl; or
  (19) -cyano;
(o) —C(O)-5 or 6 membered heterocyclo optionally substituted with one or more C$_1$ to C$_6$ alkyls aryls;
(p) —C(O)-aryl;
(q) -4, 5 or 6 membered heterocyclo optionally having a hetero atom ring member selected from sulfinyl or sulfonyl, wherein heterocyclo is substituted with one or more substituents independently selected from:
  (1) -hydroxy;
  (2) —C$_1$ to C$_6$ alkyl optionally substituted with cyclopropyl, cyclobutyl, cyclopentyl or cyclohexyl;
  (3) —SO$_2$R$_x$, wherein R$_x$ is C$_1$ to C$_6$ alkyl optionally substituted with cyclopropyl, cyclobutyl, cyclopentyl or cyclohexyl;
  (4) —C(O)-aryl; and
  (5) —C(O)OR$_x$, wherein R$_x$ is C$_1$ to C$_6$ alkyl, cyclopropyl, cyclobutyl, cyclopentyl or cyclohexyl;
(r) —OR$_{kk}$, wherein R$_{kk}$ is:
  (1) -aryl;
  (2) -5 or 6 membered heterocyclo optionally having a hetero atom ring member selected from sulfinyl or sulfonyl, wherein heterocyclo is optionally substituted with C$_1$ to C$_6$ alkyl or aryl; or
  (3) —Si(R$_x$)$_3$, wherein R$_x$ is independently selected from —C$_1$ to C$_6$ alkyl;
  (4) —CONH$_2$ optionally substituted with one or more C$_1$ to C$_6$ alkyl, cyclopropyl, cyclobutyl, cyclopentyl or cyclohexyl, wherein C$_1$ to C$_6$ alkyl is optionally substituted with alkoxy, cyclopropyl, cyclobutyl, cyclopentyl, cyclohexyl, aryl, 5 or 6 membered heterocyclo or 5 or 6 membered heteroaryl;
(s) —(O)-5 or 6 membered heterocyclo optionally substituted with one or more independently selected C$_1$ to C$_6$ alkyls; or
(t) —(O)-5 or 6 membered heteroaryl optionally substituted with one or more independently selected C$_1$ to C$_6$ alkyls.

2. The compound of claim 1, wherein:
Y is -aryl substituted with one or more substituents independently selected from: (1) -halo; (2) -hydroxy; (3) -alkoxy optionally substituted with one or more substituents independently selected from: -one or more halos; -5 or 6 membered heterocyclo; —SO$_2$-alkyl; or —C(O)NH-alkyl; (4) —C$_1$ to C$_6$ alkyl, haloalkyl, cyclopropyl; (5) -amino optionally substituted with one or more substituents independently selected from: —SO$_2$R$_x$, wherein R$_x$ is —C$_1$ to C$_6$ alkyl, cyclopropyl; and —C$_1$ to C$_6$ alkyl optionally and independently substituted with one or more alkoxy, halo, cyclopropyl, cyclohexyl, aryl, 5 or 6 membered heteroaryls wherein aryl is optionally substituted with one or more C$_1$ to C$_6$ alkyls, alkoxy, halos, haloalkyls or haloalkoxys; (6) —OC(O)NHR$_x$, wherein is R$_x$ is C$_1$ to C$_6$ alkyl; C$_2$ to C$_6$ alkenyl; -aryl optionally substituted with one or more mono- or dialkyl-amino; cyclopentyl or cyclohexyl; (7) —NR$_o$COR$_p$, wherein R$_p$ is: (i) —C$_1$ to C$_6$ alkyl; (ii) -amino optionally substituted with cyclopentyl; or one or more C$_1$ to C$_6$ alkyls which C$_1$ to C$_6$ alkyls are optionally and independently substituted with one or more aryls or alkoxys; or (iii) -cyclopropyl; and wherein R$_o$ is hydrogen; (8) —NR$_q$CONR$_q$R$_r$, wherein R$_q$ is hydrogen, and wherein R$_r$ is: (i) —C$_1$ to C$_6$ alkyl optionally substituted with one or more halos; or -aryl optionally substituted with halo; (ii) -5 or 6 membered heteroaryl substituted with cyclopropyl; (iii) -cyclobutyl; (iv) -cyclopentyl; (9) —SO$_2$R$_{aa}$, wherein R$_{aa}$ is: -5 or 6 heterocyclo optionally substituted with hydroxyl or one or more C$_1$ to C$_6$ alkyls, wherein C$_1$ to C$_6$ alkyl is optionally substituted with hydroxyl; —C$_1$ to C$_6$ alkoxy; or —C$_1$ to C$_6$ alkyl; (10) —COR$_m$, wherein R$_m$ is: (i) -amino optionally substituted with cyclopropyl, cyclobutyl, cyclopentyl or one or more C$_1$ to C$_6$ alkyls, wherein the C$_1$ to C$_6$ alkyls are optionally substituted with an aryl, 6 membered heteroaryl or a 5 or 6 membered heterocyclo, wherein aryl is optionally substituted with one or more alkoxy or halos; or (ii) -3 to 7 membered heterocyclo optionally substituted with hydroxyl or C$_1$ to C$_6$ alkyl, which alkyl is optionally substituted with -alkoxy or dialkyl-amino; (11) —NR$_t$COOR$_u$, wherein R$_t$ is hydrogen, and wherein R$_u$ is: (i) —C$_1$ to C$_{12}$ alkyl optionally substituted with one or more substituents independently selected from: cyclopropyl; cyclobutyl; cyclopentyl; -aryl optionally substituted with one or more halos or haloalkyls; -halo; —SO$_4$-alkyl; and -5 or 6 membered heteroaryl; -aryl optionally substituted with halo; or -5 or 6 membered heterocyclo; (ii) -5 or 6 membered heterocyclo optionally substituted with —C(O)-alkyl; —C(O)-alkoxy wherein alkoxy is optionally substituted with one or more alkoxys; or —SO$_2$-alkyl; —SO$_2$-cyclopropyl; (iii) -dioxo-tetrahydro-thiopyran; (iv) -cyclobutyl; or (v) -cyclopentyl; (12) —NHR$_{bb}$, wherein R$_{bb}$ is: —C(=S)NH$_2$; —C(=S)

NH-alkyl; —C(=S)NH-cyclopentyl; —C(=N—CN)—NH-cyclohexyl; —S(=O)-alkyl; —S$^+$(O$^-$)-alkyl; or —PO(OR$_x$)$_2$, wherein R$_x$ is C$_1$ to C$_6$ alkyl or -dioxo-tetrahydro-thiopyran; (13) —NR$_v$SO$_2$R$_w$, wherein R$_v$ is hydrogen, and wherein R$_w$ is: (i) —C$_1$ to C$_6$ alkyl optionally substituted with cyclobutyl or aryl, wherein aryl is optionally substituted with haloalkyl; or (ii) -amino optionally substituted with —C(O)O-alkyl, a -5 or 6 membered heterocyclo; (iii) mono- or -dialkyl-amino optionally substituted on alkyl with halo, cyclopropyl, or -5 membered heterocyclo; (iv) -aryl; (v) -cyclopropyl; (vi) -cyclobutyl; (vii) -cyclopentyl; (viii) -1-methylcyclopropyl; or (ix) -1-ethylcyclopropyl;

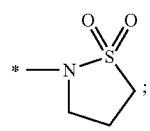

(14)

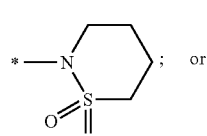 or (15)

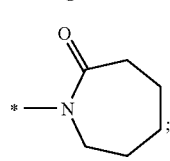

(16)

R$_1$ is:
(a) -hydrogen;
(b) —C$_1$ to C$_6$ alkoxy substituted with one or more substituents independently selected from: -5 or 6 membered heterocyclo; and -5 or 6 membered heteroaryl optionally substituted with C$_1$ to C$_6$ alkyl;
(c) —(O)-5 or 6 membered heterocyclo;
(d) —(O)-5 or 6 membered heteroaryl
optionally substituted with one or more substituents independently selected from: cyano, halo, —C$_1$ to C$_6$ alkyl; or
(e) -5 or 6 membered heterocyclo; and R$_2$ is:
(a) -alkoxy substituted with one or more substituents independently selected from: (1) -halo; (2) -hydroxy; (3) -alkoxy optionally substituted with alkoxy; (4) -amino optionally substituted with one or more substituents independently selected from 5 or 6 membered heteroaryl, 5 or 6 membered heterocyclo, and alkyl, which alkyl is optionally substituted with one or more substituents independently selected from: -5 or 6 membered heterocyclo; and -amino optionally substituted with one or more alkyl; (5) -amido optionally substituted with C$_1$ to C$_6$ alkyl; (6) —S-5 or 6 membered heteroaryl optionally substituted with C$_1$ to C$_6$ alkyl; (7) —S—C$_1$ to C$_6$ alkyl; (8) -sulfinyl-C$_1$ to C$_6$ alkyl; (9) -sulfonyl-C$_1$ to C$_6$ alkyl; (10) -5 to 7 membered heterocyclo optionally substituted with one or more substituents independently selected from hydroxy and C$_1$ to C$_6$ alkyl, which alkyl is optionally substituted with one or more independently selected C$_1$ to C$_6$ alkoxys; and (11) -5 or 6 membered heteroaryl optionally substituted with one or more C$_1$ to C$_6$ alkyls;

(b) —SO$_2$R$_x$, wherein R$_x$ is C$_1$ to C$_6$ alkyl;
(c) —S(O)R$_x$, wherein R$_x$ is C$_1$ to C$_6$ alkyl;
(d) —SR$_x$, wherein R$_x$ is C$_1$ to C$_6$ alkyl;
(e) —C(O)-5 or 6 membered heterocyclo optionally substituted with one or more C$_1$ to C$_6$ alkyls or aryls;
(f) —C(O)-aryl;
(g) -5 or 6 membered heteroaryl optionally substituted with one or more substituents independently selected from: cyano, halo, nitro, —C$_1$ to C$_6$ alkyl C$_1$ to C$_6$ alkoxy, C$_1$ to C$_6$ haloalkyl, amino optionally mono or disubstituted with —C$_1$ to C$_6$ alkyl, or 5 or 6 membered heterocyclo;
(h) -4, 5 or 6 membered heterocyclo having a hetero atom ring member selected from sulfinyl or sulfonyl, wherein heterocyclo is optionally substituted with one or more substituents independently selected from: (1) -one or more halos; (2) —C$_1$ to C$_6$ alkyl optionally substituted with cyclopropyl; (3) —SO$_2$R$_x$, wherein R$_x$ is C$_1$ to C$_6$ alkyl optionally substituted with cyclopropyl; (4) —C(O)-aryl; (5) —C(O)OR$_x$, wherein R$_x$ is C$_1$ to C$_6$ alkyl; (6) —C(O)R$_x$, wherein R$_x$ is C$_1$ to C$_6$ alkyl or cyclopropyl; and (7) oxo; or
(i) —OR$_{kk}$, wherein R$_{kk}$ is: (1) -5 or 6 membered heteroaryl optionally substituted with one or more substituents independently selected from cyano, halo, nitro, C$_1$ to C$_6$ alkyl, C$_1$ to C$_6$ alkoxy, —C(O)—C$_1$ to C$_6$ alkyl, —S—C$_1$ to C$_6$ alkyl, —C(O)O—C$_1$ to C$_6$alkyl, and C$_1$ to C$_6$ haloalkyl or -5 or 6 membered heterocyclo; or (2) -5 or 6 membered heterocyclo optionally having a sulfonyl ring member, wherein heterocyclo is optionally substituted with C$_1$ to C$_6$ alkyl, which alkyl is optionally substituted with aryl.

3. A compound of formula IIb

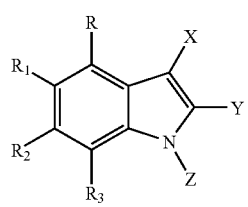

(IIb)

or a pharmaceutically acceptable salt thereof, wherein:
X is cyano;
Y is aryl substituted with one or more substituents independently selected from:
(a) —C$_1$ to C$_6$ alkyl; haloalkyl; cyclopropyl; cyclobutyl; cyclopentyl; cyclohexyl; or cyclopropylmethyl;
(b) -amino substituted with C$_1$ to C$_6$ alkyl optionally and independently substituted with one or more alkoxy, halo, cyclopropyl, cyclobutyl, cyclopentyl, cyclohexyl, aryl, or -5 or 6 membered heteroaryls, wherein aryl is optionally substituted with one or more C$_1$ to C$_6$ alkyls, alkoxy, halos, haloalkyls or haloalkoxys;
(c) —NR$_t$COOR$_u$, wherein R$_t$ is hydrogen, and wherein R$_u$ is C$_1$ to C$_{12}$ alkyl optionally substituted with one or more substituents independently selected from: cyclopropyl; cyclobutyl; cyclopentyl; cyclohexyl; -aryl optionally substituted with one or more halos or haloalkyls; -alkoxy optionally substituted with one or more alkoxys; -amino optionally substituted with one or more C$_1$ to C$_6$ alkyls; -halos; —SO$_2$-alkyl, -5 or 6 membered heteroaryl; and -5 or 6 membered heterocyclo;

(d) —NR$_v$SO$_2$R$_w$, wherein R$_v$ is hydrogen, and wherein R$_w$ is C$_1$ to C$_6$ alkyl optionally substituted with cyclopropyl, cyclobutyl, cyclopentyl, cyclohexyl or aryl, wherein aryl is optionally substituted with one or more halos or haloalkyls;

Z is C$_1$ to C$_6$ alkyl; -cyclopropyl; -cyclobutyl; -cyclopentyl; -cyclohexyl; or -cyclopropylmethyl;

R is hydrogen;

R$_1$ is hydrogen;

R$_2$ is:
  (a) -alkoxy substituted with one or more halos;
  (b) -4, 5 or 6 membered heterocyclo optionally having a hetero atom ring member selected from sulfinyl or sulfonyl, wherein heterocyclo is optionally substituted with one or more substituents independently selected from:
    (1) -hydroxy;
    (2) —C$_1$ to C$_6$ alkyl optionally substituted with cyclopropyl, cyclobutyl, cyclopentyl or cyclohexyl;
    (3) —SO$_2$R$_x$, wherein R$_x$ is C$_1$ to C$_6$ alkyl optionally substituted with cyclopropyl, cyclobutyl, cyclopentyl or cyclohexyl;
    (4) —C(O)-aryl;
    (5) —C(O)OR$_x$, wherein R$_x$ is C$_1$ to C$_6$ alkyl, cyclopropyl, cyclobutyl, cyclopentyl or cyclohexyl;
    (6) —C(O)R$_x$, wherein R$_x$ is C$_1$ to C$_6$ alkyl, cyclopropyl, cyclobutyl, cyclopentyl or cyclohexyl;
    (7) oxo;
    (8) aryl;
    (9) cyclopropyl;
    (10) cyclobutyl;
    (11) cyclopentyl; and
    (12) cyclohexyl;
  (c) -5 or 6 membered heteroaryl optionally substituted with one or more substituents independently selected from: cyano, halo, —C$_1$ to C$_6$ alkyl; —NO$_2$, —C$_1$ to C$_6$ alkoxy, C$_1$ to C$_6$ haloalkyl, amino optionally mono or disubstituted with —C$_1$ to C$_6$ alkyl, or 5 or 6 membered heterocyclo
  (d) —C(O)-3 to 7 membered heterocyclo or —C(O)-5 membered heterocyclo optionally substituted with one or more C$_1$ to C$_6$ alkyls or aryls; and
  (e) —OR$_{kk}$, wherein R$_{kk}$ is: (1) -5 or 6 membered heteroaryl optionally substituted with one or more substituents independently selected from cyano, halo, nitro, and C$_1$ to C$_6$ alkyl, C$_1$ to C$_6$ alkoxy, —C(O)—C$_1$ to C$_6$ alkyl, —S—C$_1$ to C$_6$ alkyl, —C(O)O—C$_1$ to C$_6$ alkyl, C$_1$ to C$_6$ haloalkyl; or (2) -5 or 6 membered heterocyclo optionally substituted with one or more =O; and R$_3$ is hydrogen.

4. A compound of formula IIe

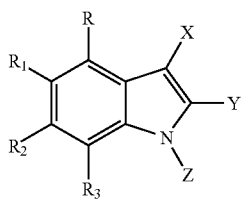

(IIe)

or a pharmaceutically acceptable salt thereof, wherein:

X is -cyano;

Y is -aryl substituted with one or more substituents independently selected from:

(1) -halo;
(2) —C$_1$ to C$_6$ alkyl; haloalkyl; cyclopropyl; cyclobutyl; cyclopentyl; cyclohexyl; or cyclopropylmethyl;
(3) -alkoxy, optionally substituted with one or more substituents independently selected from:
  (i) -halo;
  (ii) -5 or 6 membered heterocyclo;
  (iii) —C(O)NH$_2$ optionally substituted with C$_6$ to C$_8$ alkyl;
  (iv) —C(O)NH—(C$_1$ to C$_6$)-alkyl;
(4) -hydroxy;
(5) -haloalkyl;
(6) -cyano;
(7) -nitro;
(8) —COOH;
(9) —N=CHN(R$_x$)$_2$ wherein R$_x$ is independently selected from —C$_1$ to C$_6$ alkyl;
(10) -amino optionally substituted with one or more substituents independently selected from:
  (i) —SO$_2$R$_x$, wherein R$_x$ is —C$_1$ to C$_6$ alkyl, cyclopropyl, cyclobutyl, cyclopentyl or cyclohexyl;
  (ii) -6 to 8 membered aryl optionally substituted with one or more substituents independently selected from C$_1$ to C$_6$ alkyl, halo, haloalkyl, cyano, alkoxy, —COR$_x$, wherein R$_x$ is —C$_1$ to C$_6$ alkyl, and haloalkoxy;
  (iii) -5 or 6 membered heteroaryl optionally substituted with one or more substituents independently selected from C$_1$ to C$_6$ alkyl, halo, haloalkyl, cyano, alkoxy, haloalkoxy and aryl, wherein aryl is optionally substituted with halo;
  (iv) -5 or 6 membered heterocyclo optionally substituted with one or more substituents independently selected from hydroxy, =O, alkyl and haloalkyl;
  (v) —C$_1$ to C$_7$ alkyl optionally substituted with one or more substituents independently selected from: -5 or 6 membered heteroaryl, wherein heteroaryl is optionally substituted with one more substituents independently selected from C$_1$ to C$_6$ alkyl, alkoxy, haloalkoxy, halo, and haloalkyl; -aryl, wherein aryl is optionally substituted with one or more substituents independently selected from C$_1$ to C$_6$ alkyl, halo, haloalkyl; -alkoxy; and halo haloalkoxy; and
  (vi) —PO$_2$R$_x$, wherein R$_x$ is C$_1$ to C$_6$ alkyl;
(11) —OC(O)NHR$_x$ wherein R$_x$ is C$_1$ to C$_6$ alkyl optionally substituted with vinyl;
(12) —OC(O)N(R$_u$)$_2$, wherein R$_u$ is alkyl or aryl, which alkyl or aryl is optionally substituted with dialkylamino;
(13) —OC(O)NH(OR$_{uu}$), wherein R$_{uu}$ is -aryl optionally substituted with dialkylamino;
(14) —OC(O)NR$_x$(OR$_x$), wherein R$_x$ is independently selected from —C$_1$ to C$_6$ alkyl;
(15) —OC(O)N(OR$_x$)$_2$, wherein R$_x$ is independently selected from —C$_1$ to C$_6$ alkyl;
(16) —OC(O)R$_{ab}$, wherein R$_{ab}$ is a 5 or 6 membered heterocyclo optionally substituted with a 5 or 6 membered heteroaryl, which heteroaryl is optionally substituted with alkyl or haloalkyl;
(17) —NR$_o$C(O)R$_p$, wherein R$_p$ is:
  (i) —C$_1$ to C$_6$ alkyl;
  (ii) -amino optionally substituted with cyclopropyl; cyclobutyl; cyclopentyl; cyclohexyl; or one or more C$_1$ to C$_6$ alkyls, which C$_1$ to C$_6$ alkyls are optionally substituted with one or more substituents independently selected from aryl and alkoxy;

(iii) -5 or 6 membered heterocyclo optionally substituted with one or more substituents independently selected from $C_1$ to $C_6$ alkyl and aryl;
(iv) -cyclopropyl;
(v) -cyclobutyl;
(vi) -cyclopentyl;
(vii) -cyclohexyl; or
(viii) -cyclopropylmethyl;
and wherein $R_o$ is: -hydrogen; or —$C_1$ to $C_6$ alkyl;
(18) —$NR_qCONR_qR_r$, wherein $R_q$ is hydrogen, and wherein $R_r$ is:
  (i) —$C_1$ to $C_6$ alkyl optionally substituted with one or more substituents independently selected from: -halo; -hydroxy; -alkoxy; -5 or 6 membered heterocyclo; -5 or 6 membered heteroaryl; and -aryl optionally substituted with halo;
  (ii) —$C_2$ to $C_6$ alkenyl optionally substituted with one or more halos;
  (iii) —$C_1$ to $C_6$ alkoxy;
  (iv) -5 or 6 membered heterocyclo; or
  (v) -5 to 6 membered heteroaryl optionally substituted with $C_1$ to $C_6$ alkyl; cyclopropyl; cyclobutyl; cyclopentyl; cyclohexyl;
  (vi) -cyclobutyl;
  (vii) -cyclopentyl;
  (viii) -cyclopropyl;
  (ix) -cyclohexyl; or
  (x) -cyclopropylmethyl;
(19) —$SO_2R_{aa}$, wherein $R_{aa}$ is:
  (i) -5 or 6 membered heterocyclo optionally substituted with one or more substituents independently selected from: -hydroxy; —$C_1$ to $C_6$ alkoxy; and —$C_1$ to $C_6$ alkyl; or
  (ii) -amino optionally substituted with —$C_1$ to $C_6$ alkyl, which —$C_1$ to $C_6$ alkyl is optionally substituted with one or more substituents independently selected from: -alkoxy; -hydroxy; -halo;
(20) —$COR_m$, wherein $R_m$ is:
  (i) -amino optionally substituted with cyclopropyl, cyclobutyl, cyclopentyl or cyclohexyl or one or more $C_1$ to $C_6$ alkyls, which $C_1$ to $C_6$ alkyls are optionally substituted with 5 or 6 membered heterocyclo or aryl, which heterocyclo or aryl is optionally substituted with one or more substituents independently selected from halo and alkoxy;
  (ii) -3 to 7 membered heterocyclo optionally substituted with hydroxyl;
  (iii) -3 to 7 membered heterocyclo optionally substituted with $C_1$ to $C_6$ alkyl, which —$C_1$ to $C_6$ alkyl is optionally substituted with alkoxy or dialkyl-amino;
(21) —$NR_tCOOR_u$, wherein $R_t$ is hydrogen, and wherein $R_u$ is:
  (i) —$C_1$ to $C_{12}$ alkyl optionally substituted with one or more substituents independently selected from: cyclopropyl; cyclobutyl; cyclopentyl; cyclohexyl; -aryl optionally substituted with one or more halos or haloalkyls; -alkoxy optionally substituted with one or more alkoxys; -amino optionally substituted with one or more $C_1$ to $C_6$ alkyls; -halo; —$SO_2R_w$; —$SO_2R_x$, wherein $R_x$ is —$C_1$ to $C_6$ alkyl; -5 or 6 membered heteroaryl; and -5 or 6 membered heterocyclo;
  (ii) —$C_2$ to $C_6$ alkenyl;
  (iii) -aryl optionally substituted with halo;
  (iv) -4 to 7 membered heterocyclo optionally substituted with one or more substituents independently selected from: =O; —$SO_2R_w$; —$COR_p$; and —(CO)O—($C_1$ to $C_4$ alkyl)-O—($C_1$ to $C_4$ alkyl); —C(O)-alkyl;
—C(O)-alkoxy wherein alkoxy is optionally substituted with one or more alkoxys; —$SO_2$-alkyl; —$SO_2$-cyclopropyl; —$SO_2$-cyclobutyl; —$SO_2$-cyclopentyl or —$SO_2$-cyclohexyl;
  (v) -dioxo-tetrahydro-thiopyran;
  (vi) -cyclobutyl;
  (vii) -cyclopentyl;
  (viii) -cyclopropyl; or
  (ix) -cyclohexyl;
(22) —$NHR_{bb}$, wherein $R_{bb}$ is:
  (i) —C(=S)$NH_2$;
  (ii) —C(=S)$NHR_x$, wherein $R_x$ is —$C_1$ to $C_6$ alkyl; C(=S)NH-cyclopropyl; —C(=S)NH-cyclobutyl; —C(=S)NH-cyclopentyl; —C(=S)NH-cyclohexyl;
  (iii) —C(=S)$NR_xR_x$, wherein $R_x$ is independently selected from —$C_1$ to $C_6$ alkyl;
  (iv) —C(=N—CN)$NHR_x$, wherein $R_x$ is $C_1$ to $C_6$ alkyl; —C(=N—CN)—NH-cyclopropyl; —C(=N—CN)—NH-cyclobutyl; —C(=N—CN)—NH-cyclopentyl; —C(=N—CN)—NH-cyclohexyl;
  (v) —PO(OR$_x$)$_2$, wherein $R_x$ is independently selected from —$C_1$ to $C_6$ alkyl;
  (vi) —S(=O)-alkyl;
  (vii) —S$^+$(O$^-$)-alkyl; or
  (viii) -dioxo-tetrahydro-thiopyran;
(23) —N(CONHR$_w$)$_2$;
(24) —NH(SOR$_w$);
(25) —N(SO$_2$R$_w$)$_2$;
(26) —$NR_vSO_2R_w$, wherein $R_v$ is hydrogen or alkyl optionally substituted with 4 to 7 membered heterocyclo;
and wherein $R_w$ is:
  (i) —$C_1$ to $C_6$ alkyl optionally substituted with cyclopropyl, cyclobutyl, cyclopentyl, cyclohexyl or aryl, which aryl is optionally substituted with one or more substituents independently selected from haloalkyl, halo, alkoxy, and alkyl;
  (ii) -aryl;
  (iii) —$C_6$ to $C_8$ heteroaryl; or
  (iv) -amino optionally substituted with —C(O)O-alkyl, a -5 or 6 membered heterocyclo or alkyl,
  which heterocyclo or alkyl is optionally substituted with one or more substituents independently selected from halo, $C_1$ to $C_6$ alkoxy, alkoxycarbonyl, (CO)O—($C_1$ to $C_6$) alkyl), hydroxy, cyano, 5 or 6 membered heterocyclo, and 5 or 6 membered heteroaryl;
  (v) -cyclopropyl;
  (vi) -cyclobutyl;
  (vii) -cyclopentyl;
  (viii) -1-methylcyclopropyl; or —
  (ix) -1-ethylcyclopropyl;

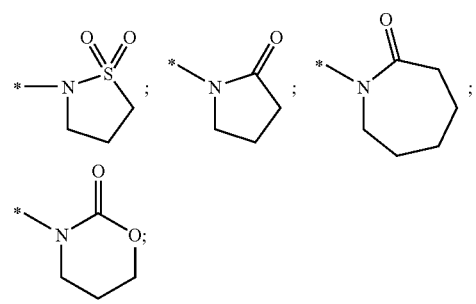

[Structures shown]

(34) -5 to 6 membered heteroaryl optionally substituted with one or more substituents independently selected from:
  (i) -halo;
  (ii) —$C_1$ to $C_6$ alkyl; haloalkyl; cyclopropyl; cyclobutyl; cyclopentyl; cyclohexyl; or cyclopropylmethyl;
  (iii) -alkoxy optionally substituted with one or more substituents independently selected from: -halo; -5 or 6 membered heterocyclo; and —C(O)NH$_2$ optionally substituted with $C_6$ to $C_8$ alkyl;
  (iv) -hydroxy;
  (v) -haloalkyl;
  (vi) -cyano;
  (vii) -nitro;
  (viii) —COOH;
  (ix) -amino optionally substituted with one or more substituents independently selected from: —SO$_2$R$_x$, wherein R$_x$ is —$C_1$ to $C_6$ alkyl; -6 to 8 membered aryl optionally substituted with one or more substituents independently selected from alkyl, halo, haloalkyl, cyano, alkoxy, —COR$_x$, wherein R$_x$ is —$C_1$ to $C_6$ alkyl and haloalkoxy; -5 or 6 membered heteroaryl optionally substituted with one or more substituents independently selected from alkyl, halo, haloalkyl, cyano, alkoxy, haloalkoxy and -aryl optionally substituted with halo; —$C_5$ to $C_6$ heterocyclo optionally substituted with one or more substituents independently selected from hydroxy, alkyl and haloalkyl; and —$C_1$ to $C_7$ alkyl optionally substituted with one or more substituents independently selected from: -5 or 6 membered heteroaryl optionally substituted with one or more alkyls, halos, or haloalkyls; -aryl optionally substituted with one or more substituents independently selected from alkyl, halo and haloalkyl; -alkoxy; and -halo;

(35) —NR$_o$COR$_p$, wherein R$_p$ is:
  (i) —$C_1$ to $C_6$ alkyl;
  (ii) -amino optionally substituted with cyclopropyl; cyclobutyl; cyclopentyl; cyclohexyl; or one or more $C_1$ to $C_6$ alkyls, which $C_1$ to $C_6$ alkyls are optionally and independently substituted with one or more aryls or alkoxys;
  (iii) -5 or 6 membered heterocyclo optionally substituted with one or more $C_1$ to $C_6$ alkyls or aryls;
  (iv) -cyclopropyl;
  (v) -cyclobutyl;
  (vi) -cyclopentyl;
  (vii) -cyclohexyl; or
  (viii) -cyclopropylmethyl;
and wherein R$_o$ is: hydrogen; or —$C_1$ to $C_6$ alkyl;

(36) —NR$_q$CONR$_q$R$_r$, wherein R$_q$ is hydrogen, and wherein R$_r$ is:
  (i) —$C_1$ to $C_6$ alkyl optionally substituted with one or more substituents independently selected from: -halo; -hydroxy; -alkoxy; -5 or 6 membered heterocyclo; -5 or 6 membered heteroaryl; and -aryl optionally substituted with halo;
  (ii) —$C_2$ to $C_6$ alkenyl optionally substituted with one or more halos;
  (iii) —$C_1$ to $C_6$ alkoxy;
  (iv) -5 or 6 membered heterocyclo; or
  (v) -5 to 6 membered heteroaryl optionally substituted with —$C_1$ to $C_6$ alkyl; cyclopropyl; cyclobutyl; cyclopentyl; or cyclohexyl;

(37) —NR$_t$COOR$_u$,
wherein R$_t$ is hydrogen,
and wherein R$_u$ is
  (i) —$C_1$ to $C_{12}$ alkyl optionally substituted with one or more substituents independently selected from: cyclopropyl; cyclobutyl; cyclopentyl; cyclohexyl; -aryl optionally substituted with one or more halos or haloalkyls; -alkoxy optionally substituted with one or more alkoxys; -amino optionally substituted with one or more $C_1$ to $C_6$ alkyls; -halo; —SO$_2$R$_w$; —SO$_2$R$_x$, wherein R$_x$ is —$C_1$ to $C_6$ alkyl; -5 or 6 membered heteroaryl; and -5 or 6 membered heterocyclo; and

(38) —NR$_v$SO$_2$R$_w$,
wherein R$_v$ is hydrogen or alkyl optionally substituted with 4 to 7 membered heterocyclo; and
wherein R$_w$ is
  (i) —$C_1$ to $C_6$ alkyl optionally substituted with cyclopropyl; cyclobutyl; cyclopentyl; cyclohexyl; or aryl, which aryl is optionally substituted with one or more substituents independently selected from haloalkyl, halo, alkoxy, and alkyl; -aryl; —$C_6$ to $C_8$ heteroaryl; or
  (ii) -amino optionally substituted with —C(O)O-alkyl or a -5 or 6 membered heterocyclo or alkyl, which heterocyclo or alkyl is optionally substituted with one or more substituents independently selected from halo, $C_1$ to $C_6$ alkoxy, alkoxycarbonyl, hydroxy, cyano, 5 or 6 membered heterocyclo and 5 or 6 membered heteroaryl;

Z is —$C_1$ to $C_6$ alkyl; -cyclopropyl; -cyclobutyl; -cyclopentyl; -cyclohexyl; or -cyclopropylmethyl;
R is hydrogen;
R$_1$ is:
  (a) -hydrogen;
  (b) -a 5 or 6 membered heterocyclo optionally substituted with one or more substituents independently selected from: (1) -hydroxy; (2) —$C_1$ to $C_6$ alkyl; (3) —SO$_2$R$_x$, wherein R$^x$ is —$C_1$ to $C_6$ alkyl; (4) —C(O)-aryl; (5) —COR$_p$; and (6) —C(O)OR$_x$, wherein R$_x$ is —$C_1$ to $C_6$ alkyl;
  (c) -5 or 6 membered heteroaryl optionally substituted with one or more substituents independently selected from: (1) —$C_1$ to $C_6$ alkyl optionally substituted with one or more substituents independently selected from halo, $C_1$ to $C_6$ alkoxy, hydroxy, 5 or 6 membered heterocyclo, and 5 or 6 membered heteroaryl; (2) -alkoxy; (3) -halo; (4) -alkylthio; (5) -haloalkyl; (6) -cyano; (7) -amino optionally substituted with alkyl, which alkyl is optionally substituted with one or more substituents independently selected from (1) halo, (ii) $C_1$ to $C_6$ alkoxy, (iii) hydroxy, (iv) cyano, (v) 5 or 6 membered heterocyclo, and (vi) 5 or 6 membered heteroaryl; (8) -heterocyclo; (9) -nitro;

(10) -hydroxy; (11) —COOH; (12) —CO$_2$R$_x$, wherein R$_x$ is —C$_1$ to C$_6$ alkyl; (13) —COR$_x$, wherein R$_x$ is —C$_1$ to C$_6$ alkyl; (14) —C(O)NH$_2$ optionally substituted with one or more C$_1$ to C$_6$ alkyls, which alkyls are optionally substituted with one or more substituents independently selected from (i) halo, (ii) C$_1$ to C$_6$ alkoxy, (iii) hydroxy, (iv) 5 or 6 membered heterocyclo, and (v) 5 or 6 membered heteroaryl; (15) -amido optionally substituted with one or more or more substituents independently selected from (i) halo, (ii) C$_1$ to C$_6$ alkoxy, (iii) hydroxy, (iv) 5 or 6 membered heterocyclo, (v) 5 or 6 membered heteroaryl, and (vi) C$_1$ to C$_6$ alkyl, which alkyl is optionally substituted with one or more C$_1$ to C$_6$ alkoxys;

(d) —C$_1$ to C$_6$ alkyl optionally substituted with one or more substituents independently selected from: (1) -amino optionally substituted with one or more substituents independently selected from (i) heterocyclo, (ii) alkoxy and (iii) alkyl, which alkyl is optionally substituted with one or more alkoxys; (2) -amido optionally substituted with C$_1$ to C$_6$ alkyl, cyclopropyl, cyclobutyl, cyclopentyl or cyclohexyl; (3) -5 or 6 membered heterocyclo optionally substituted with C$_1$ to C$_6$ alkyl; (4) -5 or 6 membered heteroaryl optionally substituted with C$_1$ to C$_6$ alkyl; and (5) -aryl; or (6) hydroxyl;

(e) —C$_2$ to C$_6$ alkenyl optionally substituted with —SO$_2$R$_x$, wherein R$_x$ is —C$_1$ to C$_6$ alkyl;

(f) —C$_1$ to C$_6$ alkoxy optionally substituted with one or more substituents independently selected from: (1) -halo; (2) -hydroxy; (3) -cyano; (4) -alkoxy optionally substituted with alkoxy; (5) -amino optionally substituted with one or more independently selected from (i) 5 or 6 membered heteroaryl, (ii) 5 or 6 membered heterocyclo and (iii) alkyl, which alkyl is optionally substituted with one or more substituents independently selected from: -5 or 6 membered heterocyclo; and -amino optionally substituted with one or more alkyl; (6) -amino optionally substituted with heterocyclo; (7) -amido optionally substituted with C$_1$ to C$_6$ alkyl; (8) -5 to 7 membered heterocyclo optionally substituted with one or more substituents independently selected from hydroxy and C$_1$ to C$_6$ alkyl, which alkyl is optionally substituted with one or more substituents independently selected from: —C$_1$ to C$_6$ alkoxy; and -aryl; (9) -5 or 6 membered heteroaryl optionally substituted with one or more substituents independently selected from: —C$_1$ to C$_6$ alkyl; and -4 to 7 membered heterocyclo; (10) -alkoxy; and (11) -aryl;

(g) —(O)-5 or 6 membered heterocyclo optionally substituted with one or more substituents independently selected from: (1) -hydroxy; (2) —C$_1$ to C$_6$ alkyl; (3) —SO$_2$R$_x$, wherein R$_x$ is —C$_1$ to C$_6$ alkyl; (4) —C(O)-aryl; (5) —COR$_x$; and (6) —C(O)OR$_x$, wherein R$_x$ is —C$_1$ to C$_6$ alkyl;

(h) —(O)-5 or 6 membered heteroaryl optionally substituted with one or more substituents independently selected from: (1) —C$_1$ to C$_6$ alkyl optionally substituted with one or more substituents independently selected from (i) halo, (ii) C$_1$ to C$_6$ alkoxy, (ii) hydroxy, (iv) 5 or 6 membered heterocyclo and (v) 5 or 6 membered heteroaryl; (2) -alkoxy; (3) -halo; (4) -alkylthio; (5) -haloalkyl; (6) -cyano; (7) -amino optionally substituted with alkyl, which alkyl is optionally substituted with one or more substituents independently selected from halo, (i) —C$_1$ to C$_6$ alkoxy, (ii) hydroxy, (iii) cyano, 5 or 6 membered heterocyclo and (iv) 5 or 6 membered heteroaryl; (8) -heterocyclo; (9) -nitro; (10) -hydroxy; (11) —COOH; (12) —CO$_2$R$_x$, wherein R$_x$ is —C$_1$ to C$_6$ alkyl; (13) —COR$_x$, wherein R$_x$ is C$_1$ to C$_6$ alkyl; (14) —C(O)NH$_2$ optionally substituted with one or more substituents independently selected from: (i) —C$_1$ to C$_6$ alkyl optionally substituted with one or more substituents independently selected from halo, C$_1$ to C$_6$ alkoxy, hydroxy, 5 or 6 membered heterocyclo and 5 or 6 membered heteroaryl; and (ii) -amido optionally substituted with one or more or more substituents independently selected from halo, C$_1$ to C$_6$ alkoxy, hydroxy, 5 or 6 membered heterocyclo, 5 or 6 membered heteroaryl, and C$_1$ to C$_6$ alkyl, which alkyl is optionally substituted with one or more C$_1$ to C$_6$ alkoxys; (15) C$_1$ to C$_6$ haloalkyl, or (16) amino optionally mono or disubstituted with —C$_1$ to C$_6$ alkyl, (i) —C(O)NH$_2$ optionally substituted with one or more C$_1$ to C$_6$ alkyls, which alkyls are optionally substituted with one or more substituents independently selected from halo, C$_1$ to C$_6$ alkoxy, hydroxy, 5 or 6 membered heterocyclo and 5 or 6 membered heteroaryl;

(j) —C(O)-3 to 7 membered heterocyclo optionally substituted with one or more substituents independently selected from: (1) -aryl; (ii) -5 or 6 membered heteroaryl; and (iii) —C$_1$ to C$_6$ alkyl further optionally substituted with one or more substituted with hydroxys;

(k) —SO$_2$R$_x$, wherein R$_x$ is —C$_1$ to C$_6$ alkyl; optionally substituted with one or more substituents independently selected from: (i) -5 or 6 membered heterocyclo; (ii) -aryl; and (iii) -5 or 6 membered heteroaryl; or (l) -alkylthio optionally substituted with one or more substituents independently selected from: (i) -5 or 6 membered heterocyclo; (ii) -aryl; and (iii) -5 or 6 membered heteroaryl;

(m) -aryl optionally substituted with one or more substituents independently selected from: (1) —C$_1$ to C$_6$ alkyl optionally substituted with one or more substituents independently selected from (i) halo, (ii) C$_1$ to C$_6$ alkoxy, (iii) hydroxy, (iv) 5 or 6 membered heterocyclo and (v) 5 or 6 membered heteroaryl; (2) -alkoxy; (3) -halo; (4) -alkylthio; (5) -haloalkyl; (6) -cyano; (7) -amino optionally substituted with alkyl, which alkyl is optionally substituted with one or more substituents independently selected from (i) halo, (ii) C$_1$ to C$_6$ alkoxy, (iii) hydroxy, (iv) cyano, (v) 5 or 6 membered heterocyclo and (vi) 5 or 6 membered heteroaryl; (8) -heterocyclo; (9) -nitro; (10) -hydroxy; (11) —COOH; (12) —CO$_2$R$_x$, wherein R$_x$ is —C$_1$ to C$_6$ alkyl; (13) —COR$_x$, wherein R$_x$ is —C$_1$ to C$_6$ alkyl; (14) —C(O)NH$_2$ optionally substituted with one or more C$_1$ to C$_6$ alkyls, which alkyls are optionally substituted with one or more substituents independently selected from (i) halo, (ii) C$_1$ to C$_6$ alkoxy, (iii) hydroxy, (iv) 5 or 6 membered heterocyclo and (v) 5 or 6 membered heteroaryl; and (15) -amido optionally substituted with one or more substituents independently selected from (i) halo, (ii) C$_1$ to C$_6$ alkoxy, (iii) hydroxy, (iv) 5 or 6 membered heterocyclo, (v) 5 or 6 membered heteroaryl, and (vi) C$_1$ to C$_6$ alkyl, which alkyl is optionally substituted with one or more C$_1$ to C$_6$ alkoxys;

(n) —C(O)-5 or 6 membered heteroaryl;
(o) —C(O)-aryl;
(p) —COOH; or
(q) —OR$_{kk}$, wherein R$_{kk}$ is: (1) -aryl optionally substituted with one or more substituents independently selected from: (i) —C$_1$ to C$_6$ alkyl optionally substituted with one or more substituents independently selected from halo, C$_1$ to C$_6$ alkoxy, hydroxy, 5 or 6 membered heterocyclo and 5 or 6 membered heteroaryl; (ii) -alkoxy; (iii) -halo; (iv) -alkylthio; (v) -haloalkyl; (vi) -cyano; (vii) -amino optionally substituted with alkyl, which alkyl is optionally substituted with one or more substituents independently selected from halo, C$_1$ to C$_6$ alkoxy, hydroxy, cyano, 5 or 6 membered heterocyclo and 5 or 6 membered heteroaryl; (viii) -heterocyclo; (ix) -nitro; (x) -hydroxy; (xi) —COOH; (xii) —CO$_2$R$_x$, wherein R$_x$ is —C$_1$ to C$_6$ alkyl; (xiii) —COR$_x$, wherein R$_x$ is —C$_1$ to C$_6$ alkyl; (xiv) —C(O)NH$_2$ optionally substituted with one or more C$_1$ to C$_6$ alkyls, which alkyls are optionally substituted with one or more substituents independently selected from halo, C$_1$ to C$_6$ alkoxy, hydroxy, 5 or 6 membered heterocyclo and 5 or 6 membered heteroaryl; and (xv) -amido optionally substituted with one or more substituents independently selected from halo, C$_1$ to C$_6$ alkoxy, hydroxy, 5 or 6 membered heterocyclo, 5 or 6 membered heteroaryl, and C$_1$ to C$_6$ alkyl, which alkyl is optionally substituted with one or more C$_1$ to C$_6$ alkoxys;

R$_2$ is:
(a) —C$_1$ to C$_6$ alkyl optionally substituted with one or more substituents independently selected from: (1) -5 or 6 membered heterocyclo; (2) -5 or 6 membered heteroaryl; (3) -aryl; (4) -amido optionally substituted with C$_1$ to C$_6$ alkyl; and (5) -amino optionally substituted with one or more substituents independently selected from (i) heterocyclo, (ii) alkoxy and (iii) alkyl, which alkyl is optionally substituted with one or more alkoxy; and (6) —SO$_2$R$_x$, wherein R$_x$ is —C$_1$ to —C$_6$ alkyl;
(b) —C$_2$ to C$_6$ alkenyl optionally substituted with SO$_2$R$_x$, wherein R$_x$ is —C$_1$ to C$_6$ alkyl;
(c)-alkylthio optionally substituted with one or more substituents independently selected from: (1) -5 or 6 membered heteroaryl optionally substituted with alkyl; (2) -5 or 6 membered heterocyclo; (3) -aryl; and (4) —C$_1$ to C$_6$ alkyl;
(d) —SO$_2$R$_x$, wherein R$_x$ is —C$_1$ to C$_6$ alkyl; optionally substituted with one or more substituents independently selected from: (1)-5 or 6 membered heteroaryl optionally substituted with one or more C$_1$ to C$_6$ alkyls; (2) -5 or 6 membered heterocyclo; (3) -aryl; and (4) —C$_1$ to C$_6$ alkyl;
(e) (1) —S(O)R$_x$, wherein R$_x$ is —C$_1$ to C$_6$ alkyl; optionally substituted with one or more substituents independently selected from: (1) -5 or 6 membered heteroaryl, which heteroaryl is optionally substituted with one or more C$_1$ to C$_6$ alkyls; (2) -5 or 6 membered heterocyclo; (3) -aryl; and (4) —C$_1$ to C$_6$ alkyl;
(ii) —SR$_x$, wherein R$_x$ is C$_1$ to C$_6$ alkyl;
(iii) —C$_2$ to C$_6$ alkenyl-SO$_2$—R$_x$, wherein R$_x$ is C$_1$ to C$_6$ alkyl;
(f)-alkoxy optionally substituted with one or more substituents independently selected from: (1) -halo; (2) -hydroxy; (3) -cyano; (4) -alkoxy optionally substituted with alkoxy; (5) -amino optionally substituted with one or more substituents independently selected from (i) —SO$_2$—C$_1$ to C$_4$ alkyl, (ii) 5 or 6 membered heteroaryl, (iii) -5 or 6 membered heterocyclo (iv) cyclopropyl, cyclobutyl, cyclopentyl, cyclohexyl, and alkyl, which alkyl is optionally substituted with one or more substituents independently selected from: -5 or 6 membered heterocyclo; and -amino optionally substituted with one or more alkyls; (6) -amido optionally substituted with C$_1$ to C$_6$ alkyl, cyclopropyl, cyclobutyl, cyclopentyl or cyclohexyl; (7) —S-5 or 6 membered heterocyclo; (8) —S-5 or 6 membered heteroaryl optionally substituted with C$_1$ to C$_6$ alkyl; (9) —S—C$_1$ to C$_6$ alkyl optionally substituted with one or more substituents independently selected from: (i) -aryl optionally substituted with one or more substituents independently selected from alkyl, haloakyl and halo; and (ii) —C$_5$ to C$_6$ heteroaryl optionally substituted with one or more substituents independently selected from alkyl, haloakyl and halo; (10) —S-aryl; (11) -sulfinyl-5 or 6 membered heterocyclo; (12) -sulfinyl-5 or 6 membered heteroaryl; (13) -sulfinyl-C$_1$ to C$_6$ alkyl optionally substituted with one or more substituents independently selected from: (i) -aryl optionally substituted with one or more substituents independently selected from alkyl, haloakyl and halo; and (ii) —C$_5$ to C$_6$ heteroaryl optionally substituted with one or more substituents independently selected from alkyl, haloakyl and halo; (14) -sulfinyl-aryl; (15) -sulfonyl-5 or 6 membered heterocyclo; (16) -sulfonyl-5 or 6 membered heteroaryl optionally substituted with C$_1$ to C$_6$ alkyl; (17) -sulfonyl-C$_1$ to C$_6$ alkyl optionally substituted with one or more substituents independently selected from: (i) -aryl optionally substituted with one or more substituents independently selected from alkyl, haloakyl and halo; and (ii) —C$_5$ to C$_6$ heteroaryl optionally substituted with one or more substituents independently selected from alkyl, haloakyl and halo; (18) -sulfonyl-aryl; (19) -5 to 7 membered heterocyclo optionally substituted with one or more substituents independently selected from hydroxy, =O, heterocyclo, and C$_1$ to C$_6$ alkyl, which alkyl is optionally substituted with one or more substituents independently selected from: —C$_1$ to C$_6$ alkoxy; and -aryl; (20) -5 or 6 membered heteroaryl optionally substituted with one or more substituents independently selected from: (i) —C$_1$ to C$_6$ alkyl optionally substituted with one or more alkoxys; (ii) -4 to 7 membered heterocyclo; and (iii) -alkoxy; and (21) -aryl;
(g)-aryl optionally substituted with one or more substituents independently selected from: (1) —C$_1$ to C$_6$ alkyl optionally substituted with one or more substituents independently selected from (i) halo, (ii) C$_1$ to C$_6$ alkoxy, (iii) hydroxy, (iv) 5 or 6 membered heterocyclo and (v) 5 or 6 membered heteroaryl; (2) -alkoxy; (3) -halo; (4) -alkylthio; (5) -haloalkyl; (6) -cyano; (7) -amino optionally substituted with alkyl, which alkyl is optionally substituted with one or more substituents independently selected from halo, C$_1$ to C$_6$ alkoxy, hydroxy, cyano, 5 or 6 membered heterocyclo and 5 or 6 membered heteroaryl; (8) -heterocyclo; (9) -nitro; (10) -hydroxy; (11) —COOH; (12) —CO$_2$R$_x$, wherein R$_x$ is —C$_1$ to C$_6$ alkyl; (13) —COR$_x$, wherein R$_1$ is —C$_1$ to C$_6$ alkyl; (14) —C(O)NH$_2$ optionally substituted with one or more C$_1$ to C$_6$ alkyls, which alkyls are optionally substituted with one or more substituents independently selected from (i) halo, (i) C$_1$ to C$_6$ alkoxy, (i) hydroxy, (ii) 5 or 6 membered heterocyclo and (iii) 5 or 6 membered heteroaryl; and (15) -amido optionally substituted with one or more substituents independently selected from (i) halo, (i) $C_1$ to $C_6$ alkoxy, (ii) hydroxy, (iii) 5 or 6 membered heterocyclo, (iv) 5 or 6 membered heteroaryl, and (v) $C_1$ to $C_6$ alkyl, which alkyl is optionally substituted with one or more $C_1$ to $C_6$ alkoxys;

(h) —(O)-5 or 6 membered heterocyclo optionally substituted with one or more substituents independently selected from: (1) -hydroxy; (2) =O; (3) —$C_1$ to $C_6$ alkyl; (4) —$SO_2R_x$, wherein $R_x$ is —$C_1$ to $C_6$ alkyl; (5) —C(O)-aryl; (6) —$COR_p$; and (7) —$C(O)OR_x$, wherein $R_x$ is —$C_1$ to $C_6$ alkyl;

(i) —(O)-5 or 6 membered heteroaryl optionally substituted with one or more substituents independently selected from: (1) —$C_1$ to $C_6$ alkyl optionally substituted with one or more substituents independently selected from (1) halo, (ii) $C_1$ to $C_6$ alkoxy, hydroxy, (iii) 5 or 6 membered heterocyclo and (iv) 5 or 6 membered heteroaryl; (2) -alkoxy; (3) -halo; (4) -alkylthio; (5) -haloalkyl; (6) -cyano; (7) -amino optionally substituted with alkyl, which alkyl is optionally substituted with one or more substituents independently selected from halo, $C_1$ to $C_6$ alkoxy, hydroxy, cyano, 5 or 6 membered heterocyclo and 5 or 6 membered heteroaryl; (8) -heterocyclo; (9) -nitro; (10) -hydroxy; (11) —COOH; (12) $CO_2R_x$, wherein $R_x$ is —$C_1$ to $C_6$ alkyl; (13) —$COR_x$, wherein $R_x$ is —$C_1$ to $C_6$ alkyl; (14) —$C(O)NH_2$ optionally substituted with one or more $C_1$ to $C_6$ alkyls, which alkyls are optionally substituted with one or more substituents independently selected from halo, $C_1$ to $C_6$ alkoxy, hydroxy, 5 or 6 membered heterocyclo and 5 or 6 membered heteroaryl; and (15) -amido optionally substituted with one or more substituents independently selected from halo, $C_1$ to $C_6$ alkoxy, hydroxy, 5 or 6 membered heterocyclo, 5 or 6 membered heteroaryl, and $C_1$ to $C_6$ alkyl, which alkyl is optionally substituted with one or more $C_1$ to $C_6$ alkoxys;

(j) —C(O)-3 to 7 membered heterocyclo optionally substituted with one or more substituents independently selected from: (1) -aryl; (2) -5 or 6 membered heteroaryl; and (3) —$C_1$ to $C_6$ alkyl optionally substituted with one or more hydroxys;

(k) —C(O)-5 or 6 membered heteroaryl;

(l) —C(O)-aryl;

(m) -amino optionally substituted with one or more substituents independently selected from: (1) —$SO_2R_x$, wherein $R_x$ is —$C_1$ to $C_6$ alkyl; (2) -6 to 8 membered aryl optionally substituted with one or more substituents independently selected from (i) alkyl, (ii) halo, (iii) haloalkyl, (iv) cyano, (v) alkoxy, (vi) $COR_x$, wherein $R_x$ is —$C_1$ to $C_6$ alkyl; and (vii) haloalkoxy; (3) -5 or 6 membered heteroaryl optionally substituted with one or more substituents independently selected from (i) alkyl, (ii) halo, (iii) haloalkyl, (iv) cyano, (v) alkoxy, (vi) haloalkoxy and (vii) -aryl optionally substituted with halo; (4) —$C_5$ to $C_6$ heterocyclo optionally substituted with one or more substituents independently selected from hydroxy, alkyl and haloalkyl; (5) —$C_1$ to $C_7$ alkyl optionally substituted with one or more substituents independently selected from: (i) -5 or 6 membered heteroaryl optionally substituted with one or more substituents independently selected from alkyl, halo and haloalkyl; (ii) -aryl optionally substituted with one or more substituents independently selected from alkyl, halo and haloalkyl; (iii) -alkoxy; and (iv) -halo;

(n) -5 or 6 membered heteroaryl optionally substituted with one or more substituents independently selected from: (1) —$C_1$ to $C_6$ alkyl optionally substituted with one or more substituents independently selected from (i) halo, (ii) $C_1$ to $C_6$ alkoxy, (iii) hydroxy, (iv) 5 or 6 membered heterocyclo and (v) -5 or 6 membered heteroaryl; (2) -alkoxy; (3) -halo; (4) -alkylthio; (5) -haloalkyl; (6) -cyano; (7) -amino optionally substituted with one more alkyls, which alkyls are optionally substituted with one or more substituents independently selected from halo, $C_1$ to $C_6$ alkoxy, hydroxy, cyano, 5 or 6 membered heterocyclo and 5 or 6 membered heteroaryl; (8) -5 or 6 membered heterocyclo; (9) -nitro; (10) -hydroxy; (11) —COOH; (12) —$CO_2R_x$, wherein $R_x$ is —$C_1$ to $C_6$ alkyl; (13) $COR_x$, wherein $R_x$ is —$C_1$ to $C_6$ alkyl; (14) —$C(O)NH_2$ optionally substituted with one or more $C_1$ to $C_6$ alkyls, which alkyls are optionally substituted with one or more substituents independently selected from (i) halo, (ii) $C_1$ to $C_6$ alkoxy, (iii) hydroxy, (iv) 5 or 6 membered heterocyclo and (v) 5 or 6 membered heteroaryl; (15) -amido optionally substituted with one or more substituents independently selected from (i) halo, (ii) $C_1$ to $C_6$ alkoxy, hydroxy, (iii) 5 or 6 membered heterocyclo, (iv) 5 or 6 membered heteroaryl, and (v) $C_1$ to $C_6$ alkyl, which alkyl is optionally substituted with one or more $C_1$ to $C_6$ alkoxys;

(o) -4, 5 or 6 membered heterocyclo optionally having a hetero atom ring member selected from sulfinyl or sulfonyl, wherein heterocyclo is optionally substituted with one or more substituents independently selected from: (1) -hydroxy; (2) =O; (3) —$C_1$ to $C_6$ alkyl optionally substituted with cyclopropyl, cyclobutyl, cyclopentyl or cyclohexyl; (4) —$SO_2R_x$, wherein $R_x$ is —$C_1$ to $C_6$ alkyl, which $C_1$ to $C_6$ alkyl is optionally substituted with cyclopropyl, cyclobutyl, cyclopentyl or cyclohexyl; (5) —C(O)-aryl; (6) —$COR_p$; (7) —$C(O)OR_x$, wherein $R_x$ is to $C_6$ alkyl, which $C_1$ to $C_6$ alkyl is optionally substituted with cyclopropyl, cyclobutyl, cyclopentyl or cyclohexyl; (8) —$C(O)R_x$, wherein $R_x$ $C_1$ to $C_6$ alkyl, cyclopropyl, cyclobutyl, cyclopentyl or cyclohexyl; (9) aryl; (10) cyclopropyl; (11) cyclobutyl; (12) cyclopentyl; and (13) cyclohexyl;

(p) —$OR_{kk}$, wherein $R_{kk}$ is: (1) -aryl optionally substituted with one or more substituents independently selected from: (i) —$C_1$ to $C_6$ alkyl optionally substituted with one or more substituents independently selected from halo, $C_1$ to $C_6$ alkoxy, hydroxy, 5 or 6 membered heterocyclo and 5 or 6 membered heteroaryl; (ii) -alkoxy; (iii) -halo; (iv) -alkylthio; (v) -haloalkyl; (vi) -cyano; (vii) -amino optionally substituted with alkyl, which alkyl is optionally substituted with one or more substituents independently selected from halo, $C_1$ to $C_6$ alkoxy, hydroxy, cyano, 5 or 6 membered heterocyclo and 5 or 6 membered heteroaryl; (viii) -heterocyclo; (ix) -nitro; (x) -hydroxy; (xi) —COOH; (xii) —$CO_2R_x$, wherein $R_x$ is —$C_1$ to $C_6$ alkyl; (xiii) —$COR_x$, wherein $R_x$ is —$C_1$ to $C_6$ alkyl; (xiv) —$C(O)NH_2$ optionally substituted with one or more $C_1$ to $C_6$ alkyls, which $C_1$ to $C_6$ alkyls are optionally substituted with one or more substituents independently selected from halo, $C_1$ to $C_6$ alkoxy, hydroxy, 5 or 6 membered heterocyclo and 5 or 6 membered heteroaryl; and (xv) -amido optionally substituted with one or more substituents independently selected from halo, $C_1$ to $C_6$ alkoxy, hydroxy, 5 or 6 membered heterocyclo, 5 or 6 membered heteroaryl, and $C_1$ to $C_6$ alkyl, which alkyl is optionally substituted with one or more $C_1$ to $C_6$ alkoxys; (2) -5 to 6 membered heterocyclo optionally having a hetero atom ring member selected from sulfinyl or sulfonyl, wherein heterocyclo is optionally substituted with $C_1$ to $C_6$ alkyl, which alkyl is optionally substituted with aryl; or (3) -5 to 6 membered heteroaryl optionally substituted with one or more substituents independently selected from cyano, halo, nitro, $C_1$ to $C_6$ alkyl, $C_1$ to $C_6$ alkoxy, —C(O)—$C_1$ to $C_6$ alkyl, —S—$C_1$ to $C_6$ alkyl, —C(O)O—$C_1$ to $C_6$ alkyl, 5 or 6 membered heterocyclo and $C_1$ to $C_6$ haloalkyl; (4) —$SO_2R_x$, wherein $R_x$ is —$C_1$ to $C_6$ alkyl; (5) —$Si(R_x)_3$, wherein $R_x$ is independently selected from —$C_1$ to $C_6$ alkyl; or (6) —$CONH_2$ optionally substituted with one or more $C_1$ to $C_6$ alkyl, cyclopropyl, cyclobutyl, cyclopentyl or cyclohexyl, wherein $C_1$ to $C_6$ alkyl is optionally substituted with alkoxy, cyclopropyl, cyclobutyl, cyclopentyl, cyclohexyl, aryl, 5 or 6 membered heterocyclo or 5 or 6 membered heteroaryl;

(q) —$OC(O)NHR_x$, wherein $R_x$ is —$C_1$ to $C_6$ alkyl and wherein $R_x$ is optionally substituted with -aryl;

(r) —$OC(O)N(R_x)_2$, wherein $R_x$ is independently —$C_1$ to $C_6$ alkyl;

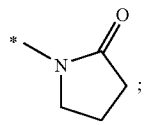
;

(t) —$CONH_2$ optionally substituted with one or more of the following:
1) $C_1$ to $C_6$ alkyl, wherein $C_1$ to $C_6$ alkyl is optionally substituted with alkoxy, cyclopropyl, cyclobutyl, cyclopentyl, cyclohexyl, 5 or 6 membered heterocyclo or 5 or 6 membered heteroaryl;
(2) alkoxy,
(3) cyclopropyl,
(4) cyclobutyl,
(5) cyclopentyl or
(6) cyclohexyl; or
(v) —C(O)OH; and $R_3$ is hydrogen; or -nitro;

with the proviso that at least one of Y, Z, $R_1$, $R_2$ and $R_3$ is selected from the following:

Y is -aryl substituted with one or more substituents independently selected from:
(1) -alkoxy substituted with one or more substituents independently selected from:
—$C(O)NH_2$ optionally substituted with $C_6$ to $C_8$ alkyl; and
—C(O)NH—($C_1$ to $C_6$)-alkyl;
(2) -haloalkyl;
(3) -cyano;
(4) —COOH;
(5) —$N=CHN(R_x)_2$, wherein $R_x$ is independently selected from —$C_1$ to $C_6$ alkyl;
(6) -amino substituted with one or more substituents independently selected from:
(i) —$SO_2R_x$, wherein $R_x$ is —$C_1$ to $C_6$ alkyl, cyclopropyl, cyclobutyl, cyclopentyl or cyclohexyl;
(ii) -6 to 8 membered aryl optionally substituted with one or more substituents independently selected from $C_1$ to $C_6$ alkyl, halo, haloalkyl, cyano, alkoxy, wherein $R_x$ is —$C_1$ to $C_6$ alkyl, and haloalkoxy;
(iii) -5 or 6 membered heteroaryl optionally substituted with one or more substituents independently selected from $C_1$ to $C_6$ alkyl, halo, haloalkyl, cyano, alkoxy, haloalkoxy and aryl, wherein aryl is optionally substituted with halo;
(iv) -5 or 6 membered heterocyclo optionally substituted with one or more substituents independently selected from hydroxy, =O, alkyl and haloalkyl;
(v) —$C_1$ to $C_7$ alkyl substituted with one or more substituents independently selected from: -5 or 6 membered heteroaryl, wherein heteroaryl is optionally substituted with one more substituents independently selected from $C_1$ to $C_6$ alkyl, alkoxy, haloalkoxy, halo, and haloalkyl; -aryl, wherein aryl is optionally substituted with one or more substituents independently selected from $C_1$ to $C_6$ alkyl, halo, haloalkyl; -alkoxy; and haloalkoxy; and
(vi) —$PO_2R_x$, wherein $R_x$ is —$C_1$ to $C_6$ alkyl;
(7) —$OC(O)NHR_x$, wherein $R_x$ is $C_1$ to $C_6$ alkyl optionally substituted with vinyl;
(8) —$OC(O)N(R_u)_2$, wherein $R_u$ is alkyl or aryl, which alkyl or aryl is optionally substituted with dialkylamino;
(9) —$OC(O)NH(OR_{uu})$, wherein $R_{uu}$ is -aryl optionally substituted with dialkylamino;
(10) —$OC(O)NR(OR_x)$, wherein $R_x$ is independently selected from —$C_1$ to $C_6$ alkyl;
(11) —$OC(O)N(OR_x)_2$, wherein $R_x$ is independently selected from —$C_1$ to $C_6$ alkyl;
(12) —$OC(O)R_{ab}$, wherein $R_{ab}$ is a 5 or 6 membered heterocyclo optionally substituted with a 5 or 6 membered heteroaryl, which heteroaryl is optionally substituted with alkyl or haloalkyl;
(13) —$NR_oC(O)R_p$, wherein $R_p$ is:
(i) -amino optionally substituted with cyclopropyl; cyclobutyl; cyclopentyl; cyclohexyl; or one or more $C_1$ to $C_6$ alkyls, which $C_1$ to $C_6$ alkyls are optionally substituted with one or more substituents independently selected from aryl and alkoxy;
(iii) -5 or 6 membered heterocyclo optionally substituted with one or more substituents independently selected from $C_1$ to $C_6$ alkyl and aryl;
(iv) -cyclopropyl;
(v) -cyclobutyl;
(vi) -cyclopentyl;
(vii) -cyclohexyl; or
(viii) -cyclopropylmethyl;
and wherein $R_o$ is: -hydrogen; or —$C_1$ to $C_6$ alkyl;
(14) —$NR_qCONR_qR_r$, wherein $R_q$ is hydrogen, and wherein $R_r$ is:
(i) —$C_1$ to $C_6$ alkyl substituted with one or more substituents independently selected from: -hydroxy; -alkoxy; -5 or 6 membered heterocyclo; -5 or 6 membered heteroaryl; and -aryl substituted with halo;
(ii) —$C_2$ to $C_6$ alkenyl optionally substituted with one or more halos;
(iii) —$C_1$ to $C_6$ alkoxy;
(iv) -5 or 6 membered heterocyclo; or
(v) -5 to 6 membered heteroaryl optionally substituted with $C_1$ to $C_6$ alkyl; cyclopropyl; cyclobutyl; cyclopentyl; cyclohexyl;
(vi) -cyclobutyl;
(vii) -cyclopentyl;
(viii) -cyclopropyl;

(ix) -cyclohexyl; or
(x) -cyclopropylmethyl;
(15) —SO$_2$R$_{aa}$, wherein R$_{aa}$ is:
  (i) -5 or 6 membered heterocyclo optionally substituted with one or more substituents independently selected from: -hydroxy; —C$_1$ to C$_6$ alkoxy; and —C$_1$ to C$_6$ alkyl; or
  (ii) -amino optionally substituted with —C$_1$ to C$_6$ alkyl, which —C$_1$ to C$_6$ alkyl is optionally substituted with one or more substituents independently selected from: -alkoxy; -hydroxy; or -halo;
(16) —COR$_m$, wherein R$_m$ is:
  (i) -amino substituted with cyclopropyl, cyclobutyl, cyclopentyl or cyclohexyl or one or more C$_1$ to C$_6$ alkyls, which alkyls are substituted with 5 or 6 membered heterocyclo or aryl, which heterocyclo is substituted with one or more substituents independently selected from halos or alkoxys; and which aryl is optionally substituted with one or more substituents independently selected from halos or alkoxys;
  (ii) -3 to 7 membered heterocyclo substituted with hydroxyl;
(17) —NR$_t$COOR$_u$,
wherein R$_t$ is hydrogen, and
wherein R$_u$ is:
  (i) —C$_1$ to C$_{12}$ alkyl substituted with one or more substituents independently selected from: cyclopropyl; cyclobutyl; cyclopentyl; cyclohexyl; -aryl substituted with one or more halos or haloalkyls; -alkoxy substituted with one or more alkoxys; -amino optionally substituted with one or more C$_1$ to C$_6$ alkyls; —SO$_2$R$_w$; —SO$_2$R$_x$, wherein R$_x$ is —C$_1$ to C$_6$ alkyl; -5 or 6 membered heteroaryl; and -5 or 6 membered heterocyclo;
  (ii) —C$_2$ to C$_6$ alkenyl;
  (iii) -4 to 7 membered heterocyclo optionally substituted with one or more substituents independently selected from: =O; —SO$_2$R$_w$; —COR$_p$; and —(CO)O—(C$_1$ to C$_4$ alkyl)-O—(C$_1$ to C$_4$ alkyl); —C(O)-alkyl; —C(O)-alkoxy wherein alkoxy is optionally substituted with one or more alkoxys; —SO, -alkyl; —SO$_2$-cyclopropyl; —SO$_2$-cyclobutyl; —SO$_2$-cyclopentyl or —SO$_2$-cyclohexyl;
  (iv) -dioxo-tetrahydro-thiopyran;
  (v) -cyclobutyl;
  (vi) -cyclopentyl;
  (vii) -cyclopropyl; or
  (viii) -cyclohexyl;
(18) —NHR$_{bb}$, wherein R$_{bb}$ is:
  (i) —C(=S)NHR$_x$, wherein R$_x$ is C$_1$ to C$_6$ alkyl; —C(=S)NH-cyclopropyl; —C(=S)NH-cyclobutyl; —C(=S)NH-cyclopentyl; —C(=S)NH-cyclohexyl;
  (ii) —C(=S)NR$_x$R$_x$, wherein R$_x$ is independently selected from —C$_1$ to C$_6$ alkyl;
  (iii) —C(=N—CN)NHR$_x$, wherein R$_x$ is —C$_1$ to C$_6$ alkyl; —C(=N—CN)—NH-cyclopropyl; —C(=N—CN)—NH-cyclobutyl; —C(=N—CN)—NH-cyclopentyl; —C(=N—CN)—NH-cyclohexyl;
  (iv) —PO(OR$_x$)$_2$, wherein R$_x$ is independently selected from —C$_1$ to C$_6$ alkyl;
  (v) —S(=O)-alkyl;
  (vi) —S$^+$(O$^-$)-alkyl; or
  (vii) -dioxo-tetrahydro-thiopyran;
(19) —N(CONHR$_w$)$_2$;
(20) —NH(SOR$_w$);
(21) —N(SO$_2$R$_w$)$_2$;
(22) —NR$_v$SO$_2$R$_w$, wherein R$_v$ is alkyl substituted with 4 to 7 membered heterocyclo; and
wherein R$_w$ is:
  (i) —C$_1$ to C$_6$ alkyl substituted with cyclopropyl, cyclobutyl, cyclopentyl, cyclohexyl or aryl, which aryl is optionally substituted with one or more substituents independently selected from haloalkyl, halo, alkoxy, and alkyl;
  (ii) -amino optionally substituted with —C(O)O-alkyl, a -5 or 6 membered heterocyclo or alkyl, which heterocyclo or alkyl is optionally substituted with one or more substituents independently selected from halo, C$_1$ to C$_6$ alkoxy, alkoxycarbonyl, (CO)O—(C$_1$ to C$_6$)alkyl), hydroxy, cyano, 5 or 6 membered heterocyclo, and 5 or 6 membered heteroaryl;
  (iii) -cyclopropyl;
  (iv) -cyclobutyl;
  (v) -cyclopentyl;
  (vi) -1-methylcyclopropyl; or
  (vii) -1-ethylcyclopropyl;

(28) -5 to 6 membered heteroaryl optionally substituted with one or more substituents independently selected from:
  (i) -halo;
  (ii) —C$_1$ to C$_6$ alkyl; haloalkyl; cyclopropyl; cyclobutyl; cyclopentyl; cyclohexyl; or cyclopropylmethyl;
  (iii) -alkoxy optionally substituted with one or more substituents independently selected from: -halo; -5 or 6 membered heterocyclo; and —C(O)NH$_2$ optionally substituted with C$_6$ to C$_8$ alkyl;
  (iv) -hydroxy;
  (v) -haloalkyl;
  (vi) -cyano;
  (vii) -nitro;
  (viii) —COOH;
  (ix) -amino optionally substituted with one or more substituents independently selected from: —SO$_2$R$_x$, wherein R$_x$ is —C$_1$ to C$_6$ alkyl; -6 to 8 membered aryl optionally substituted with one or more substituents independently selected from alkyl, halo, haloalkyl, cyano, alkoxy, —COR$_x$, wherein R$_x$ is —C$_1$ to C$_6$ alkyl and haloalkoxy; -5 or 6 membered heteroaryl optionally substituted with one or more substituents independently selected from alkyl, halo, haloalkyl, cyano, alkoxy, haloalkoxy and -aryl optionally substituted with halo; —C$_5$ to C$_6$ heterocyclo optionally substituted with one or more substituents independently selected from hydroxy, alkyl and haloalkyl; and —C$_1$ to C$_7$ alkyl optionally substituted with one or more substituents independently selected from: -5 or 6 membered heteroaryl optionally substituted with one or more alkyls, halos, or haloalkyls; -aryl optionally substituted with one or more substituents independently selected from alkyl, halo and haloalkyl; -alkoxy; and -halo;

(29) —NR$_o$COR$_p$,
wherein R$_p$ is:
  (i) -amino optionally substituted with cyclopropyl; cyclobutyl; cyclopentyl; cyclohexyl; or one or more C$_1$ to C$_6$ alkyls, which C$_1$ to C$_6$ alkyls are optionally and independently substituted with one or more aryls or alkoxys;
  (ii) -5 or 6 membered heterocyclo optionally substituted with one or more C$_1$ to C$_6$ alkyls or aryls;
  (iii) -cyclopropyl;
  (iv) -cyclobutyl;
  (v) -cyclopentyl;
  (vi) -cyclohexyl; or
  (vii) -cyclopropylmethyl;
and wherein R$_o$ is: hydrogen; or —C$_1$ to C$_6$ alkyl;

(30) —NR$_q$CONR$_q$R$_r$,
wherein R$_q$ is hydrogen, and
wherein R$_r$ is:
  (i) —C$_1$ to C$_6$ alkyl substituted with one or more substituents independently selected from: -hydroxy; -alkoxy; -5 or 6 membered heterocyclo; -5 or 6 membered heteroaryl; and -aryl optionally substituted with halo;
  (ii) —C$_2$ to C$_6$ alkenyl optionally substituted with one or more halos;
  (iii) —C$_1$ to C$_6$ alkoxy;
  (iv) -5 or 6 membered heterocyclo; or
  (v) -5 to 6 membered heteroaryl optionally substituted with —C$_1$ to C$_6$ alkyl; cyclopropyl; cyclobutyl; cyclopentyl; or cyclohexyl;

(31) —NR$_t$COOR$_u$,
wherein R$_t$ is hydrogen, and
wherein R$_u$ is
  (i) —C$_1$ to C$_{12}$ alkyl substituted with one or more substituents independently selected from: cyclopropyl; cyclobutyl; cyclopentyl; cyclohexyl; -aryl substituted with one or more halos or haloalkyls; -alkoxy substituted with one or more alkoxys; -amino optionally substituted with one or more C$_1$ to C$_6$ alkyls; —SO$_2$R$_w$; —SO$_2$R$_x$, wherein R$_x$ —C$_1$ to C$_6$ alkyl; -5 or 6 membered heteroaryl; and -5 or 6 membered heterocyclo; and

(32) —NR$_v$SO$_2$R$_w$,
wherein R$_v$ is alkyl substituted with 4 to 7 membered heterocyclo; and wherein R$_w$ is:
  (i) —C$_1$ to C$_6$ alkyl substituted with cyclopropyl; cyclobutyl; cyclopentyl; cyclohexyl; or aryl, which aryl is substituted with one or more substituents independently selected from haloalkyl, halo, alkoxy, and alkyl;
  (ii) -aryl; and
  (iii) -amino substituted with —C(O)O-alkyl or a -5 or 6 membered heterocyclo or alkyl, which heterocyclo is optionally substituted with one or more substituents independently selected from halo, C$_1$ to C$_6$ alkoxy, alkoxycarbonyl, hydroxy, cyano, 5 or 6 membered heterocyclo and 5 or 6 membered heteroaryl; and which alkyl is substituted with one or more substituents independently selected from halo, C$_1$ to C$_6$ alkoxy, alkoxycarbonyl, hydroxy, cyano, 5 or 6 membered heterocyclo and 5 or 6 membered heteroaryl;

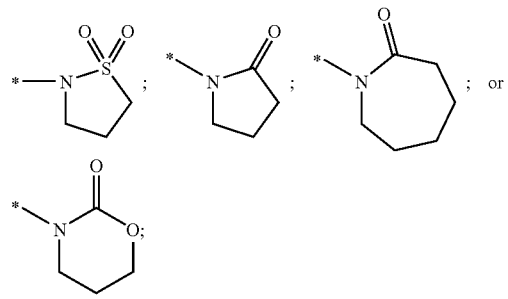

Z is —C$_1$ to C$_6$ alkyl; -cyclopropyl; -cyclobutyl; -cyclopentyl; -cyclohexyl; or -cyclopropylmethyl;

R$_1$ is:
  (a) -a 5 or 6 membered heterocyclo optionally substituted with one or more substituents independently selected from: (1) -hydroxy; (2) —C$_1$ to C$_6$ alkyl; (3) —SO$_2$R$_x$, wherein R$_x$ is —C$_1$ to C$_6$ alkyl; (4) —C(O)-aryl; (5) —COR$_p$, and (6) —C(O)OR$_x$, wherein R$_x$ is —C$_1$ to C$_6$ alkyl;
  (b) -5 or 6 membered heteroaryl substituted with one or more substituents independently selected from: (1) —C$_1$ to C$_6$ alkyl optionally substituted with one or more substituents independently selected from halo, C$_1$ to C$_6$ alkoxy, hydroxy, 5 or 6 membered heterocyclo, and 5 or 6 membered heteroaryl; (2) -alkoxy; (3) -halo; (4) -alkylthio; (5) -haloalkyl; (6) -cyano; (7) -amino optionally substituted with alkyl, which alkyl is optionally substituted with one or more substituents independently selected from (i) halo, (ii) C$_1$ to C$_6$ alkoxy, (iii) hydroxy, (iv) cyano, (v) 5 or 6 membered heterocyclo, and (vi) 5 or 6 membered heteroaryl; (8) -heterocyclo; (9) -nitro; (10) -hydroxy; (11) —COOH; (12) —CO$_2$R$_x$, wherein R$_x$ is —C$_1$ to C$_6$ alkyl; (13) —COR$_x$, wherein R$_x$ is C$_1$ to C$_6$ alkyl; (14) —C(O)NH$_2$ optionally substituted with one or more C$_1$ to C$_6$ alkyls, which alkyls are optionally substituted with one or more substituents independently selected from halo, C$_1$ to C$_6$ alkoxy, hydroxy, 5 or 6 membered heterocyclo, and 5 or 6 membered heteroaryl; (15) -amido optionally substituted with one or more or more substituents independently selected from halo, C$_1$ to C$_6$ alkoxy, hydroxy, 5 or 6 membered heterocyclo, 5 or 6 membered heteroaryl, and C$_1$ to C$_6$ alkyl, which alkyl is optionally substituted with one or more C$_1$ to C$_6$ alkoxys;
  (c) —C$_1$ to C$_6$ alkyl substituted with one or more substituents independently selected from:
    (1) -amino optionally substituted with one or more substituents independently selected from (i) heterocyclo, (ii) alkoxy and (iii) alkyl, which alkyl is substituted with one or more alkoxys; (2) -amido optionally substituted with C$_1$ to C$_6$ alkyl, cyclopropyl, cyclobutyl, cyclopentyl or cyclohexyl; (3) -5 or 6 membered heterocyclo substituted with C$_1$ to C$_6$ alkyl; (4) -5 or 6 membered heteroaryl optionally substituted with C$_1$ to C$_6$ alkyl; (5) -aryl; or (6) hydroxyl;
  (d) —C$_2$ to C$_6$ alkenyl optionally substituted with —SO$_2$R$_x$, wherein R$_x$ is —C$_1$ to C$_6$ alkyl;

(e) —$C_1$ to $C_6$ alkoxy substituted with one or more substituents independently selected from: (i) -hydroxy; (ii) -cyano; (iii) -alkoxy optionally substituted with alkoxy; (iv) -amino optionally substituted with one or more independently selected from 5 or 6 membered heteroaryl, 5 or 6 membered heterocyclo and alkyl, which alkyl is optionally substituted with one or more substituents independently selected from: -5 or 6 membered heterocyclo; and -amino optionally substituted with one or more alkyl; (v) -amino optionally substituted with heterocyclo; (vi) -amido optionally substituted with $C_1$ to $C_6$ alkyl; (vii) -5 to 7 membered heterocyclo substituted with one or more substituents independently selected from hydroxy and $C_1$ to $C_6$ alkyl, which alkyl is optionally substituted with one or more substituents independently selected from: —$C_1$ to $C_6$ alkoxy; and —$C_6$ to $C_8$ aryl; (viii) -5 or 6 membered heteroaryl optionally substituted with one or more substituents independently selected from: —$C_1$ to $C_6$ alkyl; and -4 to 7 membered heterocyclo; and (ix) -alkoxy;

(f) —(O)-5 or 6 membered heterocyclo optionally substituted with one or more substituents independently selected from: (i) -hydroxy; (ii) —$C_1$ to $C_6$ alkyl; (iii) —$SO_2R_x$, wherein $R_x$ is —$C_1$ to $C_6$ alkyl; (iv) —C(O)-aryl; (v) —$COR_p$; and (vi) —C(O)$OR_x$, wherein $R_x$ is —$C_1$ to $C_6$ alkyl; or (g) —(O)-5 or 6 membered heteroaryl optionally substituted with one or more substituents independently selected from: (i) —$C_1$ to $C_6$ alkyl optionally substituted with one or more substituents independently selected from halo, $C_1$ to $C_6$ alkoxy, hydroxy, 5 or 6 membered heterocyclo and 5 or 6 membered heteroaryl; (ii) -alkoxy; (iii) -halo; (iv) -alkylthio; (v) -haloalkyl; (vi) -cyano; (vii) -amino optionally substituted with alkyl, which alkyl is optionally substituted with one or more substituents independently selected from halo, —$C_1$ to $C_6$ alkoxy, hydroxy, cyano, 5 or 6 membered heterocyclo and 5 or 6 membered heteroaryl; (viii) -heterocyclo; (ix) -nitro; (x) -hydroxy; (xi) —COOH; (xii) —$CO_2R_x$, wherein $R_x$ is —$C_1$ to $C_6$ alkyl; (xiii) —$COR_x$, wherein $R_x$ is —$C_1$ to $C_6$ alkyl; (xiv) —C(O)$NH_2$ optionally substituted with one or more substituents independently selected from: —$C_1$ to $C_6$ alkyl optionally substituted with one or more substituents independently selected from halo, $C_1$ to $C_6$ alkoxy, hydroxy, 5 or 6 membered heterocyclo and 5 or 6 membered heteroaryl; and -amido optionally substituted with one or more or more substituents independently selected from halo, $C_1$ to $C_6$ alkoxy, hydroxy, 5 or 6 membered heterocyclo, 5 or 6 membered heteroaryl, and $C_1$ to $C_6$ alkyl, which alkyl is optionally substituted with one or more $C_1$ to $C_6$ alkoxys;

(h) —C(O)$NH_2$ optionally substituted with one or more $C_1$ to $C_6$ alkyls, which alkyls are optionally substituted with one or more substituents independently selected from halo, $C_1$ to $C_6$ alkoxy, hydroxy, 5 or 6 membered heterocyclo and 5 or 6 membered heteroaryl;

(i) —C(O)-3 to 7 membered heterocyclo optionally substituted with one or more substituents independently selected from: (i) -aryl; (ii) -5 or 6 membered heteroaryl; and (iii) —$C_1$ to $C_6$ alkyl further optionally substituted with one or more substituted with hydroxys;

(j) —$SO_2R_x$, wherein $R_x$ is —$C_1$ to $C_6$ alkyl; optionally substituted with one or more substituents independently selected from: (i) -5 or 6 membered heterocyclo; (ii) -aryl; and (iii) -5 or 6 membered heteroaryl; or (k) -alkylthio optionally substituted with one or more substituents independently selected from: (i) -5 or 6 membered heterocyclo; (ii) -aryl; and (iii) -5 or 6 membered heteroaryl;

(l) —C(O)-5 or 6 membered heteroaryl;

(m) —C(O)-aryl;

(n) —COOH; and (o) —$OR_{kk}$, wherein $R_{kk}$ is: -aryl optionally substituted with one or more substituents independently selected from halo, $C_1$ to $C_6$ alkyl, $C_1$ to $C_6$ alkoxy, $C_1$ to $C_6$ haloalkyl;

$R_2$ is:

(a) —$C_1$ to $C_6$ alkyl substituted with one or more substituents independently selected from: (i) -5 or 6 membered heterocyclo; (ii) -5 or 6 membered heteroaryl; (iii) -aryl; (iv) -amido optionally substituted with $C_1$ to $C_6$ alkyl; and (v) -amino optionally substituted with one or more substituents independently selected from heterocyclo, alkoxy and alkyl, which alkyl is optionally substituted with one or more alkoxy; and (vi) —$SO_2R_x$, wherein $R_x$ is —$C_1$ to $C_6$ alkyl;

(b) —$C_2$ to $C_6$ alkenyl optionally substituted with $SO_2R_x$, wherein $R_x$ is $C_1$ to $C_6$ alkyl;

(c) -alkylthio optionally substituted with one or more substituents independently selected from: (i) -5 or 6 membered heteroaryl optionally substituted with alkyl; (ii) -5 or 6 membered heterocyclo; (iii) -aryl; and (iv) —$C_1$ to $C_6$ alkyl;

(d) —$SO_2R_x$, wherein $R_x$ is —$C_1$ to $C_6$ alkyl; optionally substituted with one or more substituents independently selected from: (i) -5 or 6 membered heteroaryl optionally substituted with one or more $C_1$ to $C_6$ alkyls; (ii) -5 or 6 membered heterocyclo; (iii) -aryl; and (iv) —$C_1$ to $C_6$ alkyl;

(e) (1) —S(O)$R_x$, wherein $R_x$ is —$C_1$ to $C_6$ alkyl; optionally substituted with one or more substituents independently selected from: (i) -5 or 6 membered heteroaryl, which heteroaryl is optionally substituted with one or more $C_1$ to $C_6$ alkyls; (ii) -5 or 6 membered heterocyclo; (iii) -aryl; and (iv) —$C_1$ to $C_6$ alkyl;

(2) —$SR_x$, wherein $R_x$ is $C_1$ to $C_6$ alkyl;

(3) —$C_2$ to $C_6$ alkenyl-$SO_2$—$R_x$, wherein $R_x$ $C_1$ to $C_6$ alkyl;

(f) -alkoxy substituted with one or more substituents independently selected from: (i) -halo; (ii) -hydroxy; (iii) -cyano; (iv) -alkoxy optionally substituted with alkoxy; (v) -amino substituted with one or more substituents independently selected from —$SO_2$—$C_1$ to $C_4$ alkyl and alkyl, which alkyl is substituted with one or more substituents independently selected from: -5 or 6 membered heterocyclo; and -amino optionally substituted with one or more alkyls; (vi) -amido substituted with $C_1$ to $C_6$ alkyl, cyclopropyl, cyclobutyl, cyclopentyl or cyclohexyl; (vii) —S-5 or 6 membered heterocyclo; (viii) —S-5 or 6 membered heteroaryl optionally substituted with $C_1$ to $C_6$ alkyl; (ix) —S—$C_1$ to $C_6$ alkyl optionally substituted with one or more substituents independently selected from: -aryl optionally substituted with one or more substituents independently selected from alkyl, haloakyl and halo; and —$C_5$ to $C_6$ heteroaryl optionally substituted with one or more substituents independently selected from alkyl, haloakyl and halo; (x) —S-aryl; (xi) -sulfinyl-5 or 6 membered heterocyclo; (xii) -sulfinyl-5 or 6 membered heteroaryl; (xiii) -sulfinyl-$C_1$ to $C_6$ alkyl optionally substituted with one or more substituents independently selected from: (i) -aryl optionally substituted with one or more substituents independently selected from alkyl, haloakyl and halo; and —$C_5$ to $C_6$ heteroaryl optionally substituted with one or more substituents independently selected from alkyl, haloakyl and halo; (xiv) -sulfinyl-aryl; (xv) -sulfonyl-5 or 6 membered heterocyclo; (xvi) -sulfonyl-5 or 6 membered heteroaryl optionally substituted with $C_1$ to $C_6$ alkyl; (xvii) -sulfonyl-$C_1$ to $C_6$ alkyl optionally substituted with one or more substituents independently selected from: -aryl optionally substituted with one or more substituents independently selected from alkyl, haloakyl and halo; and —$C_5$ to $C_6$ heteroaryl optionally substituted with one or more substituents independently selected from alkyl, haloakyl and halo; (xviii) -sulfonyl-aryl; (xix) -5 to 7 membered heterocyclo optionally substituted with one or more substituents independently selected from hydroxy, =O, heterocyclo, and $C_1$ to $C_6$ alkyl, which alkyl is optionally substituted with one or more substituents independently selected from: —$C_1$ to $C_6$ alkoxy; and -aryl; (xx) -5 or 6 membered heteroaryl optionally substituted with one or more substituents independently selected from: —$C_1$ to $C_6$ alkyl optionally substituted with one or more alkoxys; -4 to 7 membered heterocyclo; and -alkoxy; and (xxi) -aryl;

(g) -aryl;

(h) —(O)-5 or 6 membered heterocyclo substituted with one or more substituents independently selected from: (i) -hydroxy; (ii) =O; (iii) —$C_1$ to $C_6$ alkyl; (iv) —$SO_2R_x$, wherein $R_x$ is —$C_1$ to $C_6$ alkyl; (v) —C(O)-aryl; (vi) —$COR_p$; and (vii) —$C(O)OR_x$, wherein $R_x$ is —$C_1$ to $C_6$ alkyl;

(i) —(O)-5 or 6 membered heteroaryl substituted with one or more substituents independently selected from: (i) —$C_1$ to $C_6$ alkyl optionally substituted with one or more substituents independently selected from halo, $C_1$ to $C_6$ alkoxy, hydroxy, 5 or 6 membered heterocyclo and 5 or 6 membered heteroaryl; (ii) -alkoxy; (iii) -halo; (iv) -alkylthio; (v) -haloalkyl; (vi) -cyano; (vii) -amino optionally substituted with alkyl, which alkyl is optionally substituted with one or more substituents independently selected from halo, $C_1$ to $C_6$ alkoxy, hydroxy, cyano, 5 or 6 membered heterocyclo and 5 or 6 membered heteroaryl; (viii) -heterocyclo; (ix) -nitro; (x) -hydroxy; (xi) —COOH; (xii) $CO_2R_x$, wherein is —$C_1$ to $C_6$ alkyl; (xiii) —$COR_x$, wherein $R_x$ is —$C_1$ to $C_6$ alkyl; (xiv) —$C(O)NH_2$ optionally substituted with one or more $C_1$ to $C_6$ alkyls, which alkyls are optionally substituted with one or more substituents independently selected from halo, $C_1$ to $C_6$ alkoxy, hydroxy, 5 or 6 membered heterocyclo and 5 or 6 membered heteroaryl; and (xv) -amido optionally substituted with one or more substituents independently selected from halo, $C_1$ to $C_6$ alkoxy, hydroxy, 5 or 6 membered heterocyclo, 5 or 6 membered heteroaryl, and $C_1$ to $C_6$ alkyl, which alkyl is optionally substituted with one or more $C_1$ to $C_6$ alkoxys;

(j) —C(O)-3 to 7 membered heterocyclo optionally substituted with one or more substituents independently selected from: (i) -aryl; (ii) -5 or 6 membered heteroaryl; and (iii) —$C_1$ to $C_6$ alkyl optionally substituted with one or more hydroxys;

(k) —C(O)-5 or 6 membered heteroaryl;

(l) —C(O)-aryl;

(m) -amino substituted with one or more substituents independently selected from: (i) —$SO_2R_x$, wherein $R_x$ is $C_1$ to $C_6$ alkyl; (ii) -6 to 8 membered aryl optionally substituted with one or more substituents independently selected from alkyl, halo, haloalkyl, cyano, alkoxy, $COR_x$, wherein $R_x$ is —$C_1$ to $C_6$ alkyl; and haloalkoxy; (iii) -5 or 6 membered heteroaryl optionally substituted with one or more substituents independently selected from alkyl, halo, haloalkyl, cyano, alkoxy, haloalkoxy and -aryl optionally substituted with halo; (iv) —$C_5$ to $C_6$ heterocyclo optionally substituted with one or more substituents independently selected from hydroxy, alkyl and haloalkyl; (v) —$C_1$ to $C_7$ alkyl optionally substituted with one or more substituents independently selected from: (i) -5 or 6 membered heteroaryl optionally substituted with one or more substituents independently selected from alkyl, halo and haloalkyl; (ii) -aryl optionally substituted with one or more substituents independently selected from alkyl, halo and haloalkyl; (iii) -alkoxy; and (iv) -halo;

(n) -5 or 6 membered heteroaryl substituted with one or more substituents independently selected from: (i) —$C_1$ to $C_6$ alkyl optionally substituted with one or more substituents independently selected from halo, $C_1$ to $C_6$ alkoxy, hydroxy, 5 or 6 membered heterocyclo and 5 or 6 membered heteroaryl; (ii) -alkoxy; (iii) -halo; (iv) -alkylthio; (v) -haloalkyl; (vi) -cyano; (vii) -amino optionally substituted with one more alkyls, which alkyls are optionally substituted with one or more substituents independently selected from halo, $C_1$ to $C_6$ alkoxy, hydroxy, cyano, 5 or 6 membered heterocyclo and 5 or 6 membered heteroaryl; (viii) -5 or 6 membered heterocyclo; (ix) -nitro; (x) -hydroxy; (xi) —COOH; (xii) —$CO_2R_x$, wherein $R_x$ is —$C_1$ to $C_6$ alkyl; (xiii) $COR_x$, wherein $R_x$ is —$C_1$ to $C_6$ alkyl; (xiv) —$C(O)NH_2$ optionally substituted with one or more $C_1$ to $C_6$ alkyls, which alkyls are optionally substituted with one or more substituents independently selected from halo, $C_1$ to $C_6$ alkoxy, hydroxy, 5 or 6 membered heterocyclo and 5 or 6 membered heteroaryl; (xv) -amido optionally substituted with one or more substituents independently selected from halo, $C_1$ to $C_6$ alkoxy, hydroxy, 5 or 6 membered heterocyclo, 5 or 6 membered heteroaryl, and $C_1$ to $C_6$ alkyl, which alkyl is optionally substituted with one or more $C_1$ to $C_6$ alkoxys;

(o) -4, 5 or 6 membered heterocyclo optionally having a hetero atom ring member selected from sulfinyl or sulfonyl, wherein heterocyclo is optionally substituted with one or more substituents independently selected from: (i) -hydroxy; (ii) =O; (iii) —$C_1$ to $C_6$ alkyl optionally substituted with cyclopropyl, cyclobutyl, cyclopentyl or cyclohexyl; (iv) —$SO_2R_x$, wherein $R_x$ is —$C_1$ to $C_6$ alkyl, which $C_1$ to $C_6$ alkyl is optionally substituted with cyclopropyl, cyclobutyl, cyclopentyl or cyclohexyl; (v) C(O)-aryl; (vi) —$COR_p$, (vii) —$C(O)OR_x$, wherein $R_x$ is $C_1$ to $C_6$ alkyl, which $C_1$ to $C_6$ alkyl is optionally substituted with cyclopropyl, cyclobutyl, cyclopentyl or cyclohexyl; (viii) —C(O)R$_x$, wherein R$_x$ is C$_1$ to C$_6$ alkyl, cyclopropyl, cyclobutyl, cyclopentyl or cyclohexyl; (ix) aryl; (x) cyclopropyl; (xi) cyclobutyl; (xii) cyclopentyl; and (xiii) cyclohexyl;

(p) —OR$_{kk}$, wherein R$_{kk}$ is: (i) -aryl optionally substituted with one or more substituents independently selected from halo, C$_1$ to C$_6$ alkyl, C$_1$ to C$_6$ alkoxy, and C$_1$ to C$_6$ haloalkyl; (ii) -5 to 6 membered heterocyclo optionally substituted with C$_1$ to C$_6$ alkyl, which alkyl is optionally substituted with aryl; or (iii) -5 to 6 membered heteroaryl substituted with one or more substituents independently selected from halo, C$_1$ to C$_6$ alkyl, C$_1$ to C$_6$ alkoxy, and C$_1$ to C$_6$ haloalkyl; (iv) —SO$_2$R$_x$, or (v) —Si(R$_x$)$_3$;

(q) —OC(O)NHR$_x$, wherein R$_x$ is optionally substituted with -aryl;

(r) —OC(O)N(R$_x$)$_2$; or

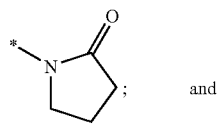
; and

R$_3$ is nitro.

5. A compound or a pharmaceutically acceptable salt thereof selected from the group consisting of:

1332

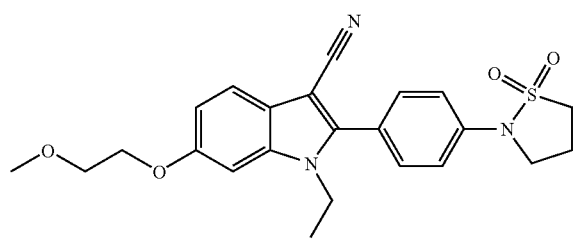

1333

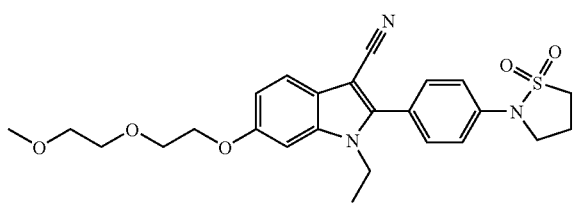

1337

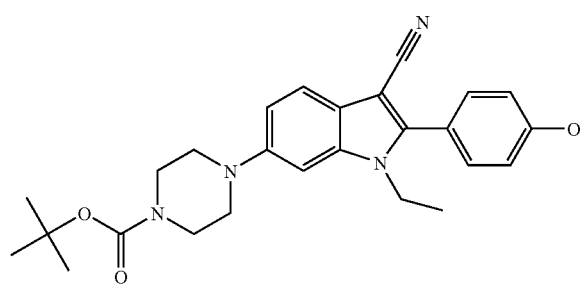

1338

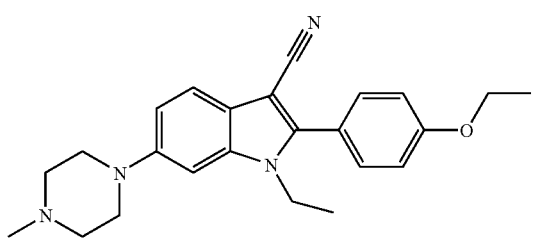

1339

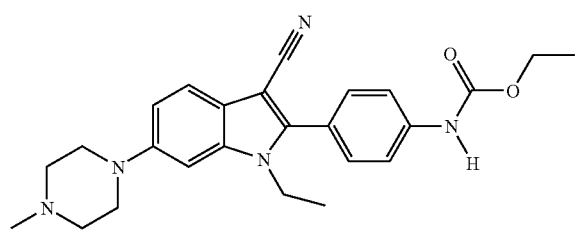

1340

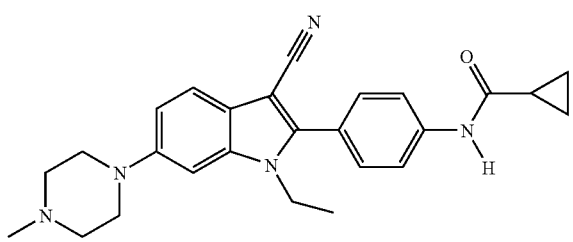

1341

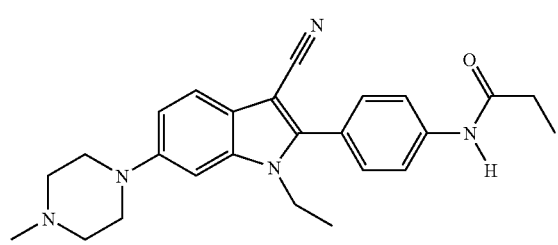

1342

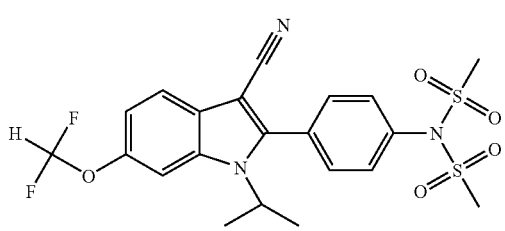

-continued
1344
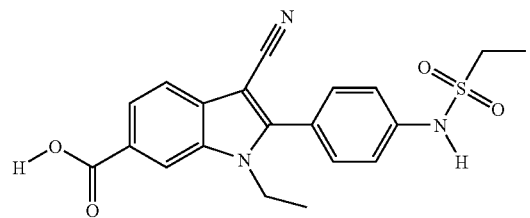
1345
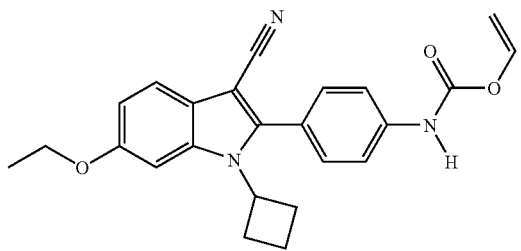
1345
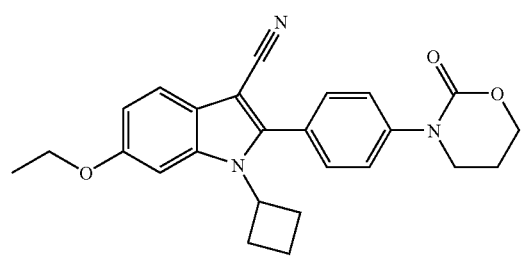
1346
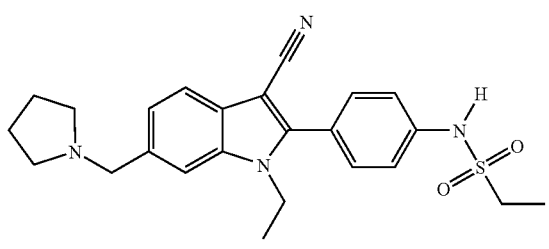
1347
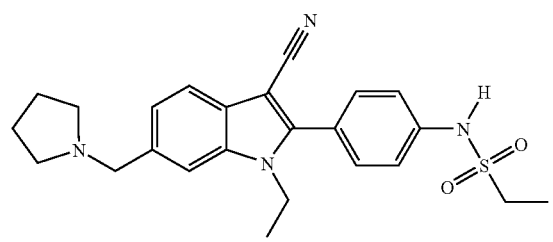
1348
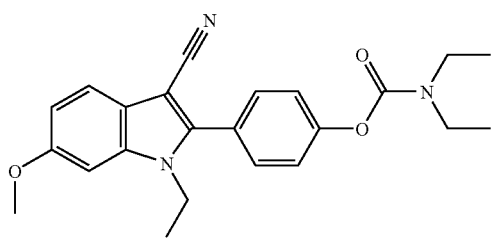
1349
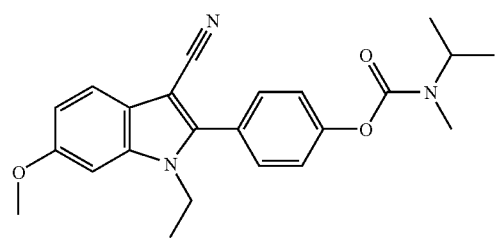
1350
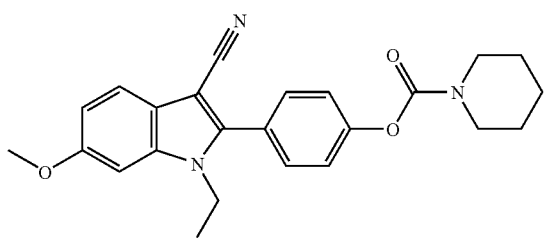
1351
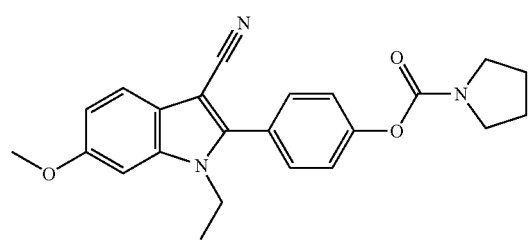
1352
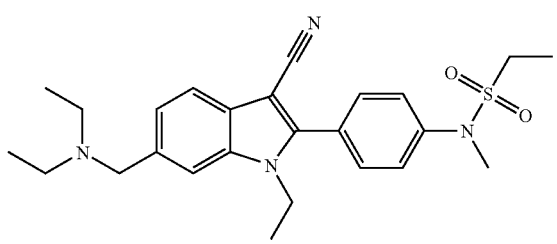
1353
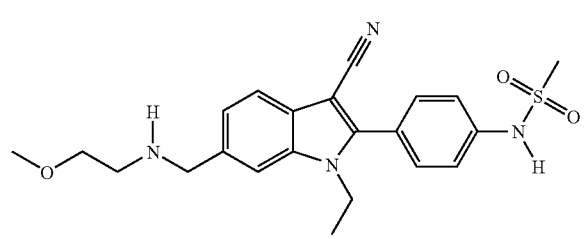
1354
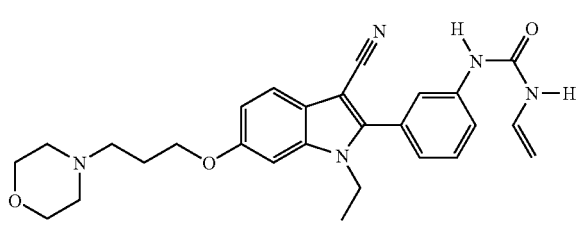

-continued
| 1355 | 1356 |
|---|---|
| 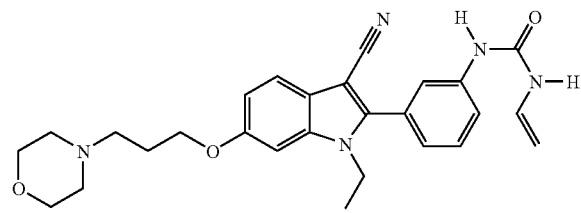 | 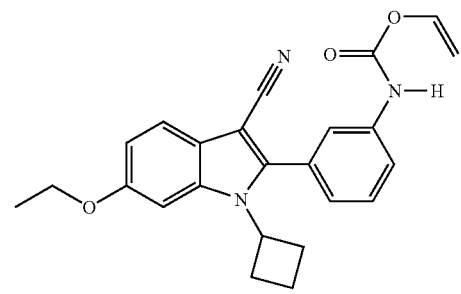 |
| 1356 | 1357 |
| 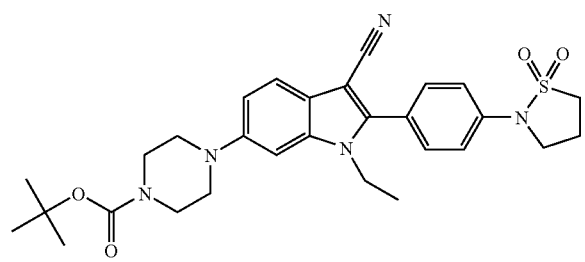 | 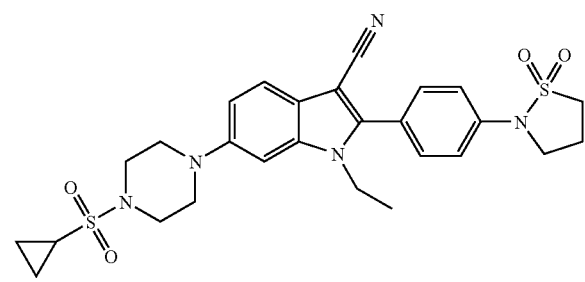 |
| 1358 | 1359 |
| 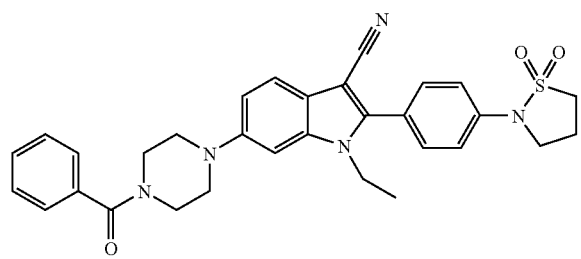 | 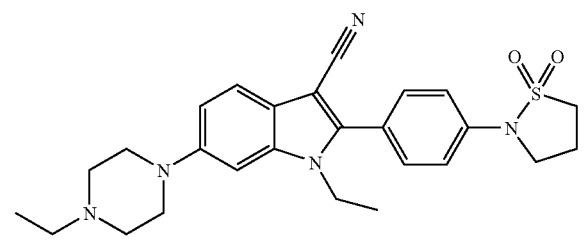 |
| 1360 | 1361 |
| 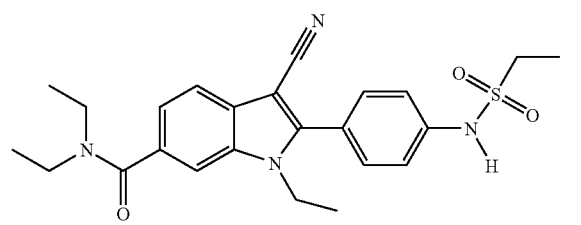 | 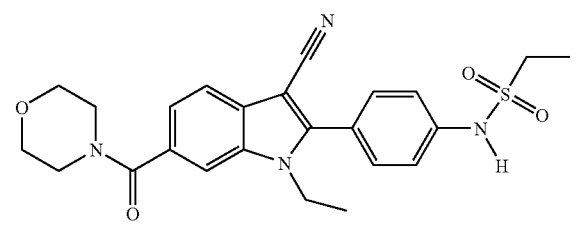 |
| 1362 | 1363 |
| 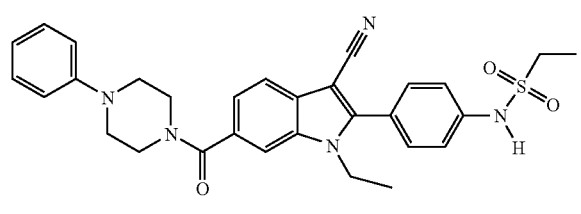 | 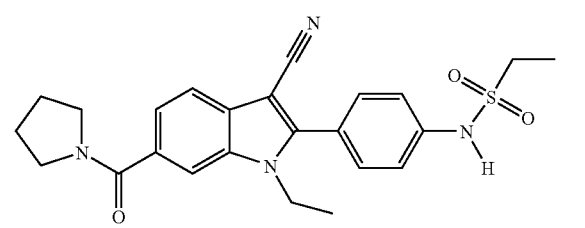 |
| 1364 | 1365 |
| 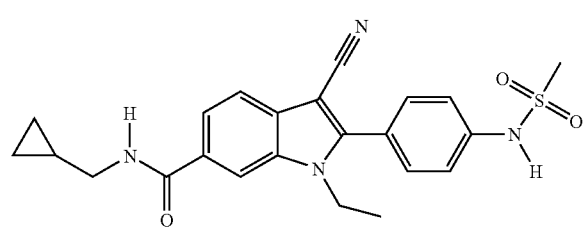 | 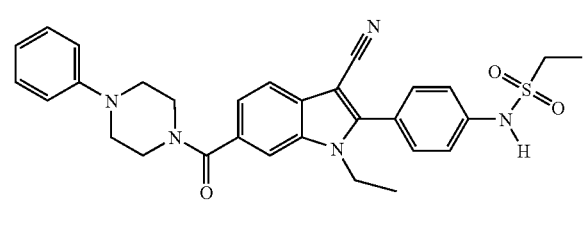 |

| 1366 | 1367 |
|---|---|
| 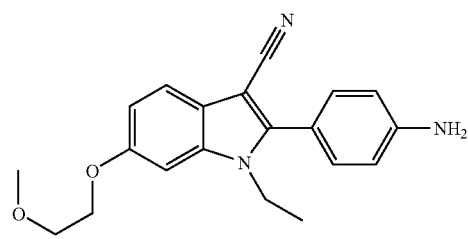 | 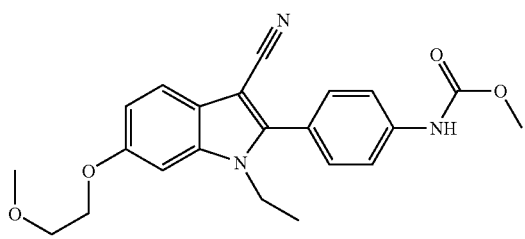 |
| 1368 | 1369 |
| 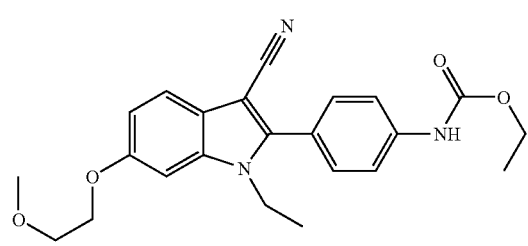 | |
| 1370 | 1371 |
| 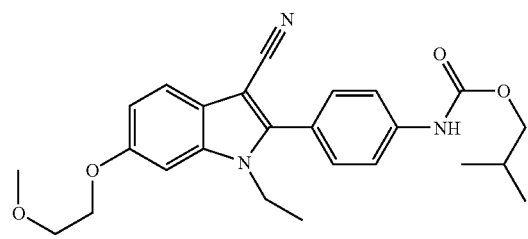 | |
| 1372 | 1373 |
| 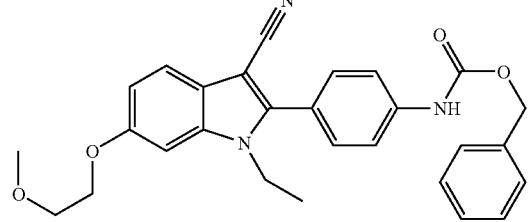 | |
| 1374 | 1375 |
| 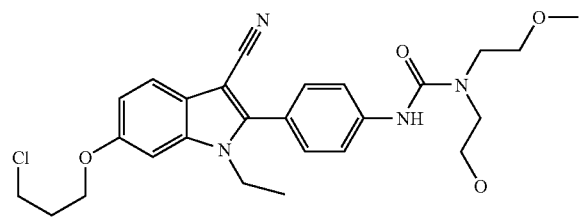 | |
| 1376 | 1377 |
| 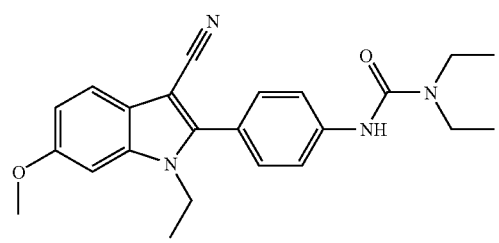 | 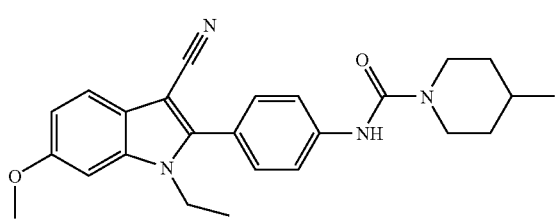 |

-continued
1378
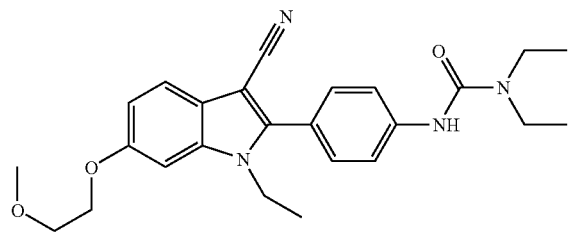
1379
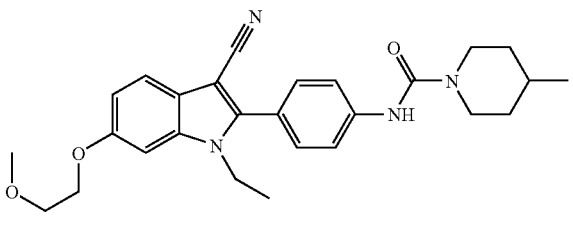
1380
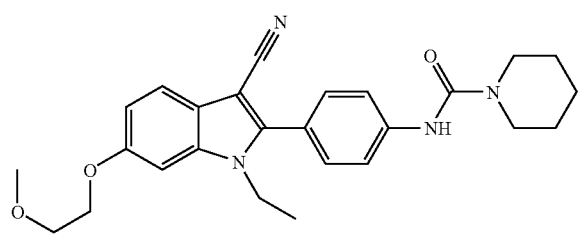
1381
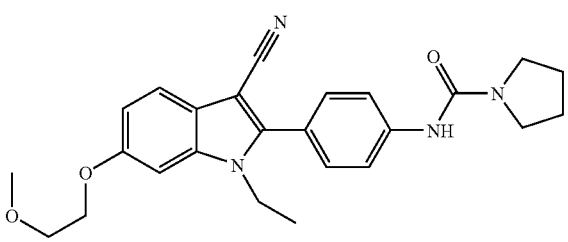
1382
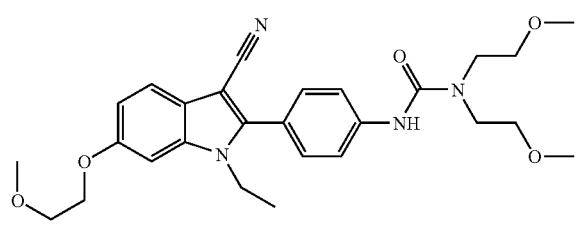
1383
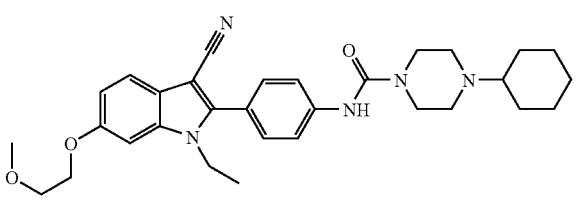
1384
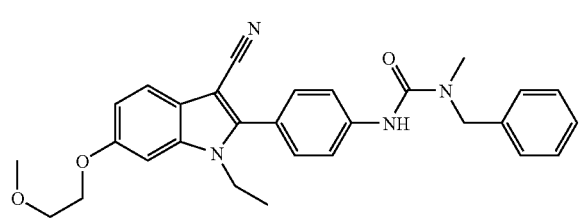
1385
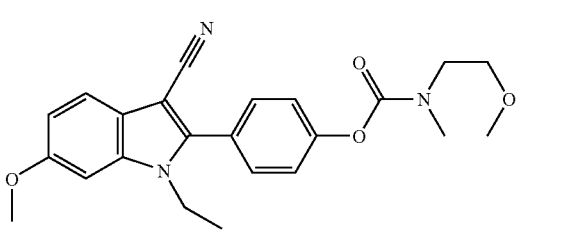
1386
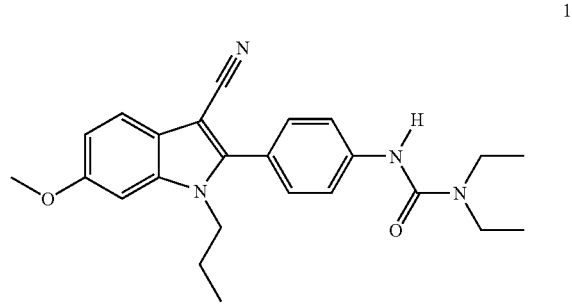
1387
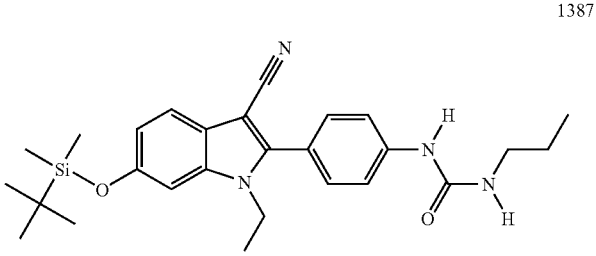
1388
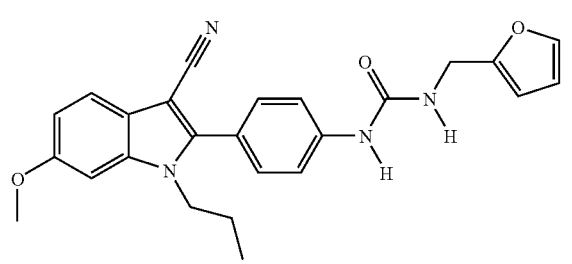
1389
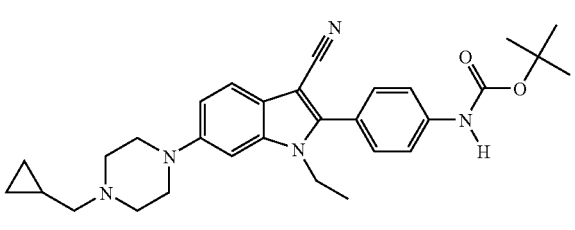

-continued
1390
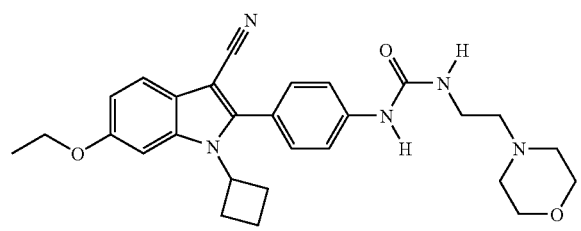
1391
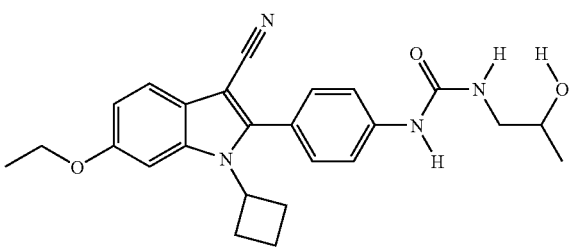
1392
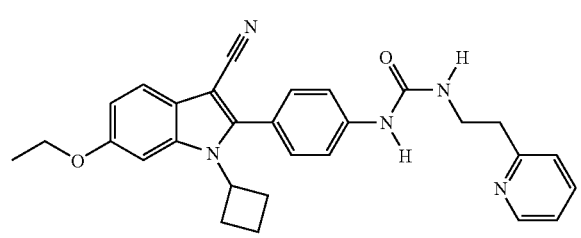
1393
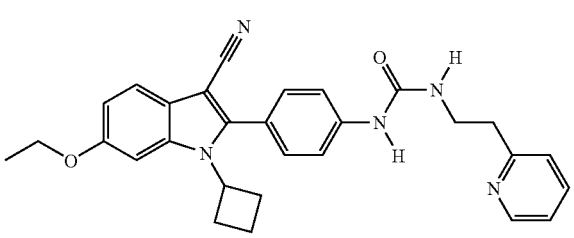
1394
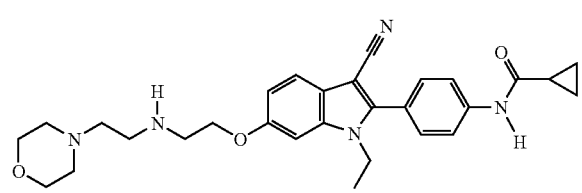
1395
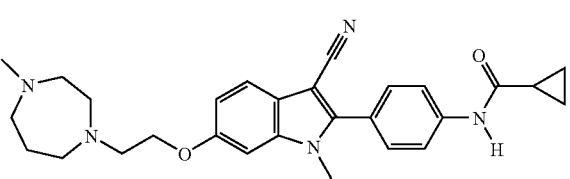
1396
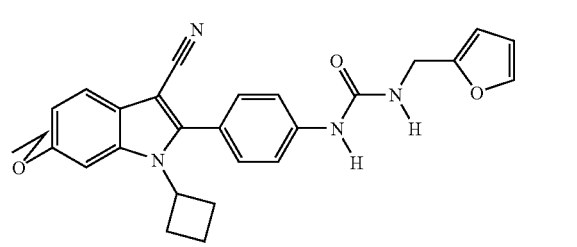
1397
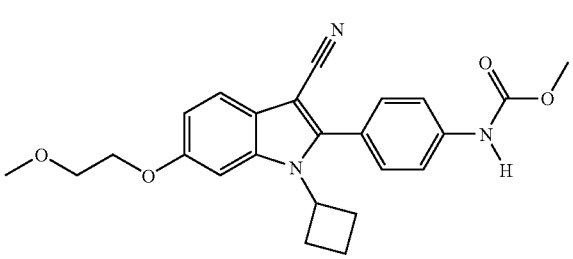
1398
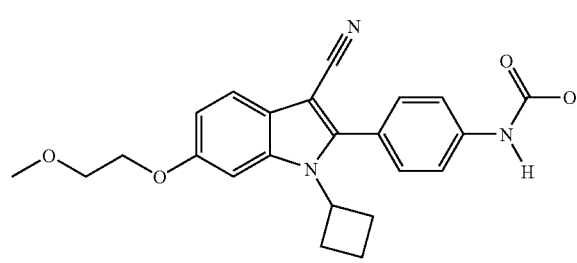
1399
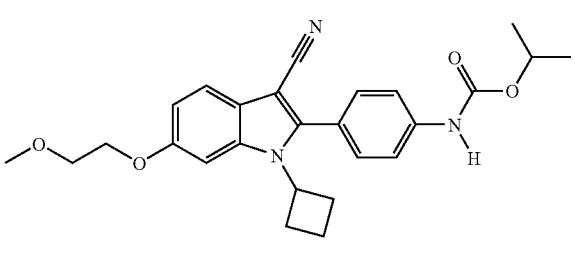
1400
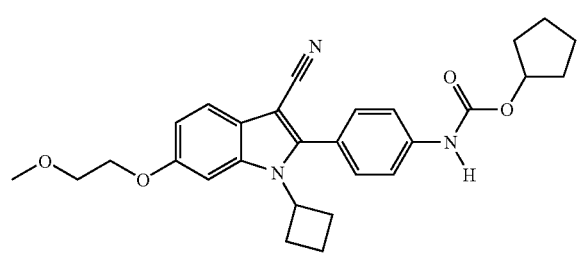
1401
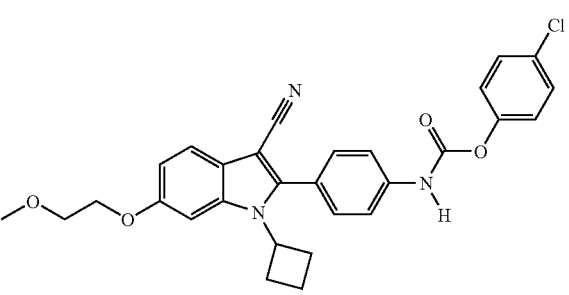

-continued
1402
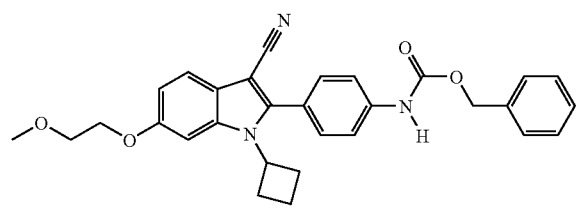
1403
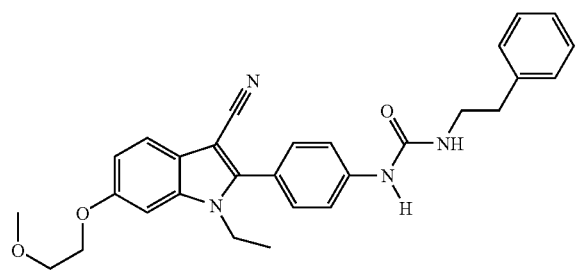
1404
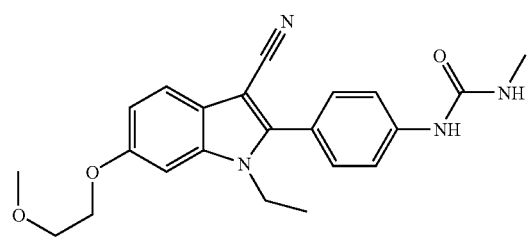
1405
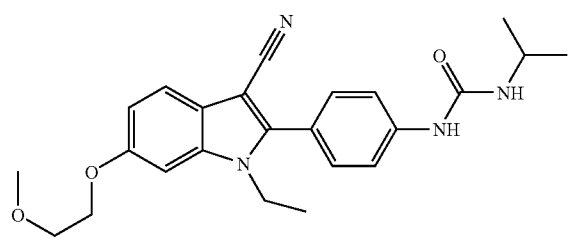
1406
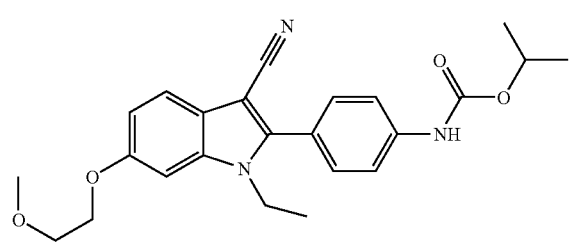
1407
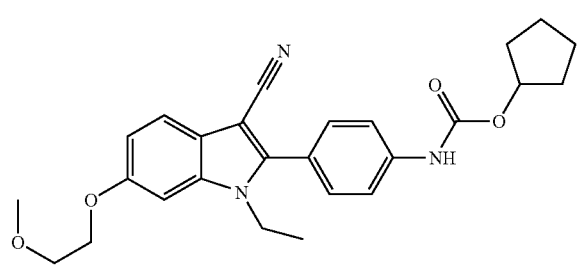
1408
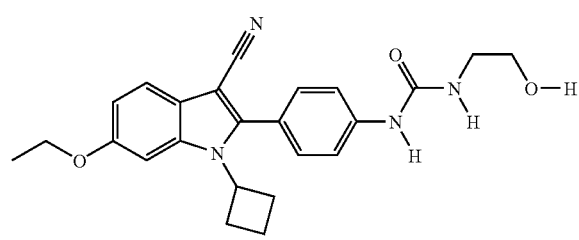
1409
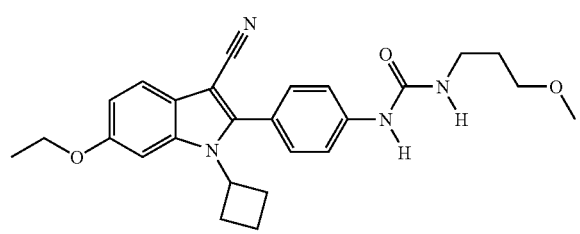
1410
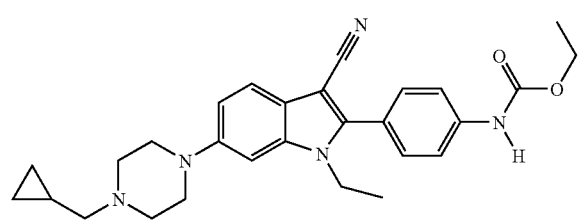
1411
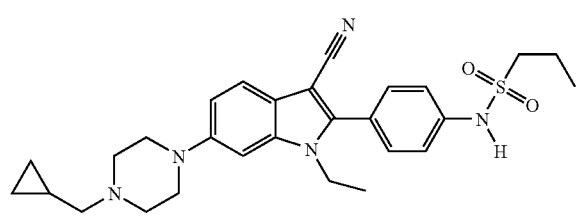
1412
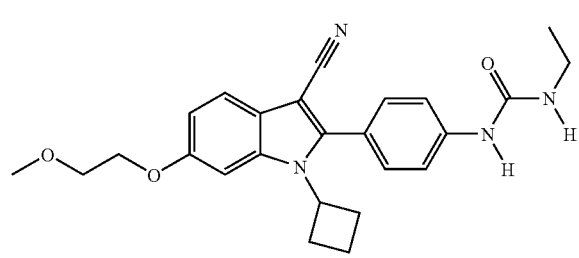
1413
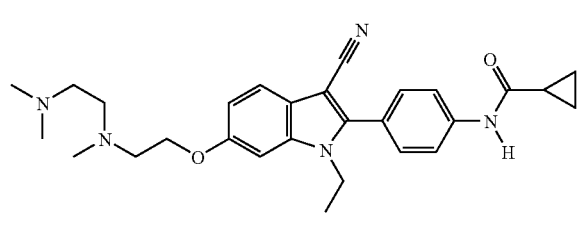

-continued
1414
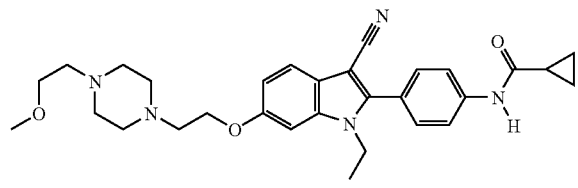
1415
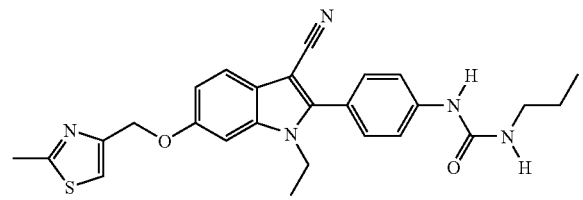
1416
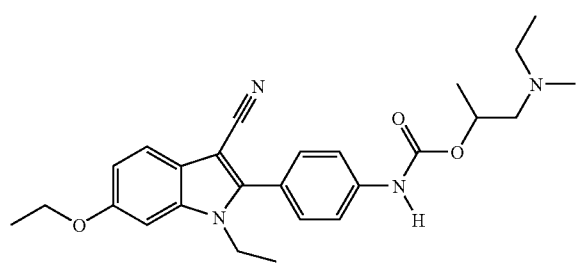
1417
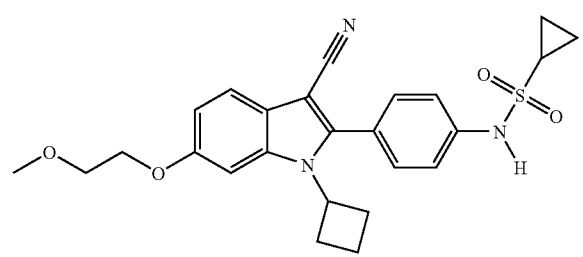
1418
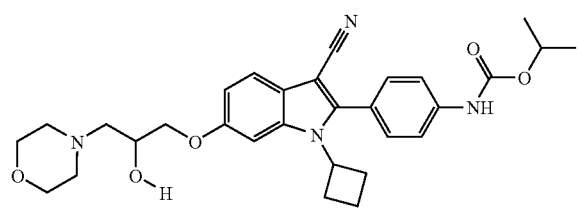
1419
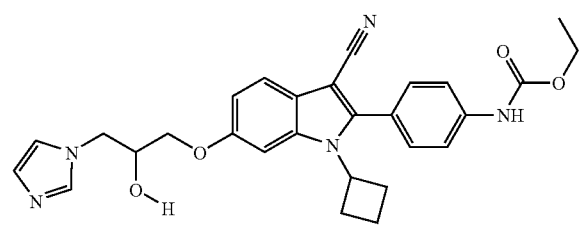
1420
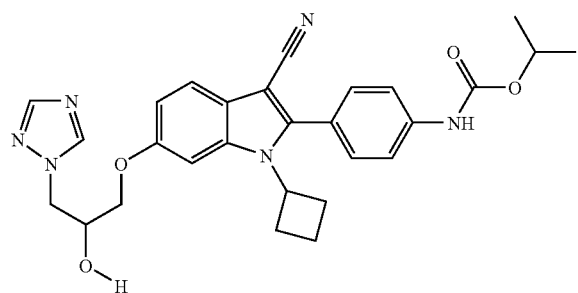
1421
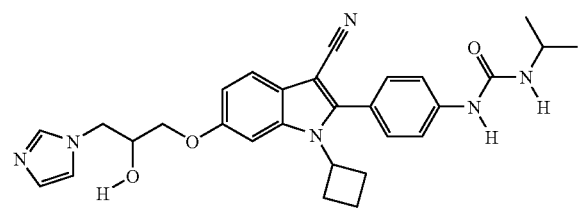
1422
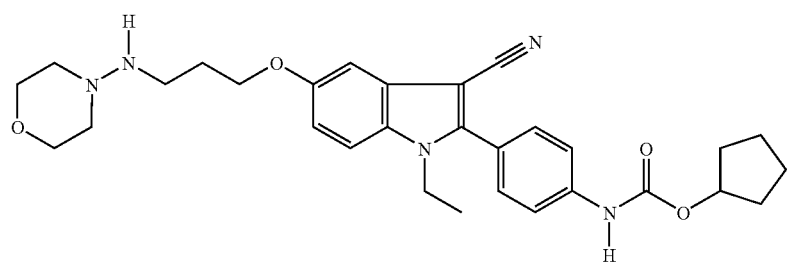

-continued
1423 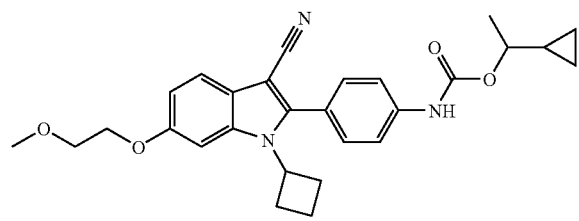
1424 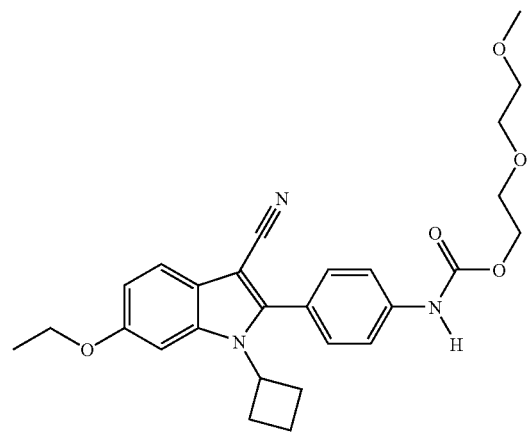
1425 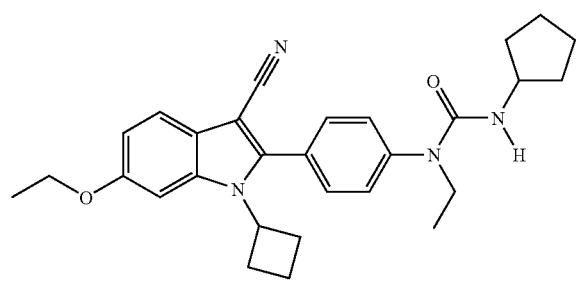
1426 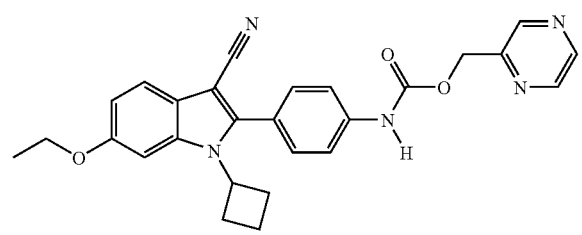
1427 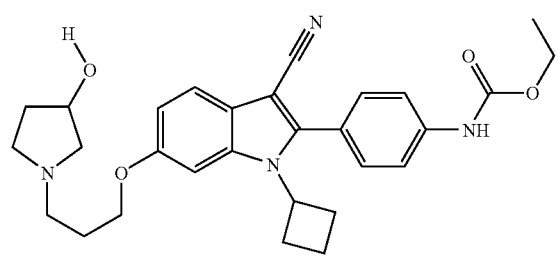
1428 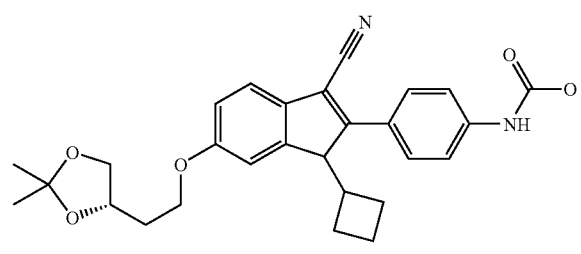
1429 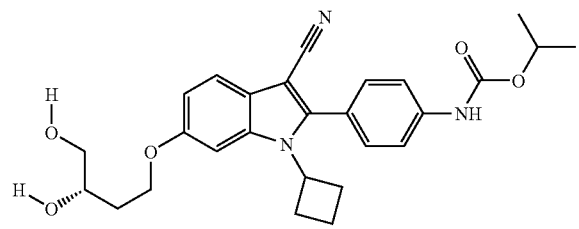
1430 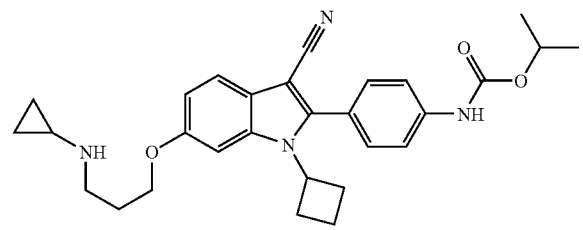
1431 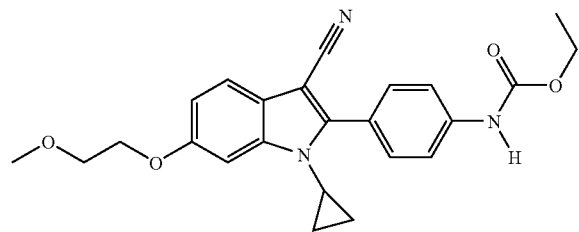
1432 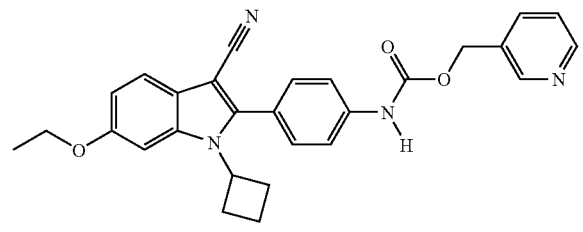

-continued
1433
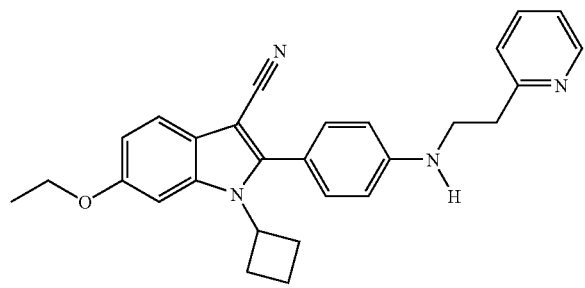
1434
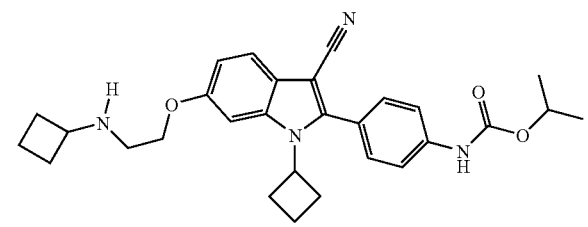
1435
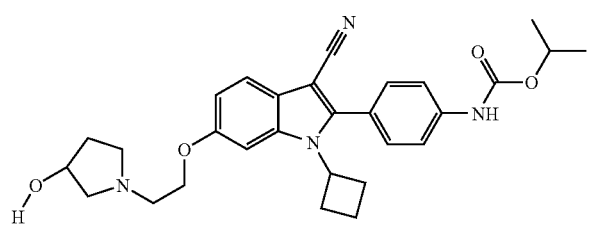
1436
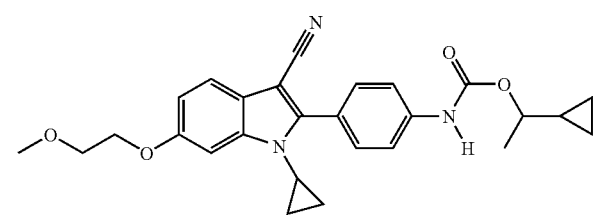
1437
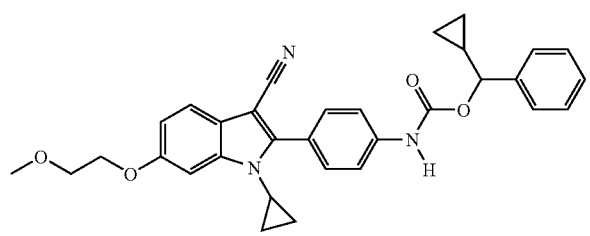
1438
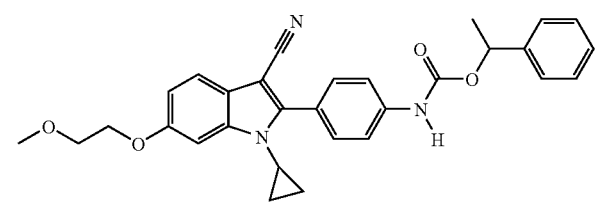
1439
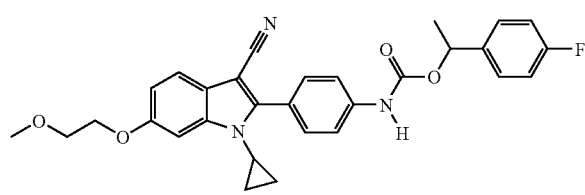
1440
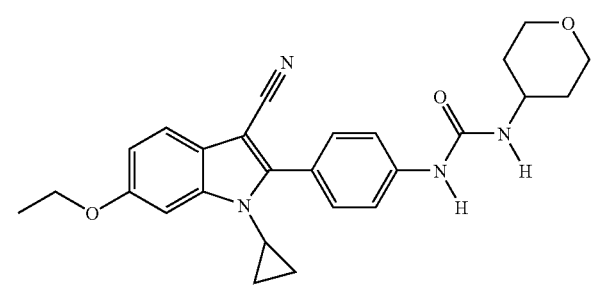
1441
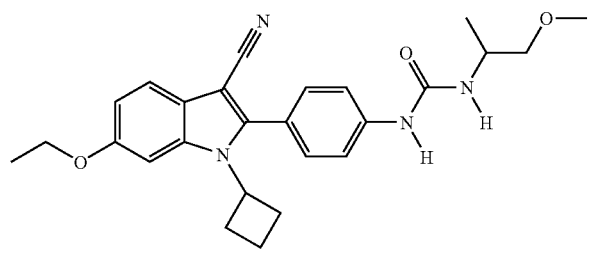
1442
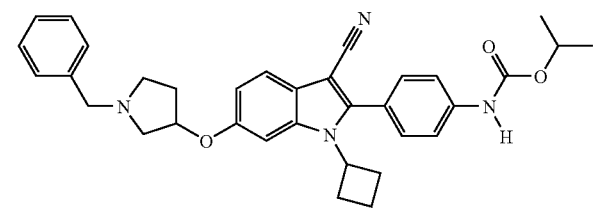

1443
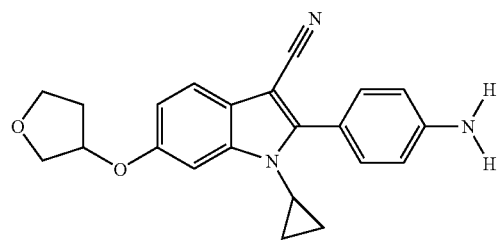
1444
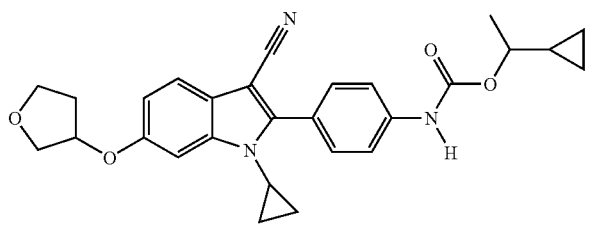
1445
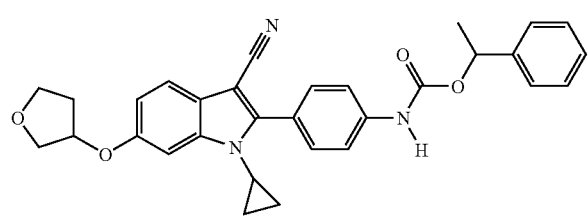
1446
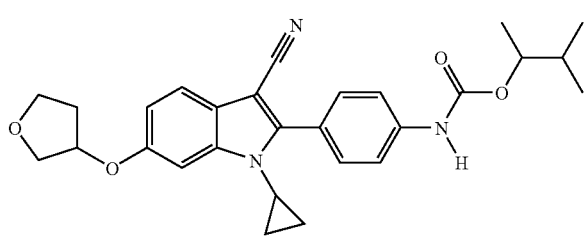
1447
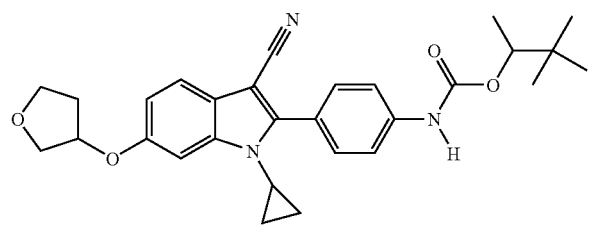
1448
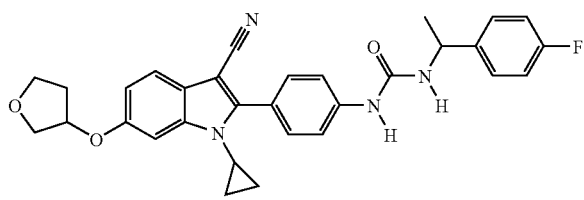
1449
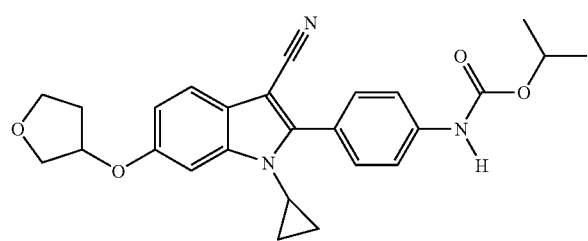
1450
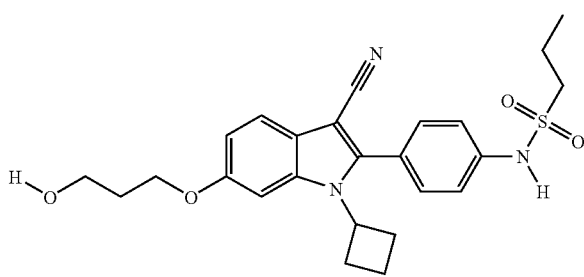
1451
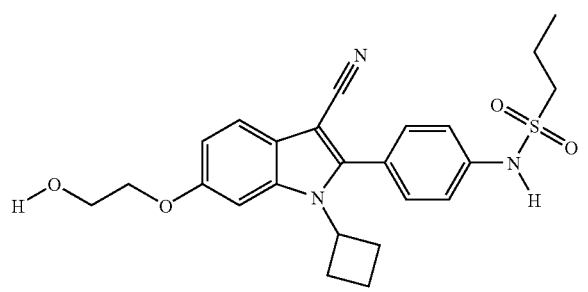
1452
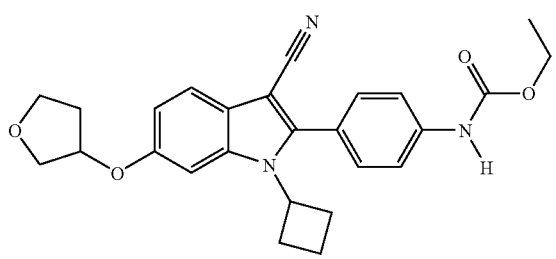

-continued
1453
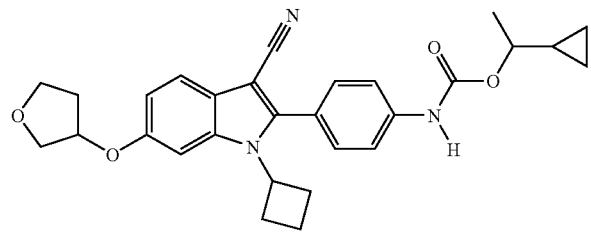
1454
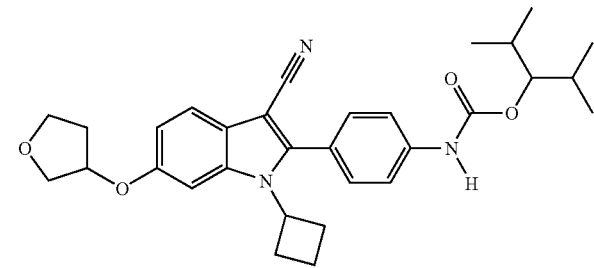
1455
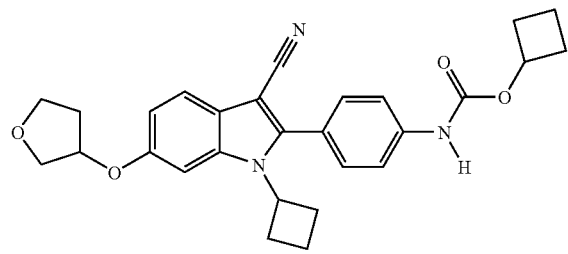
1456
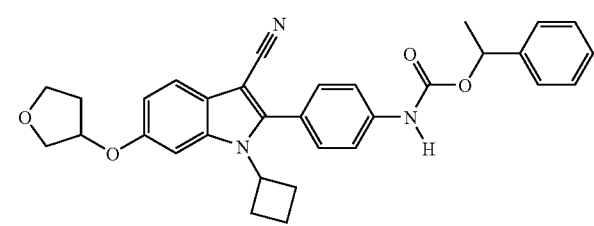
1457
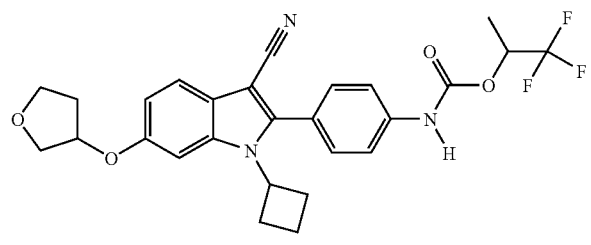
1458
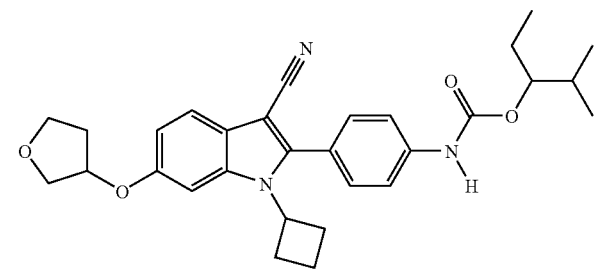
1459
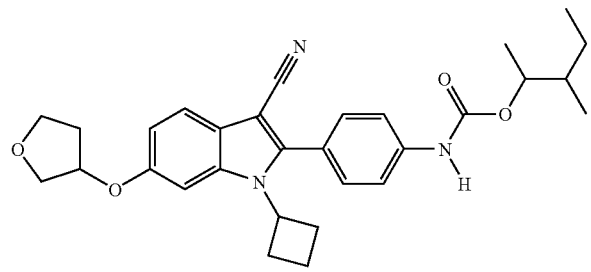
1460
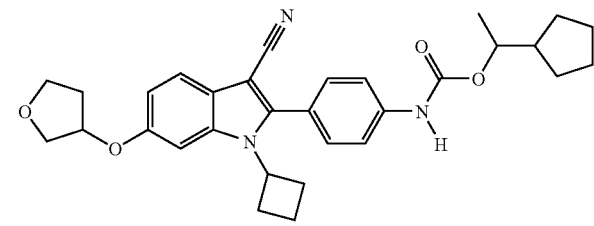
1461
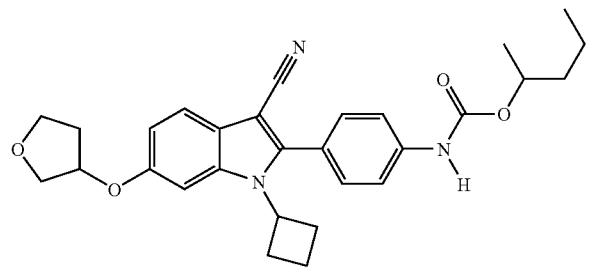
1462
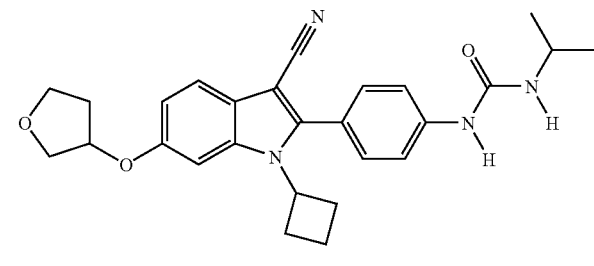

-continued
1463
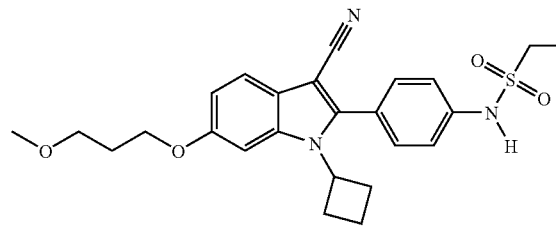
1464
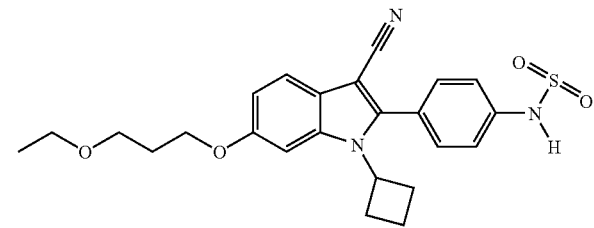
1465
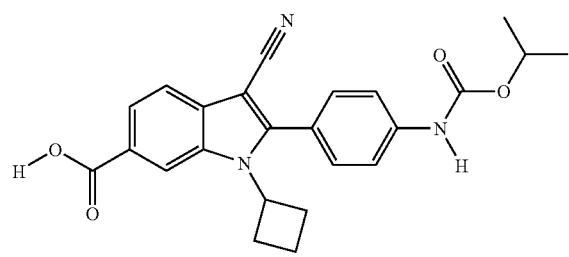
1467
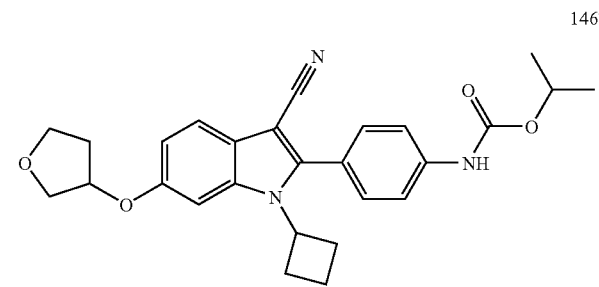
1468
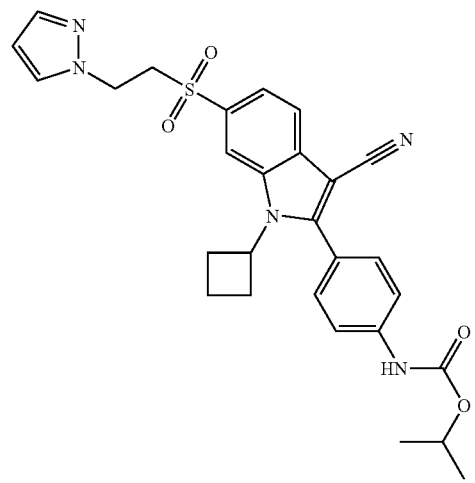
1469
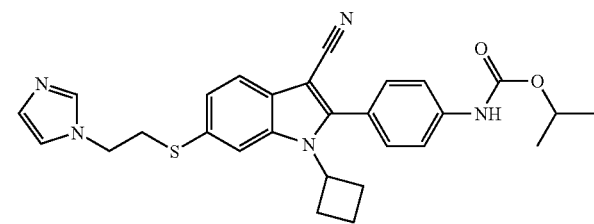
1470
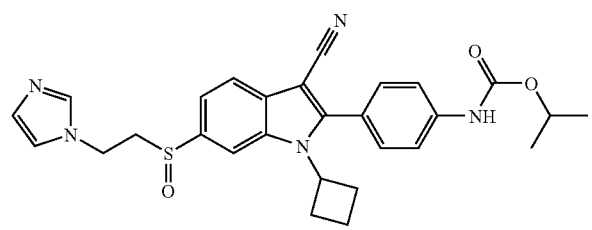
1471
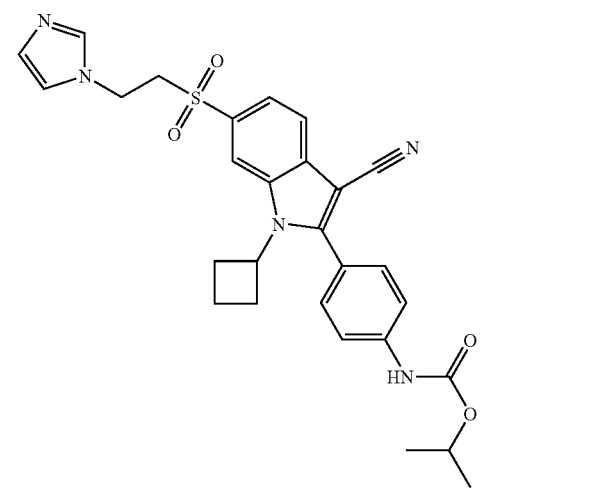

-continued
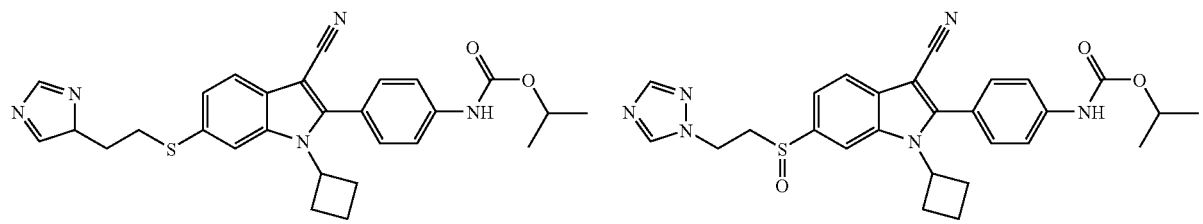
1472
1473
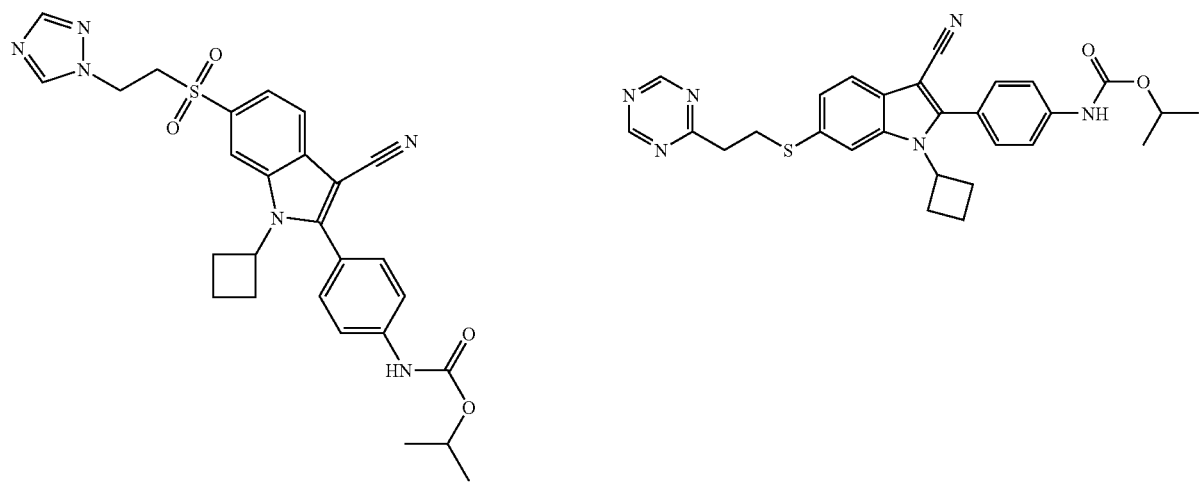
1474
1475
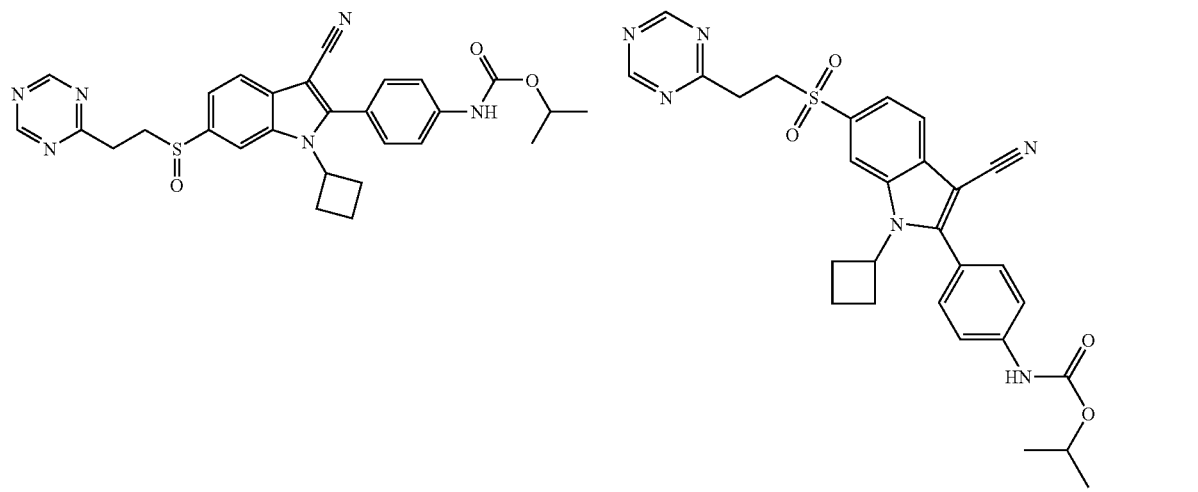
1476
1477
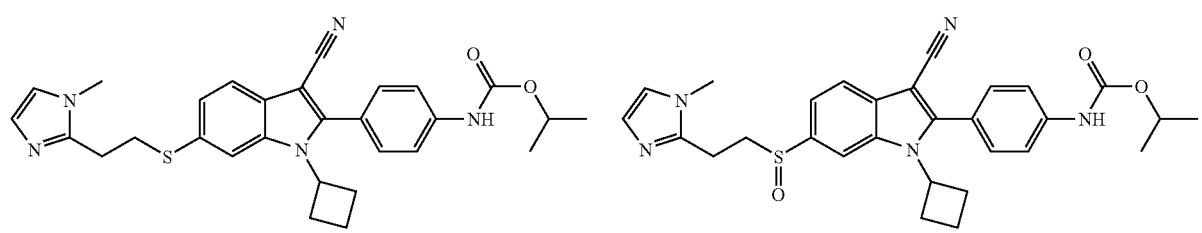
1478
1479

-continued
1480
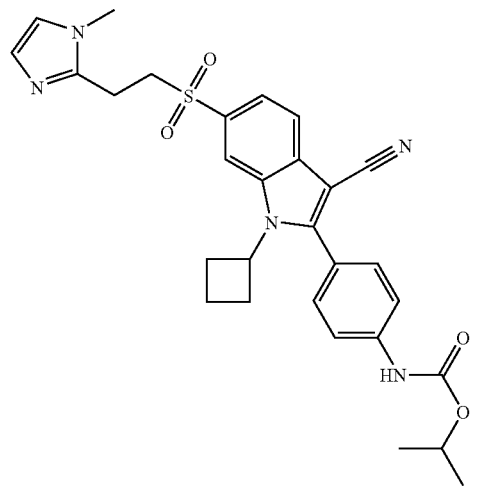
1481
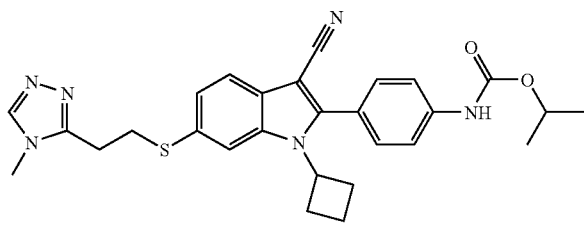
1482
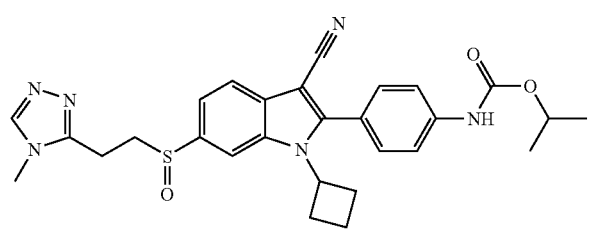
1483
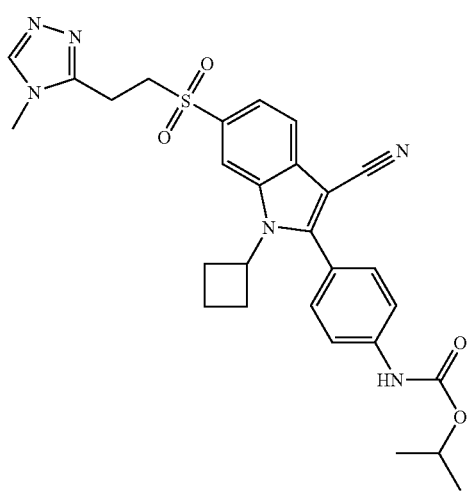
1485
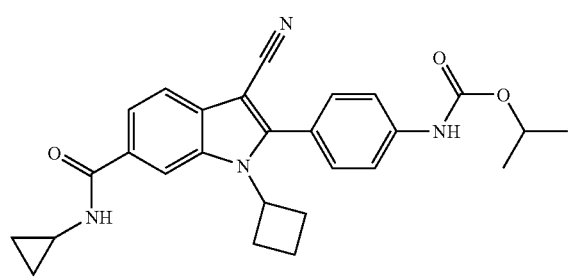
1486
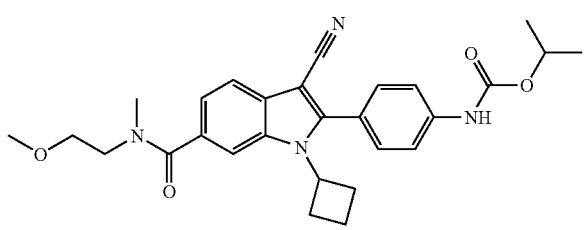
1487
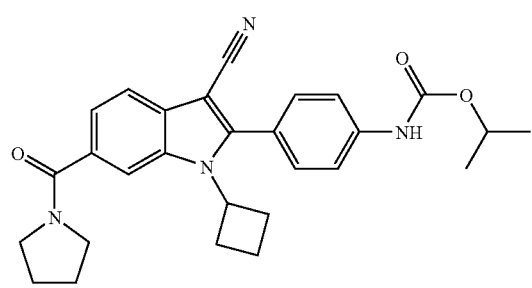
1488
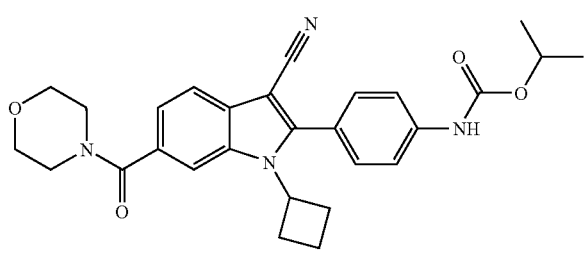

-continued
1489
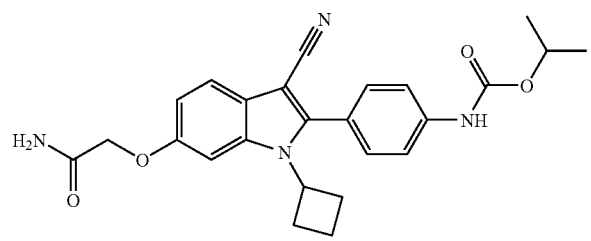
1490
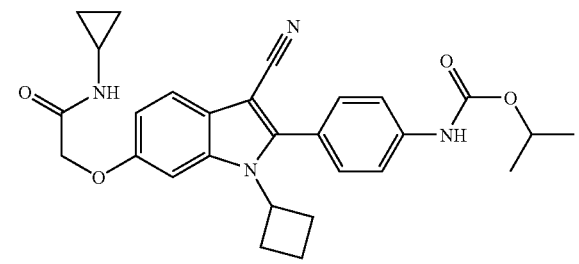
1498
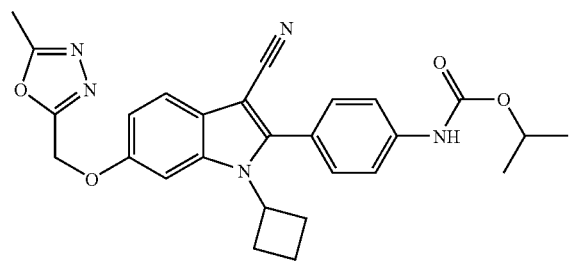
1499
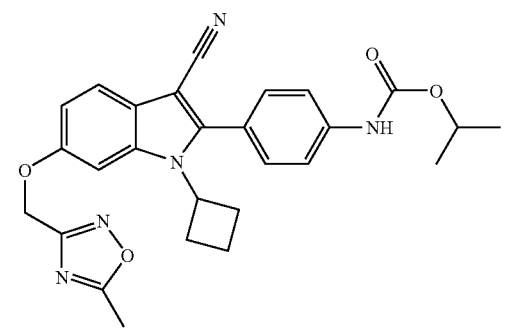
1500
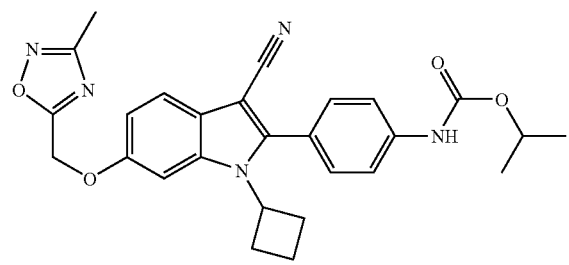
1501
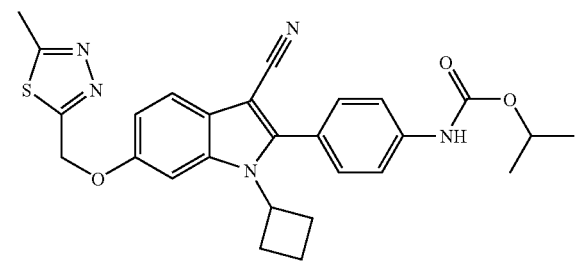
1502
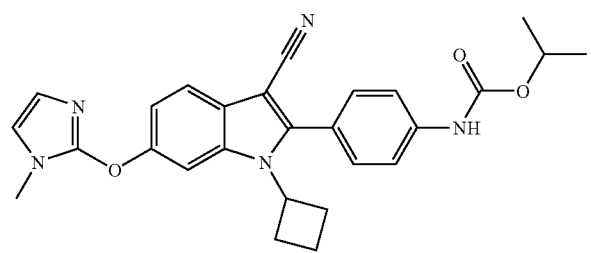
1503
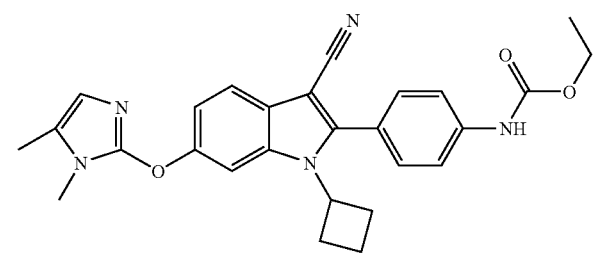
1504
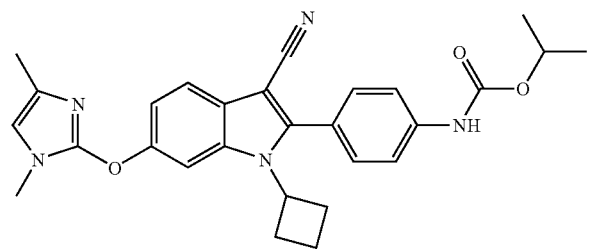
1505
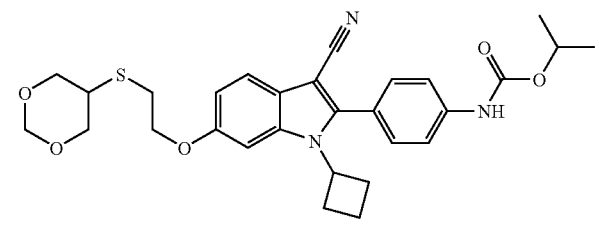

-continued
| 1508 | 1509 |
|---|---|
| 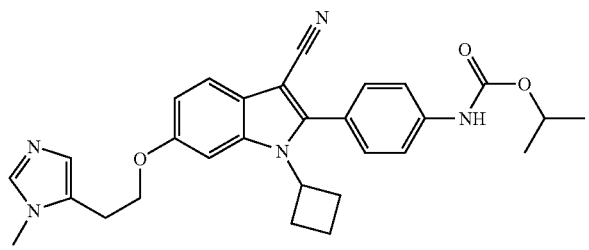 | 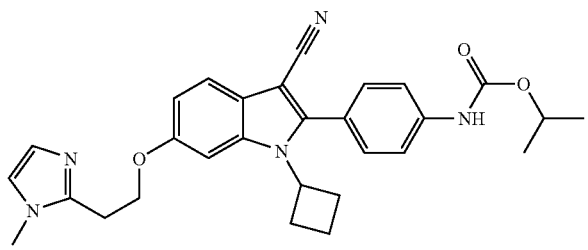 |
| 1515 | 1516 |
| 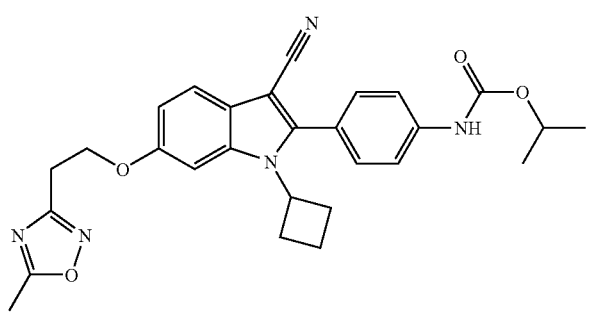 | 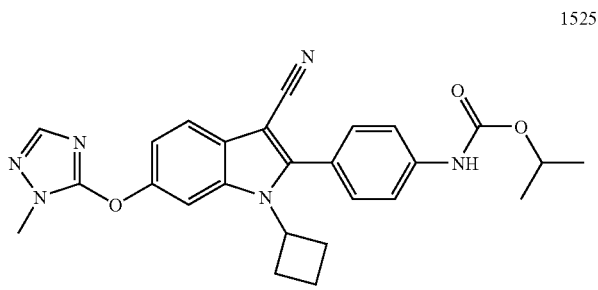 |
| 1524 | 1525 |
| 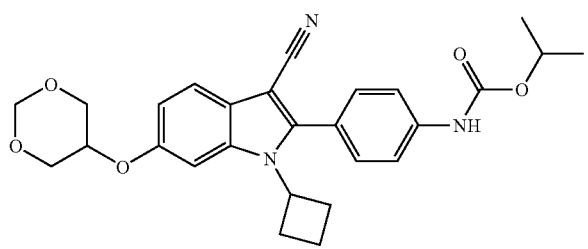 | 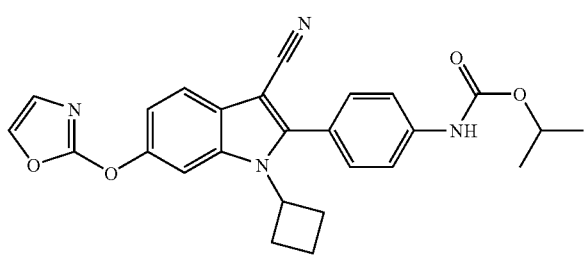 |
| 1526 | 1527 |
| 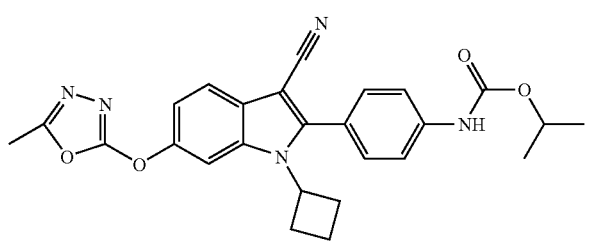 | 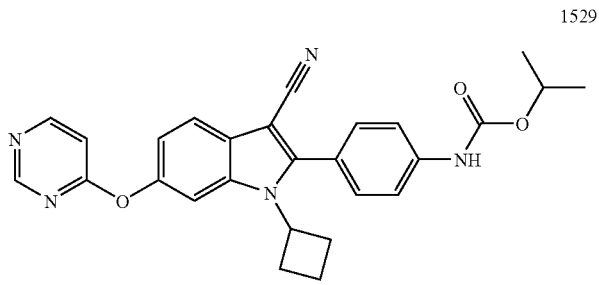 |
| 1528 | 1529 |
| 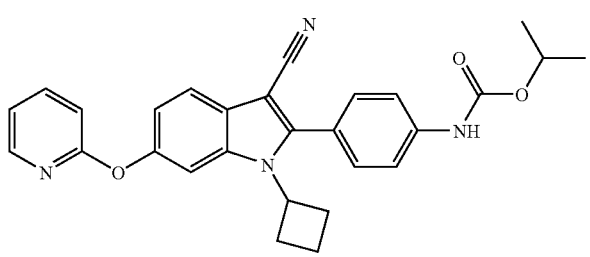 | |

-continued
1530
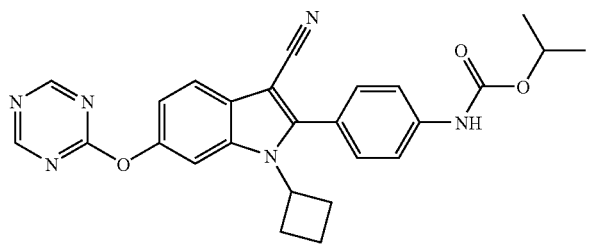
1531
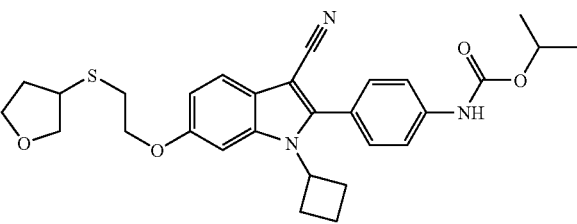
1532
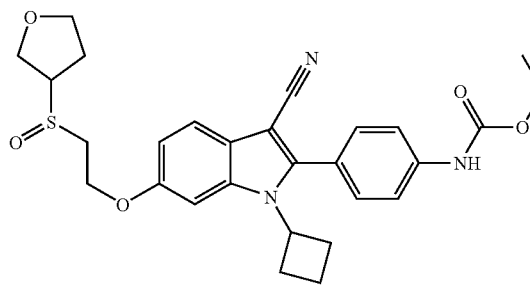
1533
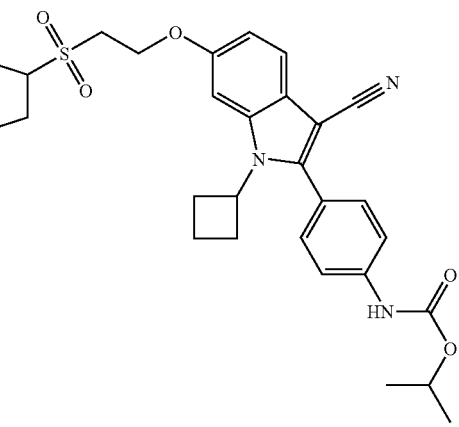
1534
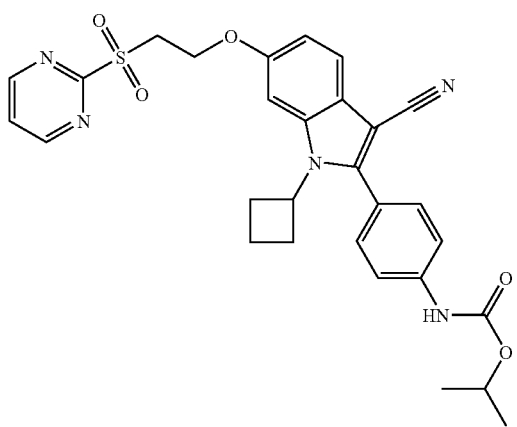
1535
1536
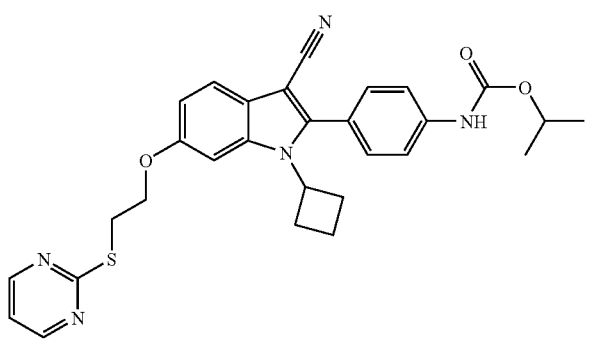
1537
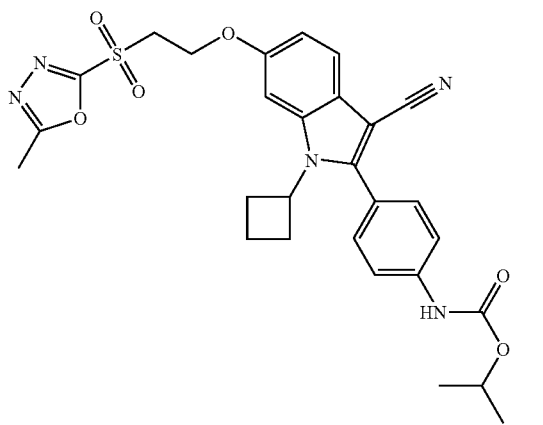

-continued
1538
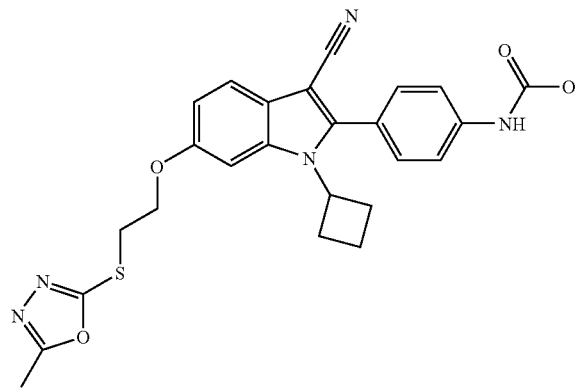
1539
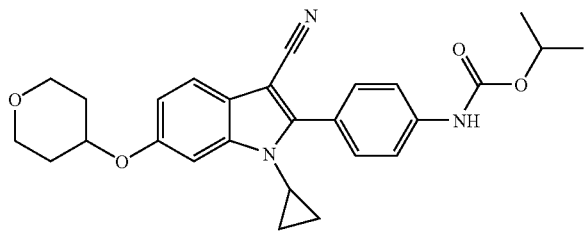
1543
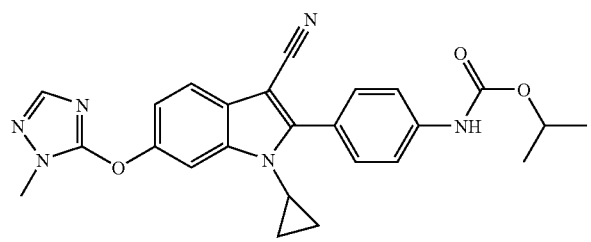
1544
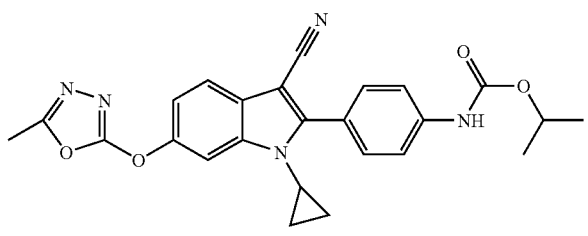
1545
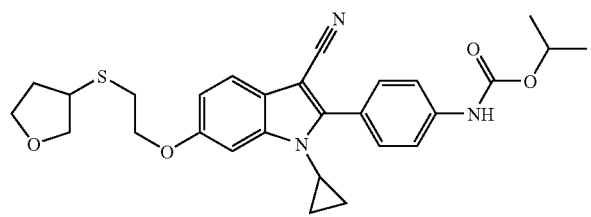
1546
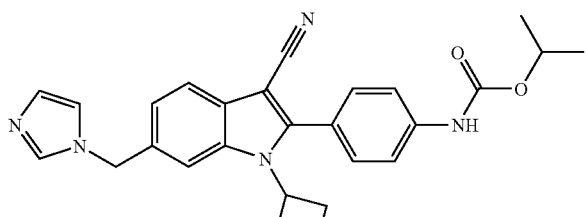
1547
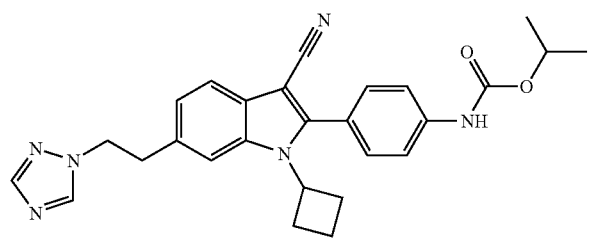
1548
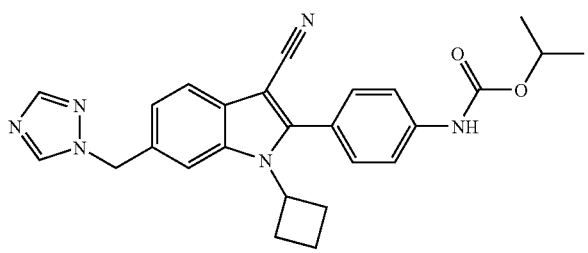
1549
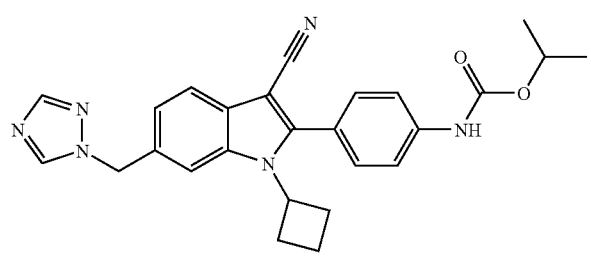
1550
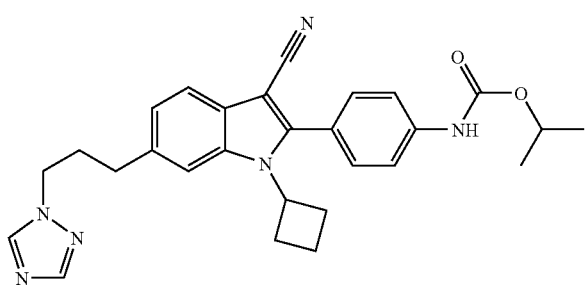

-continued
1551
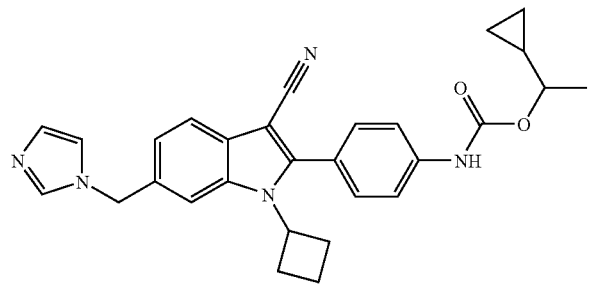
1552
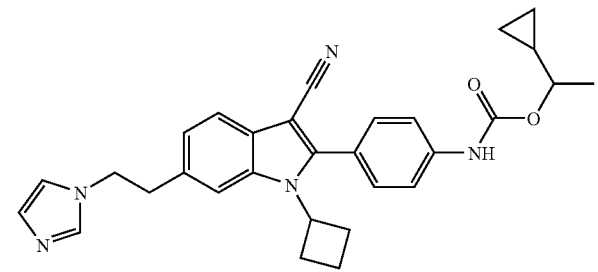
1553
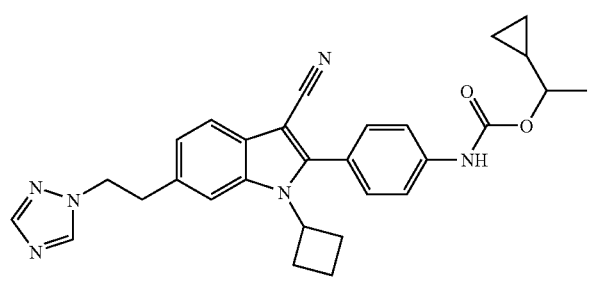
1554
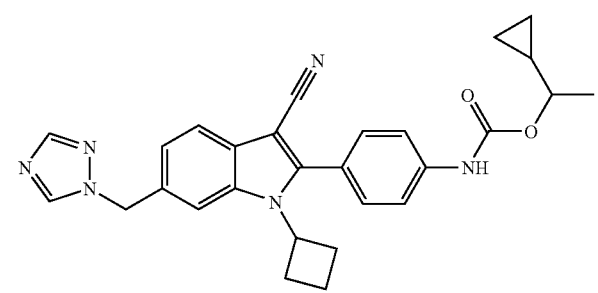
1555
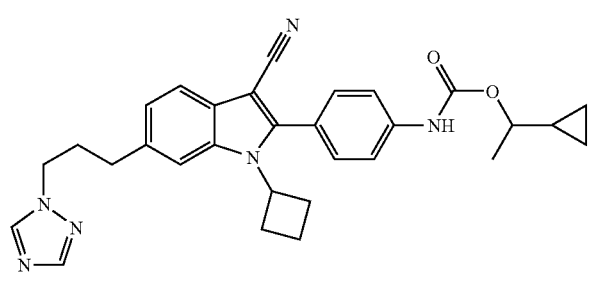
1568
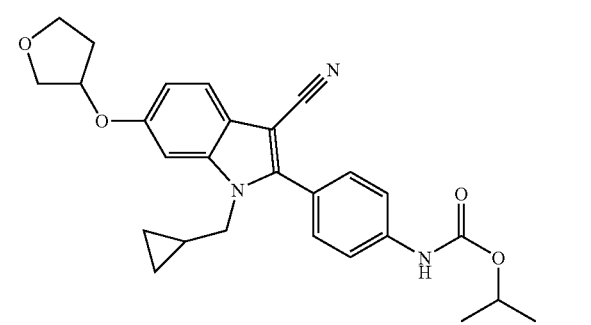
1569
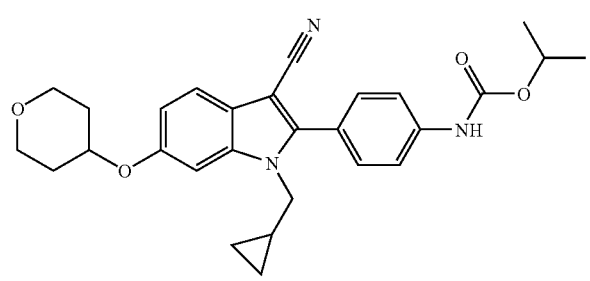
1570
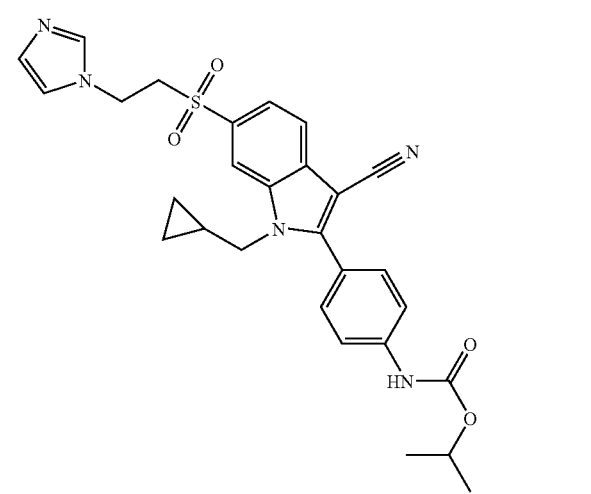

-continued
| 1571 | 1572 |
|---|---|
| 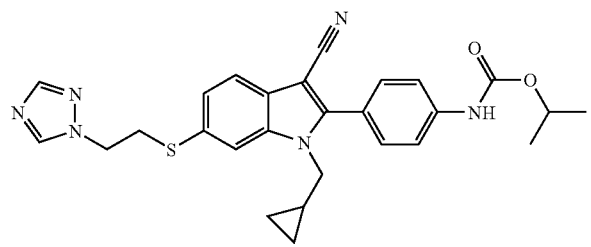 | 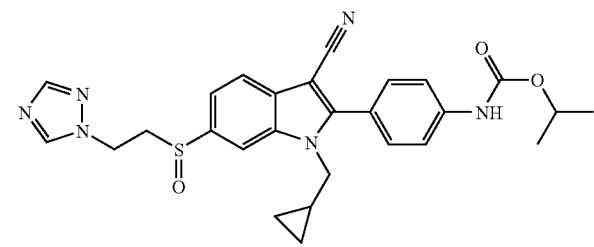 |
| 1573 | 1575 |
|---|---|
| 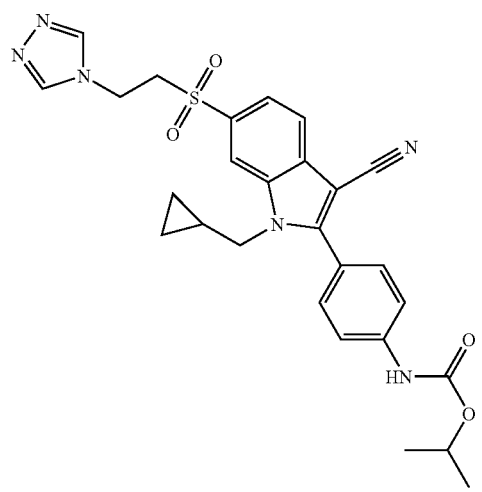 | 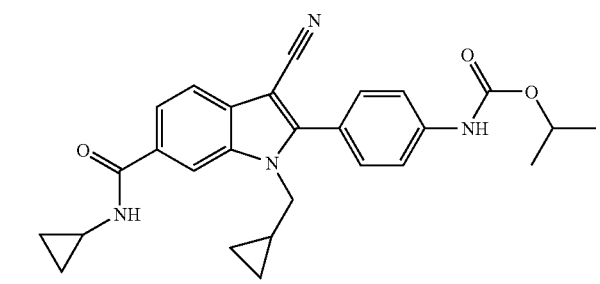 |
| 1580 | 1585 |
|---|---|
| 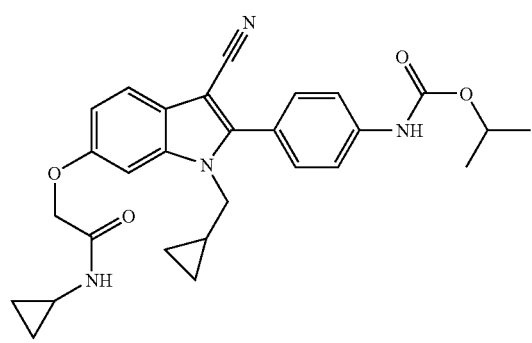 | 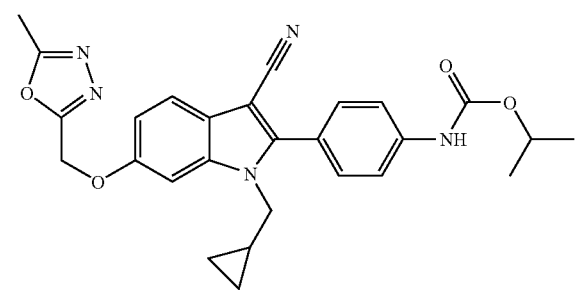 |
| 1586 | 1587 |
|---|---|
| 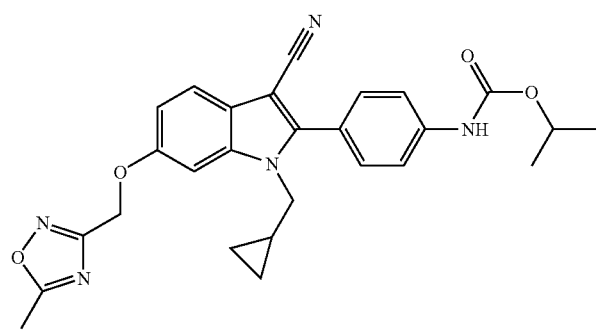 | 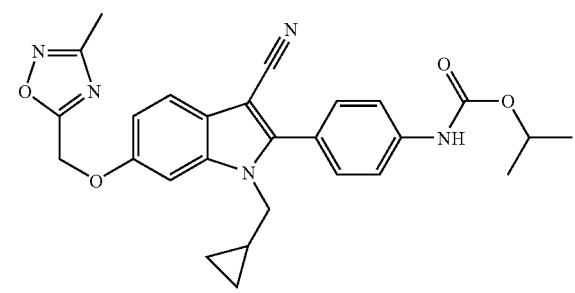 |

-continued
| 1588 | 1589 |
|---|---|
| 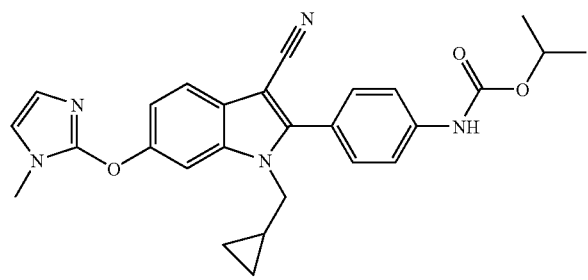 | 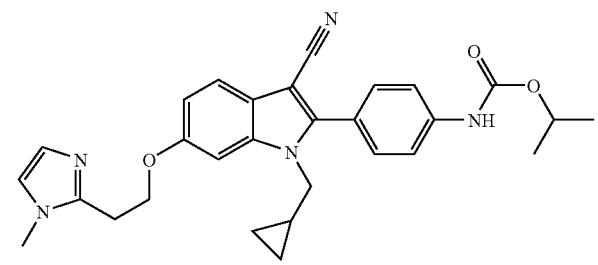 |
| 1594 | 1595 |
| 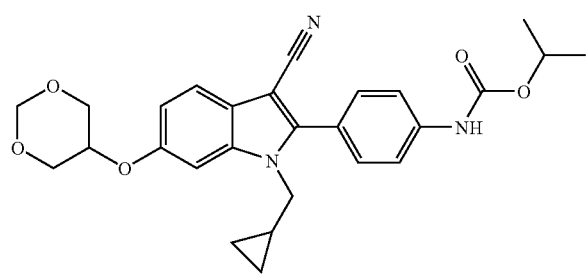 | 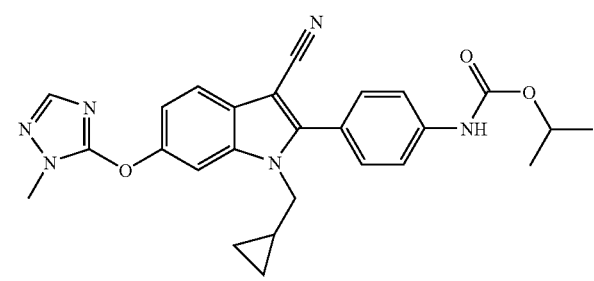 |
| 1596 | 1597 |
| 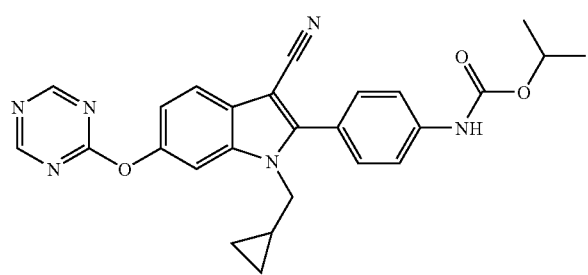 | 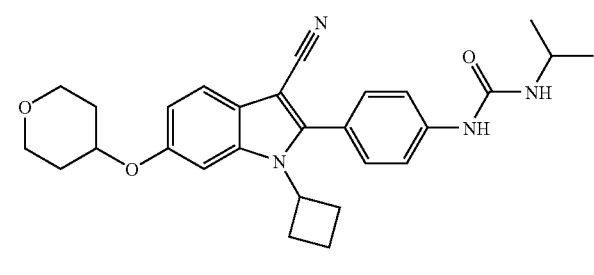 |
| 1598 | 1599 |
| 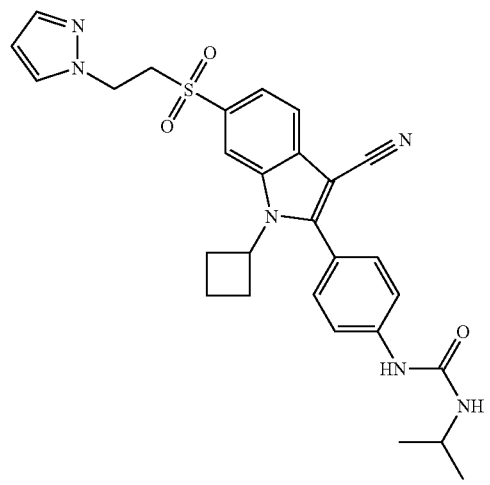 | 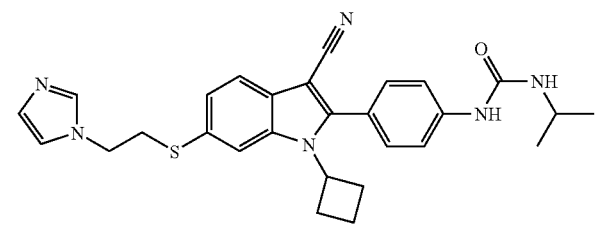 |

-continued
1600 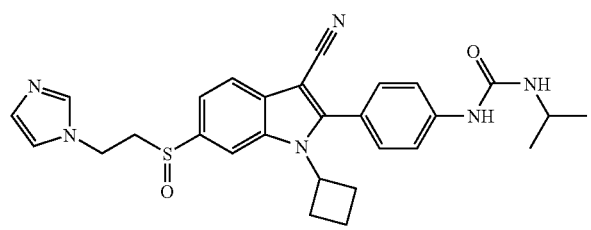
1601 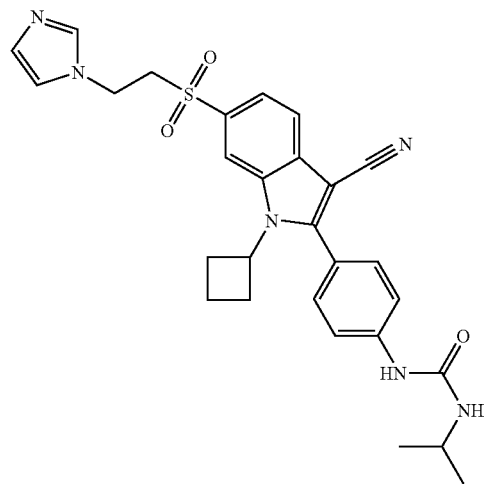
1602 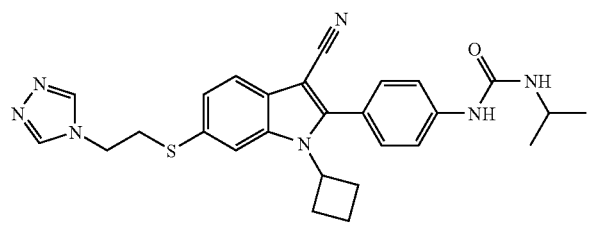
1603 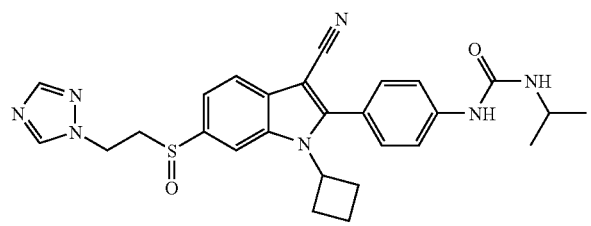
1604 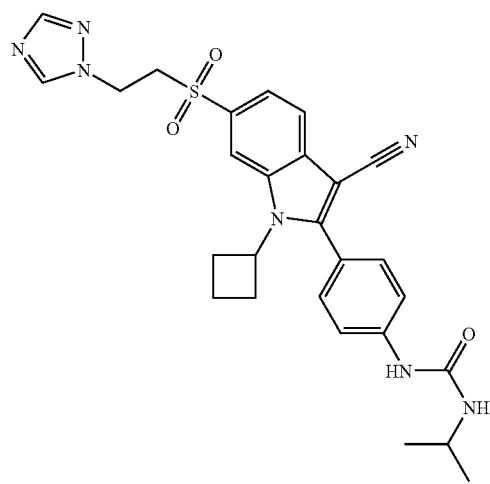
1605 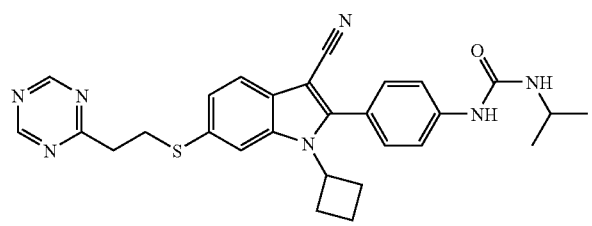

-continued
1606
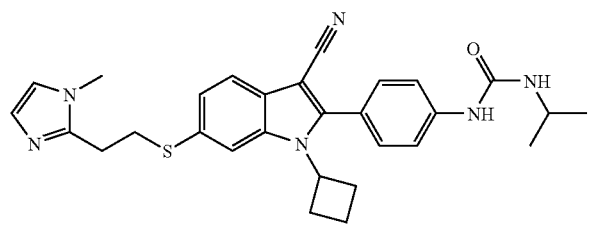
1607
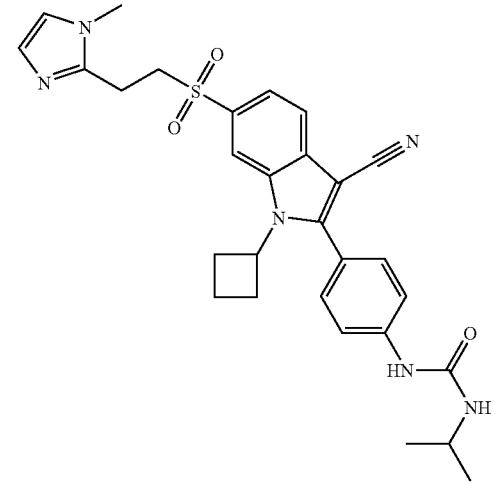
1608
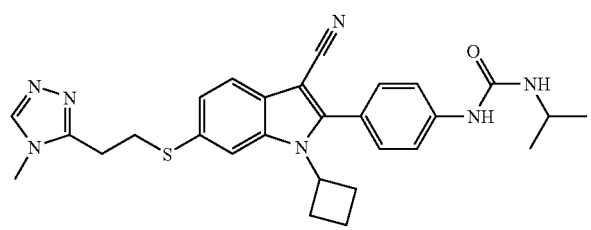
1609
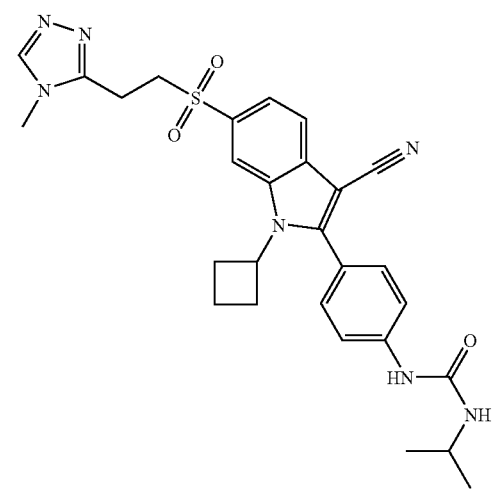
1611
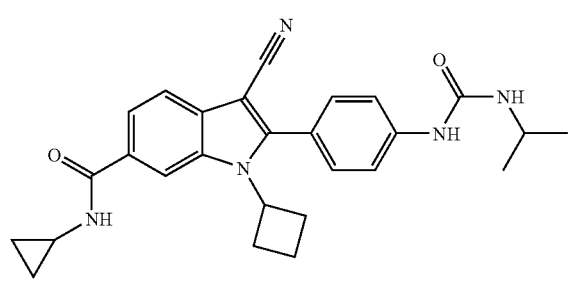
1612
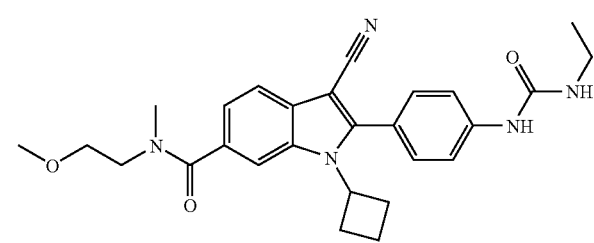
1613
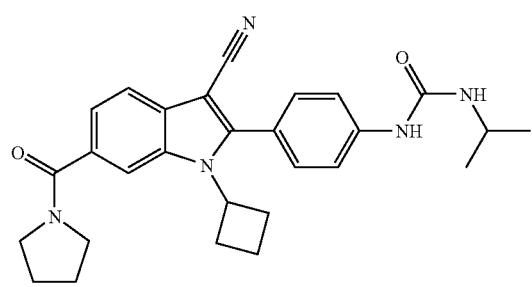
1614
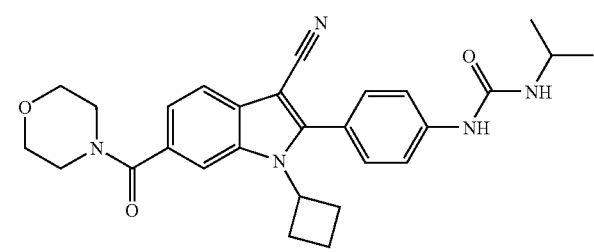

-continued
| 1615 | 1616 |
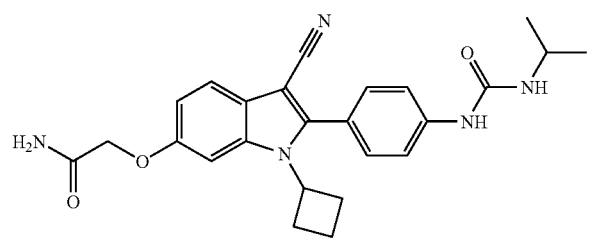
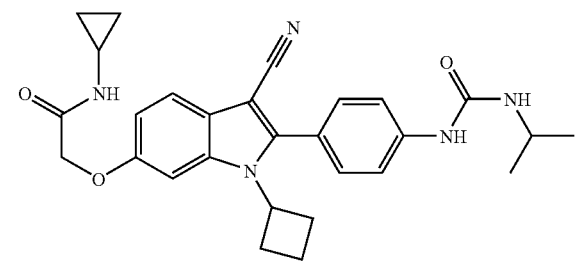
| 1624 | 1625 |
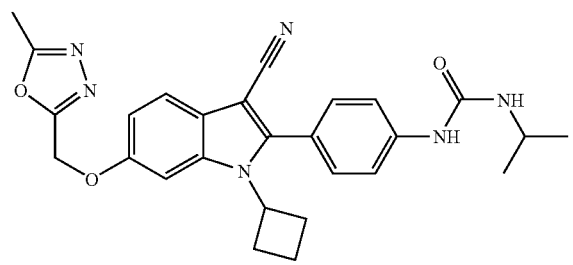
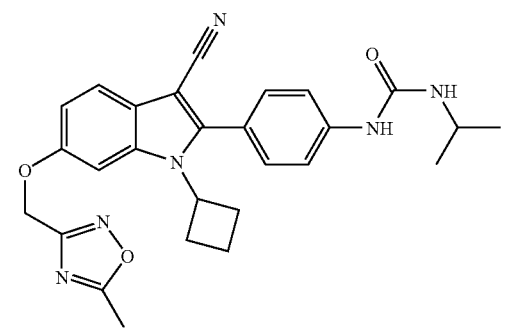
| 1626 | 1627 |
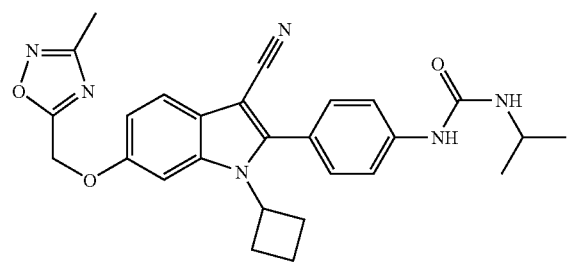
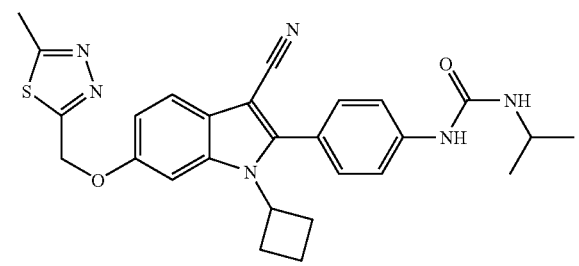
| 1628 | 1629 |
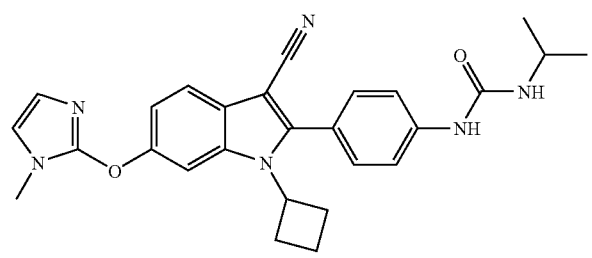
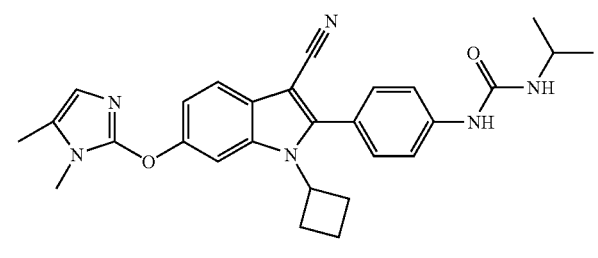
| 1630 | 1631 |
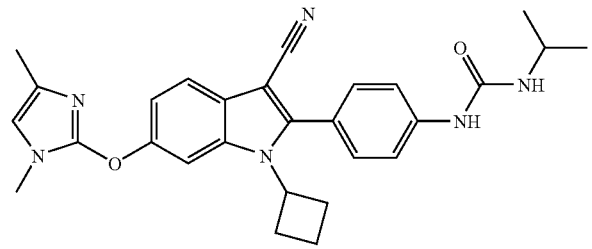
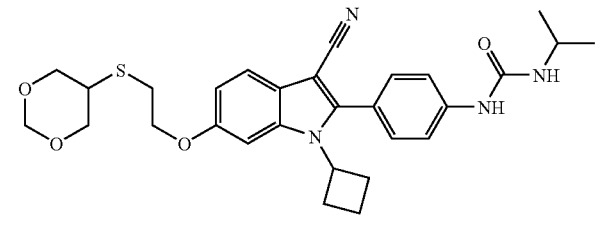

-continued
1634
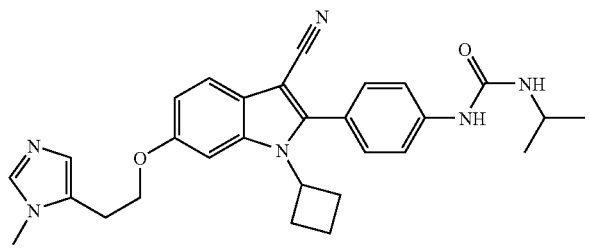
1635
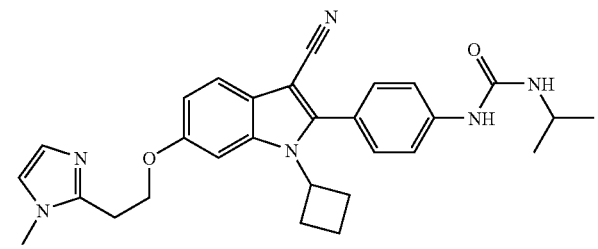
1641
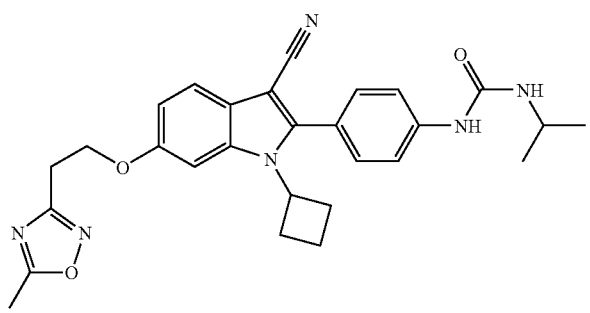
1642
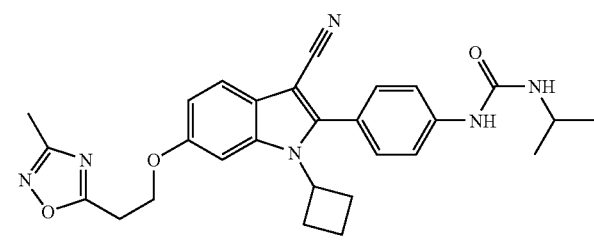
1650
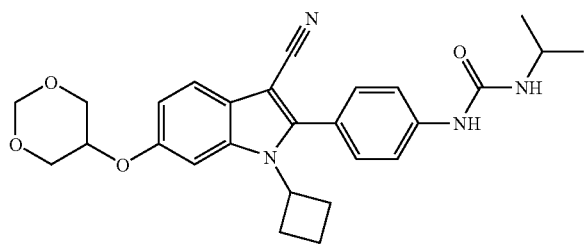
1651
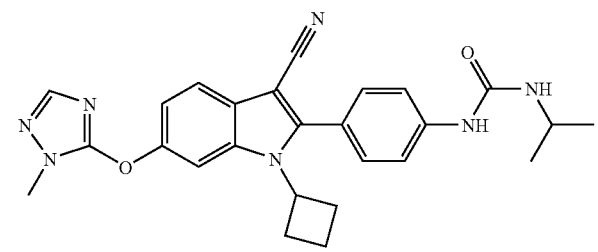
1652
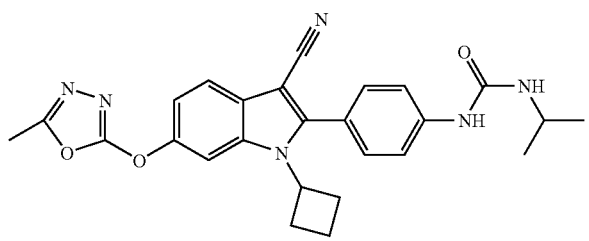
1669
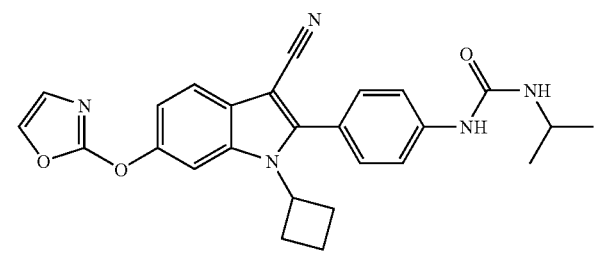
1670
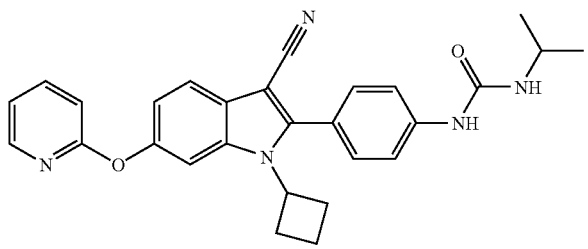
1671
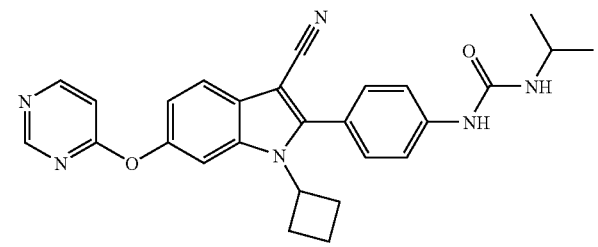

-continued
1672
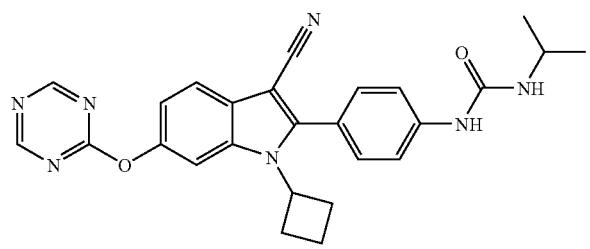
1673
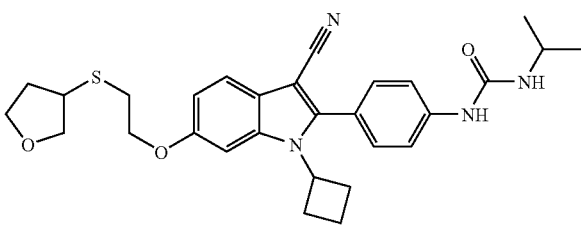
1674
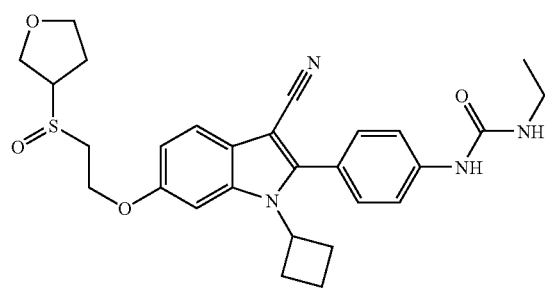
1675
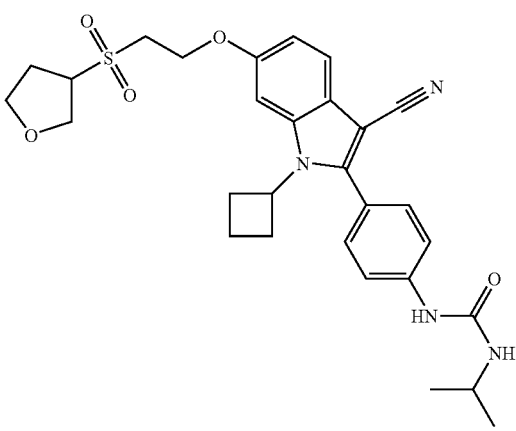
1676
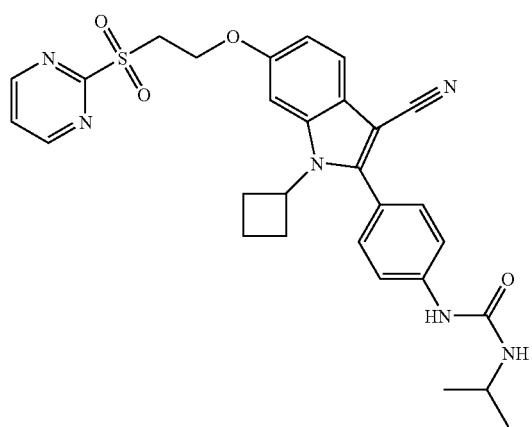
1677
1678
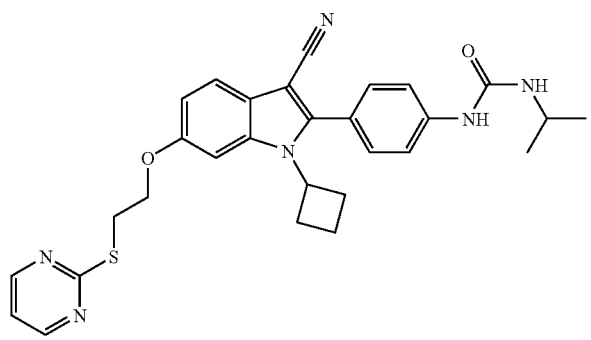
1679
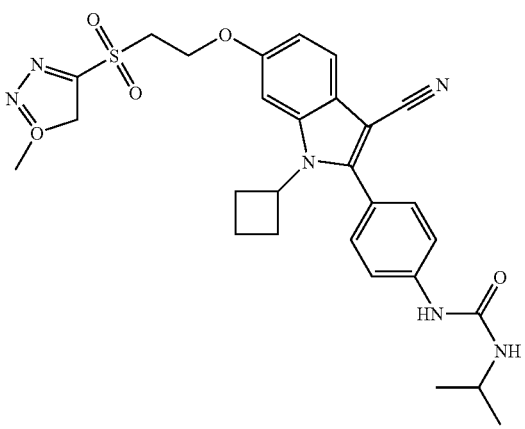

-continued
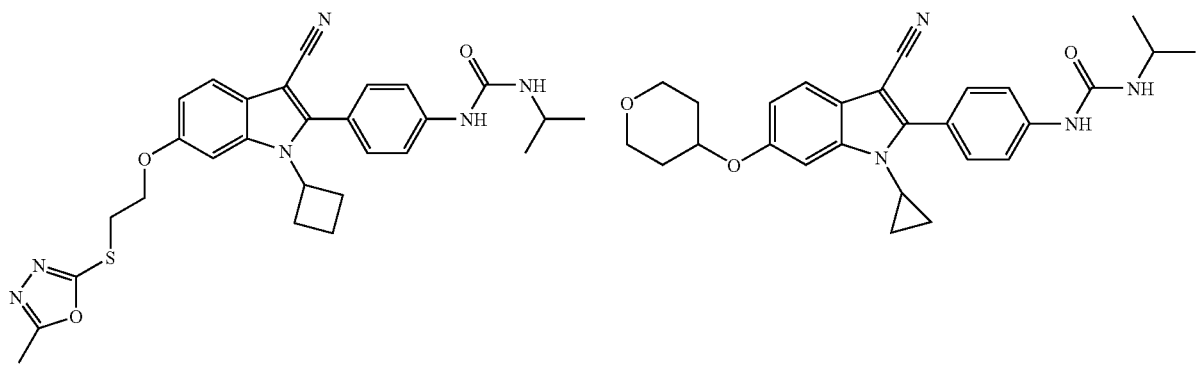
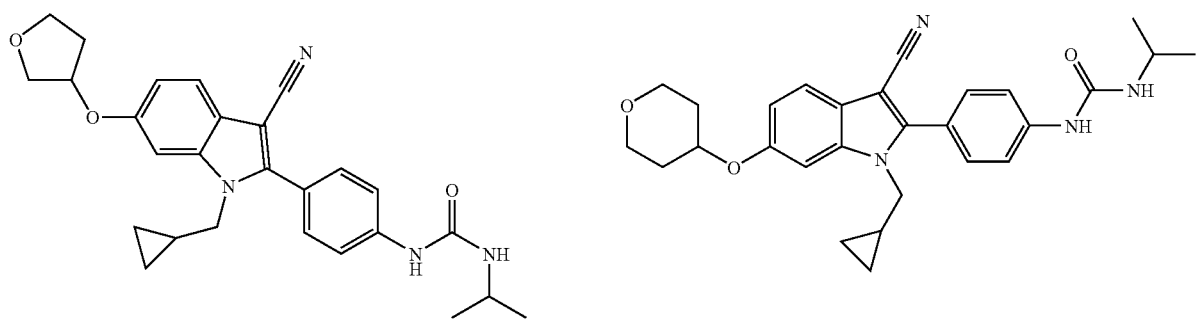
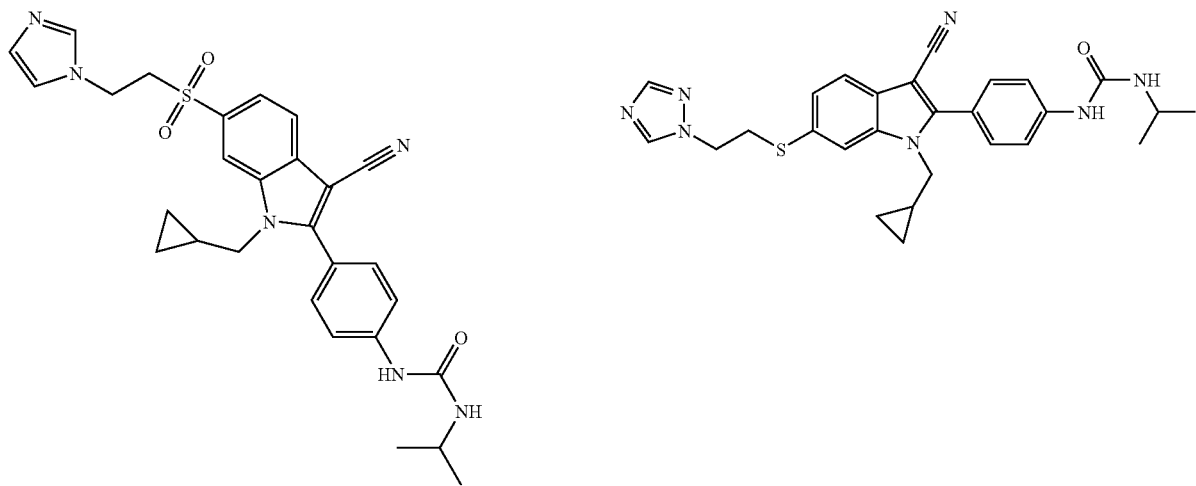
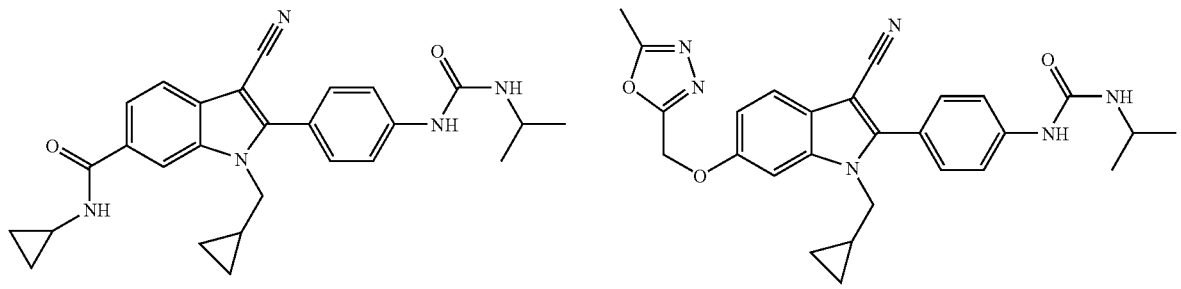

-continued
1692
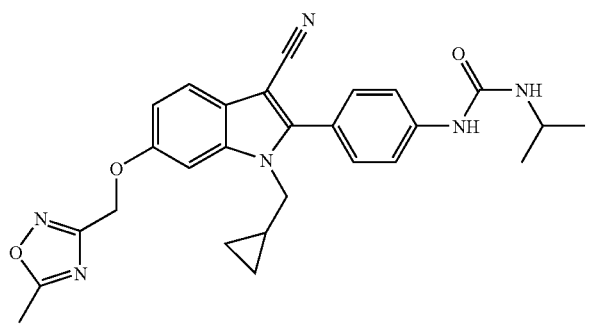
1693
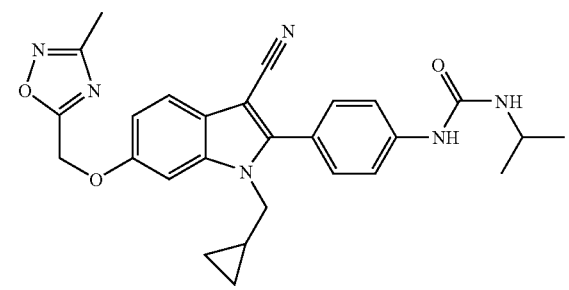
1694
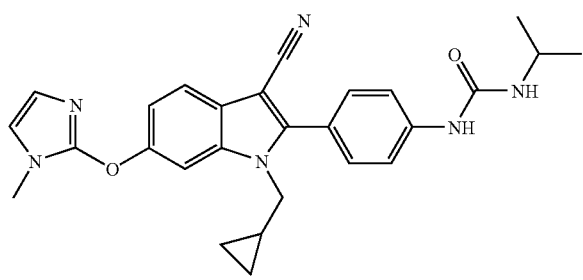
1742
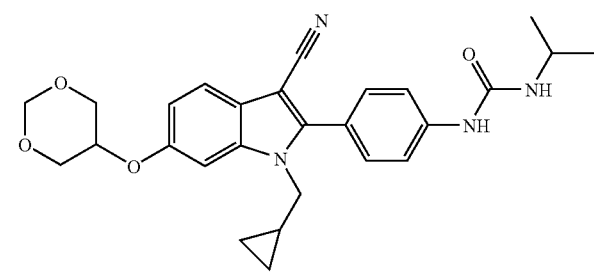
1743
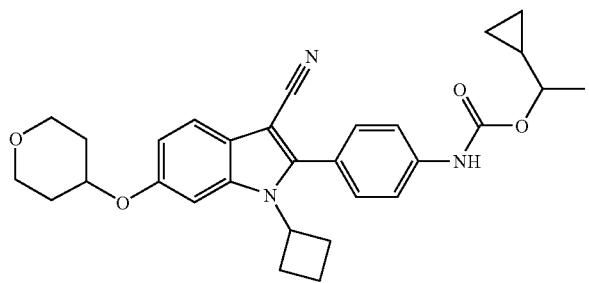
1744
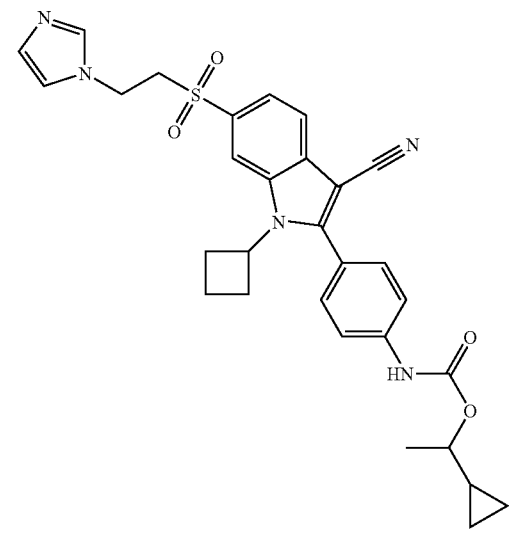
1745
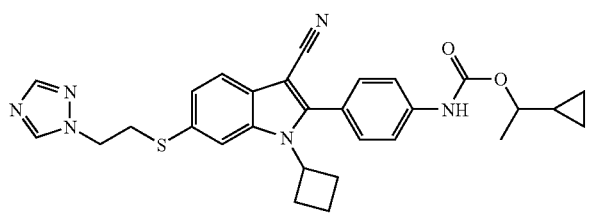
1746
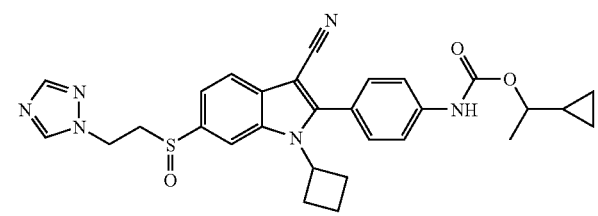

745 746
-continued
1747
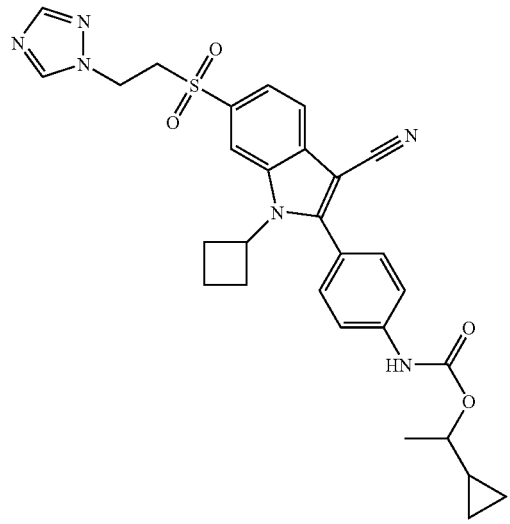
1748
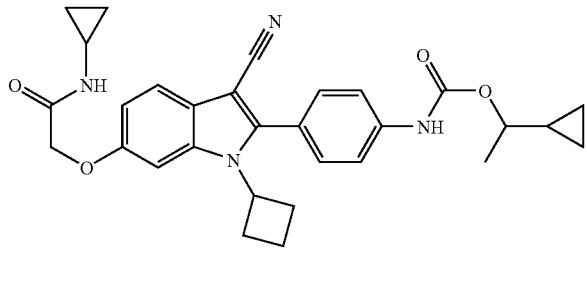
1753
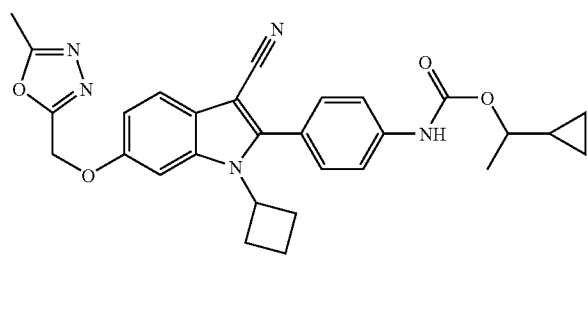
1754
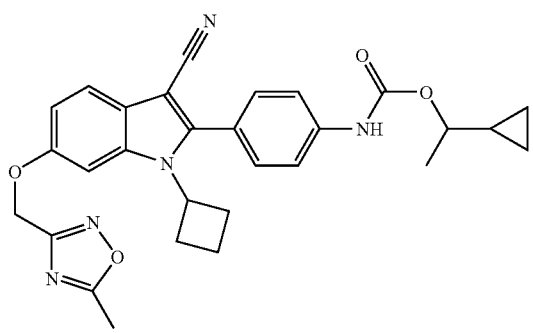
1755
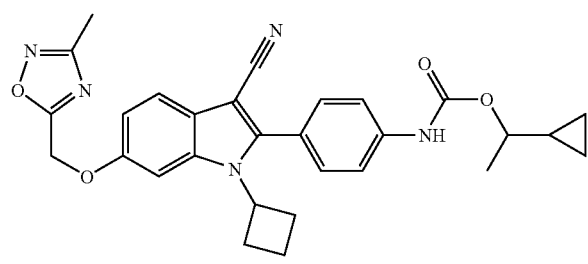
1756
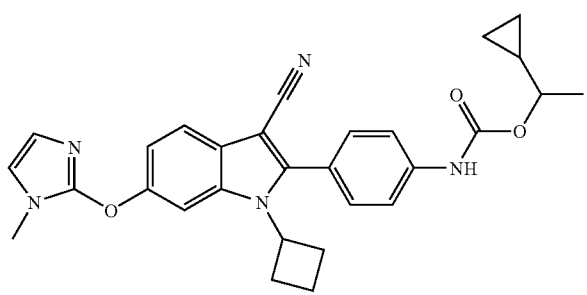
1757
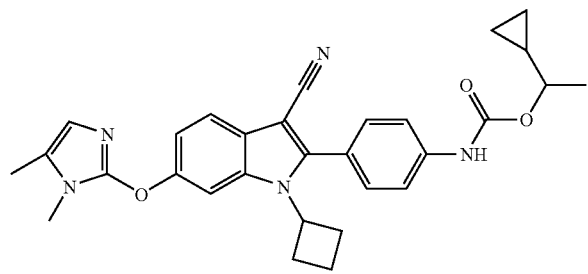
1758
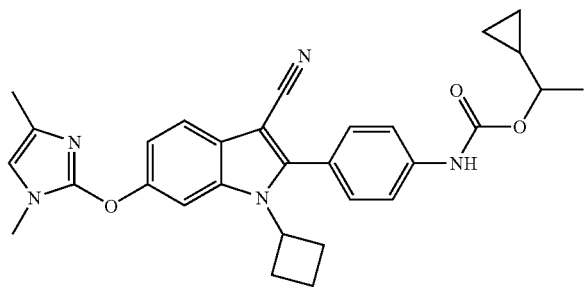

-continued
1760 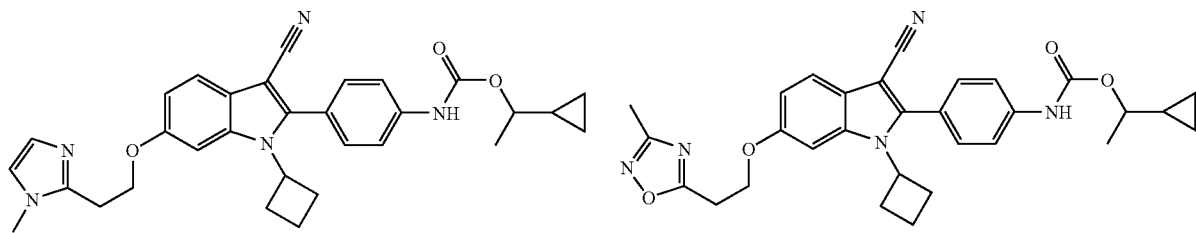 1764
1767 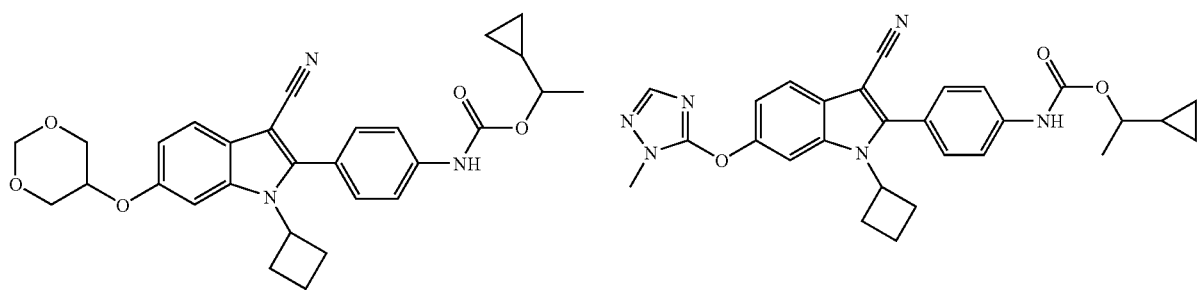 1768
1769 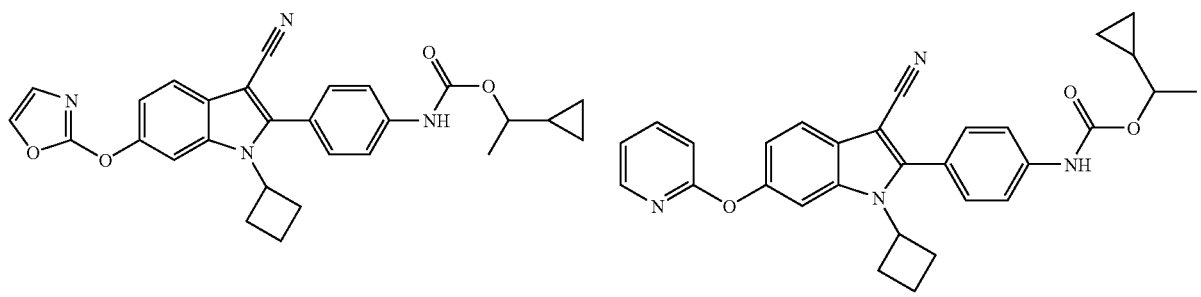 1770
1772 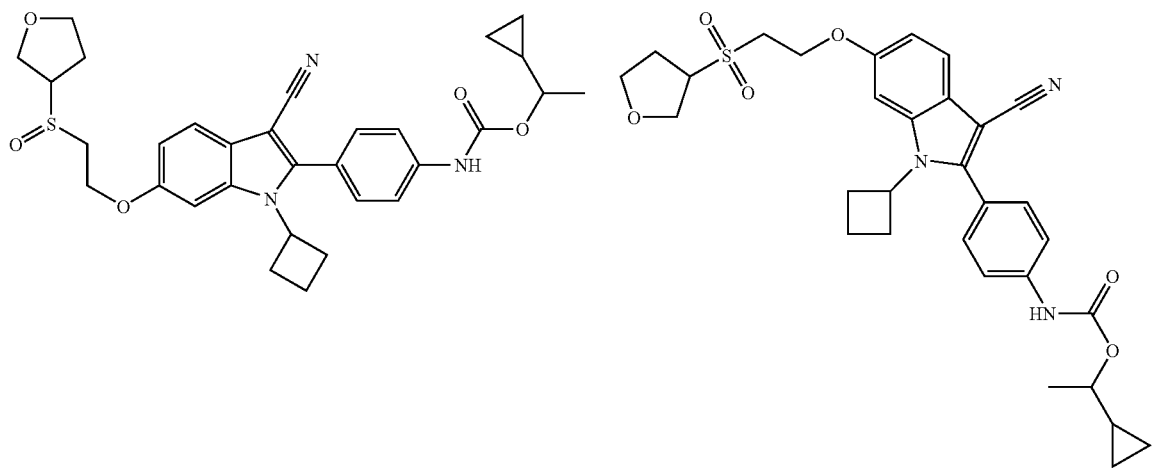 1773

-continued
1774
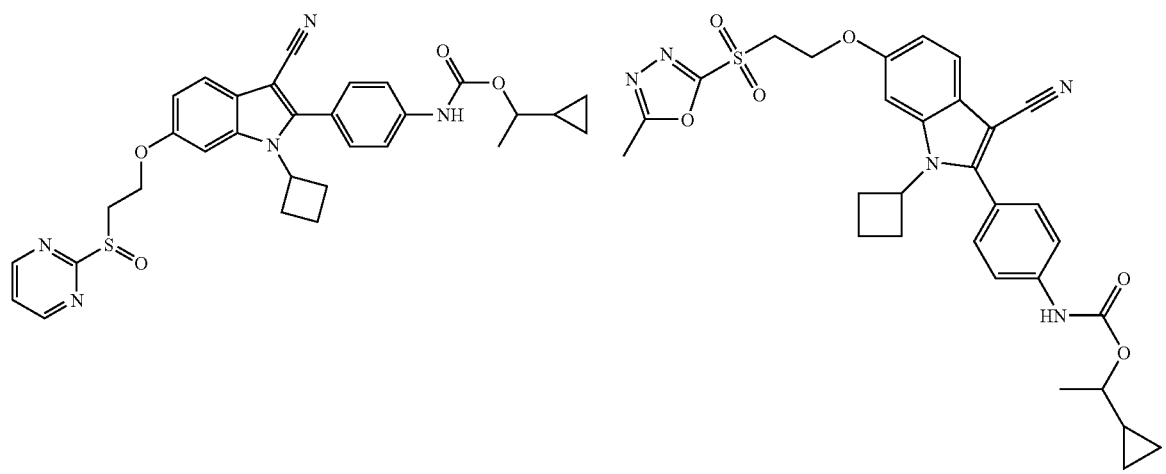
1775
1776
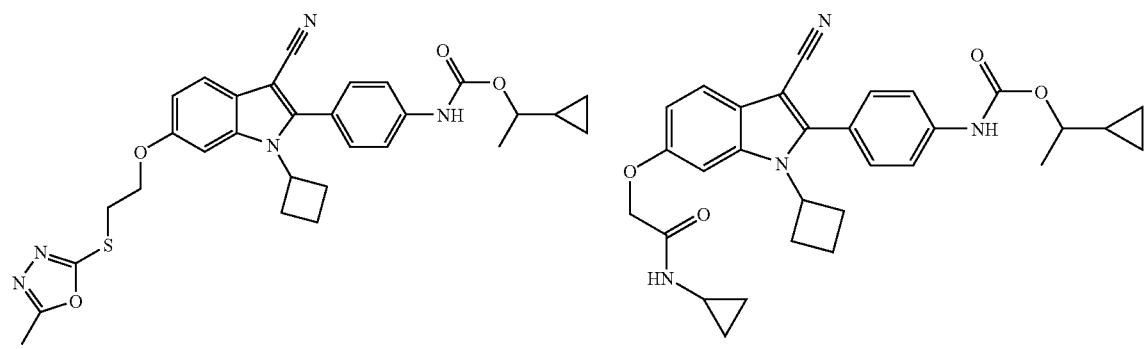
1777
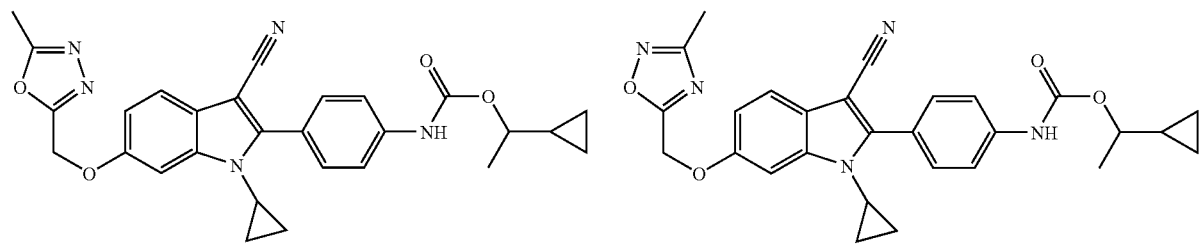
1780
1781
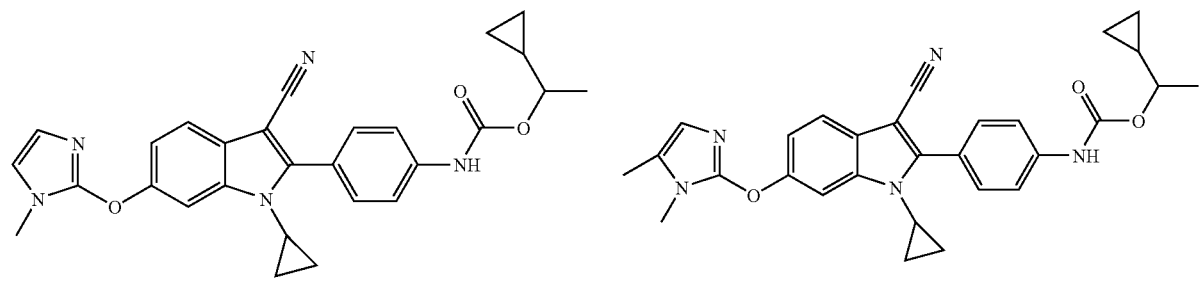
1782

-continued
1810
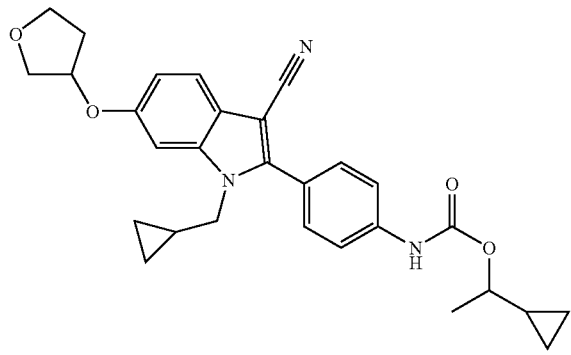
1811
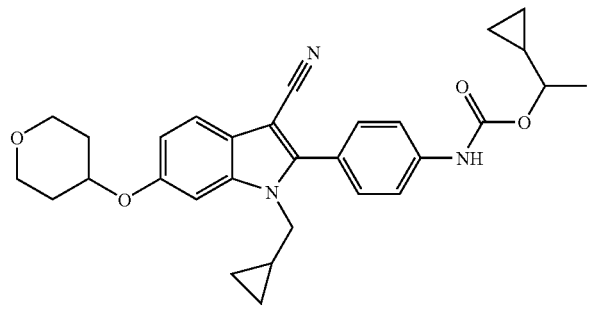
1814
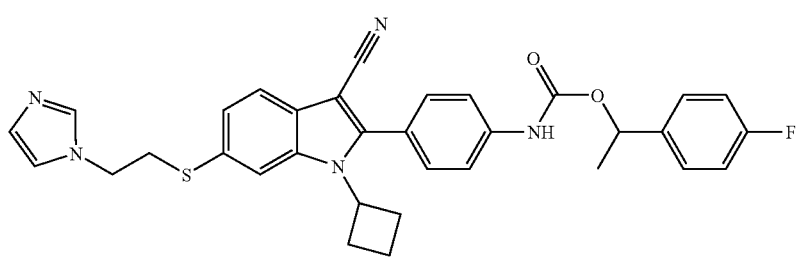
1815
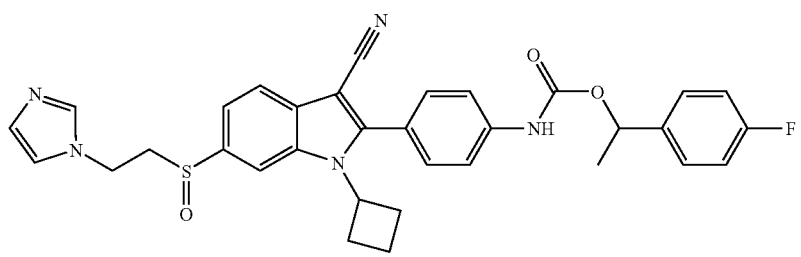
1864
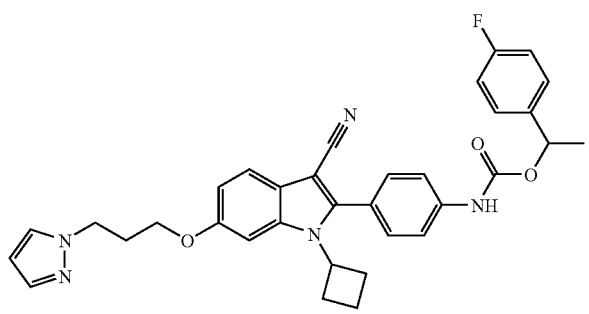
1865
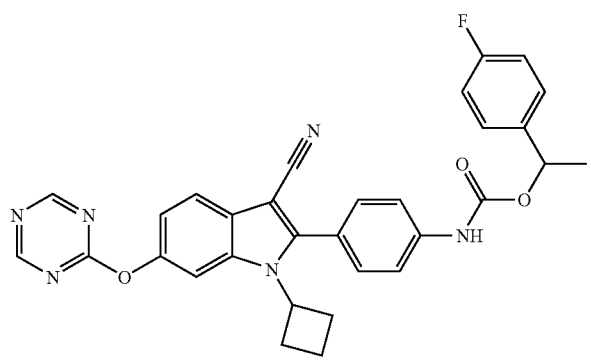
1866
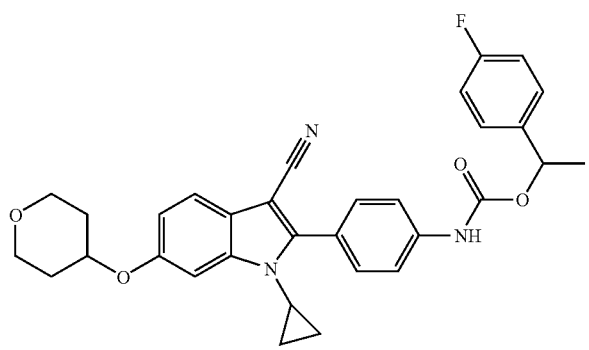
1867
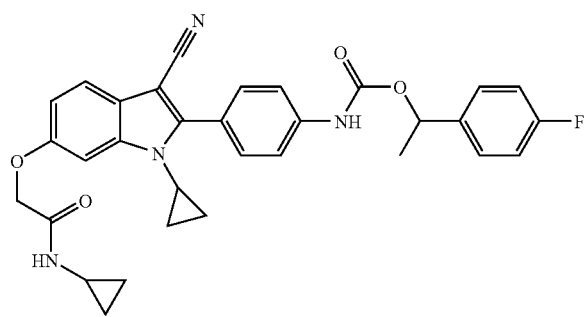

-continued
1868
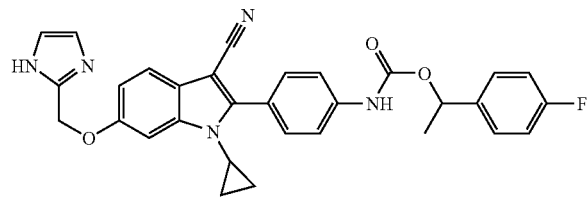
1869
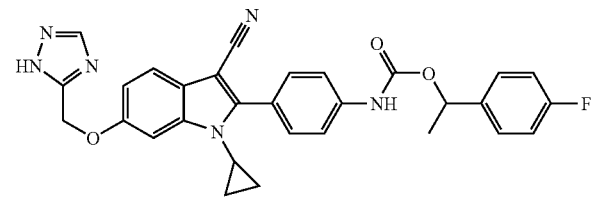
1870
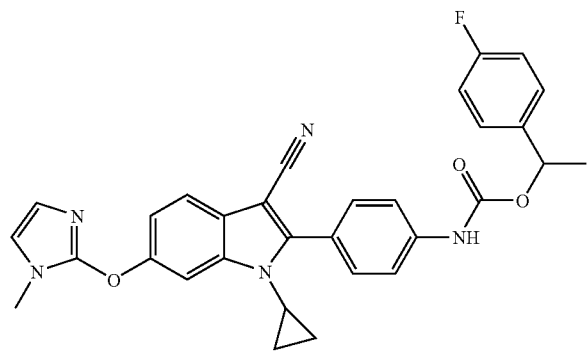
1871
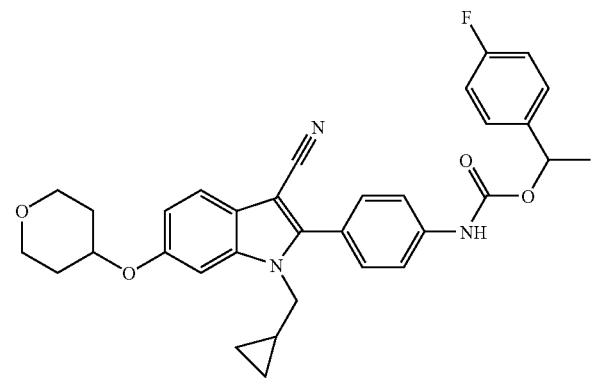
1880
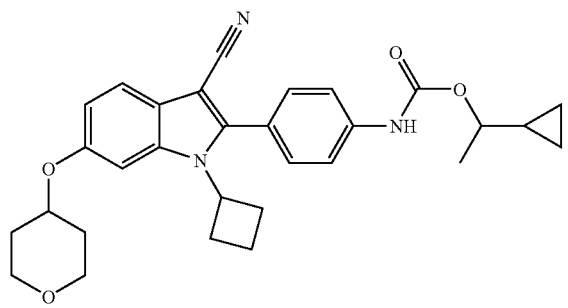
1917
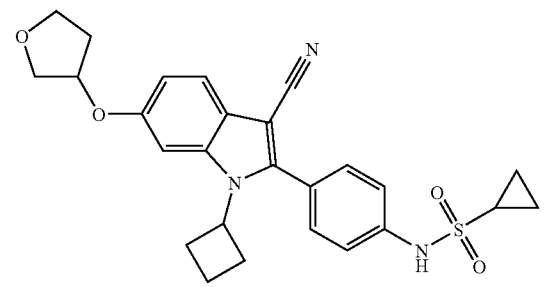
1918
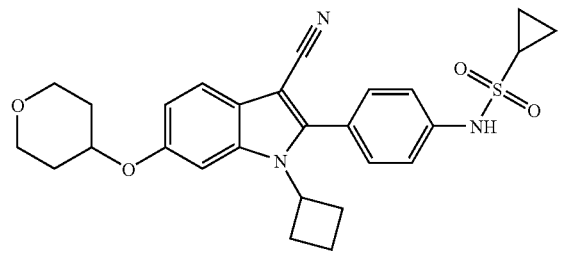
1920
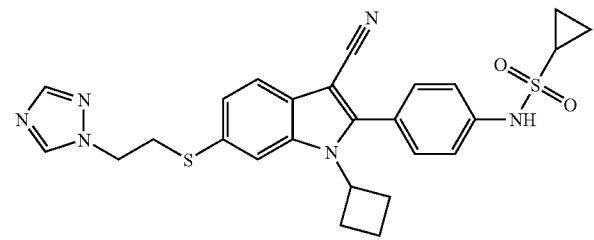

-continued
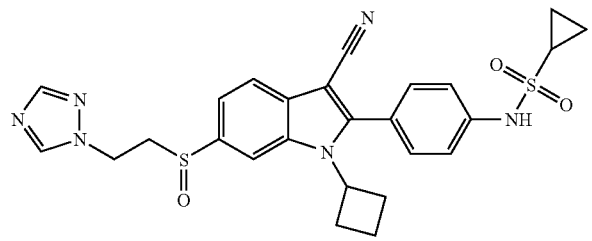
1922
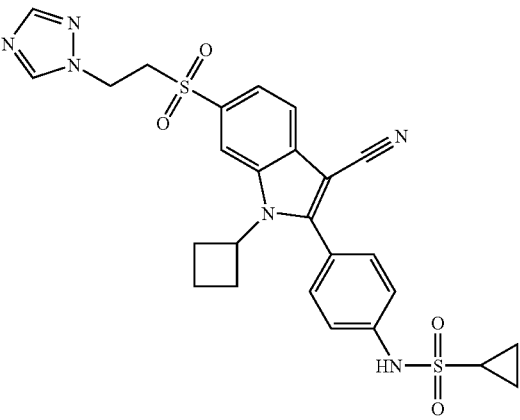
1923
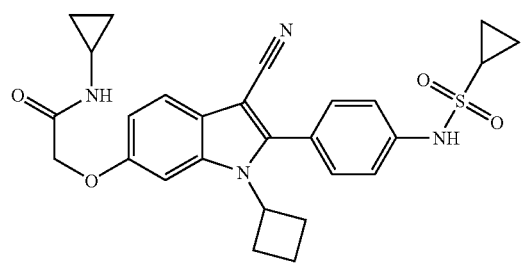
1924
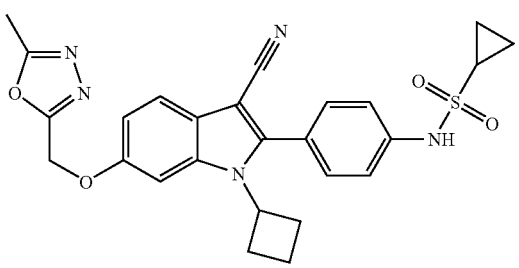
1970
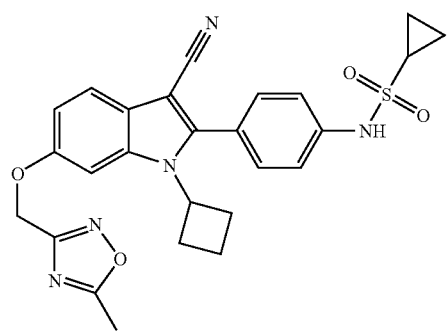
1971
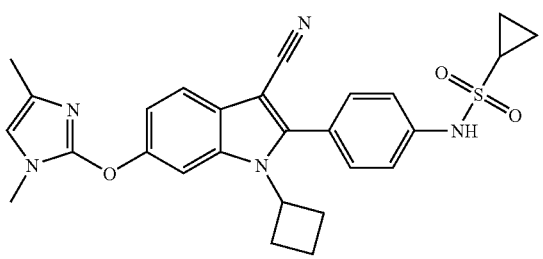
1972
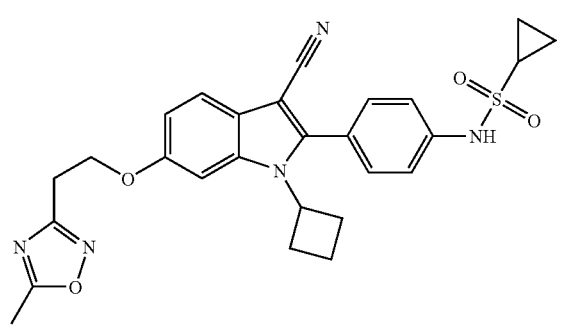
1973
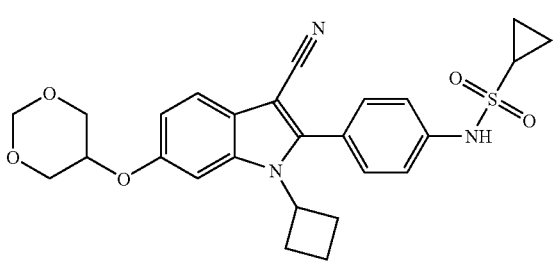
1974

-continued
1975
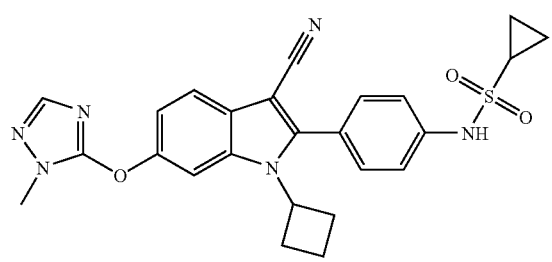
1976
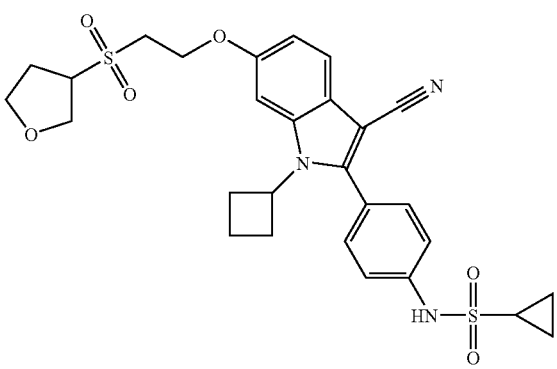
1977
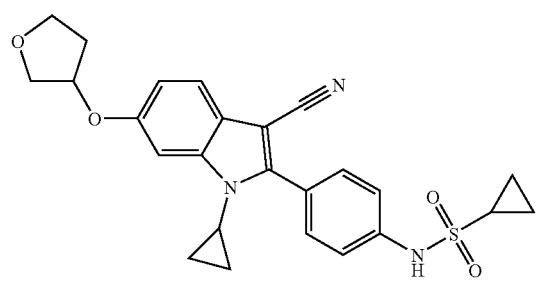
1978
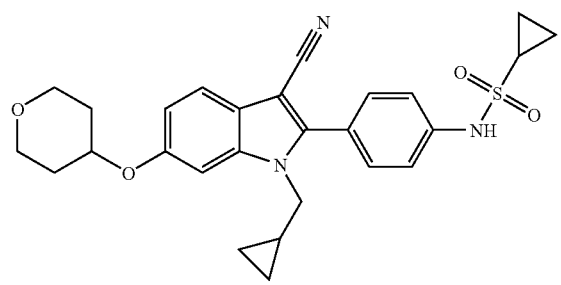
1979
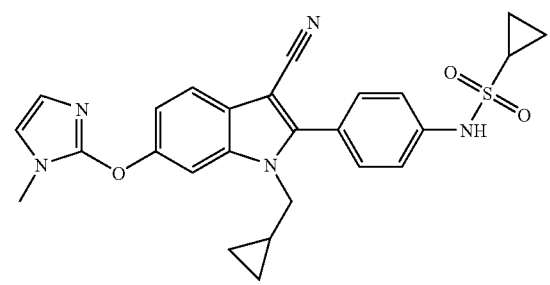
2010
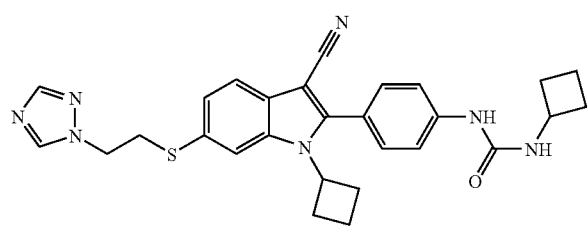
2011
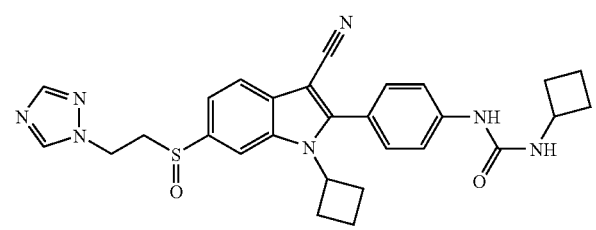
2012

-continued
2013
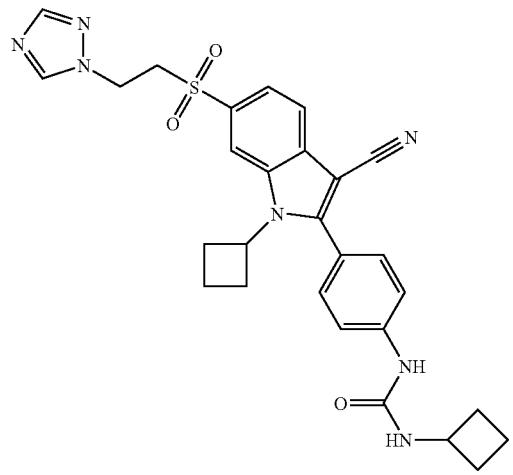
2014
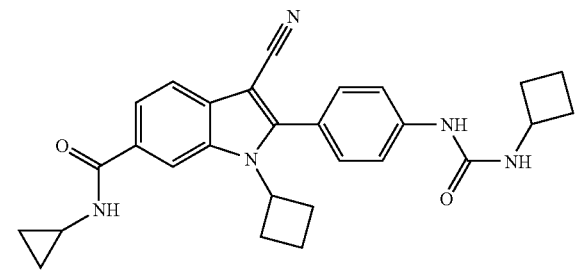
2018
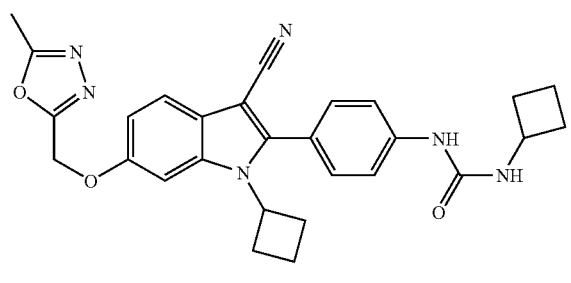
2019
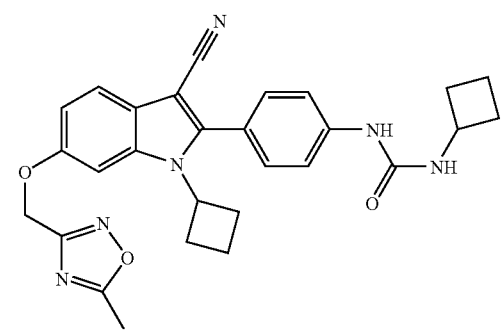
2020
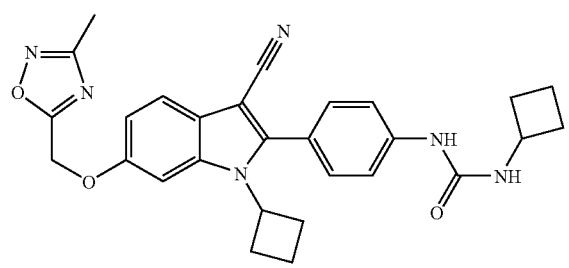
2021
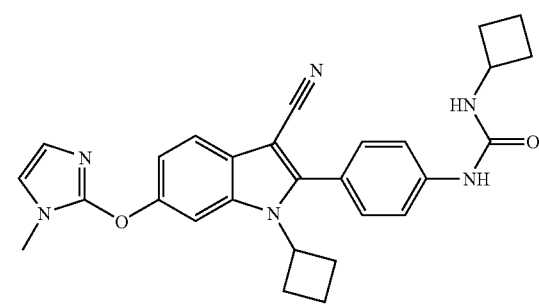
2026
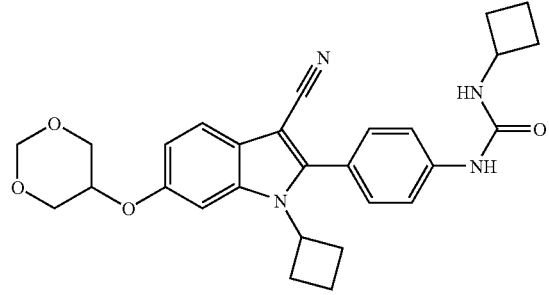
2025
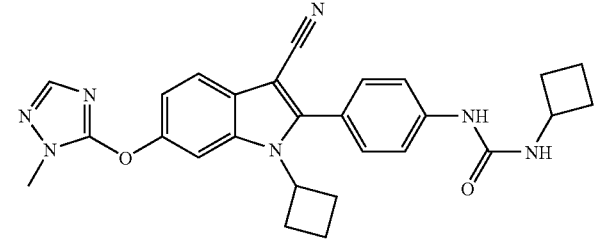

-continued
| 2027 | 2028 |
|---|---|
| 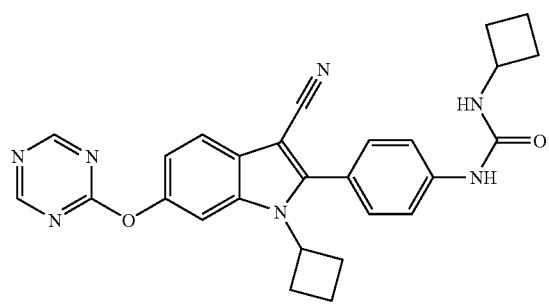 | 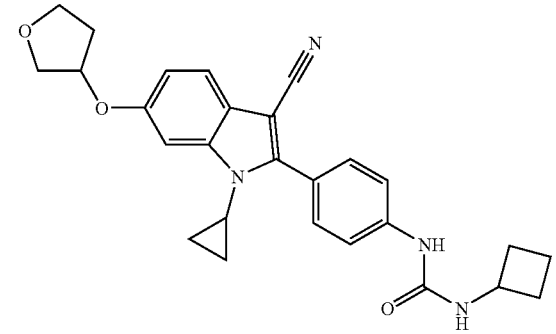 |
| 2029 | 2052 |
| 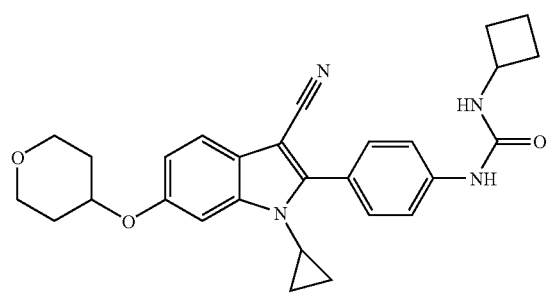 | 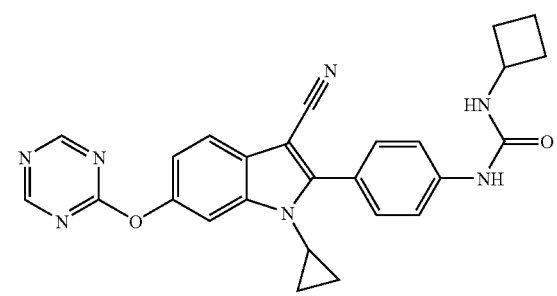 |
| 2053 | 2054 |
| 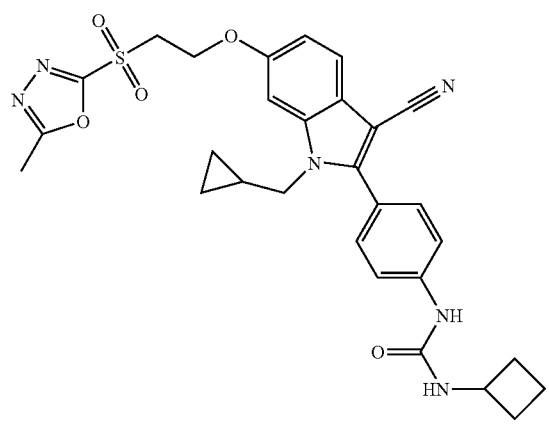 | 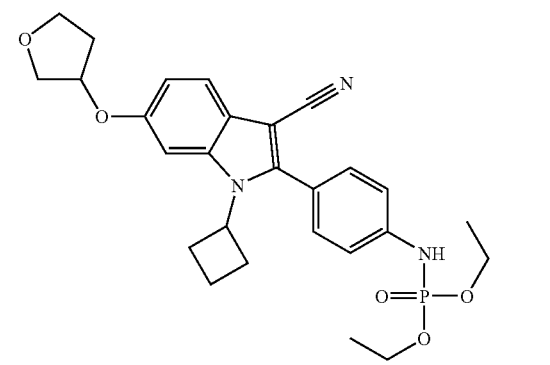 |
| 2055 | 2093 |
| 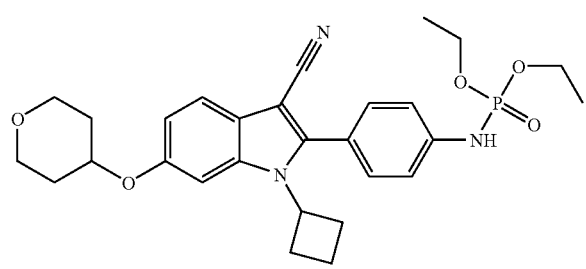 | 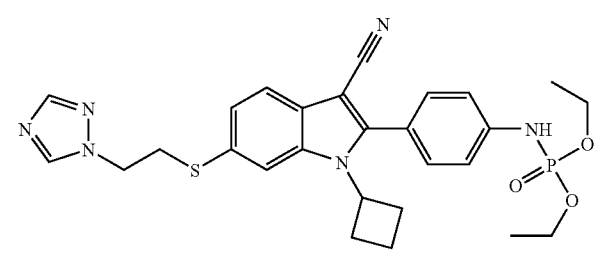 |

-continued
2094
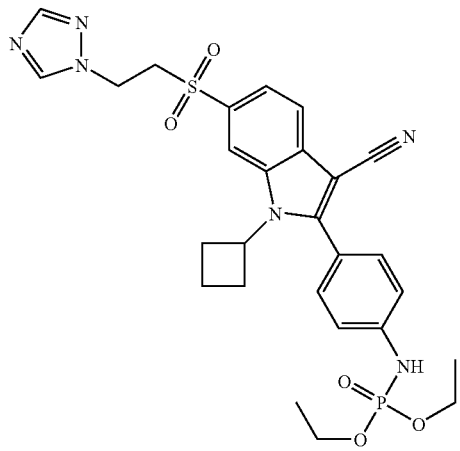
2095
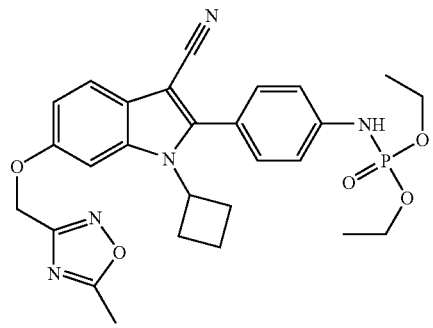
2096
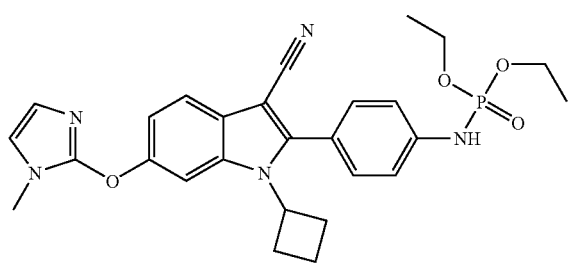
2097
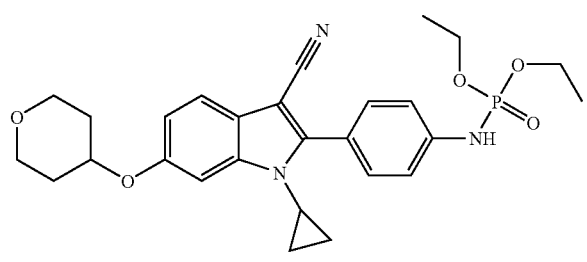
2107
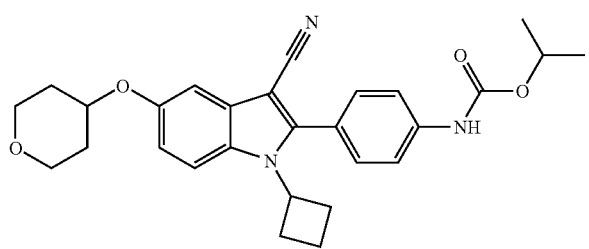
2108
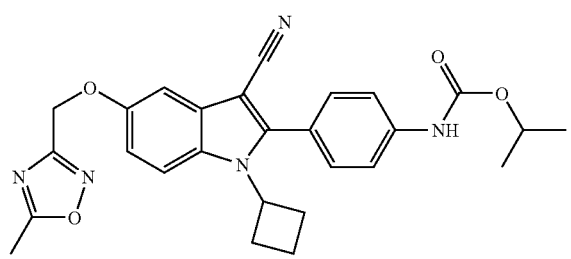
2109
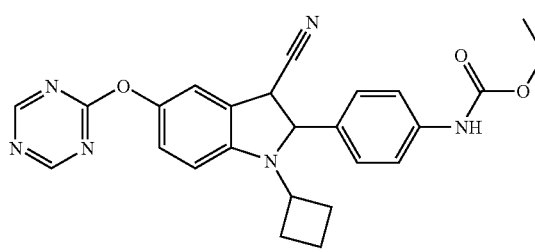
2110
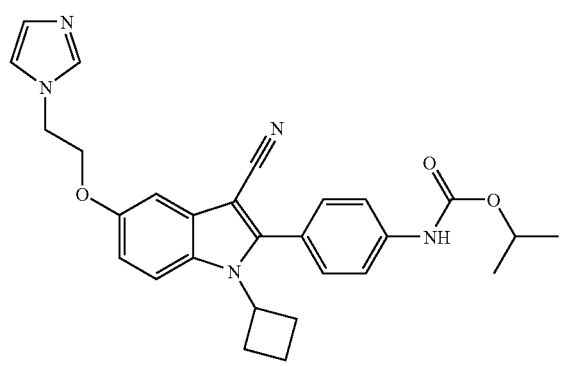

-continued
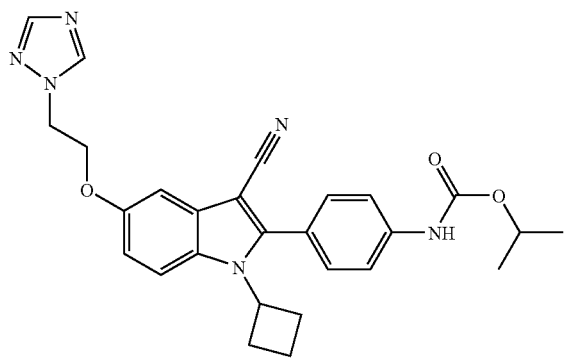
2111
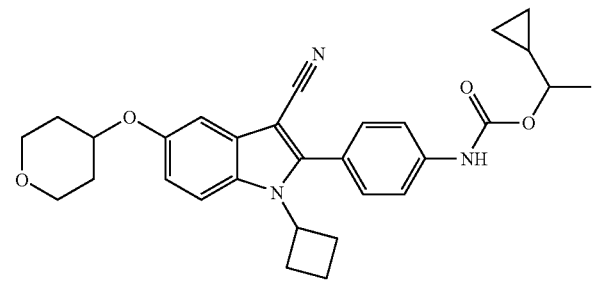
2112
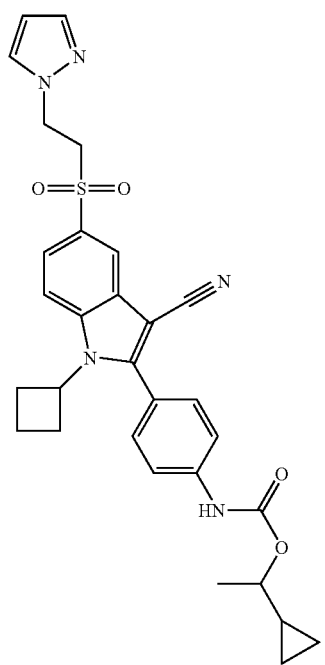
2113
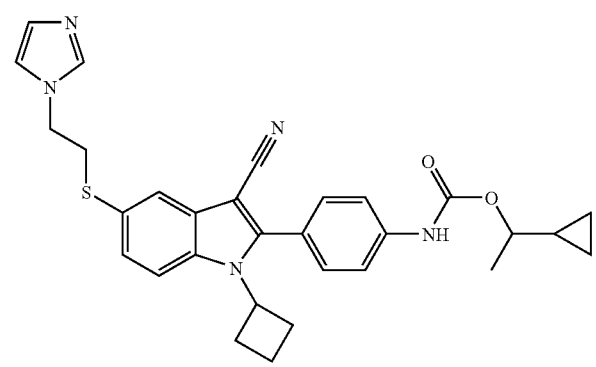
2114
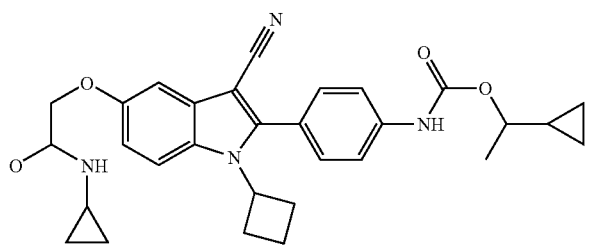
2115
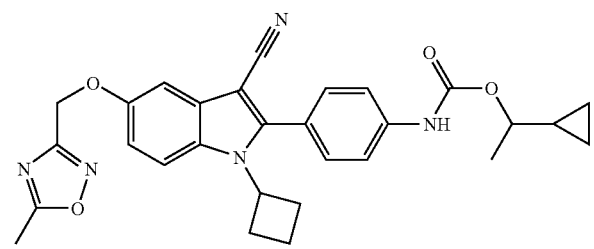
2116

-continued
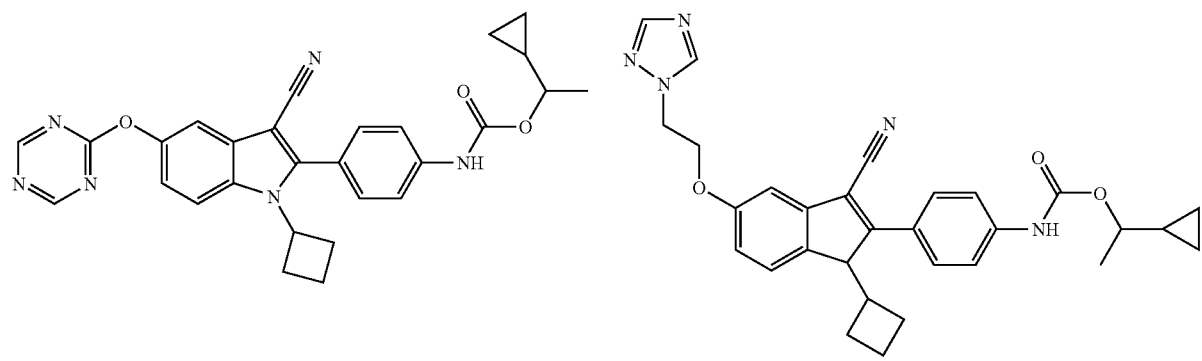
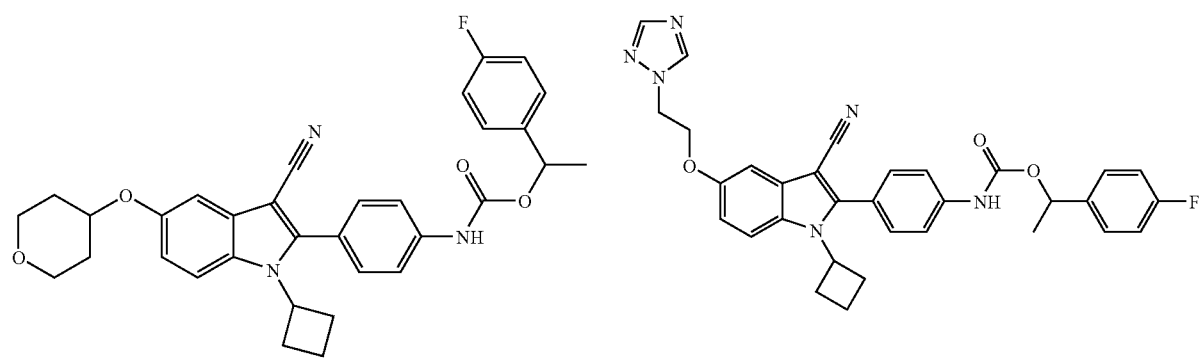
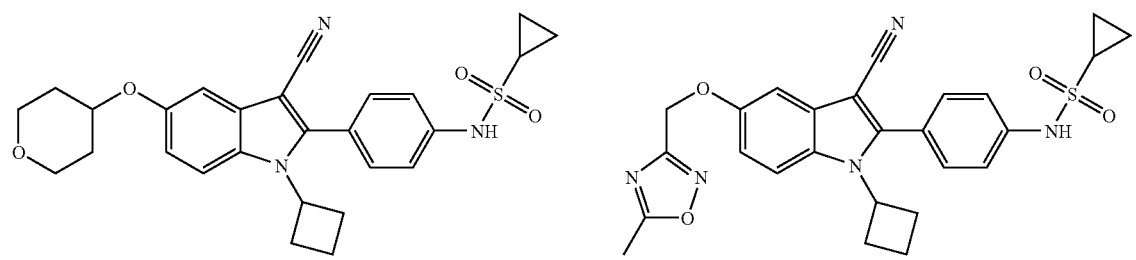
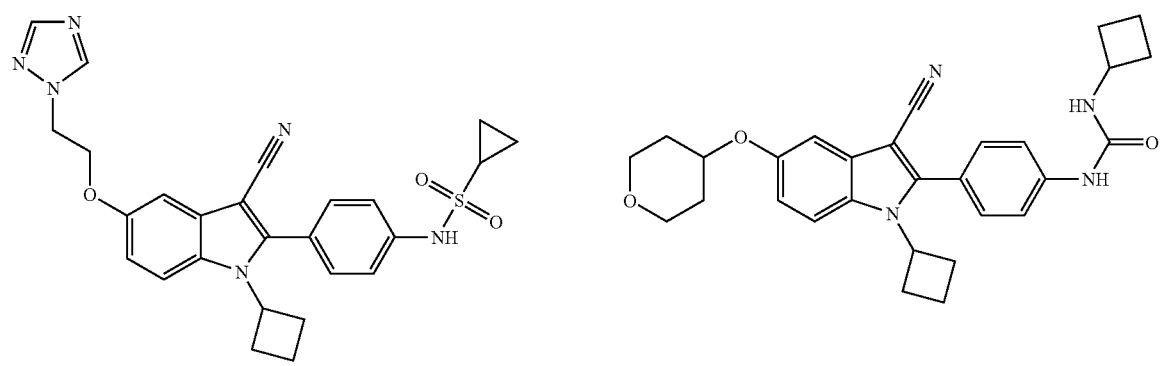

-continued
2125
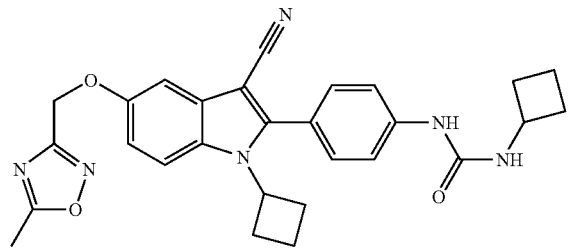
2126
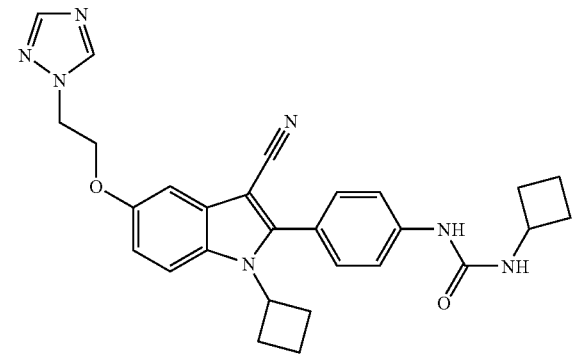
2128
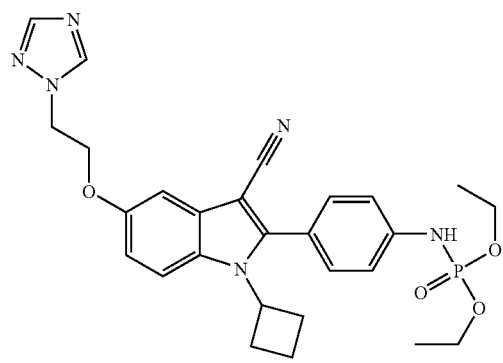
2150
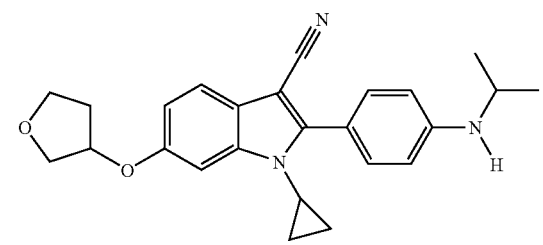
2186
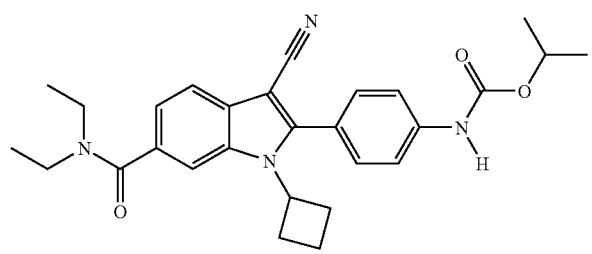
2194
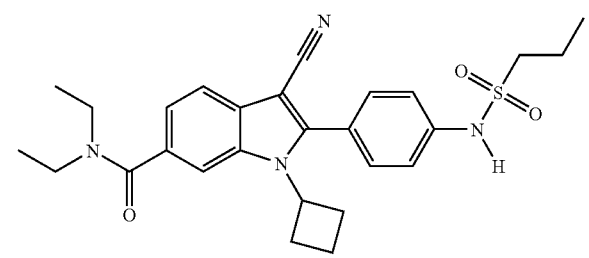
2249
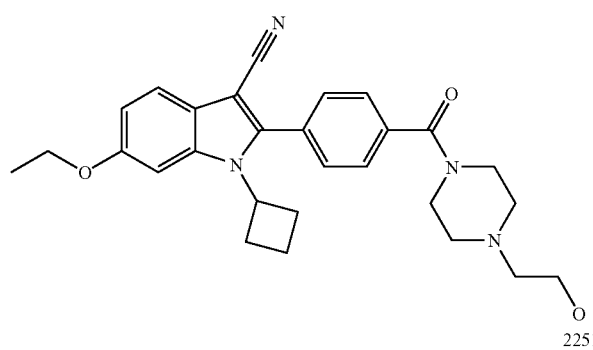
2250
2251
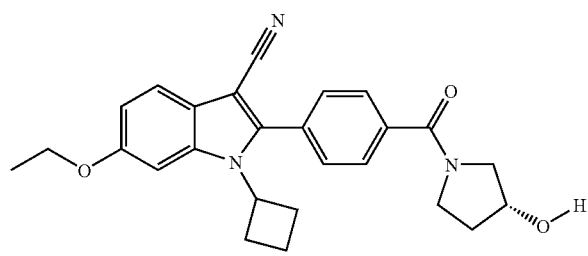
2271
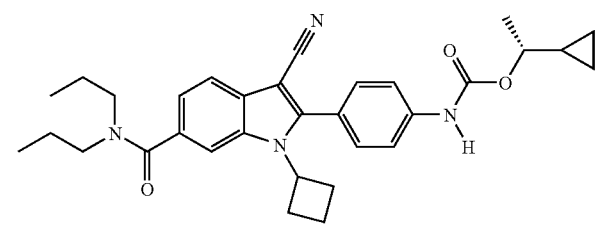

-continued
2272
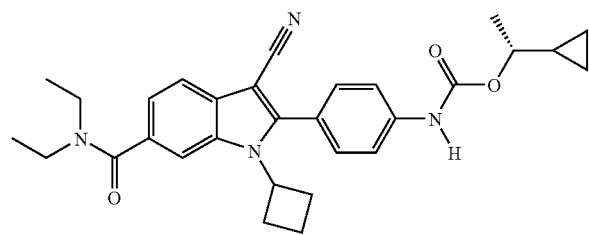
2273
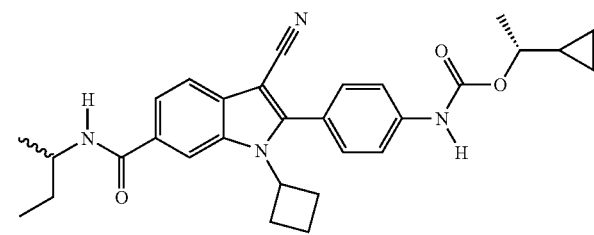
2274
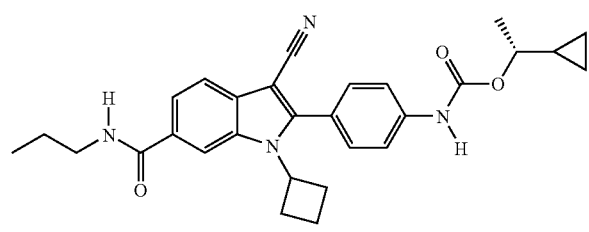
2275
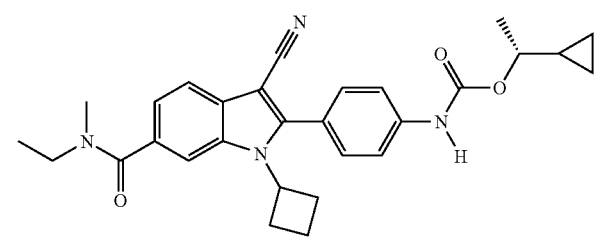
2276
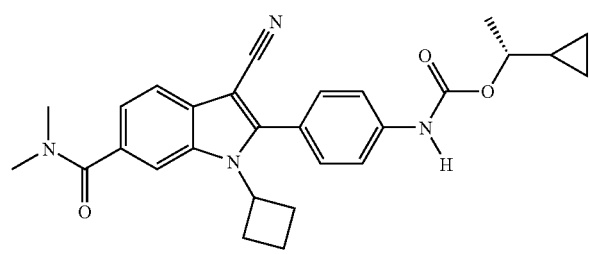
2293
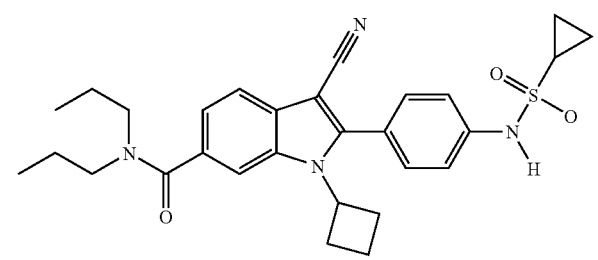
2294
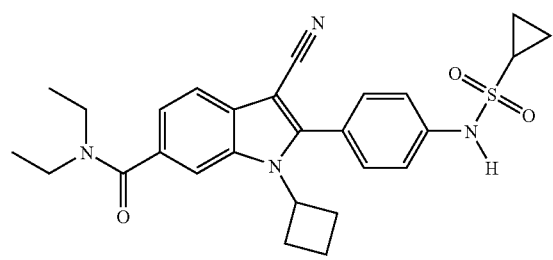
2295
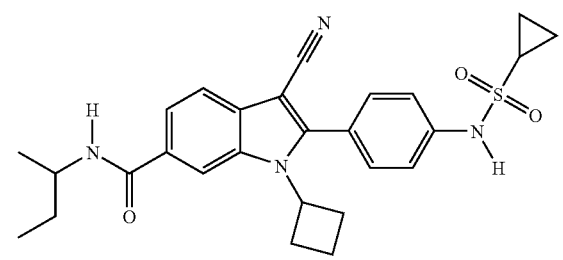
2296
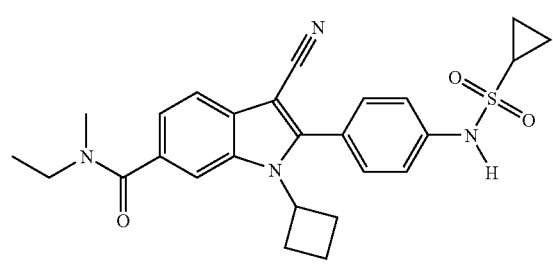
2297
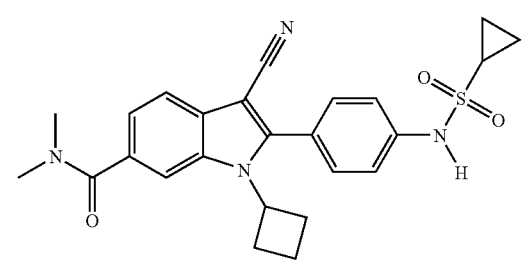

-continued
2312
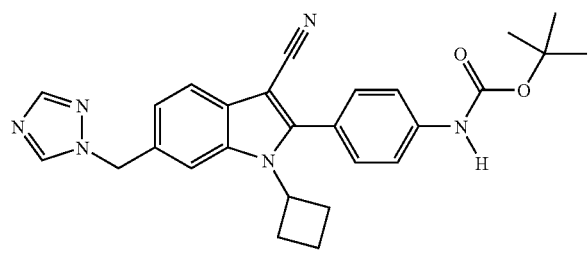
2604
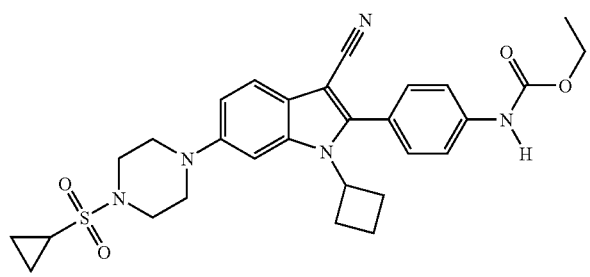
2605
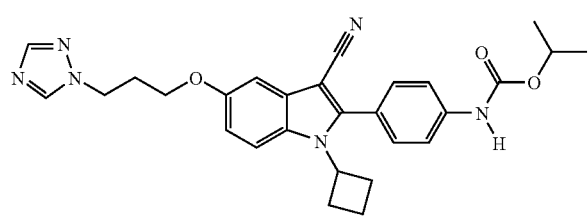
2606
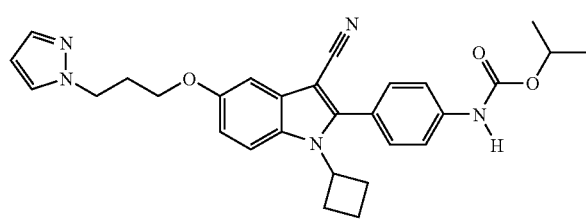
2607
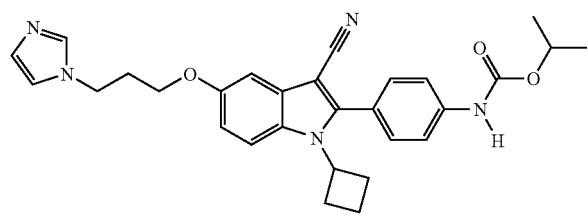
2608
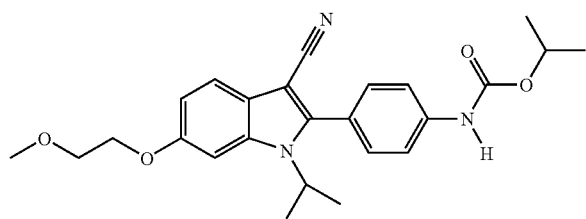
2609
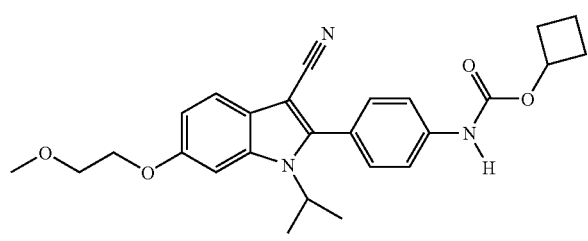
2610
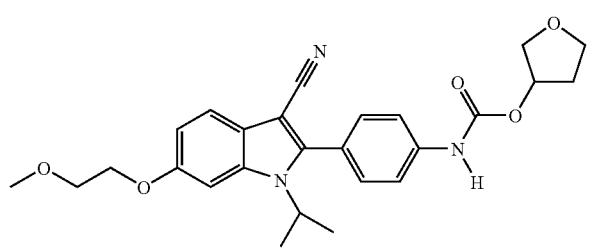
2611
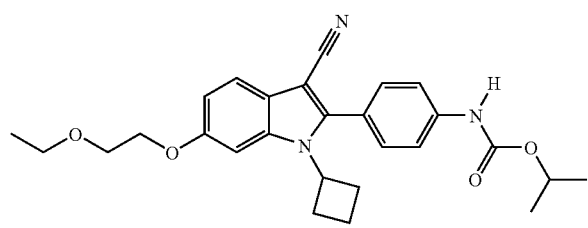
2612
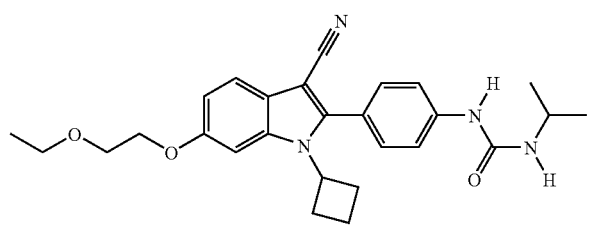
2613
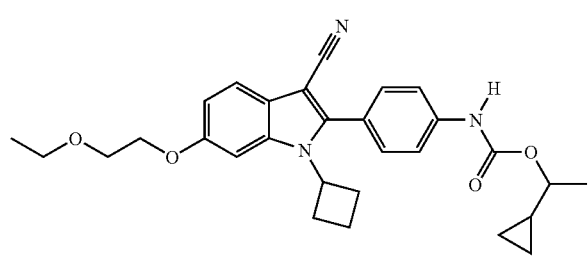
2614
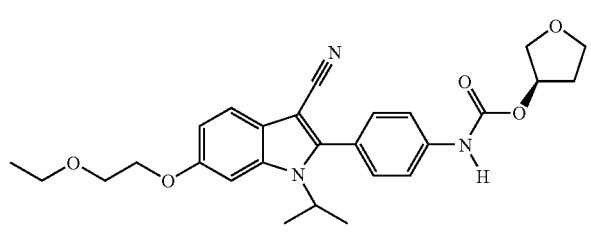

-continued
2615
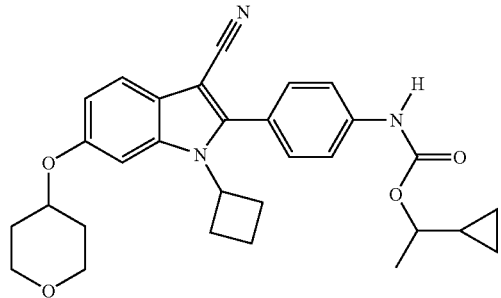
2616
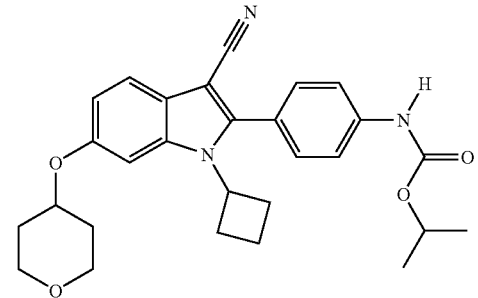
2617
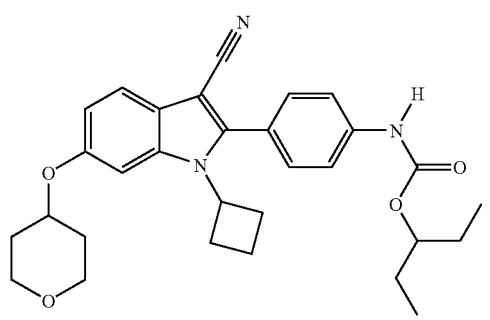
2618
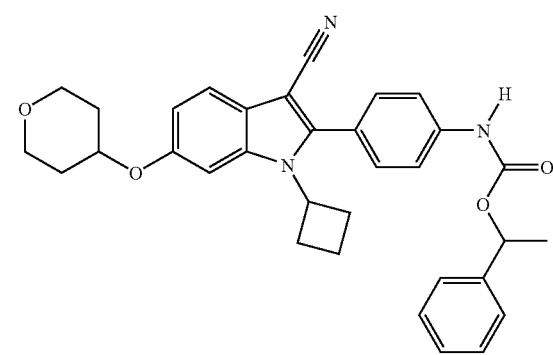
2619
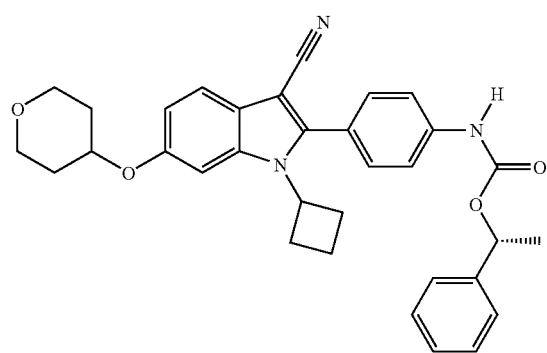
2620
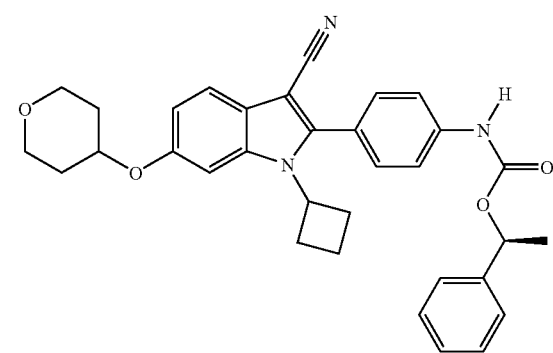
2621
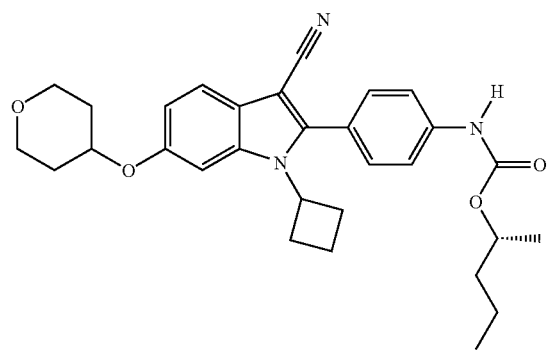
2622
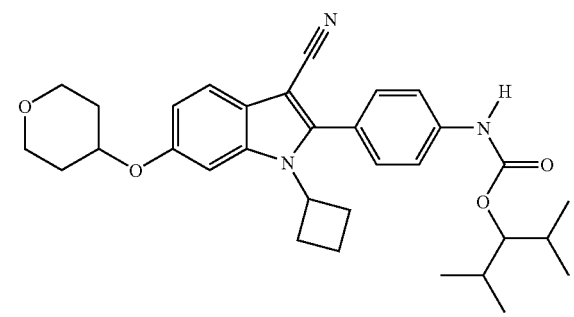

-continued
2623
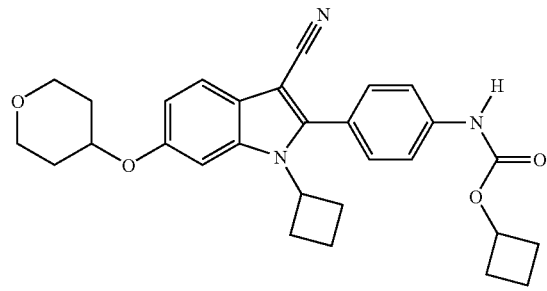
2624
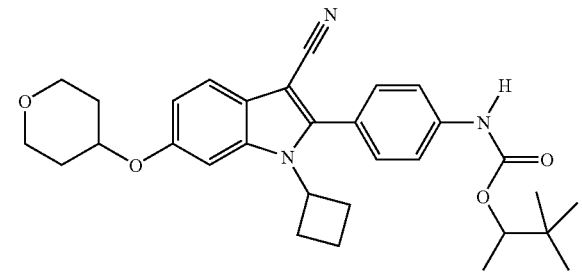
2625
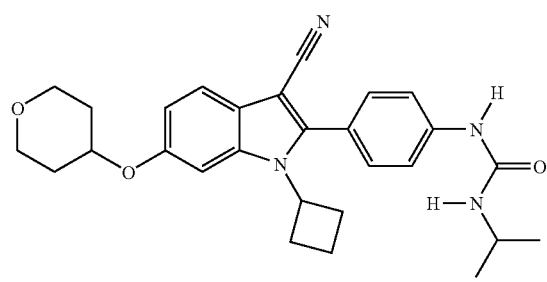
2626
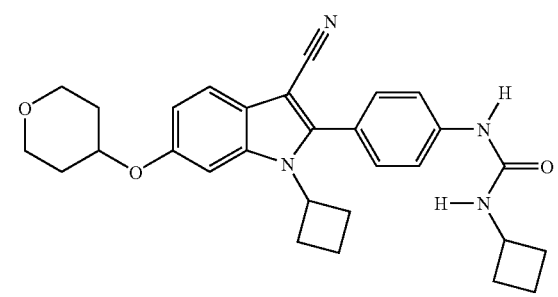
2627
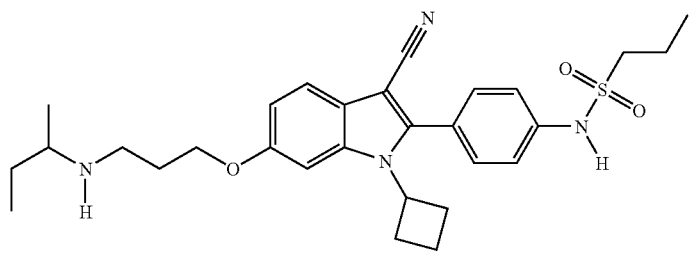
2628
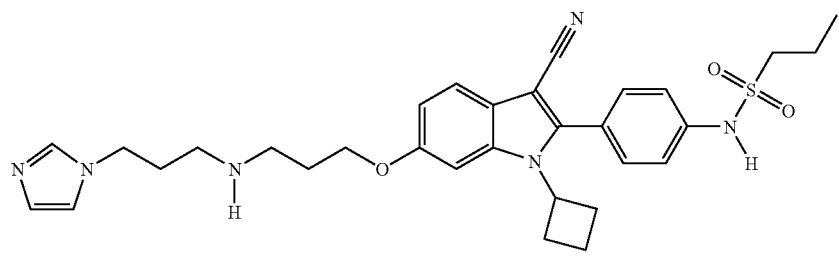
2629
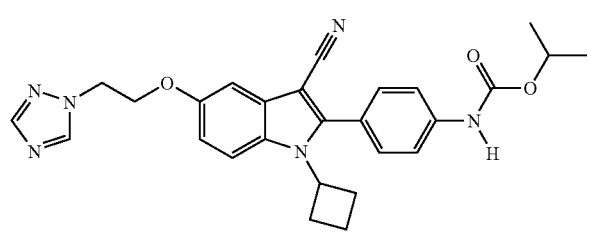
2630
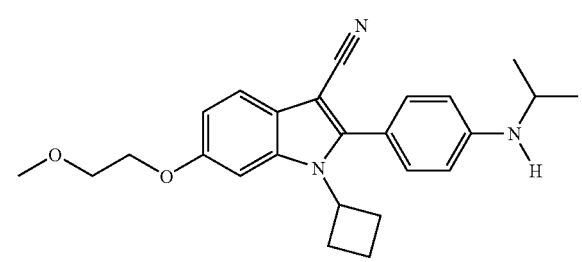

-continued
2631
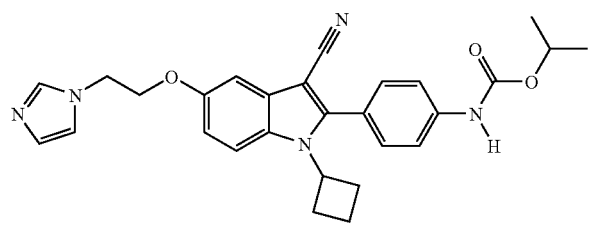
2636
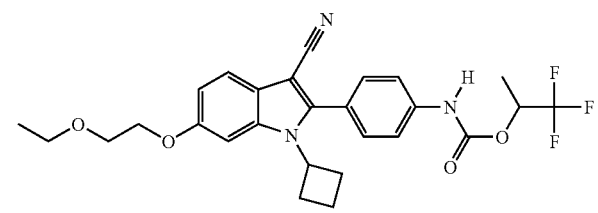
2637
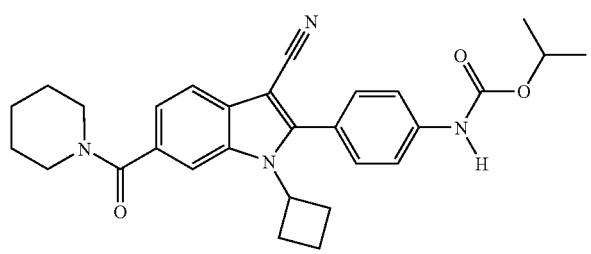
2638
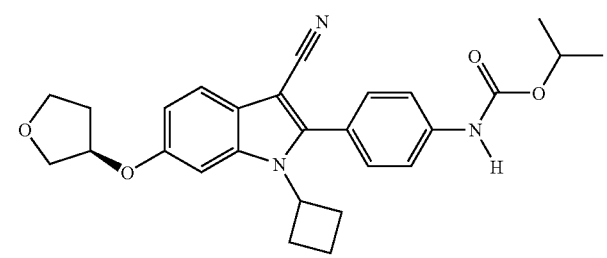
2642
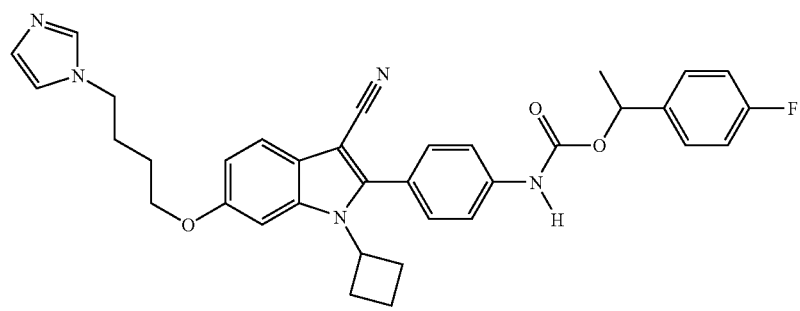
2643
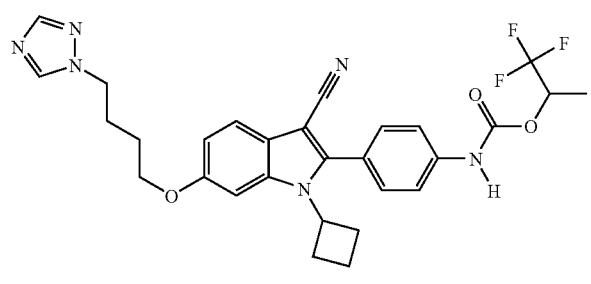
2644
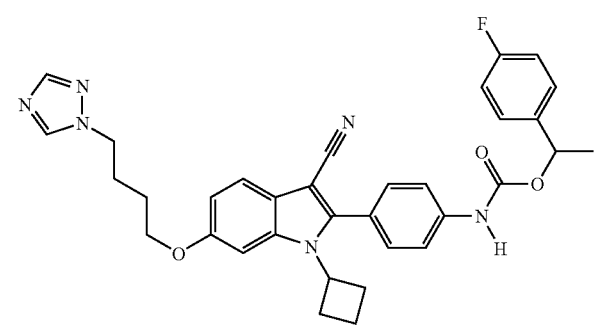
2645
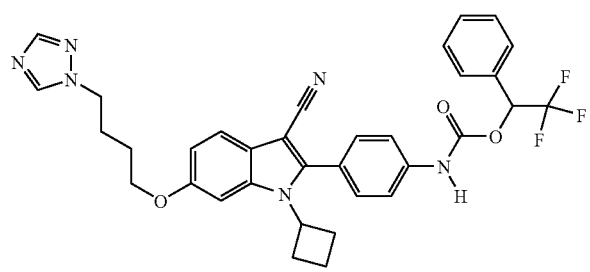
2646
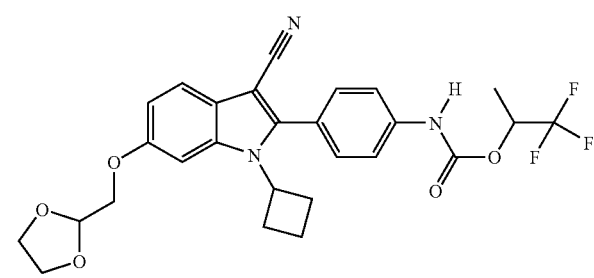

-continued
2647
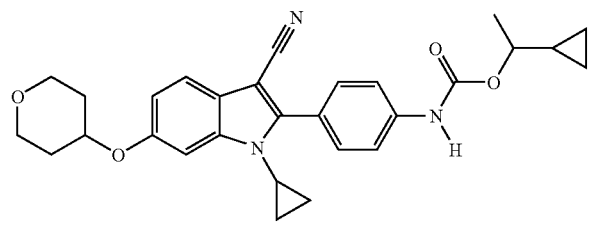
2648
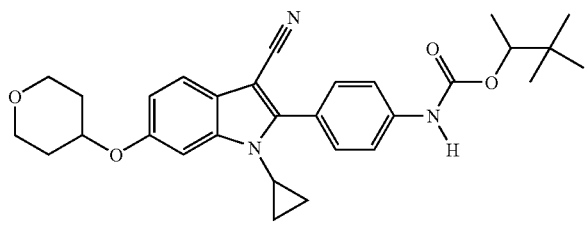
2649
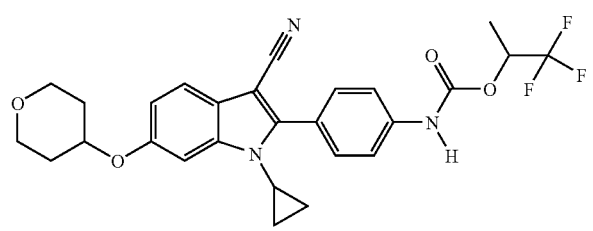
2650
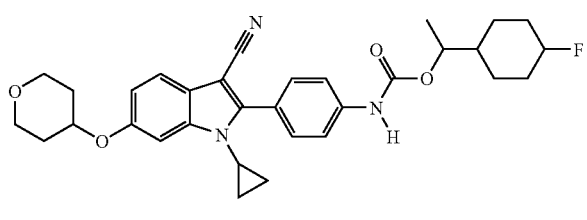
2651
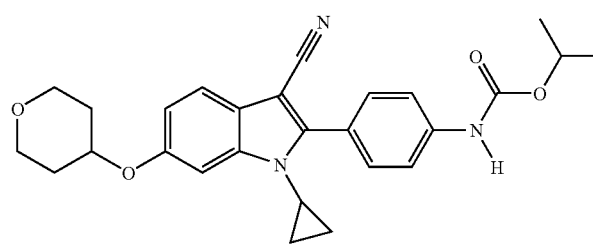
2652
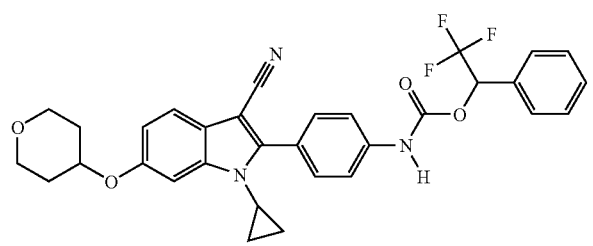
2653
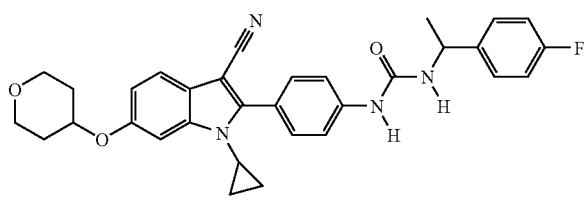
2655
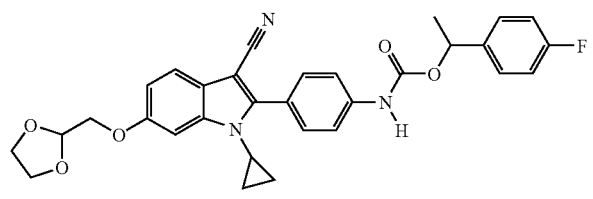
2656
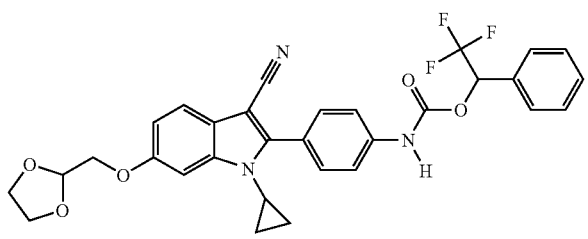
2657
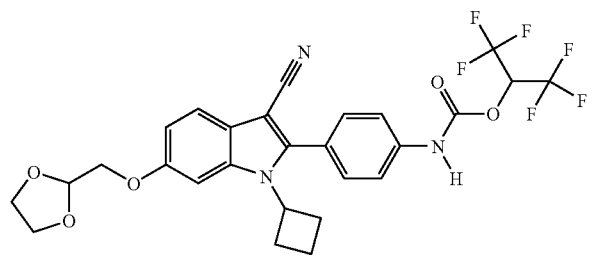
2658
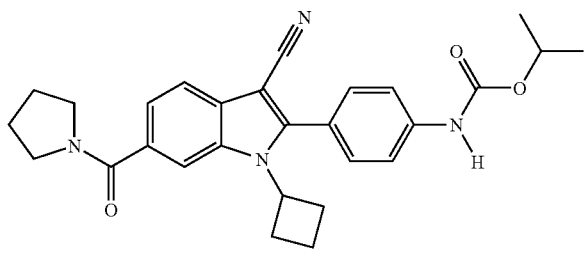

2659 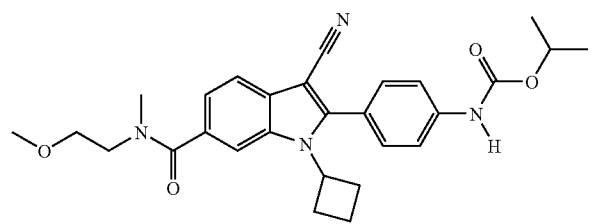
2660 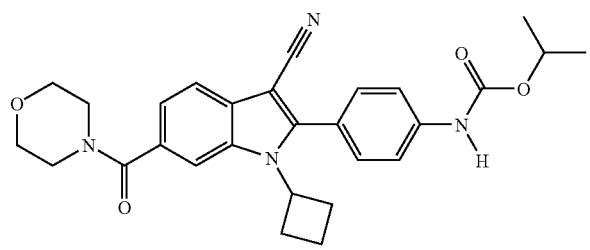
2661 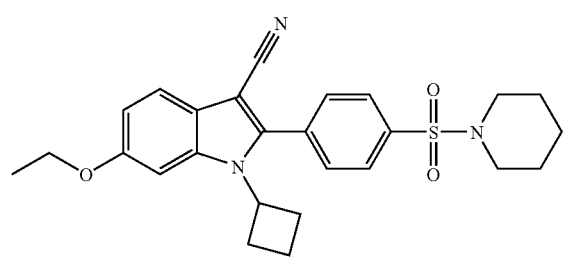
2662 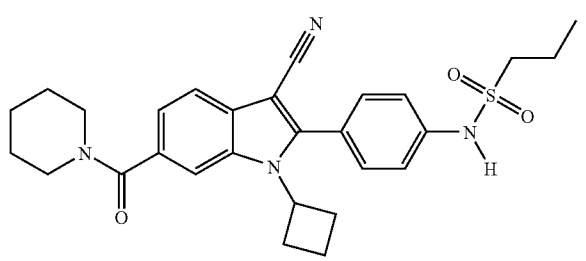
2663 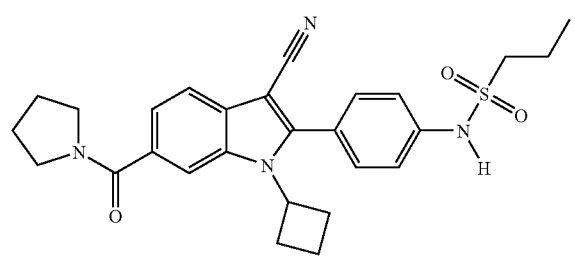
2664 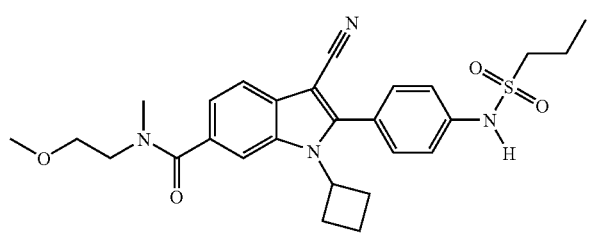
2665 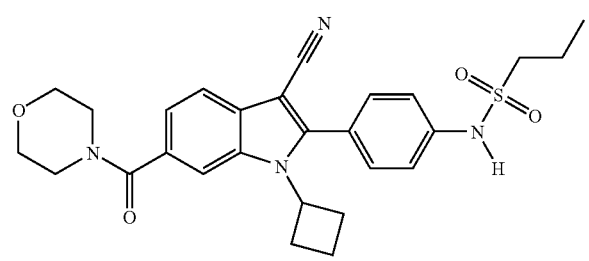
2666 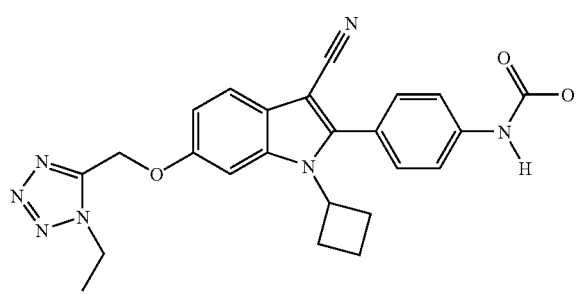
2667 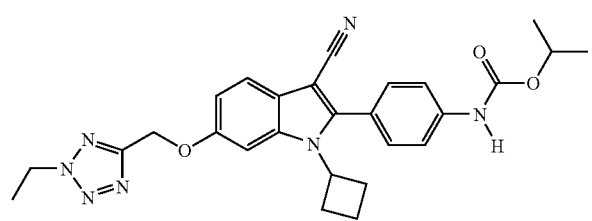
2668 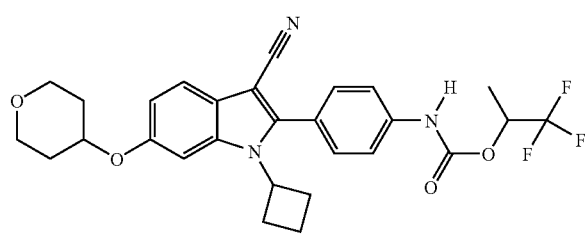

-continued
2669
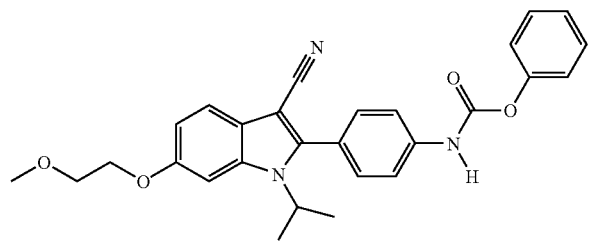
2670
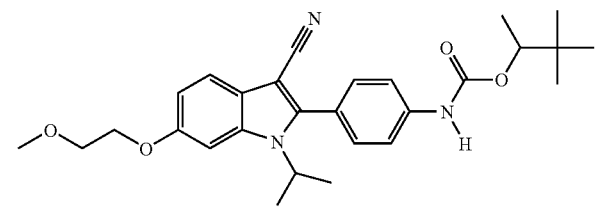
2671
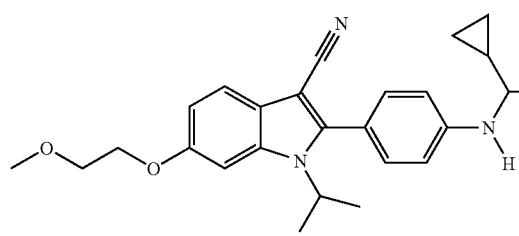
2672
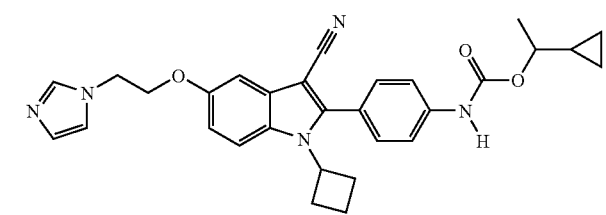
2673
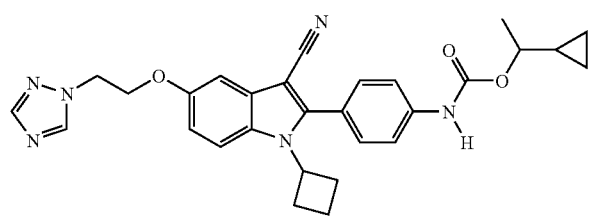
2674
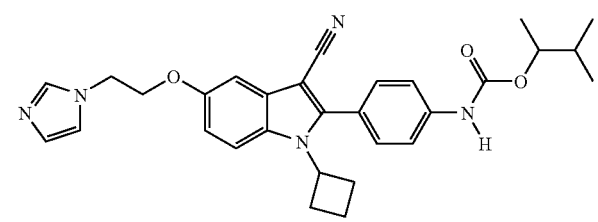
2675
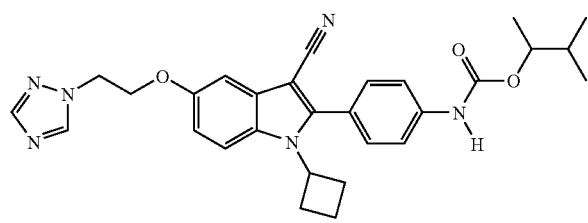
2676
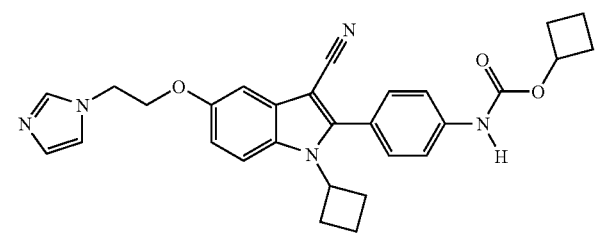
2677
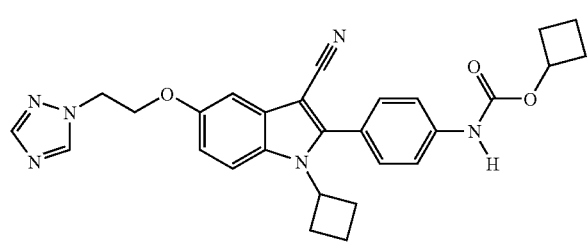
2678
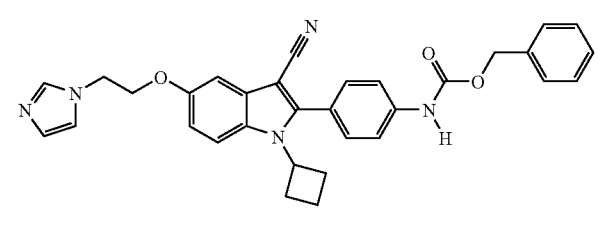
2679
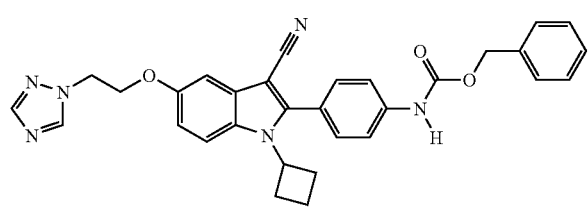
2680
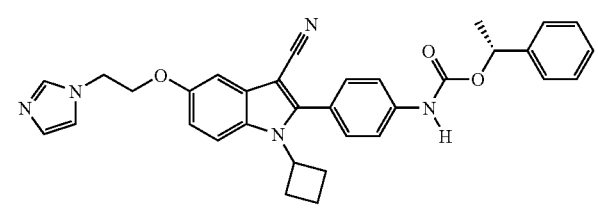

-continued
2681
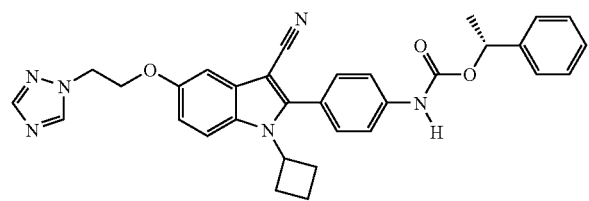
2682
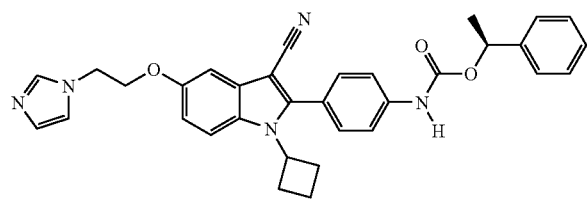
2683
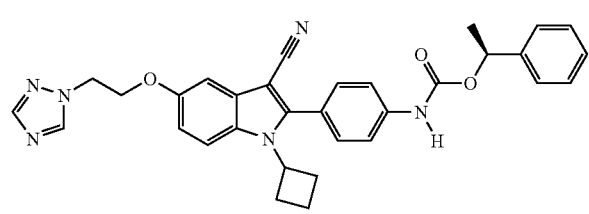
2684
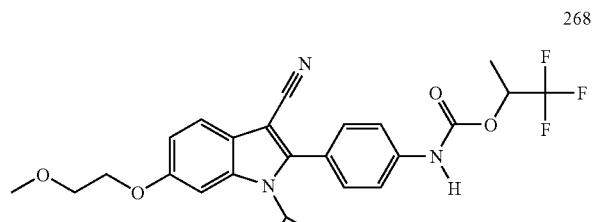
2685
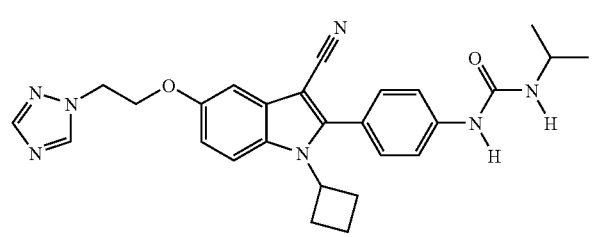
2686
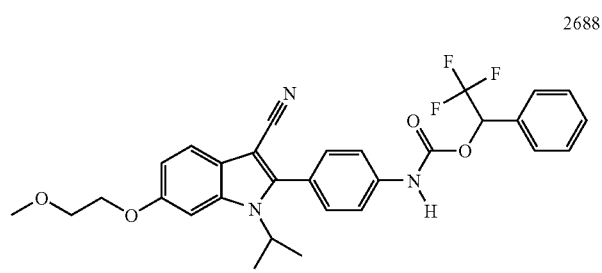
2687
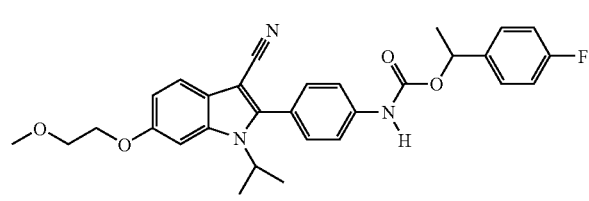
2688
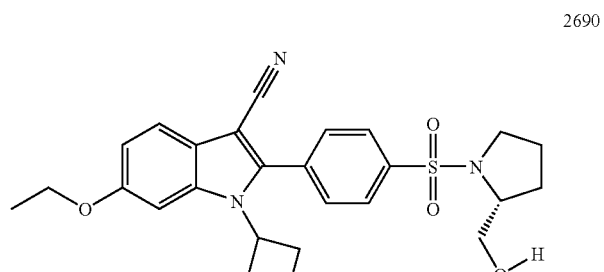
2689
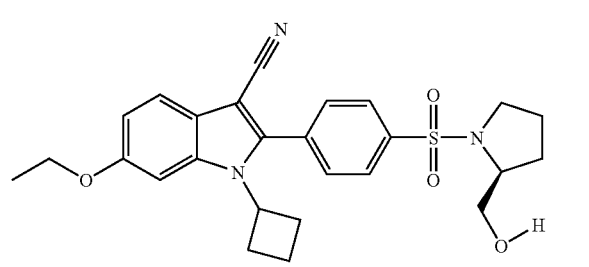
2690
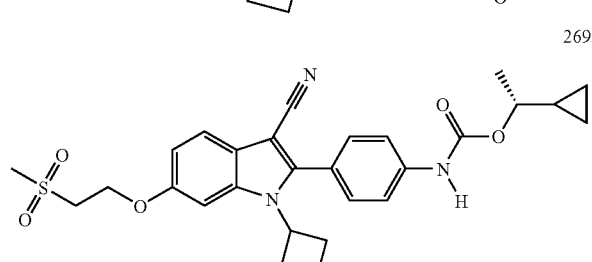
2694
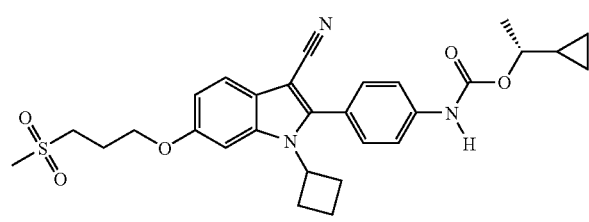
2695
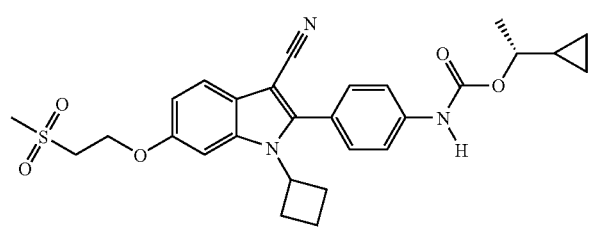

-continued
2696    2697
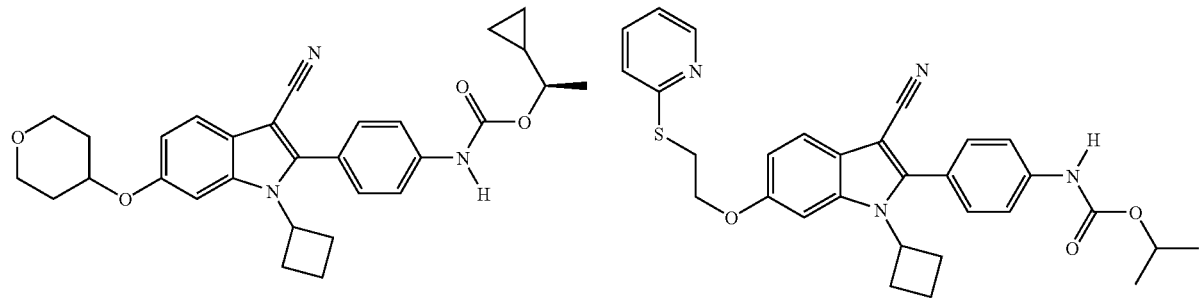
2698    2699
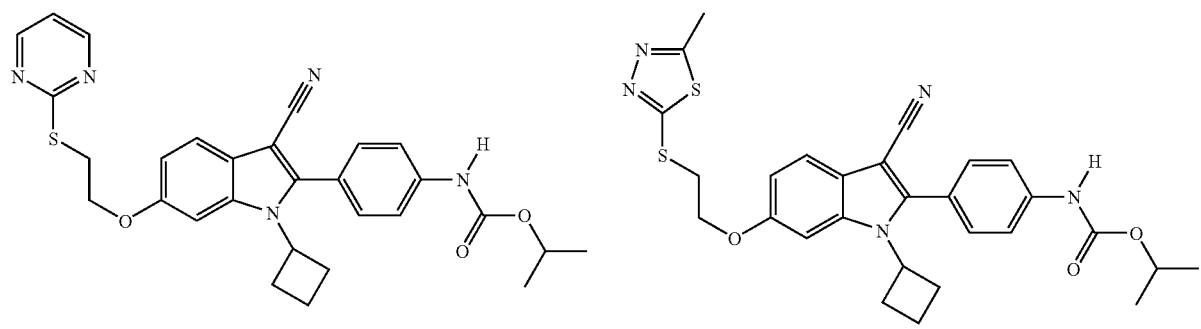
2700    2701
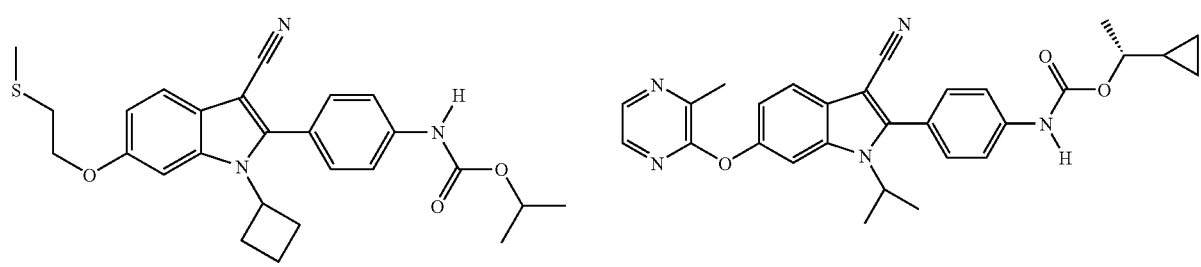
2702    2703
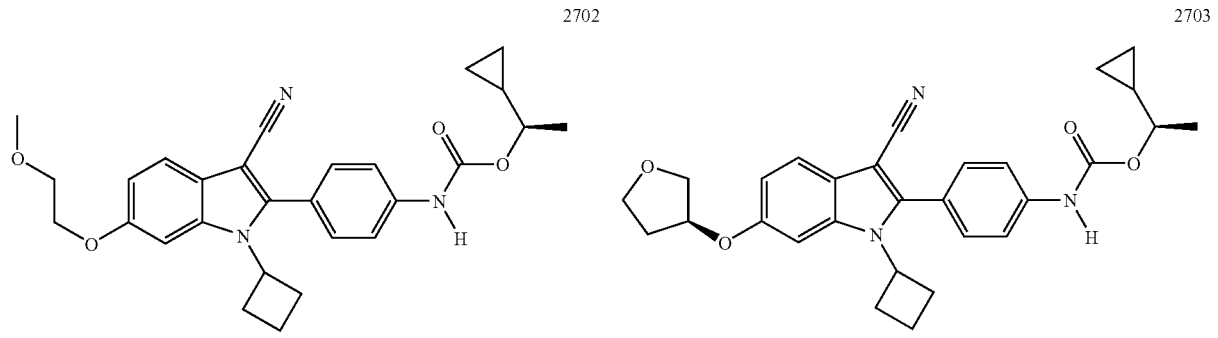
2704    2705
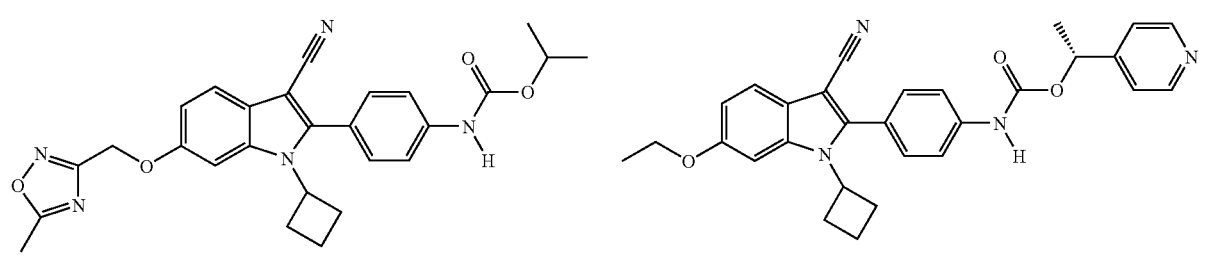

-continued
2706 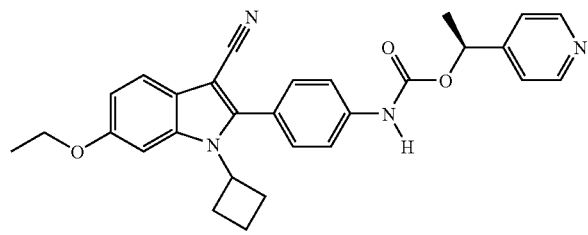
2707 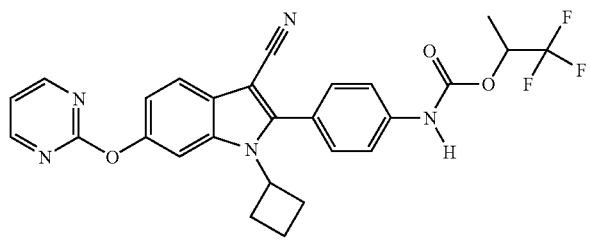
2708 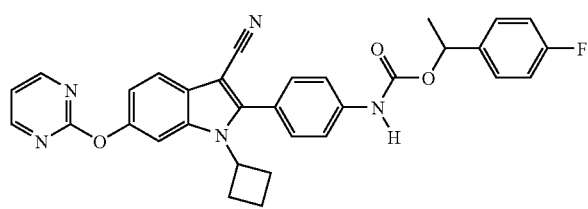
2709 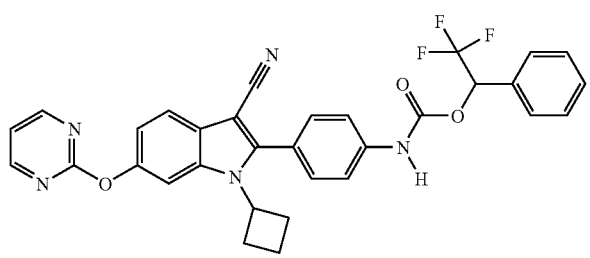
2710 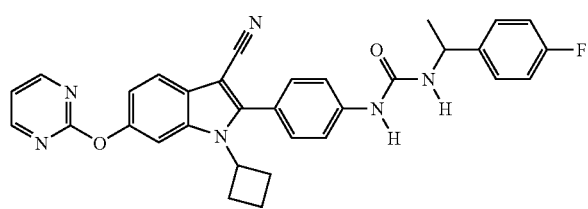
2711 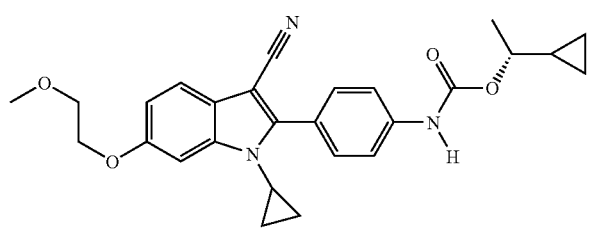
2712 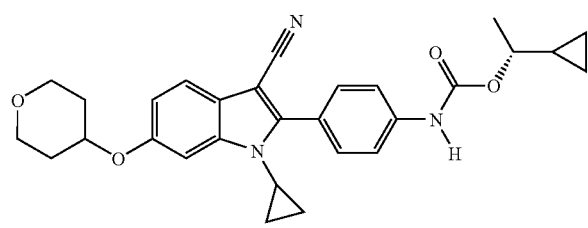
2713 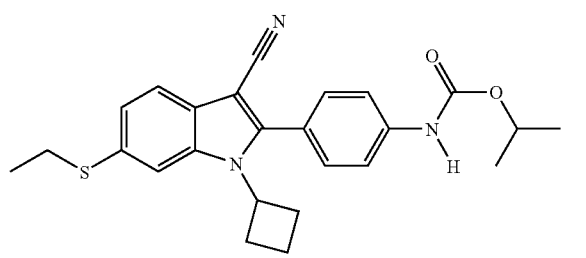
2714 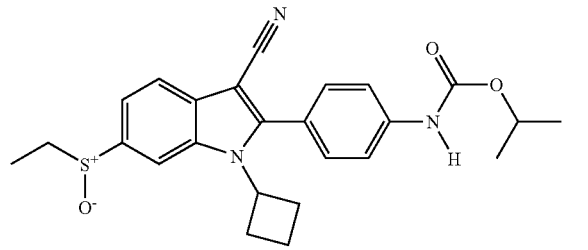
2715 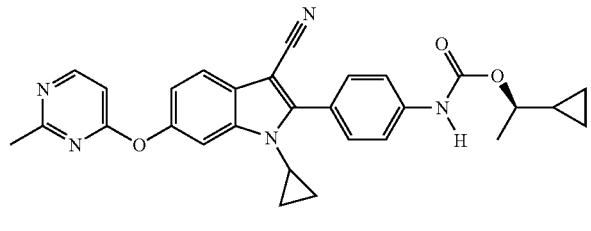
2716 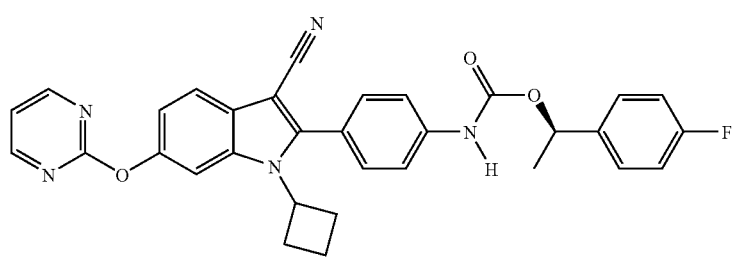

-continued
2717
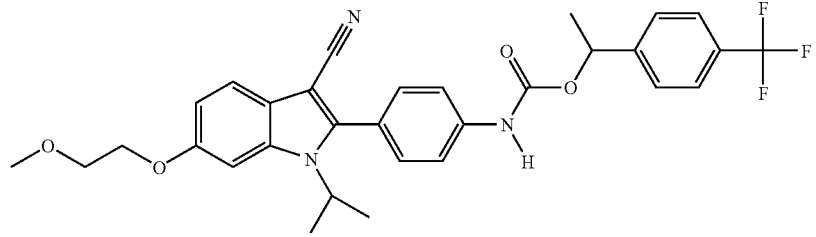
2718
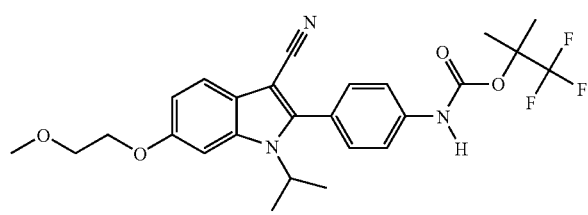
2719
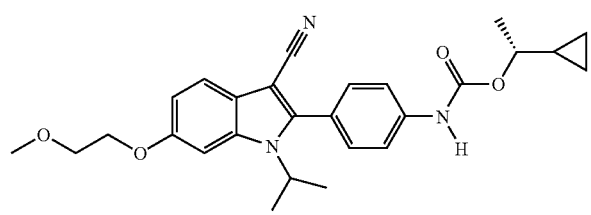
2720
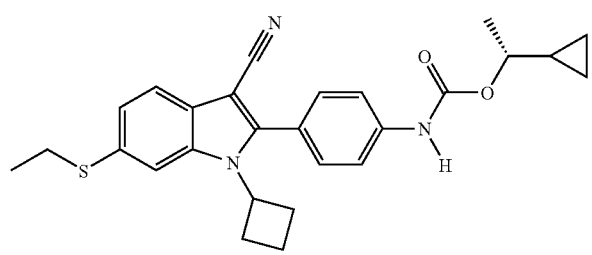
2721
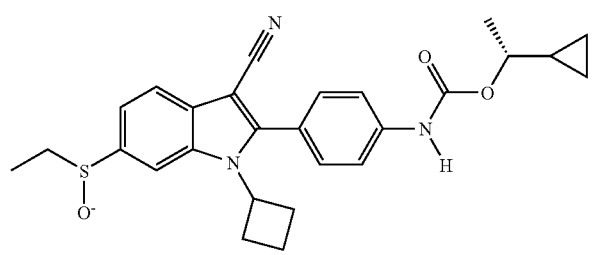
2722
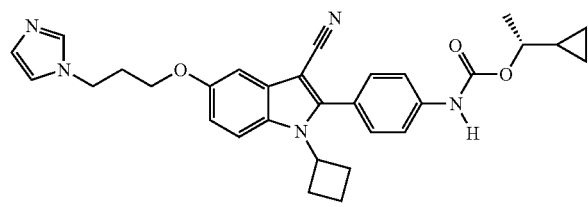
2723
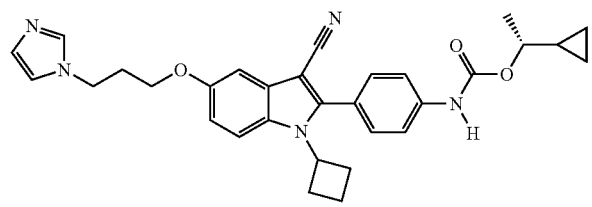
2724
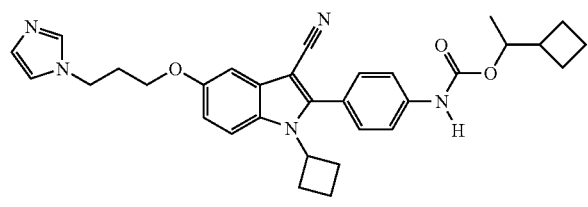
2725
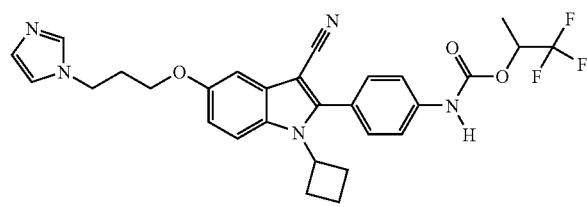
2726
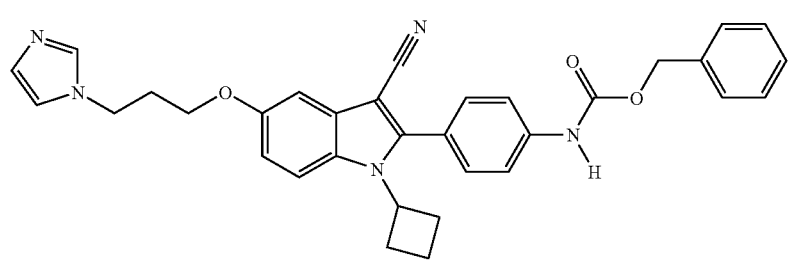

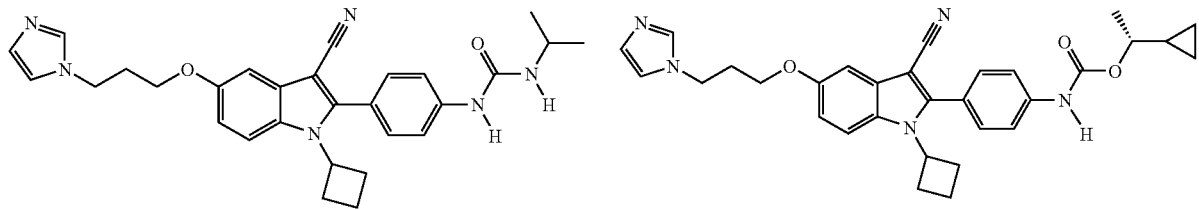
2727
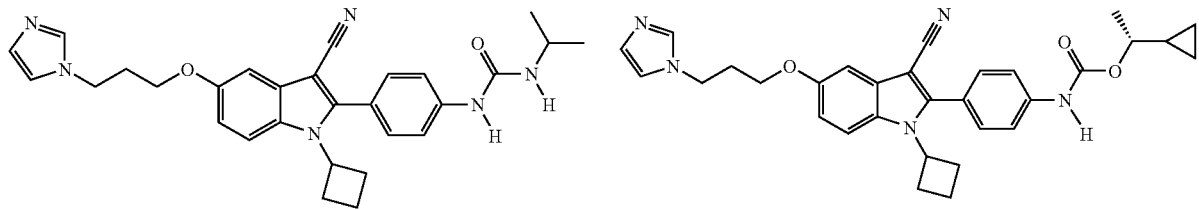
2728
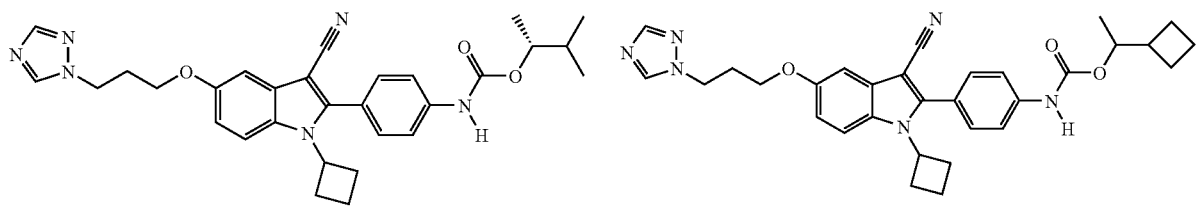
2729
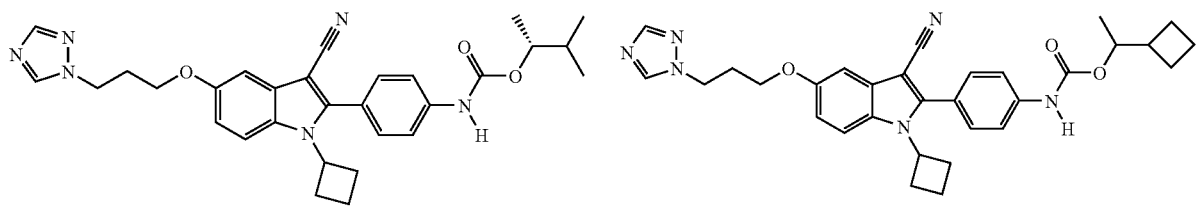
2730
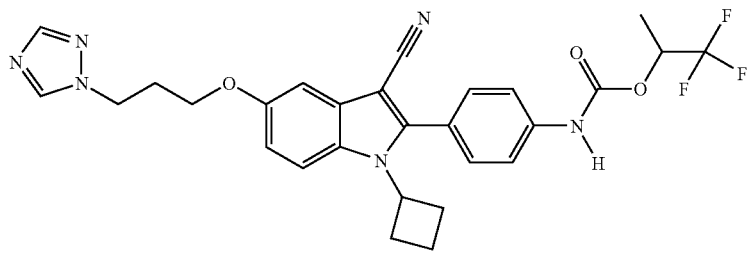
2731
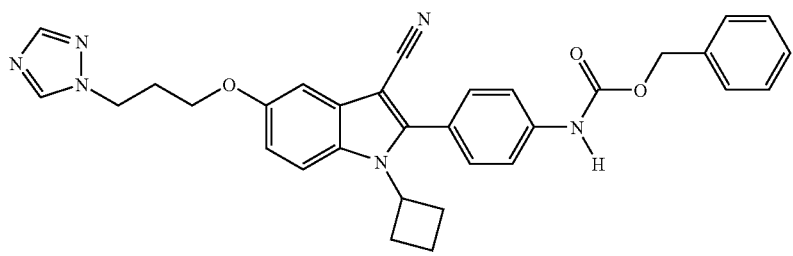
2732
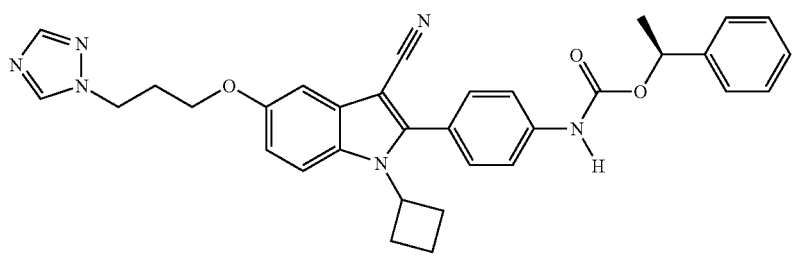
2733
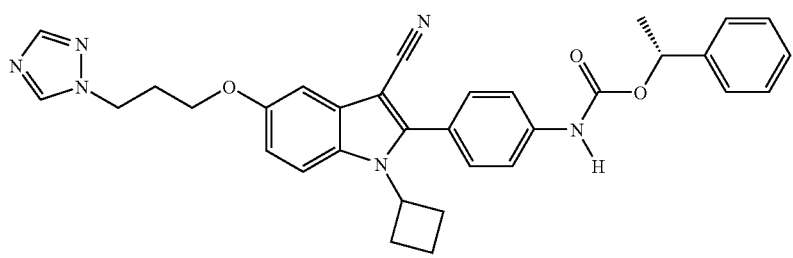
2734

-continued
2735
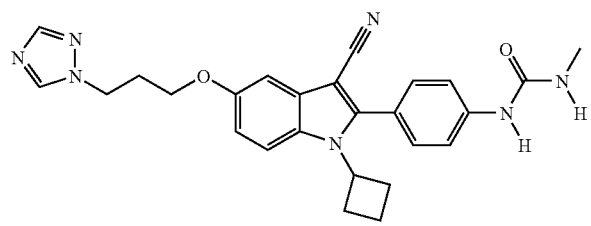
2736
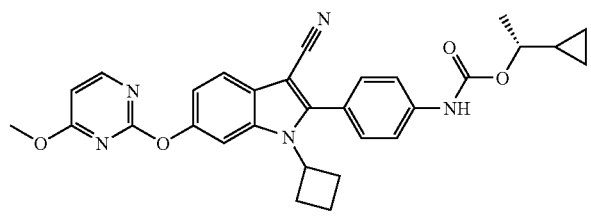
2737
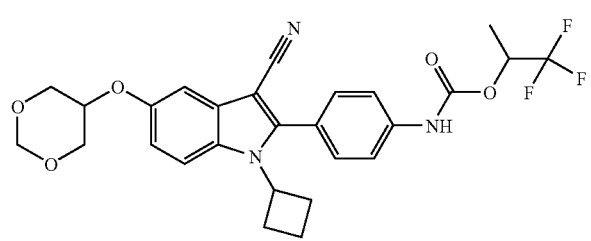
2738
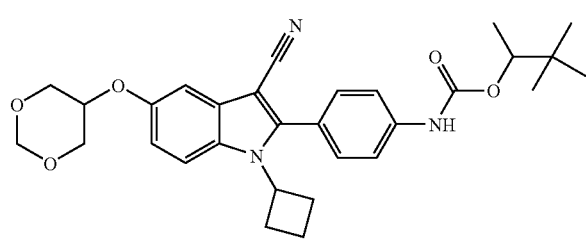
2739
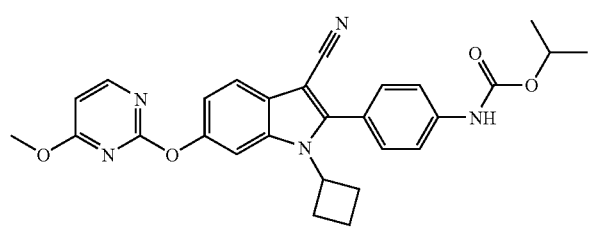
2740
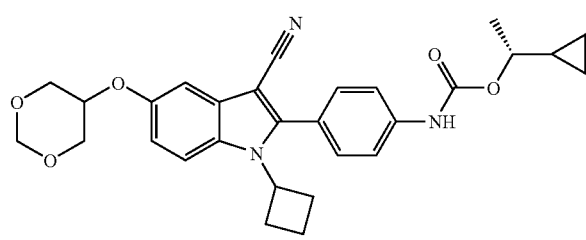
2741
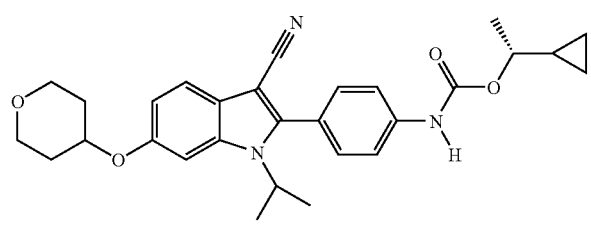
2742
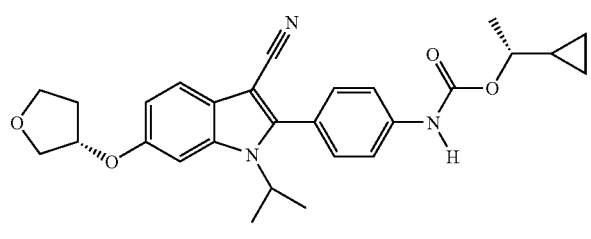
2743
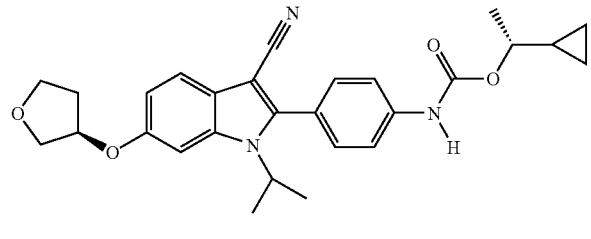
2744
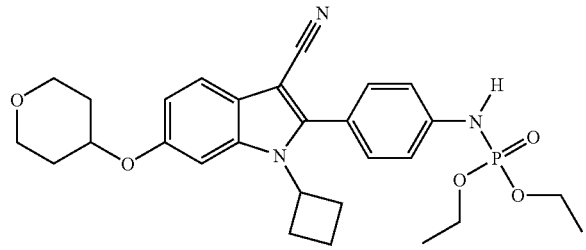
2745
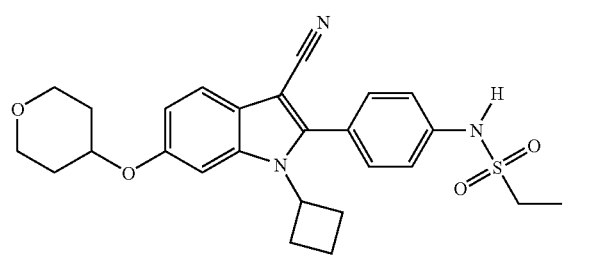
2746
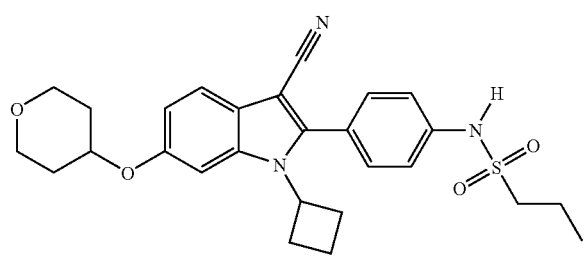

-continued
2747
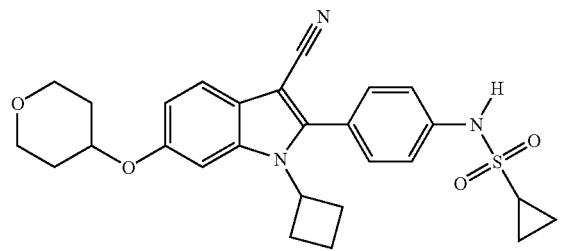
2748
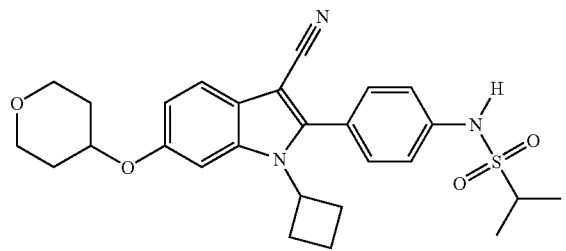
2749
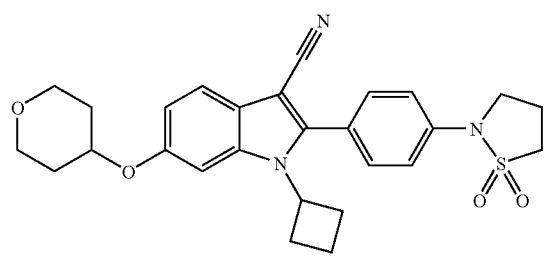
2750
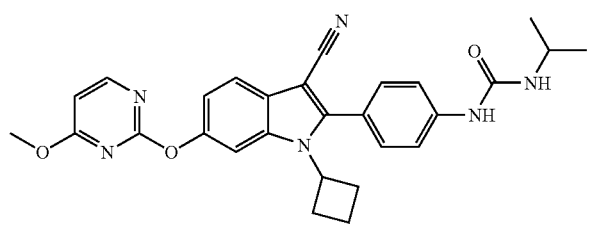
2751
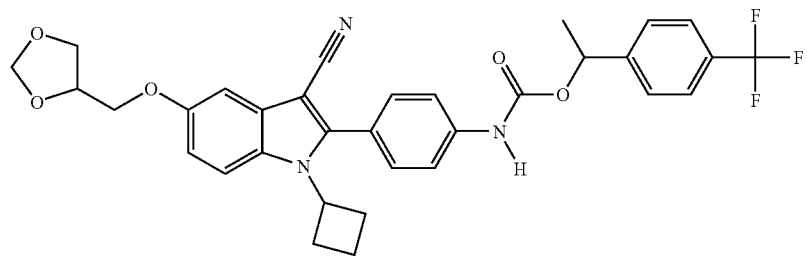
2752
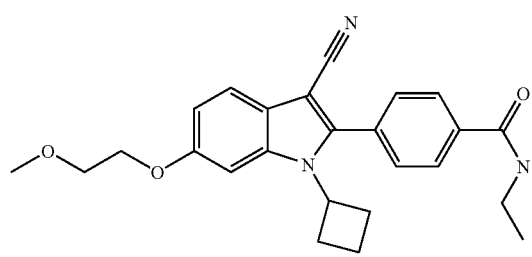
2753
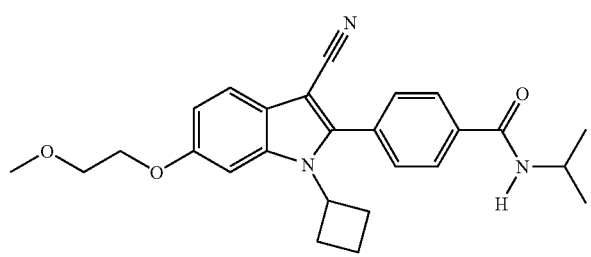
2754
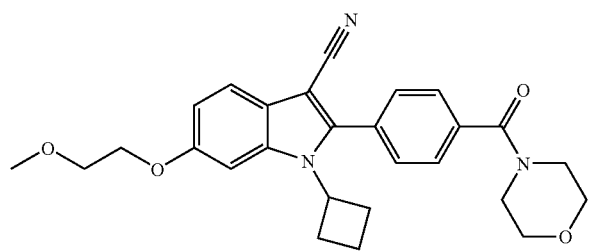
2755
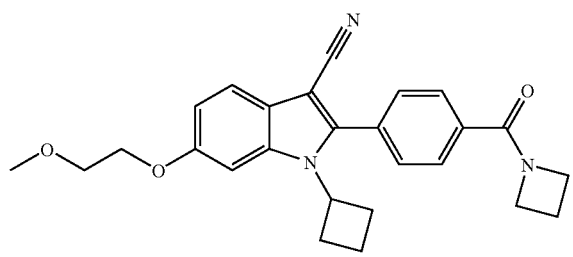
2756
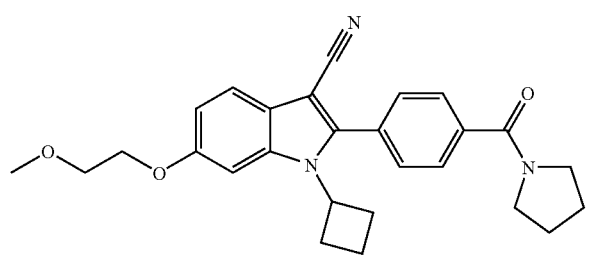
2757
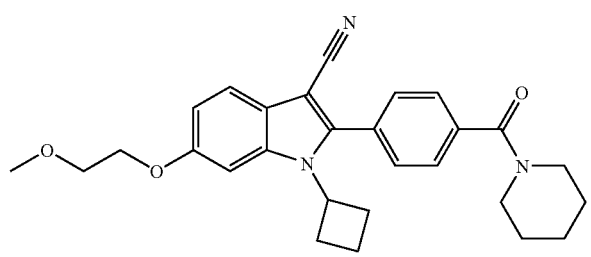

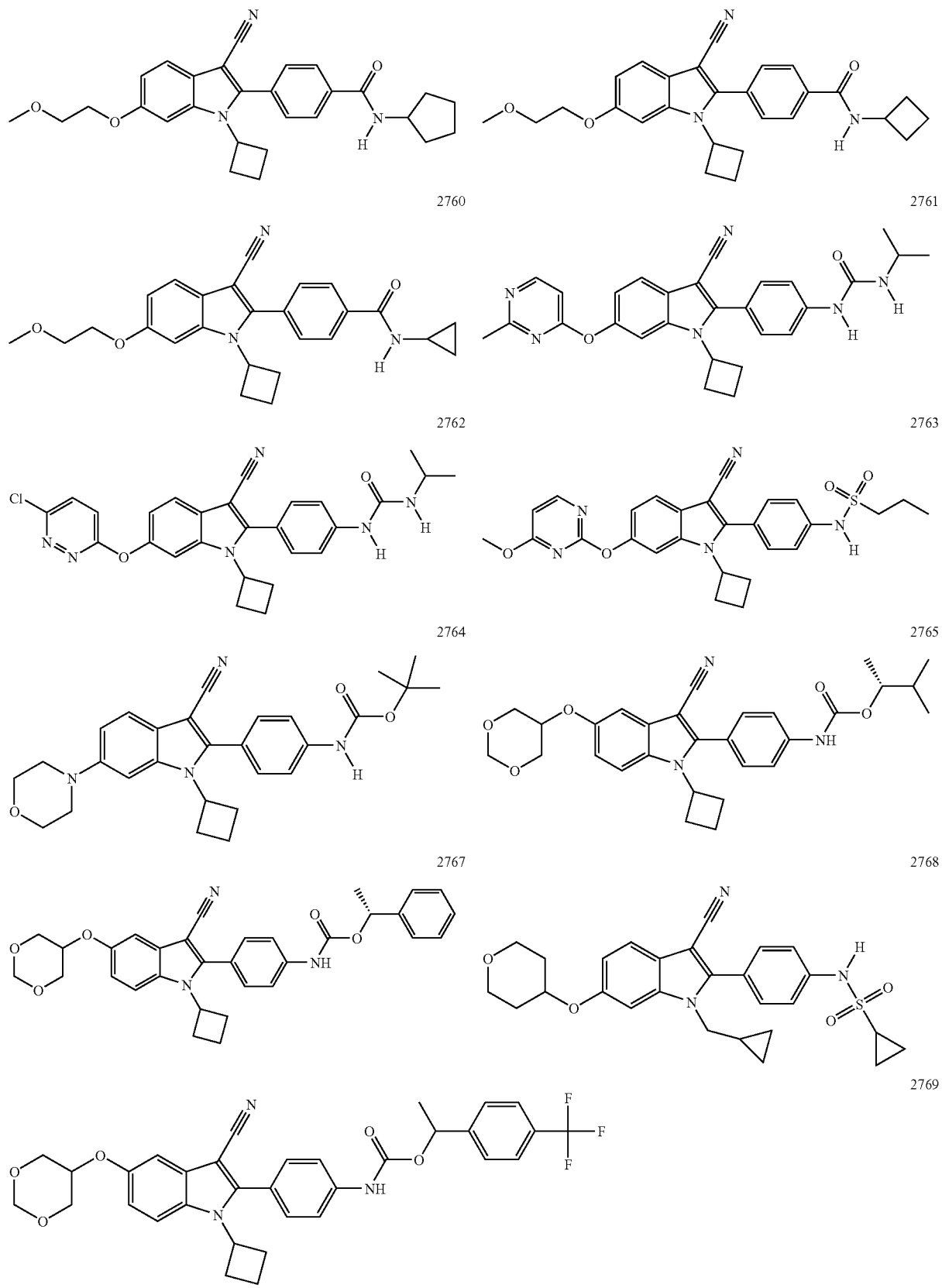

-continued
2770
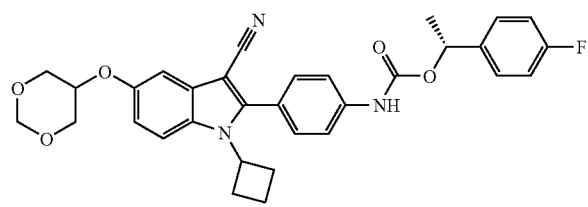
2771
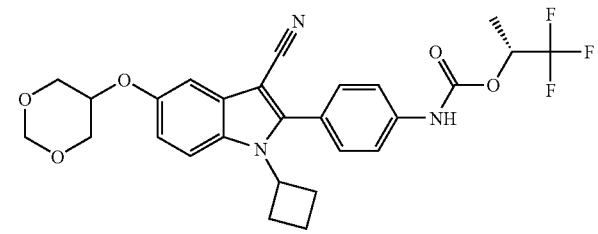
2772
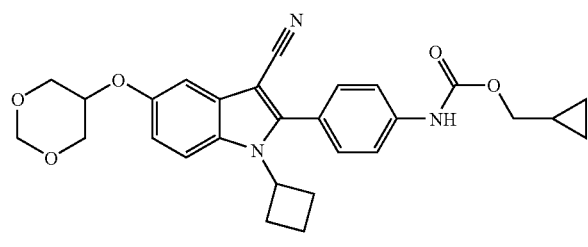
2773
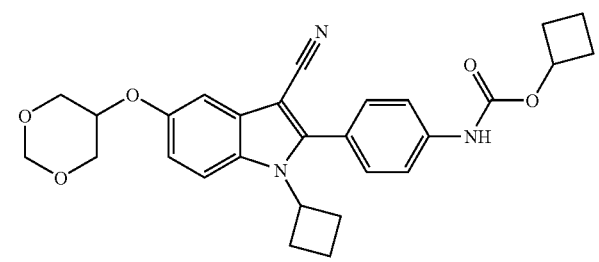
2774
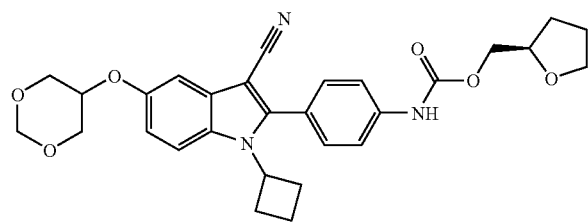
2775
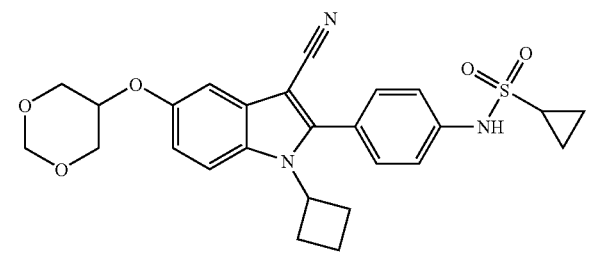
2776
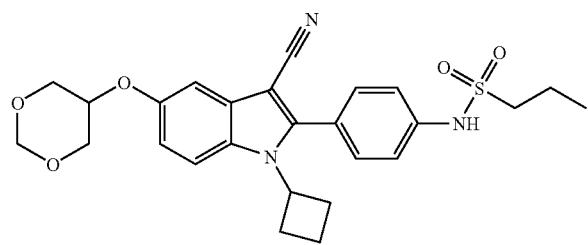
2777
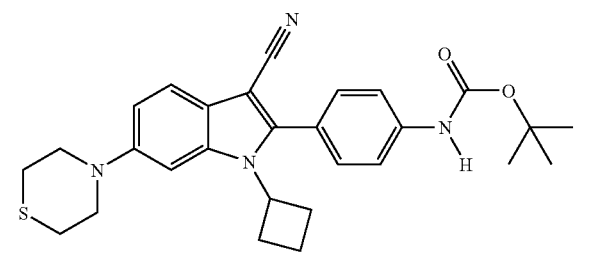
2778
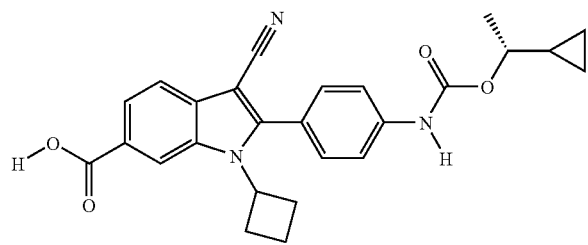
2779
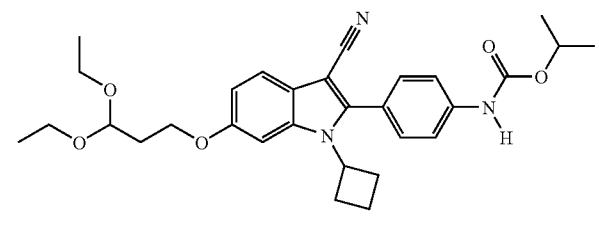

805 806
-continued
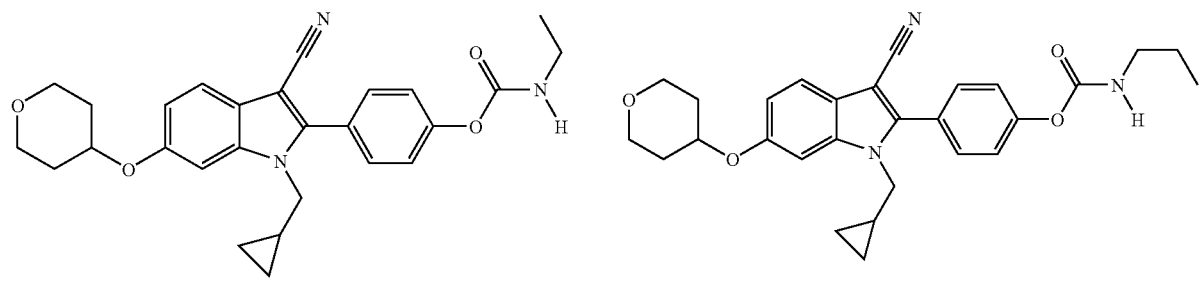
2780  2781
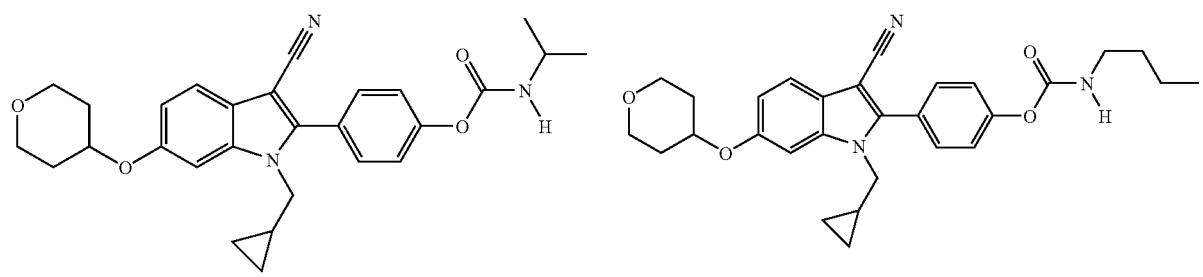
2782  2783
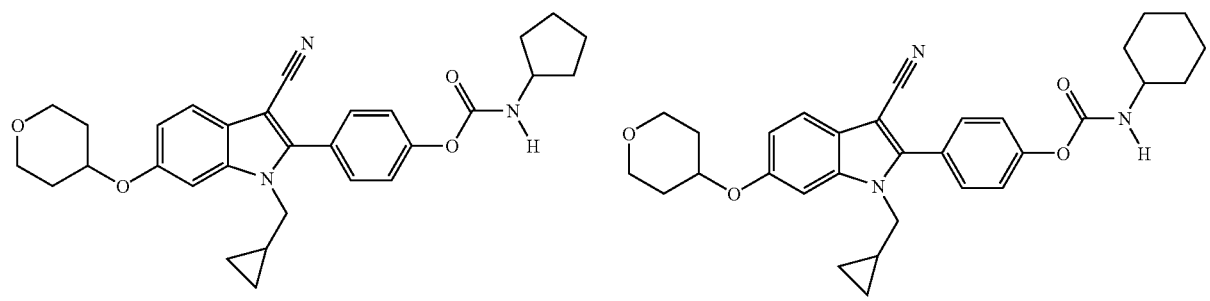
2784  2785
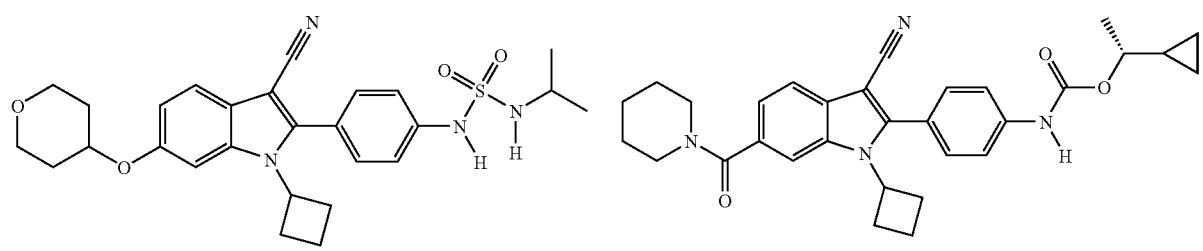
2786  2787
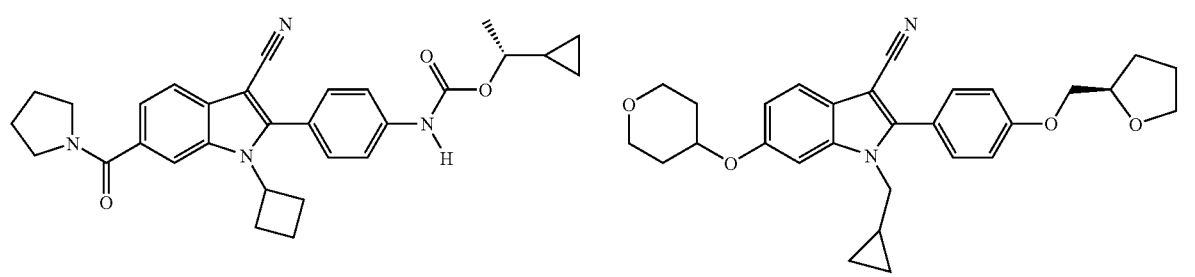
2788  2789

-continued
2790
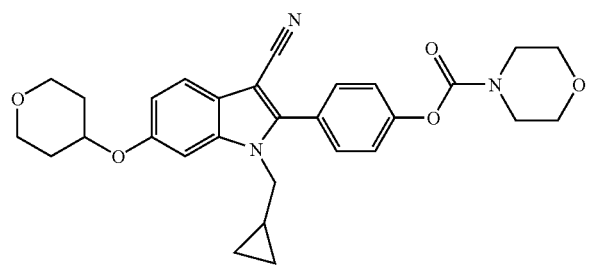
2791
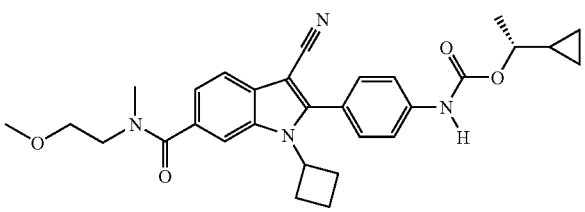
2792
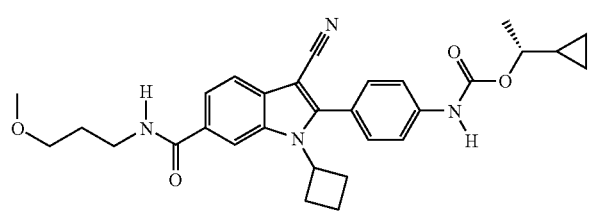
2793
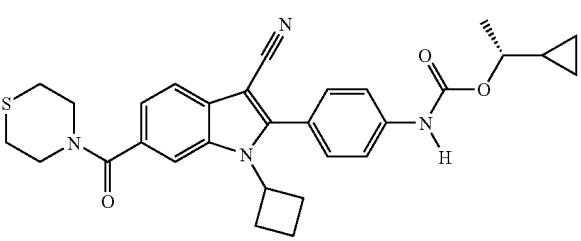
2794
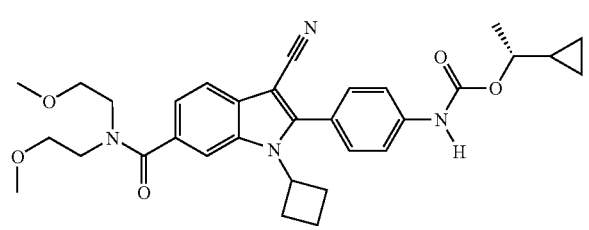
2795
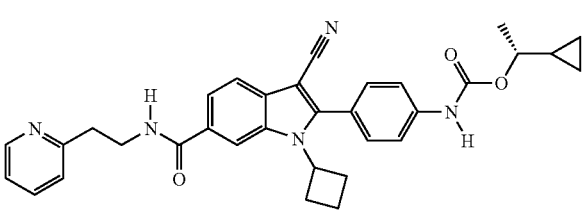
2797
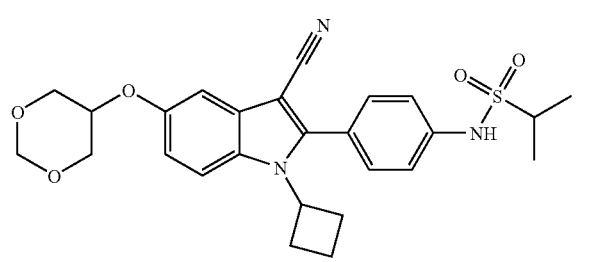
2798
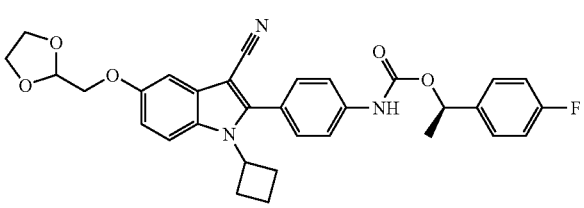
2799
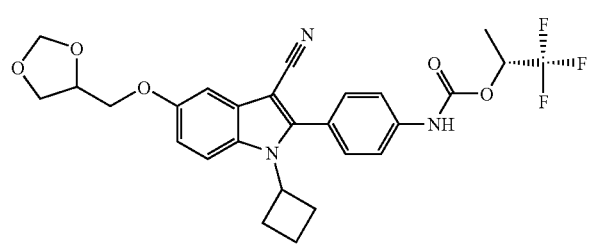
2800
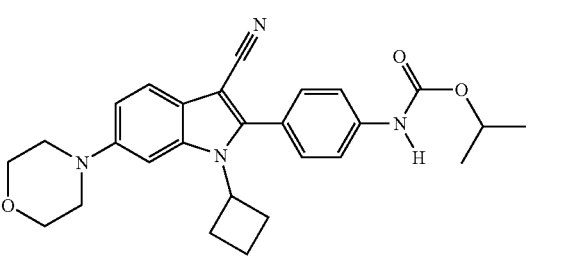
2801
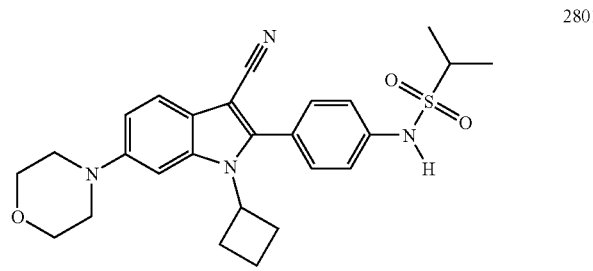
2802
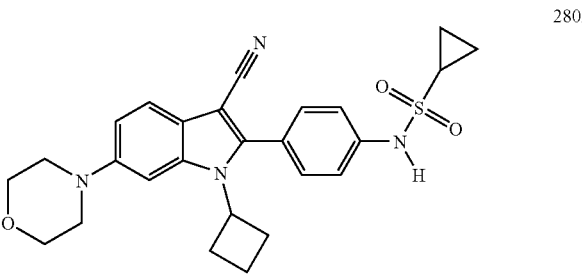

-continued
2803
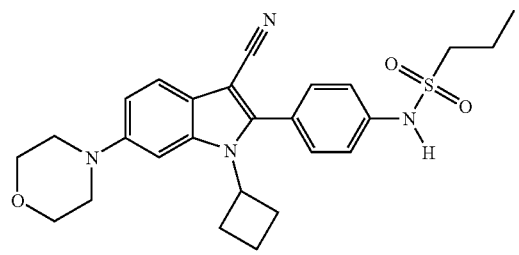
2805
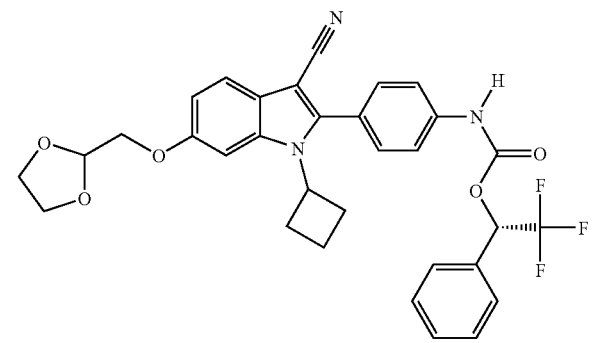
2806
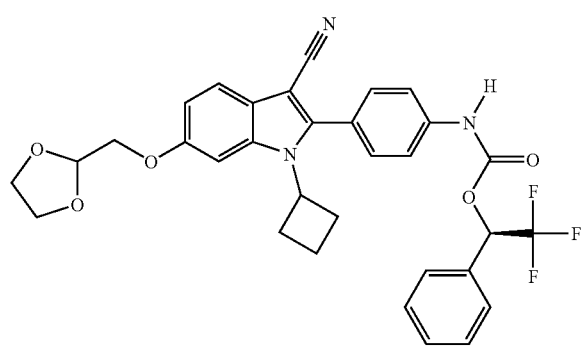
2807
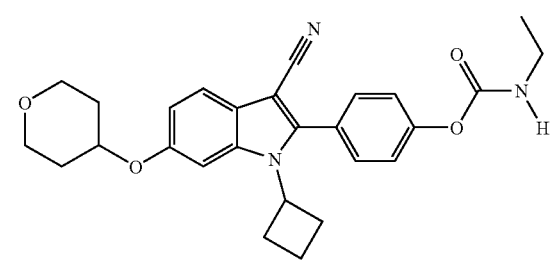
2808
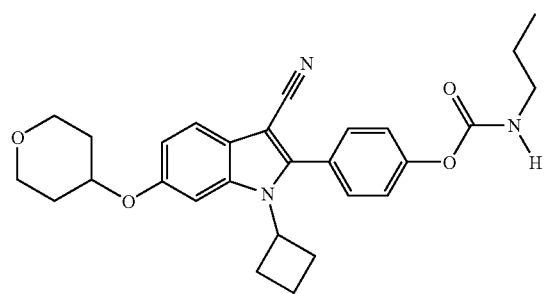
2809
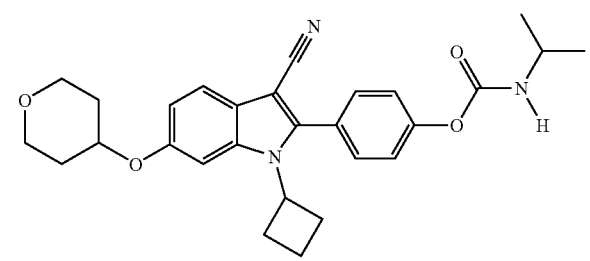
2810
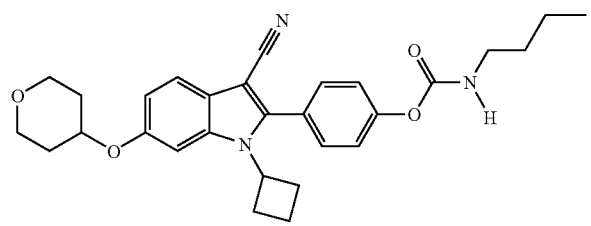
2811
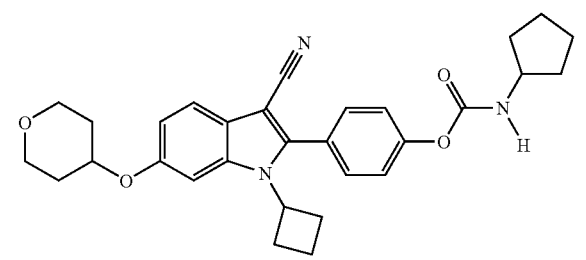
2812
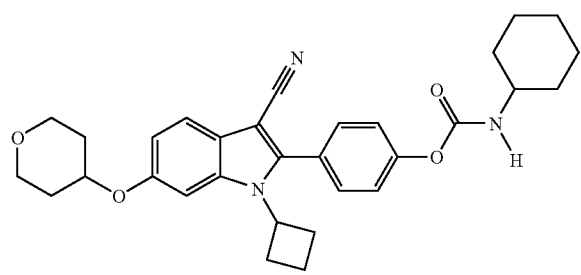
22813
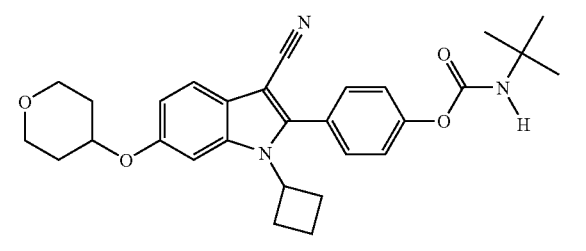

-continued
2814
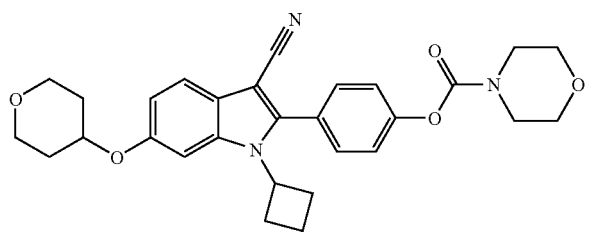
2815
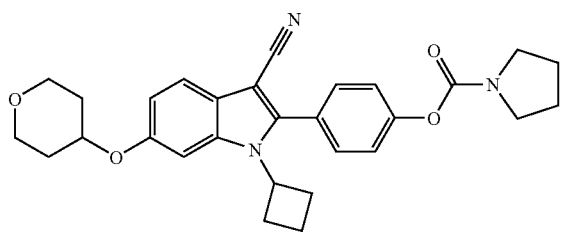
2816
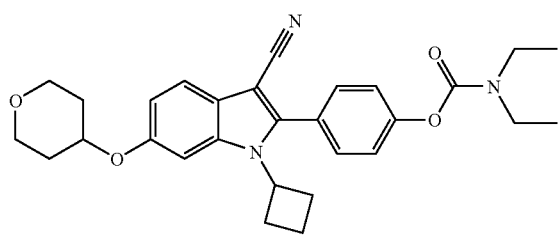
2817
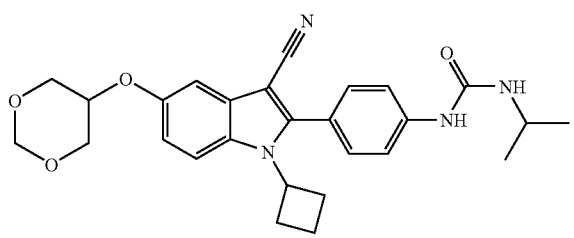
2818
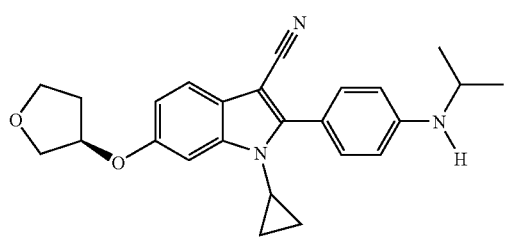
2819
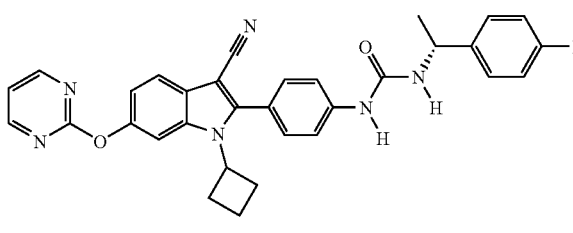
2820
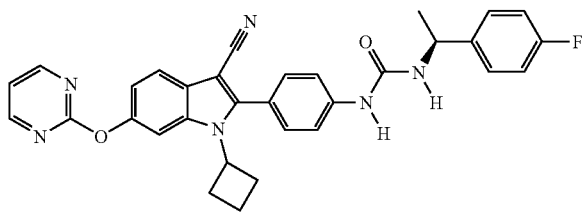
2821
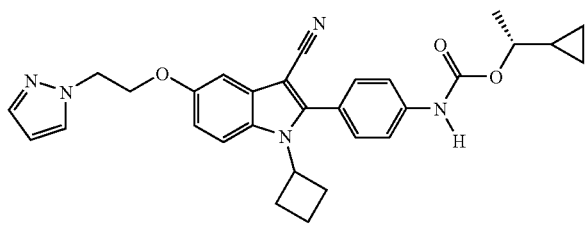
2822
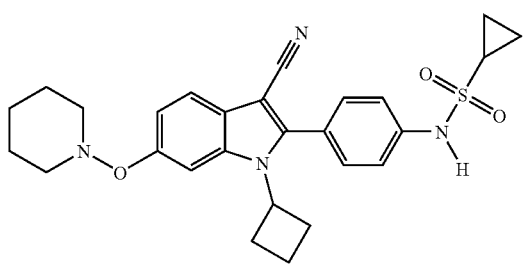
2823
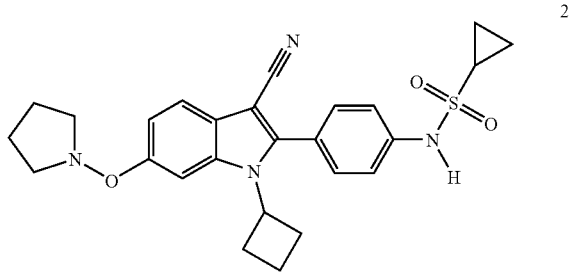
2824
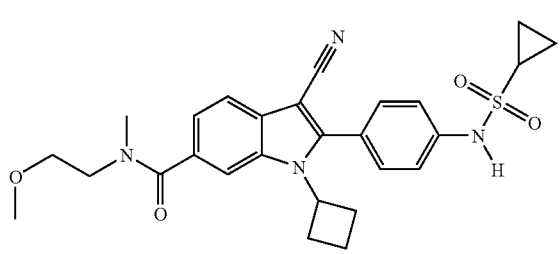
2825
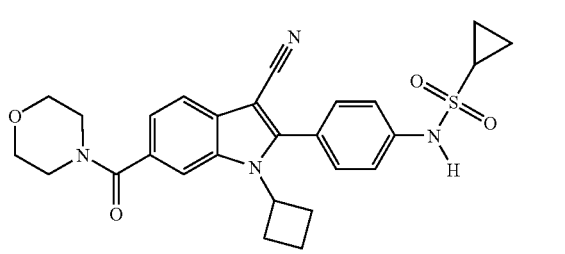

-continued
2826
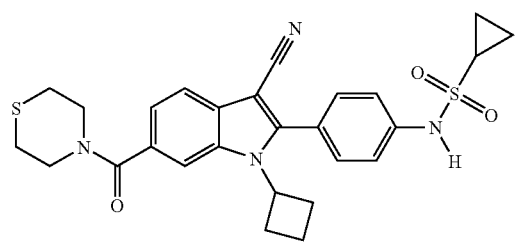
2828
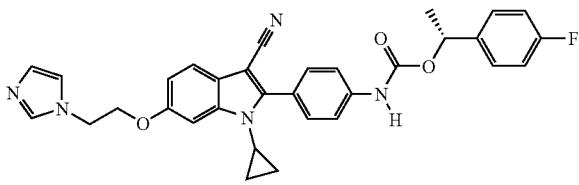
2829
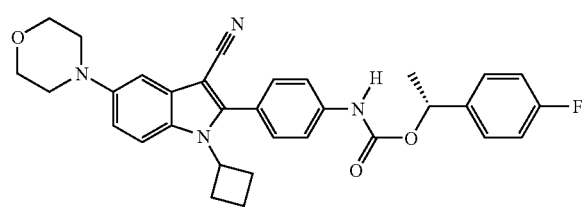
2830
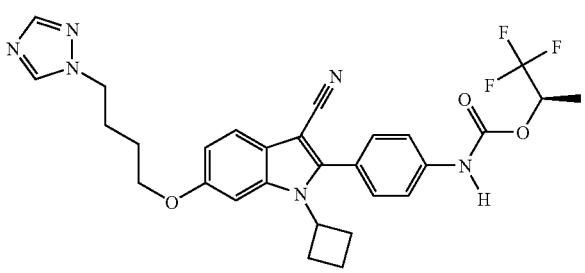
2831
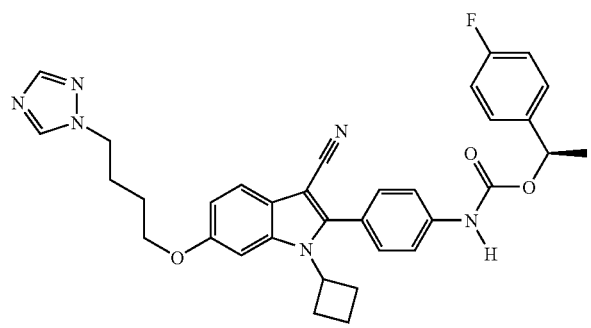
2832
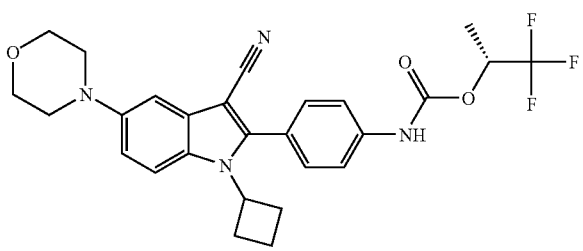
2833
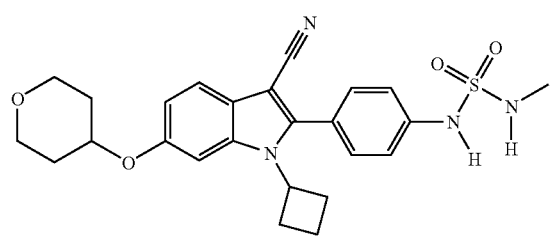
2834
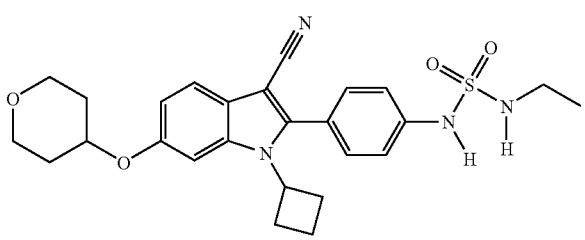
2835
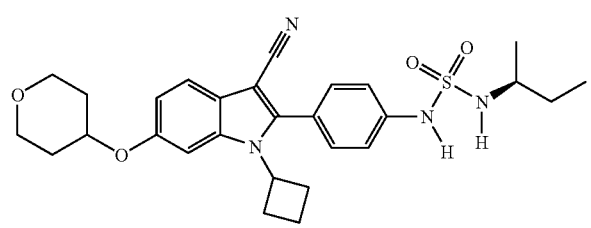
2836
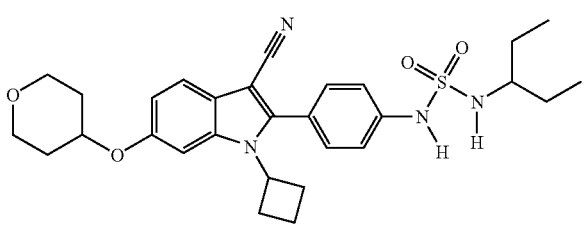

-continued
2837
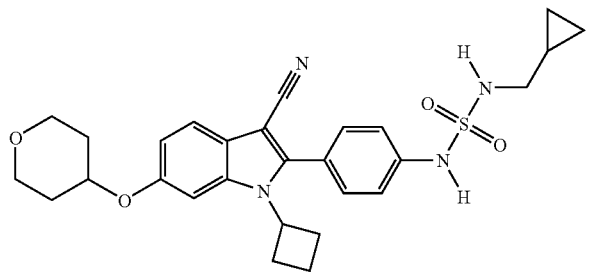
2838
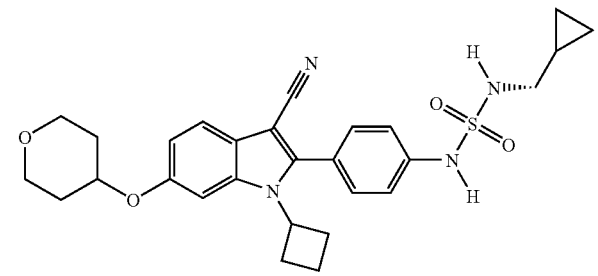
2839
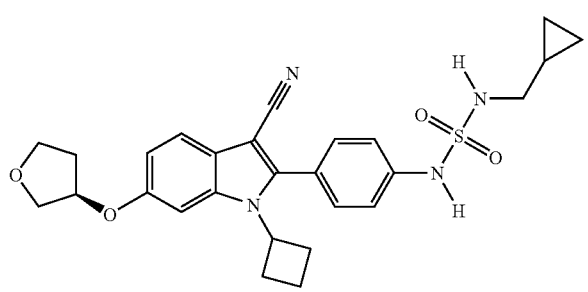
2840
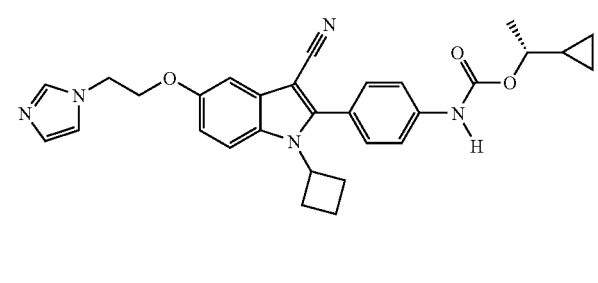
2842
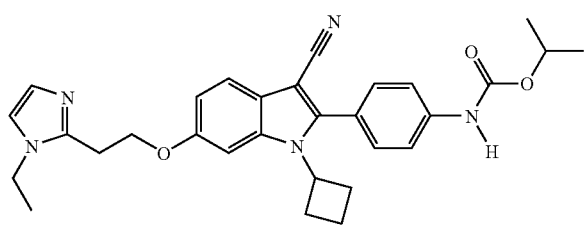
2843
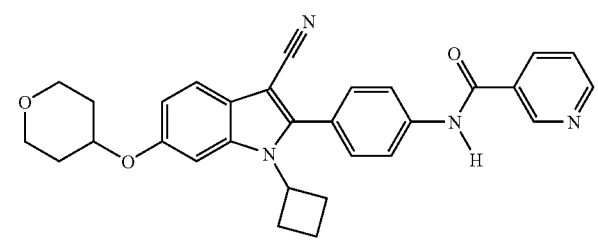
2844
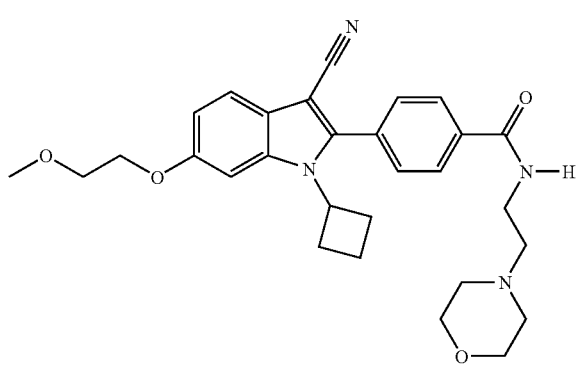
2845
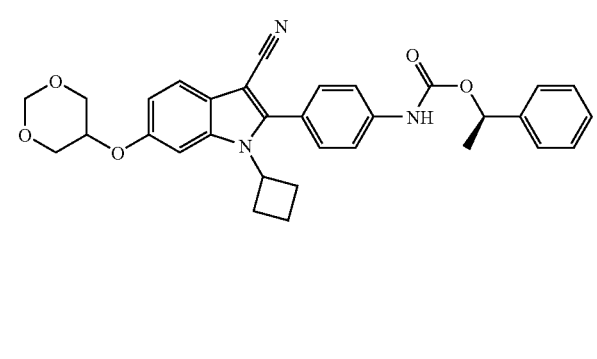
2846
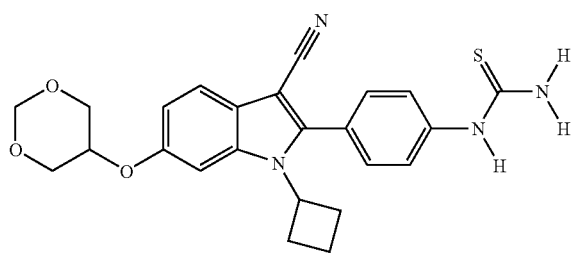
2847
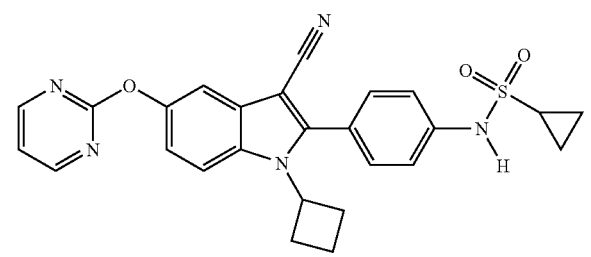

-continued
| 2848 | 2849 |
|---|---|
| 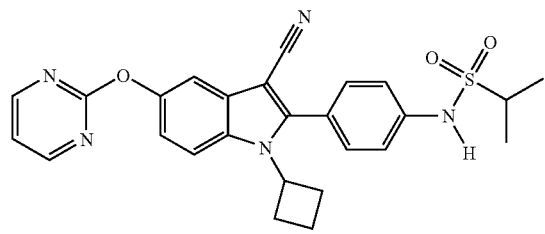 | 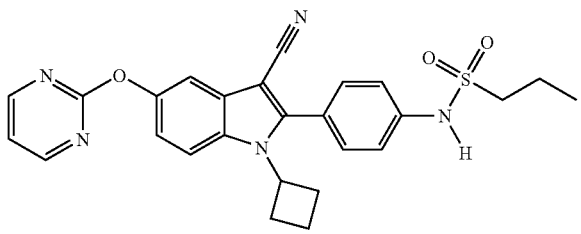 |
| 2850 | 2851 |
| 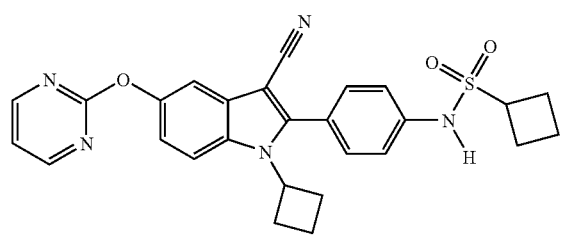 | 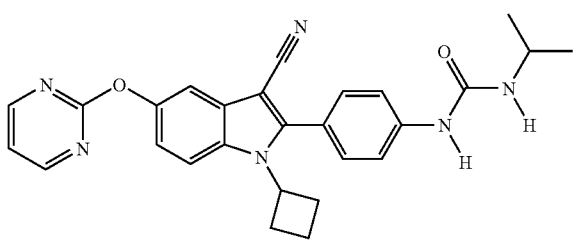 |
| 2852 | 2853 |
| 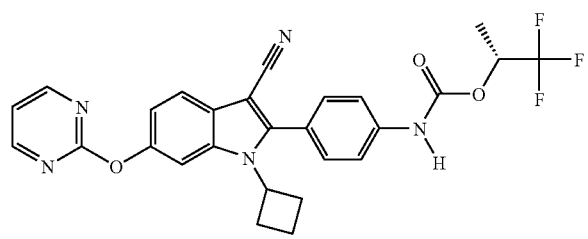 | 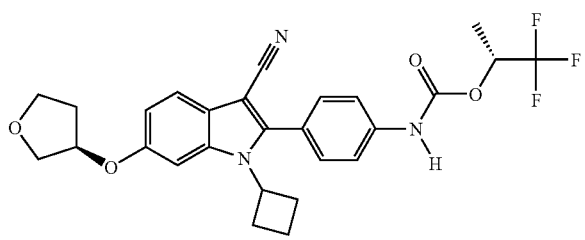 |
| 2854 | 2855 |
| 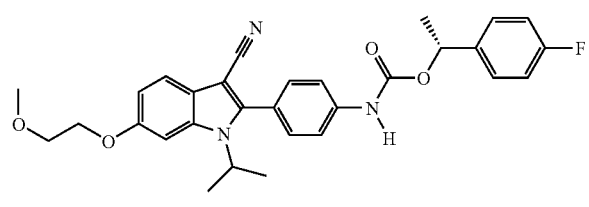 | 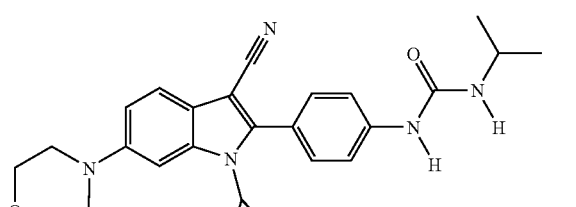 |
| 2856 | 2857 |
| 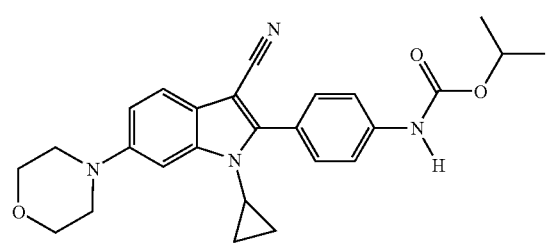 | 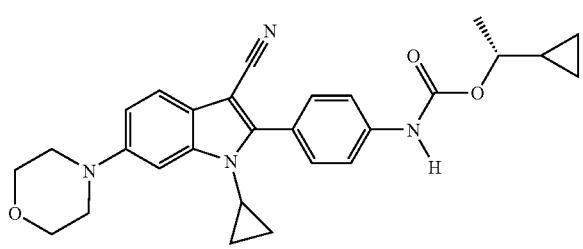 |
| 2858 | 2859 |
| 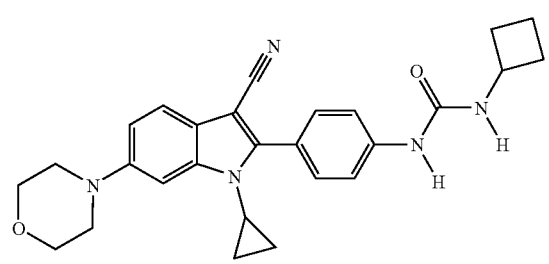 | 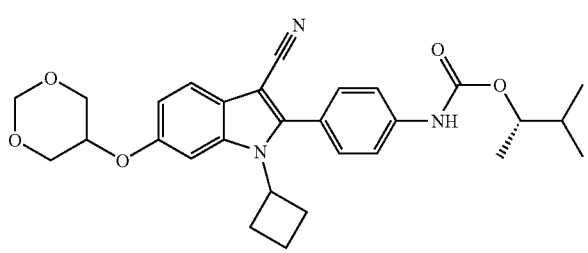 |

-continued
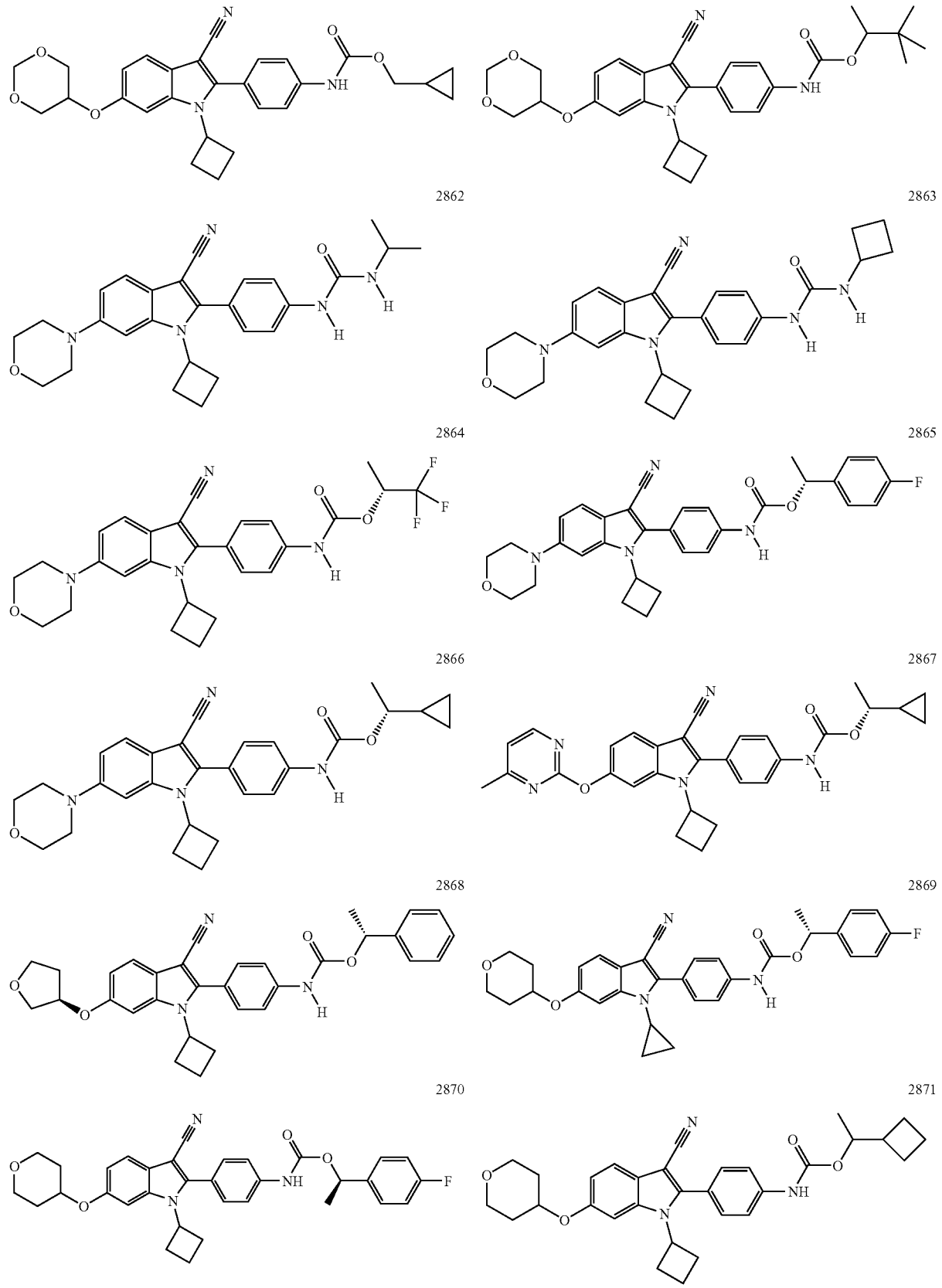

-continued
| | |
|---|---|
| 2872 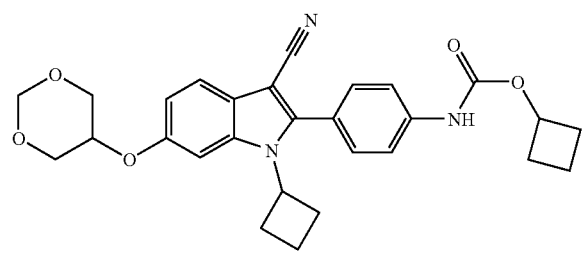 | 2873 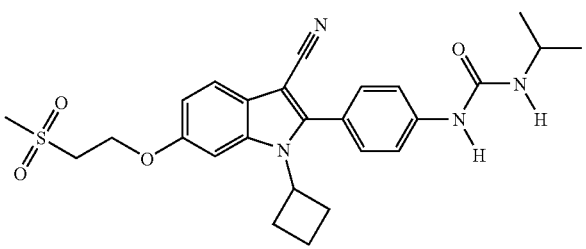 |
| 2874 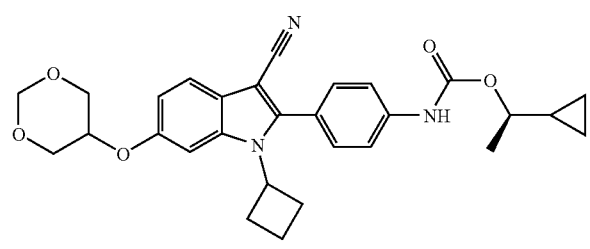 | 2875 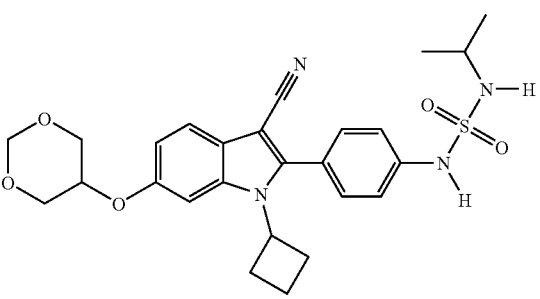 |
| 2876 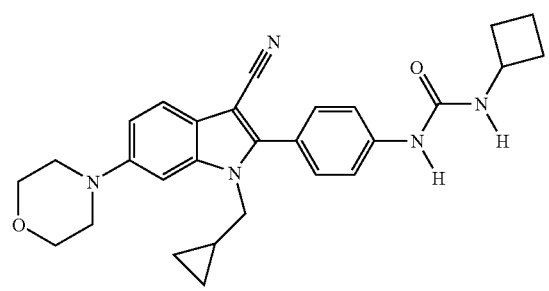 | 2877 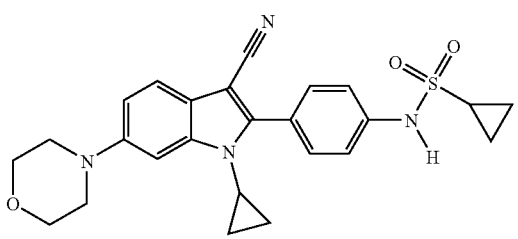 |
| 2878 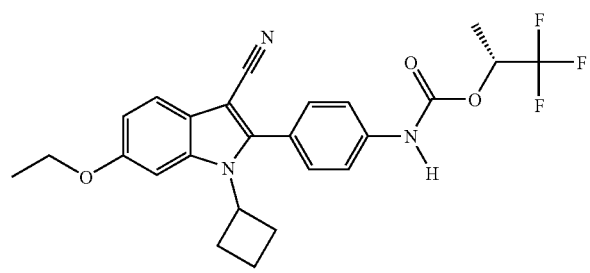 | 2879 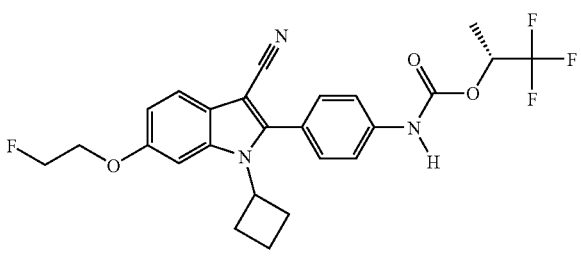 |
| 2880 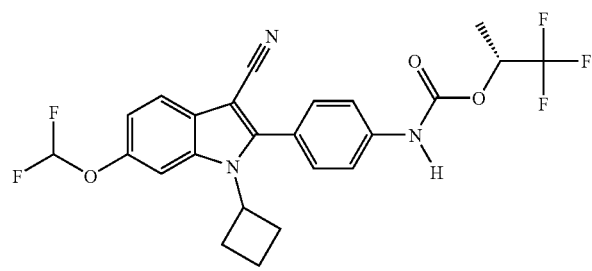 | 2881 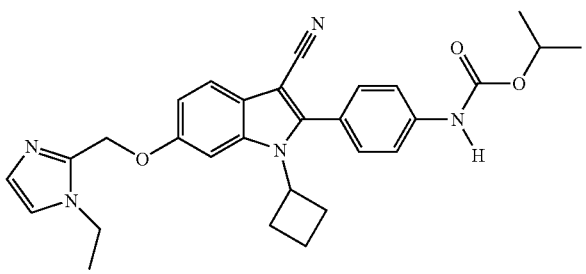 |

-continued
2882
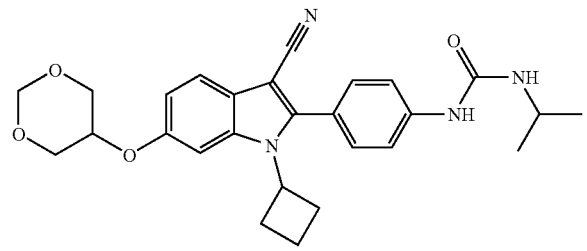
2883
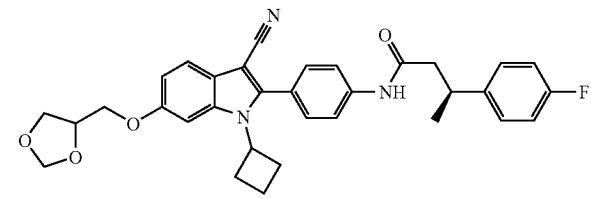
2884
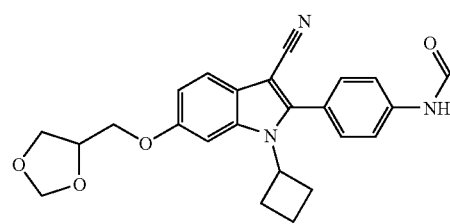
2885
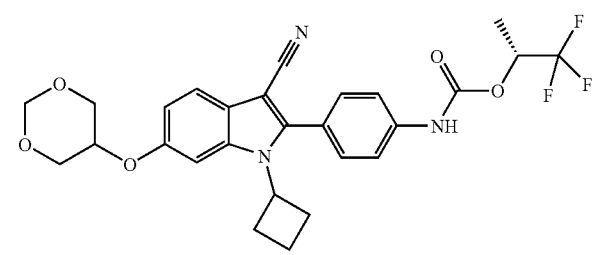
2886
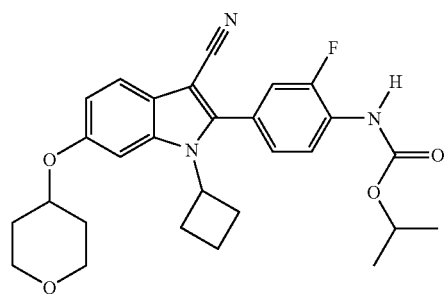
2887
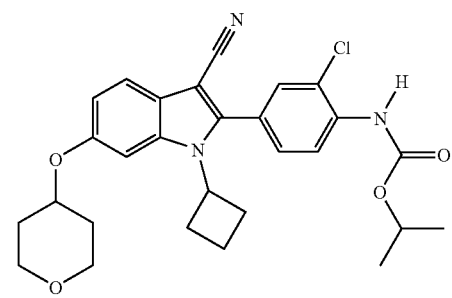
2889
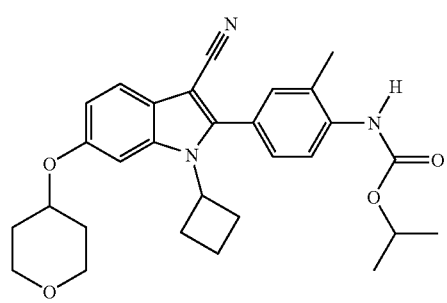
2890
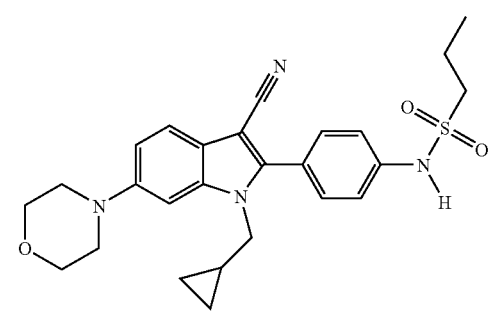
2891
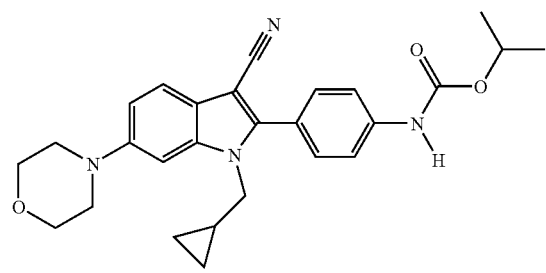
2892
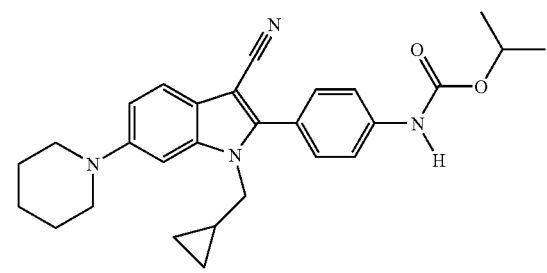

-continued
2893
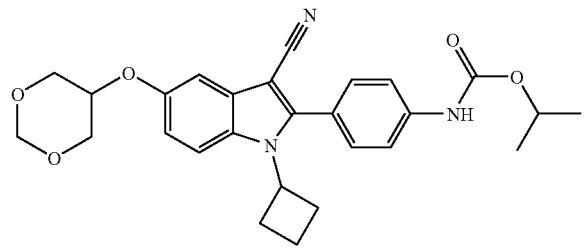
2894
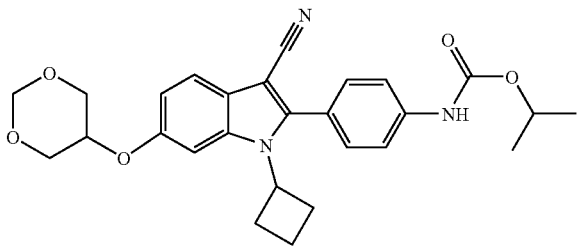
2895
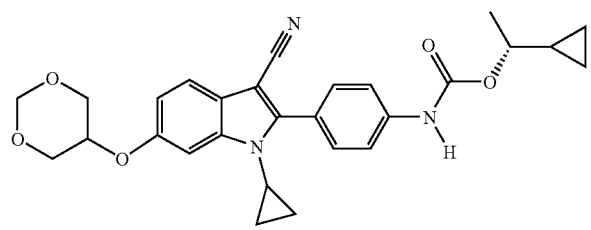
2896
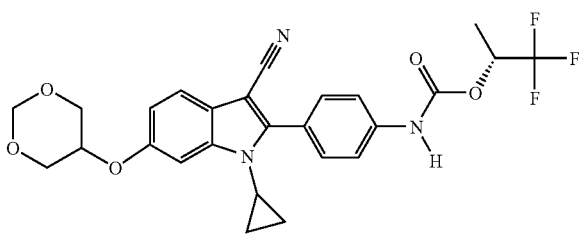
2897
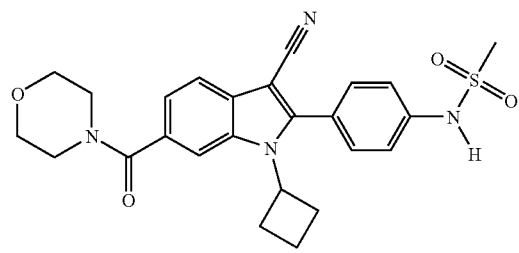
2898
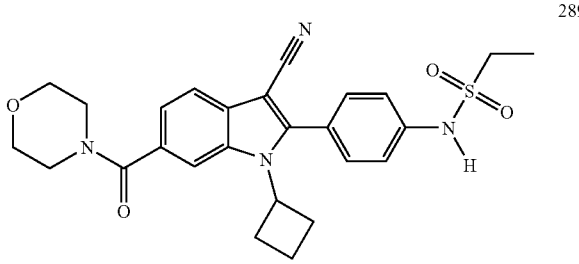
2899
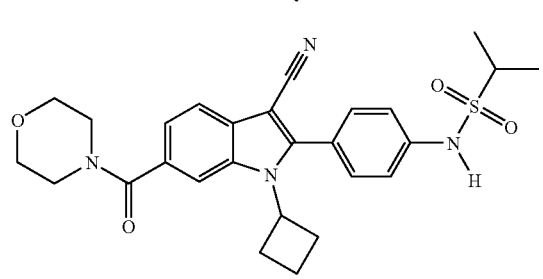
2900
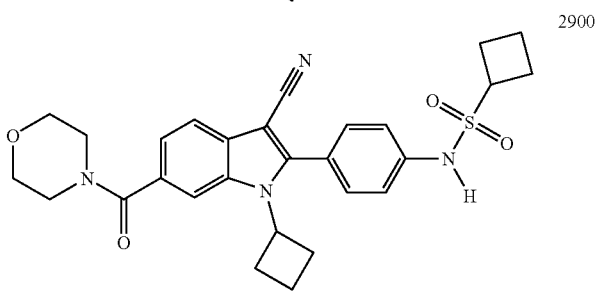
2901
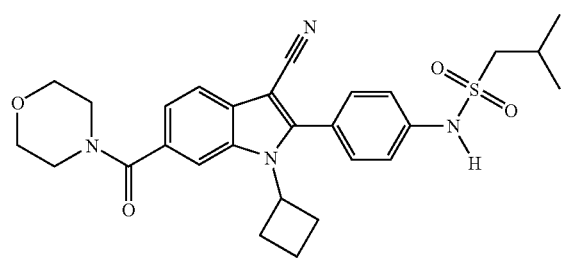
2902
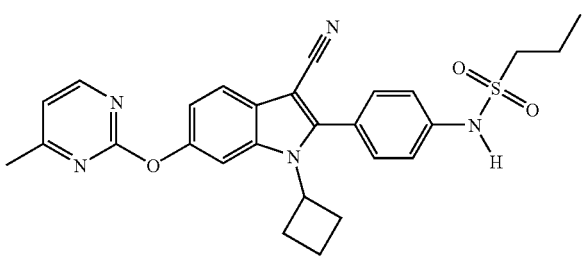
2903
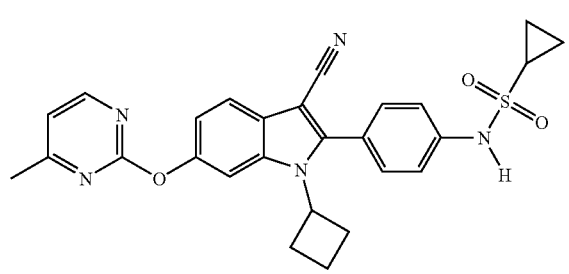
2904
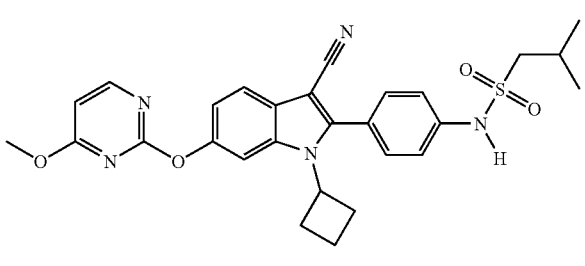

| 827 | 828 |
|---|---|
| 2905 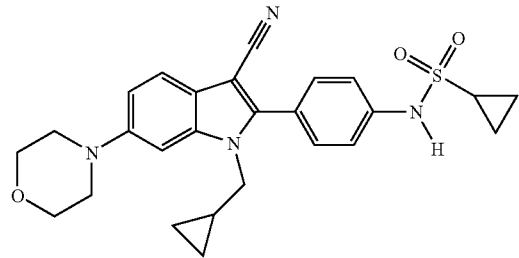 | 2906 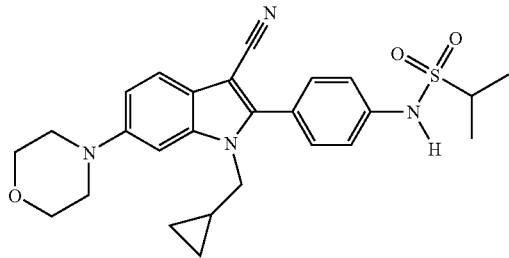 |
| 2907 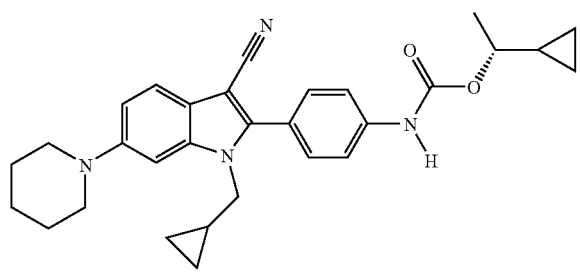 | 2908 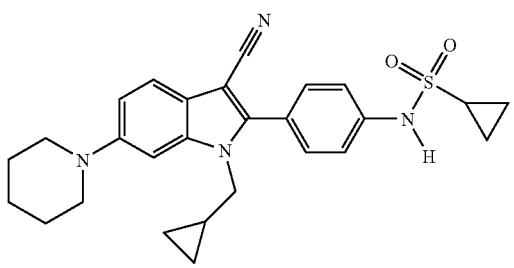 |
| 2909 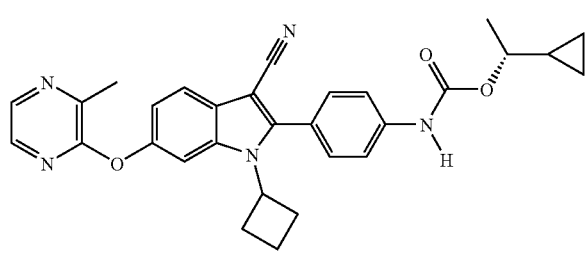 | 2910 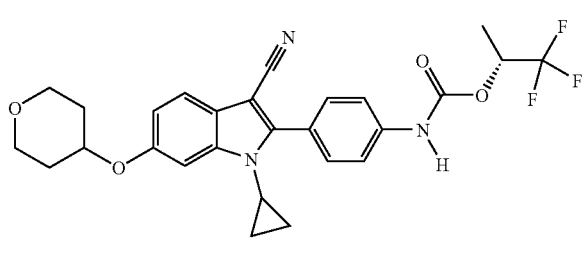 |
| 2911 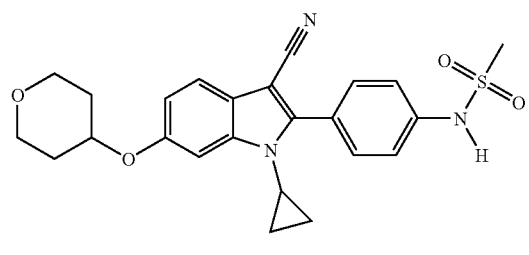 | 2912 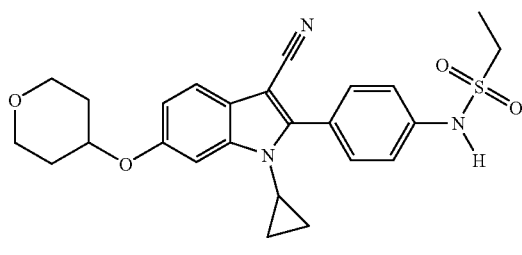 |
| 2913 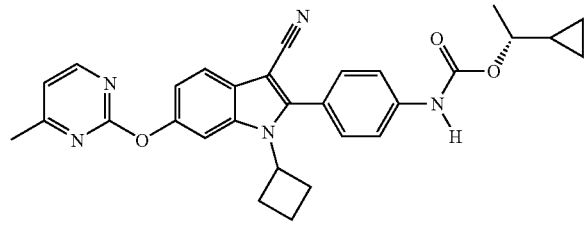 | 2914 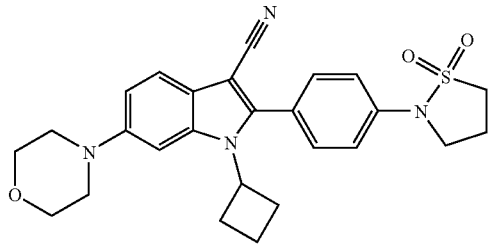 |
| 2915 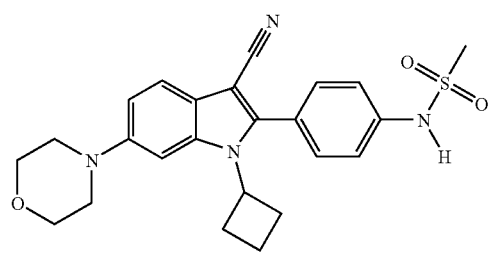 | 2916 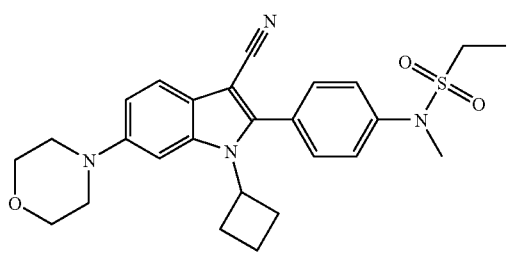 |

-continued
| 2917 | 2918 |
|---|---|
| 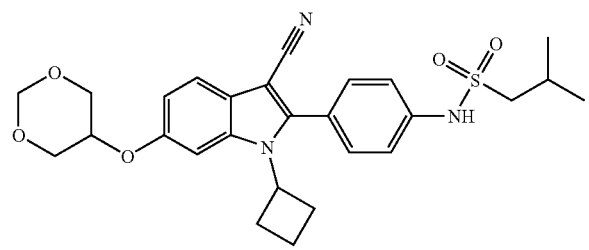 | 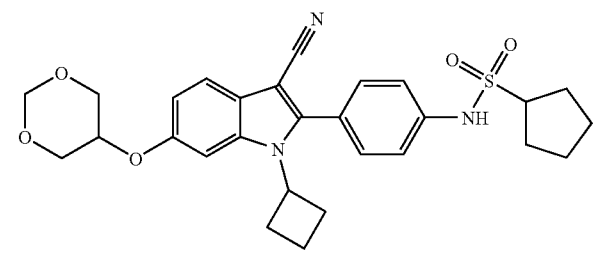 |
| 2919 | 2920 |
| 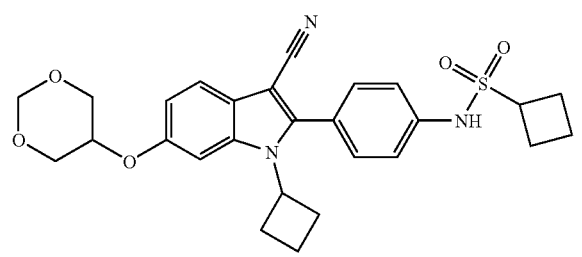 | 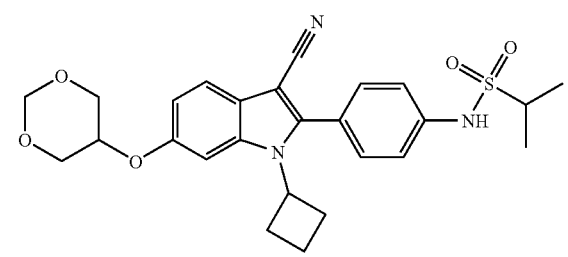 |
| 2918 | 2919 |
| 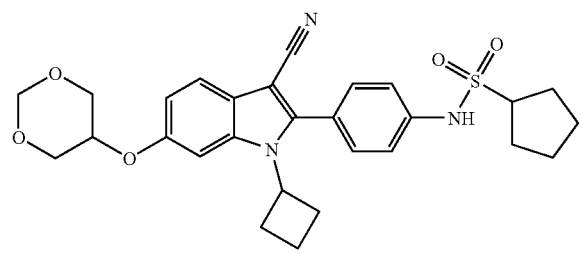 | 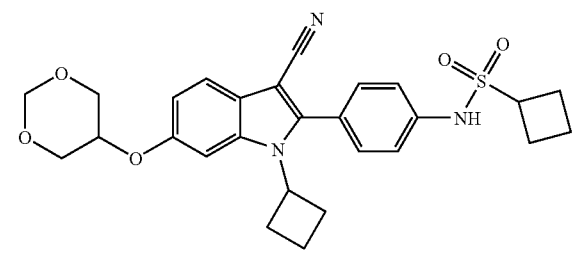 |
| 2920 | 2921 |
| 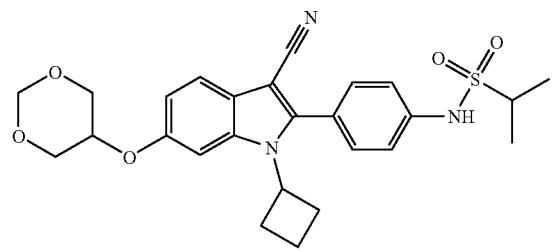 | 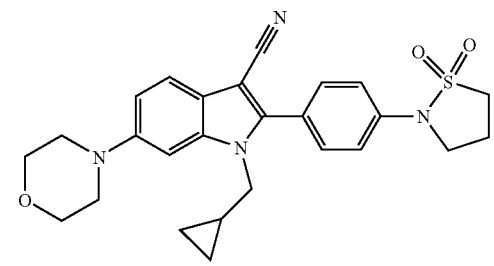 |
| 2922 | 2923 |
| 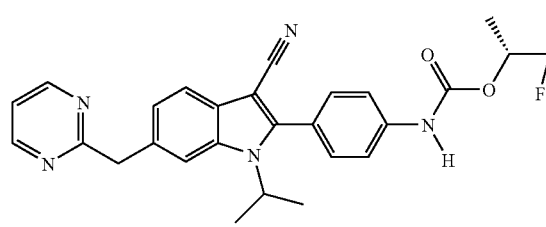 | 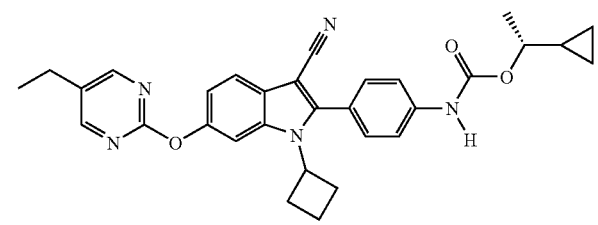 |

-continued
2924
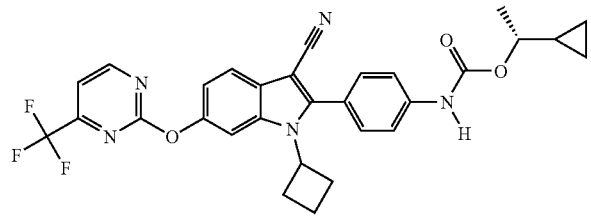
2925
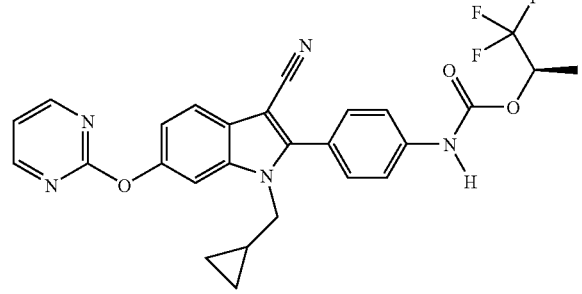
2926
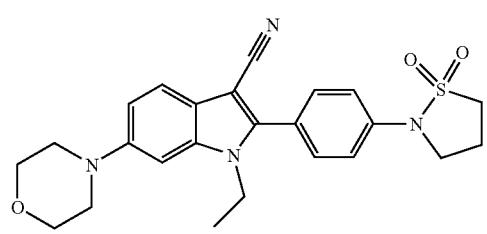
2927
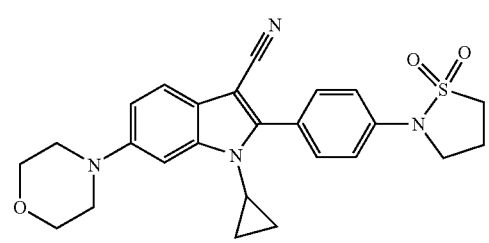
2928
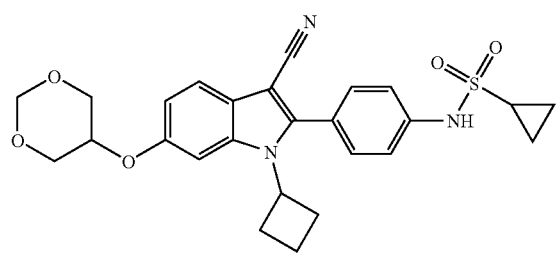
2929
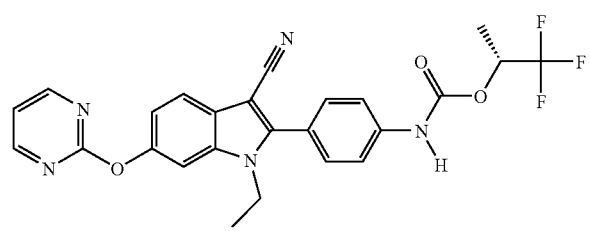
2930
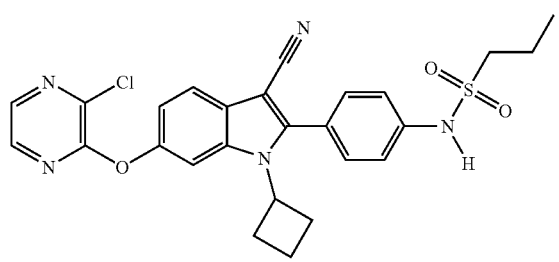
2931
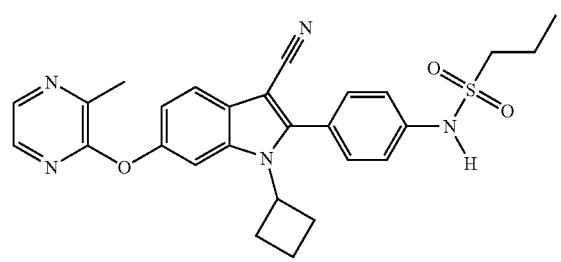
2932
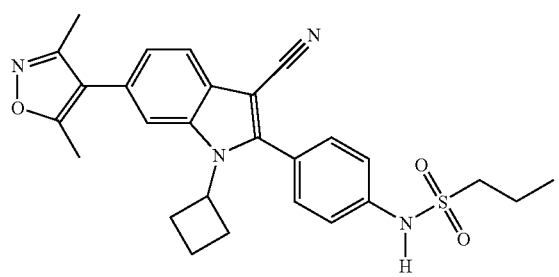
2933
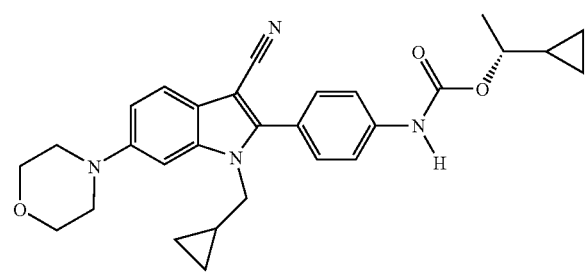

-continued
2934
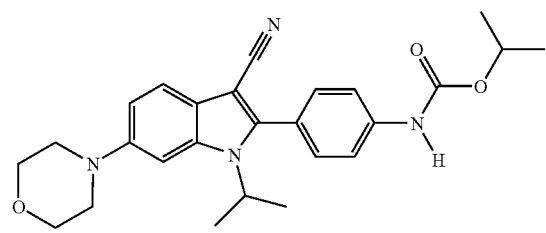
2935
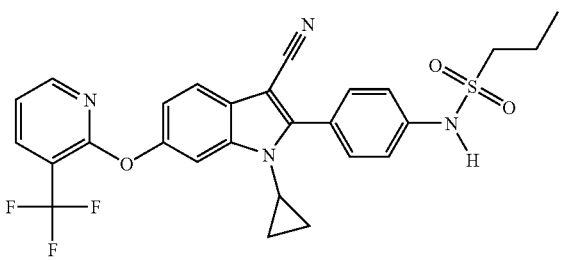
2936
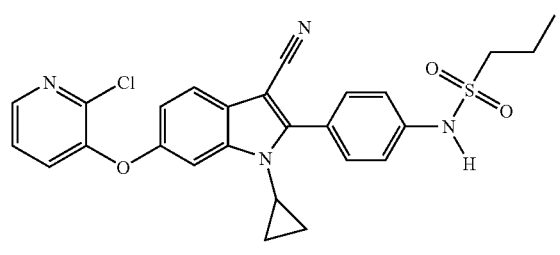
2937
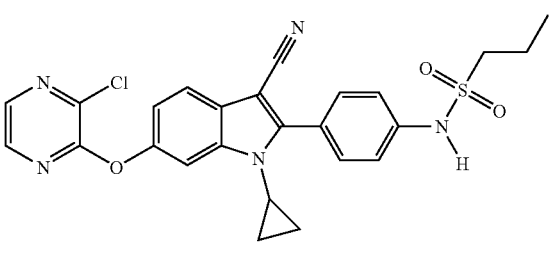
2938
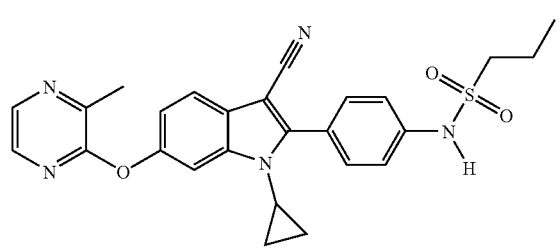
2939
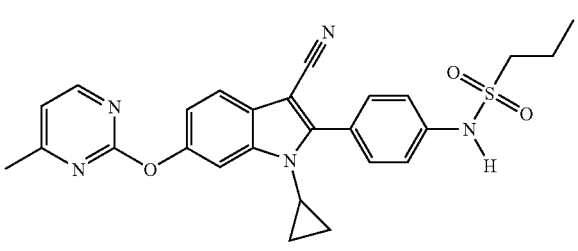
2940
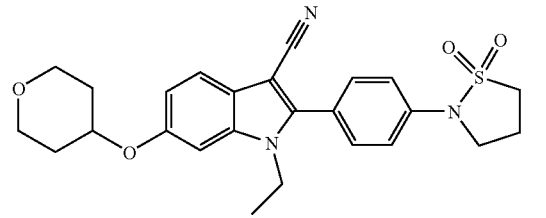
2941
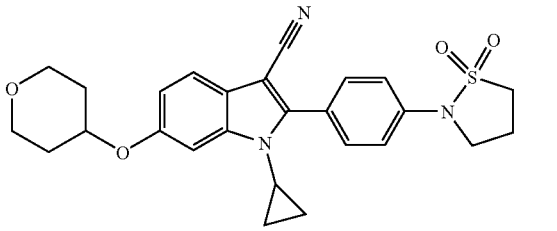
2942
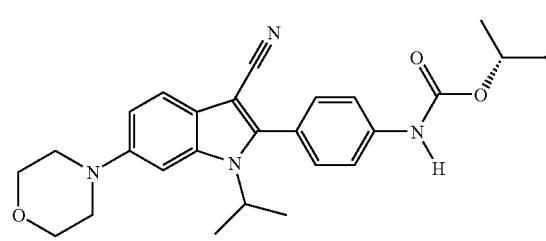
2943
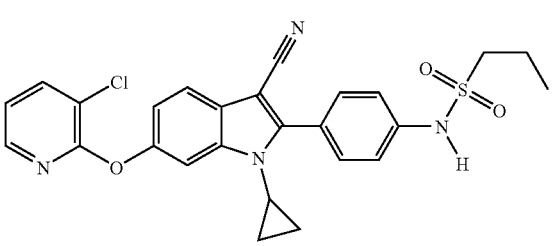
2944
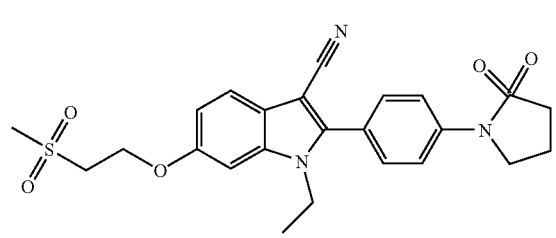
2945
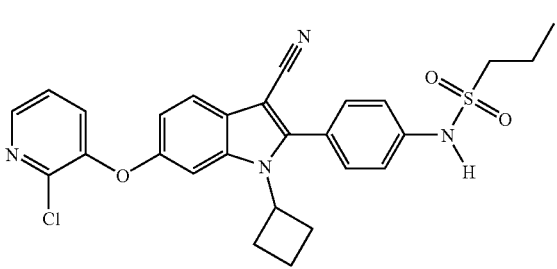

835 836
-continued
| 2946 | 2947 |
|---|---|
| 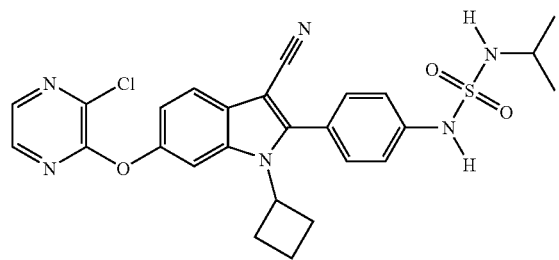 | 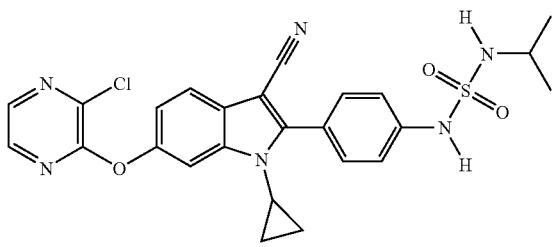 |
| 2948 | 2949 |
| 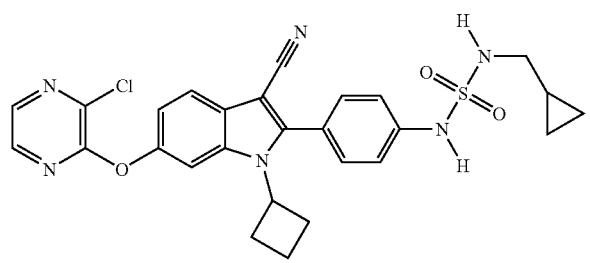 | 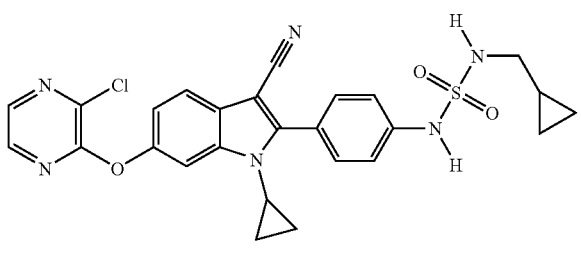 |
| 2950 | 2951 |
| 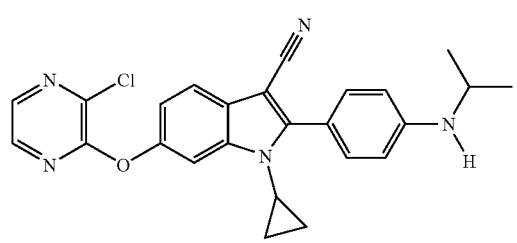 | 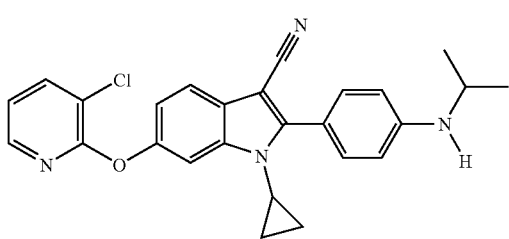 |
| 2952 | 2953 |
| 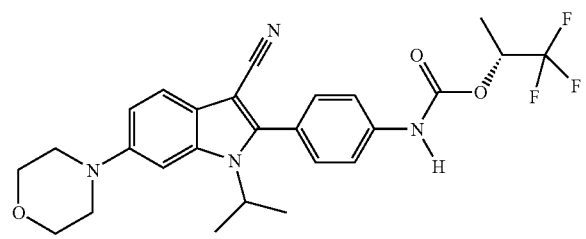 | 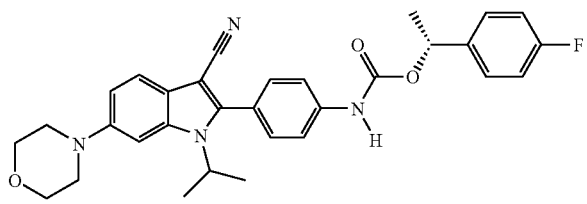 |
| 2954 | 2955 |
| 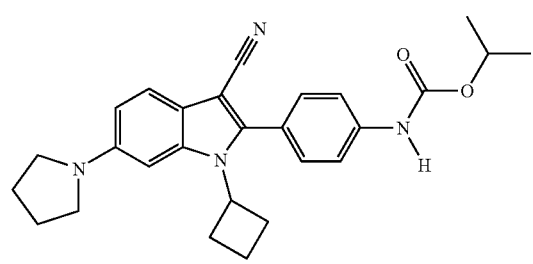 | 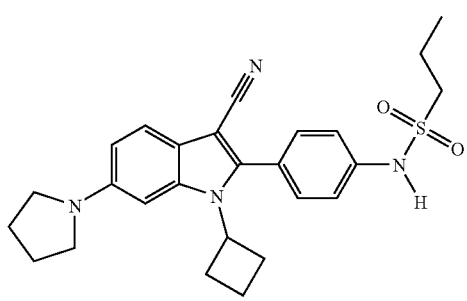 |
| 2956 | 2957 |
| 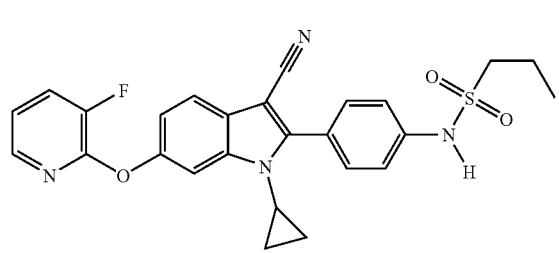 | 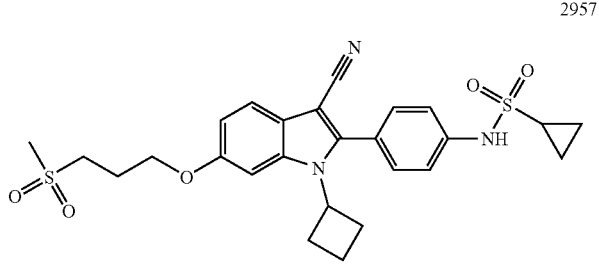 |

-continued
2958
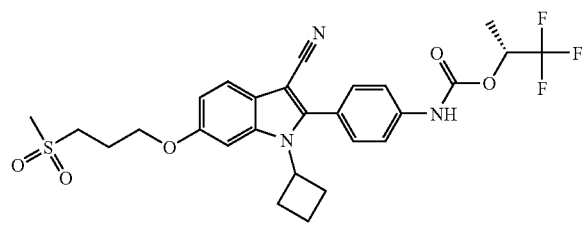
2959
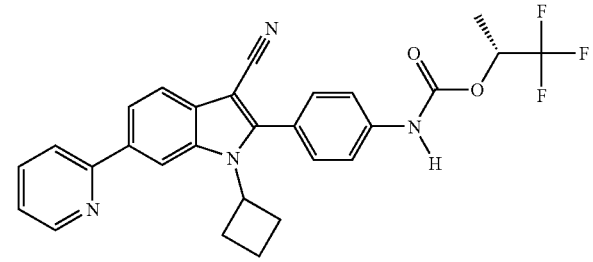
2960
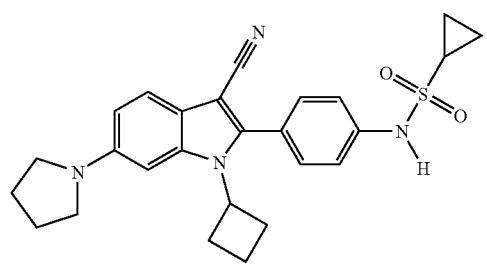
2961
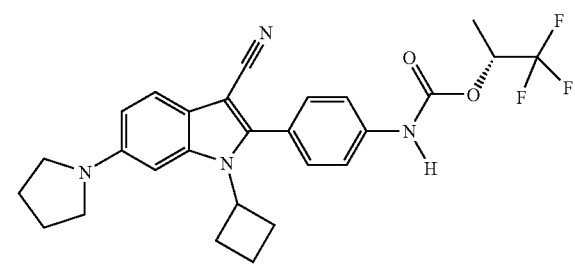
2962
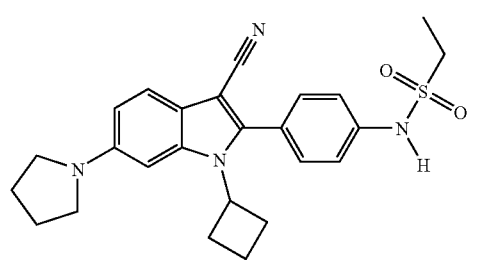
2963
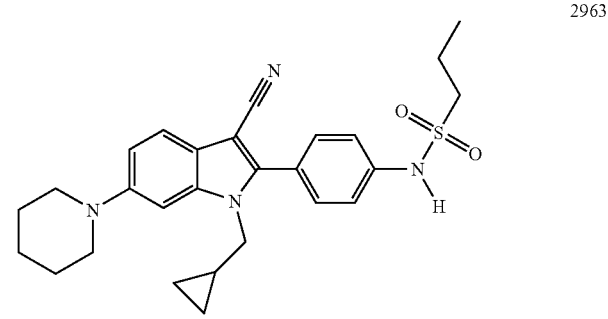
2964
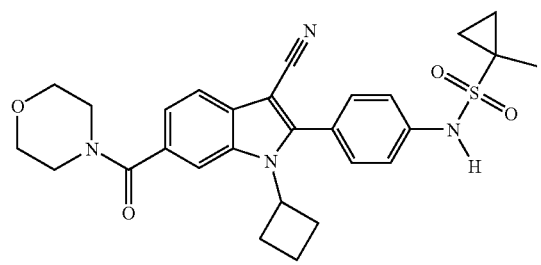
2965
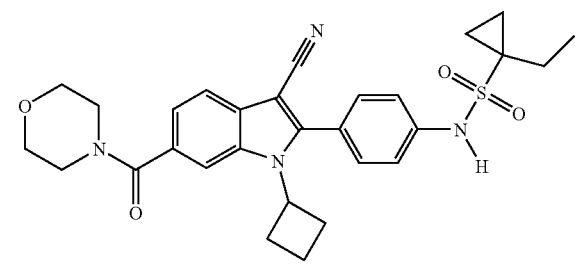
2966
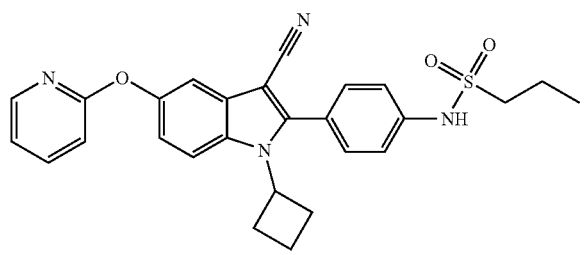
2967
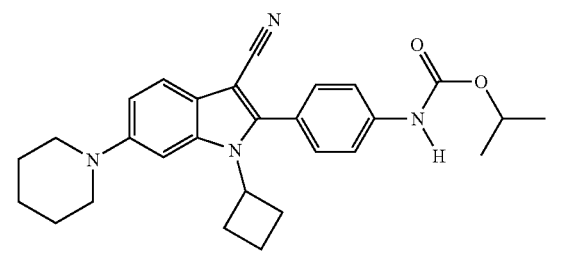

-continued
| 2968 | 2969 |
|---|---|
| 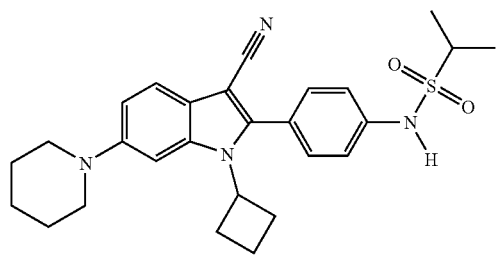 | 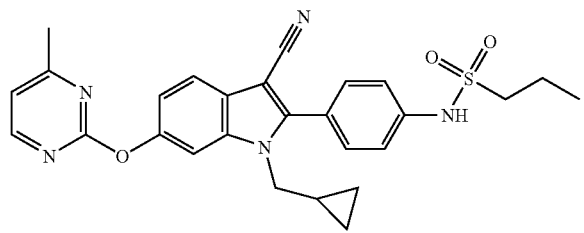 |
| 2970 | 2971 |
| 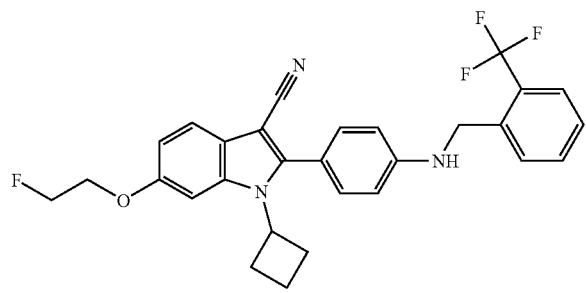 | 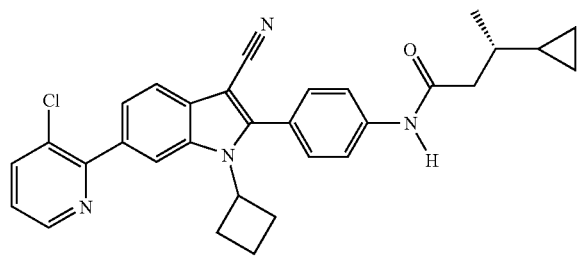 |
| 2972 | 2973 |
| 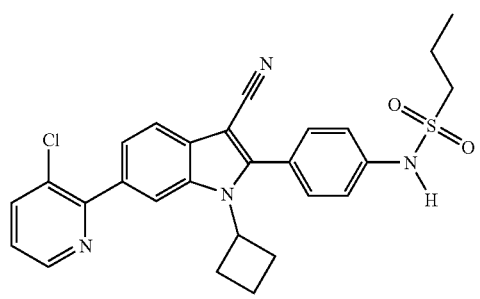 | 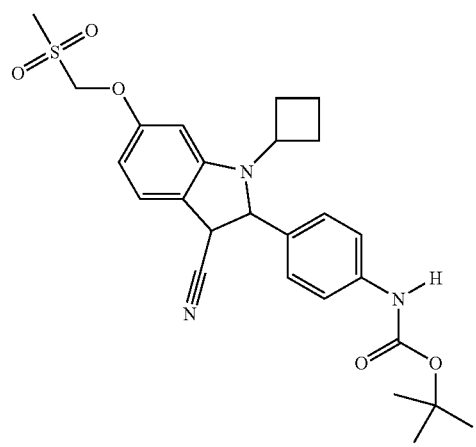 |
| 2974 | 2975 |
| 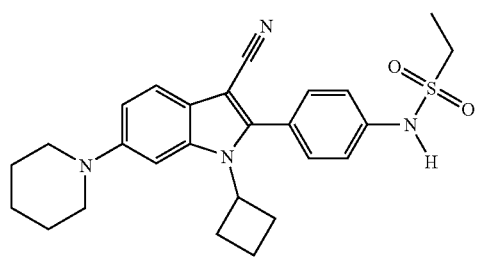 | 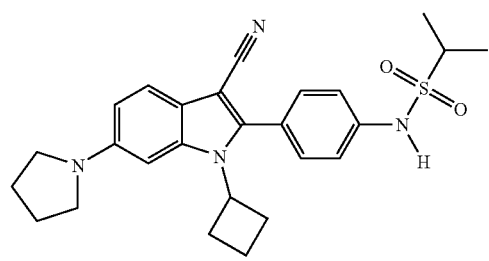 |
| 2976 | 2977 |
| 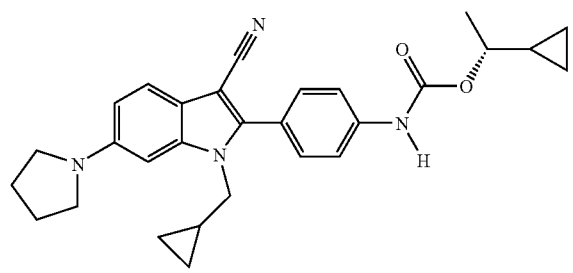 | 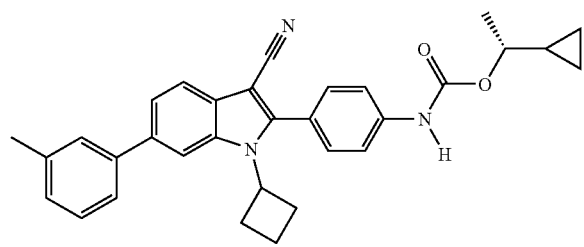 |

-continued
2978
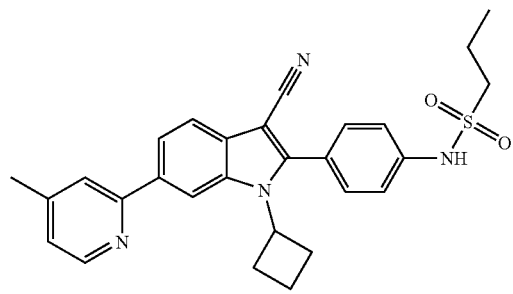
2979
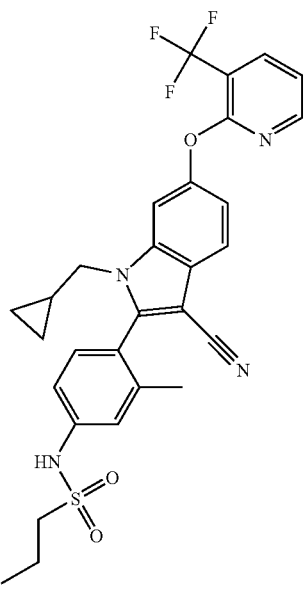
2980
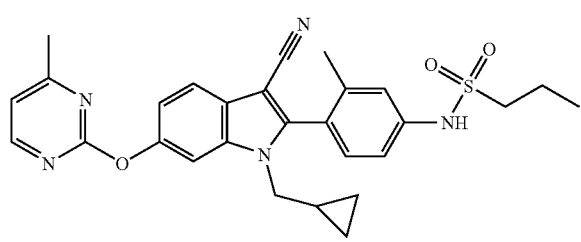
2981
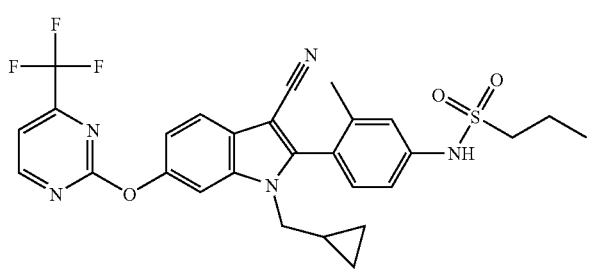
2982
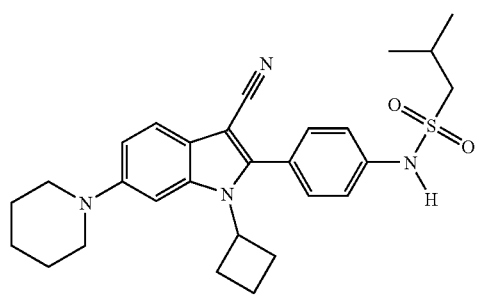
2983
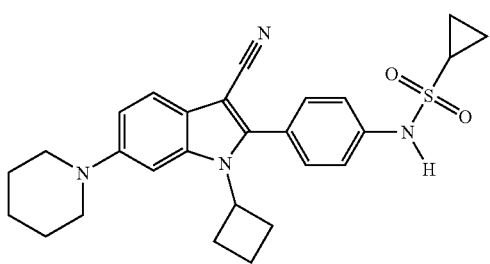
2984
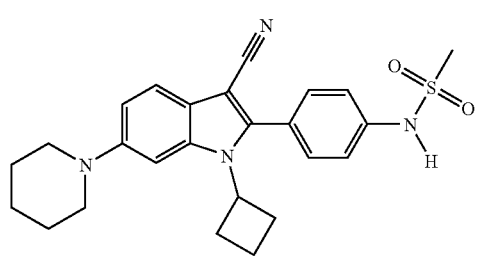
2985
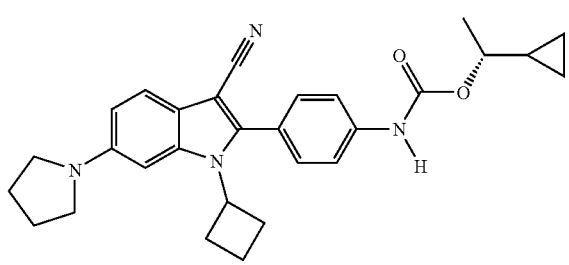

-continued
| 843 | 844 |
|---|---|
| 2986 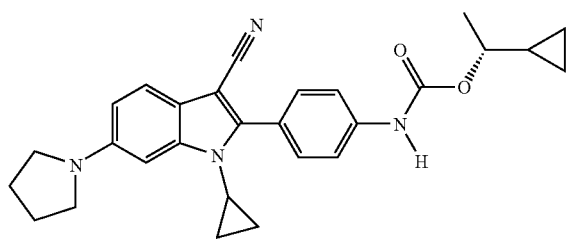 | 2987 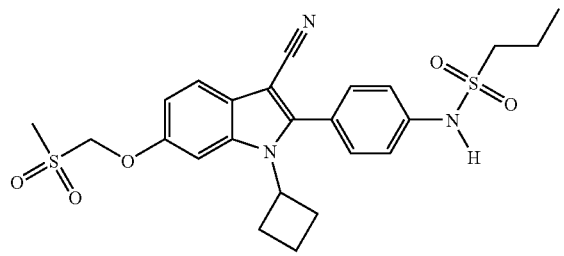 |
| 2988 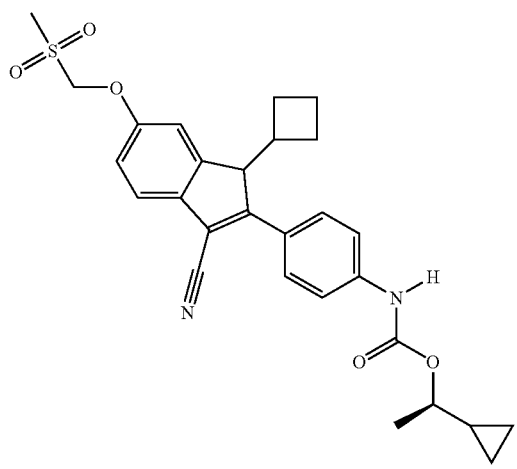 | 2989 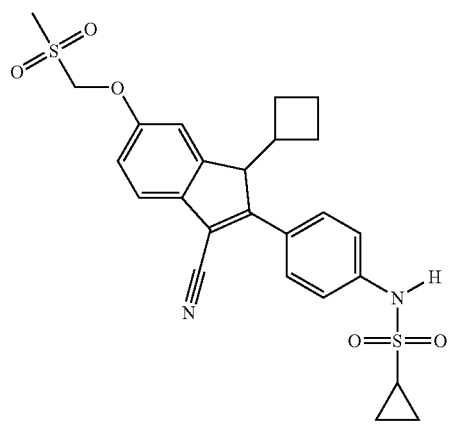 |
| 2990 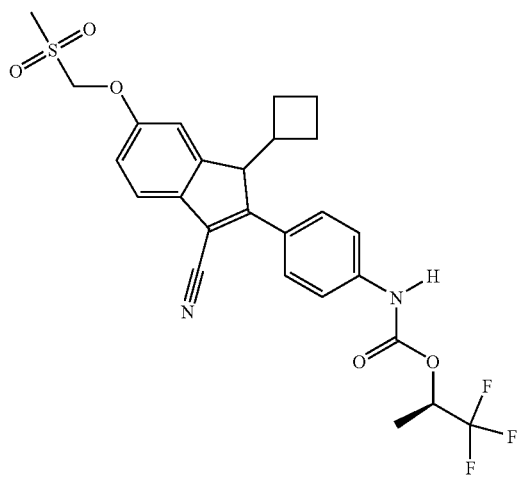 | 2991 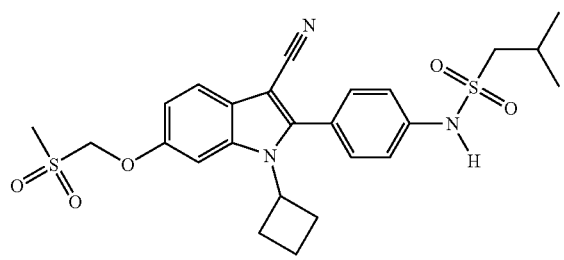 |

-continued
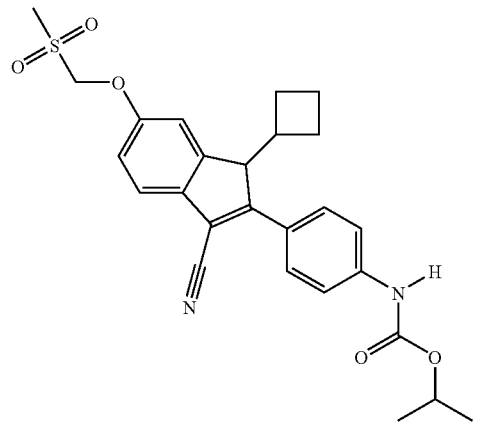
2992
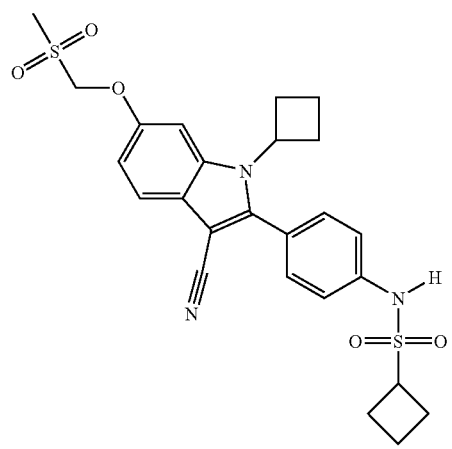
2993
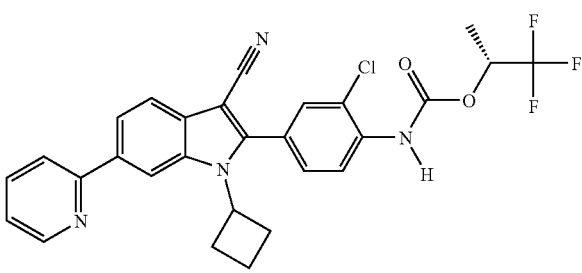
2994
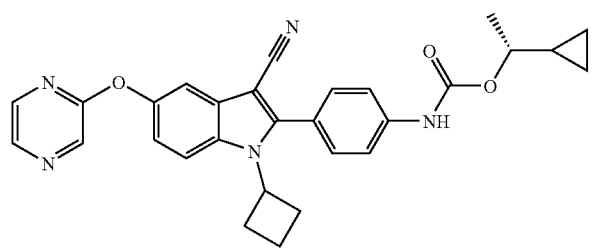
2995
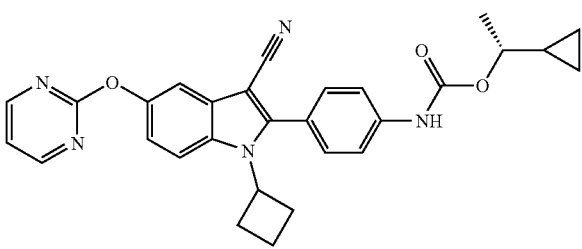
2996
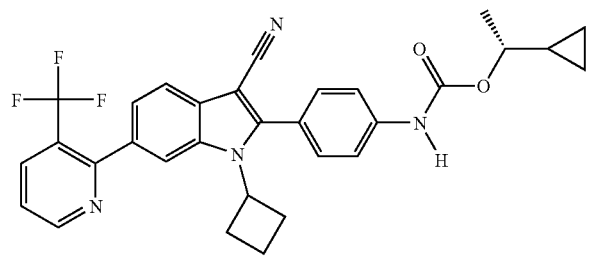
2997
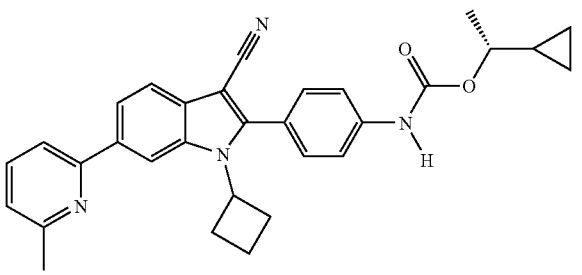
2998

-continued
2999
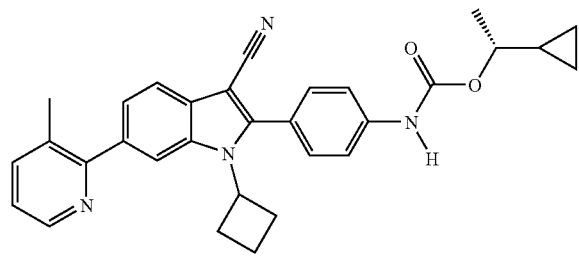
3000
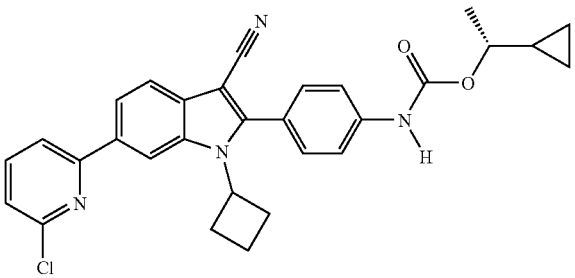
3001
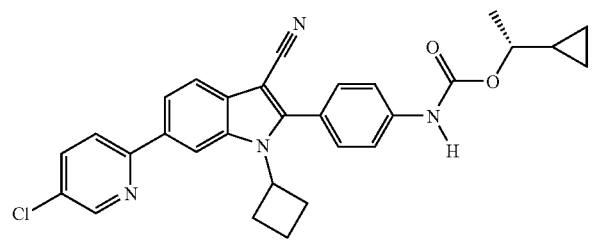
3002
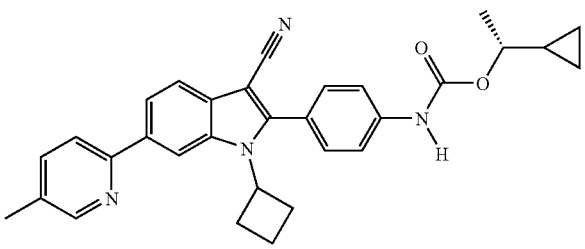
3003
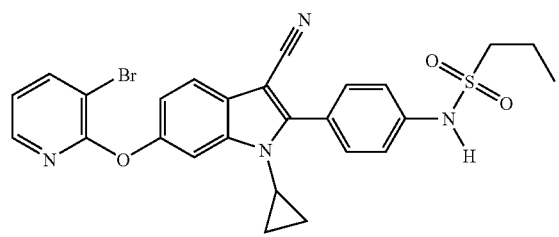
3004
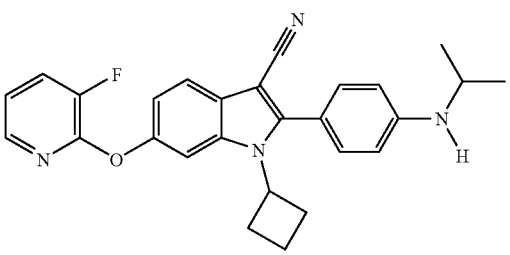
3005
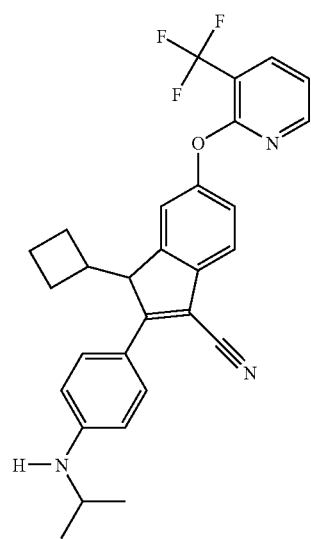
3006
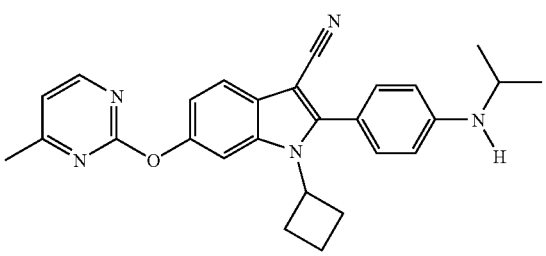

-continued
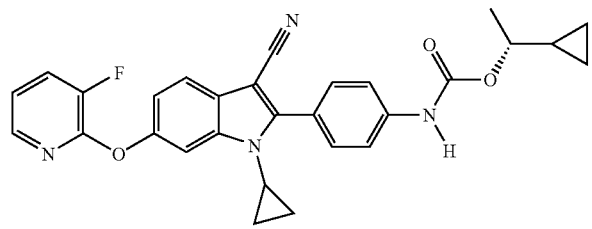
3007
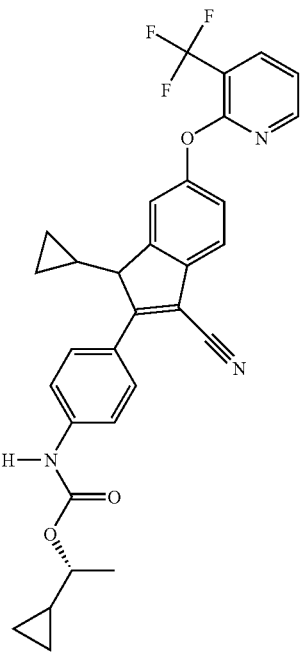
3008
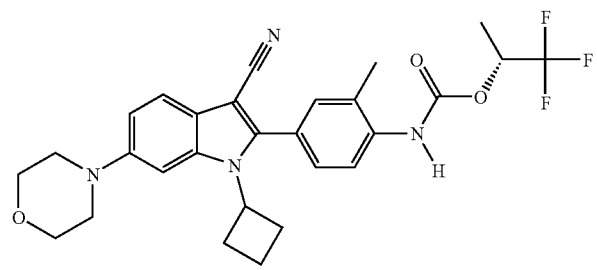
3009
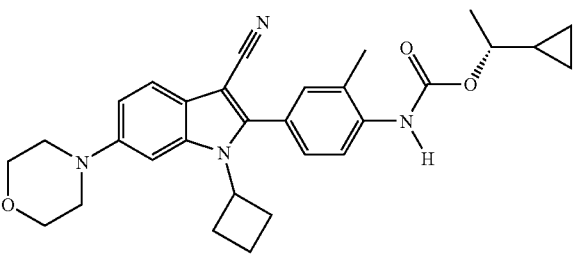
3010
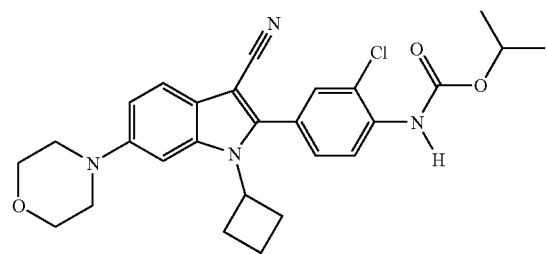
3011
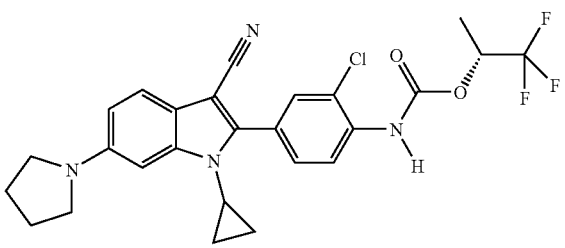
3012
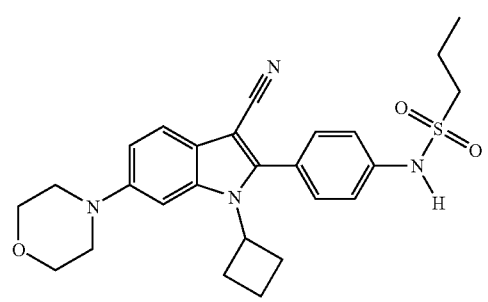
3013
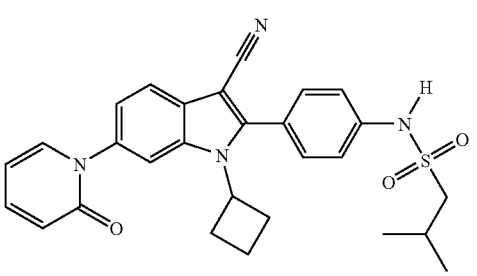
3015

-continued
3016
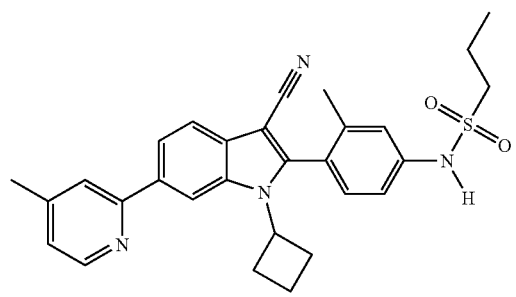
3017
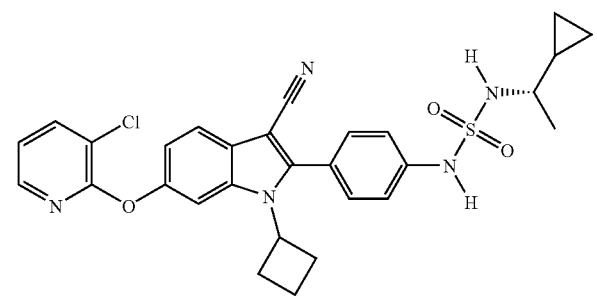
3018
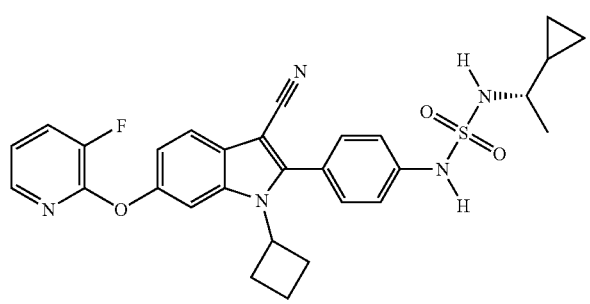
3019
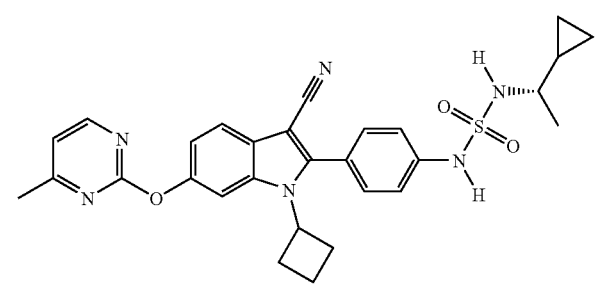
3020
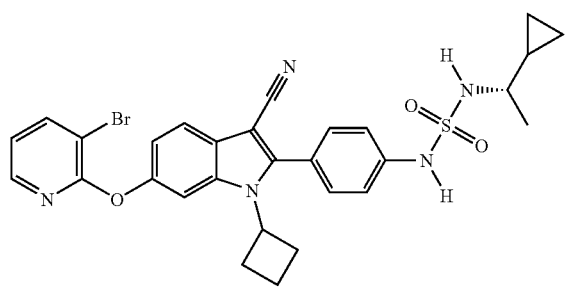
3021
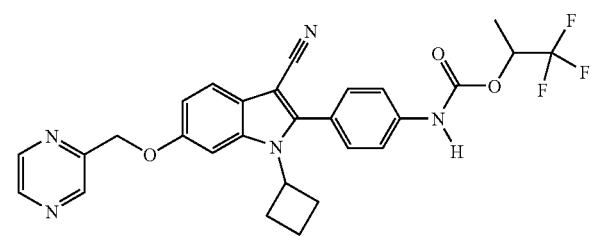
3022
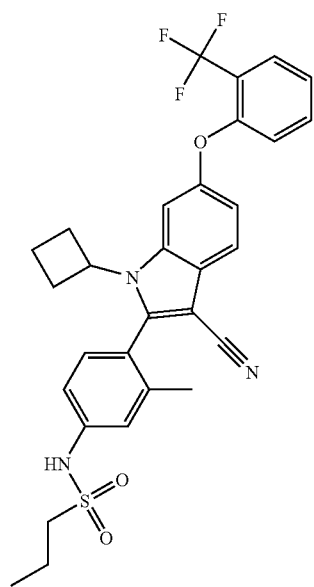
3023
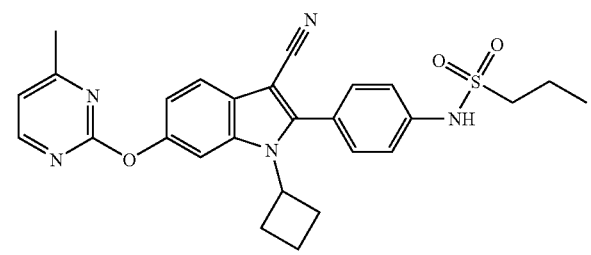

-continued
| 2304 | 3025 |
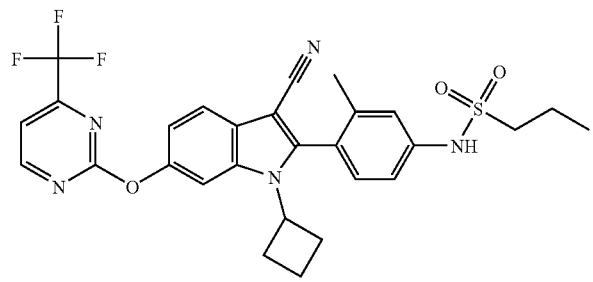
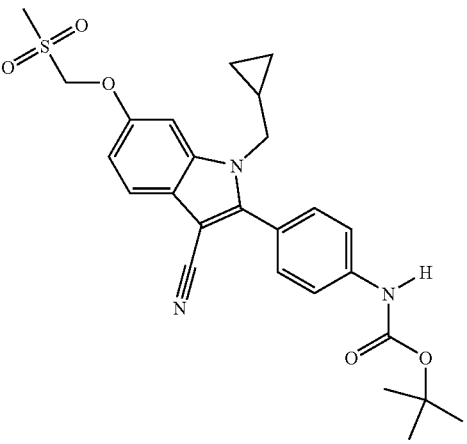
| | 3026 | 3027 |
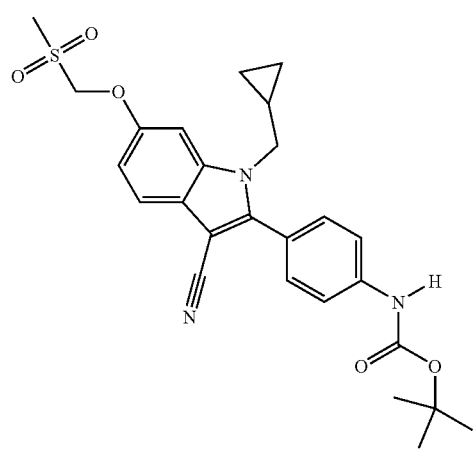
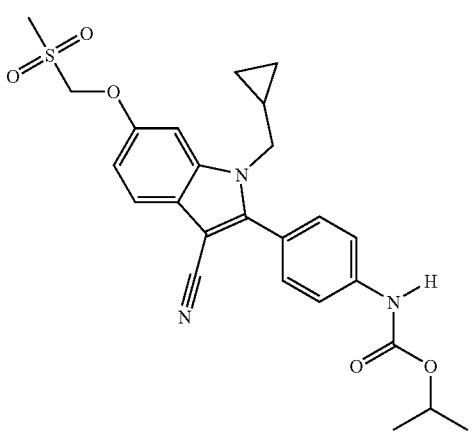
| 3027 | 3028 |
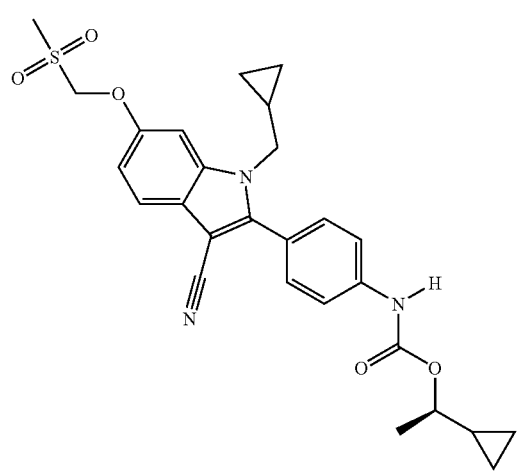
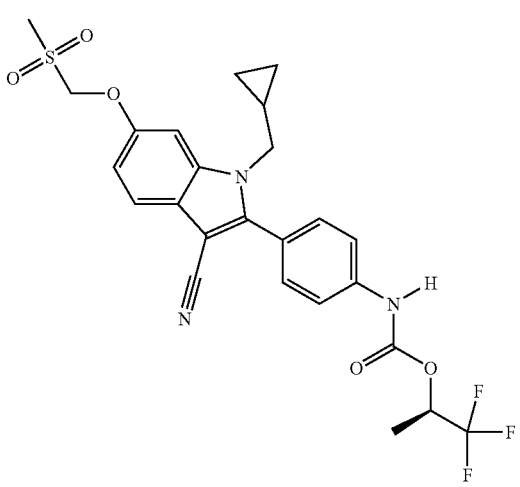

-continued
3029
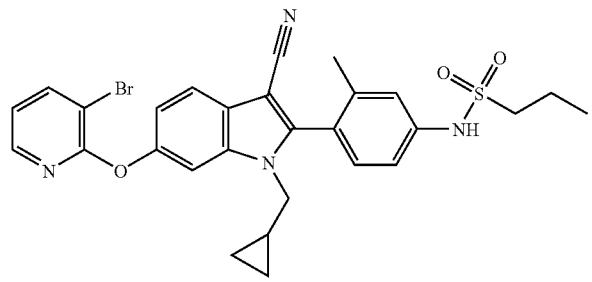
3030
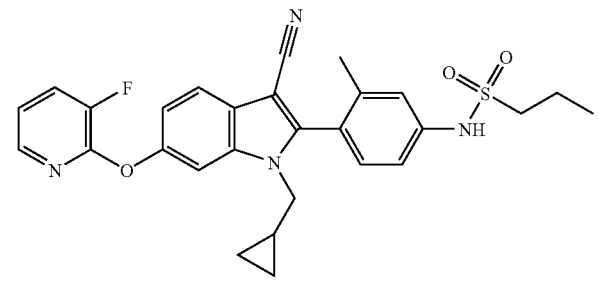
3031
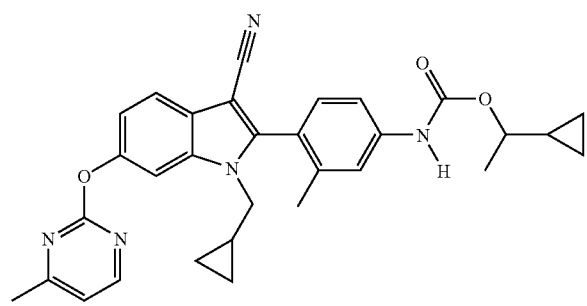
3032
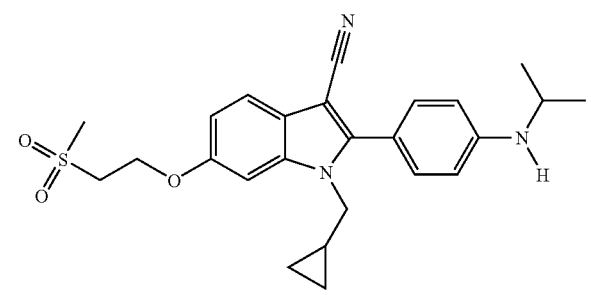
3033
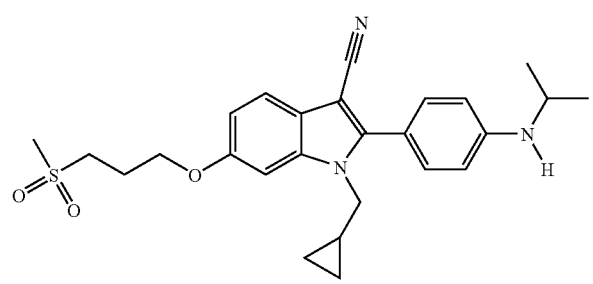
3034
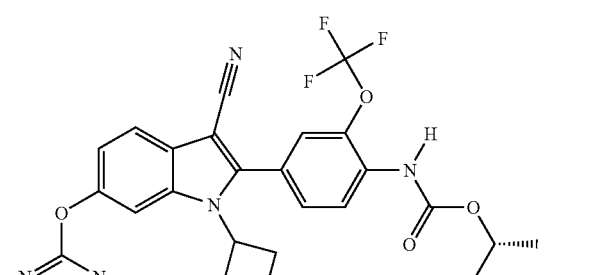
3035
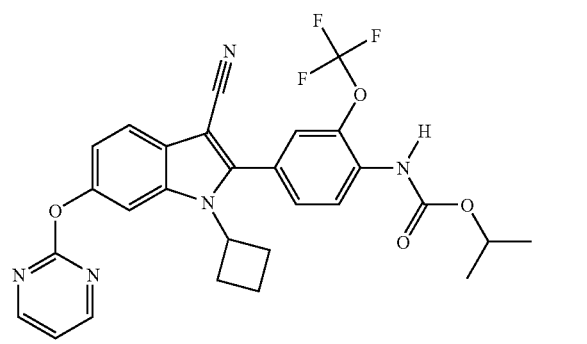
3036
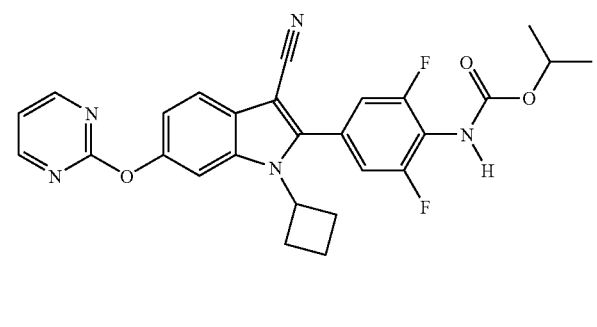
3037
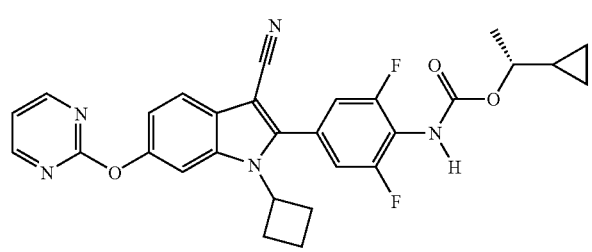
3038
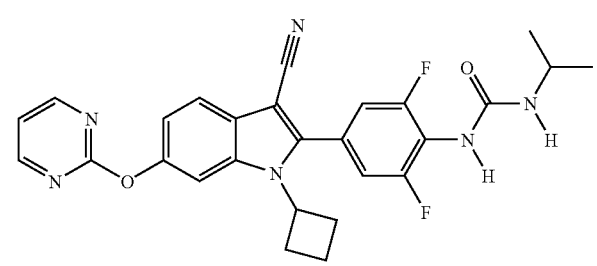

-continued
3039
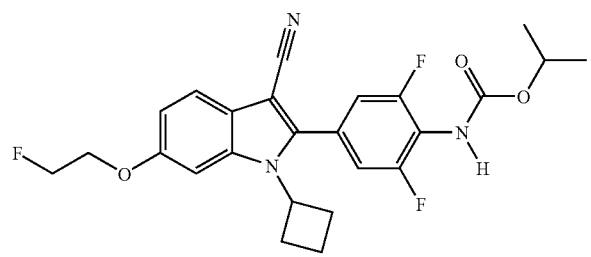
3040
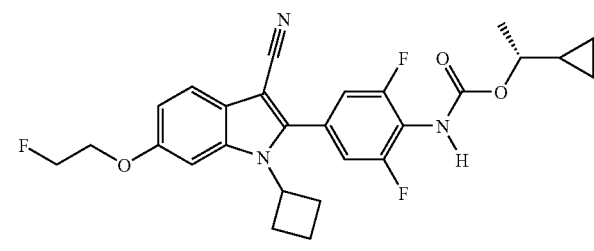
3041
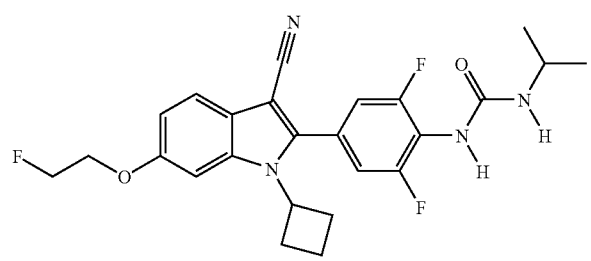
3042
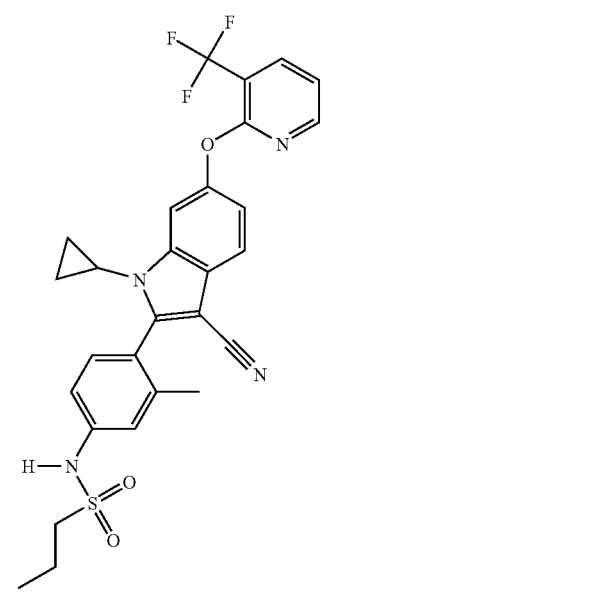
3043
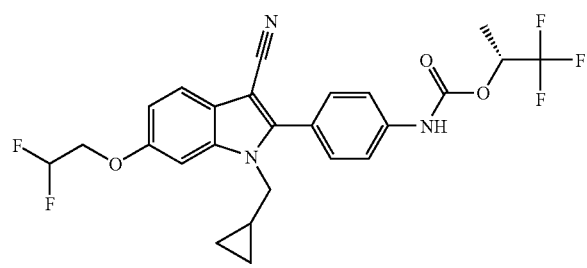
3044
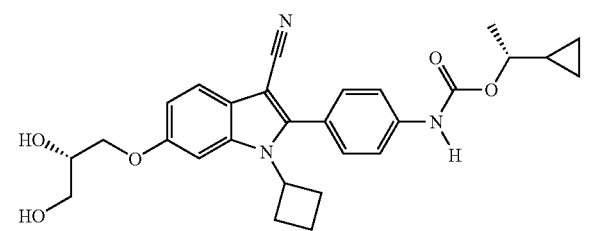
3045
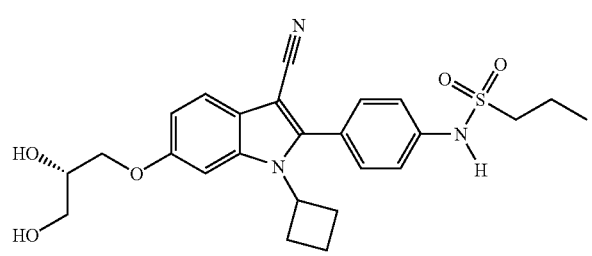
3046
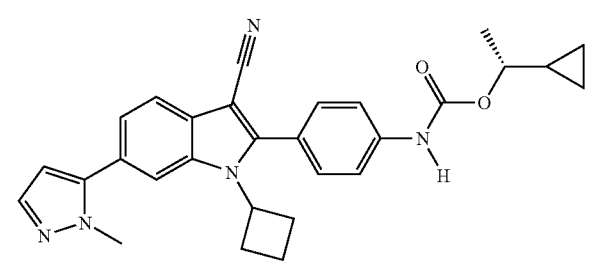

-continued
3047
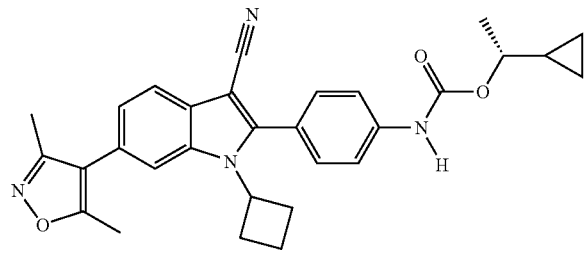
3048
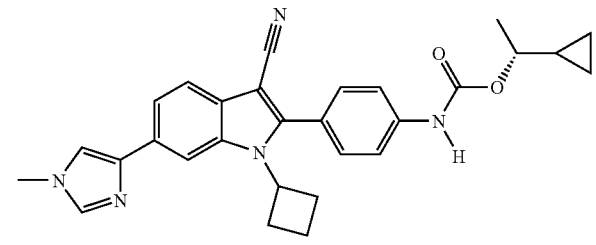
3049
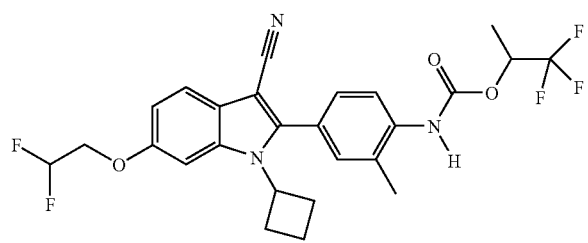
3050
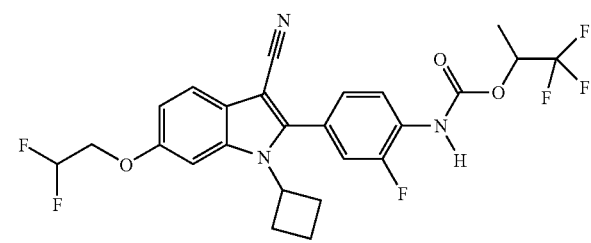
3051
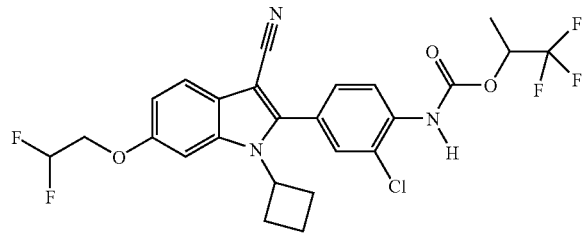
3052
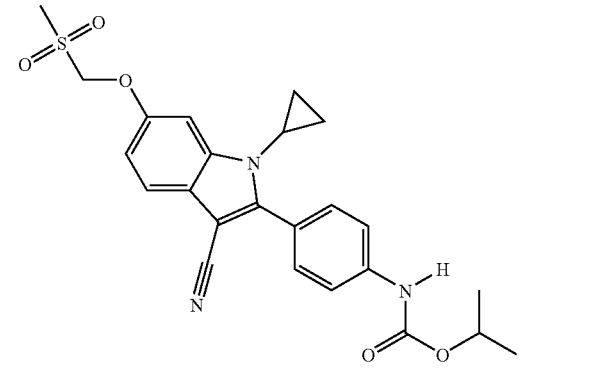
3053
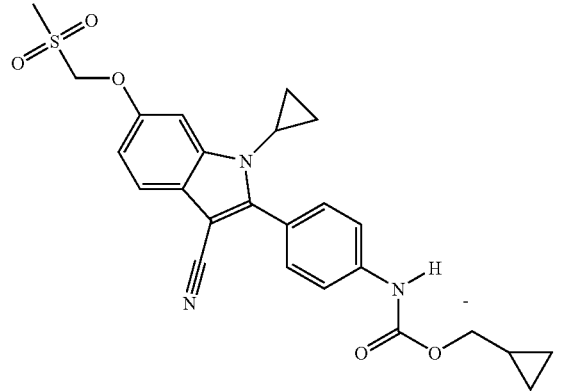
3054
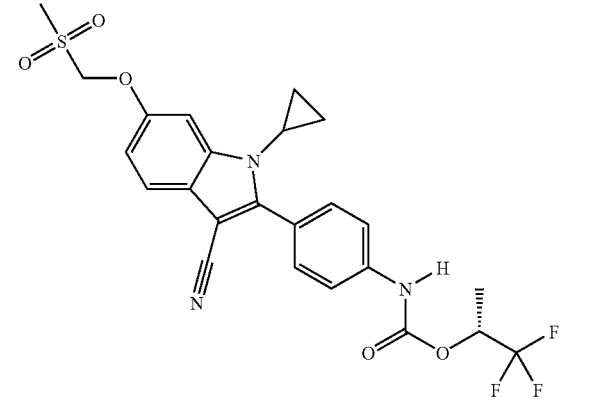

-continued
3056
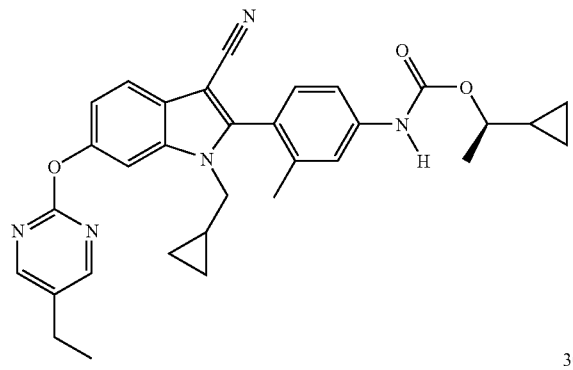
3057
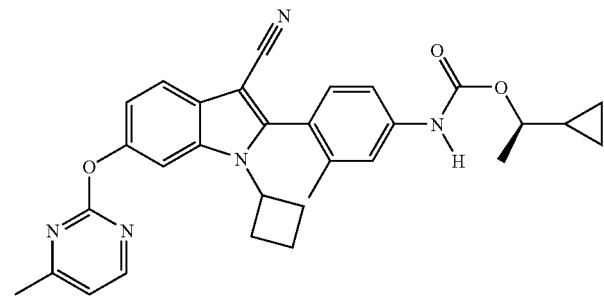
3058
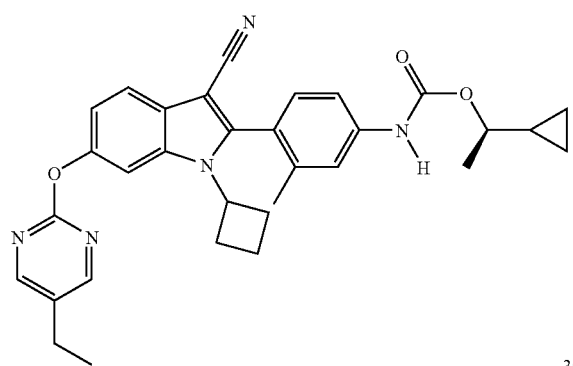
3059
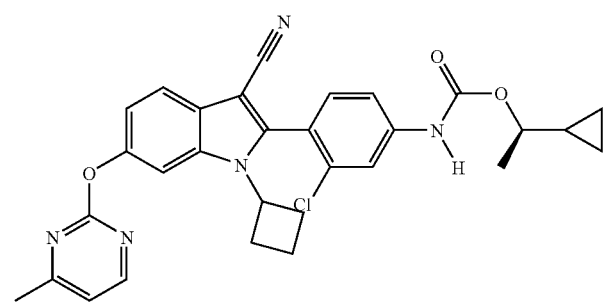
3060
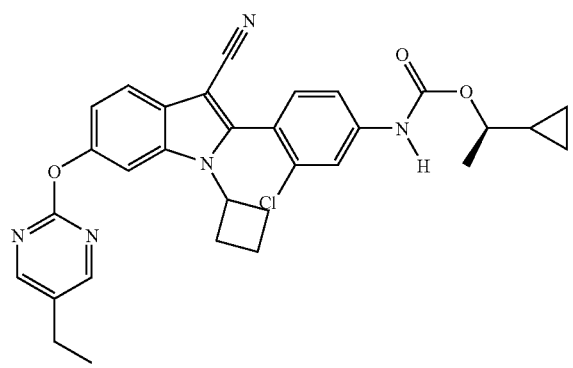
3066
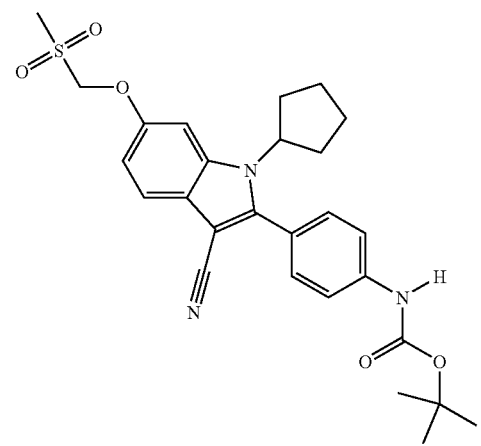
3067
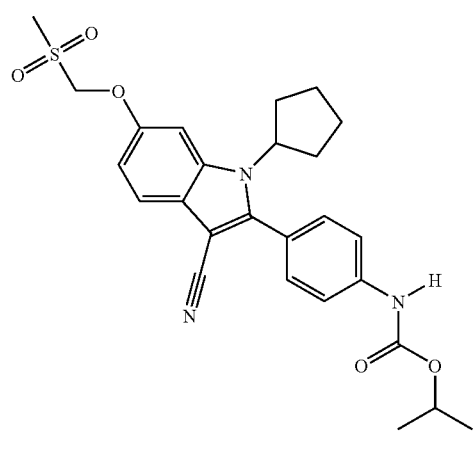
3068
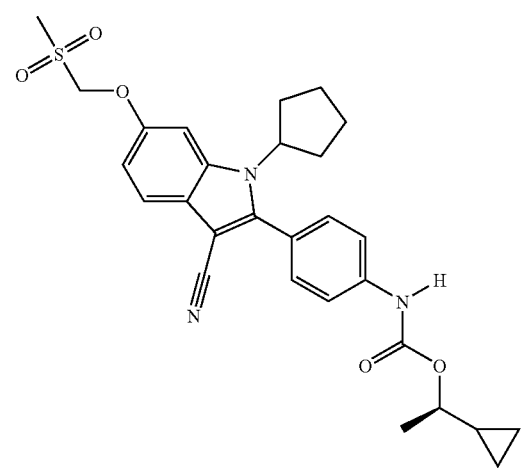

-continued
3069
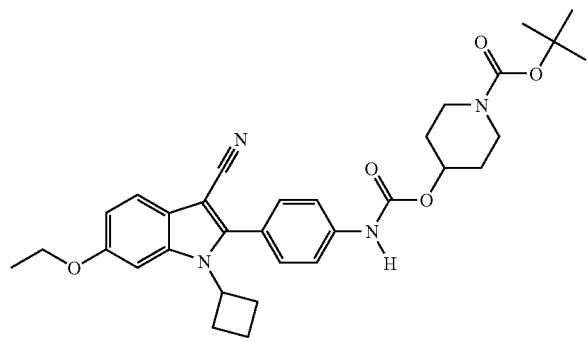
3070
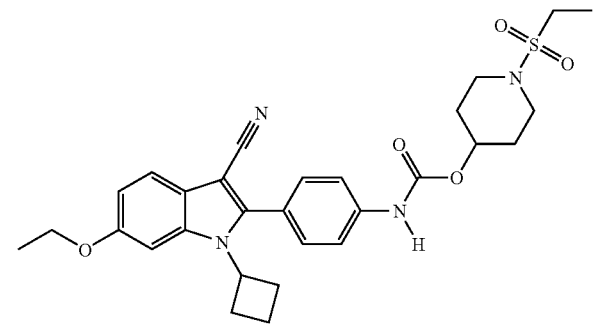
3071
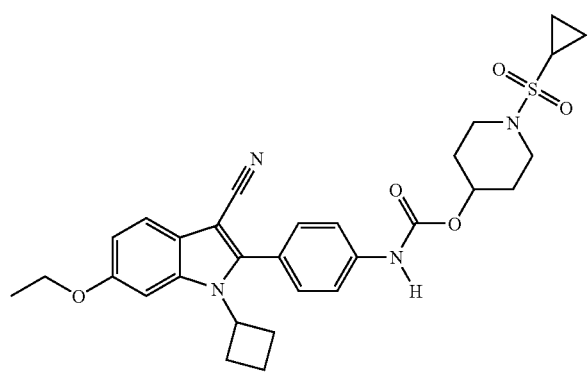
3072
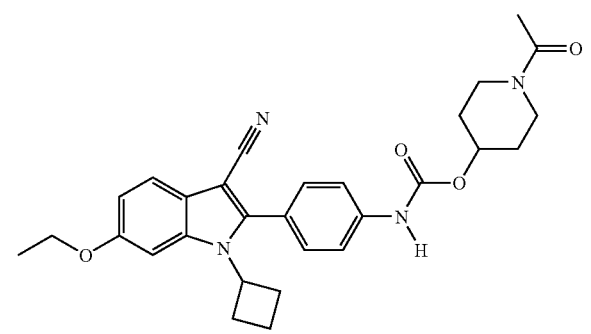
3073
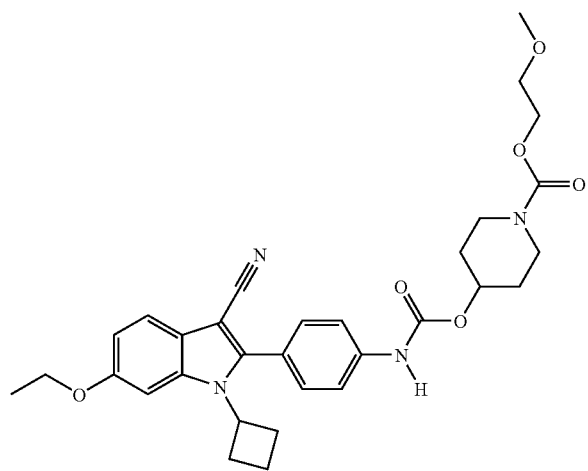
3074
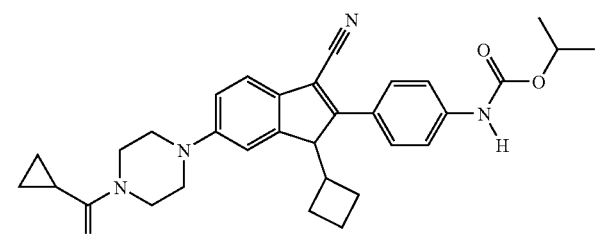
3075
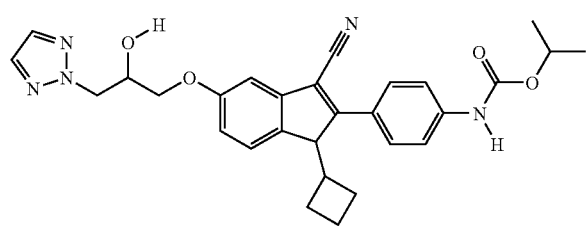
3076
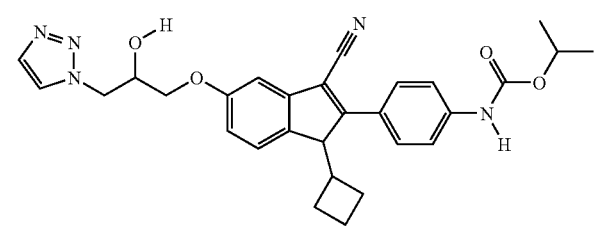

-continued
3077
3078
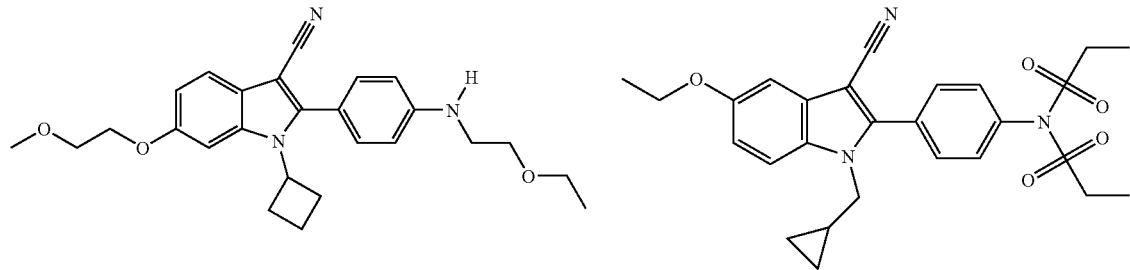
3079
3080
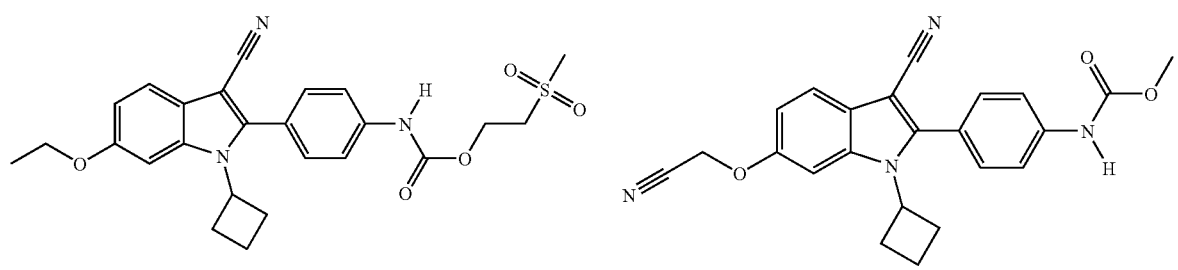
3081
3082
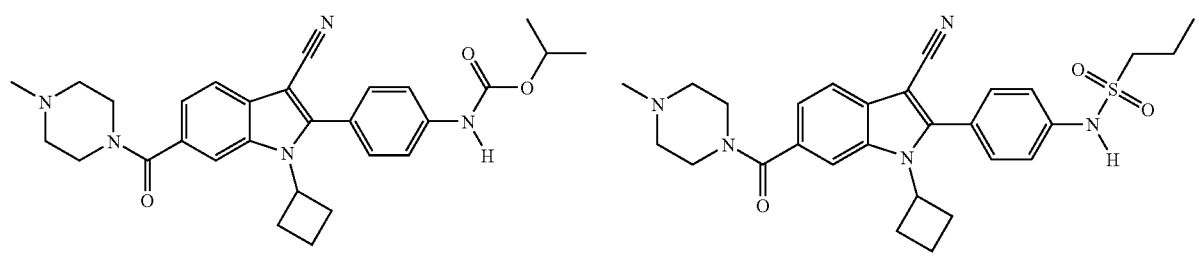
3083
3084
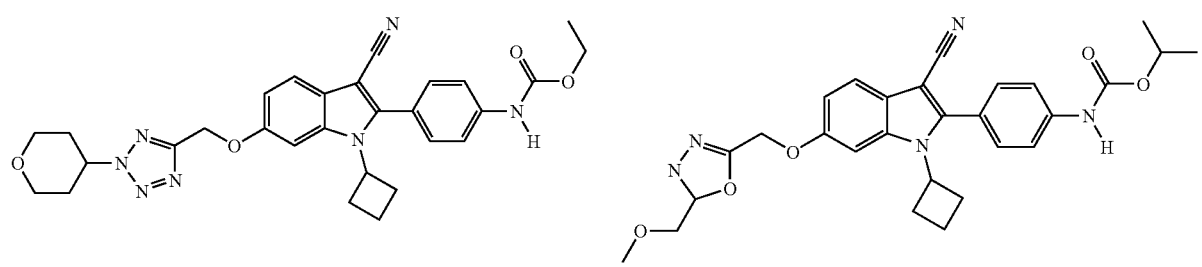
30850
3086
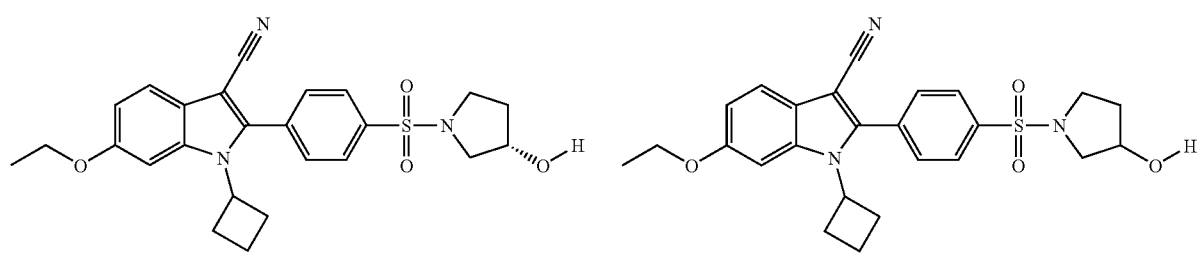

867 868
-continued
3087
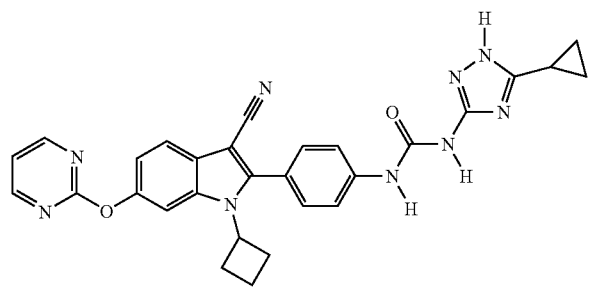
3088
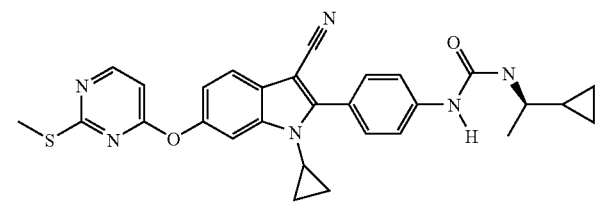
3089
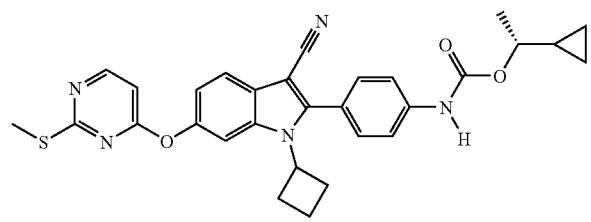
3090
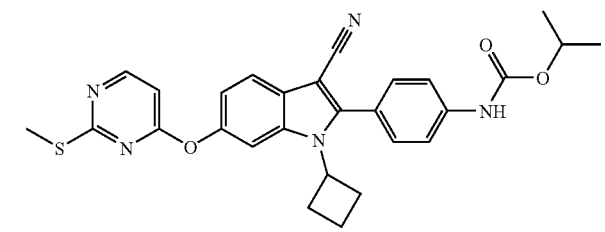
3091
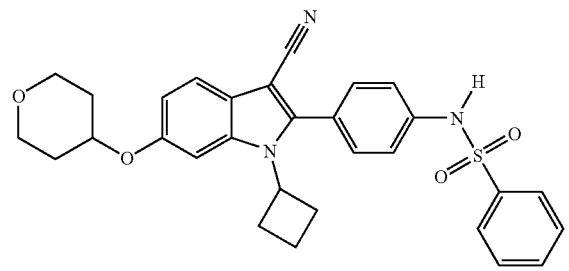
3092
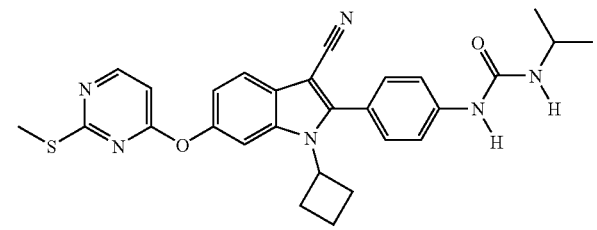
3094
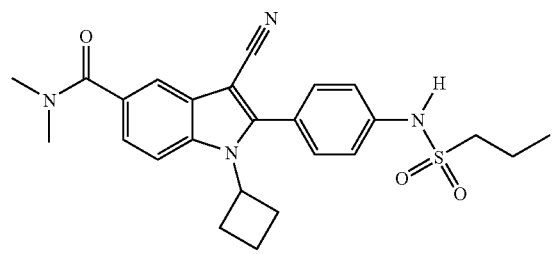
3095
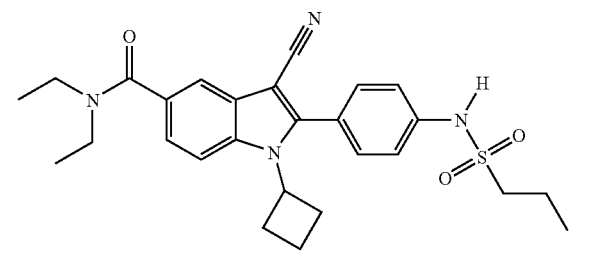
3096
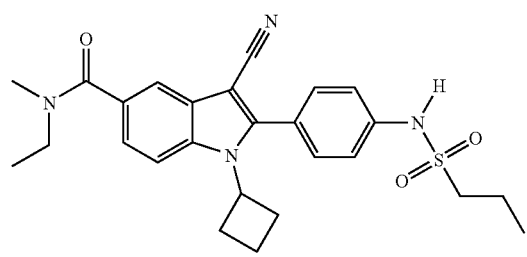
3097
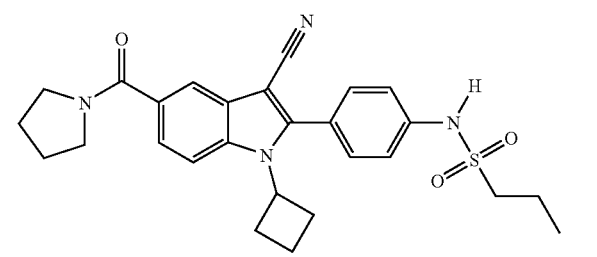

-continued
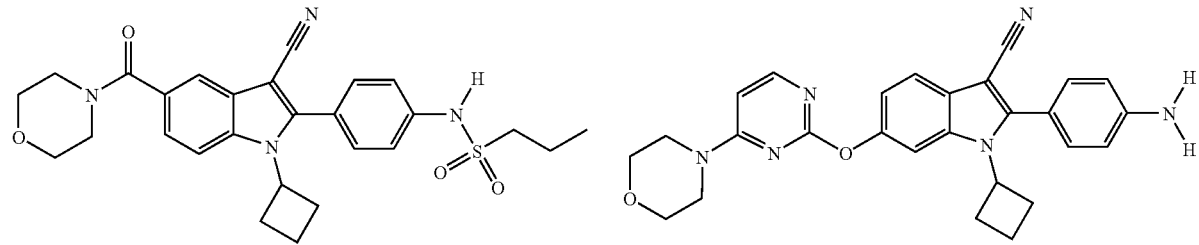
3098
3099
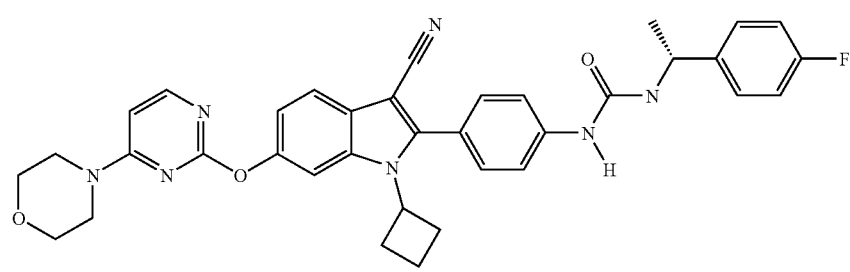
3100
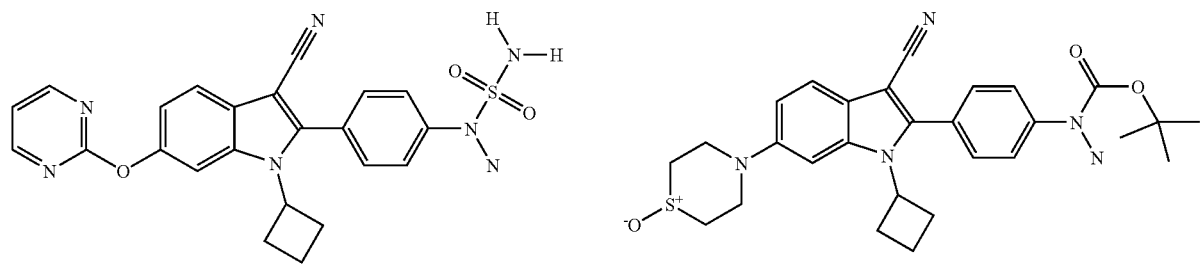
3101
3102
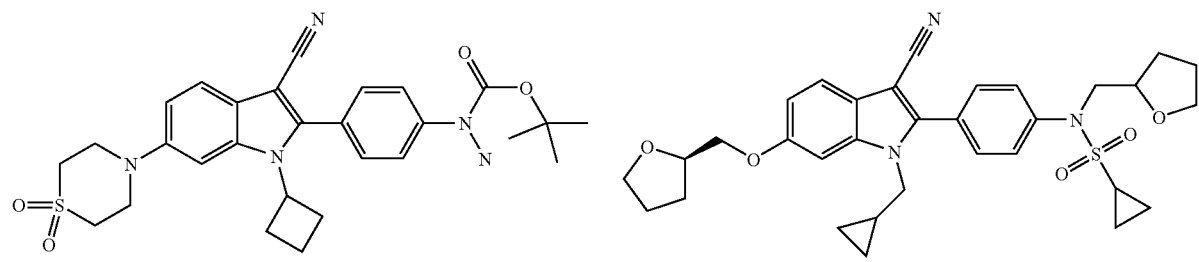
3103
3104
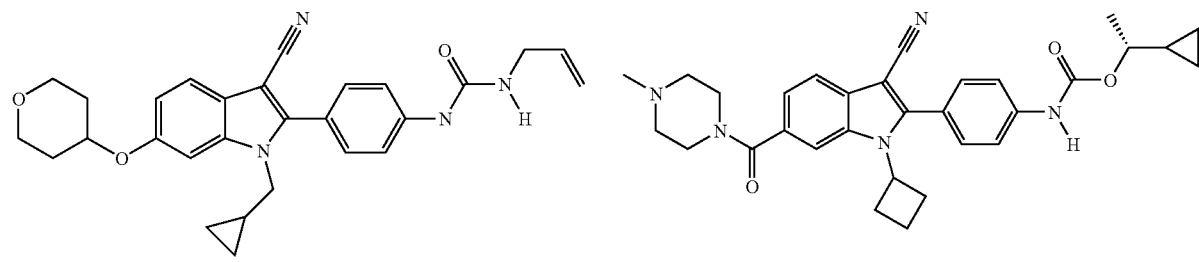
3105
3106

-continued
| 3107 | 3108 |
|---|---|
| 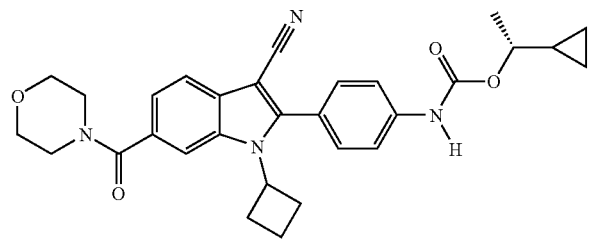 | 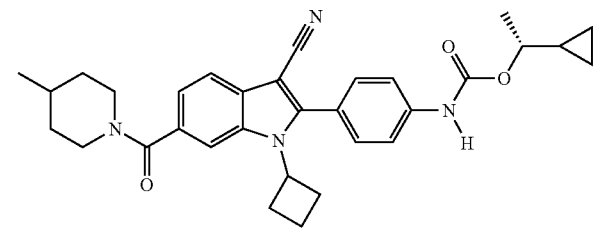 |
| 3109 | 3110 |
| 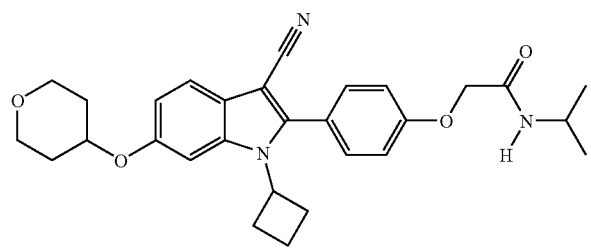 | 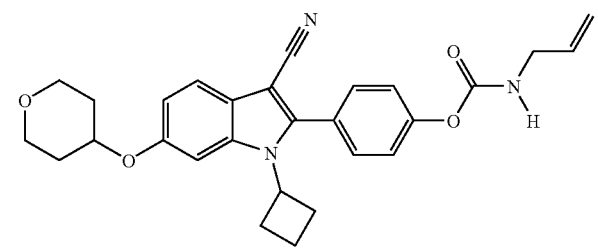 |
| 3111 | 3112 |
| 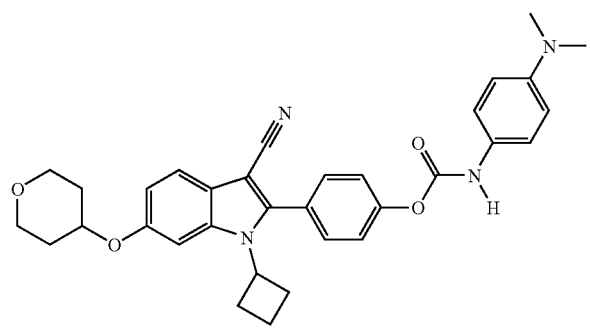 | 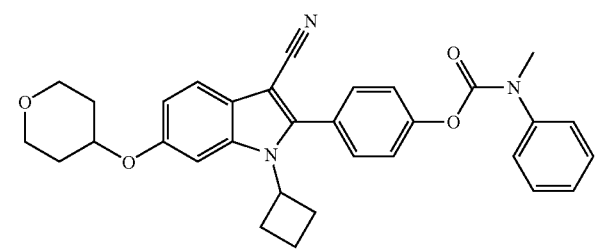 |
| 3113 | 3114 |
| 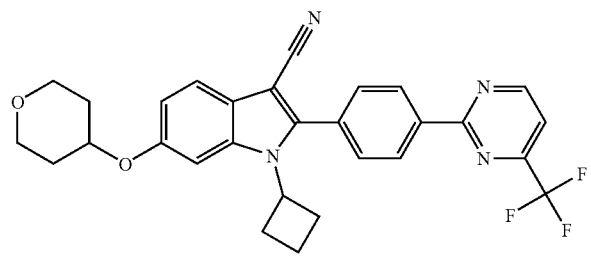 | 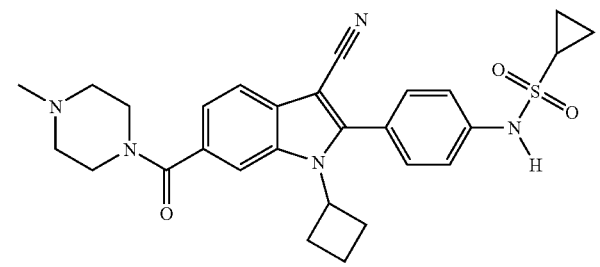 |
| 3115 | 3116 |
| 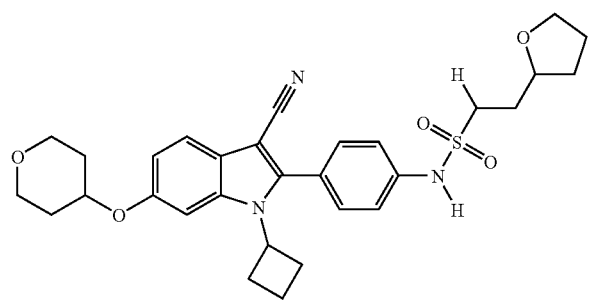 | 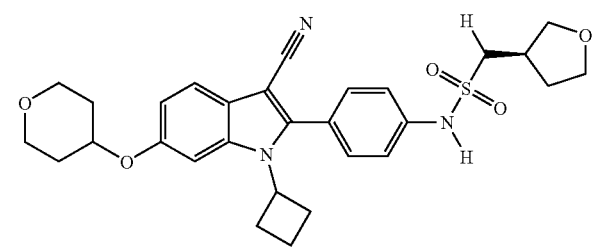 |

-continued
3117
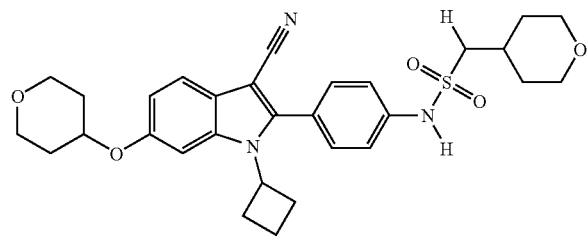
3118
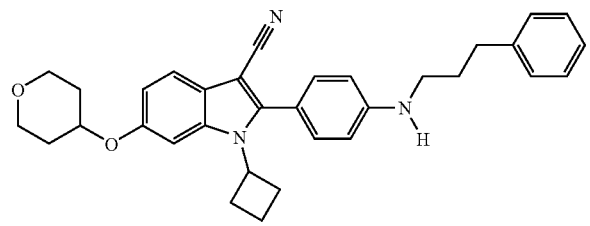
3119
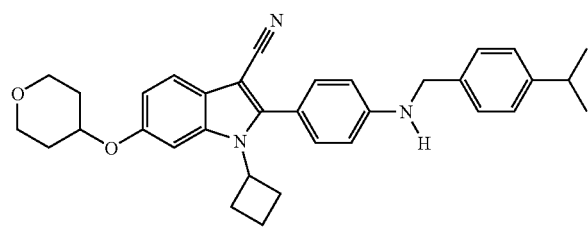
3120
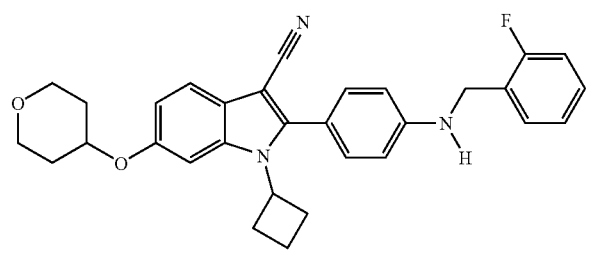
3121
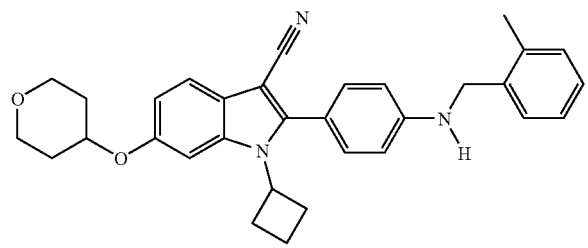
3122
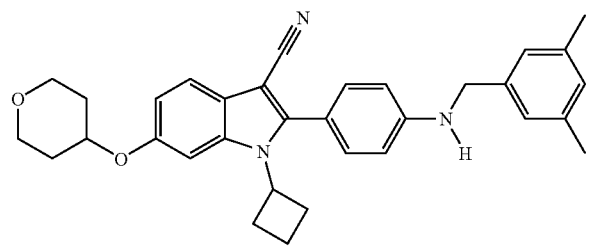
3123
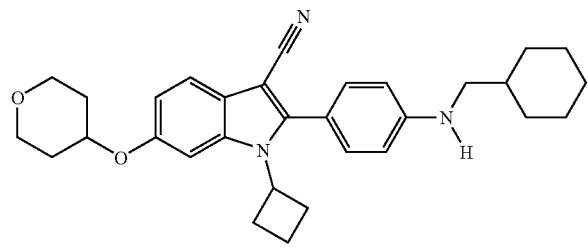
3124
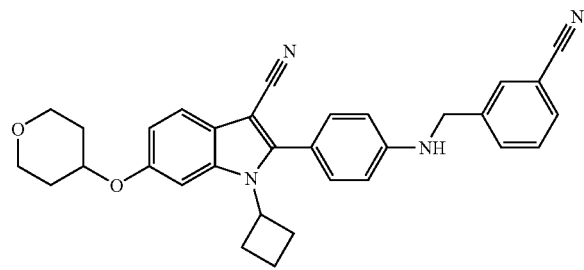
3125
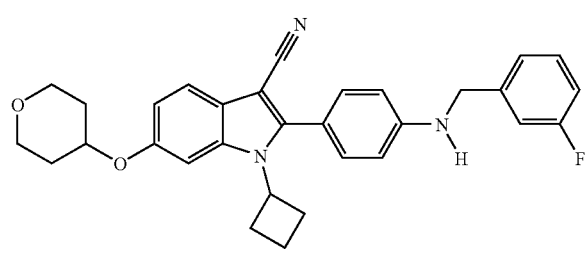
3126
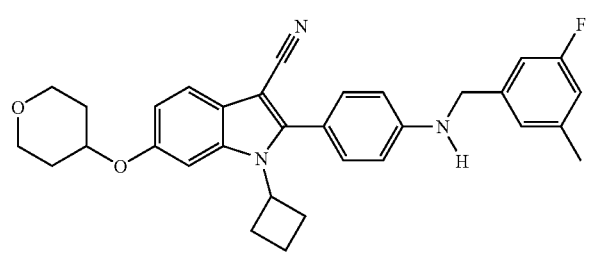

-continued
3127
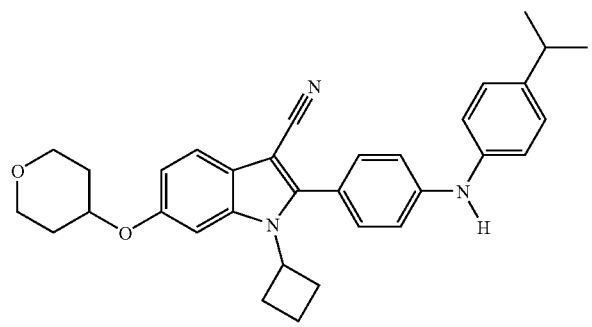
3128
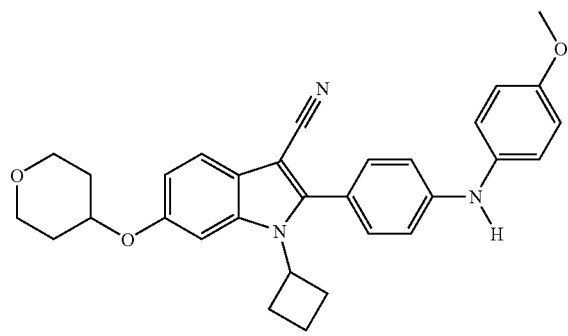
3129
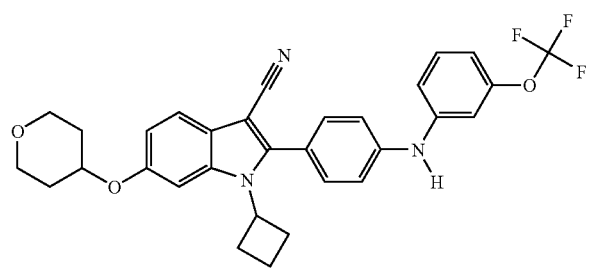
3130
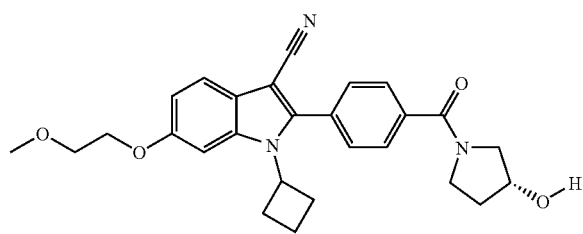
3131
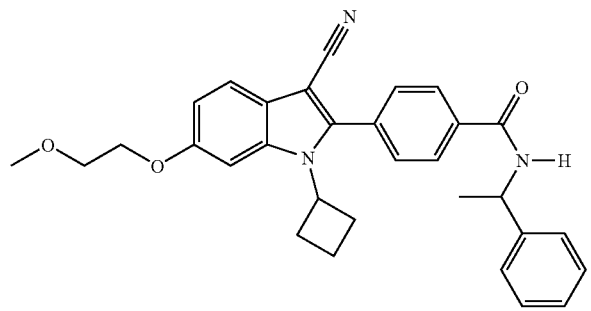
3132
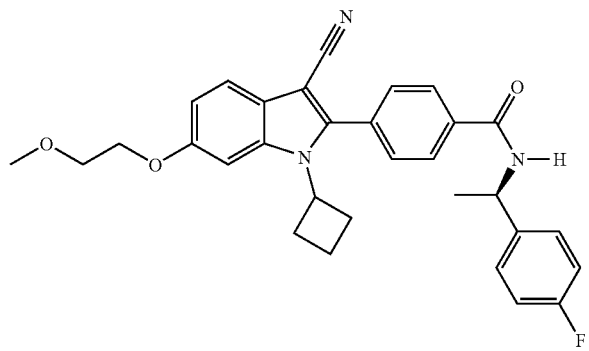
3133
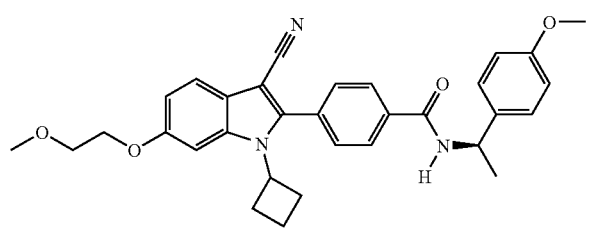
3134
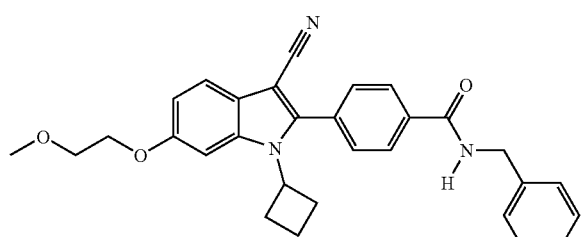
3135
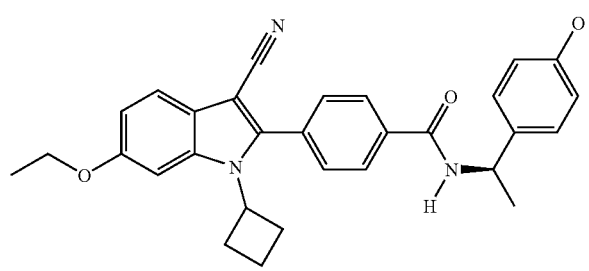
3136
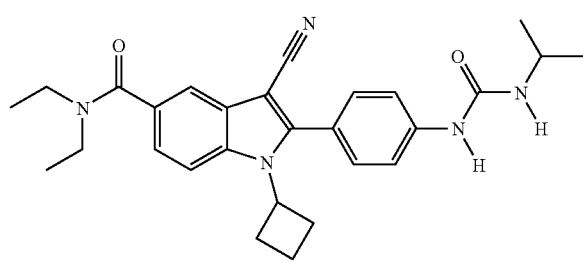

877 878
-continued
| 3137 | 3138 |
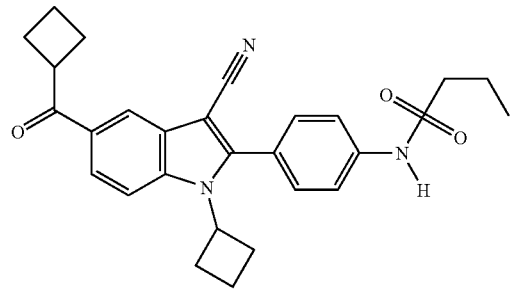 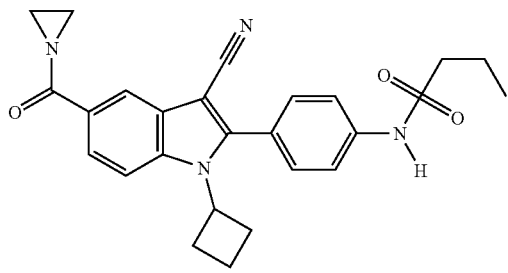
| 3139 | 3140 |
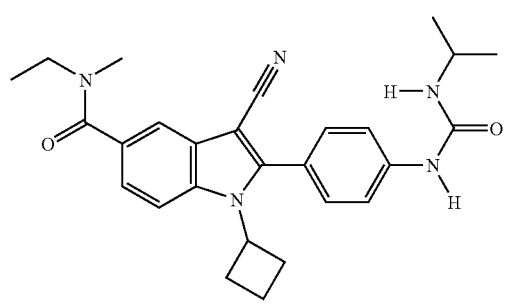 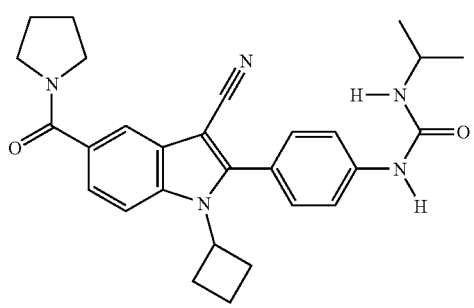
| 3141 | 3142 |
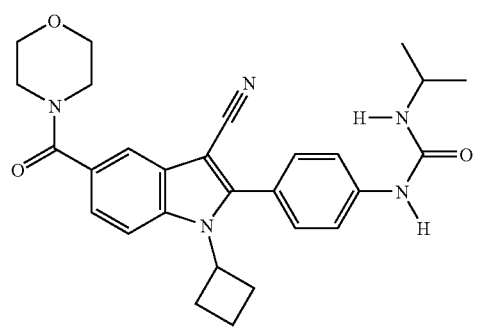 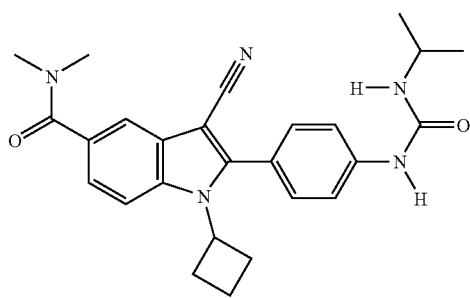
| 3143 | 3144 |
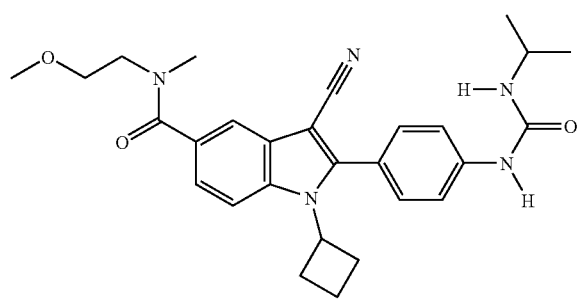 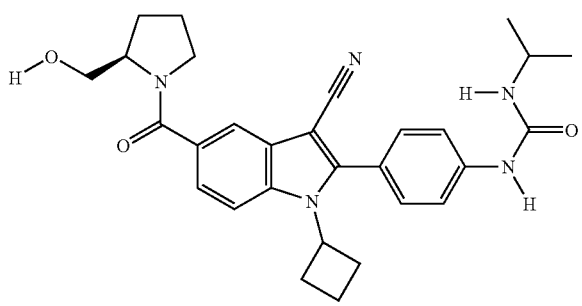
| 3145 | 3146 |
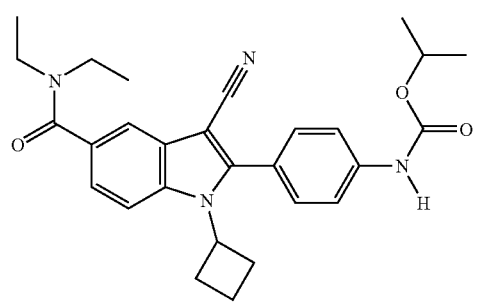 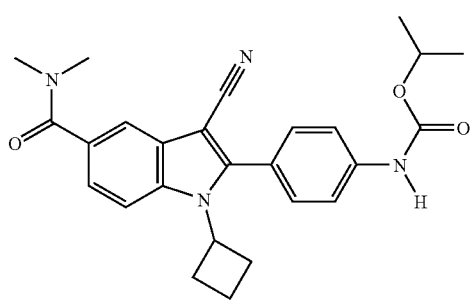

-continued
3147
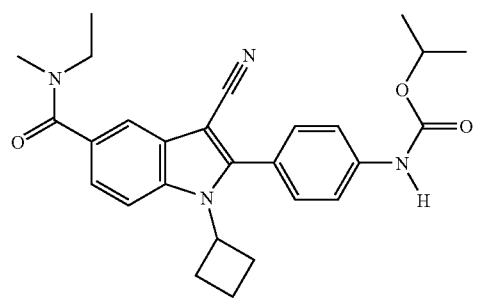
3148
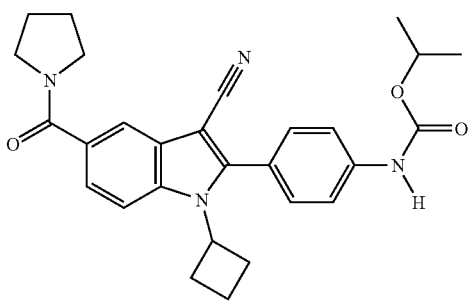
3149
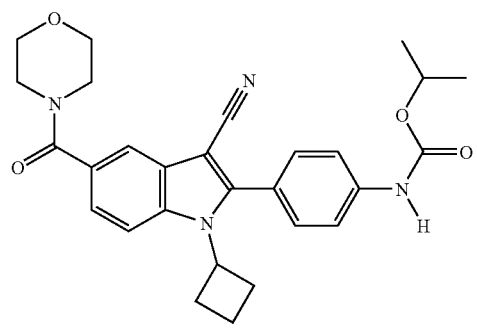
3150
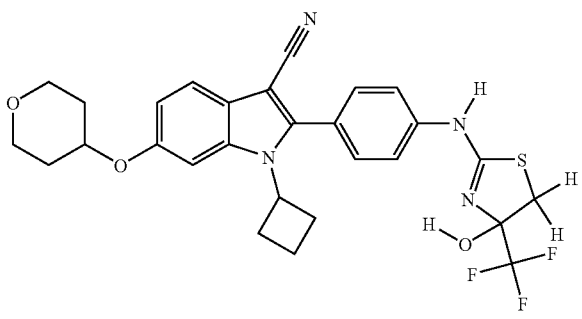
3151
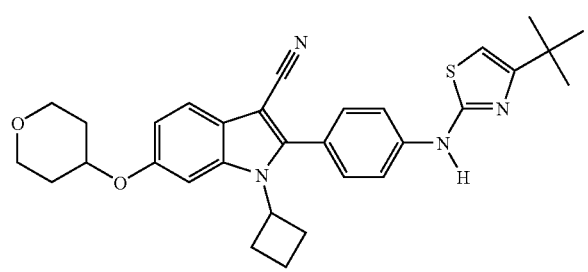
3152
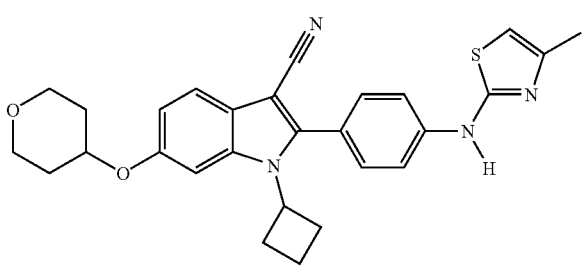
3153
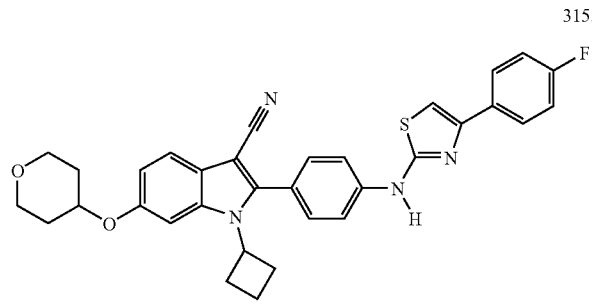
3154
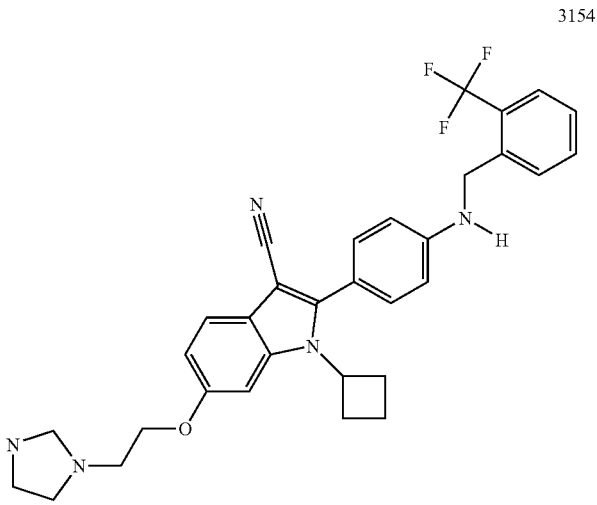

-continued
3155
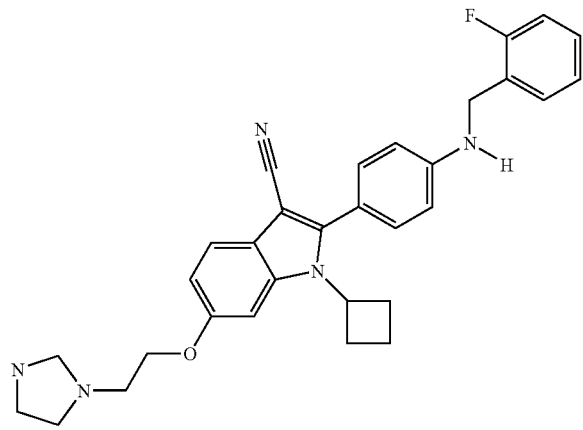
3156
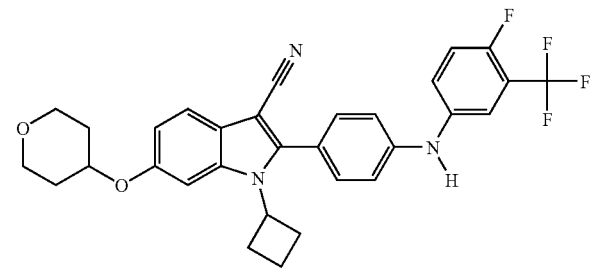
3157
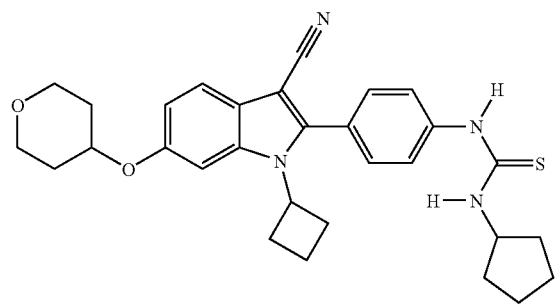
3158
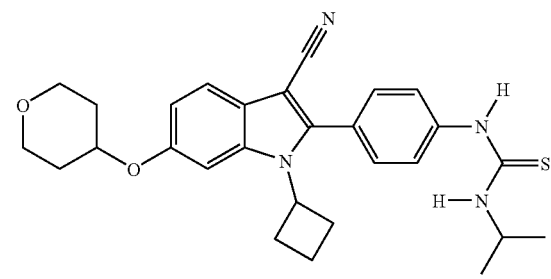
3159
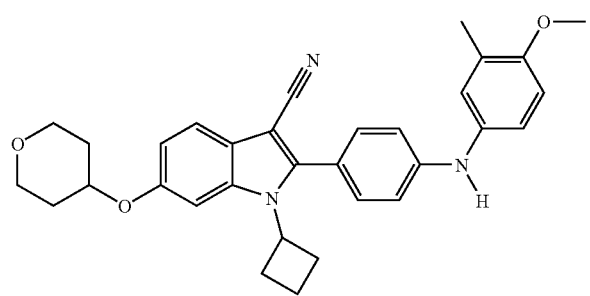
3160
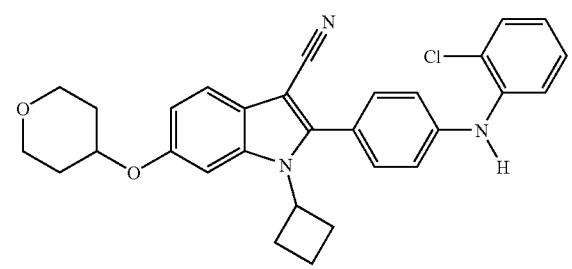
3161
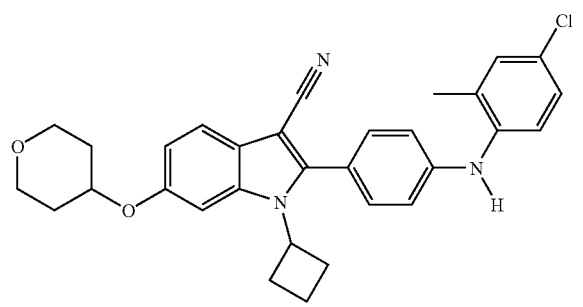
3162
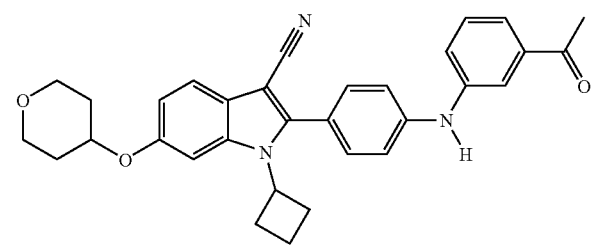

-continued
| 3163 | 3164 |
|---|---|
| 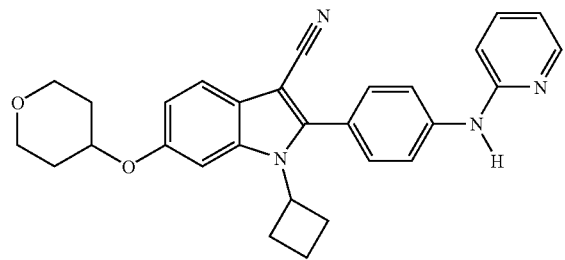 | 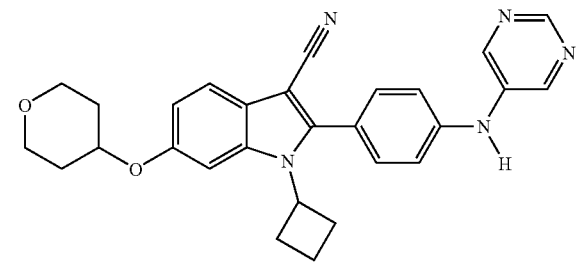 |
| 3165 | 3166 |
| 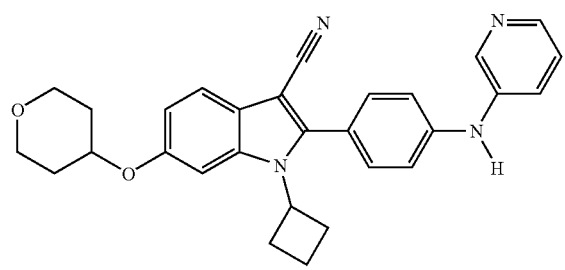 | 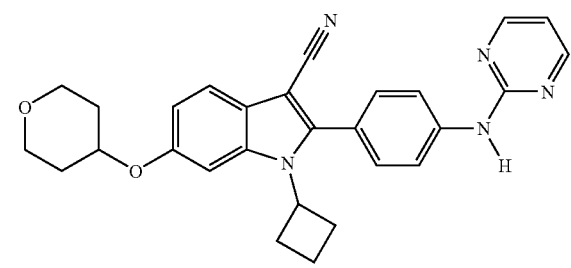 |
| 3167 | 3168 |
| 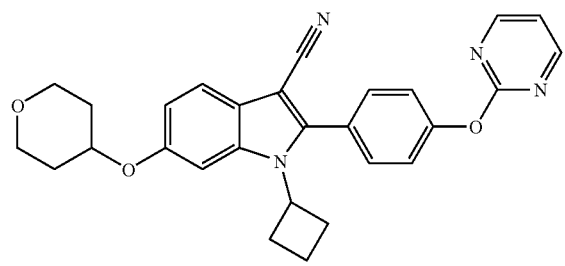 | 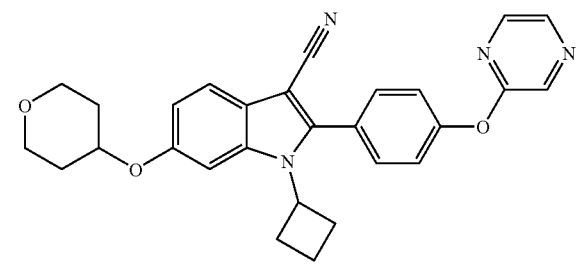 |
| 3169 | 3170 |
| 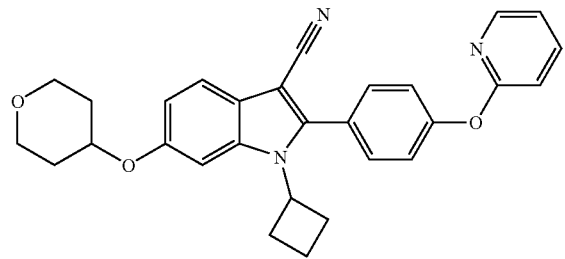 | 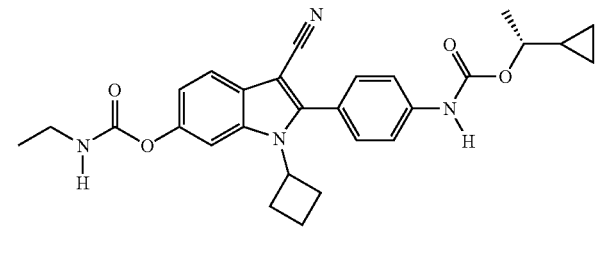 |
| 3171 | 3172 |
| 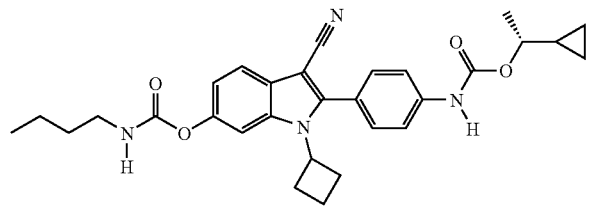 | 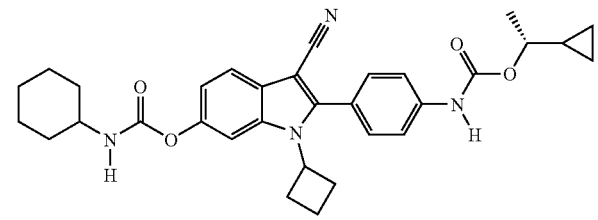 |

-continued
3173
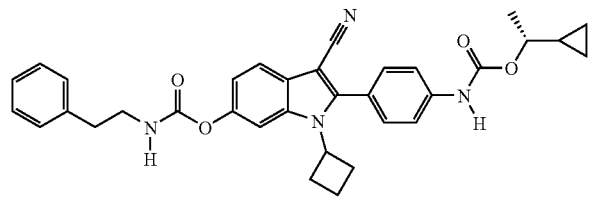
3174
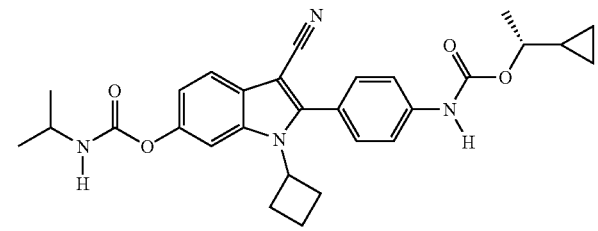
3175
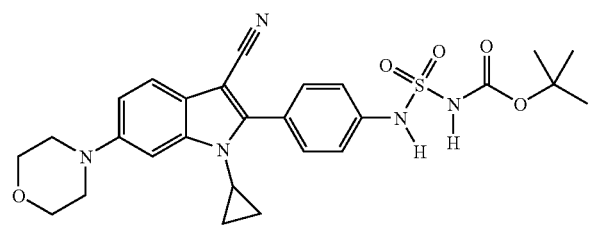
3176
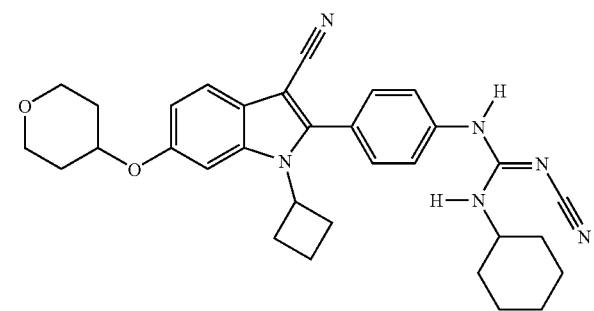
3177
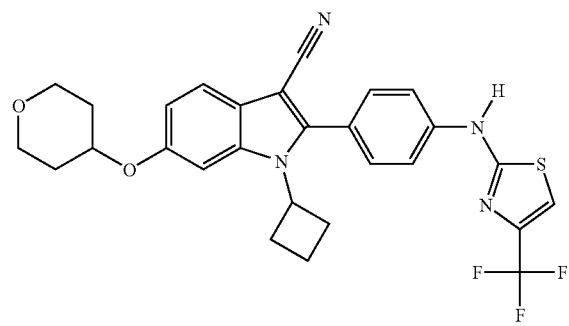
3178
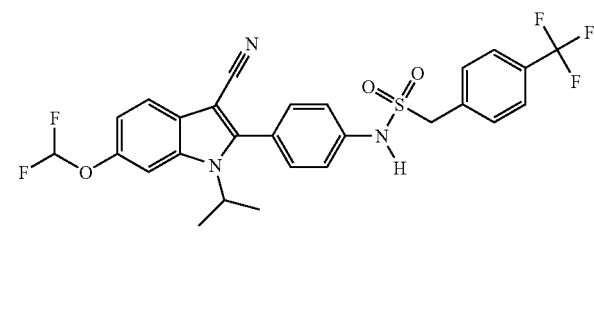
3179
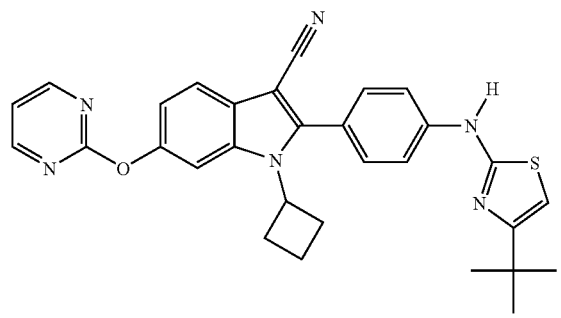
3180
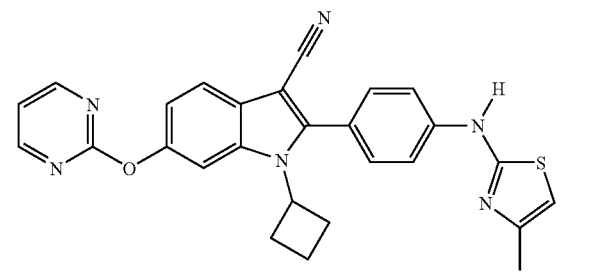
3181
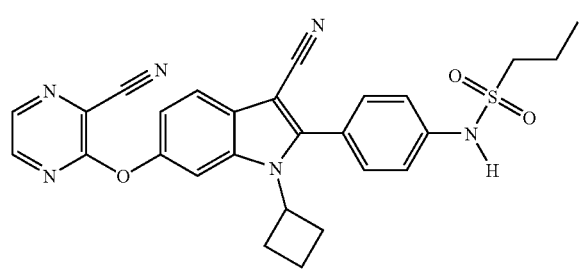
3182
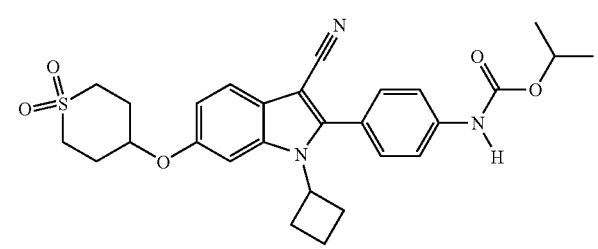

-continued
3183
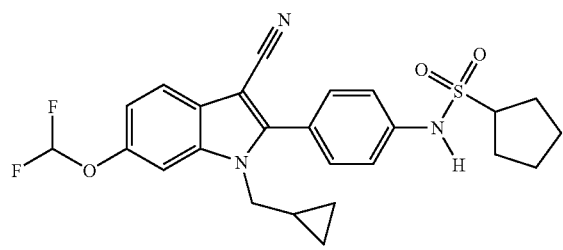
3184
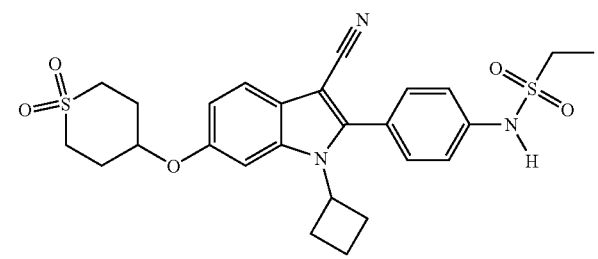
3185
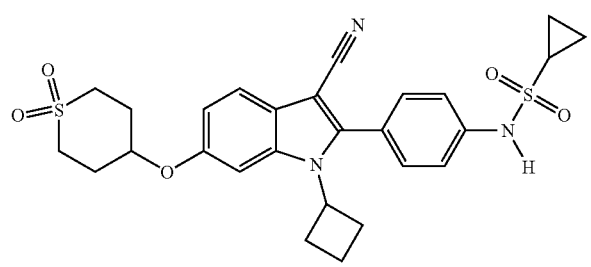
3186
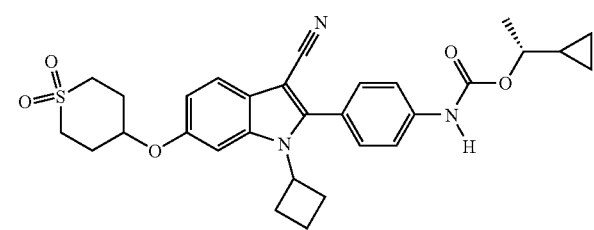
3187
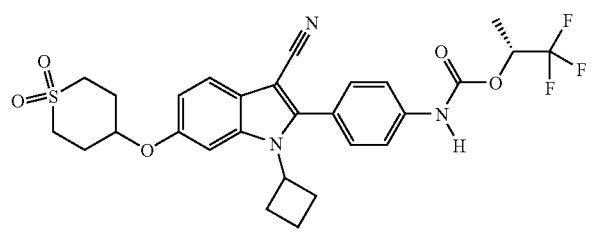
3188
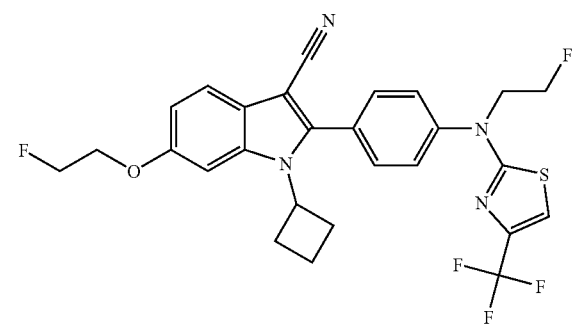
3189
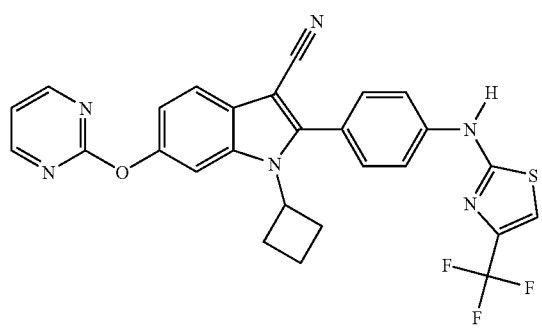
3190
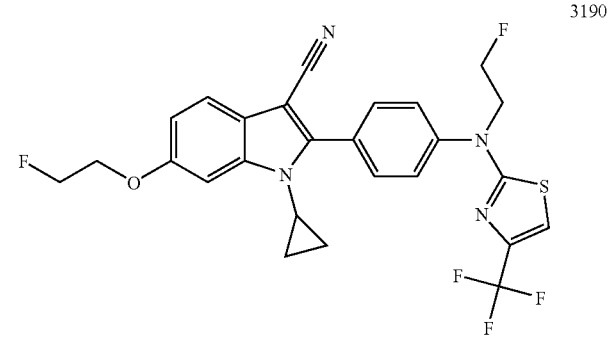
3191
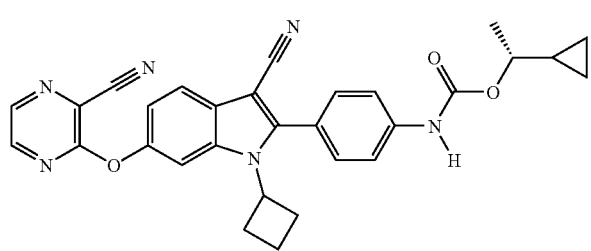
3192
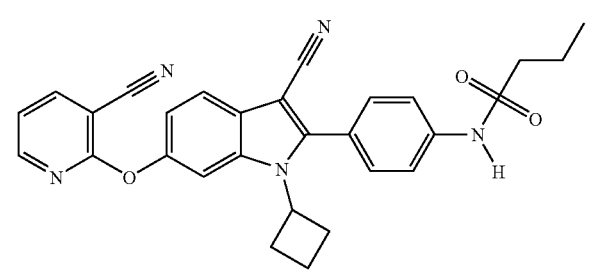

-continued
3193
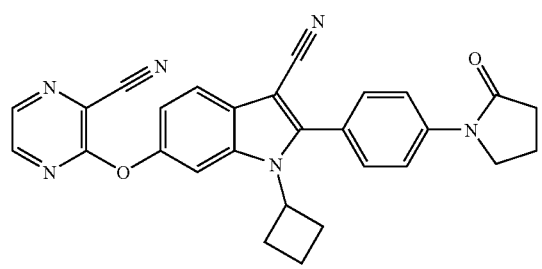
3194
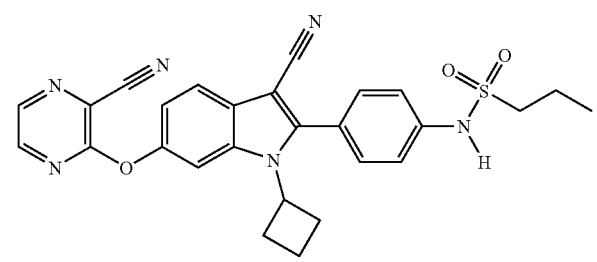
3195
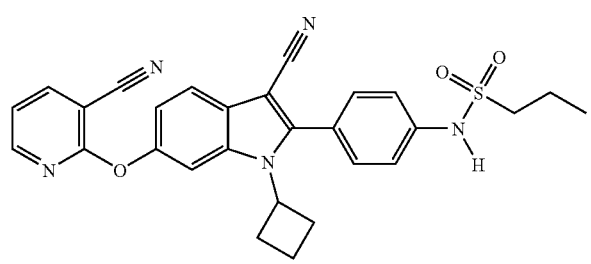
3196
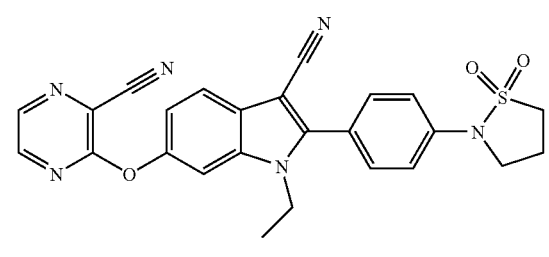
3197
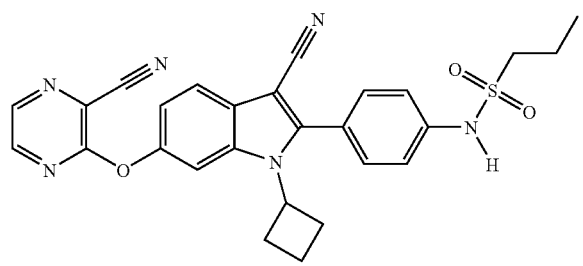
3198
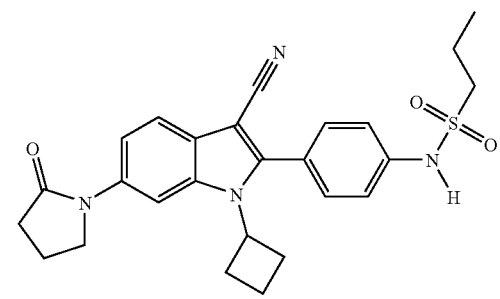
3199
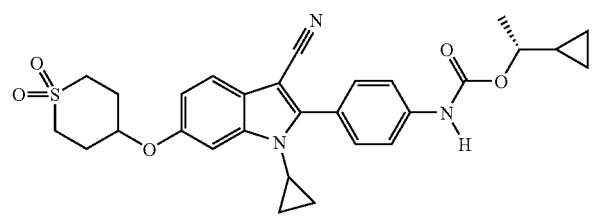
3200
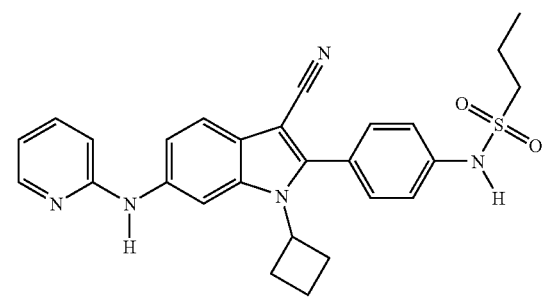
3201
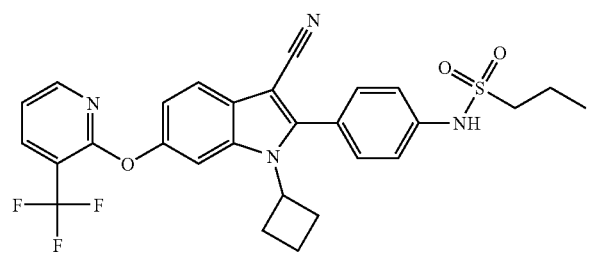
3202
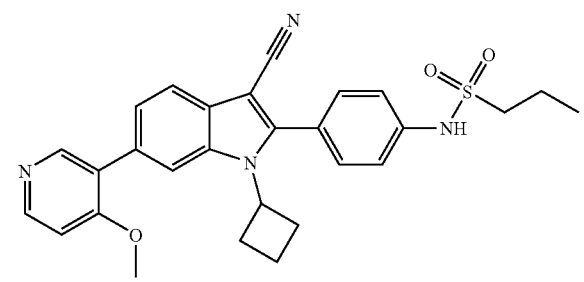

-continued
3203
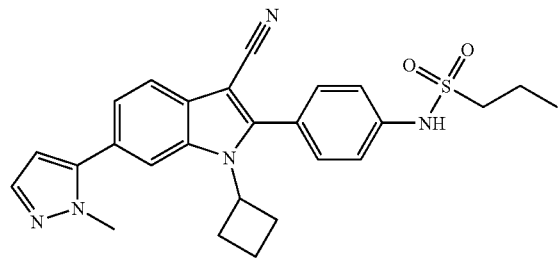
3204
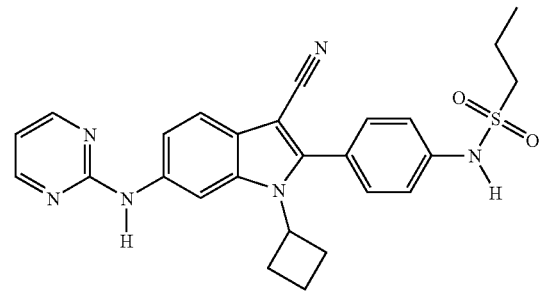
3205
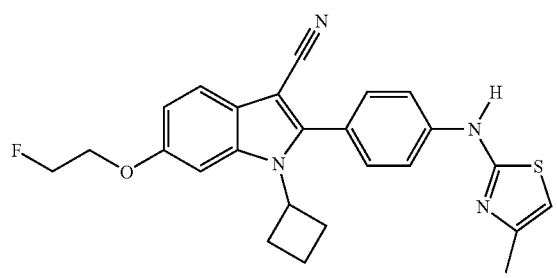
3206
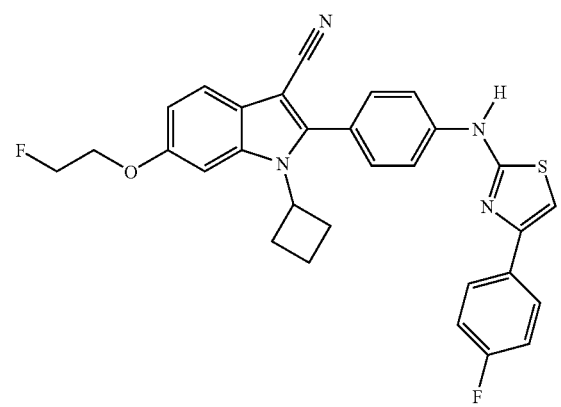
3207
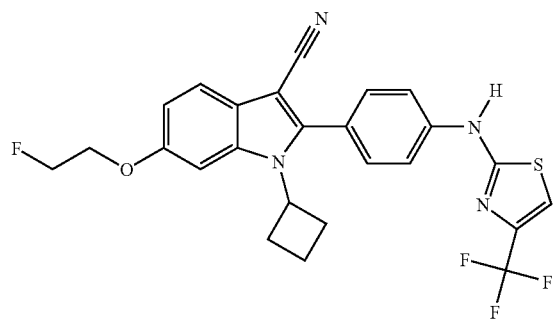
3208
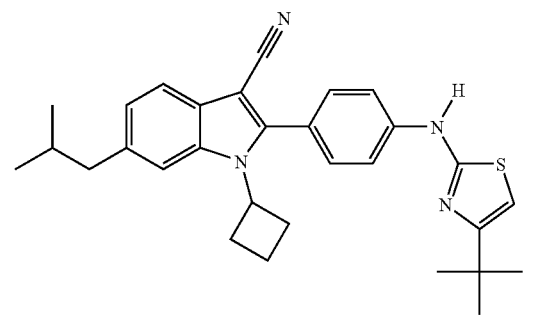
3209
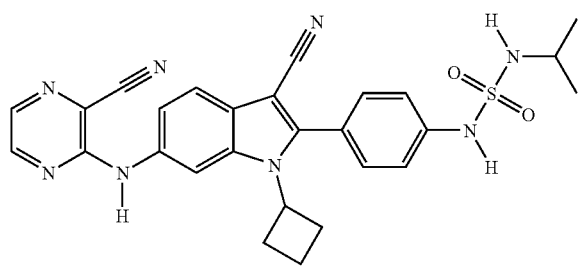
3210
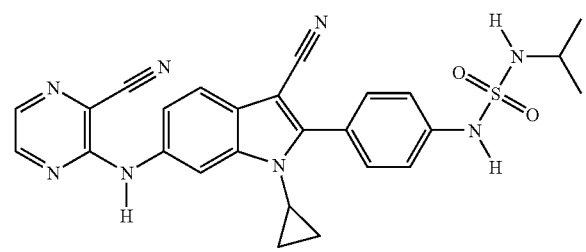
3211
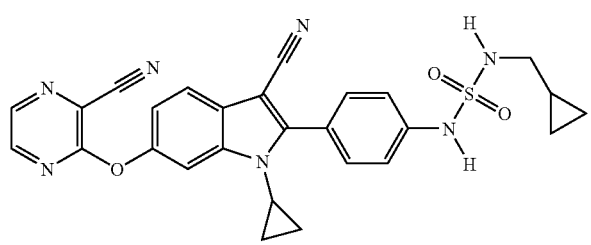
3212
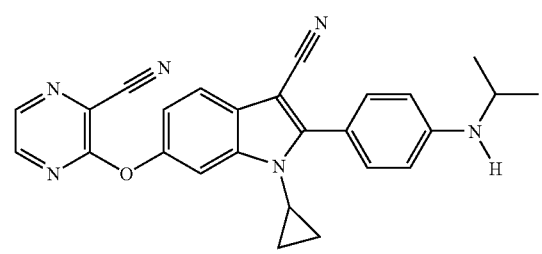

893 894
-continued
3213 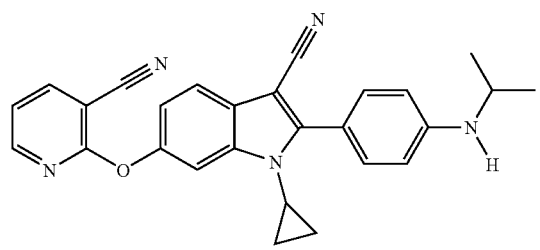 3214 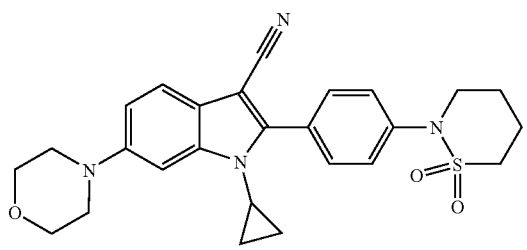
3215 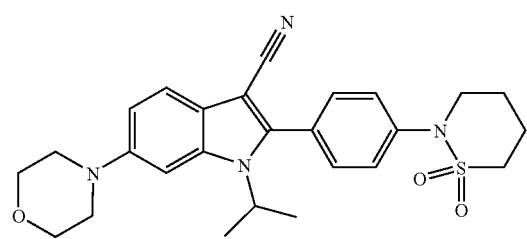 3216 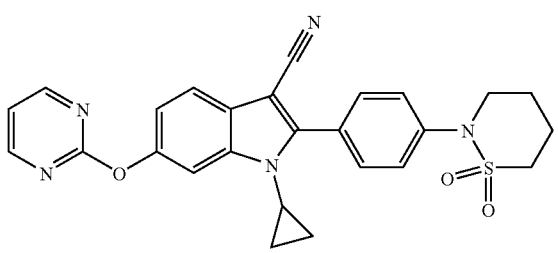
3217 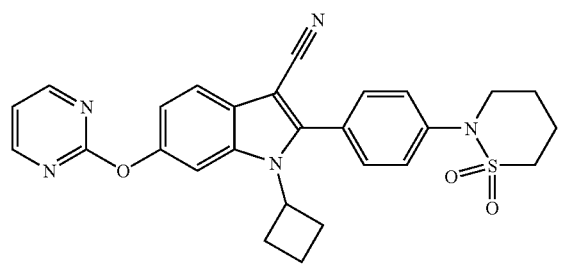 3218 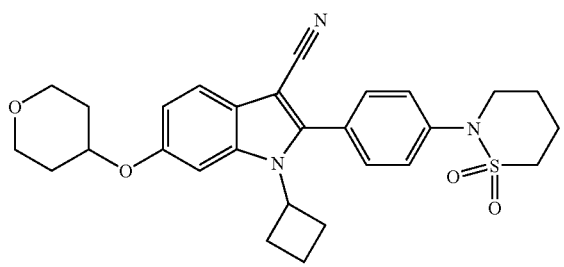
3219 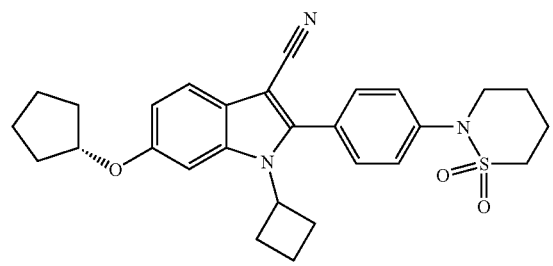 3220 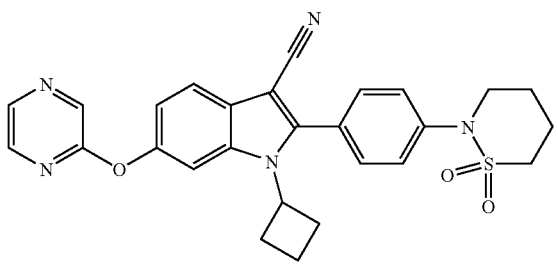
3223 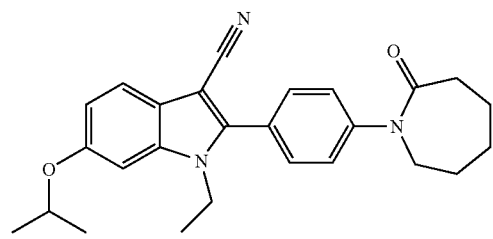 3224 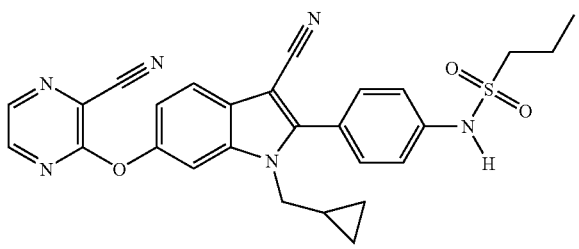

3225 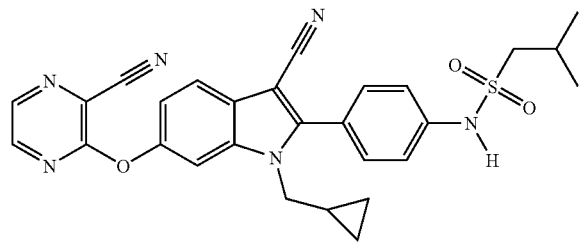
3226 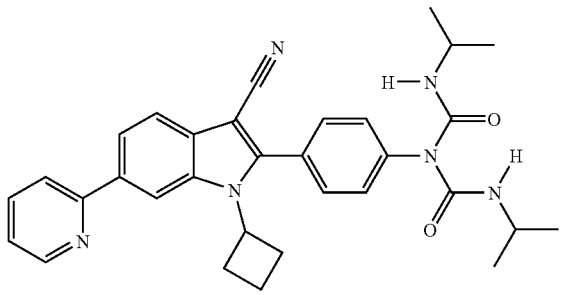
3228 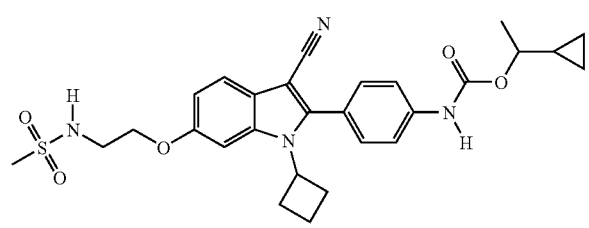
3229 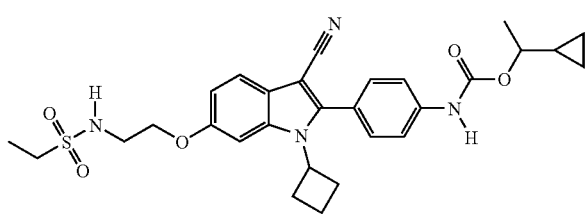
3230 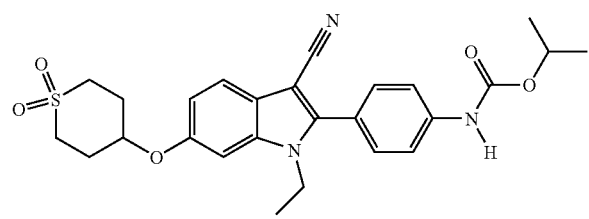
3231 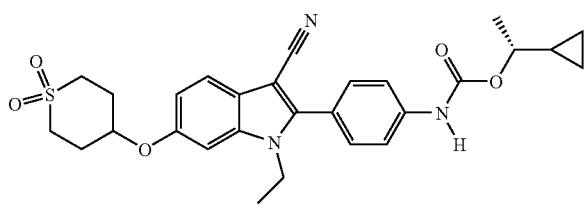
3232 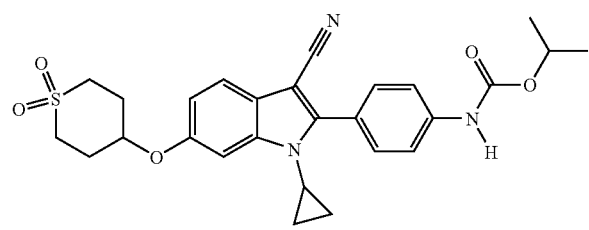
3233 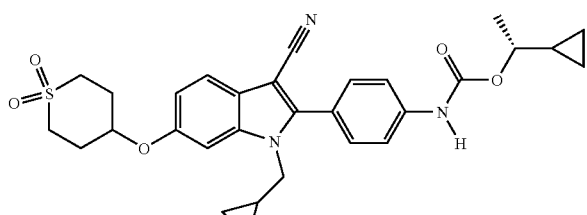
3234 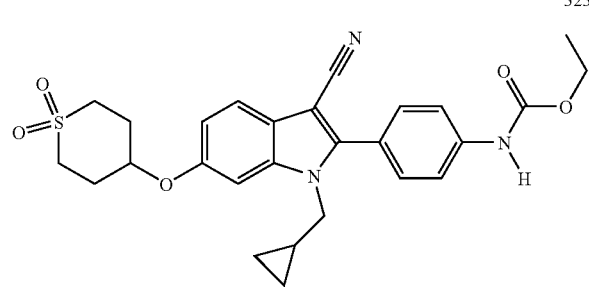
3235 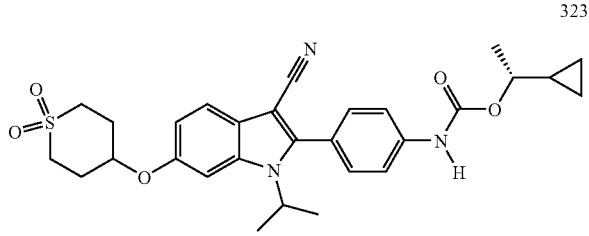
3236 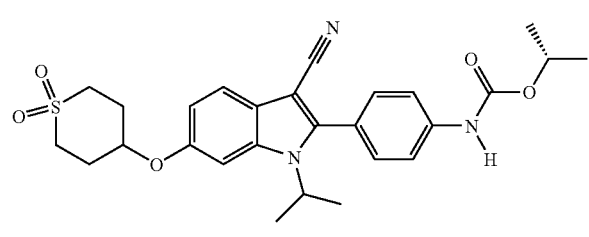
3237 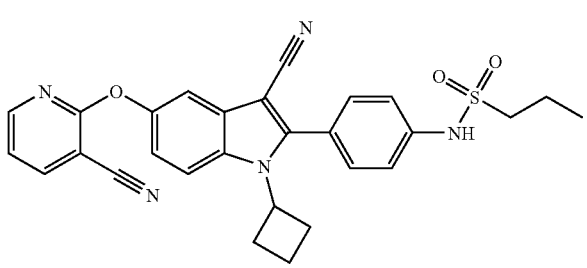

-continued
3238
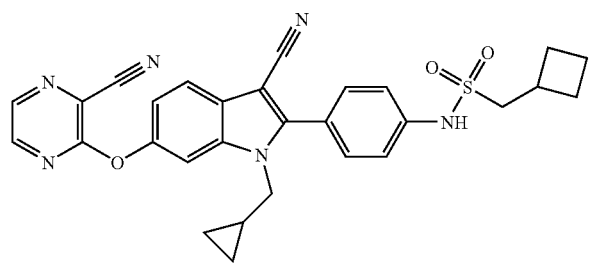
2339
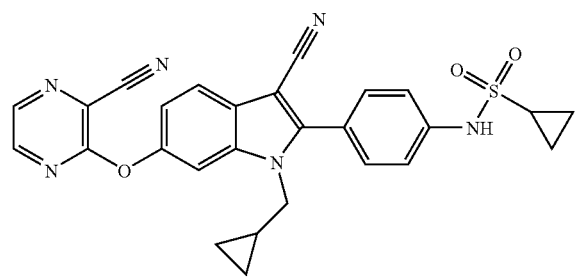
3240
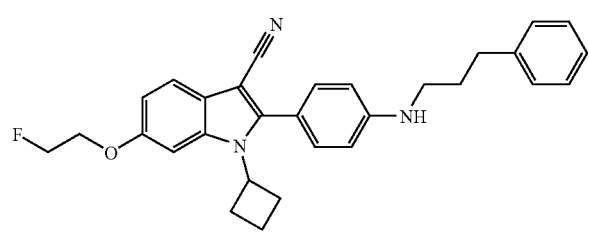
3241
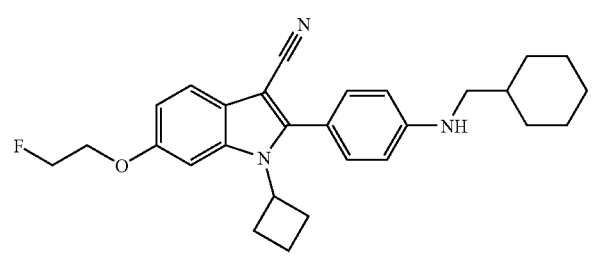
3242
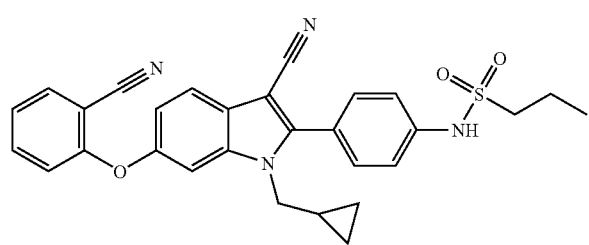
3243
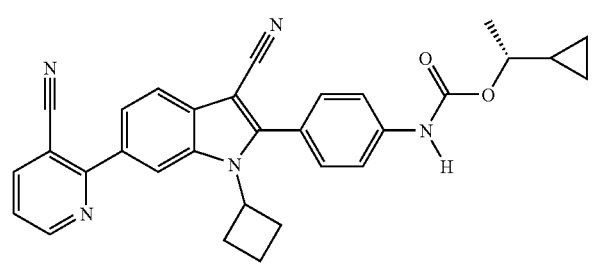
3244
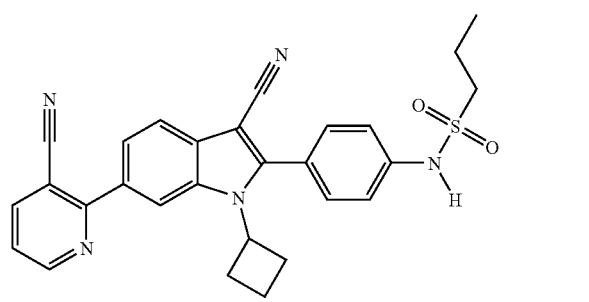
3245
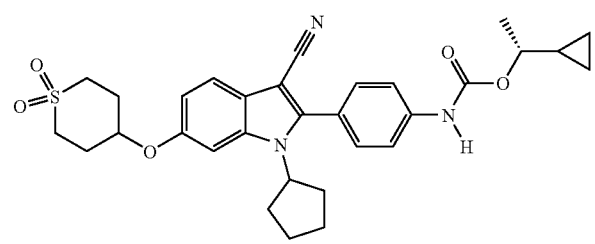
3246
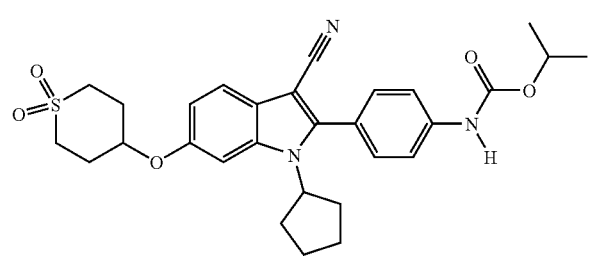
3247
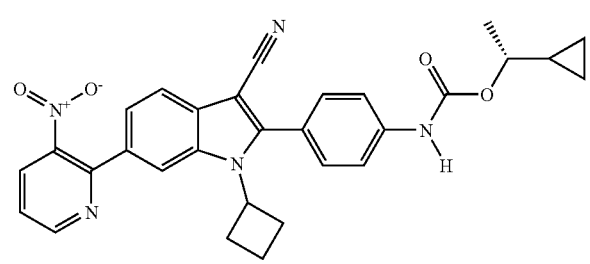

-continued
899
900
3248
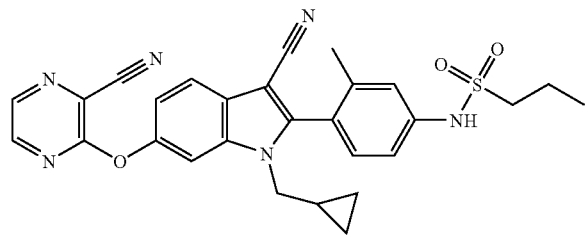
3249
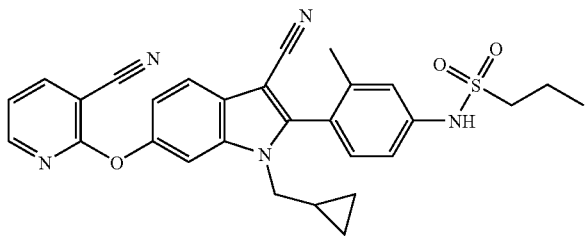
3250
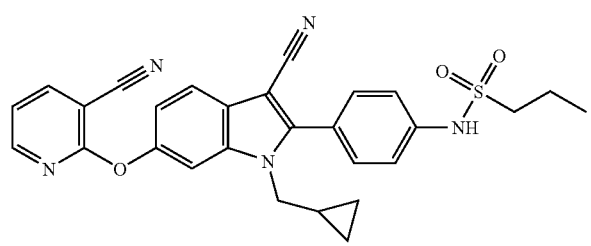
3251
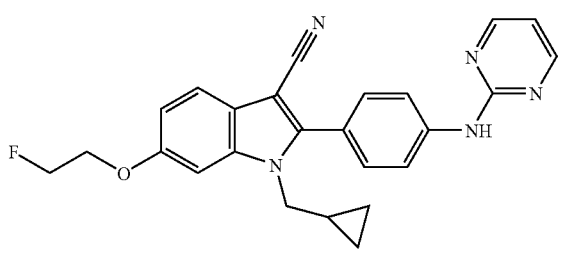
2352
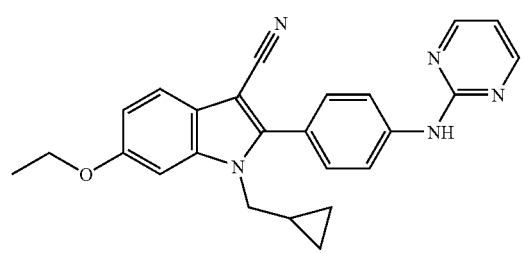
2353
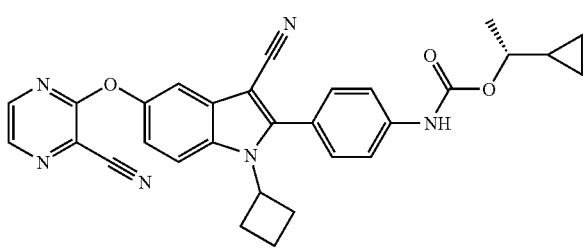
2354
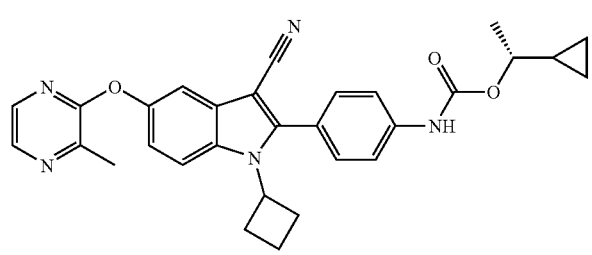
2355
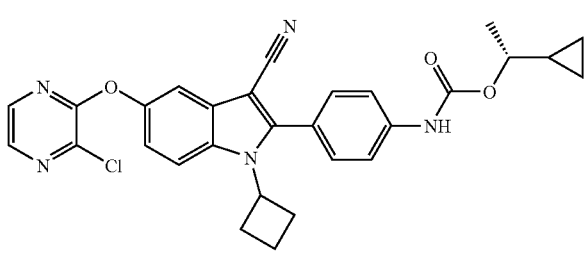
3256
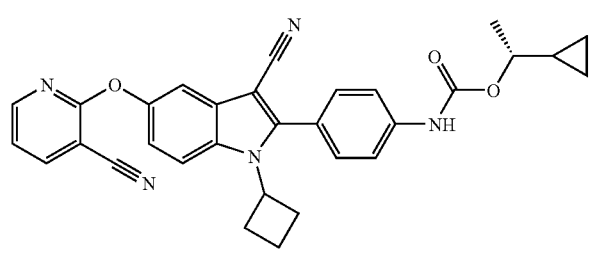
2357
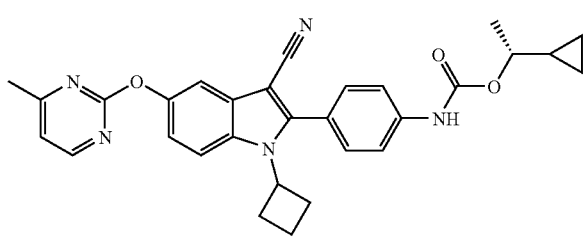

-continued
| 2358 | 3259 |
| 3260 | 3261 |
| 3262 | 3263 |
| 3264 | 3265 |
| 3266 | 2367 |
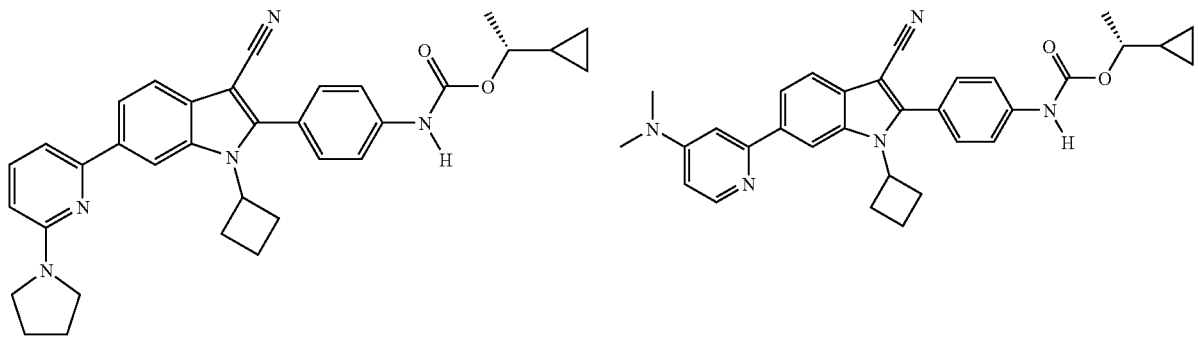
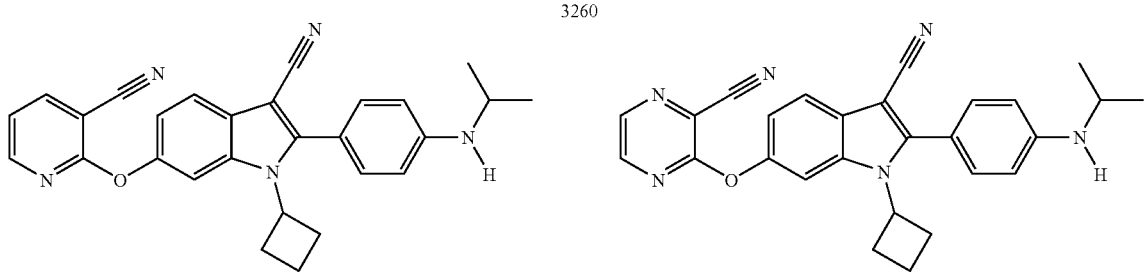
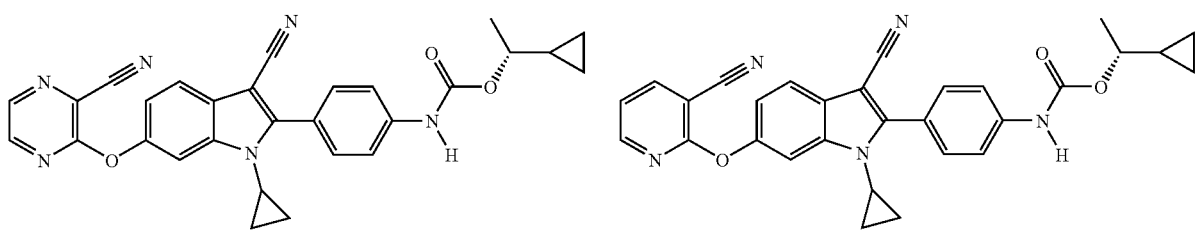
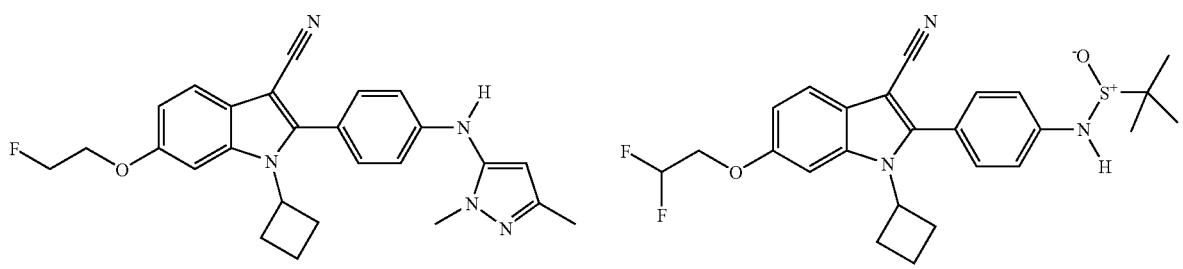
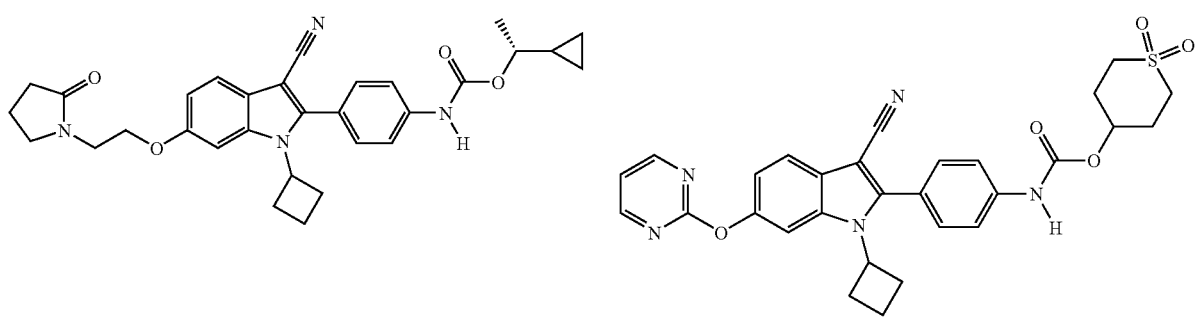

-continued
3268
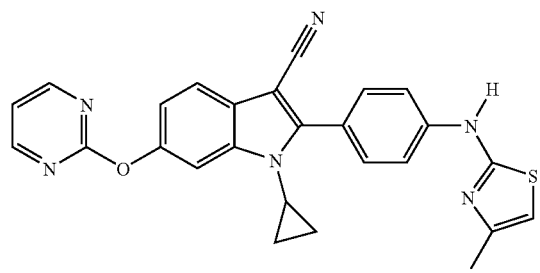
3269
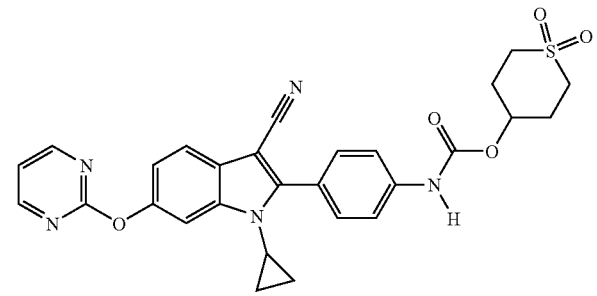
3270
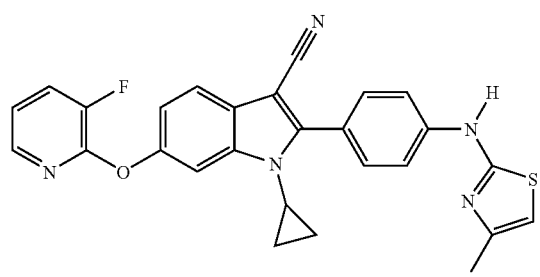
3271
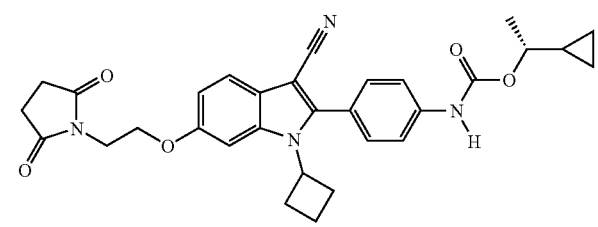
3272
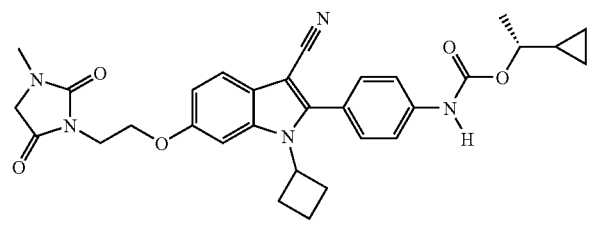
3273
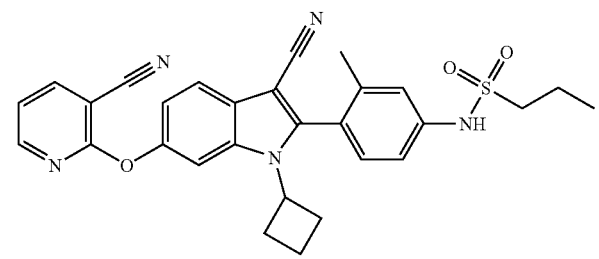
3274
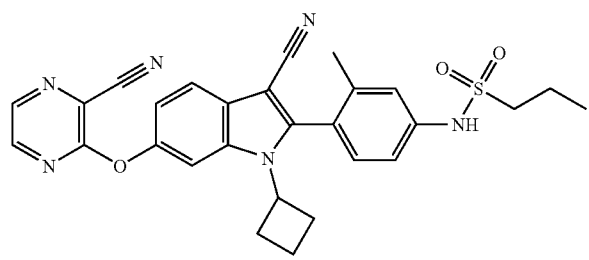
3275
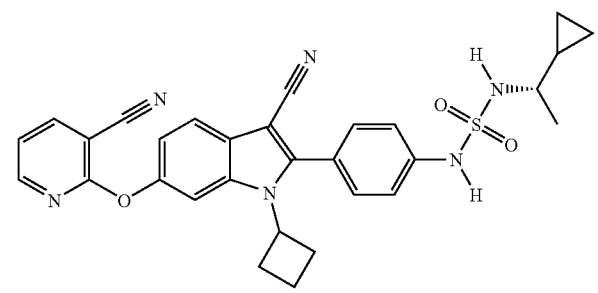
2376
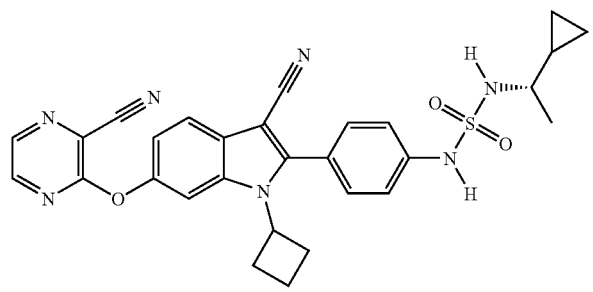
3277
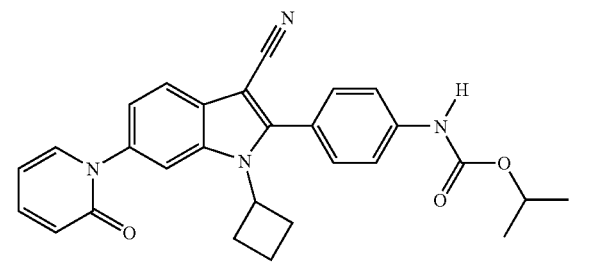

-continued
3278
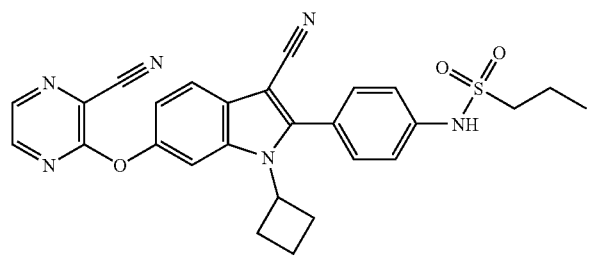
3279
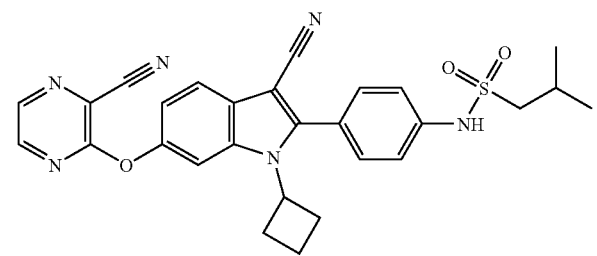
3280
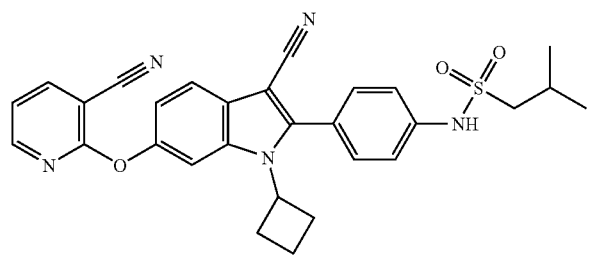
3281
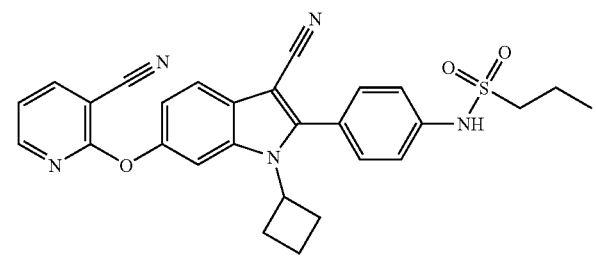
3285
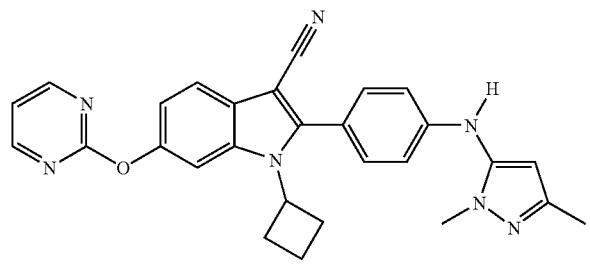
3286
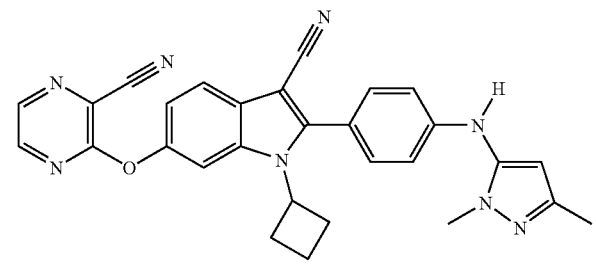
3287
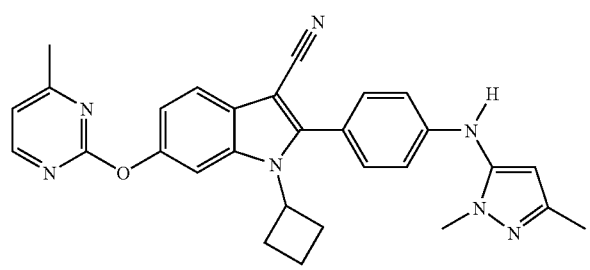
3288
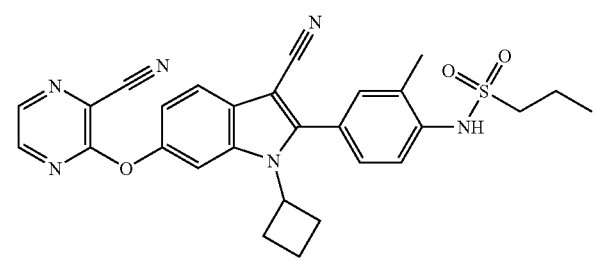
3289
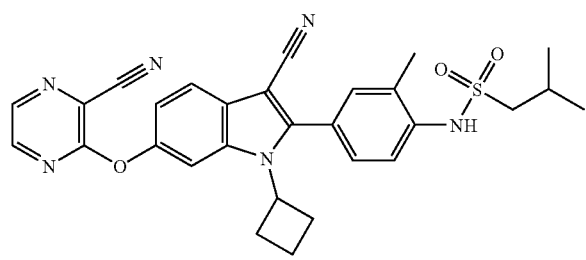
3290
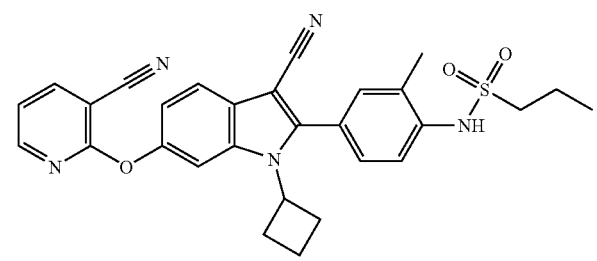

-continued
3291
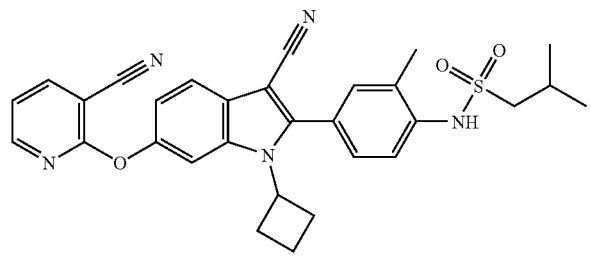
3292
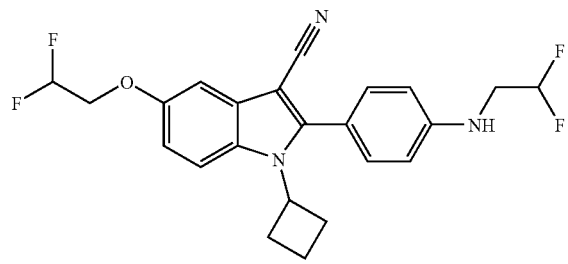
3293
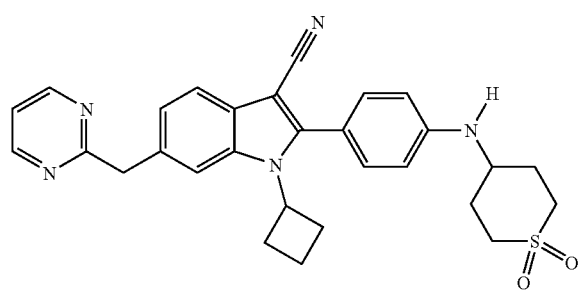
3294
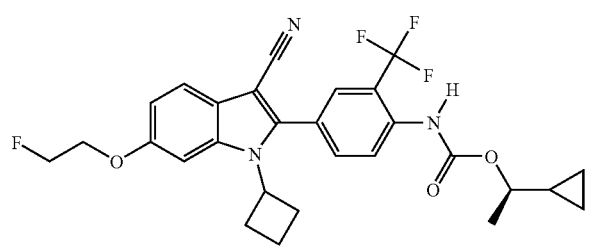
3295
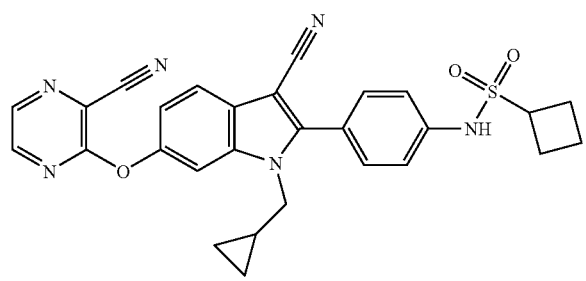
3296
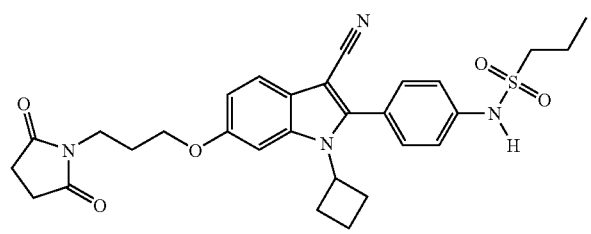
3297
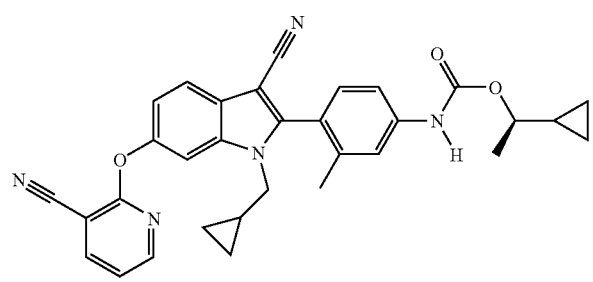
3298
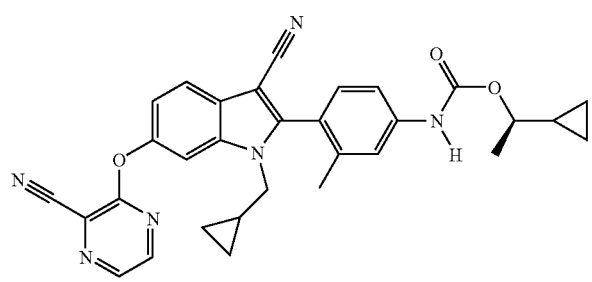
3299
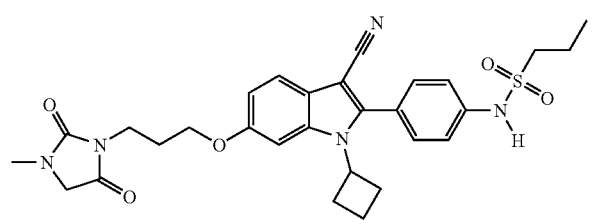
3300
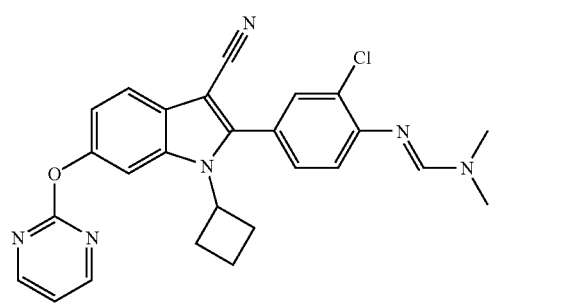

-continued
3301
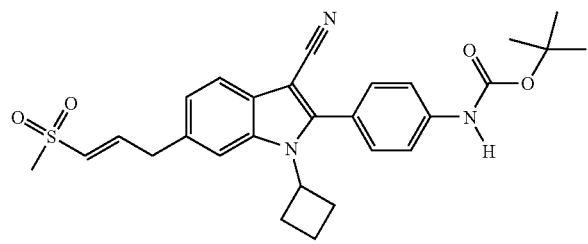
3302
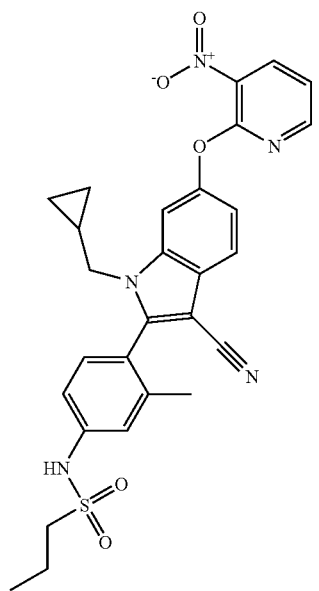
3303
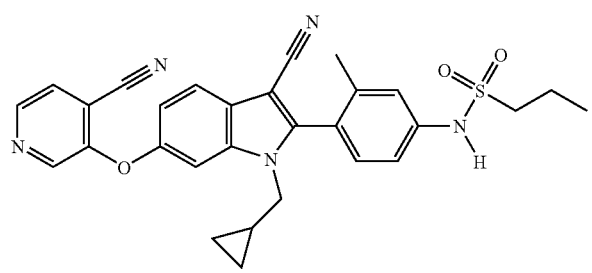
3304
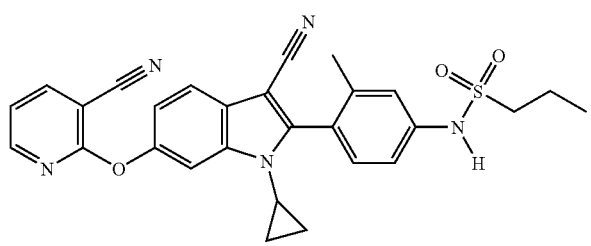
3305
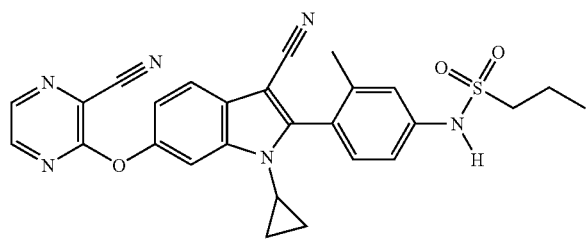
3306
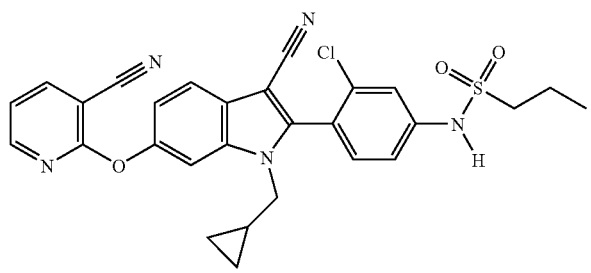

911 912
-continued
| 3307 | 3308 |
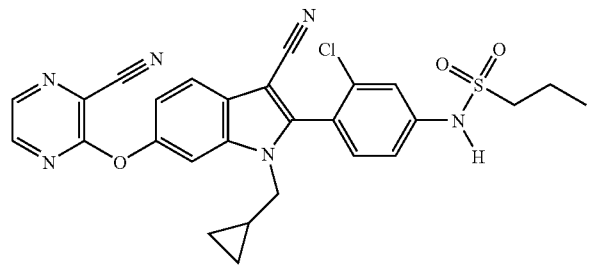
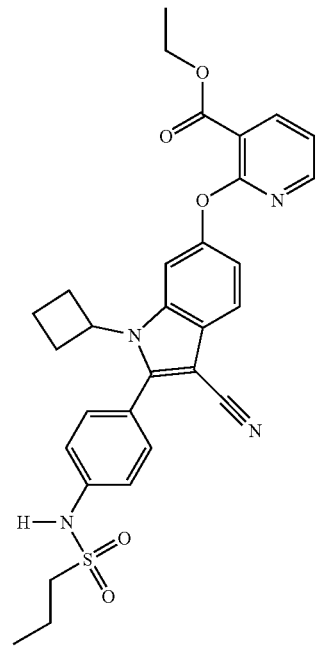
| 3309 | 3310 |
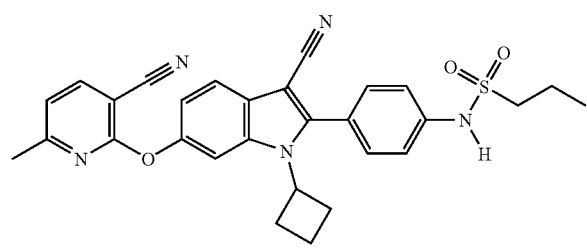
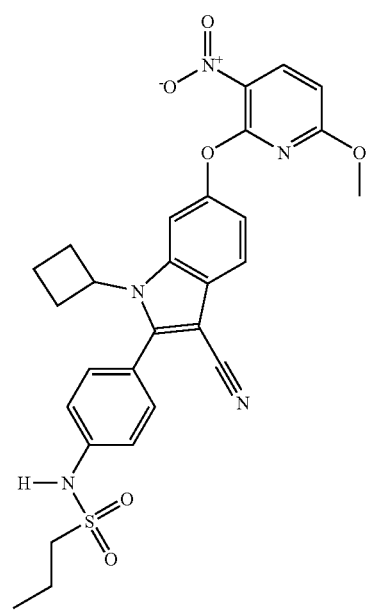

913                                          914
-continued
3311                                                      3314
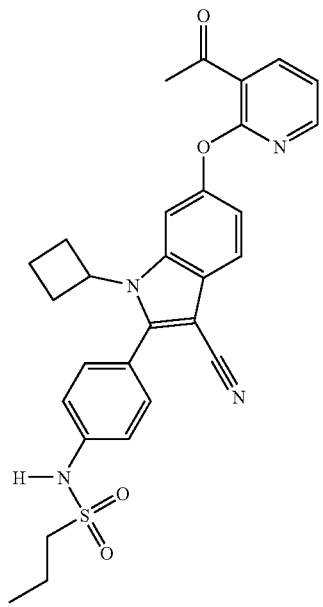                        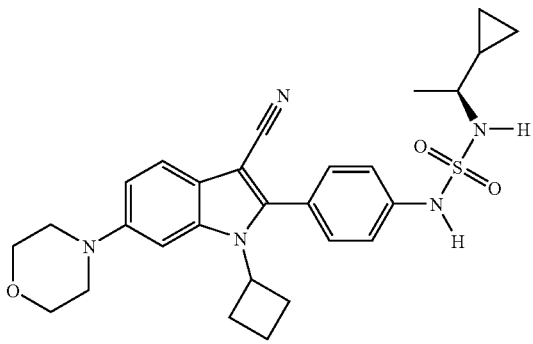
3315                                         3316
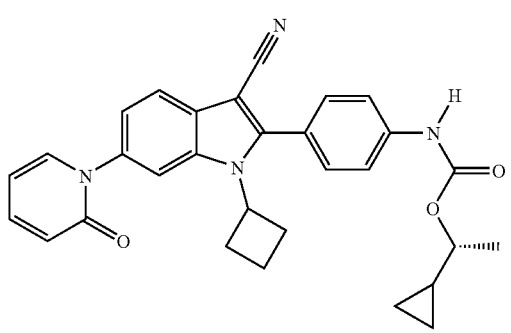                        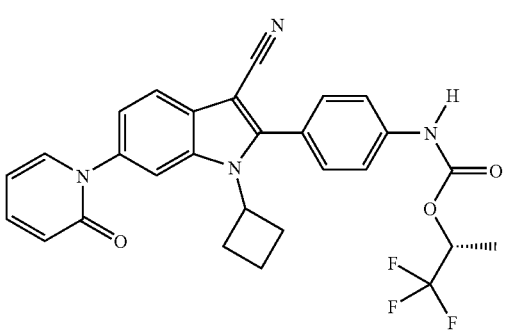
3317                                         3318
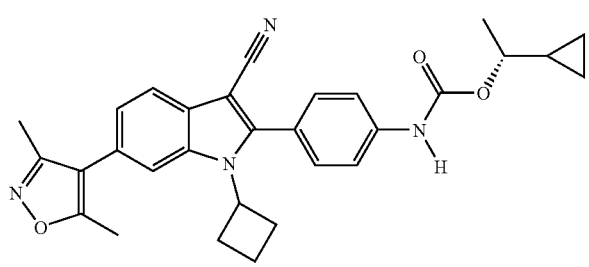                        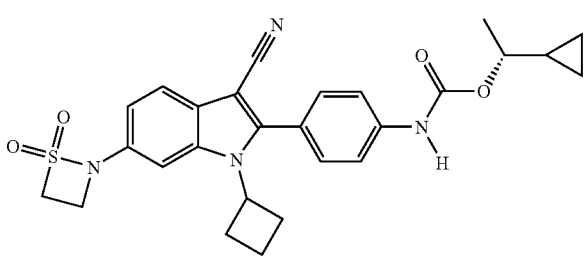
3319                                         3320
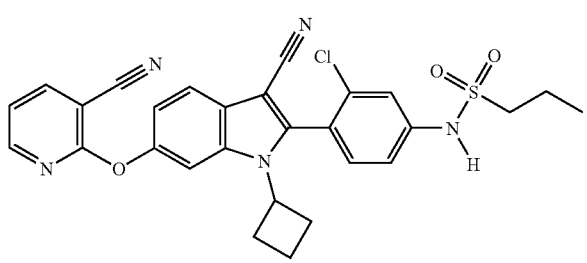                        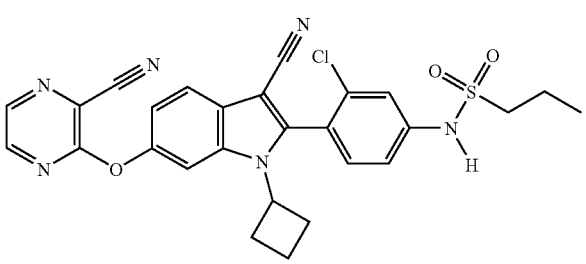

-continued
| 3323 | 3324 |
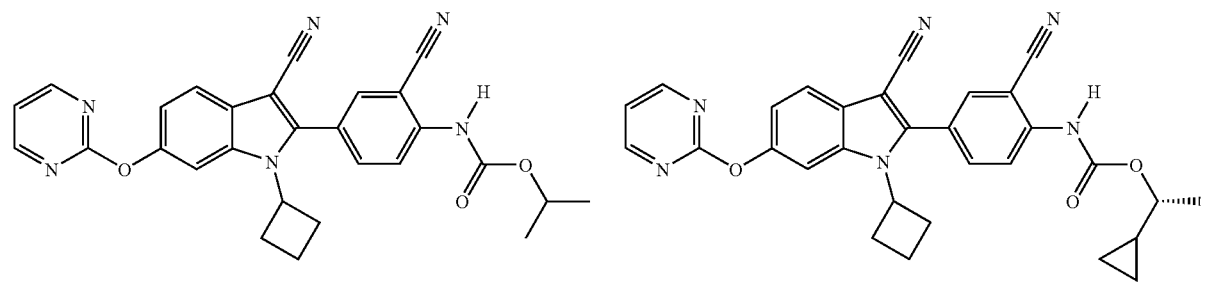
| 3325 | 3332 |
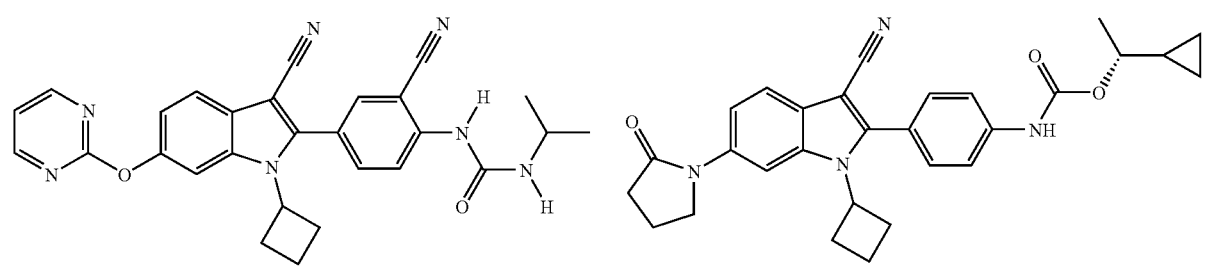
| 3333 | 3334 |
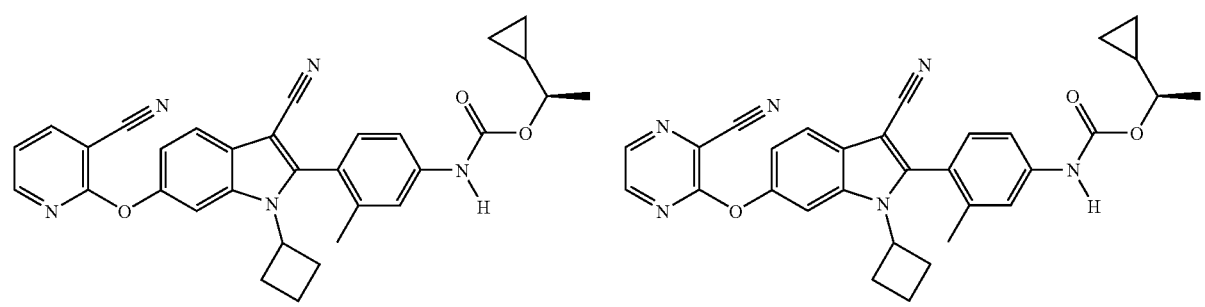
| 3335 | 3336 |
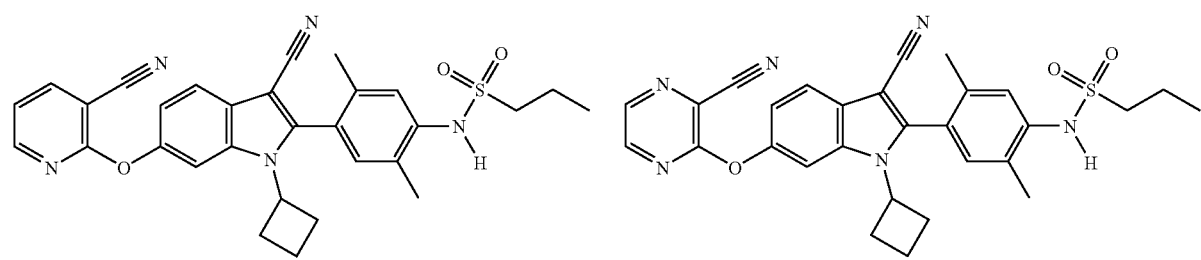

-continued
917
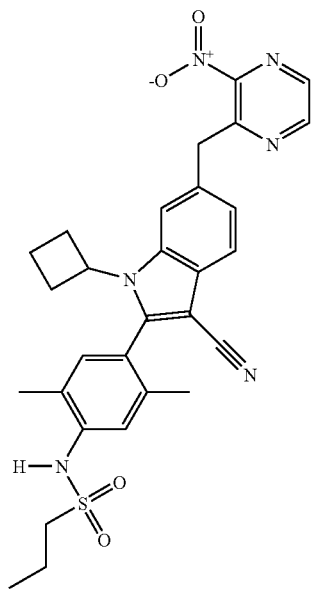
3337
3338
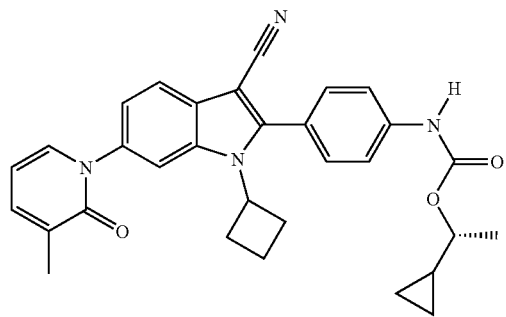
3339
3340
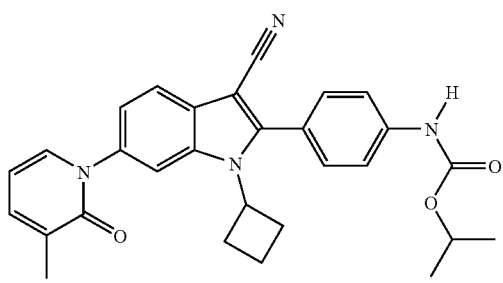
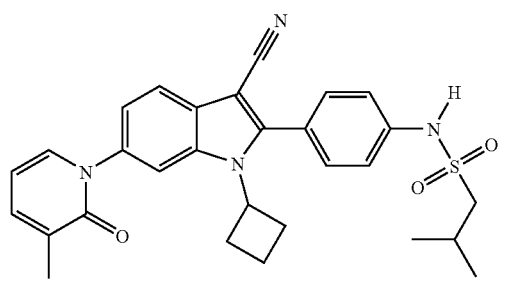
3341
3342
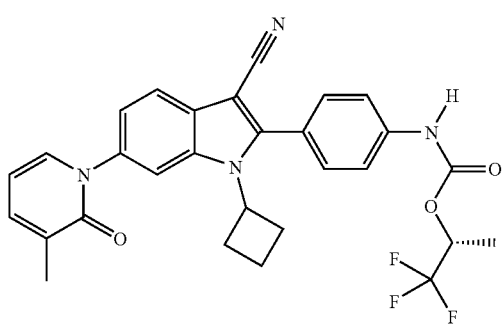
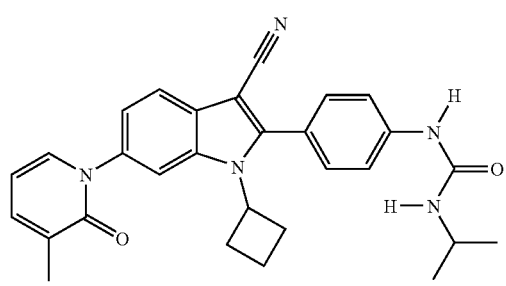
3343
3344
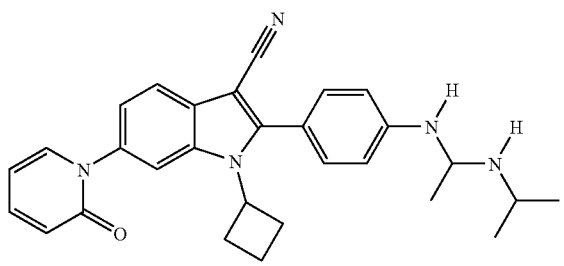
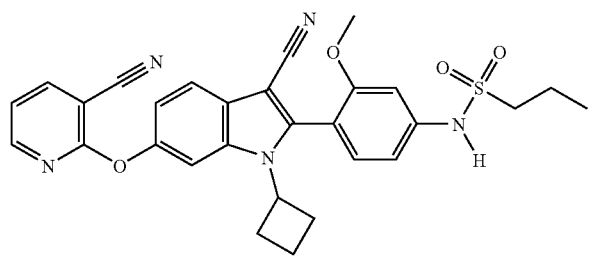

-continued

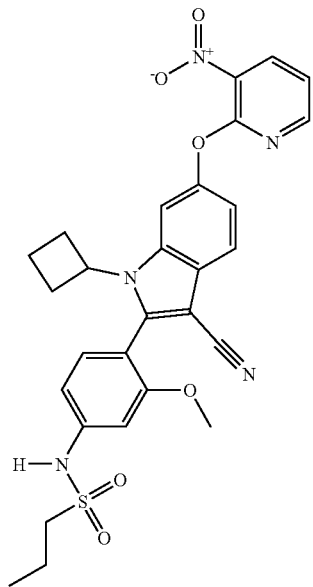
3345

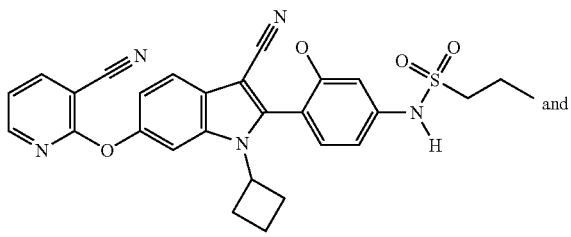
3346 and

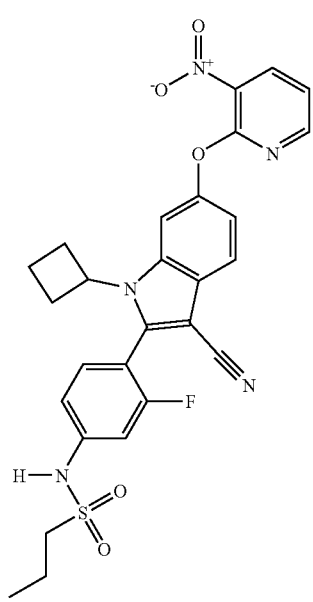
3347

6. A pharmaceutical composition comprising the compound of claim 1 or a pharmaceutically acceptable salt thereof and one or more pharmaceutically acceptable excipients.

7. A method for treating a viral infection in a subject in need thereof comprising administering an effective amount of the compound of claim 1 or a pharmaceutically acceptable salt thereof to the subject, wherein said viral infection is a Hepatitis C viral infection.

* * * * *